US007208517B1

(12) United States Patent
Winn et al.

(10) Patent No.: US 7,208,517 B1
(45) Date of Patent: *Apr. 24, 2007

(54) ENDOTHELIN ANTAGONISTS

(75) Inventors: Martin Winn, Deerfield, IL (US);
Steven A. Boyd, Longmont, CO (US);
Charles W. Hutchins, Green Oaks, IL (US); Hwan-Soo Jae, Glencoe, IL (US); Andrew S. Tasker, Simi Valley, CA (US); Thomas W. von Geldern, Richmond, IL (US); Jeffrey A. Kester, Deerfield, IL (US); Bryan K. Sorensen, Waukegan, IL (US); Bruce G. Szczepankiewicz, Gages Lake, IL (US); Kenneth J. Henry, Carmel, IN (US); Gang Liu, Waukegan, IL (US); Steven J. Wittenberger, Mundelein, IL (US); Steven A. King, Gurnee, IL (US); Todd J. Janus, Gurnee, IL (US); Robert J. Padley, Lake Bluff, IL (US)

(73) Assignee: Abbott Labortories, Abbott Park, IL (US)

( * ) Notice: Subject to any disclaimer, the term of this patent is extended or adjusted under 35 U.S.C. 154(b) by 639 days.

This patent is subject to a terminal disclaimer.

(21) Appl. No.: 09/653,563

(22) Filed: Aug. 31, 2000

Related U.S. Application Data

(63) Continuation-in-part of application No. 09/634,661, filed on Aug. 7, 2000, now abandoned, which is a continuation-in-part of application No. 09/048,955, filed on Mar. 27, 1998, now abandoned, which is a continuation-in-part of application No. 08/794,506, filed on Feb. 4, 1997, now abandoned, which is a continuation-in-part of application No. 08/600,625, filed on Feb. 13, 1996, now abandoned, which is a continuation-in-part of application No. 08/497,998, filed on Aug. 2, 1995, now abandoned, which is a continuation-in-part of application No. 08/442,575, filed on May 30, 1995, now Pat. No. 5,767,144, which is a continuation-in-part of application No. 08/334,717, filed on Nov. 4, 1994, now abandoned, which is a continuation-in-part of application No. 08/293,349, filed on Aug. 19, 1994, now abandoned.

(51) Int. Cl.
*A61K 31/40* (2006.01)

(52) U.S. Cl. .................................................. 514/422

(58) Field of Classification Search ................ 514/422, 514/423, 424, 425, 426, 428, 429; 548/412, 548/413, 517, 518, 526, 531, 543, 544, 557, 548/566, 567, 570, 571, 572, 577
See application file for complete search history.

(56) References Cited

U.S. PATENT DOCUMENTS 3,342,833 A 9/1967 Fremery et al.
3,719,667 A 3/1973 Gutowski
3,840,556 A 10/1974 Kukolja
4,132,709 A 1/1979 Santrouch et al.
4,216,218 A 8/1980 Ehrogott et al.
4,279,918 A * 7/1981 Eistetter et al. .............. 514/408
4,340,715 A 7/1982 Grounder et al.
5,482,960 A 1/1996 Berryman et al.
5,668,164 A 9/1997 Ma et al.
5,767,144 A * 6/1998 Winn et al. .................. 514/422
5,998,468 A 12/1999 Cheng et al.
6,017,951 A 1/2000 Patt et al.
6,048,893 A 4/2000 Smith et al.

FOREIGN PATENT DOCUMENTS

EP 0 439 444 7/1991

(Continued)

OTHER PUBLICATIONS

Liu, Gang et al., "Design Synthesis and Activity of a Series of Pyrrolidine—3 carboxylic Acid—Based, Highly Specific, Orally Active ETB Antagonists Containing a Diphenylmethylamine Acetamide Side Chain" J. Med. Chem. (1999), 42 (18), 3679-3689.
Aktan et al., BQ-123, A Specific Endothelin (ETA) Receptor Antagonist, Prevents Ischemia-reperfusion injury in Kidney Transplantation, *Transplant Int*, vol. 9, 1996, pp. 201-207.
Benigni et al., "A Specific Endothelin Subtype A Receptor Antagonist Protects Against Injury in Renal Disease Progression", *Kidney International*, vol. 44, 1993, pp. 440-444.
Berliner et al., *Journal of the American Chemical Society*, vol. 72, 1950, pp. 222-227.
Berridge et al., "Lithium Amplifies Agonist-dependent Phosphatidylinositol Responses in Brain and Salivary Glands", *Biochem. J.*, vol. 206, 1982, pp. 587-595.
Bhagwat, S., "Synthesis of Enantiomerically Pure Pyrrolidinones as Endothelin Receptor Antagonists", Tetrahedron Letters, 37(27), 1996, pp. 4627-4630.

(Continued)

*Primary Examiner*—Kamal A. Saeed
*Assistant Examiner*—Robert Shiao
(74) *Attorney, Agent, or Firm*—B. Gregory Donner

(57) ABSTRACT

A compound of the formula (I):

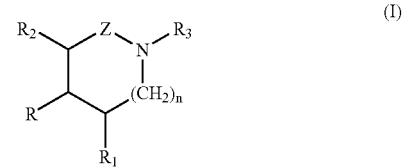

or a pharmaceutically acceptable salt thereof is disclosed, as well as processes for and intermediates in the preparation thereof, a method of antagonizing endothelin, methods for the inhibition of bone metastases, methods for the prevention of growth of new metastases, methods for the inhibition of bone turnover, and methods for the prevention of bone loss in patients, including cancer patients, using an endothelin ET-A receptor antagonist.

8 Claims, 7 Drawing Sheets

FOREIGN PATENT DOCUMENTS

| | | |
|---|---|---|
| GB | 2275926 | 9/1994 |
| WO | 93/08799 | 5/1993 |
| WO | 94/02474 | 2/1994 |
| WO | 94/14434 | 7/1994 |
| WO | 95/04534 | 2/1995 |
| WO | 95/05372 | 2/1995 |
| WO | 95/05376 | 2/1995 |
| WO | 95/33748 | 12/1995 |
| WO | 95/33752 | 12/1995 |
| WO | 95/35107 | 12/1995 |
| WO | 96/06095 | 2/1996 |
| WO | 97/30045 | 8/1997 |
| WO | 97/30046 | 8/1997 |

OTHER PUBLICATIONS

Bobik et al., "Growth Factor Activity of Endothelin on Vascular Smooth Muscle", *American Journal of Physiology*, vol. 258, 1990, pp. C408-C415.

Bonvallet et al., *American Journal of Physiology*, vol. 266, 1994, pp. H1327-H1331.

Borch et al., "The Cyanohydridoborate Anion as a Selective Reducing Agent", *J. Am. Chem. Soc.*, vol. 93, No. 12, 1971, pp. 2897-2904.

Bourguignon et al., *Canadian Journal of Chemistry*, vol. 63, 1985, pp. 2354-2361.

Bowman, *J. Chem. Soc.*, 1950, pp. 1346-1349.

Bram et al., *Bull. Chem. Soc. France*, 1964, pp. 945-951.

Bredereck et al., *Chem. Berichte*, vol. 97, 1964, pp. 3397-3406.

Brintzinger et al., *Chem. Berichte*, vol. 85, 1952, pp. 455-457.

Bunchman et al., "Smooth Muscle Cell Proliferation by Conditioned Media from Cyclosponne-Treated Endothelial Cells: A Role of Endothelin", *Transplantation Proceedings*, vol. 23, No. 1, 1991, pp. 967-968.

Bunting et al., *J. Am. Chem. Soc.*, vol. 115, 1993, pp. 11705-11715.

Cahiez et al., Copper-Catalyzed Conjugate Addition of Organomagnesium Reagents to α, β-Ethylenic Esters: A Simple High Yield Procedure, *Tetrahedron Letters*, vol. 31, No. 51, 1990, pp. 7425-7428.

*Chemical Abstract*, vol. 74, No. 9, 1971, p. 304.

*Chemical Abstract*, vol. 119, No. 21, 1993, p. 999.

Chobanian et al., Antiatherogenic Effect of Captopril in the Watanabe Heritable Hyperlipidermic Rabbit, *Hypertension*, vol. 15, No. 3, 1990, pp. 327-331.

Clozel et al., Pathophysiological Role of Endothelin Revealed by the First Orally Active Endothelin Receptor Antagonist , *Nature*, vol. 365, 1993, pp. 759-761.

Corey et al., *Tetrahedron Letters*, vol. 36, 1972, pp. 3769-3772.

Cottrell et al., *J. Chem. Soc., Perkin Trans. 1*, vol. 5, 1991, pp. 1091-1097.

Craig et al., "Modern Pharmacology, Third Edition", Little, Brown and Company, Boston, US, p. 33, col. 2-p. 35, col. 1.

Ferro et al., The Clinical Potential of Endothelin Receptor Antagonists in Cardiovascular Medicine , *Drugs*, vol. 51, No. 1, 1996, pp. 12-27.

Foegh et al., "Inhibition of Coronary Artery Transplant Atherosclerosis in Rabbits with Angiopeptin, an Octapeptide", *Atherosclerosis*, vol. 78, 1989, pp. 229-236.

Fung et al., "Nonpeptide Renin Inhibitors Employing a Novel 3-Aza (or oxa)-2,4-dialkyl Glutaric Acid Moiety as a P2/P3 Amide Bona Replacement", *J. Med. Chem.*, vol. 35, No. 10, 1992, pp. 1722-1734.

Ge, et al., Yaoxue Xuebao, 20 427-432 (1985).

Gershon et al., *J. Heterocyclic Chem.*, vol. 24, 1987, pp. 205-209.

Greene et al., "Protective Groups in Organic Synthesis", 2nd Ed., 1991, pp. 152-186.

Gupton et al., *Synthetic Communications*, vol. 12, No. 1, 1982, pp. 35-41.

Hara et al., Amelioration of Brain Damage after Focal Ischemia in the Rat by a Novel Inhibitor of Lipid Peroxidation , *European J. Pharmacol.*, vol. 197, 1991, pp. 75-82.

Hatt, *Journal of the Chemical Society*, vol. 132, 1929, pp. 1623-1632.

Heistad et al., *Circulation Research*, vol. 54, No. 6, 1984, pp. 711-718.

Higuchi et al., "Pro-drugs as Novel Delivery Systems", A.C.S. Symposium Series, *American Chemical Society*, vol. 14, (1975).

Hirata et al., *Biochem. Biophys. Res. Commun.*, vol. 154, No. 3, 1988, pp. 868-875.

Hogaboam et al., An Orally Active Non-selective Endothelin Receptor Antagonist, Bosentan, Markedly Reduces Injury in a Rat Model fo Colitis, *European J. Pharmacol.*, vol. 309, 1996, pp. 261-269.

Hoshino et al., A Convenient Preparation of Certain N,N-Dialkylcarbamoyl Chlorides , *Synthetic Communications*, vol. 17, No. 16, 1987, pp. 1887-1892.

Hudlicky et al., *Synthetic Communications*, vol. 16, No. 2, 1986, pp 169-182.

Imbriaco et al., *Clinical Cancer Research*, vol. 4, 1998, pp. 1765-1772.

Ishida et al., *Biochem. Pharmacol.*, vol. 44, No. 7, 1992, pp. 1431-1436.

Itoh et al., *Biochemical and Biophysical Research Communications*, vol. 195, No. 2, 1993, pp. 969-975.

Itoh et al., *FEBS Letters*, vol. 231, No. 2, 1988, pp. 440-444.

"IUPAC 1974 Recommendations for Section E, Fundamental Stereochemistry", *Pure Appl. Chem.*, vol. 45, pp. 13-30 (1976).

Jae, et al., "Pyrrolidine-3-carboxylic acids as Endothelin Antagonists. 2. Sulfonamide-Based ETA-ETB Mixed Antagonists." Journal of Medicinal Chemistry, vol. 40, No. 20, 1997, pp. 3217-3227.

Kaldor et al., "A Mild, Osmium Tetraoxide-Catalyzed Method for the Oxidation of Sulfides to Sulfones", *Tetrahedron Letters*, vol. 32, No. 38, 1991, pp. 5043-5046.

Kanemasa et al., "Nonstabilized Azomethine Ylides Generated by Decarboxylative Condensation of α-Amino Acids. Structural Variation, Reactivity, and Stereoselectivity", *Bull. Chem. Soc. Of Japan*, vol. 62, No. 6, 1989, pp. 1960-1968.

Klemm et al., Endothelin 1 Mediates ex vivo Coronary Vasoconstriction Caused by Exogenous and Endogenous Cytokines , *Proc. Natl. Acad. Sci.*, vol. 92, 1995, pp. 2691-2695.

Kon et al., Glomerular Actions of Endothelin In Vivo , *J. Clin. Invest.*, vol. 83, 1989, pp. 1762-1767.

Kon et al., Role of Endothelin in Cyclosporine-induced Glomerular Dysfunction , *Kidney International*, vol. 37, 1990, pp. 1487-1491.

Krapcho et al., *Organic Syntheses*, vol. 47, 1967, pp. 20-23.

Margulies et al., *Circulation*, vol. 82, No. 6, 1990, pp. 2226-2230.

Matsumura et al., *European Journal of Pharmacology*, vol. 185, 1990, pp. 103-106.

Matsumura et al., *Life Sciences*, vol. 49, 1991, pp. 841-848.

McMurdo et al., *European Journal of Pharmacology*, vol. 259, 1994, pp. 51-55.

Nakagomi et al., *J. Neurosurg.*, vol. 66, 1987, pp. 915-923.

Nelson et al., *Nature Medicine*, vol. 1, No. 9, 1995, pp. 944-949.

Nelson et al., *Urology*, vol. 53, No. 5, 1999, pp. 1063-1069.

Potvin et al., *Canadian Journal of Physiol. And Pharmacol.*, vol. 67, 1989, pp. 1213-1218.

Prescott, ed., *Methods in Cell Biology*, vol. XIV, pp. 33 et seq., Academic Press, New York, NY (1976).

Rahman, *Indian J. Chem.*, Sec. B, 19B 828-830 (1980).

Rapoport et al., *J. Org. Chem.*, 1986, vol. 51, pp. 5106-5110.

Roche, E.B, Editor: "Bioreversible Carriers in Drug Design: Theory and Application", pp. 13-21, Pergamon Press, New York (1987).

Seydal et al., "ChemiStruktur und biologische Aktivitat von Wirkstoffen." Verlag Chemie, Weinheim, DE, 1979, p. 124, paragraph 2-p. 126, paragraph 2.

Shichiri et al., *J. Clin. Invest.*, vol. 87, 1991, pp. 1867-1871.

Streitwieser et al., *Tetrahedron Letters*, vol. 42, 1971, pp. 3927-3930.

Takahashi et al., *Clinical Science*, vol. 79, 1990, pp. 619-623.

Tasker, et al., "Potent and Selective Non-Benzodioxole Containing Endothelin- A Receptor Antagonists" 1997, Journal of Medicinal Chemistry.

Taylor et al., *J. Org. Chem.*, vol. 54, 1989, pp. 3618-3624.

Topliss, "Quantitative Structure-Activity Relationships of Drugs", Academic Press, New York, p. 453, paragraph 2-p. 456, paragraph 2.
Tsuge, et al. Chemistry Letters, 801-804 (1984).
Tsuge, et al. Bull. Chem. Soc. Jpn 59 2537 (1986).
Tsuge et al., *Chemistry Letters*, 1983, pp. 1131-1134.
Tsuge et al., *J. Org. Chem.*, 1987, vol. 52, pp. 2523-2530.
*U.S. Department of Health and Human Services.* "Management of Cancer Pain Clinical Guideline No. 9." AHCPR Publication No. 94-0592: Mar. 1994.
Vilsmaier et al., *Leibigs Ann. Chem.*, 1980, pp. 1055-1063.
Wallace et al., *Am. J. Physiol.*, 1989, vol. 256, pp. G661-G666.
Watanabe et al., *Nature*, vol. 344, 1990, p. 114.
Weaver et al., *J. Amer. Chem. Soc.*, vol. 69, 1947, pp. 515-516.
Wenkert et al., *J. Org. Chem.*, vol. 48, 1983, pp. 5006-5009.
Winn, et al., "2,4-Diarylpyrrolidine-3-carboxylic Acids-Potent Et▲ Selective Endothelin Receptor Antagonists. 1. Discovery of A-127722.", *Journal of Medicinal Chemistry*, vol. 39, No. 5, 1996, pp. 1039-1048.

Wu-wong et al., *Life Sciences*, vol. 58, No. 21, 1996, pp. 1839-1847.
Yamagishi et al., *Biochem. Biophys. Res. Comm.*, vol. 191, No. 3, 1993, pp. 840-846.
Yamamoto et al., *J. Pharmacol. Exp. Therapeutics*, vol. 271, 1994, pp. 156-163.
Yanagisawa et al., *Nature*, vol. 332, 1988, pp. 411-415.
U.S. Appl. No. 09/634,661, filed Aug. 7, 2000.
U.S. Appl. No. 09/048,955, filed Mar. 27, 1998.
U.S. Appl. No. 08/794,506, filed Feb. 4, 1997.
U.S. Appl. No. 08/600,625, filed Feb. 13, 1996.
U.S. Appl. No. 08/497,998, filed Aug. 2, 1995.
U.S. Appl. No. 08/442,575, filed May 30, 1995.
U.S. Appl. No. 08/334,717, filed Nov. 4, 1994.
U.S. Appl. No. 08/293,349, filed Aug. 19, 1994.

\* cited by examiner

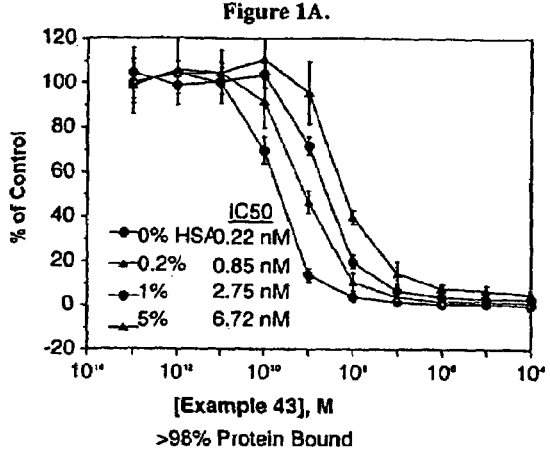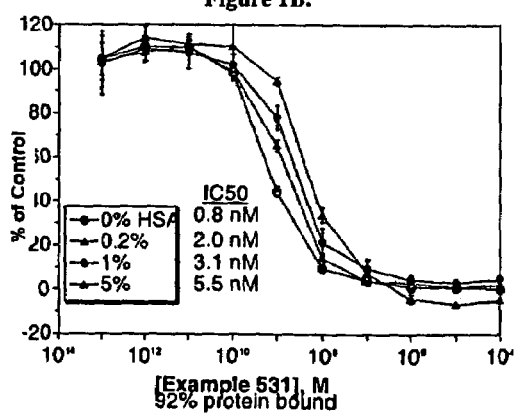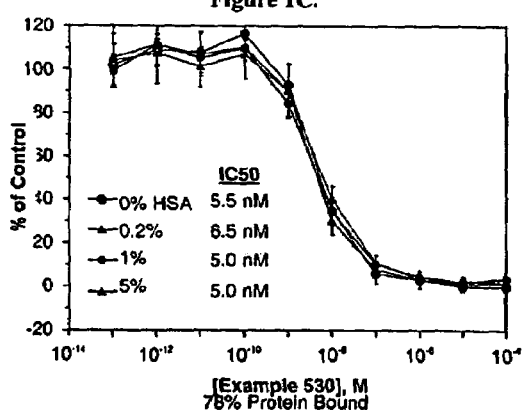
Figure 1

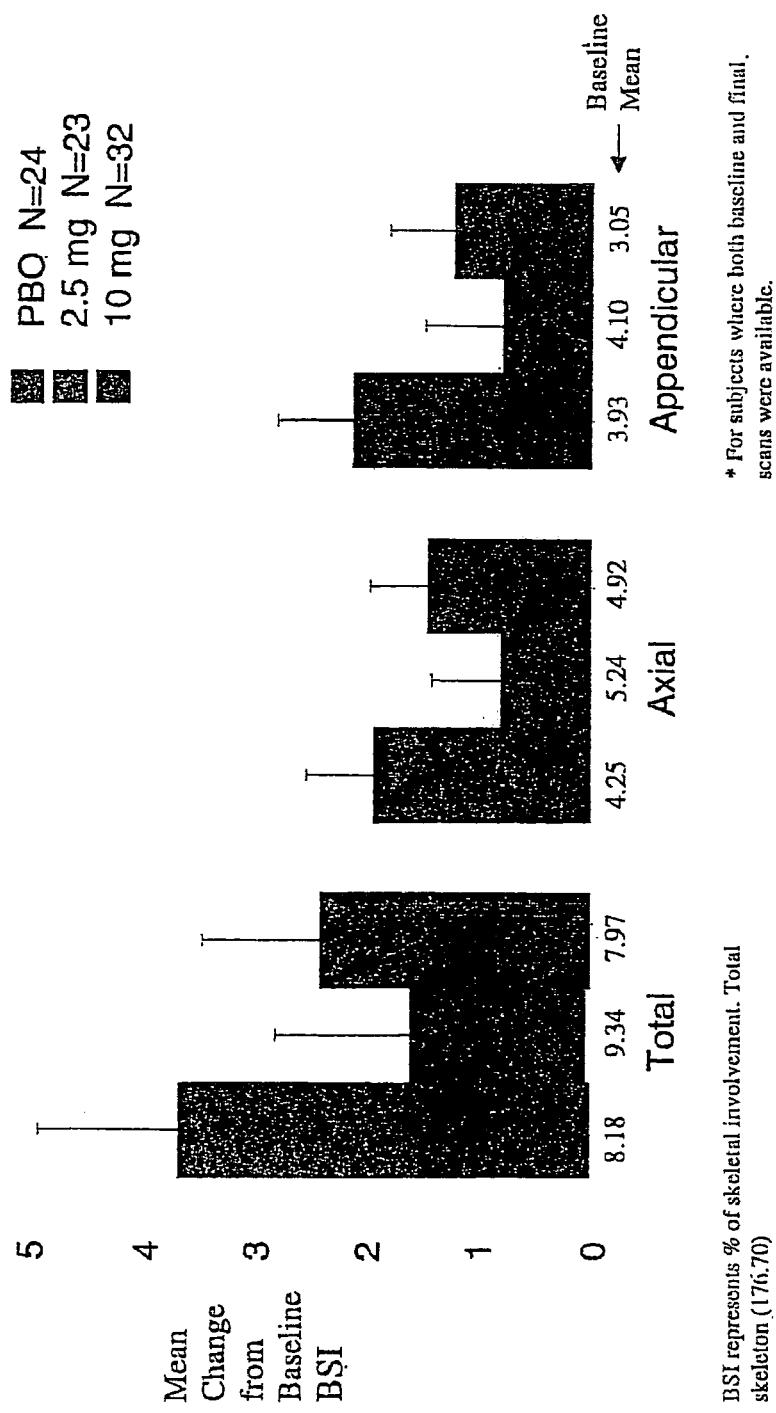

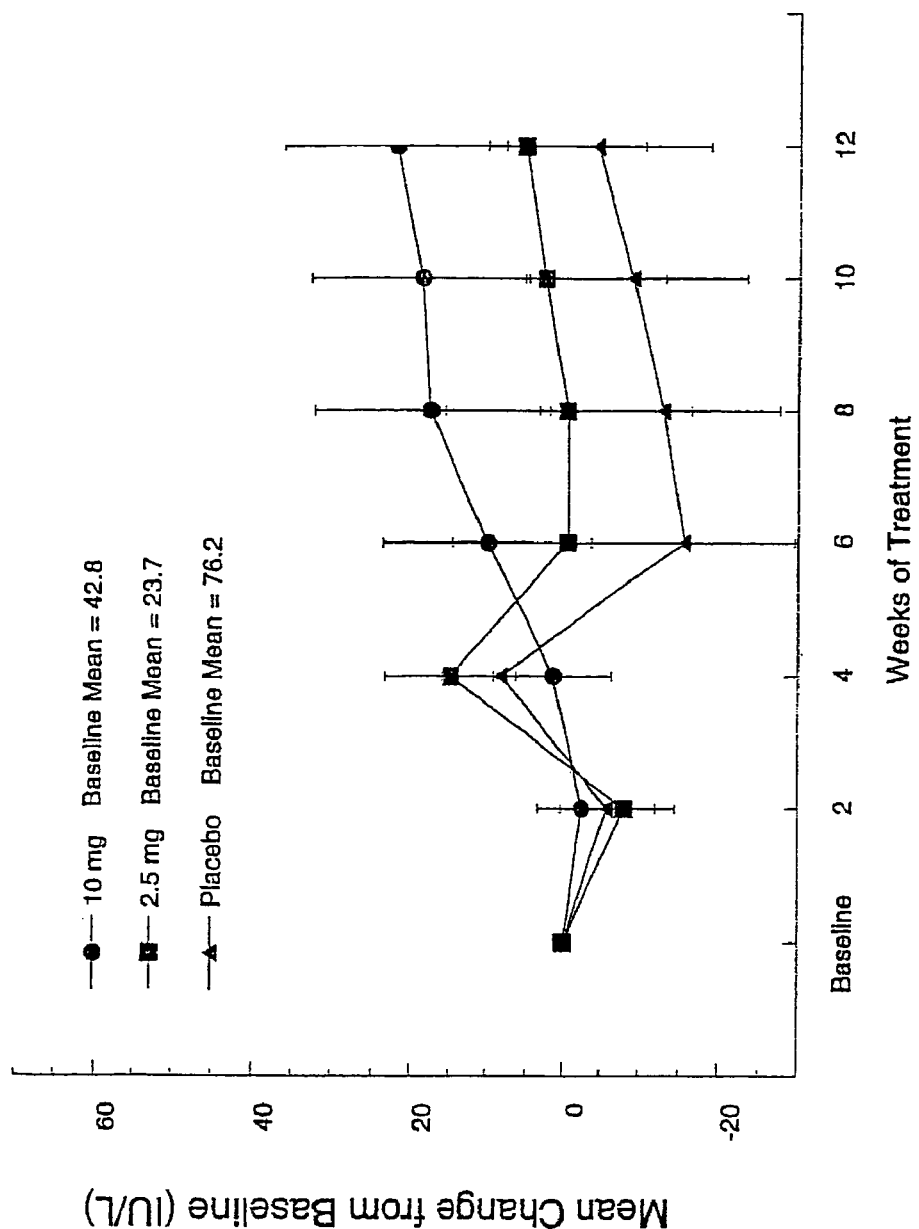

ENDOTHELIN ANTAGONISTS

This application is a continuation-in-part application of U.S. patent application Ser. No. 09/634,661, filed Aug. 7, 2000, which is a continuation-in-part application of U.S. patent application Ser. No. 09/048,955, filed Mar. 27, 1998, which is a continuation-in-part application of U.S. patent application Ser. No. 08/794,506, filed Feb. 4, 1997 now abandoned which is a continuation-in-part of U.S. patent application Ser. No. 08/600,625, filed Feb. 13, 1996 now abandoned, which is a continuation-in-part of U.S. patent application Ser. No. 08/497,998, filed Aug. 2, 1995 now abandoned, which is a continuation-in-part of U.S. patent application Ser. No. 08/442,575, filed May 30, 1995 now U.S. Pat. No. 5,767,144, which is a continuation-in-part of U.S. patent application Ser. No. 08/334,717, filed Nov. 4, 1994 now abandoned, which is a continuation-in-part of U.S. patent application Ser. No. 08/293,349, filed Aug. 19, 1994 now abandoned.

TECHNICAL FIELD

The present invention relates to compounds which are endothelin antagonists, processes for making such compounds, synthetic intermediates employed in these processes, methods and compositions for antagonizing endothelin, methods for the inhibition of bone metastases, methods for the prevention of growth of new metastases, methods for the inhibition of bone turnover, and methods for the prevention of bone loss in patients, including cancer patients, using an endothelin ET receptor antagonist.

BACKGROUND OF THE INVENTION

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin converting enzyme (ECE). Endothelin has been shown to constrict arteries and veins, increase mean arterial blood pressure, decrease cardiac output, increase cardiac contractility in vitro, stimulate mitogenesis in vascular smooth muscle cells in vitro, contract non-vascular smooth muscle including guinea pig trachea, human urinary bladder strips and rat uterus in vitro, increase airway resistance in vivo, induce formation of gastric ulcers, stimulate release of atrial natriuretic factor in vitro and in vivo, increase plasma levels of vasopressin, aldosterone and catecholamines, inhibit release of renin in vitro and stimulate release of gonadotropins in vitro.

It has been shown that vasoconstriction is caused by binding of endothelin to its receptors on vascular smooth muscle (Nature 332 411 (1988), FEBS Letters 231 440 (1988) and Biochem. Biophys. Res. Commun. 154 868 (1988)). An agent which suppresses endothelin production or an agent which binds to endothelin or which inhibits the binding of endothelin to an endothelin receptor will produce beneficial effects in a variety of therapeutic areas. In fact, an anti-endothelin antibody has been shown, upon intrarenal infusion, to ameliorate the adverse effects of renal ischemia on renal vascular resistance and glomerular filtration rate (Kon, et al., J. Clin. Invest. 83 1762 (1989)). In addition, an anti-endothelin antibody attenuated the nephrotoxic effects of intravenously administered cyclosporin (Kon, et al., Kidney Int. 37 1487 (1990)) and attenuated infarct size in a coronary artery ligation-induced myocardial infarction model (Watanabe, et al., Nature 344 114 (1990)).

Clozel et al. (Nature 365: 759–761 (1993)) report that Ro 46–2005, a nonpeptide ET-A/B antagonist, prevents post-ischaemic renal vasoconstriction in rats, prevents the decrease in cerebral blood flow due to subarachnoid hemorrhage (SAH) in rats, and decreases MAP in sodium-depleted squirrel monkeys when dosed orally. A similar effect of a linear tripeptide-like ET-A antagonist, BQ-485, on arterial caliber after SAH has also been recently reported (S. Itoh, T. Sasaki, K. Ide, K. Ishikawa, M. Nishikibe, and M. Yano, Biochem. Biophys. Res. Comm., 195: 969–75 (1993). These results indicate that agents which antagonize ET/ET receptor binding will provide therapeutic benefit in the indicated disease states.

Agents with the ability to antagonize ET/ET receptor binding have been shown to be active in a number of animal models of human disease. For example, Hogaboam et al (EUR. J. Pharmacol. 1996, 309, 261–269), have shown that an endothelin receptor antagonist reduced injury in a rat model of colitis. Aktan et al (Transplant Int 1996, 9, 201–207) have demonstrated that a similar agent prevents ischemia-reperfusion injury in kidney transplantation. Similar studies have suggested the use of endothelin antagonists in the treatment of angina, pulmonary hypertension, Raynaud's disease, and migraine. (Ferro and Webb, Drugs 1996, 51,12–27).

Abnormal levels of endothelin or endothelin receptors have also been associated with a number of disease states, including prostate cancer (Nelson et al, Nature Medicine 1995, 1, 944–949) and as a modulator in osteoblastic bone lesion (UROLOGY 53:1063–1069, 1999). suggesting a role of endothelin in the pathophysiology of these diseases.

Wu-Wong et al (Lfe Sciences 1996, 58, 1839–1847) have shown that both endothelin and endothelin antagonists bind tightly to plasma proteins, e.g., serum albumin. This plasma protein binding can decrease the effectiveness with which the antagonists inhibit endothelin's action. Thus, endothelin antagonists with reduced plasma protein binding may be more effective than highly bound congeners.

DISCLOSURE OF THE INVENTION

In accordance with the present invention there are compounds of the formula (I):

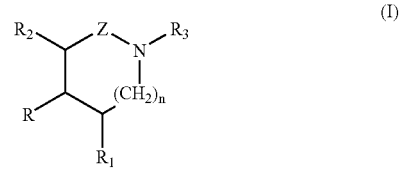

wherein

Z is —C($R_{18}$)($R_{19}$)— or —C(O)— wherein $R_{18}$ and $R_{19}$ are independently selected from hydrogen and loweralkyl;

n is 0 or 1;

R is —(CH$_2$)$_m$—W wherein m is an integer from 0 to 6 and W is
 (a) —C(O)$_2$-G wherein G is hydrogen or a carboxy protecting group,
 (b) —PO$_3$H$_2$,
 (c) —P(O)(OH)E wherein E is hydrogen, loweralkyl or arylalkyl,
 (d) —CN, (e) —C(O)NHR$_{17}$ wherein R$_{17}$ is loweralkyl,
(f) alkylaminocarbonyl,
(g) dialkylaminocarbonyl,
(h) tetrazolyl,
(i) hydroxy,
(j) alkoxy,
(k) sulfonamido,
(l) —C(O)NHS(O)$_2$R$_{16}$ wherein R$_{16}$ is loweralkyl, haloalkyl, aryl or dialkylamino,
(m) —S(O)$_2$NHC(O)R$_{16}$ wherein R$_{16}$ is defined as above,

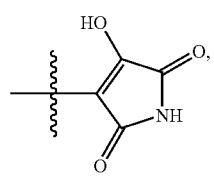(n)

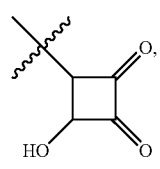(o)

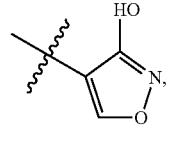(p)

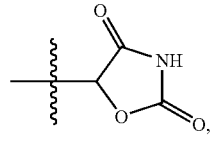(q)

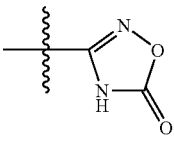(r)

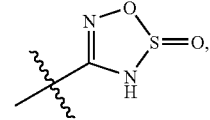(s)

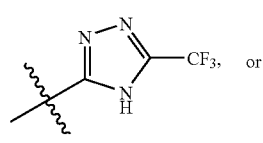(t)

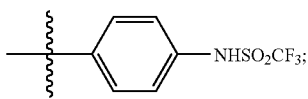(u)

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonyl alkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocylic, (heterocyclic)alkyl and (R$_{aa}$)(R$_{bb}$)N—R$_{cc}$— wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

R$_3$ is (a) R$_4$—C(O)—R$_5$—, R$_4$—R$_{5a}$—, R$_4$—C(O)—R$_5$—N(R$_6$)—, R$_6$—S(O)$_2$—R$_7$— or R$_{26}$—S(O)—R$_{27}$—
wherein R$_5$ is (i) a covalent bond, (ii) alkylene,
(iii) alkenylene, (iv) —N(R$_{20}$)—R$_8$— or —R$_{8a}$—N(R$_{20}$)—R$_8$— wherein R$_8$ and R$_{8a}$ are independently selected from the group consisting of alkylene and alkenylene
and R$_{20}$ is hydrogen, loweralkyl, alkenyl, haloalkyl, alkoxyalkyl, haloalkoxyalkyl, cylcoalkyl or cycloalkylalkyl or (v) —O—R$_9$— or —R$_{9a}$—O—R$_9$ $_9$— wherein R$_9$ and R$_{9a}$ are independently selected from alkylene;

R$_{5a}$ is (i) alkylene or (ii) alkenylene;

R$_7$ is (i) a covalent bond, (ii) alkylene, (iii) alkenylene or
(iv) —N(R$_{21}$)—R$_{10}$— or —R$_{10a}$—N(R$_{21}$)—R$_{10}$—
wherein R$_{10}$ and R$_{10a}$ are independently selected from the group consisting of alkylene and alkenylene and R$_{21}$ is hydrogen, loweralkyl, alkenyl, haloalkyl, alkoxyalkyl, haloalkoxyalkyl, aryl or arylalkyl;

R$_4$ and R$_6$ are independently selected from the group consisting of
(i) (R$_{11}$)(R$_{12}$)N— wherein R$_{11}$ and R$_{12}$ are independently selected from
(1) hydrogen,
(2) loweralkyl,
(3) haloalkyl,
(4) alkoxyalkyl,
(5) haloalkoxyalkyl,
(6) alkenyl,
(7) alkynyl,
(8) cycloalkyl,
(9) cycloalkylalkyl,
(10) aryl,
(11) heterocyclic,
(12) arylalkyl,
(13) (heterocyclic)alkyl,
(14) hydroxyalkyl,
(15) alkoxy,
(16) aminoalkyl,
(17) trialkylaminoalkyl,
(18) alkylaminoalkyl,
(19) dialkylaminoalkyl,
(20) carboxyalkyl, and
(21) diarylalkyl,
(ii) loweralkyl,
(iii) alkenyl,
(iv) alkynyl,
(v) cycloalkyl,
(vi) cycloalkylalkyl,
(vii) aryl,
(viii) arylalkyl,
(ix) heterocyclic,
(x) (heterocyclic)alkyl,
(xi) alkoxyalkyl,
(xii) hydroxyalkyl,
(xiii) haloalkyl,
(xiv) haloalkenyl,
(xv) haloalkoxyalkyl,
(xvi) haloalkoxy,
(xvii) alkoxyhaloalkyl, (xviii) alkylaminoalkyl,
(xix) dialkylaminoalkyl,
(xx) alkoxy,

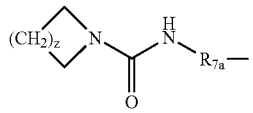

(xxi)

wherein z is 0–5 and $R_{7a}$ is alkylene, and
(xxii) $(R_{11a})(R_{12a})N$—N(H)—
wherein $R_{11a}$ and $R_{12a}$ are independently selected from aryl and alkyl, $R_{26}$ is (i) loweralkyl, (ii) haloalkyl, (iii) alkenyl, (iv) alkynyl, (v) cycloalkyl, (vi) cycloalkylalkyl, (vii) aryl, (viii) arylalkyl, (ix) heterocyclic, (x) (heterocyclic)alkyl, (xi) alkoxyalkyl or (xii) alkoxy-substituted haloalkyl; and $R_{27}$ is alkylene or alkenylene;

(b) $R_{22}$—O—C(O)—$R_{23}$— wherein $R_{22}$ is a carboxy protecting group or heterocyclic and $R_{23}$ is (i) a covalent bond, (ii) alkylene, (iii) alkenylene or (iv) —N($R_{24}$)—$R_{25}$— wherein $R_{25}$ is alkylene and $R_{24}$ is hydrogen or loweralkyl, (c) loweralkyl,
(d) alkenyl,
(e) alkynyl,
(f) cycloalkyl,
(g) cycloalkylalkyl,
(h) aryl,
(i) arylalkyl,
(j) aryloxyalkyl,
(k) heterocyclic,
(l) (heterocyclic)alkyl,
(m) alkoxyalkyl,
(n) alkoxyalkoxyalkyl, or
(o) $R_{13}$—C(O)—CH($R_{14}$)—
wherein $R_{13}$ is amino, alkylamino or dialkylamino and $R_{14}$ is aryl or $R_{15}$—C(O)— wherein $R_{15}$ is amino, alkylamino or dialkylamino;

or a pharmaceutically acceptable salt thereof.

A preferred embodiment of the invention is a compound of formula (II)

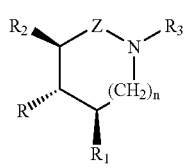

(II)

wherein the substituents —$R_2$, —R and —$R_1$ exist in a trans,trans relationship and Z, n, R, $R_1$, $R_2$, and $R_3$ are as defined above.

Another preferred embodiment of the invention is a compound of formula (I) or (II) wherein n is 0 and Z is —CH$_2$—.

Another preferred embodiment of the invention is a compound of formula (I) or (II) wherein n is 1 and Z is —CH$_2$—.

Another preferred embodiment of the invention is a compound of formula (I) or (II) wherein n is 0, Z is —CH$_2$—, and $R_3$ is $R_4$—C(O)—$R_5$—, $R_6$—S(O)$_2$—$R_7$— or $R_{26}$—S(O)—$R_{27}$— wherein $R_4$, $R_5$, $R_6$, $R_7$, $R_{26}$ and $R_{27}$ are as defined above.

Another preferred embodiment of the invention is a compound of formula (I) or (II) wherein n is 0, Z is —CH$_2$—, and $R_3$ is alkoxyalkyl or alkoxyalkoxyalkyl.

Another preferred embodiment of the invention is a compound of formula (I) or formula (II) wherein n is zero; Z is —CH$_2$— wherein $R_{18}$ and $R_{19}$ are hydrogen; R is C(O)-G wherein G is hydrogen; $R_1$ is aryl substituted with one substituent selected from methoxy, methoxyethoxy, and isopropoxyethoxy; $R_2$ is 1,3-benzodiox-5-yl; $R_3$ is $R_4$—C(O)—$R_5$— wherein $R_5$ is methylene and $R_4$ is selected from $(R_{11})(R_{12})N$— and $(R_{11a})(R_{12a})N$—N(H)—; one of $R_{11}$ and $R_{12}$ is hydrogen and the other is selected from arylalkyl and diarylalkyl wherein each aryl group of the diarylalkyl is substituted with methyl or ethyl; and one of $R_{11a}$ or $R_{12a}$ is alkyl and the other is aryl.

Another preferred embodiment of the invention is a compound of formula (I) or formula (II) wherein n is zero; Z is —CH$_2$— wherein $R_{18}$ and $R_{19}$ are hydrogen; R is C(O)-G wherein G is hydrogen; $R_1$ is phenyl substituted with one substituent selected from methoxy, methoxyethoxy, and isopropoxyethoxy; $R_2$ is 1,3-benzodiox-5-yl; $R_3$ is $R_4$—C(O)—$R_5$— wherein $R_5$ is methylene and $R_4$ is selected from $(R_{11})(R_{12})N$— and $(R_{11a})(R_{12a})N$—N(H)—; one of $R_{11}$ and $R_{12}$ is hydrogen and the other is selected from phenylalkyl and diphenylalkyl wherein each phenyl group of the diphenylalkyl is substituted with methyl or ethyl; and one of $R_{11a}$ or $R_{12a}$ is alkyl and the other is phenyl.

A more preferred embodiment of the invention is a compound of formula (I) or (II) wherein n is 0, Z is —CH$_2$—, and $R_3$ is $R_4$—C(O)—$R_5$— wherein $R_4$ is $(R_{11})(R_{12})N$— as defined above and $R_5$ is alkylene or $R_3$ is $R_6$—S(O)$_2$—$R_7$— or $R_{26}$—S(O)—$R_{27}$— wherein $R_7$ is alkylene, $R_{27}$ is alkylene and $R_6$ and $R_{26}$ are defined as above.

Another more preferred embodiment of the invention is a compound of formula (I) or (II) wherein n is 0, Z is —CH$_2$— and $R_3$ is $R_4$—C(O)—N($R_{20}$)—$R_8$— or $R_6$—S(O)$_2$—N($R_{21}$)—$R_{10}$— wherein $R_8$ and $R_{10}$ are alkylene and $R_4$, $R_6$, $R_{20}$ and $R_{21}$ are defined as above.

An even more preferred embodiment of the invention is a compound of formula (I) or (II) wherein n is 0, R is tetrazolyl or —C(O)$_2$-G wherein G is hydrogen or a carboxy protecting group or R is tetrazolyl or R is —C(O)—NHS(O)$_2$R$_{16}$ wherein $R_{16}$ is loweralkyl, haloalkyl or aryl, Z is —CH$_2$—, $R_1$ and $R_2$ are independently selected from (i) loweralkyl, (ii) cycloalkyl, (iii) substituted aryl wherein aryl is phenyl substituted with one, two or three substituents independently selected from loweralkyl, alkoxy, halo, alkoxyalkoxy and carboxyalkoxy, (iv) substituted or unsubstituted heterocyclic, (v) alkenyl, (vi) heterocyclic (alkyl), (vii) arylalkyl, (viii) aryloxyalkyl, (ix) (N-alkanoyl-N-alkyl) aminoalkyl and (x) alkylsulfonylamidoalkyl, and $R_3$ is $R_4$—C(O)—$R_5$— wherein $R_4$ is $(R_{11})(R_{12})N$— wherein $R_{11}$ and $R_{12}$ are independently selected from loweralkyl, haloalkyl, alkoxyalkyl, haloalkoxyalkyl, aryl, arylalkyl, heterocyclic, hydroxyalkyl, alkoxy, aminoalkyl, and trialkylaminoalkyl, and $R_5$ is alkylene; or $R_3$ is $R_4$—C(O)—N($R_{20}$)—$R_8$— or $R_6$—S(O)$_2$—N($R_{21}$)—$R_{10}$— wherein $R_4$ is loweralkyl, aryl, alkoxy, alkylamino, aryloxy or arylalkoxy and $R_6$ is loweralkyl, haloalkyl, alkoxyalkyl, haloalkoxyalkyl, aryl or arylalkyl, $R_8$ and $R_{10}$ are alkylene and $R_{20}$ and $R_{21}$ are loweralkyl; or $R_3$ is $R_6$—S(O)$_2$—$R_7$— or $R_{26}$—S(O)—$R_{27}$— wherein $R_6$ is loweralkyl or haloalkyl, $R_7$ is alkylene, $R_{26}$ is loweralkyl and $R_{27}$ is alkylene.

A yet more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) alkoxyalkyl, (iv) cycloalkyl, (v) phenyl, (vi) pyridyl, (vii) furanyl, (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, (ix) heterocyclic (alkyl), (x) arylalkyl, (xi) aryloxyalkyl, (xii) (N-alkanoyl-N-alkyl)aminoalkyl, or (xiii) alkylsulfonylamidoalkyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and R$_3$ is R$_4$—C(O)—N(R$_{20}$)—R$_8$— or R$_6$—S(O)$_2$—N(R$_{21}$)—R$_{10}$— wherein R$_8$ and R$_{10}$ are alkylene, R$_{20}$ and R$_{21}$ are loweralkyl, R$_4$ is loweralkyl, aryl, alkoxy, alkylamino, aryloxy or arylalkoxy and R$_6$ is loweralkyl, haloalkyl, alkoxyalkyl, aryl or arylalkyl.

Another yet more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) alkoxyalkyl, (iv) cycloalkyl, (v) phenyl, (vi) pyridyl, (vii) furanyl, (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from alkoxy, alkoxyalkoxy and carboxyalkoxy, (ix) heterocyclic (alkyl), (x) arylalkyl, (xi) aryloxyalkyl, (xii) (N-alkanoyl-N-alkyl)aminoalkyl, or (xiii) alkylsulfonylamidoalkyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from loweralkyl, haloalkyl, alkoxyalkyl, haloalkoxyalkyl, aryl, arylalkyl, heterocyclic, hydroxyalkyl, alkoxy, aminoalkyl, and trialkylaminoalkyl.

Another yet more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) loweralkyl, (ii) alkenyl, (iii) heterocyclic (alkyl), (iv) aryloxyalkyl, (v) arylalkyl, (vi) aryl, (vii) (N-alkanoyl-N-alkyl)aminoalkyl, or (viii) alkylsulfonylamidoalkyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen and R$_3$ is R$_4$—C(O)—R$_5$— wherein R$_5$ is alkylene and R$_4$ is (R$_{11}$)(R$_{12}$)N— wherein R$_{11}$ is loweralkyl and R$_{12}$ is aryl, arylalkyl, hydroxyalkyl, alkoxy, aminoalkyl, trialkylaminoalkyl, or heterocyclic.

Another yet more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_6$ wherein R$_{16}$ is loweralkyl, haloalkyl or aryl, Z is —CH$_2$—, R$_1$ is (i) loweralkyl, (ii) alkenyl, (iii) heterocyclic (alkyl), (iv) aryloxyalkyl, (v) arylalkyl, (vi) (N-alkanoyl-N-alkyl)aminoalkyl, or (vii) alkylsulfonylamidoalkyl, (vii) phenyl, or (ix) substituted or unsubstituted 4-methoxyphenyl, 3-fluoro-4-methoxyphenyl, 3-fluorophenyl, 3-fluoro-4-ethoxyphenyl, 2-fluorophenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is R$_6$—S(O)$_2$—N(R$_{21}$)—R$_{10}$— wherein R$_{10}$ is alkylene, R$_6$ is loweralkyl, haloalkyl, alkoxyalkyl, haloalkoxyalkyl, aryl or arylalkyl and R$_{21}$ is loweralkyl, haloalkyl, alkoxyalkyl, haloalkoxyalkyl, aryl or arylalkyl.

Another yet more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl, haloalkyl or aryl, Z is —CH$_2$—, R$_1$ is (i) substituted or unsubstituted 4-methoxyphenyl, 3-fluoro-4-methoxyphenyl, 3-fluorophenyl, 3-fluoro-4-ethoxyphenyl, 4-methoxymethoxyphenyl, 1,3-benzodioxolyl or 1,4-benzodioxanyl wherein the substituent is selected from loweralkyl, haloalkyl, alkoxy and alkoxyalkoxy, (ii) loweralkyl, (iii) alkenyl, (iv) heterocyclic (alkyl), (v) aryloxyalkyl, (vi) arylalkyl, (vii) (N-alkanoyl-N-alkyl)aminoalkyl, (viii) alkylsulfonylamidoalkyl, or (ix) phenyl, R$_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and R$_3$ is alkoxycarbonyl or R$_6$—S(O)$_2$—N(R$_{21}$)—R$_{10}$— wherein R$_{10}$ is alkylene, R$_6$ is loweralkyl, haloalkyl, alkoxyalkyl or haloalkoxyalkyl and R$_{21}$ is loweralkyl, haloalkyl, alkoxyalkyl or haloalkoxyalkyl.

Another yet more preferred embodiment of the invention is a =compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl or haloalkyl, Z is —CH$_2$—, R$_1$ is loweralkyl, alkenyl, heterocyclic (allkyl), aryloxyalkyl, aryalkyl, aryl, (N-alkanoyl-N-alkyl)aminoalkyl, or alkylsulfonylamidoalkyl, and R$_3$ is R$_4$—C(O)—R$_5$— wherein R$_5$ is alkylene and R$_4$ is (R$_{11}$)(R$_{12}$)N— wherein R$_{11}$ and R$_{12}$ are independently selected from alkyl, aryl, hydroxyalkyl, alkoxy, aminoalkyl, trialkylaminoalkyl, and heterocyclic.

A still more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein R$_{16}$ is loweralkyl or haloalkyl, Z is —CH$_2$—, R$_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4- benzodioxanyl or dihydrobenzofuranyl wherein the substituent is selected from alkoxy, alkoxyalkoxy and carboxyalkoxy, (ii) loweralkyl, (iii) alkenyl, (iv) heterocyclic (alkyl), (v) aryloxyalkyl, (vi) arylalkyl, (vii) (N-alkanoyl-N-alkyl)aminoalkyl, (viii) alkylsulfonylamidoalkyl, or (ix) phenyl, $R_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is $(R_{11})(R_{12})N$— wherein $R_{11}$ and $R_{12}$ are independently selected from loweralkyl, aryl, arylalkyl, hydroxyalkyl, alkoxy, aminoalkyl, trialkylaminoalkyl, or heterocyclic.

Another still more preferred embodiment of the invention is a compound of formula (I) or (II) wherein n is 0, R is —C(O)$_2$-G wherein G is hydrogen or a carboxy protecting group, tetrazolyl or —C(O)—NHS(O)$_2$R$_{16}$ wherein $R_{16}$ is loweralkyl or haloalkyl, Z is —CH$_2$—, $R_1$ is loweralkyl, alkenyl, heterocyclic (alkyl), aryloxyalkyl, arylalkyl, (N-alkanoyl-N-alkyl)aminoalkyl, alkylsulfonylamidoalkyl, phenyl, or alkoxyalkyl, $R_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is $(R_{11})(R_{12})N$— wherein $R_{11}$ and $R_{12}$ are independently selected from loweralkyl, aryl, arylalkyl, hydroxyalkyl, alkoxy, aminoalkyl, trialkylaminoalkyl, or heterocyclic.

A most highly preferred embodiment of the invention is a compound of formula (I) or (II) wherein n is 0, R is —C(O)$_2$-G wherein G is hydrogen or a carboxy protecting group, Z is —CH$_2$—, $R_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is $(R_{11})(R_{12})N$— wherein $R_{11}$ and $R_{12}$ are independently selected from loweralkyl.

Another most highly preferred embodiment of the invention is a compound of formula (I) or (II) wherein n is 0, R is —C(O)$_2$-G wherein G is hydrogen or a carboxy protecting group, Z is —CH$_2$—, $R_1$ is substituted or unsubstituted 4-methoxyphenyl, 4-fluorophenyl, 2-fluorophenyl, 4-methylphenyl, 4-trifluoromethylphenyl, 4-pentafluoroethylphenyl, 4-methoxymethoxyphenyl, 4-hydroxyphenyl, 4-ethylphenyl, 1,3-benzodioxolyl, 1,4-benzodioxanyl or dihydrobenzofuranyl wherein the substituent is selected from alkoxy, alkoxyalkoxy and carboxyalkoxy, $R_2$ is 1,3-benzodioxolyl, 1,4-benzodioxanyl, dihydrobenzofuranyl, benzofuranyl, 4-methoxyphenyl, dimethoxyphenyl, fluorophenyl or difluorophenyl and $R_3$ is $R_4$—C(O)—$R_5$— wherein $R_5$ is alkylene and $R_4$ is $(R_{11})(R_{12})N$— wherein $R_{11}$ is loweralkyl and $R_{12}$ is aryl.

Another most highly preferred embodiment of the invention is a compound of formula (I) or (II) wherein n is 0, R is —C(O)$_2$-G wherein G is hydrogen or a carboxy protecting group, Z is —CH$_2$—, $R_1$ is substituted or unsubstituted 4-methoxyphenyl, 3-fluoro-4-methoxyphenyl, 3-fluorophenyl, 2-fluorophenyl, 3-fluoro-4-ethoxyphenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and $R_3$ is $R_6$—S(O)$_2$—N($R_{21}$)—$R_{10}$— wherein $R_{10}$ is alkylene, $R_6$ is loweralkyl, haloalkyl, alkoxyalkyl or haloalkoxyalkyl and $R_{21}$ is loweralkyl, haloalkyl or alkoxyalkyl.

Another most highly preferred embodiment of the invention is a compound of formula (I) or (II) wherein n is 0, R is —C(O)$_2$-G wherein G is hydrogen or a carboxy protecting group, Z is —CH$_2$—, $R_1$ is substituted or unsubstituted 4-methoxyphenyl, 3-fluoro-4-methoxyphenyl, 3-fluorophenyl, 2-fluorophenyl, 3-fluoro-4-ethoxyphenyl, 4-methoxymethoxyphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, 4-methoxyphenyl, dimethoxyphenyl, fluorophenyl or difluorophenyl wherein the substituent is selected from loweralkyl, alkoxy and halogen and $R_3$ is $R_4$—C(O)—$R_5$— wherein $R_5$ is alkylene and $R_4$ is $(R_{11})(R_{12})N$— wherein $R_{11}$ is alkyl and $R_{12}$ is selected from aryl, aminoalkyl, trialkylaminoalkyl, and heterocyclic.

Another most highly preferred embodiment of the invention is a compound of formula (I) or (II) wherein n is 0, R is —C(O)$_2$-G wherein G is hydrogen or a carboxy protecting group, Z is —CH$_2$—, $R_1$ is loweralkyl, alkenyl, heterocyclic (alkyl), aryloxyalkyl, arylalkyl, aryl, (N-alkanoyl-N-alkyl) aminoalkyl, or alkylsulfonylamidoalkyl, and $R_3$ is $R_4$—C(O)—$R_5$— wherein $R_5$ is alkylene and $R_4$ is $(R_{11})(R_{12})N$— wherein $R_{11}$ and $R_{12}$ are independently selected from alkyl, aryl, hydroxyalkyl, alkoxy, aminoalkyl, trialkylaminoalkyl, and heterocyclic, with the proviso that one or $R_{11}$ and $R_{12}$ is alkyl.

Another most highly preferred embodiment of the invention is a compound of formula (I) or (II) wherein n is 0, Z is —CH$_2$—, and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —CH$_2$—, $R_1$ is loweralkyl, and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —CH$_2$—, $R_1$ is alkenyl, and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —CH$_2$—, $R_1$ is heterocyclic (alkyl), and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —CH$_2$—, $R_1$ is aryloxyalkyl, and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —CH$_2$—, $R_1$ is arylalkyl, and $R_3$ is $R_4$—C(O)—$R_5$— wherein $R_4$ is $(R_{11})(R_{12})N$— as defined therein and $R_5$ is alkylene.

Another most highly preferred embodiment of the invention is a compound of formula (I) or (II) wherein n is 0, Z is —$CH_2$—, $R_1$ is aryl, and $R_3$ is $R_4$—C(O)—$R_5$— wherein $R_4$ is ($R_{11}$)($R_{12}$)N— as defined therein and $R_5$ is alkylene.

Another most highly preferred embodiment of the invention is a compound of formula (I) or (II) wherein n is 0, Z is —$CH_2$—, $R_1$ is (N-alkanoyl-N-alkyl)aminoalkyl, and $R_3$ is $R_4$—C(O)—$R_5$— wherein $R_4$ is ($R_{11}$)($R_{12}$)N— as defined therein and $R_5$ is alkylene.

Another most highly preferred embodiment of the invention is a compound of formula (I) or (II) wherein n is 0, Z is —$CH_2$—, $R_1$ is alkylsulfonylamidoalkyl, and $R_3$ is $R_4$—C(O)—$R_5$— wherein $R_4$ is ($R_{11}$)($R_{12}$)N— as defined therein and $R_5$ is alkylene.

The present invention also relates to processes for preparing the compounds of formula (I) and (II) and to the synthetic intermediates employed in these processes.

The present invention also relates to a method of antagonizing endothelin in a mammal (preferably, a human) in need of such treatment, comprising administering to the mammal a therapeutically effective amount of a compound of formula (I) or (II).

The invention further relates to endothelin antagonizing compositions comprising a pharmaceutical carrier and a therapeutically effective amount of a compound of formula (I) or (II).

In another embodiment of the invention is disclosed a method for inhibiting bone metastases in a patient which comprises administering to the patient in need thereof a therapeutically effective amount of an endothelin ET-A receptor antagonist.

In another embodiment of the invention is disclosed a method for preventing new bone metastases in a patient which comprises administering to the patient in need thereof a therapeutically effective amount of an endothelin ET-A receptor antagonist.

In another embodiment of the instant invention, therefore, is disclosed a method for inhibiting metastatic growth in a patient which comprises administering to the patient in need thereof a therapeutically effective amount of an endothelin ET-A receptor antagonist.

In another embodiment of the invention is disclosed a method for inhibiting bone loss in a patient which comprises administering to the patient in need thereof a therapeutically effective amount of an endothelin ET-A receptor antagonist.

In another embodiment of the instant invention, is disclosed a method for inhibiting bone turnover in a patient which comprises administering to the patient in need thereof a therapeutically effective amount of an endothelin ET-A receptor antagonist.

In another embodiment of the invention is disclosed a method for the reduction of cancer related pain in a patient in need thereof which comprises administering to the patient a therapeutically effective amount of an endothelin ET-A receptor antagonist.

In another embodiment of the instant invention is disclosed therapeutically acceptable formulations of an endothelin ET-A receptor antagonist, optionally in the presence of a co-therapeutic agent, for use in these methods.

BRIEF DESCRIPTION OF THE DRAWINGS

FIG. 1 illustrates levels of interleukin-6 (IL-6) in a subject population treated with a placebo or 2.5 mg or 10 mg ABT-627.

FIG. 6 illustrates skeletal involvement in a subject population treated with a placebo or 10 mg ABT-627.

FIG. 7 illustrates acid phosphatase levels in a subject population treated with a placebo or 10 mg ABT-627.

Figure 2:
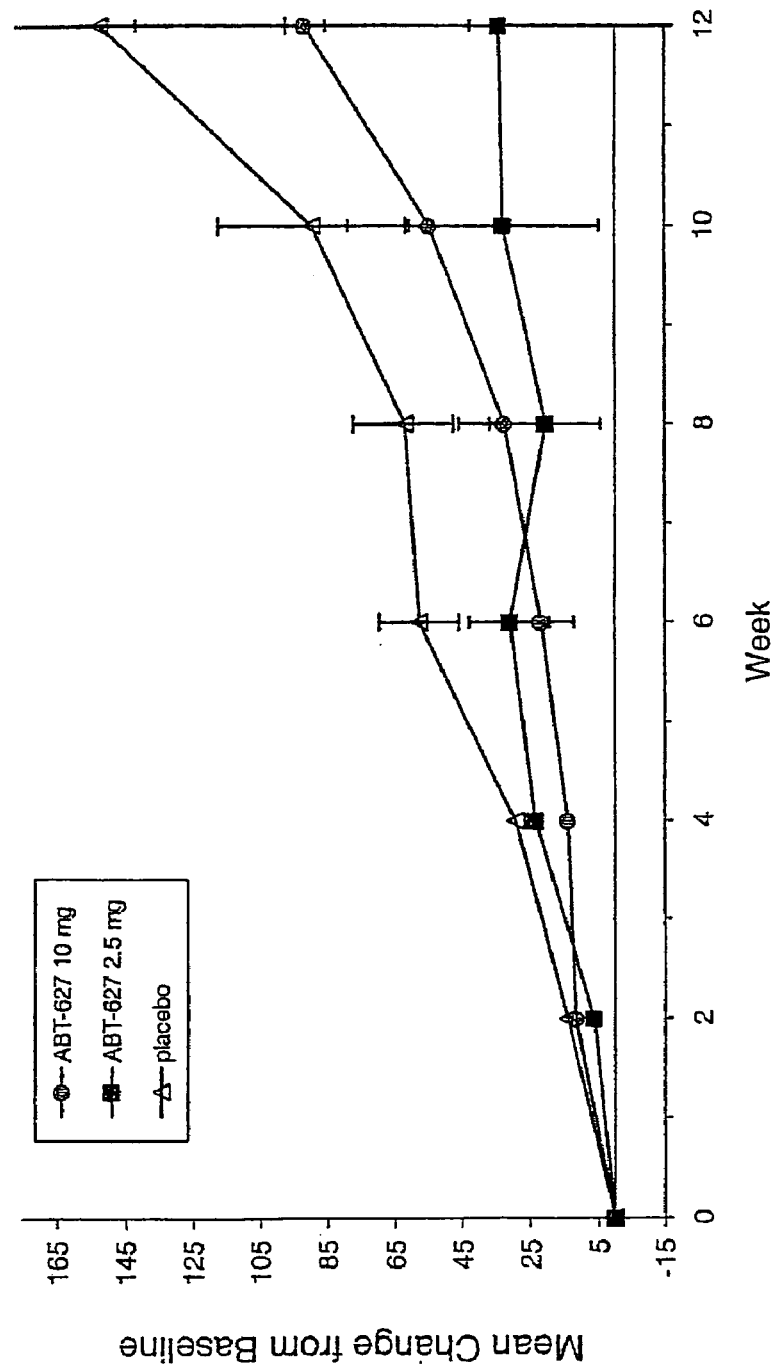
FIG. 2 illustrates levels of prostate specific antigen (PSA) in a subject population treated with a placebo or 2.5 mg or 10 mg of ABT-627.

The compounds of the invention comprise two or more asymmetrically substituted carbon atoms. As a result, racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cylcopentyl and the like; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to an alkyl group as previously defined appended to the parent molecular moiety through a carbonyl (—C(O)—) group. Examples of alkanoyl include acetyl, propionyl and the like.

The term "alkanoylamino" as used herein refers to an alkanoyl group as previously defined appended to an amino group. Examples alkanoylamino include acetamido, propionylamido and the like.

The term "alkanoylaminoalkyl" as used herein refers to $R_{43}$—NH—$R_{44}$— wherein $R_{43}$ is an alkanoyl group and $R_{44}$ is an alkylene group.

The term "alkanoyloxyalkyl" as used herein refers to $R_{30}$—O—$R_{31}$— wherein $R_{30}$ is an alkanoyl group and $R_{31}$ is an alkylene group. Examples of alkanoyloxyalkyl include acetoxymethyl, acetoxyethyl and the like.

The term "alkenyl" as used herein refers to a straight or branched chain hydrocarbon radical containing from 2 to 15 carbon atoms and also containing at least one carbon—carbon double bond. Alkenyl groups include, for example, vinyl (ethenyl), allyl (propenyl), butenyl, 1-methyl-2-buten-1-yl and the like.

The term "alkenylene" denotes a divalent group derived from a straight or branched chain hydrocarbon containing from 2 to 15 carbon atoms and also containing at least one carbon—carbon double bond. Examples of alkenylene include —CH=CH—, —CH$_2$CH=CH—, —C(CH$_3$)=CH—, —CH$_2$CH=CHCH$_2$—, and the like.

The term "alkenyloxy" as used herein refers to an alkenyl group, as previously defined, connected to the parent molecular moiety through an oxygen (—O—) linkage. Examples of alkenyloxy include allyloxy, butenyloxy and the like.

The term "alkoxy" as used herein refers to $R_{41}$O— wherein $R_{41}$ is a loweralkyl group, as defined herein. Examples of alkoxy include, but are not limited to, ethoxy, tert-butoxy, and the like.

The term "alkoxyalkoxy" as used herein refers to $R_{80}$O—$R_{81}$O— wherein $R_{80}$ is loweralkyl as defined above and $R_{81}$ is alkylene. Representative examples of alkoxyalkoxy groups include methoxymethoxy, ethoxymethoxy, t-butoxymethoxy and the like.

The term "alkoxyalkoxyalkyl" as used herein refers to an alkoxyalkoxy group as previously defined appended to an alkyl radical. Representative examples of alkoxyalkoxyalkyl groups include methoxyethoxyethyl, methoxymethoxymethyl, and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylalkenyl" as used herein refers to an alkoxycarbonyl group as previously defined appended to an alkenyl radical. Examples of alkoxycarbonylalkenyl include methoxycarbonylethenyl, ethoxycarbonylethenyl and the like.

The term "alkoxycarbonylalkyl" as used herein refers to $R_{34}$—C(O)—$R_{35}$— wherein $R_{34}$ is an alkoxy group and $R_{35}$ is an alkylene group. Examples of alkoxycarbonylalkyl include methoxycarbonylmethyl, methoxcarbonylethyl, ethoxycarbonylmethyl and the like.

The term "alkoxycarbonylaminoalkyl" as used herein refers to $R_{38}$—C(O)—NH—$R_{39}$— wherein $R_{38}$ is an alkoxy group and $R_{39}$ is an alkylene group.

The term "alkoxycarbonyloxyalkyl" as used herein refers to $R_{36}$—C(O)—O—$R_{37}$— wherein $R_{36}$ is an alkoxy group and $R_{37}$ is an alkylene group.

The term "(alkoxycarbonyl)thioalkoxy" as used herein refers to an alkoxycarbonyl group as previously defined appended to a thioalkoxy radical. Examples of (alkoxycarbonyl)thioalkoxy include methoxycarbonylthiomethoxy, ethoxycarbonylthiomethoxy and the like.

The term "alkoxyhaloalkyl" as used herein refers to a haloalkyl radical to which is appended an alkoxy group.

The terms "alkyl" and "loweralkyl" as used herein refer to straight or branched chain alkyl radicals containing from 1 to 15 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "(N-alkanoyl-N-alkyl)aminoalkyl" as used herein refers to $R_{85}C(O)N(R_{86})R_{87}$— wherein $R_{85}$ is an alkanoyl as previously defined, $R_{86}$ is loweralkyl, and $R_{87}$ is alkylene.

The term "alkylamino" as used herein refers to $R_{51}NH$— wherein $R_{51}$ is a loweralkyl group, for example, ethylamino, butylamino, and the like.

The term "alkylaminoalkyl" as used herein refers to a loweralkyl radical to which is appended an alkylamino group.

The term "alkylaminocarbonyl" as used herein refers to an alkylamino group, as previously defined, appended to the parent molecular moiety through a carbonyl (—C(O)—) linkage. Examples of alkylaminocarbonyl include methylaminocarbonyl, ethylaminocarbonyl, isopropylaminocarbonyl and the like.

The term "alkylaminocarbonylalkenyl" as used herein refers to an alkenyl radical to which is appended an alkylaminocarbonyl group.

The term "alkylaminocarbonylalkyl" as used herein refers to a loweralkyl radical to which is appended an alkylaminocarbonyl group.

The term "alkylaminocarbonylaminoalkyl" as used herein refers to $R_{40}$—C(O)—NH—$R_{41}$— wherein $R_{40}$ is an alkylamino group and $R_{41}$ is an alkylene group.

The term "alkylene" denotes a divalent group derived from a straight or branched chain saturated hydrocarbon having from 1 to 15 carbon atoms by the removal of two hydrogen atoms, for example —CH$_2$—, —CH$_2$CH$_2$—, —CH(CH$_3$)—, —CH$_2$CH$_2$CH$_2$—, —CH$_2$C(CH$_3$)$_2$CH$_2$— and the like.

The term "alkylsulfonylamidoalkyl" as used herein refers $R_{88}S(O)_2NHR_{89}$— wherein $R_{88}$ is loweralkyl and $R_{89}$ is alkylene.

The term "alkylsulfonylamino" as used herein refers to an alkyl group as previously defined appended to the parent molecular moiety through a sulfonylamino (—S(O)$_2$—NH—) group. Examples of alkylsulfonylamino include methylsulfonylamino, ethylsulfonylamino, isopropylsulfonylamino and the like.

The term "alkynyl" as used herein refers to a straight or branched chain hydrocarbon radical containing from 2 to 15 carbon atoms and also containing at least one carbon—carbon triple bond. Examples of alkynyl include —C≡C—H, H—C≡C—CH$_2$—, H—C≡C—CH(CH$_3$)— and the like.

The term "alkynylene" refers to a divalent group derived by the removal of two hydrogen atoms from a straight or branched chain acyclic hydrocarbon group containing from 2 to 15 carbon atoms and also containing a carbon—carbon triple bond. Examples of alkynylene include —C≡C—, —C≡C—CH$_2$—, —C≡C—CH(CH$_3$)— and the like.

The term "aminoalkyl" as used herein refers to a —NH$_2$, alkylamino, or dialkylamino group appended to the parent molecular moiety through an alkylene.

The term "aminocarbonyl" as used herein refers to H$_2$N—C(O)—.

The term "aminocarbonylalkenyl" as used herein refers to an alkenyl radical to which is appended an aminocarbonyl (NH$_2$C(O)—) group.

The term "aminocarbonylalkoxy" as used herein refers to H$_2$N—C(O)— appended to an alkoxy group as previously defined. Examples of aminocarbonylalkoxy include aminocarbonylmethoxy, aminocarbonylethoxy and the like.

The term "aminocarbonylalkyl" as used herein refers to a loweralkyl radical to which is appended an aminocarbonyl (NH$_2$C(O)—) group.

The term "trialkylaminoalkyl" as used herein refers to $(R_{90})(R_{91})(R_{92})N(R_{93})$— wherein $R_{90}$, $R_{91}$, and $R_{92}$ are independently selected from loweralkyl and $R_{93}$ is alkylene.

The term "aroyloxyalkyl" as used herein refers to $R_{32}$—C(O)—O—$R_{33}$— wherein $R_{32}$ is an aryl group and $R_{33}$ is an alkylene group. Examples of aroyloxyalkyl include benzoyloxymethyl, benzoyloxyethyl and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, haloalkoxy, hydroxyalkyl, alkenyloxy, alkoxy, alkoxyalkoxy, alkoxycarbonyl, alkoxycarbonylalkenyl, (alkoxycarbonyl)thioalkoxy, thioalkoxy, amino, alkylamino, dialkylamino, aminoalkyl, trialkylaminoalkyl, aminocarbonyl, aminocarbonylalkoxy, alkanoylamino, arylalkoxy, aryloxy, mercapto, cyano, nitro, carboxaldehyde, carboxy, carboxyalkenyl, carboxyalkoxy, alkylsulfonylamino, cyanoalkoxy, (heterocyclic)alkoxy, hydroxy, hydroxalkoxy, phenyl and tetrazolylalkoxy. In addition, substituted aryl groups include tetrafluorophenyl and pentafluorophenyl.

The term "arylalkenyl" as used herein refers to an alkenyl radical to which is appended an aryl group, for example, phenylethenyl and the like.

The term "arylalkoxy" as used herein refers to $R_{42}O$— wherein $R_{42}$ is an arylalkyl group, for example, benzyloxy, and the like.

The term "arylalkoxyalkyl" as used herein refers to a loweralkyl radical to which is appended an arylalkoxy group, for example, benzyloxymethyl and the like.

The term "arylalkyl" as used herein refers to an aryl group as previously defined, appended to a loweralkyl radical, for example, benzyl, phenethyl, 2,2-dimethyl-1-phenyl-1-propyl, 3,3-dimethyl-1-phenyl-1-butyl, and the like.

The term "aryloxy" as used herein refers to $R_{45}O$— wherein $R_{45}$ is an aryl group, for example, phenoxy, and the like.

The term "arylalkylcarbonyloxyalkyl" as used herein refers to a loweralkyl radical to which is appended an arylalkylcarbonyloxy group (i.e., $R_{62}C(O)O$— wherein $R_{62}$ is an arylalkyl group).

The term "aryloxyalkyl" refers to an aryloxy group as previously defined appended to an alkyl radical. Examples of aryloxyalkyl include phenoxymethyl, 2-phenoxyethyl and the like.

The term "carboxaldehyde" as used herein refers to a formaldehyde radical, —C(O)H.

The term "carboxy" as used herein refers to a carboxylic acid radical, —C(O)OH.

The term "carboxyalkenyl" as used herein refers to a carboxy group as previously defined appended to an alkenyl radical as previously defined. Examples of carboxyalkenyl include 2-carboxyethenyl, 3-carboxy-1-ethenyl and the like.

The term "carboxyalkoxy" as used herein refers to a carboxy group as previously defined appended to an alkoxy radical as previously defined. Examples of carboxyalkoxy include carboxymethoxy, carboxyethoxy and the like.

The term "cyanoalkoxy" as used herein refers to an alkoxy radical as previously defined to which is appended a cyano (—CN) group. Examples of cyanoalkoxy include 3-cyanopropoxy, 4-cyanobutoxy and the like.

The term "cycloalkanoyloxyalkyl" as used herein refers to a loweralkyl radical to which is appended a cycloalkanoyloxy group (i.e., $R_{60}$—C(O)—O— wherein $R_{60}$ is a cycloalkyl group).

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "dialkylamino" as used herein refers to $R_{56}R_{57}N$— wherein $R_{56}$ and $R_{57}$ are independently selected from loweralkyl, for example diethylamino, methyl propylamino, and the like.

The term "dialkylaminoalkyl" as used herein refers to a loweralkyl radical to which is appended a dialkylamino group.

The term "dialkylaminocarbonyl" as used herein refers to a dialkylamino group, as previously defined, appended to the parent molecular moiety through a carbonyl (—C(O)—) linkage. Examples of dialkylaminocarbonyl include dimethylaminocarbonyl, diethylaminocarbonyl and the like.

The term "dialkylaminocarbonylalkenyl" as used herein refers to an alkenyl radical to which is appended a dialkylaminocarbonyl group.

The term "dialkylaminocarbonylalkyl" as used herein refers to $R_{50}$—C(O)—$R_{51}$— wherein $R_{50}$ is a dialkylamino group and $R_{51}$ is an alkylene group.

The term "diarylalkyl," as used herein, refers to two aryl groups, as defined herein, attached to the parent molecular moiety through an alkyl group. The aryl groups of the diaryl can be optionally substituted with 1–5 alkyl substituents. Examples of "diaryl" include diphenylmethyl (benzhydryl), 2,2-diphenylethyl, 1,2-diphenylethyl, bis(2-methylphenyl)methyl, and the like.

The term "halo" or "halogen" as used herein refers to I, Br, Cl or F.

The term "haloalkenyl" as used herein refers to an alkenyl radical to which is appended at least one halogen substituent.

The term "haloalkoxy" as used herein refers to an alkoxy radical as defined above, bearing at least one halogen substituent, for example, 2-fluoroethoxy, 2,2,2-trifluoroethoxy, trifluoromethoxy, 2,2,3,3,3-pentafluoropropoxy and the like.

The term "haloalkoxyalkyl" as used herein refers to a loweralkyl radical to which is appended a haloalkoxy group.

The term "haloalkyl" as used herein refers to a lower alkyl radical, as defined above, to which is appended at least one halogen substituent, for example, chloromethyl, fluoroethyl, trifluoromethyl or pentafluoroethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like). Heterocyclics include: aziridinyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, oxetanyl, furyl, tetrahydrofuranyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

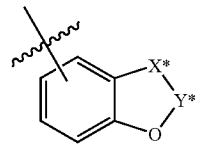

where X* is —CH$_2$— or —O— and Y* is —C(O)— or [-C(R")$_2$—]$_v$ where R" is hydrogen or C$_1$–C$_4$-alkyl and v is 1, 2 or 3 such as 1,3-benzodioxolyl, 1,4-benzodioxanyl and the like. Heterocyclics also include bicyclic rings such as quinuclidinyl and the like.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, aminoalkyl, trialkylaminoalkyl, haloalkyl, cycloalkyl, aryl, arylalkyl, —COOH, —SO$_3$H, alkoxycarbonyl, nitro, cyano and loweralkyl. In addition, nitrogen containing heterocycles can be N-protected.

The term "(heterocyclic)alkoxy" as used herein refers to a heterocyclic group as defined above appended to an alkoxy radical as defined above. Examples of (heterocyclic)alkoxy include 4-pyridylmethoxy, 2-pyridylmethoxy and the like.

The term "(heterocyclic)alkyl" as used herein refers to a heterocyclic group as defined above appended to a loweralkyl radical as defined above.

The term "heterocycliccarbonyloxyalkyl" as used herein refers to $R_{46}$—C(O)—O—$R_{47}$— wherein $R_{46}$ is a heterocyclic group and $R_{47}$ is an alkylene group.

The term "hydroxy" as used herein refers to —OH.

The term "hydroxyalkenyl" as used herein refers to an alkenyl radical to which is appended a hydroxy group.

The term "hydroxyalkoxy" as used herein refers to an alkoxy radical as previously defined to which is appended a hydroxy (—OH) group. Examples of hydroxyalkoxy include 3-hydroxypropoxy, 4-hydroxybutoxy and the like.

The term "hydroxyalkyl" as used herein refers to a loweralkyl radical to which is appended a hydroxy group.

The term "leaving group" as used herein refers to a halide (for example, Cl, Br or I) or a sulfonate (for example, mesylate, tosylate, triflate and the like).

The term "mercapto" as used herein refers to —SH.

The terms "methylenedioxy" and "ethylenedioxy" refer to one or two carbon chains attached to the parent molecular moiety through two oxygen atoms. In the case of methylenedioxy, a fused 5 membered ring is formed. In the case of ethylenedioxy, a fused 6 membered ring is formed. Methylenedixoy substituted on a phenyl ring results in the formation of a benzodioxolyl radical.

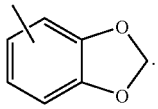

Ethylenedioxy substituted on a phenyl ring results in the formation of a benzodioxanyl radical

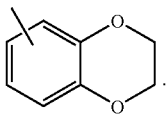

The term "substantially pure" as used herein means 95% or more of the specified compound.

The term "tetrazolyl" as used herein refers to a radical of the formula

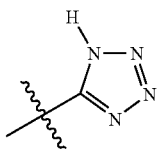

or a tautomer thereof.

The term "tetrazolylalkoxy" as used herein refers to a tetrazolyl radical as defined above appended to an alkoxy group as defined above. Examples of tetrazolylalkoxy include tetrazolylmethoxy, tetrazolylethoxy and the like.

The term "thioalkoxy" as used herein refers to $R_{70}S$— wherein $R_{70}$ is loweralkyl. Examples of thioalkoxy include, but are not limited to, methylthio, ethylthio and the like.

The term "thioalkoxyalkoxy" as used herein refers to $R_{80}S$—$R_{81}O$— wherein $R_{80}$ is loweralkyl as defined above and $R_{81}$ is alkylene. Representative examples of alkoxyalkoxy groups include $CH_3SCH_2O$—, $EtSCH_2O$—, $t$-$BuSCH_2O$— and the like.

The term "thioalkoxyalkoxyalkyl" as used herein refers to a thioalkoxyalkoxy group appended to an alkyl radical. Representative examples of alkoxyalkoxyalkyl groups include $CH_3SCH_2CH_2OCH_2CH_2$—, $CH_3SCH_2OCH_2$—, and the like.

The term "trans,trans" as used herein refers to the orientation of substituents ($R_1$ and $R_2$) relative to the central substituent R as shown

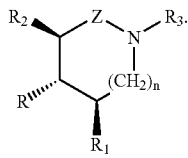

The term "trans,cis" as used herein refers to the orientation of substituents ($R_1$ and $R_2$) relative to the central substituent R as shown

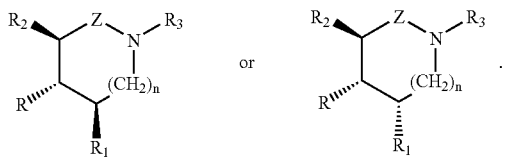

This definition encompasses both the case where R and $R_2$ are cis and R and $R_1$ are trans and the case where $R_2$ and R are trans and R and $R_1$ are cis.

The term "cis,cis" as used herein refers to the orientation of substituents ($R_1$ and $R_2$) relative to the central substituent R as shown

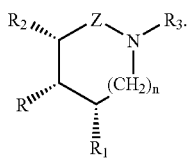

Preferred compounds of the invention are selected from the group consisting of:

trans—trans-2-(4-Methoxyphenyl)-4-(1,3-benzodioxol-5-yl)-1-[3-(N-propyl-N-n-pentanesulfonylamino)propyl]-pyrrolidine-3-carboxylic acid;

trans,trans-2-(4-Methoxymethoxyphenyl)-4-(1,3-benzodioxol-5-yl)--(2-(N-propyl-N-n-pentanesulfonylamino)ethyl]pyrrolidine-3-carboxylic acid;

trans,trans-2-(3,4-Dimethoxyphenyl)-4-(1,3-benzodioxol-5-yl)-1-[2-(N-propyl-N-n-pentanesulfonylamino)ethyl]pyrrolidine-3-carboxylic acid;

trans,trans-2-(3,4-Dimethoxyphenyl)-4-(1,3-benzodioxol-5-yl)-1-[2-(N-propyl-N-n-hexanesulfonylamino)ethyl]pyrrolidine-3-carboxylic acid;

trans,trans-2-(4-Propoxyphenyl)-4-(1,3-benzodioxol-5-yl)-1-[2-(N-propyl-N-n-pentanesulfonylamino)ethyl]pyrrolidine-3-carboxylic acid;

trans,trans-2-(3,4-Difluorophenyl)-4-(1,3-benzodioxol-5-yl)-1-(N,N-di(n-butyl)aminocarbonylmethyl)-pyrrolidine-3-carboxylic acid;

trans,trans-2-(3,4-Difluorophenyl)-4-(1,3-benzodioxol-5-yl)-1-[2-(N-propyl-N-n-pentanesulfonylamino)ethyl]pyrrolidine-3-carboxylic acid;

trans,trans-2-(3-Fluoro-4-methoxyphenyl)-4-(1,3-benzodioxol-5-yl)-1-[2-(N-propyl-N-n-hexanesulfonylamino)ethyl]pyrrolidine-3-carboxylic acid;

trans,trans-2-(3-Fluoro-4-methoxyphenyl)-4-(1,3-benzodioxol-5-yl)-1-(2-(N-propyl-N-(3-chloropropanesulfonyl)amino)ethyl)-pyrrolidine-3-carboxylic acid;

trans,trans-2-(3-Fluoro-4-methoxyphenyl)-4-(1,3-benzodioxol-5-yl)-1-(2-(N-isobutyl-N-(3-chloropropanesulfonyl)amino)ethyl)pyrrolidine-3-carboxylic acid;

trans,trans-2-(3-Fluoro-4-methoxyphenyl)-4-(1,3-benzodioxol-5-yl)-1-[2-(N-propyl-N-(4-methylbutanesulfonyl)amino)ethyl]pyrrolidine-3-carboxylic acid;

trans,trans-2-(4-Methoxy-3-fluorophenyl)-4-(7-methoxy-1,3-benzodioxol-5-yl)-1-[2-(N-propyl-N-(n-pentanesulfonyl)amino)ethyl]pyrrolidine-3-carboxylic acid;

trans,trans-2-(3-Fluoro-4-methoxyphenyl)-4-(1,3-benzodioxol-5-yl)-1-[2-(N-propyl-N-(2,2,3,3,3-pentafluoropropoxyethanesulfonyl)-amino)ethyl]pyrrolidine-3-carboxylic acid;

trans,trans-2-(1,4-Benzodioxan-6-yl)-4-(7-methoxy-1,3-benzodioxol-5-yl)-1-[2-(N-propyl-N-(n-pentanesulfonyl)amino)ethyl]pyrrolidine-3-carboxylic acid;

trans,trans-2-(3-Fluoro-4-methoxyphenyl)-4-(1,3-benzodioxol-5-yl)-1-(2-(N-isobutyl-N-(pentanesulfonylamino)ethyl)pyrrolidine-3-carboxylic acid;

trans,trans-2-(3-Fluoro-4-methoxyphenyl)-4-(1,3-benzodioxol-5-yl)-1-(2-(N-(2-methoxyethyl)-N-(3-chloropropanesulfonyl)amino)-ethyl)pyrrolidine-3-carboxylic acid;

trans,trans-2-(3-Fluoro-4-methoxyphenyl)-4-(1,3-benzodioxol-5-yl)-1-(2-(N-(2-methoxyethyl)-N-(pentanesulfonyl)amino)ethyl)pyrrolidine-3-carboxylic acid;

trans,trans-2-(3-Fluoro-4-methoxyphenyl)-4-(1,3-benzodioxol-5-yl)-1-[2-(N-propyl-N-((2,2,2-trifluoroethoxyethane)sulfonyl)amino)-ethyl]pyrrolidine-3-carboxylic acid;

trans,trans-2-(3-Fluoro-4-methoxyphenyl)-4-(1,3-benzodioxol-5-yl)-1-(2-(N-(2-methoxyethyl)-N-(butanesulfonylamino)ethyl)-pyrrolidine-3-carboxylic acid;

trans,trans-2-(3-Fluoro-4-methoxyphenyl)-4-(1,3-benzodioxol-5-yl)-1-[2-(N-propyl-N-(2-methylpropanesulfonyl)amino)ethyl]pyrrolidine-3-carboxylic acid;

trans,trans-2-(3-Fluoro-4-methoxyphenyl)-4-(1,3-benzodioxol-5-yl)-1-(2-(N-isobutyl-N-(butanesulfonylamino))ethyl)pyrrolidine-3-carboxylic acid;

trans,trans-2-(2-Methylpentyl)-4-(1,3-benzodioxol-5-yl)-1-(N,N-di(n-butyl)aminocarbonylmethyl)-pyrrolidine-3-carboxylic acid;

trans,trans-2-(2,2-Dimethylpentyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxo-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(2-Tetrahydro-2H-pyran)ethyl)-4-(1,3-benzodioxol-5-yl)-1-(N,N-di(n-butyl)aminocarbonylmethyl)-pyrrolidine-3-carboxylic acid;

trans,trans-2-(2,2,4-Trimethyl-3-pentenyl)-4-(1,3-benzodioxol-5-yl)-1-(N,N-di(n-butyl)aminocarbonylmethyl)-pyrrolidine-3-carboxylic acid;

trans,trans-2-(2,2,-Dimethyl-2-(1,3-dioxolan-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxo-2-yl)ethyl)-4-(1,3-benzodioxol-5-yl)-1-[[N-4-heptyl-N(2 methyl-3-fluorophenyl)]aminocarbonylmethyl]-pyrrolidine-3-carboxylic acid;

trans,trans-2-(2-(1,3-Dioxol-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-((2-Methoxyphenoxy)-methyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2-(2-Oxopyrrolidin-1-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2-dimethylpentyl)-4-(2,3-dihydro-benzofuran-5-yl)-1-(N,N-di(n-butyl)aminocarbonylmethyl)-pyrrolidine-3-carboxylic acid;

trans,trans-2-(2,2,-Dimethyl-2-(1,3-dioxolan-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-Methoxyphenyl)-ethyl)-4-(1,3-benzodioxol-5-yl)-1-(N,N-di(n-butyl)aminocarbonylmethyl)-pyrrolidine-3-carboxylic acid;

trans,trans-2-(2,2-Dimethyl-3-(E)-pentenyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-pyridyl)ethyl)-4-(1,3-benzodioxol-5-yl)-1-(N,N-di(n-butyl)aminocarbonylmethyl)-pyrrolidine-3-carboxylic acid;

(2S,3R,4S)-2-(2-(2-oxopyrrolidin-1-yl)ethyl)-4-(1,3-benzodioxol-5-yl)-1-(N,N-di(n-butyl)aminocarbonylmethyl)-pyrrolidine-3-carboxylic acid;

(2S,3R,4S)-2-(2-(2-oxopyrrolidin-1-yl)ethyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2-(1-pyrazolyl)ethyl)-4-(1,3-benzodioxol-5-yl)-1-(N,N-di(n-butyl)aminocarbonylmethyl)-pyrrolidine-3-carboxylic acid;

trans,trans-2-(4-Methoxyphenyl)-4-(1,3-benzodioxol-5-yl)-1-[(N-butyl-N-(4-dimethylaminobutyl)amino)carbonylmethyl]-pyrrolidine-3-carboxylic acid;

(2R,3R,4S)-2-(3-Fluoro-4-methoxyphenyl)-4-(1,3-benzodioxol-5-yl) 1-(2-(N-propyl-N-pentanesulfonylamino)ethyl)-pyrrolidine-3-carboxylic acid;

trans,trans-2-(2,2-Dimethylpentyl)-4-(1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpentyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpent-3-enyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpent-3-enyl)-4-(1,3-benzodioxol-5-yl)-1-((N-butyl-N-(4-dimethylamino)butyl)aminocarbonylmethyl)-pyrrolidine-3-carboxylic acid;

trans,trans-2-(2,2-Dimethylpent-3-enyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2-Dimethylpent-3-enyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpent-3-enyl)-4-(7-methoxy-1,3-benzodioxol-5-yl)-1-((N-butyl-N-(4-dimethylamino)butyl)aminocarbonylmethyl)-pyrrolidine-3-carboxylic acid;

trans,trans-2-(2,2,4-Trimethylpent-3-enyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2,4-Trimethylpent-3-enyl)-4-(1,3-benzo-dioxol-5-yl)-1-((N-butyl-N-(4-dimethylamino)butyl)ami-nocarbonylmethyl)-pyrrolidine-3-carboxylic acid;

trans,trans-2-(2,2,4-Trimethylpent-3-enyl)-4-(7-methoxy-1,3-benzodioxol-5-yl)-1-(N,N-di(n-butyl)aminocarbonyl-methyl)-pyrrolidine-3-carboxylic acid;

trans,trans-2-(2,2,4-Trimethylpent-3-enyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2,4-Trimethylpent-3-enyl)-4-(7-methoxy-1,3-benzodioxol-5-yl)-1-((N-butyl-N-(4-dimethylamino)butyl)aminocarbonylmethyl)-pyrrolidine-3-carboxylic acid;

trans,trans-2-(2-(1,3-Dioxol-2-yl)ethyl)-4-(1,3-benzo-dioxol-5-yl)-1-[(N-butyl-N-(4-dimethylaminobutyl)amino)carbonylmethyl]-pyrrolidine-3-carboxylic acid;

trans,trans-2-(2-(1,3-Dioxol-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2,2,-Dimethyl-2-(1,3-Dioxol-2-yl)ethyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethyl-2-(1,3-dioxolan-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2,2,-Dimethyl-2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethyl-2-(1,3-dioxolan-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Methoxyphenyl)-ethyl)-4-(1,3-benzo-dioxol-5-yl)-1-(N-4-heptyl-N-(4-fluoro-3-methylphenyl))amino)carbonylmethyl]-pyrrolidine-3-carboxylic acid;

trans,trans-2-(2-(2-Methoxyphenyl)-ethyl)-4-(1,3-benzo-dioxol-5-yl)-1-[(N-butyl-N-(4-dimethylaminobutyl)amino)carbonylmethyl]-pyrrolidine-3-carboxylic acid;

trans,trans-2-(2-(2-Methoxyphenyl)-ethyl)-4-(7-methoxy-1,3-benzodioxol-5-yl)-1-(N,N-di(n-butyl)aminocarbonyl-methyl)-pyrrolidine-3-carboxylic acid;

trans,trans-2-(2-(2-Methoxyphenyl)-ethyl)-4-(7-methoxy-1,3-benzodioxol-5-yl)-1-(N-4-heptyl-N-(4-fluoro-3-methylphenyl))aminocarbonylmethyl]-pyrrolidine-3-carboxylic acid;

trans,trans-2-(2-(2-Methoxyphenyl)-ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-((2-Methoxyphenoxy)-methyl)-4-(1,3-benzo-dioxol-5-yl)-1-(N-4-heptyl-N-(4-fluoro-3-methylphenyl))amino)carbonylmethyl]-pyrrolidine-3-carboxylic acid;

trans,trans-2-((2-Methoxyphenoxy)-methyl)-4-(1,3-benzo-dioxol-5-yl)-1-[(N-butyl-N-(4-dimethylaminobutyl)amino)carbonylmethyl]-pyrrolidine-3-carboxylic acid;

trans,trans-2-((2-Methoxyphenoxy)-methyl)-4-(7-methoxy-1,3-benzodioxol-5-yl)-1-(N,N-di(n-butyl)aminocarbonyl-methyl)-pyrrolidine-3-carboxylic acid;

trans,trans-2-((2-Methoxyphenoxy)-methyl)-4-(7-methoxy-1,3-benzodioxol-5-yl)-1-(N-4-heptyl-N-(4-fluoro-3-methylphenyl))amino)carbonylmethyl]-pyrrolidine-3-carboxylic acid;

trans,trans-2-(2-(2-Methoxyphenoxy)-methyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxo 1,2-dihydro pyridin-1-yl)-ethyl)-4-(1,3-benzodioxol-5-yl)-1-(N,N-di(n-butyl)aminocarbon-ylmethyl)-pyrrolidine-3-carboxylic acid;

trans,trans-2-(2-(2-Oxopyridin-1-yl)-ethyl)-4-(1,3-benzo-dioxol-5-yl)-1-[(N-4-heptyl-N-(4-fluoro-3-methylphe-nyl)amino)carbonylmethyl]-pyrrolidine-3-carboxylic acid;

trans,trans-2-(2-(2-Oxopyridin-1-yl)-ethyl)-4-(1,3-benzo-dioxol-5-yl)-1-[(N-butyl-N-(4-dimethylaminobutyl)amino)carbonylmethyl]-pyrrolidine-3-carboxylic acid;

trans,trans-2-(2-(2-Oxopyridin-1-yl)-ethyl)-4-(7-methoxy-1,3-benzodioxol-5-yl)-1-(N,N-di(N-butyl)aminocarbon-ylmethyl)-pyrrolidine-3-carboxylic acid;

trans,trans-2-(2-(2-Oxopyridin-1-yl)-ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyridin-1-yl)-ethyl)-4-(7-methoxy-1,3-benzodioxol-5-yl)-1-[(N-butyl-N-(4-dimethylami-nobutyl)amino)carbonylmethyl]-pyrrolidine-3-carboxylic acid;

trans,trans-2-(2(–2-Oxopiperidin-1-yl)-ethyl)-4-(1,3-benzo-dioxol-5-yl)-1-(N,N-di(N-butyl)aminocarbonylmethyl)-pyrrolidine-3-carboxylic acid;

trans,trans-2-(2-(2-Oxopiperidin-1-yl)-ethyl)-4-(1,3-benzo-dioxol-5-yl)-1-[(N-4-heptyl-N-(4-fluoro-3-methylphe-nyl)amino)carbonylmethyl]-pyrrolidine-3-carboxylic acid;

trans,trans-2-(2-(2-Oxopiperidin-1-yl)-ethyl)-4-(7-meth-oxy-1,3-benzodioxol-5-yl)-1-(N,N-di(N-butyl)aminocar-bonylmethyl)-pyrrolidine-3-carboxylic acid;

trans,trans-2-(2-(2-Oxopiperidin-1-yl)-ethyl)-4-(7-meth-oxy-1,3-benzodioxol-5-yl)-1-(N,N-di(N-butyl)aminocar-bonylmethyl)-pyrrolidine-3-carboxylic acid;

trans,trans-2-(2-(2-Oxopiperidin-1-yl)-ethyl)-4-(7-meth-oxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopiperidin-1-yl)-ethyl)-4-(7-meth-oxy-1,3-benzodioxol-5-yl)-1-[(N-butyl-N-(4-dimethy-laminobutyl)amino)carbonylmethyl]-pyrrolidine-3-car-boxylic acid;

trans,trans-2-(2-(2-Oxopyrrolidin-1-yl)ethyl)-4-(1,3-benzo-dioxol-5-yl)-1-[(N-butyl-N-(3-hydroxypropyl)amino)car-bonylmethyl]-pyrrolidine-3-carboxylic acid;

trans,trans-2-(2-(2-Oxopyrrolidin-1-yl)ethyl)-4-(1,3-benzo-dioxol-5-yl)-1-[(N-butyl-N-(propoxy)amino)carbonylm-ethyl]-pyrrolidine-3-carboxylic acid;

trans,trans-2-(2-(2-Oxopyrrolidin-1-yl)ethyl)-4-(1,3-benzo-dioxol-5-yl)-1-[(N-butyl-N-(4 dimethylaminobutyl)amino)carbonylmethyl]-pyrrolidine-3-carboxylic acid;

trans,trans-2-(2-(2-Oxopyrrolidin-1-yl)ethyl)-4-(1,3-benzo-dioxol-5-yl)-1-[(N-butyl-N-(4-trimethylammoniobutyl)amino)carbonylmethyl]-pyrrolidine-3-carboxylic acid;

trans,trans-2-(2-(2-Oxopyrrolidin-1-yl)ethyl)-4-(7-meth-oxy-1,3-benzodioxol-5-yl)-1-(N,N-di(N-butyl)aminocar-bonylmethyl)-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(3-hydroxypropyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(propoxy)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(2-Oxopyrrolidin-1-yl)ethyl)-4-(7-methoxy-1,3-benzodioxol-5-yl)-1-[(N-butyl-N-(4-trimethylammoniobutyl)amino)carbonylmethyl]-pyrrolidine-3-carboxylic acid;

trans,trans-2-(2-(2-Oxopyrrolidin-1-yl)ethyl)-4-(2,3-dihydro-benzofuran-5-yl)-1-(N,N-di(N-butyl)aminocarbonylmethyl)-pyrrolidine-3-carboxylic acid;

trans,trans-2-(2-(2-Oxopyrrolidin-1-yl)ethyl)-4-(2,3-dihydro-benzofuran-5-yl)-1-[(N-4-heptyl-N-(4-fluoro-3-methylphenyl)amino)carbonylmethyl]-pyrrolidine-3-carboxylic acid;

trans,trans-2-(2-(2-Oxopyrrolidin-1-yl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(3,3-Dimethyl-2-oxopyrrolidin-1-yl)ethyl)-4-(1,3-benzodioxol-5-yl)-1-(N,N-di(N-butyl)aminocarbonylmethyl)pyrrolidine-3-carboxylic acid;

trans,trans-2-(2-(3,3-Dimethyl-2-oxopyrrolidin-1-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(3,3-Dimethyl-2-oxopyrrolidin-1-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(4,4-Dimethyl-2-oxopyrrolidin-1-yl)ethyl)-4-(1,3-benzodioxol-5-yl)-1-(N,N-di(N-butyl)aminocarbonylmethyl)-pyrrolidine-3-carboxylic acid;

trans,trans-2-(2-(4,4-Dimethyl-2-oxopyrrolidin-1-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(4,4-Dimethyl-2-oxopyrrolidin-1-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(1-propanesultamyl)ethyl)-4-(1,3-benzodioxol-5-yl)-1-(N,N-dibutylaminocarbonylmethyl)-pyrrolidine-3-carboxylic acid;

trans,trans-2-(2-(1-propanesultamyl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(propoxy)amino)carbonylmethyl]-pyrrolidine-3-carboxylic acid;

trans,trans-2-(2-(1-propanesultamyl)ethyl)-4-(1,3-benzodioxol-5-yl)-1-[(N-butyl-N-(4 dimethylaminobutyl)amino)carbonylmethyl]-pyrrolidine-3-carboxylic acid;

trans,trans-2-(2-(1-propanesultamyl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(1-propanesultamyl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-propanesultamyl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(1-propanesultamyl)ethyl)-4-(2,3-dihydro-benzofuran-5-yl)-1-(N,N-di(n-butyl)aminocarbonylmethyl)-pyrrolidine-3-carboxylic acid;

trans,trans-2-(2-(1-propanesultamyl)ethyl)-4-(2,3-dihydro-benzofuran-5-yl)-1-[(N-4-heptyl-N-(4-fluoro-3-methylphenyl)amino)carbonylmethyl]-pyrrolidine-3-carboxylic acid;

trans,trans-2-(2-(1-propanesultamyl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(1-pyrazolyl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-pyrazolyl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(1-pyrazolyl)ethyl)-4-(1,3-benzodioxol-5-yl)-1-(N-butyl-N-(propoxy)amino)carbonylmethyl]-pyrrolidine-3-carboxylic acid;

trans,trans-2-(2-(1-pyrazolyl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(1-pyrazolyl)ethyl)-4-(7-methoxy-1,3-benzodioxol-5-yl)-1-(N,N-dibutylaminocarbonylmethyl)-pyrrolidine-3-carboxylic acid;

trans,trans-2-(2-(1-pyrazolyl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(1-pyrazolyl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(1-pyrazolyl)ethyl)-4-(2,3-dihydro-benzofuran-5-yl)-1-(N,N-dibutylaminocarbonylmethyl)-pyrrolidine-3-carboxylic acid;

trans,trans-2-(2-(1-pyrazolyl)ethyl)-4-(2,3-dihydro-benzofuran-5-yl)-1-[(N-4-heptyl-N-(4-fluoro-3-methylphenyl)amino)carbonylmethyl]-pyrrolidine-3-carboxylic acid;

trans,trans-2-(2-(1-pyrazolyl)ethyl)-4-(2,3-dihydro-benzofuran-5-yl)-1-[(N-butyl-N-(4-dimethylaminobutyl)amino)carbonylmethyl]-pyrrolidine-3-carboxylic acid;

trans,trans-2-(2-(2-oxazolyl)ethyl)-4-(1,3-benzodioxol-5-yl)-1-(N,N-di(n-butyl)aminocarbonylmethyl)-pyrrolidine-3-carboxylic acid;

trans,trans-2-(2-(Oxazol-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Oxazol-2-yl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(Oxazol-2-yl)ethyl)-4-(1,3-benzodioxol-5-yl)-1-[(N-butyl-N-(propoxy)amino)carbonylmethyl]-pyrrolidine-3-carboxylic acid;

trans,trans-2-(2-(Oxazol-2-yl)ethyl)-4-(1,3-benzodioxol-5-yl)-1-[(N-butyl —N-(4-dimethylaminobutyl)amino)carbonylmethyl]-pyrrolidine-3-carboxylic acid;

trans,trans-2-(2-(Oxazol-2-yl)ethyl)-4-(7-methoxy-1,3-benzodioxol-5-yl)-1-(N,N-di(n-=butyl)aminocarbonylmethyl)-pyrrolidine-3-carboxylic acid;

trans,trans-2-(2-(Oxazol-2-yl)ethyl)-4-(7-methoxy-1,3-benzodioxol-5-yl)-1-[(N-4-heptyl —N-(4-fluoro-3-methylphenyl)amino)carbonylmethyl]-pyrrolidine-3-carboxylic acid;

trans,trans-2-(2-(Oxazol-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(5-Methyloxazol-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(5-Methyloxazol-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(5-Methyloxazol-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-(N,N-di(n-butyl)aminocarbonylmethyl)-pyrrolidine-3-carboxylic acid;

trans,trans-2-(2-(2,5-Dioxopyrrolidin-1-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-[(N-butyl-N-(propoxy)amino)carbonylmethyl]-pyrrolidine-3-carboxylic acid;

trans,trans-2-(2-(2,5-Dioxopyrrolidin-1-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(2,5-Dioxopyrrolidin-1-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2,5-Dioxopyrrolidin-1-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyridin-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyridin-2-yl)ethyl)-4-(1,3-benzodioxol-5-yl)-1-[(N-butyl-N-(3-hydroxypropyl)amino)carbonylmethyl]-pyrrolidine-3-carboxylic acid;

trans,trans-2-(2-(Pyridin-2-yl)ethyl)-4-(1,3-benzodioxol-5-yl)-1-[(N-butyl-N-(propoxy)amino)carbonylmethyl]-pyrrolidine-3-carboxylic acid;

trans,trans-2-(2-(Pyridin-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(Pyridin-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(Pyridin-2-yl)ethyl)-4-(7-methoxy-1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyridin-2-yl)ethyl)-4-(7-methoxy-1,3-benzodioxol-5-yl)-1-[(N-butyl-N-(4-dimethylaminobutyl)amino)carbonylmethyl]-pyrrolidine-3-carboxylic acid;

trans,trans-2-(2-(Pyrimidin-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(Pyrimidin-2-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid;

trans,trans-2-(2-(Pyrimidin-2-yl)ethyl)-4-(1,3-benzodioxol-5-yl)-1-[(N-butyl-N-(4-dimethylaminobutyl)amino)carbonylmethyl]-pyrrolidine-3-carboxylic acid;

trans,trans-2-(2-(1,3-benzodioxol-4-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-benzodioxol-4-yl)ethyl)-4-(1,3-benzodioxol-5-yl)-1-[(N-4-heptyl-N-(4-fluoro-3-methylphenyl)amino)carbonylmethyl]-pyrrolidine-3-carboxylic acid; and trans,trans-2-(2-(1,3-benzodioxol-4-yl)ethyl)-4-(1,3-benzodioxol-5-yl)-1-[(N-butyl-N-(4 dimethylaminobutyl)amino)carbonylmethyl]-pyrrolidine-3-carboxylic acid;

(2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(7-methoxy-1,3-benzodioxol-5-yl)-1-(N,N-di(n-butyl)aminocarbonylmethyl)-pyrrolidine-3-carboxylic acid;

(2S,3R,4S)-2-((2-Methoxyphenoxy)-methyl)-4-(1,3-benzodioxol-5-yl)-1-(N,N-di(n-butyl)aminocarbonylmethyl)-pyrrolidine-3-carboxylic acid;

(2S,3R,4S)-2-(2-(2-Methoxyphenyl)ethyl)-4-(1,3-benzodioxol-5-yl)-1-(N,N-di(n-butyl)aminocarbonylmethyl)-pyrrolidine-3-carboxylic acid;

or a pharmaceutically acceptable salt.

Most preferred compounds of the invention are selected from the group consisting of:

trans,trans-2-(2-(1,3-Dioxol-2-yl)ethyl)-4-(1,3-benzodioxol-5-yl)-1-(N,N-di(n-butyl)aminocarbonylmethyl)-pyrrolidine-3-carboxylic acid;

trans,trans-2-(2,2,-Dimethyl-2-(1,3-dioxolan-2-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxol-2-yl)ethyl)-4-(1,3-benzodioxol-5-yl)--1-[[N-4-heptyl-N-(2-methyl-3-fluorophenyl)]aminocarbonylmethyl]-pyrrolidine-3-carboxylic acid;

trans,trans-2-(2-(1,3-Dioxol-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-((2-Methoxyphenoxy)-methyl)-4-(1,3-benzodioxol-5-yl)-1-(N,N-di(n-butyl)aminocarbonylmethyl)-pyrrolidine-3-carboxylic acid;

trans,trans-2-(2-(2-Oxopyrrolidin-1-yl)ethyl)-4-(1,3-benzodioxol-5-yl)-1-(N,N-di(n-butyl)aminocarbonylmethyl)-pyrrolidine-3-carboxylic acid;

trans,trans-2-(2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2,2-Dimethylpentyl)-4-(7-methoxy-1,3-benzodioxol-5-yl)-1-(N,N-di(n-butyl)aminocarbonylmethyl)-pyrrolidine-3-carboxylic acid;

trans,trans-2-(2,2,-Dimethyl-2-(1,3-dioxolan-2-yl)ethyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-Methoxyphenyl)-ethyl)-4-(1,3-benzodioxol-5-yl)-1-(N,N-di(n-butyl)aminocarbonylmethyl)-pyrrolidine-3-carboxylic acid;

trans,trans-2-(2,2-Dimethyl-3-(E)-pentenyl)-4-(7-methoxy-1,3-benzodioxol-5-yl)-1-(N,N-di(n-butyl)aminocarbonylmethyl)-pyrrolidine-3-carboxylic acid;

trans,trans-2-(2-(2-pyridyl)ethyl)-4-(1,3-benzodioxol-5-yl)-1-(N,N-di(n-butyl)aminocarbonylmethyl)-pyrrolidine-3-carboxylic acid;

(2S,3R,4S)-2-(2-(2-oxopyrrolidin-1-yl)ethyl)-4-(1,3-benzodioxol-5-yl)-1-(N,N-di(n-butyl)aminocarbonylmethyl)-pyrrolidine-3-carboxylic acid;

(2S,3R,4S)-2-(2-(2,2 Dimethylpentyl)-4-(7-methoxy-1,3-benzodioxol-5-yl)-1-(N,N-di(n-butyl)aminocarbonylmethyl)-pyrrolidine-3-carboxylic acid;

(2S,3R,4S)-2-(2-(2-oxopyrrolidin-1-yl)ethyl)-4-(1,3-benzodioxol-5-yl)-1-(N-4-heptyl-N-(4-fluoro-3-methylphenyl))aminocarbonylmethyl)-pyrrolidine-3-carboxylic acid;

trans,trans-2-(2-(1-pyrazolyl)ethyl)-4-(1,3-benzodioxol-5-yl)-1-(N,N-di(n-butyl)aminocarbonylmethyl)-pyrrolidine-3-carboxylic acid;

(2R,3R,4S)-2-(3-Fluoro-4-methoxyphenyl)-4-(1,3-benzodioxol-5-yl)-1-[((N-propyl-N-pentanesulfonyl)amino)ethyl]-pyrrolidine-3-carboxylic acid;

(2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(1,3-benzodioxol-5-yl)-1-(N,N-di(n-butyl)aminocarbonylmethyl)-pyrrolidine-3-carboxylic acid;

(2S,3R,4S)-2-(2,2-Dimethylpent-(E)-3-enyl)-4-(7-methoxy-1,3-benzodioxol-5-yl)-1-(N,N-di(n-butyl)aminocarbonylmethyl)-pyrrolidine-3-carboxylic acid;

(2S,3R,4S)-2-((2-Methoxyphenoxy)-methyl)-4-(1,3-benzodioxol-5-yl)-1-(N,N-di(n-butyl)aminocarbonylmethyl)-pyrrolidine-3-carboxylic acid; and (2S,3R,4S)-2-(2-(2-Methoxyphenyl)ethyl)-4-(1,3-benzodioxol-5-yl)-1-(N,N-di(n-butyl)aminocarbonylmethyl)-pyrrolidine-3-carboxylic acid;

trans,trans-2-(4-methoxyphenyl)-4-(1,3-benzodioxol-5-yl)-1-(N-((bis-(o-tolyl)methyl)amino)carbonylmethyl)-(pyrrolidine-3-carboxylic acid;

trans,trans-2-[4-(2-methoxyethoxy)phenyl]-4-(1,3-benzodioxol-5-yl)-1-(N-(2,2-dimethyl-1-phenylpropyl)-1-amino)carbonylmethyl)-pyrrolidine-3-carboxylic acid;

trans,trans-2-[4-(2-methoxyethoxy)phenyl]-4-(1,3-benzodioxol-5-yl)-1-(N-((bis-(o-tolyl)methyl)amino)carbonylmethyl)-pyrrolidine-3-carboxylic acid;

trans,trans-2-[4-(2-isopropoxyethoxy)phenyl]-4-(1,3-benzodioxol-5-yl)-1-(N-(2,2-dimethyl-1-phenylpropyl)-1-amino)carbonylmethyl)-pyrrolidine-3-carboxylic acid;

trans,trans-2-(4-methoxyphenyl)-4-(1,3-benzodioxol-5-yl)-1-(N-(3,3-dimethyl-1-phenylbutyl)-1-amino)carbonylmethyl)-pyrrolidine-3-carboxylic acid;

trans,trans-2-[4-(2-isopropopoxyethoxy)phenyl]-4-(1,3-benzodioxol-5-yl)-1-(N-((1-(o-tolyl)-1-(o-ethylphenyl)-methyl)amino)carbonylmethyl)-pyrrolidine-3-carboxylic acid;

trans,trans-2-(4-(2-(2-propoxy)ethoxy)phenyl)-4-(1,3-benzodioxol-5-yl)-1-N-phenyl-N-t-butylhydrazino carbonylmethyl)-pyrrolidine-3-carboxylic acid; and trans,trans-2-(4-(2-methoxyethoxy)phenyl)-4-(1,3-benzodioxol-5-yl)-1-(N-phenyl-N-t-butylhydrazino carbonylmethyl)-pyrrolidine-3-carboxylic acid;

or a pharmaceutically acceptable salt thereof.

Methods for preparing the compounds of the invention are shown in Schemes I–XXIII.

Scheme I illustrates the general procedure for preparing the compounds of the invention when n and m are 0, Z is —$CH_2$— and W is —$CO_2H$. A alpha-ketoester 1, where E is loweralkyl or a carboxy protecting group is reacted with a nitro vinyl compound 2, in the presence of a base (for example, 1,8-diazabicyclo[5.4.0]undec-7-ene (DBU) or sodium ethoxide or sodium hydride and the like) in an inert solvent such as toluene, benzene, tetrahydrofuran or ethanol and the like. The condensation product 3 is reduced (for example, hydrogenation using a Raney nickel or platinum catalyst). The resulting amine cyclizes to give the dihydro pyrrole 4. Reduction of 4 (for example, sodium cyanoborohydride or catalytic hydrogenation and the like) in a protic solvent such as ethanol or methanol and the like gives the pyrrolidine compound 5 as a mixture of cis—cis, trans,trans and cis,trans products. Chromatographic separation removes the cis—cis isomer leaving a mixture of the trans,trans and cis,trans isomers which is further elaborated. The cis—cis isomer can be epimerized (for example, using sodium ethoxide in ethanol) to give the trans,trans isomer and then carried on as described below. The pyrrolidine nitrogen is (1) acylated or sulfonylated with $R_3$—X ($R_3$ is $R_4$—C(O)— or $R_6$—$S(O)_2$— and X is a leaving group such as a halide (Cl is preferred) or X taken together with $R_4$—C(O)— or $R_6$—$S(O)_2$— forms an activated ester including esters or anhydrides derived from formic acid, acetic acid and the like, alkoxycarbonyl halides, N-hydroxysuccinimide, N-hydroxyphthalimide, N-hydroxybenzotriazole, N-hydroxy-5-norbornene-2,3-dicarboxamide, 2,4,5-trichlorophenol and the like) or (2) alkylated with $R_3$—X where X is a leaving group (for example, X is a halide (for example, Cl, Br or I) or X is a leaving group such as a sulfonate (for example, mesylate, tosylate, triflate and the like)) in the presence of a base such as diisopropyl ethylamine or triethylamine and the like to give the N-derivatized pyrrolidine 6 which is still a mixture of trans,trans and cis,trans isomers. Hydrolysis of the ester 6 (for example, using a base such a sodium hydroxide in EtOH/$H_2O$) selectively hydrolyzes the trans,trans ester to give a mixture of 7 and 8, which are readily separated.

Scheme II illustrates a general procedure for preparing the compounds of the invention when n is 1, m is 0, Z is —$CH_2$— and W is —$CO_2H$. A substituted benzyl chloride 9 is reacted with a lithio dithiane 10 in an inert solvent such as THF or dimethoxyethane to give the alkylated adduct 11. The anion of compound 11 is formed using a base such as n-butyllithium and then reacted with $R_1$—$CH_2$—X' wherein X' is a leaving group such as a halide or sulfonate to give compound 12. The dithiane protecting group is cleaved (for example, using a mercuric salt in water) to give the keto compound 13. Reaction of ketone 13 with benzyl amine and formaldehyde gives the keto piperidine compound 14. Treatment of compound 14 with an activated nitrile such as trimethylsilyl cyanide followed by a dehydrating agent such as phosphorous oxychloride provides the isomeric ene nitriles 15. Reduction of the double bond (for example, using sodium borohydride) affords the piperidinyl nitrile 16. Hydrolysis of the nitrile using hydrochloric acid in the presence of a carboxy protecting reagent (for example, an alkyl alcohol) affords ester 17 (where E is a carboxy protecting group). Debenzylation by catalytic hydrogenation under acidic conditions affords the free piperidine compound 18. Compound 18 is further elaborated by the procedures described in Scheme I for compound 5 to give the final product compound 19.

Scheme III illustrates a general procedure for preparing the compounds of the invention when m and n are 0, Z is —C(O)— and W is —CO$_2$H. alpha-Keto ester 20 (wherein E is loweralkyl or a carboxy protecting group) is reacted with an alpha-haloester 21 (where J is lower alkyl or a carboxy protecting group and the halogen is bromine, iodine or chlorine) in the presence of a base such as NaH or potassium tert-butoxide or lithium diisopropylamide in an inert solvent such as THF or dimethoxyethane to give diester 22. Treating compound 22 with R$_3$—NH$_2$ and heating in acetic acid gives the cyclic compound 23. The double bond is reduced (for example, by catalytic hydrogenation using a palladium on carbon catalyst or sodium cyanoborohydride reduction) to give pyrrolidone 24. Epimerization with sodium ethoxide in ethanol to give the desired trans,trans configuration, followed by sodium hydroxide hydrolysis of the ester, affords the desired trans,trans carboxylic acid 25.

Scheme IV illustrates a general procedure for preparing the compounds of the invention when n is 0, m is 1, Z is —CH$_2$— and W is —CO$_2$H. The trans,trans compound 7, prepared in Scheme I, is homologated by the Arndt-Eistert synthesis. The carboxy terminus is activated (for example, by making the acid chloride using thionyl chloride) to give compound 52, where L is a leaving group (in the case of an acid chloride, L is Cl). Compound 52 is treated with diazomethane to give the diazo ketone 53. Rearrangement of compound 53 (for example, using water or an alcohol and silver oxide or silver benzoate and triethylamine, or heating or photolysis in the presence of water or an alcohol) affords the acetic acid compound 54 or an ester which may be hydrolyzed. Compounds where m is from 2 to 6 can be obtained by repetition of the above described process.

A preferred embodiment is shown in Schemes V and VI. A benzoyl acetate 26 is reacted with a nitro vinyl benzodioxolyl compound 27 using 1,8-diazabicyclo[5.4.0]undec-7-ene (DBU) as the base in toluene to give compound 28. Catalytic hydrogenation using Raney nickel leads to reduction of the nitro group to an amine and subsequent cyclization to give the dihydropyrrole 29. The double bond is reduced with sodium cyanoborohydride to give the pyrrolidine compound 30 as a mixture of cis—cis, trans,trans and cis,trans isomers. Chromatography separates out the cis—cis isomer, leaving a mixture of the trans,trans and cis,trans isomers (31).

Scheme VI illustrates the further elaboration of the trans, trans isomer. The mixture (31) of trans,trans and cis,trans pyrrolidines described in Scheme IV is reacted with N-propyl bromoacetamide in acetonitrile in the presence of ethyldiisopropylamine to give the alkylated pyrrolidine compound 32, still as a mixture of trans,trans and cis,trans isomers. Sodium hydroxide in ethanol-water hydrolyzes the ethyl ester of the trans,trans compound but leaves the ethyl ester of the cis,trans compound untouched, thus allowing separation of the trans,trans carboxylic acid 33 from the cis,trans ester 34.

Scheme VII illustrates the preparation of a specific piperidinyl compound. Benzodioxolyl methyl chloride 35 is reacted with lithio dithiane 36 to give the alkylated compound 37. Treatment of compound 37 with 4-methoxybenzyl chloride in the presence of lithium diisopropylamide gives compound 38. Cleavage of the dithiane protecting group using a mercuric salt in aqueous solution gives ketone 39. Treatment of 39 with benzylamine and formaldehyde gives the keto piperidine 40. Treatment of compound 40 with trimethylsilyl cyanide followed by phosphorous oxychloride gives the ene nitrile as a mixture of isomers 41. Sodium borohydride reduction of the double bond gives the piperidinyl nitrile 42. Hydrochloric acid hydrolysis in the presence of ethanol gives ethyl ester 43. The N-benzyl protecting group is removed by catalytic hydrogenation to give the free piperidine compound 44. Compound 44 is further elaborated by the procedures described in Scheme V for compound 31 resulting in the formation of the N-derivatized carboxylic acid 45.

A preferred embodiment of the process shown in Scheme III is shown in Scheme VIII. 4-Methoxybenzoylacetate 46 (wherein E is loweralkyl or a carboxy protecting group) is reacted with an benzodioxolyl alpha-bromoacetate 47 (wherein E is lower alkyl or a carboxy protecting group) in the presence of NaH in THF to give diester 48. Treating compound 48 with ethoxypropylamine and heating in acetic acid gives the cyclic compound 49. The double bond is reduced by catalytic hydrogenation using a palladium on carbon catalyst to give pyrrolidone 50. Epimerization with sodium ethoxide in ethanol to give the desired trans,trans configuration is followed by sodium hydroxide hydrolysis of the ester to afford the desired trans,trans carboxylic acid 51.

Scheme IX illustrates the preparation of compounds where n is 0, Z is —CH$_2$—, and W is other than carboxylic acid. Compound 55, which can be prepared by the procedures described in Scheme IV, is converted (for example, using peptide coupling condition, e.g. N-methylmorpholine, EDCI and HOBt, in the presence of ammonia or other amide forming reactions) to give carboxamide 56. The carboxamide is dehydrated (for example, using phosphorus oxychloride in pyridine) to give nitrile 57. Nitrile 57 under standard tetrazole forming conditions (sodium azide and triethylamine hydrochloride or trimethylsilylazide and tin oxide) is reacted to give tetrazole 58. Alternatively nitrile 57 is reacted with hydroxylamine hydrochloride in the presence of a base (for example, potassium carbonate, sodium carbonate, sodium hydroxide, triethylamine, sodium methoxide or NaH) in a solvent such as DMF, DMSO, or dimethylacetamide to give amidoxime 59. The amidoxime 59 is allowed to react with a methyl or ethyl chloroformate in a conventional organic solvent (such as, chloroform, methylene chloride, dioxane, THF, acetonitrile or pyridine) in the presence of a base (for example, triethylamine, pyridine, potassium carbonate and sodium carbonate) to give an O-acyl compound. Heating of the O-acyl amidoxime in an inert solvent (such as benzene, toluene, xylene, dioxane, THF, dichloroethane, or chloroform and the like) results in cyclization to compound 60. Alternatively reacting the amidoxime 59 with thionyl chloride in an inert solvent (for example, chloroform, dichloromethane, dixoane and THF and the like) affords the oxathiadiazole 61.

Scheme X illustrates the preparation of compounds in which R$_3$ is an acylmethylene group. A carboxylic acid 62 (where R$_4$ is as previously defined herein) is treated with oxalyl chloride in a solution of methylene chloride containing a catalytic amount of N,N-dimethylformamide to give the acid chloride. Treatment of the acid chloride with excess ethereal diazomethane affords a diazoketone, and then treatment with anhydrous HCl in dioxane gives the alpha-chloroketone 63. Pyrrolidine ester 5 where E is lower alkyl or a carboxy protecting group, prepared in Scheme I, is alkylated with the alpha-chloroketone 63 to provide alkylated pyrrolidine 64. Carboxy deprotection (for example, hydrolysis of an alkyl ester using lithium or sodium hydroxide in ethanol-water) gives the alkylated pyrrolidine acid 65.

Scheme XI illustrates the preparation of "reverse amides and sulfonamides". The carboxy protected pyrrolidine 5, prepared in Scheme I, is reacted with a difunctionalized compound X—$R_8$—X where $R_8$ is alkylene and X is a leaving group (for example a halide where Br is preferred) to give N-alkylated compound 66. Treatment of 66 with an amine ($R_{20}NH_2$) affords secondary amine 67. This amine (67) can be reacted with an activated acyl compound (for example, $R_4$—C(O)—Cl) and then carboxy deprotected (for example, hydrolysis of an ester or hydrogenation of a benzyl moiety) to afford amide 68. Alternatively amine 67 can be reacted with an activated sulfonyl compound (for example, $R_6$—S(O)$_2$—Cl) and then carboxy deprotected (for example, hydrolysis of an ester or hydrogenation of a benzyl moiety) to afford sulfonamide 69.

Scheme XII illustrates a method for synthesizing pyrrolidines by an azomethine ylide type [3+2]-cycloaddition to an acrylate. General structures such as compound 70 are known to add to unsaturated esters such as 71 to provide pyrrolidines such as compound 72 (O. Tsuge, S. Kanemasa, K. Matsuda, Chem. Lett. 1131–4 (1983), O. Tsuge, S. Kanemasa, T. Yamada, K. Matsuda, J. Org. Chem. 52 2523–30 (1987), and S. Kanemasa, K. Skamoto, O. Tsuge, Bull. Chem. Soc. Jpn. 62 1960–68 (1989)). A specific example is also shown in Scheme XII. Silylimine 73 is reacted with acrylate 74 in the presence of trimethylsilyl triflate and tetrabutylammonium fluoride to give the desired pyrrolidine 75 as a mixture of isomers. This method can be modified to provide the N-acetamido derivatives directly by reacting 73 and 74 with the appropriate bromoacetamide (for example, dibutyl bromoacetamide) in the presence of tetrabutylammonium iodide and cesium fluoride to give compound 76.

Scheme XIII illustrates a method for producing an enantiomerically pure pyrrolidine 80, which can be further elaborated on the pyrrolidine nitrogen. Intermediate racemic pyrrolidine ester 77 (for example, prepared by the procedure described in Scheme V) is Boc-nitrogen protected (for example, by treatment with Boc$_2$O) and then the ester is hydrolyzed (for example, using sodium or lithium hydroxide in ethanol and water) to give t-butyl carbamoyl pyrrolidine carboxylic acid 78. The carboxylic acid is converted to its (+)-cinchonine salt, which can be recrystallized (for example from ethyl acetate and hexane or chloroform and hexane) to afford the diastereomerically pure salt. This diastereomerically pure salt can be neutralized (for example, with sodium carbonate or citric acid) to afford enantiomerically pure carboxylic acid 79. The pyrrolidine nitrogen can be deprotected (for example, using trifluoroacetic acid) and the ester reformed by the use of ethanolic hydrochloric acid to give salt 80. Alternatively one can use ethanol HCl to cleave the protecting group and form the ester in one step. The pyrrolidine nitrogen can be further elaborated (for example, by treatment with the dibutyl amide of bromoacetamide in acetonitrile in the presence of diisopropylethylamine) to give optically active compound 81. The use of (−)-cinchonine will give the opposite enantiomer.

Scheme XIV describes another procedure for preparation of pyrrolidines. Pyrrolidines may be synthesized by the use of an azomethine ylide cycloaddition to an acrylate derivative as described by Cottrell, I. F., et. al., J. Chem. Soc., Perkin Trans. 1, 5: 1091–97 (1991). Thus, the azomethine ylide precursor 82 (where $R_{55}$ is hydrogen or methyl) is condensed with a substituted acrylate 83 (wherein $R_2$ is as described herein and $R_{56}$ is loweralkyl) under acidic conditions to afford the substituted pyrrolidine 84. The N-protecting group can be removed (for example, by hydrogenolysis of an N-benzyl group) to give 85, which can be alkylated under the conditions described above to provide the N-substituted pyrrolidine 86. Standard ester hydrolysis of 86 produces the desired pyrrolidine carboxylic acid 87.

A preferred process is shown in Scheme XV. Nitro vinyl compound (88) is reacted with beta-keto ester 89 in the presence of a base such as sodium ethoxide and the like or a trialkylamine such as triethylamine or diisopropylethylamine and the like or an amidine such as DBU and the like in an inert solvent such as THF, toluene, DMF, acetonitrile, ethyl acetate, isopropyl acetate or methylene chloride and the like at a temperature of from about 0° C. to about 100° C. for a period of time from about 15 minutes to overnight to give compound 90. Reduction of the nitro group followed by cyclization was effected for example by catalytic hydrogenation with a hydrogen pressure of from about atmospheric pressure to 300 p.s.i. over from about 1 hour to about 1 day of compound 90 in an inert solvent such as THF, ethyl acetate, toluene, ethanol, isopropanol, DMF or acetonitrile and the like, using a hydrogenation catalyst such as Raney nickel, palladium on carbon, a platinum catalyst, such as platinum oxide, platinum on carbon or platinum on alumina and the like, or a rhodium catalyst, such as rhodium on carbon or rhodium on alumina and the like, and the like affords intermediate nitrone 91a or a mixture of nitrone 91a and imine 91b. The reaction mixture comprising the nitrone or nitrone/imine mixture is treated with an acid such as trifluoroacetic acid or acetic acid or sulfuric acid or phosphoric acid or methanesulfonic acid and the like, and the hydrogenation is continued to give pyrrolidine compound 92 as the cis,cis-isomer. Epimerization at C-3 is effected by treatment of compound 92 with a base such as sodium ethoxide, potassium t-butoxide, lithium t-butoxide or potassium t-amyloxide and the like or a trialkylamine such as triethylamine or diisopropylethylamine and the like or an amidine such as DBU and the like in an inert solvent such as ethanol, ethyl acetate, isopropyl acetate, THF, toluene or DMF and the like at a temperature of from about −20° C. to about 120° C. to give the trans,trans compound 93. Compound 93 itself can optionally be resolved into enantiomers prior to reacting with X—$R_3$. The substantially pure (i.e., at least 95% of the desired isomer) optically active (+)-isomer of compound 93 is obtained by treatment of a mixture of the (+)-isomer and the (−)-isomer of 93 with S-(+)-mandelic acid, D-tartaric acid or D-dibenzoyl tartaric acid and the like in a solvent such as acetonitrile, ethyl acetate, isopropyl acetate, ethanol or isopropanol and the like. The (+)-isomer of 93 selectively crystallizes as the salt, leaving the (−)-isomer of 93 in solution. Alternatively, the substantially pure (i.e., at least 95% of the desired isomer) optically active (−)-isomer of compound 93 can be selectively crystallized by reaction of a mixture of the (+)-isomer and the (−)-isomer of 93 with L-tartaric acid, L-dibenzoyl tartaric acid or L-pyroglutamic acid and the like, leaving the desired (+)-isomer of compound 93 in solution.

Compound 93 (racemic or optically active) is reacted with X—$R_3$ (where X is a leaving group (for example, a halide or a sulfonate) and $R_3$ is as previously defined) using a base such as diisopropylethylamine, triethylamine, sodium bicarbonate or potassium carbonate and the like in an inert solvent such as acetonitrile, THF, toluene, DMF or ethanol and the like at a temperature of from about 0° C. to about 100° C. to give the intermediate ester 94. The ester can be isolated or converted in situ to the carboxylic acid (95) using hydrolysis conditions such as a base such as sodium hydroxide or lithium hydroxide or potassium hydroxide and the like in a solvent such as ethanol-water or THF-ethanol and the like.

A more detailed description of the preparation of some specific analogs is provided in Schemes XVI–XXI. Aliphatic alpha-ketoesters (Scheme XVI) may be prepared by copper-catalyzed addition of a Grignard reagent (for example, propylmagnesium bromide) to an unsaturated ester, for example, ethyl 3,3-dimethylacrylate. The resultant ester is hydrolyzed, for example with sodium hydroxide in aqueous alcohol, and is homologated in stepwise fashion to the corresponding alpha-ketoester, for example by activation using carbonyldiimidazole and condensation with magnesio-ethoxymalonate. Alternatively, olefinic alpha-ketoesters may be prepared by Claisen rearrangement of the corresponding allylic alcohols; hydrolysis and homologation as described above produce the desired alpha-ketoester.

N-alkyl,O-alkyl bromohydroxamates are prepared according to Scheme XVII. N-Boc-O-allyl hydroxylamine is alkylated with and alkyl halide, for example using sodium hydride as base; the double bond is selectively reduced, for example using hydrogen and a palladium catalyst. After removal of the Boc protecting group, for example with TFA, the resultant amine is acylated, for example using bromoacetyl bromide.

The alpha-ketoesters described in Scheme XVI may be converted to pyrrolidine derivatives as described in Scheme XVIII. Michael addition onto a nitrostyrene derivative can be catalyzed with base, for example DBU or potassium t-butoxide; the resultant adduct is hydrogenated, for example using Raney Nickel as catalyst, to give an imine, which is reduced further, for example using sodium cyanoborohydride under controlled pH. A mixture of isomers are generated, in which the trans—trans is generally preferred.

Scheme XIX describes several strategies for resolving the racemic pyrrolidines described above. Treatment with a chiral acid, for example (S)-(+)-mandelic acid, may provide a crystalline derivative, which can be further enriched through recrystallization. The salt may be washed with base to extract the resolving agent and return the optically active pyrrolidine product. Alternatively, the amino ester can be N-protected (for example with Boc-anhydride) and hydrolyzed (for example with sodium hydroxide) to give the corresponding N-protected amino acid. Activation of the acid, for example as the pentafluorophenyl ester, followed by coupling with a chiral nonracemic oxazolidinone anion, provides the corresponding acyloxazolidinone diastereomers, which may be separated chromatographically. Alcoholysis of one acyloxazolidinone diastereomer, followed by cleavage of the N-protecting group, returns an optically enriched amino ester. A similar transformation may be accomplished through coupling of the protected amino acid with a chiral nonracemic amino alcohol. After chromatographic separation of the resultant diastereomers, the amide is cleaved and the protecting group is removed to provide optically enriched product.

Optically active amino esters prepared as described above may be alkylated (Scheme XX) with a variety of electrophiles, for example dibutyl bromoacetamide, N-butyl,N-alkoxy bromoacetamide, N-(4-heptyl)-N-(3-methyl-4-fluorophenyl) bromoacetamide, or N-(Ω-hydroxyalkyl)-N-alkyl haloacetamide. Hydrolysis of the resultant ester, for example using sodium hydroxide in aqueous alcohol, provides the product.

For one particular class of electrophile, N-(Ω-hydroxyalkyl)-N-alkyl haloacetamides, further transformations of the alkylation product are possible (Scheme XXI). Activation (for example using methanesulfonyl chloride) of the alcohol, followed by displacement with halogen (for example, using lithium bromide) provides the corresponding halide. Displacement of halide with an amine, for example dimethylamine, provides the corresponding amino ester, which may be hydrolyzed as previously described to provide product.

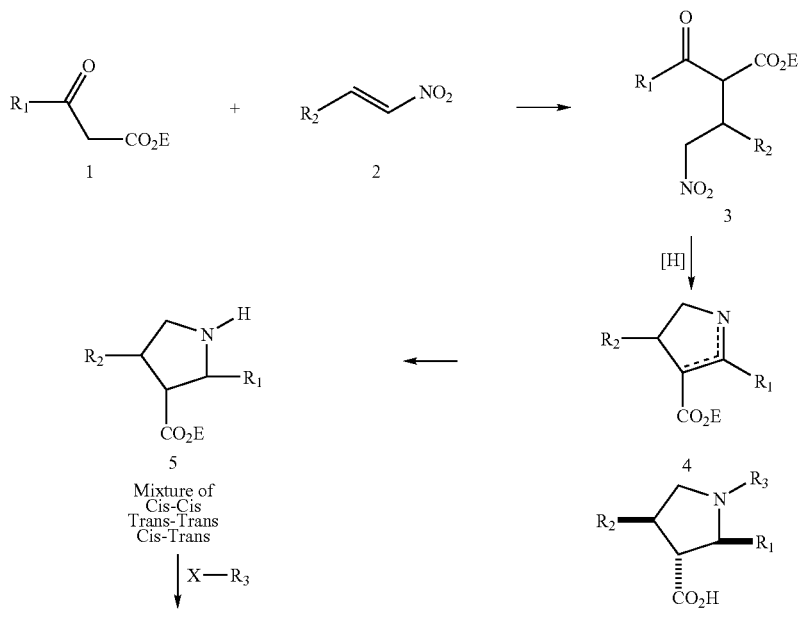

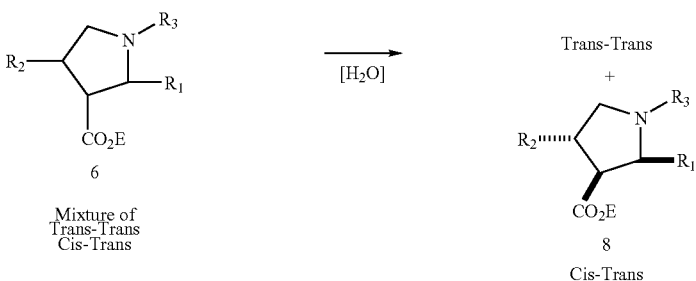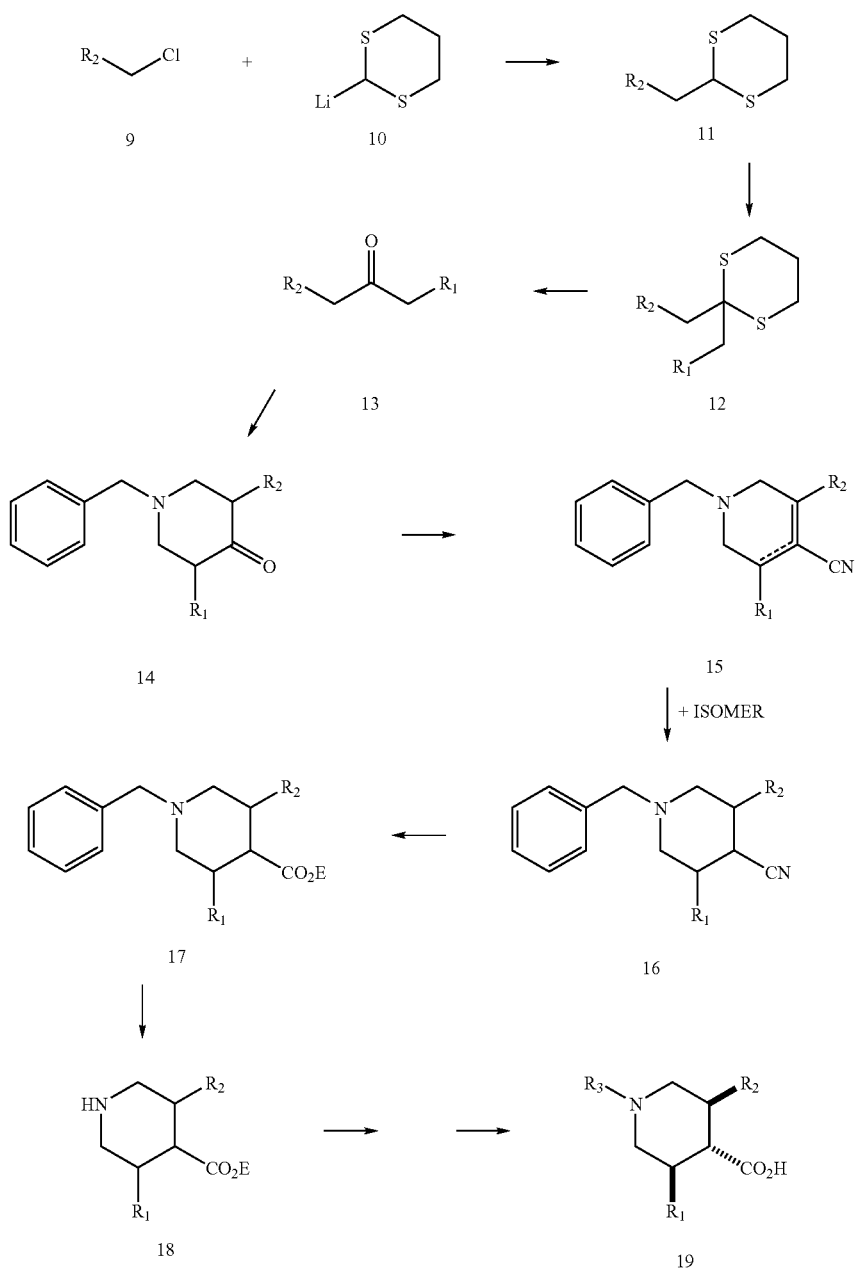

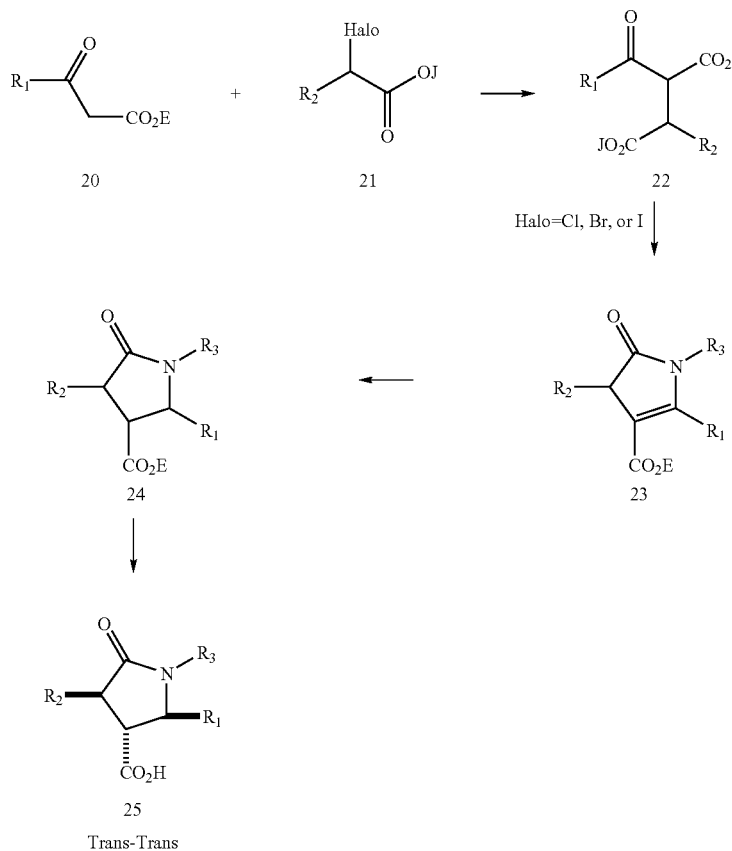
Scheme III
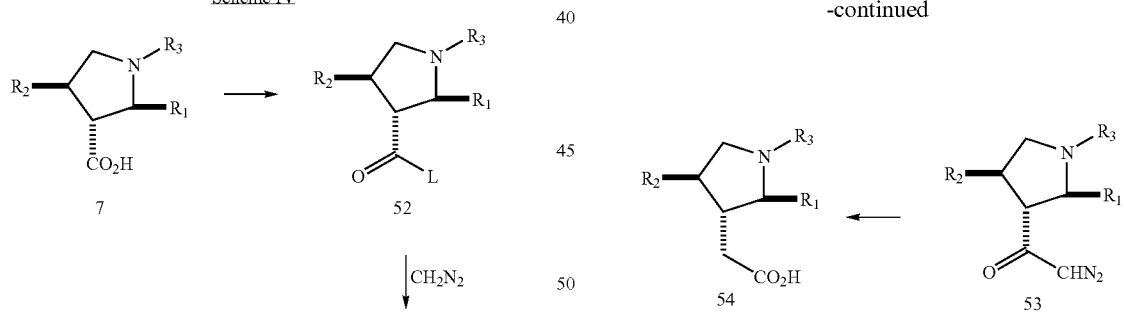
Scheme IV
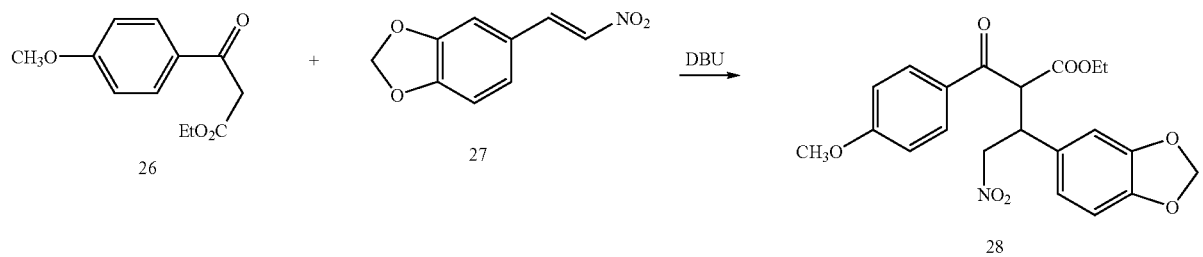
Scheme V

-continued
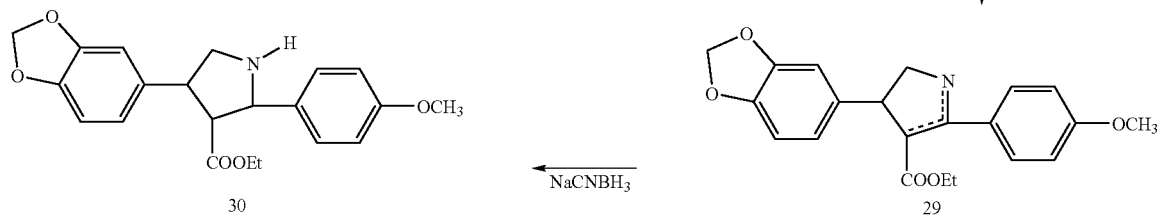
Scheme VI
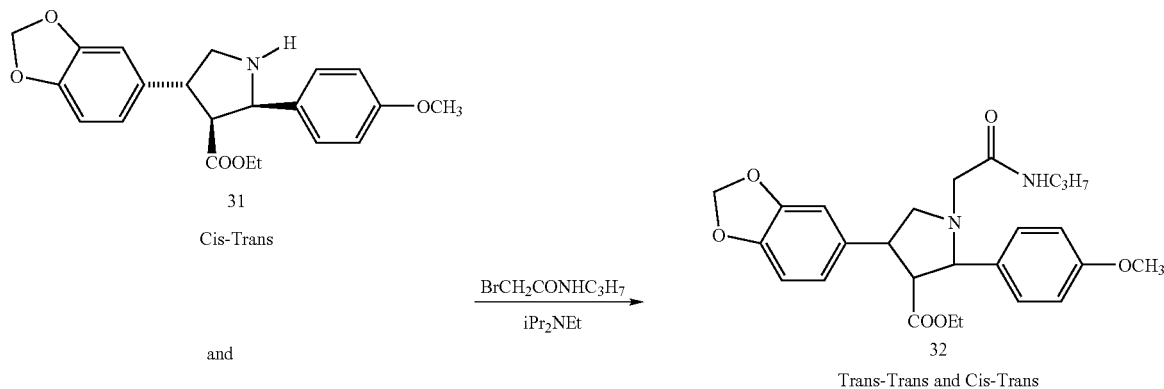
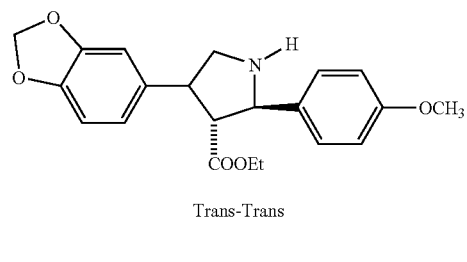
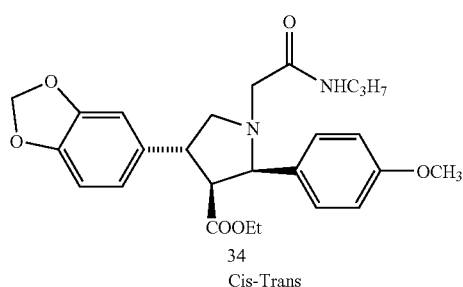

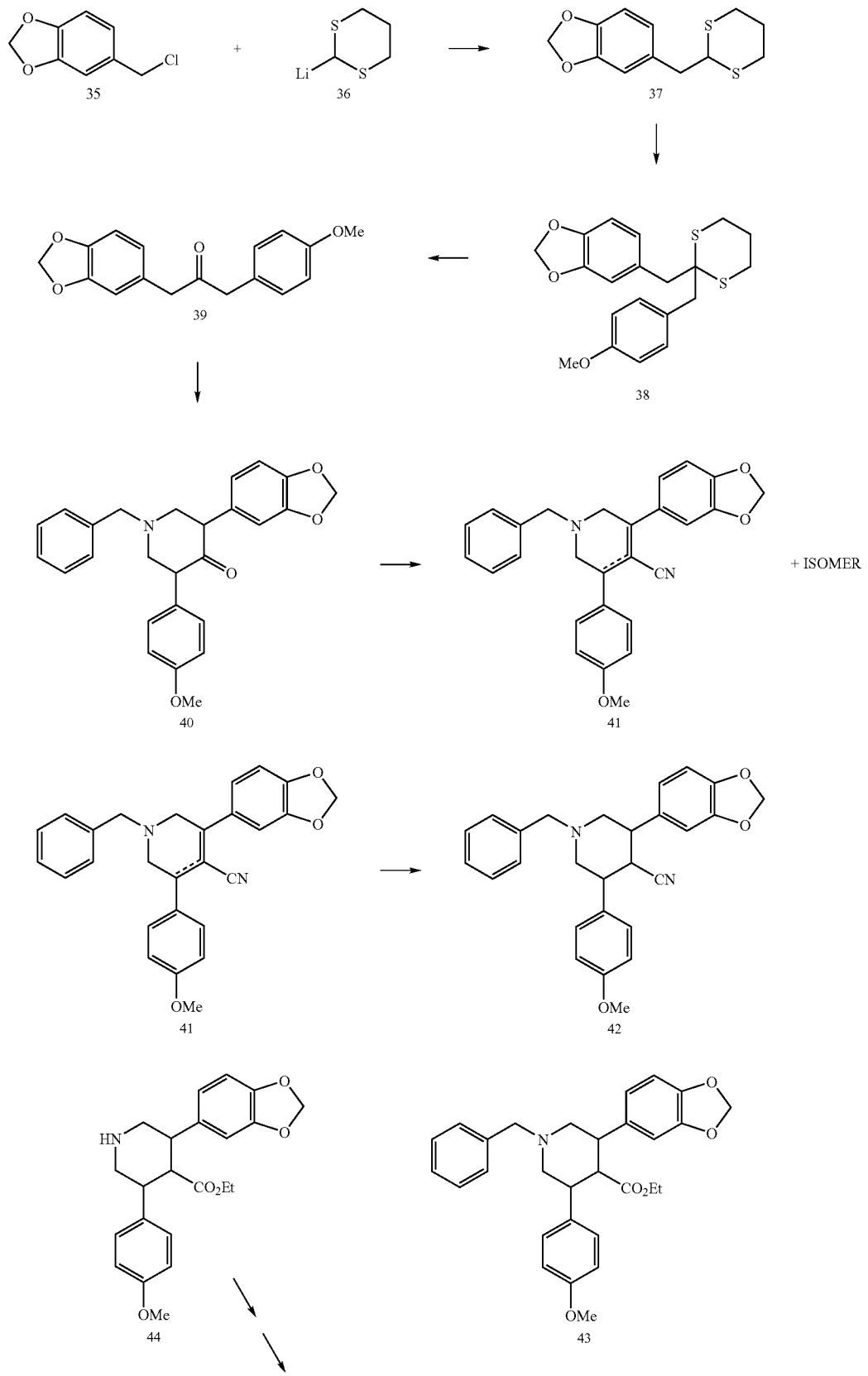
Scheme VII

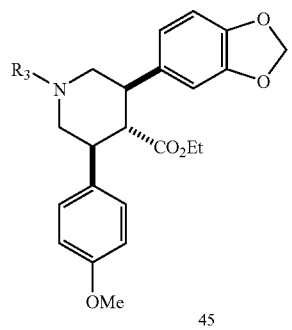
45
Scheme VIII
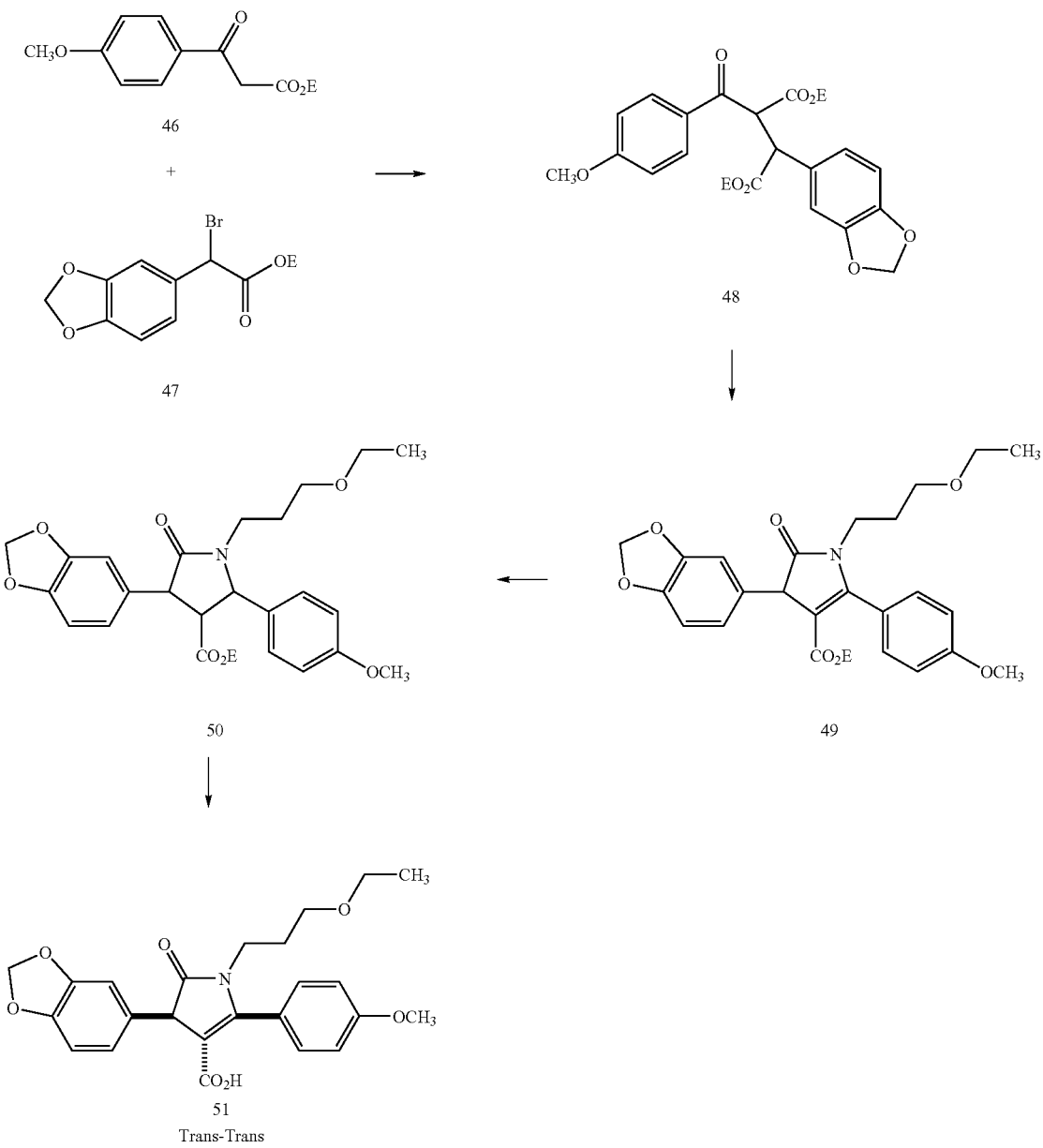
51
Trans-Trans

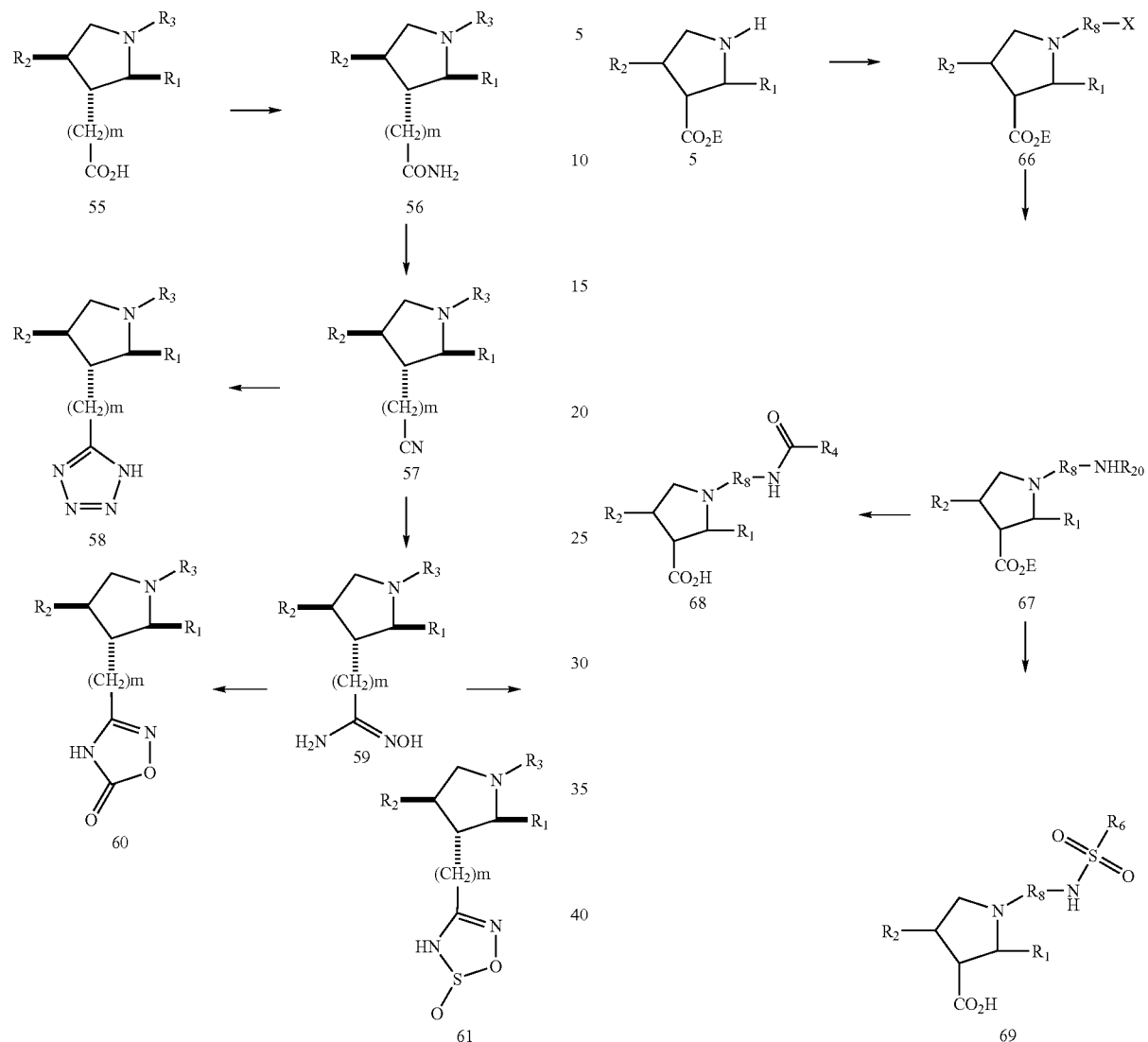

Scheme XII
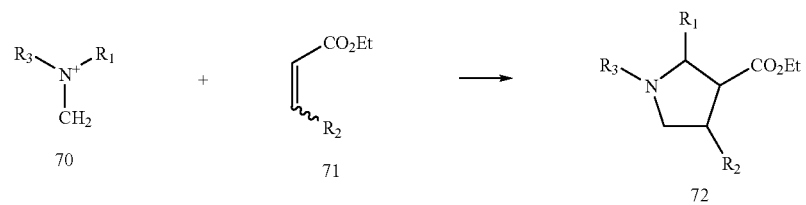
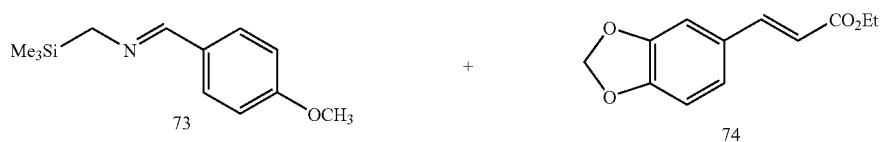
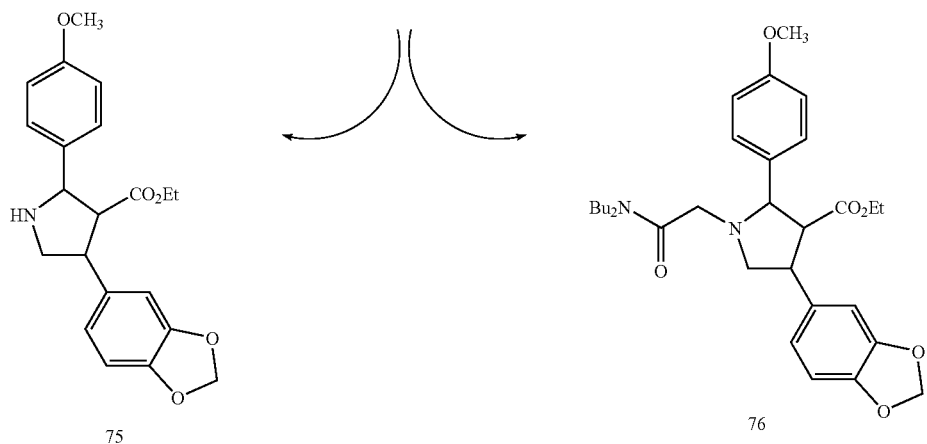
Scheme XIII
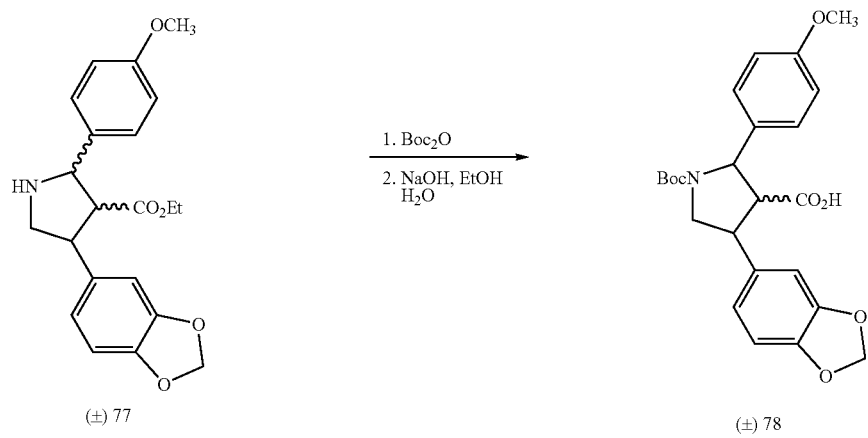

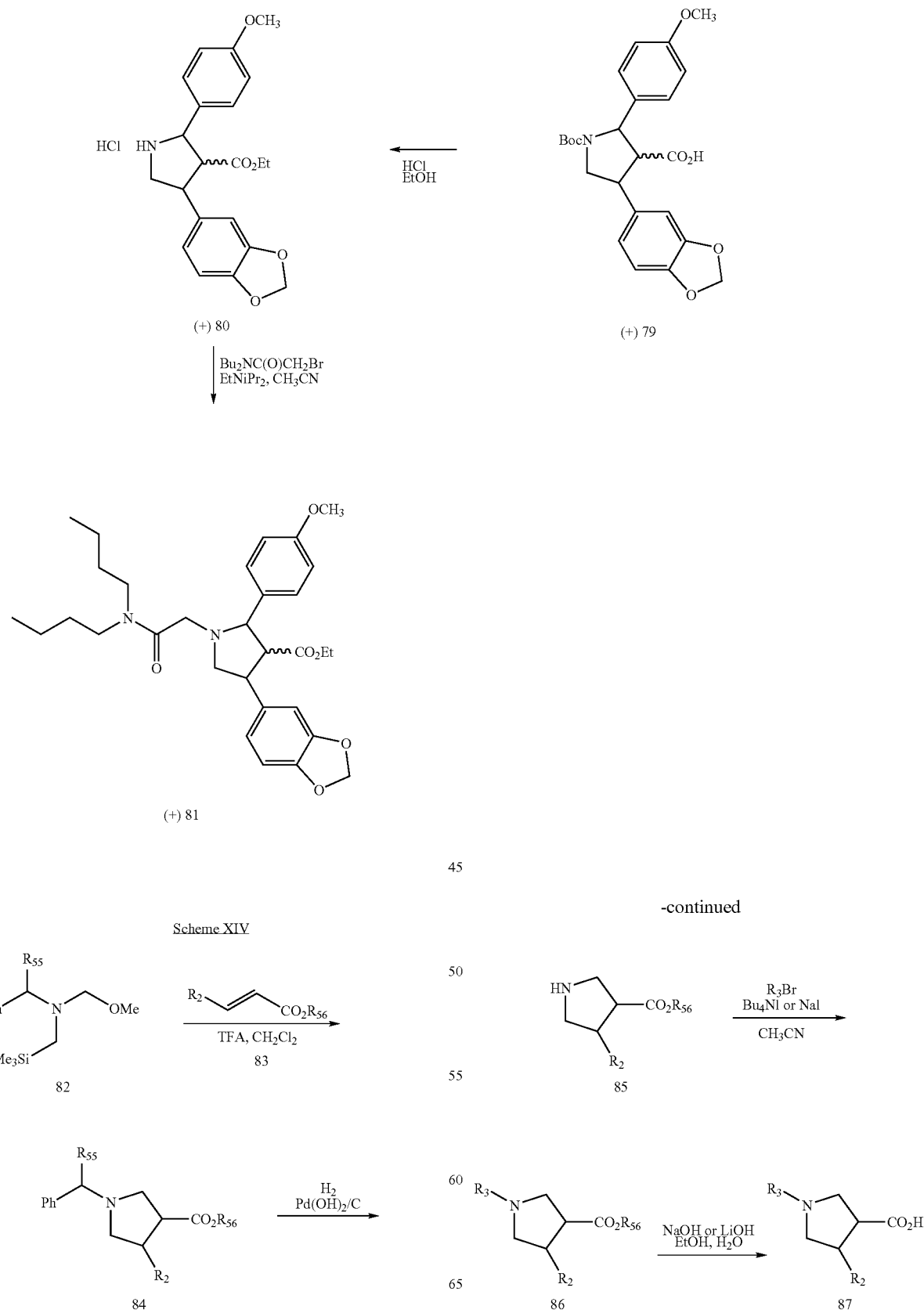

Scheme XV
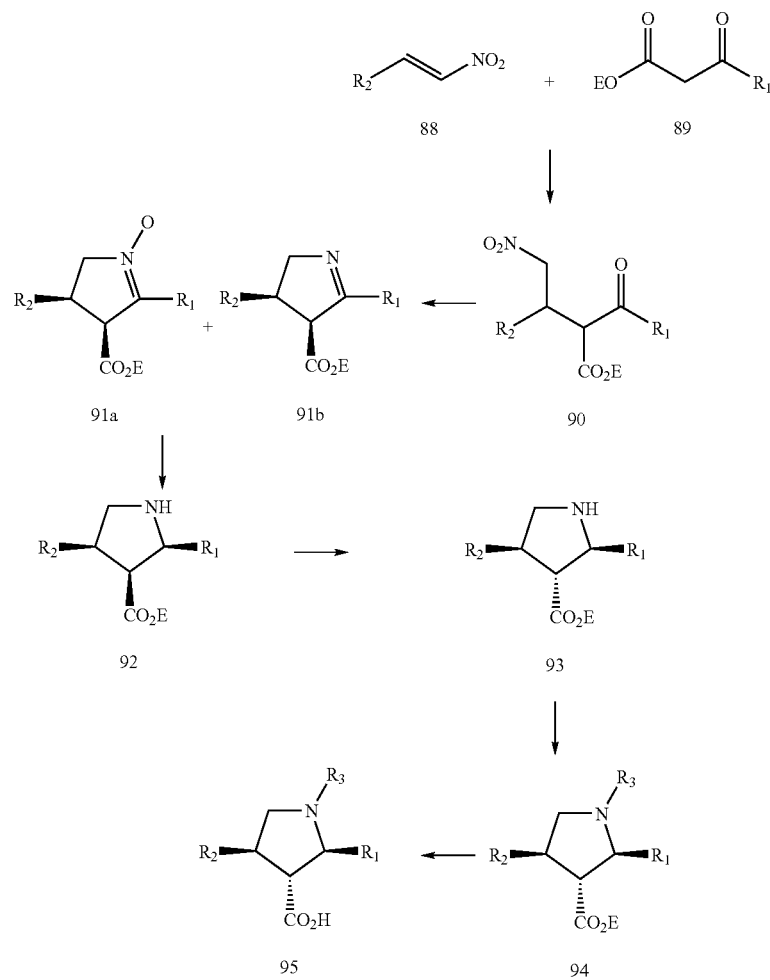
SCHEME XVI
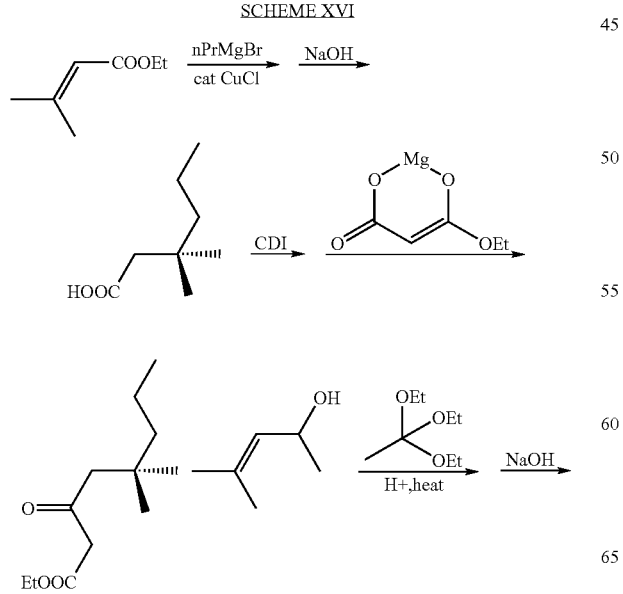
-continued
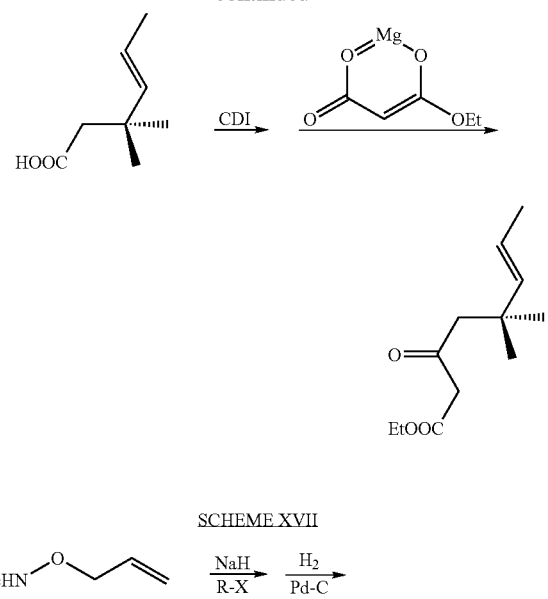
SCHEME XVII

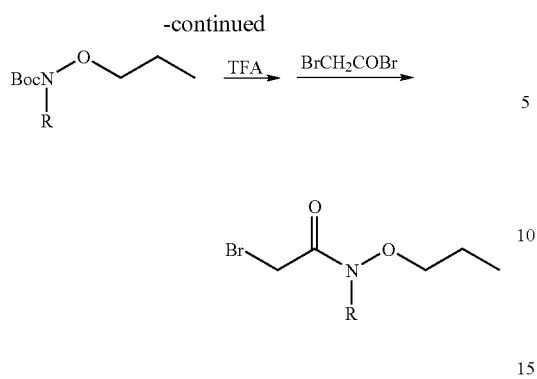
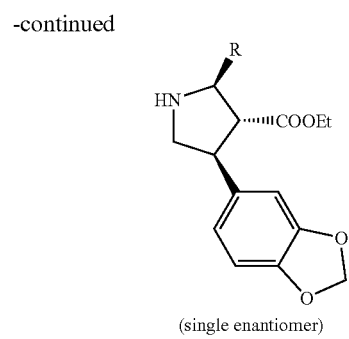
SCHEME XVIII
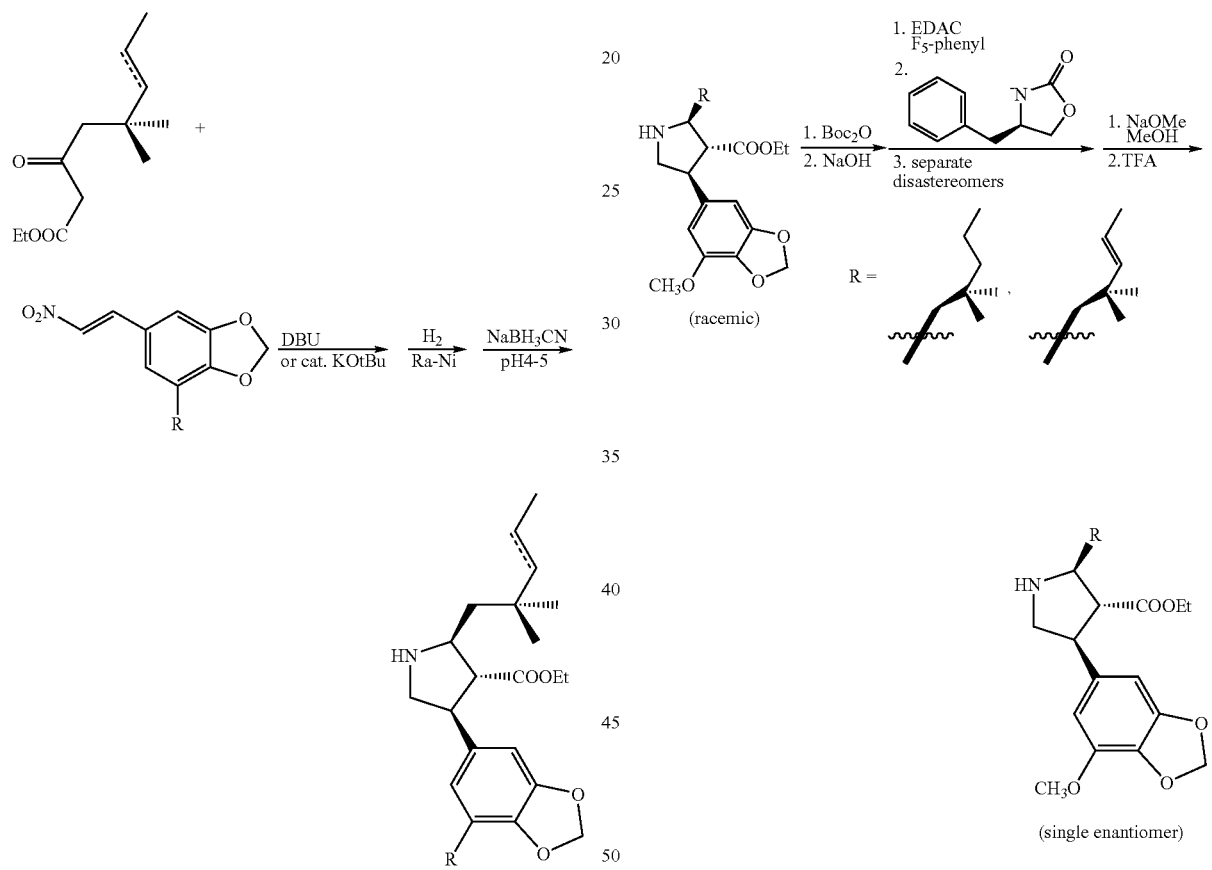
SCHEME XIX
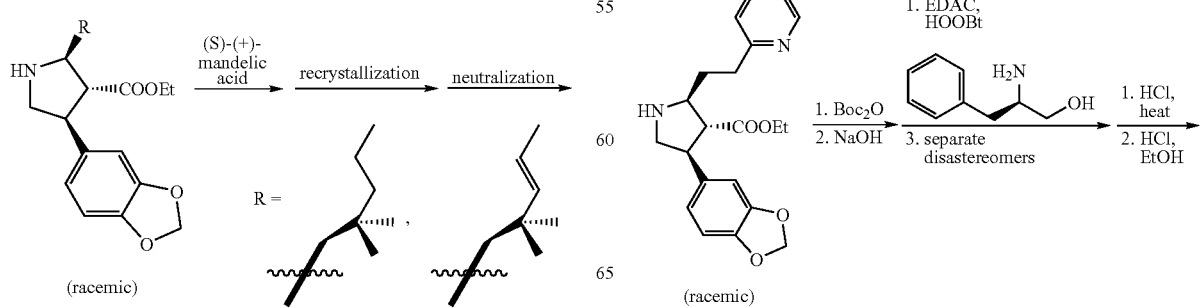

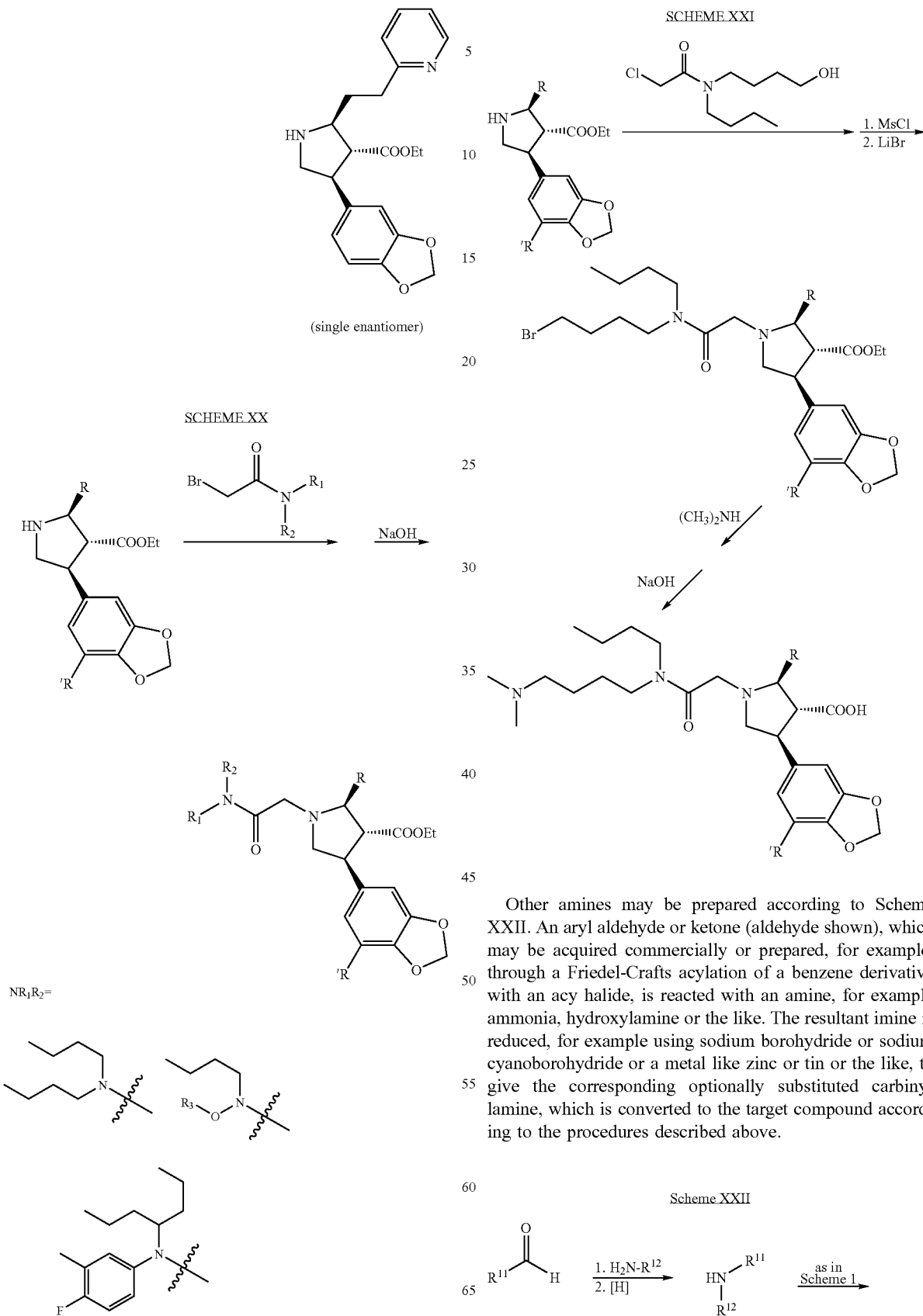

Other amines may be prepared according to Scheme XXII. An aryl aldehyde or ketone (aldehyde shown), which may be acquired commercially or prepared, for example, through a Friedel-Crafts acylation of a benzene derivative with an acy halide, is reacted with an amine, for example ammonia, hydroxylamine or the like. The resultant imine is reduced, for example using sodium borohydride or sodium cyanoborohydride or a metal like zinc or tin or the like, to give the corresponding optionally substituted carbinylamine, which is converted to the target compound according to the procedures described above.

-continued

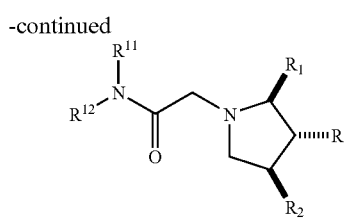

Still other amines may be prepared according to Scheme XXIII. An optionally substituted aryl halide ($R_{11a}$ is the optionally substituted aryl and X is bromo or iodo) is reacted with a metallated amine (for example, lithium tert-butylamide, or sodium benzylamide, or the like) to provide an optionally substituted aniline. This compound is reacted with an oxidized nitrogen compound, for example nitrous acid or the like, and the resultant compound is reduced using a metal like zinc or tin or palladium or the like to provide an N,N-disubstituted hydrazine, which is converted to the target compound according to the procedures described above.

Scheme XXIII

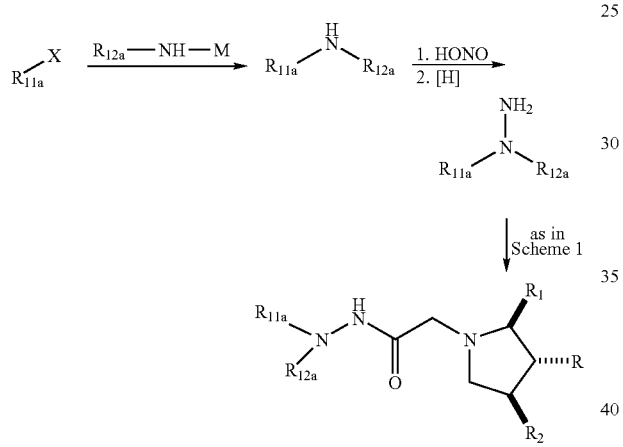

Compounds which are useful as intermediates for the preparation of compounds of the invention are:

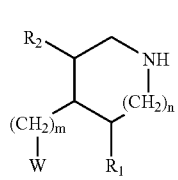

(III)

wherein n is 0 or 1;

m is 0 to 6;

W is (a) —C(O)$_2$-G where G is hydrogen or a carboxy protecting group, (b) —PO$_3$H$_2$,
  (c) —P(O)(OH)E where E is hydrogen, loweralkyl or arylalkyl,
  (d) —CN,
  (e) —C(O)NHR$_{17}$ where R$_{17}$ is loweralkyl,
  (f) alkylaminocarbonyl,
  (g) dialkylaminocarbonyl,
  (h) tetrazolyl,
  (i) hydroxy,
  (j) alkoxy,
  (k) sulfonamido,
  (l) —C(O)NHS(O)$_2$R$_{16}$ where R$_{16}$ is loweralkyl, haloalkyl, phenyl or dialkylamino,
  (m) —S(O)$_2$NHC(O)R$_{16}$,

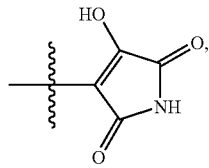
(n)

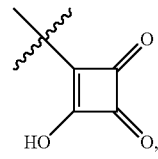
(o)

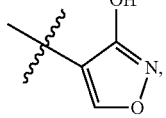
(p)

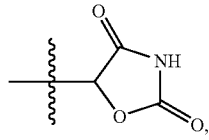
(q)

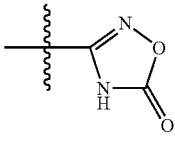
(r)

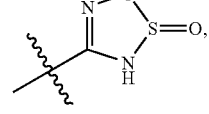
(s)

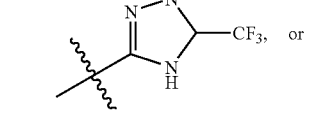
(t)

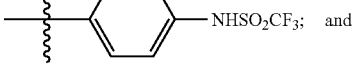
(u)

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonyl alkenyl, alkylaminocarbonylalkenyl, di alkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonyl amidoalkyl, heterocyclic, (heterocyclic)alkyl and ($R_{aa}$)($R_{bb}$)N—$R_{cc}$— wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof;

or a compound of the formula:

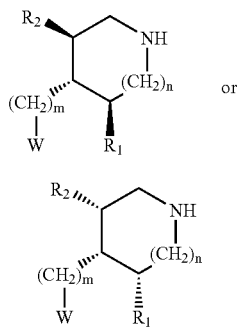

(VII)

or (VIII)

wherein n is 0 or 1;

m is 0 to 6;

W is (a) —C(O)$_2$-G where G is hydrogen or a carboxy protecting group, (b) —PO$_3$H$_2$,
- (c) —P(O)(OH)E where E is hydrogen, loweralkyl or arylalkyl,
- (d) —CN,
- (e) —C(O)NHR$_{17}$ where R$_{17}$ is loweralkyl,
- (f) alkylaminocarbonyl,
- (g) dialkylaminocarbonyl,
- (h) tetrazolyl,
- (i) hydroxy,
- (j) alkoxy,
- (k) sulfonamido,
- (l) —C(O)NHS(O)$_2$R$_{16}$ where R$_{16}$ is loweralkyl, haloalkyl, phenyl or dialkylamino, —S(O)$_2$NHC(O)R$_{16}$, (m)

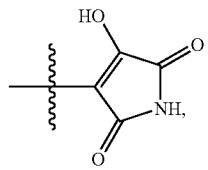 (n)

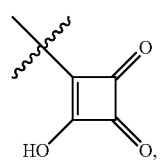 (o)

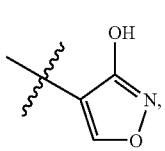 (p)

-continued

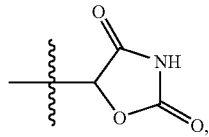 (q)

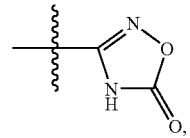 (r)

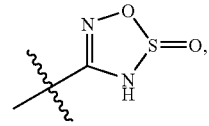 (s)

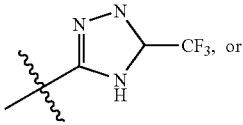 (t)

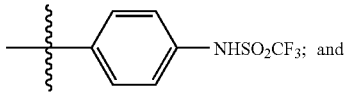 (u)

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and ($R_{aa}$)($R_{bb}$)N—$R_{cc}$— wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen; or a salt thereof.

Preferred intermediates include compounds of formula (III), (IV) and (V) wherein m is zero or 1;

W is —CO$_2$-G wherein G is hydrogen or a carboxy protecting group, and R$_1$ and R$_2$ are as defined above; or the substantially pure (+)- or (−)-isomer thereof.

Particularly preferred intermediates are compounds of formula (III), (IV) and (V) wherein n and m are both 0;

W is —CO$_2$-G wherein G is hydrogen or a carboxy protecting group;

and R$_1$ is (i) loweralkyl, (ii) alkenyl, (iii) alkoxyalkyl, (iv) cycloalkyl, (v) phenyl, (vi) pyridyl, (vii) furanyl or (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy (ix) aryalkyl, (x) aryloxyalkyl, (xi) heterocyclic (alkyl), (xii) (N-alkanoyl-N-alkyl)aminoalkyl, and (xiii) alkylsulfonylamidoalkyl, and $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

Other compounds which are useful as intermediates for the preparation of compounds of the invention are:

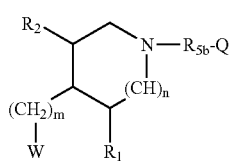
(VI)

wherein n is 0 or 1;

m is 0 to 6;

$R_{5b}$ is alkylene;

Q is a leaving group;

W is (a) —C(O)$_2$-G where G is hydrogen or a carboxy protecting group, (b) —PO$_3$H$_2$,
  (c) —P(O)(OH)E where E is hydrogen, loweralkyl or arylalkyl,
  (d) —CN,
  (e) —C(O)NHR$_{17}$ where R$_{17}$ is loweralkyl,
  (f) alkylaminocarbonyl,
  (g) dialkylaminocarbonyl,
  (h) tetrazolyl,
  (i) hydroxy,
  (j) alkoxy,
  (k) sulfonamido,
  (l) —C(O)NHS(O)$_2$R$_{16}$ where R$_{16}$ is loweralkyl, haloalkyl, phenyl or dialkylamino, —S(O)$_2$NHC(O)R$_{16}$, (m)

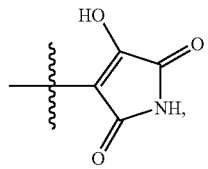
(n)

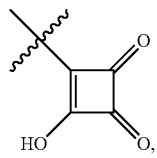
(o)

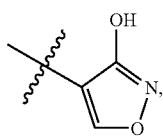
(p)

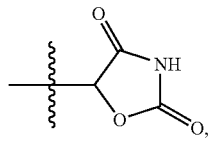
(q)

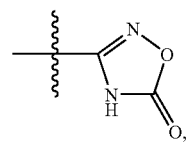
(r)

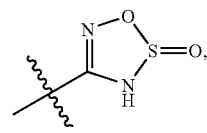
(s)

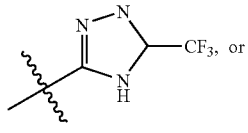
(t)

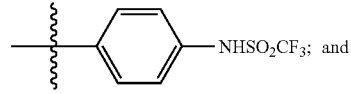
(u)

$R_1$ and $R_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and $(R_{aa})(R_{bb})N—R_{cc}—$ wherein $R_{aa}$ is aryl or arylalkyl, $R_{bb}$ is hydrogen or alkanoyl and $R_{cc}$ is alkylene, with the proviso that one or both of $R_1$ and $R_2$ is other than hydrogen;

or a salt thereof;

or a compound of the formula:

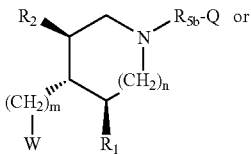
(VII)

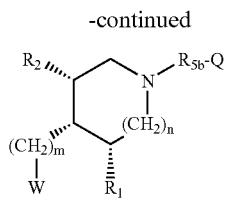
(VIII)

wherein n is 0 or 1;

m is 0 to 6;

$R_{5b}$ is alkylene;

Q is a leaving group;

W is (a) —C(O)$_2$-G where G is hydrogen or a carboxy protecting group, (b) —PO$_3$H$_2$,
- (c) —P(O)(OH)E where E is hydrogen, loweralkyl or arylalkyl,
- (d) —CN,
- (e) —C(O)NHR$_{17}$ where R$_{17}$ is loweralkyl,
- (f) alkylaminocarbonyl,
- (g) dialkylaminocarbonyl,
- (h) tetrazolyl,
- (i) hydroxy,
- (j) alkoxy,
- (k) sulfonamido,
- (l) —C(O)NHS(O)$_2$R$_{16}$ where R$_{16}$ is loweralkyl, haloalkyl, phenyl or dialkylamino, —S(O)$_2$NHC(O)R$_{16}$, (m)

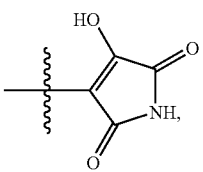 (n)

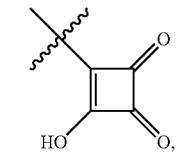 (o)

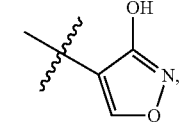 (p)

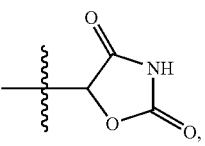 (q)

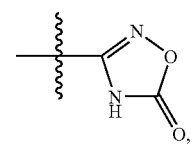 (r)

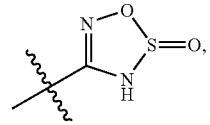 (s)

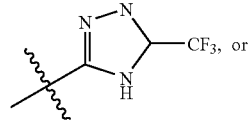 (t)

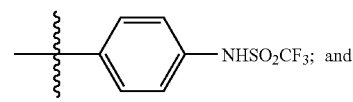 (u)

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and (R$_{aa}$)(R$_{bb}$)N—R$_{cc}$— wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

or a salt thereof.

Preferred intermediates include compounds of formula (VI), (VII) and (VIII) wherein m is zero or 1;

$R_{5b}$ is alkylene;

Q is a leaving group;

W is —CO$_2$-G wherein G is hydrogen or a carboxy protecting group, and R$_1$ and R$_2$ are as defined above; or the substantially pure (+)- or (−)-isomer thereof.

Particularly preferred intermediates are compounds of formula (VI), (VII) and (VIII) wherein n and m are both 0;

$R_{5b}$ is alkylene;

Q is a leaving group;

W is —CO$_2$-G wherein G is hydrogen or a carboxy protecting group;

and R$_1$ is (i) loweralkyl, (ii) alkenyl, (iii) alkoxyalkyl, (iv) cycloalkyl, (v) phenyl, (vi) pyridyl, (vii) furanyl or (viii) substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, (ix) arylalkyl, (x) aryloxyalkyl, (xi) heterocyclic (alkyl), (xii) (N-alkanoyl-N-alkyl)aminoalkyl, and (xiii) alkylsulfonylamidoalkyl, and R₂ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

Other compounds which are useful as intermediates for the preparation of compounds of the invention are:

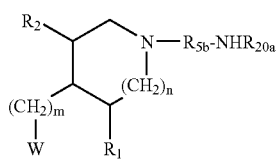

(IX)

wherein n is 0 or 1;

m is 0 to 6;

$R_{5b}$ is alkylene;

$R_{20a}$ is hydrogen, loweralkyl, alkenyl, haloalkyl, alkoxyalkyl, haloalkoxyalkyl, cycloalkyl, cycloalkylalkyl, aryl or arylalkyl;

W is (a) —C(O)₂-G where G is hydrogen or a carboxy protecting group, (b) —PO₃H₂,
 (c) —P(O)(OH)E where E is hydrogen, loweralkyl or arylalkyl,
 (d) —CN,
 (e) —C(O)NHR₁₇ where R₁₇ is loweralkyl,
 (f) alkylaminocarbonyl,
 (g) dialkylaminocarbonyl,
 (h) tetrazolyl,
 (i) hydroxy,
 (j) alkoxy,
 (k) sulfonamido,
 (l) —C(O)NHS(O)₂R₁₆ where R₁₆ is loweralkyl, haloalkyl, phenyl or dialkylamino, —S(O)₂NHC(O)R₁₆, (m)

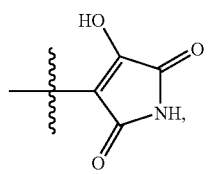

(n)

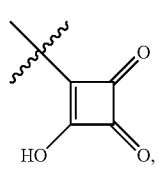

(o)

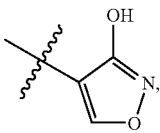

(p)

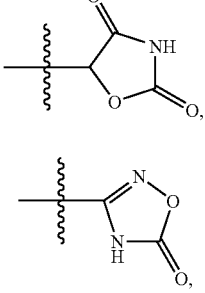

(q)

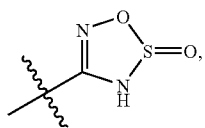

(r)

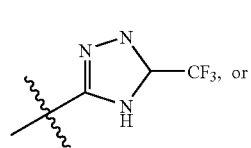

(s)

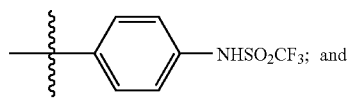

(t)

—NHSO₂CF₃; and (u)

R₁ and R₂ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and (R_{aa})(R_{bb})N—R_{cc}— wherein R_{aa} is aryl or arylalkyl, R_{bb} is hydrogen or alkanoyl and R_{cc} is alkylene, with the proviso that one or both of R₁ and R₂ is other than hydrogen;

or a salt thereof;

or a compound of the formula:

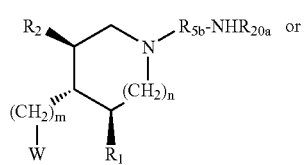

(X)

(XI)

$$\text{structure with } R_2, R_{5b}\text{-NHR}_{20a}, (CH_2)_m, (CH_2)_n, W, R_1 \text{ on piperidine ring}$$

wherein n is 0 or 1;

m is 0 to 6;

$R_{5b}$ is alkylene;

$R_{20a}$ is hydrogen, loweralkyl, alkenyl, haloalkyl, alkoxyalkyl, haloalkoxyalkyl, cycloalkyl, cycloalkylalkyl, aryl or arylalkyl;

W is (a) —C(O)$_2$-G where G is hydrogen or a carboxy protecting group, (b) —PO$_3$H$_2$, (c) —P(O)(OH)E where E is hydrogen, loweralkyl or arylalkyl, (d) —CN, (e) —C(O)NHR$_{17}$ where R$_{17}$ is loweralkyl, (f) alkylaminocarbonyl, (g) dialkylaminocarbonyl, (h) tetrazolyl, (i) hydroxy, (j) alkoxy, (k) sulfonamido, (l) —C(O)NHS(O)$_2$R$_{16}$ where R$_{16}$ is loweralkyl, haloalkyl, phenyl or dialkylamino, (m) —S(O)$_2$NHC(O)R$_{16}$, (n) hydroxy-maleimide group, (o) hydroxy-cyclobutenedione group, (p) hydroxy-isoxazole group, (q) oxazolidinedione group, (r) oxadiazolone group, (s) oxathiadiazole S-oxide group, (t) triazoline-CF$_3$ group, or (u) —C$_6$H$_4$—NHSO$_2$CF$_3$; and R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulfonylamidoalkyl, heterocyclic, (heterocyclic)alkyl and (R$_{aa}$)(R$_{bb}$)N—R$_{cc}$— wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

or a salt thereof.

Preferred intermediates include compounds of formula (IX), (X) and (XI) wherein m is zero or 1;

R$_{5b}$ is alkylene;

R$_{20a}$ is hydrogen, loweralkyl, alkenyl, haloalkyl, alkoxyalkyl, haloalkoxyalkyl, cycloalkyl, cycloalkylalkyl, aryl or arylalkyl;

W is —CO$_2$-G wherein G is hydrogen or a carboxy protecting group, and R$_1$ and R$_2$ are as defined above; or the substantially pure (+)- or (−)-isomer thereof.

Particularly preferred intermediates are compounds of formula (IX), (X) and (XI) wherein n and m are both 0;

R$_{5b}$ is alkylene;

R$_{20a}$ is hydrogen, loweralkyl, alkenyl, haloalkyl, alkoxyalkyl, haloalkoxyalkyl, cycloalkyl, cycloalkylalkyl, aryl or arylalkyl;

W is —CO$_2$-G wherein G is hydrogen or a carboxy protecting group;

and R$_1$ is (i) loweralkyl, (ii) alkenyl, (iii) alkoxyalkyl, (iv) cycloalkyl, (v) phenyl, (vi) pyridyl, (vii) furanyl or (viii)

substituted or unsubstituted 4-methoxyphenyl, 4-fluorophenyl, 3-fluorophenyl, 4-ethoxyphenyl, 4-ethylphenyl, 4-methylphenyl, 4-trifluoromethylphenyl, 4-pentafluoroethylphenyl, 3-fluoro-4-methoxyphenyl, 3-fluoro-4-ethoxyphenyl, 2-fluorophenyl, 4-methoxymethoxyphenyl, 4-hydroxyphenyl, 4-t-butylphenyl, 1,3-benzodioxolyl, 1,4-benzodioxanyl or dihydrobenzofuranyl wherein the substituent is selected from loweralkyl, haloalkyl, alkoxy, alkoxyalkoxy and carboxyalkoxy, (ix) aryalkyl, (x) aryloxyalkyl, (xi) heterocyclic (alkyl), (xii) (N-alkanoyl-N-alkyl)aminoalkyl, and (xiii) alkylsulfonylamidoalkyl, and $R_2$ is substituted or unsubstituted 1,3-benzodioxolyl, 7-methoxy-1,3-benzodioxolyl, 1,4-benzodioxanyl, 8-methoxy-1,4-benzodioxanyl, dihydrobenzofuranyl, benzofurnayl, 4-methoxyphenyl, dimethoxyphenyl, fluorophenyl or difluorophenyl wherein the substituent is selected from loweralkyl, alkoxy and halogen; or the substantially pure (+)- or (−)-isomer thereof.

The foregoing may be better understood by reference to the following examples which are provided for illustration and not intended to limit the scope of the inventive concept. The following abbreviations are used: Boc for tert-butyloxycarbonyl, Cbz for benzyloxycarbonyl, DBU for 1,8-diazabicyclo[5.4.0]undec-7-ene, EDCI for 1-(3-dimethylaminopropyl-3-ethylcarbodiimide hydrochloride, EtOAc for ethyl acetate, EtOH for ethanol, HOBt for 1-hydroxybenzotriazole, $Et_3N$ for triethylamine, TFA for trifluoroacetic acid and THF for tetrahydrofuran.

EXAMPLE 1 trans,trans-2-(4-Methoxyphenyl)-4-(1,3-benzodioxol-5-yl)-1-(propylaminocarbonylmethyl)-pyrrolidine-3-carboxylic acid

EXAMPLE 1A

Ethyl 2-(4-methoxybenzoyl)-4-nitromethyl-3-(1,3-benzodioxole-5-yl)butyrate

To ethyl (4-methoxybenzoyl)acetate (23.0 g, 0.104 mol), prepared by the method of Krapcho et al., Org. Syn. 47, 20 (1967), and 5-(2-nitrovinyl)-1,3-benzodioxole (17.0 g, 0.088 mol) dissolved in 180 mL of toluene and heated to 80° C. was added 1,8-diazabicyclo[5,4,0]undec-7-ene (DBU, 0.65 g) with stirring. The mixture was heated until all the nitro starting material dissolved. The solution was stirred without heating for 30 minutes (min) and then an additional 0.65 g of DBU was added. After stirring an additional 45 minutes, thin layer chromatography (5% ethyl acetate in methylene chloride) indicated the absence of nitro starting material. Toluene (200 mL) was added, and the organic phase was washed with dilute hydrochloric acid and NaCl solution. The organic phase was dried over sodium sulfate and then concentrated under reduced pressure. The residue obtained was chromatographed on silica gel eluting with 3:1 hexane-ethyl acetate to give 21.22 g of the desired product as a mixture of isomers and 9.98 g. of recovered ethyl (4-methoxybenzoyl)acetate.

EXAMPLE 1B

Ethyl 2-(4-methoxyphenyl)-4-(1,3-benzodioxol-5-yl)-4,5-dihydro-3H-pyrrole-3-carboxylate The compound resulting from Example 1A (21 g) in 500 mL of ethanol was hydrogenated under 4 atmospheres of hydrogen pressure using a Raney nickel 2800 catalyst (51 g). (The Raney nickel was washed with ethanol three times before use.) The catalyst was removed by filtration, and the solution was concentrated under reduced pressure. The residue obtained was chromatographed on silica gel eluting with 8.5% ethyl acetate in methylene chloride to give 12.34 g of the desired product.

EXAMPLE 1C

Ethyl 2-(4-methoxyphenyl-4-(1,3-benzodioxol-5-yl)-pyrrolidine-3-carboxylate) as a Mixture of cis—cis; trans,trans; and cis,trans-isomers The compound resulting from Example 1B (11.89 g, 0.324 mol) was dissolved in 27 mL of tetrahydrofuran and 54 mL of ethanol. Sodium cyanoborohydride (2.35 g, 0.374 mol) and 5 mg bromocresol green were added. To this blue solution was added dropwise a solution of 1:2 concentrated HCl in ethanol at such a rate that the color was kept at light yellow-green. After the yellow color persisted without additional HCl, the solution was stirred an additional 20 minutes. The solution was concentrated in vacuo and then partitioned between chloroform and an aqueous potassium bicarbonate solution. The organic phase was separated, dried over sodium sulfate, and concentrated under reduced pressure. The residue was chromatographed on silica gel eluting with 85:15 ethyl acetate-hexane to give 5.96 g. of a mixture of 64% trans,trans-compound and 34% cis,trans-compound. Further elution with pure ethyl acetate gave 0.505 g of an unknown solid followed by 3.044 g of pure cis,cis-compound.

EXAMPLE 1D trans,trans-2-(4-Methoxyphenyl)-4-(1,3-benzodioxol-5-yl)-1-(propylaminocarbonylmethyl)-pyrrolidine-3-carboxylic acid The mixture of 64% trans,trans- and 34% cis,trans-pyrrolidines (the mixture resulting from Example 1C) (5.72 g, 15.50 mmol), ethyldiisopropylamine (4.20 g, 32.56 mmol), and N-propyl bromoacetamide (3.42 g, 19.0 mmol), prepared by the method of Weaver, W. E. and Whaley, W. M., J. Amer. Chem. Soc., 69: 515 (1947), in 30 mL of acetonitrile was heated at 50° C. for 1 hour. The solution was concentrated in vacuo. The residue was dissolved in toluene, shaken with potassium bicarbonate solution, dried over sodium sulfate and concentrated in vacuo to give 7.16 g of product as a mixture of trans,trans- and cis,trans-ethyl esters.

This mixture was dissolved in a solution of 50 mL of ethanol and 15 mL of water containing 5.00 g of sodium hydroxide and stirred for 3 hours at room temperature. The solution was concentrated in vacuo and 60 mL of water added. The mixture was extracted with ether to remove the unreacted cis,trans-ethyl ester. The aqueous phase was treated with hydrochloric acid until slightly cloudy. It was then further neutralized with acetic acid to give the crude acid product. The crude product was filtered and purified by dissolving it in tetrahydrofuran, drying over sodium sulfate, concentrating in vacuo, and crystallizing from ether to give 3.230 g of the title compound. m.p. 151–153° C. $^1H$ NMR ($CD_3OD$, 300 MHz) δ 0.87 (t, J=7 Hz, 3H), 1.49 (sextet, J=7 Hz, 2H), 2.84 (d, J=16 Hz, 1H), 2.95–3.20 (m, 4H), 3.20 (d, J=16 Hz, 1H), 3.34–3.42 (m, 1H), 3.58–3.66 (m, 1H), 3.78 (s, 3H), 3.88 (d, J=10 Hz, 1H), 5.92 (s, 2H), 6.75 (d, J=8 Hz, 1H), 6.86 (dd, J=8 Hz, J=Hz, 1H), 6.90 (d, J=9 Hz, 2H), 7.02 (d, J=1 Hz, 1H), 7.40 (d, J=9 Hz, 2H).

EXAMPLE 2 trans,trans-2-(4-Methoxyphenyl)-4-(1,3-benzodioxol-5-yl)-1-(aminocarbonylmethyl)-pyrrolidine-3-carboxylic acid Using the method described in Example 1D, 300 mg of the mixture of 64% trans,trans- and 34% cis,trans-pyrrolidines (the mixture resulting from Example 1C), 220 mg of diisopropylethylamine and 184 mg iodoacetamide were reacted at 45° C. in 1 mL acetonitrile to give 291 mg of a mixture of trans,trans- and cis,trans-N-alkylated esters. A portion (270 mg.) was hydrolyzed with 200 mg NaOH in 1 mL of water and 3 mL of ethanol; a chloroform extraction was used to remove the unreacted cis,trans-ethyl ester. The isolation and purification procedures described in Example 1D were used to give 134 mg of the title compound. m.p. 246–248° C. $^1$H NMR (DMSO-$d_6$, 300 MHz) δ 2.61 (d, J=16 Hz, 1H), 2.71 (t, J=9 Hz, 1H), 2.90 (t, J=9 Hz, 1H), 2.98 (d, J=16 Hz, 1H), 3.25–3.35 (m, 1H), 3.45–3.55 (m, 1H), 3.71 (s, 3H), 3.75 (d, J=10 Hz, 1H), 6.00 (s, 2H), 6.81 (s, 2H), 6.90 (d, J=8 Hz, 2H), 7.10 (s, 1H), 7.17 (s, 1H), 7.34 (s, 1H), 7.38 (d, J=8 Hz, 2H).

EXAMPLE 3 trans,trans-2-(4-Methoxyphenyl)-4-(1,3-benzodioxol-5-yl)-1-(4-fluorobenzyl)-pyrrolidine-3-carboxylic acid Using the method described in Example 1D, 300 mg of the mixture of 64% trans,trans- and 34% cis,trans-pyrrolidines (the mixture resulting from Example 1C), 220 mg of diisopropylethylamine and 185 mg of 4-fluorobenzyl bromide were reacted at room temperature for 3 hours in 1 mL of acetonitrile to give 387 mg of a mixture of trans,trans- and cis,trans-N-alkylated esters. A portion (360 mg) was hydrolyzed with 250 mg NaOH in 1 mL of water and 4 mL of ethanol to give 160 mg of the title compound as an amorphous powder. $^1$H NMR (CDCl$_3$, 300 MHz) δ 2.74 (t, J=9 Hz, 1H), 2.95 (t, J=7 Hz, 1H), 2.98 (d, J=14, 1H), 3.07 (dd, J=9 Hz, 1 Hz, 1H), 3.42–3.53 (m, 1H), 3.70 (d, J=9 Hz, 1H), 3.78 (d, J=14, 1H), 3.81 (s, 3H), 5.92 (s, 2H), 6.70 (d, J=8 Hz, 1H), 6.77 (dd, J=8 Hz, 1 Hz, 1H), 6.91 (d, J=9 Hz, 2H), 6.94–7.00 (m, 3H), 7.20–7.25 (M, 1H), 7.44 (d, J=9 Hz, 2H).

EXAMPLE 4 trans,trans-2-(4-Methoxyphenyl)-4-(1,3-benzodioxol-5-yl)-1-(2-ethoxyethyl)-pyrrolidine-3-carboxylic acid Using the method described in Example 1D, 300 mg. of the mixture of 64% trans,trans- and 34% cis,trans-pyrrolidines (the mixture resulting from Example 1C), 220 mg of diisopropylethylamine and 152 mg of 2-bromoethyl ethyl ether were refluxed in 1.5 mL acetonitrile for 3 hours (bath temperature at 95° C.) to give 346 mg of a mixture of trans,trans- and cis, trans-esters. Hydrolysis with 250 mg NaOH in 1 mL of water and 3 mL of ethanol afforded 140 mg of the title compound. m.p. 88–90° C. $^1$H NMR (CDCl$_3$, 300 MHz) δ 1.25 (t, J=7 Hz, 3H), 2.21–2.32 (m, 1H), 2.70–2.80 (m, 1H), 2.85–2.94 (m, 2H), 3.38–3.55 (m, 6H), 3.67 (d, J=10 Hz, 1H), 3.79 (s, 3H), 5.94 (s, 2H), 6.72 (d, J=8 Hz, 1H), 6.84 (m, 1H), 6.84 (d, J=9 Hz, 2H), 7.08 (d, J=1 Hz, 1H), 7.33 (d, J=9 Hz, 2H).

EXAMPLE 5 trans,trans-2-(4-Methoxyphenyl)-4-(1,3-benzodioxol-5-yl)-1-(2-propoxyethyl)-pyrrolidine-3-carboxylic acid Using the method described in Example 1D, 520 mg of the mixture resulting from Example 1C, 364 mg of diisopropylethylamine, 50 mg potassium iodide and 350 mg 2-chloroethyl propyl ether were reacted at 125° C. in 0.5 mL acetonitrile for 4 hours to give 517 mg of a mixture of trans,trans- and cis,trans-esters. A portion (500 mg) was hydrolyzed with 315 mg NaOH in 1 mL of water and 4 mL of ethanol to give 225 mg of the title compound as an amorphous powder. $^1$H NMR (CDCl$_3$, 300 MHz) δ 0.87 (t, J=7 Hz, 3H), 1.53 (sextet, J=7 Hz, 2H), 2.28–2.41 (m, 1H), 2.71–2.83 (m, 1H), 2.92–3.08 (m, 2H), 3.30 (t, J=7 Hz, 2H), 3.40–3.60 (m, 4H), 3.72–3.83 (m, 1H), 3.76 (s, 3H), 5.92 (s, 2H), 6.71 (d, J=8 Hz, 2H), 6.74 (dd, J=8 Hz, 1 Hz), 6.71 (d, J=9 Hz, 2H), 7.07 (d, J=9 Hz, 2H), 7.73 (d, J=9 Hz, 2H).

EXAMPLE 6 trans,trans-2-(4-Methoxyphenyl)-4-(1,3-benzodioxol-5-yl)-1-[2-(2-methoxyethoxy)ethyl]-pyrrolidine-3-carboxylic acid

EXAMPLE 6A

Ethyl trans,trans-2-(4-methoxyphenyl)-4-(1,3-benzodioxol-5-yl) pyrrolidine-3-carboxylate To the pure cis,cis-compound resulting from Example 1C (3.02 g) dissolved in 10 mL of ethanol was added 20 drops of a solution of 21% sodium ethoxide in ethanol. The reaction mixture was refluxed overnight, at which time thin layer chromatography in ethyl acetate indicated the absence of starting material. The NaOEt was neutralized with HCl in ethanol, and the solution was concentrated in vacuo. The residue was taken up in toluene and extracted with potassium bicarbonate in water. The toluene was dried over sodium sulfate and concentrated under reduced pressure to give 2.775 of the title compound which was pure by TLC (ethyl acetate).

EXAMPLE 6B trans,trans-2-(4-Methoxyphenyl)-4-(1,3-benzodioxol-5-yl)-1-[2-(2-methoxyethoxy)ethyl]-pyrrolidine-3-carboxylic acid Using the method described in Example 1D, 250 mg of the compound resulting from Example 6A, 150 mg of 2-(2-methoxyethoxy)ethyl bromide and 175 mg diisopropylethylamine in 1 mL acetonitrile were heated at 100° C. for 3 hours to give 229 mg of the trans,trans-ester. A portion (200 mg) was hydrolyzed with 125 mg NaOH in 1 mL of water and 2 mL of ethanol to give 151 mg of the title compound as an amorphous powder. $^1$H NMR (CD$_3$OD, 300 MHz) δ 2.9–3.9 (m, 13H), 3.81 (s, 3H), 4.49 (d, J=10 Hz, 1H), 5.94 (s, 2H), 6.79 (d, J=8 Hz, 1H), 6.89 (dd, J=8 Hz, 1 Hz, 1H), 7.00 (d, J=9 Hz, 2H), 7.05 (d, J=1 Hz, 1H), 7.49 (d, J=9 Hz, 2H).

EXAMPLE 7 trans,trans-2-(4-Methoxyphenyl)-4-(1,3-benzo-dioxol-5-yl)-1-[2-(2-pyridyl)ethyl]-pyrrolidine-3-carboxylic acid The compound resulting from Example 6A (250 mg), 2-vinyl pyridine (355 mg) and one drop of acetic acid were dissolved in 2-methoxyethanol, and stirred at 100° C. for 2.5 hours. Toluene was added, and the solution was washed with potassium bicarbonate solution. The solution was dried over potassium bicarbonate and concentrated in vacuo. Toluene was added and the solution re-concentrated. This was done until the odor of 2-vinylpyridine was gone. The residue was taken up in hot heptane, filtered to remove a small amount of insoluble impurity, and concentrated in vacuo to give 225 mg of intermediate ester. The ester was hydrolyzed by the method described in Example 1D to give 202 mg of the title compound as the dihydrate. m.p. 77–80° C. $^1$H NMR (CD$_3$OD, 300 MHz) δ 2.8–3.3 (m, 6H), 3.55–3.70 (m, 2H), 3.76 (s, 3H), 3.99 (d, J=10 Hz, 1H), 5.92 (d, J=1 Hz, 2H), 6.72 (d, J=8 Hz, 1H), 6.80 (dd, J=8 Hz, 1 Hz), 6.85 (d, J=9 Hz, 2H), 6.92 (d, J=1 Hz, 1H), 7.20 (d, J=9 Hz, 2H), 7.20–7.32 (m, 2H), 7.70–7.80 (m, 2H), 8.40 (d, J=4 Hz, 1H).

EXAMPLE 8 trans,trans-2-(4-Methoxyphenyl)-4-(1,3-benzo-dioxol-5-yl)-1-(morpholin-4-ylcarbonyl)-pyrrolidine-3-carboxylic acid To the compound resulting from Example 6A (300 mg) and 164 mg triethylamine dissolved in 2 mL of methylene chloride and cooled in an ice bath was added 146 mg 1-morpholinocarbonyl chloride. The mixture was stirred 3 hours at room temperature. Toluene was added and the solution was washed with potassium bicarbonate solution, dried over sodium sulfate and concentrated in vacuo to give the intermediate ester. The ester was hydrolyzed by the method described in Example 1D to give 288 mg of the title compound. m.p. 244–246° C. $^1$H NMR (DMSO-d$_6$, 300 MHz) δ 2.96 (dd, J=12,Hz, 13 Hz, 1H), 3.03–3.13 (m, 2H), 3.20–3.30 (m, 2H), 3.40–3.60 (m, 5H), 3.74 (s, 3H), 3.70–3.85 (m, 3H), 5.10 (d, J=10 Hz, 1H), 5.99 (d, J=1 Hz, 2H), 6.80–6.90 (m, 2H), 6.87 (d, J=9 Hz, 2H), 7.07 (s, 1H), 7.25(d, J=9 Hz, 2H).

EXAMPLE 9 trans,trans-2-(4-Methoxyphenyl)-4-(1,3-benzodiox-ole-5-yl)-1-(butylaminocarbonyl)-pyrrolidine-3-carboxylic acid To the compound resulting from Example 6A (300 mg) dissolved in 2 mL tetrahydrofuran and cooled in an ice bath was added 88 mg of butyl isocyanate. After 40 minutes at room temperature, toluene was added, and the solution was concentrated in vacuo to give the intermediate ester. The ester was hydrolyzed by the method described in Example 1D to give 232 mg of the title compound. m.p. 220–221° C. $^1$H NMR (DMSO-d$_6$, 300 MHz) δ 0.78 (t, J=7 Hz, 3H), 1.10 (sextet, J=7 Hz, 2H), 1.22 (quintet, J=7 Hz, 2H), 2.78–3.05 (m, 3H), 3.40–3.56 (m, 2H), 3.74 (s, 3H), 3.95–4.05 (m, 1H), 4.93 (d, J=9 Hz, 1H), 5.80 (t, broad, J=7 Hz, 1H), 5.99 (s, 2H), 6.78–6.86 (m, 2H), 6.88 (d, J=9 Hz, 2H), 7.00 (d, J=1 Hz, 1H), 7.12 (d, J=9 Hz, 2H).

EXAMPLE 10 trans,trans-2-(4-Methoxyphenyl)-4-(1,3-benzo-dioxol-5-yl)-1-(4-methoxyphenylaminocarbonyl)-3-pyrrolidine-3-carboxylic acid The compound resulting from Example 6A (300 mg) was treated with 133 mg of 4-methoxyphenyl isocyanate by the procedure described in Example 9. The resulting ester was hydrolyzed with NaOH using the method described in Example 1D to give 279 mg of the title compound. m.p. 185–187° C. $^1$H NMR (CDCl$_3$, 300 MHz) δ 3.23 (dd, J=12 Hz, 13 Hz, 1H), 3.55–3.68 (m, 2H), 3.72 (s, 3H), 3.83 (s, 3H), 4.50–4.65 (m, 1H), 5.06 (d, J=10 Hz, 1H), 5.90 (s, 1H), 5.95 (s, 1H), 6.72 (d, J=9 Hz, 2H), 6.7–6.8 (m, 3H), 6.92 (d, J=9 Hz, 2H), 6.97 (d, J=9 Hz, 2H), 7.37 (d, J=9 Hz, 2H).

EXAMPLE 11 trans,trans-2-(4-Methoxyphenyl)-4-(1,3-benzo-dioxol-5-yl)-1-acetylpyrrolidine-3-carboxylic acid The compound resulting from Example 6A (250 mg) in 0.5 mL of toluene was treated with 200 mg of acetic anhydride. After stirring 2 hours at room temperature, water was added and the acetic acid neutralized with potassium bicarbonate. The mixture was extracted with toluene to give 273 mg of the intermediate ester. A portion of the ester (200 mg) was hydrolyzed using the method of Example 1D to give 211 mg of the title compound. m.p. 248–250° C. Rotational isomers are seen in the NMR. $^1$H NMR (DMSO-d$_6$, 300 MHz) δ 1.55 and 2.00 (s, 3H), 2.94 and 3.03 (dd, J=12 Hz, 13 Hz, 1H), 3.3–3.6 (m, 2H), 3.72 and 3.76 (s, 3H), 4.12 and 4.28 (dd, J=12 Hz, 7 Hz, 1H), 4.95 and 5.04 (d, J=10 Hz, 1H), 6.00 (s, 2H), 6.75–6.87 (m, 3H), 6.95 and 7.04 (d, J=9 Hz, 2H), 7.18 and 7.32 (d, J=9 Hz, 2H).

EXAMPLE 12 trans,trans-2-(4-Methoxyphenyl)-4-(1,3-benzo-dioxol-5-yl)-1-(2-furoyl)-pyrrolidine-3-carboxylic acid To the compound resulting from Example 6A (300 mg) and 164 mg triethylamine dissolved in 2 mL methylene chloride and cooled in an ice bath was added 138 mg of 2-furoyl chloride. The mixture was stirred 30 minutes at room temperature and then worked up by the procedures described in Example 8 to give the intermediare ester. The ester was hydrolyzed by the procedure described in Example 1D to give 269 mg of the title compound as an amorphous powder. $^1$H NMR (DMSO-d$_6$, 300 MHz) δ 3.06 (dd, J=12 Hz, 13 Hz, 1H), 3.3–3.6 (m, 2H), 4.25 (m, 1H), 5.19 (d, J=10 Hz, 1H), 6.67.4 (m, 8H), 7.8–7.9 (m, 1H).

EXAMPLE 13 trans,trans-2-(4-Methoxyphenyl)-4-(1,3-benzo-dioxol-5-yl)-1-(phenylaminocarbonyl)-pyrrolidine-3-carboxylic acid Starting with the compound resulting from Example 6A, phenyl isocyanate and the procedures described in Example 9, the title compound was prepared. m.p. 209–211° C. $^1$H NMR (DMSO-d$_6$, 300 MHz) δ 3.03 (dd, 1H), 3.55 (m, 1H), 3.70 (m, 1H), 3.72 (s, 3H), 4.15 (m, 1H), 5.13 (d, 1H), 6.00 (s, 2H), 6.88 (m, 5H), 7.07–7.20 (m, 3H), 7.30 (d, 2H), 7.38 (d, 2H), 8.20 (bs, 1H).

EXAMPLE 14 trans,trans-2-(4-Methoxyphenyl)-4-(1,3-benzodioxol-5-yl)-1-(allylaminocarbonylmethyl)-pyrrolidine-3-carboxylic acid Using the procedures described in Example 1 the title compound was prepared. m.p. 138–140° C. $^1$H NMR (CDCl$_3$, 300 MHz) δ 2.84 (d, 1H), 2.90–3.10 (dt, 2H), 3.28 (d, 1H), 3.35 (dd, 1H), 3.62 (m, 1H), 3.72–3.97 (m, 3H), 3.80 (s, 3H), 5.13 (bd, 2H), 5.80 (m, 1H), 5.97 (s, 2H), 6.74–6.97 (m, 5H), 7.38 (d, 2H).

EXAMPLE 15 trans,trans-2-(4-Methoxyphenyl)-4-(1,3-benzodioxol-5-yl)-1-(n-butylaminocarbonylmethyl)-pyrrolidine-3-carboxylic acid Using the procedures described in Example 1 the title compound was prepared. m.p. 105–107° C. $^1$H NMR (CDCl$_3$, 300 MHz) δ 0.90 (t, 3H), 1.30 (m, 2H), 1.45 (m, 2H), 2.80 (d, 1H), 2.87–3.35 (m, 6H), 3.62 (m, 1H), 3.80 (s, 3H), 5.97 (s, 2H), 6.75–6.92 (m, 5H), 7.28 (d, 2H).

EXAMPLE 16 trans,trans-2-(4-Methoxyphenyl)-4-(1,3-benzodioxol-5-yl)-1-(N-(n-propyl)-N-methylaminocarbonylmethyl)-pyrrolidine-3-carboxylic acid Using the procedures described in Example 1 the title compound was prepared as an amorphous solid. Rotational isomers are seen in the NMR. $^1$H NMR (CDCl$_3$, 300 MHz) δ 0.73, 0.84 (2t, 3H), 1.49 (m, 2H), 2.80 (dd, 1H), 2.85 (2s, 3H), 2.95–3.20 (m, 3H), 3.20–3.40 (m, 1H), 3.40 (d, 1H), 3.60 (m, 1H), 3.79 (s, 3H), 5.93 (s, 2H), 6.73 (d, 1H), 6.86 (m, 2H), 7.03 (m, 1H), 7.32 (d, 2H).

EXAMPLE 17 trans,trans-2-(4-Methoxyphenyl)-4-(1,3-benzodioxol-5-yl)-1-(pyrrolidin-1-ylcarbonylmethyl)-pyrrolidine-3-carboxylic acid Using the procedures described in Example 1 the title compound was prepared as an amorphous solid. $^1$H NMR (CDCl$_3$, 300 MHz) δ 1.40–1.70 (m, 6H), 2.80 (d, 1H), 3.00 (m, 2H), 3.24–3.43 (m, 5H), 3.60 (m, 2H), 3.73 (d, 1H), 3.80 (s, 3H), 5.95 (s, 2H), 6.74 (d, 1H), 6.80–6.90 (m, 3H), 7.04 (d, 1H), 7.30 (d, 2H).

EXAMPLE 18 trans,trans-2-(4-Methoxyphenyl)-4-(1,3-benzodioxol-5-yl)-1-(isobutylaminocarbonylmethyl)-pyrrolidine-3-carboxylic acid Using the procedures described in Example 1 the title compound was prepared. m.p. 175–177° C. $^1$H NMR (CD$_3$OD, 300 MHz) δ 0.87 (dd, 6H), 1.75 (septet, 1H), 2.85 (d, 1H), 2.90–3.10 (m, 4H), 3.23 (d, 1H), 3.40 (m, 1H), 3.58–3.67 (m, 1H), 3.78 (s, 3H), 3.89 (d, 1H), 5.92 (s, 2H), 6.76 (d, 1H), 6.86 (dd, 1H), 6.91 (d, 2H), 7.02 (d, 1H), 7.40 (d, 2H).

EXAMPLE 19 trans,trans-2-(4-Methoxyphenyl)-4-(1,3-benzodioxol-5-yl)-1-(cyclopentylaminocarbonylmethyl)-pyrrolidine-3-carboxylic acid Using the procedures described in Example 1 the title compound was prepared. m.p. 137–139° C. $^1$H NMR (CDCl$_3$, 300 MHz) δ 1.34 (m, 2H), 1.62 (m, 4H), 1.90 (m, 2H), 2.76 (d, 1H), 2.90 (t, 1H), 3.04 (dd, 1H), 3.22 (d, 1H), 3.28 (dd, 1H), 3.40 (m, 1H), 3.80 (s, 3H), 4.15 (m, 1H), 5.97 (d, 2H), 6.75–6.95 (m, 5H), 7.27 (m, 2H).

EXAMPLE 20 trans,trans-2-(4-Methoxyphenyl)-4-(1,3-benzodioxol-5-yl)-1-(morpholin-4-ylaminocarbonylmethyl)-pyrrolidine-3-carboxylic acid Using the procedures described in Example 1 the title compound was prepared as an amorphous solid. $^1$H NMR (CDCl$_3$, 300 MHz) δ 2.82 (d, 1H), 3.00 (m, 2H), 3.24 (m, 1H), 3.30–3.52 (m, 4H), 3.52–3.75 (m, 8H), 3.80 (s, 3H), 5.95 (s, 2H), 6.75 (d, 1H), 6.84 (d, 3H), 7.00 (s, 1H), 7.28 (d, 2H).

EXAMPLE 21 trans,trans-2-(4-Methoxyphenyl)-4-(1,3-benzodioxol-5-yl)-1-(2-phenoxyethyl)-pyrrolidine-3-carboxylic acid Using the procedures described in Example 4 the title compound was prepared as an amorphous solid. $^1$H NMR (CD$_3$OD, 300 MHz) δ 2.82 (m, 1H), 2.96 (dd, 1H), 3.13 (m, 1H), 3.32 (m, 1H), 3.51–3.70 (m, 2H), 3.77 (s, 3H), 4.00 (d, 1H), 4.07 (m, 2H), 5.91 (s, 2H), 6.72 (d, 1H), 6.80–6.95 (m, 6H), 7.03 (d, 1H), 7.22 (dd, 2H), 7.39 (d, 2H).

EXAMPLE 22 trans,trans-2-(4-Methoxyphenyl)-4-(1,3-benzodioxol-5-yl)-1-(2-methoxyethylaminocarbonylmethyl)-pyrrolidine-3-carboxylic acid Using the procedures described in Example 1 the title compound was prepared. m.p. 107–109° C. $^1$H NMR (CD$_3$OD, 300 MHz) δ 2.82 (d, 1H), 2.97 (q, 2H), 3.21 (d, 1H), 3.38 (m, 1H), 3.32 (s, 3H), 3.44 (m, 4H), 3.62 (m, 1H), 3.79 (s, 3H), 3.86 (d, 1H), 5.93 (s, 2H), 6.76 (d, 1H), 6.85 (dd, 1H), 6.91 (d, 2H), 7.01 (d, 1H), 7.38 (d, 2H).

EXAMPLE 23 trans,trans-2-(4-Methoxyphenyl)-4-(1,3-benzodioxol-5-yl)-1-(2-butoxyethyl)-pyrrolidine-3-carboxylic acid Using the procedures described in Example 4 the title compound was prepared. m.p. 53–55° C. $^1$H NMR (CDCl$_3$, 300 MHz) δ 0.88 (t, J=7 Hz, 3H), 1.32 (sextet, J=7 Hz, 2H), 1.50 (pentet, J=7 Hz, 2H), 2.27 (tt, J=6 Hz, 6 Hz, 1H), 2.92 (q, J=10 Hz, 2H), 3.35 (t, J=7 Hz, 2H), 3.42–3.56 (m, 4H), 3.68 (d, J=10 Hz, 1H), 3.78 (s, 3H), 5.94 (s, 2H), 6.73 (d, J=8 Hz, 1H), 6.83 (d, J=9 Hz, 2H), 6.82–6.87 (m, 1H), 7.06 (d, J=2 Hz, 1H), 7.32 (d, J=9 Hz, 2H). MS m/e 442 (M+H)$^+$.

EXAMPLE 24 trans,trans-2-(1,3-Benzodioxol-5-yl)-4-(4-methoxyphenyl)-1-(propylaminocarbonylmethyl)-pyrrolidine-3-carboxylic acid Using the procedures described in Example 1 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5yl afforded the title compound. m.p. 97–99° C. $^1$H NMR (CDCl$_3$, 300 MHz) δ 0.78 (t, J=7 Hz, 3H), 1.39 (sextet, J=7 Hz, 2H), 2.72 (d, J=16 Hz, 1H), 2.74 (t, J=10 Hz, 1H), 2.80–3.10 (m, 4H), 3.26–3.38 (m, 1H), 3.53 (m, 1H), 3.73 (s, 3H), 3.80 (d, J=10 Hz, 2H), 7.80 (t, J=6 Hz, 1H). MS (DCI/NH$_3$) m/e 441 (M+H)$^+$.

EXAMPLE 25 trans,trans-2-(1,3-Benzodioxol-5-yl)-4-(4-methoxyphenyl)-1-(2-propoxyethyl)-pyrrolidine-3-carboxylic acid Using the procedures described in Example 5 and substituting ethyl (1,3-benzodioxol-5-ylcarbonyl)acetate for ethyl (4-methoxybenzoyl)acetate and 4-(2-nitrovinyl)anisole for 5-(2-nitrovinyl)-1,3-benzodioxol-5yl afforded the title compound. m.p. 67–69° C. $^1$H NMR (CDCl$_3$, 300 MHz) δ 0.89 (t, J=7 Hz, 3H), 1.56 (sextet, J=7 Hz, 2H), 2.33 (m, 1H), 2.78–3.00 (m, 3H), 3.32 (t, J=7 Hz, 2H), 3.45–3.57 (m, 4H), 3.73 (m, 1H), 3.79 (s, 3H), 5.93 (s, 2H), 6.22 (d, J=8 Hz, 1H), 6.85 (d, J=8 Hz, 3H), 6.98 (s, 1H), 7.37 (d, J=8 Hz, 2H). MS (DCI/NH$_3$) m/e 428 (M+H)$^+$.

EXAMPLE 26 trans,trans-2-(1,3-Benzodioxol-5-yl)-4-(4-methoxyphenyl)-1-[2-(2-methoxyethoxy)ethyl)]-pyrrolidine-3-carboxylic acid Using the procedures described in Example 4 and substituting the starting materials described in Example 25 and using 2-(2-methoxyethoxy)ethylbromide to alkylate the pyrrolidine nitrogen afforded the title compound. m.p. 85–86° C. $^1$H NMR (CD$_3$OD, 300 MHz) δ 3.18–3.90 (m, 15H), 3.79 (s, 3H), 4.57 (d, J=10 Hz, 1H), 6.02 (s, 2H), 6.91 (d, J=8 Hz, 1H), 6.95 (d, J=9 Hz, 2H), 7.06 (dd, J=8 Hz, 1H), 7.12 (dd, J=1 Hz, 1H), 7.37 (d, J=9 Hz, 2H). MS (DCI/NH$_3$) m/e 444 (M+H)$^+$.

EXAMPLE 27 trans,trans-2-(1,3-Benzodioxol-5-yl)-4-(4-methoxyphenyl)-1-(butoxyethyl)-pyrrolidine-3-carboxylic acid Using the procedures described in Example 4, substituting the starting materials described in Example 25 and using 2-ethoxyethylbromide to alkylate the pyrrolidine nitrogen afforded the title compound. m.p. 54–56° C. $^1$H NMR (CDCl$_3$, 300 MHz) δ 0.89 (t, J=7 Hz, 3H), 1.44 (sextet, J=7 Hz, 2H), 1.52 (pentet, J=7 Hz, 2H), 2.40 (m, 1H), 2.74–2.98 (m, 3H), 3.46 (t, J=7 Hz, 2H), 3.42–3.56 (m, 4H), 3.68 (d, J=10 Hz, 1H), 3.80 (s, 3H), 5.93 (dd, J=6 Hz, 1 Hz, 2H), 6.72 (d, J=8 Hz, 1H), 6.74 (dd, J=9 Hz, 1H), 6.96 (s, 1H), 7.36 (d, J=9 Hz, 2H).

EXAMPLE 28 trans,trans-2-(4-Methoxyphenyl)-4-(1,4-benzodioxan-6-yl)-1-(propylaminocarbonylmethyl)-pyrrolidine-3-carboxylic acid Using the procedures described in Example 1 and substituting 6-(2-nitrovinyl)-1,4-benzodioxane for 5-(2-nitrovinyl)-1,3-benzodioxole afforded the title compound. m.p. 80–81° C. $^1$H NMR (CDCl$_3$, 300 MHz) δ 0.89 (t, J=7 Hz, 3H), 1.49 (sextet, J=7 Hz, 2H), 2.78 (d, J=16 Hz, 1H), 2.92 (t, J=10 Hz, 1H), 3.05–3.43 (m, 5H), 3.24 (d, J=16 Hz, 1H), 3.52–3.62 (m, 1H), 3.80 (s, 3H), 3.80 (t, J=10 Hz, 1H), 4.27 (s, 4H), 6.74–6.93 (m, 5H), 7.29 (d, J=9 Hz, 2H). MS (DCI/NH$_3$) m/e 455 (M+H)$^+$.

EXAMPLE 29 trans,trans-2-(4-Methoxyphenyl)-4-(1,4-benzodioxan-6-yl)-1-(N-methyl-N-propylaminocarbonylmethyl)-pyrrolidine-3-carboxylic acid Using the procedures described in Example 1, substituting 6-(2-nitrovinyl)-1,4-benzodioxane for 5-(2-nitrovinyl)-1,3-benzodioxole and alkylating the pyrrolidine nitrogen with N-methyl-N-propyl bromoacetamide afforded the title compound. m.p. 74–76° C. Rotational isomers are seen in the NMR. $^1$H NMR (CDCl$_3$, 300 MHz) δ 0.73, 0.83 (2t, J=7 Hz, 3H), 1.48 (m, 2H), 2.78 (dd, 1H), 2.85 (2s, 3H), 2.96–3.15 (m, 3H), 3.27–3.42 (m, 3H), 3.52–3.60 (m, 1H), 3.75 (d, 1H), 3.78 (s, 3H), 4.22 (s, 4H), 6.80–6.98 (m, 5H), 7.32 (d, 2H). MS (DCI/NH$_3$) m/e 469 (M+H)$^+$.

EXAMPLE 30 trans,trans-2-(4-Methoxyphenyl)-4-(1,3-benzodioxol-5-yl)-1-(N-methyl-N-butylaminocarbonylmethyl)-pyrrolidine-3-carboxylic acid Using the procedures described in Example 1, the title compound was prepared. Rotational isomers are seen in the NMR. $^1$H NMR (CD$_3$OD, 300 MHz) δ 0.86 (2t, 3H), 1.04–1.50 (m, 4H), 2.85 (2s, 3H), 2.93–3.20 (m, 4H), 3.40 (m, 2H), 3.52 (dd, 1H), 3.60 (m, 1H), 3.80 (s, 3H), 3.85 (m, 1H), 5.91 (s, 2H), 6.74 (d, 1H), 6.83–6.95 (m, 3H), 7.03 (dd, 1H), 7.35 (dd, 2H).

EXAMPLE 31 trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic acid

EXAMPLE 31A

Ethyl 2-(4-methoxy-2-methoxymethoxyphenyl-4-(1,3-benzodioxol-5-yl)-pyrrolidine-3-carboxylate)

Using the procedures described in Examples 1A and 1B and substituting ethyl (4-methoxy-2-methoxymethoxybenzoyl)acetate for ethyl (4-methoxybenzoyl)acetate afforded ethyl 2-(4-methoxy-2-methoxymethoxyphenyl)-4-(1,3-benzodioxol-5-yl)-4,5-dihydro-3H-pyrrole-3-carboxylate.

The above dihydro pyrrole carboxylate (3.0 g, 7.0 mmol) was dissolved in 20 mL of methanol, treated with 500 mg of 10% Pd/C and placed under hydrogen atmosphere for 32 hours. The catalyst was removed by filtration and the filtrate was concentrated under reduced pressure and chromatographed on silica gel eluting with ethyl acetate to afford the title compound (1.9 g, 63%) as the cis—cis isomer.

EXAMPLE 31B trans,trans-2-(4-Methoxy-2-methoxymethoxyphenyl)-4-(1,3-benzodioxol-5-yl)-1-(N-methyl-N-butylaminocarbonylmethyl)-pyrrolidine-3-carboxylic acid The compound resulting from Example 31A was epimerized by the procedure described in Example 6A. The resulting trans,trans compound (100 mg, 0.23 mmol) was then reacted by the procedures described in Example 1D substituting N-methyl-N-butyl bromoacetamide for N-propyl bromoacetamide to give the title compound (75 mg, 62%). m.p. 65–67° C. Rotational isomers are seen in the NMR. $^1$H NMR (CDCl$_3$, 300 MHz) δ 0.64, 0.68 (2t, J=7 Hz, 3H), 1.14, 1.12 (2 sextet, J=7 Hz, 2H), 1.40–1.48 (m, 2H), 2.86, 2.89 (2s, 3H), 2.95–3.42 (m, 6H), 3.50 (s, 3H), 3.43–3.65 (m, 2H), 3.78 (s, 3H), 4.30 (t, J=7 Hz, 1H), 5.09 (q, J=7 Hz, 2H), 5.92 (s, 2H), 6.55 (dd, J=3 Hz, 1H), 6.68 (s, 1H), 6.72 (s, 1H), 6.85 (2t, J=1 Hz, 1H), 7.04 (t, J=1 Hz, 1H), 7.42 (dd, J=3 Hz, 1H).

EXAMPLE 32 trans,trans-2-(4-Methoxyphenyl)-4-(1,3-benzodioxol-5-yl)-1-(3-ethoxypropyl)-pyrrolidin-5-one-3-carboxylic acid

EXAMPLE 32A

Ethyl 2-(4-methoxybenzoyl)-3-carbomethoxy-1,3-benzodioxole-5-propionate

To ethyl (4-methoxybenzoyl)acetate (4.44 g, 0.02 mmol) dissolved in 20 mL of anhydrous THF was added in portions 480 mg of NaH. The mixture was stirred for 30 minutes under nitrogen at ambient temperature. Methyl (1,3-benzodioxol-5-yl) bromoacetate (5.46 g, 0.02 mol) in 5 mL of THF was added. The mixture was stirred overnight at ambient temperature, diluted with 200 mL of EtOAc, and washed with water and brine. The organic phase was dried over sodium sulfate and concentrated in vacuo to afford the title compound (7.67 g, 92%) which was used without further purification.

EXAMPLE 32B

Ethyl 1-(3-ethoxypropyl)-2-(4-methoxyphenyl)-4-(1,3-benzodioxol-5-yl)-4,5-dihydro-5-oxo-1H-pyrrole-3-carboxylate A mixture of the compound resulting from Example 32A (700 mg, 1.69 mmol), 3-ethoxypropylamine (348 mg, 3.38 mmol) and 1 mL of acetic acid in a sealed tube was heated for 18 hours at 125° C. After cooling the contents of the tube to ambient temperature, 5 mL of water was added and the mixture extracted with ethyl acetate (2×100 mL). The combined organic extracts were washed with saturated sodium bicarbonate solution, water and brine, dried over sodium sulfate and concentrated under reduced pressure. The residue obtained was chromatographed on silica gel eluting with 3:2 hexane-ethyl acetate to give 330 mg (42%) of the title compound.

EXAMPLE 32C

Ethyl 1-(3-ethoxypropyl)-2-(4-methoxyphenyl)-4-(1,3-benzodioxol-5-yl)-pyrrolidin-5-one-3-carboxylate The compound resulting from Example 32B (300 mg, 0.64 mmol) in 15 mL of methanol was reduced with 100 mg of 10% Pd/C under hydrogen for 3 hours at ambient temperature. The catalyst was removed by filtration and the filtrate was concentrated under reduced pressure to give the title compound.

EXAMPLE 32D trans,trans-2-(4-Methoxyphenyl)-4-(1,3-benzodioxol-5-yl)-1-(3-ethoxypropyl)-pyrrolidin-5-one-3-carboxylic acid To the compound resulting from Example 32C (100 mg, 0.21 mmol) dissolved in 1 mL of ethanol was added 3 drops of a solution of 21% sodium ethoxide in ethanol. The mixture was heated to 70–80° C. for 3 hours, and then a solution of sodium hydroxide (100 mg) in 1 mL of water was added and heating was continued for 1 additional hour. The reaction mixture was cooled to ambient temperature, the ethanol was removed under reduced pressure, and water was added to the residue which was washed with ether. The aqueous layer was neutralized with 3 M HCl and allowed to stand overnight. The white crystalline solid was collected by filtration to give the title compound (60 mg, 64%). m.p. 134–140° C. $^1$H NMR (DMSO-d$_6$, 300 MHz) δ 1.04 (t, J=7 Hz, 3H), 1.55 (sextet, J=7 Hz, 2H), 2.48–2.56 (m, 1H), 2.93 (dd, J=9 Hz, 1H), 3.25 (t, J=7 Hz, 2H), 3.28–3.40 (m, 2H), 3.48–3.57 (m, 1H), 3.78 (s, 3H), 3.88 (d, J=10 Hz, 1H), 4.72 (d, J=10 Hz, 1H), 6.02 (s, 2H), 6.74 (dd, J=8 Hz, 1 Hz, 1H), 6.87 (d, J=8 Hz, 2H), 6.98 (d, J=8 Hz, 2H), 7.38 (d, J=8 Hz, 2H). MS (DCI/NH$_3$) m/e 442 (M+H)$^+$.

EXAMPLE 33 trans,trans-2-(4-Methoxyphenyl)-4-(1,3-benzodioxol-5-yl)-1-(3-methoxybenzyl)-pyrrolidin-5-one-3-carboxylic acid Following the procedures described in Example 32 and substituting 3-methoxybenzylamine for 3-ethoxypropylamine afforded the title compound (123 mg, 65%). m.p. 150–152° C. $^1$H NMR (CD$_3$OD, 300 MHz) δ 2.96 (dd, J=8 Hz, 10 Hz, 1H), 3.72 (s, 3H), 3.80 (s, 3H), 4.06 (d, J=10 Hz, 1H), 4.58 (d, J=8 Hz, 1H), 4.92 (q, J=16 Hz, 2H), 5.92 (s, 2H), 6.55–6.63 (m, 2H), 6.82 (d, J=8 Hz, 4H), 6.94 (d, J=8 Hz, 2H), 7.15–7.22 (m, 3H). MS (DCI/NH$_3$) m/e 475 (M+H)$^+$.

EXAMPLE 34 trans,trans-2-(4-Methoxyphenyl)-4-(1,3-benzodioxol-5-yl)-1-(N,N-diisoamylaminocarbonylmethyl)-pyrrolidine-3carboxylic acid The title compound was prepared as an amorphous solid using the procedures described in Example 1. $^1$H NMR (CDCl$_3$, 300 MHz) δ 0.70–0.90 (m, 12H), 1.10–1.60 (m, 10H), 2.75 (d, J=13 Hz, 1H), 2.90–3.10 (m, 4H), 3.15–3.30 (m, 2H), 3.40 (d, J=10 Hz, 1H), 3.40–3.52 (m, 2H), 3.55–3.62 (m, 1H), 3.75 (d, J=12 Hz, 1H), 3.79 (s, 3H), 5.93

(dd, J=1 Hz, 3 Hz, 2H), 6.72 (d, J=8 Hz, 1H), 6.82–6.90 (m, 3H), 7.03 (d, J=2 Hz, 1H), 7.30 (d, J=9 Hz, 2H).

EXAMPLE 35 trans,trans-2-(4-Methoxyphenyl)-4-(1,3-benzo-dioxol-5-yl)-1-(N,N-dipentylaminocarbonylmethyl)-pyrrolidine-3-carboxylic acid The title compound was prepared as an amorphous solid using the procedures described in Example 1. $^1$H NMR (CDCl$_3$, 300 MHz) δ 0.82 (t, J=7 Hz, 6H), 0.95–1.03 (m, 2H), 1.10–1.30 (m, 8H), 1.40–1.51 (m, 2H), 2.72 (d, J=13 Hz, 1H), 2.90–3.08 (m, 4H), 3.25–3.50 (m, 3H), 3.37 (d, J=13 Hz, 1H), 3.52–3,60 (m, 1H), 3.70 (J=10 Hz, 1H), 3.75 (s, 3H), 5.92 (dd, J=2 Hz, 5 Hz, 2H), 6.72 (d, J=8 Hz, 1H), 6.80–6.88 (m, 3H), 7.03 (d, J=2 Hz, 1H), 7.30 (d, J=9 Hz, 2H).

EXAMPLE 36 trans,trans-2-(4-Methoxyphenyl)-4-(1,3-benzo-dioxol-5-yl)-1-(N,N-di(2-methoxyethyl)aminocarbonylmethyl)-pyrrolidine-3-carboxylic acid The title compound was prepared using the procedures described in Example 1. m.p. 120–122° C. $^1$H NMR (CDCl$_3$, 300 MHz) δ 2.82 (d, J=13, 1H), 2.94–3.08 (m, 2H), 3.12 (s, 3H), 3.23 (s, 3H), 3.20–3.70 (m, 11H), 3.73 (d, J=10 Hz, 1H), 3.79 (s, 3H), 5.92 (dd, J=2 Hz, 2 Hz, 2H), 6.72 (d, J=8 Hz, 1H), 6.80–6.90 (m, 3H), 7.04 (d, J=2 Hz, 1H), 7.30 (d, J=9 Hz, 2H).

EXAMPLE 37 trans,trans-2-(4-Methoxyphenyl)-4-(1,3-benzo-dioxol-5-yl)-1-(2-hexynyl)-pyrrolidine-3-carboxylic acid Using the procedures described in Example 4, 200 mg. of the pure trans,trans isomer, the compound resulting from Example 6A was reacted with 109 mg of 1-bromo-2-hexyne, prepared by the method described in Perkin I, 2004 (1987), for 1 hour at 55° C., to give 226 mg of the intermediate ester. The ester was hydrolyzed using NaOH in ethanol-water for 3 hours at room temperature to give 175 mg of the title compound. $^1$H NMR (CDCl$_3$, 300 MHz) δ 1.00 (t, J=7 Hz, 3H), 1.54 (m, 2H), 2.14–2.22 (m, 2H), 2.96 (dd, J=7 Hz, 13 Hz, 1H), 3.07 (dd, J=18 Hz, 2 Hz, 1H), 3.15 (dd, J=9 Hz, 2 Hz, 1H), 3.26 (t, J=9 Hz, 1H), 3.36 (dd, J=18 Hz, 2 Hz, 1H), 3.47–3.55 (m, 1H), 3.79 (s, 3H), 3.88 (d, J=9 Hz, 1H), 5.95 (s, 2H), 6.72 (d, J=8 Hz, 1H), 6.80–6.88 (m, 3H), 7.03 (d, J=2 Hz, 1H), 7.22 (d, J=9 Hz, 2H).

EXAMPLE 38 trans,trans-2-(4-Methoxyphenyl)-4-(1,3-benzo-dioxol-5-yl)-1-(N-cyclopropylmethyl-N-propylaminocarbonylmethyl)-pyrrolidine-3-carboxylic acid The title compound was prepared using the procedures described in Example 1. m.p. 167–169° C. Rotational isomers were seen in the NMR. $^1$H NMR (CDCl$_3$, 300 MHz) δ −0.1 (m), 0.05 (m), 0.12–0.25 (m), 0.32–0.51 (m), 0.67 and 0.74 (2 triplets, 3H), 0.90–1.00 (m), 1.20–1.55 (m), 2.72 (d, J=13 Hz, 1H), 2.85–3.29 (m, 4H), 3.30–3.50 (m, 3H), 3.52–3.62 (m, 1H), 3.65–3.73 (2 doublets, J=10 Hz, 2 Hz, 1H), 3.78 (s, 3H), 5.95 (2 singlets, 2H), 6.72 (2 doublets, 2H), 6.80–6.90 (m, 3H), 7.00 and 7.05 (2 doublets, J=9 Hz, 2H).

EXAMPLE 39 trans,trans-2-(4-Methoxyphenyl)-4-(1,3-benzo-dioxol-5-yl)-1-(N-methyl-N-pentylaminocarbonylmethyl)-pyrrolidine-3-carboxylic acid The title compound was prepared as an amorphous solid using the procedures described in Example 1. Rotational isomers were seen in the NMR. $^1$H NMR (CDCl$_3$, 300 MHz) δ 0.85 (t, J=7 Hz, 3H), 1.00–1.08 (m), 1.13–1.32 (m), 1.35–1.50 (m), 2.72–2.82 (2 doublets, J=13 Hz, 1H), 2.83 and 2.86 (2 singlets, 3H), 2.92–3.20 (m, 3H), 3.22–3.45 (m, 3H), 3.52–3.62 (m, 1H), 3.72 (2 doublets, 1H), 3.75 and 3.76 (2 singlets, 3H), 5.92 (2 singlets, 2H), 6.72 (d, J=8 Hz, 1H), 6.80–6.87 (m, 3H), 7.03 (2 doublets, J=2 Hz, 1H), 7.30 (d, J=9 Hz, 2H).

EXAMPLE 40 trans,trans-2-(4-Methoxyphenyl)-4-(1,3-benzo-dioxol-5-yl)-1-(N,N-diisobutylaminocarbonylmethyl)-pyrrolidine-3-carboxylic acid The title compound was prepared using the procedures described in Example 1. m.p. 141–143° C. $^1$H NMR (CDCl$_3$, 300 MHz) δ 0.54 (d, J=7 Hz, 3H), 0.70–0.90 (3 doublets, J=7 Hz, 9H), 1.60–1.75 (m, 1H), 1.90–2.02 (m, 1H), 2.67 (d, J=13 Hz, 1H), 2.70 (d, J=13 Hz, 1H), 2.84 (dd, J=6 Hz, 15 Hz, 1H), 2.96–3.06 (m, 2H), 3.20 (dd, J=9 Hz, 15 Hz, 1H), 3.35 (dd, J=2 Hz, 10 Hz, 1H), 3.44–3.60 (m, 4H), 3.70 (d, J=9 Hz, 1H), 3.79 (s, 3H), 5.94 (dd, J=2 Hz, 2 Hz, 2H), 6.72 (d, J=9 Hz, 1H), 6.82–6.90 (m, 3H), 7.03 (d, J=2 Hz, 1H), 7.31 (d, J=9 Hz, 2H).

EXAMPLE 41 trans,trans-2-(4-Methoxyphenyl)-4-(1,3-benzo-dioxol-5-yl)-1-(N-methyl-N-(2-propynyl)aminocarbonylmethyl)-pyrrolidine-3-carboxylic acid The title compound was prepared as an amorphous solid using the procedures described in Example 1. Rotational isomers were seen in the NMR. $^1$H NMR (CDCl$_3$, 300 MHz) δ 2.09 and 2.32 (2 triplets, J=2 Hz, 1H), 2.80–3.10 (m, 3H), 2.90 and 2.99 (2 singlets, 3H), 3.35–3.50 (m, 2H), 3.52–3.62 (m, 1H), 3.78 (s, 3H), 4.03 (d, J=13 Hz, 1H), 4.00–4.30 (m, 3H), 5.93 (s, 2H), 6.72 (2 doublets, J=8 Hz, 1H), 6.80–6.90 (m, 3H), 7.02 and 7.11 (2 doublets, J=2 Hz, 1H), 7.30 (2 doublets, J=9 Hz, 2H).

EXAMPLE 42 trans,trans-2-(4-Methoxyphenyl)-4-(1,3-benzo-dioxol-5-yl)-1-(N-methyl-N-(n-hexyl)aminocarbonylmethyl)-pyrrolidine-3-carboxylic acid The title compound was prepared as an amorphous solid using the procedures described in Example 1. $^1$H NMR (CDCl$_3$, 300 MHz) δ 0.85 (2 triplets, J=7 Hz, 3H), 1.00–1.50 (m, 8H), 2.72–2.82 (2 doublets, J=13 Hz, 1H), 2.81 and 2.86 (2 singlets, 3H), 2.92–3.20 (m, 3H), 3.22–3.45 (m, 3H), 3.52–3.62 (m, 1H), 3.72 (2 doublets, 1H), 3.75 and 3.76 (2 singlets 3H), 5.94 (2 singlets, 2H), 6.72 (d, J=8 Hz, 1H), 6.80–6.87 (m, 3H), 7.03 (2 doublets, J=2 Hz, 1H), 7.30 (d, J=9 Hz, 1H).

EXAMPLE 43 trans,trans-2-(4-Methoxyphenyl)-4-(1,3-benzo-dioxol-5-yl)-1-(N,N-di(n-butyl)aminocarbonylmethyl)-pyrrolidine-3-carboxylic acid The title compound was prepared using the procedures described in Example 1. m.p. 123–125° C. $^1$H NMR (CDCl$_3$, 300 MHz) δ 0.79 (t, J=7 Hz, 3H), 0.85 (t, J=7 Hz, 3H), 1.00–1.50 (m, 8H), 2.74 (d, J=13 Hz, 1H), 2.90–3.09 (m, 4H), 3.23–3.50 (m, 3H), 3.38 (d, J=13 Hz, 1H), 3.52–3.62 (m, 1H), 3.75 (d, J=10 Hz, 1H), 3.78 (s, 3H), 5.93 (dd, J=2 Hz, 4 Hz), 6.71 (d, J=8 Hz, 1H), 6.81–6.89 (m, 3H), 7.03 (d, J=2 Hz, 1H), 7.30 (d, J=9 Hz, 2H). MS (DCI/NH$_3$) m/e 511 (M+H)$^+$. Anal calcd for $C_{29}H_{38}N_2O_6$: C, 68.21; H, 7.50; N, 5.49. Found: C, 68.07; H, 7.47; N, 5.40.

EXAMPLE 44 trans,trans-2-(4-Methoxyphenyl)-4-(1,3-benzo-dioxol-5-yl)-1-(N,N-diethylaminocarbonylmethyl)-pyrrolidine-3-carboxylic acid The title compound was prepared using the procedures described in Example 1. m.p. 132–134° C. $^1$H NMR (CDCl$_3$, 300 MHz) δ 0.98 (t, J=7 Hz, 3H), 1.06 (t, J=7 Hz, 3H), 2.78 (d, J=13 Hz, 1H), 2.95–3.20 (m, 4H), 3.30–3.50 (m, 4H), 3.55–3.65 (m, 1H), 3.76 (d, J=12 Hz, 1H), 3.79 (s, 3H), 5.93 (s, 2H), 6.72 (d, J=8 Hz, 1H), 6.80–6.90 (m, 3H), 7.02 (d, J=2 Hz, 1H), 7.32 (d, J=9 Hz, 2H).

EXAMPLE 45 trans,trans-2-(4-Methoxyphenyl)-4-(1,3-benzo-dioxol-5-yl)-1-(N-methyl-N-phenylaminocarbonylmethyl)-pyrrolidine-3-carboxylic acid The title compound was prepared as an amorphous solid using the procedures described in Example 1. $^1$H NMR (CD$_3$OD, 300 MHz) δ 2.75–2.85 (m, 2H), 3.05–3.13 (m, 1H), 3.18 (s, 3H), 3.40–3.58 (m, 2H), 3.78 (s, 3H), 3.88 (d, J=12 Hz, 1H), 5.92 (s, 2H), 6.72 (d, J=8 Hz, 1H), 6.75–6.85 (m, 3H), 7.00–7.12 (m, 5H), 7.82–7.92 (m, 3H).

EXAMPLE 46 trans,trans-2-(4-Methoxyphenyl)-4-(1,3-benzo-dioxol-5-yl)-1-(N-methyl-N-cyclohexylaminocarbonylmethyl)-pyrrolidine-3-carboxylic acid The title compound was prepared as an amorphous solid using the procedures described in Example 1. Rotational isomers were seen in the NMR. $^1$H NMR (CD$_3$OD, 300 MHz) δ 1.00–1.85 (m, 10H), 2.72 and 2.78 (2 singlets, 3H), 2.75–2.82 (2 doublets, J=12 Hz, 1H), 2.96–3.22 (m, 3H), 3.40–3.65 (m, 3H), 3.68 and 3.82 (2 doublets, J=10 Hz, 1H), 3.77 and 3.78 (2 singlets, 3H), 5.92 (s, 2H), 6.72 (2 doublets, J=8 Hz, 1H), 6.82–6.88 (m, 3H), 7.02 (2 doublets, J=2 Hz, 1H), 7.30–7.40 (2 doublets, J=9 Hz, 2H).

EXAMPLE 47 trans,trans-2-(4-Methoxyphenyl)-4-(1,3-benzo-dioxol-5-yl)-1-(N,N-di(n-propyl)aminocarbonylmethyl)-pyrrolidine-3-carboxylic acid The title compound was prepared using the procedures described in Example 1. m.p. 170–172° C. $^1$H NMR (CDCl$_3$, 300 MHz) δ 0.69 (t, J=7 Hz, 3H), 0.85 (t, J=7 Hz, 3H), 1.20–1.55 (m, 4H), 2.72 (d, J=13 Hz, 1H), 2.90–3.10 (m, 4H), 3.25–3.47 (m, 4H), 3.35–3.62 (m, 1H), 3.72 (d, J=9 Hz, 1H), 3.79 (s, 3H), 5.94 (s, 2H), 6.72 (d, d, J=8 Hz, 1H), 6.80–6.90 (m, 3H), 7.02 (d, J=2 Hz, 1H), 7.30 (d, J=9 Hz, 2H).

EXAMPLE 48 trans,trans-2-(4-Methoxyphenyl)-4-(1,3-benzo-dioxol-5-yl)-1-(N-methyl-N-isobutylaminocarbonylmethyl)-pyrrolidine-3-carboxylic acid The title compound was prepared as an amorphous solid using the procedures described in Example 1. Rotational isomers were seen in the NMR. $^1$H NMR (CD$_3$OD, 300 MHz) δ 0.65–0.85 (4 doublets, J=7 Hz, 6H), 1.75–1.95 (m, 1H), 2.80 and 2.90 (2 singlets, 3H), 2.90–3.10 (m, 4H), 3.10–3.65 (m, 4H), 3.74 9S, 3H), 3.81 and 3,88 (2 doublets, J=10 Hz, 1H), 5.93 (s, 2H), 6.72 (d, J=8 Hz, 1H), 6.80–6.90 (m, 3H), 7.02 (2 doublets, J=2 Hz, 1H), 7.80–7.90 (2 doublets, J=9 Hz, 2H).

EXAMPLE 49

Alternate Prepration of Ethyl 2-(4-methoxybenzoyl)-4-nitromethyl-3-(1,3-benzodioxole-5-yl)butyrate

EXAMPLE 49A

E-2-(3,4-Methylenedioxyphenyl)-1-nitroethene

To a stirred solution of piperonal (75 g, 500 mmol) in methanol (120 mL) at 10° C. was added nitromethane (27.1 mL, 500 mmol, 1 eq) followed by the dropwise addition of sodium hydroxide (21 g, 525 mmol, 1.05 eq) in sufficient water to achieve a total volume of 50 mL while maintaining the temperature between 10–15° C. The reaction mixture became cloudy, turning to a thick paste. The mixture was stirred for 30 minutes upon completion of the addition, and the mixture was then diluted with ice-water (~350 mL) maintaining the temperature below 5° C., until solution was achieved. The resultant solution was poured in a narrow stream (such that it just failed to break into drops) into a rapidly stirred solution of 36% hydrochloric acid (100 mL) in water (150 mL). A yellow solid precipitated (nitrostyrene), and this was collected by filtration, washed with water (1.5 L) until the filtrate was neutral. The filter cake was air dried and then recrystallized from hot ethanol (3 L) to yield E-2-(3,4-methylenedioxy)-nitrostyrene as yellow needles (53 g, 55%). $^1$H NMR (300 MHz, CDCl$_3$) δ 7.94 (1H, d, J=13.5 Hz), 7.47 (1H, d, J=13.5 Hz), 7.09 (1H, dd, J=7.5&2 Hz), 7.01 (1H, d, J=2 Hz), 6.87 (1H, d, J=7.5 Hz), 6.06 (2H, s). MS (DCI/NH$_3$) m/e 194 (M+H)$^+$, 211 (M+H+ NH$_3$)$^+$.

EXAMPLE 49B

Ethyl 2-(4-methoxyphenyl)oxo-4-nitro-3-(3,4-methylenedioxyphenyl)butyrate

To a stirred solution of the nitrostyrene resulting from Example 49A (14.17 g, 73.34 mmol, 1.2 eq) in a mixture of propan-2-ol (75 mL) and tetrahydrofuran (175 mL) at room temperature was added successively a solution of ethyl (4-methoxybenzoyl)acetate (11.5 g, 51.7 mmol) in THF (50 mL) followed by 1,8-diazabicyclo[5,4,0]undec-7-ene (DBU) (0.45 mL, 3.0 mmol, 0.05 eq). The resultant mixture was stirred at room temperature for 1 hour, then additional DBU (0.45 mL, 3.0 mmol, 0.05 eq) was added. The mixture was stirred a further 1 hour, then the volatiles were removed in vacuo and the residue purified by flash chromatography on 500 g silica gel, eluting with 20% ethyl acetate-hexanes changing to 25% ethyl acetate-hexanes as the product eluted. The solvents were removed in vacuo to yield the nitroketoester (19.36 g, 76%) as a viscous oil. Diastereomers were seen in the NMR. $^1$H NMR (300 MHz, CDCl$_3$,) δ 8.06 (2H, d, J=9 Hz), 7.89 (2H, d, J=9 Hz), 6.96 (2H, d, J=9 Hz), 6.91 (2H, d, J=9 Hz), 6.77 (1H, dd, J=9 Hz, 3 Hz), 6.73 (1H, d, J=9 Hz), 6.65 (1H, d, J=3 Hz), 5.95 (2H, s), 5.89 (1H, d, J=4 Hz), 5.88 (1H, d, J=4 Hz), 4.90–4.60 (3H, m), 4.39 (1H, m), 4.18 (2H, q, J=7 Hz), 3.94 (2H, m), 3.80 (3H, s), 3.78 (3H, s), 1.19 (3H, t, J=7 Hz), 0.99 (3H, t, J=7 Hz), MS (DCI/NH$_3$) m/e 416 (M+H)$^+$, 433 (M+H+ NH$_3$)$^+$.

EXAMPLE 50 trans,trans-2-(4-Methoxyphenyl)-4-(1,3-benzodioxol-5-yl)-1-(t-butyloxycarbonyl methyl)-pyrrolidine-3-carboxylic acid To a stirred solution of the compound resulting from Example 1C (100 mg, 0.27 mmol) in acetonitrile (2 mL) was added successively diisopropylethylamine (70 μL, 0.40 mmol, 1.5 eq) and t-butyl bromoacetate (48 μL, 0.29 mmol, 1.1 eq). The mixture was stirred 2 hours, then the solvent was removed in vacuo to yield the crude diester. To a stirred solution of the diester in ethanol (1 mL) at room temperature was added 50% w/w sodium hydroxide (300 mg, 3.75 mmol) in water. The mixture was stirred 2 hours, then the volatiles were removed in vacuo. The residue was dissolved in water (5 mL), and the solution was washed with ether. The aqueous phase was acidified with acetic acid (300 μL), and then extracted with ethyl acetate (2×). The combined organic extracts were dried (Na$_2$SO$_4$), filtered, and concentrated to yield the title compound (74 mg, 60%) as a white solid. $^1$H NMR (300 MHz, CDCl$_3$) δ 7.36 (2H, d, J=8 Hz), 7.13 (1H, d, J=3 Hz), 6.90 (1H, dt, J=3 Hz, 8 Hz), 6.88 (2H, d, J=8 Hz), 6.76 (1H, d, J=8 Hz), 5.96 (2H, s), 3.96 (1H, d, J=9 Hz), 3.81 (3H, s), 3.58 (1H, ddd, J=12, 10 Hz,3 Hz), 3.52 (1H, dd, J=9 Hz,3 Hz), 3.32 (1H, d, J=17 Hz), 3.08 (1H, t, J=10 Hz), 2.92 (1H, dd, J=9 Hz,7 Hz), 2.83 (1H, d, J=17 Hz). MS (DCI/NH$_3$) m/e 456 (M+H)$^+$.

Anal calc for C$_{29}$H$_{29}$NO$_7$.0.3H$_2$O: C, 65.07; H, 6.48; N, 3.04. Found: C, 65.02; H, 6.42; N, 2.93.

EXAMPLE 51 trans,trans-2-(4-Methoxyphenyl)-4-(1-naphthyl)-1-(N-methyl-N-propyl)aminocarbonylmethyl)-pyrrolidine-3-carboxylic acid The title compound was prepared by the procedures described in Examples 1 and 49 substituting naphthalene-1-carboxaldehyde for piperonyl in Example 49A. Rotational isomers are seen in the NMR. $^1$H NMR (300 MHz, CDCl$_3$) δ 8.29 (1H, bd, J=8 Hz), 7.86 (2H, d, J=8 Hz),7.75 (1H, d, J=8 Hz), 7.49 (3H, m), 7.34 (2H, dd, J=3 Hz,9 Hz), 6.83 (2H, dd, J=9 Hz,2 Hz), 4.50 (1H, m), 3.94 (1H, dd, J=9 Hz,2 Hz), 3.78 (3H, s), 3.65 (1H, m), 3.49 (1H, d, J=14 Hz), 3.40–2.93 (5H, m), 2.91, 2.83 (3H, s), 1.48 (2H, sept, J=7 Hz), 0.83, 0.77 (3H, t, J=7 Hz). MS (DCI/NH$_3$) m/e 461 (M+H)$^+$. Anal calcd for C$_{29}$H$_{29}$NO$_7$.0.5 HOAc: C, 71.00; H, 6.99; N, 5.71. Found: C, 70.95; H, 7.00; N, 5.46.

EXAMPLE 52 trans,trans-2-(4-Methoxyphenyl)-4-(2,3-dihydrobenzofuran-5-yl)-1-(N-methyl-N-propyl)aminocarbonylmethyl)-pyrrolidine-3-carboxylic acid

EXAMPLE 52A 2,3-Dihydrobenzofuran-5-carboxaldehyde

To a stirred solution of α,α-dichloromethyl methyl ether (2.15 g, 19 mmol, 1.35 eq) in methylene chloride (30 mL) at −40° C. was added successively stannic chloride (1.65 g, 17 mmol, 1.2 eq) and 15 minutes later, a solution of 2,3-dihydrobenzofuran (1.68 g, 14 mmol) in CH$_2$Cl$_2$ (5 mL) maintaining the temperature at or below −35° C. The mixture was warmed to 0° C., stirred 1 hour, then poured into ice-water, and stirred a further 30 minutes. The mixture was diluted with ether, and the phases separated. The organic phase was concentrated in vacuo, and the residue purified by vacuum distillation to yield the title compound (1.25 g, 60%) as a colorless liquid. b.p. 119–121° C. at 0.3 mm Hg.

EXAMPLE 52B trans,trans-2-(4-Methoxyphenyl)-4-(2,3-dihydrobenzofuran-5-yl)-1-(N-methyl-N-propyl)aminocarbonylmethyl)-pyrrolidine-3-carboxylic acid The title compound was prepared by the procedures described in Examples 1 and 49 substituting the compound resulting from Example 52A for piperonal in Example 49A. Rotational isomers are seen in the NMR. $^1$H NMR (300 MHz, CDCl$_3$) δ 7.33 (1H, d, J=8 Hz), 7.28 (1H, m), 7.19 (1H, m), 6.87 (1H, d, J=8 Hz), 6.73 (1H, d, J=8 Hz), 4.56 (1H, t, J=8 Hz), 3.83 (1H, d, J=10 Hz), 3.80 (3H, s), 3.63 (1H, m), 3.4–3.0 (9H, m), 2.87, 2.84 (3H, s), 1.51 (2H, septet, J=7 Hz), 0.88, 0.78 (3H, t, J=7 Hz). MS (DCI/NH$_3$) m/e 453 (M+H)$^+$. Anal calc for C$_{26}$H$_{32}$N$_2$O$_5$.0.25H$_2$O: C, 68.33; H, 7.17; N, 6.13. Found: C, 68.60; H, 6.88; N, 5.80.

EXAMPLE 53 trans,trans-2,4-Bis(4-methoxyphenyl)-1-(N-methyl-N-propyl)aminocarbonylmethyl)-pyrrolidine-3-carboxylic acid The title compound was prepared by the procedures described in Examples 1 and 49 substituting 4-methoxybenzaldehyde for piperonal in Example 49A. Rotational isomers are seen in the NMR. $^1$H NMR (300 MHz, CDCl$_3$) δ 7.37 (2H, d, J=7.5 Hz), 7.32 (2H, d, J=7.5 Hz), 6.86 (4H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCI/NH$_3$) m/e 441 (M+H)$^+$. Anal calc for C$_{25}$H$_{32}$N$_2$O$_5$.0.5H$_2$O: C, 66.80; H, 7.40; N, 6.23. Found: C, 67.15;H, 7.31; N, 6.00.

EXAMPLE 54 trans,trans-2-(4-Methoxyphenyl)-4-(3,4-dimethoxyphenyl)-1-(N-methyl-N-propyl)aminocarbonylmethyl)-pyrrolidine-3-carboxylic acid The title compound was prepared by the procedures described in Examples 1 and 49 substituting 3,4-dimethoxybenzaldehyde for piperonal in Example 49A. Rotational isomers are seen in the NMR. $^1$H NMR (300 MHz, CDCl$_3$) δ 7.33 (2H, d, J=7.5 Hz), 7.07 (1H, d, J=2.0 Hz), 6.98 (1H, m), 6.85 (1H, d, 7.5 Hz), 6.82 (2H, d, 7.5 Hz), 3.91 (3H, s), 3.86 (3H, s), 3.83 (1H, m), 3.79 (3H, s), 3.64 (1H, m), 3.50–2.95 (6H, m), 2.87 (1H, m), 2.85, 2.83 (3H, s), 1.45 (2H, m), 0.84, 0.74 (3H, t, J=7.5 Hz). MS (DCI/NH$_3$) m/e 471 (M+H)$^+$. Anal calc for C$_{26}$H$_{34}$N$_2$O$_6$.0.5H$_2$O: C, 65.12; H, 7.36; N, 5.84. Found: C, 65.22; H, 7.27; N, 5.59.

EXAMPLE 55 trans,trans-2-(4-Methoxyphenyl)-4-(3-methoxyphenyl)-1-(N-methyl-N-propyl)aminocarbonylmethyl)-pyrrolidine-3-carboxylic acid The title compound was prepared by the procedures described in Examples 1 and 49 substituting 3-methoxybenzaldehyde for piperonal in Example 49A. Rotational isomers are seen in the NMR. $^1$H NMR (300 MHz, CDCl$_3$) δ 7.33 (2H, d, J=7.5 Hz), 7.24 (1H, t, J=7.5 Hz), 7.05 (2H, m), 6.85 (2H, dd, J=7.5&2 Hz), 6.76 (1H, m), 3.83 (1H, m), 3.81 (3H, s), 3.79 (3H, s), 3.64 (1H, m), 3.48–2.97 (6H, m), 2.87, 2.83 (3H, s), 2.85 (1H, m), 1.45 (2H, m), 0.84, 0.74 (3H, t, J=7.5 Hz). MS (DCI/NH$_3$) m/e 441 (M+H)$^+$. Anal calc for C$_{25}$H$_{32}$N$_2$O$_5$.0.5H$_2$O: C, 66.80; H, 7.40; N, 6.23. Found: C, 66.76; H, 7.36; N, 6.05.

EXAMPLE 56 trans,trans-2-(4-Methoxyphenyl)-4-(2-naphthyl)-1-(N-methyl-N-propyl)aminocarbonylmethyl)-pyrrolidine-3-carboxylic acid The title compound was prepared by the procedures described in Examples 1 and 49 substituting naphthylene-2-carboxaldehyde for piperonal in Example 49A. Rotational isomers are seen in the NMR. $^1$H NMR (300 MHz, CDCl$_3$) δ 7.82 (4H, m), 7.69 (1H, m), 7.47 (2H, m), 7.37 (2H, dd, J=7.5&2 Hz), 6.85 (2H, dd, J=7.5&2 Hz), 3.90 (1H, d, J=8 Hz), 3.78 (3H, s), 3.57 (1H, m), 3.52–2.97 (6H, m), 2.93, 2.85 (3H, s), 2.90 (1H, m), 1.52 (2H, m), 0.86, 0.76 (3H, t, J=7.5 Hz). MS (DCI/NH$_3$) m/e 461 (M+H)$^+$. Anal calc for C$_{28}$H$_{32}$N$_2$O$_4$ 0.5H$_2$O: C, 71.62; H, 7.08; N, 5.97. Found: C, 71.58; H, 7.11; N, 6.01.

EXAMPLE 57 trans,trans-2-(4-Methoxyphenyl)-4-(1,3-benzodioxol-5-yl)-1-(2-(ethylsulfinyl)ethyl)-pyrrolidine-3-carboxylic acid To the compound resulting from Example 1C (100 mg, 0.27 mmol) and 2-chloroethyl ethyl sulfide (67.5 mg, 0.5 mmol, 2 equivalents) dissolved in 6 mL of acetonitrile was added 10 mg of KI and 0.5 mL of diisopropylethylamine. The mixture was refluxed for 4 hours and then concentrated in vacuo. The residue obtained was purified by flash chromatography on silica gel eluting with 4:1 hexane-ethyl acetate to afford 93 mg (75%) of the ethylthioethyl compound.

To the sulfide (90 mg, 0.2 mmol) dissolved in 5 mL of CH$_2$Cl$_2$ in an ice bath was added 68 mg of 3-chloroperoxybenzoic acid. The mixture was stirred for 40 minutes in the ice bath and for 3 hours at room temperature. A 10% solution of sodium hydroxide (2 mL) was added, and the mixture was extracted with EtOAc (2×50 mL). The combined organic extracts were washed with water and brine, dried over sodium sulfate and concentrated in vacuo. The residue obtained was chromatographed on silica gel eluting with EtOAc and 10% MeOH in CH$_2$Cl$_2$ to afford the sulfoxide (62 mg, 65%).

The ethyl ester was hydrolyzed by the procedure described in Example 1D to afford the title compound as a diastereomeric mixture. m.p. 61–63° C. MS (DCI/NH$_3$) m/e 446 (M+H)$^+$. $^1$H NMR (CDCl$_3$, 300 MHz) δ 1.25, 1.32 (t, J=9 Hz, 3H), 2.45–2.75 (m, 4H), 2.84–2.96 (m, 3H), 3.02–3.08 (m, 1H), 3.32, 3.36 (d, J=3 Hz, 1H), 3.47–3.58 (m, 2H), 3.65, 3.68 (d, J=7.5 Hz, 1H), 3.76, 3.80 (s, 3H), 5.94 (s, 2H), 6.72 (d, J=7.5 Hz, 1H), 3.84–3.89 (m, 3H), 7.02 (d, J=6 Hz, 1H), 7.30, 7.34 (d, J=7.5 Hz, 2H).

EXAMPLE 58 trans,trans-2-(4-Methoxyphenyl)-4-(1,3-benzodioxol-5-yl)-1-(2-(isopropylsulfonylamino)ethyl)-pyrrolidine-3-carboxylic acid To 2-bromoethylamine hydrobromide (1 mmol) suspended in anhydrous CH$_3$CN was added 1 equivalent of Et$_3$N. The mixture was stirred for 30 minutes and then 1 equivalent of isopropyl sulfonyl chloride and 1 equivalent of Et$_3$N were added. The resulting mixture was stirred for 2 hours at room temperature and then added to a solution of the compound resulting from Example 1C (185 mg, 0.5 mmol) in 3 mL of CH$_3$CN. The mixture was warmed at 50–60° C. for 2 hours, cooled to room temperature, treated with water and extracted with EtOAc. The combined organic extracts were washed with water and brine, dried and concentrated in vacuo. The residue obtained was chromatographed on silica gel eluting with 3:2 hexane-EtOAc to give 195 mg (75%) of the ethyl ester. The ethyl ester (160 mg, 0.31 mmol) was hydrolyzed by the procedure described in Example 1D to afford the title compound (133 mg, 88%). m.p. 94–96° C. $^1$H NMR (CD$_3$OD, 300 MHz) δ 1.26 (d, J=6 Hz, 6H), 1.97 (s, 1H), 2.38 (m, 1H), 2.77 (m, 1H), 2.88 (t, J=9 Hz, 1H), 3.04 (m, 1H), 3.14 (t, J=7.5 Hz, 2H), 3.35 (m, 2H), 3.46 (m, 1H), 3.58 (m, 1H), 3.78 (s, 3H), 5.92 (s, 2H), 6.74 (d, J=9 Hz, 1H), 6.86 (dd, J=9 Hz,3 Hz, 1H), 6.92 (d, J=9 Hz, 2H), 7.00 (d, J=3 Hz, 1H), 7.36 (d, J=9 Hz, 2H). MS (DCI/NH$_3$) m/e (M+H)$^+$.

EXAMPLE 59 trans,trans-2-(4-Methoxyphenyl)-4-(1,3-benzodioxol-5-yl)-1-(2-(isobutoxy)ethyl)-pyrrolidine-3-carboxylic acid The title compound was prepared by the procedures described in Example 1D from the compound resulting from Example 1C and 2-(isobutoxy)ethyl bromide. m.p. 68–70° C. $^1$H NMR (CDCl$_3$, 300 MHz) δ 0.88 (d, J=6 Hz, 6H), 1.82 (quintet, J=6 Hz, 1H), 2.22 (m, 2H), 2.72–2.79 (m, 1H), 2.86–2.95 (m, 2H), 3.13 (d, J=6 Hz, 2H), 3.45–3.56 (m, 4H), 3.68 (d, J=9 Hz, 1H), 3.79 (s, 3H), 5.94 (s, 2H), 6.72 (d, J=7.5 Hz, 1H), 6.85 (dd, J=9 Hz, 7.5 Hz, 3H), 7.08 (s, 1H), 7.34 (d, J=9 Hz, 2H). MS (DCI/NH$_3$) m/e 442 (M+H)$^+$.

EXAMPLE 60 trans,trans-2-(4-Methoxyphenyl)-4-(1,3-benzo-dioxol-5-yl)-1-(butylsulfonyl)-pyrrolidine-3-carboxylic acid To 100 mg (0.271 mmol) of the compound resulting from Example 1C dissolved in 10 mL of THF was added 1-butanesulfonyl chloride (46.7 mg, 1.1 equivalents) and diisopropylethylamine (53 mg, 1.5 equivalents). The resulting mixture was stirred for 2.5 hours at room temperature and then the solvent evaporated. The crude product was purified by flash chromatography on silica gel eluting with 3:2 hexane-EtOAc to afford 120 mg (90%) of the ethyl ester.

The ester (120 mg, 0.244 mmol) was dissolved in 1 mL of EtOH, and a solution of 100 mg of NaOH in 1 mL of water was added. The mixture was stirred for 3 hours at room temperature and then concentrated under reduced pressure. Water (5 mL) was added and the solution was washed with ether to remove any unhydrolyzed trans-cis isomer. The aqueous solution was acidified to pH~6 with acetic acid and then extracted with EtOAc (2×50 mL). The combined organic extracts were washed with brine, dried over sodium sulfate and concentrated under reduced pressure to afford the pure title compound (60 mg, 53%) as a white solid. m.p. 67–69° C. $^1$H NMR (CDCl$_3$, 300 MHz) δ 0.82 (t, J=7.5 Hz, 3H), 1.20–1.33 (m, 2H), 1.58–1.68 (m, 2H), 2.48–2.69 (m, 2H), 3.28 (dd, J=9 Hz, 1H), 3.49 (t, J=12 Hz, 1H), 3.65 (dd, J=12 Hz, 1H), 3.82 (s, 3H), 4.32 (dd, J=12 Hz, 1H), 5.17 (d, J=9 Hz, 2H), 5.95 (s, 2H), 6.70–6.78 (m, 3H), 6.92 (d, J=9 Hz, 2H), 7.35 (d, J=9 Hz, 2H). MS (DCI/NH$_3$) m/e 462 (M+H)$^+$.

EXAMPLE 61 trans,trans-2-(4-Methoxyphenyl)-4-(1,3-benzo-dioxol-5-yl)-1-(2-(N-methyl-N-isopropylcarbonylamino)ethyl)-pyrrolidine-3-carboxylic acid

EXAMPLE 61A trans,trans-2-(4-Methoxyphenyl)-4-(1,3-benzo-dioxol-5-yl)-1-(2-bromoethyl)-pyrrolidine-3-carboxylic acid ethyl ester To the mixture of cis,trans and trans,trans pyrrolidines resulting from Example 1C (400 mg) dissolved in 9 mL of 1,2-dibromoethane was added 0.7 mL of diisopropylethylamine and 30 mg of sodium iodide. The resultant mixture was heated at 100° C. for 1 hour, and then the solvents were removed in vacuo. The residue was taken up in EtOAc and washed sequentially with water and brine, dried and concentrated under reduced pressure. The crude product was purified by flash chromatography on silica gel eluting with 4:1 hexane-EtOAc to give 470 mg of the title product.

EXAMPLE 61B trans,trans-2-(4-Methoxyphenyl)-4-(1,3-benzo-dioxol-5-yl)-1-(2-(methylamino)ethyl)-pyrrolidine-3-carboxylic acid ethyl ester To the compound resulting from Example 61A (450 mg) dissolved in 10 mL of EtOH was added 0.5 mL of 40% aqueous methylamine and 50 mg of sodium iodide. The mixture was heated at 80° C. for 1 hour, and then the solvents were removed in vacuo. The residue was taken up in EtOAc and washed sequentially with water and brine, dried and concentrated in vacuo. The resultant product was carried on without further purification.

EXAMPLE 61C trans,trans-2-(4-Methoxyphenyl)-4-(1,3-benzo-dioxol-5-yl)-1-(2-(N-methyl-N-isobutyrylamino) ethyl)-pyrrolidine-3-carboxylic acid To the compound resulting from Example 61B (~150 mg) dissolved in 5 mL of 1,2-dichloroethane was added 0.3 mL of diisopropylethylamine. The solution was cooled to −40° C., isobutyryl chloride (0.17 mL) was added, the bath was removed, and the solution was allowed to warm to ambient temperature and stirred for 15 hours. The solvent was removed in vacuo; the residue was taken up in EtOAc and washed sequentially with 1:1 sodium bicarbonate solution/water and brine, dried and concentrated in vacuo. The product was purified by flash chromatography on silica gel eluting with a gradient 1:1 EtOAc-hexanes going to EtOAc and finally using 10% MeOH-EtOAc.

The ester was dissolved in 1.5 mL of EtOH; 0.75 mL of a 17% aqueous NaOH solution was added, and the resultant mixture was stirred at ambient temperature for 3 hours. The solvents were removed in vacuo; the residue was taken up in water and washed with ether. The aqueous phase was acidified with 1 N H$_3$PO$_4$ to pH 3 and extracted twice with ether. The combined organic extracts were washed with brine and dried over Na$_2$SO$_4$. The solvents were removed in vacuo to provide 82 mg of the title compound as a white foam. Rotamers were seen in the NMR. $^1$H NMR (CDCl$_3$, 300 MHz) of the major rotamer δ 1.06 (d, 3H, J=10 Hz), 1.12 (d, 3H, J=10 Hz), 2.15 (m, 1H), 2.5–3.0 (m, 3H), 2.91 (s, 3H), 3.32 (m, 2H), 3.50 (m, 2H), 3.65 (m, 2H), 3.77 (s, 3H), 5.92 (s, 2H), 6.73 (d, 1H, J=8 Hz), 6.75–6.9 (m, 4H), 6.96 (d, 1H, J=2 Hz), 7.29 (m, 1H). MS (DCI/NH$_3$) m/z 469 (M+H)$^+$. Analysis calcd for C$_{26}$H$_{32}$N$_2$O$_6$.0.3 TFA: C, 63.55; H, 6.48; N, 5.57. Found: C, 63.44; H, 6.71; N, 5.24.

EXAMPLE 62 trans,trans-2-(4-Methoxyphenyl)-4-(1,3-benzo-dioxol-5-yl)-1-(2-(N-methyl-N-propionylamino) ethyl)-pyrrolidine-3-carboxylic acid The title compound was prepared by the procedures described in Example 61 substituting propionyl chloride for isobutyryl chloride in Example 61C. $^1$H NMR (CDCl$_3$, 300 MHz) of the major rotamer δ 1.13 (t, 3H, J=8 Hz), 2.19 (m, 1H), 2.30 (m, 2H), 2.65–3.0 (m, 3H), 2.85 (s, 3H), 3.25–3.4 (m, 2H), 3.5–3.7 (m, 3H), 3.79 (s, 3H), 5.92 (s, 2H), 6.74 (d, 1H, J=8 Hz), 6.75–6.9 (m, 4H), 7.00 (bd s, 1H), 7.29 (bd s, 1H). MS (DCI/NH$_3$) m/z 455 (M+H)$^+$. Analysis calcd for C$_{25}$H$_{30}$N$_2$O$_6$.1.0H$_2$O: C, 63.55; H, 6.83; N, 5.93. Found: C, 63.55; H, 6.52; N, 5.73.

EXAMPLE 63 trans,trans-2-(4-Methoxyphenyl)-4-(1,3-benzo-dioxol-5-yl)-1-(N-methyl-N-benzylaminocarbonylmethyl)-pyrrolidine-3-carboxylic acid Using the procedures described in Example 1 the title compound was prepared. $^1$H NMR (CDCl$_3$, 300 MHz) of the major rotamer δ 2.79 (s, 3H), 2.8–3.2 (m, 2H), 3.48 (m, 2H), 3.61 (m, 2H), 3.77 (s, 3H), 3.78 (m, 1H), 4.3–4.5 (m, 2H), 5.95 (d, 2H, J=2 Hz), 6.7–6.9 (m, 4H), 7.00 (m, 1H), 7.15–7.35 (m, 7H). MS (FAB/NBA) m/z 503 (M+H)+. Anal calcd for $C_{29}H_{30}N_2O_6 \cdot 0.5H_2O$: C, 68.36; H, 5.74; N, 5.50. Found: C, 68.41; H, 5.74; N, 5.36.

EXAMPLE 64 trans,trans-2-(4-Methoxyphenyl)-4-(1,3-benzo-dioxol-5-yl)-1-(N-ethyl-N-butylaminocarbonylmethyl)-pyrrolidine-3-carboxylic acid Using the procedures described in Example 1 the title compound was prepared. $^1$H NMR (CDCl$_3$, 300 MHz) of the major rotamer δ 0.88 (t, 3H, J=7 Hz), 1.06 (t, 3H, J=7 Hz), 1.27 (m, 2H), 1.45 (m, 2H), 2.8–3.6 (m, 11H), 3.79 (s,3H), 3.80 (m, 1H), 5.92 (bd s, 2H), 6.75 (d, 1H, J=8 Hz), 6.85 (d, 1H, J=8 Hz), 6.92 (d, 2H, J=8 Hz), 7.03 (s, 1H), 7.33 (d, 1H, J=8 Hz). MS (DCI/NH$_3$) m/z 483 (M+H)+. Anal calcd for $C_{27}H_{34}N_2O_6 \cdot 0.5$ HOAc: C, 65.61; H, 7.08; N, 5.46. Found: C, 65.51; H, 6.70; N, 5.66.

EXAMPLE 65 trans,trans-2-(4-Methoxyphenyl)-4-(1,3-benzo-dioxol-5-yl)-1-(N-methyl-N-(2,2-dimethylpropyl) aminocarbonyl methyl)-pyrrolidine-3-carboxylic acid Using the procedures described in Example 1 the title compound was prepared. $^1$H NMR (CDCl$_3$, 300 MHz) of the major rotamer δ 0.90 (s, 9H), 2.8–3.1 (m, 4H), 2.94 (s, 3H), 3.3–3.5 (m, 3H), 3.61 (m, 1H), 3.80 (s, 3H), 3.82 (m, 1H), 5.94 (bd s, 2H), 6.74 (d, 1H, J=8 Hz), 6.86 (d, 2H, J=8 Hz), 6.87 (m, 1H), 7.03 (d, 1H, J=2 Hz), 7.33 (d, 2H, J=8 Hz). MS (DCI/NH$_3$) m/z 483 (M+H)+.

EXAMPLE 66 trans,trans-2-(4-Methoxyphenyl)-4-(1,3-benzo-dioxol-5-yl)-1-(2-(N-methyl-N-butylsulfonylamino) ethyl)-pyrrolidine-3-carboxylic acid To the compound resulting from Example 61B (60 mg, 0.13 mmol) dissolved in 5 mL of CH$_3$CN was added 0.2 mL of Et$_3$N and 22 mg (0.143 mmol, 1.1 equivalents) of 1-butanesulfonyl chloride. The mixture was stirred for 1 hour at room temperature and then concentrated in vacuo. The crude product was purified by column chromatography on silica gel eluting with 1:1 EtOAc-hexane to yield 64 mg (90%) of the ester. Ester hydrolysis by the procedure described in Example 1D afforded the title compound. m.p. 64–66° C. $^1$H NMR (CDCl$_3$, 300 MHz) δ 0.92 (t, J=7.5 Hz, 3H), 1.39 (hexad, J=7.5 Hz, 2H), 1.68–1.76 (m, 2H), 2.16–2.25 (m, 1H), 2.72 (s, 3H), 2.75–2.92 (m, 5H), 3.12–3.20 (m, 1H), 3.25–3.34 (m, 1H), 3.46–3.55 (m, 2H), 3.65 (d, J=9 Hz, 1H), 3.78 (s, 3H), 5.53 (s, 2H), 6.72 (d, J=7.5 Hz, 1H), 6.82 (dd, J=7.5 Hz,3 Hz, 1H), 6.86 (d, J=9 Hz, 2H), 7.02 (d, J=3 Hz, 1H), 7.34 (d, J=9 Hz, 2H). MS (DCI/NH$_3$) m/e 519 (M+H)+.

EXAMPLE 67 trans,trans-2-(4-Methoxyphenyl)-4-(1,3-benzo-dioxol-5-yl)-1-(2-(N-methyl-N-propylsulfonylamino)ethyl)-pyrrolidine-3-carboxylic acid The title compound was prepared by the procedures described in Example 66 substituting 1-propanesulfonyl chloride for 1-butanesulfonyl chloride. m.p. 69–70° C. $^1$H NMR (CDCl$_3$, 300 MHz) δ 1.02 (t, J=7.5 Hz, 3H), 1.78 (hexad, J=7.5 Hz, 2H), 2.18–2.26 (m, 1H), 2.72 (s, 3H), 2.75–2.95 (m, 6H), 3.13–3.22 (m, 1H), 3.25–3.35 (m, 1H), 3.47–3.58 (m, 2H), 3.66 (d, J=9 Hz, 1H), 3.80 (s, 3H), 5.96 (s, 2H), 6.74 (d, J=7.5 Hz, 1H), 6.84 (d,d, J=7.5 Hz, 3 Hz, 1H), 6.87 (d, J=9 Hz, 2H), 7.04 (d, J=3 Hz, 1H), 7.43 (d, J=9 Hz, 2H). MS (DCI/NH$_3$) m/e 505 (M+H)+.

EXAMPLE 68 trans,trans-2-(4-Methoxyphenyl)-4-(1,3-benzo-dioxol-5-yl)-1-(2-(propylsulfonyl)ethyl)-pyrrolidine-3-carboxylic acid To 1-propanethiol (3.5 g, 46.05 mmol) dissolved in 10 mL of anhydrous THF was added 632 mg (26.32 mmol) of NaH in portions under a nitrogen atmosphere. The mixture was heated at 60–70° C. for 1 hours. To this mixture was added the compound resulting from Example 61A (180 mg, 0.38 mmol) in 2 mL THF. Heating was continued at 60–70° C. for an additional 2 hours, and then the volatiles were removed under reduced pressure. The crude propylthioethyl adduct was purified by flash chromatography on silica gel eluting with 3:2 hexane-EtOAc to give 170 mg (95%).

To a solution of 170 mg (0.36 mmol) of the sulfide and 93 mg (0.8 mmol) of N-methylmorpholine N-oxide (NMO) in a mixture of 20 mL of acetone and 5 mL of H$_2$O was added a solution of osmium tetroxide (10 mg) in 0.3 mL of t-butanol. The resulting mixture was stirred overnight at room temperature and then concentrated under reduced pressure. The residue was partitioned between EtOAc and H$_2$O. The organic phase was washed with brine, dried over Na$_2$SO$_4$ and concentrated in vacuo. Flash chromatography afforded 177 mg (98%) of the ethyl ester which was hydrolyzed by the procedures described in Example 1D to afford the title compound. m.p. 73–75° C. $^1$H NMR (CDCl$_3$, 300 MHz) δ 1.04 (t, J=7.5 Hz, 3H), 1.78 (hexad, J=7.5 Hz, 2H), 2.59–2.66 (m, 1H), 2.84–3.08 (m, 7H), 3.43 (dd, J=9 Hz, 3 Hz, 1H), 3.53–3.60 (m, 1H), 3.68 (d, J=9 Hz, 1H), 3.82 (s, 3H), 5.96 (s, 2H), 6.75 (d, J=7.5 Hz, 1H), 6.82 (dd, J=7.5 Hz, 3 Hz, 1H), 6.88 (d, J=9 Hz, 2H), 6.99 (d, J=3 Hz, 1H), 7.32 (d, J=9 Hz, 2H). MS (DCI/NH$_3$) m/e 476 (M+H)+.

EXAMPLE 69 trans,trans-2-(4-Methoxyphenyl)-4-(1,3-benzo-dioxol-5-yl)-1-N-(trans-5-methylhex-2-enyl)-pyrrolidine-3-carboxylic acid

EXAMPLE 69A trans-5-Methylhex-2-enoic acid ethyl ester

Oil dispersion sodium hydride (0.85 g) was washed with hexanes and suspended in THF (20 mL), and the mixture was cooled in an ice bath to 0° C. Diisopropyl(ethoxycarbonylmethyl) phosphonate (5.0 mL) was added slowly and the mixture stirred for 20 minutes at 0° C. Isovaleraldehyde (2.0 mL) in THF (5 mL) was added dropwise over five minutes. The ice bath was removed and the mixture stirred for 18 hours at ambient temperature. Saturated ammonium chloride solution (50 mL) was added and the mixture extracted with diethyl ether (3×50 mL). The ether extracts were combined, dried with Na$_2$SO$_4$, and evaporated to give a colorless oil which was purified by flash chromatography on silica gel eluting with hexanes. The title compound was isolated as a colorless oil (2.1 g).

EXAMPLE 69B trans-5-Methylhex-2-en-1-ol

The compound resulting from Example 69A (2.0 g) was dissolved in toluene and cooled to 0° C. in an ice bath. Diisobutylaluminum hydride (1.5 $\underline{N}$ in toluene, 20 mL) was added dropwise and the solution stirred at 0° C. for two hours. Citric acid solution (25 mL) was added very slowly to the cooled solution. The resulting mixture was stirred for 18 hours at ambient temperature. Diethyl ether (50 mL) was added, the solids removed by filtration and washed with additional ether (2×25 mL). The filtrate was extracted with ether (2×25 mL). The ether extractions and washings were combined, dried, and evaporated to give a colorless oil which was purified by flash chromatography on silica gel eluting with 25% EtOAc-hexanes. The title compound was isolated as a colorless oil (1.25 g).

EXAMPLE 69C trans-1-Bromo-5-methylhex-2-ene

The compound resulting from Example 69B (1.0 g) was dissolved in diethyl ether and cooled to 0° C. in an ice bath. Phosphorus tribromide (2.5 g, 0.87 mL) was added dropwise and the solution stirred at 0° C. for two hours. The solution was poured onto ice, the layers separated, and the aqueous layer extracted with additional ether (3×25 mL). The ether layers were combined, dried, and evaporated to give a colorless oil which was used without further purification (0.95 g).

EXAMPLE 69D trans,trans-2-(4-Methoxyphenyl)-4-(1,3-benzo-dioxol-5-yl)-1-N-(trans-5-methylhex-2-enyl)-pyrrolidine-3-carboxylic acid The title compound was synthesized using the methods detailed in Example 1D but substituting the compound resulting from Example 69C for N-propyl bromoacetamide. $^1$H NMR (CDCl$_3$, 300 MHz) δ 0.84 (d, 6H, J=8 Hz), 1.57 (heptet, 1H, J=8 Hz), 1.87 (t, 2H, J=6 Hz), 2.60 (dd, 1H, J=8 Hz,14 Hz), 2.86 (t, 1H, J=10 Hz), 2.96 (dd, 1H, J=8 Hz,10 Hz), 3.20 (dd, 1H, J=5 Hz,14 Hz), 3.29 (dd, 1H, J=3 Hz,10 Hz), 3.50 (m, 1H), 3.70 (d, 1H, J=10 Hz), 3.78 (s, 3H), 5.47 (m, 2H), 5.93 (s, 2H), 6.71 (d, 1H, J=8 Hz), 6.83 (d, 3H, J=9 Hz), 7.05 (s, 1H), 7.32 (d, 2H, J=9 Hz). MS (DCI/NH$_3$) m/e 438 (M+H)$^+$. Anal calcd for C$_{26}$H$_{31}$NO$_5$: C, 71.37; H, 7.14; N, 3.20. Found: C, 71.16; H, 7.24; N, 3.17.

EXAMPLE 70 trans,trans-2-(4-Methoxyphenyl)-4-(1,3-benzo-dioxol-5-yl)-1-N-(trans-3,5-dimethylhex-2-enyl)-pyrrolidine-3-carboxylic acid The title compound was prepared by the procedures described in Example 69 but substituting 4-methyl-2-pentanone for isovaleraldehyde in Example 69A, which gave ~7:1 mixture of trans/cis olefins. The crude product was purified by preparative HPLC (Vydac μC18) eluting with a 10–70% gradient of CH$_3$CN in 0.1% TFA. The desired fractions were lyophilized to give the product (and its diastereomer) as a white solid. $^1$H NMR of the major (trans) isomer: (CDCl$_3$, 300 MHz) δ 0.83 (d, 6H, J=8 Hz), 1.56 (s,3H), 1.74 (m, 1H), 1.92 (d, 2H, J=6 Hz), 3.3–3.5 (m, 3H), 3.6–3.8 (m,4H), 3.78 (s, 3H), 3.9–4.0 (m, 1H), 5.22 (m, 1H), 5.90 (d, 2H, J=12 Hz), 6.63 (m, 1H), 6.78 (m, 3H), 6.95 (s, 1H), 7.45 (d, 3H, J=8 Hz). MS (DCI/NH$_3$) m/e 438 (M+H)$^+$. Anal calcd for C$_{27}$H$_{33}$NO$_5$ 1.0 TFA: C, 61.59; H, 6.06; N, 2.48. Found: C, 61.36; H, 6.10; N, 2.34.

EXAMPLE 71 trans,trans-2-(4-Methoxyphenyl)-4-(1,3-benzo-dioxol-5-yl)-1-(4-heptylcarbonylmethyl)-pyrroli-dine-3-carboxylic acid

EXAMPLE 71A

1-Chloro-3-propyl-2-hexanone

To 2-propylpentanoic acid (156.6 μl, 1.00 mmol) dissolved in anhydrous dichloromethane (2 mL) was added DMF (3 μL, 4 mole %), and the solution was cooled to 0° C. under a nitrogen atmosphere. To the solution was added oxalyl chloride (94.3 μL, 1.08 mmol) dropwise over a few minutes. The reaction was stirred 18 hours while warming to ambient temperature. The mixture was cooled to 0° C. and excess ~0.3 $\underline{M}$ ethereal diazomethane solution was added. The reaction mixture was stirred 18 hours while warming to ambient temperature. The reaction mixture was washed with 1 $\underline{M}$ aqueous sodium carbonate solution (30 mL), dried over anhydrous sodium sulfate, filtered and concentrated under reduced pressure. The residue was dissolved in ether (2 mL) and cooled to 0° C. under a nitrogen atmosphere. Hydrogen chloride as a 4 $\underline{N}$ solution in dioxane (275 μL, 1.10 mmol) was added dropwise over a few minutes. The reaction was stirred 18 hours while warming to ambient temperature. The reaction mixture was concentrated under reduced pressure and the residual oil was used in the next step without further purification.

EXAMPLE 71B trans,trans-Ethyl 2-(4-methoxyphenyl)-4-(1,3-benzo-dioxol-5-yl)-1-(4-heptylcarbonylmethyl)-pyrroli-dine-3-carboxylate To the compound resulting from Example 71A (1.00 mmol, maximum theoretical yield) was added a solution of the trans,trans ethyl carboxylate from Example 1C (295 mg, 0.80 mmol as a 50% solution in toluene), diisopropylethylamine (700 μL, 4.00 mmol) and acetonitrile (4 mL). To the resulting solution was added sodium iodide (12 mg, 10 mole %), and the reaction mixture was stirred 18 hours under a nitrogen atmosphere at ambient temperature. Additional sodium iodide (24 mg, 20 mole %) and acetonitrile (4 mL) were added, and the reaction mixture was heated at 45–50° C. with stirring for 18 hours. The reaction mixture was concentrated under reduced pressure, and the residue was chromatographed on silica gel eluting with 1:9 ethyl acetate-hexane to give 237 mg (46%) of the title compound as a yellow oil.

EXAMPLE 71C trans,trans-2-(4-Methoxyphenyl)-4-(1,3-benzo-dioxol-5-yl)-1-(4-heptylcarbonylmethyl)-pyrroli-dine-3-carboxylic acid To the compound resulting from Example 71B (231 mg, 0.4532 mmol) dissolved in ethanol (10 mL) was added a solution of lithium hydroxide (38 mg, 0.9065 mmol) in water (2.5 mL). The solution was stirred for 18 hours under a nitrogen atmosphere, additional lithium hydroxide (19 mg, 0.4532 mmol) in water (0.5 mL) was added, and stirring was continued 24 hours. The reaction mixture was concentrated under reduced pressure to remove the ethanol, and the aqueous residue was diluted with water (45 mL) and washed with ether (50 mL). The aqueous layer was neutralized with 1 N hydrochloric acid to cloudiness and then 10% aqueous citric acid was added to adjust the pH to ~5. This solution was then extracted with 10% ethanol in chloroform (4×25 mL). The combined organic extracts were dried over anhydrous sodium sulfate, filtered and concentrated under reduced pressure. The residue was purified by preparative TLC on silica gel eluted with 1:1 ethyl acetate-hexane to give 86 mg (39%) of the title compound as an off white powder. $^1$H NMR (CDCl$_3$, 300 MHz) δ 0.73–0.97 (m, 6H), 1.03–1.33 (m, 6H), 1.36–1.58 (m, 2H), 2.46 (m, 1H), 2.80–2.98 (m, 3H), 3.38–3.64 (m, 3H), 3.75–3.90 (m, 1H), 3.79 (s, 3H), 5.94 (s, 2H), 6.75 (d, 1H), 6.86 (d, 2H), 6.92 (d, 1H), 7.12 (s, 1H), 7.32 (d, 2H). MS (FAB) m/e 482 (M+H)$^+$. Anal calcd for C$_{28}$H$_{35}$NO$_6$: C, 69.83; H, 7.32; N, 2.91. Found: C, 69.57; H, 7.41; N, 2.73.

EXAMPLE 72 trans,trans-2-(4-Methoxyphenyl)-4-(1,3-benzo-dioxol-5-yl)-1-(valerylmethyl)-pyrrolidine-3-carboxylic acid

EXAMPLE 72A

1-Chloro-2-hexanone

Using the procedure described in Example 71A and substituting pentanoic acid for 2-propylpentanoic acid afforded the title compound as an oil which was used in the next step without further purification.

EXAMPLE 72B trans,trans-Ethyl 2-(4-methoxyphenyl)-4-(1,3-benzo-dioxole-5-yl)-1-(valerylmethyl)-pyrrolidine-3-carboxylate Substituting the compound resulting from Example 72A for 1-chloro-3-propyl-2-hexanone and using the procedure described in Example 71B, except deleting the first addition of sodium iodide, stirring 18 hours at ambient temperature and purifying by silica gel chromatography eluting with 3:17 ethyl acetate-hexane, the title compound 305 mg (65%) was obtained as a yellow oil.

EXAMPLE 72C trans,trans-2-(4-Methoxyphenyl)-4-(1,3-benzo-dioxol-5-yl)-1-(valerylmethyl)-pyrrolidine-3-carboxylic acid By substituting the compound resulting from Example 72B for trans,trans-Ethyl 2-(4-methoxyphenyl)-4-(1,3-benzodioxol-5-yl)-1-(4-heptylcarbonylmethyl)-pyrrolidine-3-carboxylate and using the procedure described in Example 71C, except only one solution of lithium hydroxide (81.5 mg, 1.942 mmol) in water (3.5 mL) was added followed by stirring for 18 hours, the title compound 130 mg (46%) was obtained as an off white powder. $^1$H NMR (CDCl$_3$, 300 MHz) δ 0.87 (t, 3H), 1.26 (m, 2H), 1.49 (m, 2H), 2.37 (m, 2H), 2.79–2.98 (m, 3H), 3.31–3.49 (m, 2H), 3.56 (m, 1H), 3.77, 3.79 (d,s, 4H), 5.94 (s, 2H), 6.75 (d, 1H), 6.81–6.93 (m, 3H), 7.09 (d, 1H), 7.33 (d, 2H). MS (FAB) m/e 440 (M+H)$^+$. Anal. calcd for C$_{25}$H$_{29}$NO$_6$: C, 68.32; H, 6.65; N, 3.19. Found: C, 67.95; H, 6.64; N, 3.05.

EXAMPLE 73 trans,trans-2-(4-Methoxyphenyl)-4-(1,3-benzo-dioxol-5-yl)-1-(N-(3,4-dimethoxybenzyl)-N-methylaminocarbonylmethyl)pyrrolidine-3-carboxylic acid

EXAMPLE 73A trans,trans- and cis, trans-2-(4-Methoxyphenyl)-4-(1,3-benzodioxol-5-yl)-1-((3,4-dimethoxybenzyl)aminocarbonylmethyl)pyrrolidine-3-carboxylic acid ethyl ester Using the procedure of Example 1D, paragraph 1, substituting 3,4-dimethoxybenzyl bromoacetamide for dipropyl bromoacetamide, the desired product mixture was obtained as a white foam in 81% yield.

EXAMPLE 73B trans,trans- and cis, trans-2-(4-Methoxyphenyl)-4-(1,3-benzodioxol-5-yl)-1-(N-(3,4-dimethoxybenzyl)-N-methylaminocarbonylmethyl)pyrrolidine-3-carboxylic acid ethyl ester The resultant product from Example 73A (220 mg, 0.404 mmol) was dissolved in 2 mL dry THF and added dropwise to a stirred, cooled (0° C.) suspension of sodium hydride (23 mg of a 60% by weight mineral oil suspension, 16.5 mg, 0.69 mmol) in 0.2 mL THF, under an argon atmosphere. The resulting mixture was stirred at 0° C. for 1 hour, then methyl iodide (28 μL, 64 mg, 0.45 mmol) was added. The reaction mixture was stirred at 0° C. for 45 minutes. TLC (Et$_2$O) indicated incomplete reaction. An additional portion of methyl iodide (28 μL, 64 mg, 0.45 mmol) and dry 1,3-dimethyl-3,4,5,6-tetrahydro-2(1H)pyrimidinone (50 μL, 0.41 mmol) were added. The reaction mixture was stirred at ambient temperature for 2 days. The reaction was poured into 25 mL of 0.5 M aqueous citric acid and extracted with 2×25 mL EtOAc. The combined organic exttracts were washed sequentially with 30 mL water and 30 mL brine, then dried (Na$_2$SO$_4$), filtered and concentrated under reduced pressure to produce 270 mg of crude material. Flash chromatography on silica gel eluting with Et$_2$O gave the title compounds as an inseparable mixture in 43% yield. $^1$H NMR (CDCl$_3$, 300 MHz) δ 2.79 (s) and 2.81 (s), for the N—CH$_3$ signals. MS m/z 591 (M+H)$^+$.

EXAMPLE 73C trans,trans-2-(4-Methoxyphenyl)-4-(1,3-benzo-dioxol-5-yl)-1-(N-(3,4-dimethoxybenzyl)-N-methylaminocarbonylmethyl)pyrrolidine-3-carboxylic acid To the resultant compound from Example 73B (98 mg, 0.17 mmol) dissolved in 1 mL EtOH and cooled to 0° C. was added a solution of lithium hydroxide monohydroxide (17 mg, 0.41 mmol) in 0.5 mL H$_2$O. The resulting solution was stirred under a nitrogen atmosphere for 16 hours. The solution was concentrated in vacuo, and the residue was partitioned between 15 mL H$_2$O and 15 mL Et$_2$O. The aqueous phase was extracted with 5 mL Et$_2$O, then the aqueous phase was acidified with 10% aqueous citric acid. The acidic aqueous phase was saturated with NaCl and extracted with 3×15 mL EtOAc. The EtOAc extracts were combined, dried (Na$_2$SO$_4$), then filtered and concentrated in vacuo to give 40 mg (42%) of the title compound as a white foam. $^1$H NMR (CD$_3$OD, 300 MHz, two rotameric forms) 2.85 (s, 3H), 2.94–3.25 (br m, 3H), 3.35–3.70 (br m) and 3.64 (s, 4H total), 3.70–3.97 (br m), 3.74 (s), 3.76 (s), 3.78 (s), 3.79 (s), 3.81 (s), and 4.03 (br d, J=14 Hz, 8H total), 4.43 (AB, 1H), 5.91 (s) and 5.93 (s, 2H total), 6.50–6.60 (m, 1H), 6.67–7.02 (br m, 6H), 7.29 (br d) and 7.35 (br d, 2H total). HRMS calcd for C$_{31}$H$_{35}$N$_2$O$_8$ (M+H)$^+$: 563.2393. Found: 563.2385.

EXAMPLE 74 trans,trans-2-(4-Methoxyphenyl)-4-(1,3-benzo-dioxol-5-yl)-1-(N-(3,4-dimethoxybenzyl)aminocarbonylmethyl)pyrrolidine-3-carboxylic acid The procedure of Example 73C was used, with the substitution of the resultant compound from Example 73A for the resultant compound from Example 73B, to provide the title compound. $^1$H NMR (CD$_3$OD, 300 MHz) δ 2.85 (d, J=16 Hz, 1H), 2.92 (br t, J=9 Hz, 1H), 2.98 (br t, J=10 Hz, 1H), 3.32–3.39 (br m, 2H), 3.54–3.65 (br m, 1H), 3.67 (s, 3H), 3.78 (s, 3H), 3.80 (s, 3H), 3.85 (d, J=10 Hz, 1H), 4.21 (d, J=15 Hz, 1H), 4.41 (d, J=15 Hz, 1H), 5.91 (s, 2H), 6.67 (d, J=8 Hz, 1H), 6.75–6.95 (m, 7H), 7.33–7.40 (m, 2H). HRMS calcd for C$_{30}$H$_{32}$N$_2$O$_8$ (M+H)$^+$: 549.2237. Found: 549.2224.

EXAMPLE 75

(2R,3R,4R)-2-(4-Methoxyphenyl)-4-(1,3-benzo-dioxol-5-yl)-1-((1R)-1-(N,N-dipropylaminocarbonyl)-1-butyl)pyrrolidine-3-carboxylic acid

EXAMPLE 75A trans,trans-2-(4-Methoxyphenyl)-4-(1,3-benzo-dioxol-5-yl)-1-((1R)-1-(benzyloxycarbonyl)butyl)pyrrolidine-3-carboxylic acid ethyl ester The procedure of Fung, et. al., J. Med. Chem., 35(10): 1722–34 (1992) was adapted. The resultant compound from Example 6A (103 mg, 0.279 mmol) was dissolved in 0.7 mL of nitromethane and 0.7 mL of H$_2$O, and ammonium carbonate (34 mg, 0.35 mmol) and (2S)-benzyl 2-bromopentanoate (78 mg, 0.30 mmol) were added. The reaction was refluxed for 24 hours. The reaction was partitioned between 15 mL of 1 M aqueous Na$_2$CO$_3$ and 25 mL of CH$_2$Cl$_2$. The aqueous phase was extracted with 2×10 mL CH$_2$Cl$_2$, and the combined organic phases were washed with 15 mL brine, dried (Na$_2$SO$_4$), then filtered and concentrated under reduced pressure to a brown oil (169 mg). The crude product was purified by silica gel chromatography eluting with 3:1 CH$_2$Cl$_2$-hexane to produce 106 mg (68%) of the title compound as a waxy solid. $^1$H NMR indicated the presence of two diastereomeric products.

EXAMPLE 75B trans,trans-2-(4-Methoxyphenyl)-4-(1,3-benzo-dioxol-5-yl)-1-((1R)-1-(N,N-dipropylaminocarbonyl)-1-butyl)pyrrolidine-3-carboxylic acid ethyl ester The resultant compound from Example 75A (101 mg, 0.180 mmol) and 30 mg of 10% palladium on charcoal were stirred in 2 mL EtOAc under 1 atmosphere of H$_2$ for 4 hours. The reaction mixture was filtered through a plug of Celite, using 15 mL MeOH to wash the catalyst. The combined filtrate and wash were concentrated in vacuo to give 81.4 mg (96%) of the crude acid as a white solid.

The above crude acid was combined with HOBt hydrate (41 mg, 0.27 mmol), dipropylamine (26 mg, 0.26 mmol), and 4-methylmorpholine (37 mg, 0.37 mmol) in 2 mL dry DMF. The solution was cooled to −15° C., then 1-ethyl-3-(3-dimethylaminopropyl)carbodiimide hydrochloride (44 mg, 0.23 mmol) was added. The mixture was stirred at −15° C. and allowed to warm slowly to room temperature overnight. The solvent was removed by distillation under reduced pressure, and the residue was partitioned between 20 mL EtOAc and 10 mL of 1 M aqueous Na$_2$CO$_3$. The organic phase was washed with 10 mL of brine, dried (Na$_2$SO$_4$), then filtered and concentrated in vacuo. The crude product was purified by flash chromatography on silica gel, eluting with 1:2 Et$_2$O-hexane. Further purification of overlap fractions by preparative TLC eluting with 1:2 Et$_2$O-hexane yielded 32 mg (34%) of a less polar product, and 44 mg (46%) of a more polar product.

EXAMPLE 75C (2R,3R,4R)-2-(4-Methoxyphenyl)-4-(1,3-benzo-dioxol-5-yl)-1-((1R)-1-(N,N-dipropylaminocarbonyl)-1-butyl)pyrrolidine-3-carboxylic acid The procedure of Example 73C was followed, with the substitution of the less polar isomer from Example 75B for the resultant product from Example 73B, to provide the title compound in 94% yield. [α]$_D$=−52° (c=0.235, CH$_3$OH). $^1$H NMR (CD$_3$OD, 300 MHz) δ 0.55 (t, J=7 Hz, 3H), 0.87 (t, J=7 Hz) and 0.87–0.94 (m, 6H total), 1.03–1.25 (br m, 2H), 1.25–1.68 (br m, 4H), 1.90–2.07 (br m, 1H), 2.75–2.94 (br m, 2H), 2.94–3.02 (br m, 2H), 3.20–3.40 (m, overlapping with CD$_2$HOD signal), 3.40–3.60 (br m, 2H), 3.79 (s, 3H), 4.04 (br d, J=9 Hz, 1H), 5.92 (dd, J=3,5 Hz, 2H), 6.72 (d, J=8 Hz, 1H), 6.79 (dd, J=1,5,8 Hz, 1H), 6.92–6.98 (br m, 3H), 7.29–7.39 (m, 2H). MS m/z 525 (M+H)$^+$.

EXAMPLE 76

(2S,3S,4S)-2-(4-Methoxyphenyl)-4-(1,3-benzo-dioxol-5-yl)-1-((1R)-1-(N,N-dipropylaminocarbonyl)-1-butyl)pyrrolidine-3-carboxylic acid The procedure of Example 73C was followed, with the substitution of the more polar isomer from Example 75B for the resultant product from Example 73B, to provide the title compound in 88% yield. [α]$_D$=+58° (c=0.37, CH$_3$OH). $^1$H NMR (CD$_3$OD, 300 MHz) 0.57 (br t, J=7 Hz, 3H), 0.88–0.98 (m, 6H), 1.08–1.35 (br m, 2H), 1.35–1.68 (br m, 4H), 1.75–1.90 (br m, 1H), 2.75–2.86 (br m, 2H), 3.10–3.30

(br m, 2H), 3.51–3.65 (br m, 2H), 3.69 (s, 3H), 4.03–4.16 (br m, 2H), 5.91 (s, 2H), 6.71–6.83 (m, 2H), 6.86–6.97 (m, 3H), 7.32 (br d, J=9 Hz, 2H). MS m/z 525 (M+H)$^+$.

EXAMPLE 77

(2S,3S,4S)-2-(4-Methoxyphenyl)-4-(1,3-benzo-dioxol-5-yl)-1-((1S)-1-(N,N-dipropylaminocarbo-nyl)-1-butyl)pyrrolidine-3-carboxylic acid

EXAMPLE 77A trans,trans-2-(4-Methoxyphenyl)-4-(1,3-benzo-dioxol-5-yl)-1-((1S)-1-(N,N-dipropylaminocarbo-nyl)-1-butyl)pyrrolidine-3-carboxylic acid ethyl ester (2R)-N,N-dipropyl 2-hydroxypentanamide (106 mg, 0.528 mmol, made by standard procedure) was dissolved in 2 mL THF under an argon atmosphere, diisopropylethylamine (75 mg, 0.58 mmol) was added, then the solution was cooled to −20° C. Trifluoromethanesulfonic anhydride (95 μL, 159 mg, 0.565 mmol) was added to the cooled solution over 1 minute, and the reaction mixture was stirred at −20° C. for 1 hour, and at room temperature for an additional 1 hour. The resulting slurry was recooled to 0° C., and a solution of the resultant compound from Example 6A (195 mg, 0.528 mmol) and diisopropylethylamine (101 μL, 75 mg, 0.58 mmol) in 3 mL of CH$_2$Cl$_2$ was added. The reaction was stirred at 0° C. for 3 hours and for an additional 2 days at room temperature. TLC (Et$_2$O-hexane 1:2) indicated starting materials remained, so the mixture was warmed to reflux for 4 hours. The reaction was cooled, then partitioned between 30 mL EtOAc and 15 mL of 1 M aqueous Na$_2$CO$_3$. The aqueous phase was extracted with 15 mL EtOAc, then the combined organic phases were washed with 20 mL brine, dried (Na$_2$SO$_4$), filtered and concentrated in vacuo to a yellowish oil. Purification by flash chromatography on silica gel eluting with 1:2 Et$_2$O-hexane gave 19.9 mg (7%) of a less polar product and 20.1 mg (7%) of a more polar product. $^1$H NMR spectra and MS were the same as those of Example 76B.

EXAMPLE 77B (2S,3S,4S)-2-(4-Methoxyphenyl)-4-(1,3-benzo-dioxol-5-yl)-1-((1S)-1-(N,N-dipropylaminocarbo-nyl)-1-butyl)pyrrolidine-3-carboxylic acid The procedure of Example 73C was followed, with the substitution of the less polar isomer from Example 77A for the resultant product from Example 73B, to provide the title compound in 100% yield. $^1$H NMR (CD$_3$OD, 300 MHz) and MS identical to those of Example 75C.

EXAMPLE 78

(2R,3R,4R)-2-(4-Methoxyphenyl)-4-(1,3-benzo-dioxol-5-yl)-1-((1S)-1-(N,N-dipropylaminocarbo-nyl)-1-butyl)pyrrolidine-3-carboxylic acid The procedure of Example 73C was followed, with the substitution of the more polar isomer from Example 77A for the resultant product from Example 73B, to provide the title compound in 88% yield. $^1$H NMR (CD$_3$OD, 300 MHz) and MS identical to those of Example 76.

EXAMPLE 79 trans,trans-2-(4-Methoxyphenyl)-4-(1,3-benzo-dioxol-5-yl)-1-(N,N-di(n-butyl)aminocarbonylm-ethyl)-3-(5-tetrazolyl)pyrrolidine Carbonyldiimidazole (510 mg, 3.148 mmol) was added to 1.020 g (2.00 mmol) of the compound resulting from Example 43 in 2.7 mL THF, and the mixture was heated for 40 minutes at 50° C. The reaction mixture was cooled in an ice bath, and 25% solution of ammonia in methanol was added. After 30 minutes, the solid which had formed was filtered, washed with ethanol and finally with ether to yield 850 mg (83%) of the 3-carboxamide compound. m.p. 194–196° C.

Phosphorus oxychloride (1.06 g) was added to this amide in 7 mL of pyridine, and the mixture was stirred 1 hour at room temperature. Dichloromethane was added, and the solution was washed with potassium bicarbonate solution, dried over sodium sulfate, and concentrated. The residue was chromatographed on silica gel eluting with 2:1 hexane-ethyl acetate to give 790 mg (96%) of the 3-carbonitrile compound.

To this nitrile in 5 mL toluene was added 385 mg of trimethyl tin chloride and 126 mg sodium azide. The mixture was heated 20 hours at 125° C. (bath temp). After cooling, methanol (5 mL) was added, and the solution was concentrated in vacuo. To the resulting residue was added 6 mL of methanol and 6 mL of water containing 0.2 g phosphoric acid. After stirring 1 hour at room temperature, water was added and the mixture extracted with dichloromethane. The combined organic extracts were dried and concentrated, and the resulting residue was crystallized from ether to give a solid. The solid was dissolved in sodium hydroxide solution, filtered from insoluble material and acidified with acetic acid to get 532 mg (62%) of the title compound. m.p. 165–167° C. $^1$H NMR (CDCl$_3$, 300 MHz) δ 0.85 (t, J=7 Hz, 3H), 0.87 (t, J=7 Hz, 3H), 1.10–1.50 (m, 8H), 3.0–3.6 (m, 8H), 3.70 (s, 3H), 3.7–3.8 (m, 1H), 3.90 (t, J=9 Hz, 1H), 4.37 (d, J=9 Hz, 1H), 5.86 (s, 2H), 6.62 (d, J=8 Hz, 1H), 6.65–6.73 (m, 3H), 6.95 (d, J=2 Hz, 1H), 7.11 (d, J=9 Hz, 2H).

EXAMPLE 80 trans,trans-2-(4-Fluorophenyl)-4-(1,3-benzodioxol-5-yl)-1-(N,N-di(n-butyl)aminocarbonylmethyl)pyr-rolidine-3-carboxylic acid The title compound was prepared as an amorphous solid from methyl (4-flourobenzoyl) acetate and 5-(2-nitrovinyl)-1,3-benzodioxole using the procedures described in Examples 1 and 43. $^1$H NMR (CDCl$_3$, 300 MHz) δ 0.81 (t, J=7 Hz, 3H), 0.90 (t, J=7 Hz, 3H), 1.0–1.55 (m, 8H), 2.81 (d, J=13 Hz, 1H), 2.90–3.10 (m, 4H), 3.15–3.30 (m, 1H), 3.32–3.45 (m, 3H), 3.55–3.65 (m, 1H), 3.86 (d, J=10 Hz, 1H), 5.94 (dd, J=2 Hz, 4 Hz, 2H), 6.72 (d, J=8 Hz, 1H), 6.86 (d, J=8 Hz, 1H), 6.95–7.07 (m, 3H), 7.32–7.45 (m, 2H).

EXAMPLE 81 trans,trans-2-(4-Methoxyphenyl)-4-(1,3-benzo-dioxol-5-yl)-1-(N,N-di(n-butyl)aminocarbonylm-ethyl)pyrrolidine-3-carboxylic acid N,N-Dibutyl glycine (150 mg, 0.813 mmol), prepared by the method of Bowman, R. E., J. Chem. Soc. 1346 (1950), in 0.7 mL of THF was treated with 138 mg (0.852 mmol)

carbonyldiimidazole and heated for 30 minutes at 50° C. After cooling to room temperature, 250 mg (0.678 mmol) of ethyl trans,trans-2-(4-methoxyphenyl)-4-(1,3-benzodioxol-5-yl)-pyrrolidine-3-carboxylate, the compound resulting from Example 6A, was added, and the mixture was heated at 45° C. for 30 minutes. The product was chromatographed on silica gel, eluting with 1:1 hexane-ethyl acetate to give 306 mg of the intermediate ethyl ester.

The ester was hydrolyzed with sodium hydroxide in water and ethanol to give 265 mg of the title compound as a white powder. $^1$H NMR (CDCl$_3$, 300 MHz) δ rotational isomers −0.75 and 0.85 (2 t, J=7 Hz, 3H), 1.05–1.5 (m, 8H), 2.65–3.20 (m, 6H) 3.43–3.70 (m, 3H), 3.72 (s, 3H), 3.87 (d, J=15 Hz, 1H), 4.49 (dd, J=12 Hz, 6 Hz) and 5.23 (dd, J=12 Hz, 8 Hz) 2H, 5.90 (dd, J=2 Hz, 4 Hz, 2H), 6.63–6.78 (m, 3H), 6.86 and 7.04 (d, J=9 Hz, 2H), 7.22 (d, J=9 Hz, 2H).

EXAMPLE 82 trans,trans-2-(4-Methoxyphenyl)-4-(1,3-benzo-dioxol-5-yl)-1-(N-n-butyl)-N-(n-propyl)aminocarbonylmethyl)pyrrolidine-3-carboxylic acid The title compound was prepared using the procedures described in Example 1. m.p. 160–162° C. $^1$H NMR (CDCl$_3$, 300 MHz) rotational isomers δ 0.69, 0.80, 0.84, 0.87 (four triplets, J=7 Hz, 6H), 1.00–1.52 (m, 6H), 2.63 and 2.66 (two doublets, J=13 Hz, 1H), 2.90–3.10 (m, 4H), 3.23–3.61 (m, 5H), 3.71 and 3.75 (two doublets, J=10 Hz, 1H), 3.78 (s, 3H), 5.92–5.96 (m, 2H), 6.72 (d, J=8 Hz, 1H), 6.83–6.89 (m, 3H), 7.03 (d, J=2 Hz, 1H), 7.81 (d, J=9 Hz, 2H).

EXAMPLE 83 trans,trans-2-(4-Methoxyphenyl)-4-(1,3-benzo-dioxol-5-yl)-1-[2-(N,N-di(n-propyl)aminocarbonyl)ethyl]pyrrolidine-3-carboxylic acid The compound resulting from Example 6A (250 mg, 0.677 mmol), 205 mg (1.36 mmol) diallyl acrylamide (Polysciences, Inc.), and 10 mg acetic acid were heated at 85° C. in 0.75 mL of methoxyethanol for one hour. Toluene was added, and the solution was washed with bicarbonate solution, dried, and concentrated. Chromatography on silica gel eluting with 3:1 hexane-ethyl acetate gave 283 mg (80%) of the diallyl compound.

The diallyl compound was hydrogenated using 10% Pd/C catalyst (27 mg) in ethyl acetate (25 mL) under a hydrogen atmosphere. The catalyst was removed by filtration, and the filtrate was concentrated to afford the dipropyl amide ethyl ester in 100% yield.

The ester was hydrolyzed to the title compound by the method of Example 1D in 83% yield. $^1$H NMR (CDCl$_3$, 300 MHz) δ 0.82 and 0.83 (two triplets, J=7 Hz, 6H), 1.39–1.54 (m, 4H), 2.35–2.60 (m, 3H), 2.80–3.07 (m, 5H), 3.14–3.21 (m, 2H), 3.31–3.38 (m, 1H), 3.51–3.61 (m, 1H), 3.73 (d, J=12H, 1H), 3.75 (s, 3H), 5.94 (s, 2H), 6,71 (d, J=9 Hz, 1H), 6.79–6.85 (m, 3H), 7.04 (d, J=2 Hz, 1H)<7.32 (d, J=9 Hz, 2H).

EXAMPLE 84 trans,trans-2-(4-Methoxyphenyl)-4-(1,3-benzo-dioxol-5-yl)-1-(N,N-di(n-butyl)aminocarbonyl)pyrrolidine-3-carboxylic acid The title compound was prepared by the procedures described in Example 8 using dibutyl carbamoyl chloride, prepared by the method of Hoshino et al., Syn. Comm., 17: 1887–1892 (1987), as a starting material. $^1$H NMR (CDCl$_3$, 300 MHz) δ 0.86 (t, J=7 Hz, 6H), 1.14–1.28 (m, 4H), 1.35–1.48 (m, 4H), 2.81–2.94 (m, 2H), 3.11 (t, J=12 Hz, 1H), 3.30–3.41 (m, 2H), 3.59–3.68 (m, 2H), 3.76 (s, 3H), 3.78–3.85 (m, 1H), 5.81 (d, J=9 Hz, 1H), 5.94 (s, 2H), 6.73–6.86 (m, 5H), 7.24 (d, J=9 Hz, 2H).

EXAMPLE 85 trans,trans-2-(4-Methoxyphenyl)-4-(1,3-benzo-dioxol-5-yl)-1-(N,N-di(n-butyl)aminocarbonylmethyl)pyrrolidine-3-carboxylic acid sodium salt Sodium hydroxide (48.2 mg of 98.3% pure, 1.184 mmol) in 2 mL of MeOH was added to the compound resulting from Example 43 (610 mg, 1.196 mmol.) in 5 mL MeOH. The solution was concentrated to dryness, and the resulting powder was stirred with heptane. The heptane was removed in vacuo to give a powder which was dried in the vacuum oven for 2 hours at 60° C. to yield 627.5 mg of the title compound.

EXAMPLE 86 trans,trans-2-(4-Methoxyphenyl)-4-(1,3-benzo-dioxol-5-yl)-1-[2-(N,N-di(n-butyl)amino)ethyl]pyrrolidine-3-carboxylic acid A solution of the bromoethyl compound resulting from Example 61A (150 mg), dibutylamine (150 mg) and sodium iodide (18 mg) in 0.75 mL ethanol was heated at 80° C. for 1 hour. After cooling, toluene was added, and the solution was washed with potassium bicarbonate solution, dried over Na$_2$SO$_4$ and concentrated. More toluene was added, and the solution was again concentrated to get rid of excess dibutylamine. The residue was dissolved in warm heptane and filtered from a small amount of insoluble material. The hepane was removed in vacuo to give 143 mg (87%) of the intermediate ethyl ester.

The ester was hydrolyzed by the method of Example 1D to give the title compound as a white powder. $^1$H NMR (CD$_3$OD, 300 MHz) δ 0.89 (t, J=7 Hz, 6H), 1.16–1.30 (m, 4H), 1.44–1.56 (m, 4H), 2.48–2.57 (m, 1H), 2.80–3.08 (m, 8H), 3.14–3.25 (m, 1H), 3.31–3.38 (m, 1H), 3.59–3.60 (m, 1H), 3.74 (s, 3H), 3.75 (d, J=10 Hz, 1H), 5.89 (s, 2H), 6.71 (d, J=9 Hz, 1H), 6.81 (dd, J=9 Hz, 2 Hz, 1H), 6.90 (d, J=10 Hz, 2H), 6.96 (d, J=2 Hz, 1H), 7.37 (d, J=10 Hz, 2H).

EXAMPLE 87 trans,trans-2-(4-Methoxyphenyl)-4-(1,3-benzo-dioxol-5-yl)-1-[2-[N-(N,N-di(n-butyl)aminocarbonyl)-N-methylamino]ethyl]pyrrolidine-3-carboxylic acid Dibutyl carbamoyl chloride (135 mg) was added to the compound resulting from Example 61B (250 mg) and 150 mg triethylamine in 1 mL dichloromethane. After stirring 1 hour at room temperature, toluene was added, and the solution was washed with potassium bicarbonate solution, dried over Na$_2$SO$_4$ and concentrated. The residue was chromatographed on silica gel, eluting with a mixture of 38% EtOAc and 62% hexane to give 194 mg of the ethyl ester intermediate.

The ester was hydrolyzed by the method of Example 1D to afford 141 mg of the title compound. $^1$H NMR (CD$_3$OD, 300 MHz) δ 0.92 (t, J=7 Hz, 6H), 1.21–1.32 (m, 4H), 1.42–1.53 (m, 4H), 2.62 (s, 3H), 2.65–2.76 (m, 1H), 3.00–3.20 (m, 8H), 3.44–3.55 (m, 1H), 3.62–3.78 (m, 2H), 3.80 (s, 3H), 4.07 (d, J=12 Hz, 1H), 5.93 (s, 2H), 6.75 (d, J=9 Hz, 1H), 6.87 (dd, J=9 Hz, 2 Hz, 1H), 6.94 (d, J=10 Hz, 2H), 7.04 (d, J=2 Hz, 1H), 7.40 (d, J=10 Hz, 2H).

EXAMPLE 88 trans,trans-2-(4-Methoxyphenyl)-4-(1,3-benzo-dioxol-5-yl)-1-(N,N-di(n-butyl)aminocarbonylmethyl)pyrrolidine-3-(N-methanesulfonyl)carboxamide Carbonyldiimidazole (75 mg, 0.463 mmol) was added to 150 mg (0.294 mmol) of the compound resulting from Example 43 in 0.4 mL of tetrahydrofuran, and the solution was stirred at 60° C. for 2 hours. After cooling, 50 mg (0.526 mmol) of methanesulfonamide and 68 mg (0.447 mmol) of DBU in 0.3 mL of THF were added. The mixture was stirred at 45° C. for 2 hours. The solvents were removed in vacuo, and the residue was dissolved in water. A few drops of acetic acid were added, and the solution was lyophilized to give 121 mg (70%) of the title compound. m.p. 170–173° C. $^1$H NMR (CDCl$_3$, 300 MHz) δ 0.82 (t, J=7 Hz, 3H), 0.88 (t, J=7 Hz, 3H), 1.05–1.51 (m, 8H), 2.75–2.86 (m, 2H), 2.83–3.25 (m, 4H), 3.17 (s, 3H), 3.32–3.50 (m, 3H), 3.70–3.78 (m, 1H), 3.80 (s, 3H), 3.87 (d, J=10 Hz, 1H), 5.96 (dd, J=2 Hz, 4 Hz, 2H), 6.74 (d, J=9 Hz, 1H), 6.84 (dd, J=9 Hz, 2 Hz, 1H), 6.90 (d, J=10 Hz, 2H), 7.01 (d, J=2 Hz, 1H), 7.34 (d, J=10 Hz, 2H).

EXAMPLE 89 trans,trans-2-(4-Methoxyphenyl)-4-(1,3-benzo-dioxol-5-yl)-1-(N,N-di(n-butyl)aminocarbonylmethyl)pyrrolidine-3-(N-benzenesulfonyl)carboxamide The compound resulting from Example 43 was converted to the title compound by the method of Example 88 substituting benzenesulfonamide for methanesulfonamide. m.p. 169–171° C. for a sample recrystallized from acetonitrile. $^1$H NMR (CDCl$_3$, 300 MHz) δ 0.81(t, J=7 Hz, 3H), 0.89 (t, J=7 Hz, 3H), 1.02–1.50 (m, 8H), 2.65–2.80 (m, 2H), 2.90–3.25 (m, 4H), 3.80–3.95 (m, 3H), 3.50–3.60 (m, 1H), 3.65 (d, J=10 Hz, 1H), 3.81 (s, 3H), 5.94 (s, 2H), 6.70 (s, 2H), 6.81–6.90 (m, 3H), 7.17 (d, J=10 Hz, 2H), 7.55 (t, J=7 Hz, 2H), 7.66 (t, J=7 Hz, 1H), 8.95 (d, J=7 Hz, 2H).

EXAMPLE 90 trans,trans-2-(4-Methoxyphenyl)-4-(1,3-benzo-dioxol-5-yl)-1-[N,N-di(n-butyl) aminosulfonylmethyl]-pyrrolidine-3-carboxylic acid Chloromethyl sulfenyl chloride, prepared by the method of Brintzinger et. al., Chem. Ber. 85: 455–457 (1952), is reacted with dibutylamine by the method of E. Vilsmaier described in Liebigs Ann. Chem. 1055–1063 (1980) to give N,N-dibutyl chloromethyl sulfenyl chloride. Alternatively dimethyl(methylthio)sulfonium tetraflouroborate is reacted with dibutylamine to give N,N-dibutyl methylsulfenyl chloride which is chlorinated with N-chlorosuccinimide to give chloromethyl sulfenyl chloride by the method of E. Vilsmaier, described in the above reference.

The N,N-dibutyl chloromethyl sulfenyl chloride is reacted with the compound resulting from Example 6A to give ethyl trans,trans-2-(4-Methoxyphenyl)-4-(1,3-benzodioxol-5-yl)-1-[N,N-di(n-butyl)aminosulfenylmethyl]-pyrrolidine-3-carboxylate. This is oxidized with osmium tetroxide and N-methyl morpholine N-oxide by the method of S. Kaldor and M. Hammond, Tet. Lett. 32: 5043–5045 (1991) to give the title compound after hydrolysis of the ethyl ester.

EXAMPLE 91 trans,trans-2-(4-Methoxyphenyl)-4-(1,3-benzo-dioxol-5-yl)-1-[(N,N-di(n-butyl)aminocarbonyl-1-(RS)-ethyl]pyrrolidine-3-carboxylic acid

EXAMPLE 91A (+)-Dibutyl 2-bromopropanamide

2-Bromopropanoic acid (510 mg, 3.33 mmol) and 4-methylmorpholine (0.74 mL, 6.73 mmol) were dissolved in 10 mL of CH$_2$Cl$_2$, the solution was cooled to 0° C. under a N$_2$ atmosphere, and then treated dropwise with isobutyl chloroformate (0.45 mL, 3.5 mmol). After 10 minutes at 0° C., dibutylamine (0.57 mL, 3.4 mmol) was added. The reaction was stirred at 0° C. for 1 hour and for an additional 16 hours at room temperature. The mixture was partitioned with 25 mL of 1.0 M aqueous Na$_2$CO$_3$ solution, then the organic phase was washed sequentially with 25 mL of 1 M aqueous NaHSO$_4$ and 25 mL brine, dried (Na$_2$SO$_4$), filtered, and concentrated under reduced pressure to afford 698 mg (2.64 mmol, 79%) of the crude bromoamide as a colorless oil. $^1$H NMR (CDCl$_3$, 300 MHz) δ 0.93 (t, J=7 Hz) and 0.97 (t, J=7.5 Hz, 6H total), 1.26–1.60 (m, 7H), 1.60–1.78 (m, 1H), 1.82 (d, J=6 Hz, 3H), 3.04–3.27 (m, 2H), 3.42–3.64 (m, 2H), 4.54 (q, J=7H, 1H). MS (DCI/NH$_3$) m/e 264 and 266 (M+H)$^+$.

EXAMPLE 91B trans,trans- and cis, trans-2-(4-Methoxyphenyl)-4-(1,3-benzodioxol-5-yl)-1-((N,N-di(n-butyl)amino) carbonyl-1-(RS)-ethyl)pyrrolidine-3-carboxylic acid ethyl ester A solution of the resultant mixture of trans,trans and cis,trans compounds from Example 1C (232 mg, 0.628 mmol) and the resultant compound from Example 91A (183 mg, 0.693 mmol) in 2 mL of CH$_3$CN was treated with diisopropylethylamine (0.22 mL, 1.3 mmol). The solution was stirred at 60–80° C. under a N$_2$ atmosphere for 16 hours. The reaction was concentrated under reduced pressure, then the residue was partitioned between 30 mL Et$_2$O and 10 mL of 1 M aqueous Na$_2$CO$_3$ solution. The organic phase was washed with 20 mL water and 20 mL brine, dried over Na$_2$SO$_4$, filtered and concentrated under reduced pressure to afford the crude amino amide as a brown oil (339 mg, 98% crude). The product was obtained by flash chromatography on silica gel eluting with 20% EtOAc-hexane to provide 224 mg (70%) of the title compounds as a mixture of 4 diastereomers. $^1$H NMR (CDCl$_3$, 300 MHz) δ 0.66–1.55 (several m, 19H), 2.63–3.00 (m, 3H), 3.05–3.39 (m, 2H), 3.40–3.76 (m, 4H), 3.78–3.80 (4 s, 3H), 3.84–4.25 (m, 2.6H), 4.38 (d, J=10.5 Hz, 0.2H) and 4.58 (d, J=10.5 Hz, 0.2H), 5.90–5.97 (m, 2H), 6.68–6.96 (m, 5H), 7.38–7.43 (m, 2H). MS (DCI/NH$_3$) m/e 553 (M+H)$^+$.

EXAMPLE 91C trans,trans-2-(4-Methoxyphenyl)-4-(1,3-benzodioxol-5-yl)-1-((N,N-dibutylamino)carbonyl-1-(RS)-ethyl)pyrrolidine-3-carboxylic acid The procedure of Example 73C was used, substituting the resultant compound from Example 91B for the resultant compound from Example 73B to give the title compound in 61% yield. $^1$H NMR (CD$_3$OD, 300 MHz) δ 0.70–1.05 (several m, 8H), 1.14 (d, J=6 Hz, 2H), 1.17–1.55 (m, 6H), 2.79–3.03 (m, 3.5H), 3.20–3.65 (br m, 4.6H plus CD$_2$HOD), 3.70–3.78 (m, 0.4H), 3.79 (s, 3H), 3.98 (d, J=8 Hz, 0.6H), 4.06 (t, J=7.5 Hz, 0.4H), 4.25 (d, J=8 Hz, 0.4H), 5.92 (s) and 5.94 (s, 2H total 6H), 6.73 (d, J=2.5 Hz) and 6.75 (d, J=3 Hz,1H total), 6.78–6.85 (m,1H), 6.91–7.00 (m, 3H), 7.30–7.38 (m, 2H). MS (DCI/NH$_3$) m/e 525 (M+H)$^+$. Anal calcd for C$_{30}$H$_{40}$N$_2$O$_6$·0.5H$_2$O: C, 67.52; H, 7.74; N, 5.25. Found: C, 67.63; H, 7.65; N, 5.21.

EXAMPLE 92 trans,trans-2-(Pentyl)-4-(1,3-benzodioxol-5-yl)-1-(N,N-di(n-butyl)aminocarbonylmethyl)pyrrolidine-3-carboxylic acid

EXAMPLE 92A

Methyl 2-(4-hexenoyl)-4-nitro-3-(1,3-benzodioxole-5-yl)butyrate

A solution of methyl 3-oxo-6-octenoate (502 mg, 2.95 mmol) in 10 mL of isopropanol was added to a solution of 5-(2-nitrovinyl)-1,3-benzodioxole (712 mg, 3.69 mmol) in 10 mL THF, then DBU (22 μL, 0.15 mmol) was added. The resulting reddish solution was stirred at room temperature for 20 minutes. TLC (ethyl acetate-hexane, 1:3) indicated complete consumption of ketoester. The solution was concentrated in vacuo and flash chromatographed on silica gel eluting with 18% ethyl acetate in hexane to produce 879 mg (2.42 mmol, 82%) of the title compound as a mixture of diastereomers in a 1:1 ratio. $^1$H NMR (CDCl$_3$, 300 MHz) δ 1.55–1.66 (m, 3H), 2.02–2.17 (br m, 1H), 2.20–2.37 (m, 1.5H), 2.49–2.76 (m, 1.5H), 3.57 (s, 1.5H), 3.74 (s, 1.5H), 3.97 (d, J=7.5H, 0.5H) and 4.05 (d, J=8 Hz, 0.5H), 4.10–4.20 (m, 1H), 4.68–4.82 (m, 2H), 5.06–5.52 (m, 2H), 5.95 (2s, 2H), 6.65 (m, 1H), 6.68 (br s,1H), 6.75 (d, 7.5 Hz, 1H). MS (DCI/NH$_3$) m/e 381 (M+NH$_4$)$^+$. Anal calcd for C$_{18}$H$_{21}$NO$_7$: C, 59.50; H, 5.82; N, 3.85. Found: C, 59.32; H, 5.71; N, 3.72.

EXAMPLE 92B

Methyl trans,trans-2-(pentyl)-4-(1,3-benzodioxol-5-yl)pyrrolidine-3-carboxylate

The procedures of Example 1B and Example 1C were followed, with the substitution of the resultant compound from Example 92A for the resultant compound from Example 1A, and the substitution of the this resultant compound for the resultant compound from Example 1B, to provide the title compound in crude form as a yellow oil. This crude compound was epimerized under the following conditions. A solution of the crude compound (660 mg, 2.07 mmol) in 3 mL methanol was treated with a solution of sodium methoxide (made by the addition of sodium metal (14 mg, 0.61 mmol) to 1 mL of methanol). The resultant solution was heated at reflux for 18 hours. The reaction was concentrated under reduced pressure, and the residue was partitioned between 25 mL saturated NaHCO$_3$ diluted with 10 mL water and 30 mL of CH$_2$Cl$_2$. The aqueous phase was extracted (2×30 mL CH$_2$Cl$_2$), then the combined organic phases were washed with 20 mL brine, dried over Na$_2$SO$_4$, filtered and the filtrate concentrated under reduced pressure to afford the crude product. Purification by flash chromatography on silica gel eluting with 3.5% methanol in CH$_2$Cl$_2$ gave 336 mg (57%) the title compound as a yellow oil. $^1$H NMR (CDCl$_3$, 300 MHz) δ 0.90 (br t, 3H), 1.25–1.70 (br m, 8H), 1.83–2.02 (br s, 2H), 2.58 (dd, J=8,9 Hz, 1H), 2.99 (dd, J=8,14 Hz, 1H), 3.34–3.45 (m, 2H), 3.53 (q, J=9 Hz, 1H), 3.66 (s, 3H), 5.94 (s, 2H), 6.65–6.75 (m, 3H). MS (DCI/NH$_3$) m/e 320 (M+H)$^+$. Anal calcd for C$_{18}$H$_{25}$NO$_4$: C, 67.69; H, 7.89; N, 4.39. Found: C, 67.39; H, 7.84; N, 4.37.

EXAMPLE 92C trans,trans-2-(Pentyl)-4-(1,3-benzodioxol-5-yl)-1-(N,N-di(n-butyl)aminocarbonylmethyl)pyrrolidine-3-carboxylic acid The procedures of Example 1B–1D were used, with the substitution of the resultant compound from Example 92A for the resultant compound from Example 1B, to provide the title compound as a white foam. $^1$H NMR (CDCl$_3$, 300 MHz) δ 0.87 (br t) and 0.89 (br t, 6H total), 0.97 (t, J=7.5 Hz, 3H), 1.21–1.42 (br m, 10), 1.43–1.78 (br m, 6H), 2.76 (t, J=7 Hz, 1H), 3.02–3.30 (br m, 6H), 3.40–3.60 (m, 3H), 3.73 (d, J=14 Hz, 1H), 5.98 (AB, 2H), 6.70 (d, J=7 Hz, 1H), 6.77 (dd, J=1.5,7 Hz, 1H), 6.89 (d, J=1.5 Hz, 1H). MS (DCI/NH$_3$) m/e 475 (M+H)$^+$. Anal calcd for C$_{27}$H$_{42}$N$_2$O$_5$·0.5H$_2$O: C, 67.05; H, 8.96; N, 5.79. Found: C, 67.30; H, 8.77; N, 5.68.

EXAMPLE 93 trans,trans-2-(Pentyl)-4-(1,3-benzodioxol-5-yl)-1-[2-(N-propyl-N-propylsulfonylamino)ethyl]pyrrolidine-3-carboxylic acid

EXAMPLE 93A

Methyl trans,trans-2-(pentyl)-4-(1,3-benzodioxol-5-yl)-1-(2-bromoethyl)pyrrolidine-3-carboxylate The procedure of Example 61A was used, with the substitution of the resultant compound from Example 92B for the resultant compound from Example 1C, to provide the title compound as a yellow oil. $^1$H NMR (CDCl$_3$, 300 MHz) δ 0.89 (br t, J=7 Hz, 3H), 1.24–1.40 (br m, 6H), 1.60–1.80 (br m, 2H), 2.61–2.75 (m, 2H), 2.76–2.91 (m, 2H), 3.10–3.22 (m, 2H), 3.36–3.47 (m, 2H), 3.68 (s, 3H), 5.92 (s, 2H), 6.69–6.77 (m, 2H), 6.90–6.94 (m,1H). MS (DCI/NH$_3$) m/e 426, 428 (M+H)$^+$.

EXAMPLE 93B

Methyl trans,trans-2-(Pentyl)-4-(1,3-benzodioxol-5-yl)-1-[2-(N-propyl-N-propylsulfonylamino)ethyl]pyrrolidine-3-carboxylate A solution of the resultant compound from Example 93A (102 mg, 0.24 mmol) and tetrabutylammonium iodide (6 mg, 16,mol) in 1 mL EtOH was treated with propylamine (60 μL, 0.73 mmol). The solution was warmed to 80° C. for 4 hours. The reaction was concentrated under reduced pressure, then the residue was dissolved in 35 mL ethyl acetate and extracted with 2×15 mL of 1 M aqueous $Na_2CO_3$. The organic phase was washed with 15 mL brine, then dried over $Na_2SO_4$, filtered and concentrated under reduced pressure to provide the crude secondary amine as a yellow oil (94.2 mg). The crude amine was dissolved in 1 mL of $CH_2Cl_2$, diisopropylethylamine (65 μL, 0.373 mmol) was added, followed by propylsulfonyl chloride (29 μL, 0.26 mmol). The solution was stirred at room temperature for 4 hours. The reaction was quenched with 10% aqueous citric acid (to pH 4), and the mixture was extracted with 2×3 mL $CH_2Cl_2$. The combined organic extracts were washed with 2 mL brine, then dried over $Na_2SO_4$, filtered, concentrated in vacuo. Purification by flash chromatography eluting with 20% ethyl acetate in hexane provided 65.0 mg (53%) of the title compound as a waxy solid. $R_f$=0.17 (20% EtOAc-hexane). MS (DCI/$NH_3$) m/e 511 $(M+H)^+$.

EXAMPLE 93C trans,trans-2-(Pentyl)-4-(1,3-benzodioxol-5-yl)-1-[2-(N-propyl-N-propylsulfonylamino)ethyl]pyrrolidine-3-carboxylic acid The procedure of Example 71C was followed, with the substitution of the resultant compound from Example 93B for the resultant compound from Example 71B, to provide the title compound as a white foam (47 mg, 80%), $R_f$=0.14 (5% MeOH—$CH_2Cl_2$). $^1$H NMR ($CDCl_3$, 300 MHz) δ 0.88 (br t) and 0.92 (t, J=7 Hz, 6H total), 1.22–1.52 (br m, 6H), 1.63 (sextet, J=8 Hz, 2H), 1.75–2.10 (br m, 4H), 2.89–2.98 (m, 2H), 3.05 (br t, J=9 Hz, 1H), 3.10–3.30 (m, 3H), 3.30–3.80 (br m, 7H), 5.94 (s, 2H), 6.71 (t, J=8 Hz, 1H), 6.77 (dd, J=1.5,8 Hz, 1H), 6.89 (d, J=1.5 Hz, 1H). MS (DCI/$NH_3$) m/e 497 $(M+H)^+$.

EXAMPLE 94 trans,trans-2-(Propyl)-4-(1,3-benzodioxol-5-yl)-1-(N,N-di(n-butyl)aminocarbonylmethyl)pyrrolidine-3-carboxylic acid

EXAMPLE 94A

Ethyl 2-(4-butanoyl)-4-nitro-3-(1,3-benzodioxole-5-yl)butyrate

The procedure of Example 92A was followed, with the substitution of ethyl butyryl acetate for methyl 3-oxo-6-octenoate, to provide the title compound as a mixture of trans and cis isomers (47 mg, 80%), $R_f$=0.28 (25% EtOAc-hexane). $^1$H NMR ($CDCl_3$, 300 MHz) δ 0.74 (t, J=7.5 Hz) and 0.91 (t, J=7.5 Hz, 3H total), 1.08 (t, J=7 Hz) and 1.28 (t, J=7 Hz, 3H total), 1.45 (sextet, J=7 Hz, 1.5H), 1.63 (sextet, J=7 Hz, approx. 1.5H), 2.17 (t, J=7 Hz) and 2.24 (t, J=7 Hz, 0.5H total)2.40–2.54 (m, 1H), 2.60 (t, J=7.5 Hz) and 2.67 (t, J=7.5 Hz, 0.5H total), 3.93–4.09 (m, 2H), 4.10–4.20 (br m, 1H), 4.23 (q, J=7 Hz, 1H), 4.67–4.85 9m, 2H), 5.94 (s, 2H), 6.62–6.75 (m, 3H). MS (DCI/$NH_3$) m/e 369 $(M+NH_4)^+$. Anal calcd for $C_{17}H_{21}NO_7$: C, 58.11; H, 6.02; N, 3.99. Found: C, 58.21; H, 5.98; N, 3.81.

EXAMPLE 94B

Ethyl trans,trans-2-(propyl)-4-(1,3-benzodioxol-5-yl)pyrrolidine-3-carboxylate

The procedure of Example 92B was followed, with the substitution of the resultant compound from Example 94A for the resultant compound from Example 92A, to afford the title compound. MS (DCI/$NH_3$) m/e 306 $(M+H)^+$.

EXAMPLE 94C trans,trans-2-(Propyl)-4-(1,3-benzodioxol-5-yl)-1-((N,N-di(n-butyl)aminocarbonylmethyl)-pyrrolidine-3-carboxylic acid The procedure of Example 92C was followed, with the substitution of the resultant product from Example 94B for the resultant product from Example 92B, to give the title compound. $^1$H NMR ($CDCl_3$, 300 MHz) δ 0.89 (t, J=7.5 Hz), 0.92 (t, J=7.5 Hz), and 0.97 (t, J=7.5H, 9H total), 1.22–1.80 (br m, 12H), 2.83 (t, J=7.5 Hz,1H), 3.40–3.55 (br m, 2H), 3.55–3.68 (m,1H), 3.78 (d, J=15 Hz,1H), 5.92 (q, J=1 Hz, 2H), 6.70 (d, J=8 Hz, 1H), 6.79 (dd, J=1 Hz,8 Hz, 1H), 6.90 (d, J=1 Hz, H). MS (DCI/$NH_3$) m/e 447 $(M+H)^+$. Anal calcd for $C_{25}H_{38}N_2O_5 \cdot 0.5H_2O$: C, 65.91; H, 8.63; N, 6.15. Found: C, 65.91; H, 8.68; N, 5.94.

EXAMPLE 95

(2R,3R,4S)-(+)-2-(4-Methoxyphenyl)-4-(1,3-benzodioxol-5-yl)-1-(tert-butyloxycarbonyl-aminocarbonylmethyl)-pyrrolidine-3-carboxylic acid

EXAMPLE 95A trans,trans-2-(4-Methoxyphenyl)-4-(1,3-benzodioxol-5-yl)-1-([tert-butyloxycarbonylaminocarbonylmethyl]pyrrolidine-3-carboxylic acid The resulting mixture of 64% trans,trans- and cis,trans-pyrrolidines resulting from Example 1C (3.01 g, 8.15 mmol) was dissolved in 50 mL of methylene chloride. To this was added dropwise a solution of di-tert-butyl dicarbonate (1.96 g, 8.97 mmol) in 20 mL methylene chloride under a nitrogen atmosphere, and the resulting solution was stirred 30 minutes at which point TLC (ethyl acetate:hexane, 1:1) indicated that all of the starting material was consumed. The reaction mixture was concentrated and dried under high vacuum to give 3.94 g of the ethyl ester as a yellow-brown oil. $^1$H NMR ($CDCL_3$, 300 MHz) δ 0.99, 1.07 (br t, br t, J=7 Hz, 3H), 1.11–1.62 (several br m, 9H), 3.05 (br m, 1H), 3.44–3.95 (m, 3H), 3.81 (s, 3H), 4.04 (q, J=7 Hz, 1H), 4.14–4.28 (br m, 1H), 4.89–5.24 (br m, 1H), 5.94 (d, J=3 Hz, 2H), 6.69–6.90 (m, 5H), 7.06–7.20 (m, 2H). MS (DCI/$NH_3$) m/e 470 $(M+H)^+$.

To the ethyl ester dissolved in 170 mL of ethanol was added a solution of lithium hydroxide (1.06 g, 25.17 mmol) in 60 mL of water. The reaction mixture was vigorously stirred for 18 hours under a nitrogen atmosphere. The reaction mixture was concentrated to remove ethanol, diluted with 250 mL of water and extracted three times with 250 mL of ether. The organic phase acidified to slight cloudiness (pH ~7) with 1 N hydrochloric acid, then to pH 4 with 10% citric acid and extracted with 5% ethanol in methylene chloride (3×100 mL). The combined organic layers dried ($Na_2SO_4$), filtered, concentrated and dried on high vacuum to give the title compound as a white foam (2.19 g, 60%). $^1$H NMR ($CDCl_3$, 300 MHz) δ 1.16 (v br s, 9H), 3.11 (br m, 1H), 3.50–3.64 (m, 2H), 3.81 (s, 3H), 4.24 (br m, 1H), 4.96 (br m, 1H), 5.94 (s, 2H), 6.71–6.79 (m, 3H), 6.84–6.91 (m, 2H), 7.19 (d, J=9 Hz, 2H). MS (DCI/$NH_3$) m/e 442 $(M+H)^+$.

EXAMPLE 95B (2R,3R,4S)-(+)-2-(4-Methoxyphenyl)-4-(1,3-benzodioxol-5-yl)-1-(tert-butyloxycarbonylaminocarbonylmethyl)-pyrrolidine-3-carboxylic acid The compound resulting from Example 95A (2.15 g, 4.86 mmol) and (+)-cinchonine (1.43 g, 4.86 mmol) were added to 100 mL of methylene chloride; this suspension was swirled with warming as necessary to get all solids to dissolve. The solution was then concentrated and dried on high vacuum to a white foam. This material was crystallized from a mixture of refluxing chloroform (64 mL) and hexane (360 mL). The resulting crystals were isolated by filtration and recrystallized under the same conditions seven additional times. Each time the resulting crystals and filtrate were monitored by $^1$H NMR and chiral HPLC. The amount of (2S,3S,4R)-(−)-enantiomer decreased first in the crystals and then in the filtrate with the predetermined endpoint achieved when the (2S,3S,4R)-(−)-enantiomer could no longer be detected in the filtrate. The pure (2R,3R,4S)-(+)-enantiomer thus obtained was partitioned between 100 mL of 10% citric acid and 100 mL of ether. The aqueous layer was further extracted twice with 100 mL of ether. The combined ether layers were washed with brine, dried ($Na_2SO_4$), filtered, concentrated and dried on high vacuum to a white powder (550 mg, 55% of theoretical 50% maximum, >99.5 ee). $^1$H NMR (CDCl$_3$, 300 MHz) δ 1.05–1.50 (br m, 9H), 3.12 (br m, 1H), 3.50–3.65 (m, 2H), 3.81 (s, 3H), 4.24 (m, 1H), 4.96 (br m, 1H), 5.95 (s, 2H), 6.70–6.79 (m, 3H), 6.86 (d, J=9 Hz, 2H), 7.19 (d, J=9 Hz, 2H). MS (DCI/NH$_3$) m/e 442 (M+H)$^+$.

EXAMPLE 95C (2R,3R,4S)-(+)-Ethyl 2-(4-methoxyphenyl)-4-(1,3-benzodioxol-5-vi)-pyrrolidine-3-carboxylate The compound resulting from Example 95B (251 mg, 0.568 mmol) was dissolved in 20 mL of a saturated solution of anhydrous HCl(g) in anhydrous ethanol. The resulting solution was heated at 50° C. with stirring for 18 hours at which point all of the precipitated solid had dissolved. The reaction mixture was concentrated to a solid which was partitioned between 0.8 M aqueous sodium carbonate (50 mL) and methylene chloride (50 mL). The aqueous layer was further extracted with methylene chloride (2×50 mL). The combined organic layers were dried (Na$_2$SO$_4$), filtered, concentrated and dried under high vacuum to give the title compound as an almost colorless oil (158 mg, 69%). $^1$H NMR (CDCl$_3$, 300 MHz) δ 1.11 (t, J=7 Hz, 3H), 2.18 (v br s, 1H), 2.93 (t, J=9 Hz, 1H), 3.19,3.22 (dd, J=7 Hz, 1H), 3.50–3.69 (m, 2H), 3.80 (s, 3H), 4.07 (q, J=7 Hz, 2H), 4.49 (d, J=9 Hz, 1H), 5.94 (s, 2H), 6.73 (d, J=2 Hz, 2H), 6.81–6.92 (m, 3H), 7.34–7.41 (m, 2H). MS (DCI/NH$_3$) m/e 370 (M+H)$^+$.

EXAMPLE 95D (2R,3R,4S)-(+)-2-(4-Methoxyphenyl)-4-(1,3-benzodioxol-5-yl)-1-(tert-butyloxycarbonyl-aminocarbonylmethyl)-pyrrolidine-3-carboxylic acid To the resulting compound from Example 95C (131 mg, 0.355 mmol) was added, diisopropylethylamine (137 mg, 185 μL, 1.06 mmol), acetonitrile (2 mL), N,N-di-(n-butyl) bromoacetamide (133 mg, 0.531 mmol), and the mixture was heated at 50° C. for 1.5 hours. The reaction mixture was concentrated to a solid, dried under high vacuum, and purified by chromatography on silica gel eluting with 1:3 ethyl acetate-hexane to give pure ester as a colorless oil. $^1$H NMR (CDCl$_3$, 300 MHz) δ 0.81 (t, J=7 Hz, 3H), 0.88 (t, J=7 Hz, 3H), 1.10 (t, J=7 Hz, 3H), 1.00–1.52 (m, 8H), 2.78 (d, J=14 Hz, 1H), 2.89–3.10 (m, 4H), 3.23–3.61 (m, 5H), 3.71 (d, J=9 Hz, 1H), 3.80 (s, 3H), 4.04 (q, J=7 Hz, 2H), 5.94 (dd, J=1.5 Hz, 2H), 6.74 (d, J=9 Hz, 1H), 6.83–6.90 (m, 3H), 7.03 (d, J=2 Hz, 1H), 7.30 (d, J=9 Hz, 2H). MS (DCI/NH$_3$) m/e 539 (M+H)$^+$.

To the ethyl ester dissolved in 7 mL of ethanol was added a solution of lithium hydroxide (45 mg, 1.06 mmol) in water (2.5 mL). The mixture was stirred for 1 hour at ambient temperature and then warmed slowly to 40° C. over 2.5 hours at which point all of the starting material had been consumed. The reaction mixture was concentrated to remove the ethanol, diluted with 60 mL water and extracted with ether (3×40 mL). The aqueous solution was treated with 1 N aqueous hydrochloric acid until cloudy, and the pH was then adjusted to ~4–5 with 10% aqueous citric acid. This mixture was extracted with 1:19 ethanol-methylene chloride (3×50 mL). The combined extracts were dried (Na$_2$SO$_4$), filtered, concentrated and dried under high vacuum to give the title compound as a white foam (150 mg, 83%). $^1$H NMR (CDCl$_3$, 300 MHz) δ 0.80 (t, J=7 Hz, 3H), 0.88 (t, J=7 Hz, 3H), 1.08 (m, 2H), 1.28 (m, 3H), 1.44 (m, 3H), 2.70–3.77 (svr br m, 12H), 3.79 (s, 3H), 5.95 (m, 2H), 6.75 (d, J=8 Hz, 1H), 6.87 (br d, J=8 Hz, 3H), 7.05 (br s, 1H), 7.33 (v br s, 2H). MS (DCI/NH$_3$) m/e 511 (M+H)$^+$. [α]$^{22}$=+74.42°. Anal calcd for C$_{29}$H$_{38}$N$_2$O$_6$ 0.5H$_2$O: C, 67.03; H, 7.56; N, 5.39. Found: C, 67.03; H, 7.59; N, 5.33.

EXAMPLE 95E

Alternate Preparation of (2R,3R,4S)-(+)-2-(4-Methoxyphenyl)-4-(1,3-benzodioxol-5-yl)-1-(tert-butyloxycarbonylaminocarbonylmethyl)-pyrrolidine-3-carboxylic acid The product of Example 95A (2.858 g) was suspended in 10 mL of EtOAc. 0.7833 g of R (+) alpha methyl benzylamine in 3 mL ethyl acetate was added. On swirling all of the solids were dissolved. The ethyl acetate was removed in vacuum. Ether (13 ml) was added to the residue. When all of the residue had dissolved, 5 mg of seed crystals were added and these crystals were crushed with a metal spatula while cooling in ice. The product crystallized very slowly. After 1 hour the solid was filtered and washed with ether giving 1.4213 g, m.p. 163–167°. The filtrate was concentrated, cooled and scratched with a spatula to give a second crop 0.1313 g, m.p. 164–168°. The filtrate was concentrated again and put in the refrigerator and let stand overnight giving 1.6906 g, m.p. 102–110°. (HPLC of this showed 20% of the desired enantiomer and 80% of the unwanted enantiomer.)

The first two batches of crystallized material were combined and suspended in 20 mL dichloromethane (Note: the unwanted isomer is more soluble in dichloromethane) and stirred for 2 minutes. The mixture was concentrated, but not to dryness, and ether (10 mL) was added. After stirring for a few minutes the crystals were filtered. Yield: 1.401 g, m.p. 164–1720.

Treatment of the crystalline product with 10% citric acid and ether according the method described in Example 95B provided the title compound.

EXAMPLE 96 trans,trans-2-(4-Methoxyphenyl)-4-(1,3-benzo-dioxol-5-yl)-1-[2-(N-propyl-N-butyrylamino)ethyl]pyrrolidine-3-carboxylic acid The title compound was prepared by the methods described in Example 61, but substituting propylamine for methylamine in Example 61B and butyryl chloride for isobutyryl chloride in Example 61C. The product was purified by preparative HPLC (Vydac µC18) eluting with a 10–70% gradient of $CH_3CN$ in 0.1% TFA. The desired fractions were lyophilized to give the product as a white solid. $^1$H NMR ($CDCl_3$, 300 MHz) δ 0.80 (m, 3H), 0.90 (t, 3H, J=8 Hz), 1.42 (m, 2H), 1.58 (heptet, 2H, J=8 Hz), 2.20 (t, 3H, J=8 Hz), 2.94 (br m, 2H), 3.10 (br m, 2H), 3.48 (br m, 4H), 3.76 (br m, 2H), 3.78 (s, 3H), 4.30 (br s, 1H), 5.95 (s, 2H), 6.75 (d, 1H, J=8 Hz), 6.84 (m, 1H), 6.85 (d, 2H, J=8 Hz), 7.04 (d, 1H, J=1 Hz), 7.40 (d, 2H, J=8 Hz). MS ($DCI/NH_3$) m/e 497 (M+H)$^+$. Anal calcd for $C_{28}H_{36}N_2O_6$ 1.0 TFA: C, 58.82; H, 6.42; N, 4.57. Found: C, 58.77; H, 6.30; N, 4.42.

EXAMPLE 97 trans,trans-2-(4-Methoxyphenyl)-4-(1,3-benzo-dioxol-5-yl)-1-[2-(N-propyl-N-(ethylaminocarbonyl)amino)ethyl]pyrrolidine-3-carboxylic acid The title compound was prepared by the methods described in Example 61, but substituting propylamine for methylamine in Example 61B and ethyl isocyanate for isobutyryl chloride in Example 61C. The crude product was purified by trituration with 1:1 diethyl ether-hexane. The resulting solid was dissolved in $CH_3CN$ and water and lyophilized to give the product as a white solid. $^1$H NMR ($CDCl_3$, 300 MHz) mixture of rotamers δ 0.80 (t, J=8 Hz) and 1.05 (t, J=8 Hz) and 1.20 (m) and 1.42 (m) total of 8H for the four peaks, 2.35 (br s, 1H), 2.70 (m, 1H), 3.0 (m, 3H), 3.2 (m, 3H), 3.25 (dq, 1H, J=1,8 Hz), 3.42 (m, 1H), 3.6 (m, 1H), 3.75 (m, 1H), 3.78 (s, 3H), 4.8 (br s, 1H), 5.95 (s, 2H), 6.74 (d, 1H, J=8 Hz), 6.85 (m, 3H), 7.00 (s, 1H), 7.30 (d, 2H, J=8 Hz). MS ($DCI/NH_3$) m/e 498 (M+H)$^+$. Anal calcd for $C_{27}H_{35}N_3O_6$ 0.75$H_2O$: C, 63.45; H, 7.20; N, 8.22. Found: C, 63.38; H, 7.29; N, 8.44.

EXAMPLE 98 trans,trans-2-(4-Methoxyphenyl)-4-(1,3-benzo-dioxol-5-yl)-1-[2-(N-butyl-N-butyrylamino)ethyl]pyrrolidine-3-carboxylic acid The title compound was prepared by the methods described in Example 61, but substituting butylamine for methylamine in Example 61B and butyryl chloride for isobutyryl chloride in Example 61C. The crude product was purified by trituration with 1:1 diethyl ether-hexane. The resulting solid was dissolved in $CH_3CN$ and water and lyophilized to give the product as a white solid. $^1$H NMR ($CDCl_3$, 300 MHz) δ 0.80 (m, 3H), 0.90 (t, 3H, J=8 Hz), 1.45 (m, 4H), 1.6 (m, 2H), 2.20 (t, 3H, J=8 Hz), 2.94 (br m, 2H), 3.10 (br m, 2H), 3.5 (br m, 4H), 3.80 (br m, 2H), 3.82 (s, 3H), 4.30 (br s, 1H), 5.95 (s, 2H), 6.75 (d, 1H, J=8 Hz), 6.84 (m, 1H), 6.85 (d, 2H, J=8 Hz), 7.04 (d, 1H, J=1 Hz), 7.40 (d, 2H, J=8 Hz). MS ($DCI/NH_3$) m/e 511 (M+H)$^+$. HRMS calcd for $C_{29}H_{38}N_2O_6$: 511.2808. Found: 511.2809

EXAMPLE 99 trans,trans-2-(4-Methoxyphenyl)-4-(1,3-benzo-dioxol-5-yl)-1-[2-(N-propyl-N-ethoxycarbonylamino)ethyl]pyrrolidine-3-carboxylic acid The title compound was prepared by the methods described in Example 61, but substituting propylamine for methylamine in Example 61B and ethyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1$H NMR ($CDCl_3$, 300 MHz) δ 0.80 (t, 3H, J=8 Hz), 1.05 (m, 2H), 1.22 (m, 3H), 1.45 (m, 3H), 2.08 (br s, 1H), 2.75 (m, 1H), 2.88 (br q, 2H, J=8 Hz), 3.08 (br m, 2H), 3.27 (br m, 2H), 3.44 (m, 1H), 3.54 (dt, 1H, J=1,8 Hz), 3.63 (d, 1H, J=8 Hz), 3.78 (s, 3H), 4.02 (br d, 2H), 5.93 (s, 2H), 6.72 (d, 1H, J=8 Hz), 6.81 (dd, 1H, J=1,8 Hz), 6.85 (d, 2H, J=8 Hz), 7.00 (s, 1H), 7.30 (d, 2H, J=8 Hz). MS ($DCI/NH_3$) m/e 499 (M+H)$^+$. Anal calcd for $C_{27}H_{34}N_2O_7$ 0.5$H_2O$: C, 63.89; H, 6.95; N, 5.52. Found: C, 64.03; H, 6.71; N, 5.30.

EXAMPLE 100 trans,trans-2-(4-Methoxyphenyl)-4-(1,3-benzo-dioxol-5-yl)-1-[2-(N-methyl-N-(2-ethylbutyryl)amino)ethyl]pyrrolidine-3-carboxylic acid To the compound resulting from Example 61B (190 mg) dissolved in THF (2 mL) was added HOBt (60 mg), EDCI (85 mg), N-methylmorpholine (50 µL), and DMF (2 mL). 2-Ethylbutyric acid was added and the solution stirred overnight at ambient temperature. Water (10 mL) was added, and the mixture was extracted with EtOAc (2×25 mL). The combined organic extracts were washed with saturated sodium bicarbonate solution, 1 $\underline{N}$ $H_3PO_4$, and brine, dried with $Na_2SO_4$, and evaporated to give an oil which was purified by flash chromatography on silica gel eluting with 1:3 EtOAc-hexane. The resulting ethyl ester was saponified by the procedure described in Example 61C. The crude product was dissolved in $CH_3CN$ and water and lyophilized to give the product as a white solid. $^1$H NMR ($CDCl_3$, 300 MHz) (mixture of rotamers) δ 0.66, 0.74, 0.80, 0.88 (all triplets, total of 6H, J=8 Hz), 1.05 (m, 2H), 1.25–1.75 (m, 5H), 2.16 (m, 1H), 2.32 (m, 1H), 2.45 (m, 1H), 2.70 (m, 1H), 2.86, 2.94 (s, total 3H), 2.95 (m, 1H), 3.35 (m, 1H), 3.52 (m, 2H), 3.65 (m, 1H), 3.80 (s, 3H), 5.94, 5.96 (s, total 2H), 6.73 (m, 1H), 6.84 (m, 3H), 6.97 (m, 1H), 7.30 (m, 2H). MS ($DCI/NH_3$) m/e 497 (M+H)$^+$. Anal calcd for $C_{28}H_{36}N_2O_6$ 0.25$H_2O$: C, 67.11; H, 7.34; N, 5.59. Found: C, 67.13; H, 7.24; N, 5.56.

EXAMPLE 101 trans,trans-2-(4-Methoxyphenyl)-4-(1,3-benzo-dioxol-5-yl)-1-[2-(N-methyl-N-(2-propylvaleryl)amino)ethyl]pyrrolidine-3-carboxylic acid The title compound was prepared by the procedure described in Example 100, but substituting 2-propylpentanoic acid for 2-ethylbutyric acid. The crude product was purified by preparative HPLC (Vydac µC18) eluting with a 10–70% gradient of $CH_3CN$ in 0.1% TFA. The desired fractions were lyophilized to give the product as a white solid.

$^1$H NMR ($CDCl_3$, 300 MHz) δ 0.79 (t, 3H, J=8 Hz), 0.82 (t, 3H, J=8 Hz), 1.10 (m, 4H), 1.2–1.5 (m, 4H), 2.55 (m, 1H), 2.96 (s, 3H), 3.15 (br m, 1H), 3.32 (br m, 1H), 3.56 (m, 2H), 3.68 (m, 1H) 3.68 (s, 3H), 3.70 (m, 1H), 3.80 (m, 2H), 4.65 (br d, 1H), 5.92 (s, 2H), 6.75 (d, 1H, J=8 Hz), 6.84 (m, 1H), 6.85 (d, 2H, J=8 Hz), 7.05 (s, 1H), 7.42 (d, 2H, J=8 Hz). MS (DCI/NH$_3$) m/e 525 (M+H)$^+$. Anal calcd for C$_{30}$H$_{40}$N$_2$O$_6$ 1.25 TFA: C, 58.51; H, 6.23; N, 4.20. Found: C, 58.52; H, 6.28; N, 4.33.

EXAMPLE 102 trans,trans-2-(4-Methoxyphenyl)-4-(1,3-benzo-dioxol-5-yl)-1-[2-(N-propyl-N-(tert-butyloxycarbonylmethyl)amino)ethyl]pyrrolidine-3-carboxylic acid The title compound was prepared by the methods described in Example 61, but substituting propylamine for methylamine in Example 61B and t-butyl bromoacetate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) δ 0.82 (t, 3H, J=8 Hz), 1.18 (m, 2H), 1.19 (s, 9H), 2.12 (m, 1H), 2.46 (m, 2H), 2.70 (m, 3H), 2.85 (m, 2H), 3.20 (s, 2H), 3.40 (dd, 1H, J=2,8 Hz), 3.50 (dt, 1H, J=2,8 Hz), 3.62 (d, 1H, J=8 Hz), 3.78 (s, 3H), 5.95 (s, 2H), 6.72 (d, 1H, J=8 Hz), 6.84 (m, 1H), 6.85 (d, 2H, J=8 Hz), 7.05 (s, 1H), 7.16 (d, 2H, J=8 Hz). MS (DCI/NH$_3$) m/e 541 (M+H)$^+$. Anal calcd for C$_{30}$H$_{40}$N$_2$O$_7$ 1.0H$_2$O: C, 64.50; H, 7.58; N, 5.01. Found: C, 64.75; H, 7.35; N, 4.86.

EXAMPLE 103 trans,trans-2-(4-Methoxyphenyl)-4-(1,3-benzo-dioxol-5-yl)-1-[2-(N-propyl-N-(n-propylaminocarbonylmethyl)amino)ethyl]pyrrolidine-3-carboxylic acid The title compound was prepared by the methods described in Example 61, but substituting propylamine for methylamine in Example 61B and N-propyl bromoacetamide for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.78 (t, 3H, J=8 Hz), 0.88 (t, 3H, J=8 Hz), 1.45 (m, 2H), 1.48 (m, 3H, J=8 Hz), 2.55–2.7 (m, 2H), 2.90 (m, 1H), 3.04 (m, 1H), 3.15 (m, 3H), 3.28 (t, 1H, J=8 Hz), 3.45 (t, 1H, J=8 Hz), 3.60 (m, 2H), 3.70 (d, 2H, J=8 Hz), 3.75 (m, 1H), 3.80 (s, 3H), 4.25 (d, 1H, J=8 Hz), 5.95 (s, 2H), 6.75(d, 1H, J=8 Hz), 6.86 (dt, 1H, J=1,8 Hz), 6.88 (d, 2H, J=8 Hz), 7.04 (d, 1H, J=1 Hz), 7.40 (d, 2H, J=8 Hz). MS (DCI/NH$_3$) m/e 526 (M+H)$^+$. Anal calcd for C$_{29}$H$_{39}$N$_3$O$_6$ 1.85 TFA: C, 53.32; H, 5.59; N, 5.70. Found: C, 53.45; H, 5.62; N, 5.63.

EXAMPLE 104 trans,trans-2-(4-Methoxyphenyl)-4-(1,3-benzo-dioxol-5-yl)-1-[2-(N-propyl-N-(4-methoxyphenoxycarbonyl)amino)ethyl]pyrrolidine-3-carboxylic acid The title compound was prepared by the methods described in Example 61, but substituting propylamine for methylamine in Example 61B and 4-methoxyphenylchloroformate for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CD$_3$OD, 300 MHz) mixture of rotamers δ 0.88 (m,3H), 1.57 (m, 2H), 2.45 (br s) and 2.60 (br s, total of 1H), 2.90–3.15 (m, 4H), 3.42–3.7 (m, 5H), 3.78 (s, 3H), 3.80 (s, 3H), 3.85 (m) and 4.0 (m, total of 1H), 5.95 (s) and 5.98 (s, total of 2H), 6.63(m, 1H), 6.72 (d, 1H, J=8 Hz), 6.81 (m, 2H), 6.93 (m, 5H), 7.40 (m, 2H). MS (DCI/NH$_3$) m/e 577 (M+H)$^+$. Anal calcd for C$_{32}$H$_{36}$N$_2$O$_8$ 1.0H$_2$O: C, 64.63; H, 6.44; N, 4.71. Found: C, 64.70; H, 6.38; N, 4.63.

EXAMPLE 105 trans,trans-2-(4-Methoxyphenyl)-4-(1,3-benzo-dioxol-5-yl)-1-[2-(N-propyl-N-(4-methoxybenzoyl)amino)ethyl]pyrrolidine-3-carboxylic acid The title compound was prepared by the methods described in Example 61, but substituting propylamine for methylamine in Example 61B and anisoyl chloride for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) mixture of rotamers δ 0.78 (m) and 0.98 (t, J=8 Hz) total of 3H, 1.47 (m) and 1.52 (q, J=8 Hz) total of 2H, 2.25 (br s, 1H), 2.78 (br s, 1H), 2.90 (br t, 2H), 3.12–3.68 (m, 7H), 3.80 (s, 3H), 3.82 (s, 3H), 5.94 (s, 2H), 6.75(d, 1H, J=8 Hz), 6.83 (m, 5H), 6.94 (m, 1H), 7.22 (m, 4H). MS (FAB) m/e 561 (M+H)$^+$. Anal calcd for C$_{32}$H$_{36}$N$_2$O$_7$ 0.75H$_2$O: C, 66.94; H, 6.58; N, 4.88. Found: C, 67.00; H, 6.38; N, 4.59.

EXAMPLE 106 trans,trans-2-(4-Methoxyphenyl)-4-(1,3-benzo-dioxol-5-yl)-1-[2-(N-propyl-N-benzoylamino)ethyl]pyrrolidine-3-carboxylic acid The title compound was prepared by the methods described in Example 61, but substituting propylamine for methylamine in Example 61B and benzoyl chloride for isobutyryl chloride in Example 61C. The crude product was purified by trituration with 1:1 diethyl ether-hexane. The resulting solid was dissolved in CH$_3$CN and water and lyophilized to give the product as a white solid. $^1$H NMR (CDCl$_3$, 300 MHz) mixture of rotamers δ 0.65 and 0.9 (m, total of 3H), 1.4 and 1.55 (m, total of 2H), 2.05 and 2.15 (m, total of 1H), 2.6–3.6 (m, 8H), 5.92 (s, 2H), 6.70(d, 1H, J=8 Hz), 6.82 (m, 4H), 7.2–7.4 (m, 6H). MS (DCI/NH$_3$) m/e 531 (M+H)$^+$. Anal calcd for C$_{31}$H$_{34}$N$_2$O$_6$ 0.3H$_2$O: C, 69.46; H, 6.51; N, 5.23. Found: C, 69.48; H, 6.19; N, 4.84.

EXAMPLE 107 trans,trans-2-(4-Methoxyphenyl)-4-(1,3-benzo-dioxol-5-yl)-1-[2-(N-propyl-N-benzyloxycarbonylamino)ethyl]pyrrolidine-3-carboxylic acid The title compound was prepared by the methods described in Example 61, but substituting propylamine for methylamine in Example 61B and benzyl chloroformate for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.8 (m, 3H) 1.45 (m, 2H), 2.20 (br m, 1H), 2.75 (m, 1H), 2.93 (m, 1H), 3.15 (m, 2H), 3.32 (m, 3H), 3.52 (m, 2H), 3.66 (m, 1H), 3.78 (s, 3H), 5.00 (m, 2H), 5.94 (s, 2H), 6.72(d, 1H, J=8 Hz), 6.82 (m, 3H), 7.0 (br d, 1H, J=15 Hz), 7.2 (s, 4H), 7.30 (m, 3H). MS (FAB) m/e 561 (M+H)+. Anal calcd for $C_{32}H_{36}N_2O_7$ 1.0 TFA: C, 60.53; H, 5.53; N, 4.15. Found: C, 60.66; H, 5.34; N, 4.28.

EXAMPLE 108 trans,trans-2-(4-Methoxyphenyl)-4-(1,3-benzo-dioxol-5-yl)-1-[2-(N-propyl-N-(4-methoxybenzyloxycarbonyl)amino)ethyl]pyrrolidine-3-carboxylic acid The title compound is prepared by the methods described in Example 61, substituting propylamine for methylamine in Example 61B and 4-methoxybenzyl chloroformate for isobutyryl chloride in Example 61C.

EXAMPLE 109 trans,trans-2-(4-Methoxyphenyl)-4-(1,3-benzo-dioxol-5-yl)-1-[2-(N-butyl-N-ethoxycarbonylamino)ethyl]pyrrolidine-3-carboxylic acid The title compound was prepared by the methods described in Example 61, but substituting butylamine for methylamine in Example 61B and ethyl chloroformate for isobutyryl chloride in Example 61C. The crude product was purified by preparative HPLC (Vydac μC18) eluting with a 10–70% gradient of $CH_3CN$ in 0.1% TFA. The desired fractions were lyophilized to give the product as a white solid. $^1$H NMR ($CDCl_3$, 300 MHz) δ 0.82 (t, 3H, J=8 Hz), 1.20 (m, 5H), 1.34 (m, 2H), 3.08 (m, 2H), 3.17 (m, 2H), 3.52 (m, 2H), 3.75 (m, 2H), 3.78 (s, 3H), 4.06 (q, 2H, J=8 Hz), 4.35 (br s, 1H), 5.94 (s, 2H), 6.76 (d, 1H, J=8 Hz), 6.92 (d, 2H, J=8 Hz), 7.03 (br s, 1H), 7.17 (br s, 1H), 7.7 (br s, 2H). MS (FAB) m/e 513 (M+H)+. Anal calcd for $C_{28}H_{36}N_2O_7$ 0.5 TFA: C, 61.15; H, 6.46; N, 4.92. Found: C, 60.99; H, 6.80; N, 4.93.

EXAMPLE 110 trans,trans-2-(4-Methoxyphenyl)-4-(1,3-benzo-dioxol-5-yl)-1-[2-(N-butyl-N-propoxycarbony-lamino)ethyl]pyrrolidine-3-carboxylic acid The title compound was prepared by the methods described in Example 61, but substituting butylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1$H NMR ($CDCl_3$, 300 MHz) δ 0.80 (br s, 1H), 0.85 (t, 3H, J=8 Hz), 0.92 (br s, 1H), 1.22 (m, 3H), 1.40 (m, 3H), 1.62 (br m, 1H), 2.15 (br s, 1H), 2.72 (m, 1H), 2.87 (m, 1H), 3.1–3.45 (m, 5H), 3.55 (m, 1H), 3.64 (d, 1H, J=8 Hz), 3.79 (s, 3H), 3.88 (br s, 1H), 3.97 (br s, 1H), 5.95 (s, 2H), 6.73(d, 1H, J=8 Hz), 6.85 (m, 3H, 7.0 (s, 1H), 7.30 (d, 2H, J=8 Hz). MS (FAB) m/e 527 (M+H)+. Anal calcd for $C_{29}H_{38}N_2O_7$ 0.15$H_2O$: C, 65.80; H, 7.29; N, 5.29. Found: C, 65.79; H, 7.30; N, 5.21.

EXAMPLE 111 trans,trans-2-(4-Methoxyphenyl)-4-(1,3-benzo-dioxol-5-yl)-1-[2-(N-propyl-N-propoxycarbony-lamino)ethyl]pyrrolidine-3-carboxylic acid The title compound was prepared by the methods described in Example 61, but substituting propylamine for methylamine in Example 61B and propyl chloroformate for isobutyryl chloride in Example 61C. The crude product was purified by trituration with 1:1 diethyl ether-hexane. The resulting solid was dissolved in $CH_3CN$ and water and lyophilized to give the product as a white solid. $^1$H NMR ($CDCl_3$, 300 z) δ 0.80 (t, 3H, J=8 Hz), 093 (m, 3H), 1.43 (m, 3H), 1.62 (m, 1H), 2.15 (br s, 1H), 2.68–3.45 (m, 8H), 3.54 (m, 1H), 3.66 (m, 1H), 3.78 (s, 3H), 3.94 (m, 2H), 5.94 (s, 2H), 6.72 (d, 1H, J=8 Hz), 6.82 (m, 1H), 6.84 (d, 2H, J=8 Hz), 7.00 (br s, 1H), 7.33 (m, 2H). MS (DCI/$NH_3$) m/e 513 (M+H)+. Anal calcd for $C_{28}H_{36}N_2O_7$ 0.15$H_2O$: C, 65.26; H, 7.10; N, 5.44. Found: C, 65.22; H, 6.74; N, 5.06.

EXAMPLE 112 trans,trans-1-(N,N-Di(n-butyl)aminocarbonylm-ethyl)-2,4-di(1,3-benzodioxol-5-yl)pyrrolidine-3-carboxylic acid Ethyl (3,4-methylenedioxybenzoyl)acetate, prepared by the method of Krapcho et al., Org. Syn. 47, 20 (1967) starting with 3,4-methylenedioxyacetophenone instead of 4-methoxyacetophenone, was reacted by the procedures described in Example 1 to give the title compound as a white solid. m.p. 58–60° C. $^1$H NMR ($CDCl_3$, 300 MHz) δ 0.87 (quintet, J=6 Hz, 6H), 1.12 (sextet, J=6 Hz, 2H), 1.24–1.51 (m, 6H), 2.80 (d, J=13 Hz, 1H), 2.94–3.12 (m, 4H), 3.28–3.50 (m, 4H), 3.58–3.62 (m, 1H), 3.78 (d, J=9 Hz, 1H), 5.95 (s, 4H), 6.73 (dd, J=8 Hz, 3 Hz, 2H), 6.84–6.89 (m, 2H), 6.92 (d, J=1 Hz, 1H), 7.01 (d, H=1 Hz, 1H). MS (DCI/$NH_3$) m/e 525 (M+H)+.

EXAMPLE 113 trans,trans-1-(2-(N-(n-Butyl)-N-propylsulfony-lamino)ethyl)-2-(4-methoxyphenyl)-4-(1,3-benzo-dioxol-5-yl)pyrrolidine-3-carboxylic acid Using the procedures described in Example 66, the title compound was prepared as a white solid. m.p. 64–65° C. $^1$H NMR ($CDCl_3$, 300 MHz) δ 0.83 (t, J=7 Hz, 3H), 0.98 (t, J=7 Hz, 3H), 1.12–1.25 (m, 2H), 1.32–1.41 (m, 2H), 1.75 (sextet, J=7 Hz, 2H), 2.23–2.31 (m, 2H), 2.72–3.32 (m, 8H), 3.43 (dd, J=9 Hz, 3 Hz, 1H), 3.53–3.59 (m, 1H), 3.65 (d, J=9 Hz, 1H), 3.80 (s, 3H), 5.95 (s, 2H), 6.73 (d, J=8 Hz, 1H), 6.83 (dd, J=8 Hz, 1 Hz, 1H), 6.88 (d, J=9 Hz, 2H), 7.02 (d, J=1 Hz, 1H), 7.33 (d, J=9 Hz, 2H). MS (DCI/$NH_3$) m/e 547 (M+H)+.

EXAMPLE 114 trans,trans-1-(N,N-Di(n-butyl)aminocarbonylm-ethyl)-2-(4-methoxyphenyl)-4-(1,3-benzodioxol-5-yl)pyrrolidine-3-carboxylic acid Using the procedures described in Examples 28 and 43, the title compound was prepared as a white solid. m.p. 74–76° C. $^1$H NMR ($CDCl_3$, 300 MHz) δ 0.80 (t, J=6 Hz, 3H), 0.88 (t, J=8 Hz, 3H), 1.08 (sextet, J=8 Hz, 2H), 1.21–1.48 (m, 6H), 2.75 (d, J=12 Hz, 1H), 2.95–3.09 (m, 4H), 3.26–3.59 (m, 5H), 3.75 (d, J=9 Hz, 1H), 3.79 (s, 3H), 4.28 (s, 4H), 6.78 (d, J=9 Hz, 1H), 6.85 (d, J=9 Hz, 2H), 6.91 (d,d, J=3 Hz, 9 Hz, 1H), 6.98 (d, J=3 Hz, 1H), 7.32 (d, J=9 Hz, 2H). MS (DCI/$NH_3$) m/e 525 (M+H)+.

EXAMPLE 115 trans,trans-1-(2-(N-Propyl-N-propylsulfonylamino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 72–73° C. $^1$H NMR (CDCl$_3$, 300 MHz) δ 0.79 (t, J=8 Hz, 3H), 0.98 (t, J=8 Hz, 3H), 1.43 (sextet, J=8 Hz, 2H), 1.75 (sextet, J=8 Hz, 2H), 2.22–2.32 (m, 1H), 2.69–3.32 (m, 9H), 3.42 (dd, J=3 Hz, 12 Hz, 1H), 3.52–3.58 (m, 1H), 3.64 (d, J=12 Hz, 1H), 3.80 (s, 3H), 5.95 (s, 2H), 6.73 (d, J=11 Hz, 1H), 6.83 (dd, J=1 Hz, 11 Hz, 1H), 6.87 (d, J=11 Hz, 2H), 7.0 (d, J=2 Hz, 1H), 7.32 (d, J=11 Hz, 2H). MS (DCI/NH$_3$) m/e 533 (M+H)$^+$.

EXAMPLE 116 trans,trans-1-(2-(N-Butyl-N-butylsulfonylamino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 62–63° C. $^1$H NMR (CDCl$_3$, 300 MHz) δ 0.82 (t, J=6 Hz, 3H), 0.91)t, J=6 Hz, 3H), 1.20 (sextet, J=6 Hz, 2H), 1.33–1.42 (m, 4H), 1.68 (quintet, J=6 Hz, 3H), 2.23–2.32 (m, 1H), 2.70–3.28 (m, 9H), 3.41 (d, J=8 Hz, 1H), 3.52–3.58 (m, 1H), 3.65 (d, J=8 Hz, 1H), 3.79 (s, 3H), 5.95 (s, 2H), 6.72 (d, J=8 Hz, 1H), 6.82 (d, J=8 Hz, 1H), 6.87 (d, J=8 Hz, 2H), 7.01 (s, 1H), 7.32 (d, J=8 Hz, 2H). MS (DCI/NH$_3$) m/e 561 (M+H)$^+$.

EXAMPLE 117 trans,trans-1-(2-(N,N-Di(n-butyl)aminocarbonylmethyl)-2-(4-methoxymethoxyphenyl)-4-(1,3-benzodioxol-5-yl)pyrrolidine-3-carboxylic acid 4-Hydroxyacetophenone was treated with chloromethyl methyl ether and triethylamine in THF at room temperature to give ethyl 4-methoxymethoxybenzoylacetate which was treated by the procedures described in Example 1 to afford the title compound as a white solid. m.p. 48–49° C. $^1$H NMR (CDCl$_3$, 300 MHz) δ 0.81 (t, J=7 Hz, 3H), 0.88 (t, J=7 Hz, 3H), 1.06 (sextet, J=7 Hz, 2H), 1.20–1.35 (m, 4H), 1.44 (quintet, J=7 Hz, 2H), 2.75 (d, J=12 Hz, 1H), 2.94–3.10 (m, 4H), 3.25–3.35 (m, 1H), 3.40 (d, J=12 Hz, 1H), 3.43–3.52 (m, 2H), 3.47 (s, 3H), 3.55–3.62 (m, 1H), 3.77 (d, J=9 Hz, 1H), 5.15 (s, 2H), 5.94 (m, 2H), 6.73 (d, J=8 Hz, 1H), 6.86 (dd, J=1 Hz, 8 Hz, 1H), 7.0 (d, J=8 Hz, 2H), 7.04 (d, J=1 Hz, 1H), 7.32 (d, J=8 Hz, 2H). MS (DCI/NH$_3$) m/e 541 (M+H)$^+$.

EXAMPLE 118 trans,trans-1-(2-(N,N-Di(n-butyl)aminocarbonylmethyl)-2-(4-hydroxyphenyl)-4-(1,3-benzodioxol-5-yl)pyrrolidine-3-carboxylic acid hydrochloride salt The compound resulting from Example 116 was treated with concentrated HCl in 1:1 THF-isopropanol to give the title compound as a white solid. m.p. 211–212° C. $^1$H NMR (CD$_3$OD, 300 MHz) δ 0.90 (t, J=8 Hz, 6H), 1.12–1.27 (m, 6H), 1.36–1.45 (m, 2H), 3.04 (bs, 1H), 3.14–3.35 (t, J=9 Hz, 1H), 3.90 (bs, 3H), 4.17 (d, J=15 Hz, 1H), 5.96 (s, 2H), 6.82–6.93 (m, 4H), 7.03 (d, J=1 Hz, 1H), 7.42 (bs, 2H). MS (DCI/NH$_3$) m/e 497 (M+H)$^+$.

EXAMPLE 119 trans,trans-1-(2-(N-Isobutyl-N-propylsulfonylamino)ethyl)-2-(4-methoxyphenyl)-4-(1,3-benzodioxol-5-yl) pyrrolidine-3-carboxylic acid Using the procedures described in Example 66, the title compound was prepared as a white solid. m.p. 73–74° C. $^1$H NMR (CDCl$_3$, 300 MHz) δ 0.80 (d, J=6 Hz, 6H), 0.98 (t, J=8 Hz, 3H), 1.62 (sextet, J=6 Hz, 1H), 1.74 (sextet, J=8 Hz, 2H), 2.23–2.34 (m, 1H), 2.68–2.98 (m, 7H), 3.08–3.18 (m, 1H), 3.26–3.42 (m, 2H), 3.52–3.58 (m, 1H), 3.65 (d, J=9 Hz, 1H), 3.80 (s, 3H), 5.90 (s, 2H), 6.74 (d, J=8 Hz, 1H), 6.82 (d, J=8 Hz, 1H), 6.86 (d, J=8 Hz, 2H), 6.98 (d, J=1 Hz, 1H), 7.33 (d, J=8 Hz, 2H). MS (DCI/NH$_3$) m/e 547 (M+H)$^+$.

EXAMPLE 120 trans,trans-1-(2-(N-Benzenesulfonyl-N-propylamino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 89–91° C. $^1$H NMR (CDCl$_3$, 300 MHz) δ 0.74 (t, J=6 Hz, 3H), 1.33 (sextet, J=6 Hz, 2H), 2.20–2.30 (m, 1H), 2.62–2.72 (m, 1H), 2.85–3.05 (m, 4H), 3.12–3.22 (m, 1H), 3.38 (dd, J=3 Hz, 9 Hz, 1H), 3.49–3.57 (m, 1H), 3.62 (d, J=9 Hz, 1H), 3.82 (s, 3H), 5.96 (s, 2H), 6.73 (d, J=8 Hz, 1H), 6.84 (dd, J=1 Hz, 8 Hz, 1H), 6.85 (d, J=9 Hz, 2H), 7.02 (d, J=1 Hz, 1H), 7.28 (d, J=9 Hz, 2H), 7.39–7.54 (m, 3H), 7.70 (d, J=7 Hz, 2H). MS (DCI/NH$_3$) m/e 567 (M+H)$^+$.

EXAMPLE 121 trans,trans-1-(2-(N-(4-Methoxybenzenesulfonyl)-N-propylamino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 96–97° C. $^1$H NMR (CDCl$_3$, 300 MHz) δ 0.73 (t, J=7 Hz, 3H), 1.34 (sextet, J=7 Hz, 2H), 2.20–2.30 (m, 1H), 2.62–2.71 (m, 1H), 2.82–3.03 (m, 4H), 3.08–3.18 (m, 2H), 3.38 (dd, J=3 Hz, 9 Hz, 1H), 3.48–3.56 (m, 1H), 3.62 (d, J=9 Hz, 1H), 3.81 (s, 3H), 3.86 (s, 3H), 5.95 (s, 2H), 6.73 (d, J=8 Hz, 1H), 6.81–6.89 (m, 5H), 7.01 (d, J=1 Hz, 1H), 7.28 (d, J=8 Hz, 2H), 7.62 (d, J=8 Hz, 2H). MS (DCI/NH$_3$) m/e 597 (M+H)$^+$.

EXAMPLE 122 trans,trans-1-(N,N-Di(n-butyl)aminocarbonylmethyl)-2-(2-methoxyethoxy-4-methoxyphenyl)-4-(1,3-benzodioxol-5-yl)pyrrolidine-3-carboxylic acid 2-Hydroxy-5-methoxyacetophenone was treated with sodium hydride and bromoethyl methyl ether in THF at 70° C. to provide ethyl 2-methoxyethoxy-4-methoxybenzoylacetate which was treated by the procedures described in Example 1 to provide the title compound as a white solid. m.p. 63–65° C. $^1$H NMR (CDCl$_3$, 300 MHz) δ 0.84 (t, J=7 Hz, 3H), 0.89 (t, J=7 Hz, 3H), 1.16 (sextet, J=7 Hz, 2H), 1.28 (sextet, J=7 Hz, 2H), 1.45–1.52 (m, 4H), 2.87–2.94 (m, 2H), 3.00–3.16 (m, 3H), 3.26–3.36 (m, 2H), 3.43 (s, 3H), 3.47–3.54 (m, 3H), 3.66–3.72 (m, 3H), 3.78 (s, 3H), 3.76–3.84 (m, 1H), 4.02–4.10 (m, 2H), 4.25 (d, J=9 Hz, 1H), 5.92 (s, 2H), 6.40 (d, J=2 Hz, 1H), 6.52 (dd, J=2 Hz, 9 Hz, 1H), 6.70 (d, J=8 Hz, 1H), 6.83 (dd, J=1 Hz, 8 Hz, 1H), 5.98 (d, J=2 Hz, 1H), 7.53 (d, J=9 Hz, 1H). MS (DCI/NH$_3$) m/e 585 (M+H)$^+$.

EXAMPLE 123 trans,trans-1-(2-(N-Propyl-N-(2,4-dimethylbenzene-sulfonyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 88–90° C. $^1$H NMR (CDCl$_3$, 300 MHz) δ 0.69 (t, J=7 Hz, 3H), 1.32 (sextet, J=7 Hz, 2H), 2.12–2.20 (m, 1H), 2.32 (s, 3H), 2.47 (s, 3H), 2.62–2.69 (m, 1H), 2.78 (t, J=9 Hz, 1H), 2.89 (dd, J=8 Hz, 1H), 3.02 (sextet, J=9 Hz, 2H), 3.15–3.32 (m, 3H), 3.46–3.55 (m, 1H), 3.60 (d, J=9 Hz, 1H), 3.82 (s, 3H), 5.96 (s, 2H), 6.72 (d, J=7 Hz, 1H), 6.80 (dd, J=1 Hz, 9 Hz, 1H), 6.86 (d, J=9 Hz, 2H), 6.97 (d, J=1 Hz, 1H), 7.03 (bs, 2H), 7.29 (d, J=9 Hz, 1H). MS (DCI/NH$_3$) m/e 595 (M+H)$^+$.

EXAMPLE 124 trans,trans-1-(2-(N-Propyl-N-(3-chloropropylsulfo-nyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 75–76° C. $^1$H NMR (CDCl$_3$, 300 MHz) δ 0.80 (t, J=7 Hz, 3H), 1.45 (sextet, J=7 Hz, 2H), 2.15–2.31 (m, 3H), 2.70–2.80 (m, 1H), 2.85–3.10 (m, 6H), 3.23–3.31 (m, 2H), 3.43 (bd, J=9 Hz, 1H), 3.55–3.66 (m, 4H), 3.81 (s, 3H), 5.94 (s, 2H), 6.73 (d, J=8 Hz, 1H), 6.82 (d, J=8 Hz, 1H), 6.86 (d, J=8 Hz, 2H), 7.00 (s, 1H), 7.33 (d, J=8 Hz, 2H). MS (DCI/NH$_3$) m/e 567 (M+H)$^+$.

EXAMPLE 125 trans,trans-1-(2-(N-Propyl-N-(2-methoxyethylsulfo-nyl)amino)ethyl)-2-(4-methoxyphenyl)-4-(1,3-benzodioxol-5-yl)pyrrolidine-3-carboxylic acid Using the procedures described in Example 66, trans, trans-1-(2-(N-Propyl-N-(vinylsulfonyl)amino)ethyl)-2-(4-methoxyphenyl)-4-(1,3-benzodioxol-5-yl)pyrrolidine-3-carboxylic acid was prepared. Ester hydrolysis using aqueous sodium hydroxide in methanol afforded the title compound as a white solid. m.p. 62–64° C. $^1$H NMR (CDCl$_3$, 300 MHz) δ 0.78 (t, J=7 Hz, 3H), 1.42 (sextet, J=7 Hz, 2H), 2.23–2.32 (m, 1H), 2.72–2.79 (m, 1H), 2.86–3.05 (m, 4H), 3.10–3.27 (m, 4H), 3.32 (s, 3H), 3.43 (dd, J=3 Hz, 9 Hz, 1H), 3.53–3.58 (m, 1H), 3.65 (d, J=9 Hz, 1H), 3.69 (t, J=6 Hz, 2H), 3.80 (s, 3H), 5.94 (s, 2H), 6.73 (d, J=8 Hz, 1H), 6.82 (dd, J=1 Hz, 8 Hz, 1H), 6.87 (d, J=8 Hz, 2H), 7.02 (d, J=1 Hz, 1H), 7.33 (d, J=8 Hz, 2H). MS (DCI/NH$_3$) m/e 549 (M+H)$^+$.

EXAMPLE 126 trans,trans-1-(2-(N-Propyl-N-(2-ethoxyethylsulfo-nyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 58–60° C. $^1$H NMR (CDCl$_3$, 300 MHz) δ 0.78 (t, J=7 Hz, 3H), 1.18 (t, J=7 Hz, 3H), 1.43 (sextet, J=7 Hz, 2H), 2.24–2.33 (m, 1H), 2.70–2.80 (m, 1H), 2.87–3.05 (m, 4H), 3.13–3.20 (m, 2H), 3.22–3.32 (m, 2H), 3.42 (dd, J=2 Hz, 9 Hz, 1H), 3.46 (q, J=7 Hz, 2H), 3.52–3.58 (m, 1H), 3.65 (d J=9 Hz, 1H), 3.72 (t, J=6 Hz, 2H), 3.80 (s, 3H), 5.95 (s, 2H), 6.73 (d, J=7 Hz, 1H), 6.83 (dd, J=1 Hz, 7 Hz, 1H), 6.87 (d, J=8 Hz, 2H), 7.00 (d, J=1 Hz, 1H), 7.32 (d, J=8 Hz, 2H). MS (DCI/NH$_3$) m/e 563 (M+H)$^+$.

EXAMPLE 127 trans,trans-1-(2-(N-Propyl-N-(5-dimethylamino-1-naphthylsulfonyl)amino)ethyl)-2-(4-methoxyphe-nyl)-4-(1,3-benzodioxol-5-yl)pyrrolidine-3-carboxy-lic acid Using the procedures described in Example 66, the title compound was prepared as a yellow solid. m.p. 102–104° C. $^1$H NMR (CDCl$_3$, 300 MHz) δ 0.62 (t, J=7 Hz, 3H), 1.28 (sextet, J=7 Hz, 2H), 2.12–2.20 (m, 1H), 2.78 (t, J=9 Hz, 1H), 2.88 (s, 6H), 2.72–2.89 (m, 1H), 3.05–3.12 (m, 2H), 3.26–3.45 (m, 3H), 3.45–3.52 (m, 1H), 3.58 (d, J=9 Hz, 1H), 6.97 (d, J=1 Hz, 1H), 7.13 (d, J=7 Hz, 1H), 7.26 (d, J=8 Hz, 1H), 7.42–7.50 (m, 2H), 8.08 (dd, J=1 Hz, 7 Hz, 1H), 8.20 (d, J=8 Hz, 1H), 8.48 (d, J=8 Hz, 1H). MS (DCI/NH$_3$) m/e 660 (M+H)$^+$.

EXAMPLE 128 trans,trans-1-(2-(N-Propyl-N-(ethylsulfonyl)amino) ethyl)-2-(4-methoxyphenyl)-4-(1,3-benzodioxol-5-yl)pyrrolidine-3-carboxylic acid Using the procedures described in Example 66, the title compound was prepared as a white solid. m.p. 70–72° C. $^1$H NMR (CDCl$_3$, 300 MHz) δ 0.79 (t, J=8 Hz, 3H), 1.28 (t, J=7 Hz, 3H), 1.43 (q, J=8 Hz, 2H), 2.22–2.30 (m, 1H), 2.71–2.80 (m, 1H), 2.82–3.10 (m, 6H), 3.18–3.32 (m, 2H), 3.43 (dd, J=3 Hz, 9 Hz, 1H), 3.53–3.60 (m, 1H), 3.65 (d, J=9 Hz, 1H), 3.80 (s, 3H), 5.96 (s, 2H), 6.73 (d, J=7 Hz, 1H), 6.82 (dd, J=1 Hz, 7 Hz, 1H), 6.88 (d, J=8 Hz, 2H), 7.00 (d, J=1 Hz, 1H), 7.32 (d, J=8 Hz, 2H). MS (DCI/NH$_3$) m/e 519 (M+H)$^+$.

EXAMPLE 129 trans,trans-1-(2-(N-Propyl-N-(4-methylbenzene-sulfonyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 78–79° C. $^1$H NMR (CDCl$_3$, 300 MHz) δ 0.73 (t, J=7 Hz, 3H), 1.33 (sextet, J=7 Hz, 2H), 2.20–2.30 (m, 1H), 2.40 (s, 3H), 2.61–2.72 (m, 1H), 2.83–3.05 (m, 4H), 3.08–3.19 (m, 2H), 3.48 (dd, J=3 Hz, 9 Hz, 1H), 3.49–3.57 (m, 1H), 3.62 (d, J=9 Hz, 1H), 3.81 (s, 3H), 5.95 (s, 2H), 6.73 (d, J=8 Hz, 1H), 6.82 (d, J=8 Hz, 1H), 6.87 (d, J=8 Hz, 2H), 7.00 (s, 1H), 7.21 (d, J=8 Hz, 2H), 7.29 (d, J=8 Hz, 2H), 7.57 (d, J=8 Hz, 2H). MS (DCI/NH$_3$) m/e 581 (M+H)$^+$.

EXAMPLE 130 trans,trans-1-(N,N-Di(n-butyl)aminocarbonylm-ethyl)-2-(3-pyridyl)-4-(1,3-benzodioxol-5-yl)pyrroli-dine-3-carboxylic acid Methyl nicotinoyl acetate was prepared by the method of Wenkert, et al., J. Org. Chem. 48: 5006 (1983) and treated by the procedures described in Example 1 to provide the title compound as a white solid. m.p. 167–168° C. $^1$H NMR (CDCl$_3$, 300 MHz) δ 0.82 (t, J=7 Hz, 3H), 0.89 (t, J=7 Hz, 3H), 1.14 (sextet, J=7 Hz, 2H), 1.23–1.48 (m, 6H), 2.86–3.20 (m, 6H), 3.34–3.43 (m, 2H), 3.57 (dd, J=3 Hz, 9 Hz, 1H), 3.75–3.83 (m, 1H), 4.08 (d, J=9 Hz, 1H), 5.93 (s, 2H), 6.73 (d, J=8 Hz, 1H), 6.90 (dd, J=2 Hz, 8 Hz, 1H), 7.03 (d, J=2 Hz, 1H), 7.38 (dd, J=4 Hz, 8 Hz, 1H), 8.04 (d, J=8 Hz, 1H), 8.48 (dd, J=2 Hz, 4 Hz, 2H). MS (DCI/NH$_3$) m/e 482 (M+H)$^+$.

EXAMPLE 131 trans,trans-1-(2-(N-Propyl-N-(n-butylsulfonyl) amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 65–66° C. $^1$H NMR (CDCl$_3$, 300 MHz) δ 0.78 (t, J=7 Hz, 3H), 0.92 (t, J=7 Hz, 3H), 1.31–1.46 (m, 4H), 1.68 (quintet, J=7 Hz, 2H), 2.21–2.32 (m, 1H), 2.70–3.08 (m, 7H), 3.12–3.23 (m, 2H), 3.42 (dd, J=2 Hz, 9 Hz, 1H), 3.52–3.58 (m, 1H), 3.64 (d, J=9 Hz, 1H), 3.80 (s, 3H), 5.96 (s, 2H), 6.72 (d, J=7 Hz, 1H), 6.83 (dd, J=1 Hz, 7 Hz, 1H), 6.86 (d, J=8 Hz, 2H), 7.00 (d, J=1 Hz, 1H), 7.32 (d, J=8 Hz, 2H). MS (DCI/NH$_3$) m/e 547 (M+H)$^+$.

EXAMPLE 132 trans,trans-1-(2-(N-Propyl-N-(4-chlorobenzenesulfonyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 105–106° C. $^1$H NMR (CDCl$_3$, 300 MHz) δ 0.72 (t, J=7 Hz, 3H), 1.34 (sextet, J=7 Hzm 2H), 2.56–2.62 (m, 1H), 2.78–2.86 (m, 1H), 2.96–3.03 (m, 3H), 3.13–3.26 (m, 3H), 3.51 (dd, J=5 Hz, 9 Hz, 1H), 3.62–3.68 (m, 1H), 3.80 (s, 3H), 3.94 (d, J=9 Hz, 1H), 5.92 (s, 2H), 6.75 (d, J=8 Hz, 1H), 6.84 (dd, J=2 Hz, 8 Hz, 1H), 6.94 (d, J=8 Hz, 2H), 6.98 (d, J=2 Hz, 1H), 7.36 (d, J=8 Hz, 1H), 7.49 (d, J=8 Hz, 1H), 7.68 (d, J=8 Hz, 1H). MS (DCI/NH$_3$) m/e 601 (M+H)$^+$.

EXAMPLE 133 trans,trans-1-(2-(N-Propyl-N-(benzylsulfonyl) amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 88–89° C. $^1$H NMR (CDCl$_3$, 300 MHz) δ 0.72 (t, J=7 Hz, 3H), 1.32 (sextet, J=7 Hz, 2H), 2.06–2.16 (m, 1H), 2.56–2.67 (m, 1H), 2.75–3.10 (m, 6H), 3.30 (dd, J=2 Hz, 9 Hz, 1H), 5.95 (s, 2H), 6.73 (d, J=7 Hz, 1H), 6.80 (dd, J=1 Hz, 7 Hz, 1H), 6.86 (d, J=8 Hz, 2H), 6.97 (d, J=1 Hz, 1H), 7.27–7.35 (m, 7H). MS (DCI/NH$_3$) m/e 581 (M+H)$^+$.

EXAMPLE 134 trans,trans-1-(2-(N-Propyl-N-(4-fluorobenzenesulfonyl)amino)ethyl)-2-(4-methoxyphenyl)-4-(1,3-benzodioxol-5-yl)pyrrolidine-3-carboxylic acid Using the procedures described in Example 66, the title compound was prepared as a white solid. m.p. 91–93° C. $^1$H NMR (CDCl$_3$, 300 MHz) δ 0.73 (t, J=7 Hz, 3H), 1.44 (sextet, J=7 Hz, 2H), 2.18–2.27 (m, 1H), 2.56–2.67 (m, 1H), 2.78–2.87 (m, 2H), 2.97 (septet, J=8 Hz, 2H), 3.11–3.16 (m, 2H), 3.33 (dd, J=2 Hz, 9 Hz, 1H), 3.43–3.50 (m, 1H), 3.57 (d, J=9 Hz, 1H), 3.78 (s, 3H), 7.08 (t, J=8 Hz, 2H), 7.24 (d, J=8 Hz, 2H), 7.69 (dd, J=5 Hz, 8 Hz, 2H). MS (DCI/NH$_3$) m/e 585 (M+H)$^+$.

EXAMPLE 135 trans,trans-1-(N-Methyl-N-propylaminocarbonylmethyl)-2-(4-methoxyphenyl)-4-(4-benzofuranyl)pyrrolidine-3-carboxylic acid

EXAMPLE 135A

Benzofuran-4-carboxaldehyde

To a suspension of 60% sodium hydride in mineral oil (4.00 g, 100 mmol, 1.25 eq) in DMF (60 mL) at 0° C. was added a solution of 3-bromophenol (13.8 g, 80 mmol) in DMF (5 mL). After 10 minutes, bromoacetaldehyde diethyl acetal (14.9 mL, 96.6 mmol, 1.24 eq) was added, and the resultant mixture then heated at 120° C. for 2.5 hours. The mixture was cooled to room temperature and was poured into water, and extracted once with ether. The organic solution was dried over MgSO$_4$, filtered, evaporated and vacuum distilled to yield a colorless liquid (17.1 g, 74%). b.p. 160–163° C. at 0.4 mm Hg.

To warm polyphosphoric acid (15.3 g) was added a solution of the above compound (17.1 g, 59.3 mmol) in benzene (50 mL). The resultant mixture was heated under reflux with vigorous stirring for 4 hours, after which time the benzene layer was carefully decanted off, and the lower layer washed once with hexanes. The combined organic solutions were concentrated in vacuo, and then vacuum distilled to yield a colorless liquid (8.13 g, 70%). b.p. 62–72° C. at 0.6 mm Hg.

To a solution of the above compounds (8.11 g, 41.5 mmol) in ether (80 mL) at −78° C. was added 1.7 M t-butyllithium (48.8 mL, 83 mmol, 2 eq) such that the temperature did not exceed −70° C. After stirring for 15 minutes, a solution of DMF (6.5 mL, 83 mmol, 2 eq) in ether (20 mL) was added, and the mixture allowed to warm to room temperaure over 2 hours. The mixture was poured into water and the phases separated. The organic solution was dried over MgSO$_4$ and concentrated in vacuo. The residue was purified by flash chromatography on silica gel eluting with 10% ether in hexanes to yield benzofuran-6-carboxaldehyde (1.22 g) and benzofuran-4-carboxaldehyde (1.86 g), both as colorless oils.

EXAMPLE 135B trans,trans-1-(N-Methyl-N-propylaminocarbonylmethyl)-2-(4-methoxyphenyl)-4-(4-benzofuranyl)pyrrolidine-3-carboxylic acid The title compound was prepared using the procedures described in Examples 1 and 49 substituting the compound resulting from Example 135A in Example 49A for piperonal. $^1$H NMR (300 MHz, CDCl$_3$) (minor rotamer) δ 7.59 (1H, t, J=3 Hz), 7.4–7.2 (6H, m), 6.8 (2H, d, J=8 Hz), 4.03 (1H, m), 3.94 (1H, dd, J=8 Hz, 3 Hz), 3.77 (3H, s), 3.61 (1H, dd, J=8 Hz, 73 Hz), 3.42 (1H, dd, J=11 Hz, 5 Hz), 3.40–2.90 (5H, m), 2.82 (2.81) (3H, s), 1.50 (2H, septet, J=7 Hz), 0.82 (0.75) (3H, t, J=7 Hz). MS (DCI/NH$_3$) m/e 451 (M+H)$^+$. Anal. calc. for C$_{26}$H$_{30}$N$_2$O$_5$.AcOH: C, 65.87; H, 6.71; N,,5.49. Found: C, 66.04; H, 6.42; N, 5.60. s

EXAMPLE 136 trans,trans-1-(N-Methyl-N-propylaminocarbonylmethyl)-2-(4-methoxyphenyl)-4-(6-benzofuranyl)pyrrolidine-3-carboxylic acid The title compound was prepared using the procedures described in Examples 1 and 49 substituting benzofuran-6-carboxaldehyde, prepared as described in Example 135A, in Example 49A for piperonal. $^1$H NMR (300 MHz, CDCl$_3$) (minor rotamer) δ 7.65 (1H, bd), 7.60 (1H, d, J=2 Hz), 7.55 (1H, d, J=8 Hz), 7.35 (3H, m), 6.85 (2H, dd, J=8 Hz, 3Hz), 6.75 (1H, dd, J=3 Hz, 2 Hz), 3.83 (2H, m), 3.79 (3H, s), 3.60–3.0 (7H, m), 2.91 (2.83) (s, 3H), 1.51 (2H, septet, J=7 Hz), 0.83 (0.78) (3H, t, J=7 Hz). MS (DCI/NH$_3$) m/e 451 (M+H)$^+$. Anal. calc. for C$_{26}$H$_{30}$N$_2$O$_5$.0.5H$_2$O: C, 67.96; H, 6.80; N, 6.10. Found: C, 67.90; H, 6.71; N, 6.07.

EXAMPLE 137 trans,trans-1-(N-Methyl-N-propylaminocarbonylmethyl)-2-(4-methoxyphenyl)-4-(6-benzo-2,3-dihydrofuranyl)pyrrolidine-3-carboxylic acid The title compound was prepared by catalytic hydrogenation (4 atmospheres of H$_2$ in AcOH, followed by preparative hplc) of the compound resulting from Example 136 $^1$H NMR (300 MHz, CDCl$_3$) (minor rotamer) δ 7.49 (7.47) (2H, d, J=8 Hz), 7.19 (1H, d, J=8 Hz), 7.00 (1H, m), 7.82 (3H, m), 5.40 (1H, dd, J=11 Hz, 7 Hz), 4.58 (2H, t, J=8 Hz), 4.18 (1H, m), 4.10 (1H, m), 3.88 (1H, m), 3.79 (3H, s), 3.60 (1H, m), 3.35 (1H, m), 3.19 (2H, t, J=8 Hz), 3.00 (4H, m), 2.91 (2.78) (s, 3H), 1.53 (1.40) (2H, septet, J=7 Hz), 0.88 (0.78) (3H, t, J=7 Hz). MS (DCI/NH$_3$) m/e 453 (M+H)$^+$. Anal. calc. for C$_{26}$H$_{32}$N$_2$O$_5$.1.25 TFA: C, 57.53; H, 5.63; N, 4.71. Found: C, 57.68; H, 5.68; N, 4.70.

EXAMPLE 138 trans,trans-1-(N,N-Di(n-butyl)aminocarbonylmethyl)-2-(4-methoxyphenyl)-4-(4-benzofuranyl)pyrrolidine-3-carboxylic acid The title compound was prepared by the procedures described in Examples 1 and 49 substituting benzofuran-4-carboxaldehyde in Example 49A for piperonal and substituting N,N-dibutyl bromoacetamide for N-methyl-N-propyl bromoacetamide. $^1$H NMR (300 MHz, CDCl$_3$) δ 7.62 (1H, d, J=3 Hz), 7.39 (1H, dt, J=8 Hz, 2 Hz), 7.34 (3H, m), 7.26 (1H, d, J=2 Hz), 7.23 (1H, d, J=8 Hz), 6.84 (2H, d, J=8 Hz), 4.02 (1H, ddd, J=8, 6 Hz,4 Hz), 3.89 (1H, d, J=9 Hz) 3.79 (3H, s), 3.67 (1H, dd, J=10 Hz, 3 Hz), 3.44 (2H, m), 3.35–3.15 (3H, m), 3.00 (2H, m), 2.84 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$. Anal. calc. for C$_{30}$H$_{38}$N$_2$O$_5$: C, 71.12; H, 7.56; N, 5.53. Found: C, 70.86; H, 7.45; N, 5.24.

EXAMPLE 139 trans,trans-1-(N,N-Di(n-butyl)aminocarbonylmethyl)-2-(4-methoxyphenyl)-4-(4-benzofuranyl)pyrrolidine-3-carboxylic acid The title compound was prepared by the procedures described in Examples 1 and 49 substituting benzofuran-5-carboxaldehyde, prepared by the procedures described in Example 135A substituted 4-bromophenol for 3-bromophenol, in Example 49A for piperonal and substituting N,N-dibutyl bromoacetamide for N-methyl-N-propyl bromoacetamide. $^1$H NMR (300 MHz, CDCl$_3$) δ 7.64 (1H, bd), 7.59 (1H, d, J=2 Hz), 7.43 (2H, m), 7.33 (2H, d, J=8 Hz), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.82 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$. Anal. calc. for C$_{30}$H$_{38}$N$_2$O$_5$: C, 71.12; H, 7.56; N, 5.53. Found: C, 70.73; H, 7.45; N, 5.29.

EXAMPLE 140 trans,trans-1-(N,N-Di(n-butyl)aminocarbonylmethyl)-2-(4-methoxyphenyl)-4-(6-benzofuranyl)pyrrolidine-3-carboxylic acid The title compound was prepared by the procedures described in Examples 1 and 49 substituting benzofuran-6-carboxaldehyde in Example 49A for piperonal and substituting N,N-dibutyl bromoacetamide for N-methyl-N-propyl bromoacetamide. $^1$H NMR (300 MHz, CDCl$_3$) δ 7.63 (1H, bd), 7.59 (1H, d, J=2 Hz), 7.53 (1H, d, J=8 Hz), 7.36 (3H, m), 6.85 (2H, d, J=8 Hz), 6.73 (1H, dd, J=3 Hz, 1 Hz), 3.82 (1H, d, J=11 Hz), 3.89 (1H, d, J=9 Hz) 3.79 (3H, s), 3.53 (1H, dd, J=10 Hz, 3 Hz), 3.44 (2H, m), 3.30 (1H, m), 3.20–2.95 (5H, m), 2.80 (1H, d, J=14 Hz), 1.43 (3H, m), 1.23 (3H, m), 1.08 (2H, m), 0.87 (3H, t, J=7 Hz), 0.82 (3H, t, J=7 Hz). MS (DCI/NH$_3$) m/e 507 (M+H)$^+$. Anal. calc. for C$_{30}$H$_{38}$N$_2$O$_5$.0.75H$_2$O: C, 69.28; H, 7.65; N, 5.39. Found: C, 69.11; H, 7.33; N, 5.32.

EXAMPLE 141 trans,trans-1-(N,N-Di(n-butyl)aminocarbonylmethyl)-2-(4-methoxyphenyl)-4-(6-benzo-2,3-dihydrofuranyl)pyrrolidine-3-carboxylic acid The title compound was prepared by catalytic hydrogenation of the compound resulting from Example 140 (4 atmospheres of H$_2$ in AcOH, followed by preparative hplc). $^1$H NMR (300 MHz, CDCl$_3$) δ 7.40 (2H, d, J=8 Hz), 7.16 (1H, d, J=8 Hz), 6.97 (1H, dd, J=8 Hz, 2 Hz), 6.89 (3H, m), 5.90 (1H, bs) 4.57 (2H, t, J=9 Hz), 4.93 (2H, m), 3.80 (3H, s), 3.70–3.58 (2H, m), 3.40 (1H, m), 3.30–2.90 (8H, m), 1.40 (2H, m), 1.29 (3H, m), 1.08 (2H, m), 0.92 (3H, t, J=7 Hz), 0.82 (3H, t, J=7 Hz). MS (DCI/NH$_3$) m/e 509 (M+H)$^+$. Anal. calc. for C$_{30}$H$_{40}$N$_2$O$_5$ 0.85 TFA: C, 62.88; H, 6.80; N, 4.63. Found: C, 63.04; H, 6.66; N, 4.60.

EXAMPLE 142 trans,trans-1-(N-Methyl-N-propylaminocarbonylmethyl)-2-(4-methoxyphenyl)-4-(5-indanyl)pyrrolidine-3-carboxylic acid

EXAMPLE 142A

Indane-5-carboxaldehyde

Indane-5-carboxaldehyde was prepared by formylation of indane under the conditions described for 2,3-dihydrobenzofuran in Example 52A. The resultant mixture of 4- and 5-carboxaldehydes was purified as follows: to a 6:1 mixture of indane-4-carboxaldehyde and indane-5-carboxaldehyde (3.46 g, 23 mmol) was added aniline (2.20 g, 23 mmol, 1 eq). The resultant solution slowly solidified to a mixture of imines which was recrystallized from hot acetonitrile to yield the 5-aldimine as a white solid. The aldimine (2.65 g) was suspended in water (6 mL), and treated with 4 N hydrochloric dioxane (10 mL). The mixture was boiled for 1 hour, cooled to room temperature, and poured into ether. The organic solution was dried over $MgSO_4$, filtered, and concentated in vacuo. Vacuum distillation of the residue afforded indane-5-carboxaldehyde (1.54 g, 88%) as a colorless liquid. b.p. 88–90° C. at 0.9 mm Hg.

EXAMPLE 142B trans,trans-1-(N-Methyl-N-propylaminocarbonylmethyl)-2-(4-methoxyphenyl)-4-(5-indanyl)pyrrolidine-3-carboxylic acid The title compound was prepared by the procedures described in Examples 1 and 49 substituting indane-5-carboxaldehyde for piperonal in Example 49A. $^1$H NMR (300 MHz, $CDCl_3$) (minor rotamer) δ 7.25–7.1 (5H, m), 6.78 (2H, d, J=8 Hz), 3.89 (1H, d, J=8 Hz), 3.75 (3H, s), 3.50–2.90 (6H, m), 2.88 (6H, t, J=6 Hz), 2.82 (2.80) (3H, s), 2.04 (2H, t, J=8 Hz), 1.48 (2H, septet, J=7 Hz), 0.83 (0.73) (3H, t, J=7 Hz). MS (DCI/$NH_3$) m/e 451 (M+H)$^+$, 473 (M+Na)$^+$. Anal. calc. for $C_{27}H_{34}N_2O_4$ 2.5$H_2$O° C., 65.44; H, 7.93; N, 5.65. Found: C, 65.36; H, 7.45; N, 5.53.

EXAMPLE 143 trans,trans-1-(N-Methyl-N-propylaminocarbonylmethyl)-2-(4-methoxyphenyl)-4-(6-indolyl)pyrrolidine-3-carboxylic acid The title compound was prepared by the procedures described in Examples 1 and 49 substituting indole-6-carboxaldehyde, prepared by the method of Rapoport, J. Org. Chem. 51: 5106 (1986), for piperonal in Example 49A. $^1$H NMR (300 MHz, $CDCl_3$) (minor rotamer) δ 8.43 (1H, brs), 7.57 (1H, d, J=8 Hz), 7.43 (1H, s), 7.31 (2H, dd, J=6 Hz, 3 Hz), 7.22 (1H, d, J=8 Hz), 7.1 (1H, t, J=3 Hz), 6.78 (2H,dd, J=6 Hz, 3 Hz), 6.45 (1H, m), 3.93 (1H, dd, J=6 Hz, 3 Hz), 3.80 (1H, m), 3.73 (3H, s), 3.60–2.90 (6H, m), 2.86 (2.82) (3H, s), 1.47 (2H, septet, J=7 Hz), 0.83 (0.73) (3H, t, J=7 Hz). MS (DCI/$NH_3$) m/e 450 (M+H)$^+$. Anal. calc. for $C_{26}H_{31}N_3O_4$ 0.75$H_2$O: C, 67.44; H, 7.07; N, 9.07. Found: C, 67.42; H, 7.09; N, 8.91.

EXAMPLE 144 trans,trans-1-(N-Methyl-N-propylaminocarbonylmethyl)-2-(4-methoxyphenyl)-4-(3,4-difluorophenyl)pyrrolidine-3-carboxylic acid The title compound was prepared by the procedures described in Examples 1 and 49 substituting 3,4-difluorobenzaldehyde for piperonal in Example 49A. $^1$H NMR (300 MHz, $CDCl_3$) (minor rotamer) δ 7.60–7.3 (4H, m), 7.13 (1H, q, J=9 Hz), 6.90 (2H, d, J=8 Hz), 3.90 (1H, m), 3.79 (3H, s), 3.60–2.95 (6H, m), 2.92 (2.78) (3H, s), 1.55 (2H, septet, J=7 Hz), 0.88 (0.73) (3H, t, J=7 Hz). MS (DCI/$NH_3$) m/e 447 (M+H)$^+$. Anal. calc. for $C_{24}H_{28}F_2N_2O_4$·1.80$H_2$O: C, 60.19; H, 6.65; N, 5.85. Found: C, 60.13; H, 6.34; N, 5.84.

EXAMPLE 145 trans,trans-1-(N-Methyl-N-propylaminocarbonylmethyl)-2-(4-methoxyphenyl)-4-(phenyl)pyrrolidine-3-carboxylic acid The title compound was prepared by the procedures described in Examples 1 and 49 substituting benzaldehyde for piperonal in Example 49A. $^1$H NMR (300 MHz, $CDCl_3$) (minor rotamer) δ 7.53 (4H, d, J=6 Hz), 7.40–7.20 (3H, m), 6.88 (2H, d, J=8 Hz), 3.90 (1H, m), 3.79 (3H, s), 3.70–2.95 (8H, m), 2.90 (2.79) (3H, s), 1.50 (2H, sept, J=7 Hz), 0.87 (0.72) (3H, t, J=7 Hz). MS (DCI/$NH_3$) m/e 411 (M+H)$^+$. Anal. calc. for $C_{24}H_{30}N_2O_4$·2.00$H_2$O: C, 64.55; H, 7.67; N, 6.27. Found: C, 64.37; H, 7.43; N, 6.29.

EXAMPLE 146 trans,trans-1-(N-Methyl-N-propylaminocarbonylmethyl)-2-(4-methoxyphenyl)-4-(4-hydroxyphenyl)pyrrolidine-3-carboxylic acid The title compound was prepared by the procedures described in Examples 1 and 49 substituting 4-hydroxybenzaldehyde for piperonal in Example 49A. $^1$H NMR (300 MHz, $CDCl_3$—$CD_3OD$) (minor rotamer) δ 7.35 (2H, d, J=8 Hz), 7.28 (2H, dd, J=7 Hz, 3 Hz), 6.90 (2H, dd, J=7 Hz, 3 Hz), 6.89 (2H, d, J=8 Hz), 3.81 (3H, s), 3.65 (1H, d, J=8 Hz), 3.70–3.00 (8H, m), 2.92 (2.83) (3H, s), 1.50 (2H, septet, J=7 Hz), 0.87 (0.77) (3H, t, J=7 Hz). MS (DCI/$NH_3$) m/e 427 (M+H)$^+$. Anal. calc. for $C_{24}H_{30}N_2O_5$·1.00$H_2$O: C, 64.85; H, 7.26; N, 6.30. Found: C, 64.82; H, 7.39; N, 6.46.

EXAMPLE 147 trans,trans-1-(N-Methyl-N-propylaminocarbonylmethyl)-2-(4-methoxyphenyl)-4-(2,4-dimethoxyphenyl)pyrrolidine-3-carboxylic acid The title compound was prepared by the procedures described in Examples 1 and 49 substituting 2,4-dimethoxybenzaldehyde for piperonal in Example 49A. $^1$H NMR (300 MHz, $CDCl_3$—$CD_3OD$) (minor rotamer) δ 7.61 (1H, d, J=8 Hz), 7.30 (2H, d, J=8 Hz), 6.82 (2H, d, J=8 Hz), 6.55 (1H, d, J=8 Hz), 6.45 (1H, d, J=3 Hz), 3.90 (1H, m), 3.81 (3H, s), 3.79 (3H, s), 3.77 (3H, s), 3.70–2.90 (8H, m), 2.85 (3H, s), 1.50 (2H, sept, J=7 Hz), 0.87 (0.77) (3H, t, J=7 Hz). MS (DCI/$NH_3$) m/e 471 (M+H)$^+$. Anal. calc. for $C_{26}H_{34}N_2O_6$ 0.75$H_2$O: C, 64.51; H, 7.39; N, 5.79. Found: C, 64.65; H, 7.07; N, 5.75.

EXAMPLE 148 trans,trans-1-(N,N-Di(n-butyl)aminocarbonylmethyl)-2-(4-methoxyphenyl)-4-(5-benzo-2,3-dihydrofuranyl)pyrrolidine-3-carboxylic acid The title compound was prepared by the procedures described in Examples 1 and 49 substituting 2,3-dihydrobenzofuran-5-carboxaldehyde for piperonal in Example 49A. $^1$H NMR (300 MHz, $CDCl_3$) δ 7.31 (2H, d, J=8 Hz), 7.27 (1H, d, J=2 Hz), 7.18 (1H, dd, J=7 Hz, 3 Hz), 6.86 (2H, d, J=8 Hz), 6.72 (1H, d, J=8 Hz), 4.56 (2H, t, J=7 Hz), 3.78 (3H, s), 3.62 (1H, m), 3.50–3.25 (4H, m), 3.17 (2H, t, J=7 Hz), 3.15–2.90 (5H, m), 2.79 (1H, d, J=14 Hz), 1.43 (3H, m), 1.26 (3H, m), 1.08 (2H, m), 0.87 (3H, t, J=7 Hz), 0.81 (3H, t, J=7 Hz). MS (DCI/$NH_3$) m/e 509 (M+H)$^+$. Anal. calc.

for C₃₀H₄₀N₂O₅·0.25H₂O: C, 70.22; H, 7.95; N, 5.46. Found: C, 70.21; H, 7.92; N, 5.36.

EXAMPLE 149 trans,trans-1-(N,N-Di(n-butyl)aminocarbonylmethyl)-2-(4-methoxyphenyl)-4-(4-methoxyphenyl)pyrrolidine-3-carboxylic acid The title compound was prepared by the procedures described in Examples 1 and 49 substituting 4-methoxybenzaldehyde for piperonal in Example 49A. $^1$H NMR (300 MHz, CDCl₃) δ 7.38 (2H, d, J=8 Hz), 7.30 (2H, d, J=8 Hz), 6.87 (4H, dd, J=7 Hz, 3 Hz), 3.78 (3H, s), 3.76 (3H, s), 3.63 (1H, m), 3.50–3.20 (4H, m), 3.15–2.90 (5H, m), 2.78 (1H, d, J=14 Hz), 1.43 (3H, m), 1.27 (3H, m), 1.09 (2H, m), 0.87 (3H, t, J=7 Hz), 0.81 (3H, t, J=7 Hz). MS (DCI/NH₃) m/e 497 (M+H)⁺. Anal. calc. for C₂₉H₄₀N₂O₅: C, 70.13; H, 8.12; N, 5.64. Found: C, 69.78; H, 8.10; N, 5.54.

EXAMPLE 150 trans,trans-1-(N,N-Di(n-butyl)aminocarbonylmethyl)-2-(4-methoxyphenyl)-4-(3,4-difluorophenyl)pyrrolidine-3-carboxylic acid The title compound was prepared by the procedures described in Examples 1 and 49 substituting 3,4-difluorobenzaldehyde for piperonal in Example 49A. $^1$H NMR (300 MHz, CDCl₃) δ 7.35 (1H, m), 7.30 (2H, d, J=8 Hz), 7.20–7.00 (2H, m), 6.87 (2H, d, J=8 Hz), 3.78 (3H, s), 3.79 (1H, m), 3.62 (1H, m), 3.50–3.30 (3H, m), 3.23 (1H, m), 3.15–2.90 (4H, m), 2.78 (1H, d, J=14 Hz), 1.43 (2H, m), 1.27 (4H, m), 1.08 (2H, m), 0.85 (3H, t, J=7 Hz), 0.80 (3H, t, J=7 Hz). MS (DCI/NH₃) m/e 503 (M+H)⁺. Anal. calc. for C₂₈H₃₆F₂N₂O₄·1H₂O: C, 64.60; H, 7.36; N, 5.38. Found: C, 64.59; H, 7.20; N, 5.35.

EXAMPLE 151 trans,trans-1-(N,N-Di(n-butyl)aminocarbonylmethyl)-2-(4-methoxyphenyl)-4-(2,4-dimethoxyphenyl)pyrrolidine-3-carboxylic acid The title compound was prepared by the procedures described in Examples 1 and 49 substituting 2,4-dimethoxybenzaldehyde for piperonal in Example 49A. $^1$H NMR (300 MHz, CDCl₃) δ 7.37 (2H, d, J=8 Hz), 7.20 (1H, d, J=8 Hz), 6.92 (2H, d, J=8 Hz), 6.60 (1H, d, J=3 Hz), 6.49 (1H, dd, J=6 Hz, 2 Hz), 5.35 (1H, d, J=8 Hz), 4.20 (3H, m), 4.10 (3H, s), 3.83 (3H, s), 3.81 (3H, s), 3.75 (3H, m), 3.17 (2H, hep, J=7 Hz), 3.05 (2H, t, J=7 Hz), 1.30 (4H, m), 1.07 (4H, m), 0.87 (3H, t, J=7 Hz), 0.80 (3H, t, J=7 Hz). MS (DCI/NH₃) m/e 527 (M+H)⁺. Anal. calc. for C₃₀H₄₂N₂O₆·1.30 TFA: C, 58.02; H, 6.47; N, 4.15. Found: C, 57.92; H, 6.43; N, 4.07.

EXAMPLE 152 trans,trans-1-(N,N-Di(n-butyl)aminocarbonylmethyl)-2-phenyl-4-(1,3-benzodioxol-5-yl)pyrrolidine-3-carboxylic acid The title compound was prepared by the procedures described in Examples 1 and 49 substituting ethyl benzoylacetate in Example 49B. $^1$H NMR (300 MHz, CDCl₃) δ 7.50–7.25 (5H, m), 7.04 (1H, d, J=3 Hz), 6.87 (1H, dd, J=7 Hz, 3 Hz), 6.74 (1H, d, J=8 Hz), 5.94 (1H, d, J=4 Hz), 5.92 (1H, d, J=4 Hz), 3.85 (1H, d, J=8 Hz), 3.64 (1H, m), 3.42 (3H, m), 3.27 (2H, m), 3.20–2.90 (5H, m), 2.81 (1H, d, J=14 Hz), 1.43 (2H, m), 1.27 (4H, m), 1.05 (2H, m), 0.85 (3H, t, J=7 Hz), 0.80 (3H, t, J=7 Hz). MS (DCI/NH₃) m/e 481 (M+H)⁺. Anal. calc. for C₂₈H₃₆N₂O₅: C, 69.98; H, 7.55; N, 5.83. Found: C, 69.69; H, 7.63; N, 5.71.

EXAMPLE 153 trans,trans-1-(N,N-Di(n-butyl)aminocarbonylmethyl)-2-phenyl-4-(5-benzo-2,3-dihydrofuranyl)pyrrolidine-3-carboxylic acid The title compound was prepared by the procedures described in Examples 1 and 49 substituting ethyl benzoylacetate in Example 49B and 2,3-dihydrobenzofuran-5-carboxaldehyde for piperonal in Example 49A. $^1$H NMR (300 MHz, CDCl₃) δ 7.53 (2H, m), 7.40 (4H, m), 7.13 (1H, dd, J=7 Hz, 3 Hz), 6.72 (1H, d, J=8 Hz), 5.40 (1H, d, J=10 Hz), 4.56 (2H, t, J=8 Hz), 4.18 (1H, d, J=14 Hz), 4.07 (2H, m), 3.79 (2H, m), 3.48 (1H, d, J=14 Hz), 3.35 (1H, m), 3.28 (3H, m), 2.95 (2H, m), 1.47 (2H, m), 1.28 (4H, m), 1.10 (2H, m), 0.93 (3H, t, J=7 Hz), 0.78 (3H, t, J=7 Hz). MS (DCI/NH₃) m/e 479 (M+H)⁺. Anal. calc. for C₂₉H₃₈N₂O₄·1.10 TFA: C, 62.04; H, 6.52; N, 4.64. Found: C, 61.89; H, 6.44; N, 4.57.

EXAMPLE 154 trans,trans-1-(N,N-Di(n-butyl)aminocarbonylmethyl)-2-(4-t-butylphenyl)-4-(5-benzo-2,3-dihydrofuranyl)pyrrolidine-3-carboxylic acid The title compound was prepared by the procedures described in Examples 1 and 49 substituting t-butyl benzoylacetate, prepared by the method of Krapcho et al., Org. Syn. 47:20 (1967) starting from 4-t-butylacetophenone, in Example 49B and 2,3-dihydrobenzofuran-5-carboxaldehyde for piperonal in Example 49A. $^1$H NMR (300 MHz, CDCl₃) δ 7.60–7.30 (6H, m), 6.90 (1H, m), 4.50 (2H, m), 3.95 (1H, m), 3.85–2.95 (11H, m), 2.90 (1H, d, J=14 Hz), 1.58 (2H, m), 1.50 (7H, m), 1.41 (6H, s), 1.10 (2H, m), 1.00 (3H, t, J=7 Hz), 0.90 (3H, t, J=7 Hz). MS (DCI/NH₃) m/e 535 (M+H)⁺. Anal. calc. for C₃₃H₄₆N₂O₄·0.25H₂O: C, 73.50; H, 8.69; N, 5.19. Found: C, 73.57; H, 8.58; N, 5.14.

EXAMPLE 155 trans,trans-2-(N,N-Di(n-butyl)aminocarbonylmethyl)-2-(4-methoxyphenyl)-4-(4-fluorophenyl)pyrrolidine-3-carboxylic acid The title compound was prepared by the procedures described in Examples 1 and 49 substituting 4-fluorobenzaldehyde for piperonal in Example 49A. $^1$H NMR (300 MHz, CDCl₃) δ 7.50 (1H, m), 7.42 (1H, dd, J=7 Hz, 3 Hz), 7.36 (2H, d, J=8 Hz), 7.01 (3H, t, J=8 Hz), 6.87 (1H, d, J=8 Hz), 3.83 (1H, m), 3.8 (3H, s), 3.67 (1H, m), 3.47 (3H, m), 3.30–2.90 (5H, m), 2.82 (1H, d, J=14 Hz), 1.43 (2H, m), 1.28 (4H, m), 1.08 (2H, m), 0.90 (3H, t, J=7 Hz), 0.82 (3H, t, J=7 Hz). MS (DCI/NH₃) m/e 485 (M+H)⁺. Anal. calc. for C₂₈H₃₇FN₂O₄: C, 69.40; H, 7.70; N, 5.78. Found: C, 69.03; H, 8.00; N, 5.74.

EXAMPLE 156 trans,trans-1-(N. N-Di(n-butyl)aminocarbonylmethyl)-2-(3-furyl)-4-(1,3-benzodioxol-5-yl)pyrrolidine-3-carboxylic acid The title compound was prepared by the procedures described in Examples 1 and 49 substituting β-oxo-3-furanpropionate in Example 49B. $^1$H NMR (300 MHz, CDCl$_3$) δ 7.41 (2H, m), 6.97 (1H, d, J=3 Hz), 6.85 (1H, dd, J=7 Hz, 3 Hz), 6.72 (1H, d, J=8 Hz), 6.42 (1H, s), 5.94 (1H, d, J=4 Hz), 5.92 (1H, d, J=4 Hz), 3.90 (1H, m), 3.70–3.25 (5H, m), 3.20–2.90 (4H, m), 2.85 (1H, d, J=14 Hz), 1.43 (2H, m), 1.40–1.05 (6H, m), 0.90 (6H, m). MS (DCI/NH$_3$) m/e 471 (M+H)$^+$. Anal. calc. for C$_{26}$H$_{34}$N$_2$O$_6$: C, 66.36; H, 7.28; N, 5.95. Found: C, 66.09; H, 7.24; N, 5.87.

EXAMPLE 157 trans,trans-1-(N,N-Di(n-butyl)aminocarbonylmethyl)-2-(isopropyl)-4-(1,3-benzodioxol-5-yl)pyrrolidine-3-carboxylic acid The title compound was prepared by the procedures described in Examples 1 and 49 substituting ethyl isobutyrylacetate in Example 49B. $^1$H NMR (300 MHz, CDCl$_3$) δ 6.85 (1H, d, J=2 Hz), 6.76 (1H, dd, J=6 Hz, 2 Hz), 6.71 (1H, d, J=8 Hz), 5.92 (2H, s), 3.75 (1H, d, J=14 Hz), 3.66 (1H, q, J=7 Hz), 3.42 (3H, m), 3.25 (3H, m), 3.11 (2H,m), 2.83 (1H, t, J=7 Hz), 1.88 (1H, m), 1.55 (4H, m), 1.32 (4H, m), 0.92 (12H, m). MS (DCI/NH$_3$) m/e 447 (M+H)$^+$. Anal. calc. for C$_{25}$H$_{38}$N$_2$O$_5$.0.50H$_2$O: C, 65.91; H, 8.63; N, 6.15. Found: C, 66.07; H, 8.10; N, 6.03.

EXAMPLE 158 trans,trans-1-(N,N-Di(n-butyl)aminocarbonylmethyl)-2-(4-t-butylphenyl)-4-(1,3-benzodioxol-5-yl)pyrrolidine-3-carboxylic acid The title compound was prepared by the procedures described in Examples 1 and 49 substituting ethyl 4-t-butylbenzoylacetate, prepared by the method of Krapcho et al., Org. Syn. 47: 20 (1967) starting with 4-t-butylacetophenone), in Example 49B. $^1$H NMR (300 MHz, CDCl$_3$) δ 7.32 (4H, d, J=3 Hz), 7.04 (1H, d, J=2 Hz), 6.87 (1H, dd, J=8 Hz, 3 Hz), 6.74 (1H, d, J=9 Hz), 5.94 (1H, d, J=4 Hz), 5.92 (1H, d, J=4 Hz), 3.77 (1H, d, J=14 Hz), 3.65–3.25 (5H, m), 3.15–2.85 (4H, m), 2.73 (1H, d, J=14 Hz), 1.45 (2H, m), 1.29 (13H, s), 1.00 (2H, m), 0.86 (3H, t, J=7 Hz), 0.76 (3H, t, J=7 Hz). MS (DCI/NH$_3$) m/e 537 (M+H)$^+$. Anal. calc. for C$_{32}$H$_{44}$N$_2$O$_5$: C, 71.61; H, 8.26; N, 5.22. Found: C, 71.43; H, 8.09; N, 5.11.

EXAMPLE 159 trans,trans-1-(N,N-Di(n-butyl)aminocarbonylmethyl)-2-(4-t-butylphenyl)-4-(5-benzo-2,3-dihydrofuranyl pyrrolidine-3-carboxylic acid The title compound was prepared by the procedures described in Examples 1 and 49 substituting ethyl isobutyrylacetate in Example 49B and 2,3-dihydrobenzofuran-5-carboxaldehyde for piperonal in Example 49A. $^1$H NMR (300 MHz, CDCl$_3$) δ 7.30 (1H, s), 7.13 (1H, dd, J=7 Hz, 2 Hz), 6.82 (1H, d, J=8 Hz), 4.68 (2H, t, J=8 Hz), 4.48 (1H, s), 3.19 (3H, m), 3.80 (3H, m), 3.48 (2H, m), 3.3 (5H, m), 2.41 (1H, m), 1.65 (4H, m), 1.44 (4H, m), 1.21 (3H, d, J=5 Hz), 1.17 (3H, d, J=5 Hz), 1.05 (6H, m). MS (DCI/NH$_3$) m/e 445 (M+H)$^+$. Anal. calc. for C$_{26}$H$_{40}$N$_2$O$_4$ 1.2 TFA: C, 58.67; H, 7.14; N, 4.8.2 Found: C, 58.54; H, 7.25; N, 4.74.

EXAMPLE 160 trans,trans-1-(N,N-Di(n-butyl)aminocarbonylmethyl)-2-(anti-4-methoxycyclohexyl)-4-(1,3-benzodioxol-5-yl)pyrrolidine-3-carboxylic acid

EXAMPLE 160A syn and anti Ethyl 4-methoxycyclohexanoylacetate

Syn, anti-4-Methoxycyclohexane carboxylic acid (5.00 g, 31.6 mmol) and carbonyldiimidazole (6.15 g, 37.9 mmol, 1.2 eq) were stirred in anhydrous tetrahydrofuran (50 mL) for 6 hours at room temperature. At the same time, magnesium chloride (3.01 g, 31.6 mmol) and ethyl malonate potassium salt (7.52 g, 44.2 mmol, 1.4 equivalents) were stirred in anhydrous tetrahydrofuran (75 mL) for 6 hours at 50° C. The mixture was cooled to room temperature, and the imidazole-acid mixture added to it. The reaction stirred overnight at room temerature. The solvents were removed under reduced pressure, and the residue was taken up in chloroform/water. The organic phase washed with 5% potassium bisulfate, water, and brine, dried with magnesium sulfate, filtered, and concentrated under reduced pressure. The residue was purified by flash chromatography on 175 g silica gel, eluting with 20% ethyl acetate in hexanes. Pure fractions of the syn and anti methoxycyclohexyl β-keto esters were obtained. The solvents were removed under reduced pressure to yield the trans-4-methoxycyclohexyl β-keto ester (914 mg) as a colorless oil and the cis 4-methoxycyclohexyl β keto ester (1.07 g) as a colorless oil.

EXAMPLE 160B trans,trans-1-(N,N-Di(n-butyl)aminocarbonylmethyl)-2-(anti-4-methoxycyclohexyl)-4-(1,3-benzodioxol-5-yl)pyrrolidine-3-carboxylic acid The title compound was prepared by the procedures described in Examples 1 and 49 substituting the anti-compound resulting from Example 160A in Example 49B. $^1$H NMR (300 MHz, CDCl$_3$) δ 6.84 (1H, d, J=2 Hz), 6.76 (1H, dd, J=7 Hz, 2 Hz), 6.61 (1H, d, J=8 Hz), 5.92 (2H, s), 3.69 (2H, m), 3.50–3.27 (5H, m), 3.26 (3H, s), 3.25–3.00 (3H, m), 2.88 (1H, m), 1.95 (2H, m), 1.62 (7H, m), 1.33 (9H, m), 0.97 (3H, t, J=7 Hz), 0.92 (3H, t, J=7 Hz). MS (DCI/NH$_3$) m/e 517 (M+H)$^+$. Anal. calc. for C$_{29}$H$_{44}$N$_2$O$_6$ 0.50H$_2$O: C, 66.26; H, 8.63; N, 5.33. Found: C, 66.27; H, 8.50; N, 5.13.

EXAMPLE 161 trans,trans-1-(N,N-Di(n-butyl)aminocarbonylmethyl)-2-(syn-4-methoxycyclohexyl)-4-(1,3-benzodioxol-5-yl)pyrrolidine-3-carboxylic acid The title compound was prepared by the procedures described in Examples 1 and 49 substituting the syn-compound resulting from Example 160A in Example 49B. $^1$H NMR (300 MHz, CDCl$_3$) δ 6.84 (1H, d, J=2 Hz), 6.77 (1H, dd, J=6 Hz, 2 Hz), 6.61 (1H, d, J=8 Hz), 5.92 (2H, s), 3.65 (2H, m), 3.42 (2H, m), 3.32 (3H, s), 3.30–3.00 (6H, m), 2.82

(1H, m), 2.10 (2H, m), 1.83 (2H, m), 1.52 (6H, m), 1.33 (4H, m), 1.20–1.00 (4H, m), 0.96 (3H, t, J=7 Hz), 0.91 (3H, t, J=7 Hz). MS (DCI/NH$_3$) m/e 517 (M+H)$^+$. Anal. calc. for C$_{29}$H$_{44}$N$_2$O$_6$·0.30H$_2$O: C, 66.72; H, 8.61; N, 5.37. Found: C, 66.76; H, 8.65; N, 5.28.

EXAMPLE 162 trans,trans-1-(N,N-Di(n-butyl)aminocarbonylmethyl)-2,4-di(5-benzo-2,3-dihydrofuranyl)pyrrolidine-3-carboxylic acid

EXAMPLE 162A

5-Acetyl-2,3-dihydrobenzofuran

To a 0° C. solution of acetyl chloride (1.64 mL, 23.0 mmol, 1.3 equivalents) in methylene chloride (30 mL) was added stannic chloride (2.49 mL, 21.3 mmol, 1.2 equivalents), maintaining the temperature below 5° C. The solution was stirred 15 minutes at 0° C., and then a solution of 2,3-dihydrofuran (2.00 mL, 17.7 mmol) in methylene chloride (5 mL) was added dropwise while maintaining the temperature below 8° C. The dark red solution was stirred 1 hour at 2° C. and then poured into 50 mL of ice water. The reaction was stirred an additional 30 minutes, and the layers were separated. The organic layer was washed with water and aqueous sodium bicarbonate, dried over magnesium sulfate, filtered, and concentrated under reduced pressure. The residue was purified by flash chromatography on 150 g silica gel, eluting with 18% ethyl acetate in hexanes. The solvents were removed under reduced pressure to yield the title compound (2.68 g, 93%) as a yellow solid.

EXAMPLE 162B trans,trans-1-(N,N-Di(n-butyl)aminocarbonylmethyl)-2,4-di(5-benzo-2,3-dihydrofuranyl)pyrrolidine-3-carboxylic acid The title compound was prepared by the procedures described in Examples 1 and 49 substituting the compound resulting from Example 162A in Example 49B and 2,3-dihydrobenzofuran-5-carboxaldehyde for piperonal in Example 49A. $^1$H NMR (300 MHz, CDCl$_3$) δ 7.43 (1H, s), 7.38 (1H, s), 7.06 (2H, m), 6.75 (1H, d, J=6 Hz), 6.70 (1H, d, J=6 Hz), 5.40 (1H, d, J=9 Hz), 4.58 (4H, q, J=7 Hz), 4.16 (1H, d, J=14 Hz), 4.09 (2H, m), 3.82 (2H, m), 3.57 (1H, d, J=14 Hz), 3.38 (1H, m), 3.30–3.05 (6H, m), 2.95 (2H, q, J=6 Hz), 1.50 (2H, m), 1.30 (4H, m), 1.15 (2H, m), 0.94 (3H, t, J=7 Hz), 0.83 (3H, t, J=7 Hz). MS (DCI/NH$_3$) m/e 521 (M+H)$^+$. Anal. calc. for C$_{31}$H$_{40}$N$_2$O$_5$ 1.25 TFA: C, 60.67; H, 6.27; N, 4.22. Found: C, 60.49; H, 6.18; N, 4.13.

EXAMPLE 163 trans,trans-1-(N,N-Di(n-butyl)aminocarbonylmethyl)-2-(3-furyl)-4-(5-benzo-2,3-dihydrofuranyl)pyrrolidine-3-carboxylic acid The title compound was prepared by the procedures described in Examples 1 and 49 substituting ethyl β-oxo-3-furanpropionate in Example 49B and 2,3-dihydrobenzofuran-5-carboxaldehyde for piperonal in Example 49A. $^1$H NMR (300 MHz, CDCl$_3$) δ 7.42 (1H, m), 7.38 (1H, m), 7.13 (1H, s), 7.16 (1H, dd, J=7 Hz, 3 Hz), 6.70 (1H, d, J=8 Hz), 6.41 (1H, m), 4.57 (2H, t, J=7 Hz), 3.95 (1H, d, J=8 Hz), 3.63 (1H, m), 3.55 (1H, d, J=14), 3.50–3.25 (4H, m), 3.18 (2H, t, J=6 Hz), 3.15–2.95 (3H, m), 2.87 (1H, d, J=14 Hz), 1.45 (4H, m), 1.35–1.10 (4H, m), 0.85 (6H, m). MS (DCI/NH$_3$) m/e 469 (M+H)$^+$. Anal. calc. for C$_{27}$H$_{36}$N$_2$O$_5$ 0.25H$_2$O: C, 68.55; H, 7.78; N, 5.92. Found: C, 68.62; H, 7.68; N, 5.82.

EXAMPLE 164 trans,trans-1-(N,N-Di(n-butyl)aminocarbonylmethyl)-2-(4-methoxyphenyl)-4-(3-fluorophenyl)pyrrolidine-3-carboxylic acid The title compound was prepared by the procedures described in Examples 1 and 49 substituting 3-fluorobenzenecarboxaldehyde for piperonal in Example 49A. $^1$H NMR (300 MHz, CDCl$_3$) δ 7.30 (2H, d, J=8 Hz), 7.22 (2H, m), 6.91 (1H, m), 6.86 (2H, d, J=8 Hz), 3.79 (1H, m), 3.78 (3H, s), 3.68 (1H, m), 3.55–3.37 (3H, m), 3.29 (1H, m), 3.15–2.90 (5H, m), 2.78 (1H, d, J=14 Hz), 1.43 (2H, m), 1.25 (4H, m), 1.07 (2H, m), 0.87 (3H, t, J=7 Hz), 0.80 (3H, t, J=7 Hz). MS (DCI/NH$_3$) m/e 485 (M+H)$^+$. Anal. calc. for C$_{28}$H$_{37}$FN$_2$O$_4$·0.25H$_2$O: C, 68.76; H, 7.73; N, 5.73. Found: C, 68.87; H, 7.69; N, 5.67.

EXAMPLE 165 trans,trans-1-(N,N-Di(n-butyl)aminocarbonylmethyl)-2-(4-methoxyphenyl)-4-(3-pyridyl)pyrrolidine-3-carboxylic acid The title compound was prepared by the procedures described in Examples 1 and 49 substituting 3-pyridinecarboxaldehyde for piperonal in Example 49A. The nitro styrene was prepared by the method of Bourguignon, et al., Can. J. Chem. 63: 2354 (1985). $^1$H NMR (300 MHz, CDCl$_3$) δ 8.82 (1H, bs), 8.73 (1H, bd, J=9 Hz), 8.62 (1H, bd, J=7 Hz), 7.78 (1H, bdd, J=9 Hz, 3 Hz), 7.38 (2H, d, J=10 Hz), 6.90 (2H, d, J=10 Hz), 4.39 (1H, d, J=12 Hz), 3.95 (1H, m), 3.80 (3H, s), 3.79 (1H, m), 3.68 (1H, d, J=18 Hz), 3.50–3.30 (3H, m), 3.25–2.90 (6H, m), 1.47 (2H, m), 1.31 (4H, m), 1.20 (2H, m), 0.92 (3H, t, J=7 Hz), 0.83 (3H, t, J=7 Hz). MS (DCI/NH$_3$) m/e 468 (M+H)$^+$. Anal. calc. for C$_{27}$H$_{37}$N$_3$O$_4$ 1.65 TFA: C, 55.50; H, 5.94; N, 6.41. Found: C, 55.53; H, 5.90; N, 6.27.

EXAMPLE 166 trans,trans-1-(N,N-Di(n-butyl)aminocarbonylmethyl)-2-(2-fluorophenyl)-4-(1,3-benzodioxol-5-yl)pyrrolidine-3-carboxylic acid The title compound was prepared by the procedures described in Examples 1 and 49 substituting ethyl 2-fluorobenzoylacetate in Example 49B. $^1$H NMR (300 MHz, CDCl$_3$) δ 7.52 (1H, dt, J=7 Hz, 3 Hz), 7.25 (1H, m), 7.13 (1H, dt, J=7 Hz, 3 Hz), 7.02 (2H, m), 6.88 (1H, dd, J=7 Hz, 3 Hz), 6.73 (1H, d, J=8 Hz), 5.93 (1H, d, J=4 Hz), 5.92 (1H, d, J=4 Hz), 4.25 (1H, d, J=9 Hz), 3.68 (1H, m), 3.42 (3H, m), 3.39 (1H, m), 3.20–2.95 (4H, m), 2.91 (1H, d, J=14 Hz), 1.45 (3H, m), 1.26 (3H, m), 1.08 (2H, m), 0.87 (3H, t, J=7 Hz), 0.81 (3H, t, J=7 Hz). MS (DCI/NH$_3$) m/e 499 (M+H)$^+$. Anal. calc. for C$_{28}$H$_{35}$FN$_2$O$_5$·0.25H$_2$O: C, 66.85; H, 7.11; N, 5.57. Found: C, 66.51; H, 6.67; N, 5.18.

EXAMPLE 167 trans,trans-1-(N,N-Di(n-butyl)aminocarbonylmethyl)-2-(3-fluorophenyl)-4-(1,3-benzodioxol-5-yl)pyrrolidine-3-carboxylic acid The title compound was prepared by the procedures described in Examples 1 and 49 substituting ethyl 3-fluorobenzoylacetate in Example 49B. $^1$H NMR (300 MHz, CDCl$_3$) δ 7.38 (1H, m), 7.18 (1H, d, J=7 Hz), 7.15 (1H, m), 7.00 (1H, d, J=2 Hz), 6.95 (1H, m), 6.86 (1H, dd, J=7 Hz, 2 Hz), 6.75 (1H, d, J=8 Hz), 5.93 (1H, d, J=4 Hz), 5.92 (1H, d, J=4 Hz), 3.94 (1H, d, J=14 Hz), 3.63 (1H, m), 3.42 (3H, m), 3.35–2.95 (5H, m), 2.87 (1H, d, J=14 Hz), 1.44 (3H, m), 1.27 (3H, m), 1.10 (2H, m), 0.88 (3H, t, J=7 Hz), 0.81 (3H, t, J=7 Hz). MS (DCI/NH$_3$) m/e 499 (M+H)$^+$. Anal. calc. for C$_{28}$H$_{35}$FN$_2$O$_5$: C, 67.45; H, 7.08; N, 5.62. Found: C, 67.32; H, 7.05; N, 5.40.

EXAMPLE 168 trans,trans-1-(4-N,N-Di(n-butyl)aminophenyl)-2-(4-methoxyphenyl)-4-(1,3-benzodioxol-5-yl)pyrrolidine-3-carboxylic acid 4-Nitro-1-fluorobenzene, ethyl trans,trans-2-(4-methoxyphenyl)-4-(1,3-benzodioxol-5-yl)-pyrrolidine-3-carboxylate (the compound resulting from Example 6A), and diisopropylethylamine are heated in dioxane to give ethyl trans,trans-2-(4-methoxyphenyl)-4-(1,3-benzodioxol-5-yl)-1-(4-nitrophenyl)-pyrrolidine-3-carboxylate. The nitro compound is hydrogenated to give the corresponding aminophenyl compound. The aminophenyl compound is reacted with butyraldehyde and sodium cyanoborohydride according to the method of Borch, J. Am Chem. Soc. 93: 2897 (1971) to give the corresponding N,N-dibutylaminophenyl compound. Hydrolysis with sodium hydroxide using the method of Example 1D affords the title compound.

EXAMPLE 169 trans,trans-1-(2-N,N-Dibutylaminopyrimidin-4-vi)-2-(4-methoxyphenyl)-4-(1,3-benzodioxol-5-yl)pyrrolidine-3-carboxylic acid 2-(Dibutylamino)-4-chloropyrimidine is prepared from 2,4-dichloropyrimidine according to the method of Gershon, J. Heterocyclic Chem. 24: 205 (1987) and reacted with ethyl trans,trans-2-(4-methoxyphenyl)-4-(1,3-benzodioxol-5-yl)-pyrrolidine-3-carboxylate (the compound resulting from Example 6A) and diisoproplyethylamine in dioxane with heating to give the intermediate ethyl ester, which is hydrolyzed with sodium hydroxide using the method of Example 1D to the title compound.

EXAMPLES 170–266

Using the procedures described in Examples 1, 4, 5, 7, 8 and 9 and Scheme X, the compounds can be prepared.

Ex. No. Name 170 trans,trans-2-(4-Methoxyphenyl)-4-(1,3-benzodioxol-5-yl)-1-(isopropylaminocarbonylmethyl)-pyrrolidine-3-carboxylic acid;

171 trans,trans-2-(4-Methoxyphenyl)-4-(1,3-benzodioxol-5-yl)-1-(ethylaminocarbonylmethyl)-pyrrolidine-3-carboxylic acid;

172 trans,trans-2-(4-Methoxyphenyl)-4-(1,3-benzodioxol-5-yl)-1-(1-methylpropylaminocarbonylmethyl)-pyrrolidine-3-carboxylic acid;

173 trans,trans-2-(4-Methoxyphenyl)-4-(1,3-benzodioxol-5-yl)-1-(phenylaminocarbonylmethyl)-pyrrolidine-3-carboxylic acid;

174 trans,trans-2-(4-Methoxyphenyl)-4-(1,3-benzodioxol-5-yl)-1-(piperidinylcarbonylmethyl)-pyrrolidine-3-carboxylic acid;

175 trans,trans-2-(4-Methoxyphenyl)-4-(1,3-benzodioxol-5-yl)-1-(1-(propylaminocarbonyl)ethyl)-pyrrolidine-3-carboxylic acid;

176 trans,trans-2-(4-Methoxyphenyl)-4-(1,3-benzodioxol-5-yl)-1-(α-(propylaminocarbonyl)benzyl)-pyrrolidine-3-carboxylic acid;

177 trans,trans-2-(4-Methoxyphenyl)-4-(1,3-benzodioxol-5-yl)-1-(bis-(propylaminocarbonyl)methyl)-pyrrolidine-3-carboxylic acid;

178 trans,trans-2-(4-Methoxyphenyl)-4-(1,3-benzodioxol-5-yl)-1-(2-(propylaminocarbonyl)ethyl)-pyrrolidine-3-carboxylic acid;

179 trans,trans-2-(4-Methoxyphenyl)-4-(1,3-benzodioxol-5-yl)-1-(propylaminosulfonylmethyl)-pyrrolidine-3-carboxylic acid;

180 trans,trans-2-(4-Methoxyphenyl)-4-(1,3-benzodioxol-5-yl)-1-(2-phenethyl)-pyrrolidine-3-carboxylic acid;

181 trans,trans-2-(4-Methoxyphenyl)-4-(1,3-benzodioxol-5-yl)-1-(pentanoylmethyl)-pyrrolidine-3-carboxylic acid;

182 trans,trans-2-(4-Methoxyphenyl)-4-(1,3-benzodioxol-5-yl)-1-(benzoylmethyl)-pyrrolidine-3-carboxylic acid;

183 trans,trans-2-(4-Methoxyphenyl)-4-(1,3-benzodioxol-5-yl)-1-(hexyl)-pyrrolidine-3-carboxylic acid;

184 trans,trans-2-(4-Methoxyphenyl)-4-(1,3-benzodioxol-5-yl)-1-(2-hexynyl)-pyrrolidine-3-carboxylic acid;

185 trans,trans-2-(4-Methoxyphenyl)-4-(1,3-benzodioxol-5-yl)-1-(propoxymethylcarbonyl-pyrrolidine-3-carboxylic acid;

186 trans,trans-2-(4-Methoxyphenyl)-4-(1,3-benzodioxol-5-yl)-1-(phenylacetyl)-pyrrolidine-3-carboxylic acid;

187 trans,trans-2-(4-Methoxyphenyl)-4-(1,3-benzodioxol-5-yl)-1-(anilinylcarbonyl)-pyrrolidine-3-carboxylic acid;

188 trans,trans-2-(4-Methoxyphenyl)-4-(1,3-benzodioxol-5-yl)-1-(2-acetylaminoethyl)-pyrrolidine-3-carboxylic acid;

189 trans,trans-2-(4-Methoxyphenyl)-4-(1,3-benzodioxol-5-yl)-1-(2-phenoxyethyl)-pyrrolidine-3-carboxylic acid;

190 trans,trans-2-(4-Methoxyphenyl)-4-(1,3-benzodioxol-5-yl)-1-(2-benzodioxanylmethyl)-pyrrolidine-3-carboxylic acid;

191 trans,trans-2-(4-Methoxyphenyl)-4-(1,3-benzodioxol-5-yl)-1-(2-tetrahydrofuranylmethyl)-pyrrolidine-3-carboxylic acid;

192 trans,trans-2-(4-Methoxyphenyl)-4-(1,3-benzodioxol-5-yl)-1-(2-(propylaminocarbonylamino)ethenyl)-pyrrolidine-3-carboxylic acid;

193 trans,trans-2-(4-Methoxyphenyl)-4-(1,3-benzodioxol-5-yl)-1-(2-(propylaminocarbonylamino)ethyl)-pyrrolidine-3-carboxylic acid;

194 trans,trans-2-(4-Methoxyphenyl)-4-(1,3-benzodioxol-5-yl)-1-(3-oxohex-1-enyl)-pyrrolidine-3-carboxylic acid;

195 trans,trans-2-(2,4-Dimethoxyphenyl)-4-(1,3-benzodioxol-5-yl)-1-(propylaminocarbonylmethyl)-pyrrolidine-3-carboxylic acid;

196 trans,trans-2-(2-Carboxy-4-methoxyphenyl)-4-(1,3-benzodioxol-5-yl)-1-(propylaminocarbonylmethyl)-pyrrolidine-3-carboxylic acid;

197 trans,trans-2-(2-Aminocarbonyl-4-methoxyphenyl)-4-(1,3-benzodioxol-5-yl)-1-(propylaminocarbonylmethyl)-pyrrolidine-3-carboxylic acid;
198 trans,trans-2-(2-Methanesulfonamido-4-methoxyphenyl)-4-(1,3-benzodioxol-5-yl)-1-(propylaminocarbonylmethyl)-pyrrolidine-3-carboxylic acid;
199 trans,trans-2-(2-Aminocarbonylmethoxy-4-methoxyphenyl)-4-(1,3-benzodioxol-5-yl)-1-(propylaminocarbonylmethyl)-pyrrolidine-3-carboxylic acid;
200 trans,trans-2-(2-Methoxyethoxy-4-methoxyphenyl)-4-(1,3-benzodioxol-5-yl)-1-(propylaminocarbonylmethyl)-pyrrolidine-3-carboxylic acid;
201 trans,trans-2-(2-Carboxymethoxy-4-methoxyphenyl)-4-(1,3-benzodioxol-5-yl)-1-(propylaminocarbonylmethyl)-pyrrolidine-3-carboxylic acid;
202 trans,trans-2-(4-Methoxy-2-tetrazolylmethoxyphenyl)-4-(1,3-benzodioxol-5-yl)-1-(propylaminocarbonylmethyl)-pyrrolidine-3-carboxylic acid;
203 trans,trans-2-(2-Allyloxy-4-methoxyphenyl)-4-(1,3-benzodioxol-5-yl)-1-(propylaminocarbonylmethyl)-pyrrolidine-3-carboxylic acid;
204 trans,trans 2,4-Bis(4-methoxyphenyl)-1-(propylaminocarbonylmethyl)-pyrrolidine-3-carboxylic acid;
205 trans,trans 2,4-Bis(1,3-benzodioxol-5-yl)-1-(propylaminocarbonylmethyl)-pyrrolidine-3-carboxylic acid;
206 trans,trans-2-(4-Methoxyphenyl)-4-(1,3-benzodioxol-5-yl)-1-(N-methyl-N-propylaminocarbonylmethyl)-pyrrolidine-3-carboxylic acid;
207 trans,trans-2-(4-Methoxyphenyl)-4-(1,3-benzodioxole-5-yl)-1-(N-methyl-N-butylaminocarbonyl)-pyrrolidine-3-carboxylic acid;
208 trans,trans-2-(4-Methoxyphenyl)-4-(1,3-benzodioxol-5-yl)-1-(N-methyl-N-(4-methoxyphenyl)aminocarbonyl)-3-pyrrolidine-3-carboxylic acid;
209 trans,trans-2-(4-Methoxyphenyl)-4-(1,3-benzodioxol-5-yl)-1-(N-methyl-N-phenylaminocarbonyl)-pyrrolidine-3-carboxylic acid;
210 trans,trans-2-(4-Methoxyphenyl)-4-(1,3-benzodioxol-5-yl)-1-(N-methyl-N-allylaminocarbonylmethyl)-pyrrolidine-3-carboxylic acid;
211 trans,trans-2-(4-Methoxyphenyl)-4-(1,3-benzodioxol-5-yl)-1-(N-methyl-N-(n-butyl)aminocarbonylmethyl)-pyrrolidine-3-carboxylic acid;
212 trans,trans-2-(4-Methoxyphenyl)-4-(1,3-benzodioxol-5-yl)-1-(N-methyl-N-isobutylaminocarbonylmethyl)-pyrrolidine-3-carboxylic acid;
213 trans,trans-2-(4-Methoxyphenyl)-4-(1,3-benzodioxol-5-yl)-1-(N-methyl-N-cyclopentylaminocarbonylmethyl)-pyrrolidine-3-carboxylic acid;
214 trans,trans-2-(4-Methoxyphenyl)-4-(1,3-benzodioxol-5-yl)-1-(N-methyl-N-(2-methoxyethyl)aminocarbonyl)-pyrrolidine-3-carboxylic acid;
215 trans,trans-2-(4-Methoxyphenyl)-4-(1,3-benzodioxol-5-yl)-1-(N-methyl-N-butoxyethylaminocarbonyl)-pyrrolidine-3-carboxylic acid;
216 trans,trans-2-(1,3-Benzodioxol-5-yl)-4-(4-methoxyphenyl)-1-(N-methyl-N-propylaminocarbonylmethyl)-pyrrolidine-3-carboxylic acid;
217 trans,trans-2-(4-Methoxyphenyl)-4-(1,4-benzodioxan-6-yl)-1-(N-methyl-N-propylaminocarbonylmethyl)-pyrrolidine-3-carboxylic acid;
218 trans,trans-2-(4-Methoxyphenyl)-4-(1,3-benzodioxol-5-yl)-1-(N-methyl-N-isopropylaminocarbonylmethyl)-pyrrolidine-3-carboxylic acid;
219 trans,trans-2-(4-Methoxyphenyl)-4-(1,3-benzodioxol-5-yl)-1-(N-methyl-N-ethylaminocarbonyl)-pyrrolidine-3-carboxylic acid;
220 trans,trans-2-(4-Methoxyphenyl)-4-(1,3-benzodioxol-5-yl)-1-(N-methyl-N-(1-methylpropyl)aminocarbonylmethyl)-pyrrolidine-3-carboxylic acid;
221 trans,trans-2-(4-Methoxyphenyl)-4-(1,3-benzodioxol-5-yl)-1-(N-methyl-N-phenylaminocarbonylmethyl)-pyrrolidine-3-carboxylic acid;
222 trans,trans-2-(4-Methoxyphenyl)-4-(1,3-benzodioxol-5-yl)-1-(1-(N-methyl-N-propylaminocarbonyl)ethyl)-pyrrolidine-3-carboxylic acid;
223 trans,trans-2-(4-Methoxyphenyl)-4-(1,3-benzodioxol-5-yl)-1-(α-(N-methyl-N-propylaminocarbonyl)benzyl)-pyrrolidine-3-carboxylic acid;
224 trans,trans-2-(4-Methoxyphenyl)-4-(1,3-benzodioxol-5-yl)-1-(N-ethyl-N-propylaminocarbonylmethyl)-pyrrolidine-3-carboxylic acid;
225 trans,trans-2-(4-Methoxyphenyl)-4-(1,3-benzodioxole-5-yl)-1-(N-ethyl-N-butylaminocarbonyl)-pyrrolidine-3-carboxylic acid;
226 trans,trans-2-(4-Methoxyphenyl)-4-(1,3-benzodioxol-5-yl)-1-(N-ethyl-N-(4-methoxyphenyl)aminocarbonyl)-3-pyrrolidine-3-carboxylic acid;
227 trans,trans-2-(4-Methoxyphenyl)-4-(1,3-benzodioxol-5-yl)-1-(N-ethyl-N-phenylaminocarbonyl)-pyrrolidine-3-carboxylic acid;
228 trans,trans-2-(4-Methoxyphenyl)-4-(1,3-benzodioxol-5-yl)-1-(N-ethyl-N-allylaminocarbonylmethyl)-pyrrolidine-3-carboxylic acid;
229 trans,trans-2-(4-Methoxyphenyl)-4-(1,3-benzodioxol-5-yl)-1-(N-ethyl-N-isobutylaminocarbonylmethyl)-pyrrolidine-3-carboxylic acid;
230 trans,trans-2-(4-Methoxyphenyl)-4-(1,3-benzodioxol-5-yl)-1-(N-ethyl-N-cyclopentylaminocarbonylmethyl)-pyrrolidine-3-carboxylic acid;
231 trans,trans-2-(4-Methoxyphenyl)-4-(1,3-benzodioxol-5-yl)-1-(N-ethyl-N-methoxyethylaminocarbonyl)-pyrrolidine-3-carboxylic acid;
232 trans,trans-2-(4-Methoxyphenyl)-4-(1,3-benzodioxol-5-yl)-1-(N-ethyl-N-butoxyethylaminocarbonyl)-pyrrolidine-3-carboxylic acid;
233 trans,trans-2-(1,3-Benzodioxol-5-yl)-4-(4-methoxyphenyl)-1-(N-ethyl-N-propylaminocarbonylmethyl)-pyrrolidine-3-carboxylic acid;
234 trans,trans-2-(4-Methoxyphenyl)-4-(1,4-benzodioxan-6-yl)-1-(N-ethyl-N-propylaminocarbonylmethyl)-pyrrolidine-3-carboxylic acid;
235 trans,trans-2-(4-Methoxyphenyl)-4-(1,3-benzodioxol-5-yl)-1-(N-ethyl-N-isopropylaminocarbonylmethyl)-pyrrolidine-3-carboxylic acid;
236 trans,trans-2-(4-Methoxyphenyl)-4-(1,3-benzodioxol-5-yl)-1-(N,N-diethylaminocarbonylmethyl)-pyrrolidine-3-carboxylic acid;
237 trans,trans-2-(4-Methoxyphenyl)-4-(1,3-benzodioxol-5-yl)-1-(N-ethyl-N-(1-methylpropyl)aminocarbonylmethyl)-pyrrolidine-3-carboxylic acid;
238 trans,trans-2-(4-Methoxyphenyl)-4-(1,3-benzodioxol-5-yl)-1-(N-ethyl-N-phenylaminocarbonylmethyl)-pyrrolidine-3-carboxylic acid;
239 trans,trans-2-(4-Methoxyphenyl)-4-(1,3-benzodioxol-5-yl)-1-(1-(N-ethyl-N-propylaminocarbonyl)ethyl)-pyrrolidine-3-carboxylic acid;
240 trans,trans-2-(4-Methoxyphenyl)-4-(1,3-benzodioxol-5-yl)-1-(α-(N-ethyl-N-propylaminocarbonyl)benzyl)-pyrrolidine-3-carboxylic acid;
241 trans,trans-2-(4-Methoxyphenyl)-4-(1,3-benzodioxol-5-yl)-1-(N-methyl-N-isobutylaminocarbonylmethyl)-pyrrolidine-3-carboxylic acid;

242 trans,trans-2-(4-Methoxyphenyl)-4-(1,3-benzodioxol-5-yl)-1-(N-methyl-N-cyclohexylaminocarbonylmethyl)-pyrrolidine-3-carboxylic acid;
243 trans,trans-2-(4-Methoxyphenyl)-4-(1,3-benzodioxol-5-yl)-1-(N,N-dipropylaminocarbonylmethyl)-pyrrolidine-3-carboxylic acid;
244 trans,trans-2-(4-Methoxyphenyl)-4-(1,3-benzodioxol-5-yl)-1-(isobutyloxyethyl)-pyrrolidine-3-carboxylic acid;
245 trans,trans-2-(4-Methoxyphenyl)-4-(1,3-benzodioxol-5-yl)-1-(butylsulfonyl)-pyrrolidine-3-carboxylic acid;
246 trans,trans-2-(4-Methoxyphenyl)-4-(1,3-benzodioxol-5-yl)-1-(isopropylsulfonylaminoethyl)-pyrrolidine-3-carboxylic acid;
247 trans,trans-2-(4-Methoxyphenyl)-4-(1,3-benzodioxol-5-yl)-1-(ethoxymethylcarbonylmethyl)-pyrrolidine-3-carboxylic acid;
248 trans,trans-2-(4-Methoxyphenyl)-4-(1,3-benzodioxol-5-yl)-1-(2-ethylbutyrylmethyl)-pyrrolidine-3-carboxylic acid;
249 trans,trans-2-(4-Methoxyphenyl)-4-(1,3-benzodioxol-5-yl)-1-(N-methyl-N-(3,4-dimethoxybenzyl)aminocarbonylmethyl)-pyrrolidine-3-carboxylic acid;
250 trans,trans-2-(4-Methoxyphenyl)-4-(1,3-benzodioxol-5-yl)-1-[(1R)-1-(N-methyl-N-propylaminocarbonyl)butyl]-pyrrolidine-3-carboxylic acid;
251 trans,trans-2-(4-Methoxyphenyl)-4-(1,3-benzodioxol-5-yl)-1-[(1S)-1-(N-methyl-N-propylaminocarbonyl)butyl]-pyrrolidine-3-carboxylic acid;
252 trans,trans-2-(4-Methoxyphenyl)-4-(1,3-benzodioxol-5-yl)-1-(3-isopropoxypropyl)-pyrrolidine-3-carboxylic acid;
253 trans,trans-2-(4-Methoxyphenyl)-4-(1,3-benzodioxol-5-yl)-1-(5-methylhexyl)-pyrrolidine-3-carboxylic acid;
254 trans,trans-2-(4-Methoxyphenyl)-4-(1,3-benzodioxol-5-yl)-1-(5-methyl-2-hexenyl)-pyrrolidine-3-carboxylic acid;
255 trans,trans-2-(4-Methoxyphenyl)-4-(1,3-benzodioxol-5-yl)-1-(5-methyl-4-hexenyl)-pyrrolidine-3-carboxylic acid;
256 trans,trans-2-(4-Methoxyphenyl)-4-(1,3-benzodioxol-5-yl)-1-(3,5-dimethyl-2-hexenyl)-pyrrolidine-3-carboxylic acid;
257 trans,trans-2-(4-Methoxyphenyl)-4-(1,3-benzodioxol-5-yl)-1-(2-(N-methyl-N-isobutyrylamino)ethyl)-pyrrolidine-3-carboxylic acid;
258 trans,trans-2-(4-Methoxyphenyl)-4-(1,3-benzodioxol-5-yl)-1-(N-methyl-N-(2,2-dimethylpropyl)aminocarbonylmethyl)-pyrrolidine-3-carboxylic acid;
259 trans,trans-2-(4-Methoxyphenyl)-4-(1,3-benzodioxol-5-yl)-1-(N-ethyl-N-butylaminocarbonylmethyl)-pyrrolidine-3-carboxylic acid;
260 trans,trans-2-(4-Methoxyphenyl)-4-(1,3-benzodioxol-5-yl)-1-(N-methyl-N-benzylaminocarbonylmethyl)-pyrrolidine-3-carboxylic acid;
261 trans,trans-2-(4-Methoxyphenyl)-4-(5-indanyl)-1-(N-methyl-N-propylaminocarbonylmethyl)-pyrrolidine-3-carboxylic acid;
262 trans,trans-2-(4-Methoxyphenyl)-4-(2,3-dihydrobenzofuran-5-yl)-1-(N-methyl-N-propylaminocarbonylmethyl)-pyrrolidine-3-carboxylic acid;
263 trans,trans-2-(4-Methoxyphenyl)-4-(1-methylindol-5-yl)-1-(N-methyl-N-propylaminocarbonylmethyl)-pyrrolidine-3-carboxylic acid;
264 trans,trans-2-(4-Methoxyphenyl)-4-(2-naphthyl)-1-(N-methyl-N-propylaminocarbonylmethyl)-pyrrolidine-3-carboxylic acid;
265 trans,trans-2-(4-Methoxyphenyl)-4-(1,2-dimethoxy-4-phenyl)-1-(N-methyl-N-propylaminocarbonylmethyl)-pyrrolidine-3-carboxylic acid;
266 trans,trans-2-(4-Methoxyphenyl)-4-(1-methoxy-3-phenyl)-1-(N-methyl-N-propylaminocarbonylmethyl)-pyrrolidine-3-carboxylic acid;

EXAMPLES 267–288

Following the procedures described in Example 1 and Scheme II, the following compounds can be prepared.

267 trans,trans-3-(4-Methoxyphenyl)-5-(1,3-benzodioxol-5-yl)-1-(propylaminocarbonylmethyl)-piperidine-4-carboxylic acid;
268 trans,trans-3-(4-Methoxyphenyl)-5-(1,3-benzodioxol-5-yl)-1-(aminocarbonylmethyl)-piperidine-4-carboxylic acid;
269 trans,trans-3-(4-Methoxyphenyl)-5-(1,3-benzodioxol-5-yl)-1-(4-fluorobenzyl)-piperidine-4-carboxylic acid;
270 trans,trans-3-(4-Methoxyphenyl)-5-(1,3-benzodioxol-5-yl)-1-(2-ethoxyethyl)-piperidine-4-carboxylic acid;
271 trans,trans-3-(4-Methoxyphenyl)-5-(1,3-benzodioxol-5-yl)-1-(2-propoxyethyl)-piperidine-4-carboxylic acid;
272 trans,trans-3-(4-Methoxyphenyl)-5-(1,3-benzodioxol-5-yl)-1-[2-(2-methoxyethoxy)ethyl]-piperidine-4-carboxylic acid;
273 trans,trans-3-(4-Methoxyphenyl)-5-(1,3-benzodioxol-5-yl)-1-[2-(2-pyridyl)ethyl]-piperidine-4-carboxylic acid;
274 trans,trans-3-(4-Methoxyphenyl)-5-(1,3-benzodioxol-5-yl)-1-(morpholin-4-ylcarbonyl)-piperidine-4-carboxylic acid;
275 trans,trans-3-(4-Methoxyphenyl)-5-(1,3-benzodioxole-5-yl)-1-(butylaminocarbonyl)-piperidine-4-carboxylic acid;
276 trans,trans-3-(4-Methoxyphenyl)-5-(1,3-benzodioxol-5-yl)-1-(4-methoxyphenylaminocarbonyl)-3-piperidine-4-carboxylic acid;
277 trans,trans-3-(4-Methoxyphenyl)-5-(1,3-benzodioxol-5-yl)-1-acetylpiperidine-3-carboxylic acid;
278 trans,trans-3-(4-Methoxyphenyl)-5-(1,3-benzodioxol-5-yl)-1-(2-furoyl)-piperidine-3-carboxylic acid;
279 trans,trans-3-(4-Methoxyphenyl)-5-(1,3-benzodioxol-5-yl)-1-(phenylaminocarbonyl)-piperidine-4-carboxylic acid;
280 trans,trans-3-(4-Methoxyphenyl)-5-(1,3-benzodioxol-5-yl)-1-(allylaminocarbonylmethyl)-piperidine-4-carboxylic acid;
281 trans,trans-3-(4-Methoxyphenyl)-5-(1,3-benzodioxol-5-yl)-1-(n-butylaminocarbonylmethyl)-piperidine-4-carboxylic acid;
282 trans,trans-3-(4-Methoxyphenyl)-5-(1,3-benzodioxol-5-yl)-1-(N-n-butyl-N-methylaminocarbonylmethyl)-piperidine-4-carboxylic acid;
283 trans,trans-3-(4-Methoxyphenyl)-5-(1,3-benzodioxol-5-yl)-1-(pyrrolidin-1-ylcarbonylmethyl)-piperidine-4-carboxylic acid;
284 trans,trans-3-(4-Methoxyphenyl)-5-(1,3-benzodioxol-5-yl)-1-(isobutylaminocarbonylmethyl)-piperidine-4-carboxylic acid;
285 trans,trans-3-(4-Methoxyphenyl)-5-(1,3-benzodioxol-5-yl)-1-(cyclopentylaminocarbonylmethyl)-piperidine-4-carboxylic acid;
286 trans,trans-3-(4-Methoxyphenyl)-5-(1,3-benzodioxol-5-yl)-1-(morpholin-4-ylaminocarbonylmethyl)-piperidine-4-carboxylic acid;
287 trans,trans-3-(4-Methoxyphenyl)-5-(1,3-benzodioxol-5-yl)-1-(2-phenoxyethyl)-piperidine-4-carboxylic acid;

288 trans,trans-3-(4-Methoxyphenyl)-5-(1,3-benzodioxol-5-yl)-1-(methoxyethylaminocarbonyl)-piperidine-4-carboxylic acid.

EXAMPLE 289 trans,trans-2-(4-Methoxyphenyl)-4-(1,3-benzodioxol-5-yl)-1-(4-dibutylaminophenyl)-pyrrolidine-3-carboxylic acid 4-Nitro-fluorobenzene, ethyl trans,trans-2-(4-methoxyphenyl)-4-(1,3-benzodioxol-5-yl)-pyrrolidine-3-carboxylate (example 6A) and di-isopropyl ethylamine are heated in dioxane to give ethyl trans,trans-2-(4-methoxyphenyl)-4-(1,3-benzodioxol-5-yl)-1-(4-nitrophenyl)-pyrrolidine-3-carboxylate. The nitro compound is hydrogenated to the corresponding aminophenyl compound. This is reacted with butyraldehyde and sodium cyanoborohydride according to the method of Borch (J. Am Chem. Soc., 93, 2897, 1971) to give the corresponding N,N-dibutylaminophenyl compound, which is hydrolyzed with sodium hydroxide using the method of example 1D to give the title compound.

EXAMPLE 290 trans,trans-2-(4-Methoxyphenyl)-4-(1,3-benzodioxol-5-yl)-1-(2-dibutylamino-pyrimidine-4-yl)-pyrrolidine-3-carboxylic acid 2-(Dibutylamino) 4-chloropyrimidine is prepared from 2-4-dichloropyrimidine according to the method of Gershon (J. Heterocyclic Chem. 24, 205, 1987). This compound, ethyl trans,trans-2-(4-methoxyphenyl)-4-(1,3-benzodioxol-5-yl)-pyrrolidine-3-carboxylate (example 6A), and di-isopropyl ethylamine are heated in dioxane to give the intermediate ethyl ester, which is hydrolyzed with sodium hydroxide using the method of example 1D to give the title compound.

EXAMPLE 291 trans,trans-2-(4-Methoxyphenyl)-4-(1,3-benzodioxol-5-yl)-1-(N-butyl-N-phenylaminocarbonylmethyl)-pyrrolidine-3-carboxylic acid The title compound was prepared according to the general procedure of Example 1. $^1$H NMR (CD$_3$OD): δ 0.87 (t,3H, J=8); 1.2–1.35 (m,2H); 1.35–1.5 (m,2H); 2.78 (m, 2H); 3.10 (t,1H, J=9); 3.26 (d,1H,J=15); 3.44 (dd,1H,J=5,10); 3.5–3.7 (m,3H); 3.77 (m,1H); 3.78 (s,3H); 5.93 (s,2H); 6.7–6.9 (m,4H); 7.0–7.2 (m,5H); 7.4 (m,3H). MS (DCI/NH$_3$): m/e 531 (M+H)$^+$. Anal calcd for C$_{31}$H$_{34}$N$_2$O$_6$: C, 70.17; H, 6.46; N, 5.28. Found: C, 70.36; H, 6.52; N, 4.99.

EXAMPLE 292

Sodium trans,trans-2-(4-Methoxyphenyl)-4-(1,3-benzodioxol-5-yl)-1-(N,N-di(n-butyl)aminocarbonylmethyl)-pyrrolidine-3-carboxylate

EXAMPLE 292A

Ethyl 3-(4-methoxyphenyl)-3-oxopropionate

Simultaneous reactions were run in both a 65-L reactor and a 35-L reactor that share the same reflux system. A nitrogen atmosphere was maintained in both. 4.0 kg (100 moles) of 60% sodium hydride in mineral oil and 32 L toluene were charged into the ambient temperature reactors. The mixture was agitated for 5 minutes and allowed to settle. 20 L of the toluene solution was aspirated. 28 L of toluene was added, agitated for 5 minutes, allowed to settle and 28 L of the toluene solution was aspirated. 68 L of toluene and 8.4 L (69.7 moles) diethyl carbonate were added. The agitation was begun and the flow of Syltherm (Note 4) in reactor jackets was initiated. A solution of 5.0 kg (33.3 moles) 4-methoxyacetophenone in 12 L toluene was added over 20 minutes. When additions were complete, the jacket temperature was reduced to 10° C. and stirring continued for 16 hours. A solution of 6.7 L (117 moles) glacial acetic acid in 23 L deionized water was fed at the same rate that was previously used for the acetophenone solution. When addition was complete, agitation was stopped and the layers separated. The aqueous layer was washed once with 13 L toluene. The combined organic layers were washed twice with 6.7 L portions of 7% (w:w) aqueous sodium bicarbonate. The toluene solution was washed once with 6.7 L of 23% (w:w) aqueous sodium chloride. The organic solution was dried over 10 kg sodium sulfate, filtered, and the solvent removed on the rotary evaporator to provide the desired product.

EXAMPLE 292B 3,4-Methylenedioxy-1-(2-nitroethenyl)-benzene

In a 45-L cryogenic reactor with a contoured, anchor stirrer was dissolved 5.537 kg (36.9 moles) piperonal in 9 L methanol and 2.252 kg (36.9 moles) nitromethane at 15°–20° C. The jacket temperature was set to −5° C. and the reaction solution cooled to a temperature of +3.5° C. A 21° C. solution of 3.10 kg (38.8 moles) 50% (w:w) aqueous sodium hydroxide diluted with 3.7 L water was pumped in. The reaction temperature was maintained between 10°–15° C. When addition was complete, the jacket temperature was reset to 1° C. and stirring continued for 30 minutes. A mixture of 7 kg ice in 19 L water was added to dissolve most of the solid. The reaction mixture was filtered through canvas and then a 27R10SV Honeycomb filter. The filtered solution was metered into a 21° C. mixture of 7.4 L concentrated hydrochloric acid in 11.1 L deionized water. The final reaction temperature was 26° C. The resulting product was centrifuged and washed until the wash pH rose to at least 6 (by pH indicating paper). The crude product was dissolved in 92 L dichloromethane and the layers separated. The aqueous layer was washed once with 8 L dichloromethane. The combined organics were dried over 1.32 kg magnesium sulfate and filtered through Whatman #1 paper. The volume was reduced to 20% and the solution cooled to 4° C. Filtration through Whatman #1 paper, followed by ambient temperature drying in vacuo with an air leak afforded 1.584 kg (22%) of a first crop Concentration of the MLS to 25% followed by similar cooling, filtration, and drying afforded 0.262 kg (4%) of a second crop. The yellow product darkened on standing in light and air.

EXAMPLE 292C

Ethyl 2-(4-methoxybenzoyl)-3-(1,3-benzodioxol-5-yl)-4-nitro-butanoate

Into a 45-L stirred reactor at ambient temperature were charged 5.819 kg (30.1 moles) 3,4-methylenedioxy-1-(2-nitroethenyl)-benzene and 24 L ethyl acetate. A solution of 5.355 kg (24.1 moles) ethyl 3-(4-methoxyphenyl)-3-oxopropionate in 16 L ethyl acetate was added. 280 g (275 ml, 1.84 moles) of 1,8-diaza-bicyclo[5.4.0]undec-7-ene in four equal portions was added over a 2.5 hour period. The reaction mixture was filtered through dicalite and the resulting filtered solution was used in the next step without any further purification.

EXAMPLE 292D

Ethyl 2-(4-methoxyphenyl)-4-(1,3-benzodioxol-5-yl)-4,5-dihydro-3H-pyrrol-3-carboxylate The product of Example 292C (1316 ml solution consisting of 300 g Ethyl 2-(4-methoxybenzoyl)-3-(3,4-methylenedioxyphenyl)-4 nitrobutanoate in ethyl acetate) was added to a glass reactor containing RaNi # 28 (300 g). The reaction mixture was shaken under a hydrogen environment of 4 atm at room temperature for 18 hours and filtered through a nylon 0.20 micron 47 mm millipore.

The filtrate was concentrated to 1.4 kg of dark solution and purified by normal phase silica gel chromatography eluting with 85:15, hexanes:ethyl acetate. The pure fractions were combined and concentrated (as above) until crystals formed. The solution was cooled to 0° C. and filtered. The solid was washed with 2 L of 85:15, hexane:ethyl acetate (0° C.). The solids were dried in vacuo at 50° C. to a constant weight of 193.4 g (21% yield, melting point 80–81° C.) of the title compound. A further 200 g (23% yield) of product was obtained from the mother liquors.

EXAMPLE 292E

Ethyl 2-(4-methoxyphenyl)-4-(1,3-benzodioxol-5-yl)-pyrrolidine 3-carboxylate

Into a 12-L flask equipped with magnetic stirring, addition funnel, temperature probe, and nitrogen inlet was charged 0.460 kg ethyl 2-(4-methoxyphenyl)-4-(3,4-methylenedioxyphenyl)-4,5-dihydro-3H-pyrrole-3-carboxylate (1.25 mol). The reaction vessel was degassed with nitrogen. Absolute 3.7 L ethanol and 1.12 L of THF were added. 31 mg bromocresol green and 94.26 g sodium cyanoborohydride (1.5 mol) were added. A solution containing 400 mL absolute ethanol and 200 mL of 12 M HCl was then added. The reaction mixture was stirred for 30 minutes after addition was complete. After the starting material was consumed, 0.5 L of 7% aq. NaHCO$_3$ was added. The reaction mixture was concentrated and diluted with 5 L ethyl acetate. The organic layer was washed twice with 2 L of 7% aq. NaHCO$_3$ and once with 2.5 L of 23% aq. NaCl, the dried over 190 g MgSO$_4$, filtered, and concentrated to give 447 g of the title compound as a thick yellow oil.

EXAMPLE 292F

Ethyl 2-(4-methoxypheny)-4-(1,3-benzodioxol-5-yl)-1-(N,N-di(n-butyl)aminocarbonylmethyl) pyrrolidine 3-carboxylate Into a 22-L flask equipped with overhead stirring, nitrogen inlet, and condenser was charged ethyl 2-(4-methoxyphenyl)-4-(3,4-methylenedioxyphenyl)-pyrrolidine-3-carboxylate (2.223 kg, 6.02 mol). The reaction vessel was degassed with nitrogen. 13.2 L of acetonitrile, 3.66 L diisopropylethylamine (2.71 kg, 20.9 mol), and 1.567 kg dibutylamidomethyl bromide (6.26 mol) were added. The mixture was refluxed at 78° C. for 17 hrs. After the disappearance of starting material, the mixture was concentrated until crystals formed. The solid was filtered and washed with 4 L ethyl acetate (0° C.). Concentrating of the filtrate was continued as above until all volatiles were removed. The residue was diluted with 40 L ethyl acetate and washed with 20 L deionized water. The organic layer was washed with 8 L of 23% aq. NaCl nad dried over 0.399 kg MgSO$_4$ and filtered. Concentration as above provided 3.112 kg (96% yield) of the title compound as a dark oil.

EXAMPLE 292G trans,trans-2-(4-Methoxyphenyl)-4-(1,3-benzodioxol-5-yl)-pyrrolidine 3-carboxylate and preparation of trans,trans 2-(4-methoxyphenyl)-4-(3,4-dioxyphenyl)-pyrrolidine-3-carboxylic acid ethyl ester Into a 35-L reactor equipped with overhead stirring, nitrogen inlet, and condenser was charged 3.112 kg ethyl 2-(4-methoxyphenyl)-4-(3,4-methylenedioxyphenyl)-pyrrolidine 3-carboxylate (5.78 mol). 16.4 L of absolute ethanol was added and the reaction vessel was degassed with nitrogen. 0.115 kg of sodium ethoxide (1.69 mol) was added and the mixture was refluxed at 79° C. for 1 hr. The mixture was cooled to 15° C. and 5 L of 7.6 M NaOH solution (38.1 mol) was added. The mixture was stirred at 15° C. for 18 hrs. The solvent was evaporated and the residue dissolved in 15.8 L of deionized water and extracted with 28 L of ether. The ether solution was washed with 9.5 L deionized water. The aqueous wash was extracted with 3 L ether. 0.340 L of 12 M HCl was added to the aqueous layer. The aqueous layer was extracted with 24 L of ethyl acetate. The organic layer was washed with 9 L of 23% aq. NaCl, dried with 0.298 kg MgSO$_4$, filtered, and concentrated to give 2.132 kg of a dark oil. The oil was triturated with 18 L ether. The undesired solids were filtered and saved for later use. The mother liquors were concentrated to obtain 1.102 kg of light foam. The foam was dissolved in 5.5 L ethyl acetate with heating to 65° C. 14 L hexane was added slowly enough to keep the solution refluxing. The reaction mixture was cooled to 10° C. and filtered. The crystals were washed with 2 L ether (0° C.) and dried to constant weight in vacuo at 50° C. to give 0.846 kg (43% yield, melting point 119–120) of crude product, which was further purified by normal phase silica gel chromatography.

EXAMPLE 292H

Sodium trans,trans-2-(4-methoxyphenyl)-4-(1,3-benzodioxol-5-yl)-1-(N,N-di(n-butyl)aminocarbonylmethyl) pyrrolidine 3-carboxylate Into a 20-L flask was charged trans,trans 2-(4-methoxyphenyl)-4-(3,4-methyledioxyphenyl)-1-(N,N-dibutylamino-carbonyl methyl) pyrrolidine 3-carboxylic acid (0.927 kg, 1.819 mol). A solution of 0.0720 kg NaOH (1.80 mol) dissolved in 4.65 L methanol was added. The reaction mixture was concentrated to an oil. Pentane (4 L) was added and the solution concentrated again. Pentane (4 L) was added again and concentration of this solution gave a light tan foam. The foam was dried in vacuo at 50° C. to a constant weight of 0.937 kg (97% yield) of the title compound.

EXAMPLE 293 trans—trans-2-(4-Methoxyphenyl)-4-(1,3-benzo-dioxol-5-yl)-1-[decahydroisoquinolin-2-carbonylmethyl]-pyrrolidine-3-carboxylic acid The title compound was prepared using the procedures described in example 1. NMR (CD$_3$OD, 300 MHz) shows a mixture of isomers. MS (DCI/NH$_3$) m/z 521. Anal calcd for C$_{30}$H$_{36}$N$_2$O$_6$.1.3 TFA: C, 58.54; H, 6.62; N, 4.19. Found: C, 58.34; H, 5.58; N, 4.00.

EXAMPLE 294 trans—trans-2-(4-Methoxyphenyl)-4-(1,3-benzo-dioxol-5-yl)-1-[3,3-dimethylpiperidinyl-carbonylmethyl]-pyrrolidine-3-carboxylic acid The title compound was prepared using the procedures described in example 1. NMR (CD$_3$OD, 300 MHz) indicates presence of rotamers. δ 0.84 (s, 3H), 0.86 (s, 3H), 1.35–1.6 (m, 4H), 3.83 (s, 3H), 5.96 (s, 2H), 6.81 (d, 1H, J=8), 6.90 (dd, 1H, J=1,8), 7.01 (d, 2H, J=9), 7.03 (s, 1H), 7.47 (d, 2H, J=9). MS (DCI/NH$_3$) m/z 495. Anal calcd for C$_{28}$H$_{34}$N$_2$O$_6$. 1.4 TFA: C, 56.55; H, 5.45; N, 4.28. Found: C, 56.52; H, 5.83; N, 4.26.

EXAMPLE 295 trans—trans-2-(4-Methoxyphenyl)-4-(1,3-benzo-dioxol-5-yl)-1-[2-(N-propyl-N-iso-butoxycarbonylamino)ethyl]-pyrrolidine-3-carboxylic acid The title compound was prepared by the methods detailed in Example 61, but substituting propylamine for methylamine in Example 61B and isobutyl chloroformate for isobutyryl chloride in Example 61C. The crude product was purified by trituration with 1:1 diethyl ether/hexane. The resulting solid was dissolved in CH$_3$CN and water and lyophilized to give the product as a white solid. $^1$H NMR (CDCl$_3$, 300 MHz) δ 0.80 (t, 3H, J=7), 0.92 (m, 3H), 1.43 (h, 2H, J=7 Hz), 1.7–1.9 (m, 1H), 2.72 (m, 1H), 2.90 (m, 2H), 3.10 (m, 2H), 3.25 (m, 2H), 3.40 (m, 1H), 3.55 (m, 1H), 3.62 (m, 1H), 3.7–3.9 (m, 2H) 3.78 (s, 3H), 5.95 (s, 2H), 6.72 (d, 1H, J=8 Hz), 6.82 (m, 3H), 7.00 (s, 1H), 7.30 (d, 2H, J=8 Hz). MS (DCI/NH$_3$) m/e 527 (M+H)$^+$. Anal calcd for C$_{29}$H$_{38}$N$_2$O$_6$ 0.5H$_2$O: C, 65.03; H, 7.34; N, 5.23. Found: C, 65.13; H, 6.96; N, 4.95.

EXAMPLE 296 trans—trans-2-(4-Methoxyphenyl)-4-(1,3-benzo-dioxol-5-yl)-1-[1,2,3,4-tetrahydroisoquinolin-2-carbonylmethyl]-pyrrolidine-3-carboxylic acid The title compound was prepared using the procedures described in example 1. NMR (CD$_3$OD, 300 MHz) indicates presence of rotamers. δ 2.97 (m, 2H), 4.68 (s, 3H), 5.97 (s, 2H), 6.83 (d, 1H, J=8), 6.9–7.0 (m, 3H), 7.03 (d, 1H, J=2), 7.1–7.3 (m, 4H), 7.4–7.5 (m, 2H). MS (DCI/NH$_3$) m/z 515.

EXAMPLE 297 trans—trans-2-(4-Methoxyphenyl)-4-(1,3-benzo-dioxol-5-yl)-1-[2-(N-propyl-N-dimethylaminocarbonylamino)ethyl]-pyrrolidine-3-carboxylic acid The title compound was prepared by the methods detailed in Example 61, but substituting propylamine for methylamine in Example 61B and dimethylcarbamyl chloride for isobutyryl chloride in Example 61C. The crude product was purified by preparative HPLC (Vydac µC18) eluting with a 10–70% gradient of CH$_3$CN in 0.1% TFA. The desired fractions were lyophilized to give the product as a white solid. $^1$H NMR (CDCl$_3$, 300 MHz) δ 0.70 (t, 3H, J=7), 1.28 (m, 2H), 2.75 (s, 3H), 2.82 (m, 2H), 3.1–3.45 (m, 4H), 3.70 (m, 1H), 3.80 (s, 3H), 3.90 (m, 3H), 4.72 (m, 1H), 5.95 (s, 2H), 6.75 (d, 1H, J=8 Hz), 6.87 (m, 3H), 7.05 (s, 1H), 7.40 (d, 2H, J=8 Hz). MS (DCI/NH$_3$) m/e 498 (M+H)$^+$. Anal calcd for C$_{27}$H$_{35}$N$_3$O$_6$ 1.25 TFA: C, 55.35; H, 5.71; N, 6.56. Found: C, 55.41; H, 5.71; N, 6.41.

EXAMPLE 298 trans,trans-2-(4-Methoxyphenyl)-4-(1,3-benzo-dioxol-5-yl)-1-(2-(N-propyl-N-(4-nitrobenzenesulfonyl)amino)ethyl)-pyrrolidine-3-carboxylic acid Using the procedures described in Eample 66, the title compound was prepared as a yellow solid. m.p. 85–87° C. $^1$H NMR (CDCl$_3$, 300 MHz) δ 0.77 (t, J=7.5 Hz, 3H), 1.38 (sextet, J=7.5 Hz, 2H), 2.20–2.29 (m, 1H), 2.57–2.66 (m, 1H), 2.82–3.15 (m, 4H), 3.22 (t, J=7.5 Hz, 2H) 3.38 (dd, J=3 Hz,J=9 Hz, 1H), 3.49–3.57 (m, 1H), 3.59 (d, J=9 Hz, 1H), 3.83 (s, 3H), 5.96 (s, 2H), 6.73 (d, J=8 Hz, 1H), 6.82 (dd, J=1 Hz,J=8 Hz, 1H), 6.87 (d, J=9 Hz, 2H), 6.98 (d, J=1 Hz, 1H), 7.27 (d, J=9 Hz, 2H), 7.82 (d, J=9 Hz, 2H), 8.23 (d, J=9 Hz,2H). MS (DCI/NH$_3$) m/e 612 (M+H)$^+$.

EXAMPLE 299 trans,trans-2-(4-Methoxyphenyl)-4-(1,3-benzo-dioxol-5-yl)-1-(2-(N-propyl-N-n-pentanesulfonylamino)ethyl)-pyrrolidine-3-carboxylic acid Using the procedures described in Example 66, the title compound was prepared as a white solid. m.p. 59–61° C. $^1$H NMR (CDCl$_3$, 300 MHz) δ 0.79 (t, J=7.5 Hz, 3H), 0.90 (t, J=6 Hz, 3H), 1.26–1.32 (m, 4H), 1.43 (sextet, J=7.5 Hz, 2H), 1.67–1.76 (m, 2H), 2.23–2.32 (m, 1H), 2.70–3.08 (m, 7H), 3.15–3.32 (m,2H), 3.42 (dd, J=3 Hz,J=9 Hz, 1H), 3.52–3.57 (m, 1H), 3.63 (d, J=9 Hz, 1H), 3.80 (s, 3H), 5.95 (s, 2H), 6.73 (d, J=7.5 Hz, 1H), 6.83 (dd, J=1 Hz,J=7.5 Hz, 1H), 6.87(d, J=8 Hz, 2H), 7.00 (d, J=1 Hz, 1H), 7.32 (d, J=8 Hz, 2H). MS (DCI/NH$_3$) m/e 561 (M+H)$^+$.

EXAMPLE 300 trans,trans-2-(4-Methoxyphenyl)-4-(1,3-benzo-dioxol-5-yl)-1-(2-(N-propyl-N-(4-trifluoromethoxy-benzenesulfonyl)amino)ethyl)-pyrrolidine-3-carboxylic acid Using the procedures described in Example 66, the title compound was prepared as a white solid. m.p. 122–124° C. $^1$H NMR (CD$_3$OD, 300 MHz) δ 0.75 (t, J=7.5 Hz, 3H), 1.26–1.45 (m, 2H), 2.96–3.08 (m, 2H), 3.23 (bs, 2H), 3.35–3.45 (m, 2H), 3.52 (t, J=10 Hz, 1H), 3.81 (d, J=9 Hz, 2H), 3.86 (s, 3H), 3.92 (t, J=9 Hz, 1H), 4.63 (d, J=10 Hz, 1H), 5.97 (s, 2H), 6.82 (d, J=9 Hz, 1H), 6.93 (dd, J=3 Hz,J=9 Hz, 1H), 7.06–7.08 (m, 3H), 7.46 (d, J=9 Hz, 2H), 7.56 (d, J=9 Hz, 2H), 7.89 (d, J=9 Hz, 2H). MS (DCI/NH$_3$), m/e 651 (M+H)$^+$.

EXAMPLE 301 trans,trans-2-(4-Methoxyphenyl)-4-(1,3-benzo-dioxol-5-yl)-1-(2-(N-propyl-N-(2-methyl-2-propene-sulfonyl)amino)ethyl)-pyrrolidine-3-carboxylic acid Using the procedures described in Example 66, the title compound was prepared as a white solid. m.p. 69–71° C. $^1$H NMR (CDCl$_3$, 300 MHz) δ 0.79 (t, J=7.5 Hz, 3H), 1.93 (sextet, J+7.5 Hz, 2H), 1.92 (s, 3H), 2.25–2.35 (m, 1H), 2.68–2.77 (m, 1H), 2.85–3.28 (m, 7H), 3.40 (d, J=9 Hz, 1H), 3.52–3.68 (m, 2H), 3.66 (d, J=9 Hz, 1H), 3.80 (s, 3H), 4.92 (s, 1H), 5.07 (s, 1H), 5.97 (s, 2H), 6.74 (d, J=7 Hz, 1H), 6.82–6.89 (m,3H), 7.01 (s,1H), 7.33 (d, J=9 Hz, 2H). MS (DCI/NH$_3$), m/e 545 (M+H)$^+$.

EXAMPLE 302 trans—trans-2-(4-Methoxyphenyl)-4-(1,3-benzo-dioxol-5-yl)-1-[2-ethylpiperidinyl-carbonylmethyl]-pyrrolidine-3-carboxylic acid The title compound was prepared using the procedures described in example 1. NMR (CD$_3$OD, 300 MHz) shows a mixture of isomers. δ 0.75 (t, 3H, J=7), 1.4–1.7 (m, 8H), 3.84 (s, 3H), 5.96 (s, 2H), 6.83 (d, 1H, J=8), 6.91 (d, 1H, J=8), 7.0–7.1 (m, 3H), 7.52 (d, 2H, J=9). MS (DCI/NH$_3$) m/z 495. Anal calcd for C$_{28}$H$_{34}$N$_2$O$_6$.1.6 TFA: C, 55.35; H, 5.30; N, 4.14. Found: C, 55.26; H, 5.37; N, 4.01.

EXAMPLE 303 trans,trans-2-(4-Methoxyphenyl)-4-(1,3-benzo-dioxol-5-yl)-1-(2-(N-propyl-N-(2-methylpropane-sulfonyl)amino)ethyl)-pyrrolidine-3-carboxylic acid Using the procedures described in Example 66, the title compound was prepared as a white solid. m.p. 72–73° C. $^1$H NMR (CDCl$_3$, 300 MHz) δ 0.82 (t, J=7.5 Hz, 3H), 1.04 (d, J=6 Hz, 6H), 1.44(q, J=7.5 Hz, 2H), 2.15–2.33 (m,2H), 2.57–2.75 (m, 2H), 2.84–3.08 (m, 3H), 3.12–3.21 (m, 1H), 3.23–3.45 (m, 1H), 3.43 (d, J=11 Hz, 1H), 3.55–3.62 (m, 1H), 3.66 (d, J=9 Hz, 1H), 3.80 (s, 3H), 5.95 (s, 2H), 6.75 (d, J=9 Hz, 1H), 6.83 (dd, J=1 Hz,J=9 Hz, 1H), 6.87(d, J=9 Hz, 2H), 7.02 (d, J=1 Hz, 1H), 7.33 (d, J=9 Hz, 2H). MS (DCI/NH$_3$) m/e 547 M+H)$^+$.

EXAMPLE 304 trans,trans-2-(4-Methoxyphenyl)-4-(1,3-benzo-dioxol-5-yl)-1-(2-(N-propyl-N-heptanesulfony-lamino)ethyl)-pyrrolidine-3-carboxylic acid Using the procedures described in Example 66, the title compound was prepared as a white solid. m.p. 58–59° C. $^1$H NMR (CDCl$_3$, 300 MHz) δ 0.80(t, J=7.5 Hz, 3H), 0.88 (t, J=7 Hz, 3H), 1.23–1.36 (m, 8H), 1.94 (q, J=7.5 Hz, 2H), 1.71(quintet, J=7 Hz, 2H), 2.23–2.32 (m, 1H), 2.70–3.09(m, 7H), 3.13–3.32 (m,2H), 3.43(dd, J=3 Hz,J=9 Hz, 1H), 3.52–3.58(m,1H), 3.65(d, J=9 Hz, 1H), 3.80 (s, 3H), 5.96(s, 2H), 6.73 (d, J=7 Hz, 1H), 6.83 (dd, J=1 Hz, J=7 Hz, 1H), 6.87(d, J=9 Hz, 2H), 7.01(d, J=1 Hz, 1H), 7.32 (d, J=9 Hz, 2H). MS (DCI/NH$_3$) m/e 589 M+H)$^+$.

EXAMPLE 305 trans—trans-2-(4-Methoxyphenyl)-4-(1,3-benzo-dioxol-5-yl)-1-[2-(N-ethyl-N-ethoxycarbonylamino) ethyl]-pyrrolidine-3-carboxylic acid Prepared by the methods detailed in Example 61, but substituting ethylamine for methylamine in Example 61B and ethyl chloroformate for isobutyryl chloride in Example 61C. The crude product was purified by preparative HPLC (Vydac μC18) eluting with a 10–70% gradient of CH$_3$CN in 0.1% TFA. The desired fractions were lyophilized to give the product as a white solid. $^1$H NMR (CDCl$_3$, 300 MHz) δ 0.90 (t, 3H, J=7), 1.22 (m, 3H), 3.0–3.2 (m, 4H), 3.42 (m, 2H), 3.78 (s, 3H), 3.82 (m, 4H), 4.10 (q, 2H, J=7 Hz), 3.5 (br s, 1H), 5.97 (dd, 2H, J=1,7 Hz), 6.72 (d, 1H, J=8 Hz), 6.84 (m, 3H), 7.00 (s, 1H), 7.42 (d, 2H, J=8 Hz). MS (DCI/NH$_3$) m/e 485 (M+H)$^+$. Anal calcd for C$_{26}$H$_{32}$N$_2$O$_7$ 1.2 TFA: C, 54.90; H, 5.39; N, 4.51. Found: C, 55.01; H, 5.36; N, 4.56.

EXAMPLE 306 trans,trans-2-(4-Methoxyphenyl)-4-(1,3-benzo-dioxol-5-yl)-1-(2-(N-propyl-N-hexanesulfony-lamino)ethyl)-pyrrolidine-3-carboxylic acid Using the procedures described in Example 66, the title compound was prepared as a white solid. m.p. 59–60° C. $^1$H NMR (CDCl$_3$, 300 MHz) δ 0.80(t, J=7.5 Hz,3H), 0.89(t, J=7 Hz, 3H), 1.25–1.36(m, 6H), 1.53(sextet, J=7.5 Hz, 2H), 1.72(quintet, J=7 Hz, 2H), 2.23–2.32(m, 1H), 2.72–3.08(m, 7H), 3.15–3.32(m, 2H), 3.43(d, J=9 Hz, 1H), 3.55–3.62(m, 1H), 3.65 (d, J=10 Hz, 1H), 3.80(s, 3H), 5.96(s, 2H), 6.74(d, J=7.5 Hz,1H), 6.82(d, J=7.5 Hz,1H), 6.87(d, J=9 Hz, 2H), 7.01(s,1H), 7.32(d, J=9 Hz,2H). MS (DCI/NH$_3$), m/e 575 (M+H)$^+$.

EXAMPLE 307 trans—trans-2-(4-Ethylphenyl)-4-(1,3-benzodioxol-5-yl)-1-[N,N-di(n-butyl)aminocarbonylmethyl]-pyr-rolidine-3-carboxylic acid The title compound was prepared using the procedures described in examples 1 and 49, substituting ethyl 4-ethyl-benzoylacetate (prepared by the method of Krapcho et al., Org. Syn. 47, 20 (1967) starting with 4'-ethylacetophenone) in procedure 49B. NMR (CDCl$_3$, 300 MHz) δ 7.31 (2H, d, J=8 Hz), 7.16 (2H, d, J=8 Hz), 7.03 (1H, d, J=3 Hz), 6.86 (1H, dd, J=8&3 Hz), 6.73 (1H, d, J=9 Hz), 5.94 (1H, d, J=4 Hz), 5.92 (1H, d, J=4 Hz), 3.77 (1H, d, J=9 Hz), 3.60 (1H, m), 3.53–3.23 (5H, m), 3.13–2.90 (4H, m), 2.73 (1H, d, J=14 Hz), 2.62 (2H, q, J=9 Hz), 1.45 (2H, m), 1.40–1.10 (6H, m), 1.02 (2H, m), 0.87 (3H, t, J=7 Hz), 0.78 (3H, t, J=7 Hz). m/e (DCI, NH$_3$) 509 (MH$^+$) Anal. calc. for C$_{30}$H$_{40}$N$_2$O$_5$ C, 70.84; H, 7.93; N, 5.51. Found C, 70.80; H, 7.85; N, 5.25.

EXAMPLE 308 trans—trans-2-(4-Methoxyphenyl)-4-(1,3-benzo-dioxol-5-yl)-1-[2-(N-propyl-N-(2-chloroethoxy)car-bonylamino)ethyl]-pyrrolidine-3-carboxylic acid Prepared by the methods detailed in Example 61, but substituting propylamine for methylamine in Example 61B and 2-chloroethyl chloroformate for isobutyryl chloride in Example 61C. The crude product was purified by trituration with 1:1 diethyl ether/hexane. The resulting solid was dissolved in $CH_3CN$ and water and lyophilized to give the product as a white solid. $^1H$ NMR ($CDCl_3$, 300 MHz) δ 0.80 (t, 3H, J=7), 1.22 (m, 3H), 2.15 (m, 1H), 2.75 (m, 1H), 2.85 (m, 1H), 3.1 (m, 2H), 3.25 (m, 2H), 3.5 (m, 3H), 3.65 (m, 2H), 3.80 (s, 3H), 4.18 (m, 1H), 4.30 (m, 1H), 5.98 (s, 2H), 6.72 (m, 1H), 6.82 (m, 3H), 7.00 (m, 1H), 7.30(m, 2H). MS (DCI/$NH_3$) m/e 533 (M+H)$^+$. Anal calcd for $C_{27}H_{33}N_2O_7Cl$: C, 60.84; H, 6.24; N, 5.26. Found: C, 60.48; H, 6.04; N, 5.10.

EXAMPLE 309 trans—trans-2-(2-Methoxyethyl)-4-(1,3-benzodioxol-5-yl)-1-[N,N-di(n-butyl)aminocarbonylmethyl]-pyrrolidine-3-carboxylic acid The title compound was prepared using the procedures described in example 1, substituting ethyl 5-methoxy-3-oxopentanoate for ethyl 4-methoxybenzoylacetate in Example 1A. The title compound is a yellow foam. $^1H$ NMR ($CDCl_3$, 300 MHz) δ 0.91 (t, J=7 Hz) and 0.95 (t, J=7 Hz, 6H total), 1.28–1.41 (br m, 4H), 1.45–1.63 (br m, 4H), 2.00–2.20 (br m, 2H), 3.06 (br t, J=9 Hz, 1H), 3.30 (s) and 3.20–3.68 (br m, 11H total), 3.72–4.10 (br m, 4H), 5.92 (s, 2H), 6.72 (d, J=8.5 Hz, 1H), 6.82 (dd, J=1.5, 8.5 Hz, 1H), 6.91 (d, J=1.5 Hz, 1H); MS (FAB) m/e 463 (M+H)$^+$. Anal calcd for $C_{25}H_{38}N_2O_5 \cdot H_2O$: C, 62.48; H, 8.39; N, 5.83. Found: C, 62.13; H, 8.15; N, 5.69.

EXAMPLE 310 trans,trans-2-(4-Methoxyphenyl)-4-(1,3-benzodioxol-5-yl)-1-(2-(N-ethyl-N-n-pentanesulfonylamino)ethyl)-pyrrolidine-3-carboxylic acid Using the procedures described in Example 66, the title compound was prepared as a white solid. m.p. 57–58° C. $^1H$ NMR ($CDCl_3$, 300 MHz) δ 0.89(t, J=7 Hz, 3H), 1.06(t, J=7.5 Hz, 3H), 1.26–1.37(m, 4H), 1.72(quintet, J=7.5 Hz, 2H), 2.22–2.32(m,1H), 2.71–2.96(m,5H), 3.08–3.30(m,4H), 3.95(d, J=9 Hz, 1H), 3.53–3.60(m, 1H), 3.67(d, J=9 Hz,1H), 3.80(s, 1H), 5.97(s, 2H), 6.73(d, J=9 Hz, 1H), 6.82(d, J=9 Hz,1H), 6.88(d, J=9 Hz, 2H), 7.02(s,1H), 7.33(d, J=9 Hz, 2H). MS (CDI/$NH_3$) m/e 547 (M+H)$^+$.

EXAMPLE 311 trans—trans-2-(4-Methoxyphenyl)-4-(1,3-benzodioxol-5-yl)-1-[N,N-dicyclohexylamino carbonylmethyl]-pyrrolidine-3-carboxylic acid The title compound was prepared using the procedures described in example 1. NMR ($CD_3OD$, 300 MHz) δ 1.0–2.0 (m, 20H), 3.0–3.1 (m, 2H), 3.80 (s, 3H), 5.95 (s, 2H), 6.75 (d, 1H, J=8), 6.86 (dd, 1H, J=2,8), 6.95 (d, 2H, J=9), 7.04 (d, 1H, J=2), 7.38 (d, 2H, J=9). MS (DCI/$NH_3$) m/z 563. Anal calcd for $C_{33}H_{42}N_2O_6 \cdot 0.5H_2O$: C, 69.33; H, 7.58; N, 4.90. Found: C, 69.42; H, 7.29; N, 4.78.

EXAMPLE 312 trans—trans-2-(4-Methoxyphenyl)-4-(1,3-benzodioxol-5-yl)-1-[2-(N-propyl-N-tert-butoxycarbonylamino)ethyl]-pyrrolidine-3-carboxylic acid The title compound was prepared using the procedures described in example 61, substituting propylamine for aqueous methylamine in Example 61B and di-tert-butyldicarbonate for isobutyryl chloride in Example 61C. NMR ($CD_3OD$, 300 MHz) suggests presence of rotamers δ 0.81 (t, 3H, J=7), 1.2–1.5 (m, 11H), 3.78 (s, 3H), 5.92 (dd, 2H, J=1,2), 6.74 (d, 1H, J=8), 6.84 (dd, 1H, J=2,8), 6.92 (d, 2H, J=9), 6.99 (bd s, 1H), 7.35 (d, 2H, J=9). MS (DCI/$NH_3$) m/z 527. Anal calcd for $C_{29}H_{38}N_2O_7$: C, 66.14; H, 7.27; N, 5.32. Found: C, 66.05; H, 7.36; N, 5.15.

EXAMPLE 313 trans—trans-2-(4-Methoxy-3-fluorophenyl)-4-(1,3-benzodioxol-5-yl)-1-[N,N-di(n-butyl)aminocarbonylmethyl]-pyrrolidine-3-carboxylic acid The title compound was prepared using the methods described in examples 1 and 43, using 4-methoxy-3-fluoro acetophenone in place of 4-methoxy acetophenone. m.p. 142–143° C. NMR ($CDCl_3$, 300 MHz) δ 0.82 (t, J=7 Hz, 3H), 0.88 (t, J=7 Hz, 3H), 1.03–1.50 (m, 8H), 2.82 (d, J=13 Hz, 1H), 2.90–3.13 (m, 4H), 3.20–3.50 (m, 3H), 3.39 (d, J=13H, 1H), 3.55–3.65 (m, 1H), 3.82 (d, J=10 Hz, 1H), 3.87 (s, 3H), 5.91 (dd, J=2 Hz, 4 Hz, 2H), 6.72 (d, J=8 Hz, 1H), 6.83–6.91 (m, 2H), 6.99 (d, J=2 Hz, 1H), 7.06 (m, 2H). Anal calcd for $C_{29}H_{37}N_2O_6F$: C, 65.89; H, 7.06; N, 5.30. Found: C, 65.82; H, 7.13; N, 5.29.

EXAMPLE 314 trans,trans-2-(Propyl)-4-(1,3-benzodioxol-5-yl)-1-(2-(N-propyl-pentanesulfonylamino)ethyl)pyrrolidine-3-carboxylic acid

EXAMPLE 314A

Propyl pentanesulfonamide

Pentane sulfonyl chloride (687 mg, 4.03 mmol) was dissolved in 5 mL $CH_2Cl_2$ and added to an ice-cooled solution of n-propylamine (0.40 mL, 4.82 mmol) and ethyldiisopropylamine (0.85 mL, 4.88 mmol) in 5 mL $CH_2Cl_2$ under a nitrogen atmosphere. The reaction was stirred at 0° C. for 30 min, then at 25° C. for 4 h. The solution was partitioned between 20 mL of 1.0 M aqeous $NaHSO_4$ and 25 mL $CH_2Cl_2$. The organic phase was washed sequentially with 25 mL $H_2O$ and 25 mL brine, then dried ($Na_2SO_4$), filtered, and concentrated in vacuo to provide 739 mg (3.83 mmol, 95%) of the title compound as a white solid. TLC (25% EtOAc-hexane) Rf 0.23; $^1H$ NMR ($CDCl_3$, 300 MHz) δ 0.92 (t, J=7 Hz, 3H), 0.97 (t, J=7 Hz, 3H), 1.28–1.50 (br m, 4H), 1.52–1.68 (m, 2H), 1.75–1.90 (br m, 2H), 2.98–3.06 (m, 2H), 3.08 (q, J=6 Hz, 2H), 4.10–4.23 (br m, 1H); MS (DCI/$NH_3$) m/e 211 (M+$NH_4$)$^+$.

EXAMPLE 3149B

Ethyl trans,trans--4-(1,3-benzodioxol-5-yl)-1-(2-bromoethyl)-2-propylpyrrolidine-3-carboxylate The title compound was prepared according the procedure of Example 61A, substituting the compound of Example 94B for the pyrrolidine mixture.

EXAMPLE 314C

Ethyltrans,trans-2-(Propyl)-4-(1,3-benzodioxol-5-yl)-1-(2-(N-propyl-pentanesulfonylamino)ethyl)pyrrolidine-3-carboxylate A solution of the compound of Example 314A (6.6 mg, 34 μmol) in 0.1 mL DMF was treated with sodium hydride (2 mg, 60% oil dispersion, 1.2 mg NaH, 50 μmol). The resulting mixture was stirred at room temperature for 15 min, then a solution of the compound of Example 189B (9.0 mg, 22 μmol) in 0.1 mL DMF was added, followed by 0.5 mg of tetra-n-butylammonium iodide. The reaction was sealed under argon and stirred at 60° C. overnight. The reaction was concentrated under high vacuum, and the residue was partitioned between 2 mL of saturated aqueous NaHCO$_3$, 1 mL water and 5 mL EtOAc. The organic phase was washed with 1 mL brine, dried by passing through a plug of Na$_2$SO$_4$, and the filtrate concentrated in vacuo to an oil. The crude product was purified by preparative TLC (silica gel, 8×20 cm, 0.25 mm thickness, eluting with 20% EtOAc-hexane, providing 8.4 mg (73%) of the title compound as a wax.

EXAMPLE 314D trans,trans-4-(1,3-benzodioxol-5-yl)-2-(Propyl)-1-(2-(N-propyl-pentanesulfonylamino)ethyl)pyrrolidine-3-carboxylic acid The title compound was prepared according to the procedure of Example 71C. $^1$H NMR (CDCl$_3$, 300 MHz) δ 0.88–1.00 (m, 9H), 1.20–1.55 (br m, 6H), 1.55–1.68 (m, 3H), 1.70–1.85 (br m, 2H), 1.90–2.16 (br m, 2H), 2.84–3.26 (br m, 6H), 3.26–3.90 (br m, 6H), 5.95 (s, 2H), 6.76 (d, J=8 Hz, 1H), 6.79 (m, 1H), 6.93 (br s, 1H); HRMS (FAB) calcd for C$_{25}$H$_{41}$N$_2$O$_6$S (M+H)+497.2685, found 497.2679.

EXAMPLE 315 trans,trans-2-(4-Methoxyphenyl)-4-(1,3-benzodioxol-5-yl)-1-(2-(N-propyl-N-dimethylsulfamoylamino)ethyl)-pyrrolidine-3-carboxylic acid Using the procedures described in Example 66, the title compound was preapred as a white solid. m.p. 59–61° C. $^1$H NMR (CDCl$_3$, 300 MHz) δ 0.79 (t, J=7.5 Hz, 3H), 1.45 (sextet, J=7.5 Hz, 2H), 2.22–2.31(m,1H), 2.65(s, 6H), 2.70–2.79(m, 1H), 2.85–3.04(m, 4H), 3.09–3.32(m, 2H), 3.40(d, J=9 Hz, 1H), 3.55 (t, J=9 Hz,1H), 3.65(d, J=9 Hz,1H), 3.81(s, 3H), 5.96(s,2H), 6.75(d, J=9 Hz, 1H), 6.83 (d, J=9 Hz, 1H), 6.88(d, J=9 Hz, 2H), 7.02(s, 1H), 7.34(d, J=9 Hz, 2H). MS (DCI/NH$_3$) m/e534 (M+H)$^+$.

EXAMPLE 316 trans—trans-2-(4-Methoxphenyl)-4-(1,3-benzodioxol-5-yl)-1-[2-(N-propyl-N-[4-methoxyphenyl]sulfonylamino)propyl]-pyrrolidine-3-carboxylic acid

EXAMPLE 316A

Ethyl trans—trans and cis-trans 2-(4-Methoxyphenyl)-4-(1,3-benzodiox-5-yl)-1-(3-bromopropyl) pyrrolidine-3-carboxylate A 2:1 mixture of trans—trans and cis-trans ethyl 2-(4-methoxyphenyl)-4-(1,3-benzodiox-5-yl)-pyrrolidine-3-carboxylate (4.00 g; prepared according to example 1C), 32 ml dibromopropane, and 200 mg sodium iodide, were heated at 100° for 1.25 hrs. The excess dibromopropane was removed in vacuo and the residue was dissolved in toluene. After shaking with potassium bicarbonate, the solution was dried (Na$_2$SO$_4$) and the solution concentrated. The residue was chromatographed on silica gel eluting with 5:1 hexane: EtOAc. yielding 5.22 (98%) of the title compound.

EXAMPLE 316B

Ethyl trans—trans and cis-trans 2-(4-Methoxyphenyl)-4-(1,3-benzodiox-5-yl)-1-(3-propylaminopropyl) pyrrolidine-3-carboxylate The compound described in Example 316A (5.22 g) was heated at 80° for 2 hrs. with 35 ml. ethanol, 2.5 g. propylamine and 35 mg. sodium iodide. The solvents were removed in vacuo. The residue was dissolved in toluene, shaken with potassium bicarbonate solution and dried (Na$_2$SO$_4$). The soilution was concentrated in vacuum to give 4.96 g of the title compound as an orange oil. This was used in the next step without purification.

EXAMPLE 316C trans—trans-2-(4-Methoxphenyl)-4-(1,3-benzodioxol-5-yl)-1-[2-(N-propyl-N-[4-methoxyphenyl]sulfonylamino)propyl]-pyrrolidine-3-carboxylic acid Using the method described in example 66, the compound prepared in Example 316B was reacted with 4-methoxybenzenesulfonyl chloride in acetonitrile containing diisopropylethylamine. The resulting product was chromatographed on silica gel (30% EtOAc in hexane), and hydrolyzed to the title compound by the method of example 1D. NMR (CDCl$_3$, 300 MHz) δ 0.83 (t, J=7 Hz, 3H), 1.40–1.52 (m, 2H), 1.56–1.70 (m, 2H), 2.00–2.11 (m, 1H), 2.40–2.51 (m, 1H), 2.69–2.78 (m, 1H), 2.84–3.03 (m, 4H), 3.19–3.34 (m, 2H), 3.48–3.59 (m, 2H), 3.80 (s, 3H), 3.86 (s, 3H), 5.95 (s, 2H), 6.74 (d, J=8 Hz, 1H), 6.85 (d, J=8 Hz, 3H), 6.93 (d, J=8 Hz, 2H), 7.02 (d, J=2 Hz, 1H), 7.29 (d, J=8 Hz, 2H), 7.69 (d, J=8 Hz, 2H). Anal calcd for C$_{32}$H$_{38}$N$_2$O$_8$S: C, 62.93; H, 6.27; N, 4.59. Found: C, 62.97; H, 6.39; N, 4.45.

EXAMPLE 317 trans—trans-2-(4-Methoxphenyl)-4-(1,3-benzodioxol-5-yl)-1-[2-(N-propyl-N-propylsulfonylamino)propyl]-pyrrolidine-3-carboxylic acid Using the method described in example 66, the propylamino compound prepared in Example 316B was reacted with propanesulfonyl chloride in acetonitrile containing diisopropylethylamine. The resuling product was chromatographed on silica gel (30% EtOAc in hexane) and hydrolyzed to the title compound by the method of example 1D. NMR (CDCl$_3$, 300 MHz) δ 0.85 (t, J=7 Hz, 3H), 1.02 (t, J=7 Hz, 3H), 1.47–1.60 (m, 2H), 1.65–1.85 (m, 4H), 2.04–2.16 (m, 1H), 2.42–2.57 (m, 1H), 2.72–3.11 (m, 5H), 3.25–3.41 (m, 2H), 3.50–3.62 (m, 2H), 3.80 (s, 3H), 5.85 (s, 2H), 6.72 (d, J=8 Hz, 1H), 6.80–6.90 (m, 3H), 7.02 (d, J=2 Hz, 1H), 7.30 (d, J=9 Hz, 2H). Anal calcd for C$_{28}$H$_{38}$N$_2$O$_7$S: C, 61.52; H, 7.01; N, 5.12. Found: C, 61.32; H, 7.01; N, 5.01.

EXAMPLE 318 trans,trans--2-(3-Fluoro-4-methoxyphenyl)-4-(1,3-benzodioxol-5-yl) 1-(2-(N-propyl-N-pentanesulfonylamino)ethyl)-pyrrolidine-3-carboxylic acid Using the procedures described in Example 313 and Example 66, the title compound was prepared as a white solid. m.p. 66–68° C. $^1$H NMR (CDCl$_3$, 300 MHz) δ 0.81(t,J=7.5 Hz, 3H), 0.89(t, J=7 Hz, 3H), 1.26–1.35(m, 4H), 1.45(sextet, J=7.5 Hz, 2H), 1.68–1.76(m, 2H), 2.25–2.33 (m, 1H), 2.72–2.92 (m, 5H), 2.97–3.12 (m, 2H), 3.16–3.33 (m, 2H), 3.43 (dd, J=3 Hz, J=9 Hz, 1H), 3.53–3.60 (m, 1H), 3.66 (d, J=10 Hz, 1H), 3.88 (s, 3H), 5.95 (s, 2H), 6.74 (d, J=8 Hz, 1H), 6.82 (dd, J=1 Hz, J=8 Hz, 1H), 6.92 (t, J=8 Hz, 1H), 6.97 (d, J=1 Hz, 1H), 7.12 (d, J=8 Hz, 1H), 7.18 (dd, J=1 Hz, J=12 Hz, 1H). MS (DCI/NH$_3$) m/e 579 (M+H)$^+$.

EXAMPLE 319 trans—trans-2-(4-Pyridinyl)-4-(1,3-benzodioxol-5-yl)-1-[N,N-di(n-butyl)aminocarbonylmethyl]-pyrrolidine-3-carboxylic acid The title compound was prepared using the methods described in examples 1 and 43, using methyl 3-oxo-3-(4-pyridyl)propanoate (J. Am. Chem. Soc. 1993, 115, 11705) in place of ethyl (4-methoxybenzoyl)acetate. m.p. 131–132° C. NMR (CDCl$_3$, 300 MHz) δ 0.82 (t, J+7 Hz, 3H), 0.88 (t, J=7 Hz, 3H), 1.05–1.50 (m, 8H), 2.90 (dd, J=7 Hz, 9 Hz, 1H), 2.97 (d, J=13 Hz, 1H), 3.00–3.25 (m, 4H), 3.32 (m, 1H), 3.39 (d, J=13 Hz, 1H), 3.45–3.52 (m, 1H), 3.67–3.78 (m, 1H), 4.10 (d, J=9 Hz, 1H), 5.92 (dd, J=2 Hz, 4 Hz, 2H), 6.75 (d, J=9 Hz, 1H), 6.90 (dd, J=9 Hz, 2 Hz, 1H), 7.02 (d, J=2 Hz, 1H), 7.45 (d, J=8 Hz, 2H), 8.50 (d, J=8 Hz, 2H). Anal calcd for C$_{27}$H$_{35}$N$_3$O$_5$: C, 67.34; H, 7.33; N, 8.73. Found: C, 67.39; H, 7.45; N, 8.61.

EXAMPLE 320 trans—trans-2-(4-Methoxyphenyl)-4-(1,3-benzodioxol-5-yl)-1-[2-(N-propyl-N-diethylaminocarbonylamino)ethyl]-pyrrolidine-3-carboxylic acid The title compound was prepared using the procedures described in example 61, substituting propylamine for aqueous methylamine in Example 61B and diethylcarbamyl chloride for isobutyryl chloride in Example 61C. NMR (CD$_3$OD, 300 MHz) δ 0.74 (t, 3H, J-7), 1.09 (t, 6H, J=7), 1.33 (m, 2H), 3.17 (q, 4H, J=7), 3.78 (s, 3H), 4.04 (m, 1H), 5.93 (s, 2H), 6.86 (d, 1H, J=8), 7.06 (dd, 1H, J=2,8), 6.94 (d, 2H, J=9), 7.04 (d, 1H, J=2), 7.40 (d, 2H, J=9). MS (DCI/NH$_3$) m/z 526. Anal calcd for C$_{29}$H$_{39}$N$_3$O$_6$ · 0.1 TFA: C, 65.31; H, 7.34; N, 7.82. Found: C, 65.33; H, 7.43; N, 8.14.

EXAMPLE 321 trans—trans-2-(4-Methoxyphenyl)-4-(1,3-benzodioxol-5-yl)-1-[3,5-dimethylpiperidinyl-carbonylmethyl]-pyrrolidine-3-carboxylic acid The title compound was prepared using the procedures described in example 1. NMR (CD$_3$OD, 300 MHz) shows mixture of isomers. δ 0.88 (d, 3H, J=7), 0.93 (d, 3H, J=7), 3.82 (s, 3H), 5.95 (s, 2H), 6.82 (d, 1H, J=8), 6.89 (dd, 1H, J=1,8), 7.00 d, 2H, J=9), 7.03 (m, 1H), 7.47 (d, 2H, J=9). MS (DCI/NH$_3$) m/z 495.

EXAMPLE 322 trans—trans-2-(4-Methoxyphenyl)-4-(1,3-benzodioxol-5-yl)-1-[N,N-di(s-butyl)aminocarbonylmethyl]-pyrrolidine-3-carboxylic acid The title compound was prepared using the procedures described in example 1. NMR (CD$_3$OD, 300 MHz) suggests a mixture of isomers. δ 0.83 (t, 6H, J=8), 1.27 (d, 6H, J=7), 1.6 (m, 2H), 3.79 (s, 3H), 5.93 (s, 2H), 6.75 (d, 1H, J=8), 6.86 (d, 1H, J=8), 6.94 (d, 2H, J=9), 7.03 (d, 1H, J=2), 7.35 (d, 2H, J=9). MS (DCI/NH$_3$) m/z 511.

EXAMPLE 323 trans—trans-2-(4-Methoxyphenyl)-4-(1,3-benzodioxol-5-yl)-1-[N-(2-Methylphenyl)-N-butylaminocarbonylmethyl]-pyrrolidine-3-carboxylic acid The title compound was prepared using the procedures described in example 1. MS (DCI/NH$_3$) m/z 545. Anal calcd for C$_{32}$H$_{36}$N$_2$O$_6$ 0.9H$_2$O: C, 68.53; H, 6.79; N, 4.99. Found: C, 68.56; H, 6.62; N, 4.71.

EXAMPLE 324 trans—trans-2-(4-Methoxyphenyl)-4-(1,3-benzodioxol-5-yl)-1-[N-(3-Methylphenyl)-N-butylaminocarbonylmethyl]-pyrrolidine-3-carboxylic acid The title compound was prepared using the procedures described in example 1. NMR (CD$_3$OD, 300 MHz) d 0.88 (t, 3H, J=7), 1.2–1.5 (m, 4H), 2.31 (s, 3H), 2.8 (m, 2H), 3.14 (t, 1H, J=10), 3.3 (m, 3H), 3.44 (dd, 1H, J=5,10), 3.53 (m, 1H), 3.60 (t, 2H, J=7), 3.79 (s, 3H), 3.82 (m, 1H), 5.93 (s, 2H), 6.74 (d, 1H, J=8), 6.8–6.9 (m, 5H), 7.06 (d, 1H, J=2), 7.09 (d, 2H, J=9), 7.18 (d, 1H, J=7), 7.27 (t, 1H, J=7). MS (DCI/NH$_3$) m/z 545. Anal calcd for C$_{32}$H$_{36}$N$_2$O$_6$·0.8H$_2$O: C, 68.75; H, 6.78; N, 5.01. Found: C, 68.70; H, 6.67; N, 4.85.

EXAMPLE 325 trans,trans-4-(1,3-Benzodioxol-5-yl)-2-(benzyloxymethyl)-1-((N,N-dibutylaminocarbonylmethyl) pyrrolidine-3-carboxylic acid

EXAMPLE 325A

Ethyl trans,trans-4-(1,3-Benzodioxol-5-yl)-2-(benzyloxymethyl)-1-((N,N-di(n-butyl)aminocarbonylmethyl)pyrrolidine-3-carboxylate The procedures of Example 1A–1D were followed, substituting ethyl 4-benzyloxy-3-oxobutyrate for 4-methoxybenzoylacetate in Example 1A, to afford the title compound as a colorless oil. TLC (30% EtOAc-hexane) Rf 0.18; $^1$H NMR (CDCl$_3$, 300 MHz) δ 0.88 (t, J=7 Hz, 6H), 1.17 (t, J=7 Hz, 3H), 1.20–1.34 (br m, 4H), 1.40–1.56 (br m, 3H), 2.85 (t, J=8 Hz, 1H), 2.98–3.30 (m, 5H), 3.39–3.60 (m, 3H), 3.64–3.75 (m, 2H), 3.92 (d, J=14 Hz, 1H), 4.10 (two overlapping q, J=6.5 Hz, 2H), 4.53 (s, 2H), 5.91 (m, 2H), 6.69 (d, J=9 Hz, 1H), 6.77 (dd, J=1.5, 9 Hz, 1H), 6.91 (d, J=1.5 Hz, 1H); MS (DCI/NH$_3$) m/e 553 (M+H)$^+$.

EXAMPLE 325B trans,trans-4-(1,3-Benzodioxol-5-yl)-2-(benzyloxymethyl)-1-((N,N-di(n-butyl)aminocarbonylmethyl)pyrrolidine-3-carboxylic acid The title compound was prepared according to the procedure of Example 71C, as a colorless glass. TLC (5% MeOH—CH$_2$Cl$_2$) Rf 0.13; $^1$H NMR (CDCl$_3$, 300 MHz) δ 0.86 (t, J=7 Hz), and 0.90 (t, J=7 Hz, 6H total), 1.15–1.52 (br m, 8H), 2.96–3.35 (br m, 5H), 3.50–3.75 (br m, 2H), 3.80 (dd, J=3, 13 Hz,1H), 3.88–4.40 (br m, 6H), 4.45 (AB, 2H), 5.90 (s, 2H), 6.70 (d, J=8 Hz, 1H), 6.84 (dd, J=1,8 Hz, 1H), 6.93 (d, J=1 Hz, 1H), 7.28–7.39 (m, 5H); MS (DCI/NH$_3$) m/e 524 (M+H)$^+$.

EXAMPLE 326 trans,trans-4-(1,3-Benzodioxol-5-yl)-2-(hydroxymethyl)-1-((N,N-di(n-butyl)aminocarbonylmethyl)pyrrolidine-3-carboxylic acid

EXAMPLE 326A

Ethyl trans,trans-4-(1,3-Benzodioxol-5-yl)-2-(hydroxymethyl)-1-((N,N-di(n-butyl)aminocarbonylmethyl)pyrrolidine-3-carboxylate The resultant product from Example 325A (128 mg, 0.232 mmol) and 25 mg of 20% Pd(OH)$_2$ on charcoal in 7 mL EtOH was stirred under 1 atm hydrogen for 48 h. The mixture was filtered through a plug of celite, and the catalyst was washed with 2×10 mL EtOH, then the combined filtrate and washes were concentrated under reduced pressure to afford the crude product. Purification by flash chromatography (40% EtOAc-hexane) provided the title compound.

EXAMPLE 326B trans,trans-4-(1,3-Benzodioxol-5-yl)-2-(hydroxymethyl)-1-((N,N-di(butyl)aminocarbonylmethyl)pyrrolidine-3-carboxylic acid The title compound was prepared according to the procedure of Example 71C.

EXAMPLE 327 trans,trans--4-(1,3-Benzodioxol-5-yl)-2-(N-methylpropenamid-3-yl)-1-((N,N-di(n-butyl)aminocarbonylmethyl)pyrrolidine-3-carboxylic acid

EXAMPLE 327A

Ethyl trans,trans--4-(1,3-Benzodioxol-5-yl)-2-(formyl)-1-((N,N-di(n-butyl)aminocarbonylmethyl)pyrrolidine-3-carboxylate The title compound is made by selective oxidation (e.g. using the Swern oxidation with DMSO, oxalyl chloride, ethyldiisopropylamine or using the Dess-Martin periodinane) of the compound of Example 326A.

EXAMPLE 327B

Ethyl trans,trans--4-(1,3-Benzodioxol-5-yl)-2-(O-tert-butylpropenoat-3-yl)-1-((N,N-di(n-butyl)aminocarbonylmethyl)pyrrolidine-3-carboxylate The title compound is produced by condensing the compound of Example 327A with tert-butyl triphenylphosphoranylidene acetate in CH$_2$Cl$_2$ solution.

EXAMPLE 327C

Ethyl trans,trans--4-(1,3-Benzodioxol-5-yl)-2-(propenoic acid-3-yl)-1-(N,N-di(n-butyl)aminocarbonylmethyl)pyrrolidine-3-carboxylate The title compound is produced by reacting the compound of Example 327B with trifluoacetic acid in CH$_2$Cl$_2$ (1:1).

EXAMPLE 327D

Ethyl trans,trans--4-(1,3-Benzodioxol-5-yl)-2-(N-methylpropenamid-3-yl)-1-(N,N-di(n-butyl)aminocarbonylmethyl)pyrrolidine-3-carboxylate The title compound is produced by condensing the compound of Example 327C with methylamine hydrochloride in the presence of a carbodiimide (e.g. N-ethyl-N-(3-dimethylamino)propylcarbodiimide, DCC).

EXAMPLE 327E trans,trans--4-(1,3-Benzodioxol-5-yl)-2-(N-methylpropenamid-3-yl)-1-(N,N-di(n-butyl)aminocarbonylmethyl)pyrrolidine-3-carboxylic acid The title compound is produced by reacting the compound of Example 327D with lithium hydroxide according to the procedure of Example 71C.

EXAMPLE 328 trans,trans--4-(1,3-Benzodioxol-5-yl)-2-(1-hydroxy-2-propen-3-yl)-1-(N,N-di(n-butyl)aminocarbonylmethyl)pyrrolidine-3-carboxylic acid

EXAMPLE 328A

Ethyl trans,trans--4-(1,3-Benzodioxol-5-yl)-2-(1-hydroxy-2-propen-3-yl)-1-(N,N-di(n-butyl)aminocarbonylmethyl)pyrrolidine-3-carboxylate The title compound is produced by reacting the compound of Example 327C with borane methyl sulfide complex.

EXAMPLE 328B trans,trans--4-(1,3-Benzodioxol-5-yl)-2-(1-hydrox-2-propen-3-yl)-1-(N,N-di(n-butyl)aminocarbonylmethyl)pyrrolidine-3-carboxylic acid The title compound is produced by condensing the compound of Example 328A with lithium hydroxide according to the procedure of Example 71C.

EXAMPLE 329 trans,trans--4-(1,3-Benzodioxol-5-yl)-2-(N-benzylaminomethyl)-1-(N,N-di(n-butyl)aminocarbonylmethyl)pyrrolidine-3-carboxylic acid

EXAMPLE 329A

Ethyl trans,trans--4-(1,3-Benzodioxol-5-yl)-2-(N-benzylaminomethyl)-1-(N,N-di(n-butyl)aminocarbonylmethyl)pyrrolidine-3-carboxylate The title compound is produced by condensing the compound of Example 327A with benzylamine in the presence of sodium cyanoborohydride in ethanol.

EXAMPLE 329B trans,trans--4-(1,3-Benzodioxol-5-yl)-2-(N-benzylaminomethyl)-1-(N,N-di(n-butyl)aminocarbonylmethyl)pyrrolidine-3-carboxylic acid The title compound is produced by reacting the compound of Example 329A with lithium hydroxide according to the procedure of Example 71C.

EXAMPLE 330 trans,trans--4-(1,3-Benzodioxol-5-yl)-2-(N-acetyl-N-benzylaminomethyl)-1-(N,N-di(n-butyl)aminocarbonylmethyl)pyrrolidine-3-carboxylic acid

EXAMPLE 330A

Ethyl trans,trans--4-(1,3-Benzodioxol-5-yl)-2-(N-acetyl-N-benzylaminomethyl)-1-(N,N-di(n-butyl)aminocarbonylmethyl)pyrrolidine-3-carboxylate The title compound is produced by reacting the compound of Example 3294A with acetic anhydride in the presence of pyridine or triethylamine.

EXAMPLE 330B trans,trans--4-(1,3-Benzodioxol-5-yl)-2-(N-acetyl-N-benzylaminomethyl)-1-(N,N-di(n-butyl)aminocarbonylmethyl)pyrrolidine-3-carboxylic acid The title compound is produced by reacting the compound of Example 330A with lithium hydroxide according to the procedure of Example 71C.

EXAMPLE 331 trans,trans--4-(1,3-Benzodioxol-5-yl)-2-(ethynyl)-1-(N. N-di(n-butyl)aminocarbonylmethyl)pyrrolidine-3-carboxylic acid

EXAMPLE 331A

Ethyl trans,trans--4-(1,3-Benzodioxol-5-yl)-2-(ethynyl)-1-(N,N-di(n-butyl)aminocarbonylmethyl)pyrrolidine-3-carboxylate The title compound is made by employing the procedure of Corey and Fuchs (Tetrahedron Lett. 1972, 3769–72), using the compound of Example 327A.

EXAMPLE 331B trans,trans--4-(1,3-Benzodioxol-5-yl)-2-(ethynyl)-1-(N,N-di(n-butyl)aminocarbonylmethyl)pyrrolidine-3-carboxylic acid The title compound is produced by reacting the compound of Example 331A with lithium hydroxide according to the procedure of Example 71C.

EXAMPLE 332 trans,trans--4-(1,3-Benzodioxol-5-yl)-2-(1-pentynyl)-1-(N,N-di(n-butyl)aminocarbonylmethyl)pyrrolidine-3-carboxylic acid

EXAMPLE 332A

Ethyl trans,trans--4-(1,3-Benzodioxol-5-yl)-2-(pentynyl)-1-(N,N-di(n-butyl)aminocarbonylmethyl)pyrrolidine-3-carboxylate The title compound is made by palladium-catalyzed coupling of the compound of Example 206A and propyl iodide, employing the procedure of Taylor, et. al. (J. Org. Chem. 1989, 54(15), 3618–24).

EXAMPLE 332B trans,trans--4-(1,3-Benzodioxol-5-yl)-2-(1-pentynyl)-1-(N,N-di(n-butyl)aminocarbonylmethyl)pyrrolidine-3-carboxylic acid The title compound is produced by reacting the compound of Example 332A with lithium hydroxide according to the procedure of Example 71C.

EXAMPLE 333 trans—trans-2-(4-Methoxphenyl)-4-(1,3-benzodioxol-5-yl)-1-[2-(2,6-dioxopiperidinyl)ethyl]-pyrrolidine-3-carboxylic acid The compound of example 61A is added to a solution of the sodium salt of glutarimide in dimethylformamide. After stirring 24 hours, water is added and the mixture is extracted with ether. The resultant glutarimide is hydrolyzed to the title compound by the method of example 1D.

EXAMPLE 334 trans—trans-2-(4-Methoxyphenyl)-4-(1,3-benzodioxol-5-yl)-1-[N,N-diphenylaminocarbonylmethyl]-pyrrolidine-3-carboxylic acid The title compound was prepared according to the procedures described in Example 1. $^1$H NMR (300 MHz, CD$_3$OD) δ 2.83 (dd, 1, J=8.1, 9.7), 2.99 (d, 1, J=15.4), 3.19 (t, 1, J=9.5), 3.49 (d, 1, J=15.3), 3.51 (dd, 1, J=4.6, 9.5), 3.57 (m, 1), 3.79 (s, 3), 3.85 (d, 1, J=9.5), 5.90 (s, 2), 6.71 (d, 1, J=8.0), 6.84 (m, 3), 7.04 (d, 1, J=1.6), 7.14–7.16 (m, 6), 7.19–7.34 (m, 6); MS (DCI/NH$_3$) m/z 551; Anal Calcd for C$_{33}$H$_{30}$N$_2$O$_6$.0.65H$_2$O.0.35C$_2$H$_5$OCOCH$_3$: C, 69.77, H, 5.77, N, 4.76. Found: C, 69.75, H, 5.55, N, 4.64.

EXAMPLE 335 trans—trans-2-(4-Methoxyphenyl)-4-(1,3-benzodioxol-5-yl)-1-[N,N-diisopropylaminocarbonylmethyl]-pyrrolidine-3-carboxylic acid The title compound was prepared according to the procedures described in Example 1. $^1$H NMR (300 MHz, CD$_3$OD) δ 0.95 (d, 3, J=6.5), 1.24 (d, 3, J=6.4), 1.30 (d, 6, J=6.8), 2.85 (d, 1, J=12.5), 3.04 (dd, 1, J=8.1, 9.8), 3.14 (t, 1, J=9.7), 3.32–3.55 (m, 3), 3.63 (m, 1), 5.92 (s, 2), 6.75 (d, 1, J=8.1), 6.85 (dd, 1, J=1.7, 8.1), 6.93 (m, 2), 7.02 (d, 1, J=1.7), 7.35 (m, 2). MS (DCI/NH₃) m/z 483. Anal Calcd for C$_{27}$H$_{34}$N$_2$O$_6$.0.65 EtOAc: C, 65.86, H, 7.32, N, 5.19. Found: C, 5.74, H, 7.26, N, 5.52.

EXAMPLE 336 trans,trans-2-(3-Fluoro-4-methoxyphenyl)-4-(1,3-benzodioxol-5-yl)-1-(2-N-propyl-N-butanesulfonylamino)ethyl)-pyrrolidine-3-carboxylic acid Using the procedures described in Example 313 and Example 66, the title compound was prepared as a white solid. m.p. 65–66° C. $^1$H NMR (CDCl$_3$, 300 MHz) δ 0.82(t, J=7.5 Hz, 3H), 0.92(t, J=7.5 Hz, 3H), 1.34–1.52(m, 4H), 1.72(quintet, J=7.5 Hz,2H), 2.25–2.35(m,1H), 2.72–2.94(m, 5H), 2.97–3.12(m, 2H), 3.19–3.46(m, 2H), 3.44(d, J=9 Hz,1H), 3.53–3.60(m, 1H), 3.67(d, J=9 Hz, 1H), 3.89(s, 3H), 5.95(s, 2H), 6.74(d, J=8 Hz, 1H), 6.82(d, J=8 Hz, 1H), 6.92(t, J=9 Hz, 1H), 6.97(s, 1H), 7.12(d, J=9 Hz, 1H), 7.18(d, J=12 Hz, 1H). MS (DCI/NH$_3$) m/e 565 (M+H)$^+$.

EXAMPLE 337

Using methods described in the above examples, the compounds disclosed in Table 1 can be prepared.

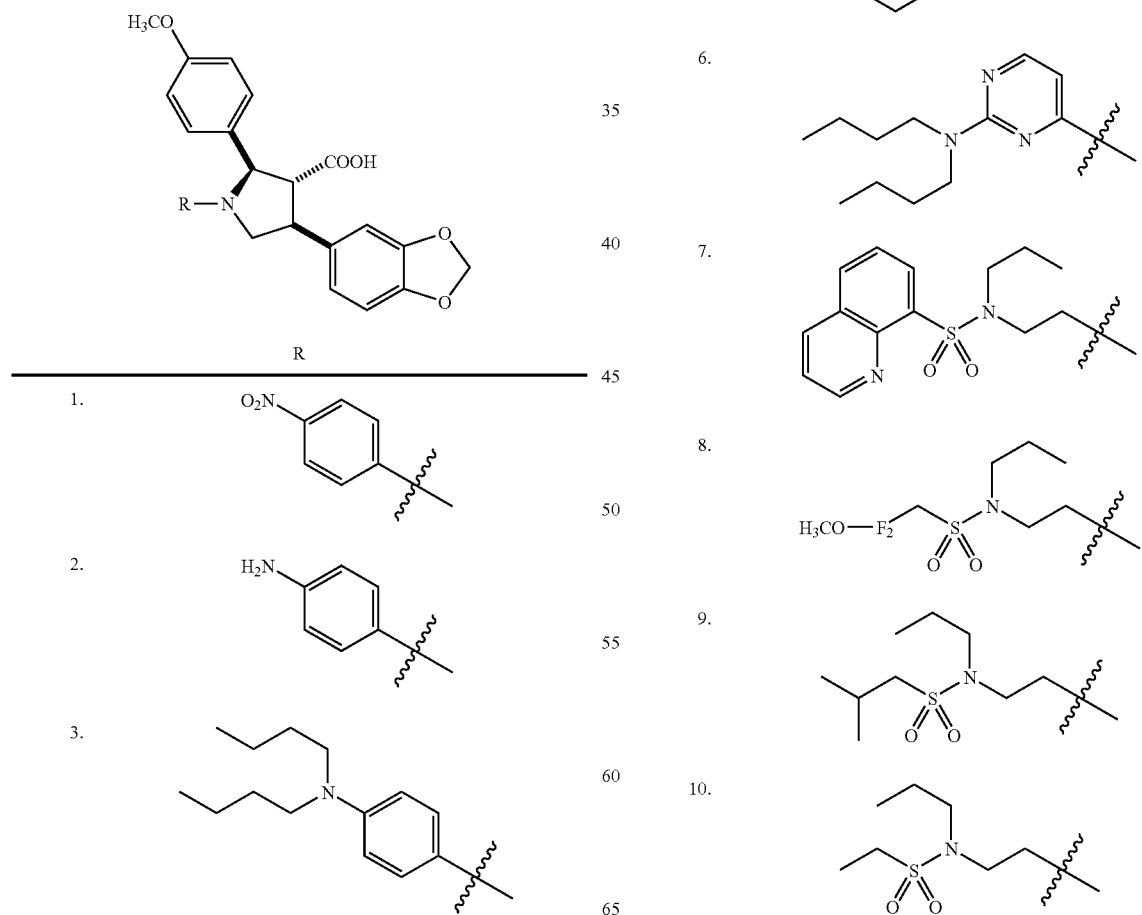

TABLE 1

TABLE 1-continued

[Structure: pyrrolidine with 2-(4-methoxyphenyl), 3-COOH, 4-(1,3-benzodioxol-5-yl), N-R substituents]

| # | R |
|---|---|
| 11. | CH₃CH₂-S(O)₂-N(butyl)-CH₂CH₂- |
| 12. | (butyl)₂N-S(O)₂- |
| 13. | propyl-S(O)₂-N(butyl)-(CH₂)₃- |
| 14. | 4-MeO-C₆H₄-S(O)₂-N(propyl)-(CH₂)₄- |
| 15. | 4-Cl-C₆H₄-S(O)₂-N(butyl)-CH₂CH₂- |
| 16. | 4-F-C₆H₄-S(O)₂-N(butyl)-CH₂CH₂- |
| 17. | 4-pyridyl-S(O)₂-N(propyl)-CH₂CH₂- |
| 18. | 4-pyridyl-S(O)₂-N(butyl)-CH₂CH₂- |
| 19. | 3-pyridyl-S(O)₂-N(propyl)-CH₂CH₂- |
| 20. | 3-pyridyl-S(O)₂-N(butyl)-CH₂CH₂- |
| 21. | 4-O₂N-C₆H₄-S(O)₂-N(propyl)-CH₂CH₂- |
| 22. | 4-O₂N-C₆H₄-S(O)₂-N(butyl)-CH₂CH₂- |
| 23. | propyl-S(O)₂-N(butyl)-CH₂CH₂- |
| 24. | Cl-(CH₂)₃-S(O)₂-N(butyl)-CH₂CH₂- |
| 25. | 4-MeO-C₆H₄-S(O)₂-N(propyl)-CH₂CH₂- |
| 26. | CH₃O-CH₂CH₂-S(O)₂-N(butyl)-CH₂CH₂- |

TABLE 1-continued
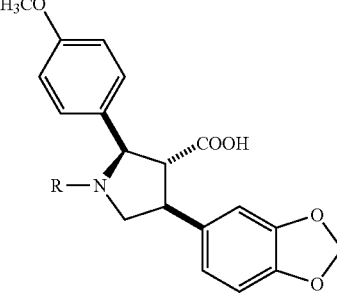
| | R |
|---|---|
| 27. | 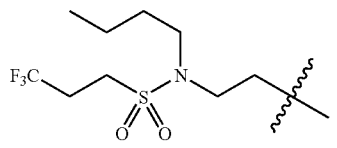 |
| 28. | 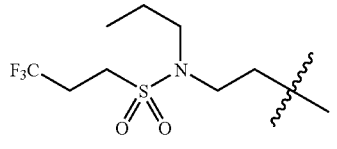 |
| 29. | 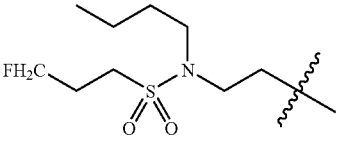 |
| 30. | 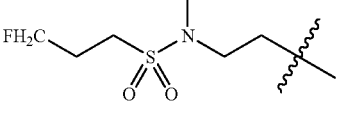 |
| 31. | 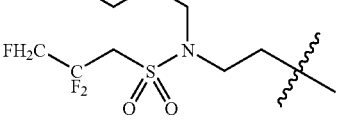 |
| 32. | 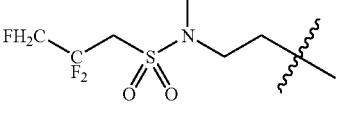 |
| 33. | 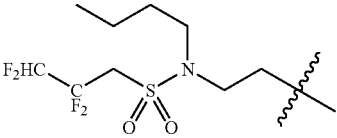 |
| 34. | 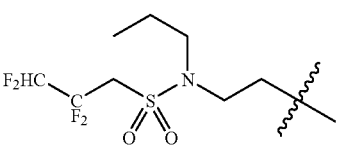 |
| 35. | 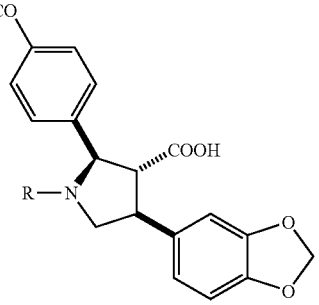 |
| 36. | 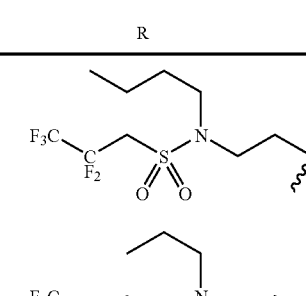 |
| 37. | 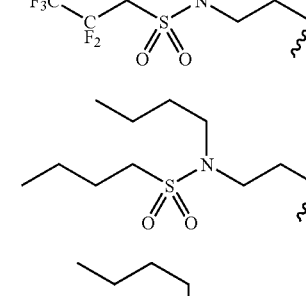 |
| 38. | 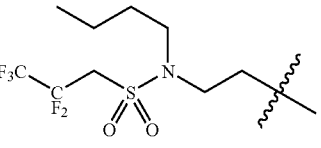 |
| 39. | 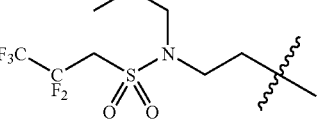 |
| 40. | 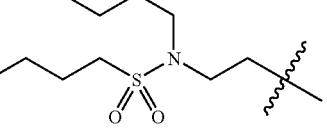 |
| 41. | 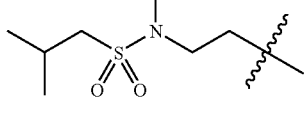 |
| 42. | 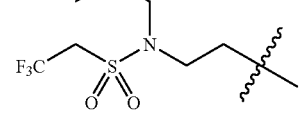 |

TABLE 1-continued

| # | R |
|---|---|
| 43. | 4-methylphenyl-SO2-N(butyl)-CH2CH2-~ |
| 44. | morpholine-SO2-N(propyl)-CH2CH2-~ |
| 45. | 4-methylpiperazine-SO2-N(propyl)-CH2CH2-~ |
| 46. | 1,2,3,4-tetrahydroisoquinoline-N-C(O)-CH2-~ |
| 47. | 1,2,3,4-tetrahydroquinoline-N-C(O)-CH2-~ |
| 48. | decahydroquinoline-N-C(O)-CH2-~ |
| 49. | 2-ethylpiperidine-N-C(O)-CH2-~ |
| 50. | 2,6-dimethylpiperidine-N-C(O)-CH2-~ |
| 51. | 3,5-dimethylpiperidine-N-C(O)-CH2-~ |
| 52. | 3,3-dimethylpiperidine-N-C(O)-CH2-~ |
| 53. | 3,3,5-trimethylazepane-N-C(O)-CH2-~ |
| 54. | N,N-dicyclohexyl-C(O)-CH2-~ |
| 55. | N-butyl-N-phenyl-C(O)-CH2-~ |

TABLE 1-continued

[Structure shown: pyrrolidine with 4-methoxyphenyl, COOH, and benzo[1,3]dioxole substituents, with R on N]

| # | R |
|---|---|
| 56. | N,N-di(sec-butyl)aminocarbonylmethyl-dimethyl |
| 57. | 2,5-dipropylpyrrolidin-1-yl-carbonyl-dimethyl |
| 58. | ethoxycarbonyl(ethyl)aminopropyl |
| 59. | propoxycarbonyl(ethyl)aminopropyl |
| 60. | cyclohexylmethoxycarbonyl(propyl)aminopropyl |
| 61. | cyclohexylmethoxycarbonyl(butyl)aminopropyl |
| 62. | cyclohexyloxycarbonyl(propyl)aminopropyl |
| 63. | cyclohexyloxycarbonyl(butyl)aminopropyl |
| 64. | cyclohexylacetyl(propyl)aminopropyl |
| 65. | cyclohexylacetyl(butyl)aminopropyl |
| 66. | cyclohexylcarbonyl(propyl)aminopropyl |
| 67. | cyclohexylcarbonyl(butyl)aminopropyl |
| 68. | (1,2,3,4-tetrahydronaphthalen-1-yloxy)carbonyl(propyl)aminopropyl |
| 69. | (1,2,3,4-tetrahydronaphthalen-1-yloxy)carbonyl(butyl)aminopropyl |

TABLE 1-continued
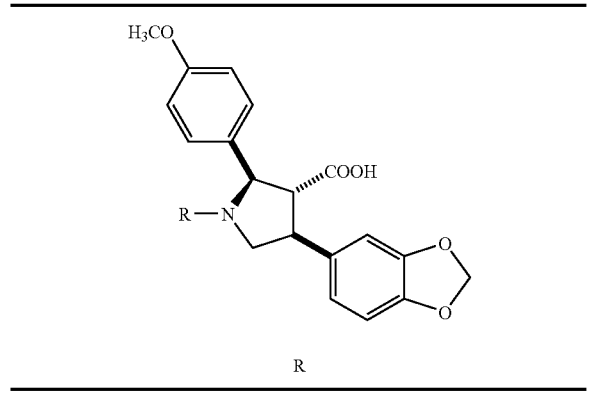
| | R |
|---|---|
| 70. | |
| 71. | |
| 72. | |
| 73. | |
| 74. | |
| 75. | |
| 76. | |
TABLE 1-continued
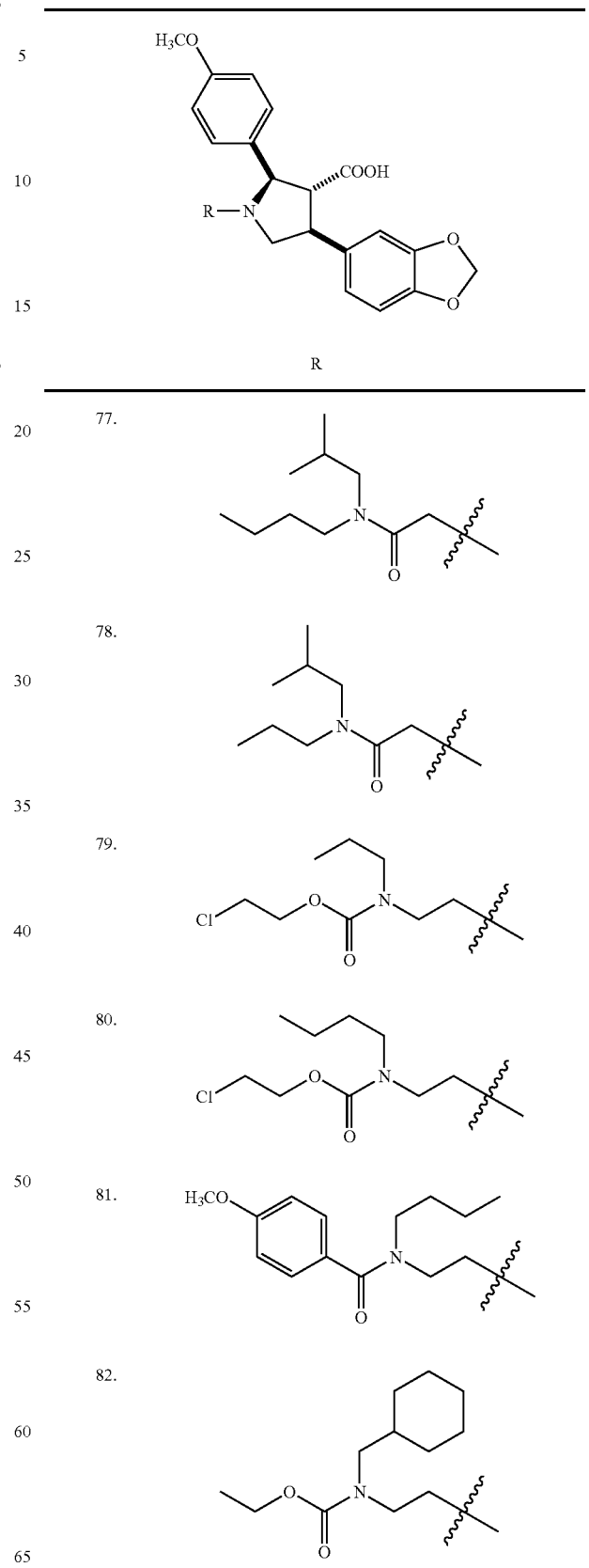

TABLE 1-continued
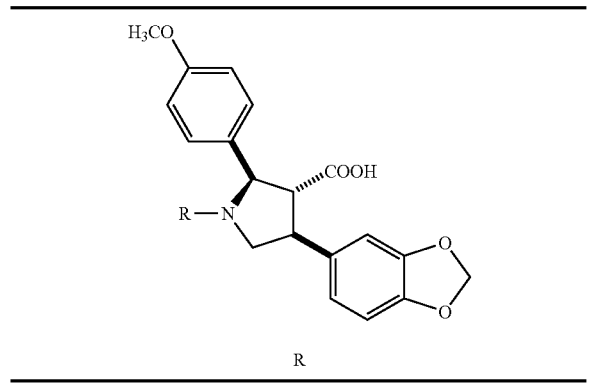
| | |
|---|---|
| 83. | |
| 84. | |
| 85. | |
| 86. | |
| 87. | |
| 88. | |
| 89. | |
| 90. | |
| 91. | |
| 92. | |
| 93. | |
| 94. | |
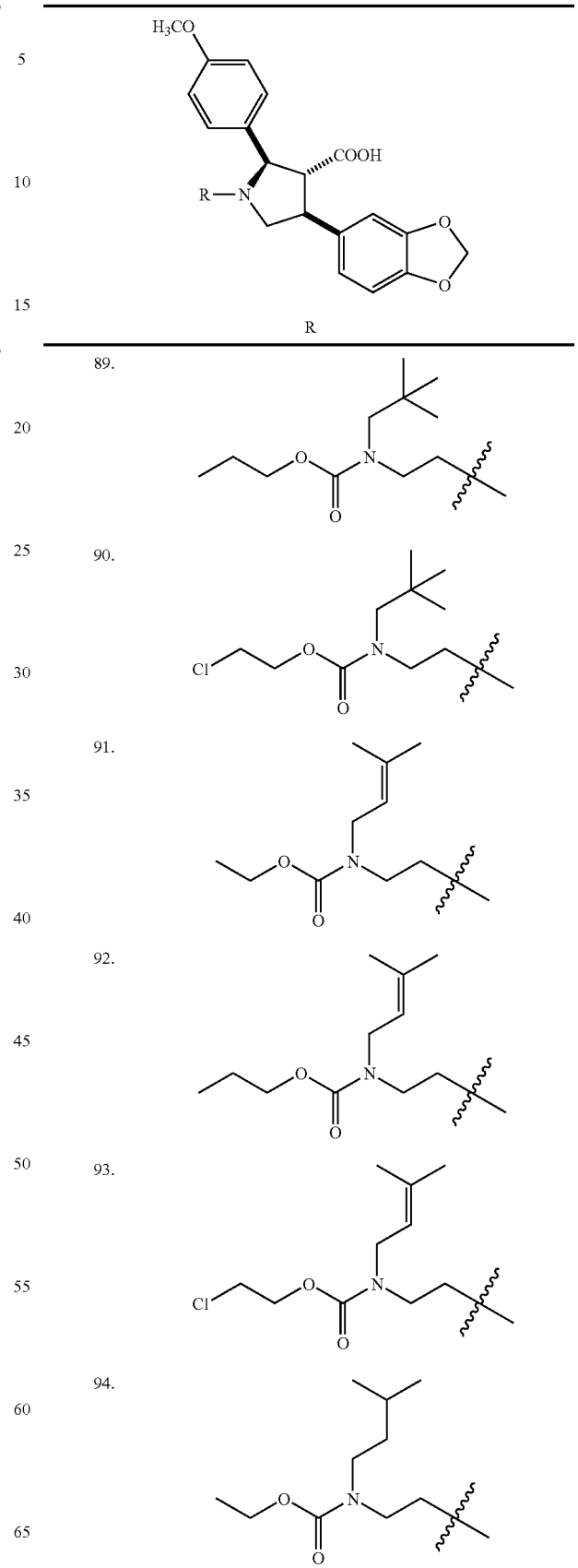

TABLE 1-continued
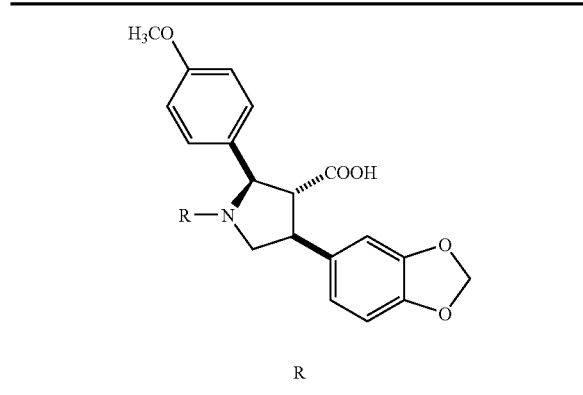
R
95. 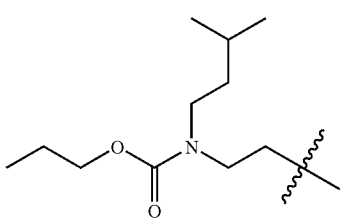
96. 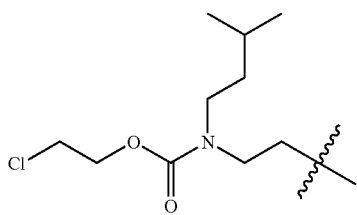
97. 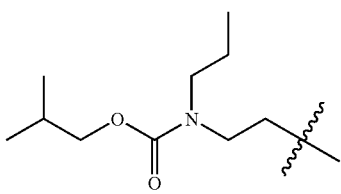
98. 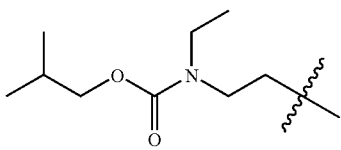
99. 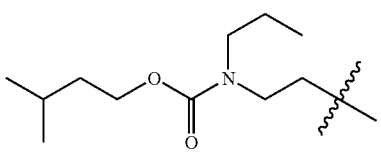
100. 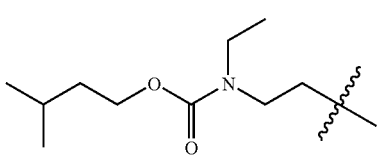
TABLE 1-continued
R
101. 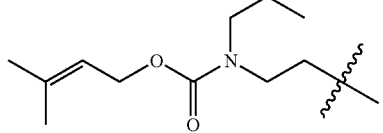
102. 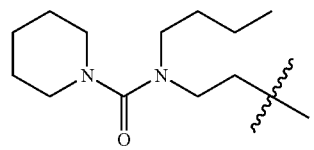
103. 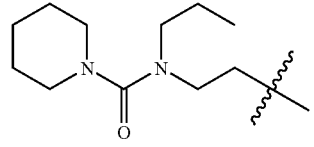
104. 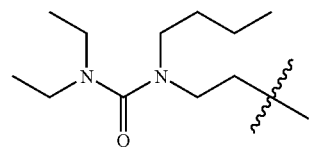
105. 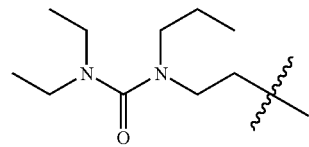
106. 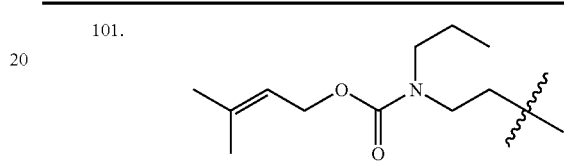
107. 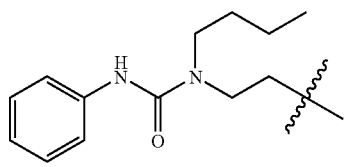

TABLE 1-continued
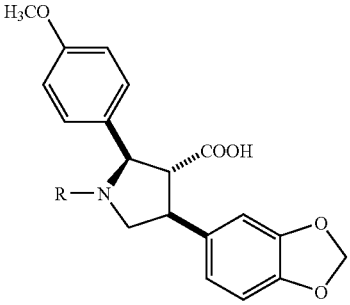
| | R |
|---|---|
| 108. | 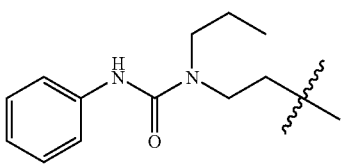 |
| 109. | 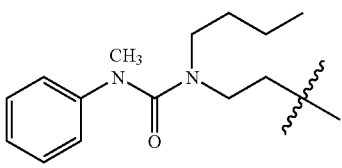 |
| 110. | 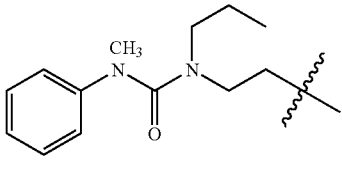 |
| 111. | 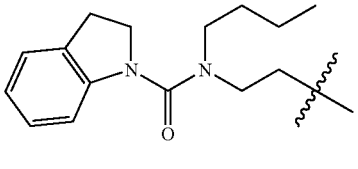 |
| 112. | 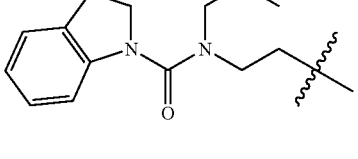 |
| 113. | 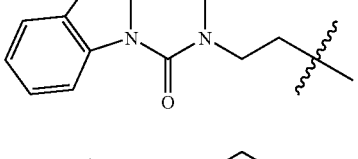 |
| 114. | 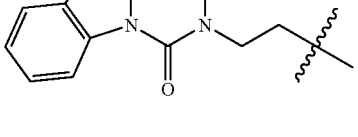 |
TABLE 1-continued
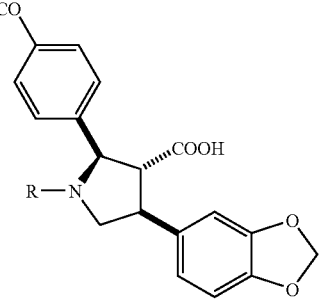
| | R |
|---|---|
| 115. | 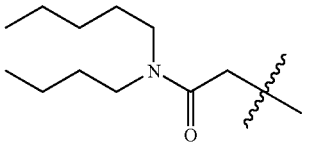 |
| 116. | 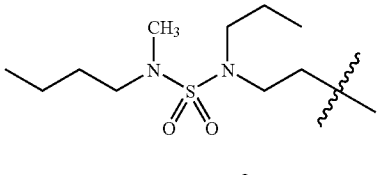 |
| 117. | 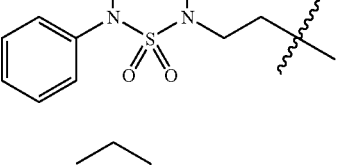 |
| 118. | 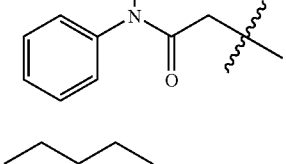 |
| 119. | 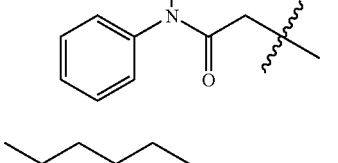 |
| 120. | 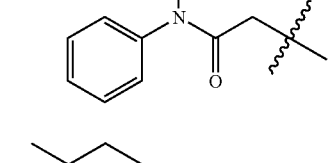 |
| 121. | 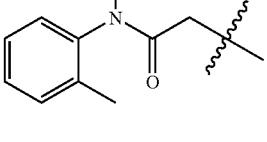 |

TABLE 1-continued

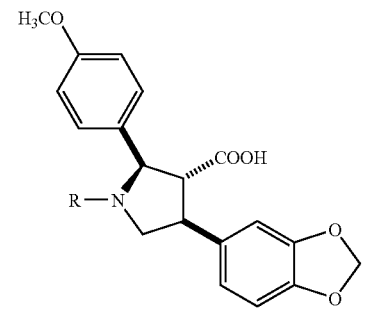

| | R |
|---|---|
| 122. | N-butyl-N-(3-methylphenyl)amide linker |
| 123. | N-butyl-N-(4-methylphenyl)amide linker |
| 124. | N-butyl-N-(2-fluorophenyl)amide linker |
| 125. | N-butyl-N-(3-fluorophenyl)amide linker |
| 126. | N-butyl-N-(4-fluorophenyl)amide linker |
| 127. | N-butyl-N-(2-chlorophenyl)amide linker |

TABLE 1-continued

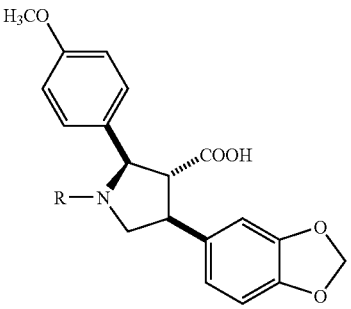

| | R |
|---|---|
| 128. | N-butyl-N-(3-chlorophenyl)amide linker |
| 129. | N-butyl-N-(4-chlorophenyl)amide linker |
| 130. | N-butyl-N-(2-methoxyphenyl)amide linker |
| 131. | N-butyl-N-(3-methoxyphenyl)amide linker |
| 132. | N-butyl-N-(4-methoxyphenyl)amide linker |
| 133. | N-butyl-N-(2-naphthyl)amide linker |

TABLE 1-continued
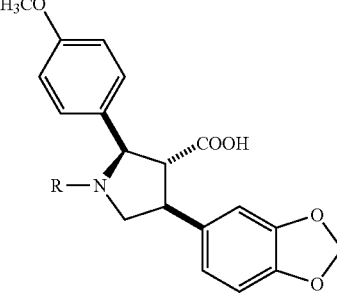
| | R |
|---|---|
| 134. | 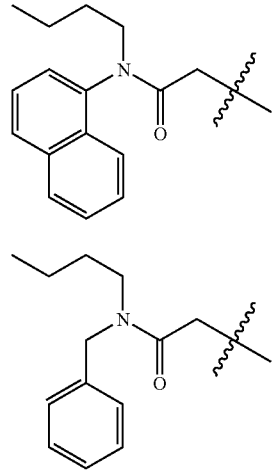 |
| 135. | 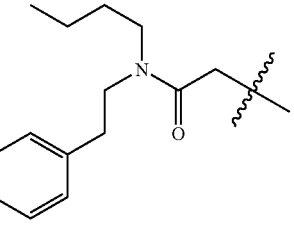 |
| 136. | 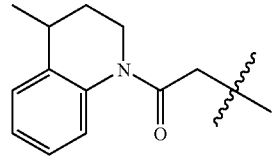 |
| 137. | 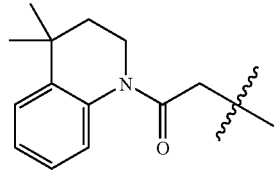 |
| 138. | 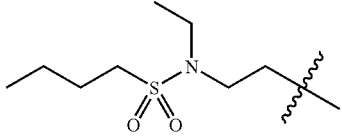 |
| 139. | 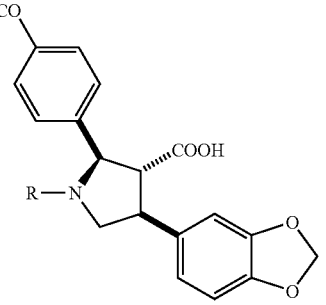 |
TABLE 1-continued
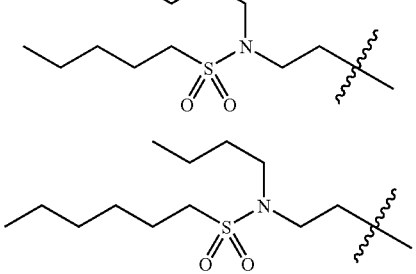
| | R |
|---|---|
| 140. | 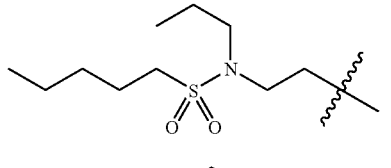 |
| 141. | 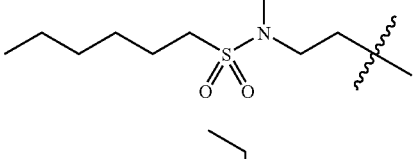 |
| 142. | 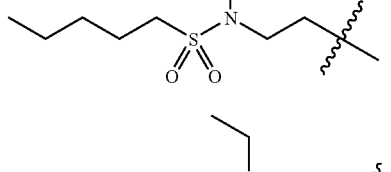 |
| 143. | 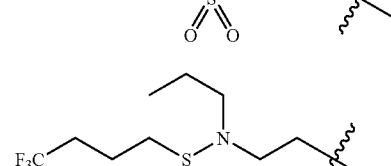 |
| 144. | 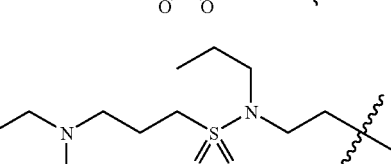 |
| 145. | 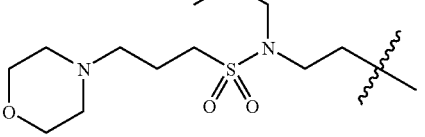 |
| 146. | |
| 147. | |

TABLE 1-continued
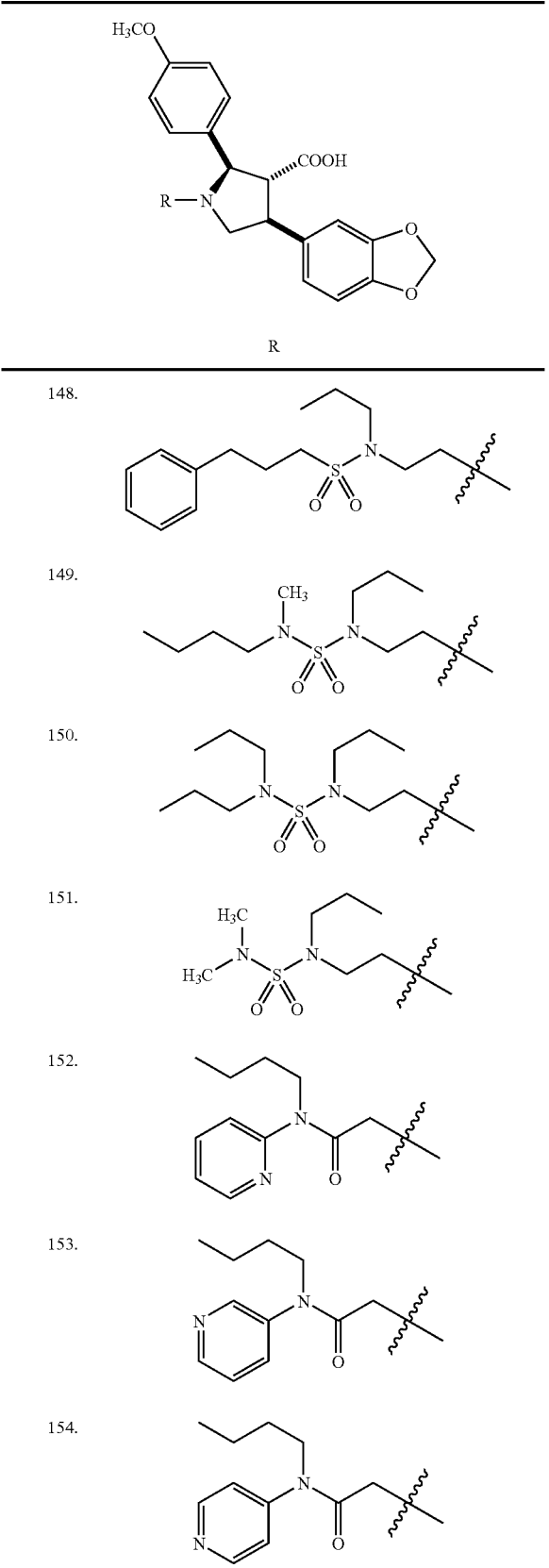
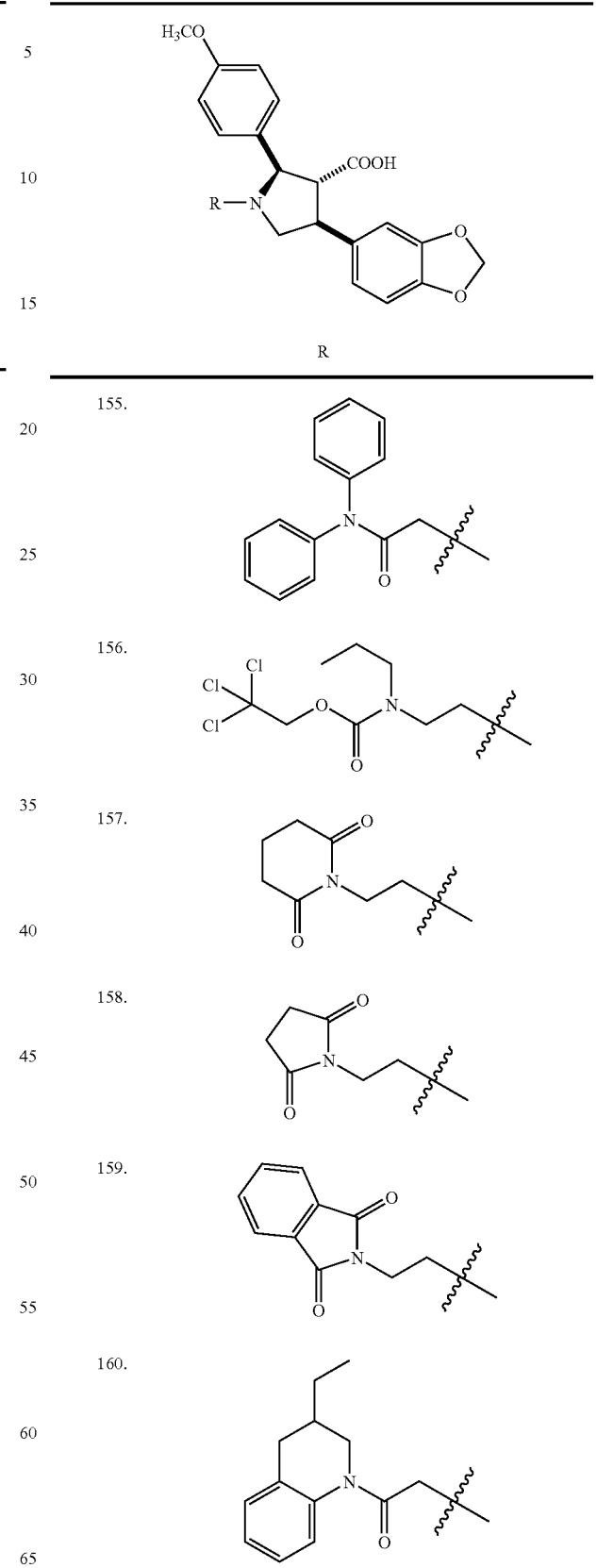

TABLE 1-continued
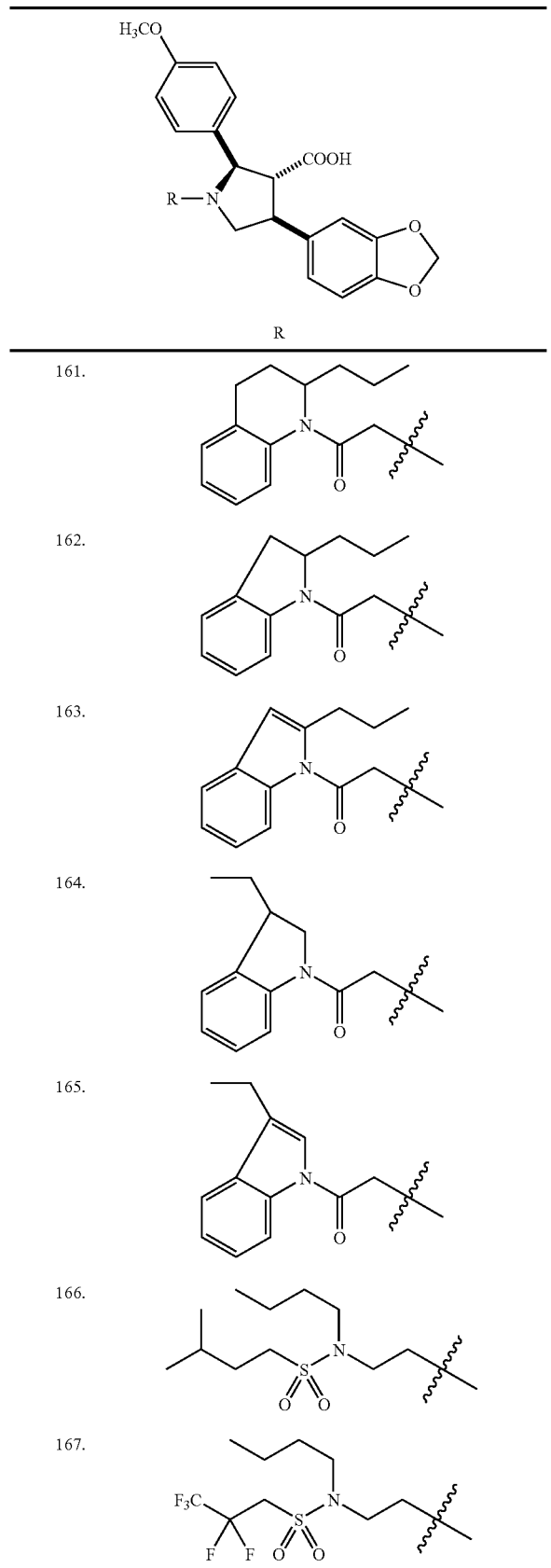
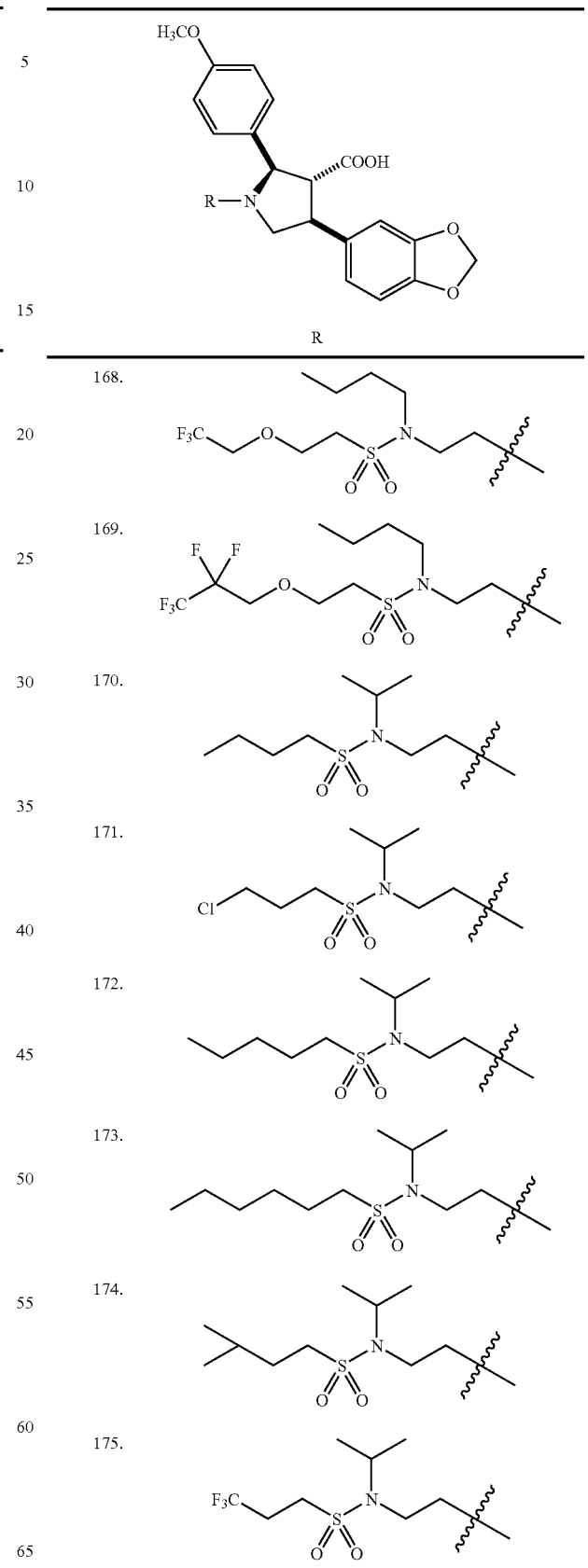

TABLE 1-continued
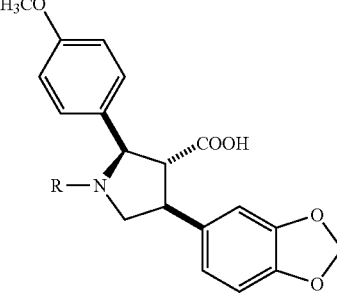
| 176. | 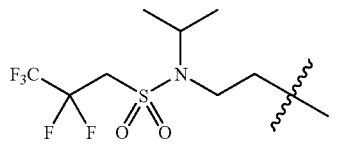 |
| 177. | 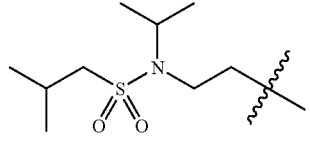 |
| 178. | 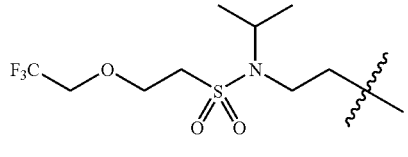 |
| 179. | 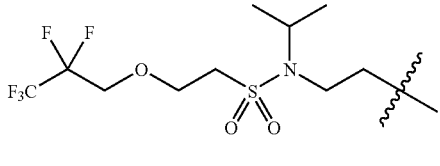 |
| 180. | 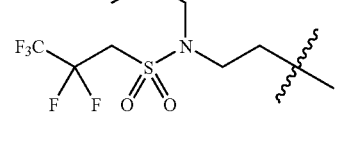 |
| 181. | 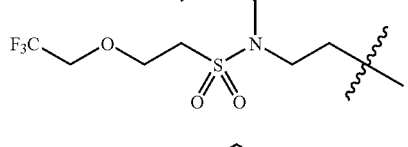 |
| 182. | 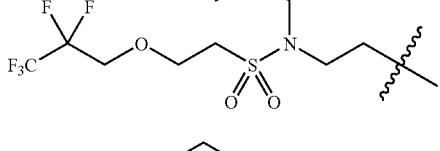 |
| 183. | 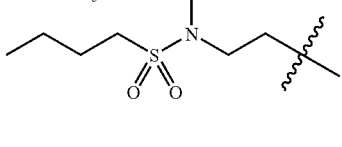 |
TABLE 1-continued
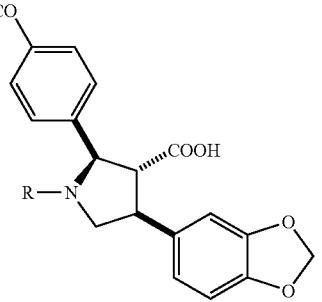
| 184. | 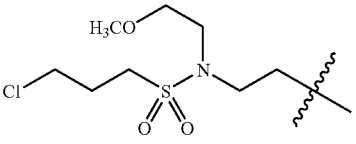 |
| 185. | 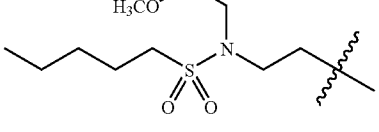 |
| 186. | 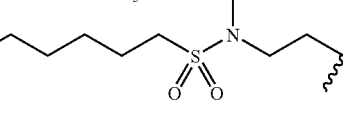 |
| 187. | 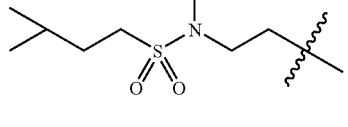 |
| 188. | 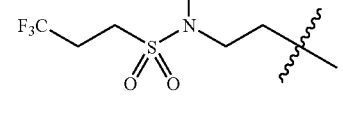 |
| 189. | 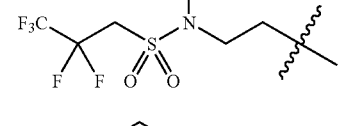 |
| 190. | 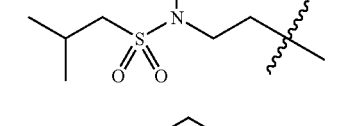 |
| 191. | 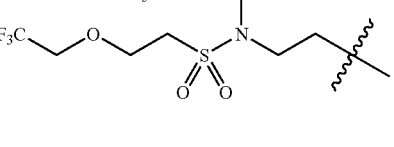 |

TABLE 1-continued
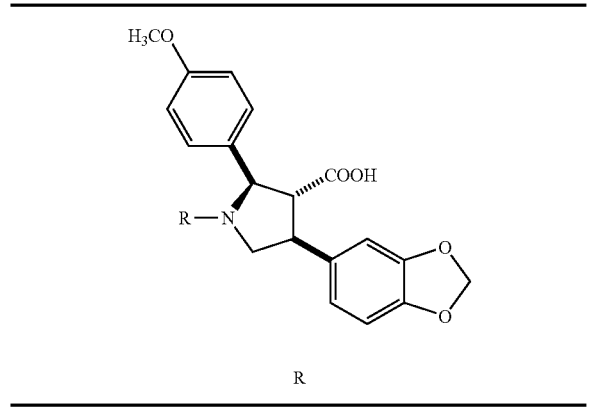
R
192. 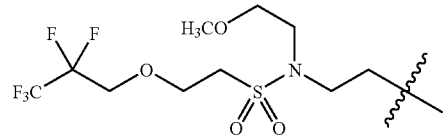
193. 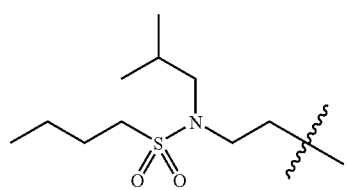
194. 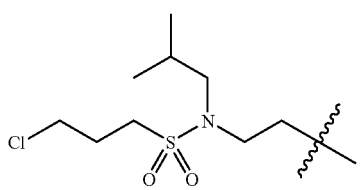
195. 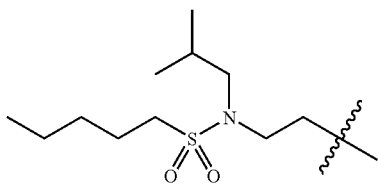
196. 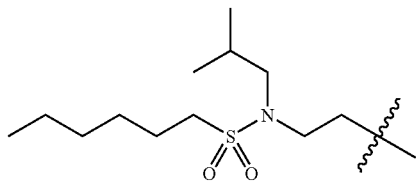
197. 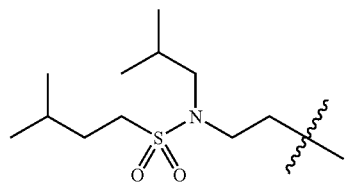
TABLE 1-continued
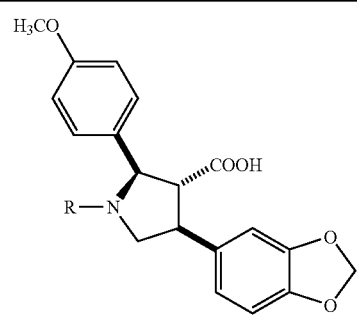
R
198. 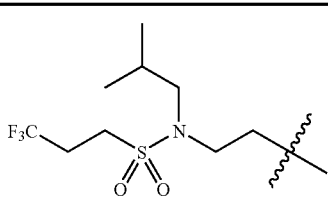
199. 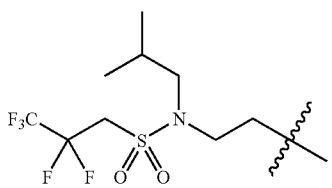
200. 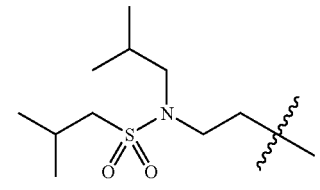
201. 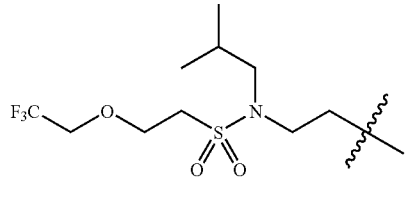
202. 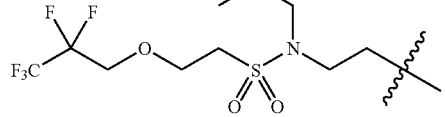
203. 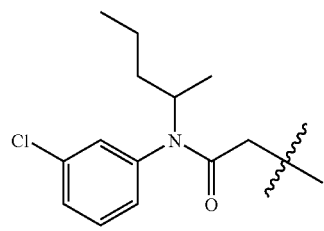

TABLE 1-continued
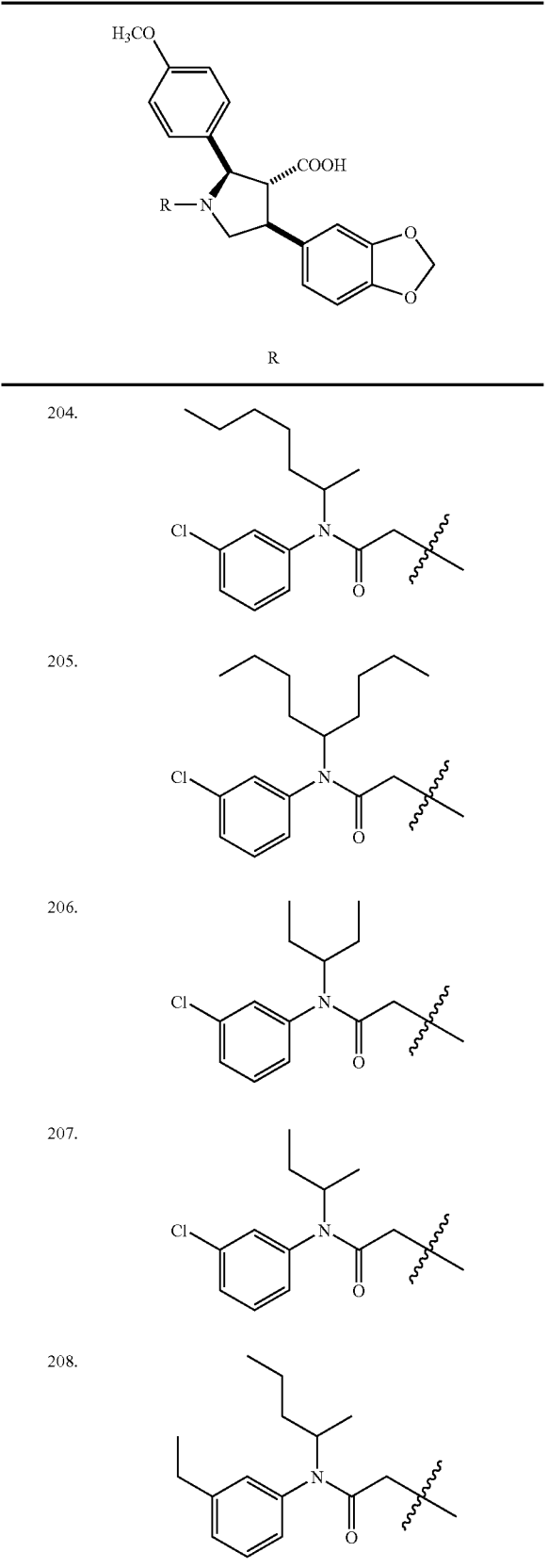
TABLE 1-continued
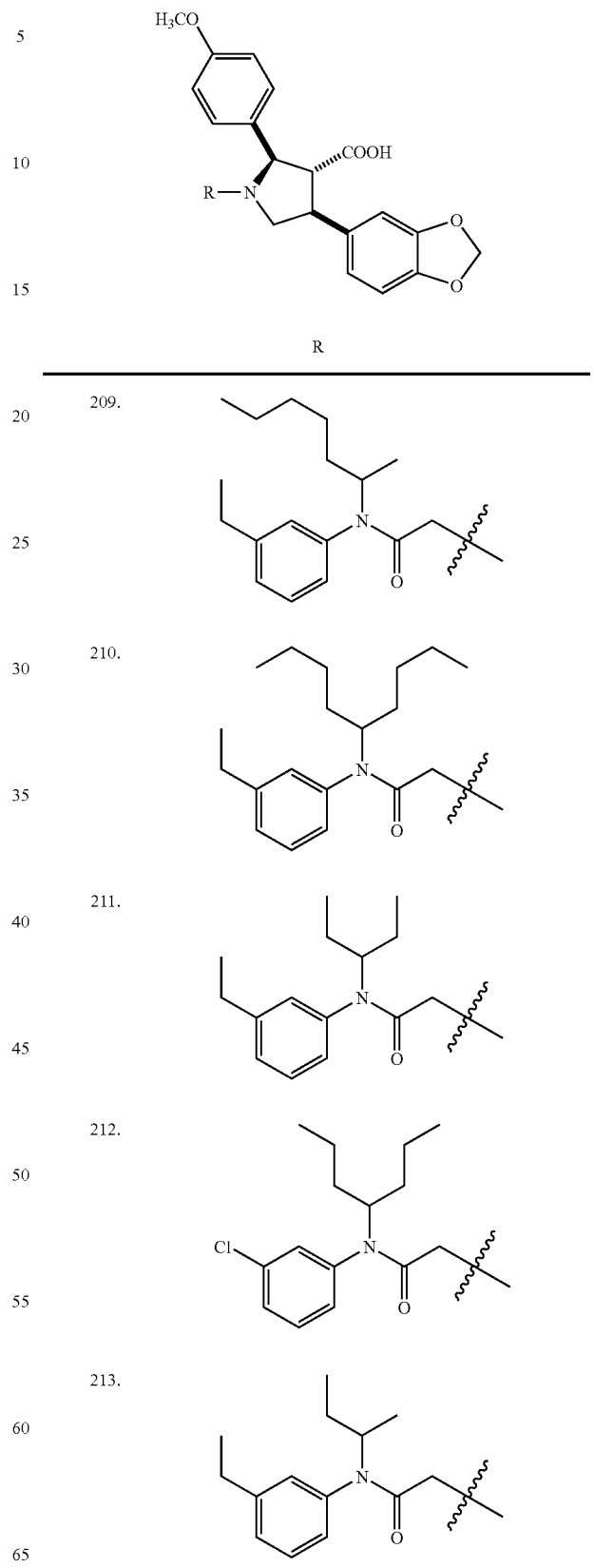

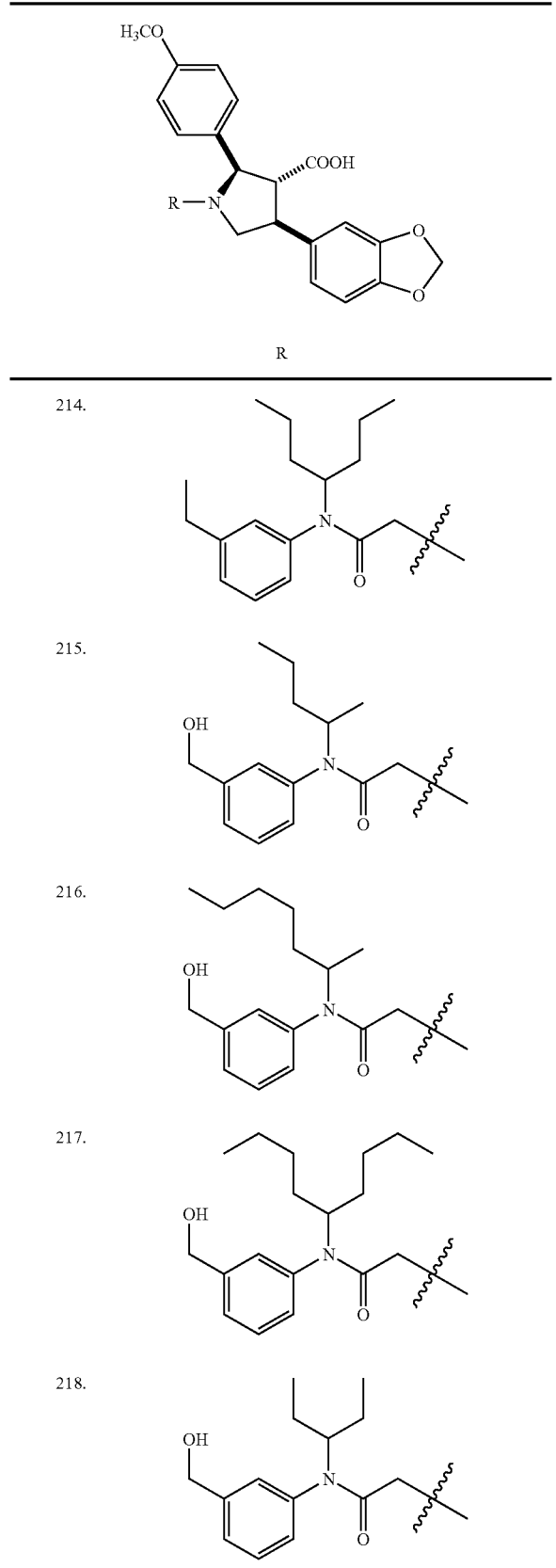
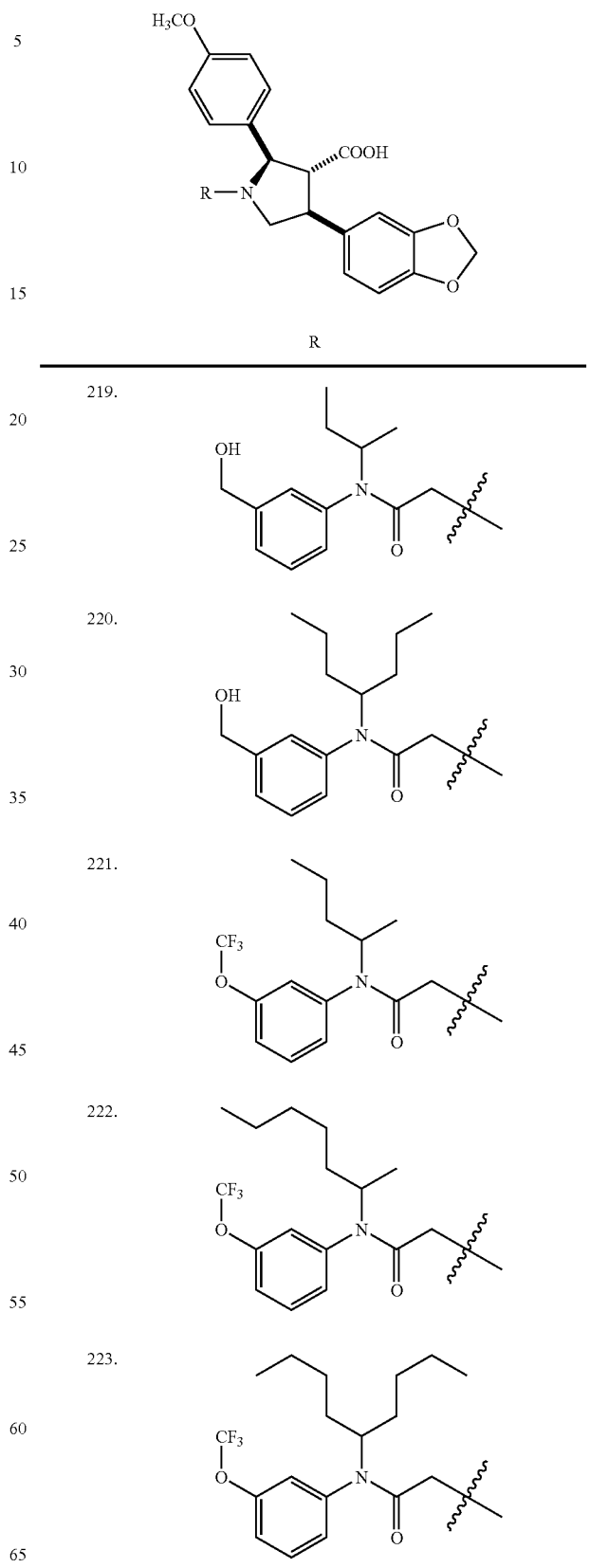

TABLE 1-continued
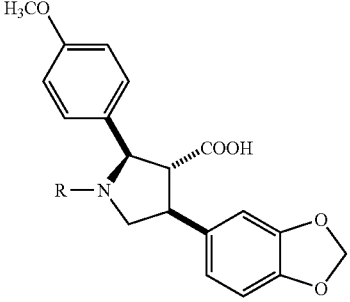
| | R |
|---|---|
| 224. | 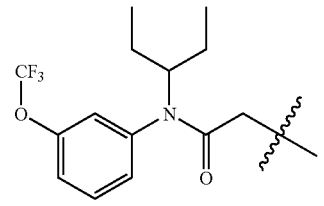 |
| 225. | 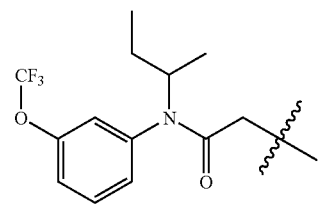 |
| 226. | 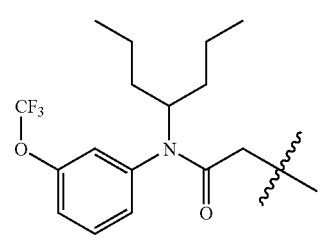 |
| 227. | 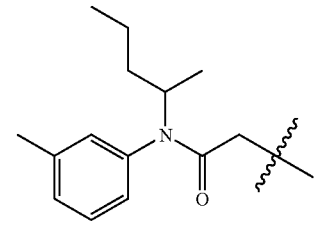 |
| 228. |  |
TABLE 1-continued
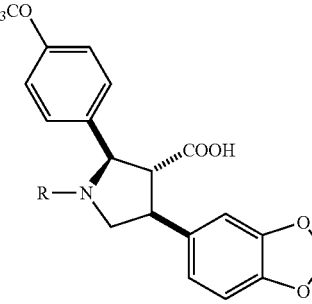
| | R |
|---|---|
| 229. | 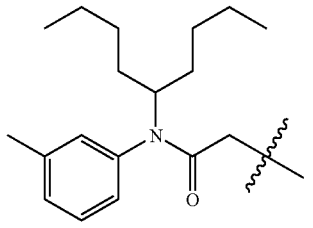 |
| 230. | 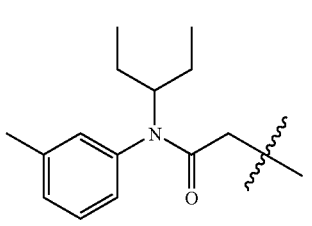 |
| 231. | 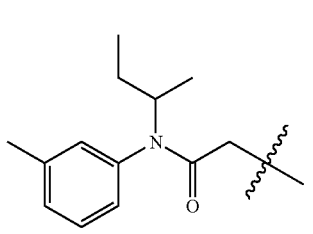 |
| 232. | 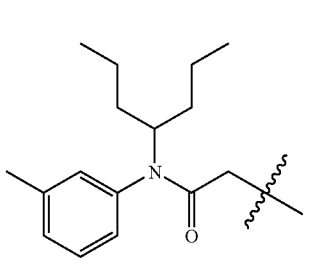 |
| 233. |  |

TABLE 1-continued
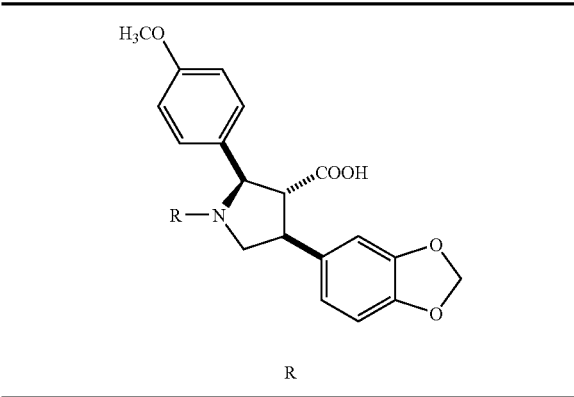
R
234. 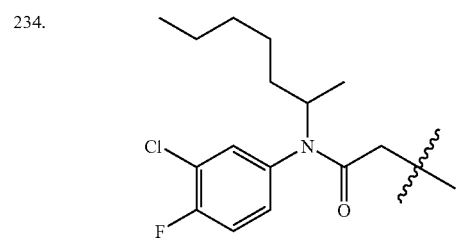
235. 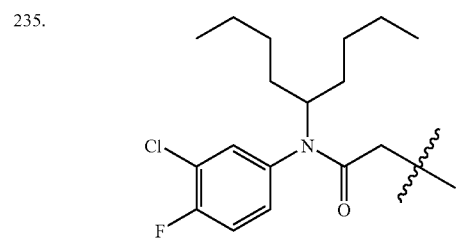
236. 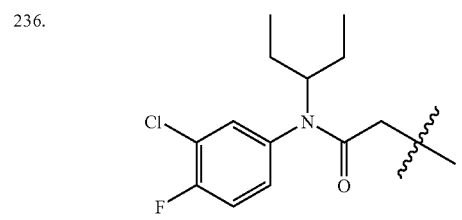
237. 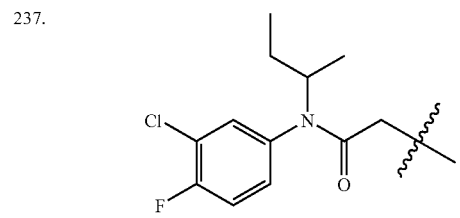
238. 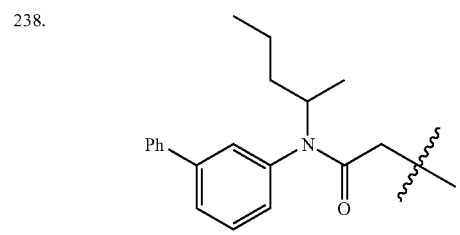
TABLE 1-continued
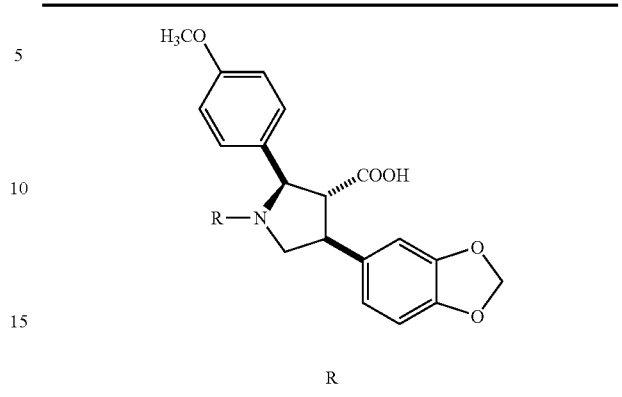
R
239. 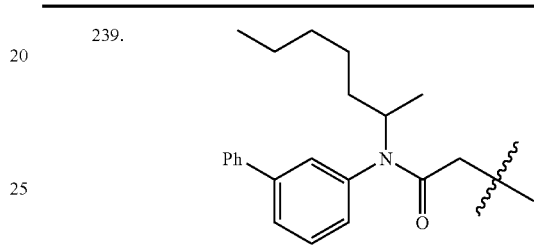
240. 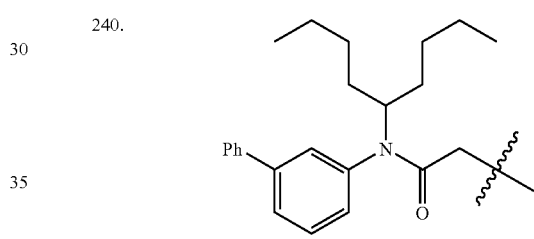
241. 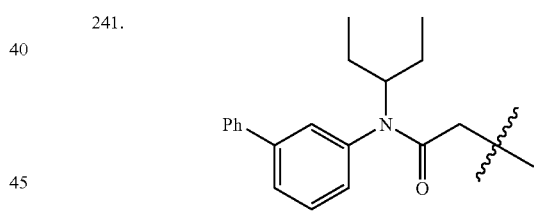
242. 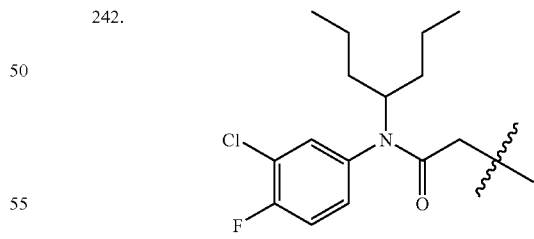
243. 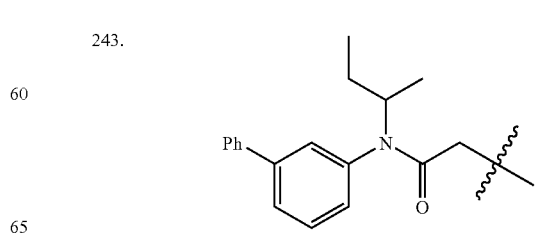

TABLE 1-continued
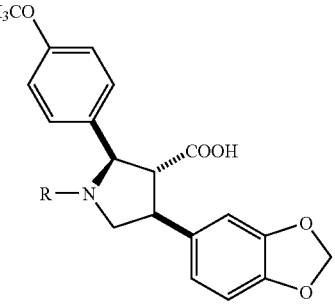
| R |
|---|
| 244. 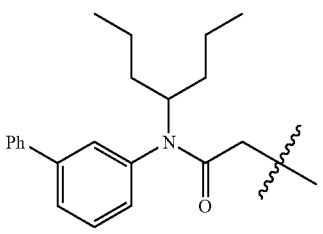 |
| 245. 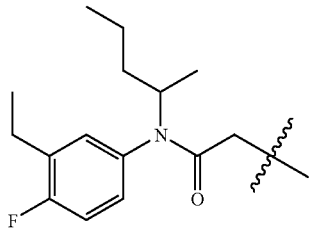 |
| 246. 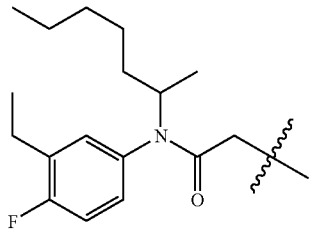 |
| 247. 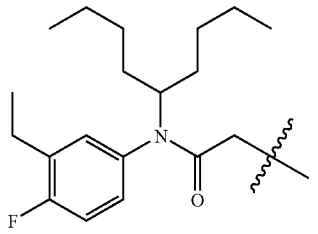 |
| 248. 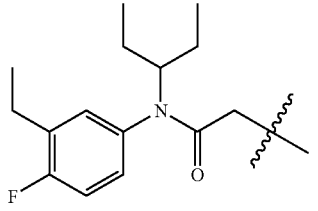 |
TABLE 1-continued
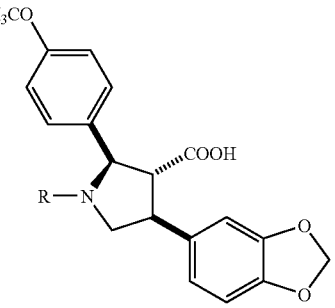
| R |
|---|
| 249. 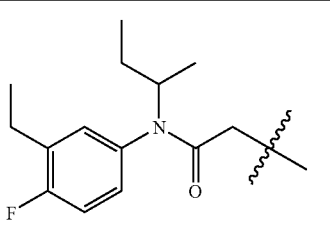 |
| 250. 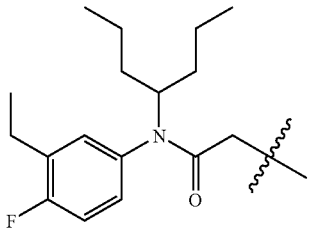 |
| 251. 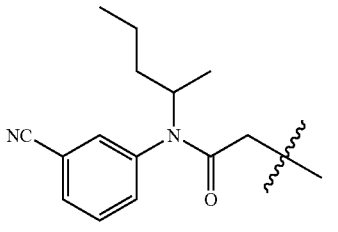 |
| 252. 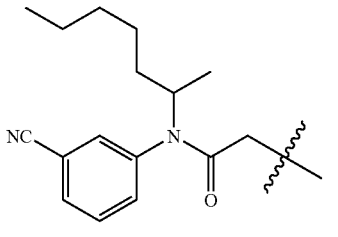 |
| 253. 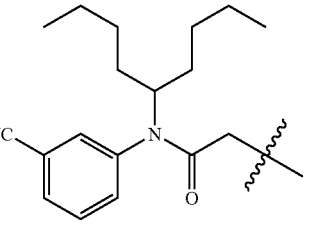 |

TABLE 1-continued
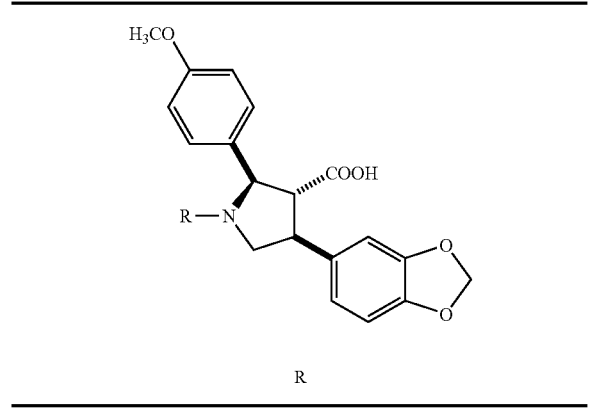
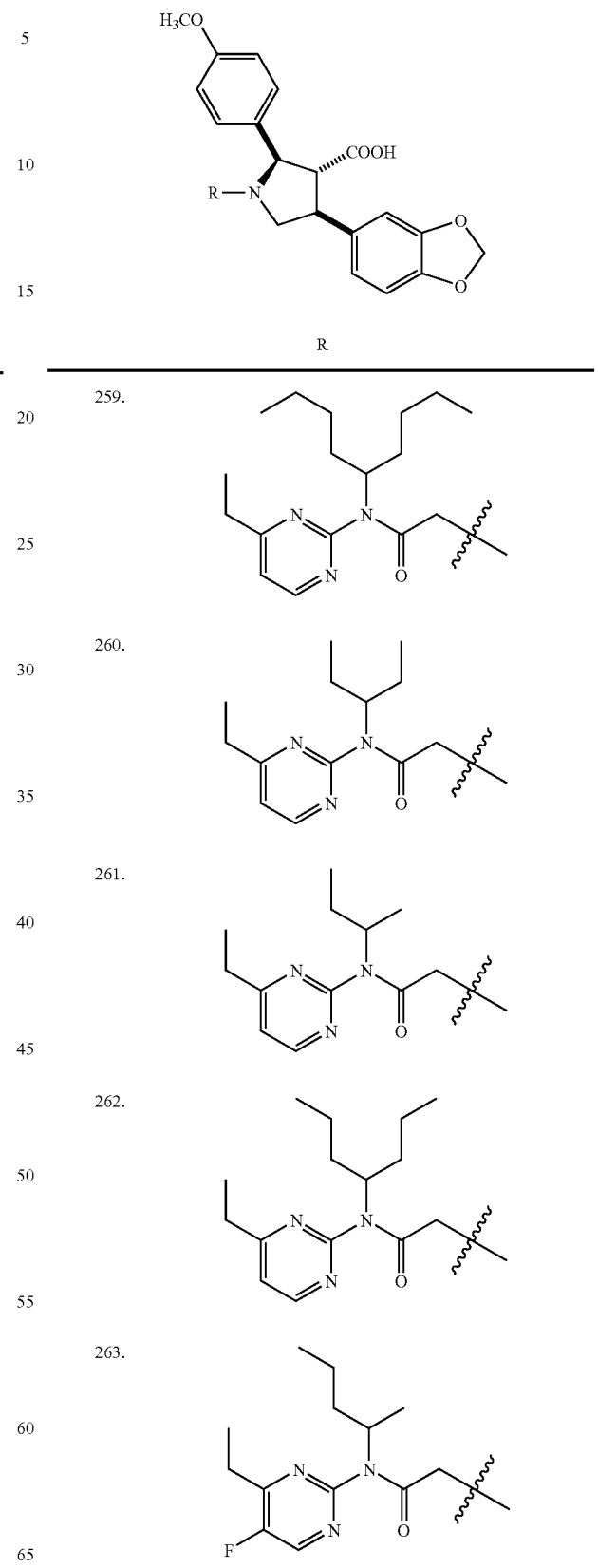
| | R |
|---|---|
| 254. | |
| 255. | |
| 256. | |
| 257. | |
| 258. | |
| 259. | |
| 260. | |
| 261. | |
| 262. | |
| 263. | |

TABLE 1-continued
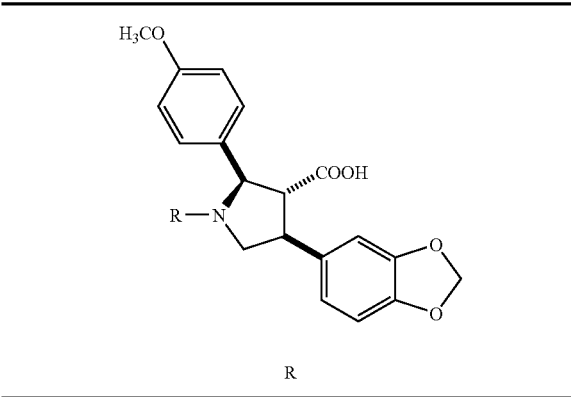
R
| | |
|---|---|
| 264. | |
| 265. | |
| 266. | |
| 267. | |
| 268. | |
TABLE 1-continued
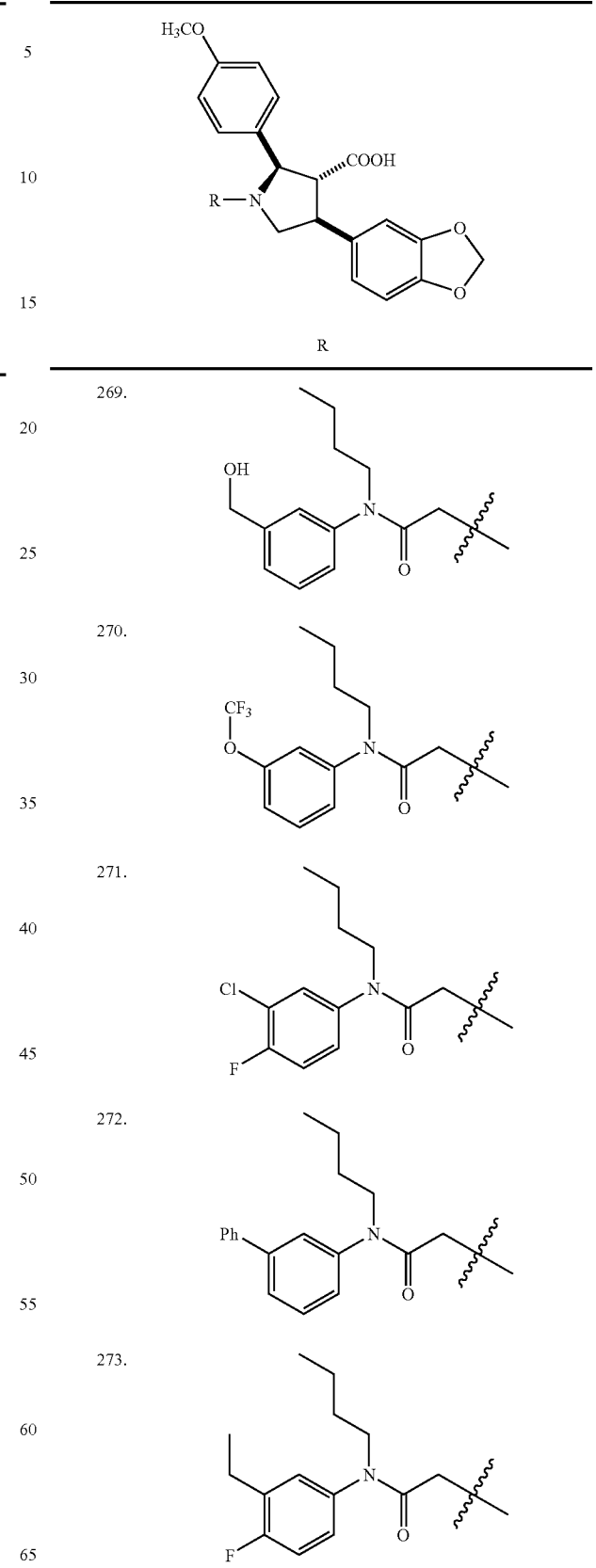
R
| | |
|---|---|
| 269. | |
| 270. | |
| 271. | |
| 272. | |
| 273. | |

TABLE 1-continued
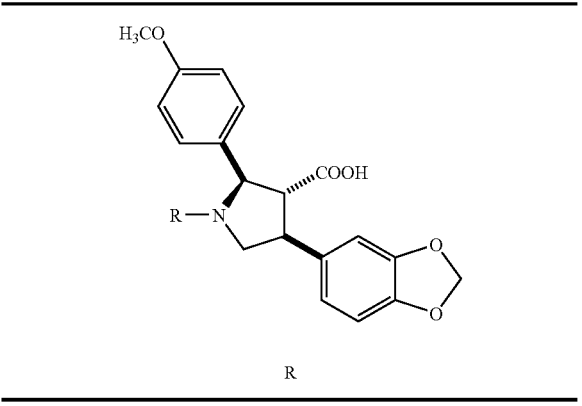
R
| | |
|---|---|
| 274. | 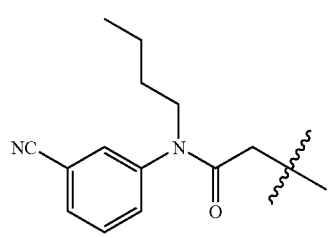 |
| 275. | 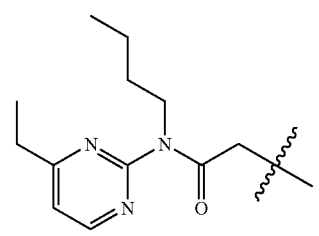 |
| 276. | 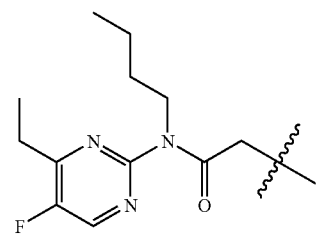 |
| 277. | 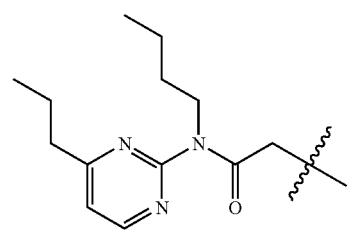 |
| 278. | 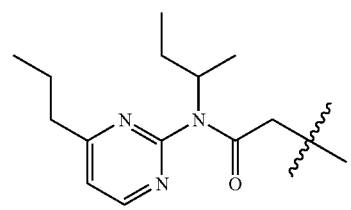 |
TABLE 1-continued
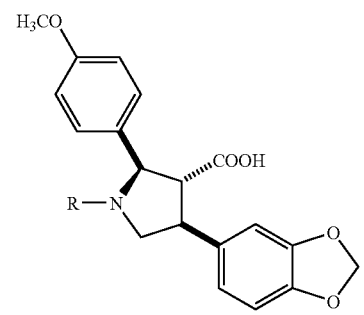
R
| | |
|---|---|
| 279. | 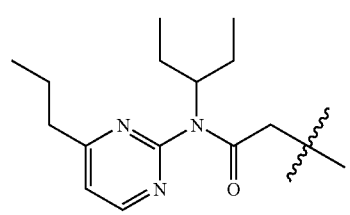 |
| 280. | 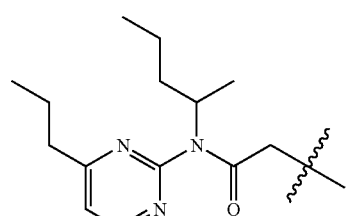 |
| 281. | 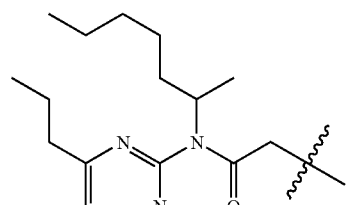 |
| 282. | 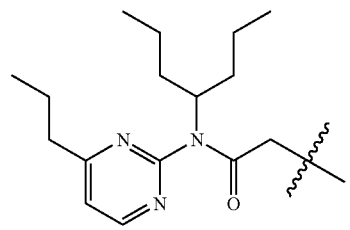 |
| 283. | 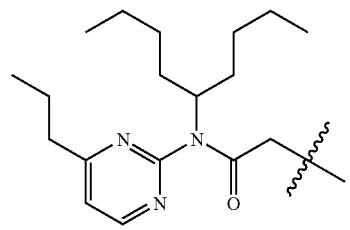 |

TABLE 1-continued
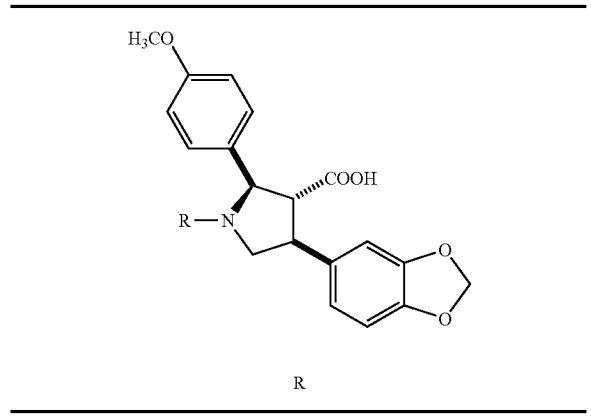
| | R |
|---|---|
| 284. | 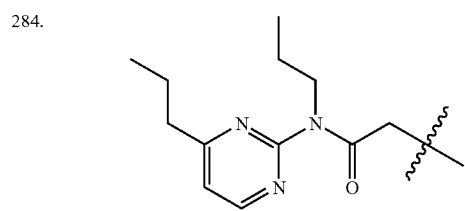 |
| 285. | 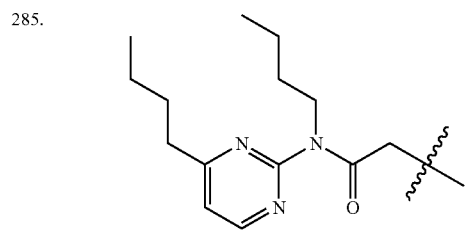 |
| 286. | 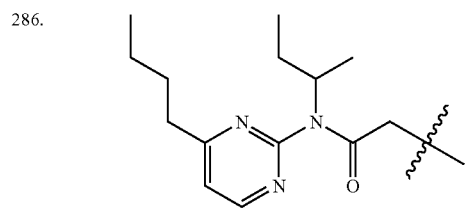 |
| 287. | 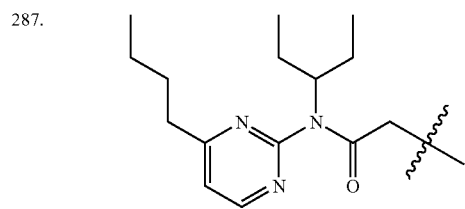 |
| 288. | 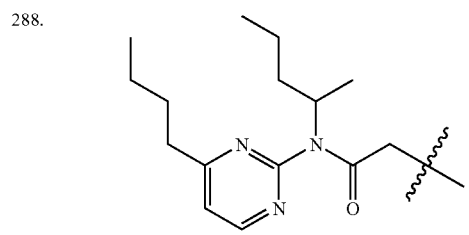 |
TABLE 1-continued
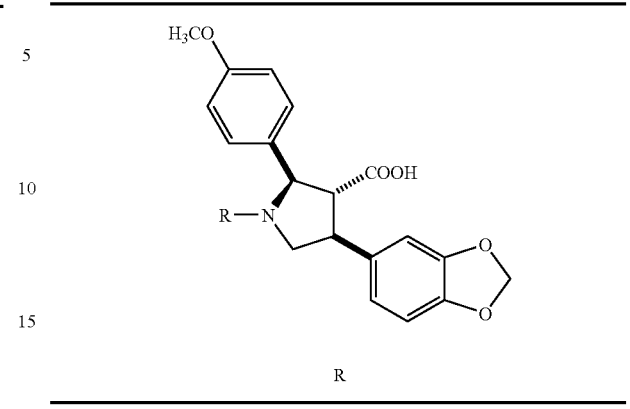
| | R |
|---|---|
| 289. | 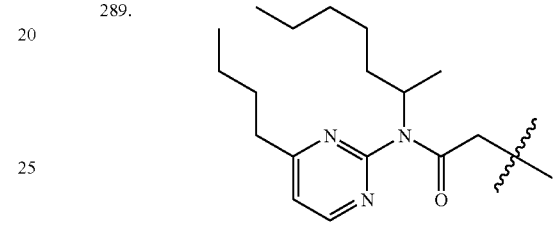 |
| 290. | 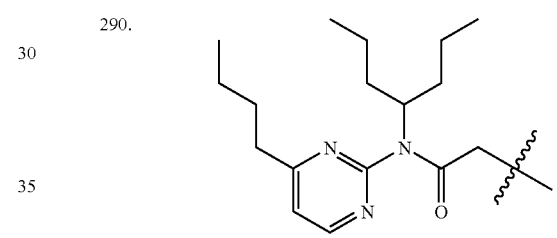 |
| 291. |  |
| 292. |  |
| 293. | 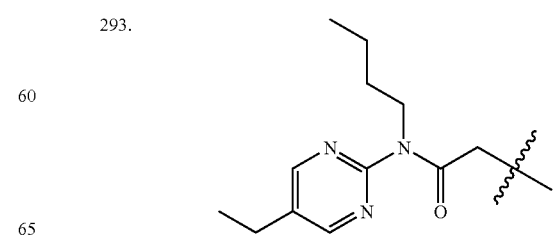 |

TABLE 1-continued
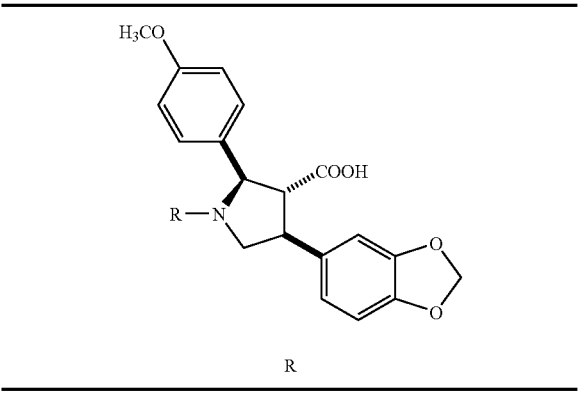
R
| | |
|---|---|
| 294. | 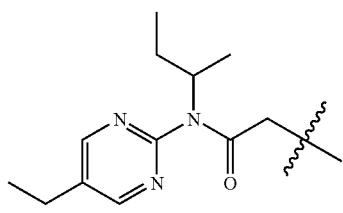 |
| 295. | 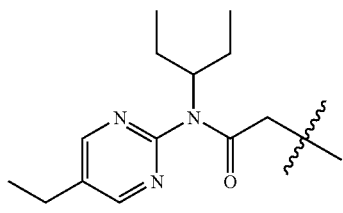 |
| 296. | 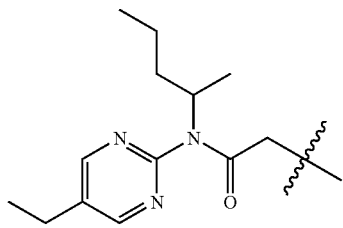 |
| 297. | 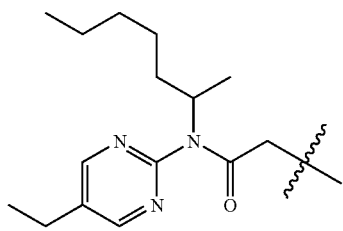 |
| 298. | 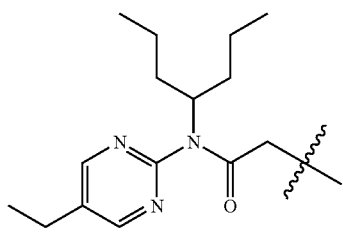 |
TABLE 1-continued
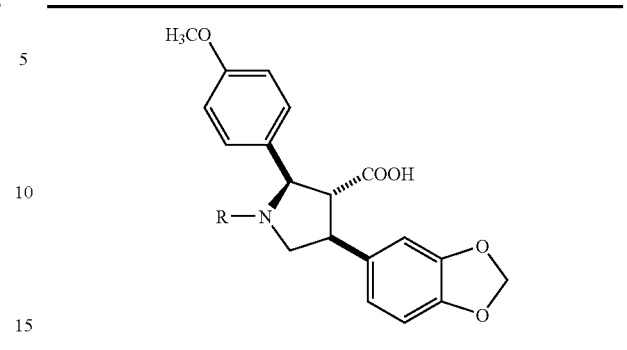
R
| | |
|---|---|
| 299. | 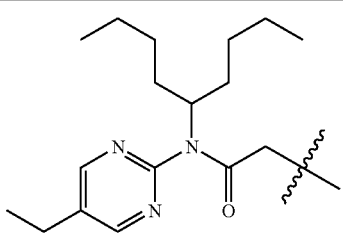 |
| 300. | 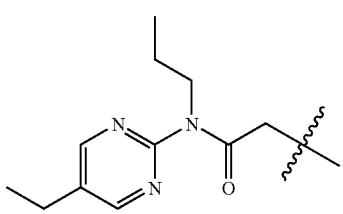 |
| 301. | 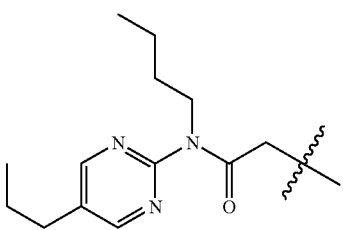 |
| 302. | 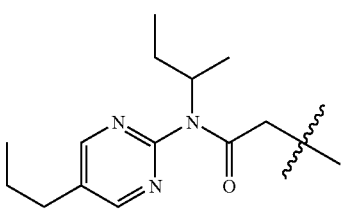 |
| 303. | 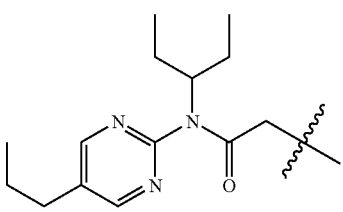 |

TABLE 1-continued
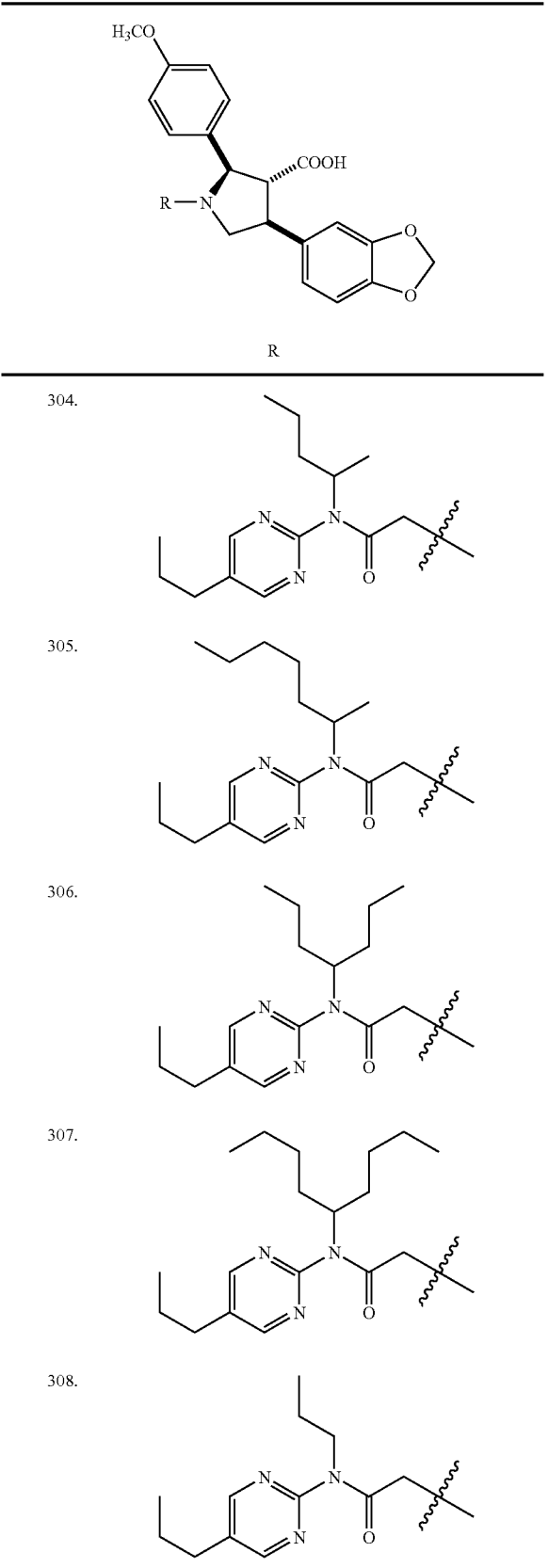
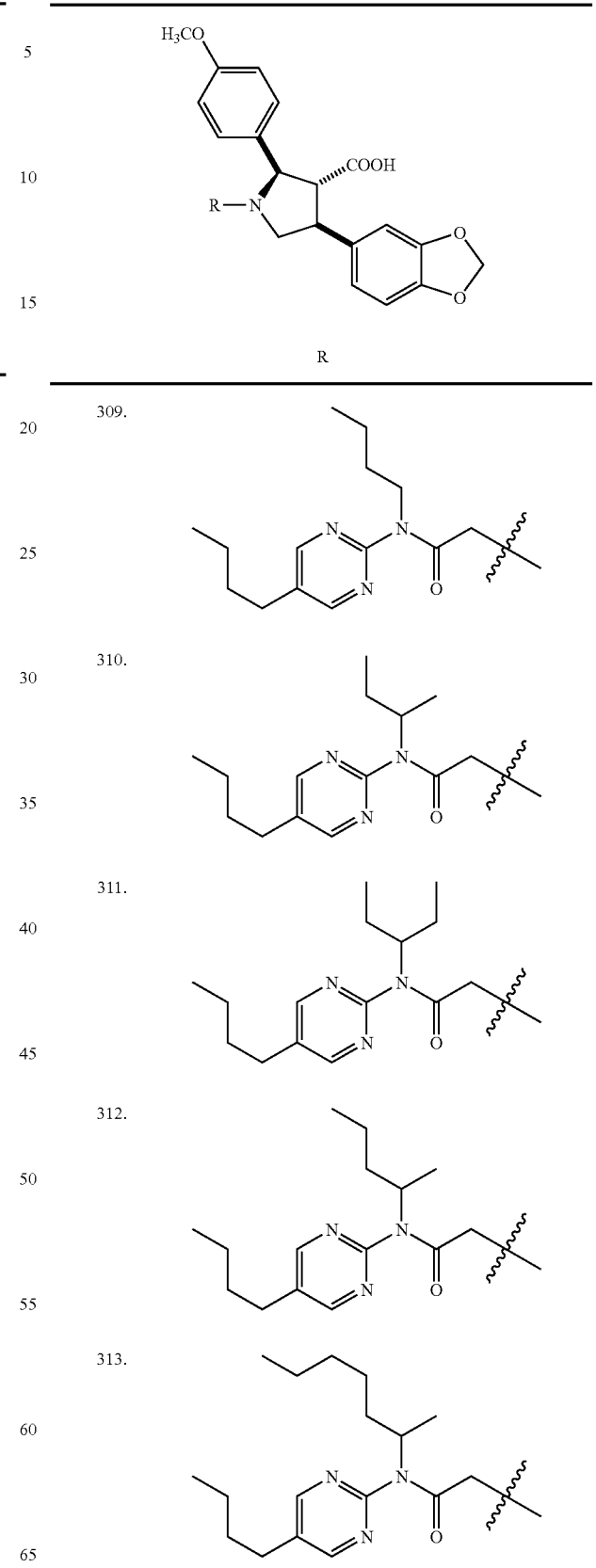

TABLE 1-continued
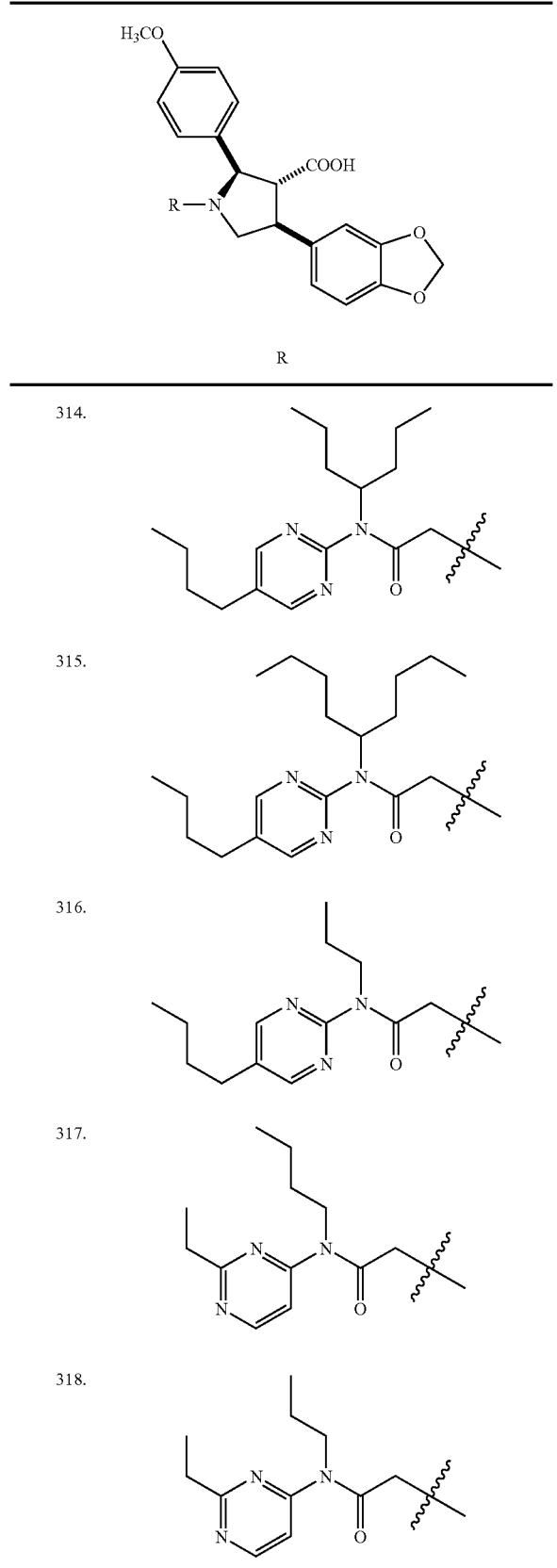
| | |
|---|---|
| 314. | |
| 315. | |
| 316. | |
| 317. | |
| 318. | |
TABLE 1-continued
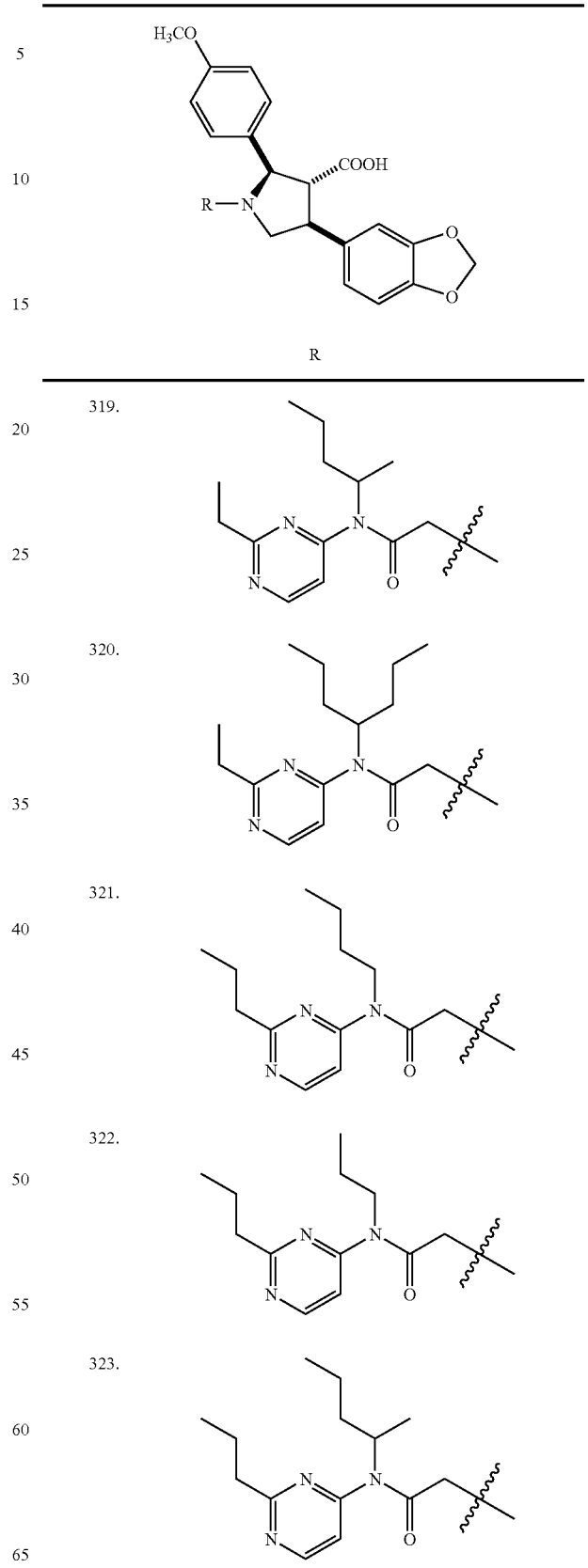
| | |
|---|---|
| 319. | |
| 320. | |
| 321. | |
| 322. | |
| 323. | |

TABLE 1-continued
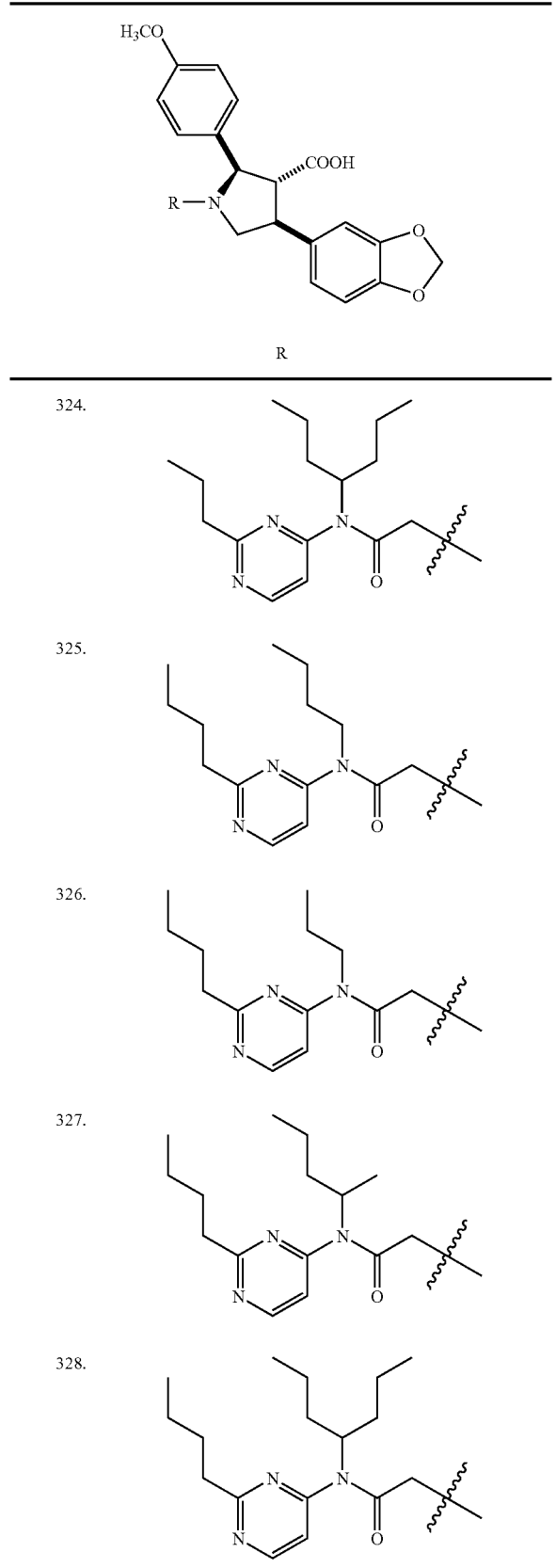
| | R |
|---|---|
| 324. | |
| 325. | |
| 326. | |
| 327. | |
| 328. | |
TABLE 1-continued
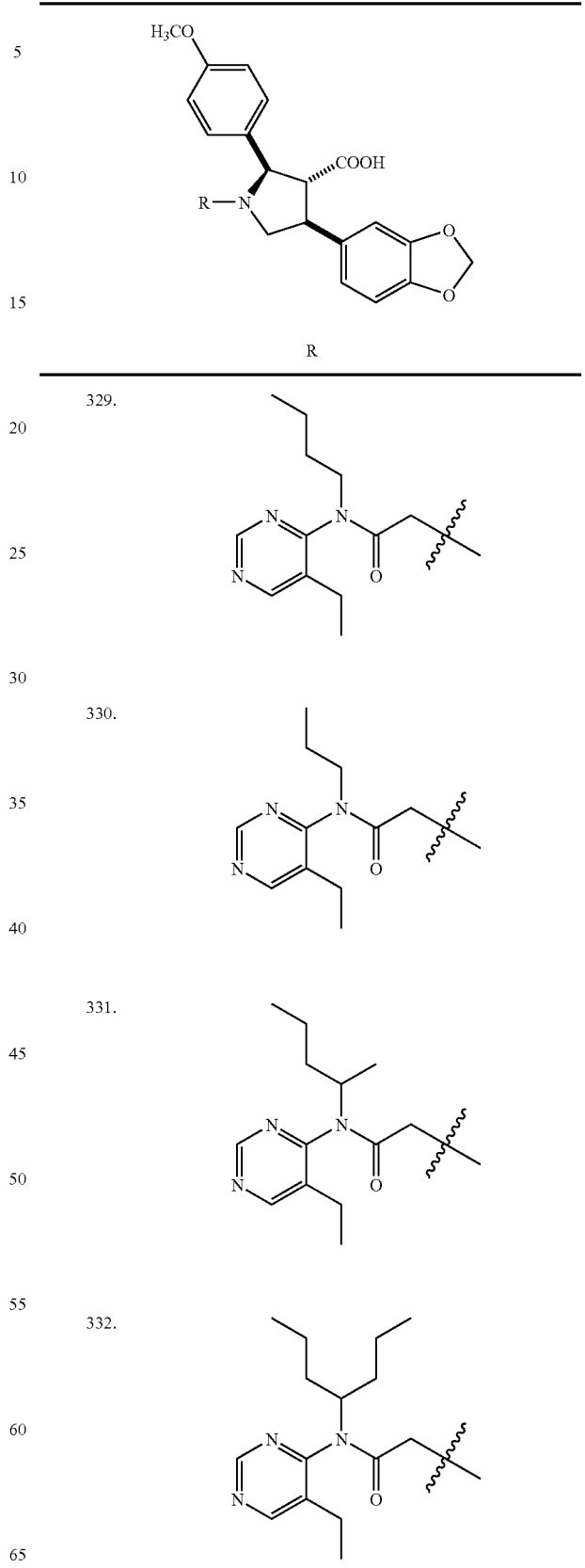
| | R |
|---|---|
| 329. | |
| 330. | |
| 331. | |
| 332. | |

TABLE 1-continued
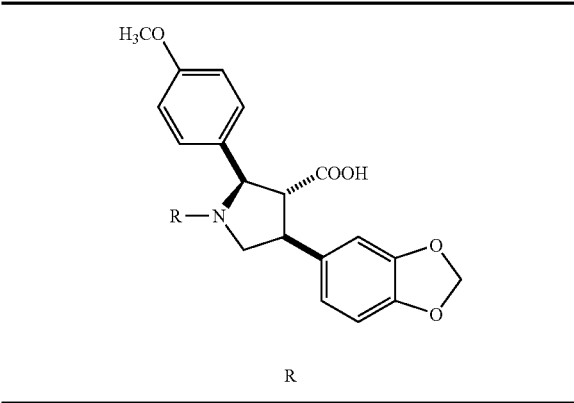
R
| | |
|---|---|
| 333. | 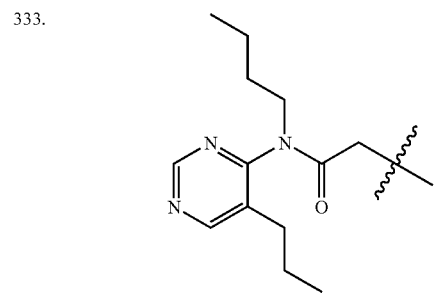 |
| 334. | 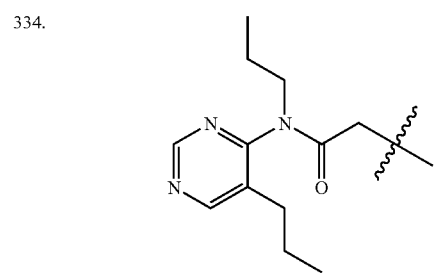 |
| 335. | 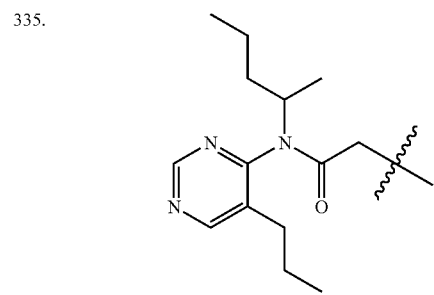 |
| 336. | 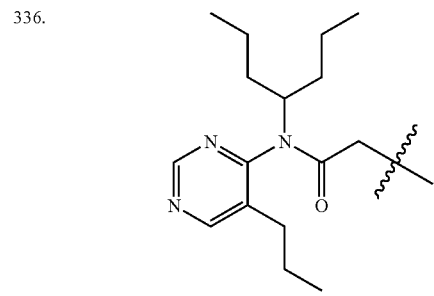 |
TABLE 1-continued
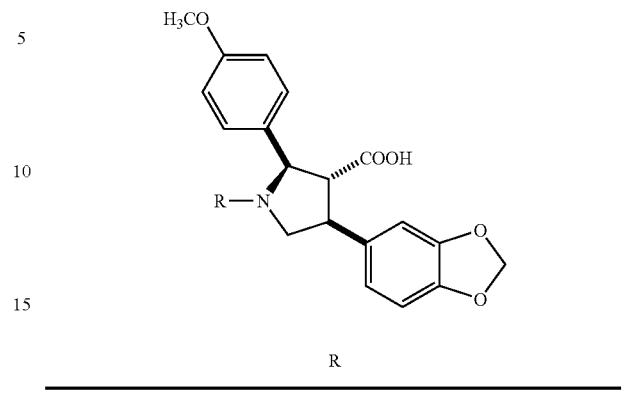
R
| | |
|---|---|
| 337. | 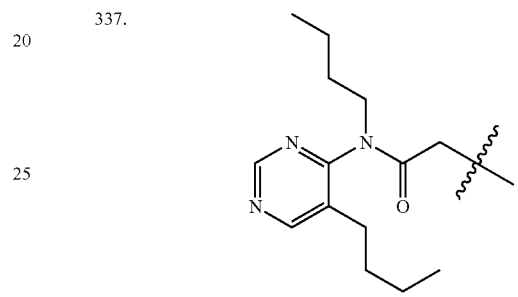 |
| 338. | 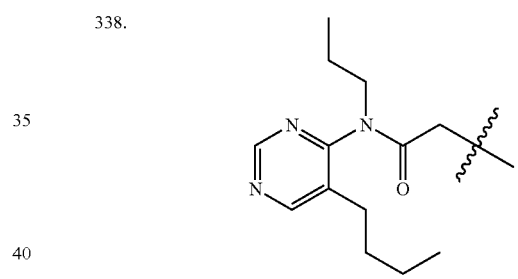 |
| 339. | 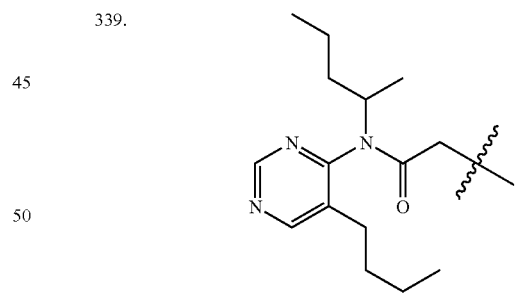 |
| 340. | 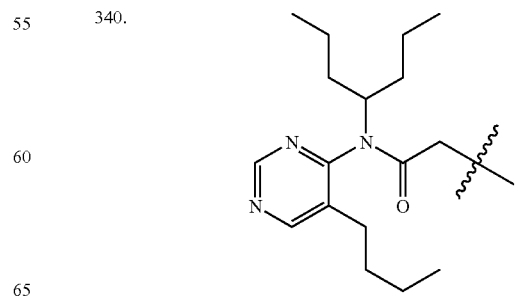 |

TABLE 1-continued
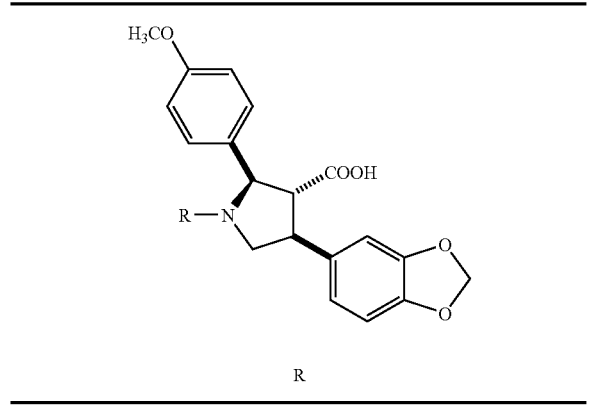
R
341. 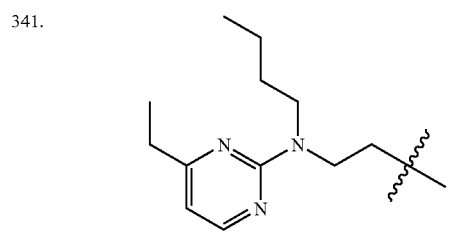
342. 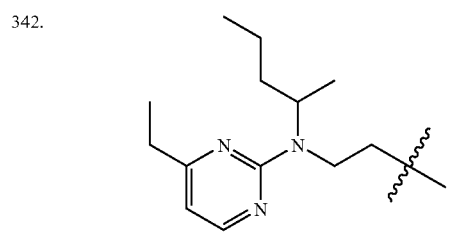
343. 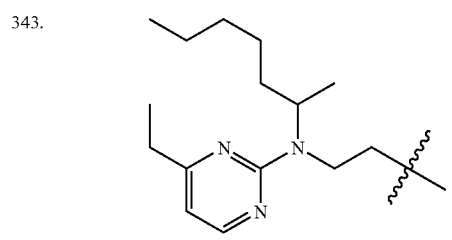
344. 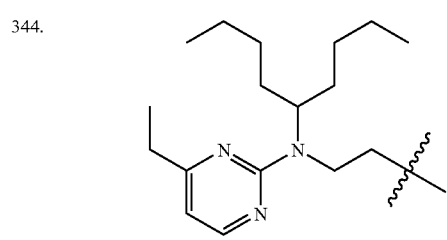
345. 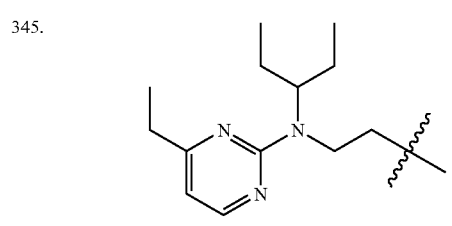
TABLE 1-continued
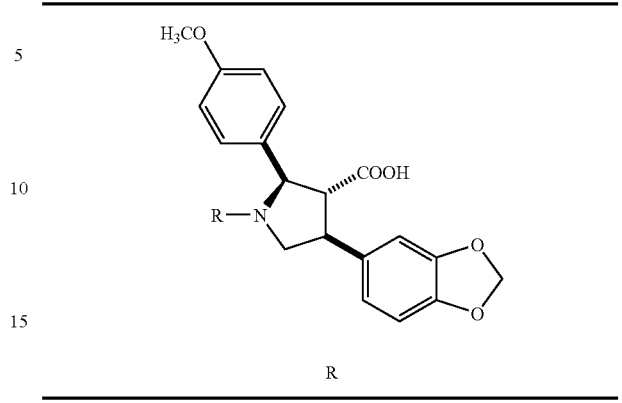
R
346. 
347. 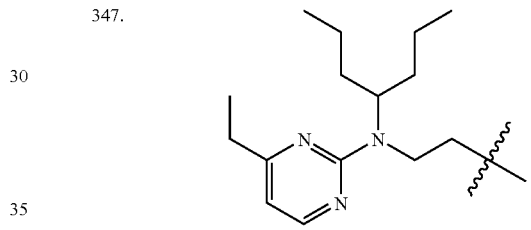
348. 
349. 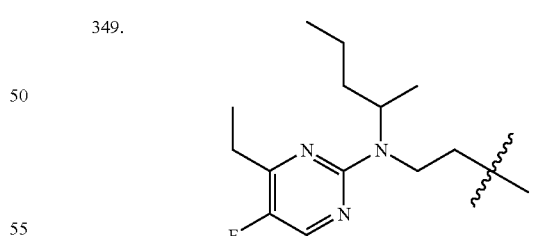
350. 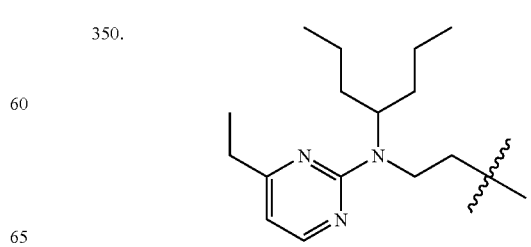

TABLE 1-continued
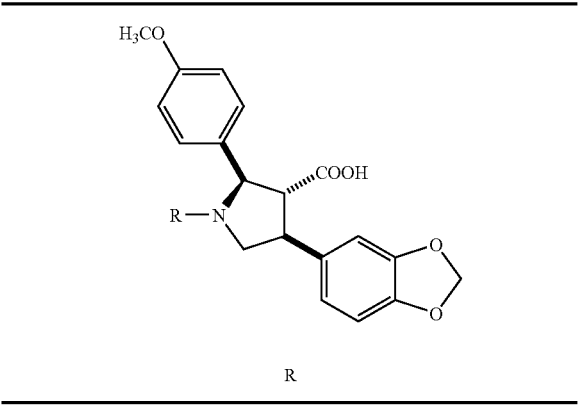
| | R |
|---|---|
| 351. | 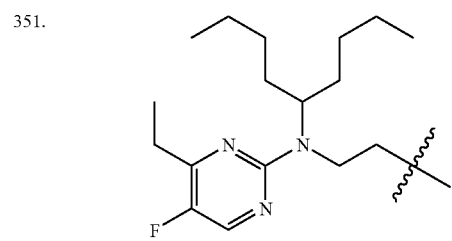 |
| 352. | 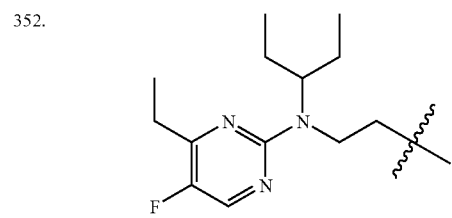 |
| 353. | 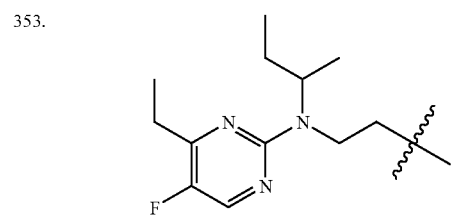 |
| 354. | 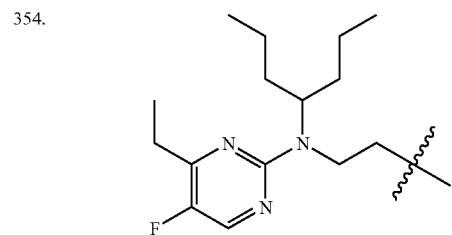 |
| 355. | 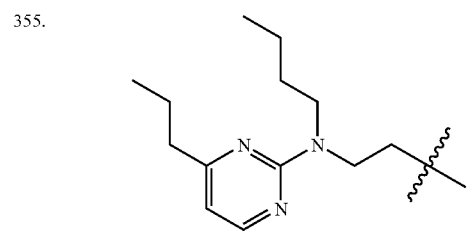 |
TABLE 1-continued
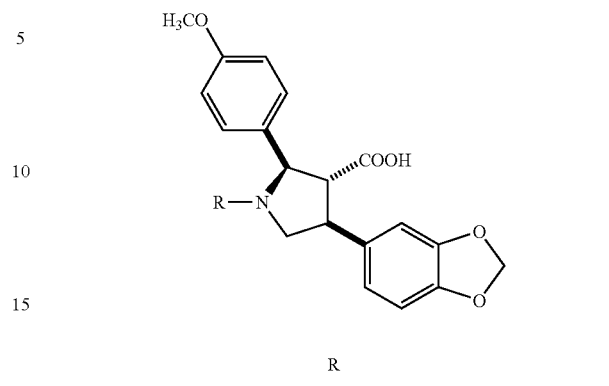
| | R |
|---|---|
| 356. | 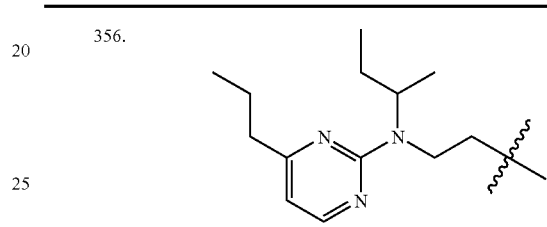 |
| 357. | 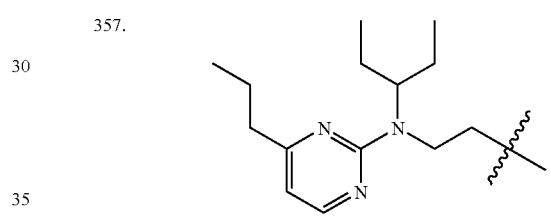 |
| 358. | 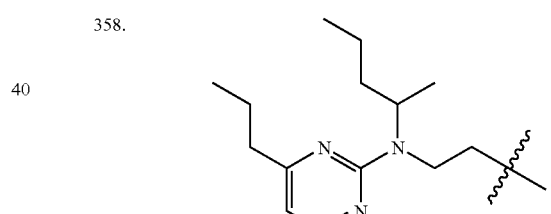 |
| 359. | 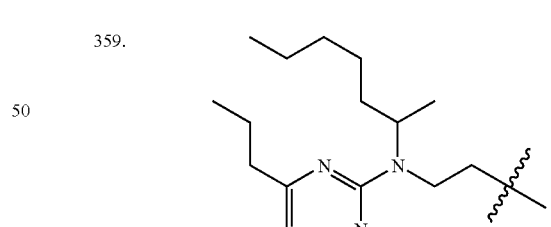 |
| 360. | 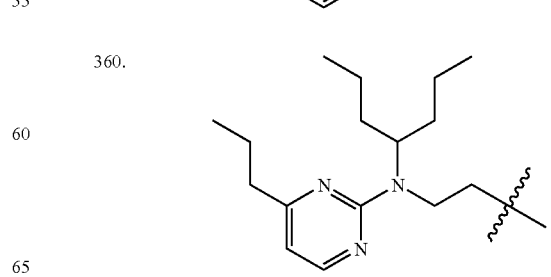 |

TABLE 1-continued
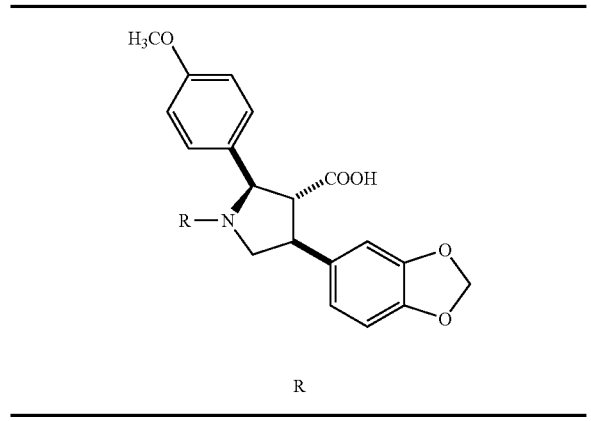
R
| 361. | 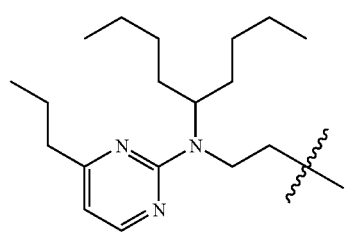 |
| --- | --- |
| 362. | 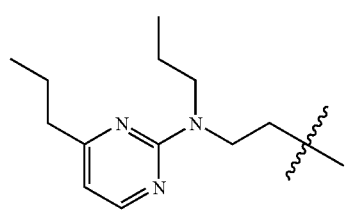 |
| 363. | 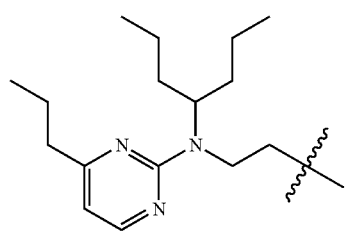 |
| 364. | 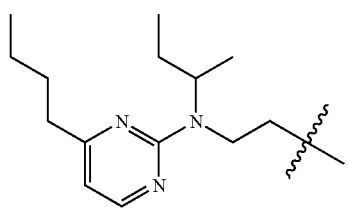 |
| 365. | 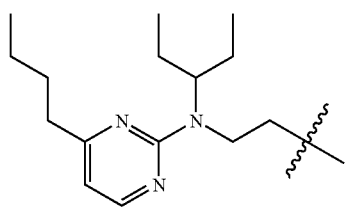 |
TABLE 1-continued
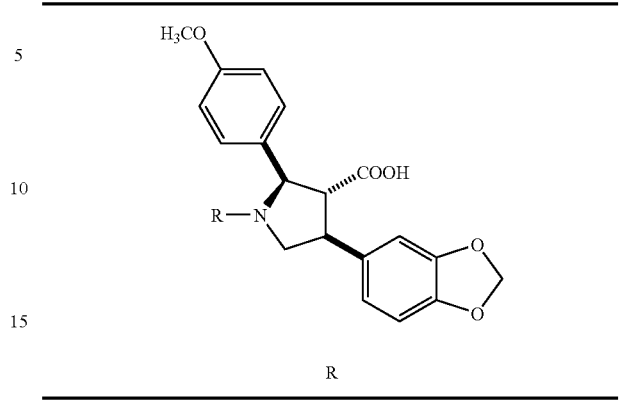
R
| 366. | 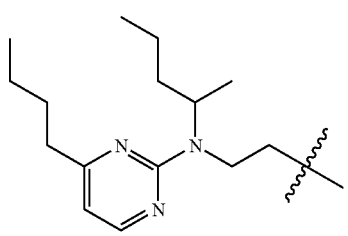 |
| --- | --- |
| 367. | 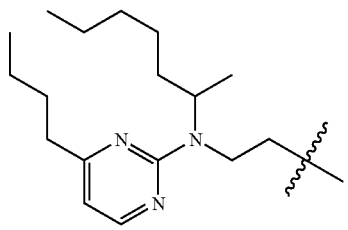 |
| 368. | 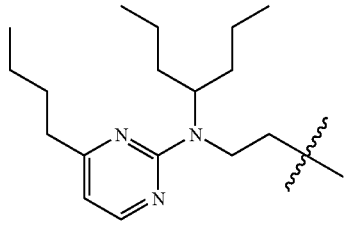 |
| 369. | 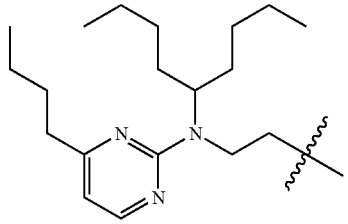 |
| 370. | 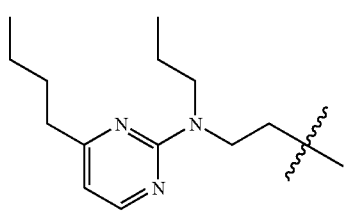 |

TABLE 1-continued
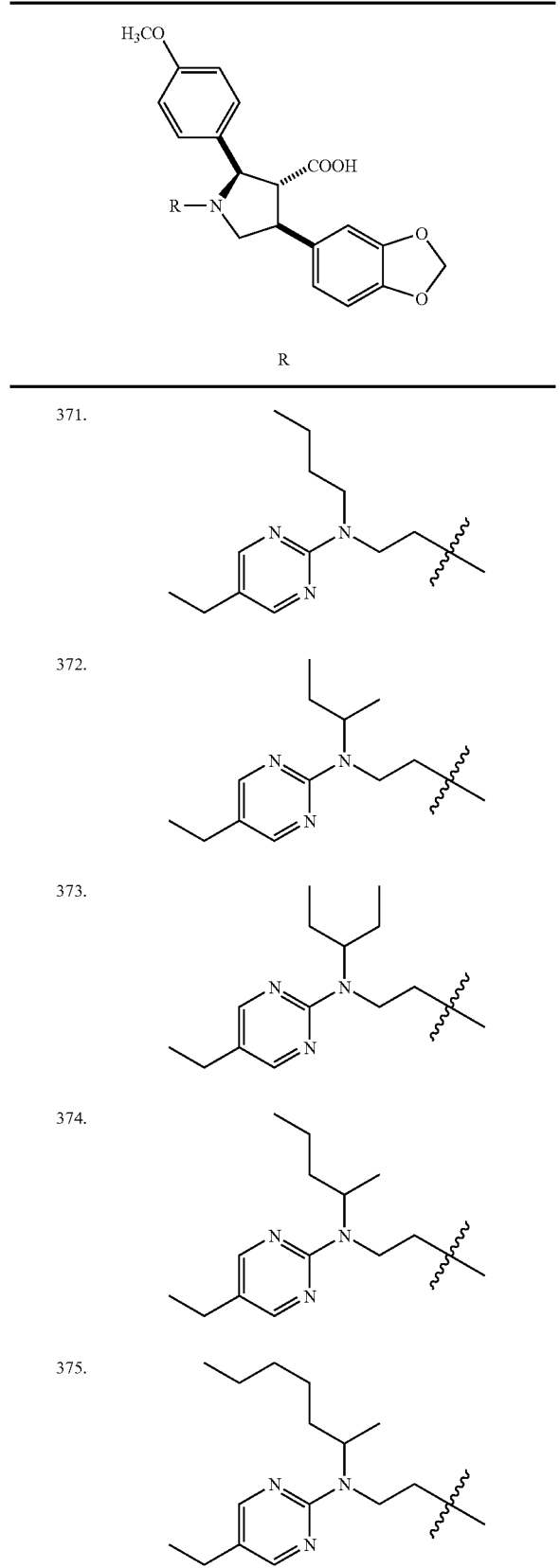
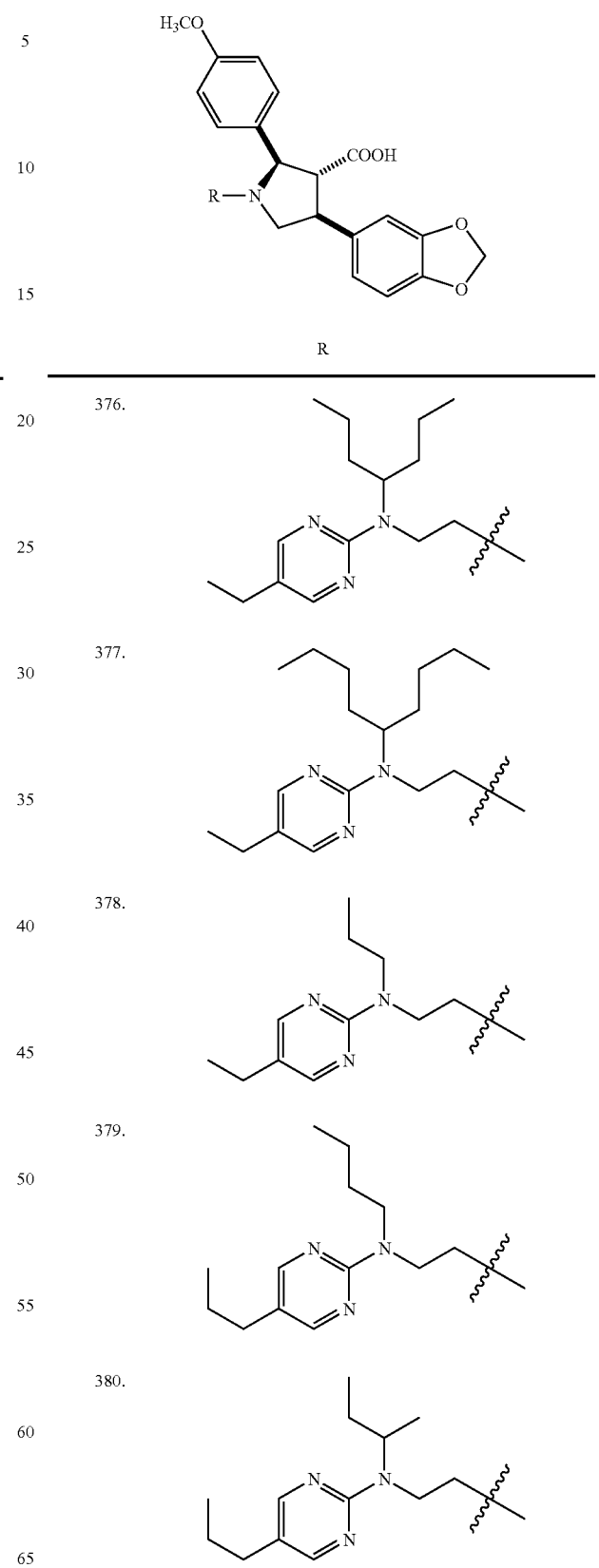

225
TABLE 1-continued
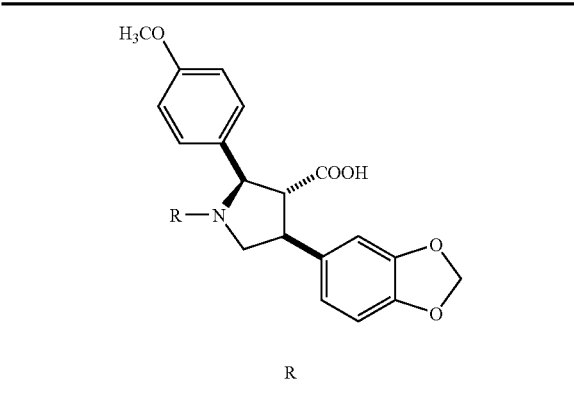
| | R |
|---|---|
| 381. | |
| 382. | |
| 383. | |
| 384. | |
| 385. | |
226
TABLE 1-continued
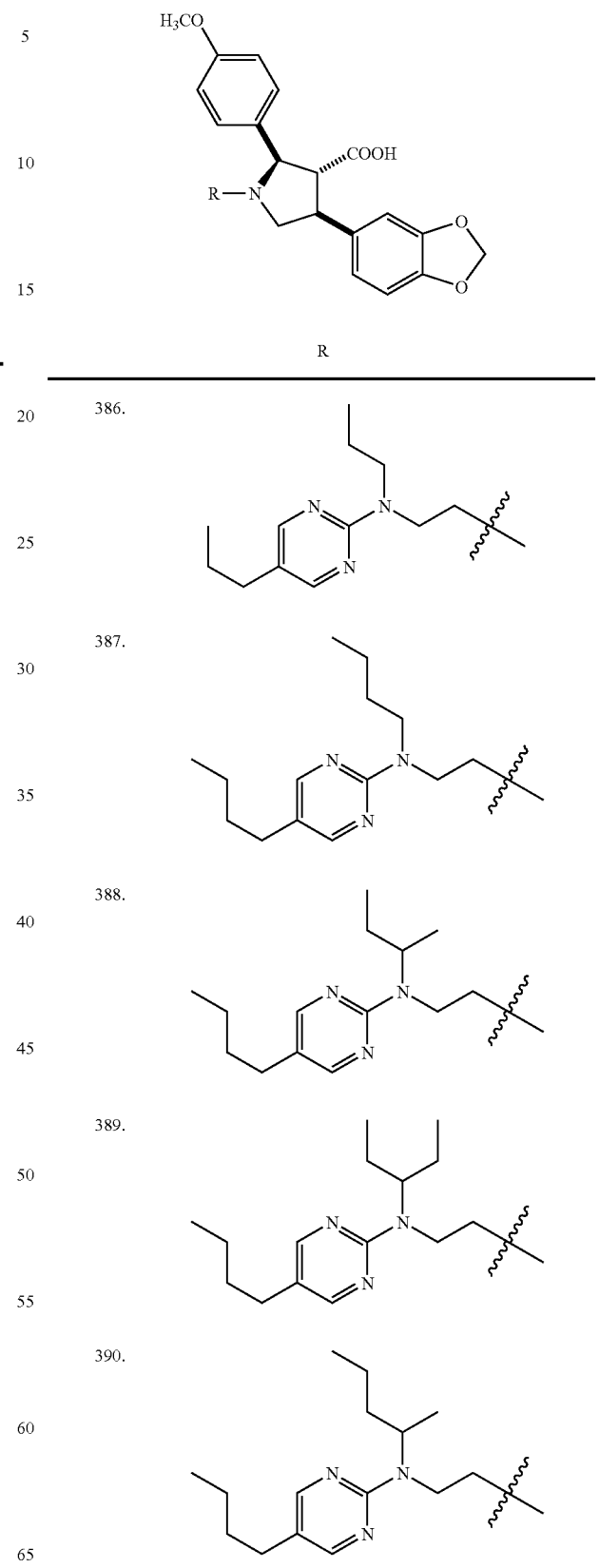
| | R |
|---|---|
| 386. | |
| 387. | |
| 388. | |
| 389. | |
| 390. | |

TABLE 1-continued
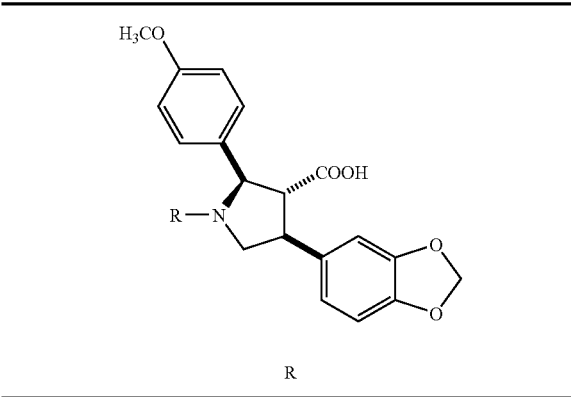
R
391. 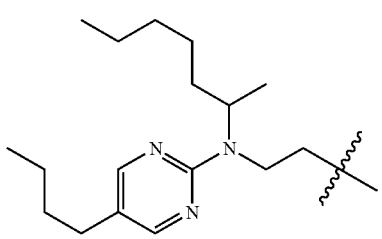
392. 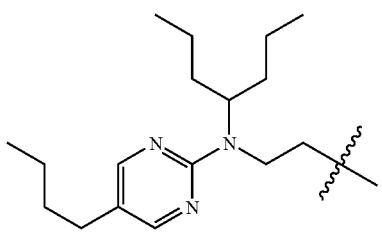
393. 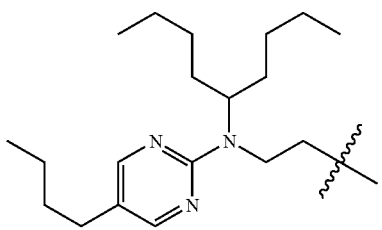
394. 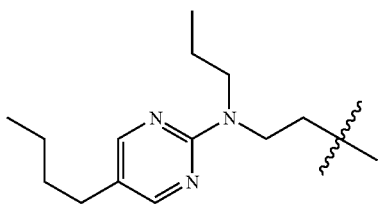
395. 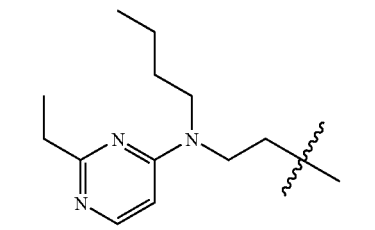
TABLE 1-continued
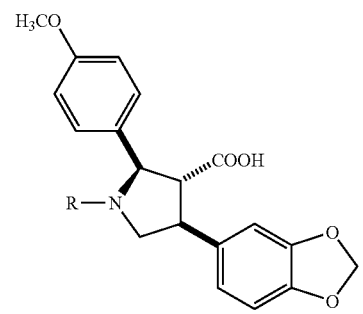
R
396. 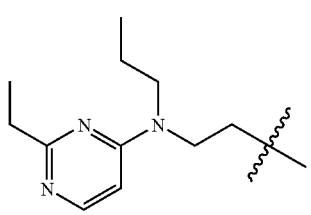
397. 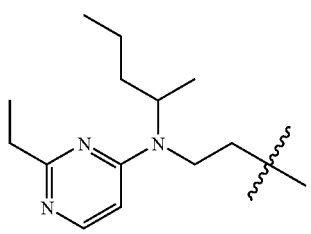
398. 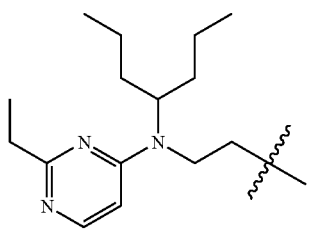
399. 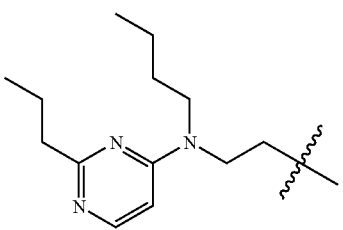
400. 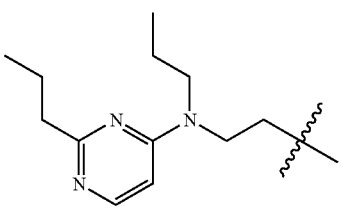

TABLE 1-continued
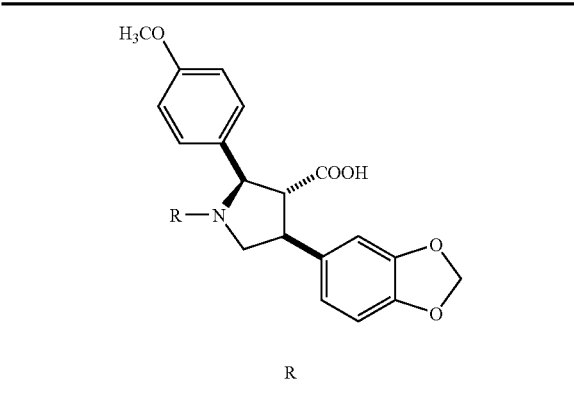
| | R |
|---|---|
| 401. | |
| 402. | |
| 403. | |
| 404. | |
| 405. | |
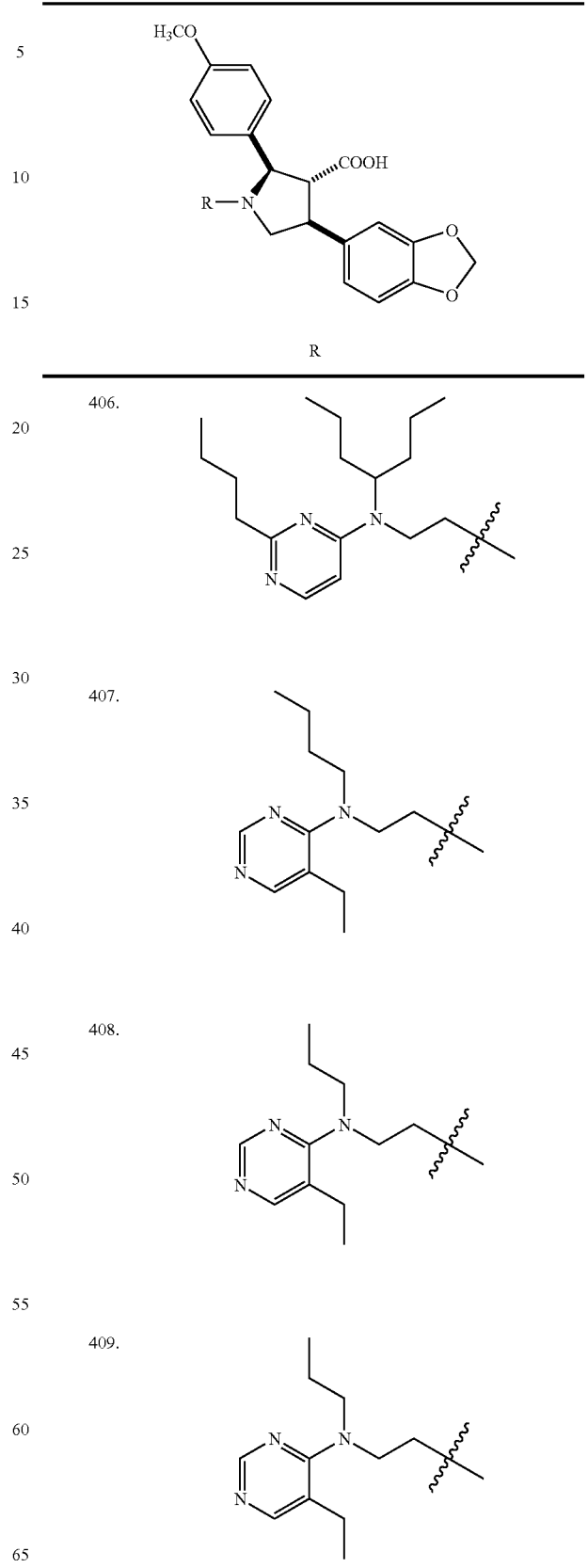

TABLE 1-continued
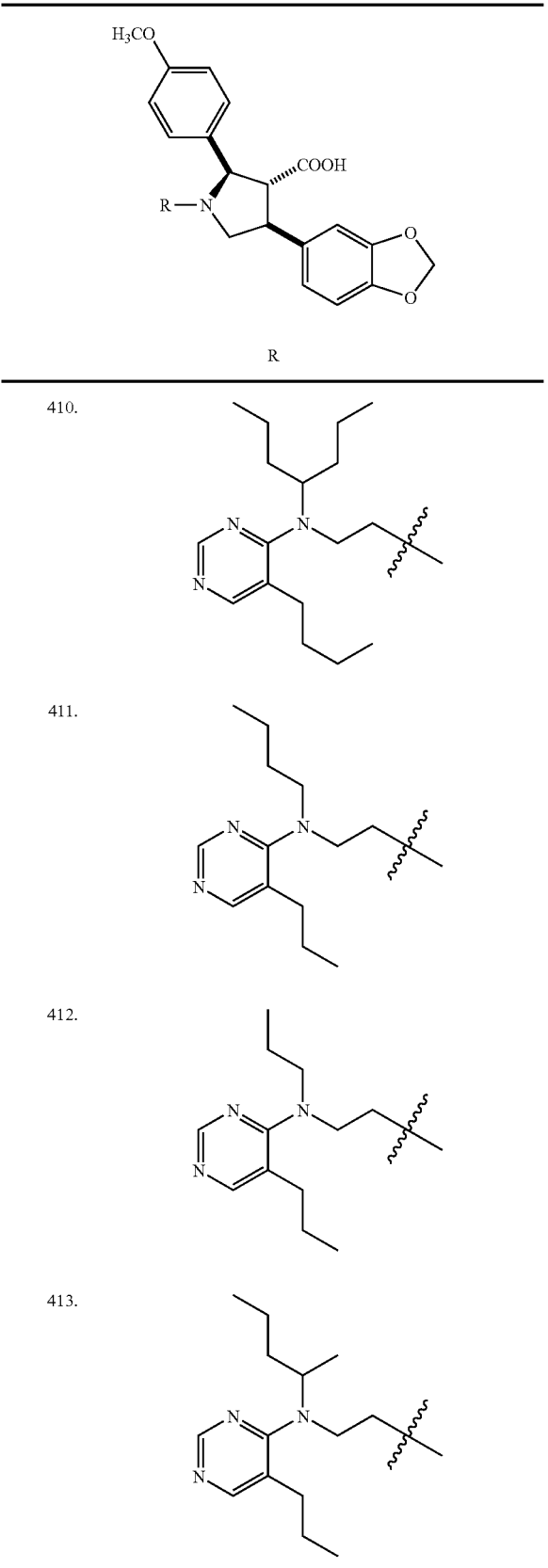
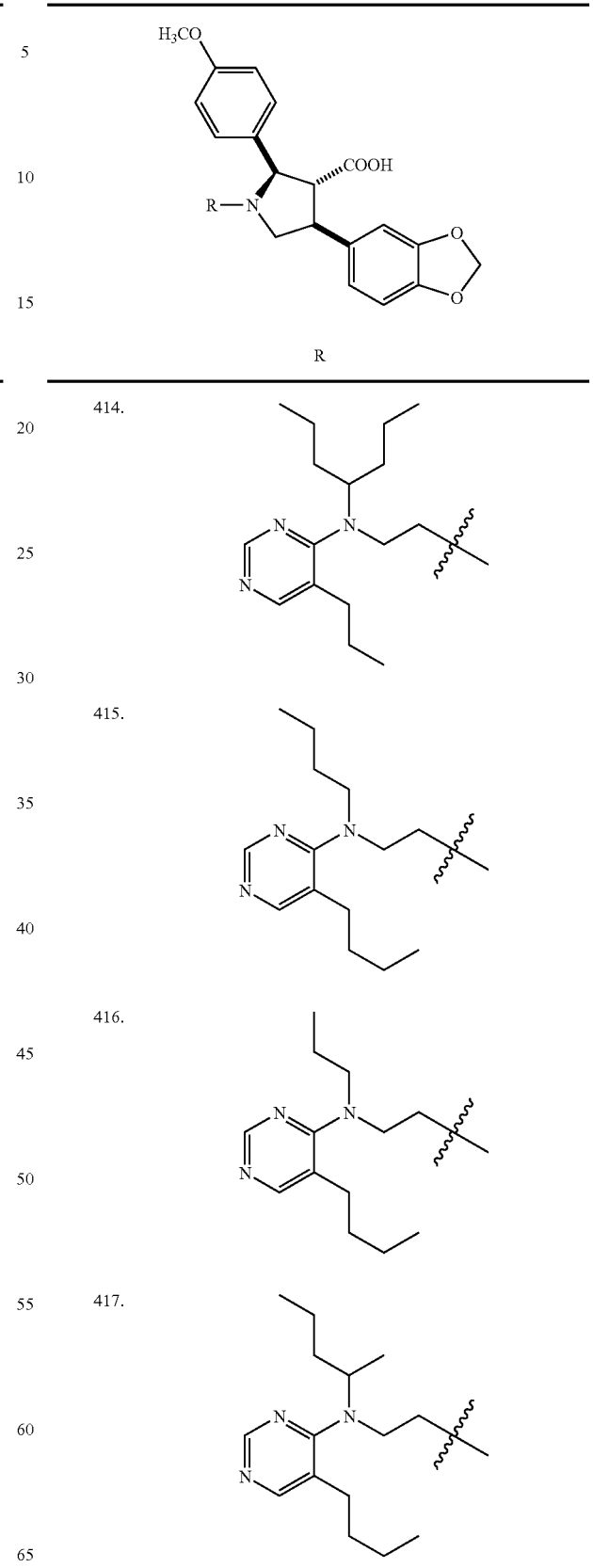

TABLE 1-continued
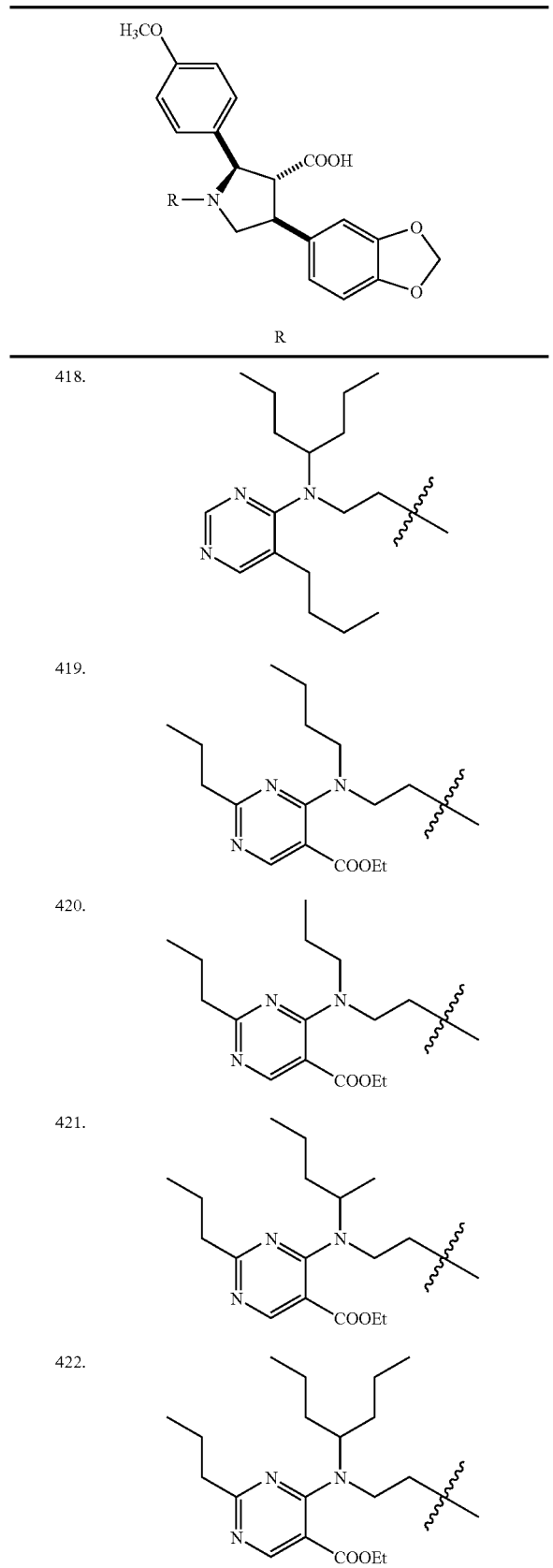
| 418. | |
| 419. | |
| 420. | |
| 421. | |
| 422. | |
TABLE 1-continued
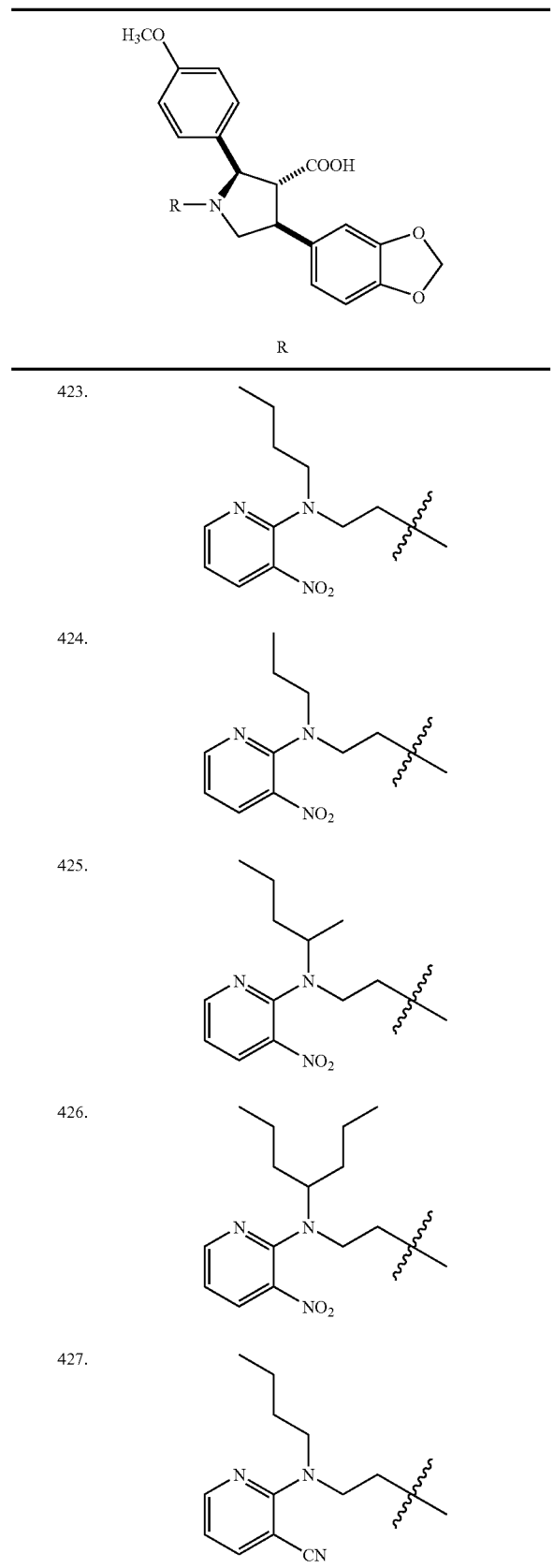
| 423. | |
| 424. | |
| 425. | |
| 426. | |
| 427. | |

TABLE 1-continued
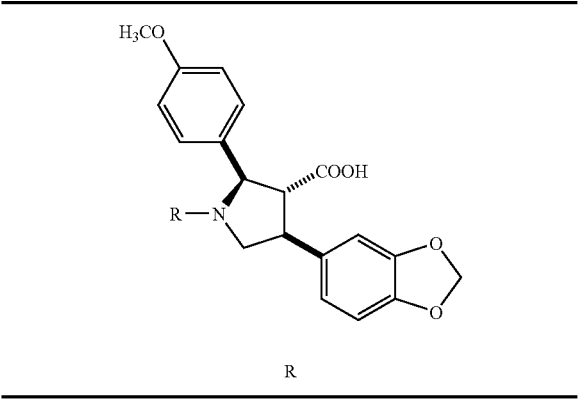
R
428. 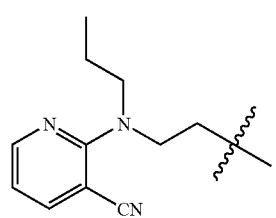
429. 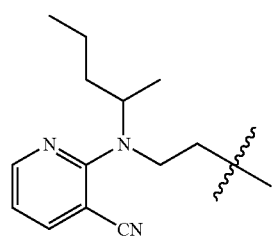
430. 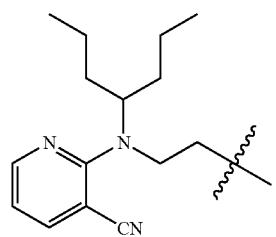
431. 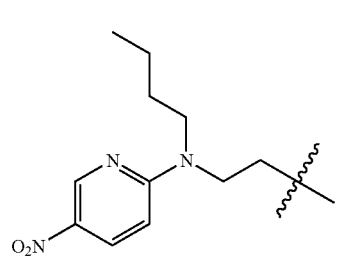
432. 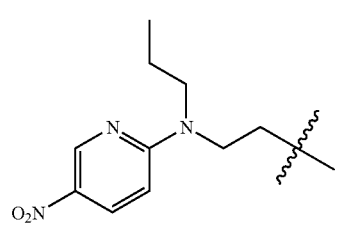
TABLE 1-continued
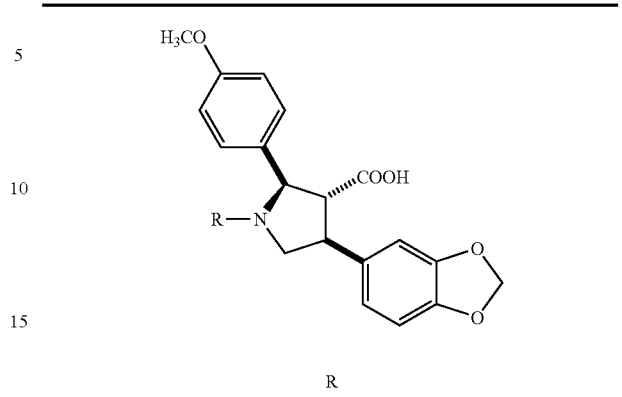
R
433. 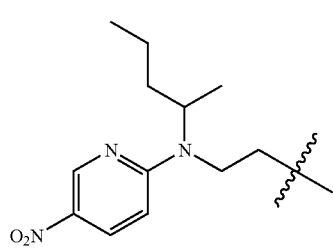
434. 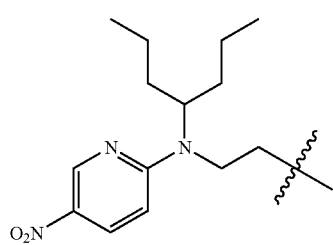
435. 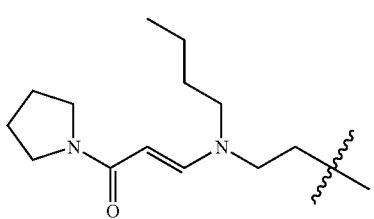
436. 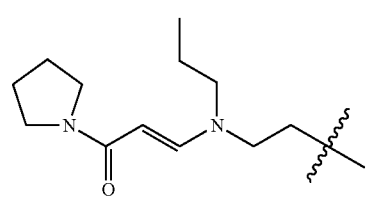
437. 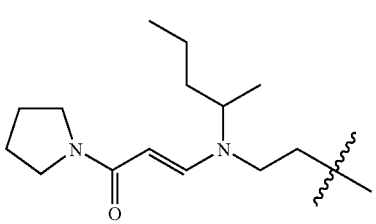

TABLE 1-continued
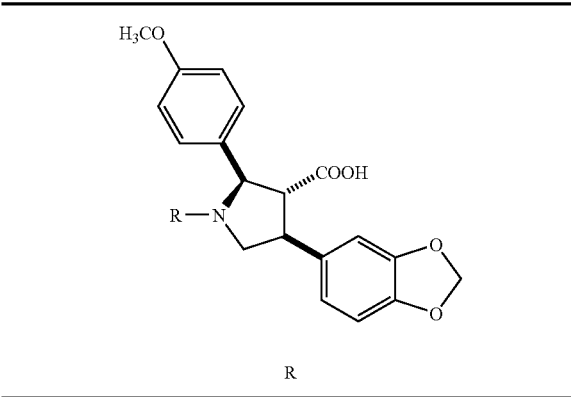
R
| | R |
|---|---|
| 438. | 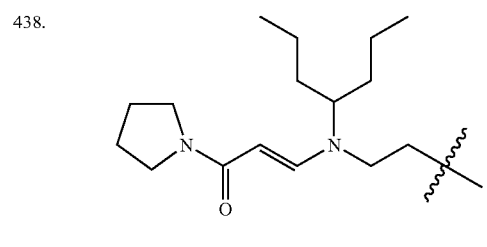 |
| 439. | 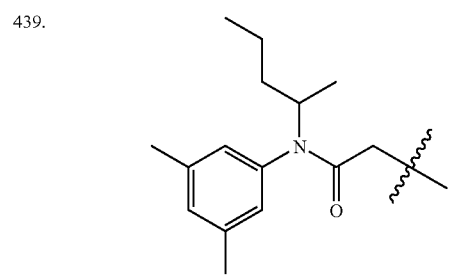 |
| 440. | 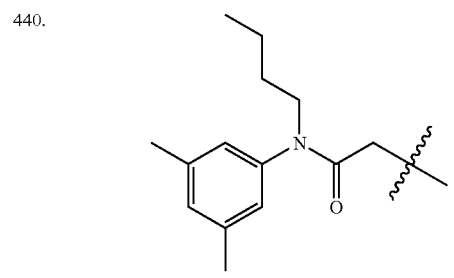 |
| 441. | 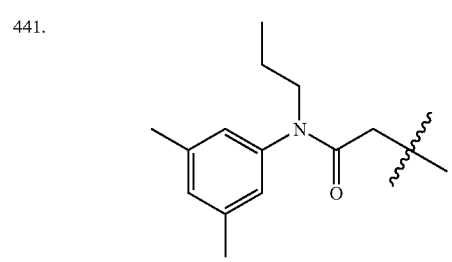 |
TABLE 1-continued
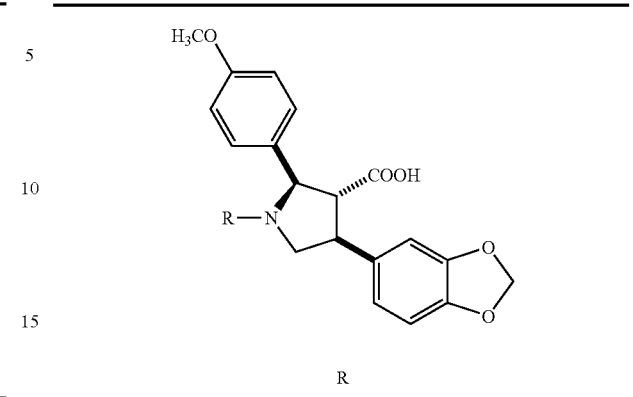
R
| | R |
|---|---|
| 442. | 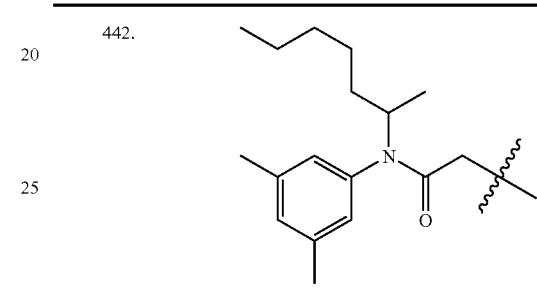 |
| 443. | 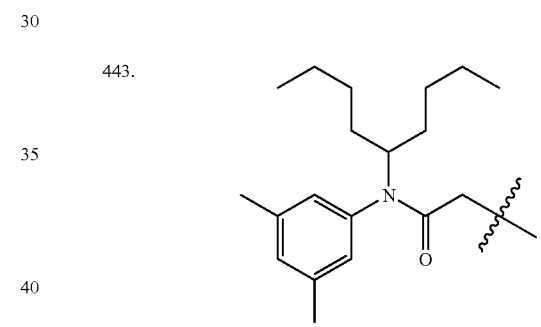 |
| 444. | 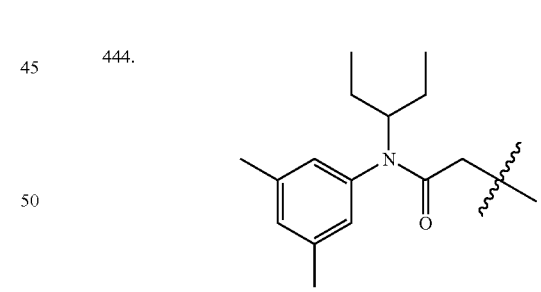 |
| 445. | 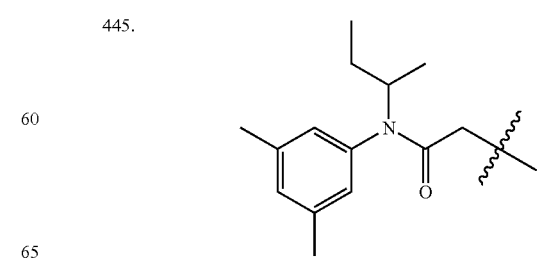 |

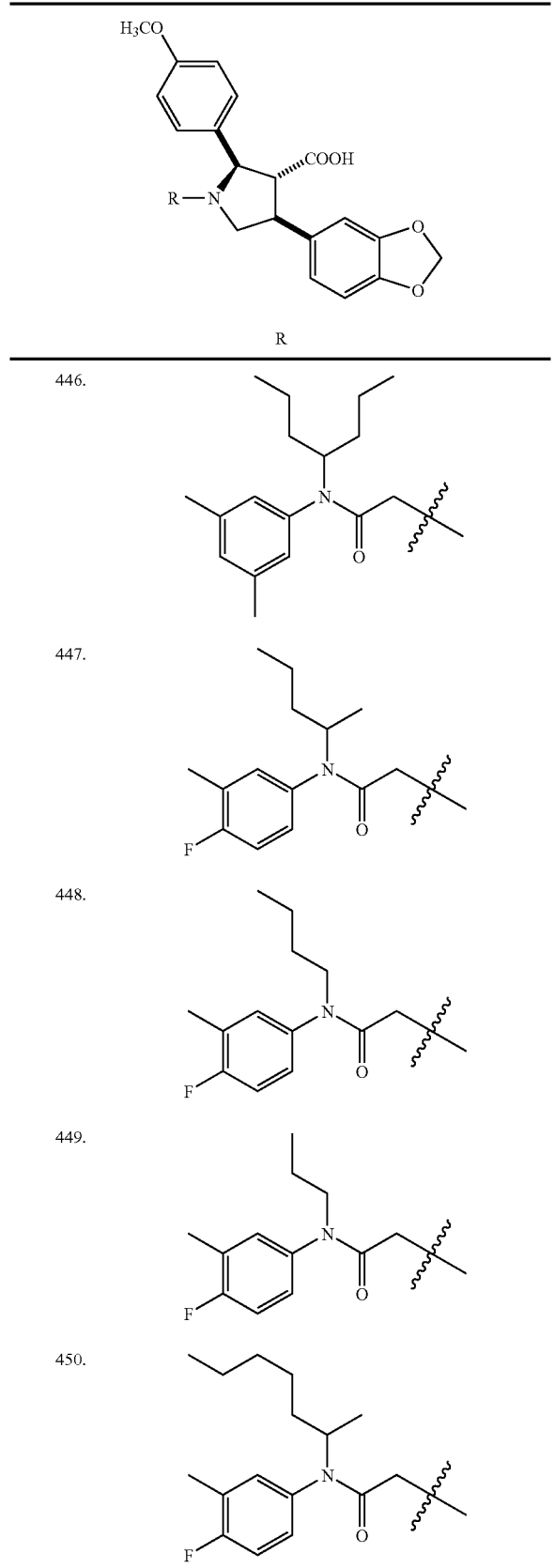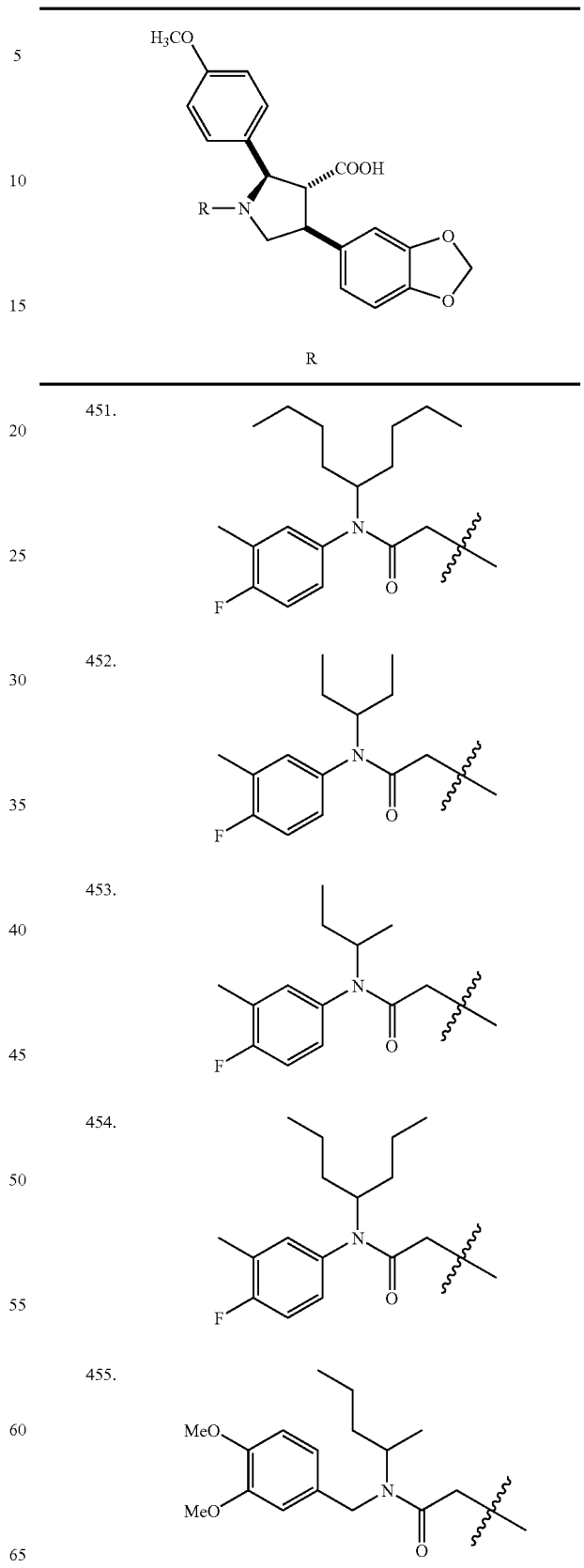

TABLE 1-continued
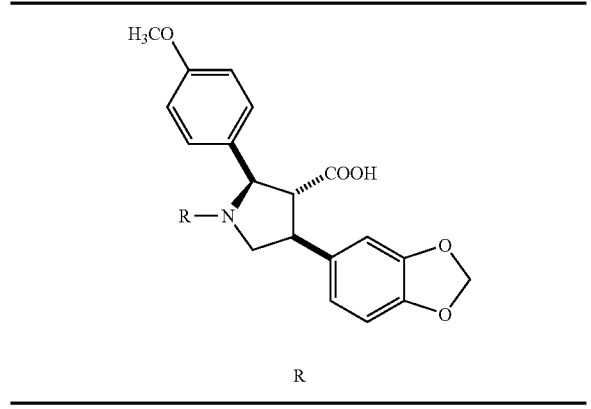
R
| | |
|---|---|
| 456. | 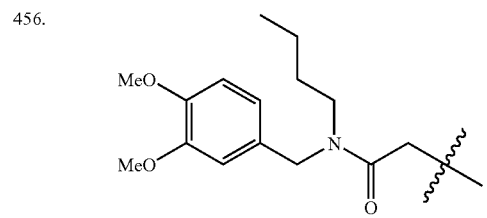 |
| 457. | 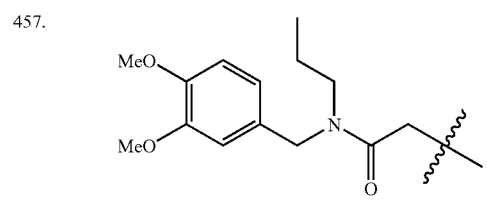 |
| 458. | 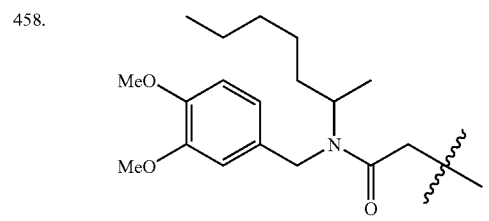 |
| 459. | 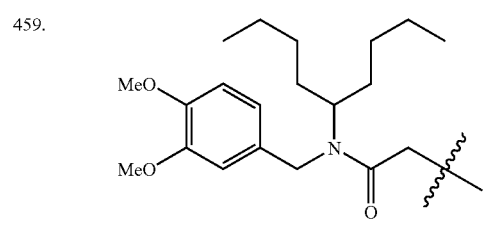 |
| 460. | 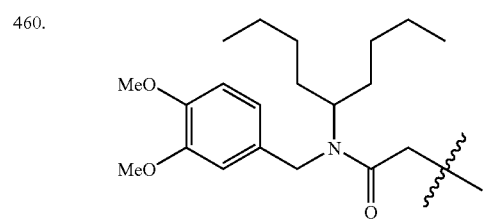 |
TABLE 1-continued
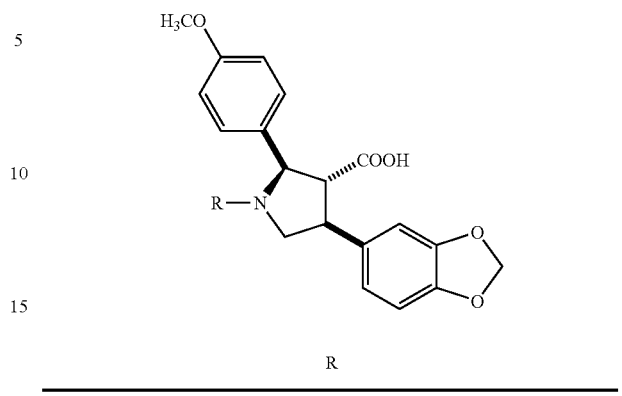
R
| | |
|---|---|
| 461. | 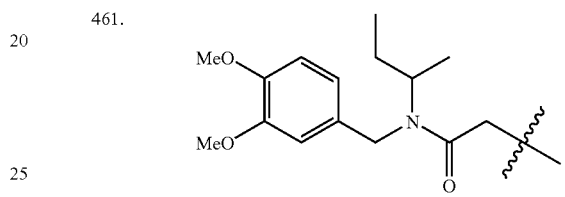 |
| 462. | 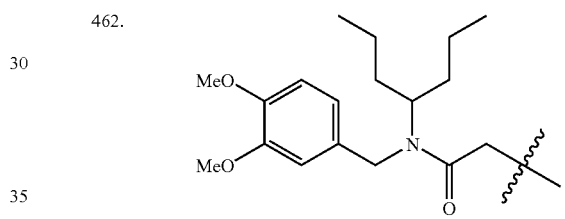 |
| 463. | 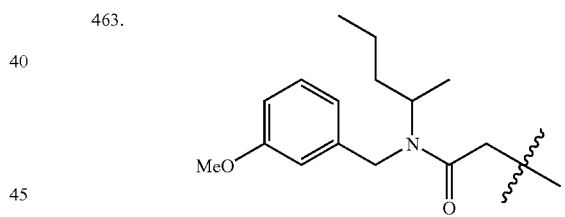 |
| 464. | 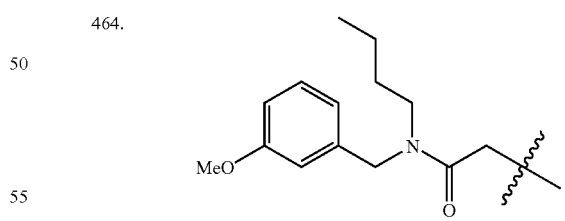 |
| 465. | 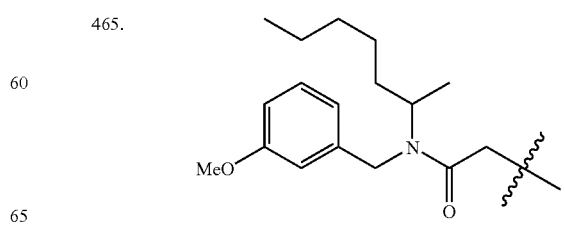 |

TABLE 1-continued
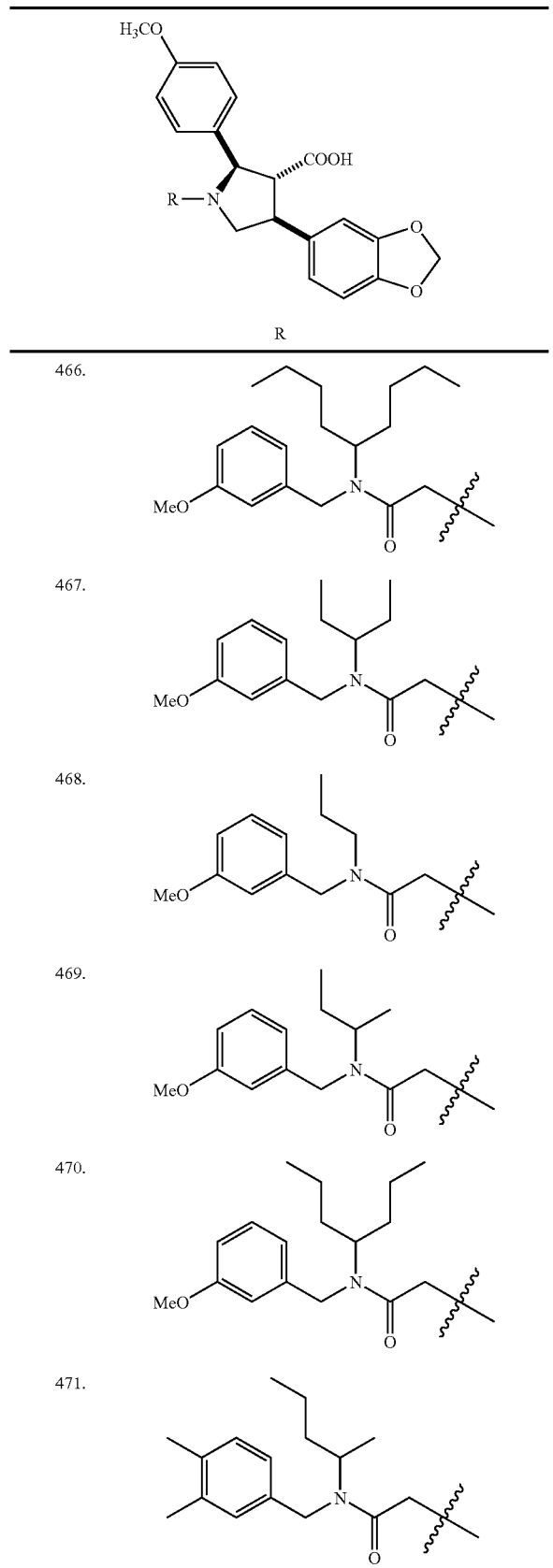
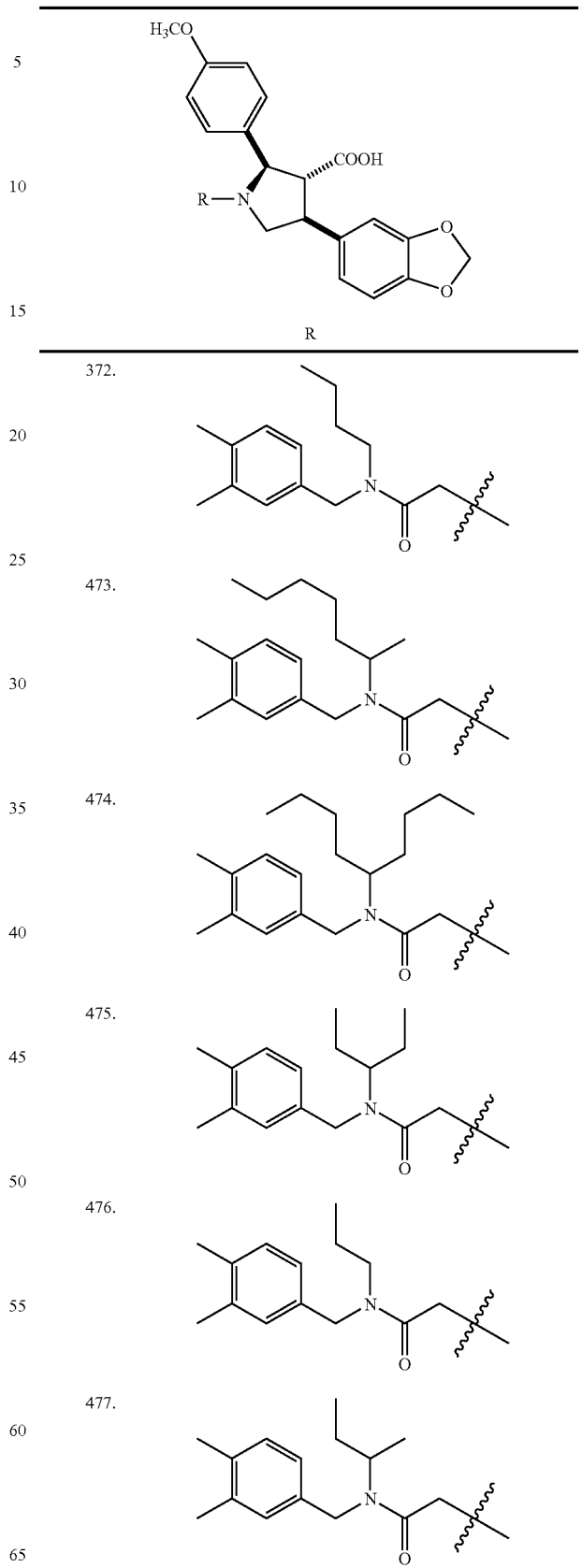

TABLE 1-continued

[Structure: pyrrolidine with 2-(4-methoxyphenyl), 3-COOH, 4-(benzo[1,3]dioxol-5-yl), N-R]

| # | R |
|---|---|
| 478 | N-(3,4-dimethylbenzyl)-N-(heptan-4-yl)acetamide linker |
| 479 | N-(3,4-dichlorobenzyl)-N-(pentan-2-yl)acetamide linker |
| 480 | N-(3,4-dichlorobenzyl)-N-butylacetamide linker |
| 481 | N-(3,4-dichlorobenzyl)-N-(heptan-2-yl)acetamide linker |
| 482 | N-(3,4-dichlorobenzyl)-N-(nonan-5-yl)acetamide linker |
| 483 | N-(3,4-dichlorobenzyl)-N-(pentan-3-yl)acetamide linker |
| 484 | N-(3,4-dichlorobenzyl)-N-propylacetamide linker |
| 485 | N-(3,4-dichlorobenzyl)-N-(butan-2-yl)acetamide linker |
| 486 | N-(3,4-dichlorobenzyl)-N-(heptan-4-yl)acetamide linker |
| 487 | N-(3,4-difluorobenzyl)-N-(pentan-2-yl)acetamide linker |
| 488 | N-(3,4-difluorobenzyl)-N-butylacetamide linker |

TABLE 1-continued
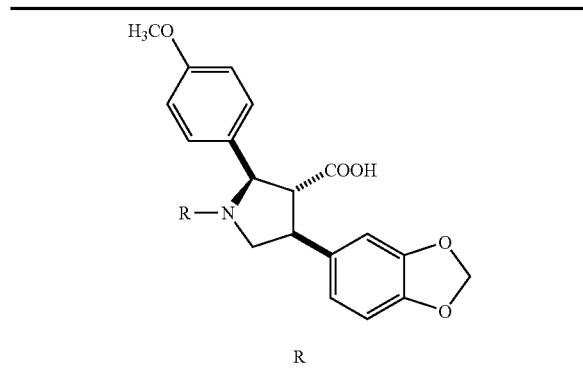
R
| | |
|---|---|
| 489. | 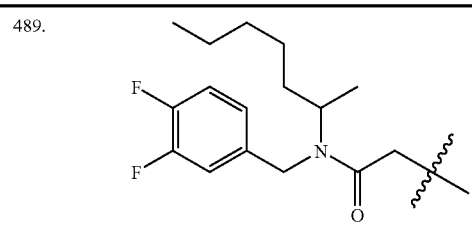 |
| 490. | 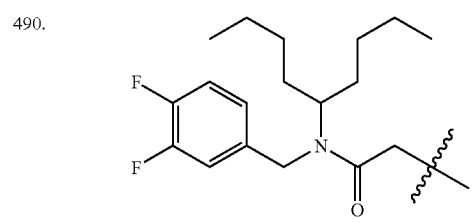 |
| 491. | 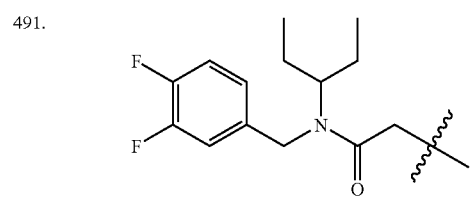 |
| 492. | 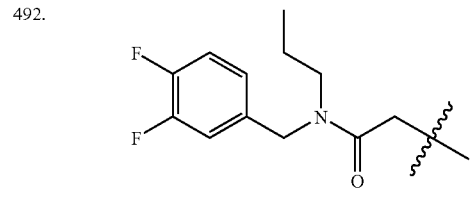 |
| 493. | 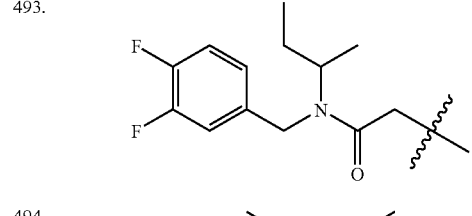 |
| 494. | |
TABLE 1-continued
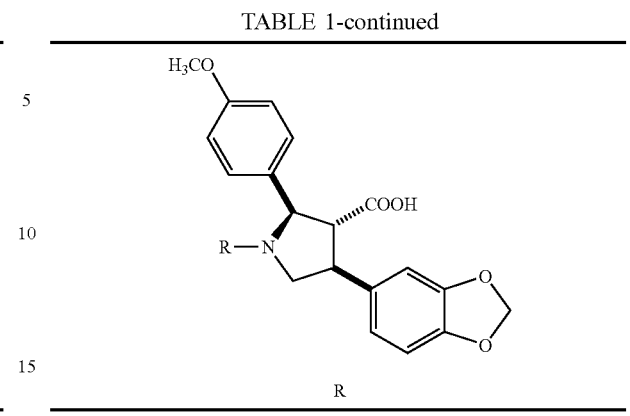
R
| | |
|---|---|
| 495. | 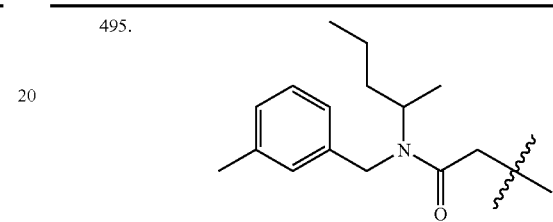 |
| 496. |  |
| 497. | 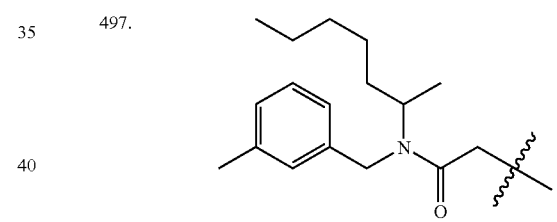 |
| 498. | 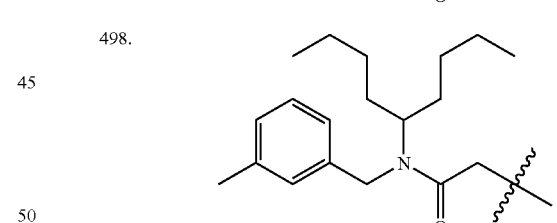 |
| 499. | 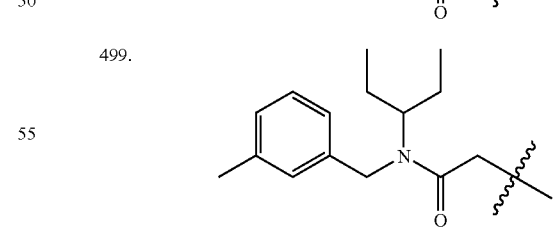 |
| 500. | |

TABLE 1-continued
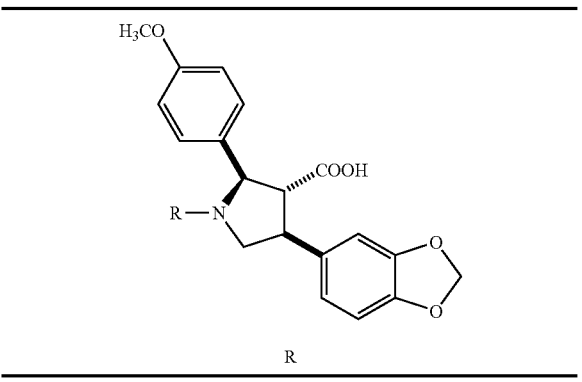
R
| | |
|---|---|
| 501. | 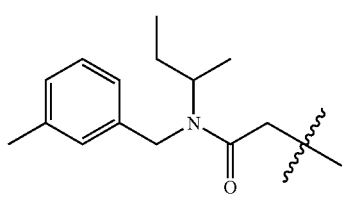 |
| 502. | 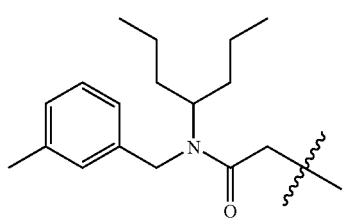 |
| 503. | 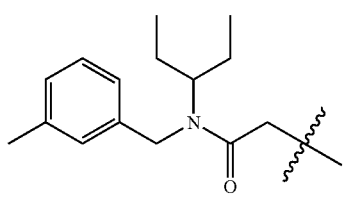 |
| 504. | 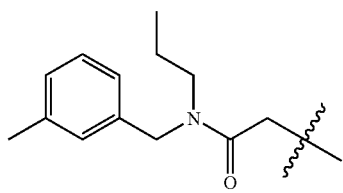 |
| 505. | 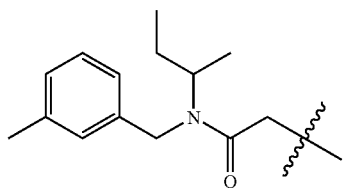 |
| 506. | 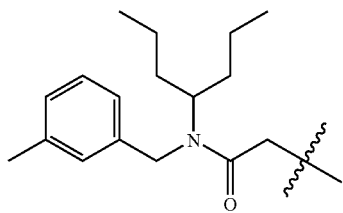 |
TABLE 1-continued
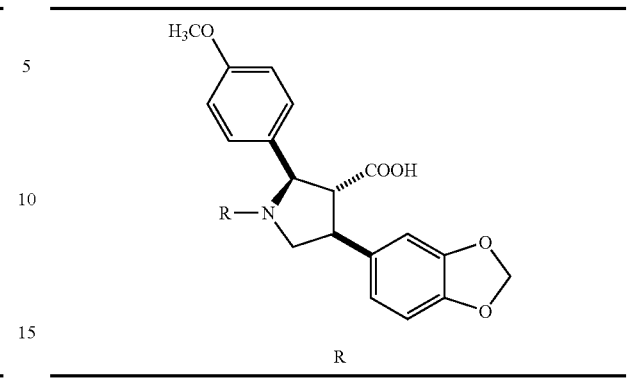
R
| | |
|---|---|
| 507. | 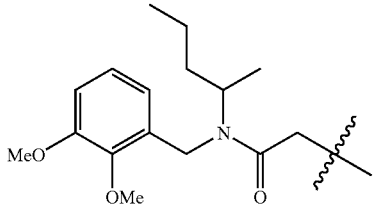 |
| 508. | 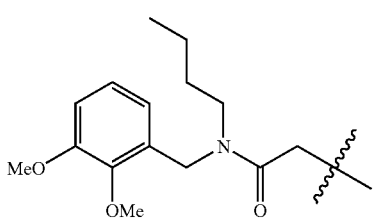 |
| 509. | 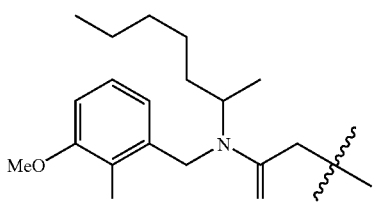 |
| 510. | 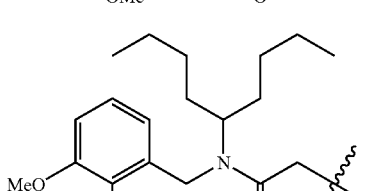 |
| 511. | 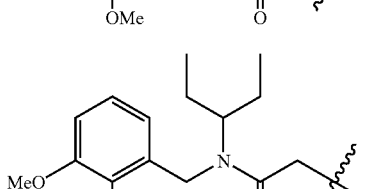 |
| 512. | |

TABLE 1-continued
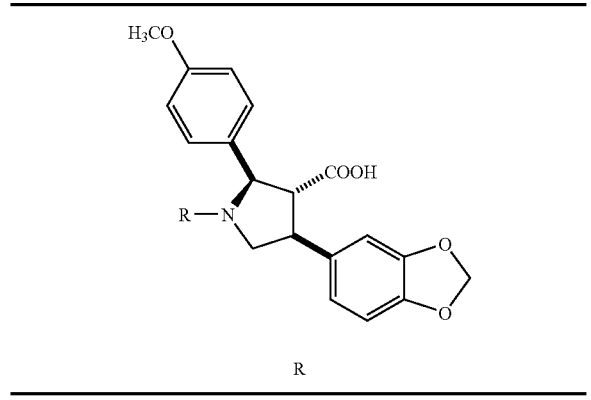
R
| | |
|---|---|
| 513. | 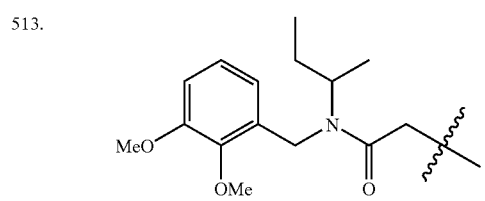 |
| 514. | 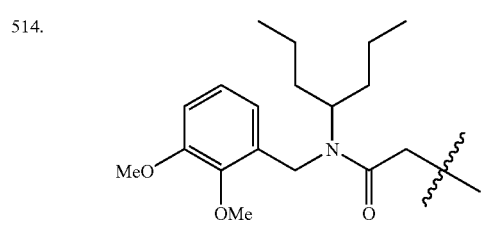 |
| 515. | 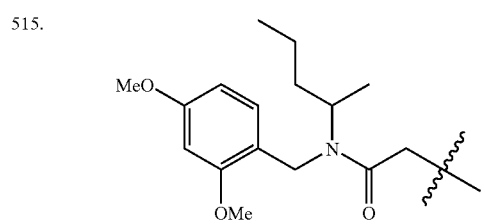 |
| 516. | 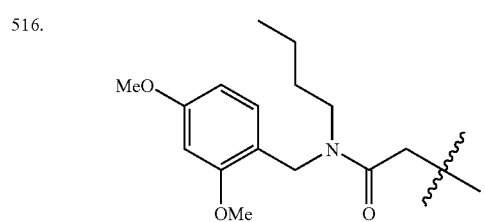 |
| 517. | 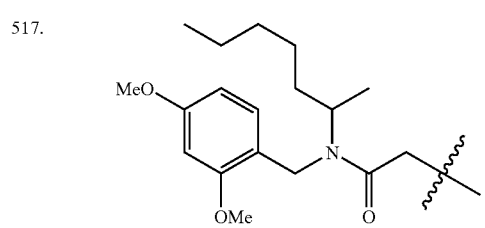 |
TABLE 1-continued
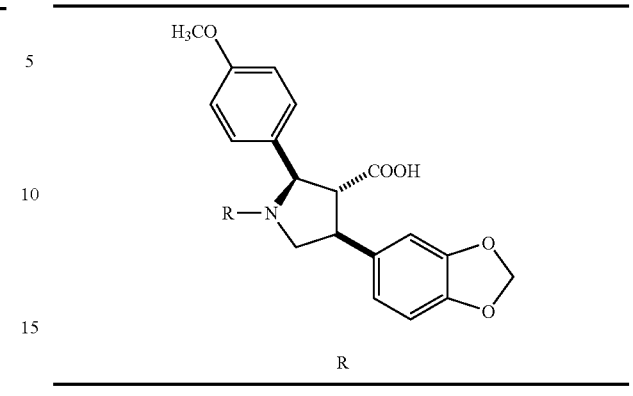
R
| | |
|---|---|
| 518. | 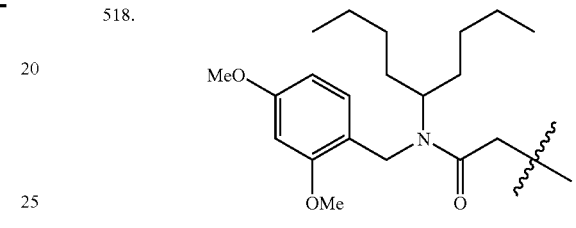 |
| 519. | 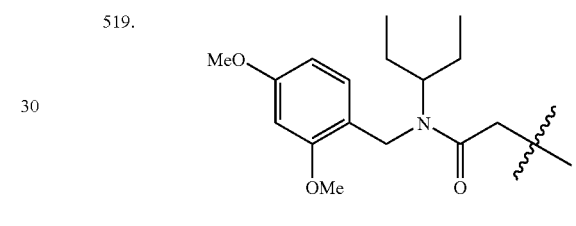 |
| 520. | 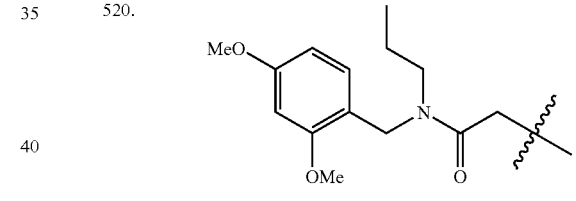 |
| 521. | 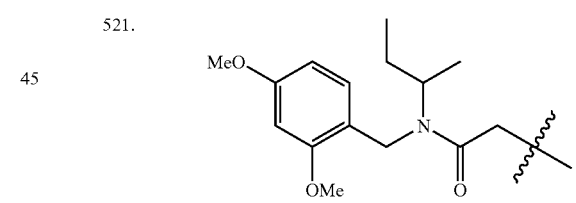 |
| 522. | 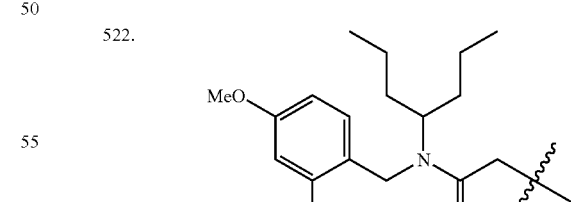 |
| 523. | 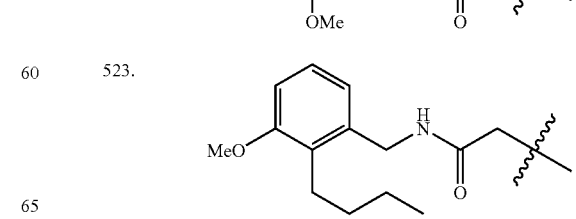 |

TABLE 1-continued
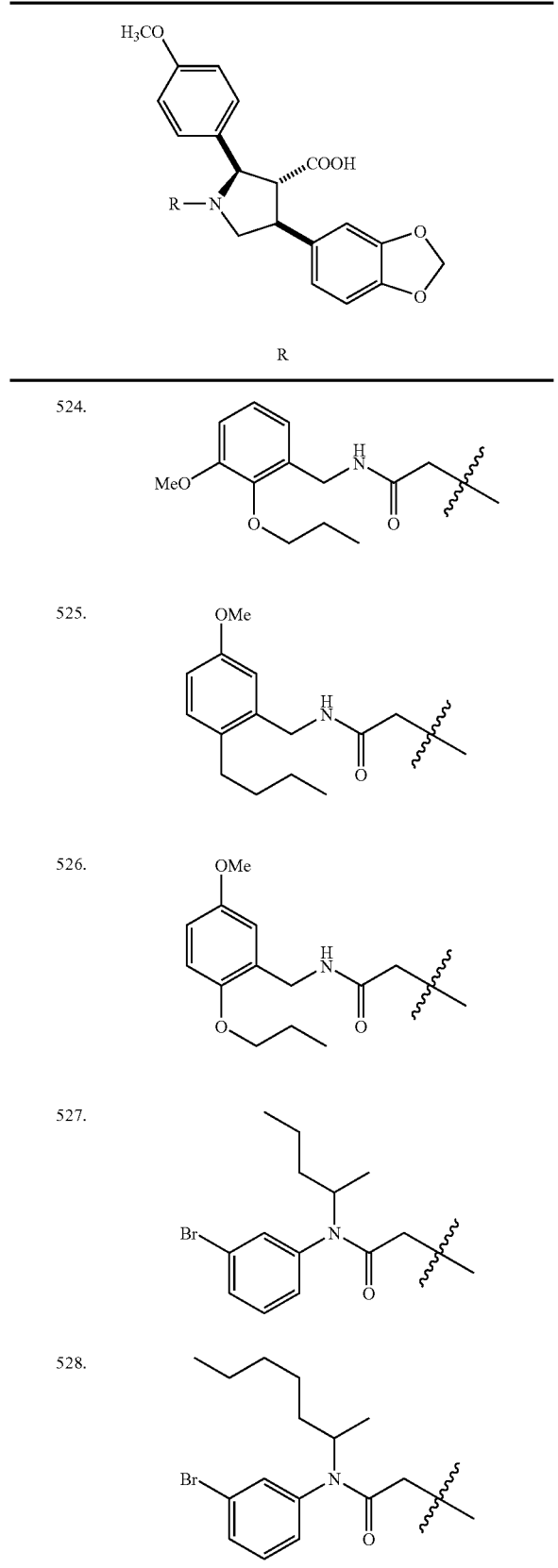
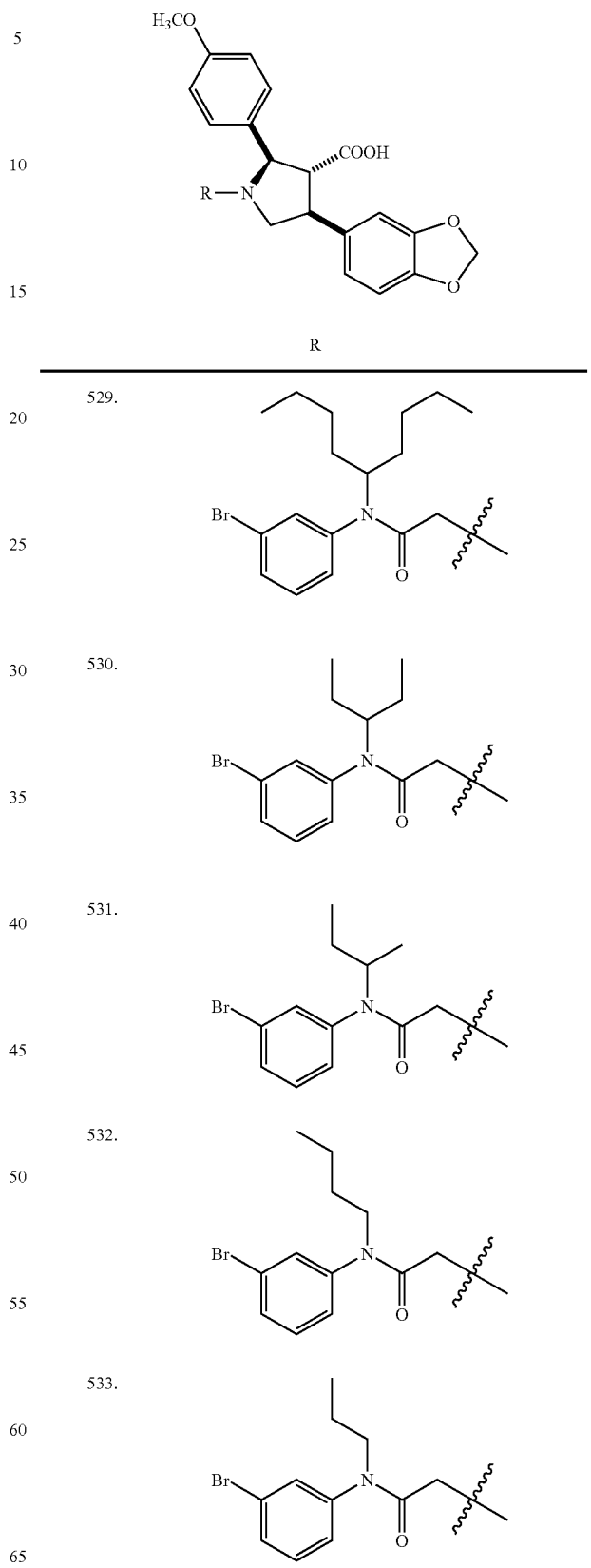

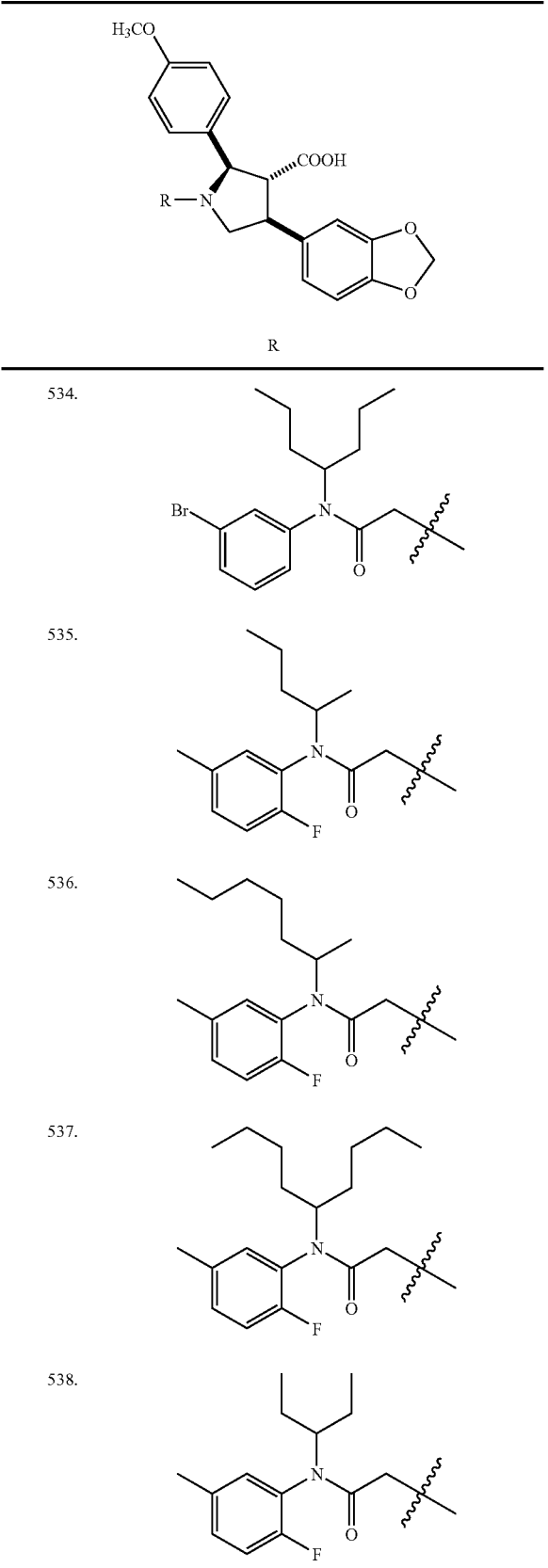
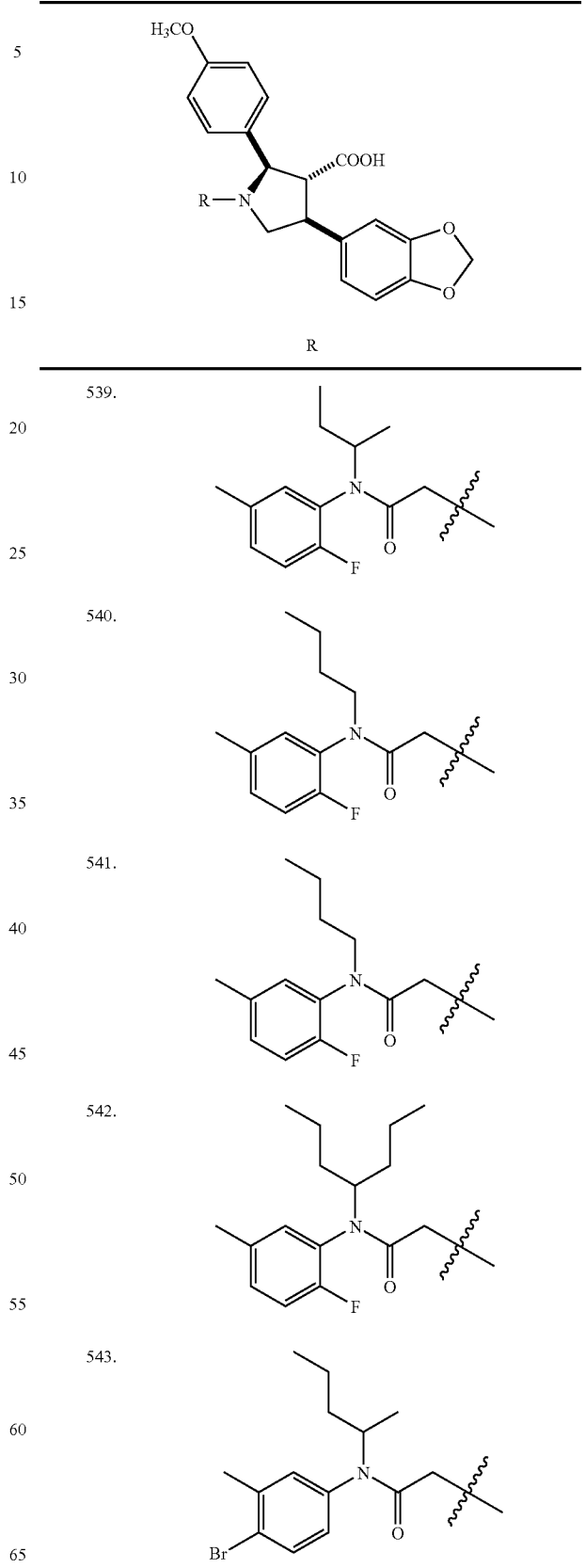

TABLE 1-continued
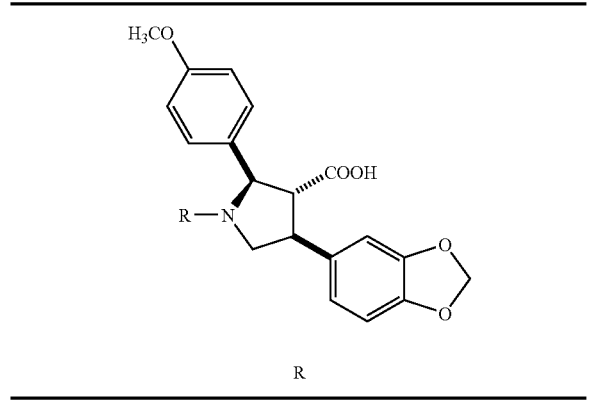
R
| 544. | 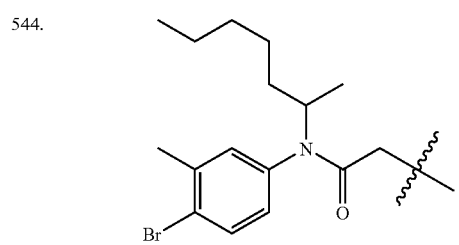 |
| --- | --- |
| 545. | 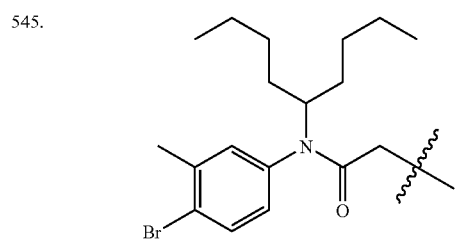 |
| 546. | 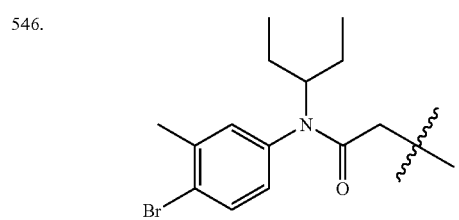 |
| 547. | 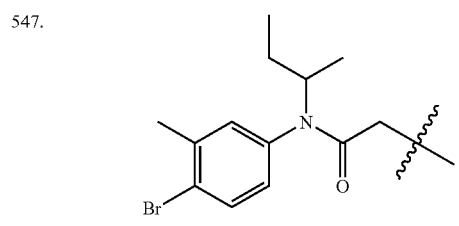 |
| 548. | 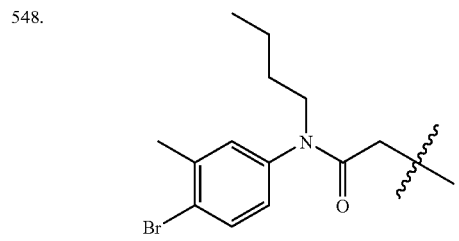 |
TABLE 1-continued
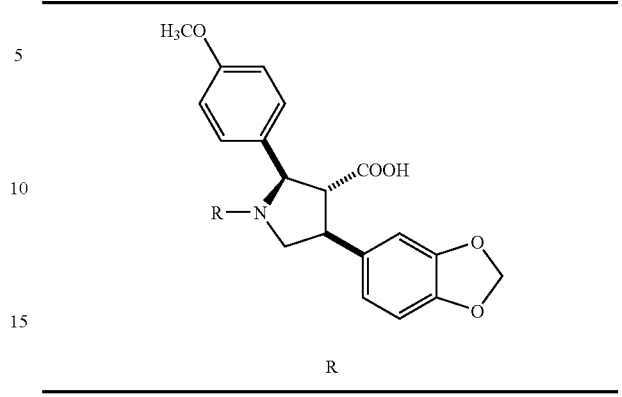
R
| 549. |  |
| --- | --- |
| 550. |  |
| 551. |  |
| 552. | 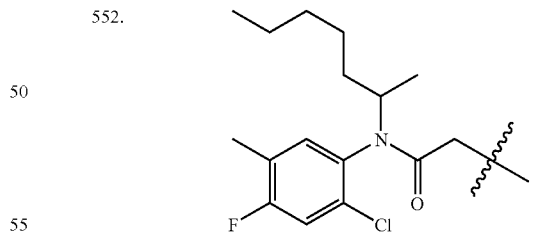 |
| 553. | 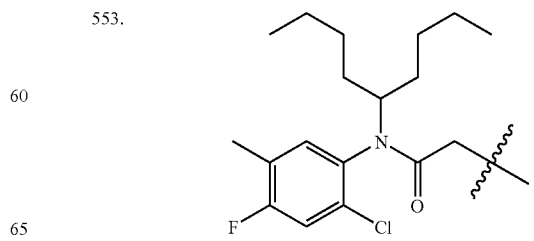 |

TABLE 1-continued (Structure shown with 4-methoxyphenyl, COOH, benzodioxole substituents on pyrrolidine with R on N)

| # | R |
|---|---|
| 554. | N-(2-chloro-4-fluoro-5-methylphenyl)-N-(pentan-3-yl)acetamide linker |
| 555. | N-(2-chloro-4-fluoro-5-methylphenyl)-N-(sec-butyl)acetamide linker |
| 556. | N-(2-chloro-4-fluoro-5-methylphenyl)-N-butylacetamide linker |
| 557. | N-(2-chloro-4-fluoro-5-methylphenyl)-N-propylacetamide linker |
| 558. | N-(2-chloro-4-fluoro-5-methylphenyl)-N-(heptan-4-yl)acetamide linker |
| 559. | N-(3-bromo-4-fluorophenyl)-N-(pentan-2-yl)acetamide linker |
| 560. | N-(3-bromo-4-fluorophenyl)-N-(heptan-2-yl)acetamide linker |
| 561. | N-(3-bromo-4-fluorophenyl)-N-(nonan-5-yl)acetamide linker |
| 562. | N-(3-bromo-4-fluorophenyl)-N-(pentan-3-yl)acetamide linker |
| 563. | N-(3-bromo-4-fluorophenyl)-N-(sec-butyl)acetamide linker |

TABLE 1-continued
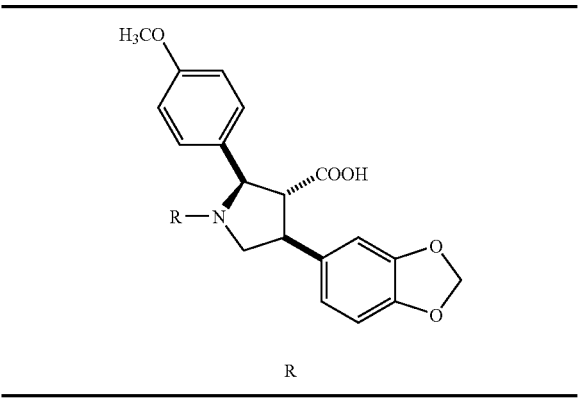
| | R |
|---|---|
| 564. | 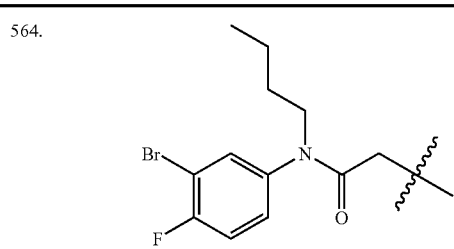 |
| 565. | 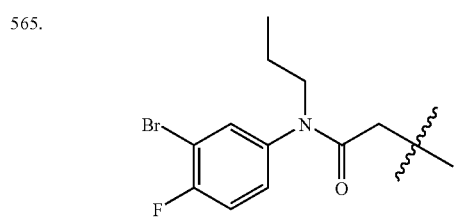 |
| 566. | 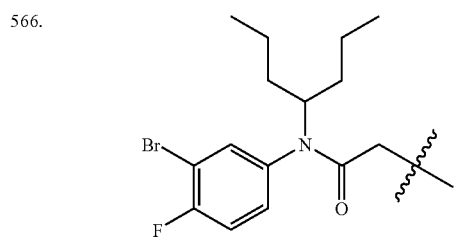 |
| 567. | 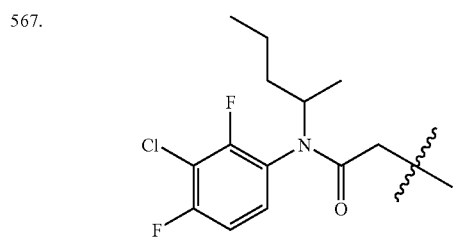 |
| 568. | 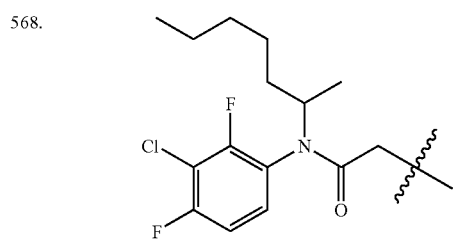 |
TABLE 1-continued
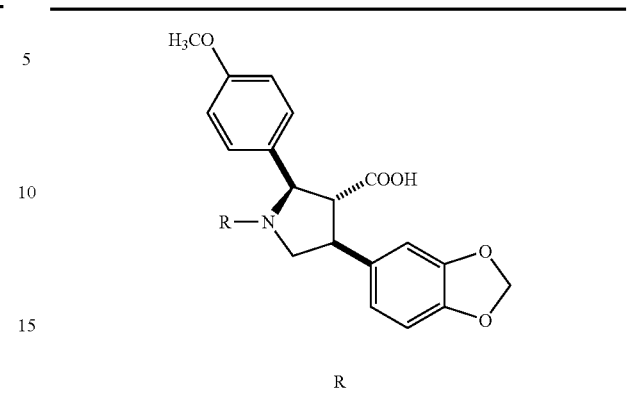
| | R |
|---|---|
| 569. | 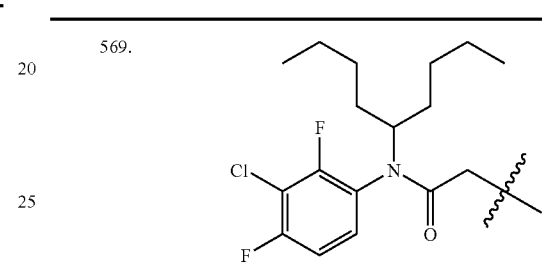 |
| 570. | 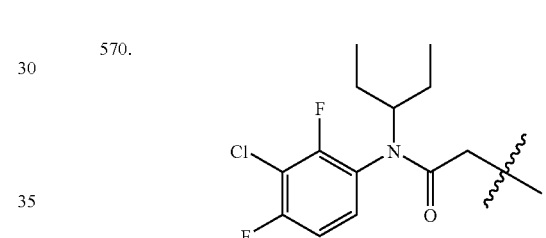 |
| 571. |  |
| 572. |  |
| 573. |  |

TABLE 1-continued
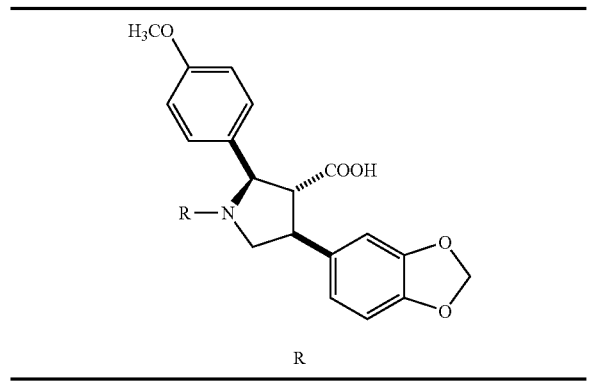
| | R |
|---|---|
| 574. | 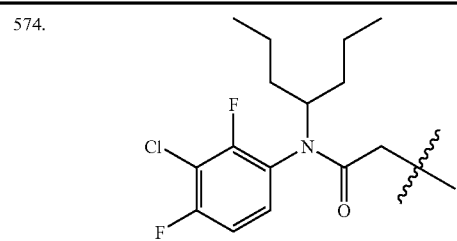 |
| 575. | 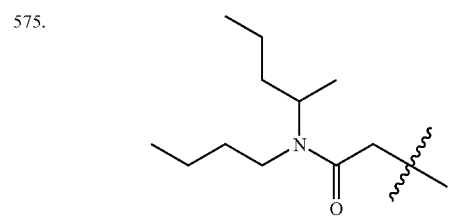 |
| 576. | 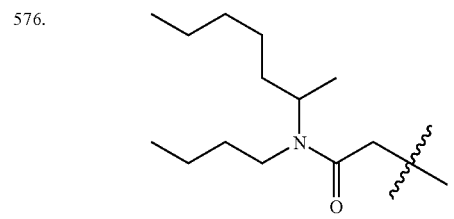 |
| 577. | 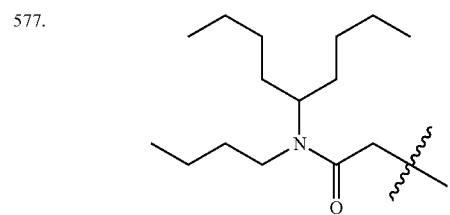 |
| 578. | 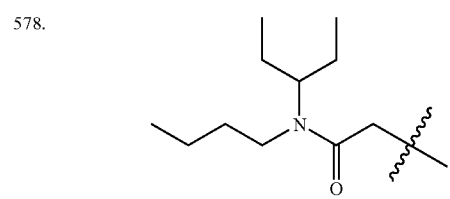 |
TABLE 1-continued
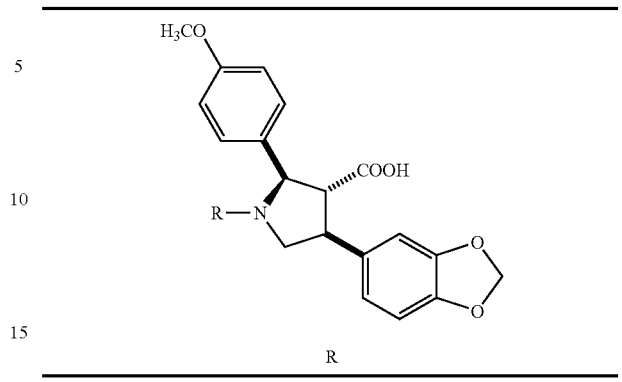
| | R |
|---|---|
| 579. | 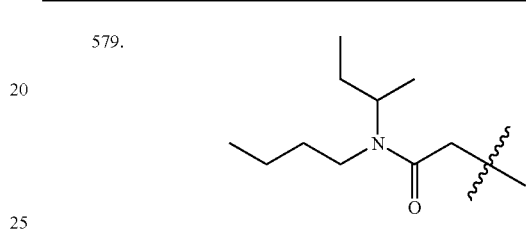 |
| 580. | 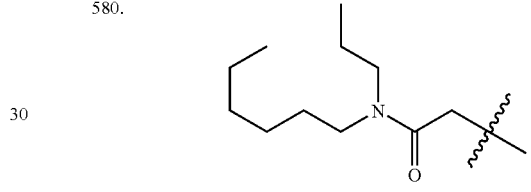 |
| 581. | 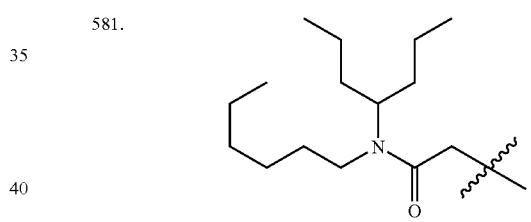 |
| 582. | 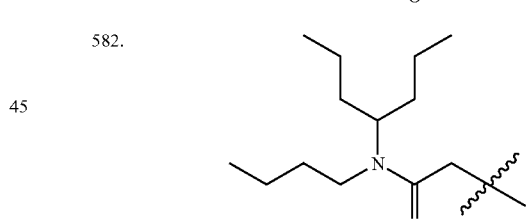 |
| 583. | 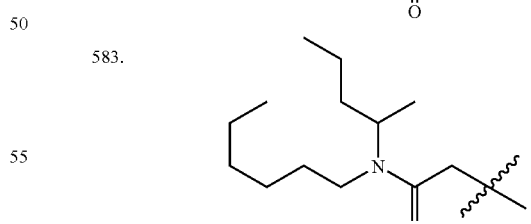 |
| 584. | 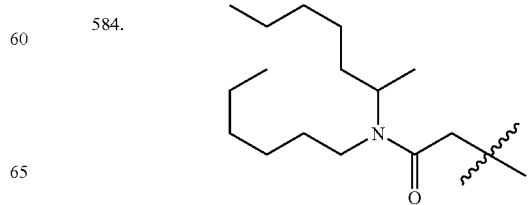 |

TABLE 1-continued
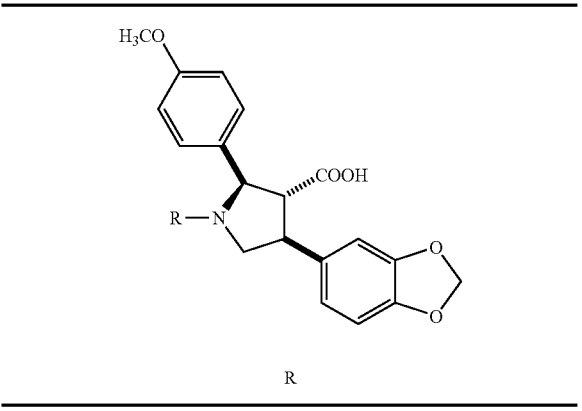
R
| | |
|---|---|
| 585. | 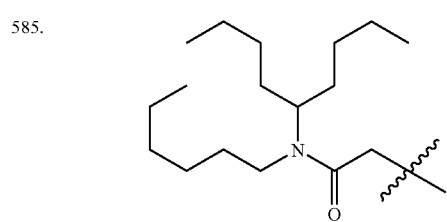 |
| 586. | 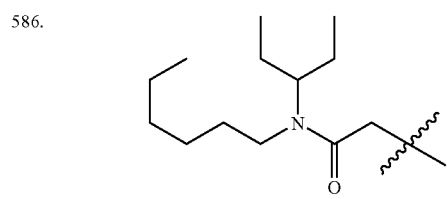 |
| 587. | 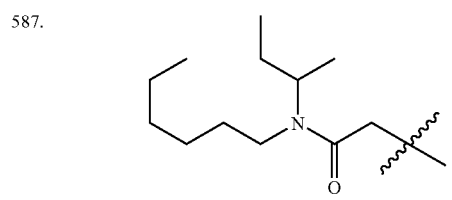 |
| 588. | 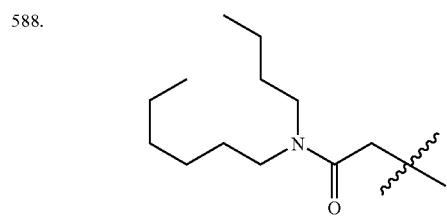 |
| 589. | 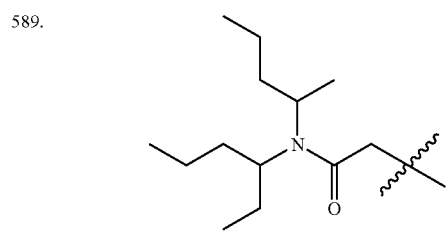 |
TABLE 1-continued
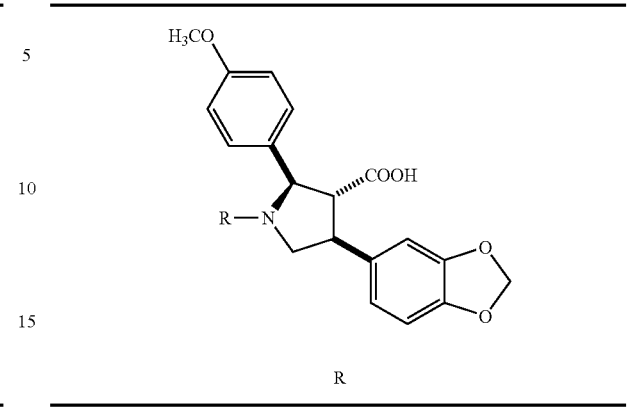
R
| | |
|---|---|
| 590. |  |
| 591. |  |
| 592. | 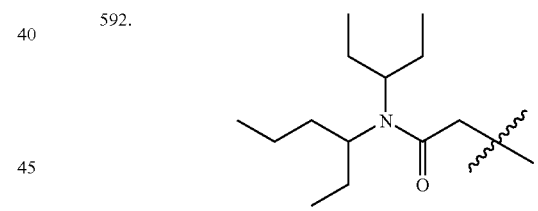 |
| 593. | 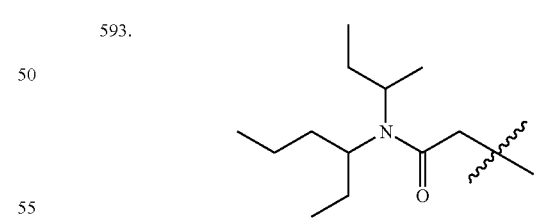 |
| 594. | 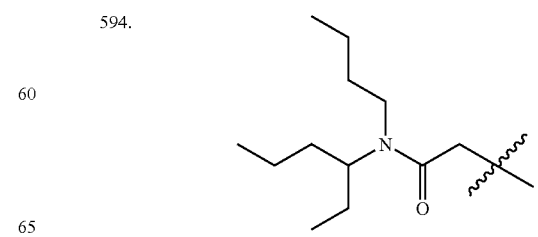 |

TABLE 1-continued
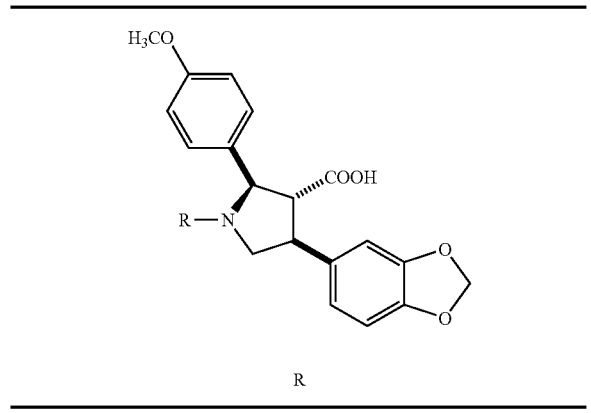
R
595. 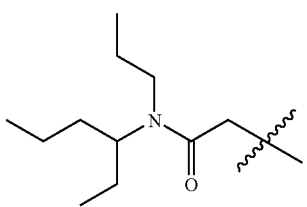
596. 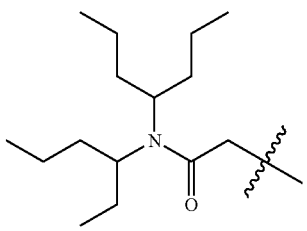
597. 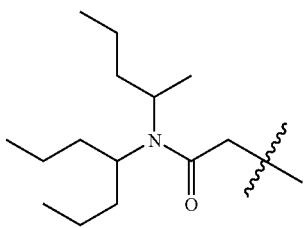
598. 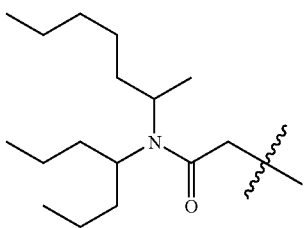
599. 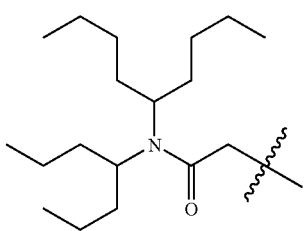
TABLE 1-continued
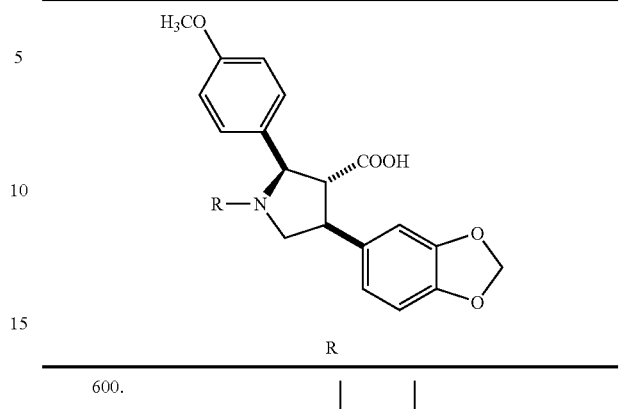
R
600. 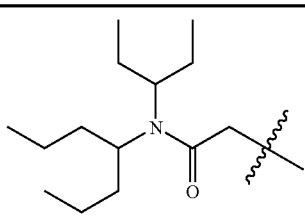
601. 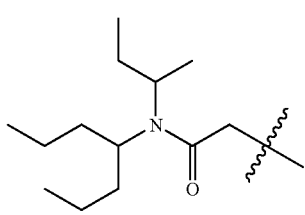
602. 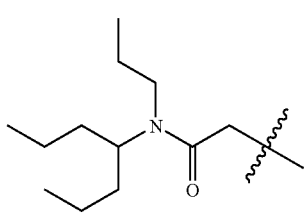
603. 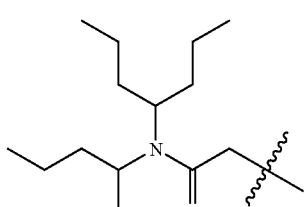
604. 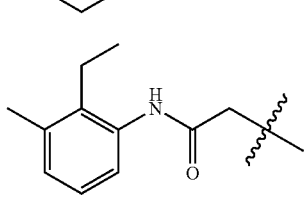
605. 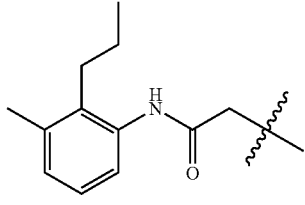

TABLE 1-continued
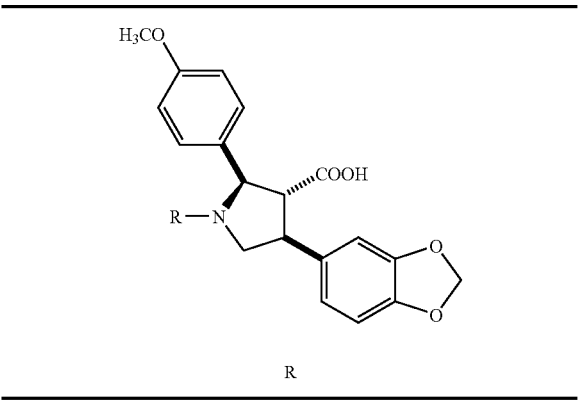
R
| 606. | 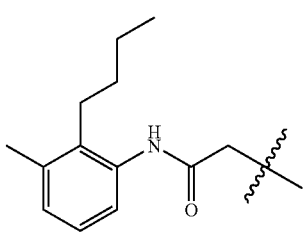 |
|---|---|
| 607. | 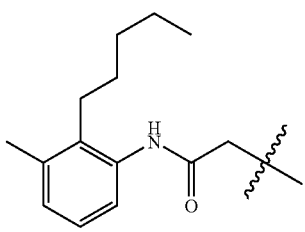 |
| 608. | 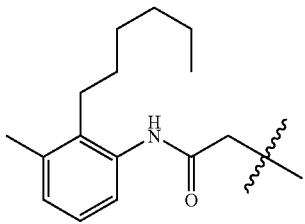 |
| 609. | 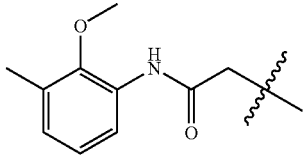 |
| 610. | 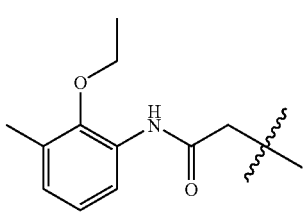 |
TABLE 1-continued
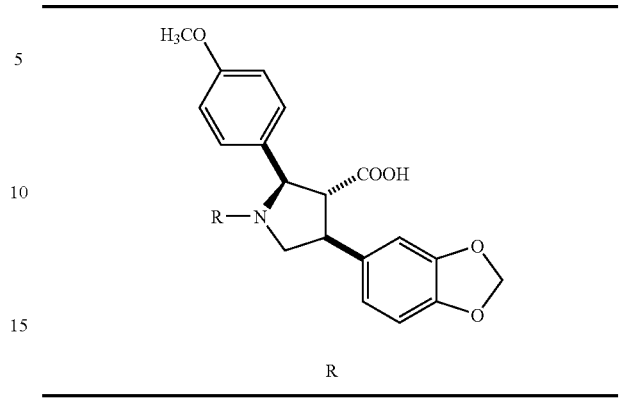
R
| 611. | 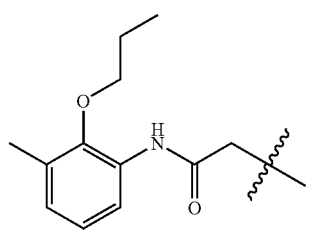 |
|---|---|
| 612. | 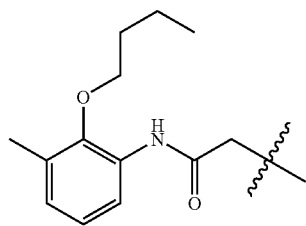 |
| 613. | 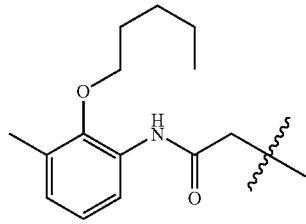 |
| 614. |  |
| 615. | 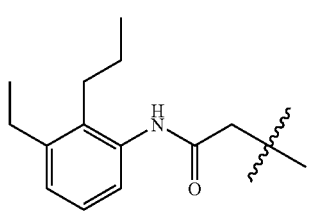 |

TABLE 1-continued
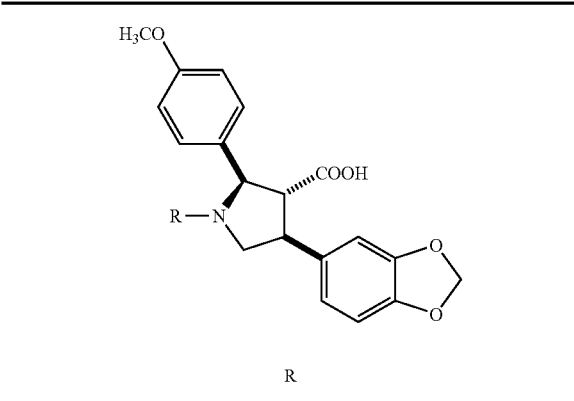
R
616.
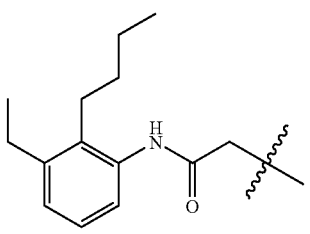
617.
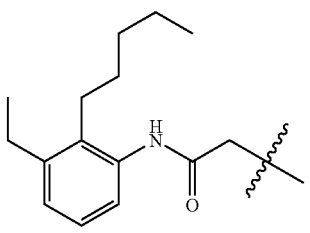
618.
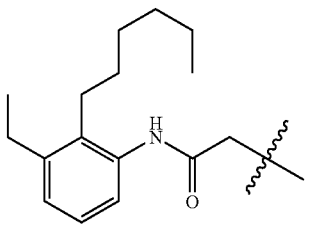
619.
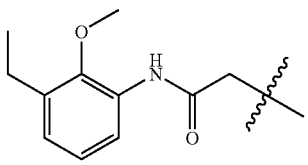
620.
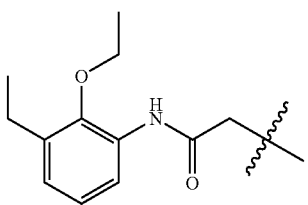
TABLE 1-continued
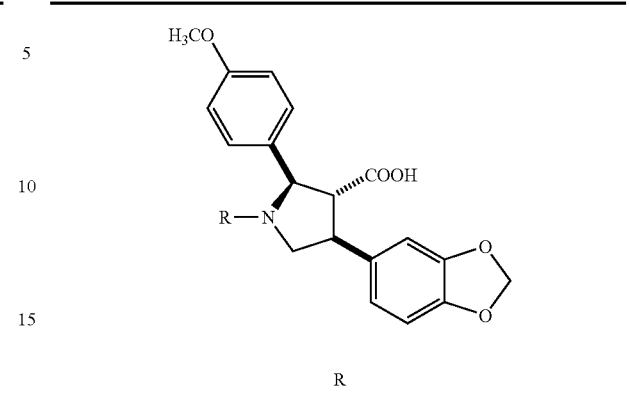
R
621.
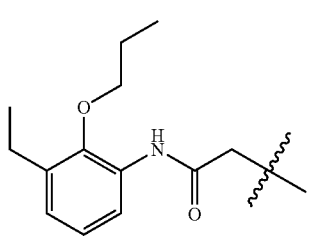
622.
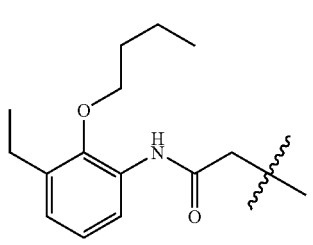
623.
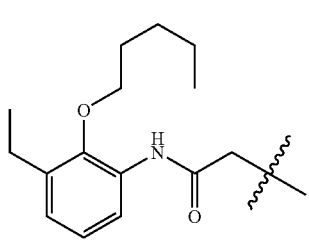
624.
625.
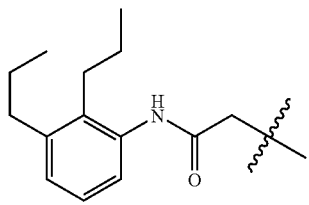

TABLE 1-continued
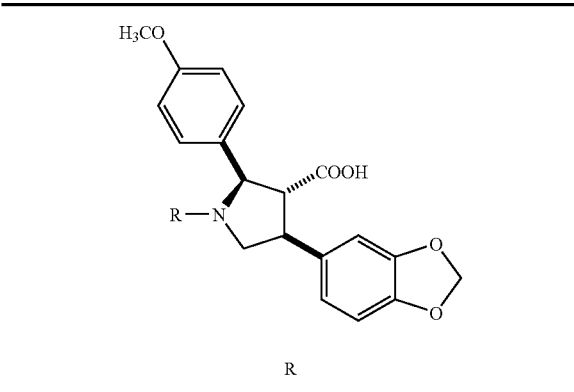
| R |
|---|
| 626. |
| 627. |
| 628. |
| 629. |
| 630. |
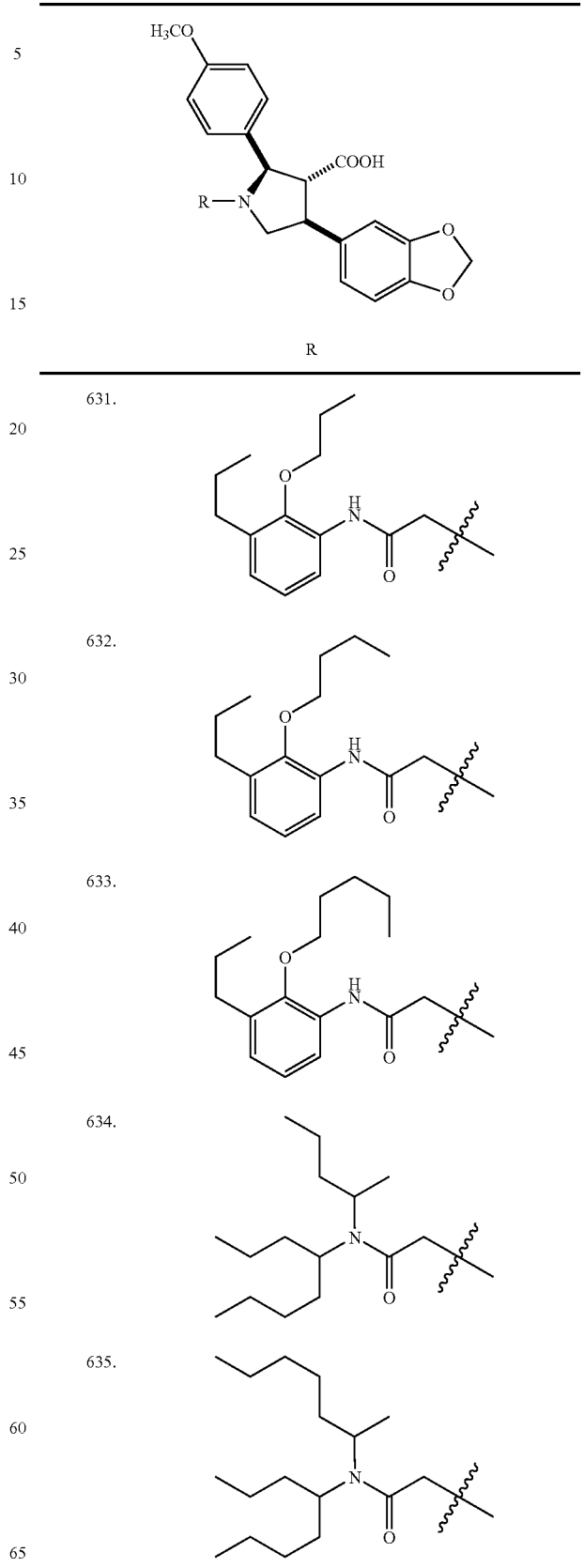
| R |
|---|
| 631. |
| 632. |
| 633. |
| 634. |
| 635. |

TABLE 1-continued
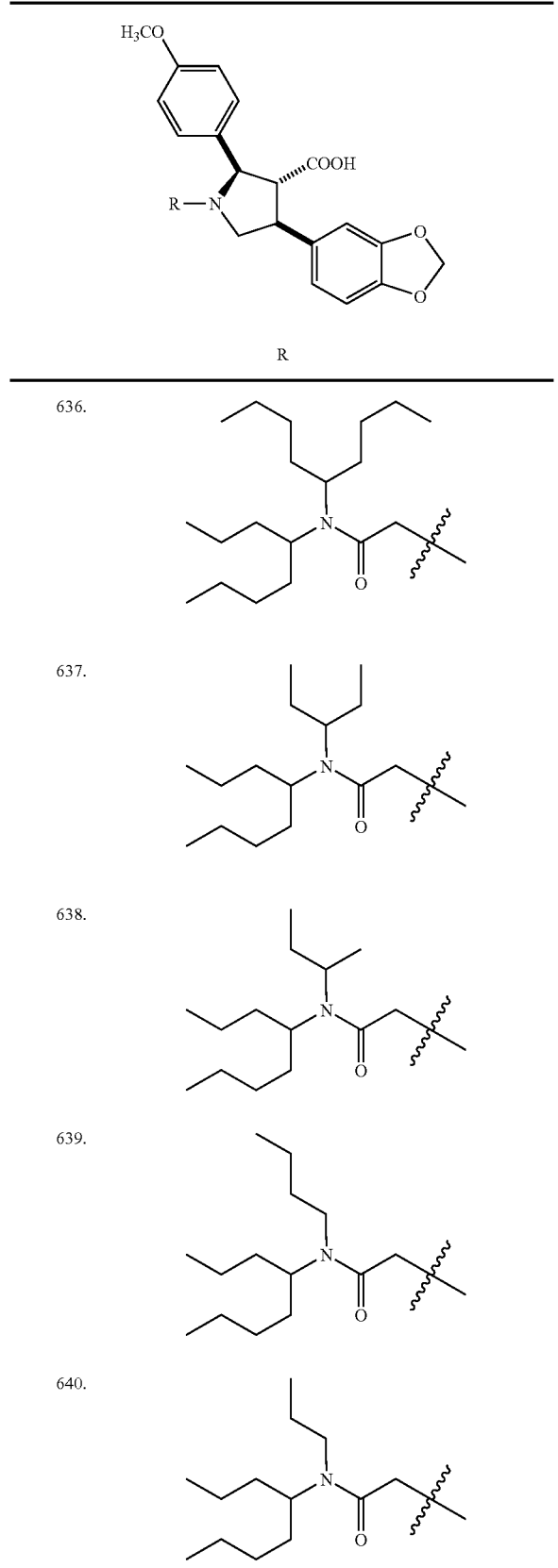
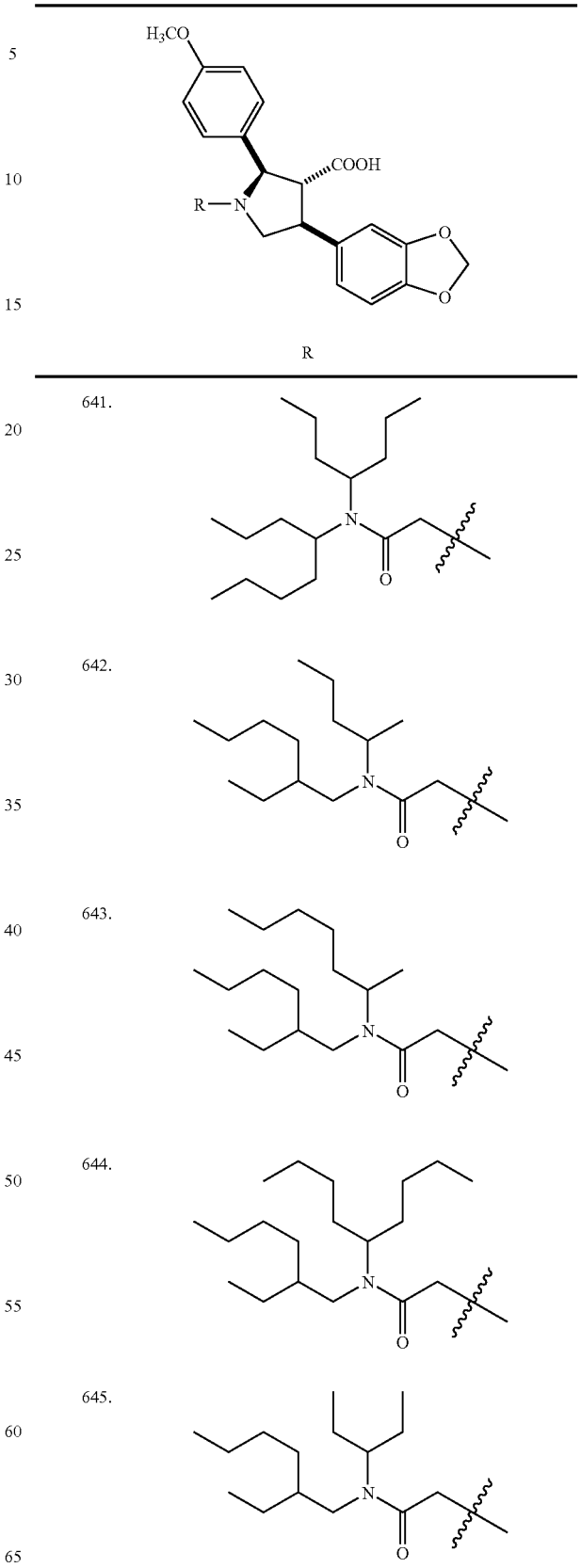

277
TABLE 1-continued
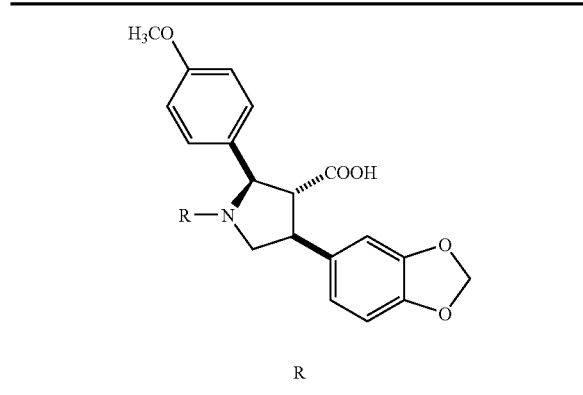
| | R |
|---|---|
| 646. | 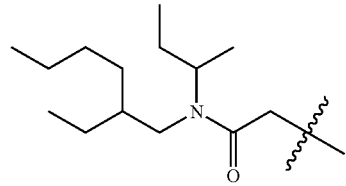 |
| 647. | 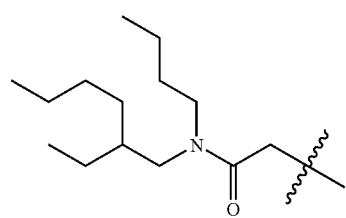 |
| 648. | 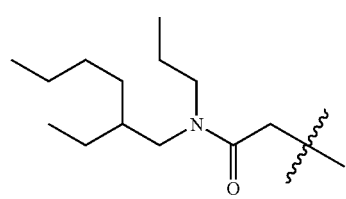 |
| 649. | 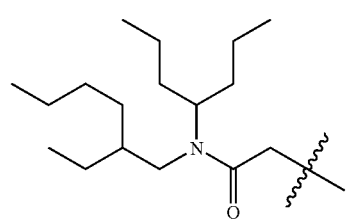 |
| 650. | 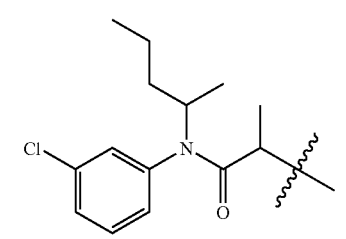 |
278
TABLE 1-continued
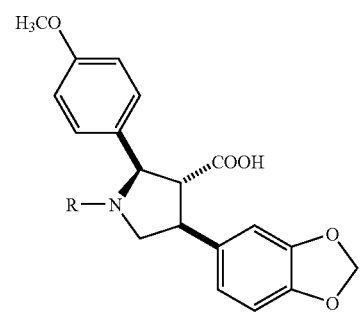
| | R |
|---|---|
| 651. | 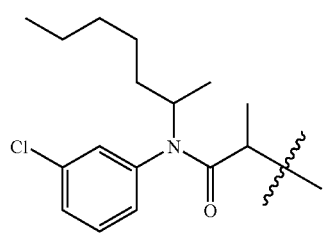 |
| 652. | 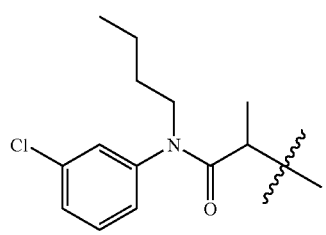 |
| 653. | 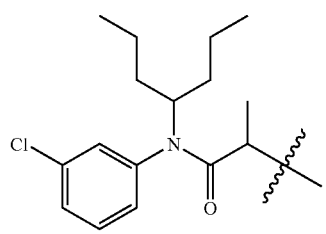 |
| 654. | 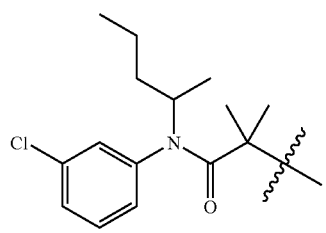 |
| 655. | 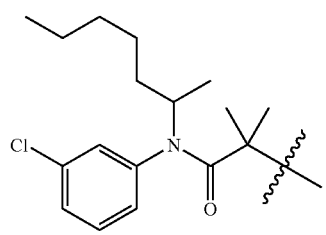 |

TABLE 1-continued
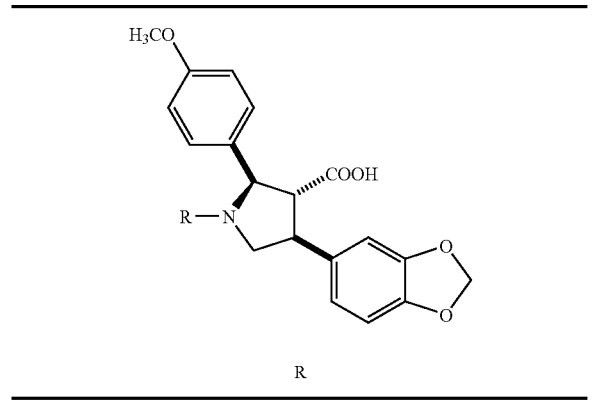
R
| 656. | 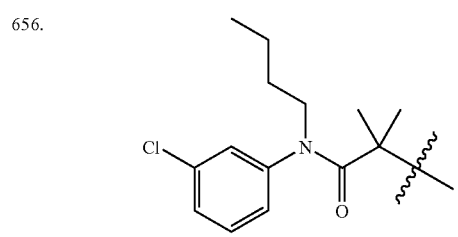 |
| --- | --- |
| 657. | 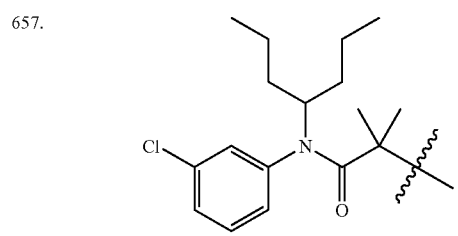 |
| 658. | 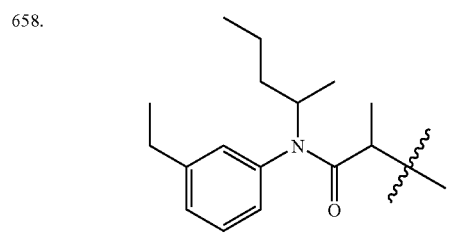 |
| 659. | 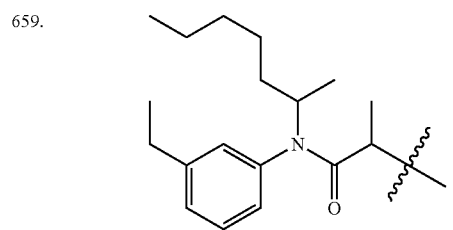 |
| 660. | 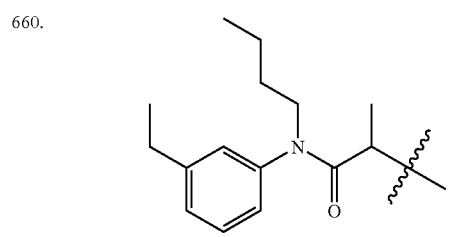 |
TABLE 1-continued
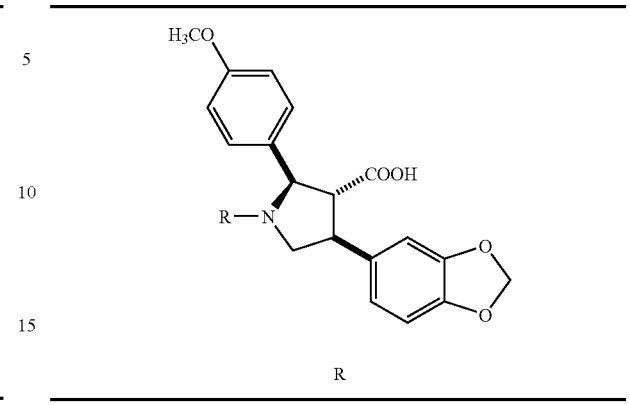
R
| 661. | 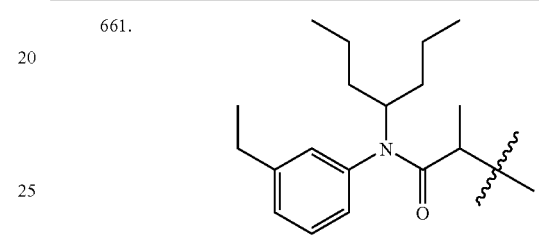 |
| --- | --- |
| 662. | 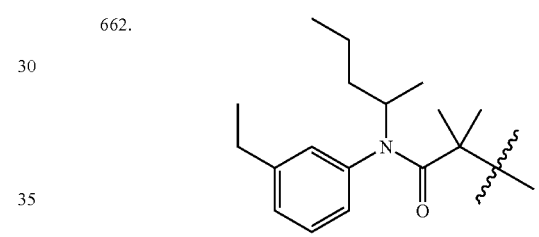 |
| 663. |  |
| 664. |  |
| 665. | 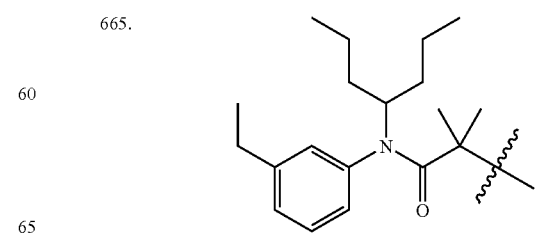 |

TABLE 1-continued
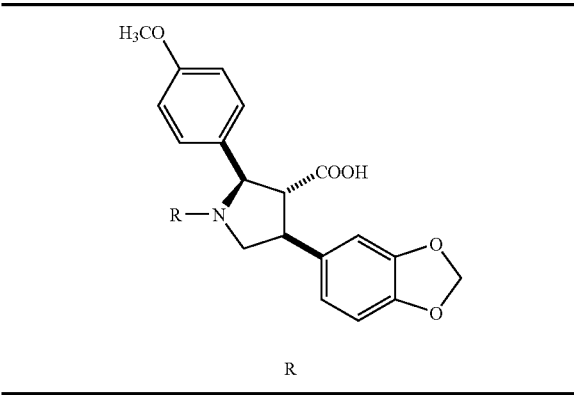
| | R |
|---|---|
| 666. | 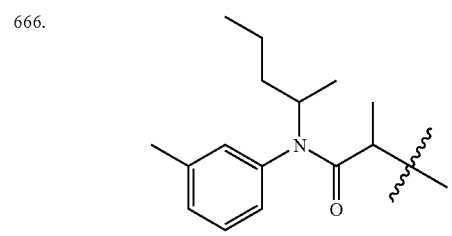 |
| 667. | 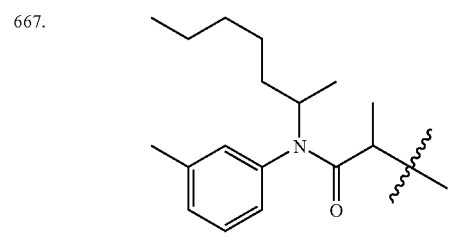 |
| 668. | 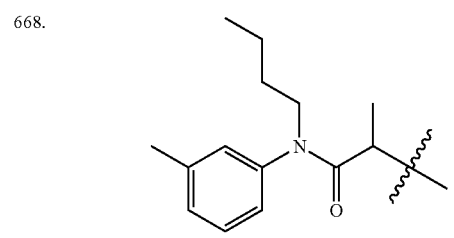 |
| 669. | 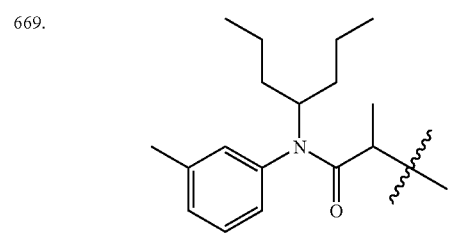 |
| 670. | 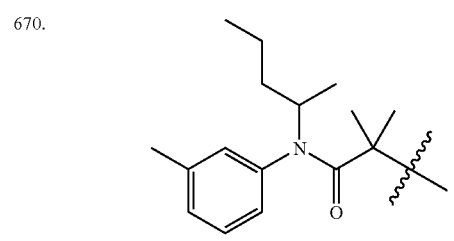 |
TABLE 1-continued
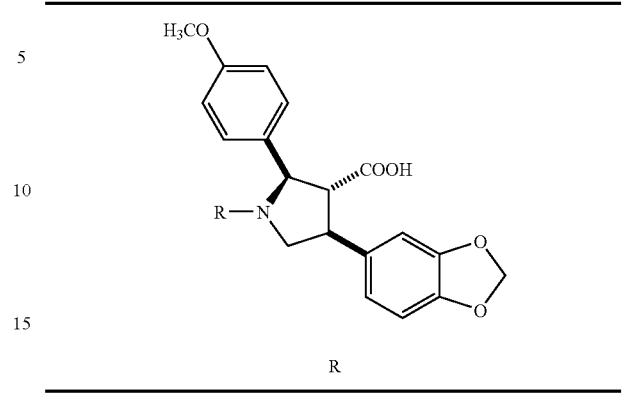
| | R |
|---|---|
| 671. | 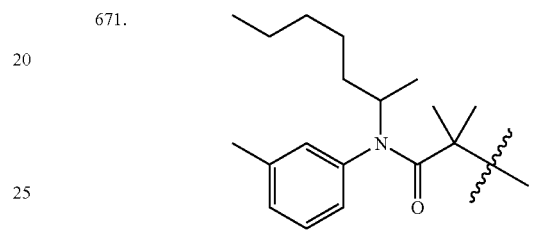 |
| 672. | 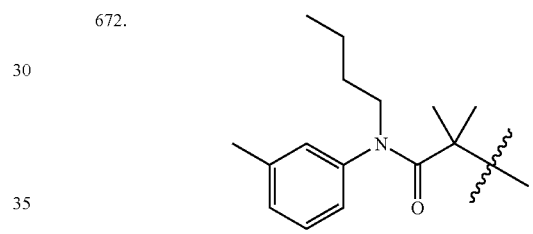 |
| 673. |  |
| 674. | 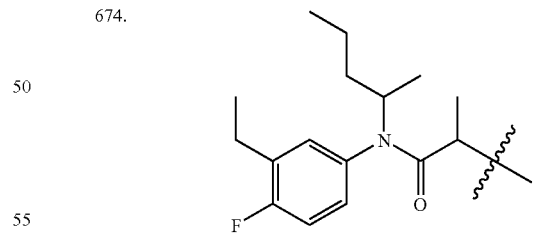 |
| 675. |  |

TABLE 1-continued
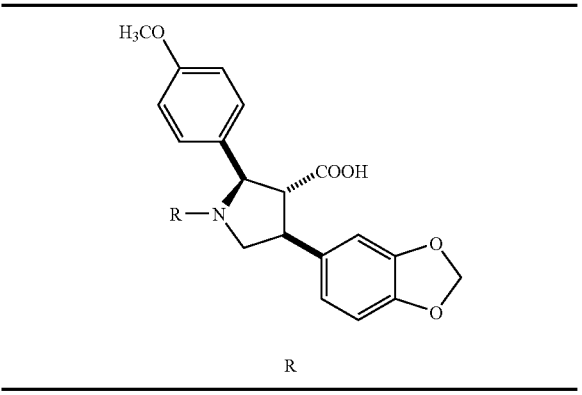
| | R |
|---|---|
| 676. | 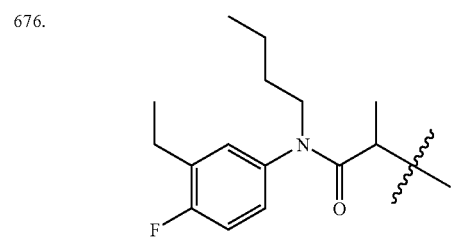 |
| 677. | 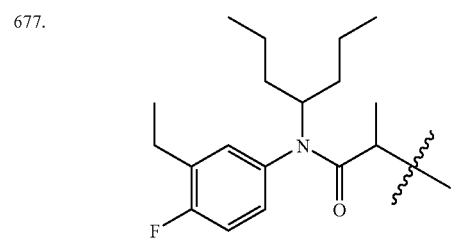 |
| 678. | 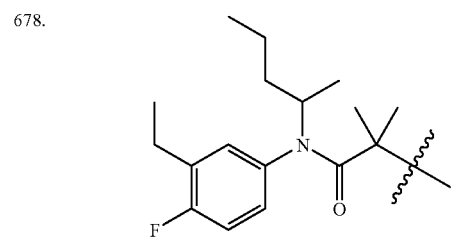 |
| 679. | 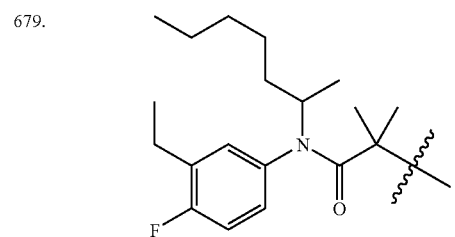 |
| 680. | 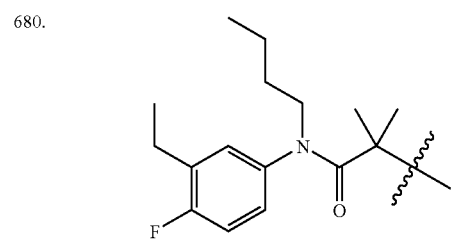 |
TABLE 1-continued
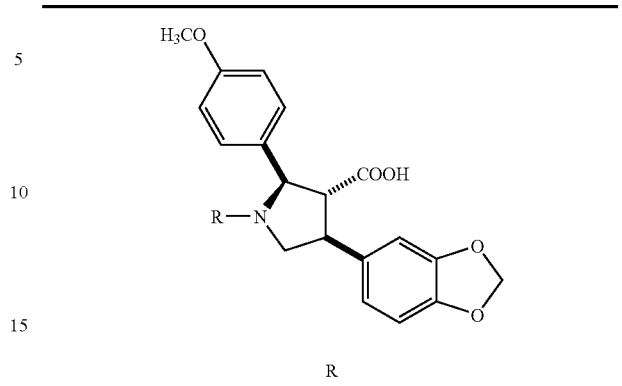
| | R |
|---|---|
| 681. | 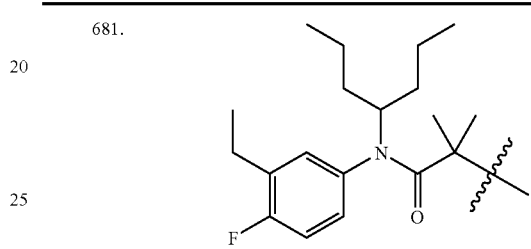 |
| 682. | 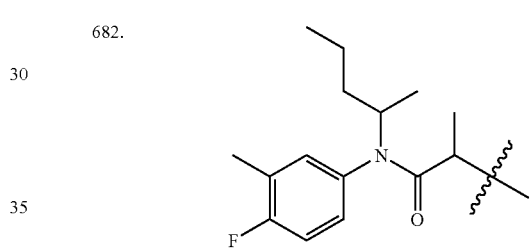 |
| 683. | 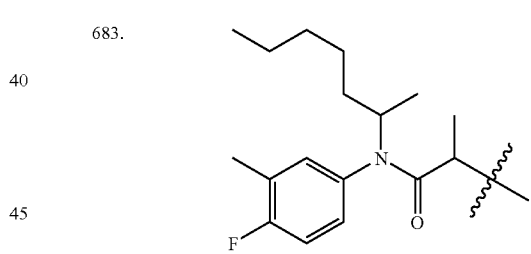 |
| 684. | 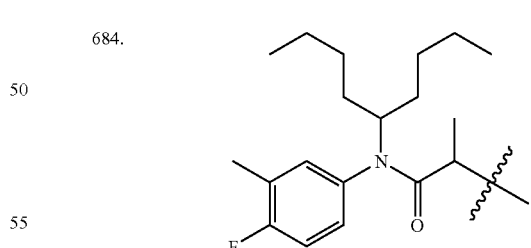 |
| 685. | 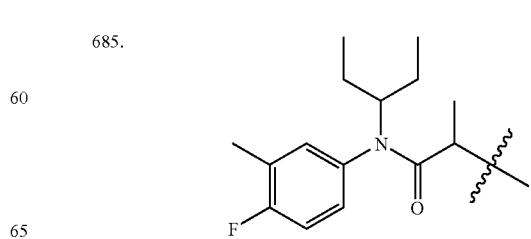 |

TABLE 1-continued
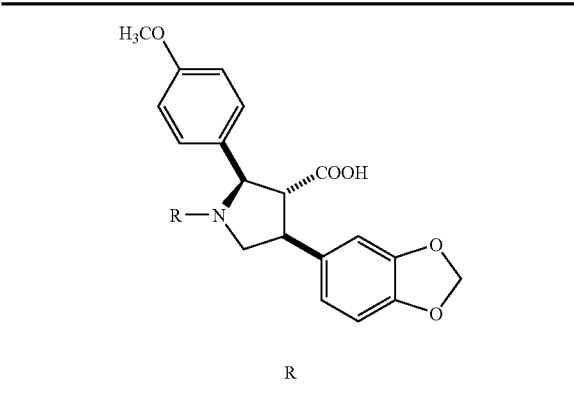
R
| | |
|---|---|
| 686. | |
| 687. | |
| 688. | |
| 689. | |
| 690. | |
| 691. | |
| 692. | |
| 693. | |
| 694. | |
| 695. | |
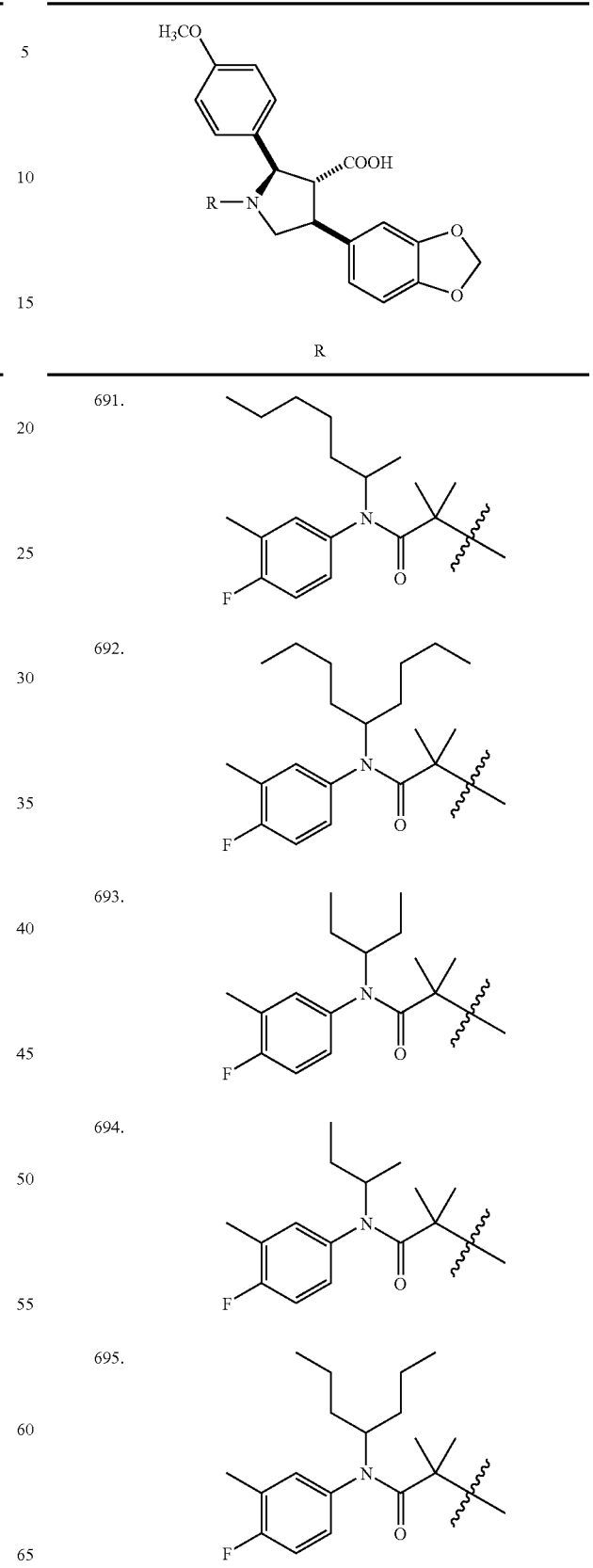

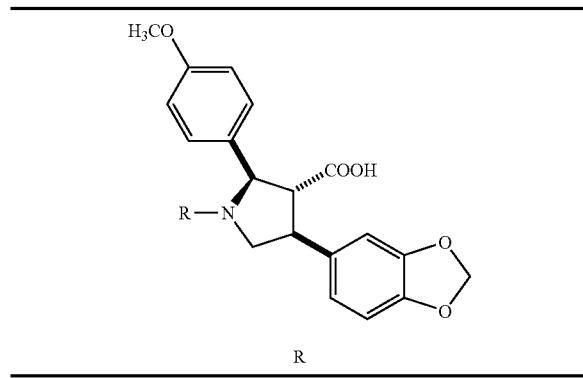

TABLE 1-continued
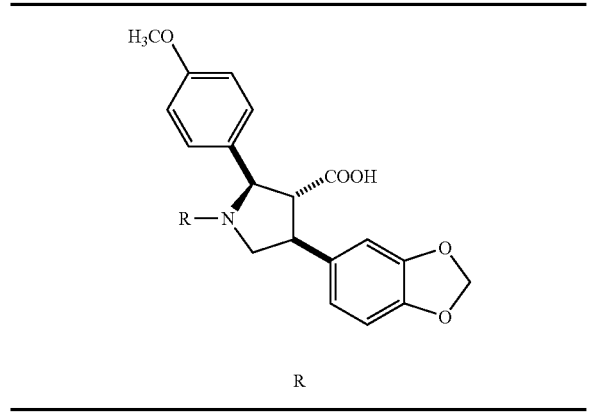
R
708. 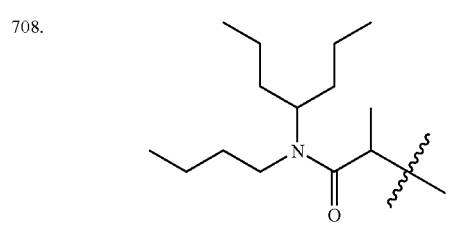
709. 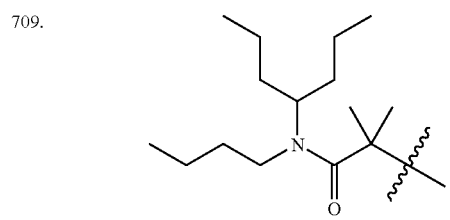
710. 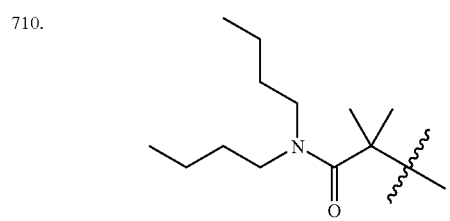
711. 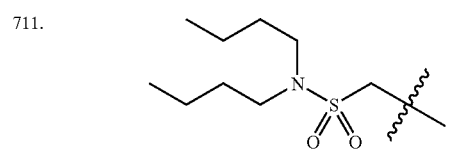
712. 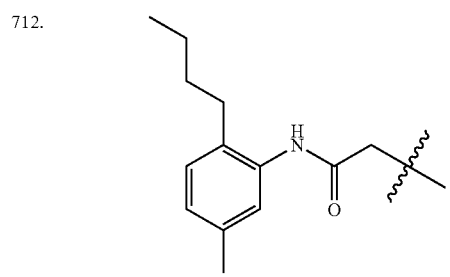
TABLE 1-continued
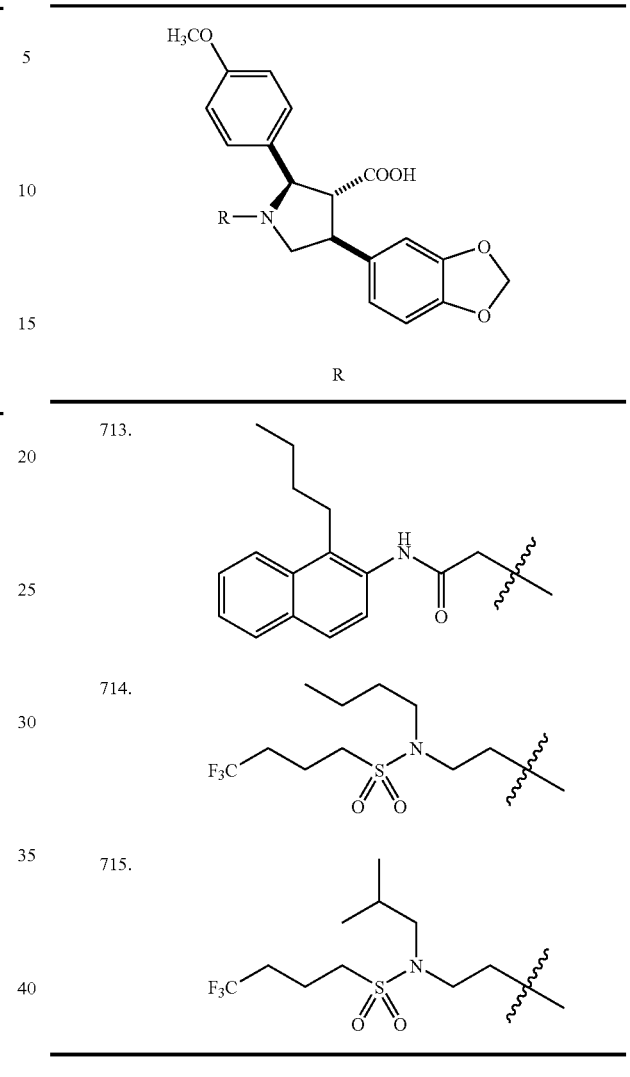
EXAMPLE 338
Using methods described in the above examples, compounds comprising a parent structure selected from those disclosed in Table 2A and an R substituent selected from those disclosed in Table 2B can be prepared.
TABLE 2A
1. 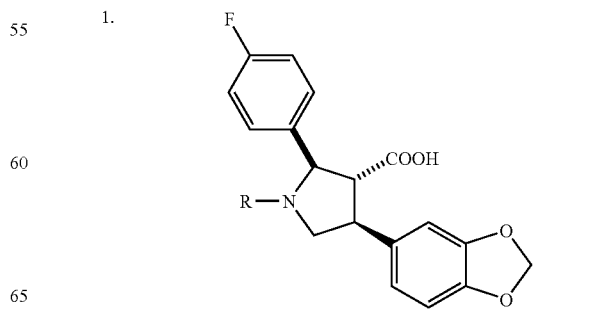

TABLE 2A-continued
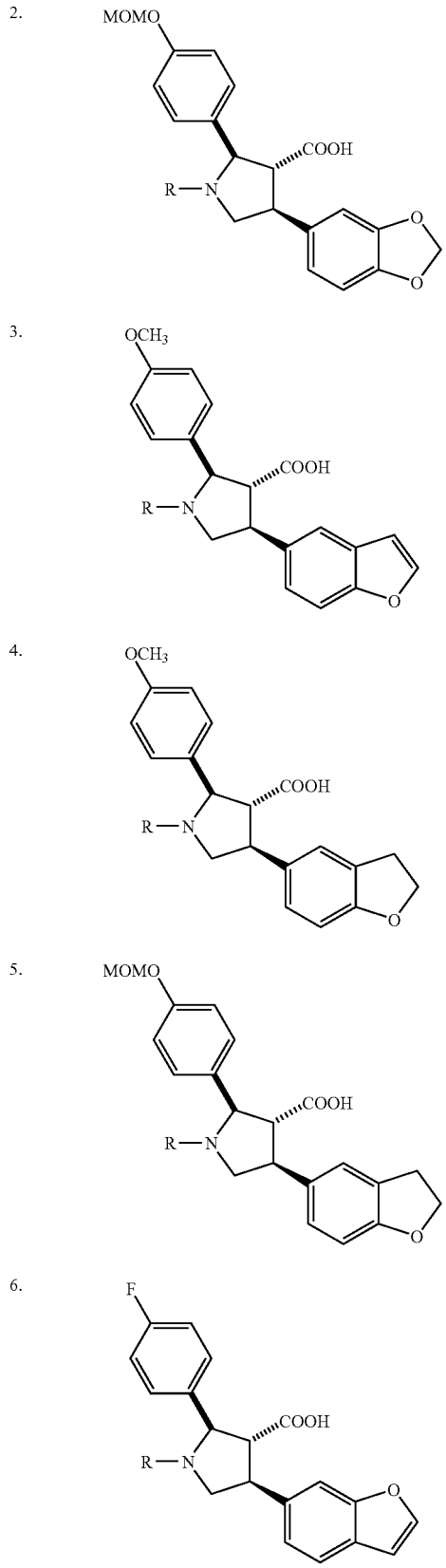
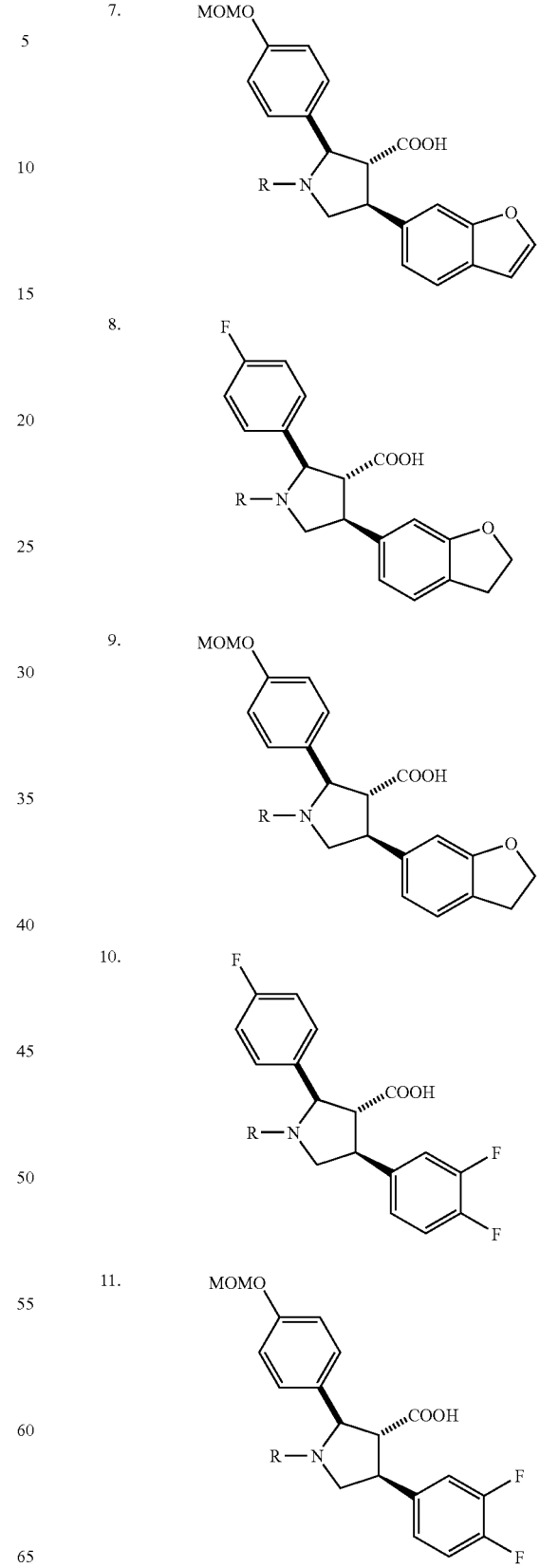

TABLE 2A-continued
12. 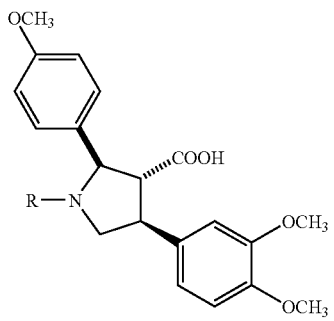
13. 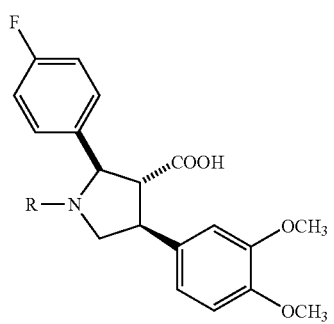
14. 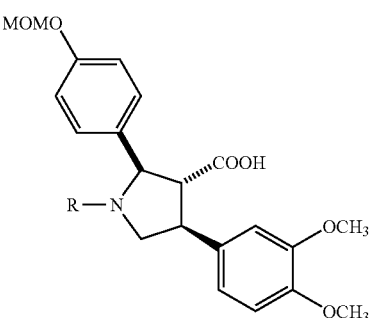
15. 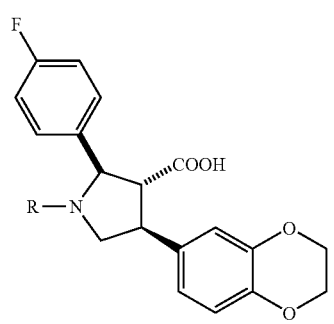
16. 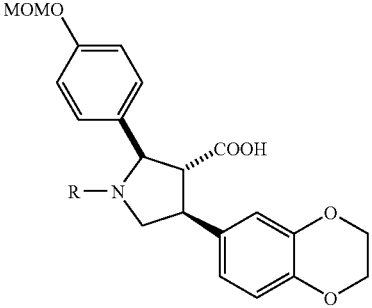
17. 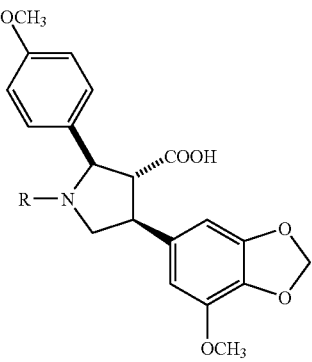
18. 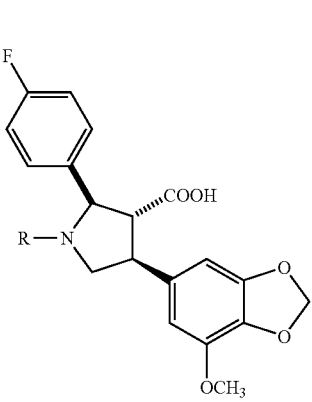
19. 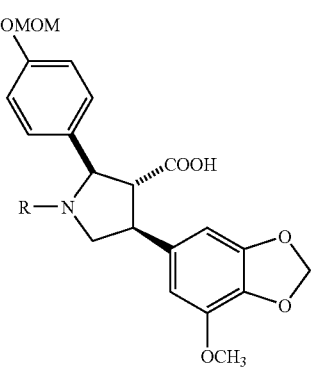
20. 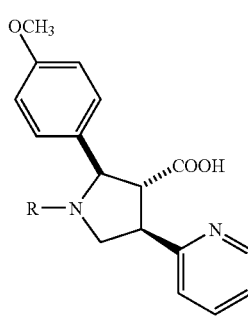

TABLE 2A-continued
| | |
|---|---|
| 21. 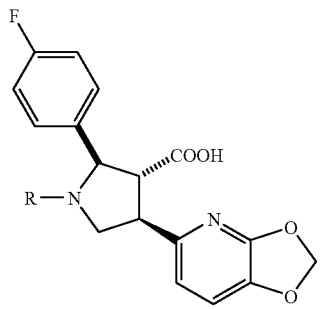 | 26. 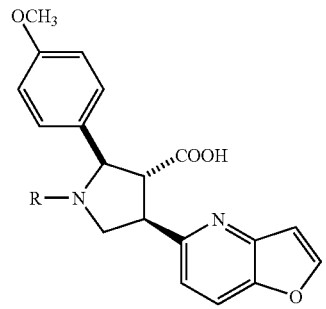 |
| 22. 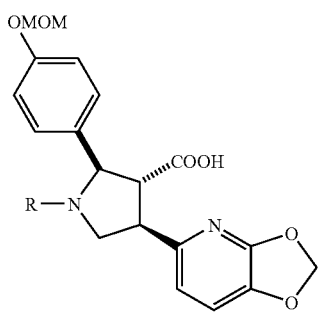 | 27. 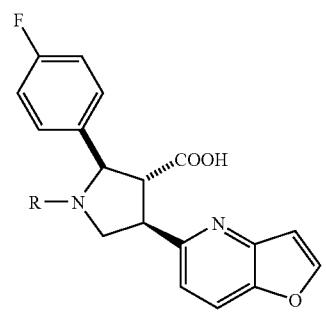 |
| 23. 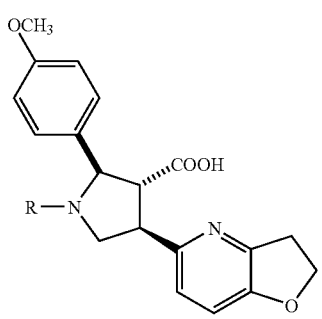 | 28. 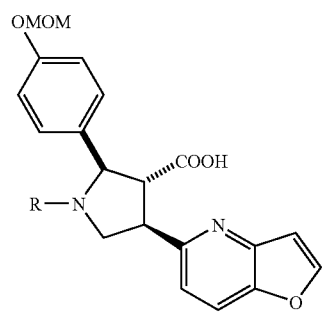 |
| 24. 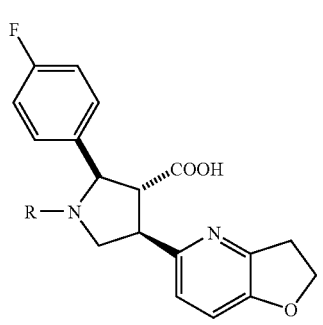 | 29. 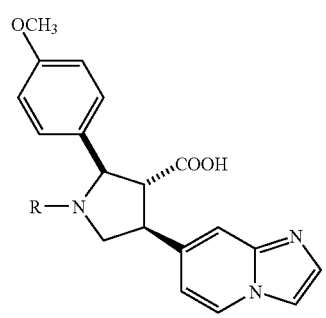 |
| 25. 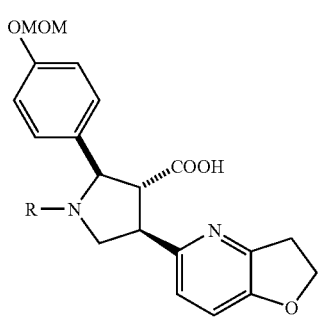 | 30. 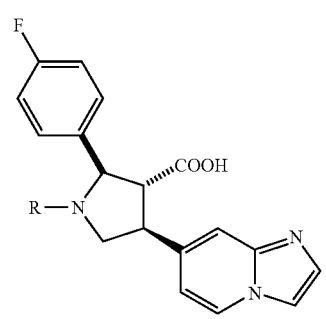 |

TABLE 2A-continued
31. 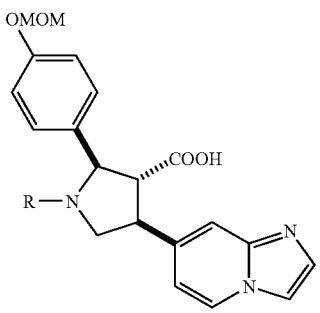
32. 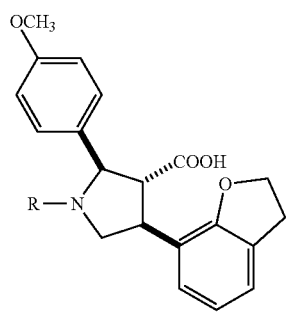
33. 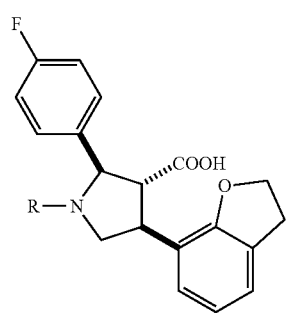
34. 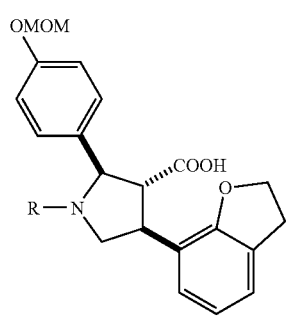
35. 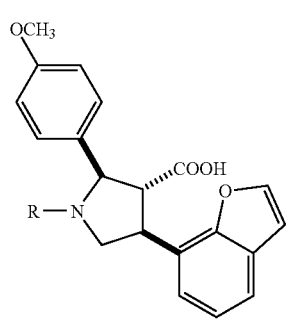
TABLE 2A-continued
36. 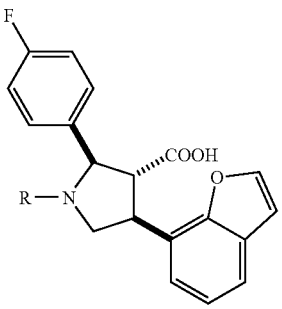
37. 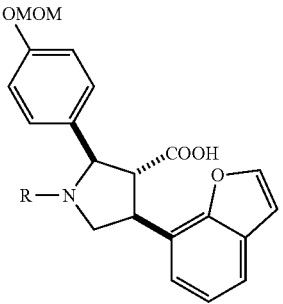
38. 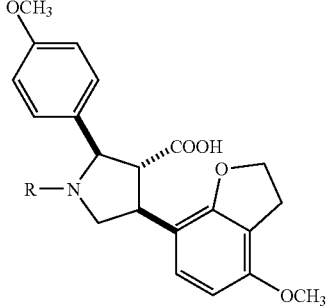
39. 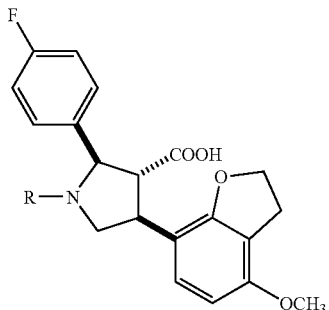
40. 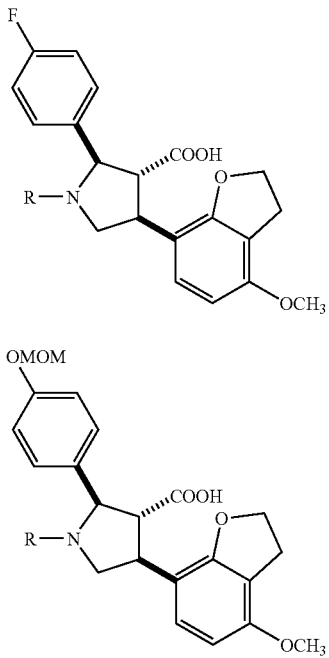

TABLE 2A-continued
| 41. | 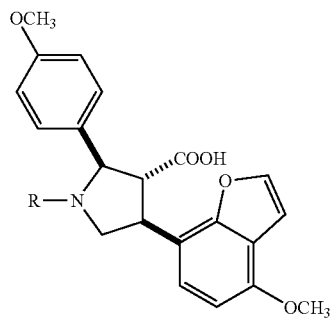 |
| --- | --- |
| 42. | 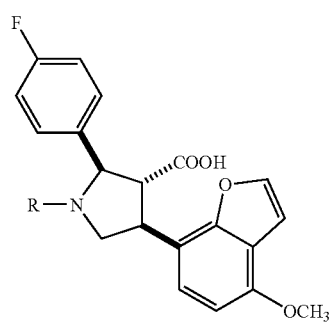 |
| 43. | 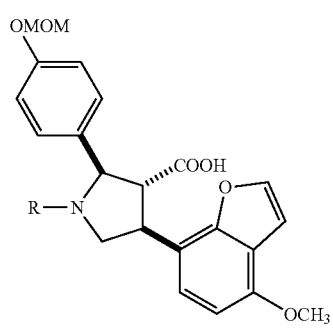 |
| 44. | 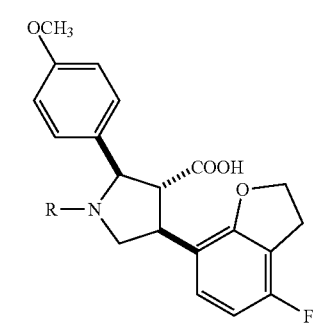 |
| 45. | 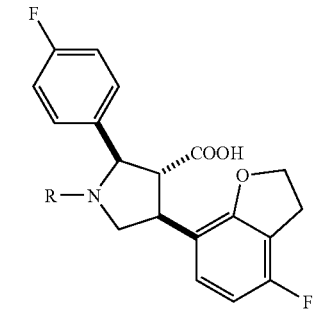 |
TABLE 2A-continued
| 46. | 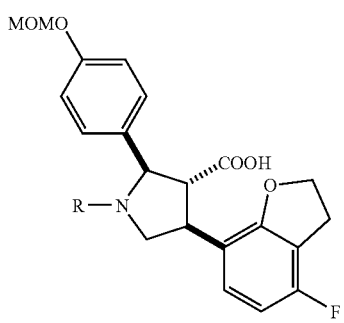 |
| --- | --- |
| 47. | 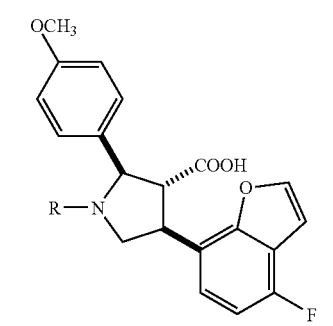 |
| 48. | 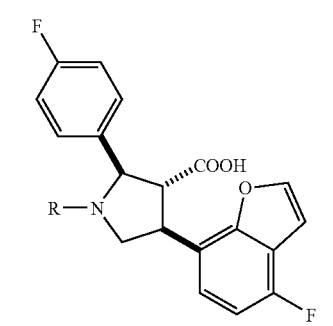 |
| 49. | 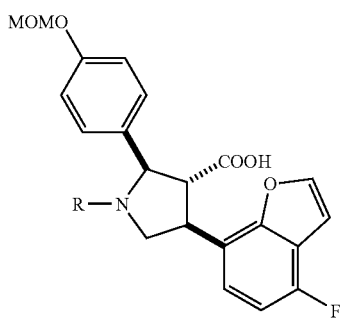 |

TABLE 2A-continued
50. 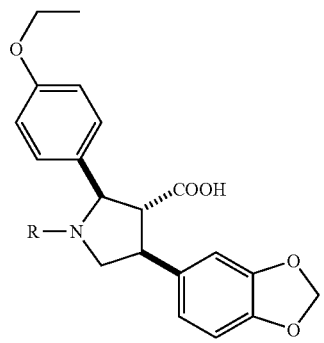
51. 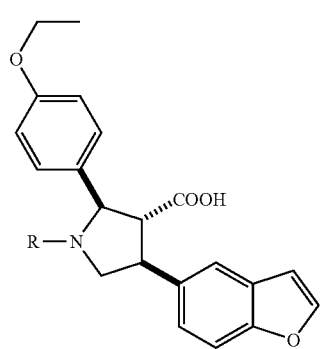
52. 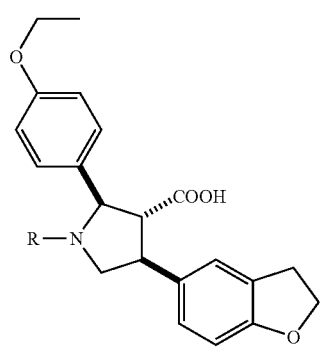
53. 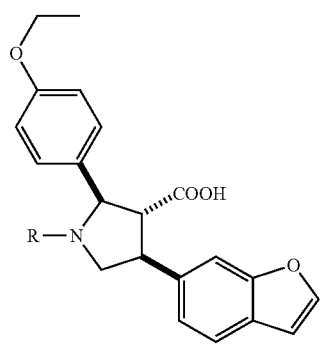
TABLE 2A-continued
54. 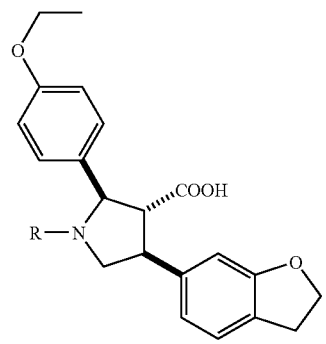
55. 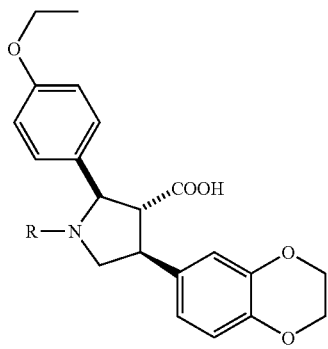
56. 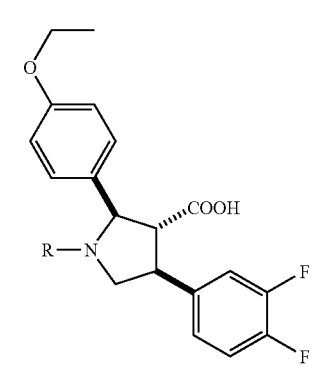
57. 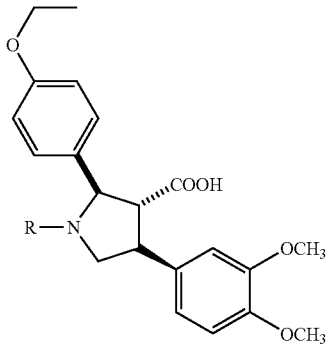

TABLE 2A-continued
58. 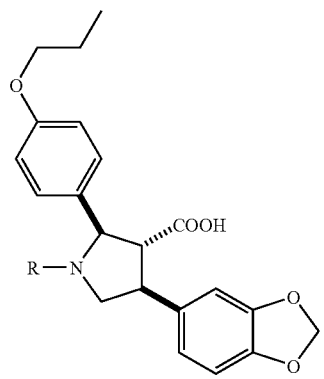
59. 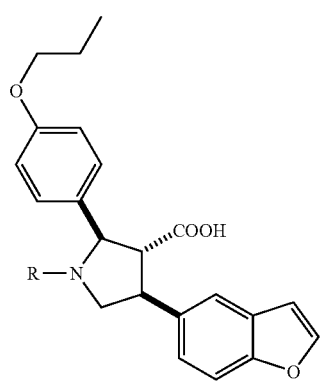
60. 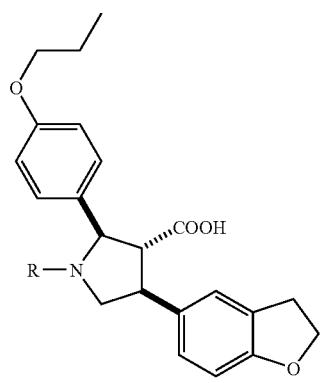
61. 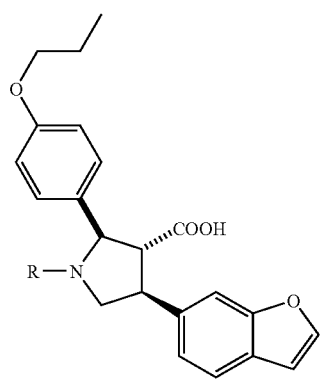
TABLE 2A-continued
62. 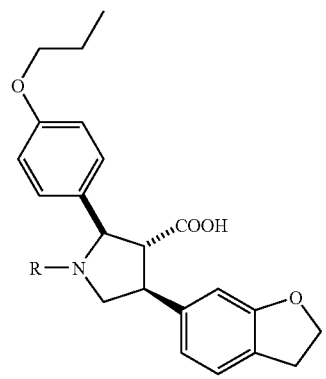
63. 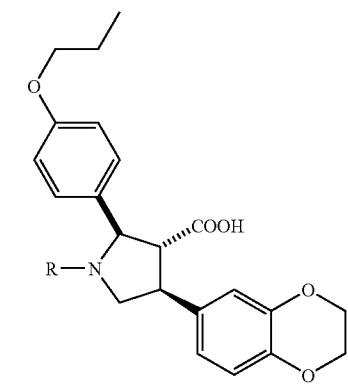
64. 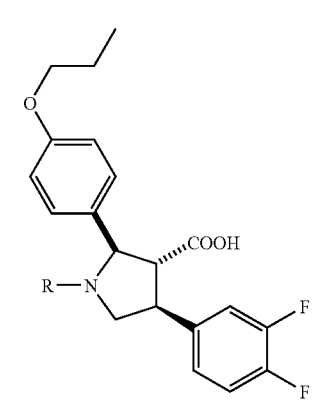
65. 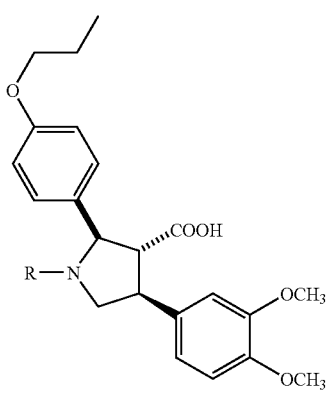

TABLE 2A-continued
66. 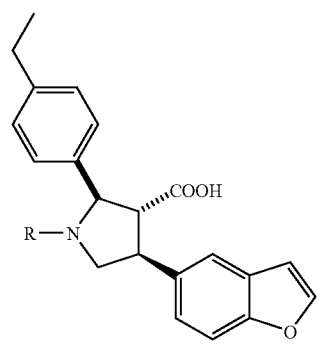
67. 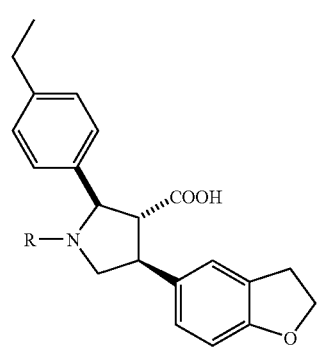
68. 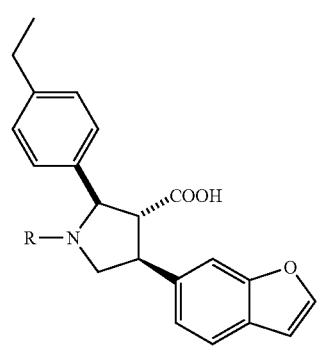
69. 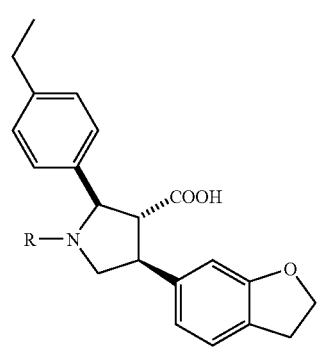
TABLE 2A-continued
70. 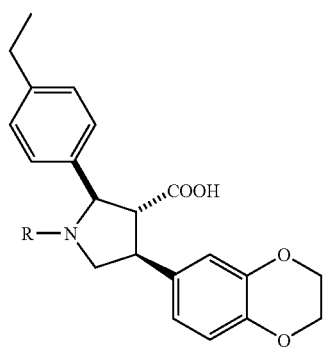
71. 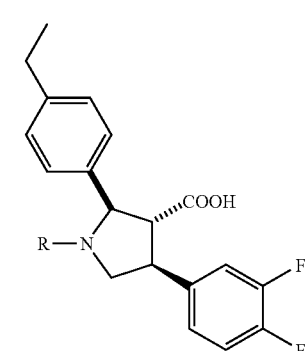
72. 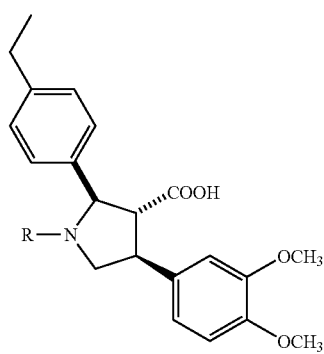
73. 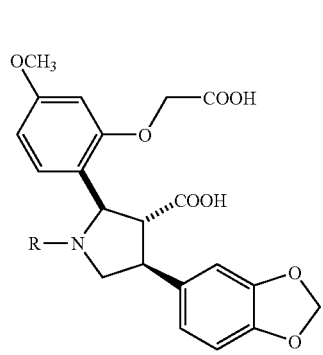

TABLE 2A-continued
| | | | | |
|---|---|---|---|---|
| 74. | 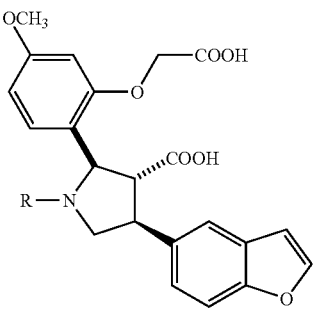 | | 79. | 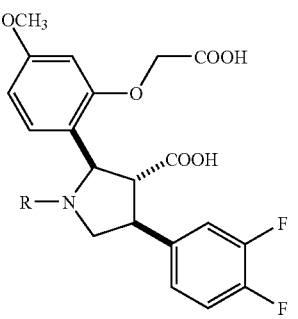 |
| 75. | 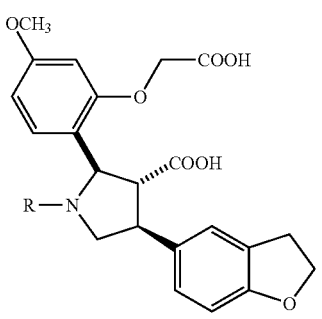 | | 80. | 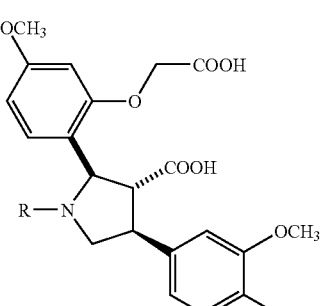 |
| 76. | 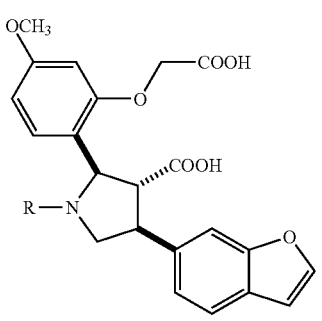 | | 81. | 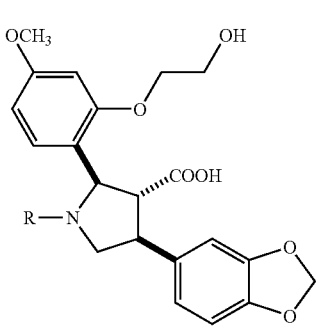 |
| 77. | 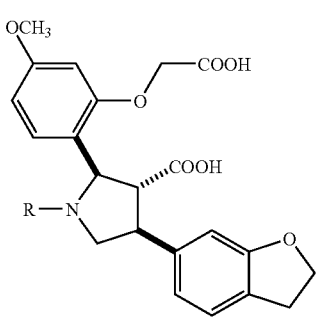 | | 82. | 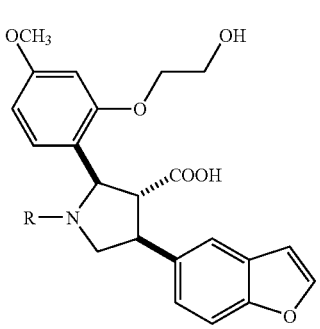 |
| 78. | 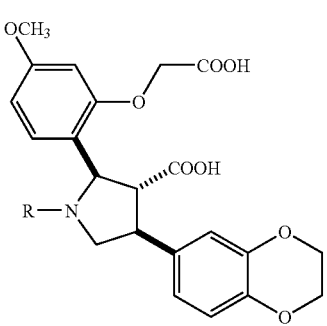 | | 83. | 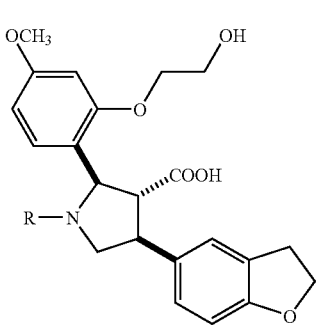 |

TABLE 2A-continued
| | |
|---|---|
| 84. | 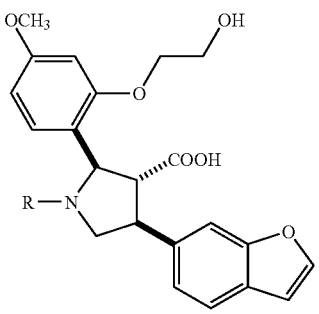 |
| 85. | 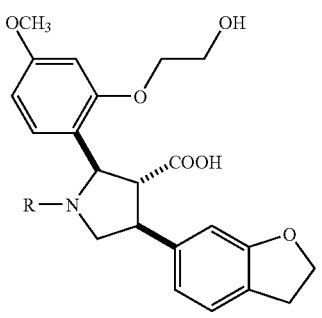 |
| 86. | 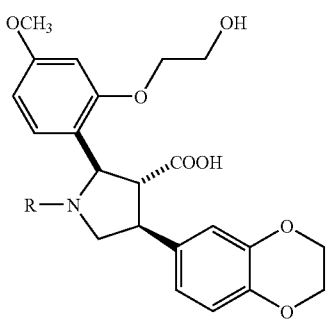 |
| 87. | 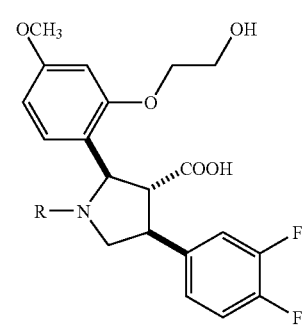 |
| 88. | 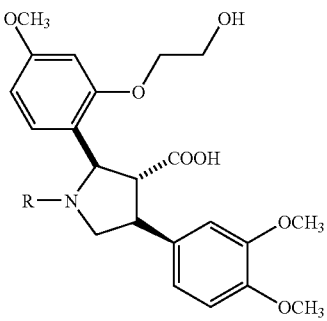 |
| 89. | 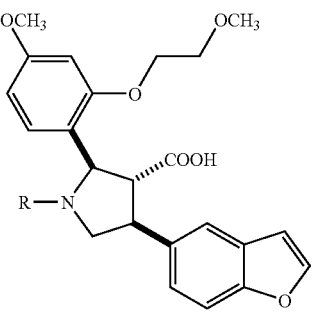 |
| 90. | 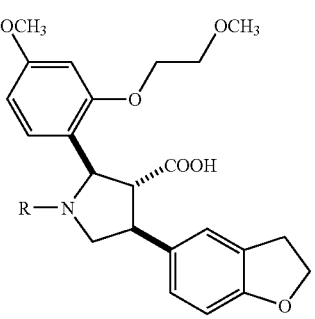 |
| 91. | 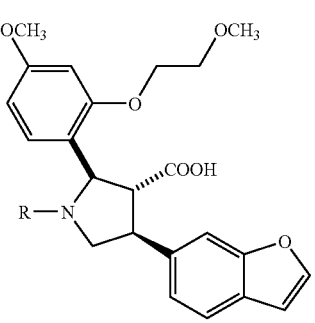 |
| 92. | 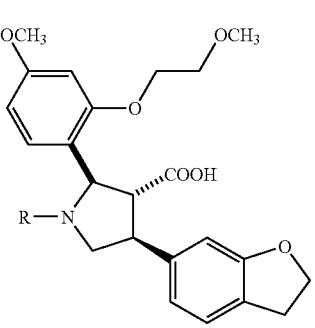 |
| 93. | 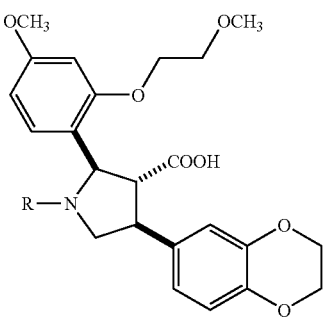 |

TABLE 2A-continued
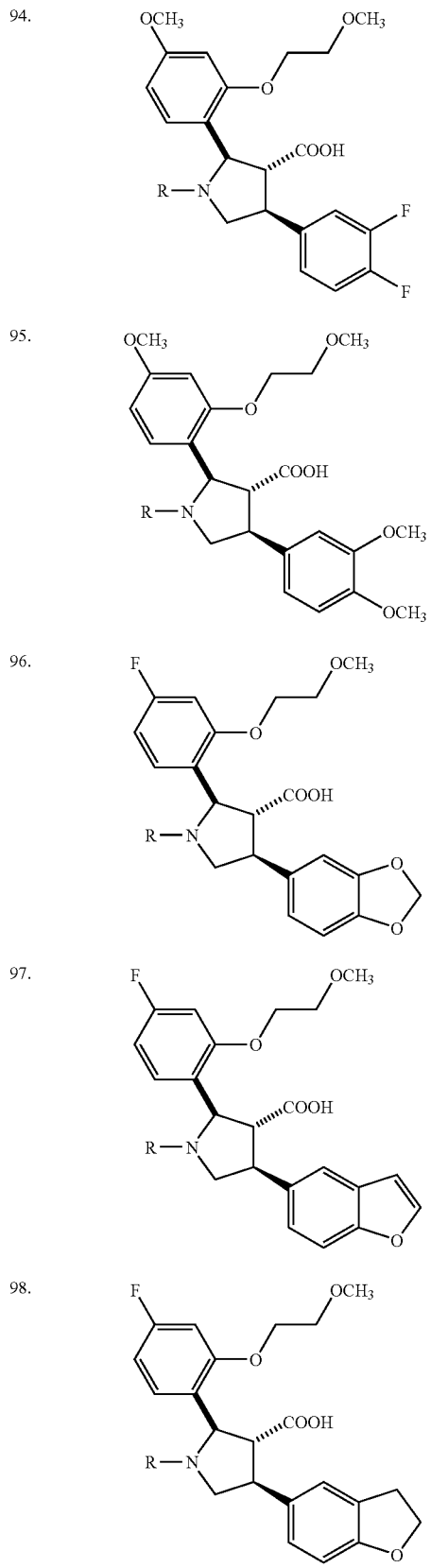
94.
95.
96.
97.
98.
TABLE 2A-continued
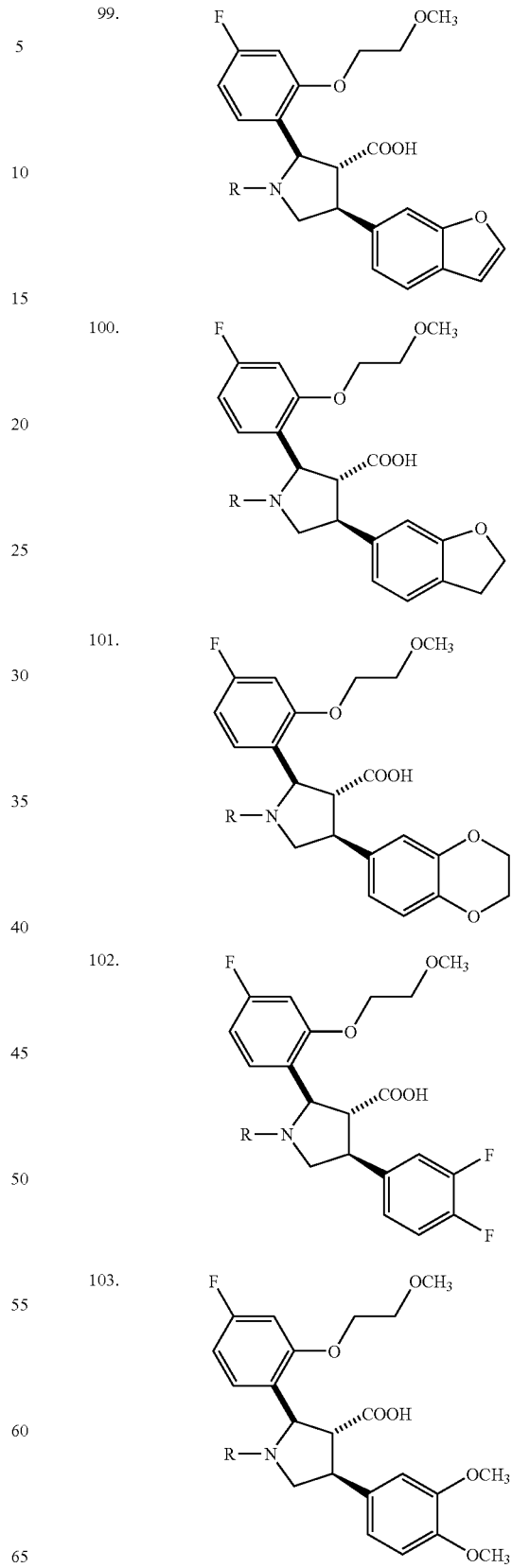
99.
100.
101.
102.
103.

TABLE 2A-continued
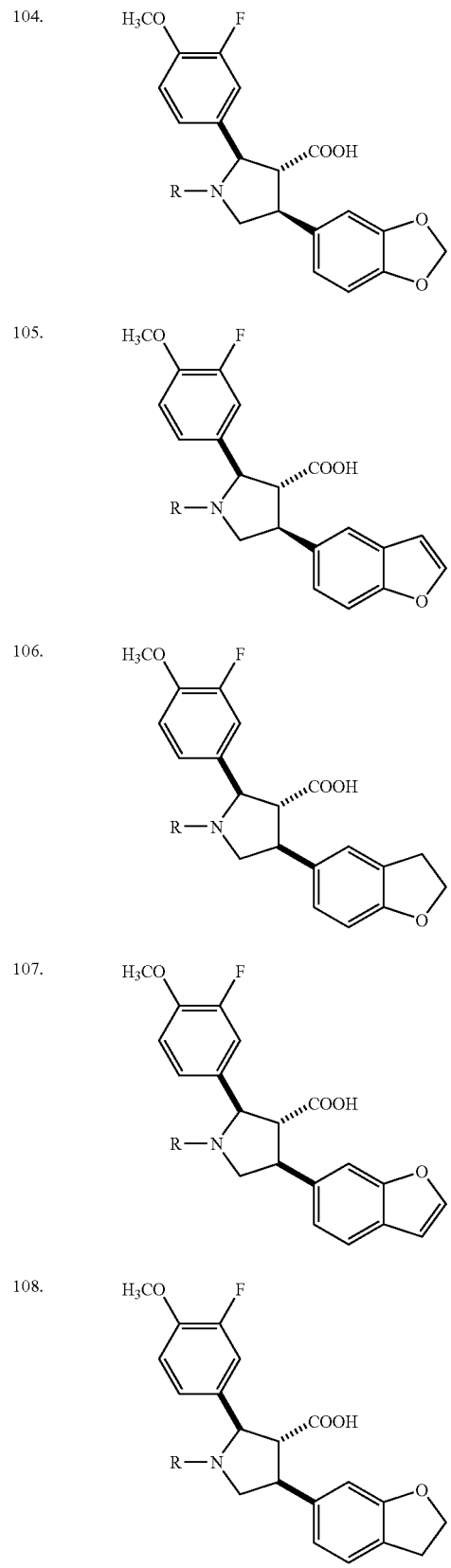
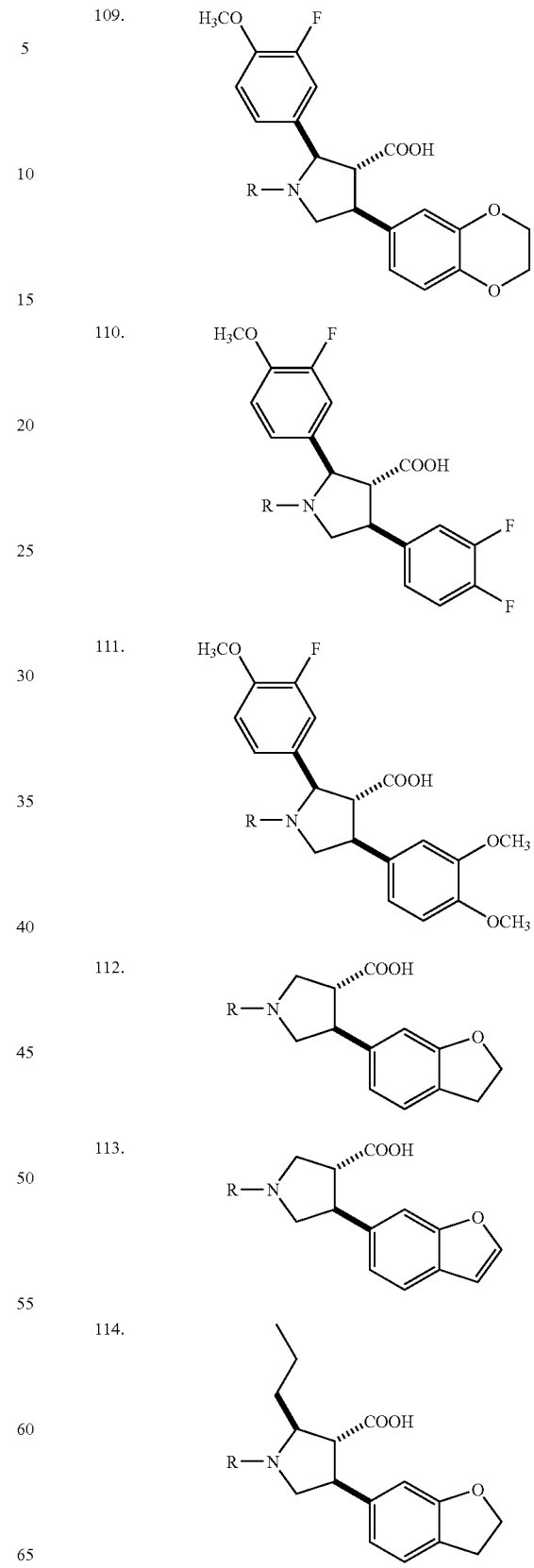

TABLE 2A-continued
| | |
|---|---|
| 115. | 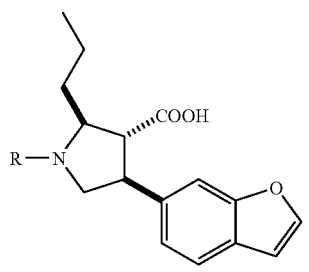 |
| 116. | 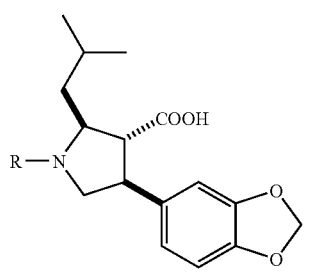 |
| 117. | 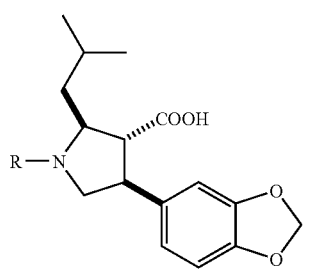 |
| 118. | 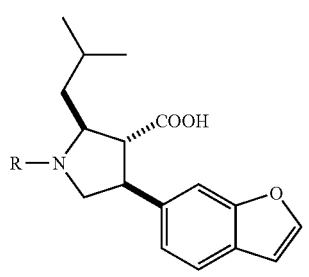 |
| 119. | 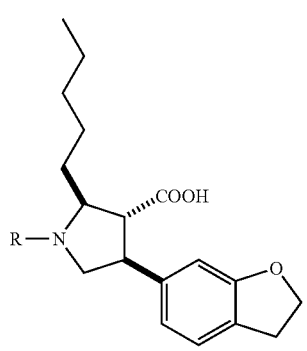 |
TABLE 2A-continued
| | |
|---|---|
| 120. | 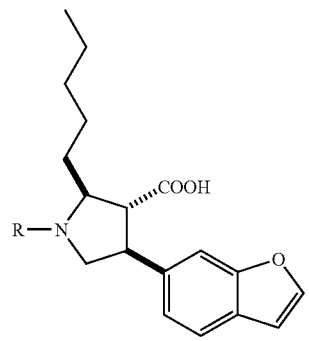 |
| 121. | 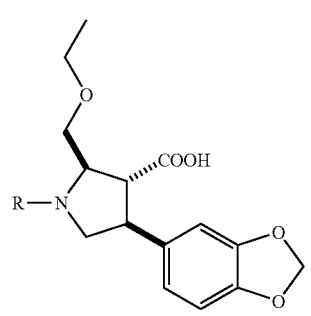 |
| 122. | 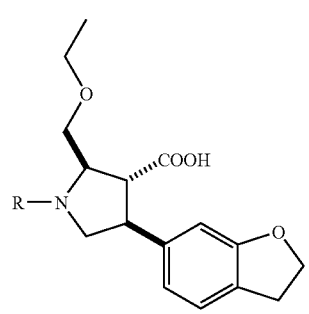 |
| 123. | 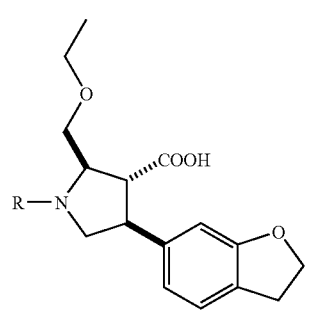 |
| 124. | 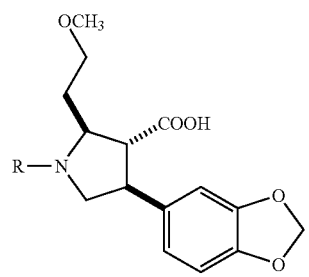 |

TABLE 2A-continued
| 125. | 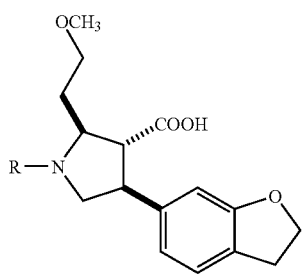 |
| --- | --- |
| 126. | 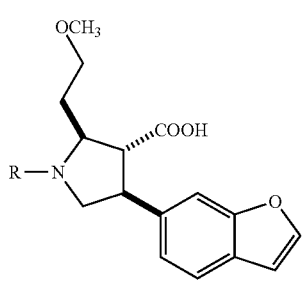 |
| 127. | 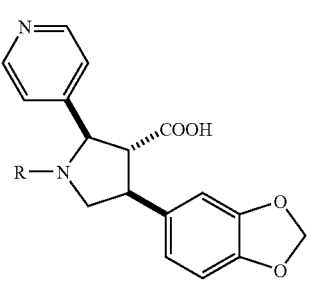 |
| 128. | 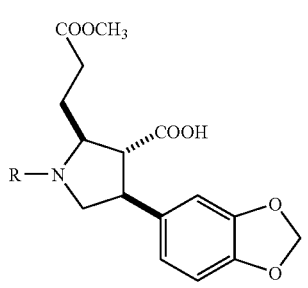 |
| 129. | 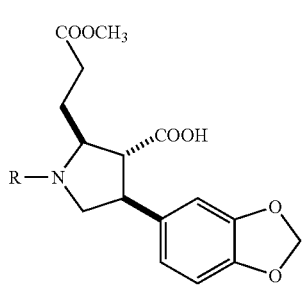 |
TABLE 2A-continued
| 130. | 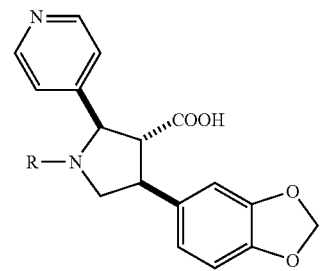 |
| --- | --- |
| 131. | 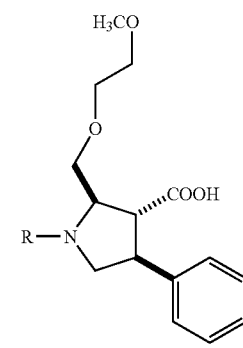 |
| 132. | 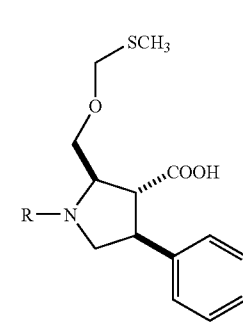 |
| 133. | 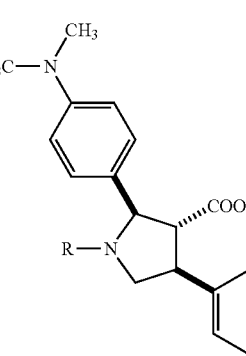 |
| 134. | 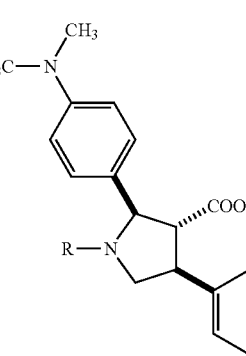 |

TABLE 2A-continued
| 135. | 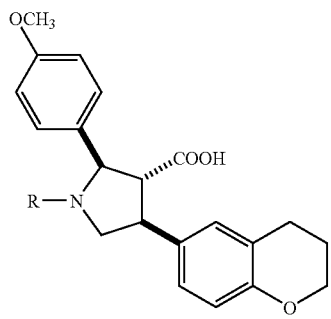 |
| --- | --- |
| 136. | 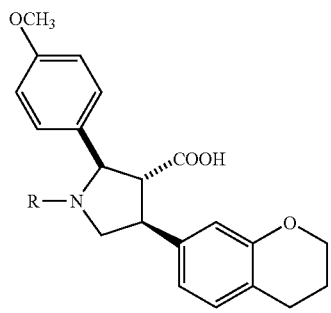 |
| 137. | 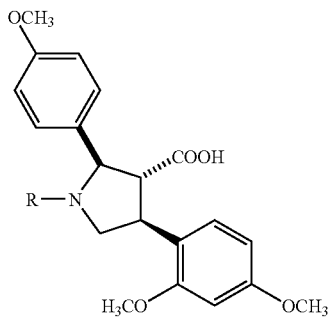 |
| 138. | 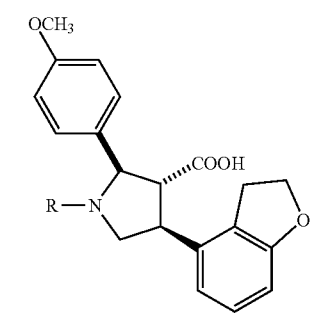 |
| 139. | 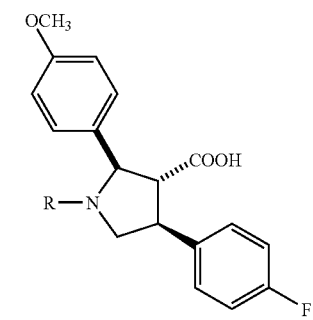 |
| 140. | 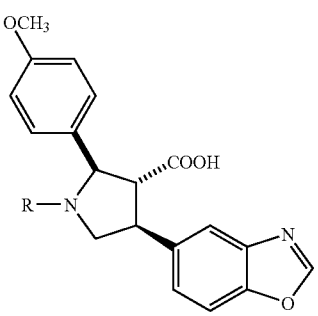 |
| 141. | 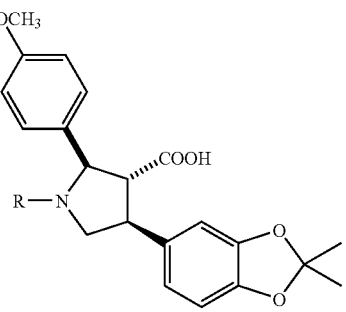 |
| 142. | 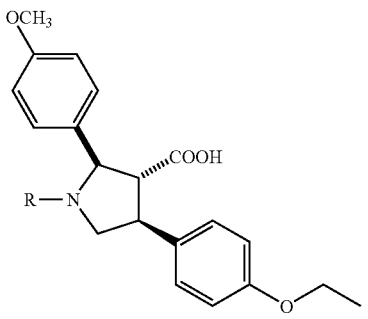 |
| 143. | 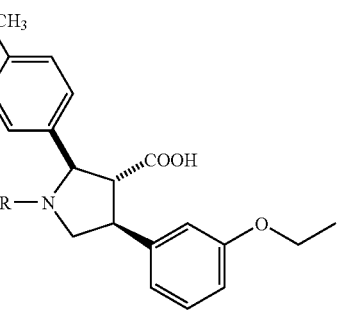 |
| 144. | 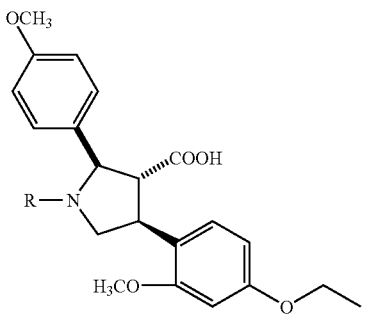 |

TABLE 2A-continued
145. 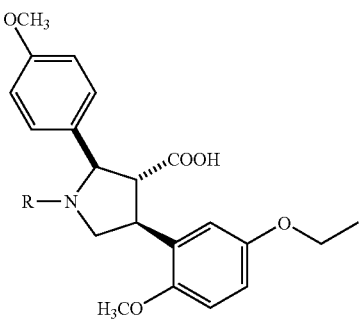
146. 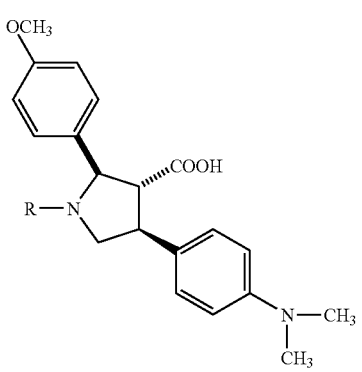
147. 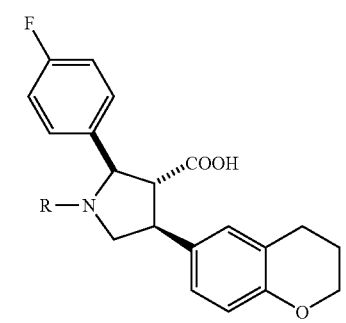
148. 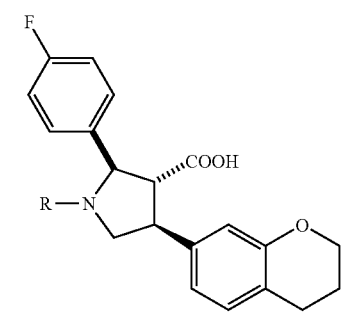
TABLE 2A-continued
149. 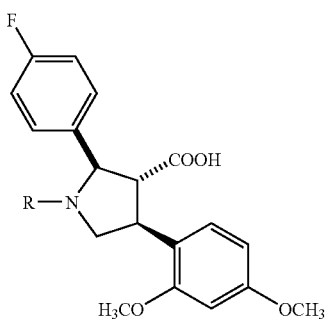
150. 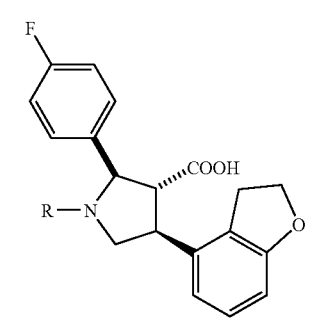
151. 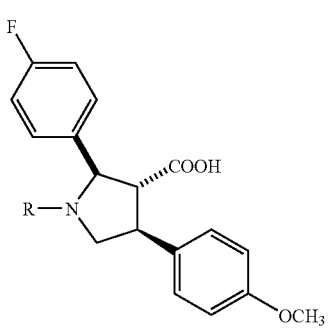
152. 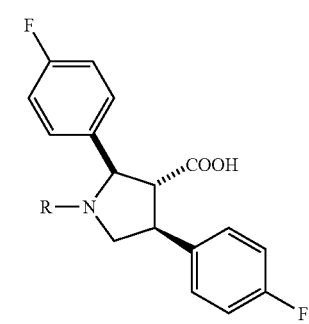
153. 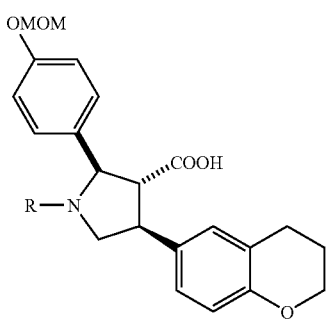

TABLE 2A-continued
| | | |
|---|---|---|
| 154. | 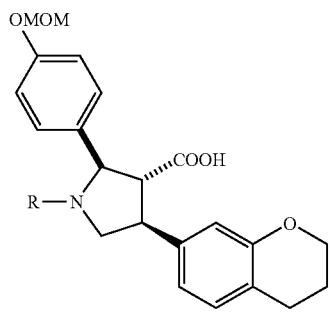 | |
| 155. | 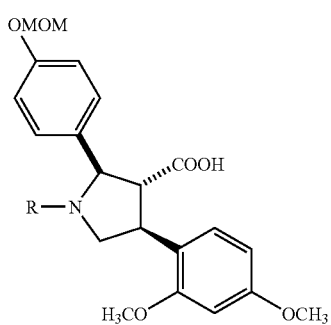 | |
| 156. | 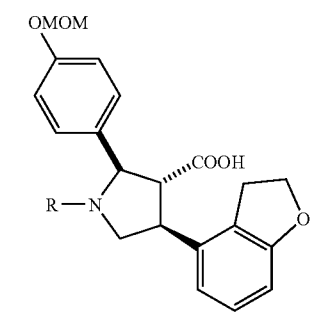 | |
| 157. | 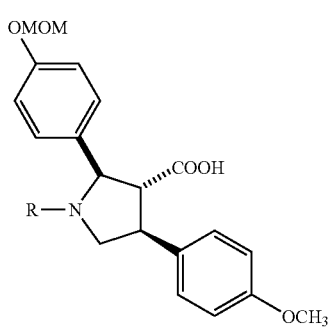 | |
| 158. | 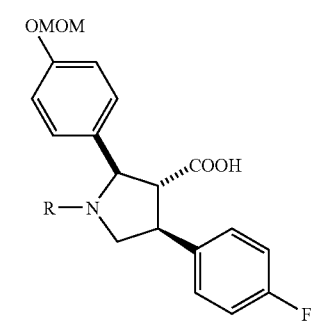 | |
TABLE 2A-continued
| | | |
|---|---|---|
| 159. | 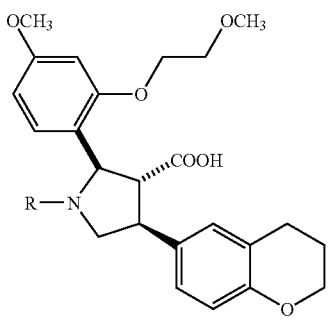 | |
| 160. | 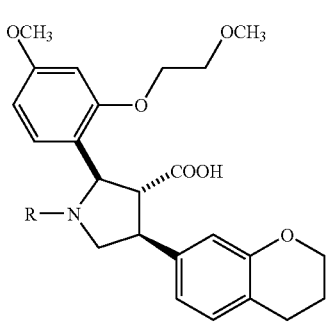 | |
| 161. | 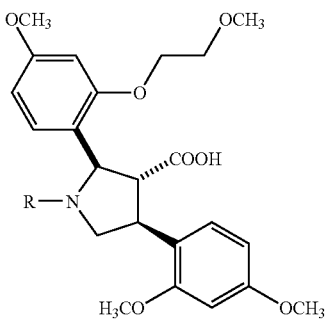 | |
| 162. | 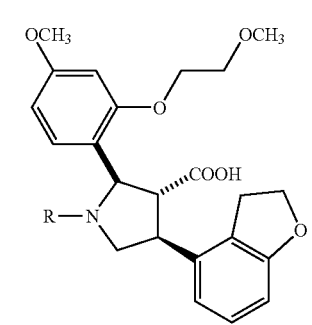 | |
| 163. | 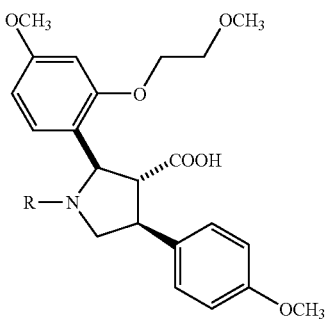 | |

TABLE 2A-continued
| | |
|---|---|
| 164. | 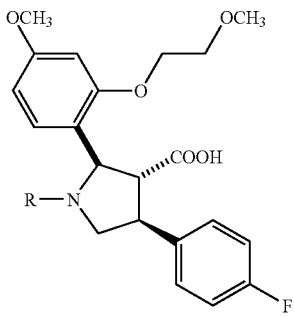 |
| 165. | 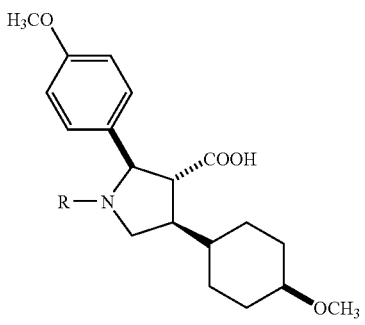 |
| 166. | 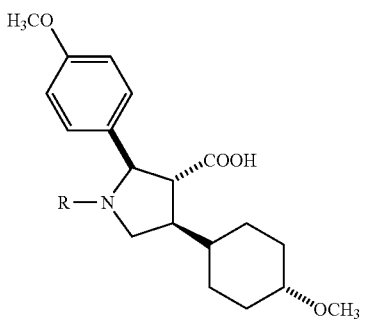 |
| 167. | 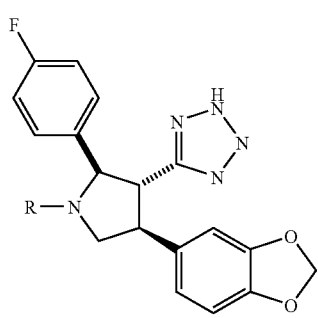 |
| 168. | 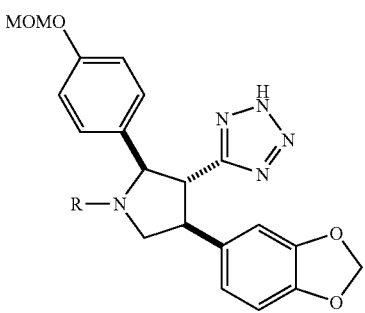 |
| 169. | 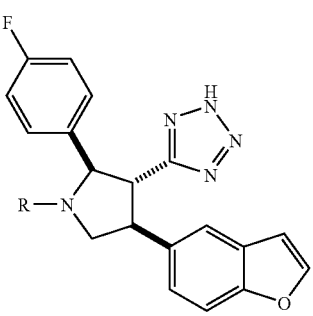 |
| 170. | 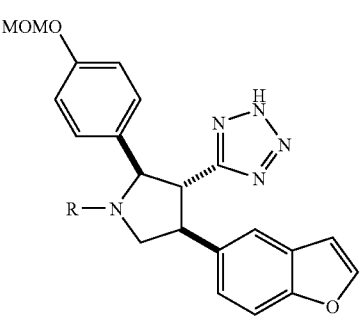 |
| 171. | 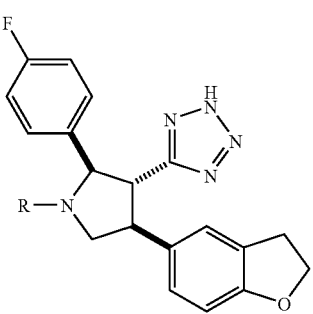 |
| 172. | 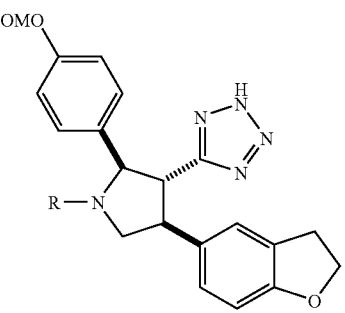 |
| 173. | 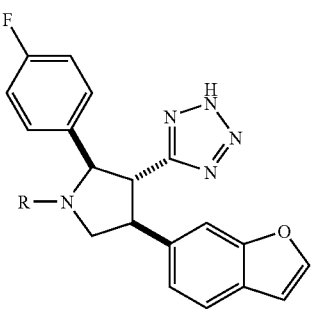 |

TABLE 2A-continued
174. 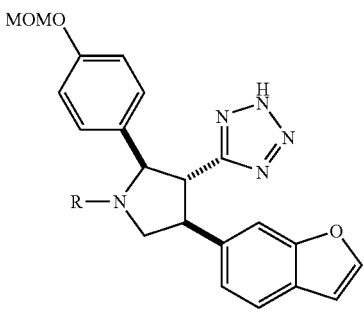
175. 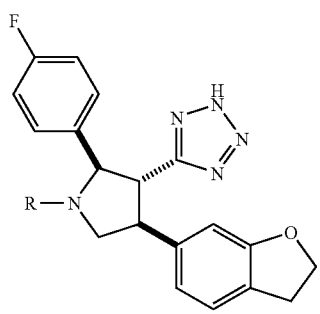
176. 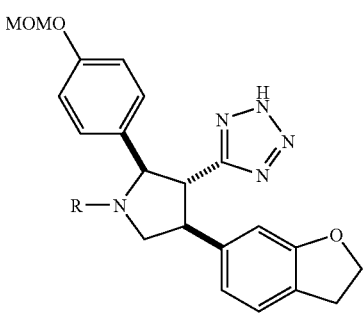
177. 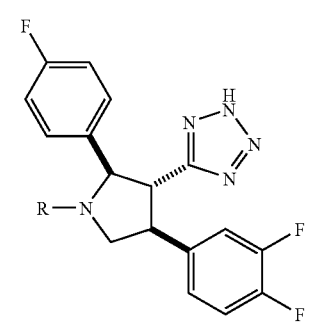
178. 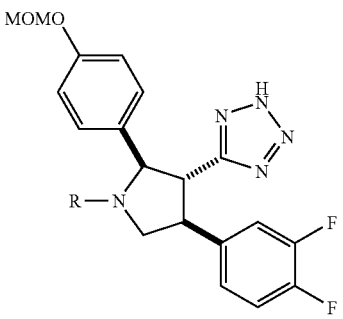
TABLE 2A-continued
179. 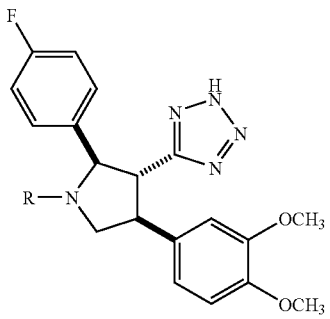
180. 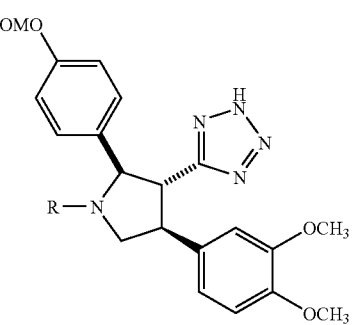
181. 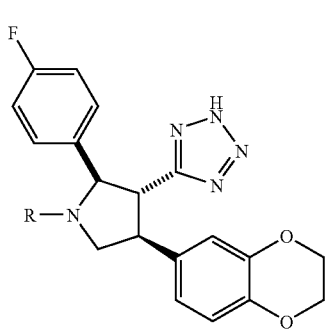
182. 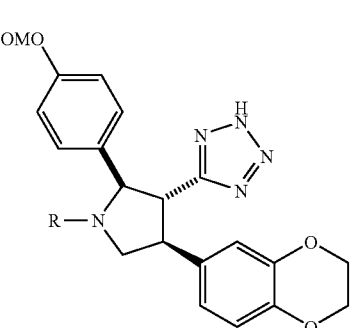
183. 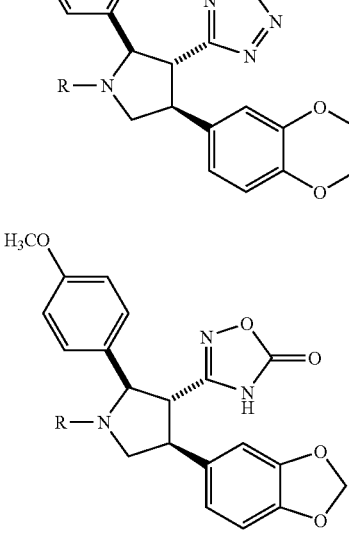

TABLE 2A-continued
184. 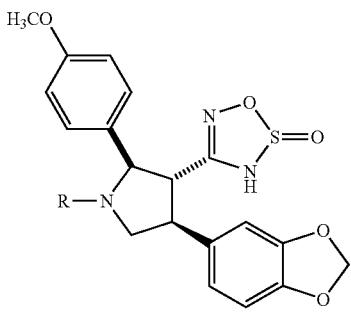
185. 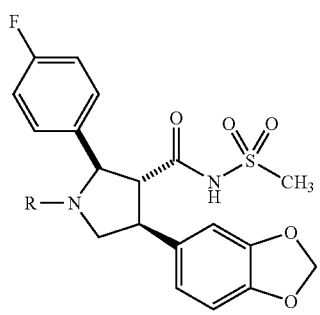
186. 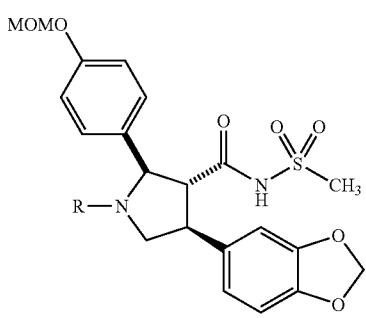
187. 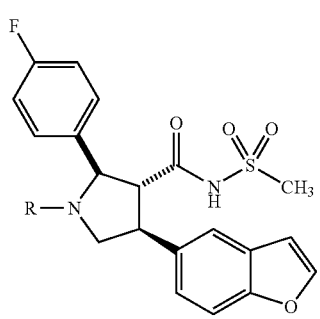
188. 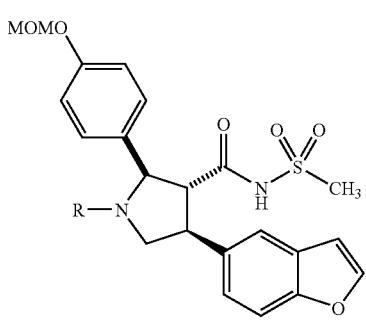
TABLE 2A-continued
189. 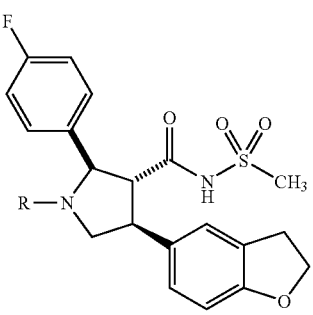
190. 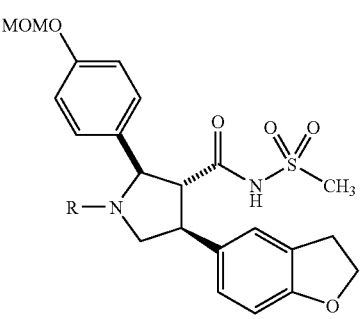
191. 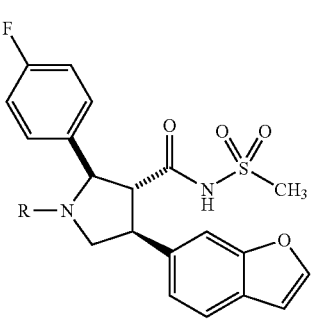
192. 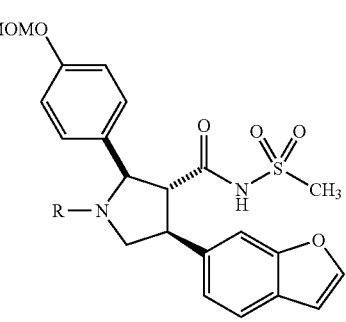
193. 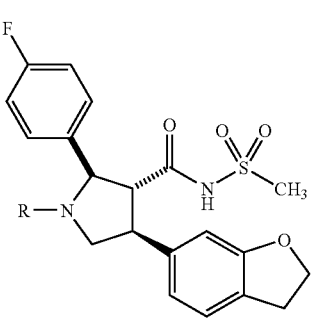

US 7,208,517 B1
TABLE 2A-continued
| 194. | 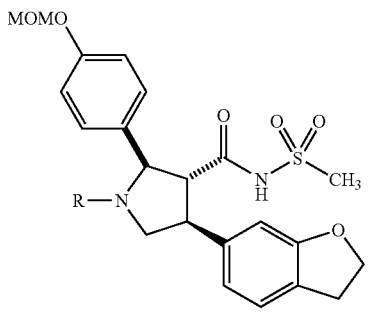 |
| --- | --- |
| 195. | 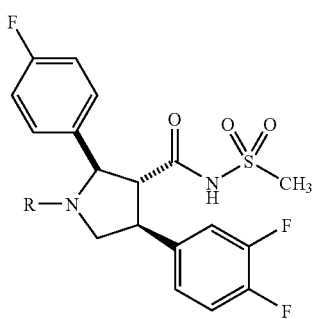 |
| 196. | 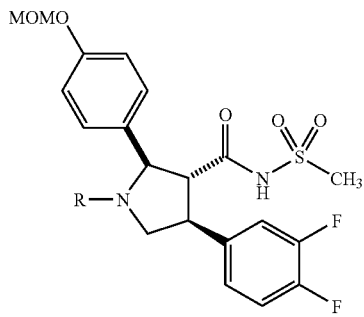 |
| 197. | 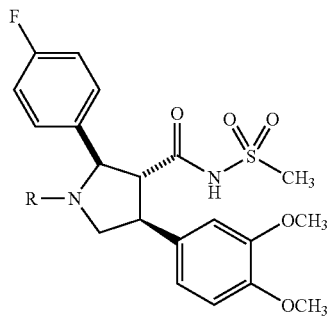 |
| 198. | 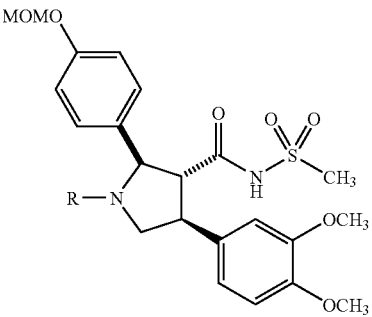 |
TABLE 2A-continued
| 199. | 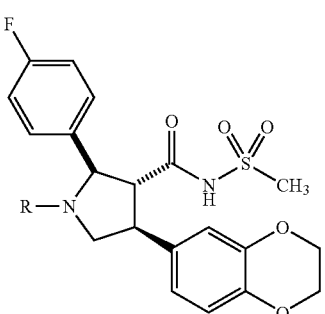 |
| --- | --- |
| 200. | 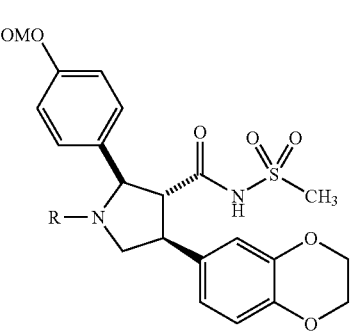 |
| 201. | 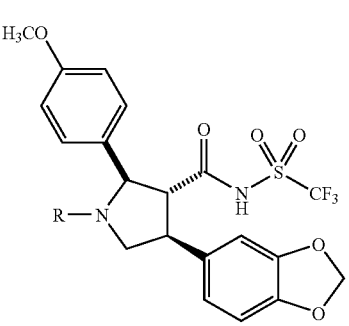 |
| 202. | 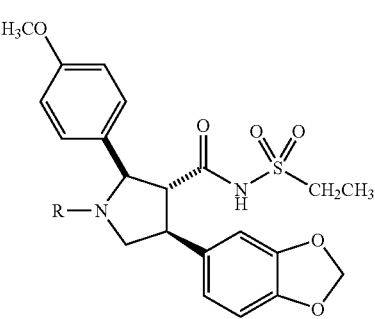 |
| 203. | 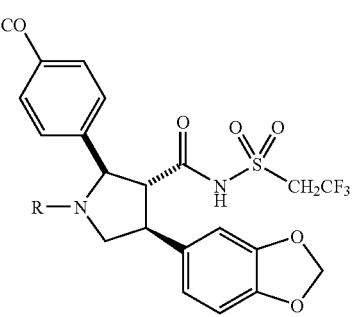 |

TABLE 2A-continued
204. 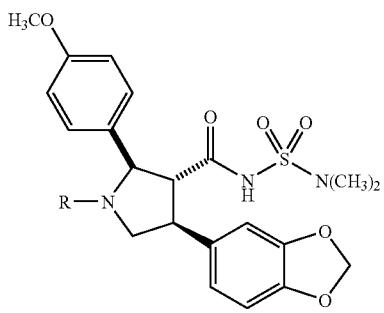
205. 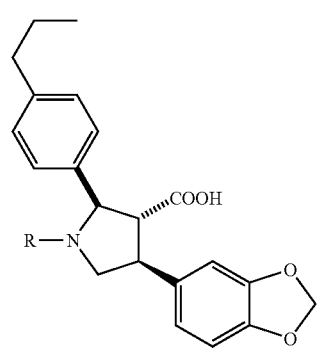
206. 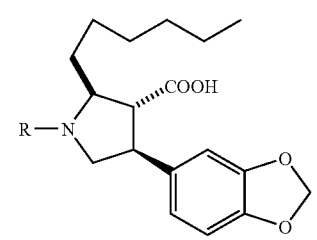
207. 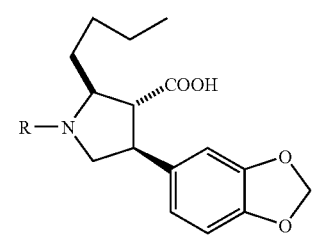
208. 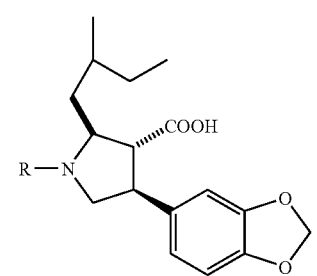
TABLE 2A-continued
209. 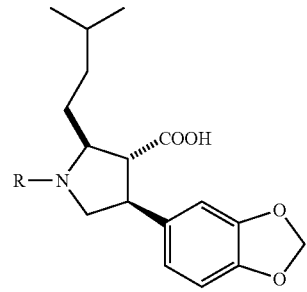
210. 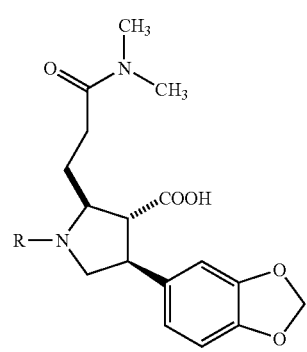
211. 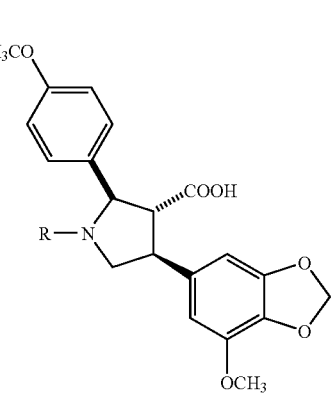
212. 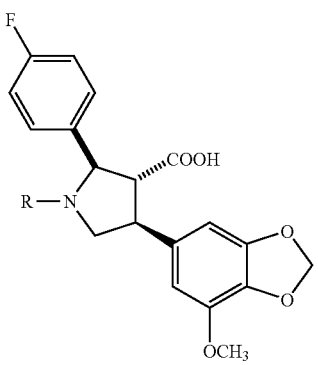

TABLE 2A-continued
| 213. | 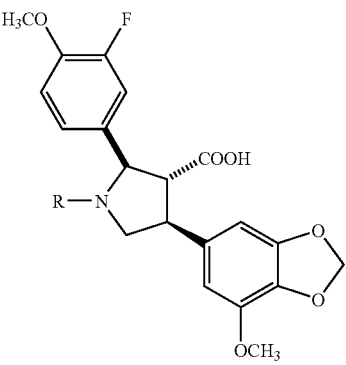 |
| --- | --- |
| 214. | 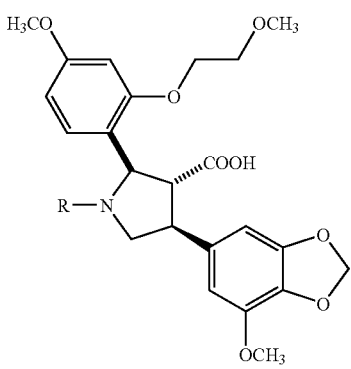 |
| 215. | 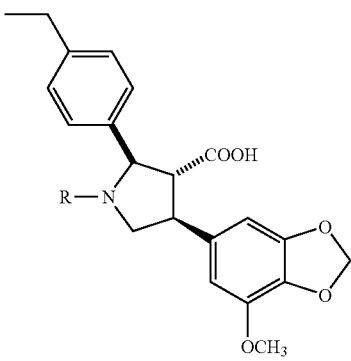 |
| 216. | 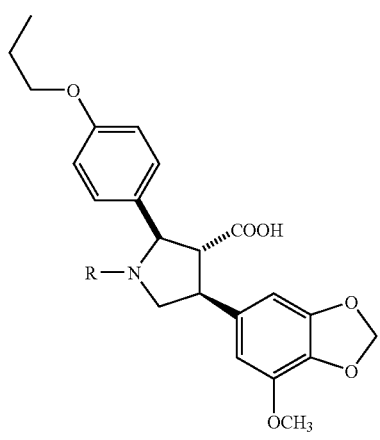 |
| 217. | 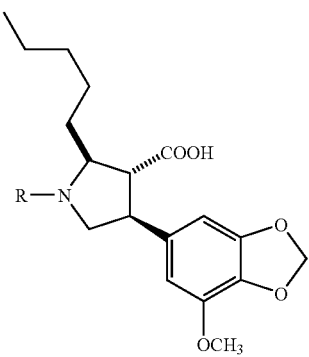 |
| 218. | 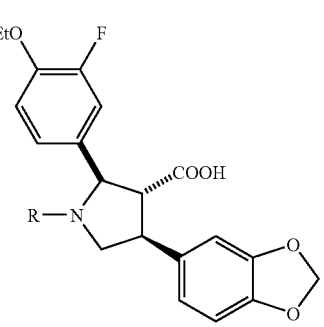 |
| 219. | 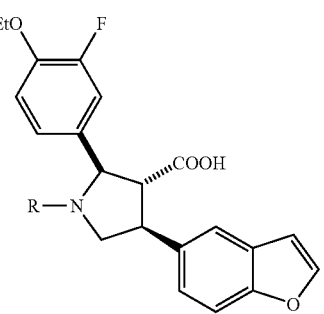 |
| 220. | 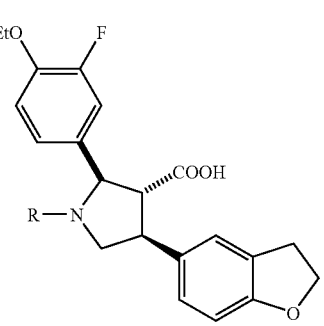 |
| 221. | 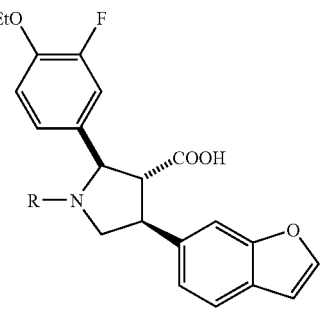 |

TABLE 2A-continued
222. 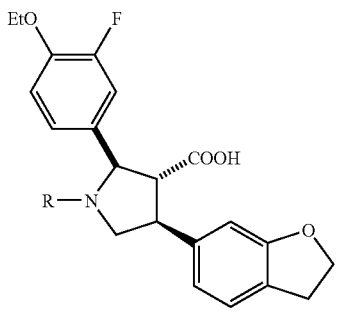
223. 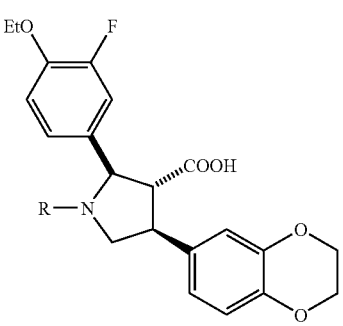
224. 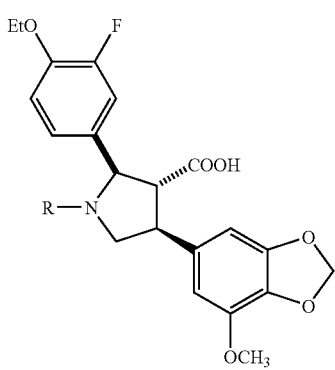
225. 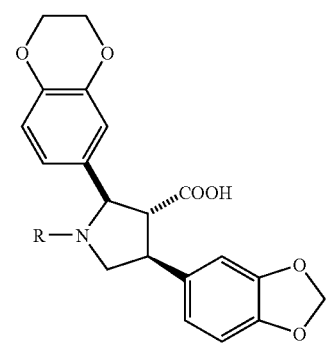
TABLE 2A-continued
226. 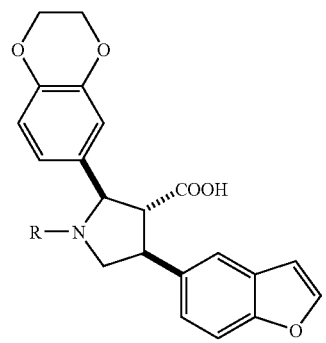
227. 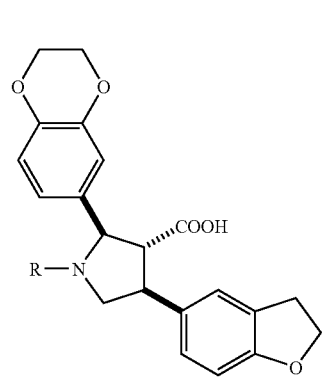
228. 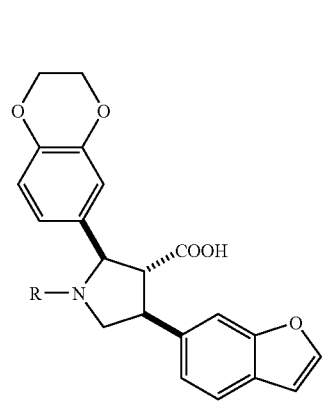
229. 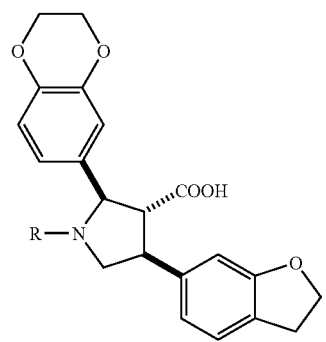

TABLE 2A-continued
| | |
|---|---|
| 230. | 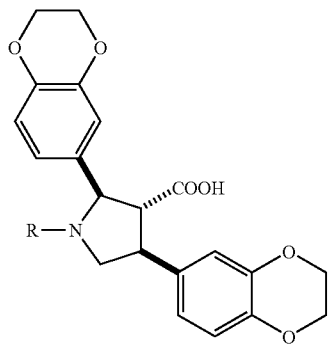 |
| 231. | 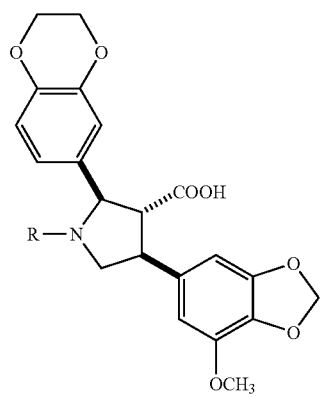 |
| 232. | 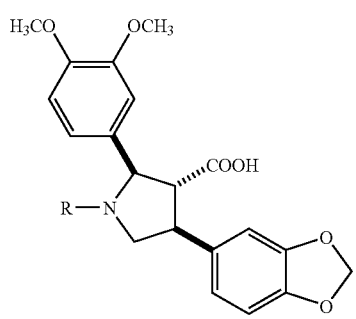 |
| 233. | 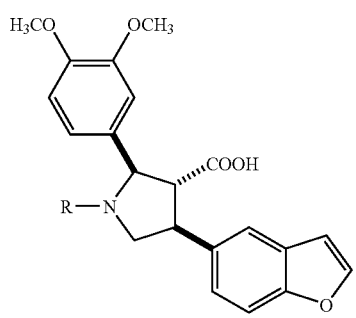 |
TABLE 2A-continued
| | |
|---|---|
| 234. | 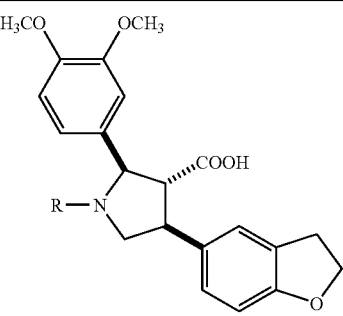 |
| 235. | 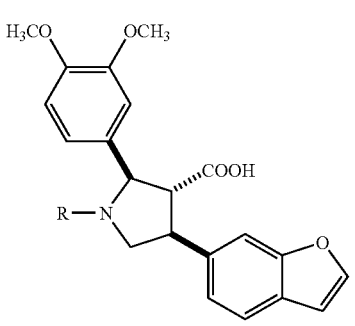 |
| 236. | 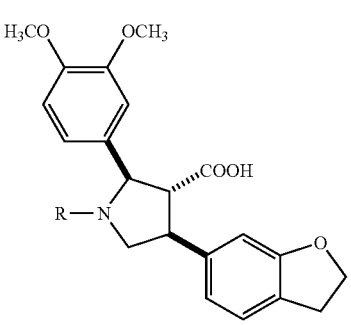 |
| 237. | 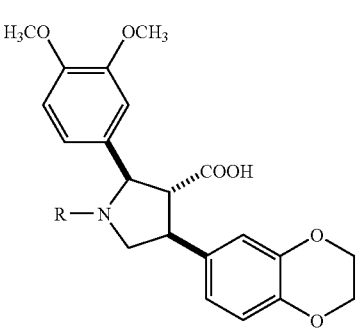 |
| 238. | 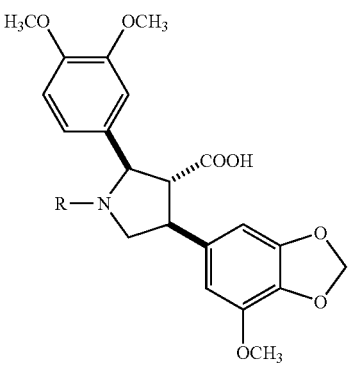 |

TABLE 2A-continued
239. 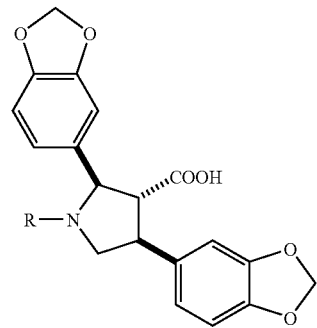
240. 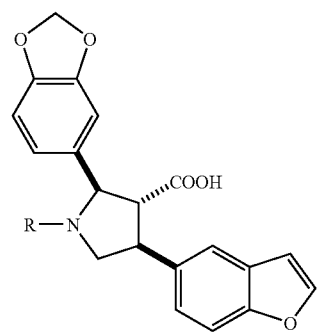
241. 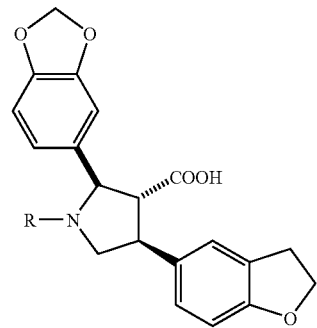
242. 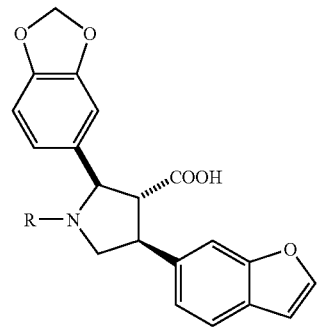
TABLE 2A-continued
243. 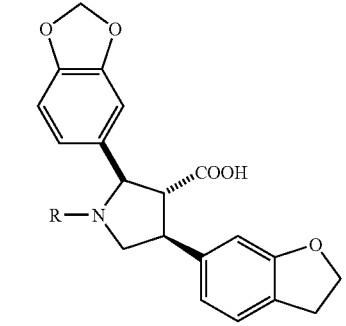
244. 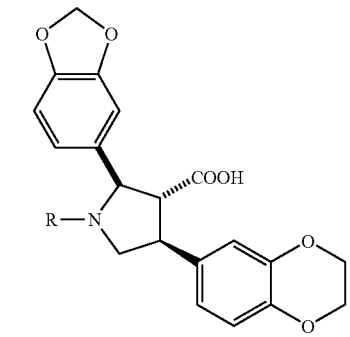
245. 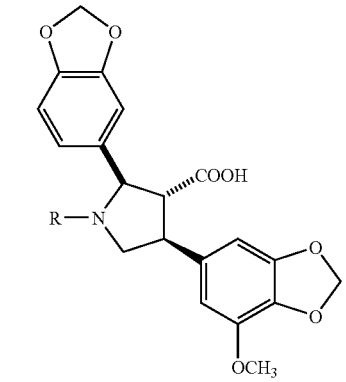
246. 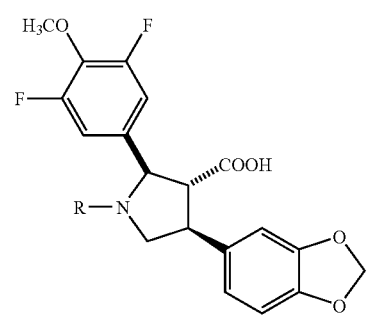

TABLE 2A-continued
247. 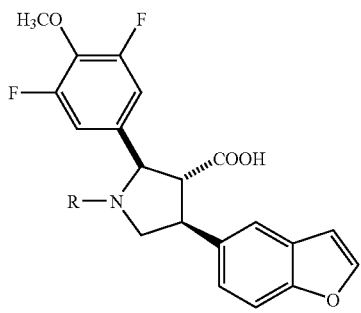
248. 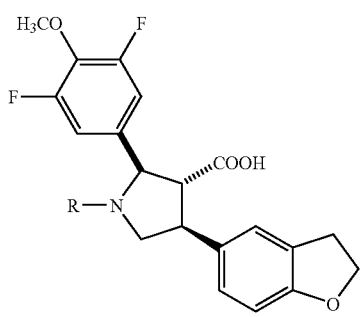
249. 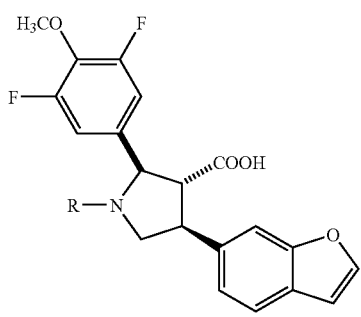
250. 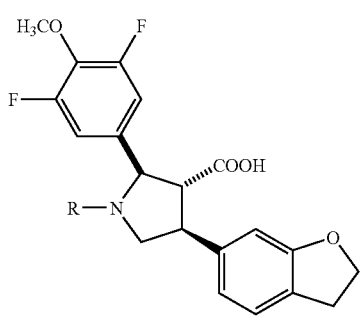
251. 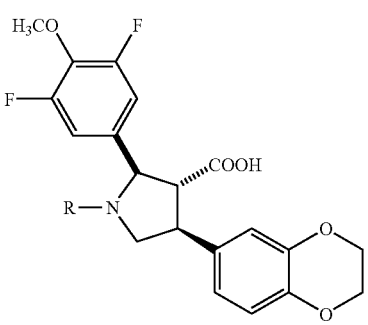
TABLE 2A-continued
252. 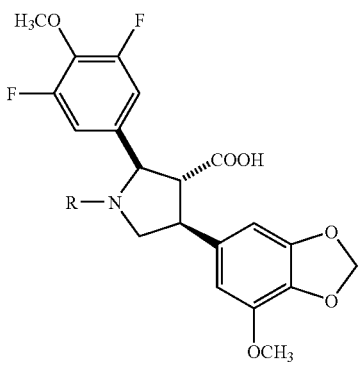
253. 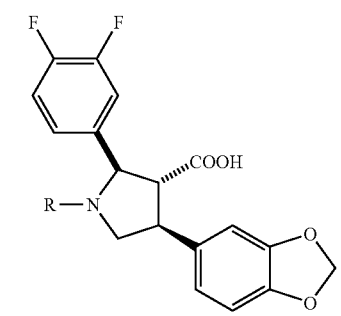
254. 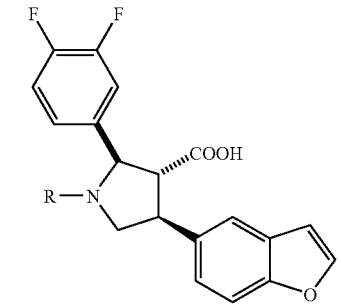
255. 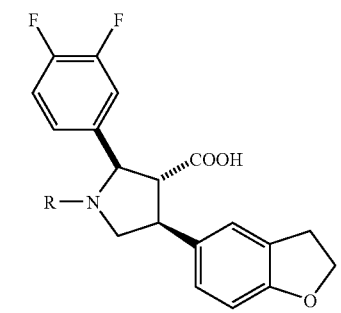
256. 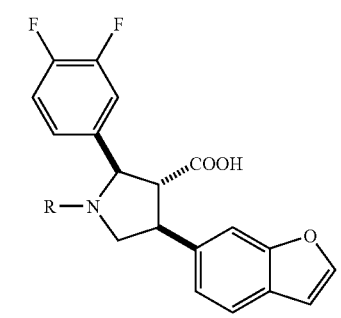

TABLE 2A-continued
257. 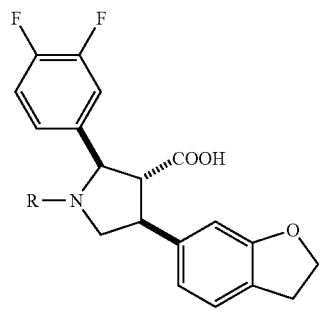
258. 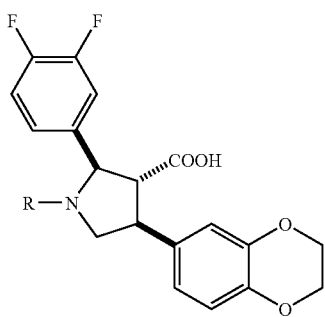
259. 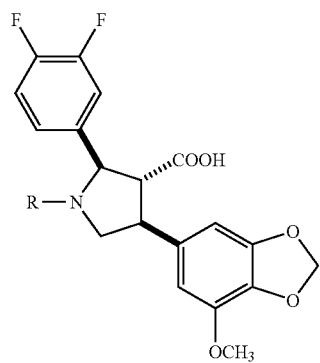
260. 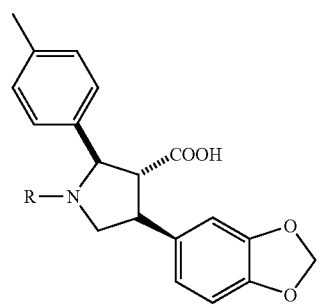
261. 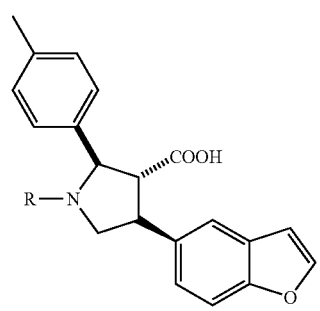
TABLE 2A-continued
262. 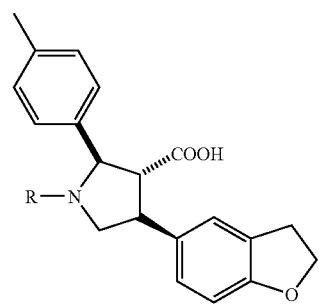
263. 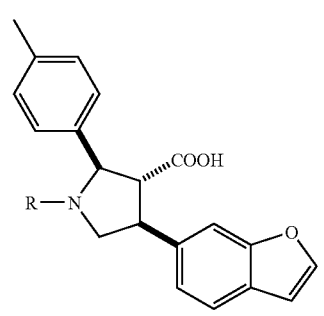
264. 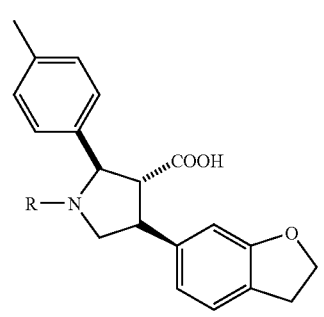
265. 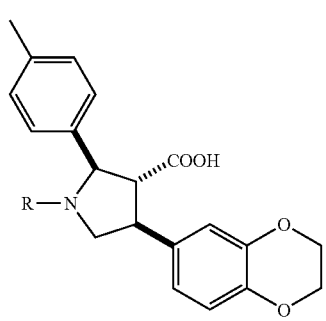
266. 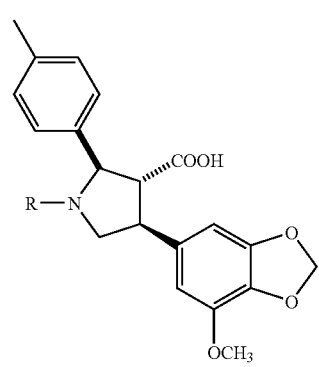

TABLE 2A-continued
267. 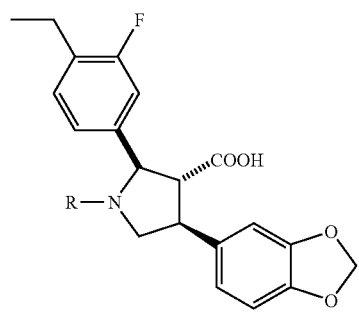
268. 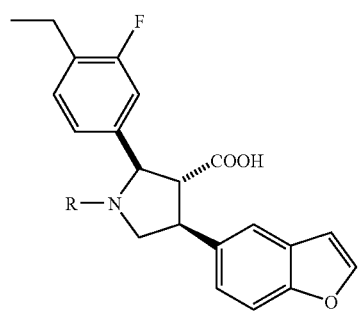
269. 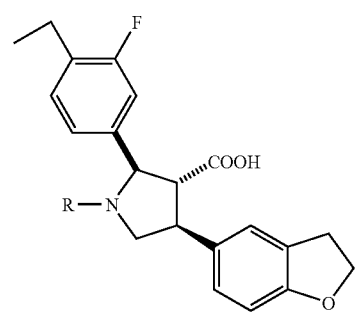
270. 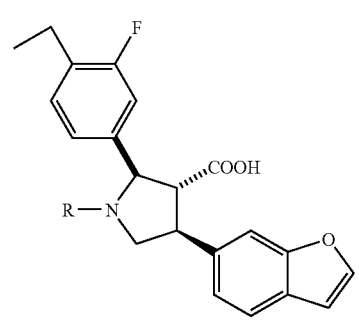
271. 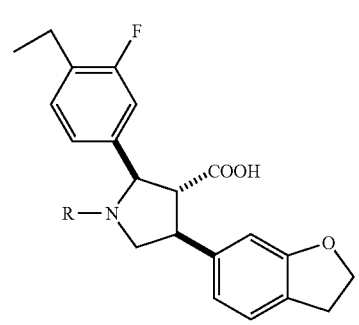
TABLE 2A-continued
272. 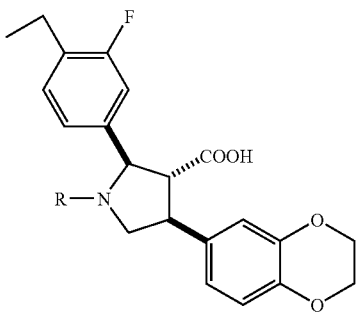
273. 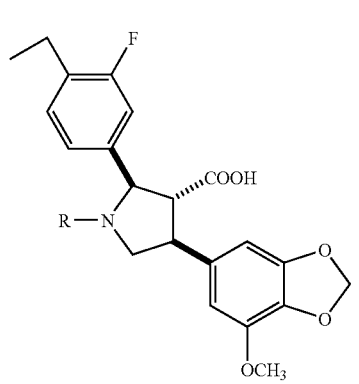
274. 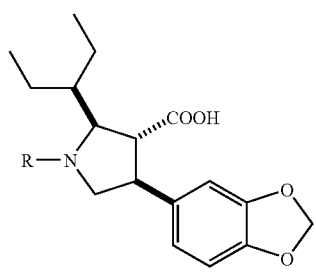
275. 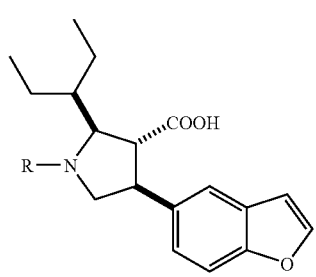
276. 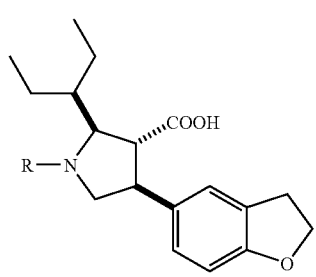

TABLE 2A-continued
277. 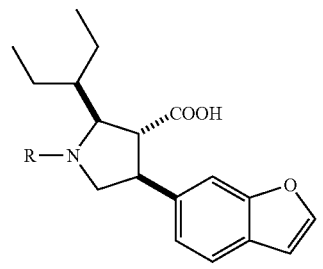
278. 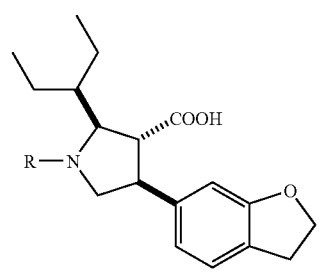
279. 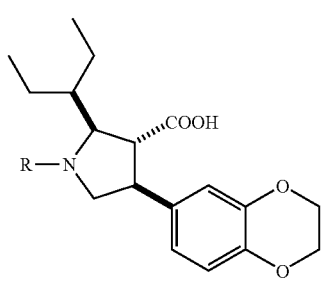
280. 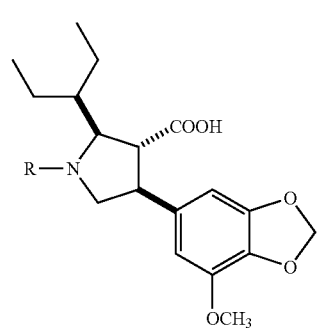
281. 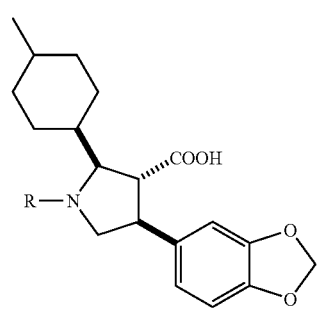
TABLE 2A-continued
282. 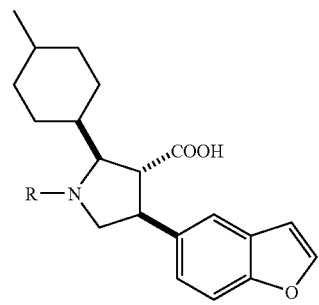
283. 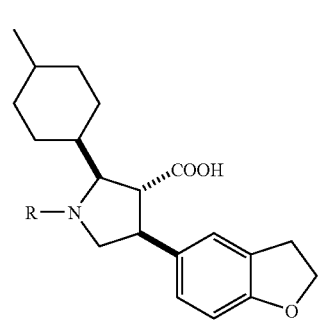
284. 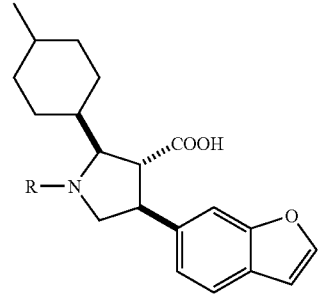
285. 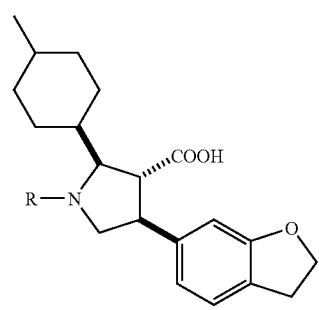
286. 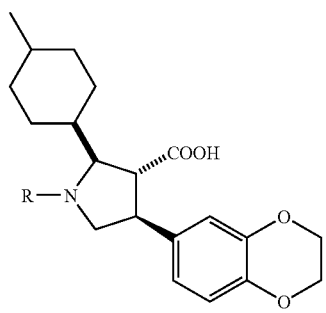

TABLE 2A-continued
287. 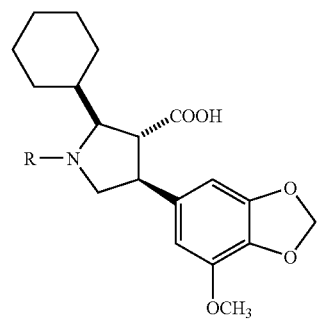
288. 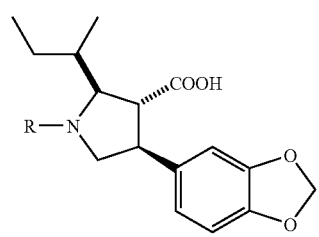
289. 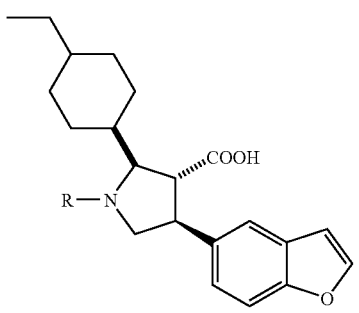
290. 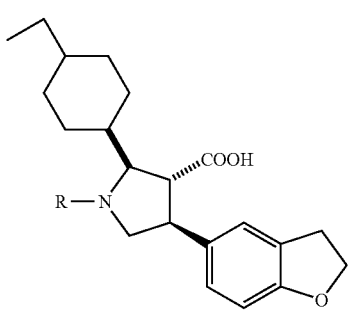
291. 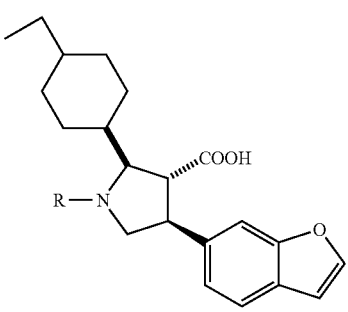
TABLE 2A-continued
292. 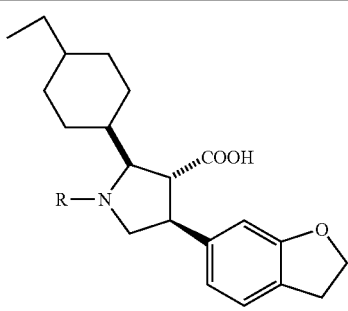
293. 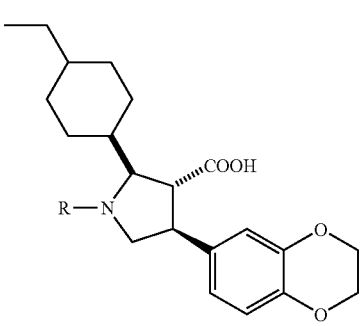
294. 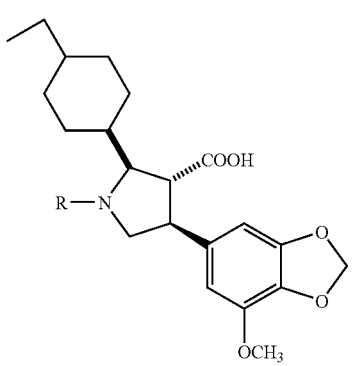
295. 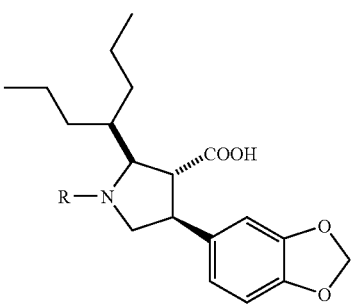
296. 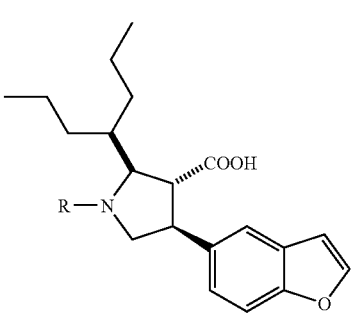

TABLE 2A-continued
| | |
|---|---|
| 297. | 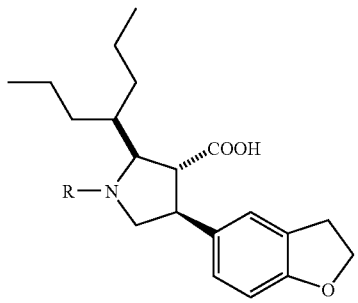 |
| 298. | 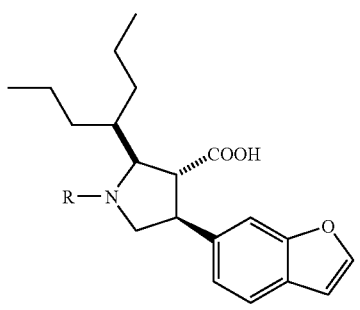 |
| 299. | 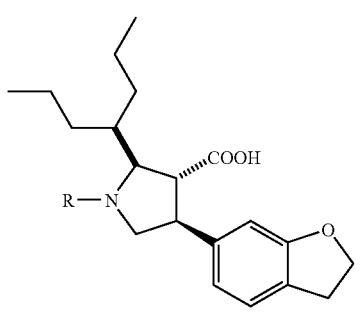 |
| 300. | 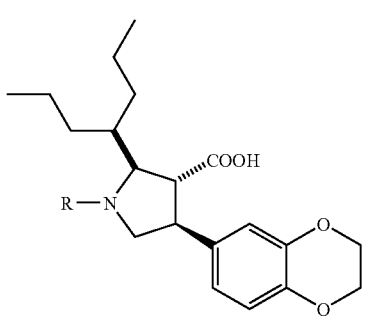 |
| 301. | 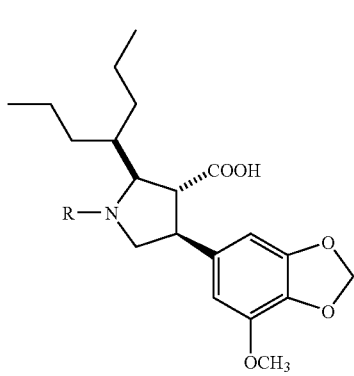 |
TABLE 2A-continued
| | |
|---|---|
| 302. | 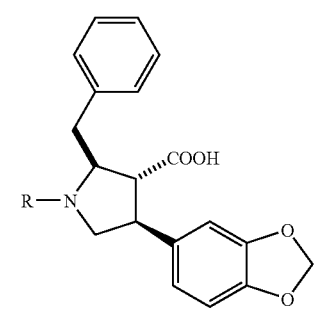 |
| 303. | 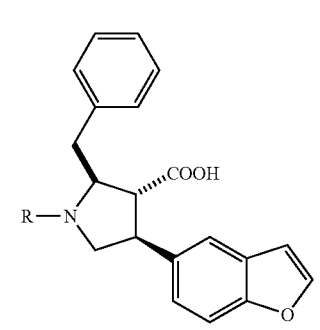 |
| 304. | 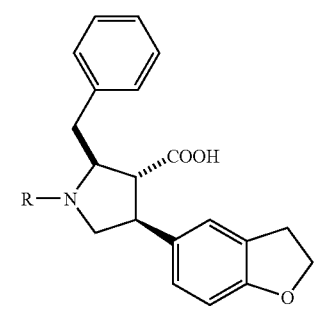 |
| 305. | 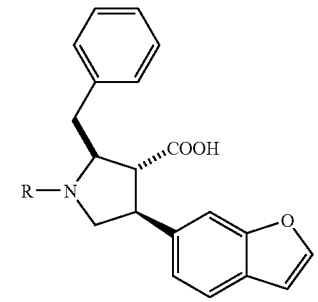 |
| 306. | 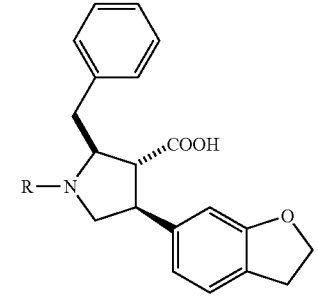 |

TABLE 2A-continued
307. 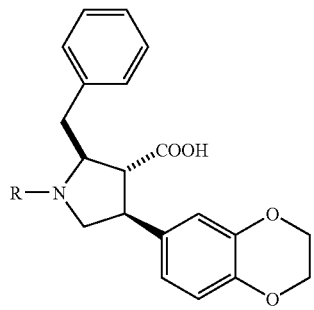
308. 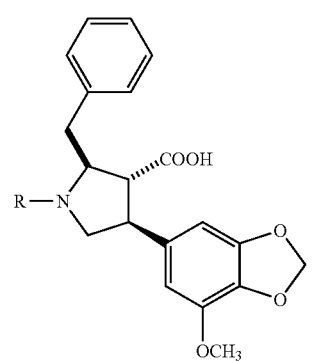
309. 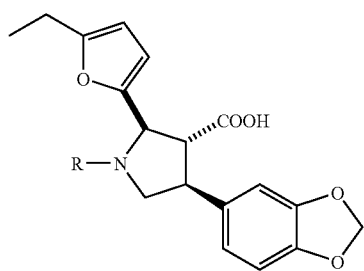
310. 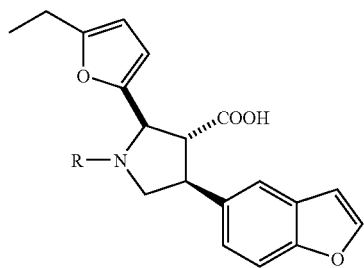
311. 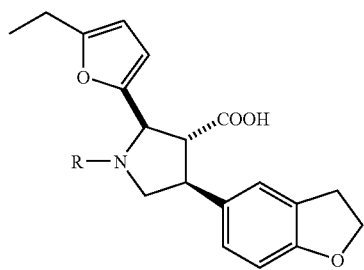
312. 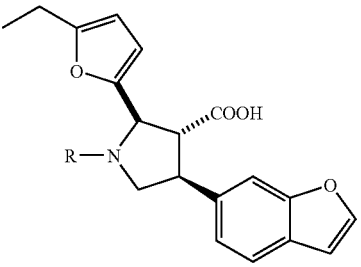
313. 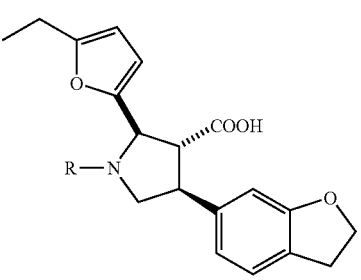
314. 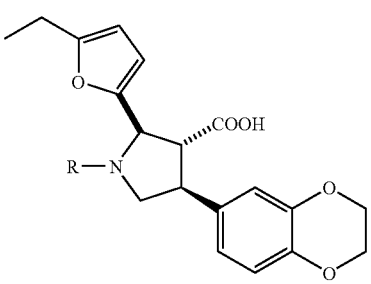
315. 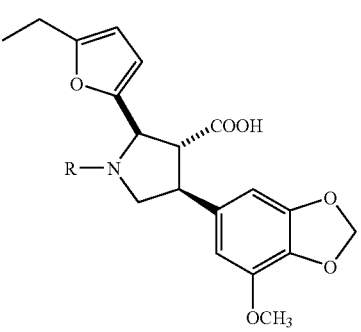
316. 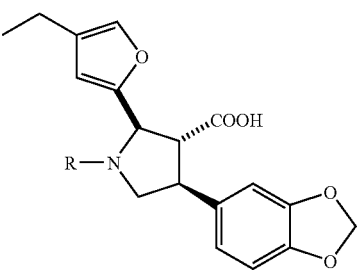

TABLE 2A-continued
317. 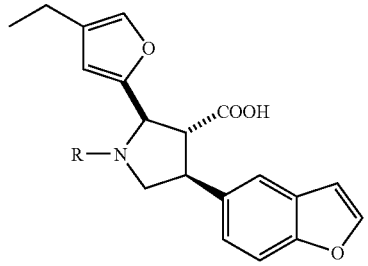
318. 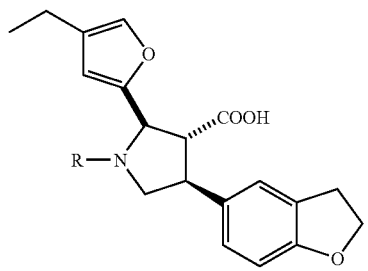
319. 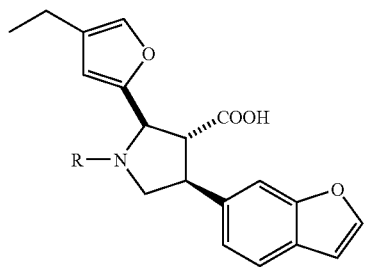
320. 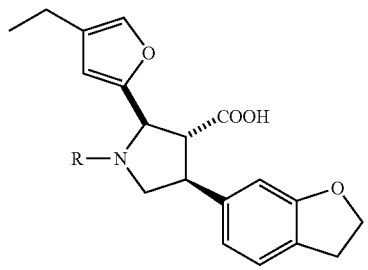
321. 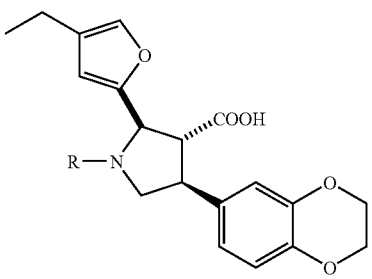
TABLE 2A-continued
322. 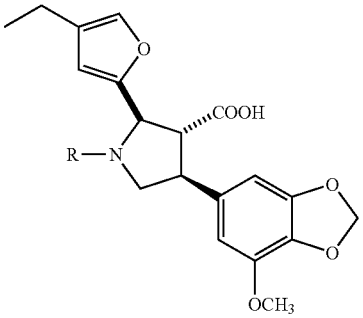
323. 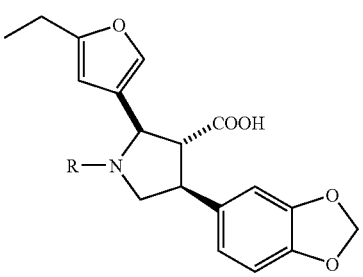
324. 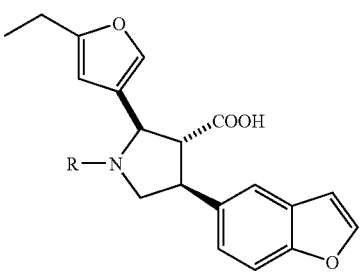
325. 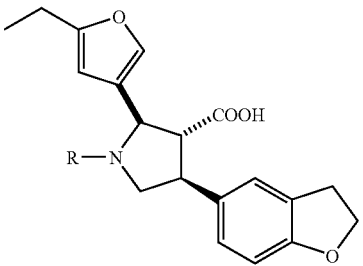
326. 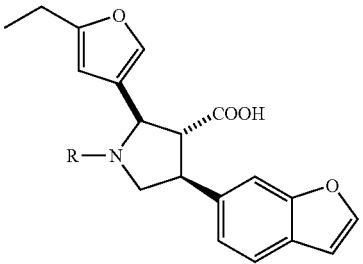

TABLE 2A-continued
327. 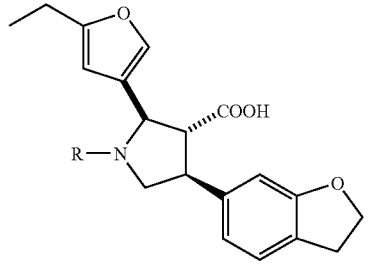
328. 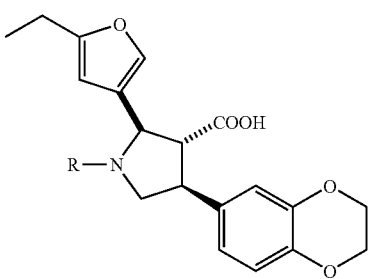
329. 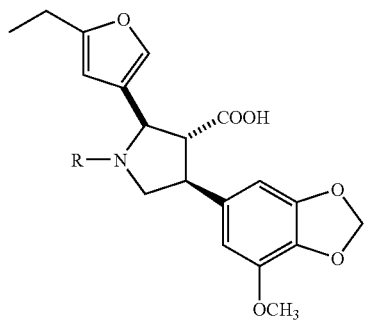
330. 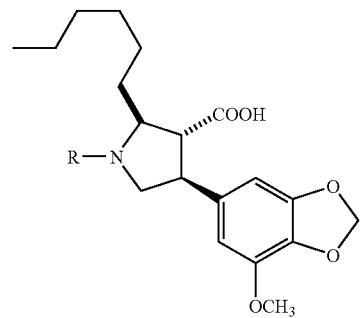
331. 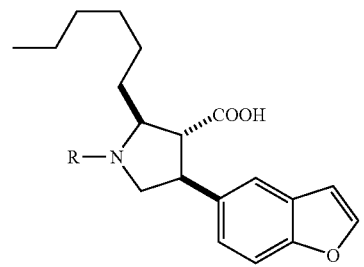
TABLE 2A-continued
332. 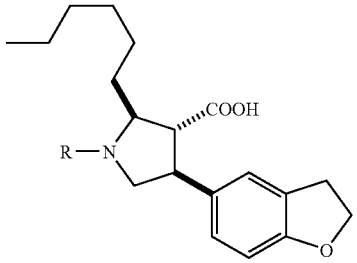
333. 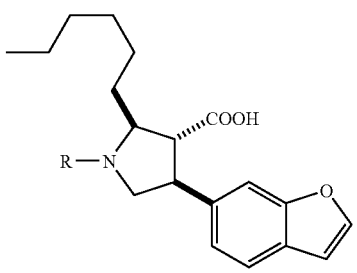
334. 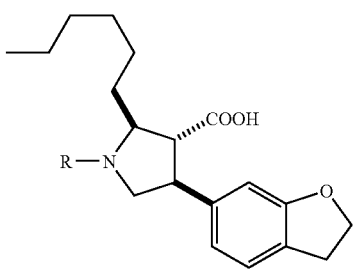
335. 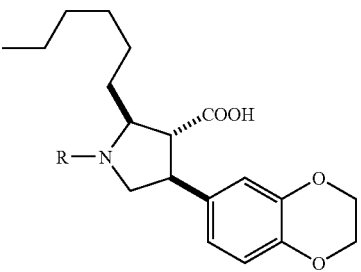
336. 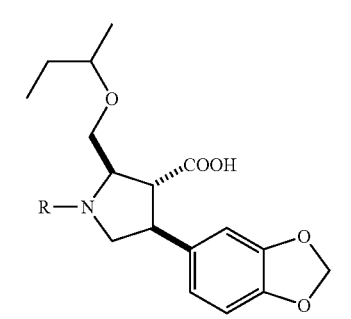

TABLE 2A-continued
| | |
|---|---|
| 337. | 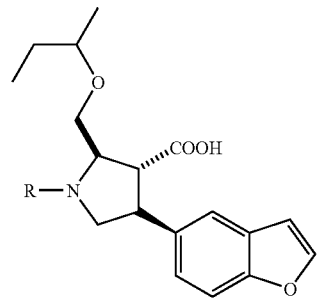 |
| 338. | 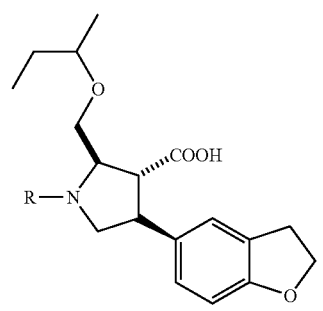 |
| 339. | 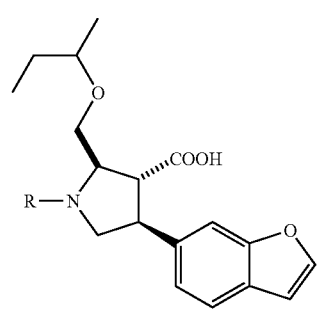 |
| 340. | 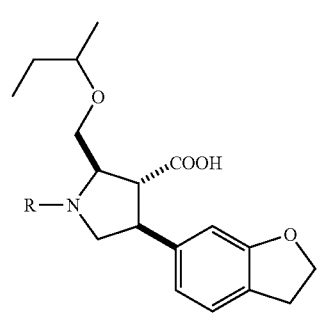 |
| 341. | 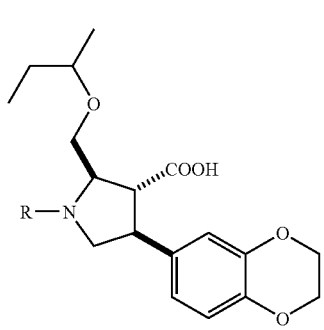 |
TABLE 2A-continued
| | |
|---|---|
| 342. | 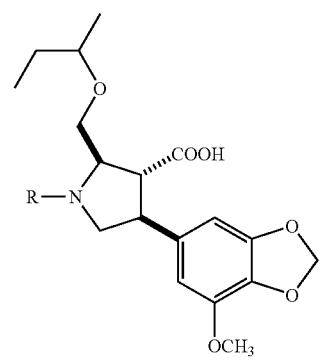 |
| 343. | 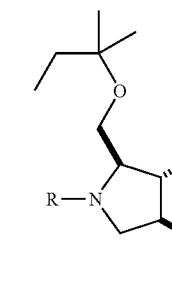 |
| 344. | 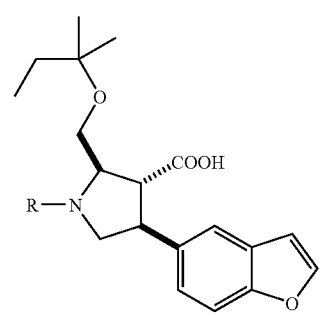 |
| 345. | 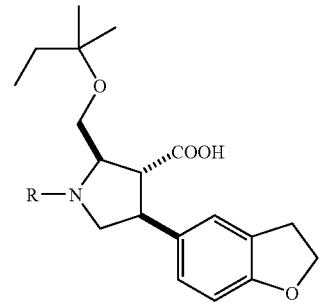 |
| 346. | 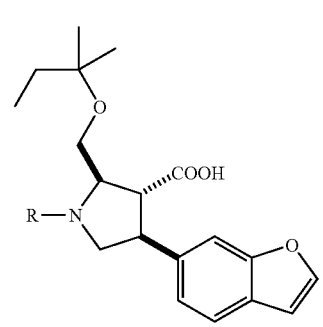 |

TABLE 2A-continued
| | |
|---|---|
| 347. | 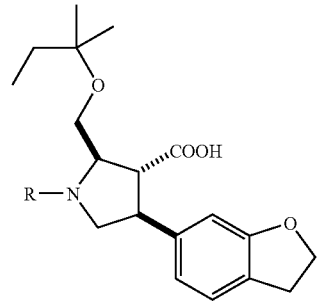 |
| 348. | 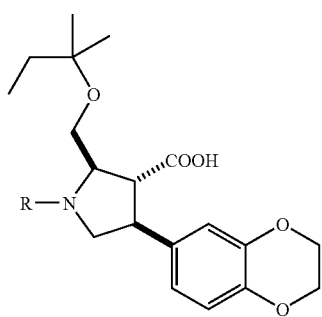 |
| 349. | 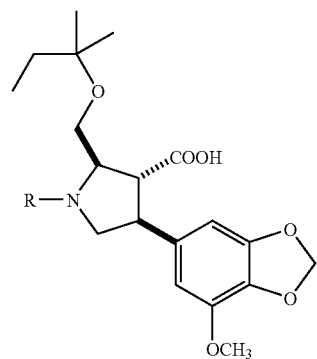 |
| 350. | 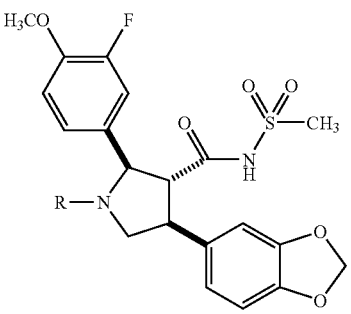 |
| 351. | 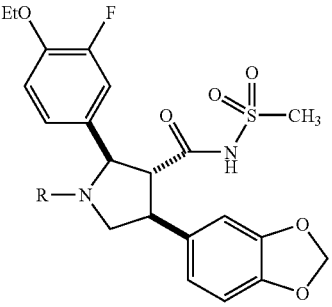 |
TABLE 2A-continued
| | |
|---|---|
| 352. | 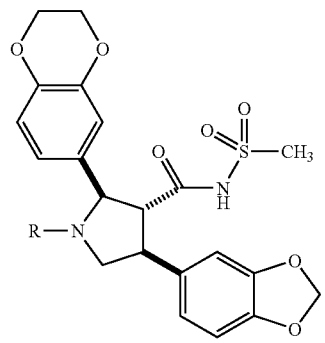 |
| 353. | 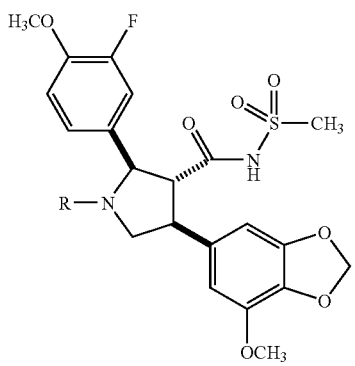 |
| 354. | 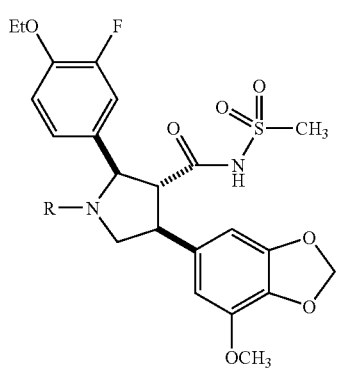 |
| 355. | 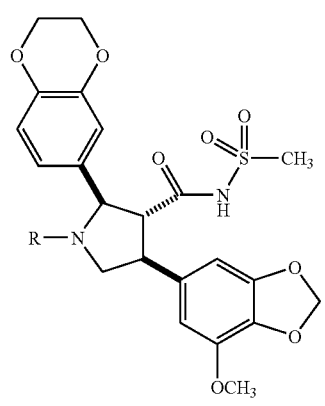 |

TABLE 2A-continued
356. 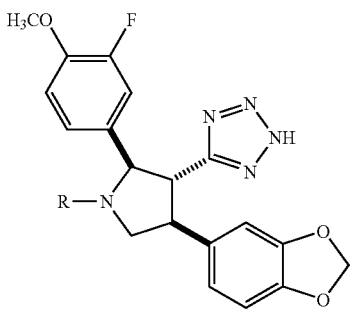
357. 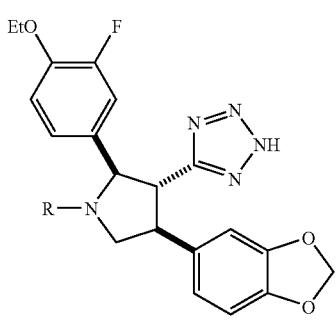
358. 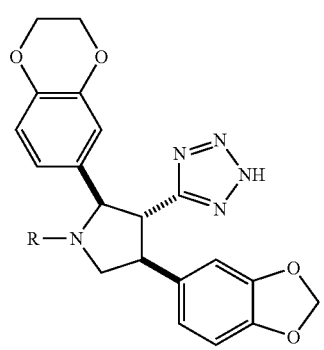
359. 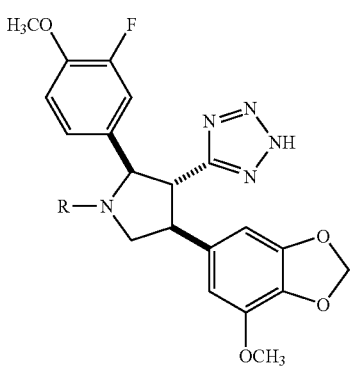
TABLE 2A-continued
360. 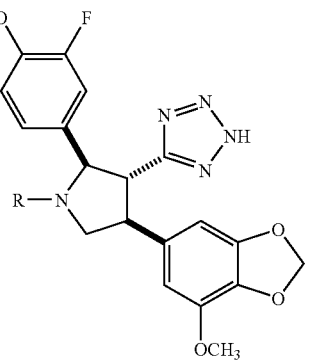
361. 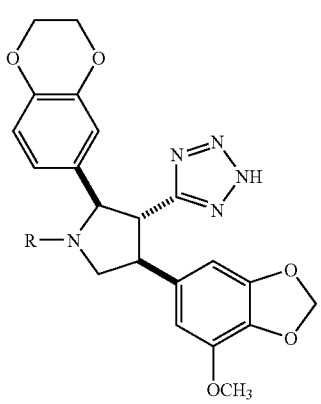
362. 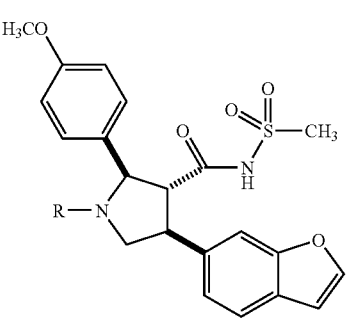
363. 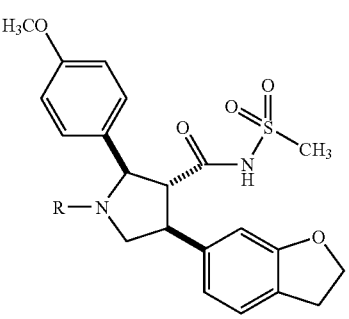

TABLE 2A-continued
| 364. | 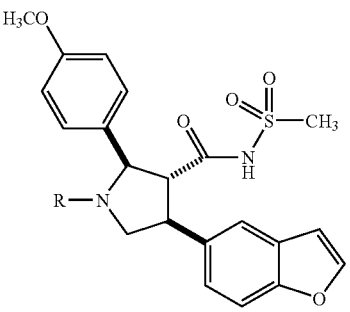 |
| --- | --- |
| 365. | 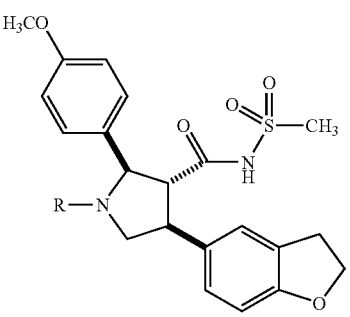 |
| 366. | 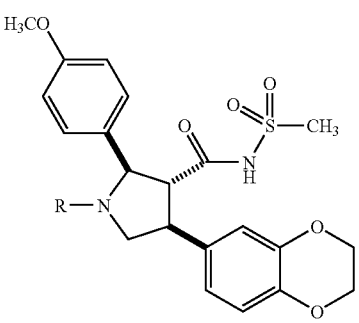 |
| 367. | 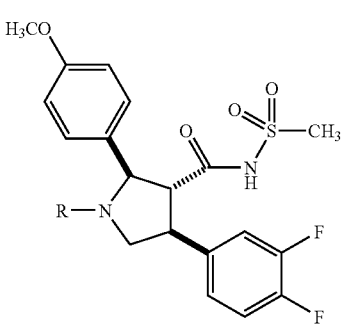 |
| 368. | 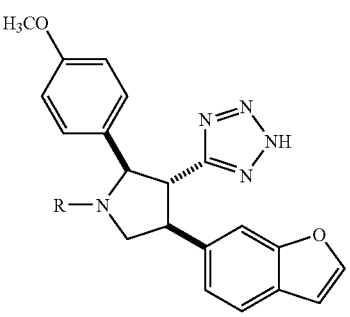 |
TABLE 2A-continued
| 369. | 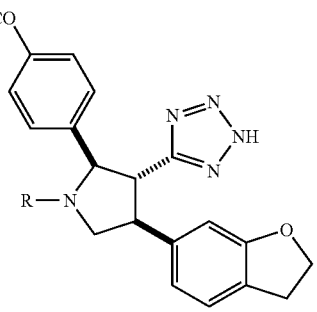 |
| --- | --- |
| 370. | 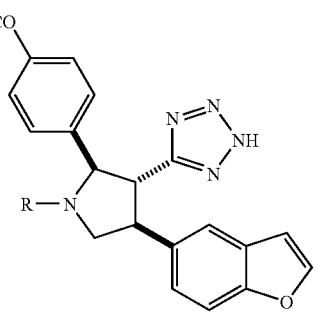 |
| 371. | 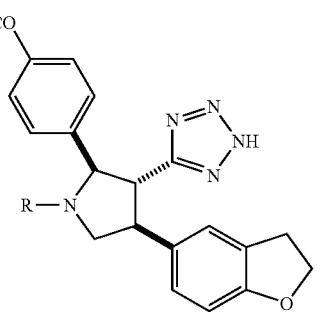 |
| 372. | 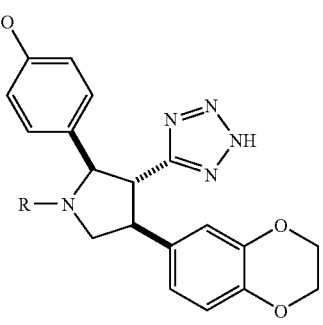 |
| 373. | 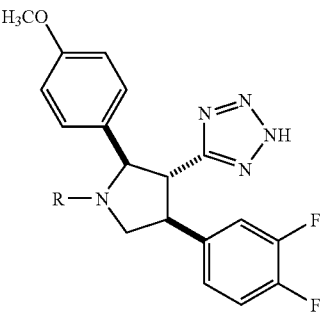 |

TABLE 2A-continued
374. 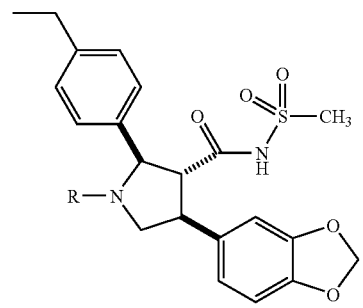
375. 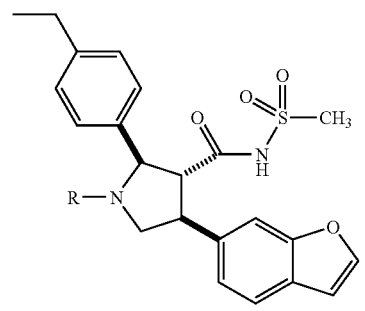
376. 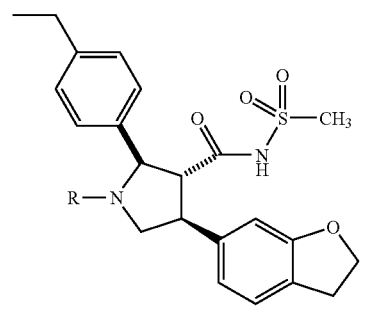
377. 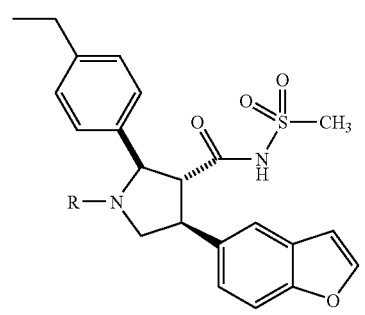
378. 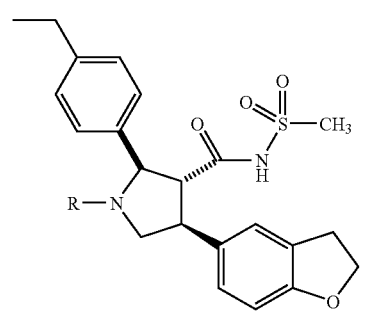
TABLE 2A-continued
379. 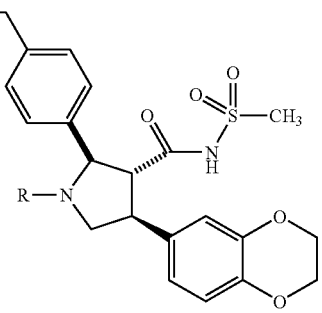
380. 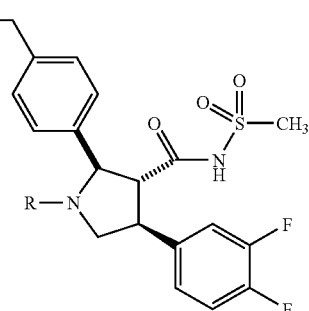
381. 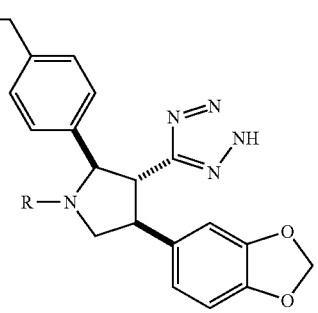
382. 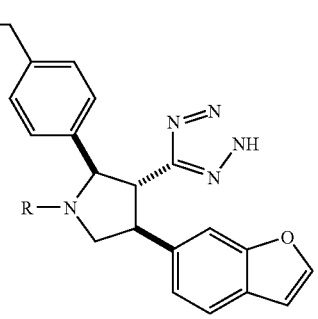
383. 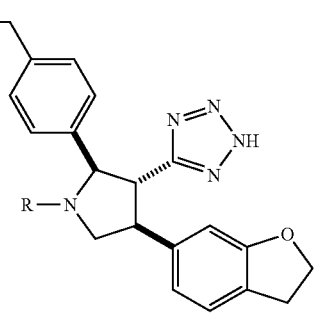

TABLE 2A-continued
384. 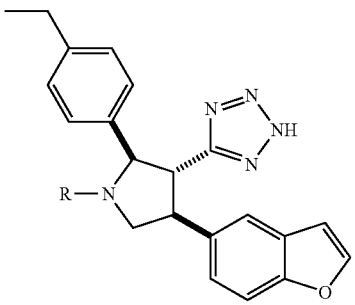
385. 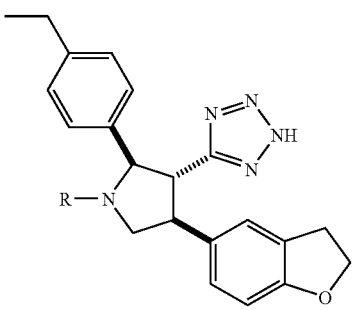
386. 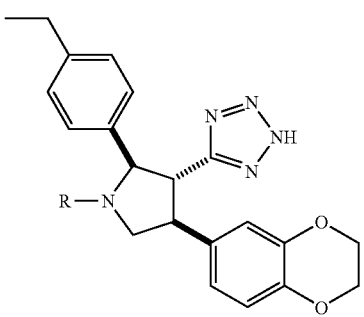
387. 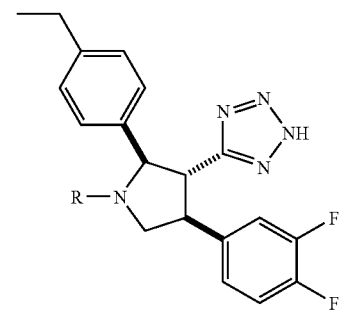
388. 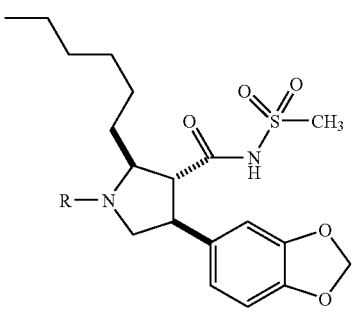
TABLE 2A-continued
389. 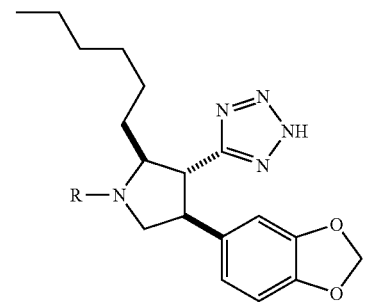
390. 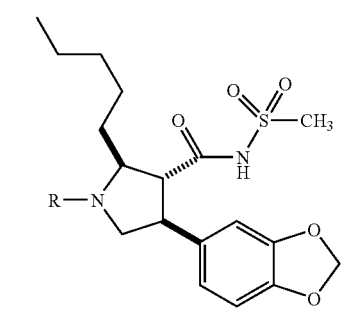
391. 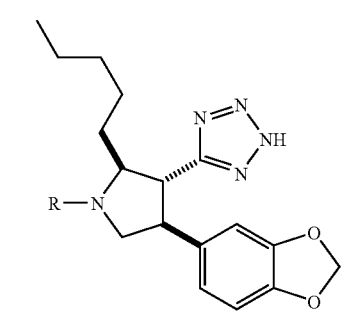
392. 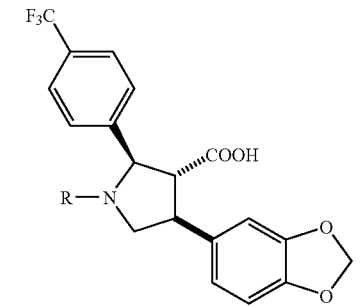
393. 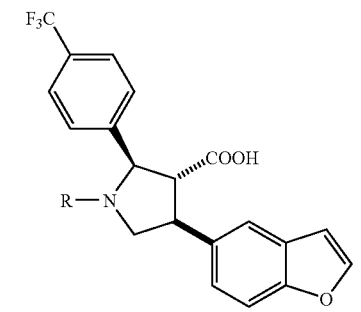

TABLE 2A-continued
| | | |
|---|---|---|
| 394. | 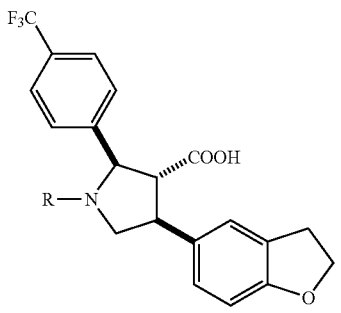 | |
| 395. | 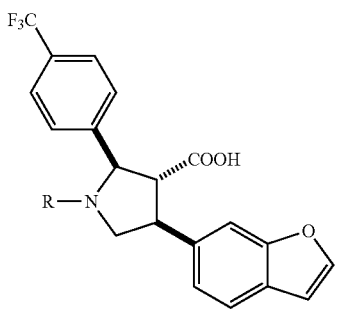 | |
| 396. | 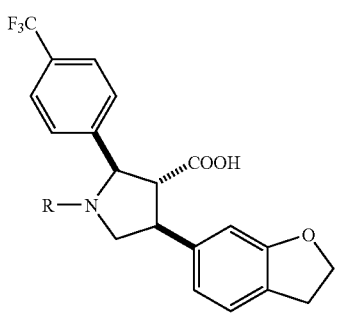 | |
| 397. | 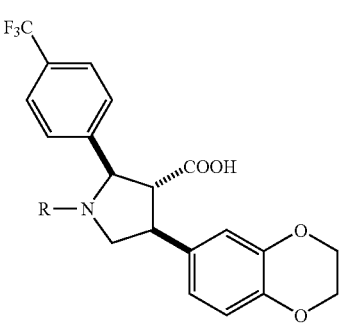 | |
| 398. | 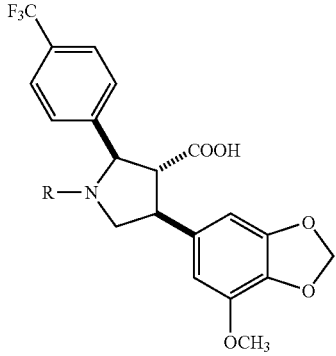 | |
TABLE 2A-continued
| | | |
|---|---|---|
| 399. | 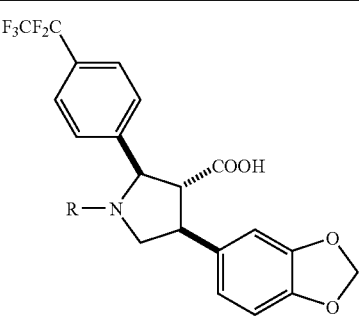 | |
| 400. | 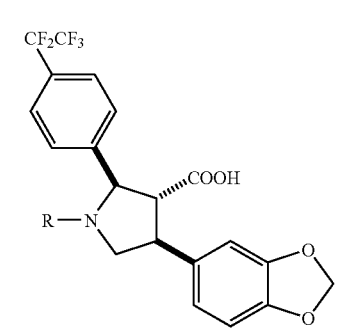 | |
| 401. | 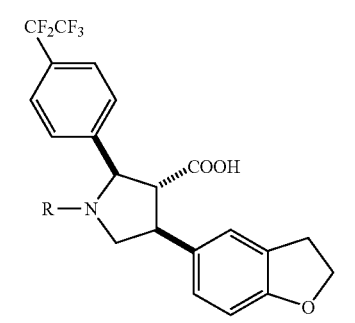 | |
| 402. | 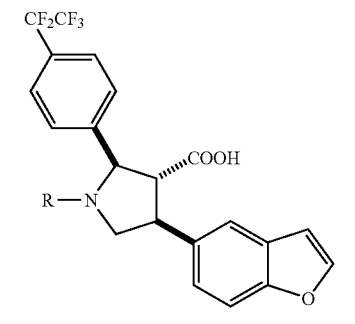 | |
| 403. | 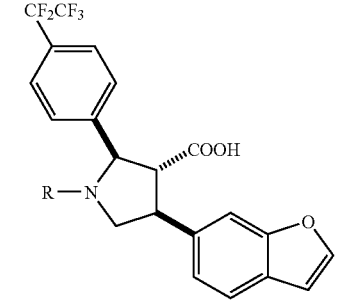 | |

TABLE 2A-continued
404. 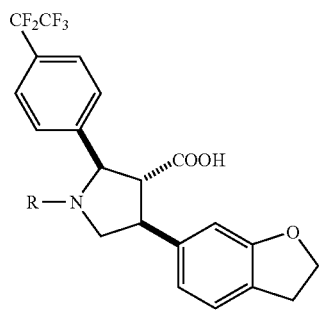
405. 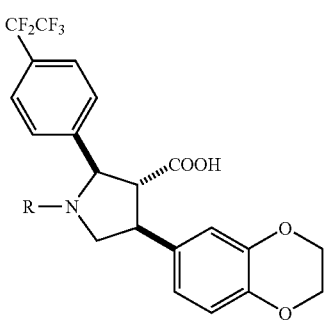
406. 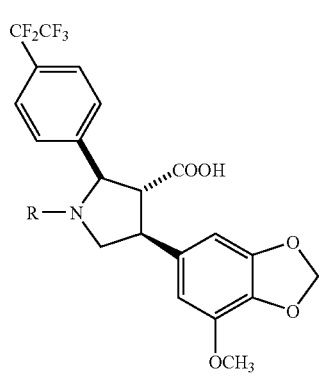
407. 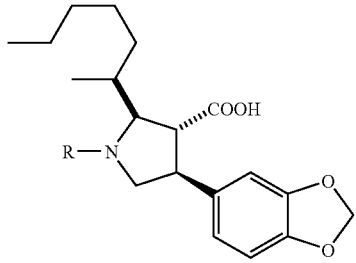
408. 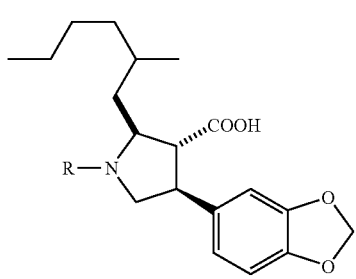
TABLE 2A-continued
409. 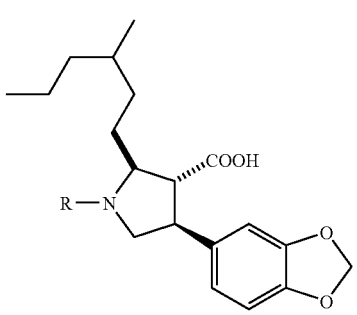
410. 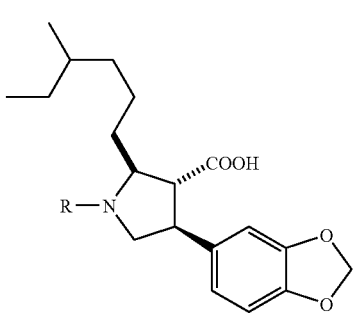
411. 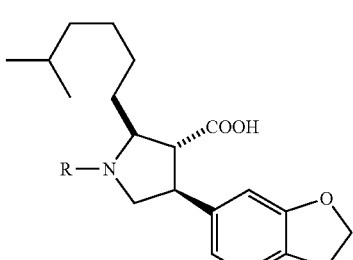
412. 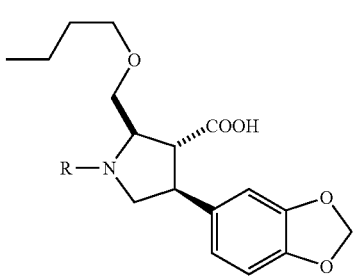
413. 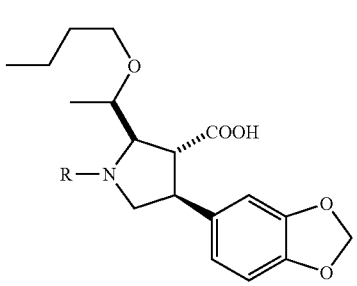

TABLE 2A-continued
| | | | | |
|---|---|---|---|---|
| 414. | 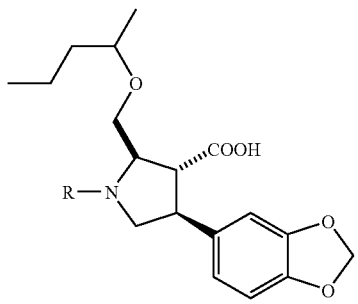 | | 419. | 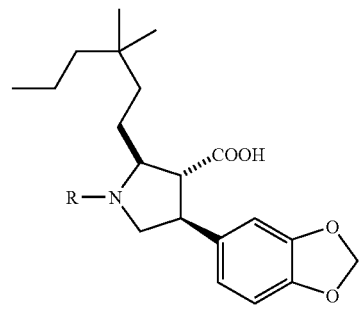 |
| 415. | 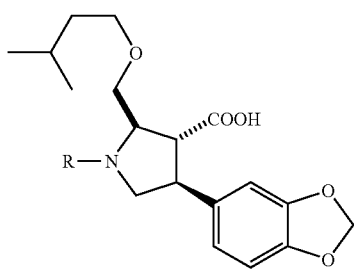 | | 420. | 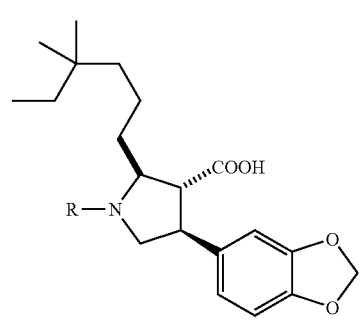 |
| 416. | 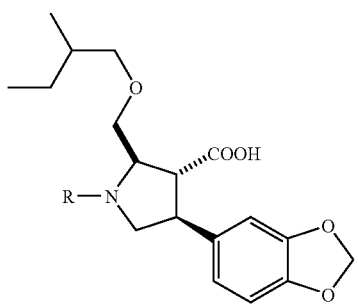 | | 421. | 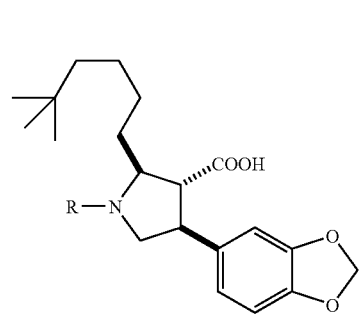 |
| 417. | 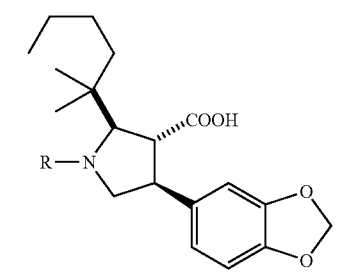 | | 422. | 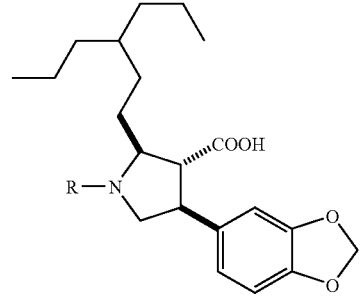 |
| 418. | 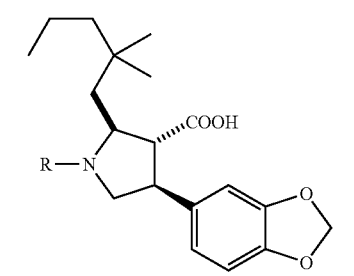 | | 423. | 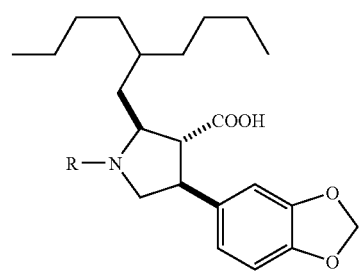 |

TABLE 2A-continued
424. 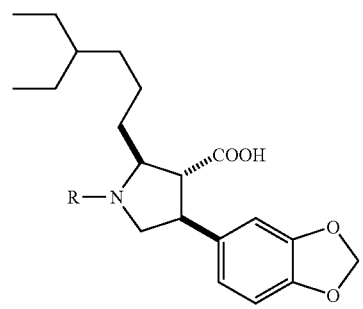
425. 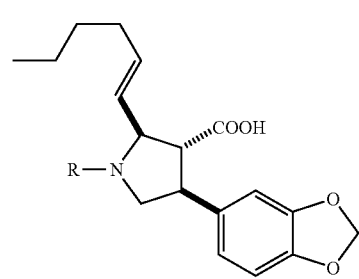
426. 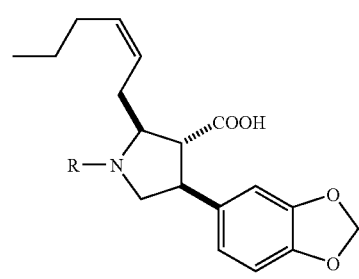
427. 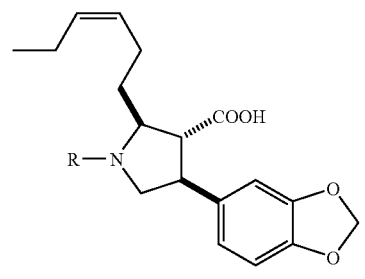
428. 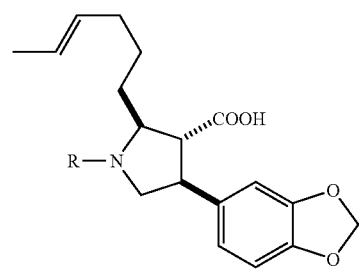
TABLE 2A-continued
429. 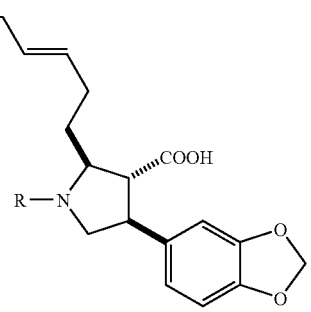
430. 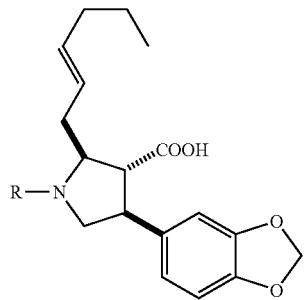
431. 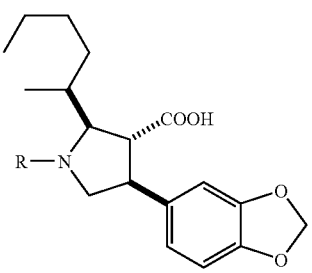
432. 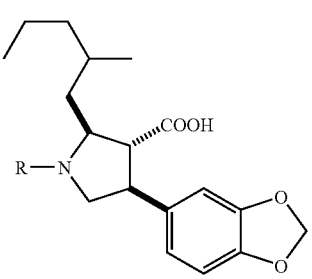
433. 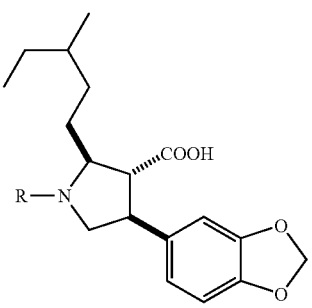

TABLE 2A-continued
434. 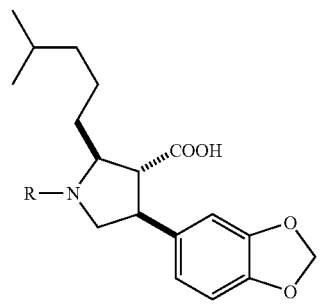
435. 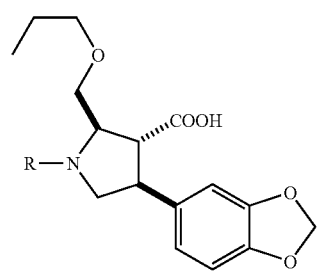
436. 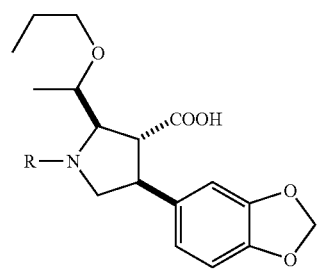
437. 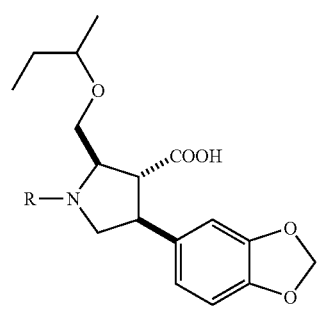
438. 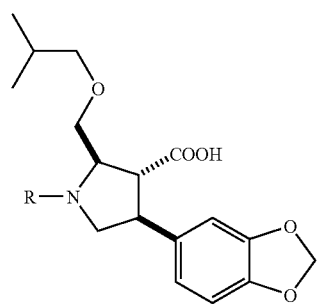
TABLE 2A-continued
439. 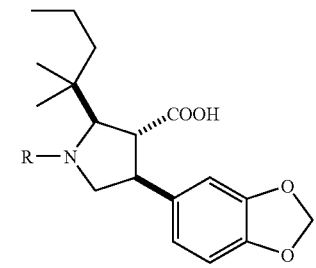
440. 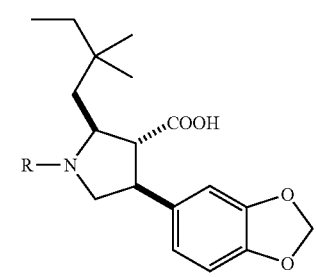
441. 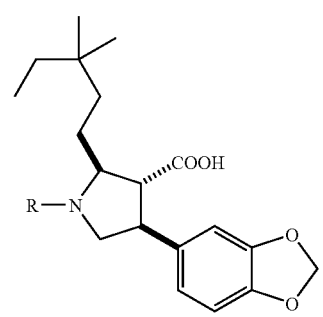
442. 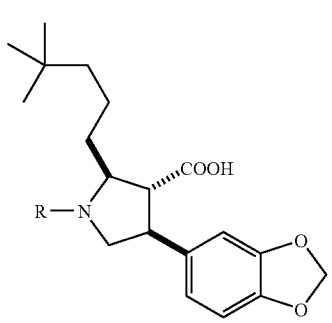
443. 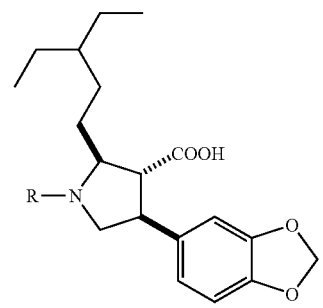

TABLE 2A-continued
444. 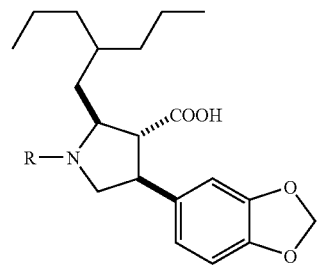
445. 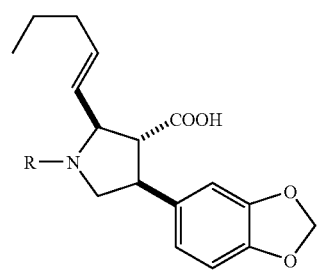
446. 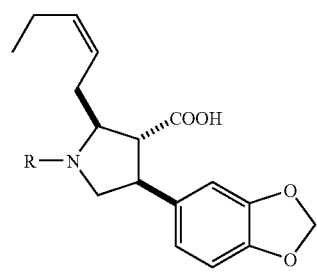
447. 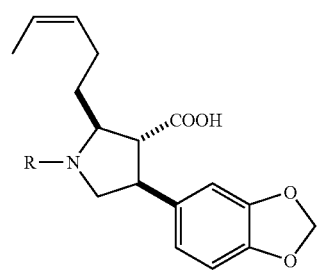
448. 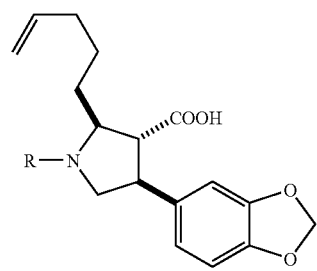
TABLE 2A-continued
449. 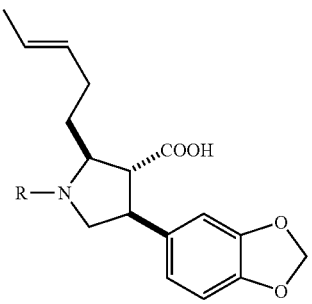
450. 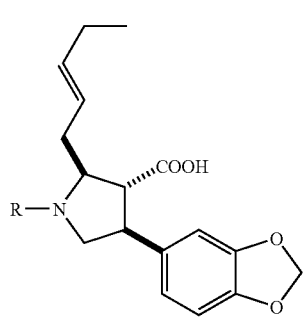
451. 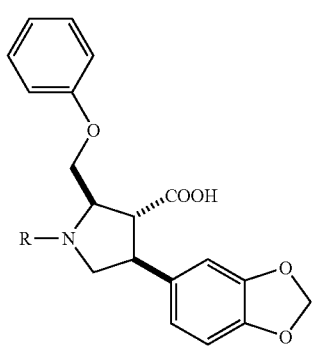
452. 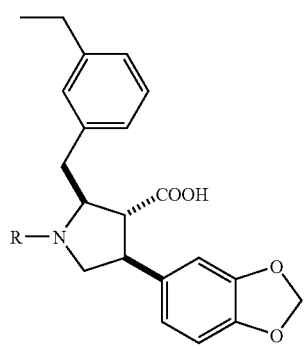
453. 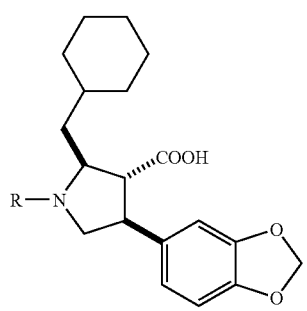

TABLE 2A-continued
454. 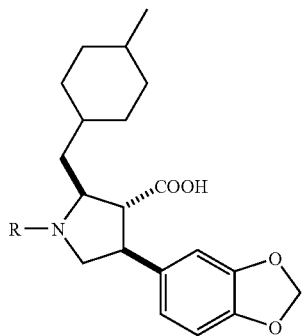
455. 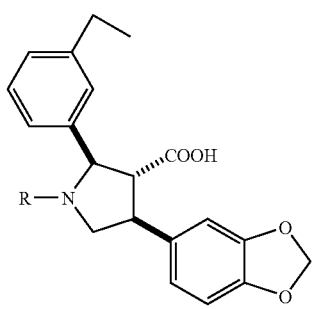
456. 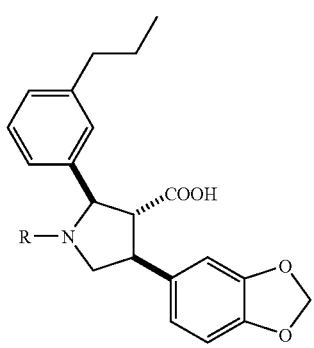
457. 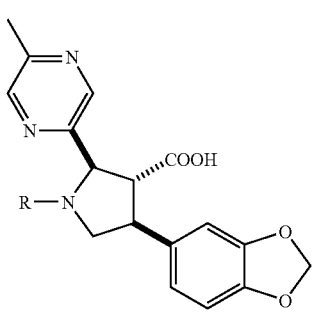
458. 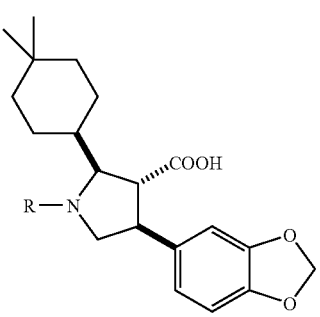
TABLE 2A-continued
459. 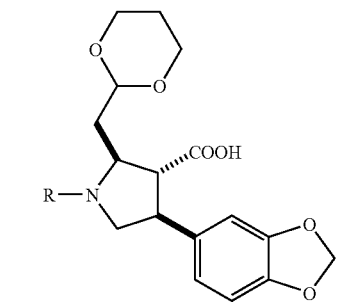
460. 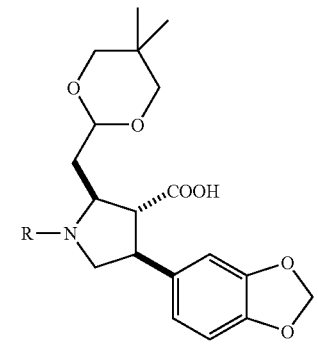
461. 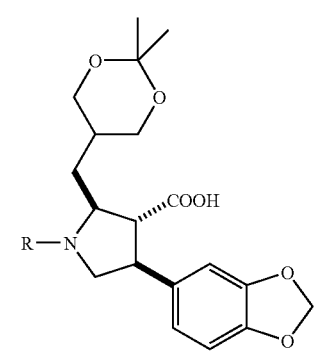
462. 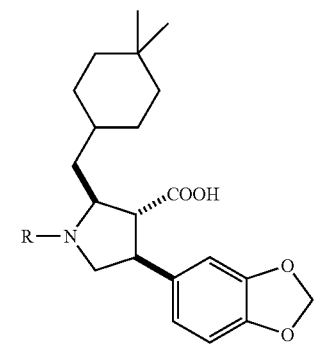

TABLE 2A-continued
| 463. | 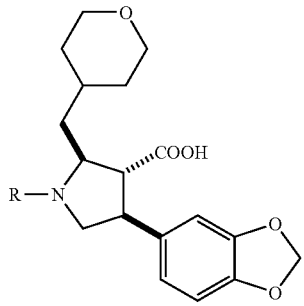 |
| --- | --- |
| 464. | 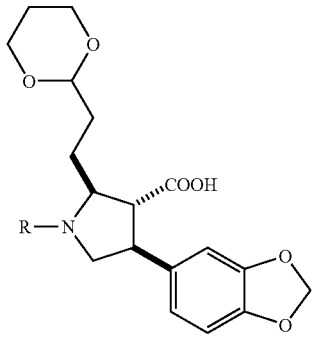 |
| 465. | 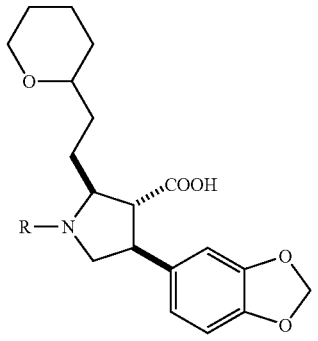 |
TABLE 2B
| | R |
| --- | --- |
| 1. | 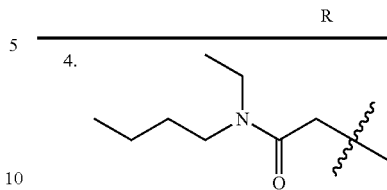 |
| 2. | 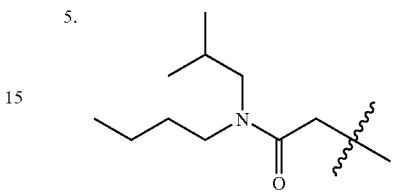 |
| 3. | 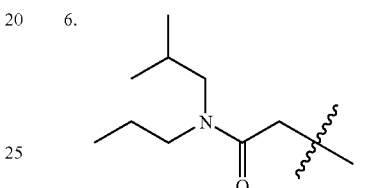 |
TABLE 2B-continued
| | R |
| --- | --- |
| 4. | 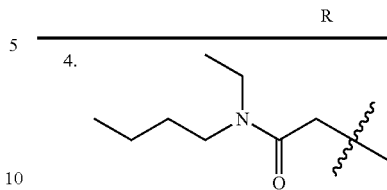 |
| 5. | 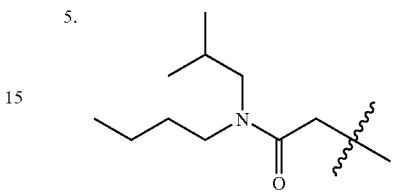 |
| 6. | 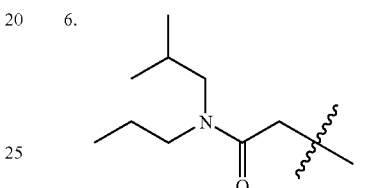 |
| 7. | 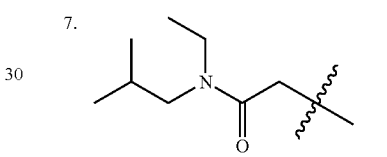 |
| 8. | 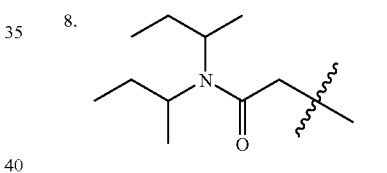 |
| 9. | 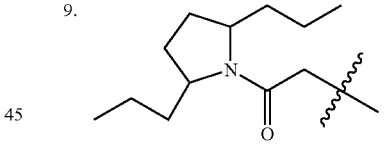 |
| 10. | 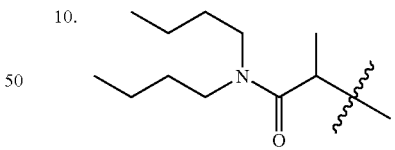 |
| 11. |  |
| 12. | 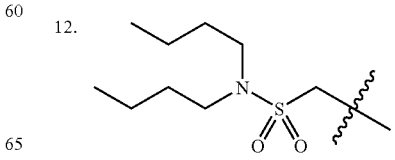 |

TABLE 2B-continued

TABLE 2B-continued
| | R |
|---|---|
| 33. | 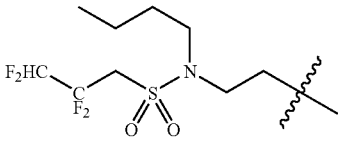 |
| 34. | 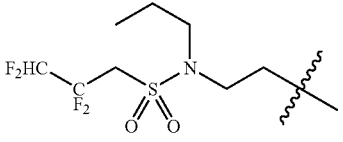 |
| 35. | 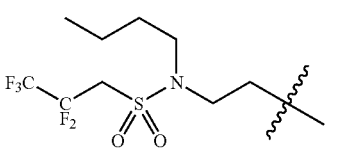 |
| 36. | 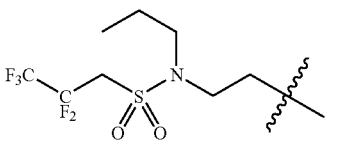 |
| 37. | 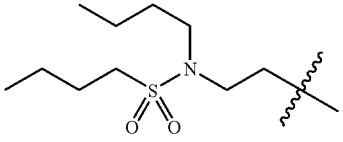 |
| 38. | 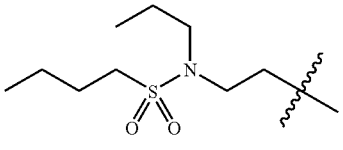 |
| 39. | 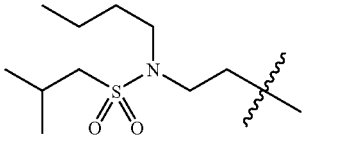 |
| 40. | 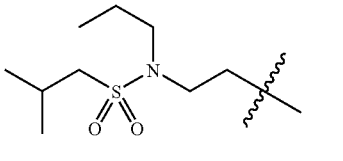 |
| 41. | 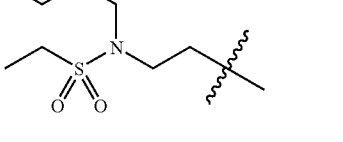 |
| 42. | 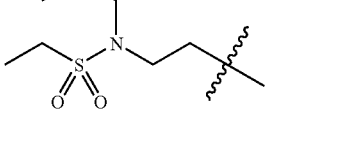 |
| 43. | 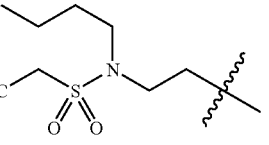 |
| 44. | 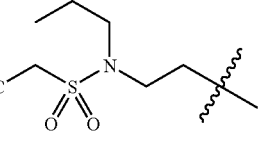 |
| 45. | 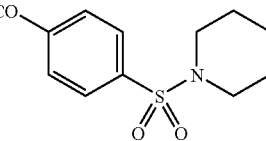 |
| 46. | 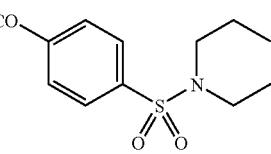 |
| 47. | 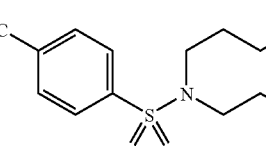 |
| 48. | 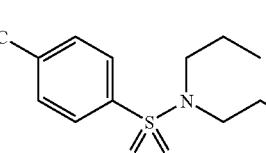 |
| 49. | 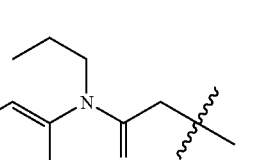 |
| 50. | 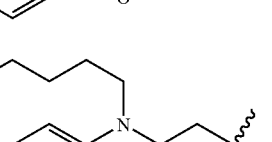 |
| 51. | 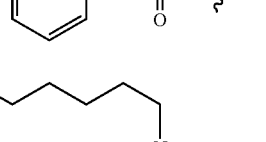 |

TABLE 2B-continued
| | R |
|---|---|
| 52. | 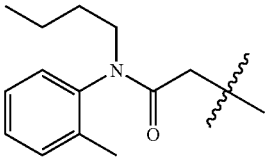 |
| 53. | 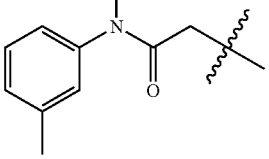 |
| 54. | 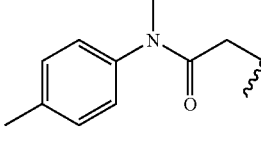 |
| 55. | 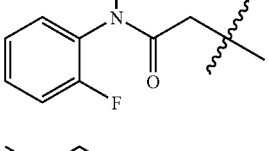 |
| 56. | 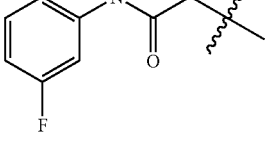 |
| 57. | 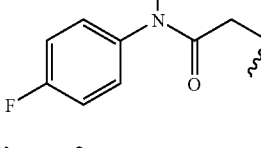 |
| 58. | 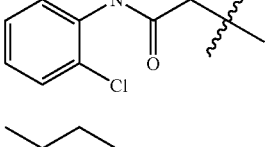 |
| 59. | 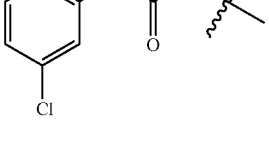 |
| 60. | 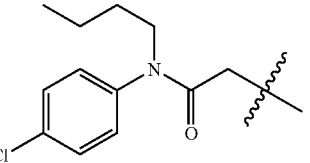 |
| 61. | 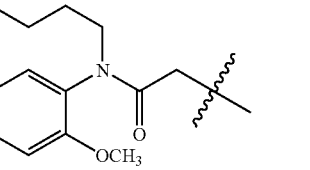 |
| 62. | 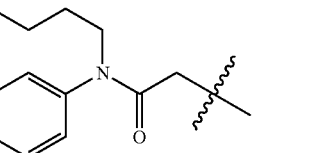 |
| 63. | 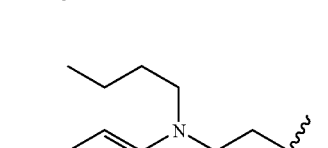 |
| 64. | 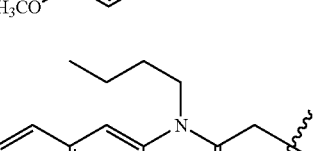 |
| 65. | 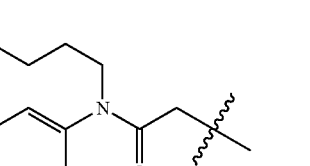 |
| 66. | 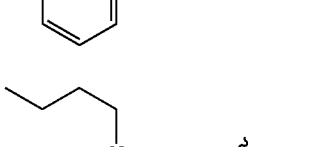 |

TABLE 2B-continued
| | R |
|---|---|
| 67. | 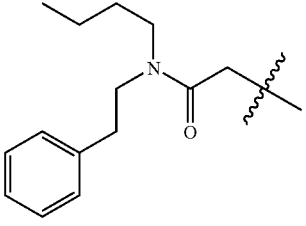 |
| 68. | 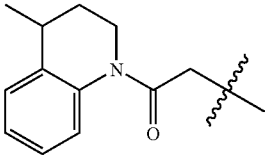 |
| 69. | 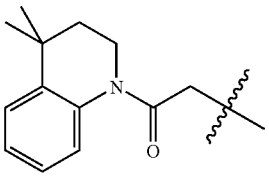 |
| 70. | 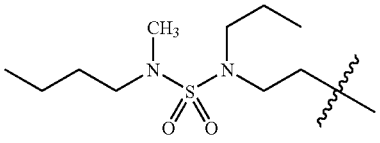 |
| 71. | 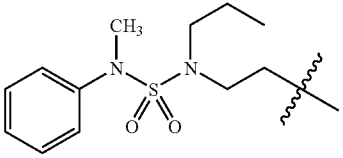 |
| 72. | 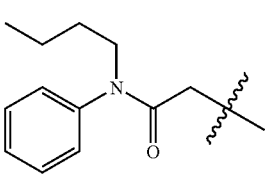 |
| 73. | 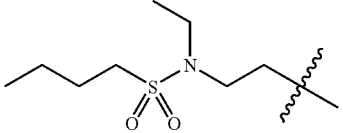 |
| 74. | 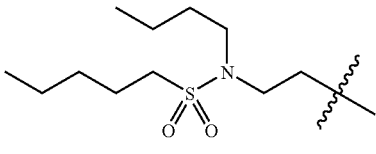 |
| 75. | 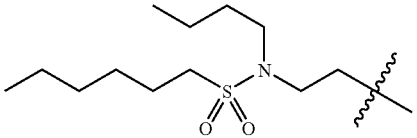 |
| 76. | 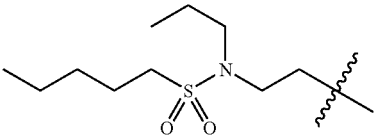 |
| 77. | 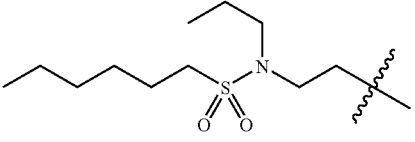 |
| 78. | 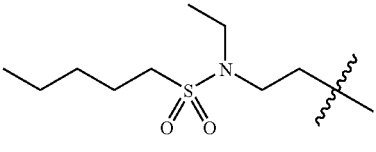 |
| 79. | 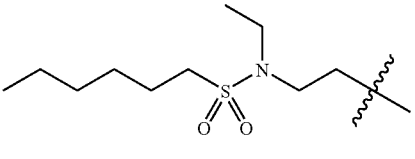 |
| 80. | 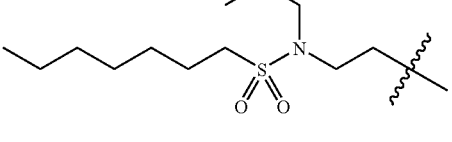 |
| 81. | 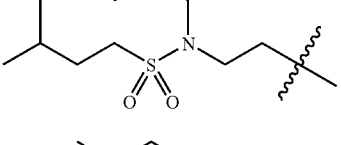 |
| 82. | 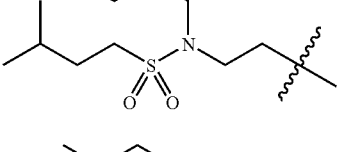 |
| 83. | 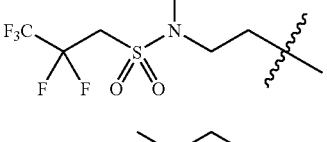 |
| 84. | 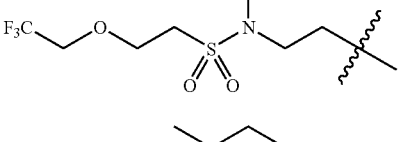 |
| 85. | 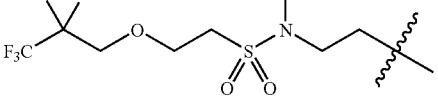 |

US 7,208,517 B1
TABLE 2B-continued
| | R |
|---|---|
| 86. | 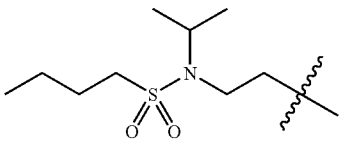 |
| 87. | 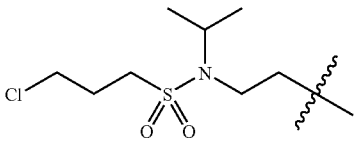 |
| 88. | 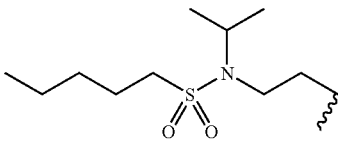 |
| 89. | 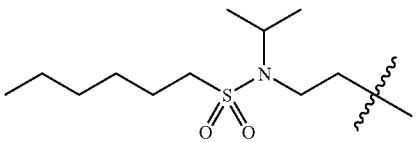 |
| 90. | 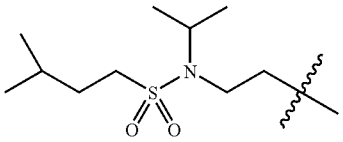 |
| 91. | 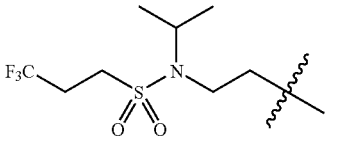 |
| 92. | 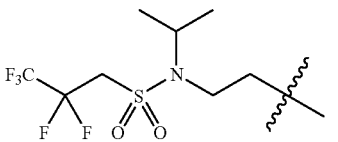 |
| 93. | 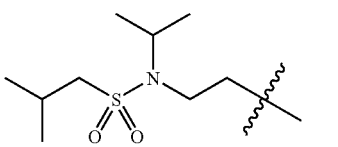 |
| 94. | 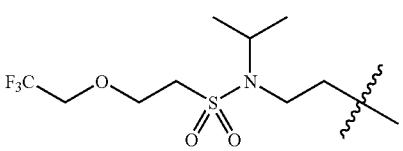 |
| 95. | 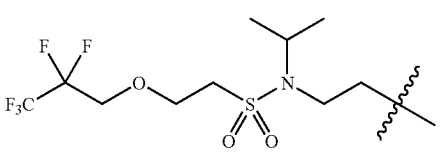 |
TABLE 2B-continued
| | R |
|---|---|
| 96. | 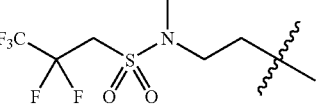 |
| 97. | 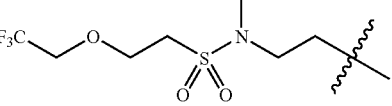 |
| 98. | 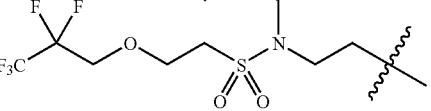 |
| 99. | 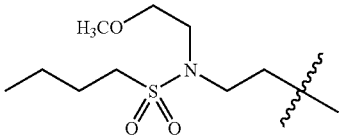 |
| 100. | 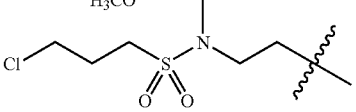 |
| 101. | 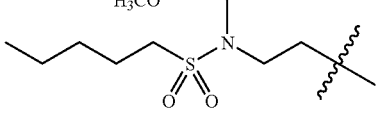 |
| 102. | 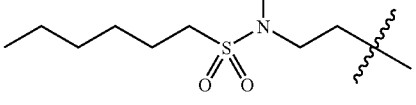 |
| 103. | 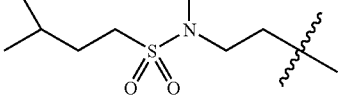 |
| 104. | 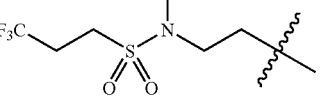 |
| 105. | 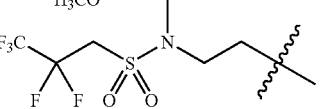 |

TABLE 2B-continued

| | R |
|---|---|
| 106. | (structure) |
| 107. | (structure) |
| 108. | (structure) |
| 109. | (structure) |
| 110. | (structure) |
| 111. | (structure) |
| 112. | (structure) |
| 113. | (structure) |
| 114. | (structure) |
| 115. | (structure) |
| 116. | (structure) |
| 117. | (structure) |
| 118. | (structure) |
| 119. | (structure) |
| 120. | (structure) |

TABLE 2B-continued
| | R | | R |
|---|---|---|---|
| 121. 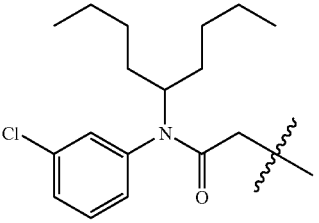 | | 127. 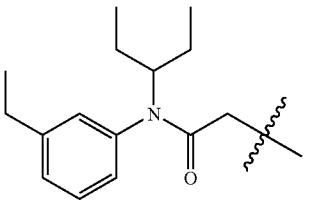 | |
| 122. 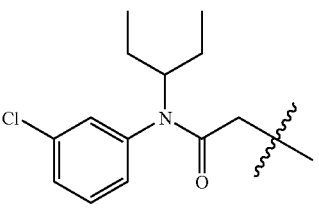 | | 128. 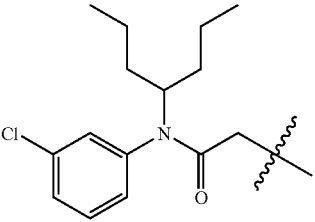 | |
| 123. 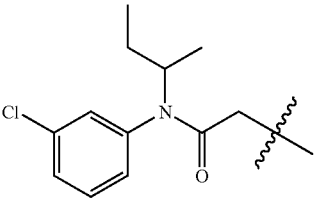 | | 129. 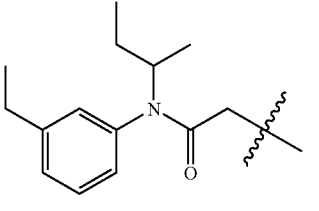 | |
| 124. 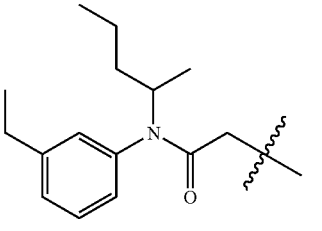 | | 130. 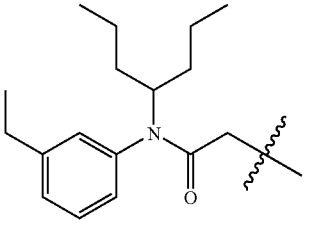 | |
| 125. 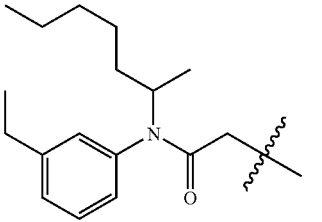 | | 131. 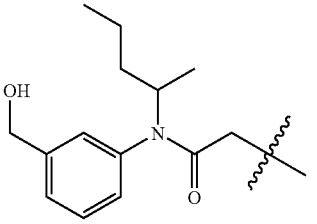 | |
| 126. 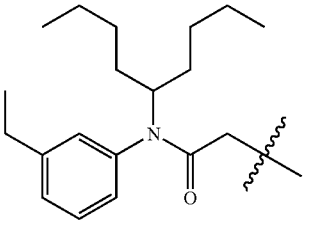 | | 132. 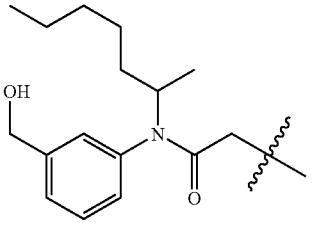 | |

TABLE 2B-continued

| | R |
|---|---|
| 133. | [structure] |
| 134. | [structure] |
| 135. | [structure] |
| 136. | [structure] |
| 137. | [structure] |
| 138. | [structure] |
| 139. | [structure] |
| 140. | [structure] |
| 141. | [structure] |
| 142. | [structure] |
| 143. | [structure] |
| 144. | [structure] |
| 145. | [structure] |

TABLE 2B-continued
| | R |
|---|---|
| 146. | 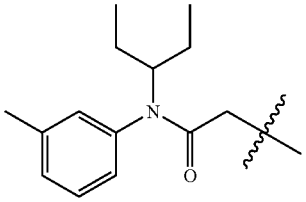 |
| 147. | 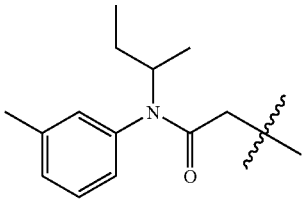 |
| 148. | 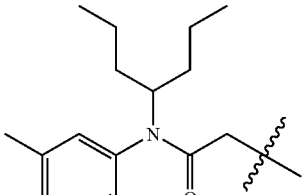 |
| 149. | 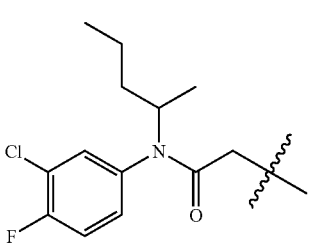 |
| 150. | 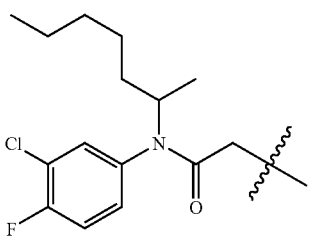 |
| 151. | 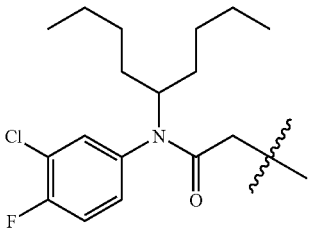 |
| 152. | 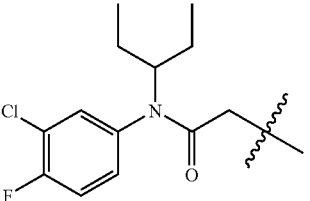 |
| 153. | 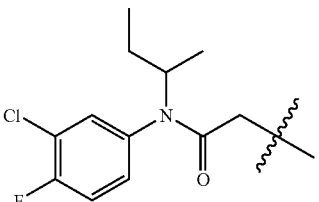 |
| 154. | 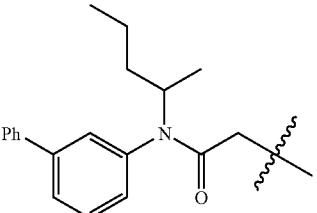 |
| 155. | 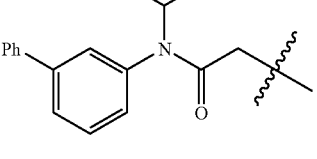 |
| 156. | 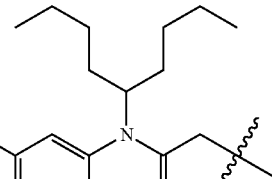 |
| 157. | 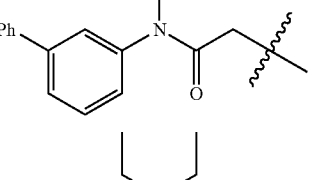 |
| 158. | 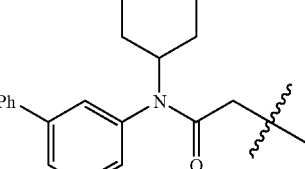 |

TABLE 2B-continued

| | R |
|---|---|
| 159. | (structure) |
| 160. | (structure) |
| 161. | (structure) |
| 162. | (structure) |
| 163. | (structure) |
| 164. | (structure) |
| 165. | (structure) |
| 166. | (structure) |
| 167. | (structure) |
| 168. | (structure) |
| 169. | (structure) |
| 170. | (structure) |
| 171. | (structure) |

TABLE 2B-continued
| | R |
|---|---|
| 172. | 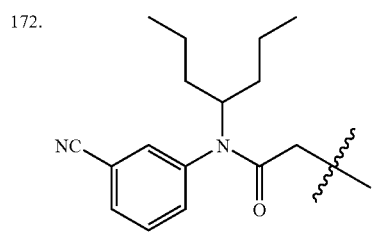 |
| 173. | 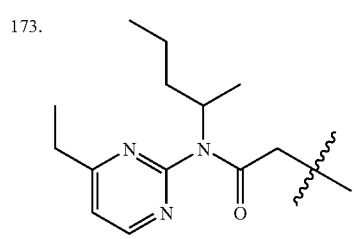 |
| 174. | 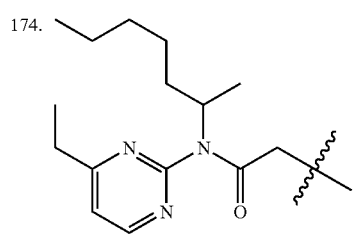 |
| 175. | 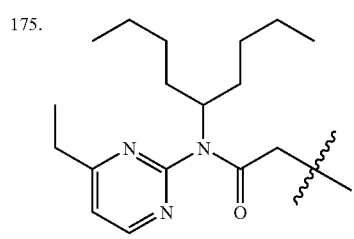 |
| 176. | 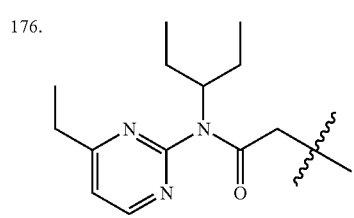 |
| 177. | 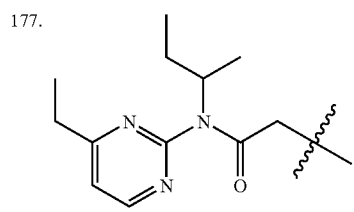 |
TABLE 2B-continued
| | R |
|---|---|
| 178. | 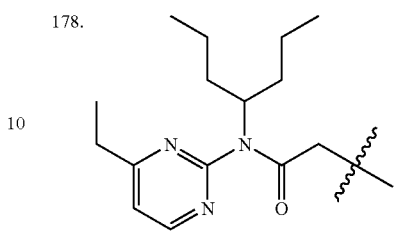 |
| 179. |  |
| 180. | 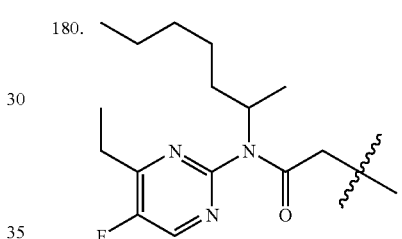 |
| 181. |  |
| 182. | 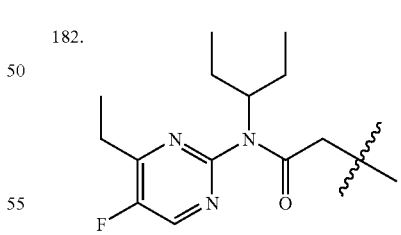 |
| 183. | 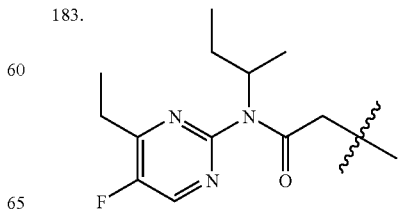 |

TABLE 2B-continued
| | R |
|---|---|
| 184. | 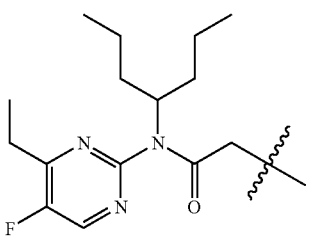 |
| 185. | 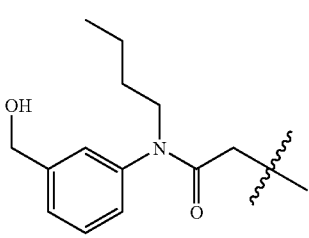 |
| 186. | 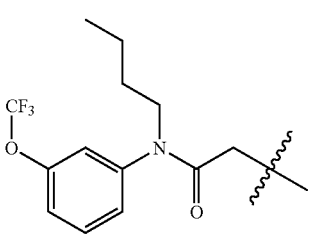 |
| 187. | 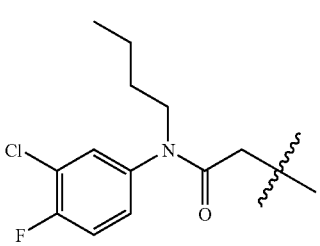 |
| 188. | 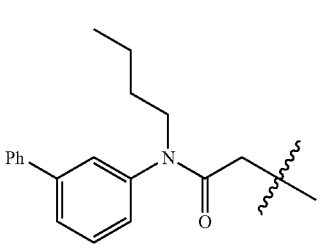 |
| 189. | 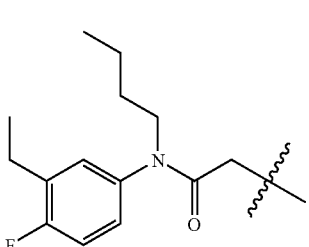 |
| 190. | 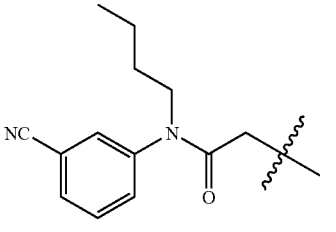 |
| 191. | 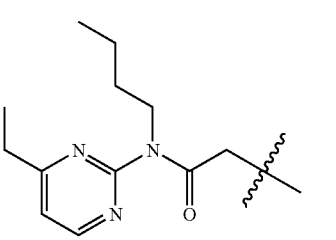 |
| 192. | 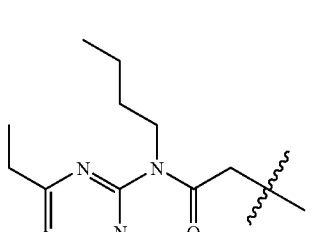 |
| 193. | 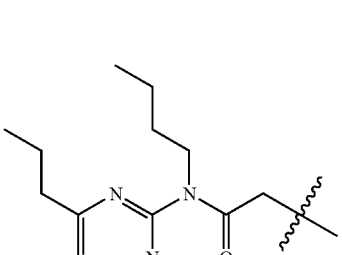 |
| 194. | 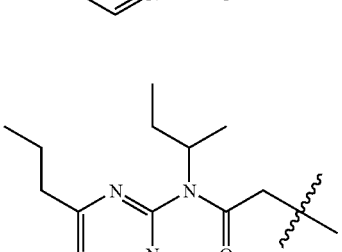 |
| 195. | 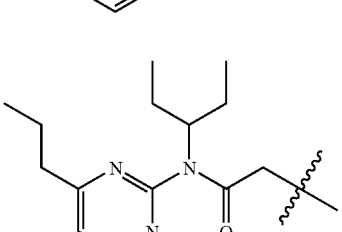 |

TABLE 2B-continued

| R |
|---|
| 196. |
| 197. |
| 198. |
| 199. |
| 200. |
| 201. |
| 202. |
| 203. |
| 204. |
| 205. |
| 206. |
| 207. |
| 208. |

TABLE 2B-continued
| | R |
|---|---|
| 209. | 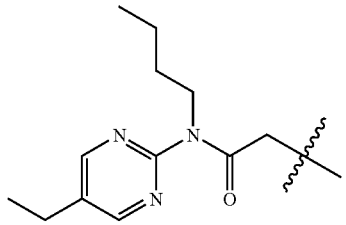 |
| 210. | |
| 211. | |
| 212. | |
| 213. | |
| 214. | |
TABLE 2B-continued
| | R |
|---|---|
| 215. | 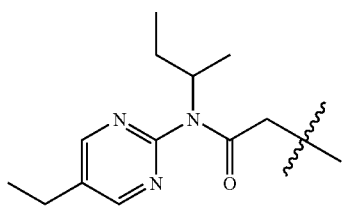 |
| 216. | |
| 217. | |
| 218. | |
| 219. | |
| 220. | |
| 221. | |

TABLE 2B-continued

| | R |
|---|---|
| 222. | (structure) |
| 223. | (structure) |
| 224. | (structure) |
| 225. | (structure) |
| 226. | (structure) |
| 227. | (structure) |
| 228. | (structure) |
| 229. | (structure) |
| 230. | (structure) |
| 231. | (structure) |
| 232. | (structure) |
| 233. | (structure) |
| 234. | (structure) |

TABLE 2B-continued

| | R |
|---|---|
| 235. | |
| 236. | |
| 237. | |
| 238. | |
| 239. | |
| 240. | |
| 241. | |
| 242. | |
| 243. | |
| 244. | |
| 245. | |
| 246. | |

TABLE 2B-continued
| | R |
|---|---|
| 247. | 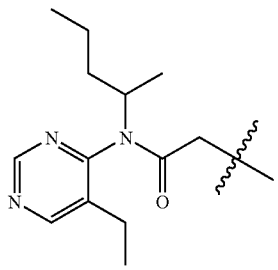 |
| 248. | |
| 249. | |
| 250. | |
| 252. | |
TABLE 2B-continued
| | R |
|---|---|
| 252. | 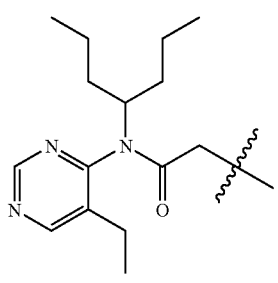 |
| 253. | |
| 254. | |
| 255. | |
| 256. | |

TABLE 2B-continued
| | R |
|---|---|
| 257. | 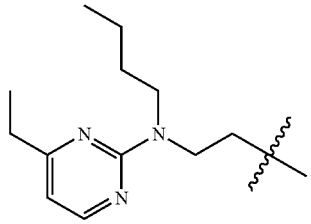 |
| 258. | 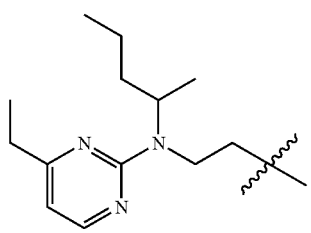 |
| 259. | 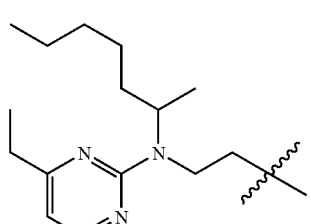 |
| 260. | 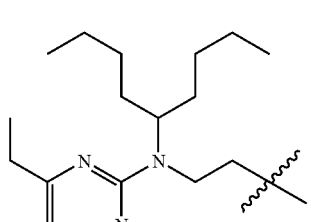 |
| 261. | 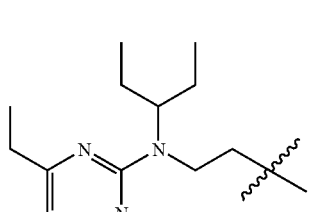 |
| 262. | 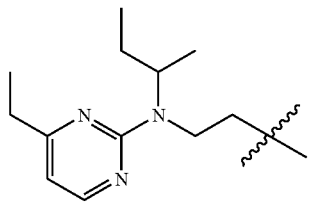 |
| 263. | 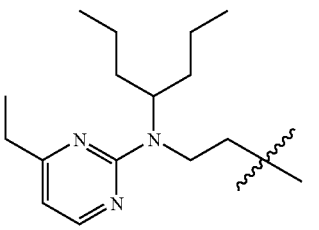 |
| 264. | 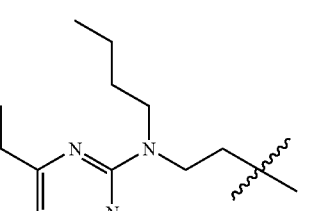 |
| 265. | 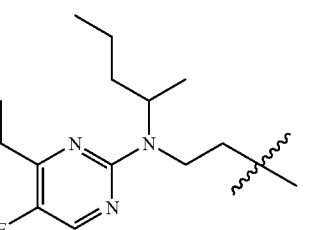 |
| 266. | 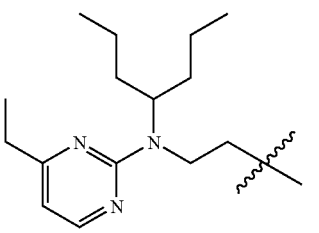 |
| 267. | 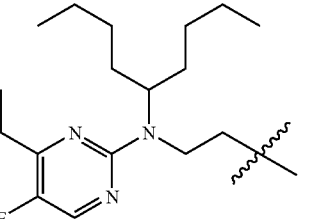 |
| 268. | 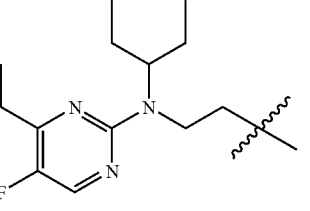 |

TABLE 2B-continued
| | R |
|---|---|
| 269. | 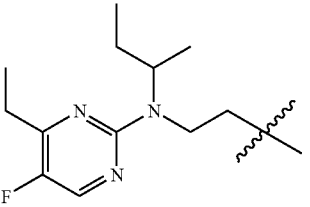 |
| 270. | 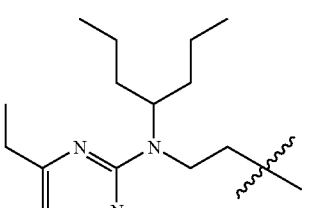 |
| 271. | 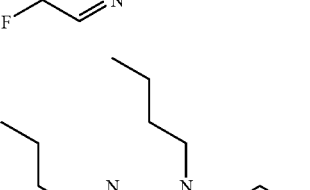 |
| 272. | 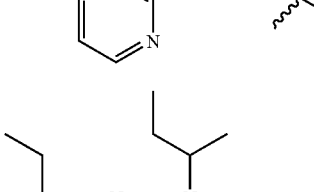 |
| 273. | 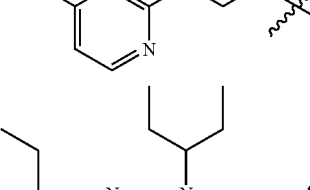 |
| 274. | 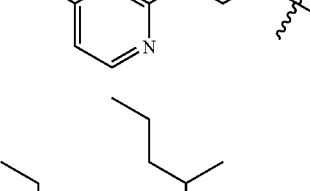 |
| 275. | 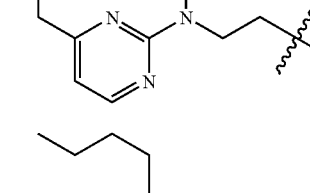 |
| 276. | 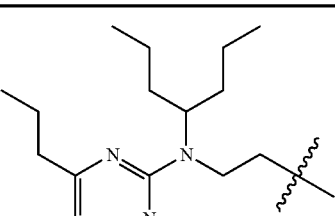 |
| 277. | 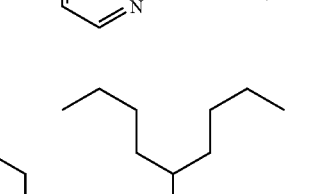 |
| 278. | 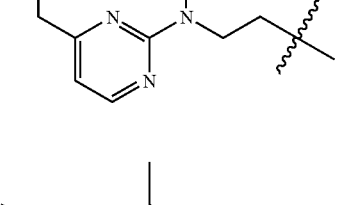 |
| 279. | 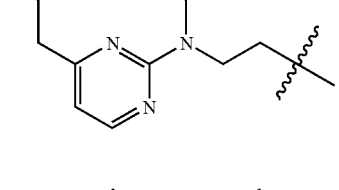 |
| 280. | 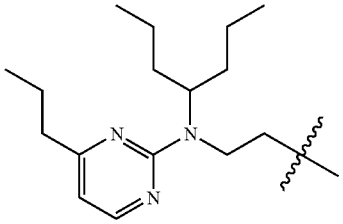 |
| 281. | 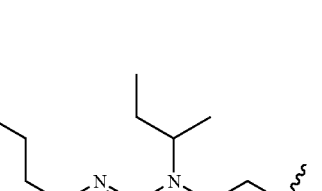 |

TABLE 2B-continued
| R |
|---|
| 282. 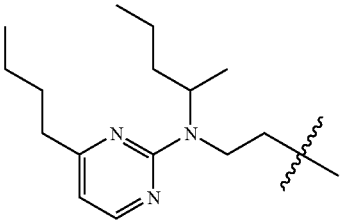 |
| 283. 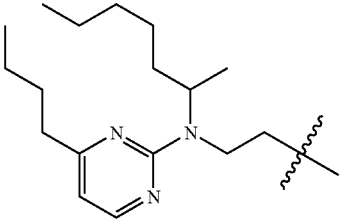 |
| 284. 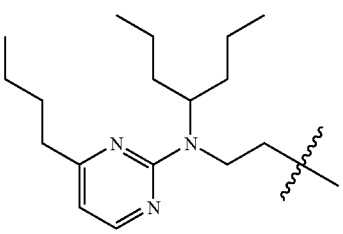 |
| 285. 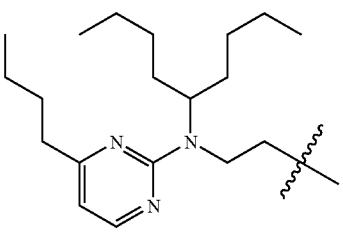 |
| 286. 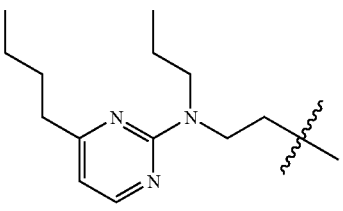 |
| 287. 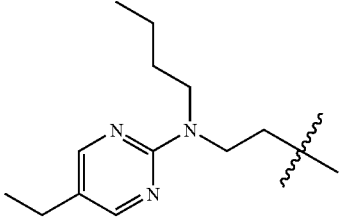 |
| 288. 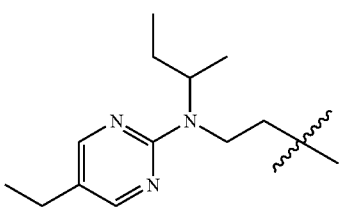 |
| 289. 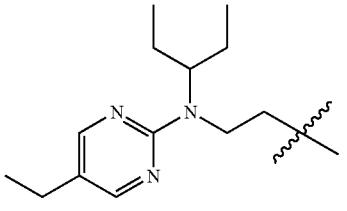 |
| 290. 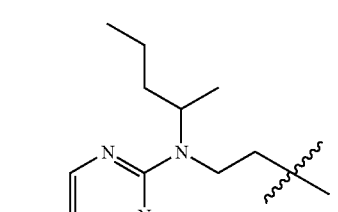 |
| 291. 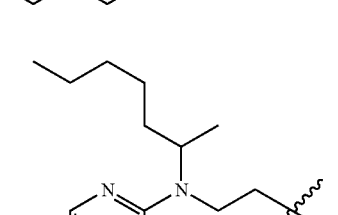 |
| 292. 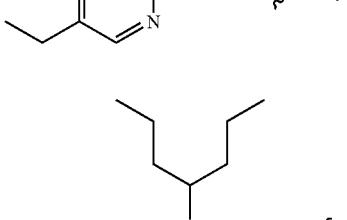 |
| 293. 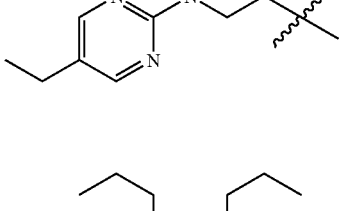 |
| 294. 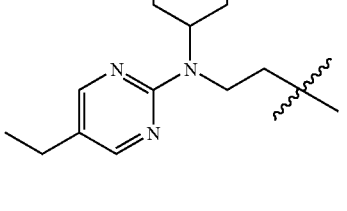 |

TABLE 2B-continued
| | R |
|---|---|
| 295. | 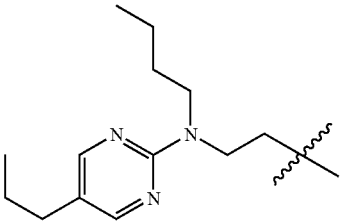 |
| 296. | 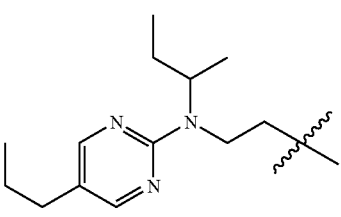 |
| 297. | 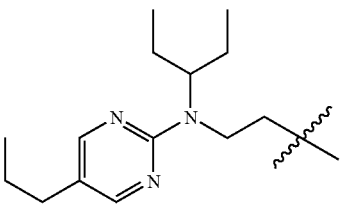 |
| 298. | 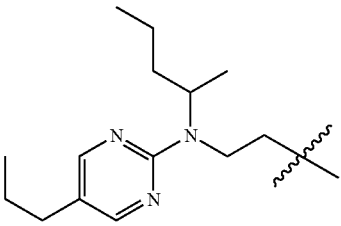 |
| 299. | 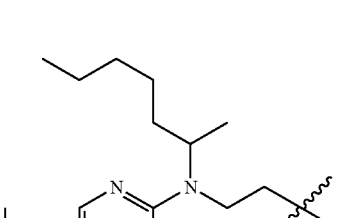 |
| 300. | 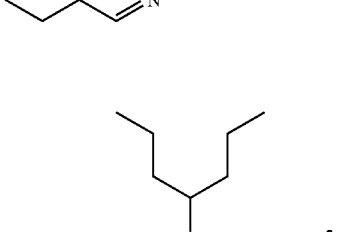 |
| 301. | 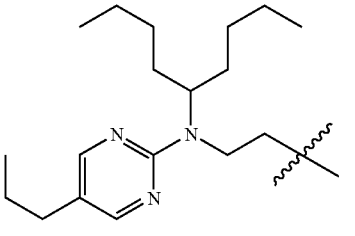 |
| 302. | 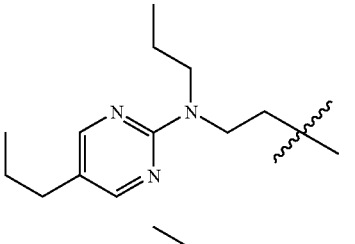 |
| 303. | 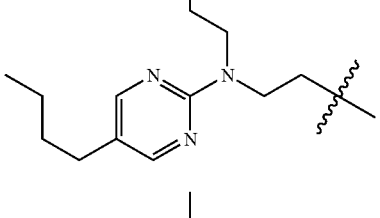 |
| 304. | 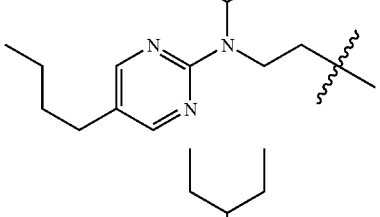 |
| 305. | 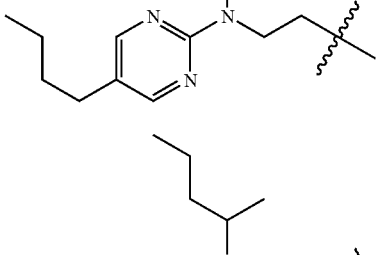 |
| 306. | 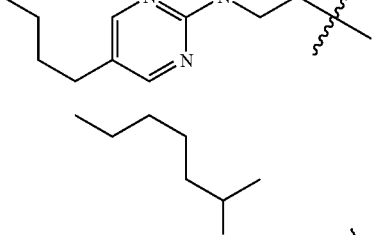 |
| 307. | 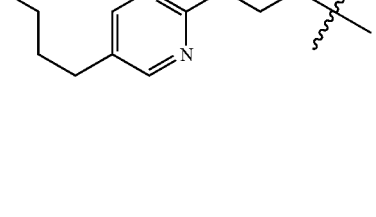 |

TABLE 2B-continued
R
308. 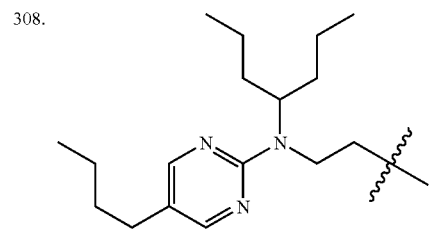
309. 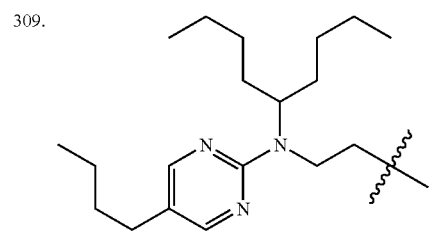
310. 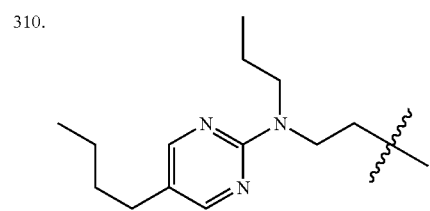
311. 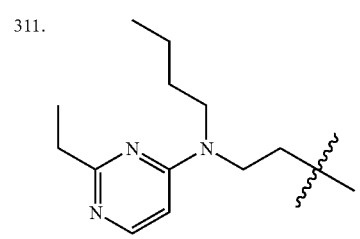
312. 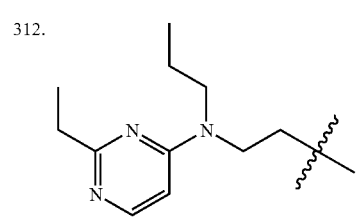
313. 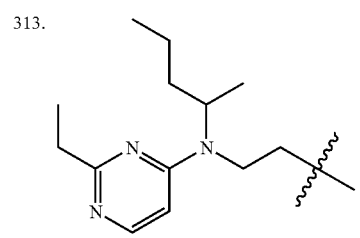
TABLE 2B-continued
R
314. 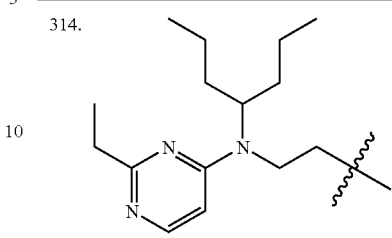
315. 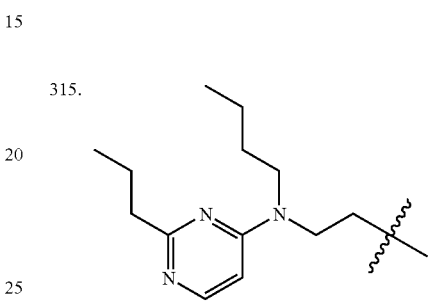
316. 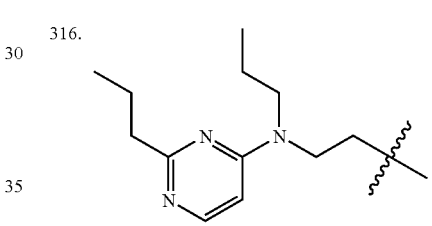
317. 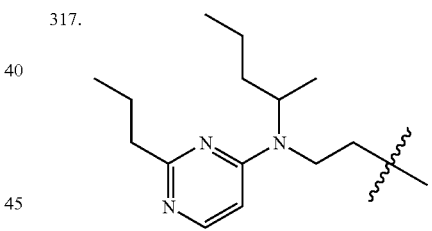
318. 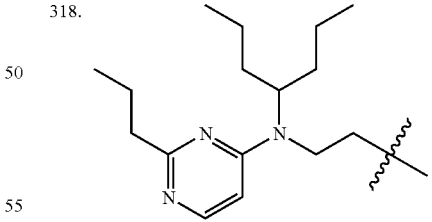
319. 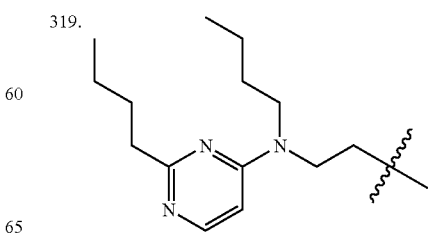

TABLE 2B-continued

| R |
|---|
| 320. [structure] |
| 321. [structure] |
| 322. [structure] |
| 323. [structure] |
| 324. [structure] |
| 325. [structure] |
| 326. [structure] |
| 327. [structure] |
| 328. [structure] |
| 329. [structure] |
| 330. [structure] |

TABLE 2B-continued
| | R |
|---|---|
| 331. | 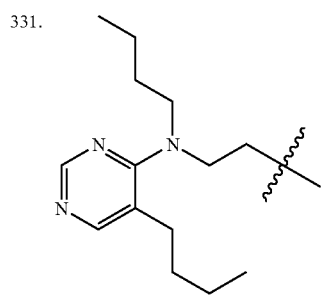 |
| 332. | 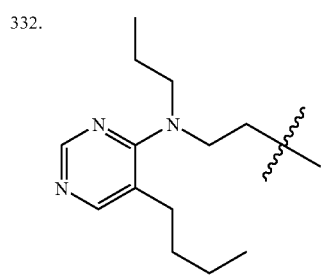 |
| 333. | 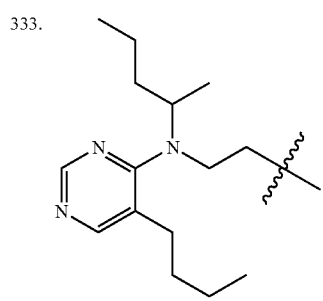 |
| 334. | 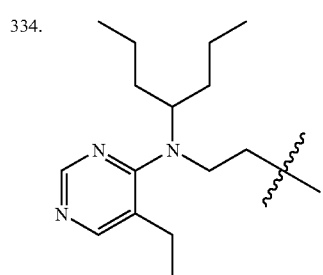 |
| 335. | 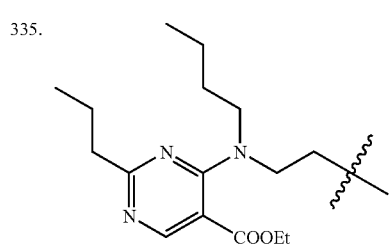 |
| 336. | 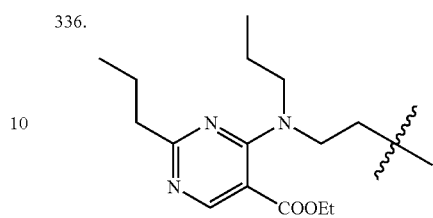 |
| 337. | 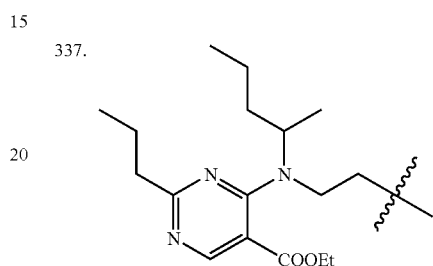 |
| 338. | 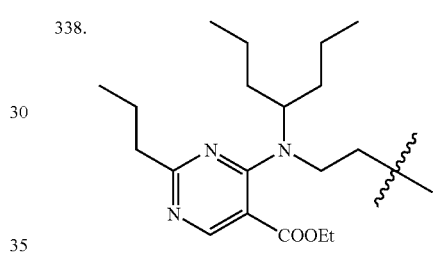 |
| 339. | 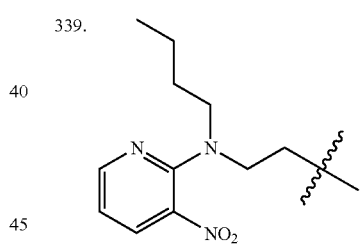 |
| 340. | 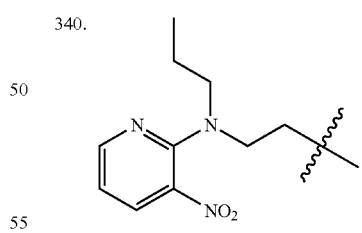 |
| 341. | 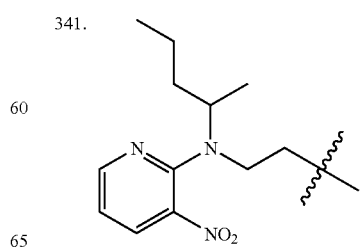 |

TABLE 2B-continued
| | R |
|---|---|
| 342. | 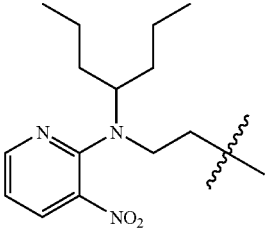 |
| 343. | 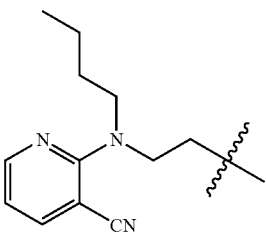 |
| 344. | 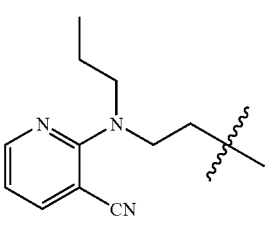 |
| 345. | 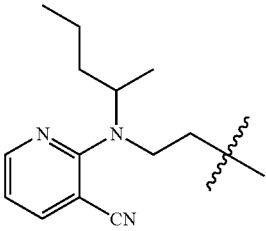 |
| 346. | 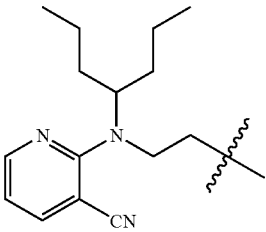 |
| 347. | 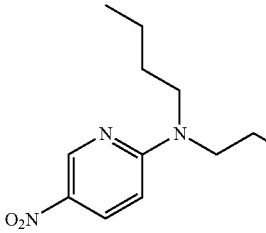 |
| 348. | 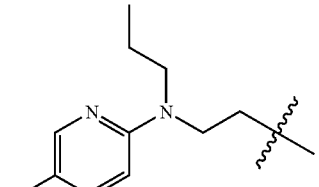 |
| 349. | 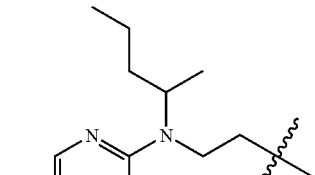 |
| 350. | 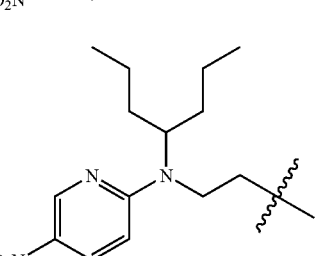 |
| 351. | 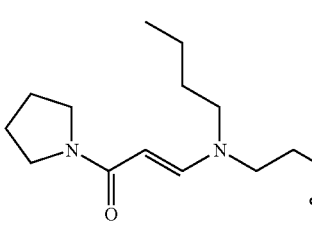 |
| 352. | 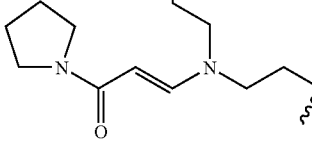 |
| 353. | 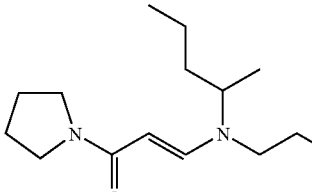 |
| 354. | 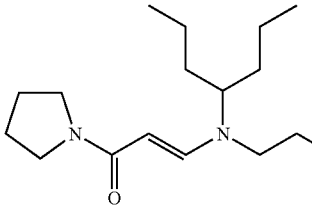 |

TABLE 2B-continued
| R |
|---|
| 355. 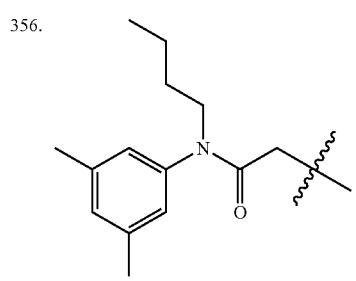 |
| 356. 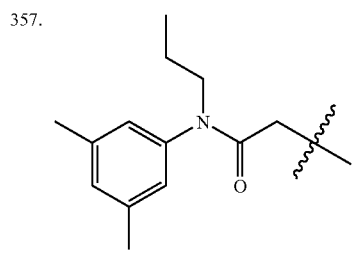 |
| 357.  |
| 358. 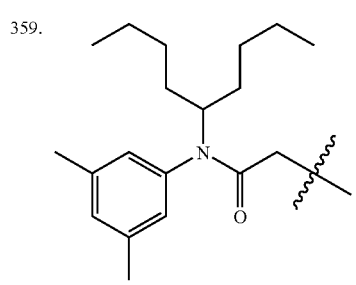 |
| 359. 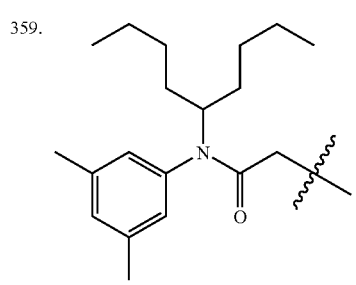 |
TABLE 2B-continued
| R |
|---|
| 360. 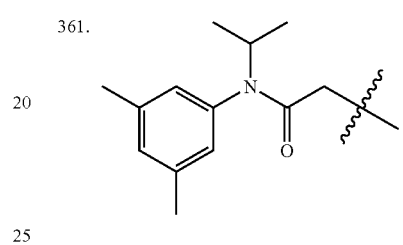 |
| 361. 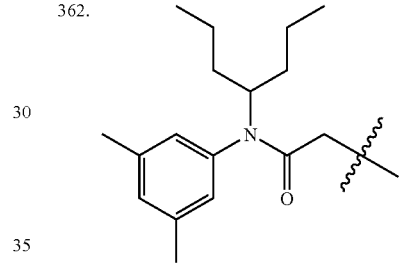 |
| 362. 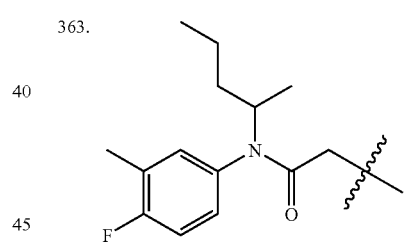 |
| 363. 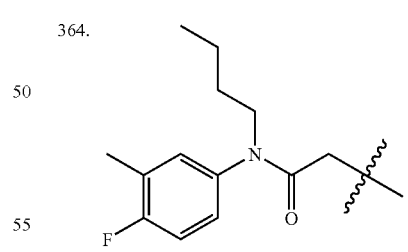 |
| 364. 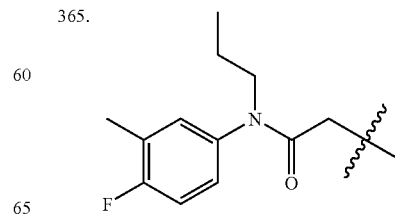 |
| 365. 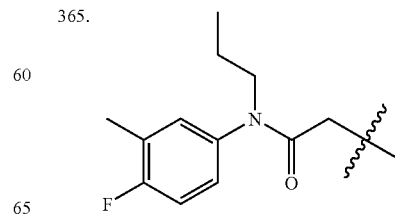 |

TABLE 2B-continued
R
366. 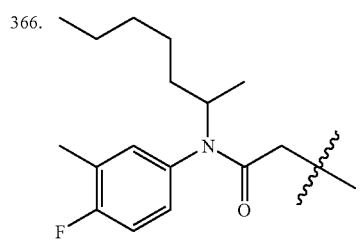
367. 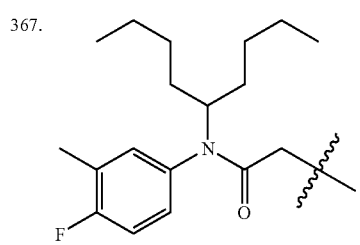
368. 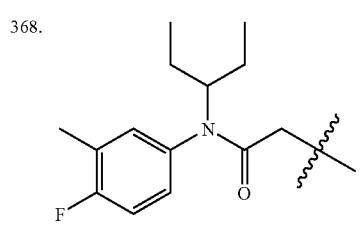
369. 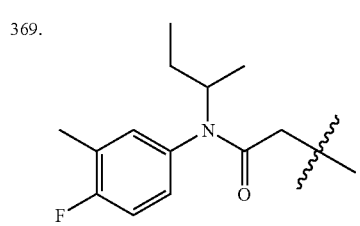
370. 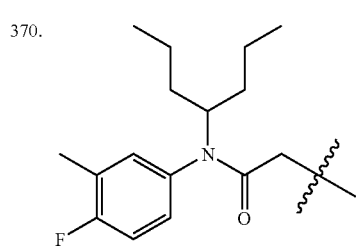
371. 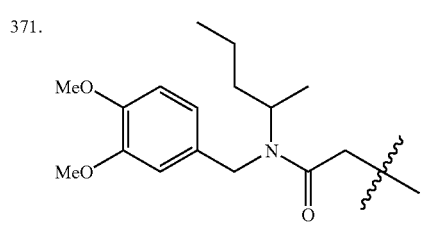
TABLE 2B-continued
R
372. 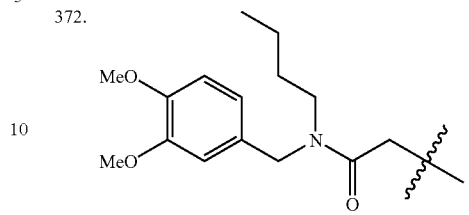
373. 
374. 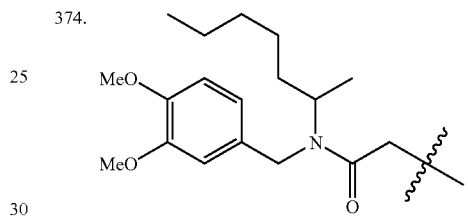
375. 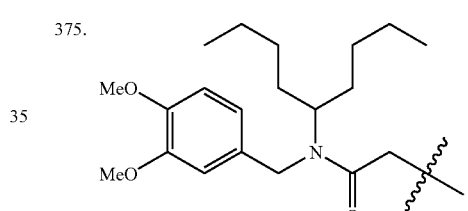
376. 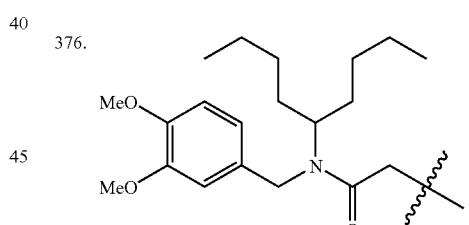
377. 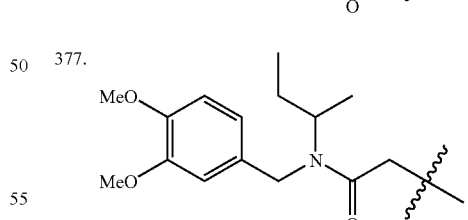
378. 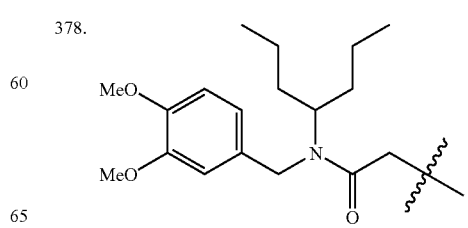

TABLE 2B-continued

| | R |
|---|---|
| 379. | (3-MeO-benzyl)(pentan-2-yl)amide |
| 380. | (3-MeO-benzyl)(butyl)amide |
| 381. | (3-MeO-benzyl)(hexan-2-yl)amide |
| 382. | (3-MeO-benzyl)(nonan-5-yl)amide |
| 383. | (3-MeO-benzyl)(pentan-3-yl)amide |
| 384. | (3-MeO-benzyl)(propyl)amide |
| 385. | (3-MeO-benzyl)(butan-2-yl)amide |
| 386. | (3-MeO-benzyl)(heptan-4-yl)amide |
| 387. | (3,4-dimethylbenzyl)(pentan-2-yl)amide |
| 388. | (3,4-dimethylbenzyl)(butyl)amide |
| 389. | (3,4-dimethylbenzyl)(hexan-2-yl)amide |
| 390. | (3,4-dimethylbenzyl)(nonan-5-yl)amide |
| 391. | (3,4-dimethylbenzyl)(pentan-3-yl)amide |
| 392. | (3,4-dimethylbenzyl)(propyl)amide |

TABLE 2B-continued
| | R |
|---|---|
| 393. | 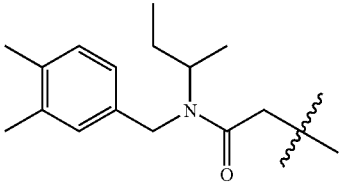 |
| 394. | 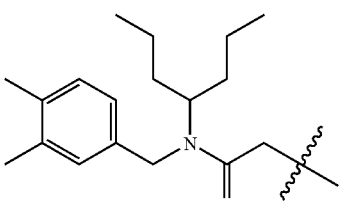 |
| 395. | 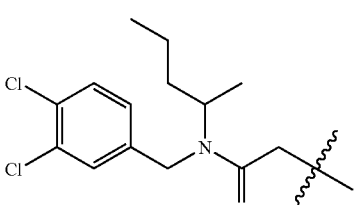 |
| 396. | 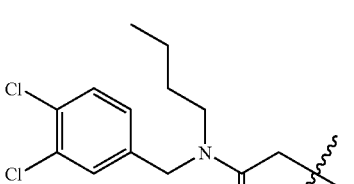 |
| 397. | 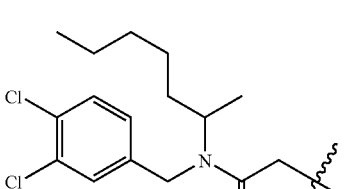 |
| 398. | 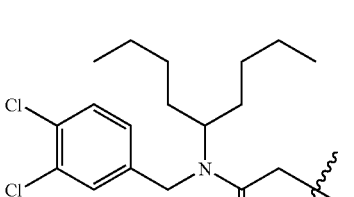 |
| 399. | 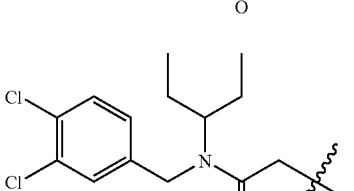 |
| 400. | 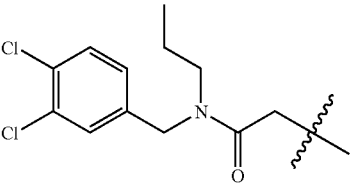 |
| 401. | 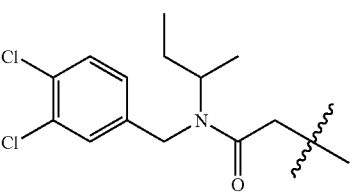 |
| 402. | 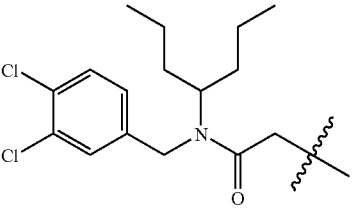 |
| 403. | 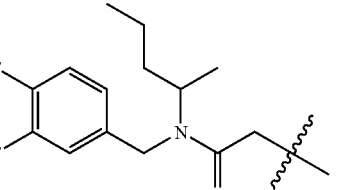 |
| 404. | 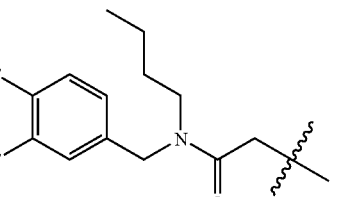 |
| 405. | 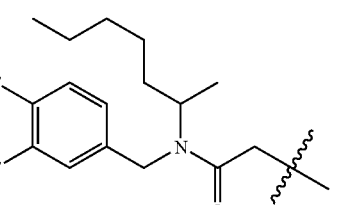 |
| 406. | 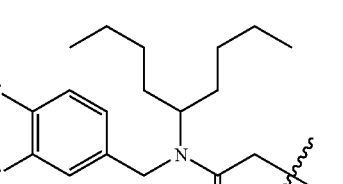 |

TABLE 2B-continued
| | R |
|---|---|
| 407. | 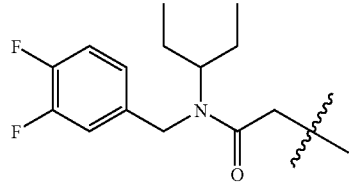 |
| 408. | 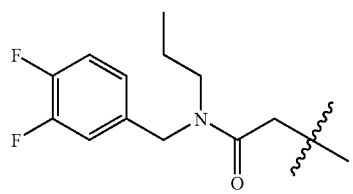 |
| 409. | 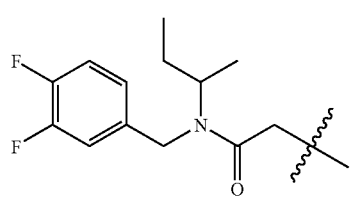 |
| 410. | 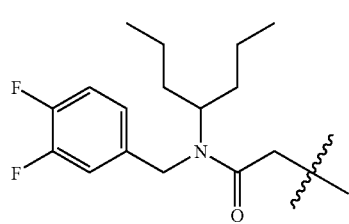 |
| 411. | 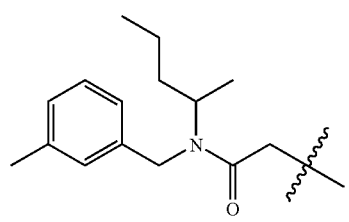 |
| 412. | 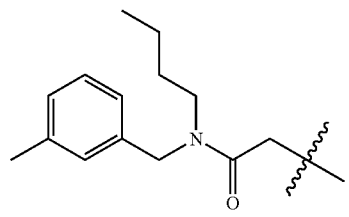 |
| 413. | 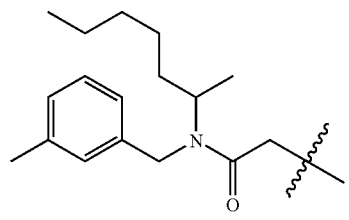 |
| 414. | 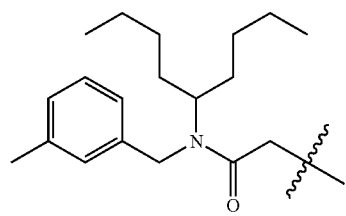 |
| 415. | 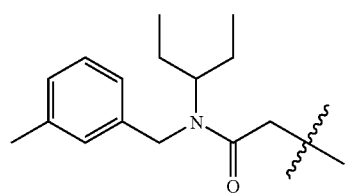 |
| 416. | 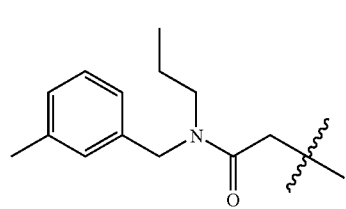 |
| 417. | 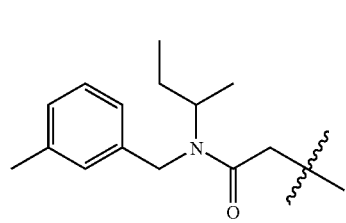 |
| 418. | 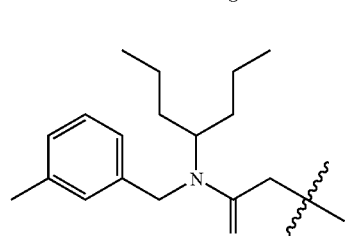 |
| 419. | 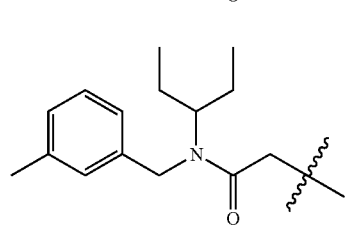 |
| 420. | 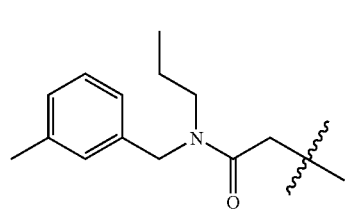 |

TABLE 2B-continued

| | R |
|---|---|
| 421. | (structure) |
| 422. | (structure) |
| 423. | (structure) |
| 424. | (structure) |
| 425. | (structure) |
| 426. | (structure) |
| 427. | (structure) |
| 428. | (structure) |
| 429. | (structure) |
| 430. | (structure) |
| 431. | (structure) |
| 432. | (structure) |
| 433. | (structure) |
| 434. | (structure) |

TABLE 2B-continued

| | R |
|---|---|
| 435. | MeO-C6H3(OMe)-CH2-N(CH(Et)2)-C(=O)-CH2-C(Me)2-⁓ |
| 436. | MeO-C6H3(OMe)-CH2-N(nPr)-C(=O)-CH2-C(Me)2-⁓ |
| 437. | MeO-C6H3(OMe)-CH2-N(CH(Me)Et)-C(=O)-CH2-C(Me)2-⁓ |
| 438. | MeO-C6H3(OMe)-CH2-N(CH(nPr)2)-C(=O)-CH2-C(Me)2-⁓ |
| 439. | MeO-C6H3(nBu)-CH2-NH-C(=O)-CH2-C(Me)2-⁓ |
| 440. | MeO-C6H3(OnPr)-CH2-NH-C(=O)-CH2-C(Me)2-⁓ |
| 441. | MeO-C6H3(nBu)-CH2-NH-C(=O)-CH2-C(Me)2-⁓ |
| 442. | MeO-C6H3(OnPr)-CH2-NH-C(=O)-CH2-C(Me)2-⁓ |
| 443. | Br-C6H4-N(CH(Et)(nPr))-C(=O)-CH2-C(Me)2-⁓ |
| 444. | Br-C6H4-N(CH(Me)(nPent))-C(=O)-CH2-C(Me)2-⁓ |
| 445. | Br-C6H4-N(CH(nBu)2)-C(=O)-CH2-C(Me)2-⁓ |
| 446. | Br-C6H4-N(CH(Et)2)-C(=O)-CH2-C(Me)2-⁓ |
| 447. | Br-C6H4-N(CH(Me)Et)-C(=O)-CH2-C(Me)2-⁓ |
| 448. | Br-C6H4-N(nBu)-C(=O)-CH2-C(Me)2-⁓ |

TABLE 2B-continued
| | R |
|---|---|
| 449. | 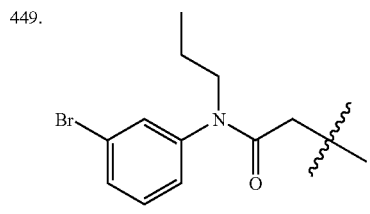 |
| 450. | 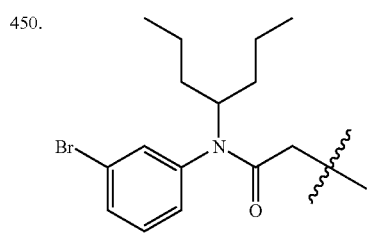 |
| 451. | 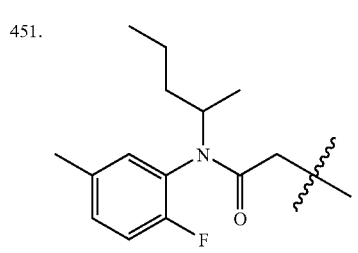 |
| 452. | 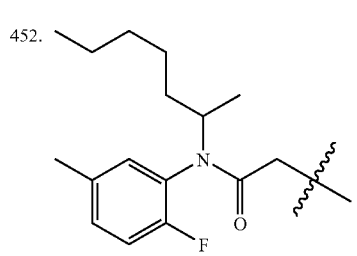 |
| 453. | 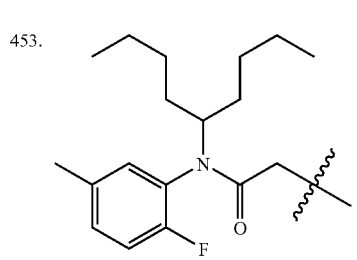 |
| 454. | 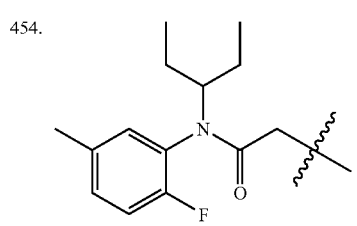 |
| 455. | 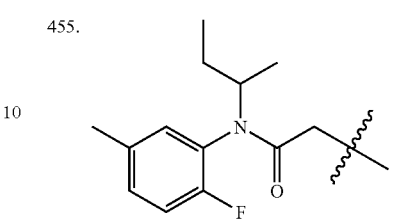 |
| 456. | 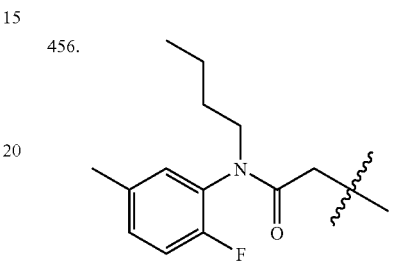 |
| 457. | 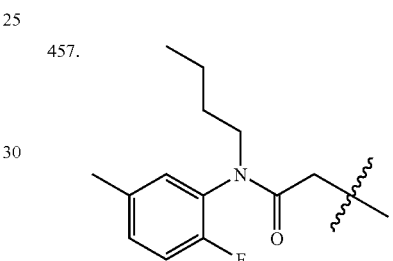 |
| 458. | 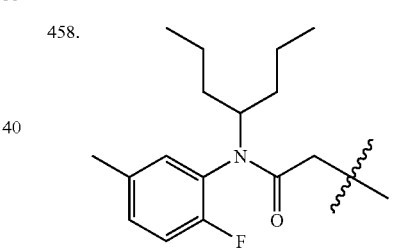 |
| 459. | 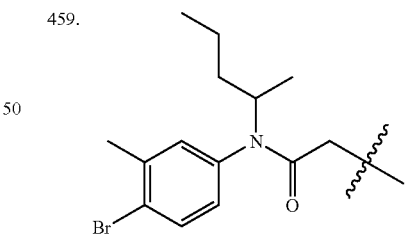 |
| 460. | 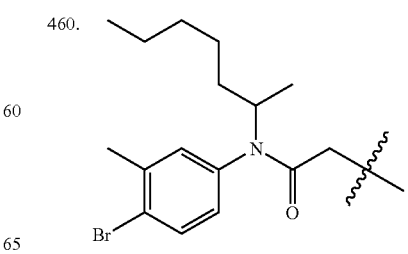 |

TABLE 2B-continued
| | R |
|---|---|
| 461. | 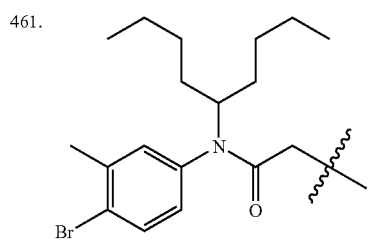 |
| 462. | 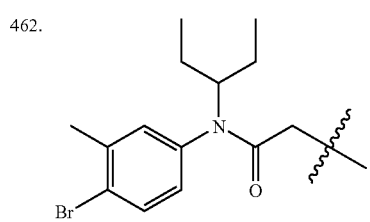 |
| 463. | 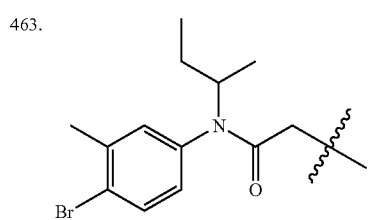 |
| 464. | 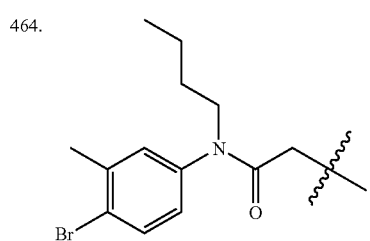 |
| 465. | 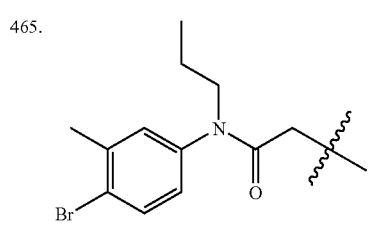 |
| 466. | 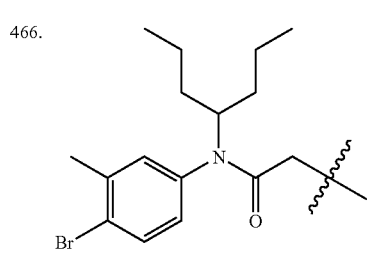 |
TABLE 2B-continued
| | R |
|---|---|
| 467. | 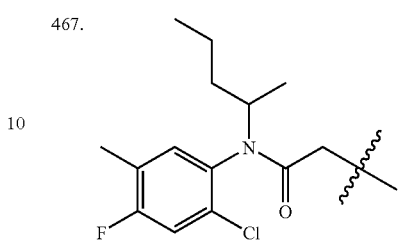 |
| 468. | 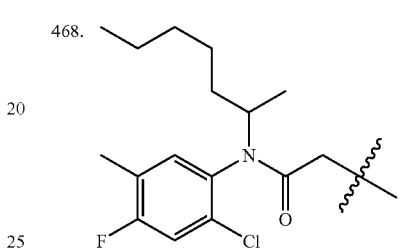 |
| 469. | 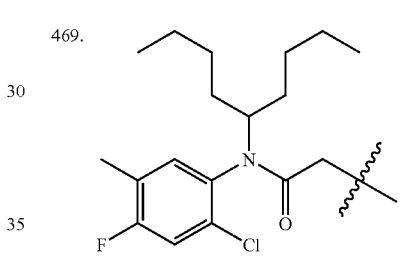 |
| 470. | 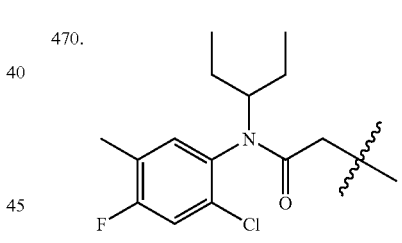 |
| 471. | 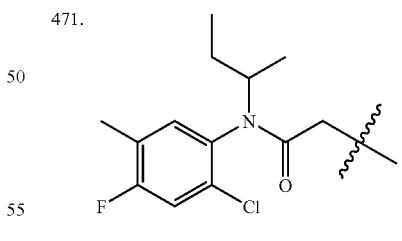 |
| 472. | 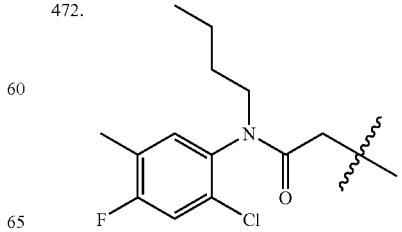 |

TABLE 2B-continued
| R |
|---|
| 473. 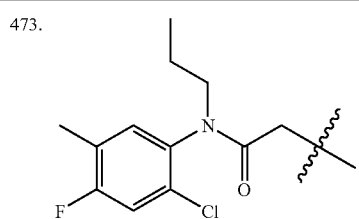 |
| 474. 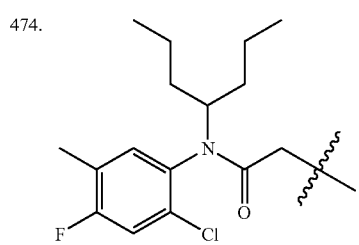 |
| 475. 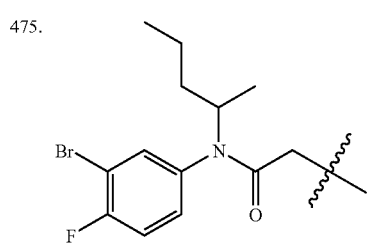 |
| 476. 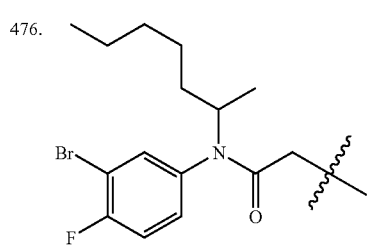 |
| 477. 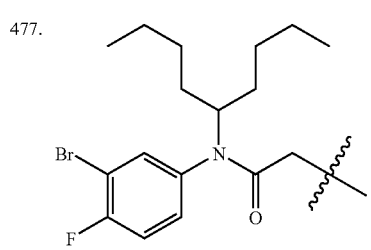 |
| 478. 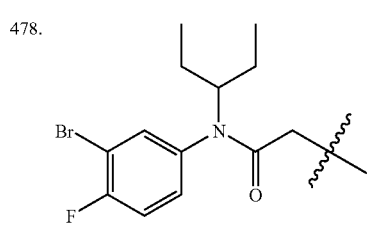 |
TABLE 2B-continued
| R |
|---|
| 479. 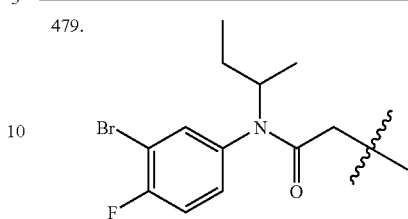 |
| 480. 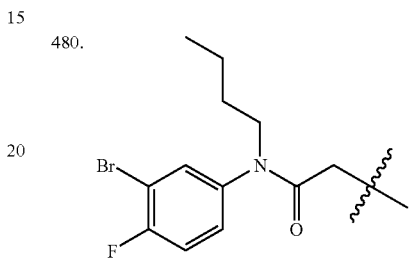 |
| 481. 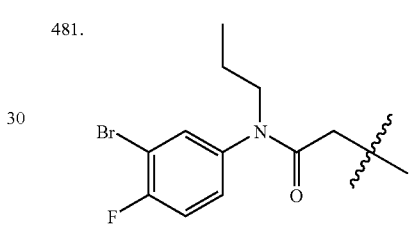 |
| 482. 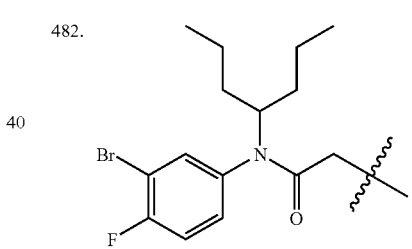 |
| 483. 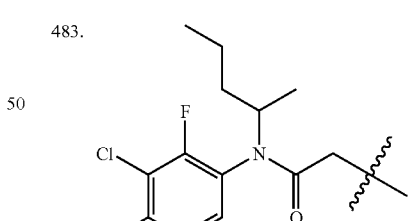 |
| 484. 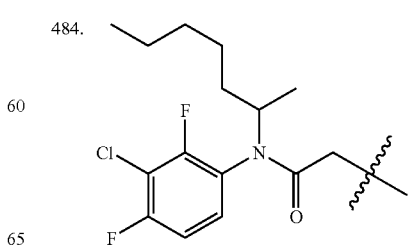 |

TABLE 2B-continued
| R |
|---|
| 485. 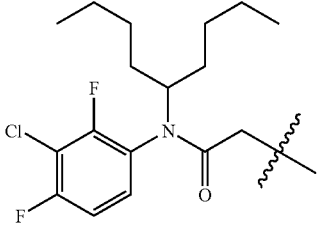 |
| 486. 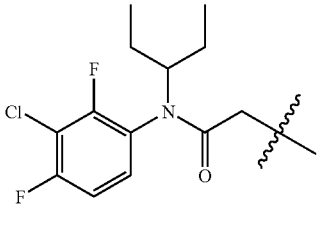 |
| 487. 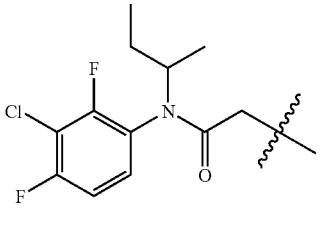 |
| 488. 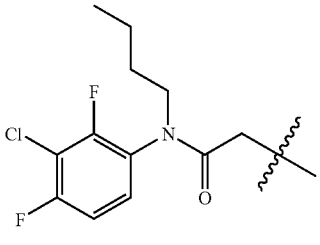 |
| 489. 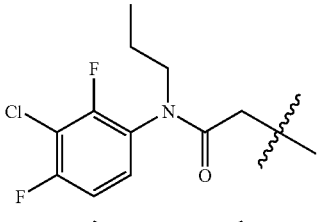 |
| 490. 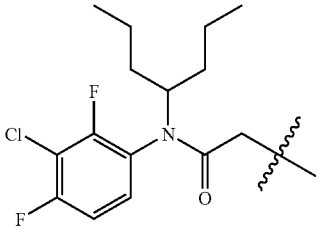 |
| 491. 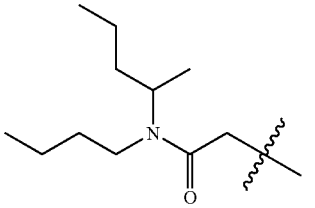 |
| 492. 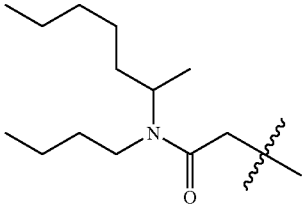 |
| 493. 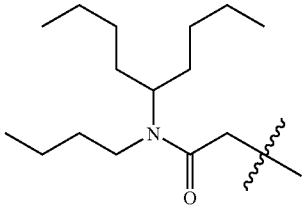 |
| 494. 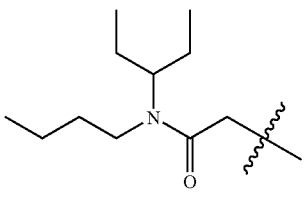 |
| 495. 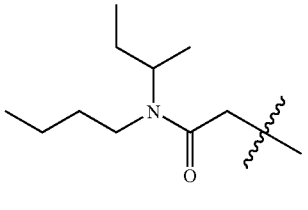 |
| 496. 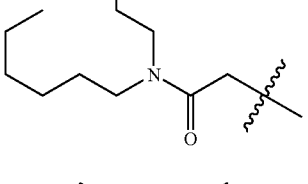 |
| 497. 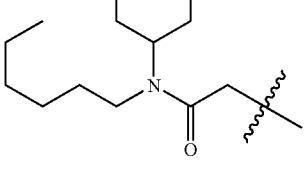 |
| 498. 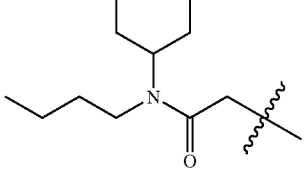 |

TABLE 2B-continued
| | R |
|---|---|
| 499. | 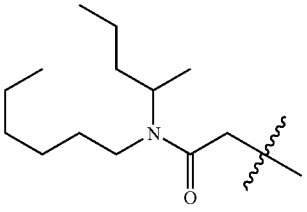 |
| 500. | 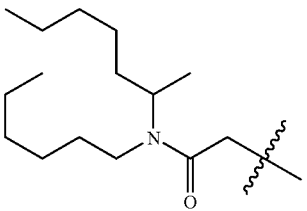 |
| 501. | 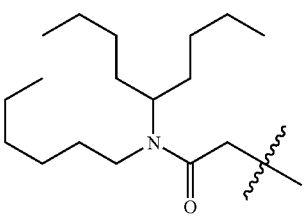 |
| 502. | 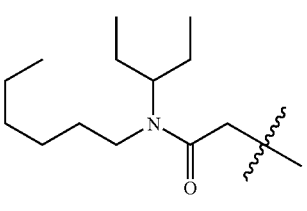 |
| 503. | 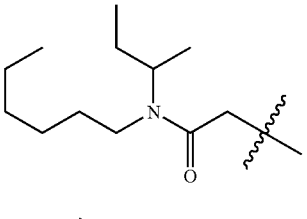 |
| 504. | 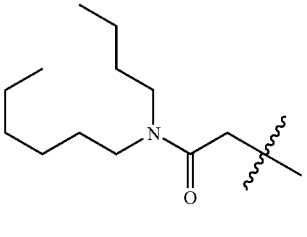 |
| 505. | 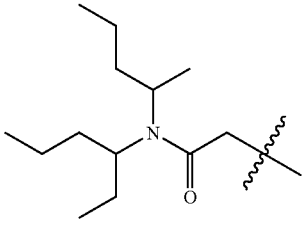 |
| 506. | 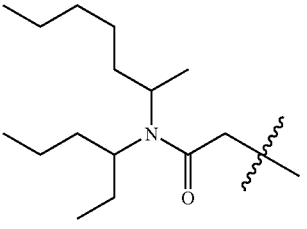 |
| 507. | 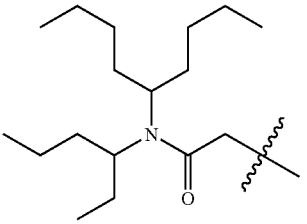 |
| 508. | 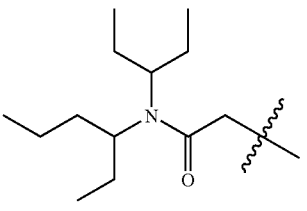 |
| 509. | 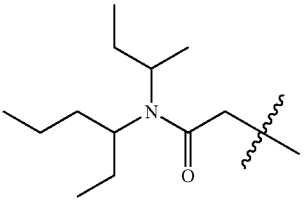 |
| 510. | 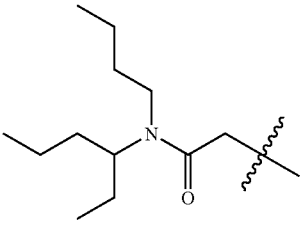 |
| 511. | 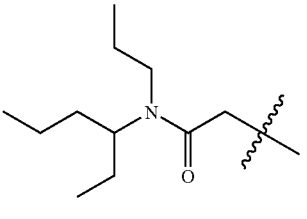 |
| 512. | 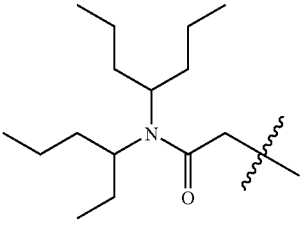 |

TABLE 2B-continued
| | R |
|---|---|
| 513. | 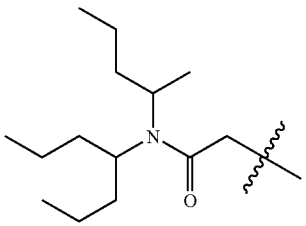 |
| 514. | 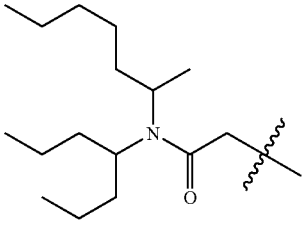 |
| 515. | 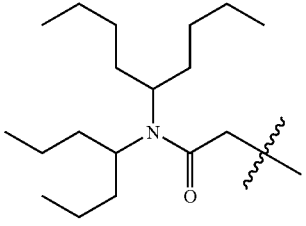 |
| 516. | 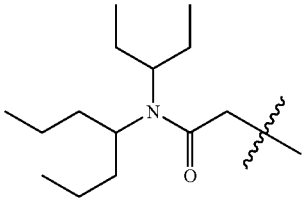 |
| 517. | 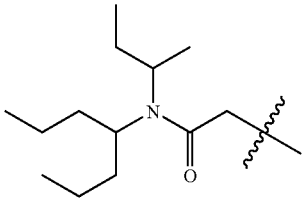 |
| 518. | 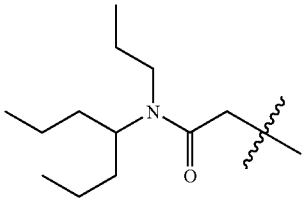 |
| 519. | 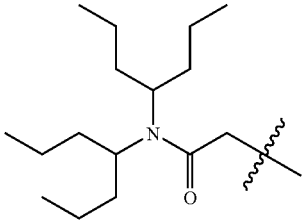 |
| 520. | 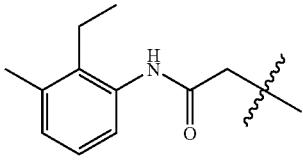 |
| 521. | 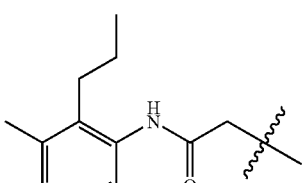 |
| 522. | 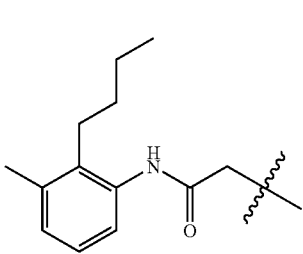 |
| 523. | 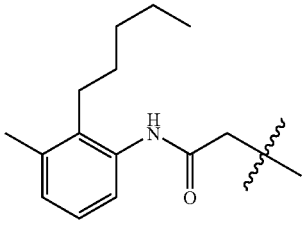 |
| 524. | 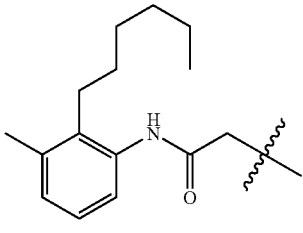 |
| 525. | 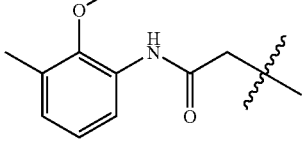 |
| 526. | 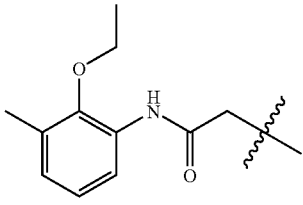 |

TABLE 2B-continued

| R |
|---|
| 527. (2-propoxy-3-methylphenyl amide) |
| 528. (2-butoxy-3-methylphenyl amide) |
| 529. (2-pentyloxy-3-methylphenyl amide) |
| 530. (2,3-diethylphenyl amide) |
| 531. (2-propyl-3-ethylphenyl amide) |
| 532. (2-butyl-3-ethylphenyl amide) |
| 533. (2-pentyl-3-ethylphenyl amide) |
| 534. (2-hexyl-3-ethylphenyl amide) |
| 535. (2-methoxy-3-ethylphenyl amide) |
| 536. (2-ethoxy-3-ethylphenyl amide) |
| 537. (2-propoxy-3-ethylphenyl amide) |
| 538. (2-butoxy-3-ethylphenyl amide) |
| 539. (2-pentyloxy-3-ethylphenyl amide) |
| 540. (2-ethyl-3-ethylphenyl amide) |

TABLE 2B-continued
| | R |
|---|---|
| 541. | 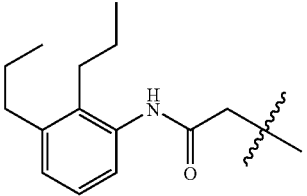 |
| 542. | 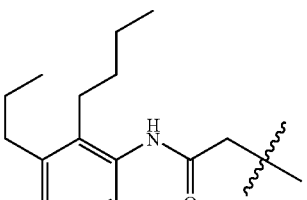 |
| 543. | 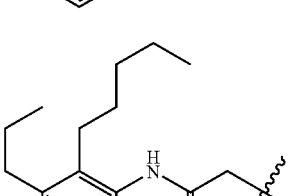 |
| 544. | 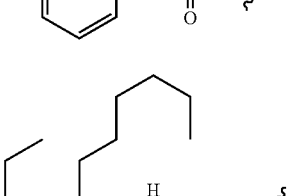 |
| 545. | 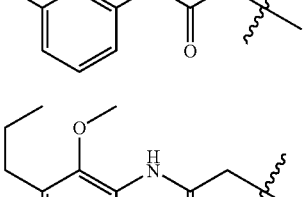 |
| 546. | 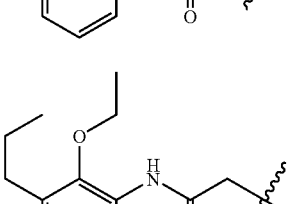 |
| 547. | 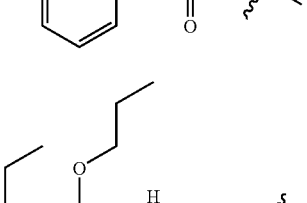 |
| 548. | 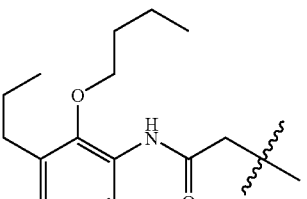 |
| 549. | 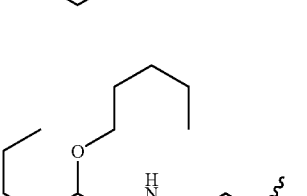 |
| 550. | 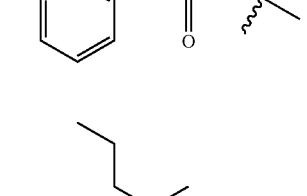 |
| 551. | 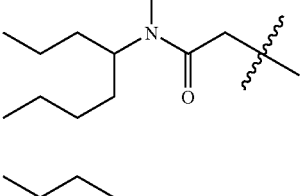 |
| 552. | 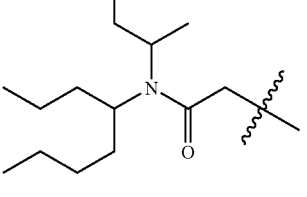 |
| 553. | 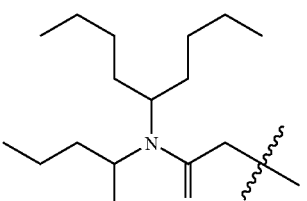 |

US 7,208,517 B1
TABLE 2B-continued
| | R |
|---|---|
| 554. | 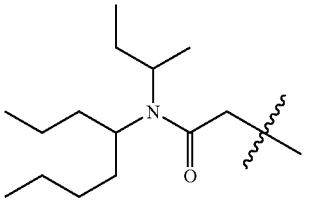 |
| 555. | 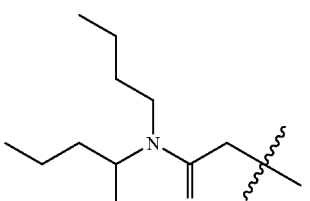 |
| 556. | 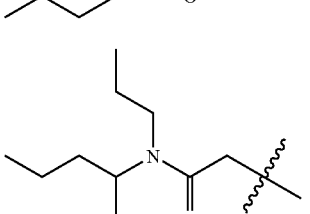 |
| 557. | 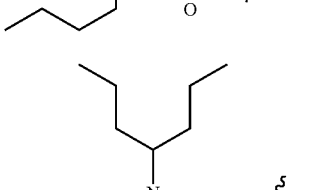 |
| 558. | 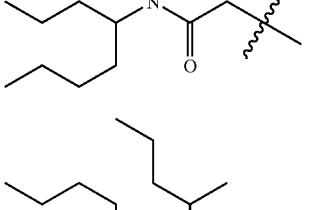 |
| 559. | 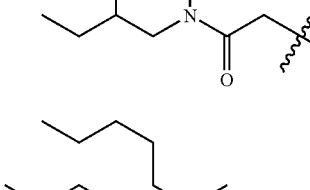 |
| 560. | 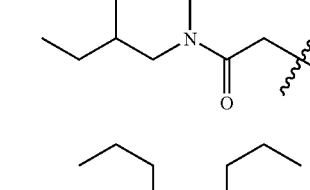 |
| 561. | 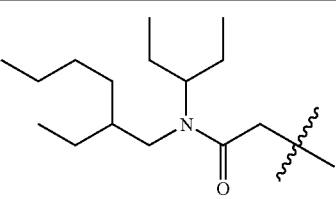 |
| 562. | 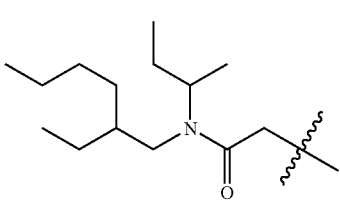 |
| 563. | 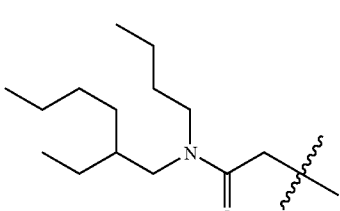 |
| 564. | 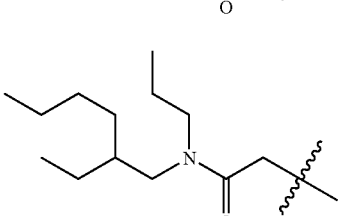 |
| 565. | 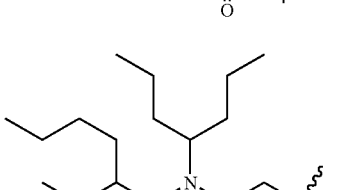 |
| 566. | 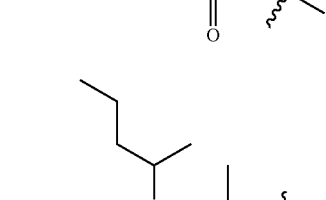 |
| 567. | 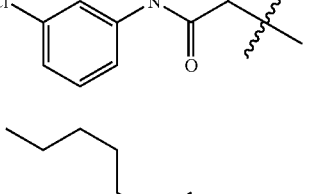 |

TABLE 2B-continued
R
568. 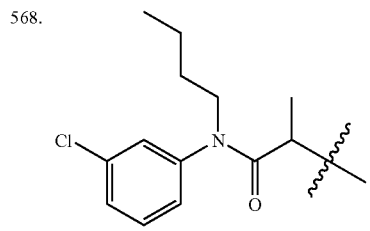
569. 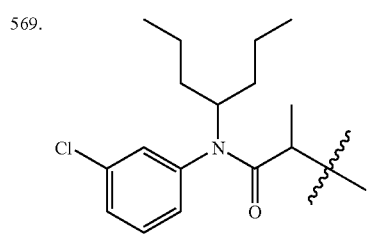
570. 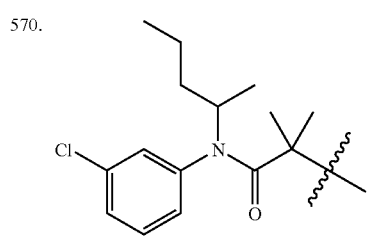
571. 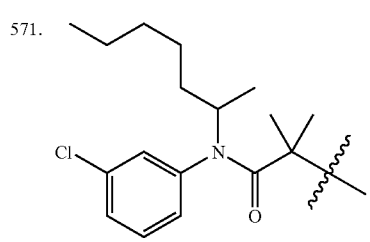
572. 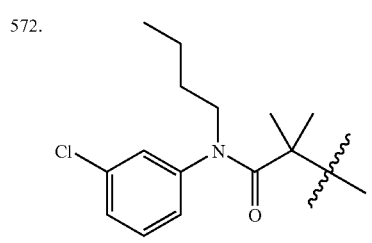
573. 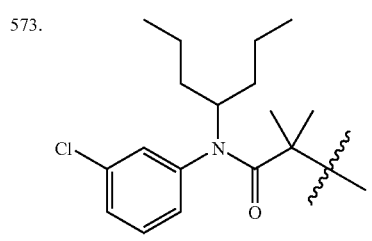
TABLE 2B-continued
R
574. 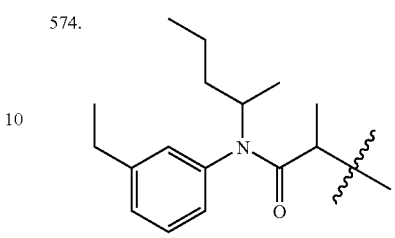
575. 
576. 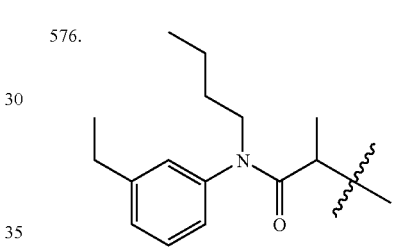
577. 
578. 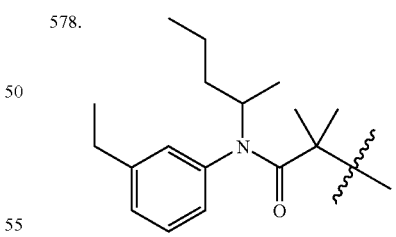
579. 

TABLE 2B-continued
| | R |
|---|---|
| 580. | 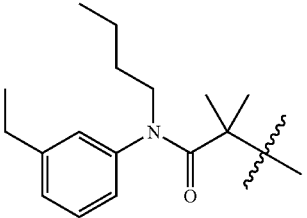 |
| 581. | 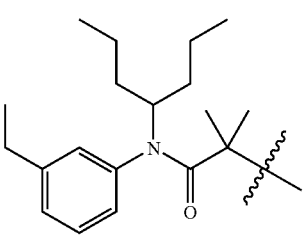 |
| 582. | 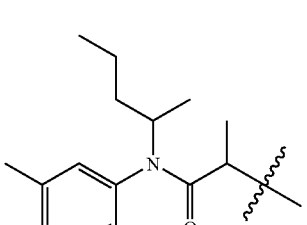 |
| 583. | 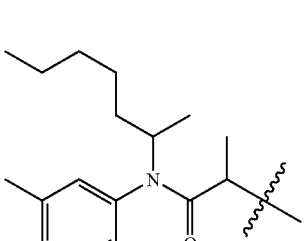 |
| 584. | 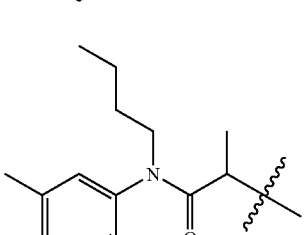 |
| 585. | 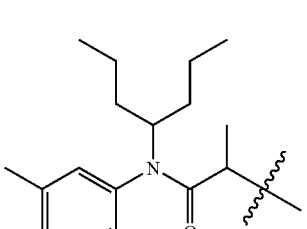 |
| 586. | 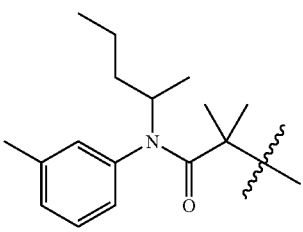 |
| 587. | 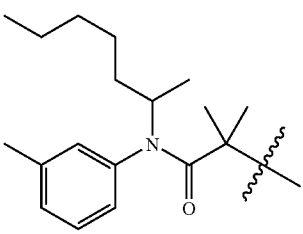 |
| 588. | 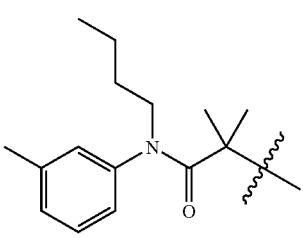 |
| 589. | 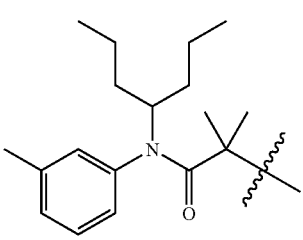 |
| 590. | 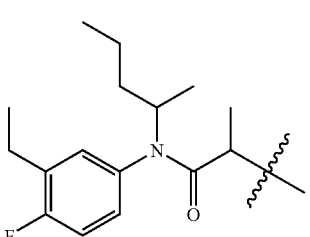 |
| 591. | 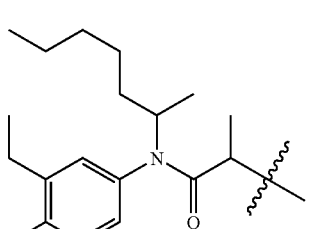 |

TABLE 2B-continued
| | R |
|---|---|
| 592. | 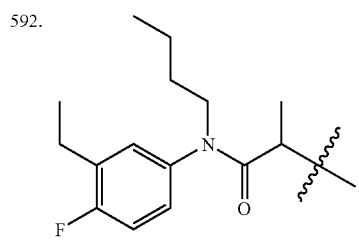 |
| 593. | 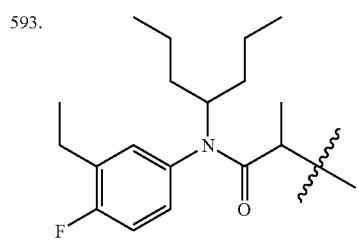 |
| 594. | 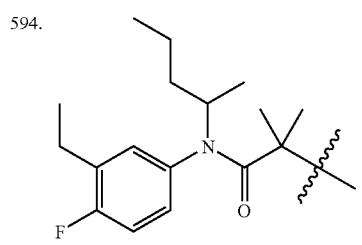 |
| 595. | 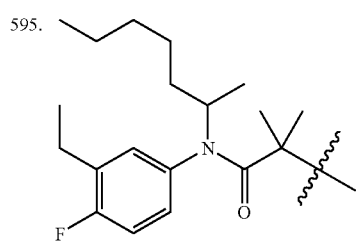 |
| 596. | 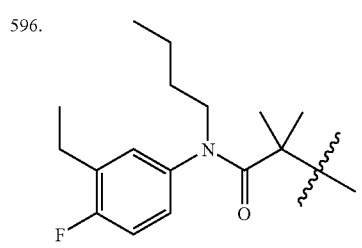 |
| 597. | 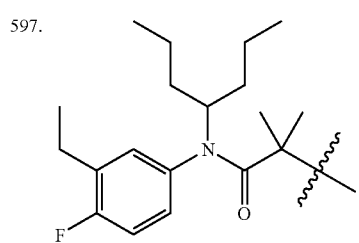 |
| 598. | 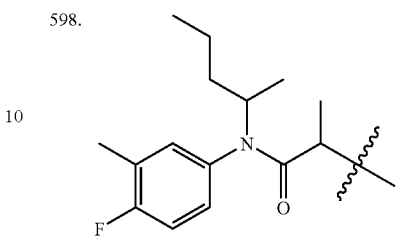 |
| 599. |  |
| 600. | 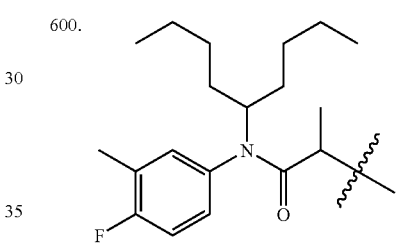 |
| 601. |  |
| 602. | 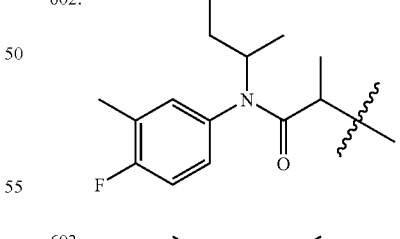 |
| 603. | 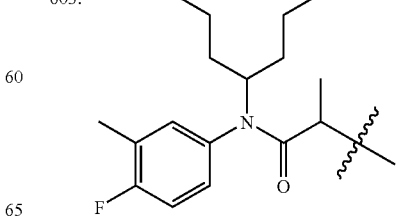 |

TABLE 2B-continued

| | R |
|---|---|
| 604. | |
| 605. | |
| 606. | |
| 607. | |
| 608. | |
| 609. | |
| 610. | |
| 611. | |
| 612. | |
| 613. | |
| 614. | |
| 615. | |
| 616. | |
| 617. | |

TABLE 2B-continued
| | R |
|---|---|
| 618. | 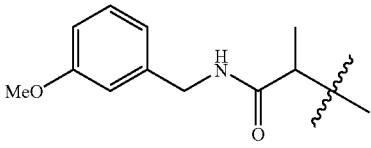 |
| 619. | 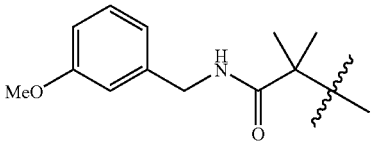 |
| 620. | 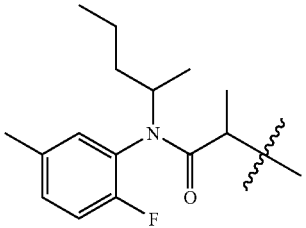 |
| 621. | 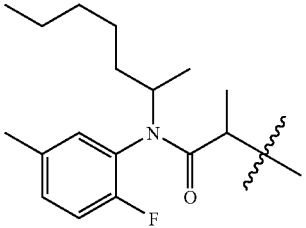 |
| 622. | 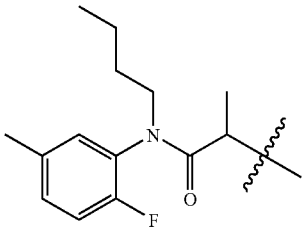 |
| 623. | 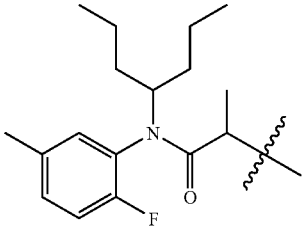 |
| 624. | 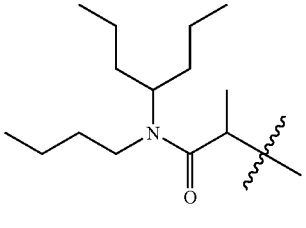 |
| 625. | 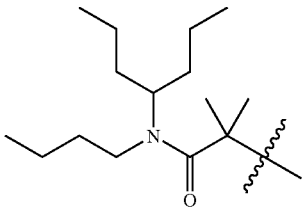 |
| 626. | 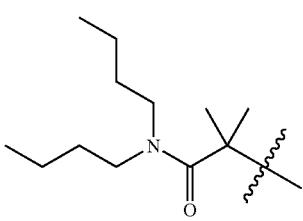 |
| 627. | 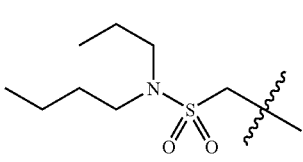 |
| 628. | 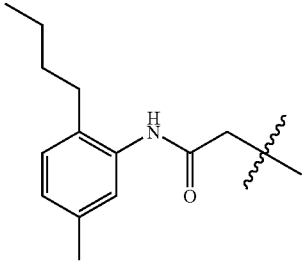 |
| 629. | 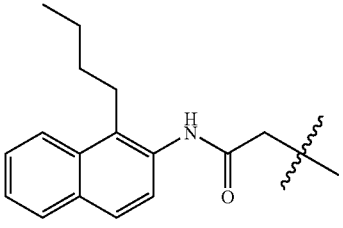 |
| 630. | 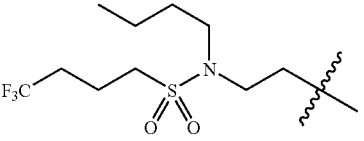 |
| 631. | 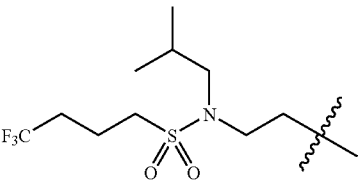 |

TABLE 2B-continued

R

632. [Structure: F₃C-(CH₂)₃-S(O)₂-N(propyl)-CH₂CH₂-C(CH₃)(wavy bond)]

EXAMPLE 339

Using methods described in the above examples, compounds comprising a parent structure selected from those disclosed in Table 3A and an R substituent selected from those disclosed in Table 3B can be prepared.

TABLE 3A

1. [Pyrrolidine with 2-(4-fluorophenyl), 3-COOH, 4-(benzofuran-5-yl); R—N]

2. [Pyrrolidine with 2-(4-MOM-O-phenyl), 3-COOH, 4-(benzofuran-5-yl); R—N]

3. [Pyrrolidine with 2-(4-fluorophenyl), 3-COOH, 4-(2,3-dihydrobenzofuran-5-yl); R—N]

TABLE 3A-continued

4. [Pyrrolidine with 2-(4-methoxyphenyl), 3-COOH, 4-(benzofuran-6-yl); R—N]

5. [Pyrrolidine with 2-(4-methoxyphenyl), 3-COOH, 4-(2,3-dihydrobenzofuran-6-yl); R—N]

6. [Pyrrolidine with 2-(4-methoxyphenyl), 3-COOH, 4-(3,4-difluorophenyl); R—N]

7. [Pyrrolidine with 2-(4-methoxyphenyl), 3-COOH, 4-(2,3-dihydro-1,4-benzodioxin-6-yl); R—N]

8. [Pyrrolidine with 2-(4-ethylphenyl), 3-COOH, 4-(1,3-benzodioxol-5-yl); R—N]

TABLE 3A-continued
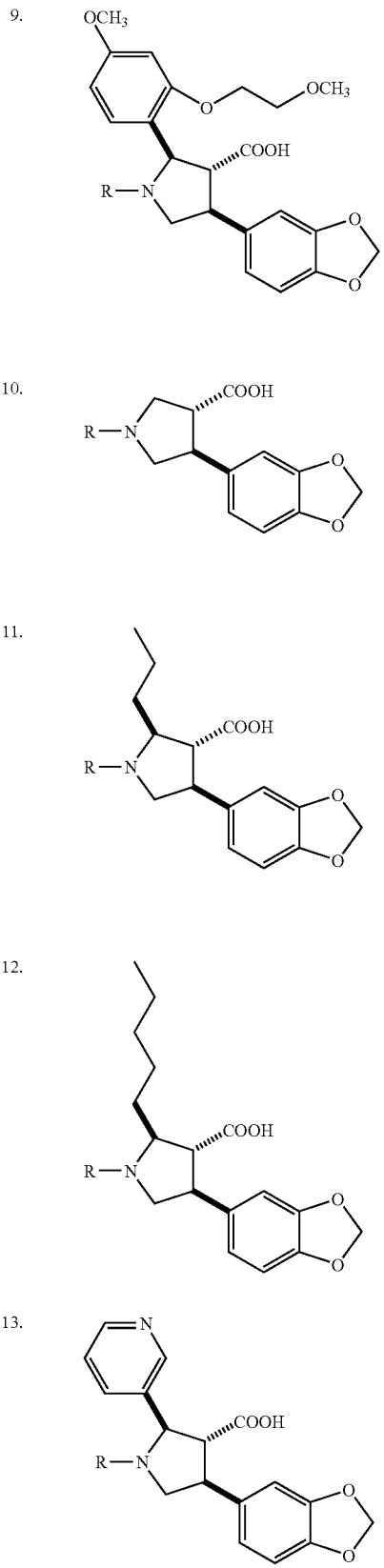
TABLE 3A-continued
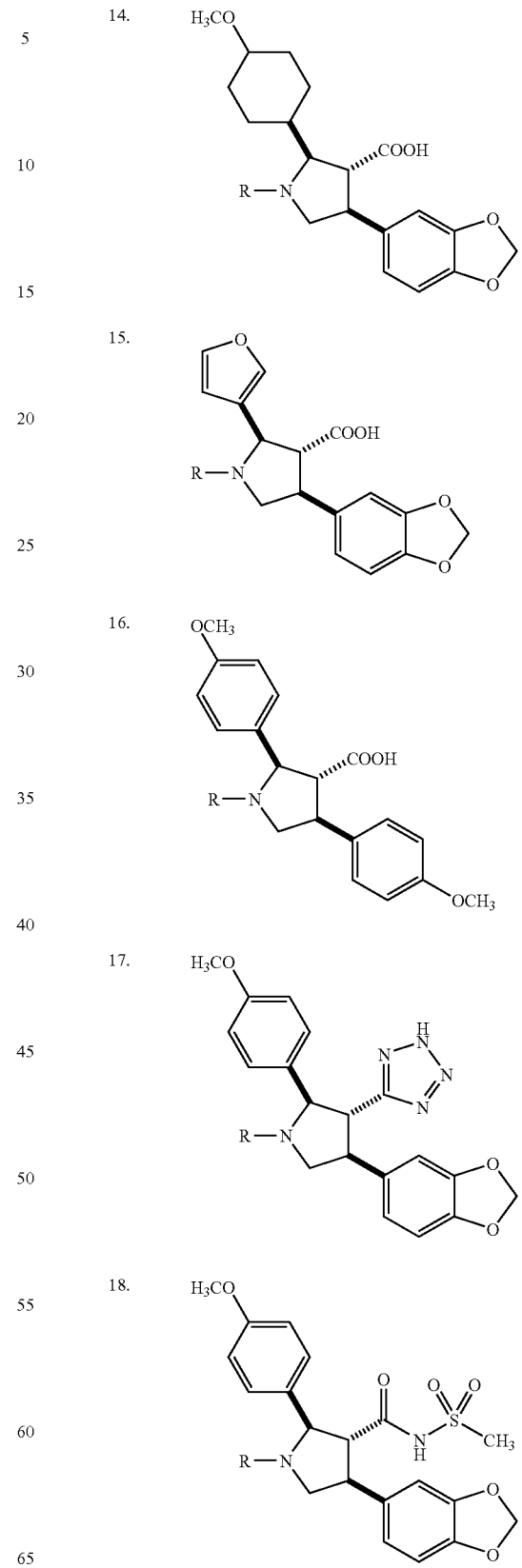

TABLE 3A-continued
| 19. | 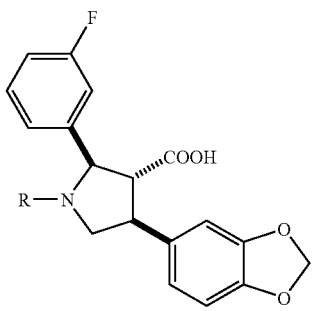 |
|---|---|
| 20. | 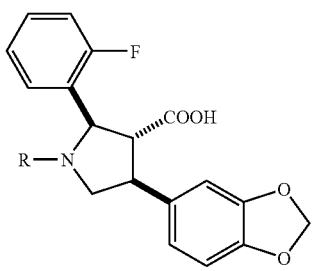 |
| 21. | 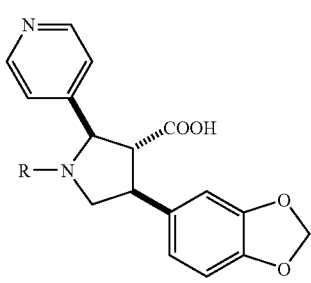 |
TABLE 3B
| | R |
|---|---|
| 1. | 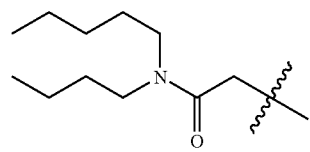 |
| 2. | 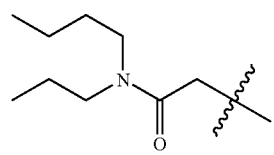 |
| 3. | 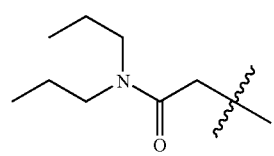 |
| 4. | 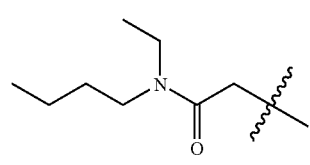 |
TABLE 3B-continued
| | R |
|---|---|
| 5. | 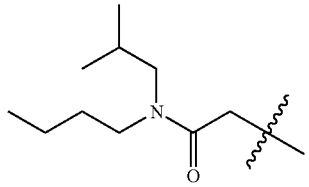 |
| 6. | 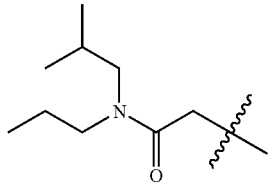 |
| 7. | 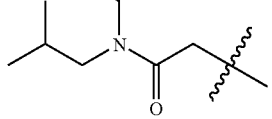 |
| 8. | 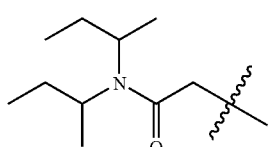 |
| 9. | 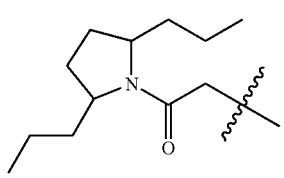 |
| 10. | 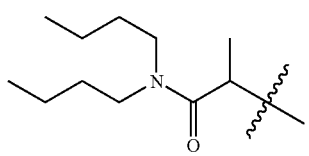 |
| 11. | 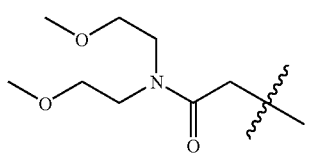 |
| 12. | 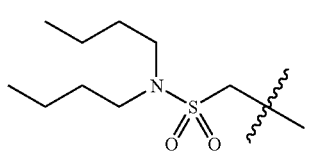 |
| 13. | 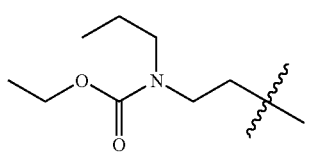 |

TABLE 3B-continued
| | R |
|---|---|
| 14. | 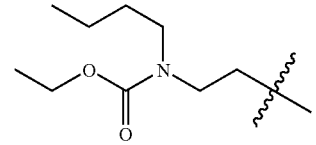 |
| 15. | 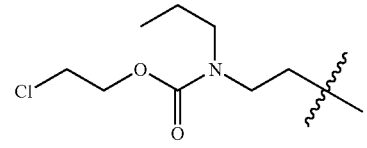 |
| 16. | 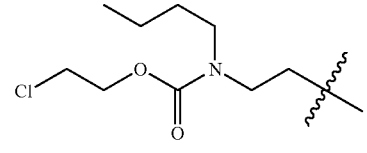 |
| 17. | 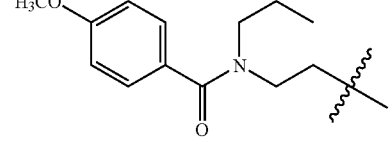 |
| 18. | 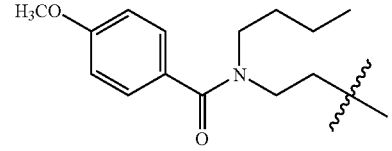 |
| 19. | 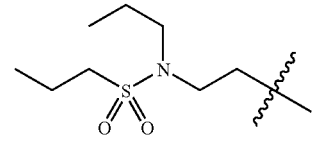 |
| 20. | 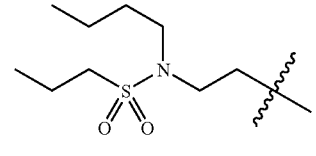 |
| 21. | 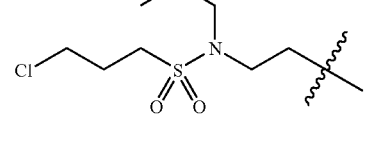 |
| 22. | 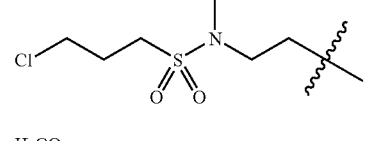 |
| 23. | 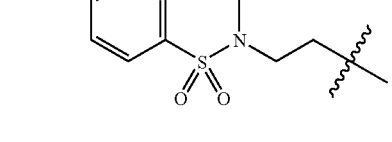 |
| 24. | |
| 25. | |
| 26. | |
| 27. | |
| 28. | |
| 29. | |
| 30. | |
| 31. | |
| 32. | |
| 33. | |

TABLE 3B-continued
| | R |
|---|---|
| 34. | 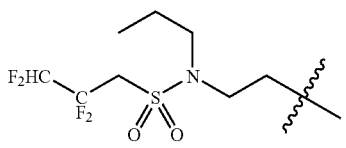 |
| 35. | 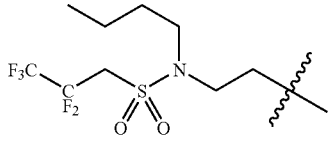 |
| 36. | 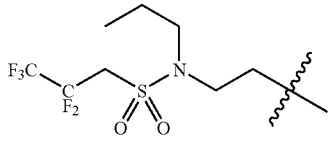 |
| 37. | 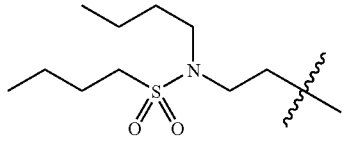 |
| 38. | 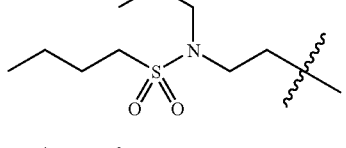 |
| 39. | 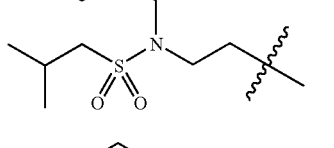 |
| 40. | 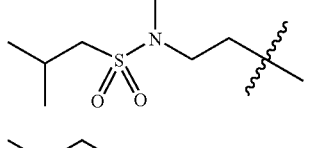 |
| 41. | 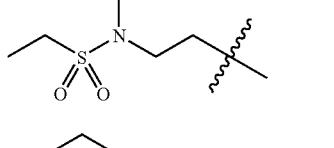 |
| 42. | 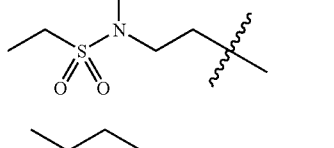 |
| 43. | 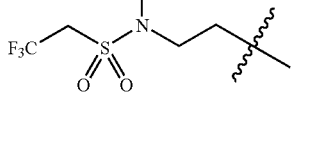 |
| 44. | 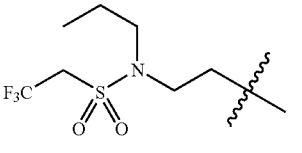 |
| 45. | 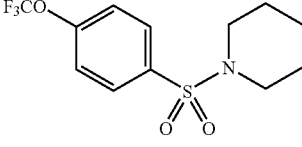 |
| 46. | 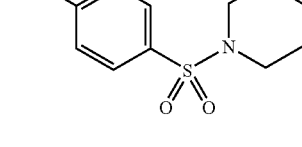 |
| 47. | 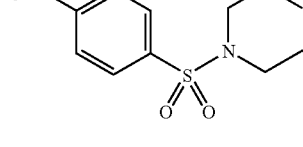 |
| 48. | 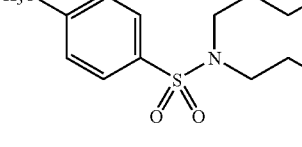 |
| 49. | 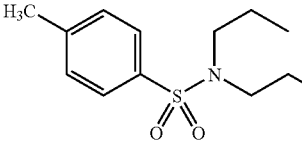 |
| 50. | 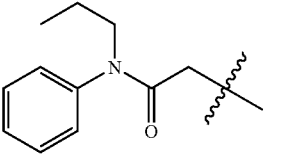 |
| 51. | 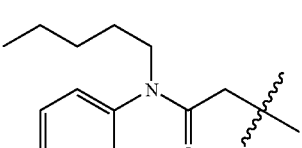 |
| 52. | 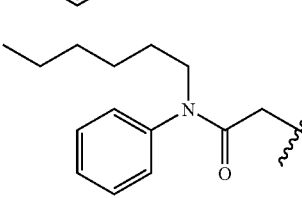 |

TABLE 3B-continued
| | R |
|---|---|
| 53. | 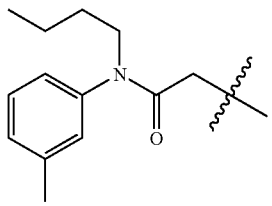 |
| 54. | 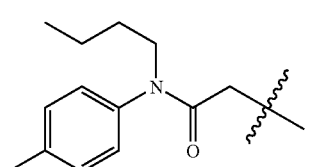 |
| 55. | 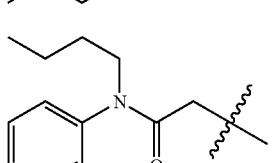 |
| 56. | 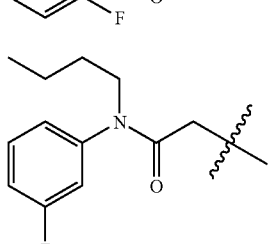 |
| 57. | 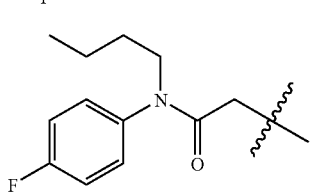 |
| 58. | 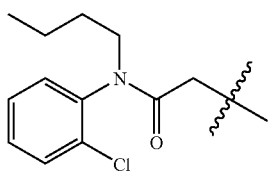 |
| 59. | 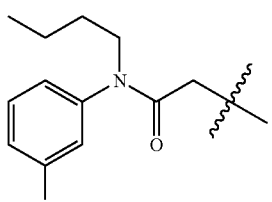 |
| 60. | 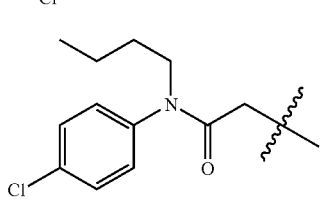 |
TABLE 3B-continued
| | R |
|---|---|
| 61. | 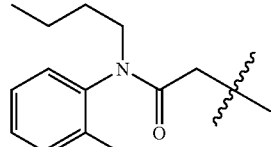 |
| 62. | 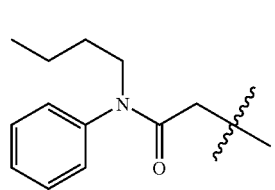 |
| 63. | 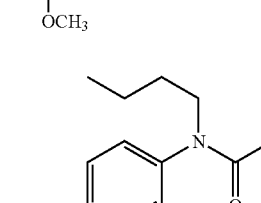 |
| 64. | 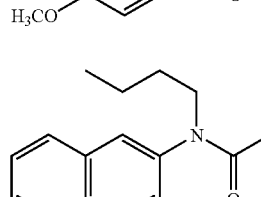 |
| 65. | 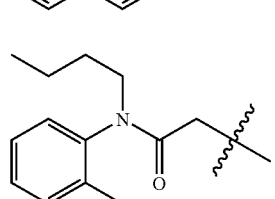 |
| 66. | 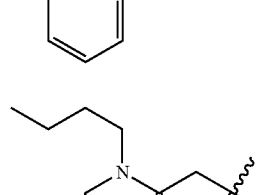 |
| 67. | 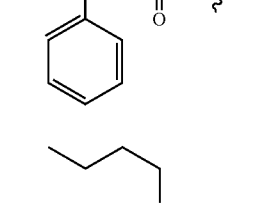 |

TABLE 3B-continued
| | R |
|---|---|
| 68. | 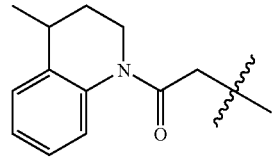 |
| 69. | 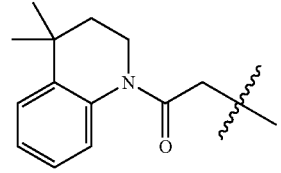 |
| 70. | 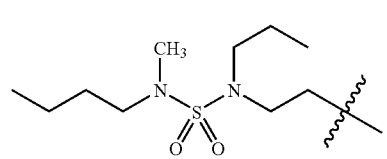 |
| 71. | 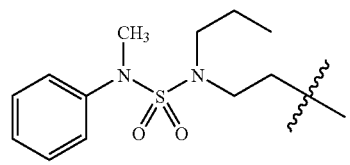 |
| 72. | 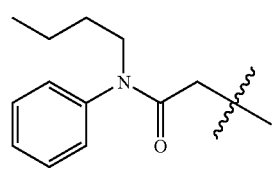 |
| 73. | 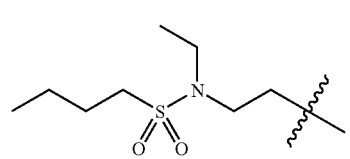 |
| 74. | 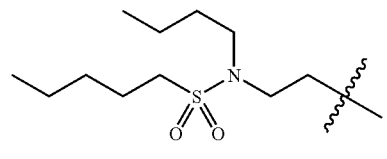 |
| 75. | 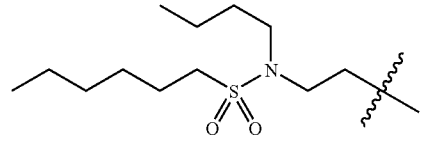 |
| 76. | 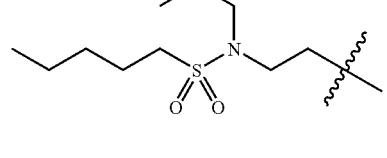 |
| 77. | 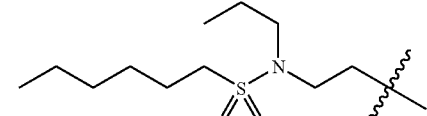 |
| 78. | 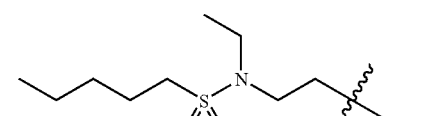 |
| 79. | |
| 80. | |
| 81. | |
| 82. | |
| 83. | |
| 84. | |
| 85. | |
| 86. | |

TABLE 3B-continued

| | R |
|---|---|
| 87. | (isopropyl)N-SO2-CH2CH2CH2-Cl, N-alkyl chain |
| 88. | (pentyl)-SO2-N(isopropyl)-alkyl |
| 89. | (hexyl)-SO2-N(isopropyl)-alkyl |
| 90. | (isopentyl)-SO2-N(isopropyl)-alkyl |
| 91. | F3C-CH2CH2-SO2-N(isopropyl)-alkyl |
| 92. | F3C-CF2-CH2-SO2-N(isopropyl)-alkyl |
| 93. | (isobutyl)-SO2-N(isopropyl)-alkyl |
| 94. | F3C-CH2-O-CH2CH2-SO2-N(isopropyl)-alkyl |
| 95. | F3C-CF2-CH2-O-CH2CH2-SO2-N(isopropyl)-alkyl |
| 96. | F3C-CF2-CH2-SO2-N(propyl)-alkyl |

TABLE 3B-continued

| | R |
|---|---|
| 97. | F3C-CH2-O-CH2CH2-SO2-N(propyl)-alkyl |
| 98. | F3C-CF2-CH2-O-CH2CH2-SO2-N(propyl)-alkyl |
| 99. | (butyl)-SO2-N(CH2CH2OCH3)-alkyl |
| 100. | Cl-CH2CH2CH2-SO2-N(CH2CH2OCH3)-alkyl |
| 101. | (pentyl)-SO2-N(CH2CH2OCH3)-alkyl |
| 102. | (hexyl)-SO2-N(CH2CH2OCH3)-alkyl |
| 103. | (isopentyl)-SO2-N(CH2CH2OCH3)-alkyl |
| 104. | F3C-CH2CH2-SO2-N(CH2CH2OCH3)-alkyl |
| 105. | F3C-CF2-CH2-SO2-N(CH2CH2OCH3)-alkyl |
| 106. | (isobutyl)-SO2-N(CH2CH2OCH3)-alkyl |

TABLE 3B-continued

| | R |
|---|---|
| 107. | (structure) |
| 108. | (structure) |
| 109. | (structure) |
| 110. | (structure) |
| 111. | (structure) |
| 112. | (structure) |
| 113. | (structure) |
| 114. | (structure) |amp TABLE 3B-continued

| | R |
|---|---|
| 115. | (structure) |
| 116. | (structure) |
| 117. | (structure) |
| 118. | (structure) |
| 119. | (structure) |
| 120. | (structure) |
| 121. | (structure) |

TABLE 3B-continued
| | R |
|---|---|
| 122. | 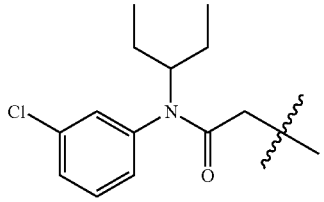 |
| 123. | 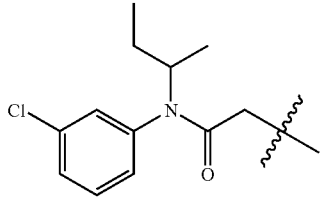 |
| 124. | 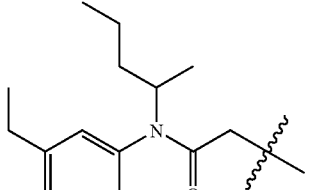 |
| 125. | 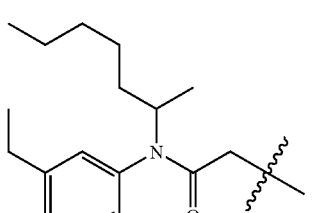 |
| 126. | 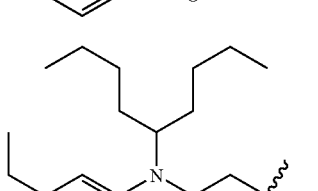 |
| 127. | 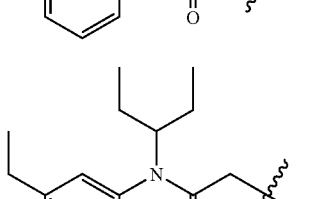 |
| 128. | 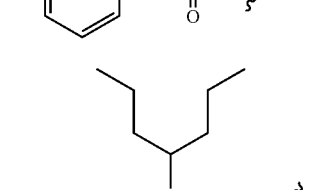 |
| 129. | 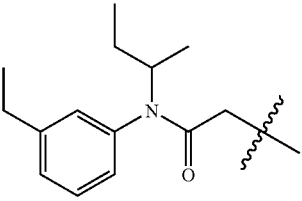 |
| 130. | 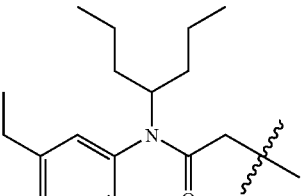 |
| 131. | 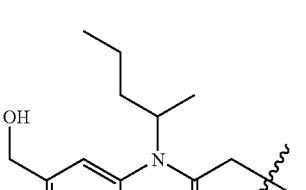 |
| 132. | 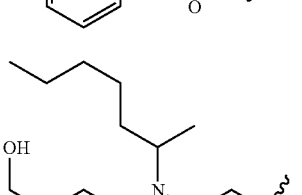 |
| 133. | 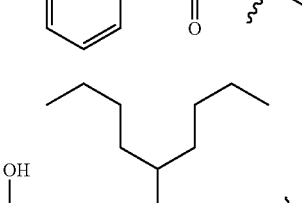 |
| 134. | 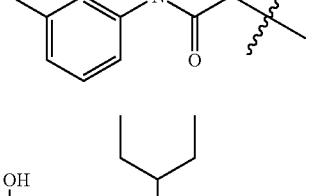 |
| 135. | 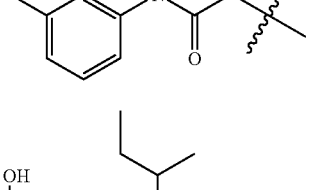 |

TABLE 3B-continued

| | R |
|---|---|
| 136. | (3-hydroxymethylphenyl)-N-(heptan-4-yl)-acetamide linker |
| 137. | (3-trifluoromethoxyphenyl)-N-(pentan-2-yl)-acetamide linker |
| 138. | (3-trifluoromethoxyphenyl)-N-(heptan-2-yl)-acetamide linker |
| 139. | (3-trifluoromethoxyphenyl)-N-(nonan-5-yl)-acetamide linker |
| 140. | (3-trifluoromethoxyphenyl)-N-(pentan-3-yl)-acetamide linker |
| 141. | (3-trifluoromethoxyphenyl)-N-(butan-2-yl)-acetamide linker |
| 142. | (3-trifluoromethoxyphenyl)-N-(heptan-4-yl)-acetamide linker |
| 143. | (3-methylphenyl)-N-(pentan-2-yl)-acetamide linker |
| 144. | (3-methylphenyl)-N-(heptan-2-yl)-acetamide linker |
| 145. | (3-methylphenyl)-N-(nonan-5-yl)-acetamide linker |
| 146. | (3-methylphenyl)-N-(pentan-3-yl)-acetamide linker |
| 147. | (3-methylphenyl)-N-(butan-2-yl)-acetamide linker |
| 148. | (3-methylphenyl)-N-(heptan-4-yl)-acetamide linker |

TABLE 3B-continued
| | R |
|---|---|
| 149. | 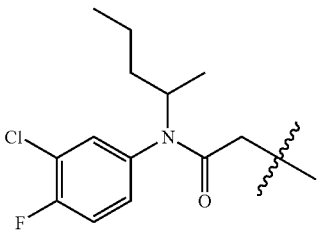 |
| 150. | 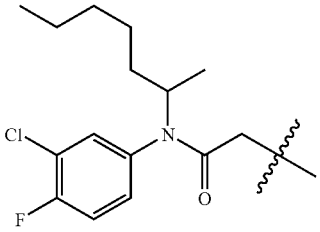 |
| 151. | 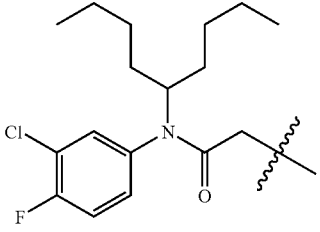 |
| 152. | 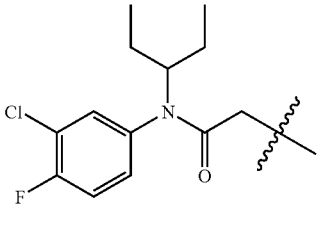 |
| 153. | 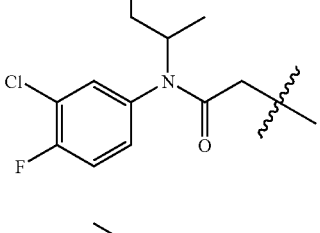 |
| 154. | 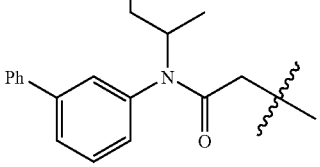 |
TABLE 3B-continued
| | R |
|---|---|
| 155. | 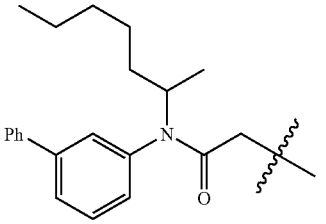 |
| 156. | 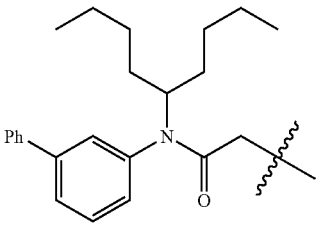 |
| 157. | 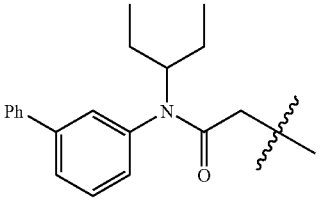 |
| 158. | 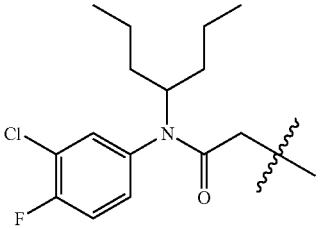 |
| 159. | 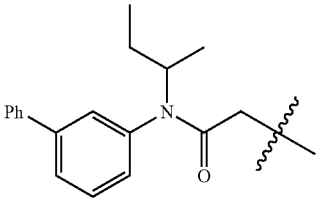 |
| 160. | 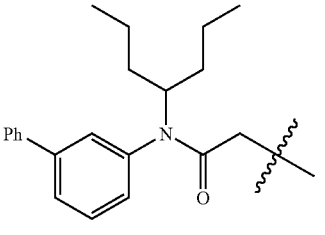 |

TABLE 3B-continued
| | R |
|---|---|
| 161. | 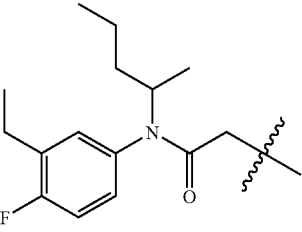 |
| 162. | 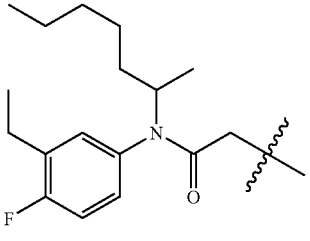 |
| 163. | 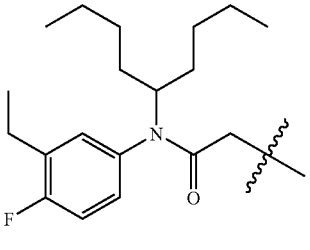 |
| 164. | 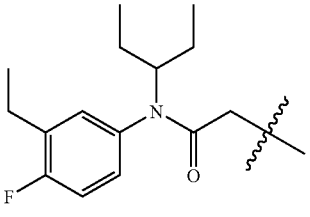 |
| 165. | 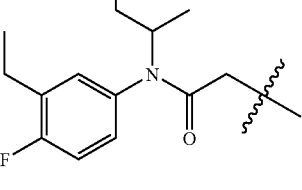 |
| 166. | 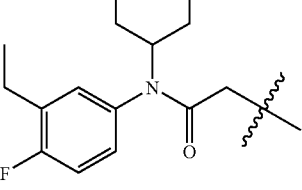 |
| 167. | 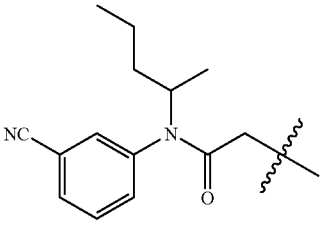 |
| 168. | 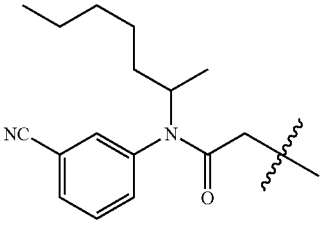 |
| 169. | 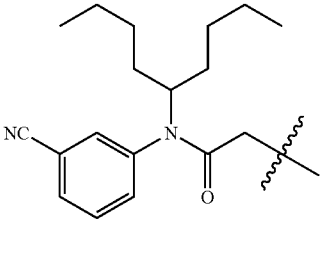 |
| 170. | 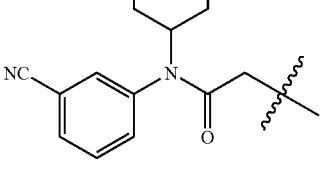 |
| 171. | 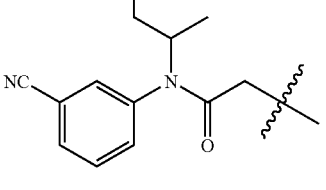 |
| 172. | 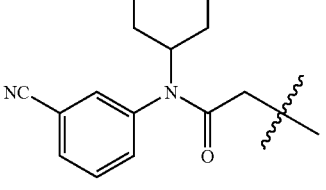 |

TABLE 3B-continued

| | R |
|---|---|
| 173. | (4-ethylpyrimidin-2-yl)(pentan-2-yl)amide structure |
| 174. | (4-ethylpyrimidin-2-yl)(hexan-2-yl)amide structure |
| 175. | (4-ethylpyrimidin-2-yl)(nonan-5-yl)amide structure |
| 176. | (4-ethylpyrimidin-2-yl)(pentan-3-yl)amide structure |
| 177. | (4-ethylpyrimidin-2-yl)(butan-2-yl)amide structure |
| 178. | (4-ethylpyrimidin-2-yl)(heptan-4-yl)amide structure |

TABLE 3B-continued

| | R |
|---|---|
| 179. | (4-ethyl-5-fluoropyrimidin-2-yl)(pentan-2-yl)amide structure |
| 180. | (4-ethyl-5-fluoropyrimidin-2-yl)(hexan-2-yl)amide structure |
| 181. | (4-ethyl-5-fluoropyrimidin-2-yl)(nonan-5-yl)amide structure |
| 182. | (4-ethyl-5-fluoropyrimidin-2-yl)(pentan-3-yl)amide structure |
| 183. | (4-ethyl-5-fluoropyrimidin-2-yl)(butan-2-yl)amide structure |
| 184. | (4-ethyl-5-fluoropyrimidin-2-yl)(heptan-4-yl)amide structure |

TABLE 3B-continued
R
185. 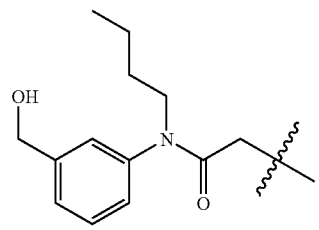
186. 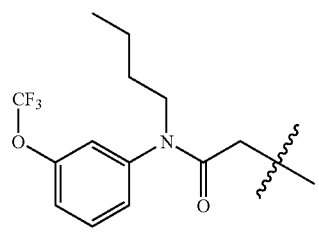
187. 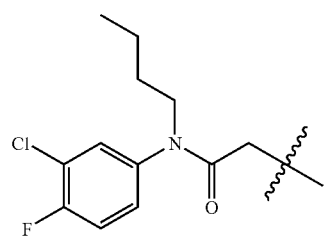
188. 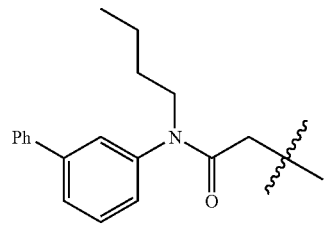
189. 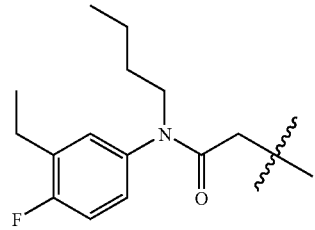
190. 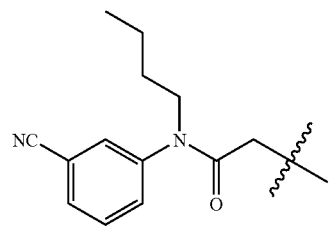
TABLE 3B-continued
R
191. 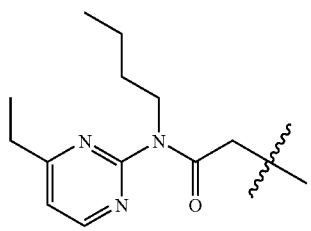
192. 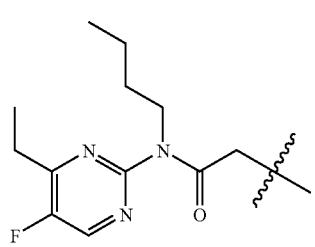
193. 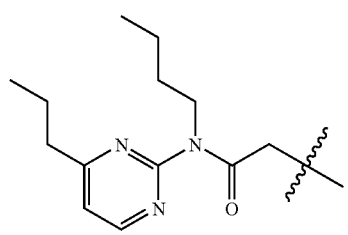
194. 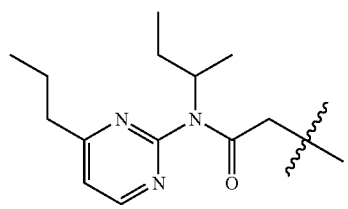
195. 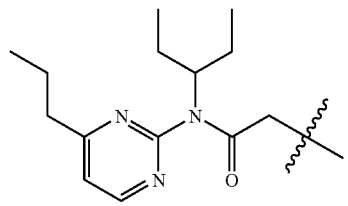
196. 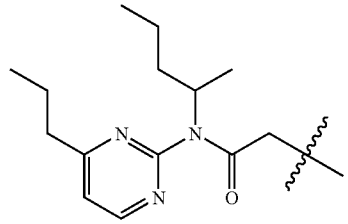

TABLE 3B-continued
| | R |
|---|---|
| 197. | 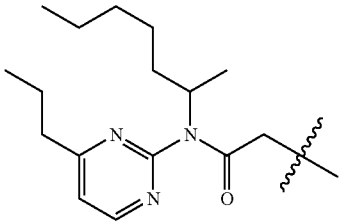 |
| 198. | 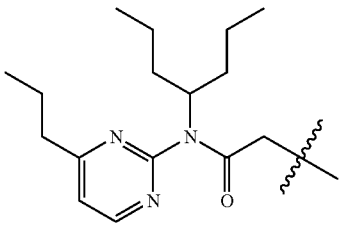 |
| 199. | 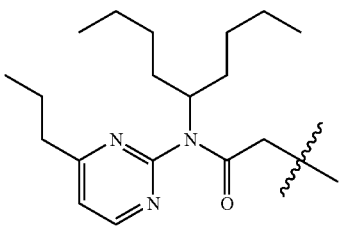 |
| 200. | 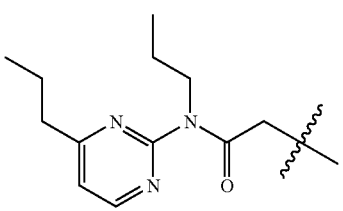 |
| 201. | 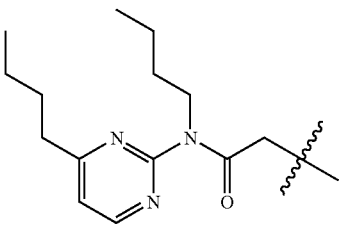 |
| 202. | 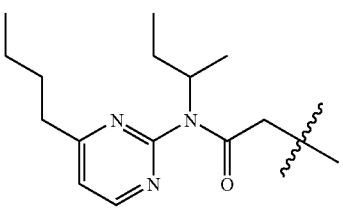 |
| 203. | 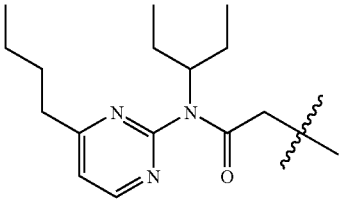 |
TABLE 3B-continued
| | R |
|---|---|
| 204. | 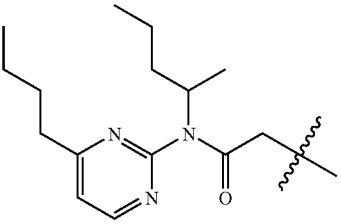 |
| 205. | 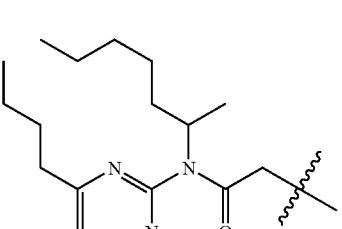 |
| 206. | 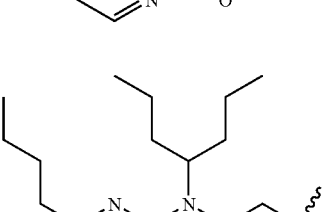 |
| 207. | 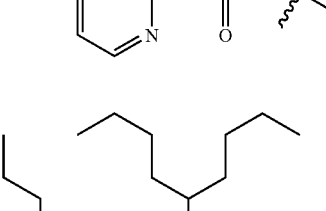 |
| 208. | 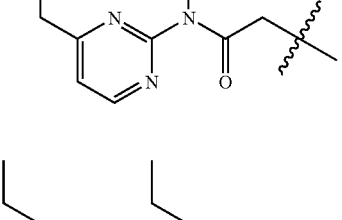 |
| 209. | 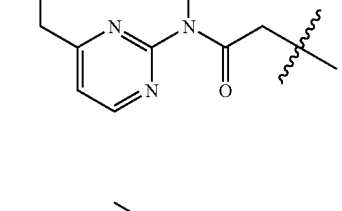 |

TABLE 3B-continued
| | R |
|---|---|
| 210. | 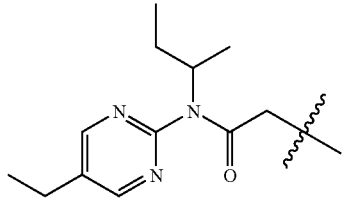 |
| 211. | 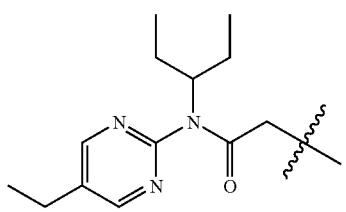 |
| 212. | 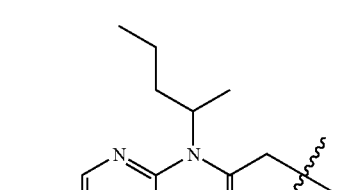 |
| 213. | 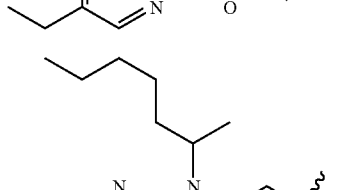 |
| 214. | 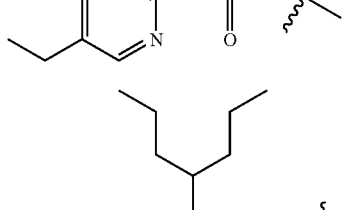 |
| 215. | 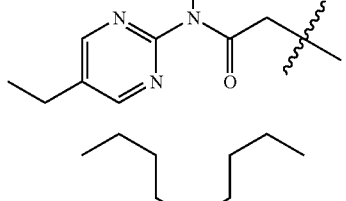 |
| 216. | 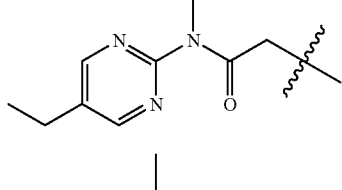 |
TABLE 3B-continued
| | R |
|---|---|
| 217. | 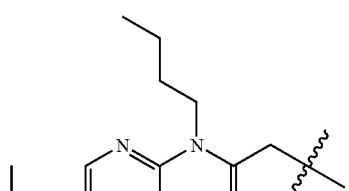 |
| 218. | 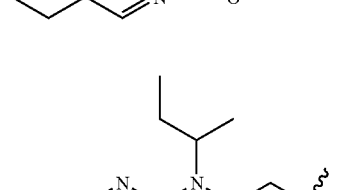 |
| 219. | 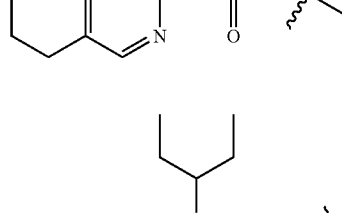 |
| 220. | 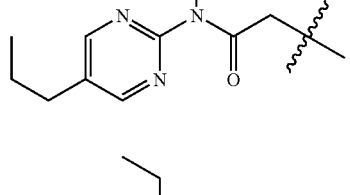 |
| 221. | 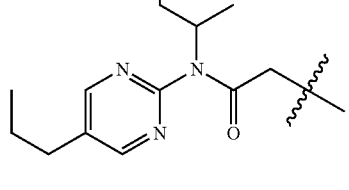 |
| 222. | 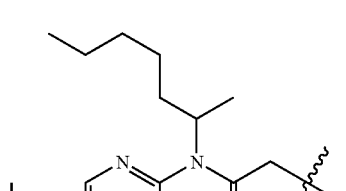 |

TABLE 3B-continued
| | R |
|---|---|
| 223. | 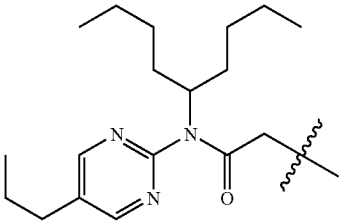 |
| 224. | 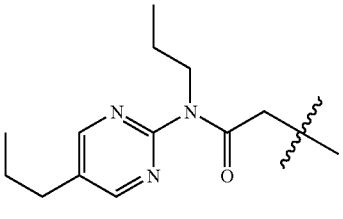 |
| 225. | 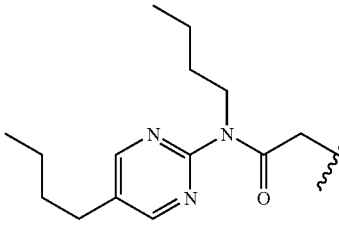 |
| 226. | 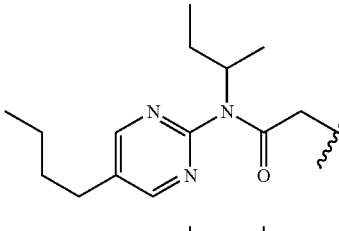 |
| 227. | 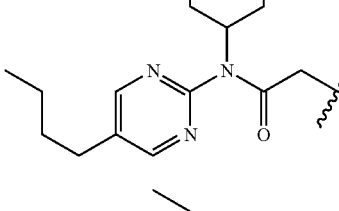 |
| 228. | 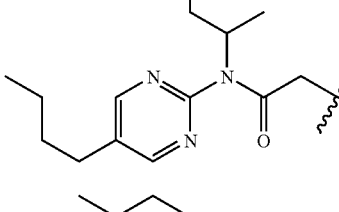 |
| 229. | 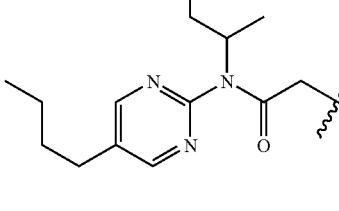 |
| 230. | 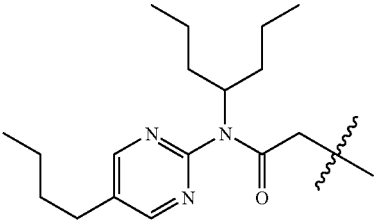 |
| 231. | 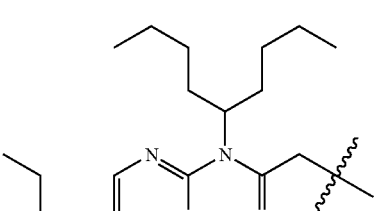 |
| 232. | 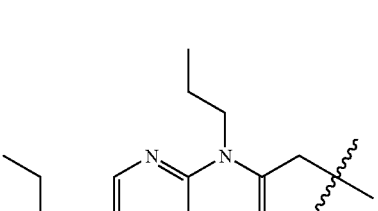 |
| 233. | 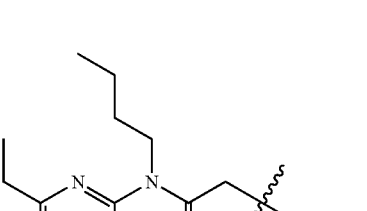 |
| 234. | 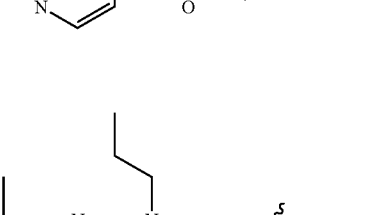 |
| 235. | 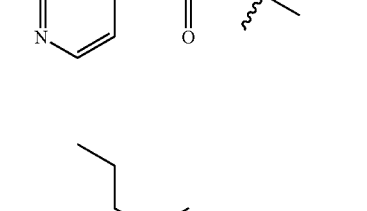 |

TABLE 3B-continued
| | R |
|---|---|
| 236. | 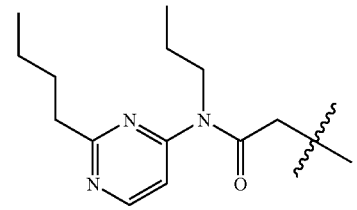 |
| 237. | |
| 238. | |
| 239. | |
| 240. | |
| 241. | |
TABLE 3B-continued
| | R |
|---|---|
| 242. | 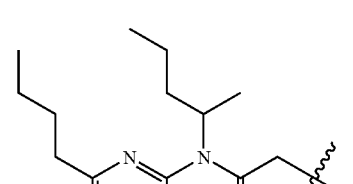 |
| 243. | |
| 244. | |
| 245. | |
| 246. | |
| 247. | |

TABLE 3B-continued
| R |
|---|
| 248. 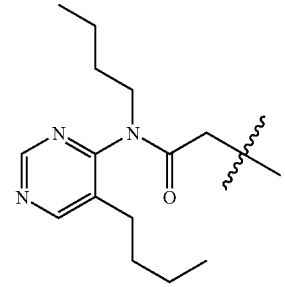 |
| 249. |
| 250. |
| 252. |
| 252. |
TABLE 3B-continued
| R |
|---|
| 253. |
| 254. |
| 255. |
| 256. |
| 257. |

TABLE 3B-continued

TABLE 3B-continued

| R |
|---|
| 270. (structure) |
| 271. (structure) |
| 272. (structure) |
| 273. (structure) |
| 274. (structure) |
| 275. (structure) |
| 276. (structure) |
| 277. (structure) |
| 278. (structure) |
| 279. (structure) |
| 280. (structure) |
| 281. (structure) |
| 282. (structure) |

TABLE 3B-continued

| | R |
|---|---|
| 283. | (structure) |
| 284. | (structure) |
| 285. | (structure) |
| 286. | (structure) |
| 287. | (structure) |
| 288. | (structure) |
| 289. | (structure) |
| 290. | (structure) |
| 291. | (structure) |
| 292. | (structure) |
| 293. | (structure) |
| 294. | (structure) |
| 295. | (structure) |

TABLE 3B-continued
| | R |
|---|---|
| 296. | 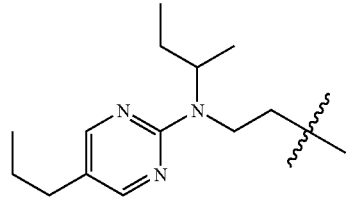 |
| 297. | |
| 298. | |
| 299. | |
| 300. | |
| 301. | |
| 302. | |
TABLE 3B-continued
| | R |
|---|---|
| 303. | 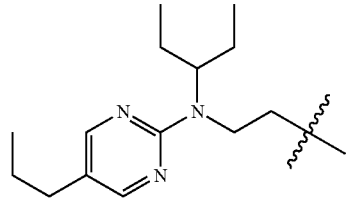 |
| 304. | |
| 305. | |
| 306. | |
| 307. | |
| 308. | |

TABLE 3B-continued

| | R |
|---|---|
| 309. | (structure) |
| 310. | (structure) |
| 311. | (structure) |
| 312. | (structure) |
| 313. | (structure) |
| 314. | (structure) |
| 315. | (structure) |
| 316. | (structure) |
| 317. | (structure) |
| 318. | (structure) |
| 319. | (structure) |
| 320. | (structure) |
| 321. | (structure) |

TABLE 3B-continued
R
322. 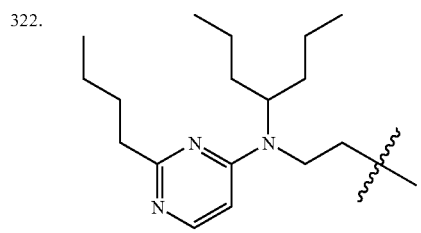
323. 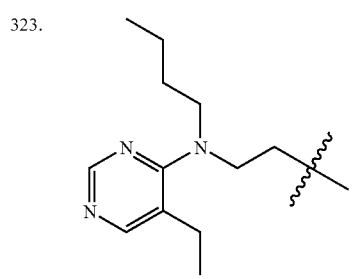
324. 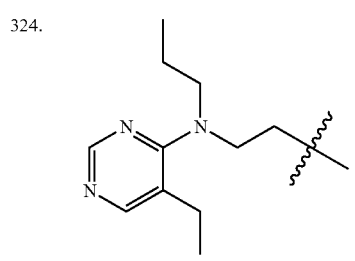
325. 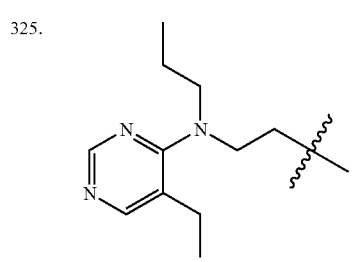
326. 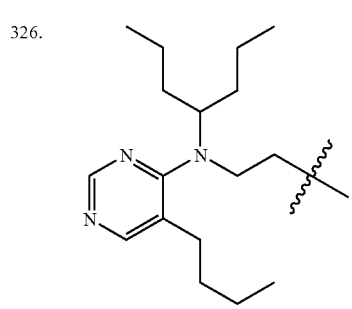
TABLE 3B-continued
R
327. 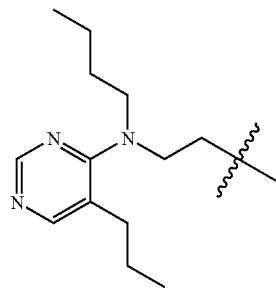
328. 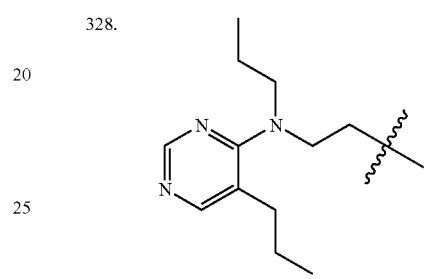
329. 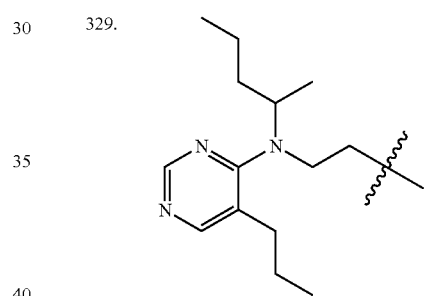
330. 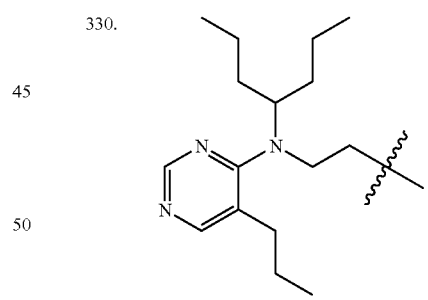
331. 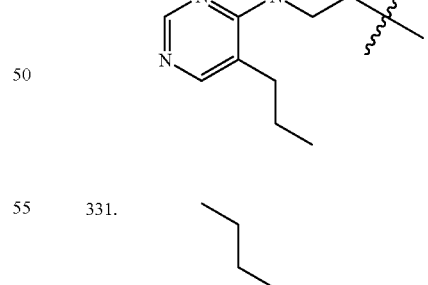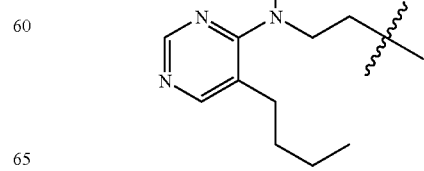

TABLE 3B-continued
| | R |
|---|---|
| 332. | 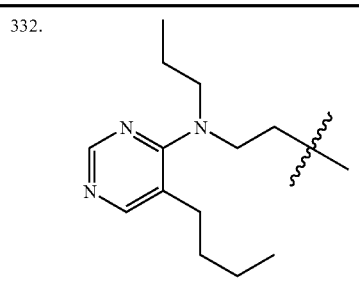 |
| 333. | 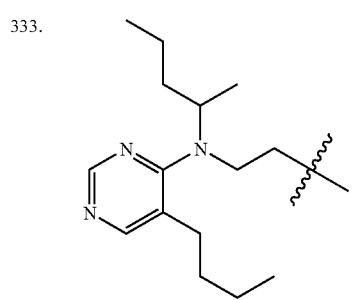 |
| 334. | 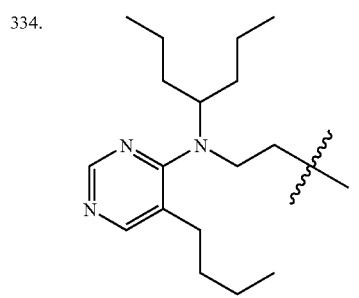 |
| 335. | 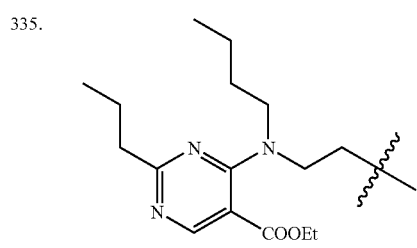 |
| 336. | 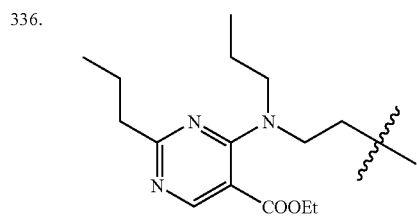 |
| 337. | 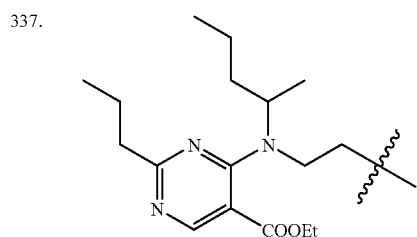 |
| 338. | 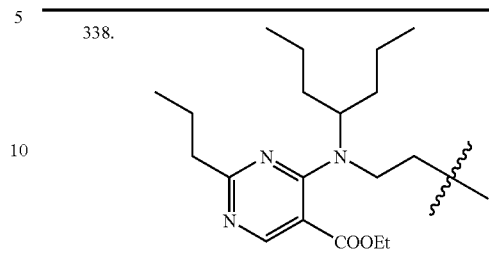 |
| 339. | 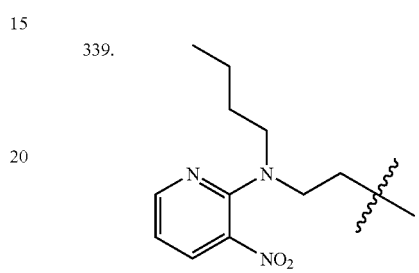 |
| 340. | 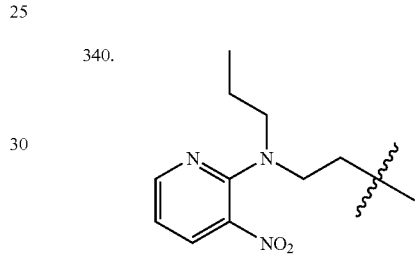 |
| 341. |  |
| 342. |  |
| 343. | 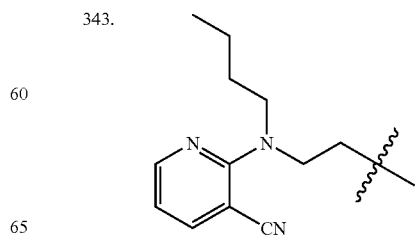 |

TABLE 3B-continued
| R |
|---|
| 344. 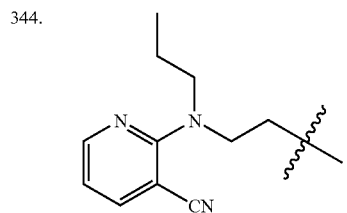 |
| 345. 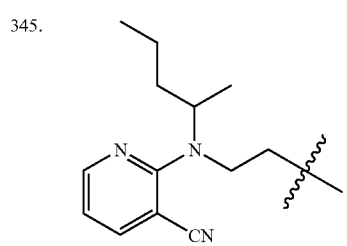 |
| 346. 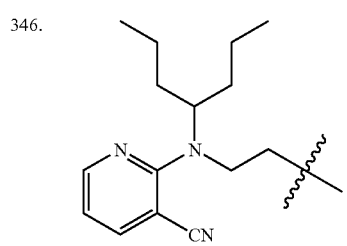 |
| 347. 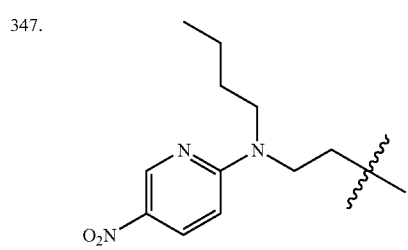 |
| 348. 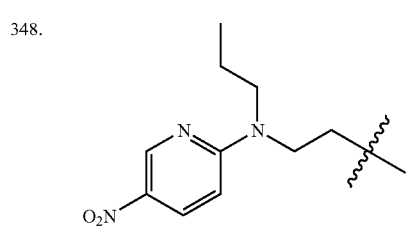 |
| 349. 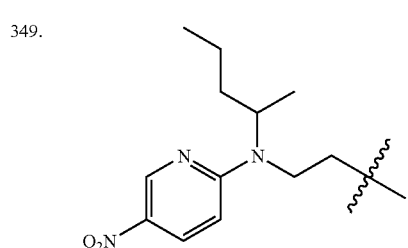 |
TABLE 3B-continued
| R |
|---|
| 350. 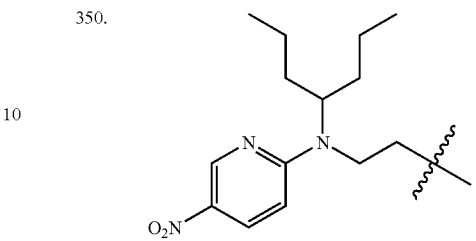 |
| 351. 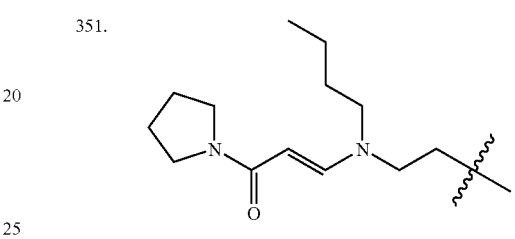 |
| 352. 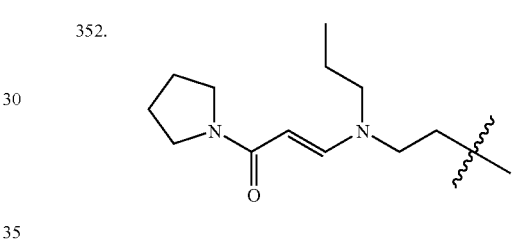 |
| 353. 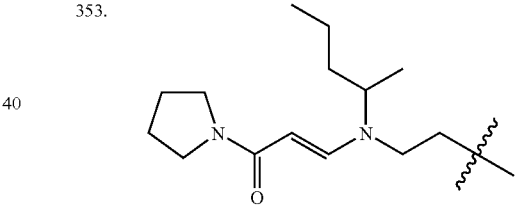 |
| 354. 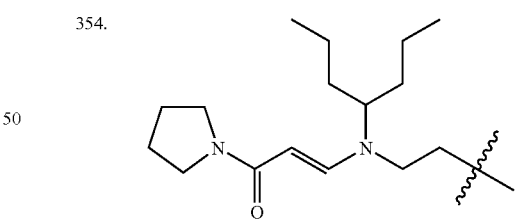 |
| 355. 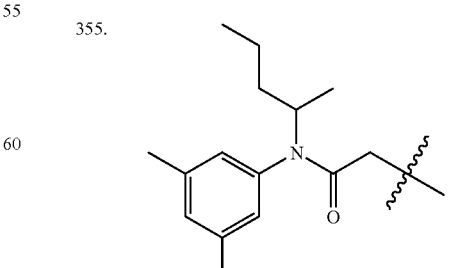 |

TABLE 3B-continued
| | R |
|---|---|
| 356. | 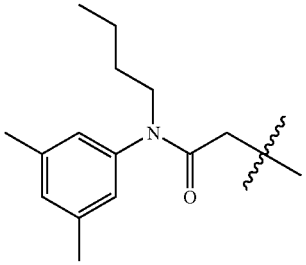 |
| 357. | 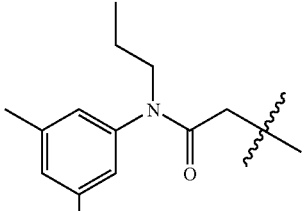 |
| 358. | 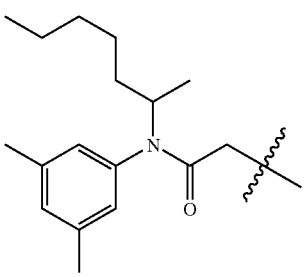 |
| 359. | 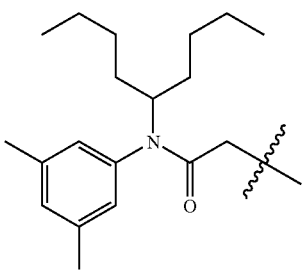 |
| 360. | 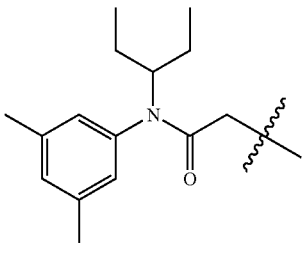 |
| 361. | 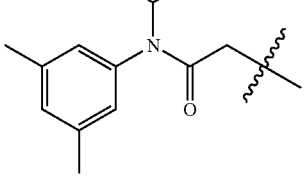 |
| 362. | 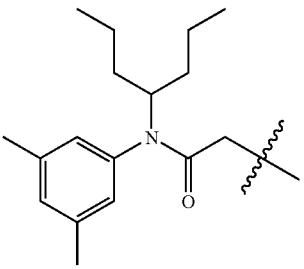 |
| 363. | 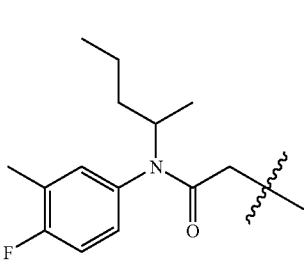 |
| 364. | 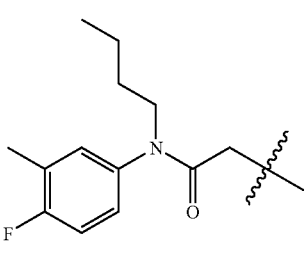 |
| 365. | 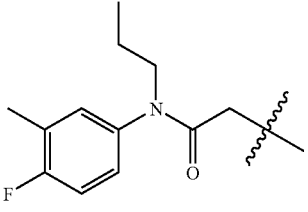 |
| 366. | 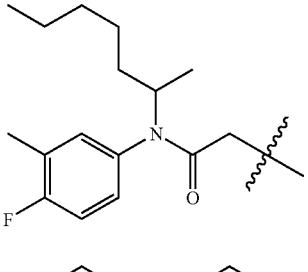 |
| 367. | 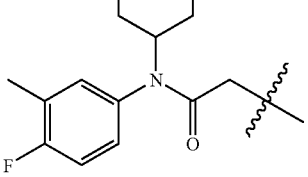 |

TABLE 3B-continued
| | R |
|---|---|
| 368. | 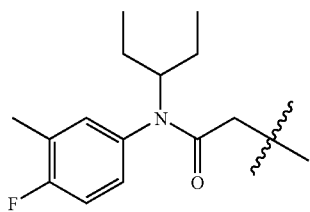 |
| 369. | 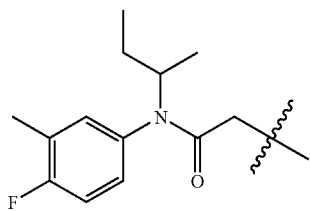 |
| 370. | 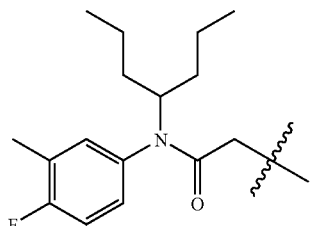 |
| 371. | 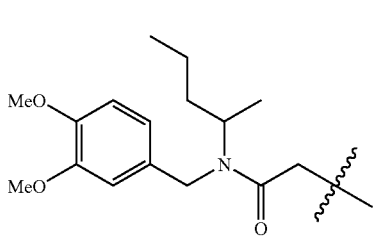 |
| 372. | 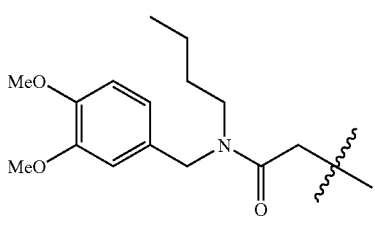 |
| 373. | 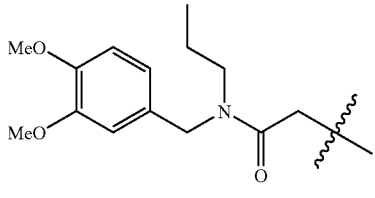 |
| 374. | 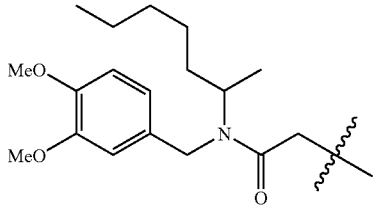 |
| 375. | 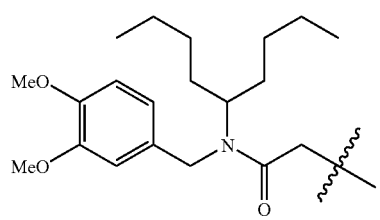 |
| 376. | 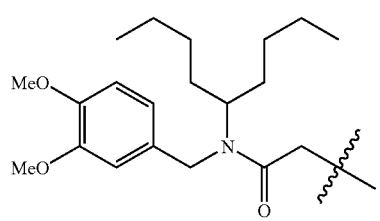 |
| 377. | 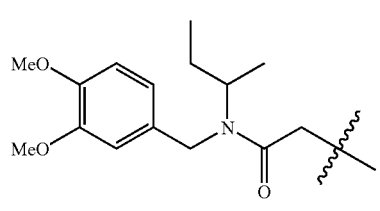 |
| 378. | 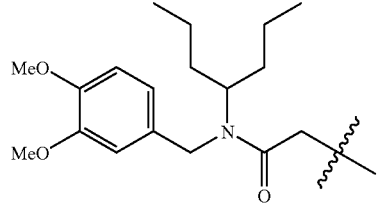 |
| 379. | 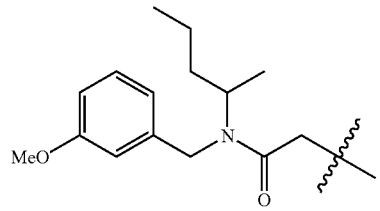 |
| 380. | 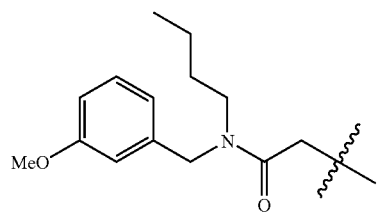 |
| 381. | 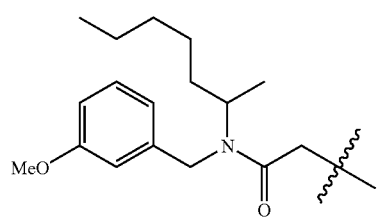 |

TABLE 3B-continued
| | R |
|---|---|
| 382. | 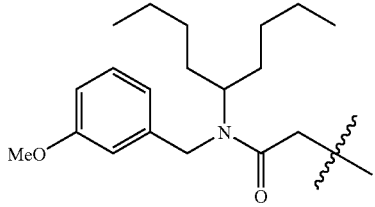 |
| 383. | 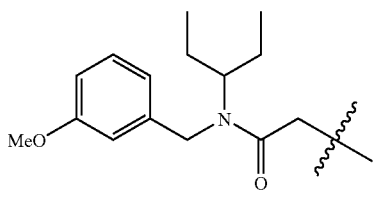 |
| 384. | 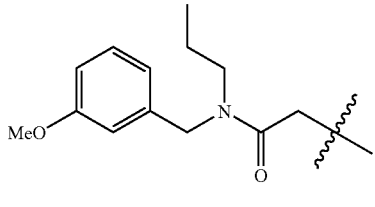 |
| 385. | 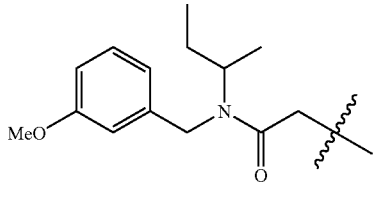 |
| 386. | 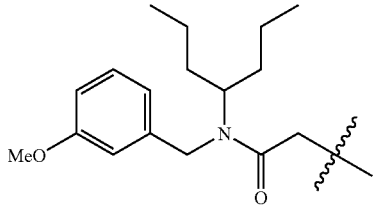 |
| 387. | 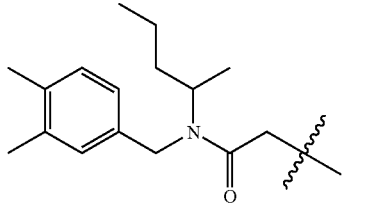 |
| 388. | 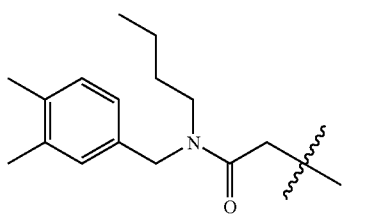 |
| 389. | 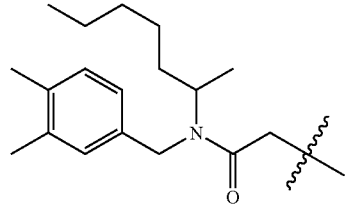 |
| 390. | 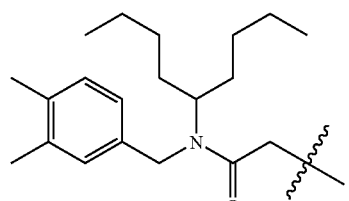 |
| 391. | 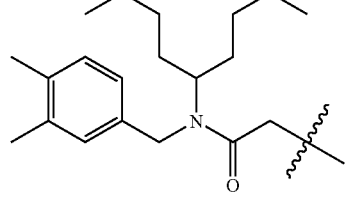 |
| 392. | 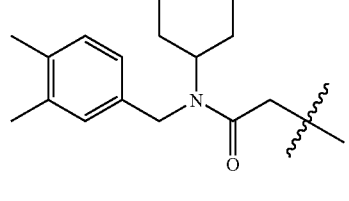 |
| 393. | 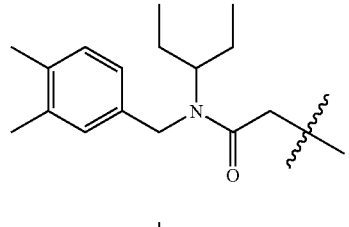 |
| 394. | 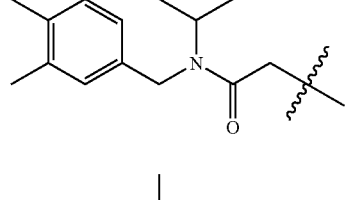 |
| 395. | 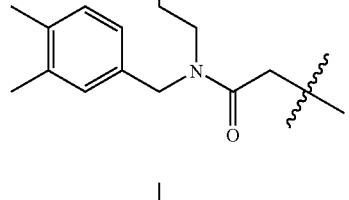 |

TABLE 3B-continued

| | R |
|---|---|
| 396. | 3,4-dichlorobenzyl, N-butyl amide |
| 397. | 3,4-dichlorobenzyl, N-(hexan-2-yl) amide |
| 398. | 3,4-dichlorobenzyl, N-(nonan-5-yl) amide |
| 399. | 3,4-dichlorobenzyl, N-(pentan-3-yl) amide |
| 400. | 3,4-dichlorobenzyl, N-propyl amide |
| 401. | 3,4-dichlorobenzyl, N-(butan-2-yl) amide |
| 402. | 3,4-dichlorobenzyl, N-(heptan-4-yl) amide |
| 403. | 3,4-difluorobenzyl, N-(pentan-2-yl) amide |
| 404. | 3,4-difluorobenzyl, N-butyl amide |
| 405. | 3,4-difluorobenzyl, N-(heptan-2-yl) amide |
| 406. | 3,4-difluorobenzyl, N-(nonan-5-yl) amide |
| 407. | 3,4-difluorobenzyl, N-(pentan-3-yl) amide |
| 408. | 3,4-difluorobenzyl, N-propyl amide |
| 409. | 3,4-difluorobenzyl, N-(butan-2-yl) amide |

TABLE 3B-continued
| | R |
|---|---|
| 410. | 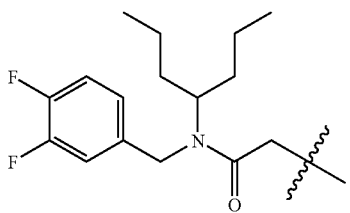 |
| 411. | 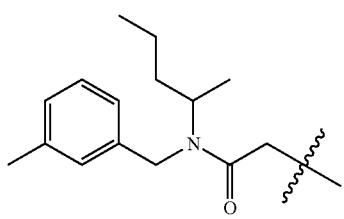 |
| 412. | 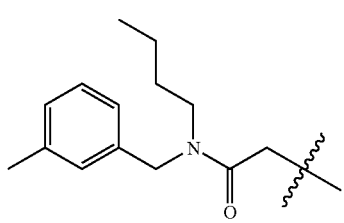 |
| 413. | 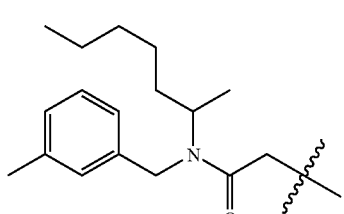 |
| 414. | 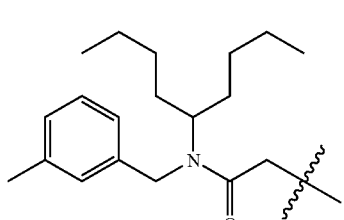 |
| 415. | 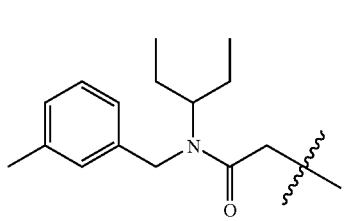 |
| 416. | 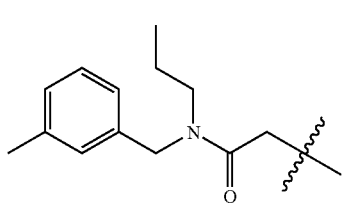 |
| 417. | 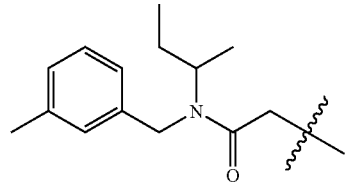 |
| 418. | 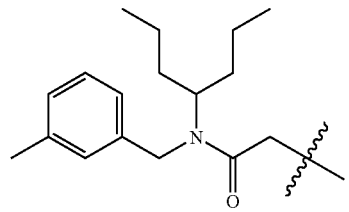 |
| 419. | 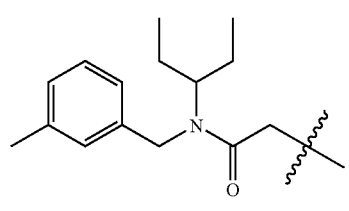 |
| 420. | 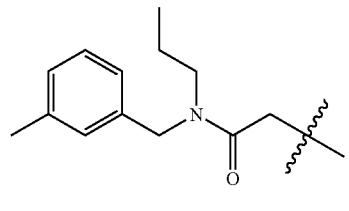 |
| 421. | 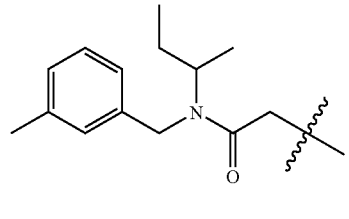 |
| 422. | 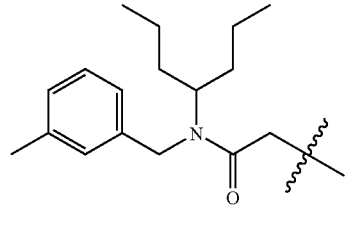 |
| 423. | 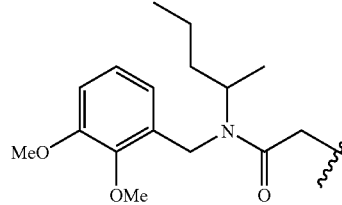 |

TABLE 3B-continued
R
424. 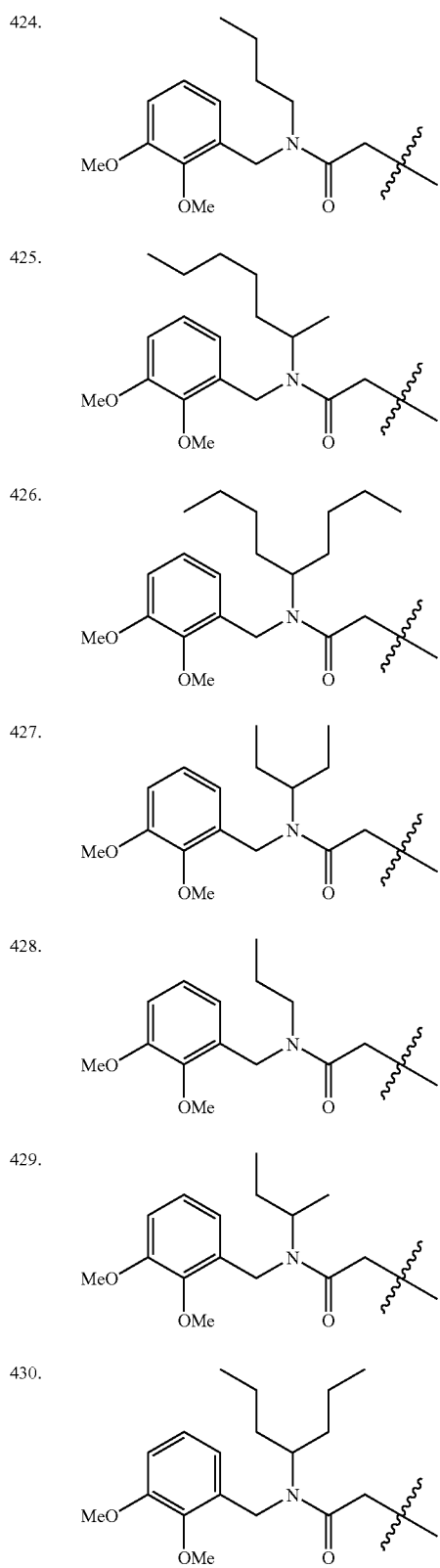
425.
426.
427.
428.
429.
430.
TABLE 3B-continued
R
431. 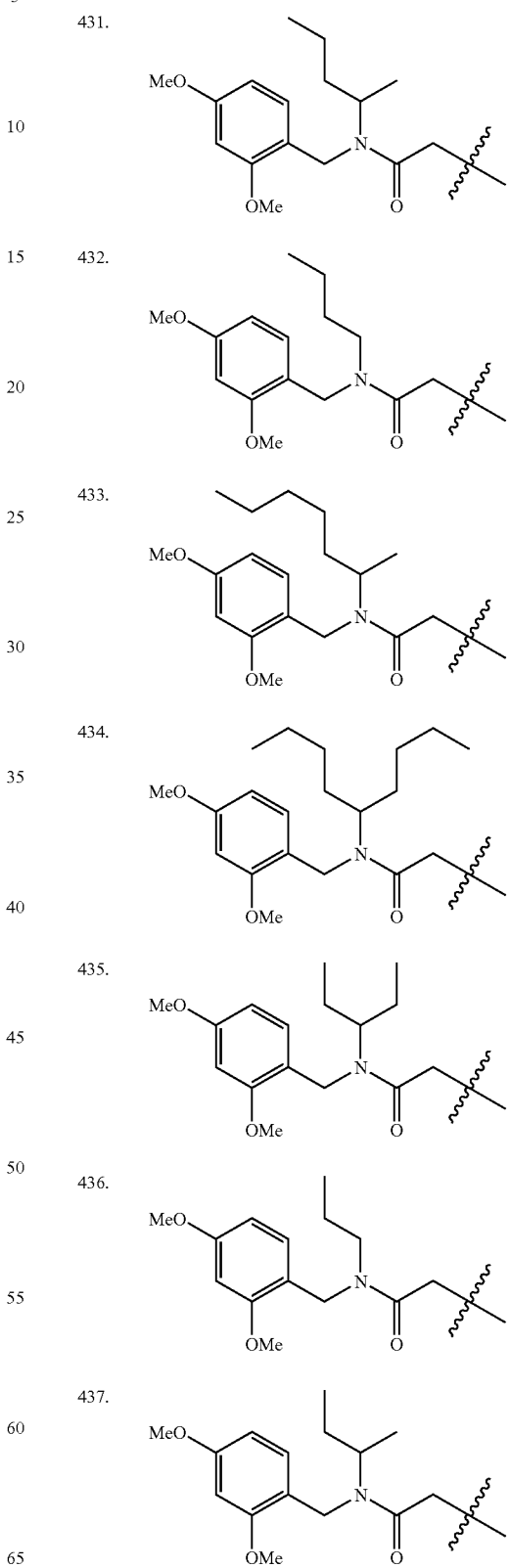
432.
433.
434.
435.
436.
437.

TABLE 3B-continued

TABLE 3B-continued

| | R |
|---|---|
| 452. | |
| 453. | |
| 454. | |
| 455. | |
| 456. | |
| 457. | |
| 458. | |
| 459. | |
| 460. | |
| 461. | |
| 462. | |
| 463. | |

TABLE 3B-continued
| | R |
|---|---|
| 464. | 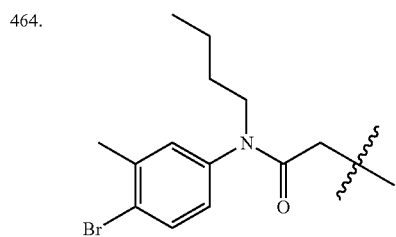 |
| 465. | 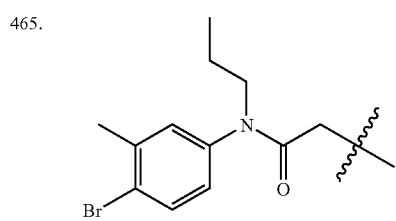 |
| 466. | 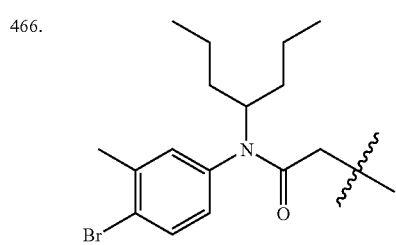 |
| 467. | 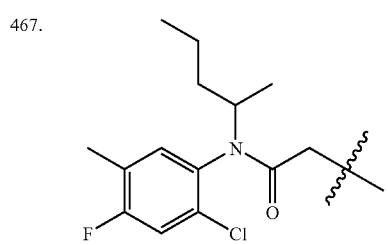 |
| 468. | 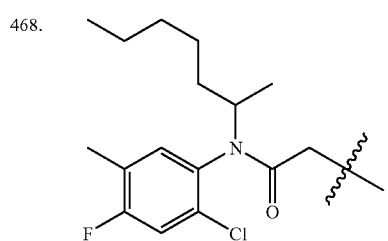 |
| 469. | 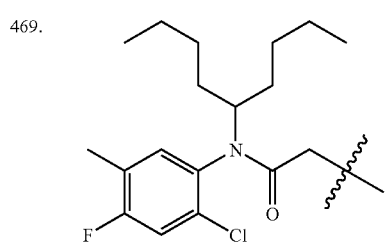 |
TABLE 3B-continued
| | R |
|---|---|
| 470. | 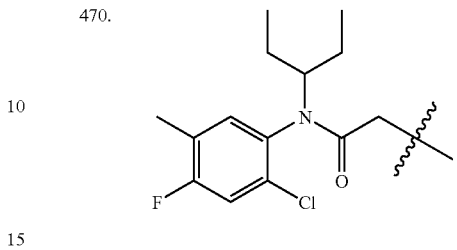 |
| 471. | 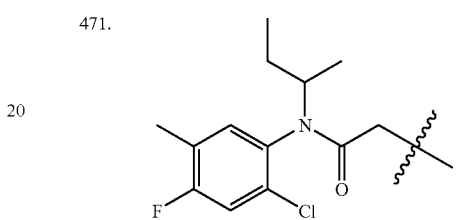 |
| 472. | 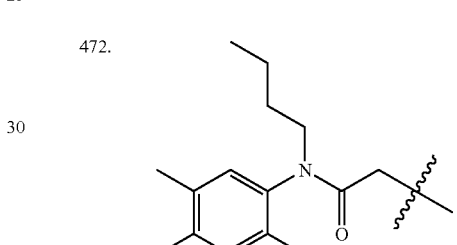 |
| 473. |  |
| 474. | 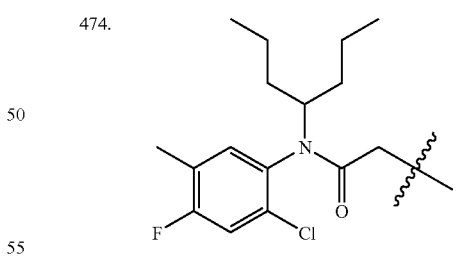 |
| 475. | 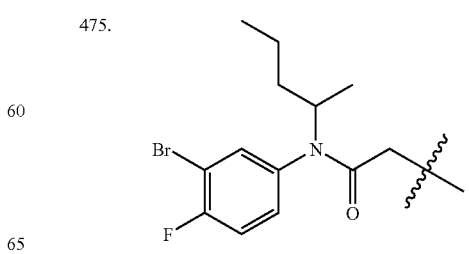 |

TABLE 3B-continued

| | R |
|---|---|
| 476. | (3-Br, 4-F phenyl)-N(hexan-2-yl)-acetamide |
| 477. | (3-Br, 4-F phenyl)-N(nonan-5-yl)-acetamide |
| 478. | (3-Br, 4-F phenyl)-N(pentan-3-yl)-acetamide |
| 479. | (3-Br, 4-F phenyl)-N(butan-2-yl)-acetamide |
| 480. | (3-Br, 4-F phenyl)-N-butyl-acetamide |
| 481. | (3-Br, 4-F phenyl)-N-propyl-acetamide |
| 482. | (3-Br, 4-F phenyl)-N(heptan-4-yl)-acetamide |
| 483. | (3-Cl, 2,4-diF phenyl)-N(pentan-2-yl)-acetamide |
| 484. | (3-Cl, 2,4-diF phenyl)-N(hexan-2-yl)-acetamide |
| 485. | (3-Cl, 2,4-diF phenyl)-N(nonan-5-yl)-acetamide |
| 486. | (3-Cl, 2,4-diF phenyl)-N(pentan-3-yl)-acetamide |
| 487. | (3-Cl, 2,4-diF phenyl)-N(butan-2-yl)-acetamide |

TABLE 3B-continued
| | R |
|---|---|
| 488. | 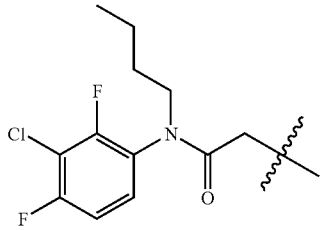 |
| 489. | 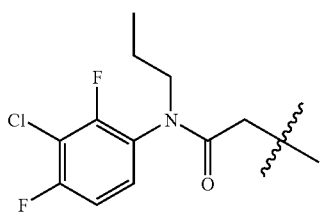 |
| 490. | 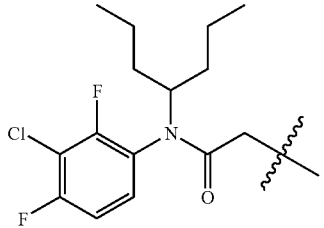 |
| 491. | 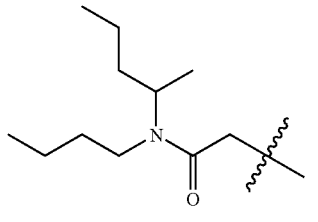 |
| 492. | 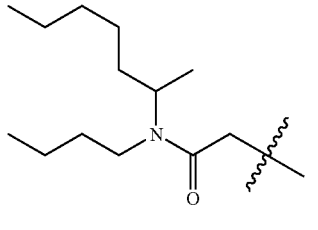 |
| 493. | 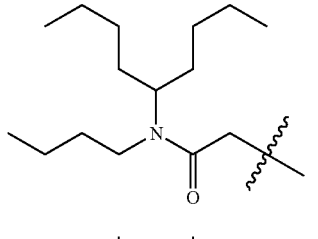 |
| 494. | 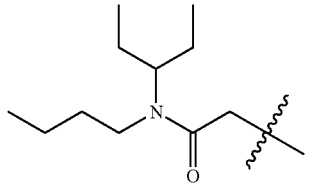 |
| 495. | 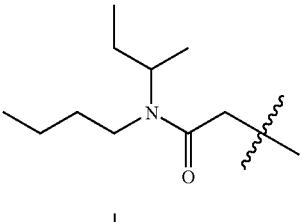 |
| 496. | 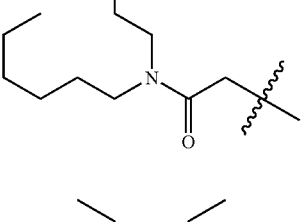 |
| 497. | 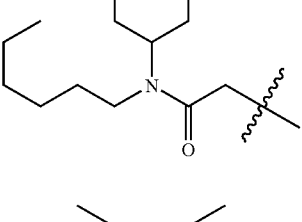 |
| 498. | 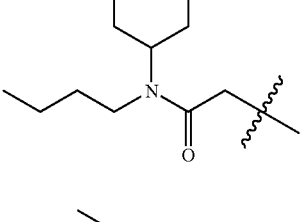 |
| 499. | 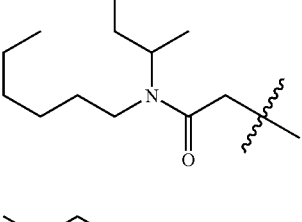 |
| 500. | 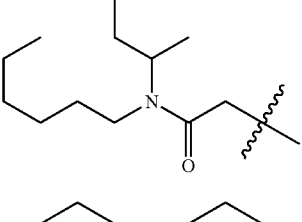 |
| 501. | 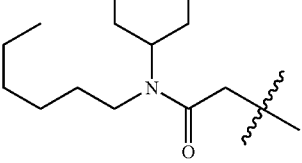 |

TABLE 3B-continued
| | R |
|---|---|
| 502. | 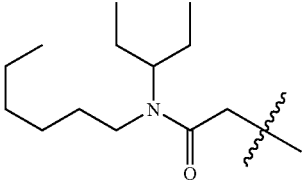 |
| 503. | 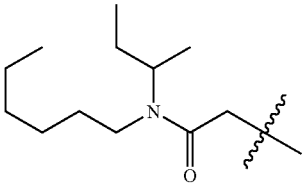 |
| 504. | 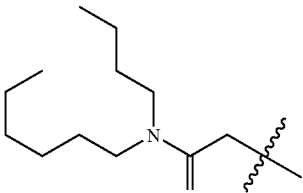 |
| 505. | 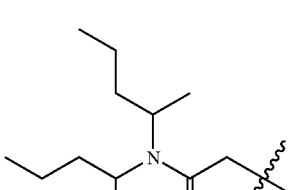 |
| 506. | 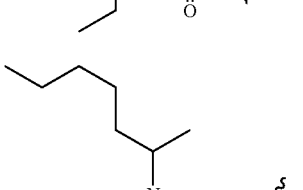 |
| 507. | 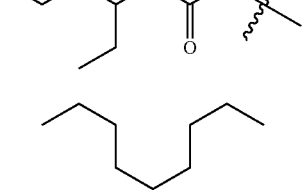 |
| 508. | 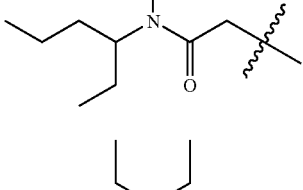 |
TABLE 3B-continued
| | R |
|---|---|
| 509. | 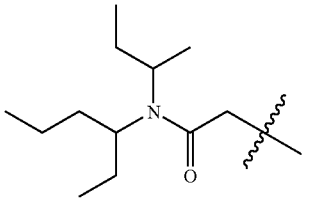 |
| 510. | 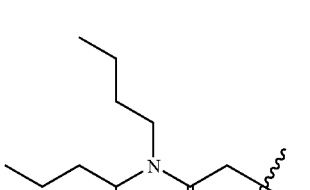 |
| 511. | 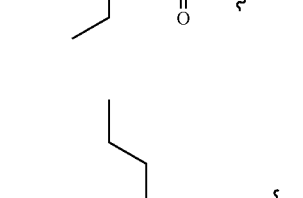 |
| 512. | 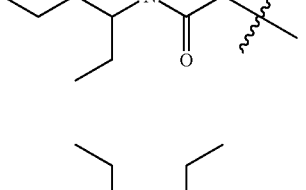 |
| 513. | 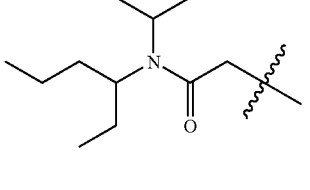 |
| 514. | 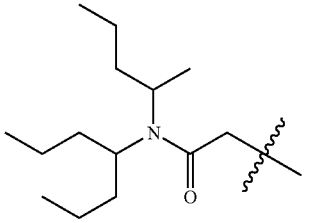 |

TABLE 3B-continued

| | R |
|---|---|
| 515. | (structure) |
| 516. | (structure) |
| 517. | (structure) |
| 518. | (structure) |
| 519. | (structure) |
| 520. | (structure) |
| 521. | (structure) |
| 522. | (structure) |
| 523. | (structure) |
| 524. | (structure) |
| 525. | (structure) |
| 526. | (structure) |
| 527. | (structure) |
| 528. | (structure) |

TABLE 3B-continued

TABLE 3B-continued
| | R |
|---|---|
| 543. | 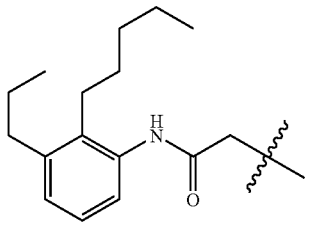 |
| 544. | 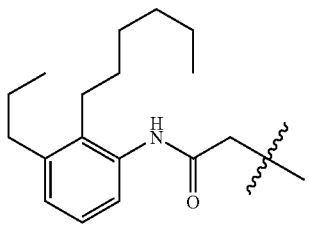 |
| 545. | 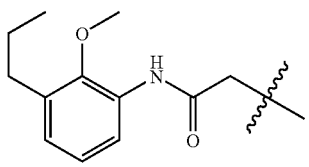 |
| 546. | 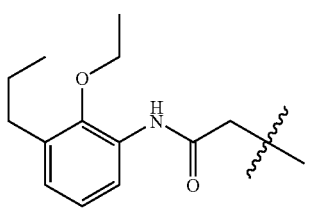 |
| 547. | 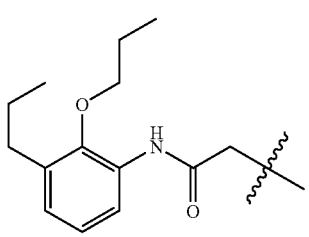 |
| 548. | 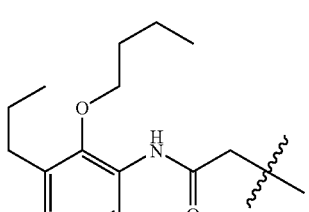 |
| 549. | 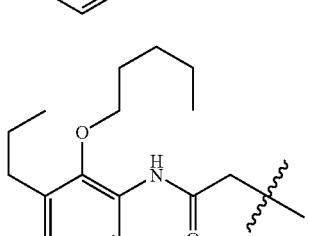 |
TABLE 3B-continued
| | R |
|---|---|
| 550. | 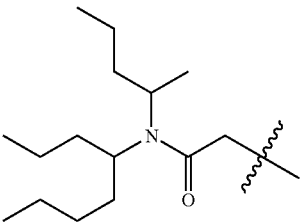 |
| 551. | 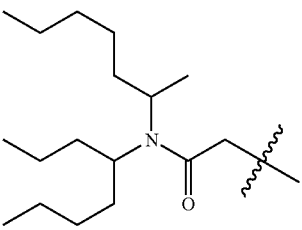 |
| 552. | 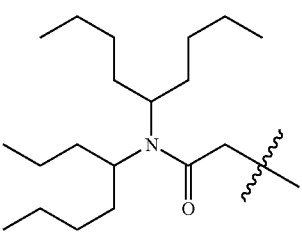 |
| 553. | 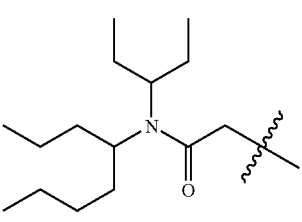 |
| 554. | 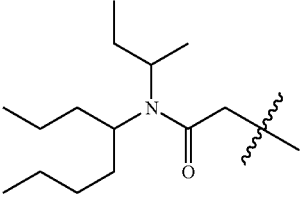 |
| 555. | 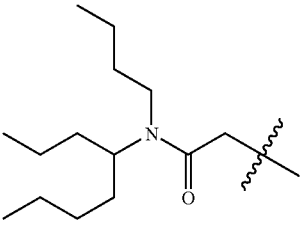 |
| 556. | 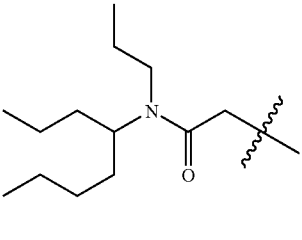 |

TABLE 3B-continued

| | R |
|---|---|
| 557. | (structure) |
| 558. | (structure) |
| 559. | (structure) |
| 560. | (structure) |
| 561. | (structure) |
| 562. | (structure) |
| 563. | (structure) |
| 564. | (structure) |
| 565. | (structure) |
| 566. | (structure) |
| 567. | (structure) |
| 568. | (structure) |
| 569. | (structure) |
| 570. | (structure) |

| 569 | 570 |
|---|---|
| TABLE 3B-continued | TABLE 3B-continued |
| R | R |
| 571. 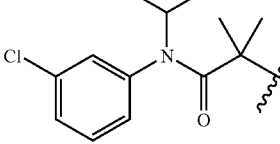 | 577. 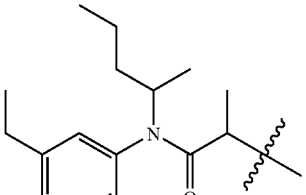 |
| 572. 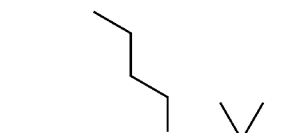 | 578. 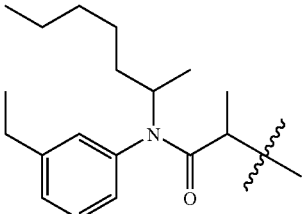 |
| 573. 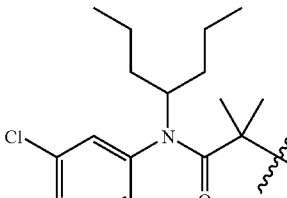 | 579. 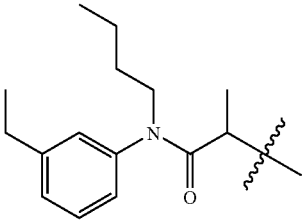 |
| 574. | 580. |
| 575. | 581. |
| 576. | 582. |

TABLE 3B-continued
| | R |
|---|---|
| 583. | 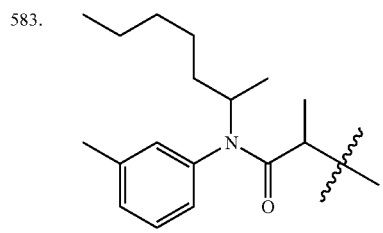 |
| 584. | 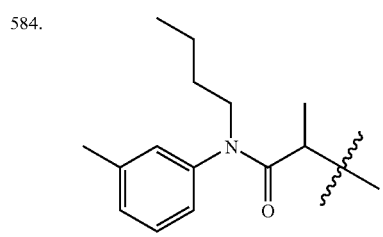 |
| 585. | 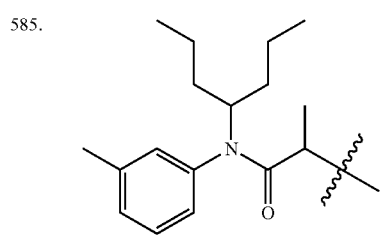 |
| 586. | 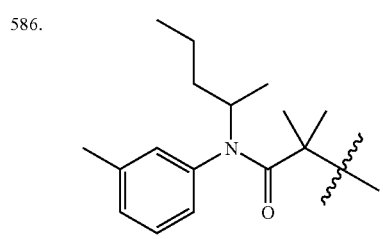 |
| 587. | 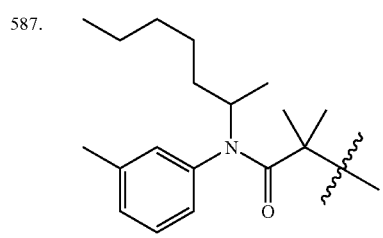 |
| 588. | 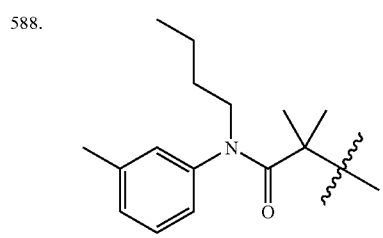 |
TABLE 3B-continued
| | R |
|---|---|
| 589. | 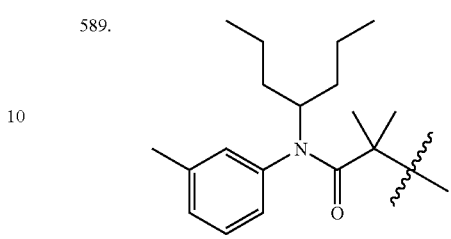 |
| 590. | 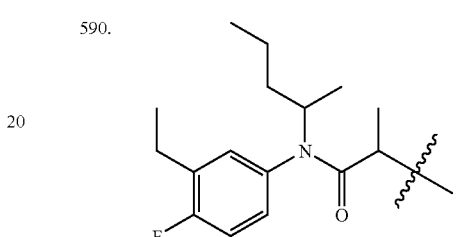 |
| 591. | 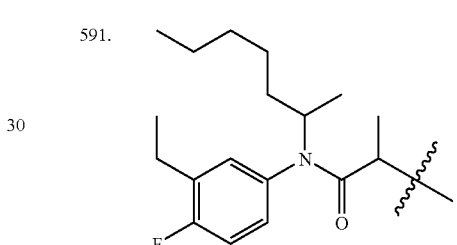 |
| 592. |  |
| 593. |  |
| 594. | 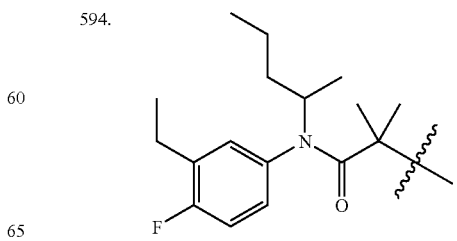 |

TABLE 3B-continued
| | R |
|---|---|
| 595. | 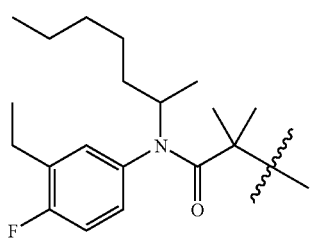 |
| 596. | 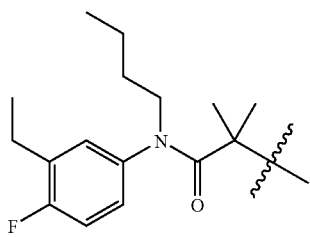 |
| 597. | 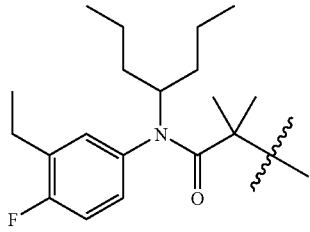 |
| 598. | 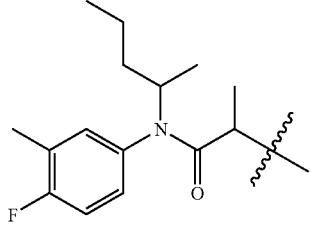 |
| 599. | 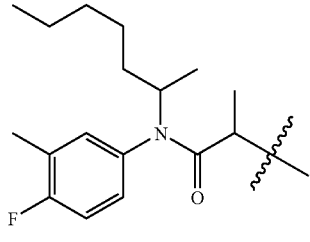 |
| 600. | 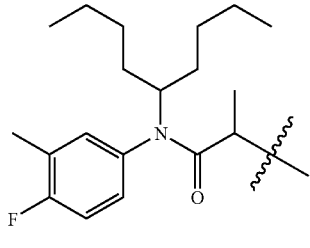 |
| 601. | 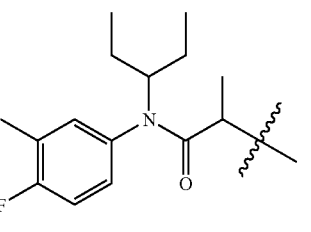 |
| 602. | 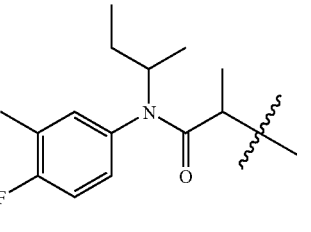 |
| 603. | 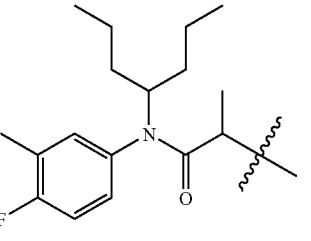 |
| 604. | 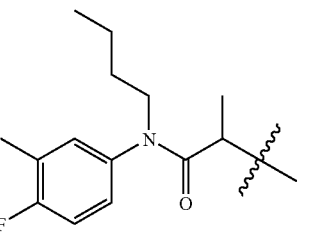 |
| 605. | 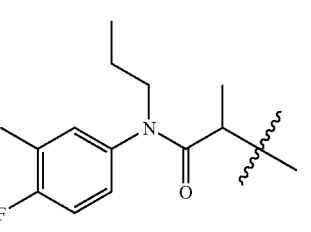 |
| 606. | 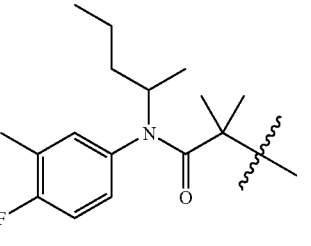 |

TABLE 3B-continued
| | R |
|---|---|
| 607. | 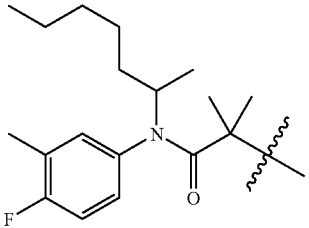 |
| 608. | 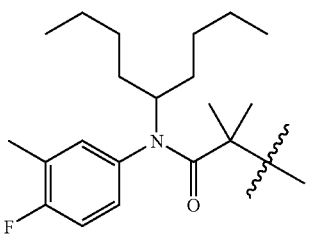 |
| 609. | 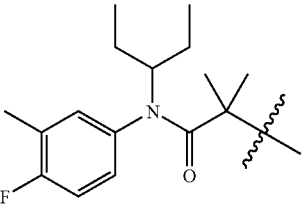 |
| 610. | 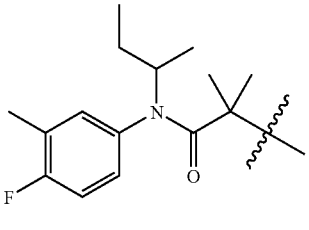 |
| 611. | 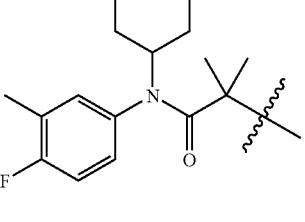 |
| 612. | 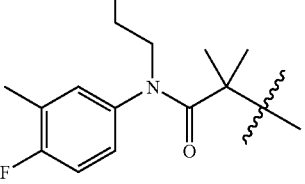 |
| 613. | 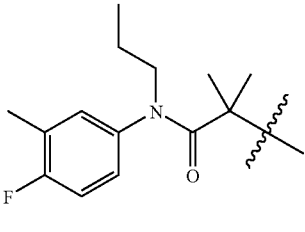 |
| 614. | 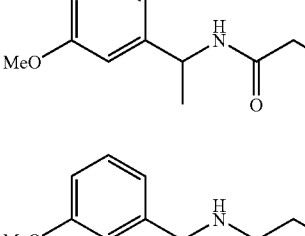 |
| 615. | 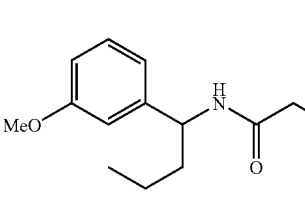 |
| 616. | 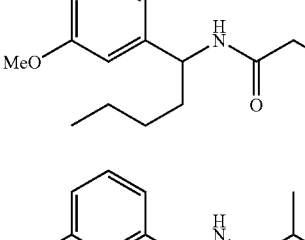 |
| 617. | 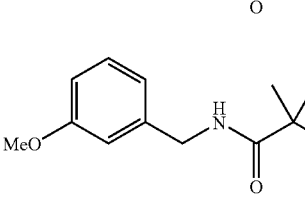 |
| 618. | 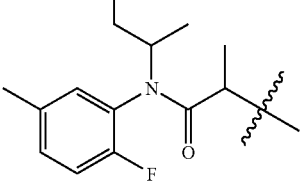 |
| 619. | 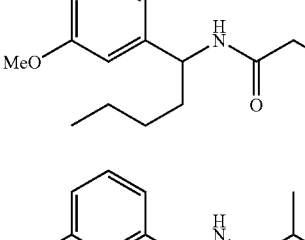 |
| 620. | 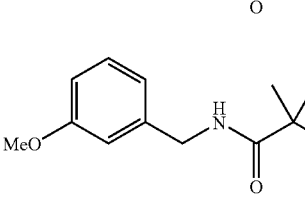 |

TABLE 3B-continued
| | R |
|---|---|
| 621. | 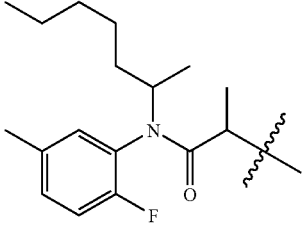 |
| 622. | 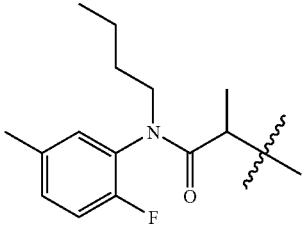 |
| 623. | 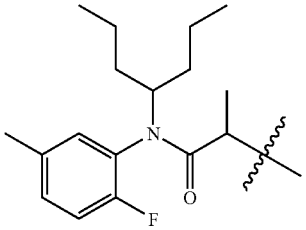 |
| 624. | 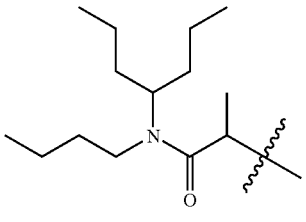 |
| 625. | 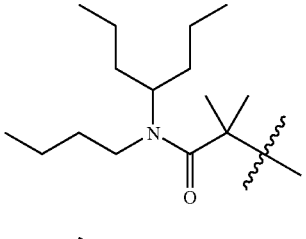 |
| 626. | 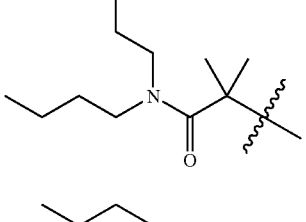 |
| 627. | 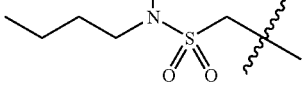 |
| 628. | 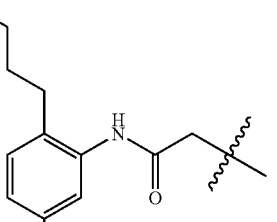 |
| 629. | 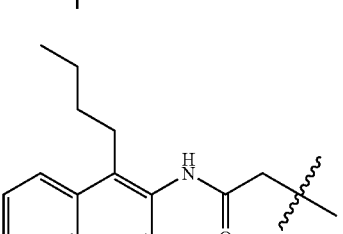 |
| 630. | 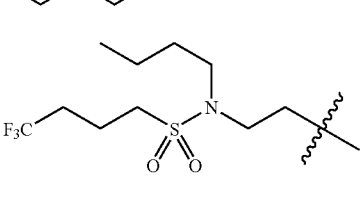 |
| 631. | 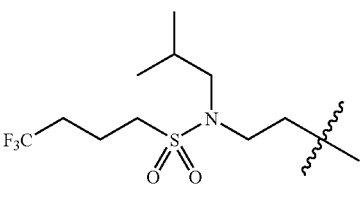 |
| 632. | 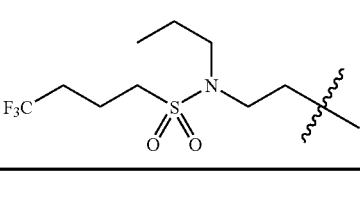 |
EXAMPLE 340
trans,trans-4-(1,3-Benzodioxol-5-yl)-2-(4-methoxyphenyl)-1-(N-(3-methylbut-1-yl)-N-phenyl)aminocarbonylmethyl)-pyrrolidine-3-carboxylic acid
Using the procedures described in Example 1, the title compound was prepared. $^1$H NMR (300 MHz, CD$_3$OD) δ 0.85 (d, J=6 Hz, 6H), 1.25 (q, J=7 Hz, 2H), 1.42–1.56 (m, 1H), 3.43–3.85 (m, 9H), 3.88s (3), 5.95 (s, 2H), 6.80 (d, J=7 Hz, 1H), 6.86 (dd, J=9 Hz, 1H), 6.89–7.00 (m, 2H), 6.97 (d, J=1 Hz, 1H), 7.04 (d, J=9 Hz, 2H), 7.37 (d, J=9 Hz, 2H), 7.40–7.47 (m, 3H). MS (C.I.) m/e C (53.12, 53.11), H (4.63, 4.80), N (3.33, 3.28).

EXAMPLE 341 trans,trans-4-(1,3-Benzodioxol-5-yl)-2-(4-methoxyphenyl)-1-(N-butyl-N-(4-methylphenylaminocarbonylmethyl)-pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.47 (m, 4H), 2.37 (s, 3H), 2.83 (q, J=7 Hz, 2H), 3.06–3.25 (m, 2H), 3.40–3.50 (m, 1H), 3.51–3.63 (m, 3H), 3.80 (s, 3H), 3.87 (d, J=9 Hz, 1H), 5.92 (s, 2H), 6.74 (d, J=8 Hz, 1H), 6.80–6.86 (m, 3H), 6.89 (d, J=8 Hz, 2H), 7.04 (d, J=2 Hz, 1H), 7.12 (d, J=8 Hz, 2H), 7.19 (d, J=8 Hz, 2H). MS (DCI) m/e 545 (M+H)$^+$. Analysis calcd for C$_{32}$H$_{36}$N$_2$O$_6$: C, 70.57; H, 6.66; N, 5.14. Found: C, 70.20; H, 6.81; N, 5.03.

EXAMPLE 342 trans,trans-4-(1,3-Benzodioxol-5-yl)-2-(4-propoxyphenyl)-1-(N,N-di(n-butyl)amino)carbonyl) methyl)-pyrrolidine-3-carboxylic acid Using the procedures described in Example 1, the title compound was prepared. $^1$H (300 MHz, CDCl$_3$) δ 7.30 (2H, d, J=9), 7.03 (1H, d, J=2), 6.83 (3H, m), 6.72 (1H, d, J=9), 5.95 (1H, d, J=2), 5.93 (1H, d, J=2), 3.88 (2H, t, J=7), 3.73 (1H, d, J=12), 3.58 (1H, m), 3.53–3.20 (4H, m), 3.10–2.90 (4H, m), 2.72 (1H, d, J=15), 1.79 (2H, q, J=8), 1.50–1.05 (8H, m), 1.02 (3H, t, J=7), 0.87 (3H, t, J=7), 0.80 (3H, t, J=7). MS (DCI/NH$_3$) m/e 539 (M+H)$^+$. Anal calcd for C$_{31}$H$_{42}$N$_2$O$_6$.0.5H$_2$O: C, 67.98; H, 7.91; N, 5.11. Found: C, 68.24; H, 7.70; N, 5.03.

EXAMPLE 343 trans,trans-4-(1,3-Benzodioxol-5-yl)-2-(4-propylphenyl)-1-(N,N-di(n-butyl)aminocarbonylmethyl)pyrrolidine-3-carboxylic acid Using the procedures described in Example 1, the title compound was prepared. $^1$H (300 MHz, CDCl$_3$) δ 7.31 (2H, d, J=9), 7.13 (2H, d, J=9), 7.03 (1H, d, J=2), 6.84 (1H, dd, J=6, 2), 6.73 (1H, d, J=9), 5.95 (1H, d, J=2), 5.93 (1H, d, J=2), 3.76 (1H, d, J=10), 3.60 (1H, m), 3.55–3.20 (4H, m), 3.13–2.88 (4H, m), 2.75 (1H, d, J=15), 2.55 (2H, t, J=8), 1.62 (2H, q, J=8), 1.50–1.00 (8H, m), 0.92 (3H, t, J=7), 0.85 (3H, t, J=7), 0.78 (3H, t, J=7). MS (DCI/NH$_3$) m/e 523 (MH$^+$). Anal calcd for C$_{31}$H$_{42}$N$_2$O$_5$.0.25H$_2$O: C, 70.63; H, 8.13; N, 5.31. Found: C, 70.55; H, 8.08; N, 5.18.

EXAMPLE 344 trans—trans-2-(4-Methoxyphenyl)-4-(1,3-benzodioxol-5-yl)-1-[3-(N-propyl-N-n-pentanesulfonylamino)propyl]pyrrolidine-3-carboxylic acid Using the procedures described in Example 316, the title compound was prepared. $^1$H NMR (300 MHz, CDCl$_3$) δ 0.85 (t, J=7 Hz, 3H), 0.90 (t, J=7 Hz, 3H), 1.3–1.4 (m, 4H), 1.5–1.6 (sextet, J=7, 2H), 1.65–1.8 (m, 4H), 2.05–2.15 (m, 1H), 2.43–2.56 (m, 1H), 2.72–3.1 (m, 7H), 3.27–3.4 (m, 2H), 3.5–3.6 (m, 2H), 3.80 (s, 3H), 5.95 (s, 2H), 6.73 (d, J=8 Hz, 1H), 6.8–6.9 (m, 1H), 6.85 (d, J=9 Hz, 2H), 7.02 (d, J=2 Hz, 1H), 7.80 (d, J=9 Hz, 2H).

EXAMPLE 345 trans,trans-4-(1,2-Dihydrobenzofuran-5-yl)-2-(4-ethylphenyl)-1-(N,N-di(n-butyl)aminocarbonylmethyl)-pyrrolidine-3-carboxylic acid Using the procedures described in Example 1, the title compound was prepared. 1H (300 MHz, CDCl$_3$) δ 7.40 (3H, m), 7.22 (2H, d, J=8), 7.13 (1H, dd, J=8, 3), 6.72 (1H, d, J=9), 5.28 (1H, d, J=12), 4.55 (2H, t, J=9), 4.15 (1H, d, J=18), 4.03 (2H, m), 3.75 (2H, m), 3.40 (2H, m), 3.20 (2H, t, J=9), 3.15 (1H, m), 3.10–2.90 (2H, m), 2.63 (2H, q, J=9), 1.47 (2H, m), 1.31 (4H, m), 1.12 (3H, t, J=8), 1.10 (2H,m), 0.92 (3H, t, J=9), 0.80 (3H, t, J=9). MS (DCI/NH$_3$) m/e 507 (M+H$^+$). Anal calcd for C$_{31}$H$_{42}$N$_2$O$_4$ 1.0 TFA: C,63.86; H, 6.98; N, 4.51. Found: C, 63.95; H, 7.12; N, 4,43.

EXAMPLE 346 trans,trans-4-(1,3-Benzodioxol-5-yl)-2-(4-methoxyphenyl)-1-(((N-(3-pentyl)-N-phenylamino)carbonyl)methyl)pyrrolidine-3-carboxylic acid Using the procedures described in Example 1, the title compound was prepared. $^1$H NMR (300 MHz, CD$_3$OD) δ 0.93 (t, J=7.3 Hz, 3H), 0.94 (t, J=7.3 Hz, 3H), 1.33 (m, 4H), 2.72 (d, J=15.2 Hz, 1H), 2.81 (m, 1H), 3.11–3.23 (m, 2H), 3.45–3.57 (m, 2H), 3.79 (s, 3H), 3.83 (d, J=9.8 Hz, 1H), 4.54 (m, 1H), 5.92 (s, 2H), 6.73 (d, J=7.8 Hz, 1H), 6.83 (m, 3H), 6.98 (bs, 2H), 7.04 (d, J=1.7 Hz, 1H), 7.07 (2), 7.37 (m, 3H). MS (DCI) m/e 545 (M+H$^+$). Anal calcd for C$_{32}$H$_{33}$N$_2$O$_6$ 0.35H$_2$O: C, 69.76; H, 6.71; N, 5.08. Found: C, 69.72; H, 6.66; N, 4.94.

EXAMPLE 347 trans,trans-4-(1,3-Benzodioxol-5-yl)-2-(4-methoxyphenyl)-1-(((N-butyl)-N-(3-trifluoromethylphenyl)amino)carbonyl)methyl)pyrrolidine-3-carboxylic acid Using the procedures described in Example 1, the title compound was prepared. $^1$H NMR (300 MHz, CD$_3$OD) δ 0.87 (t, J=6.6 Hz, 3H), 1.17–1.45 (m, 4H), 2.65 (d, J=16.5 Hz, 1H), 2.72 (m, 1H), 3.10 (t, J=9.5 Hz, 1H), 3.21–3.27 (m, 1H), 3.40 (dd, J=4.1, 9.9 Hz, 1H), 3.54 (m, 1H), 3.61–3.74 (m, 3H), 3.77 (s, 3H), 5.93 (s, 2H), 6.73–6.85 (m, 4H), 7.02 (m, 3H), 7.33 (d, J=7.5 Hz, 1H), 7.40 (s, 1H), 7.58 (t, J=7.8 Hz, 1H), 7.69 (d, J=7.5 Hz, 1H). MS (DCI) m/e 599 (M+H$^+$). Anal calcd for C$_{32}$H$_{33}$F$_3$N$_2$O$_6$: C, 64.21; H, 5.56; N, 4.68. Found: C, 64.09; H, 5.63; N, 4.57.

EXAMPLE 348 trans,trans-4-(1,3-Benzodioxol-5-yl)-2-(4-methoxyphenyl)-1-(N-propyl-N-(4-morpholinylcarbonyl)aminocarbonylmethyl)-pyrrolidine-3-carboxylic acid Using the procedures described in Example 1, the title compound was prepared. $^1$H NMR (300 MHz, CD$_3$OD) δ 0.78 (t, J=7 Hz, 3H), 1.43 (q, J=7 Hz, 2H), 2.07–3.01 (m, 1H), 2.76 (dd, J=7, 9 Hz, 2H), 2.77–3.00 (m, 5H), 3.05 (3.70, J=m Hz, 11H), 3.76 (s, 3H), 5.88 (s, 2H), 6.67 (d, J=8 Hz, 1H), 6.80 (dd, J=7 Hz, 1H), 6.83–6.90 (m, 2H), 6.98 (d, J=2 Hz, 1H), 7.32–7.39 (m, 2H). MS m/e calc'd for (M+H) C$_{29}$H$_{39}$N$_3$O$_7$: (M+H) 540.2710, Found (M+H) 540.2713.

EXAMPLE 349 trans,trans-4-(1,3-Benzodioxol-5-yl)-2-(4-methoxyphenyl)-1-(cis-2,6-dimethylpiperidin-1-yl)carbonylmethyl)-pyrrolidine-3-carboxylic acid Using the procedures described in Example 1, the title compound was prepared. $^1$H NMR (300 MHz, CD$_3$OD) δ 0.94 (d, J=7 Hz, 3H), 1.15d (7, 3H), 1.10–1.70 (m, 6H), 1.70–1.90 (m, 1H), 2.9. (d, J=13 Hz, 1H), 3.00–3.20 (m, 2H), 3.50 (3.70, J=m Hz, 2H), 3.79 (s, 3H), 3.80–4.00 (m, 1H), 4.10–4.65 (m, 2H), 5.95 (s, 2H), 6.70 (7.10, J=m Hz, 5H), 7.35 (m, 2H). MS m/e calc'd for (M+H)+C$_{28}$H$_{35}$N$_2$O$_6$: (M+H) 495.2495. Found (M+H) 495.2493.

EXAMPLE 350 trans,trans-2-(4-Methoxymethoxyphenyl)-4-(1,3-benzodioxol-5-yl)-1-[2-(N-propyl-N-n-pentanesulfonylamino)ethyl]pyrrolidine-3-carboxylic acid Using the procedures described in Example 1, the title compound was prepared and isolated as a white solid. m.p. 57–59° C. $^1$H NMR (CDCl$_3$, 300 MHz) δ 0.78 (t, J=7 Hz, 3H), 0.90 (t, J=7 Hz, 3H), 1.28–1.36 (m, 4H), 1.93 (sextet, J=7 Hz, 2H), 1.72 (t, J=7 Hz, 2H), 2.20–2.32 (m, 1H), 2.72–3.10 (m, 7H), 3.18–3.41 (m, 2H), 3.43 (dd, J=3 Hz, J=9 Hz, 1H), 3.48 (s, 3H), 3.52–3.59 (m, 1H), 3.68 (d, J=9 Hz, 1H), 5.15 (s, 2H), 5.94 (s,2H), 6.73 (d, J=8 Hz, 1H), 6.82 (dd, J=1 Hz, J=8 Hz, 1H), 6.98–7.02 (m, 3H), 7.32 (d, J=9 Hz, 2H). MS (DCI/NH$_3$) m/e 591 (M+H)$^+$.

EXAMPLE 351 trans,trans-4-(1,3-Benzodioxol-5-yl)-2-(4-methoxyphenyl)-1-(((N-(2-butyl)-N-phenylamino)carbonyl)methyl)pyrrolidine-3-carboxylic acid Using the procedures described in Example 1, the title compound was prepared. $^1$H NMR (300 MHz, CD$_3$OD) δ 0.79–0.89 (m, 6H), 1.14–1.21 (m, 1H), 1.25–1.40 (m, 1H), 2.64 (dd, J=4.6, 15.4 Hz, 1H), 2.76 (t, J=9.0 Hz, 1H), 3.05–3.13 (m, 2H), 3.37–3.49 (m, 2H), 3.70 (s, 3H), 3.80 (d, J=9.8 Hz, 1H), 4.53 (m, 1H), 5.83 (m, 2H), 6.65 (d, J=8.1 Hz, 1H), 6.72 (–6.76, J=m Hz, 3H), 6.87 (m, 2H), 6.95 (d, J=1.7 Hz, 1H), 7.03 (m, 2H), 7.29 (m, 3H). MS (DCI) m/e 531 (M+H$^+$). Anal calcd for C$_{31}$H$_{34}$N$_2$O$_6$ 0.4H$_2$O: C, 69.23; H, 6.52; N, 5.21. Found: C, 69.19; H, 6.52; N, 5.03.

EXAMPLE 352 trans,trans-4-(1,3-Benzodioxol-5-yl)-2-(4-methoxyphenyl)-1-(((N-(2-propyl)-N-phenylamino)carbonyl)methyl)pyrrolidine-3-carboxylic acid Using the procedures described in Example 1, the title compound was prepared. $^1$H NMR (300 MHz, CD$_3$OD) δ 0.99 (d, J=6.8 Hz, 6H), 2.71 (d, J=115.6 Hz, 1H), 2.84 (m, 1H), 3.13–3.18 (m, 2H), 3.45–3.58 (m, 2H), 3.79 (s, 3H), 3.88 (d, J=9.8 Hz, 1H), 4.80 (m, 1H), 5.92 (s, 2H), 6.74 (d, J=8.1 Hz, 1H), 6.83 (m, 3H), 6.96 (br s, 2H), 7.04 (d, J=1.7 Hz, 1H), 7.13 (m, 2H), 7.38 (m, 3H). MS (DCI) m/e 517 (M+H$^+$). Anal calcd for C$_{30}$H$_{32}$N$_2$O$_6$.0.4H$_2$O.0.08CH$_3$CO$_2$C$_2$H$_5$: C, 68.65; H, 6.28; N, 5.28. Found: C, 68.64; H, 6.35; N, 5.14.

EXAMPLE 353 trans,trans-4-(4-Propoxyphenyl)-2-(4-methoxyphenyl)-1-(N,N-di(n-butyl)aminocarbonylmethyl)-pyrrolidine-3-carboxylic acid Using the procedures described in Example 1, the title compound was prepared. $^1$H (300 MHz, CDCl$_3$) δ 7.42 (2H, d, J=10 Hz), 7.38 (2H, d, J=10 Hz), 6.92 (2H, d, J=10 Hz), 6.88 (2H, d, J=10 Hz), 5.13 (1H, bd, J=12 Hz), 4.02 (2H, m), 3.90 (2H, t, J=8 Hz), 3.80 (3H, s), 3.71 (3H, m), 3.40 (2H, m), 3.19 (1H, m), 3.10–2.90 (2H, m), 1.80 (2H, m), 1.48 (2H, m), 1.29 (4H, m), 1.13 (2H, m), 1.03 (3H, t, J=8 Hz), 0.92 (3H, t, J=9 Hz), 0.82 (3H, t, J=9 Hz). MS (DCI/NH$_3$) m/e 525 (MH$^+$). Anal calcd for C$_{31}$H$_{44}$N$_2$O$_5$ 1 TFA: C, 62.06H 7.10; N, 4.39. Found: C, 62.43; H, 7.28; N, 4.39.

EXAMPLE 354 trans,trans-4-(1,3-Benzodioxol-5-yl)-2-(4-methoxyphenyl)-1-((1,2,3,4-tetrahydroquinolin-1-yl)carbonyl)methyl)pyrrolidine-3-carboxylic acid Using the procedures described in Example 1, the title compound was prepared. $^1$H NMR (300 MHz, CD$_3$OD) δ 1.88 (quintet, J=6.5 Hz, 2H), 2.67 (t, J=6.4 Hz, 2H), 2.87 (t, J=8.6 Hz, 1H), 3.14 (m, 2H), 3.42 (dd, J=4.6, 9.7 Hz, 1H), 3.53–3.70 (m, 3H), 3.72–3.78 (m, 1H), 3.77 (s, 3H), 3.86 (d, J=9.6 Hz, 1H), 5.91 (s, 2H), 6.73 (d, J=8.1 Hz, 1H), 6.83 (m, 3H), 6.98 (d, J=1.1 Hz, 1H), 7.02–7.23 (m, 6H). MS (DCI) m/e 515 (M+H$^+$). Anal calcd for C$_{30}$H$_{30}$N$_2$O$_6$.0.3H$_2$O. 0.15CH$_3$CO$_2$C$_2$H$_5$: C, 68.93; H, 6.01; N, 5.25. Found: C, 68.91; H, 5.86; N, 5.19.

EXAMPLE 355 trans,trans-2-(3,4-Dimethoxyphenyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as a white solid. m.p. 64–65° C. $^1$H NMR (CDCl$_3$, 300 MHz) δ 0.79 (t, J=7 Hz, 3H), 0.88 (t, J=7 Hz, 3H), 1.07 (sextet, J=7 Hz, 2H), 1.20–1.35 (m, 4H), 1.43 (sextet, J=7 Hz, 2H), 2.83 (d, J=13.5 Hz, 1H), 2.94–3.17 (m, 4H), 3.22–3.42 (m, 1H), 3.40–3.48 (m, 3H), 3.58–3.65 (m, 1H), 3.82 (s, 3H), 3.85 (s, 4H), 5.92 (s, 2H), 6.73 (d, J=8 Hz, 1H), 6.81 (d, J=8 Hz, 1H), 6.86–6.96 (m, 3H), 7.07 (d, J=3 Hz, 1H). MS (DCI/NH$_3$) m/e 541 (M+H)$^+$.

EXAMPLE 356 trans,trans-2-(3,4-Dimethoxyphenyl)-4-(1,3-benzodioxol-5-yl)-1-[2-(N-propyl-N-n-pentanesulfonylamino)ethyl]pyrrolidine-3-carboxylic acid Using the procedures described in Example 1, the title compound was prepared and isolated as a white solid. m.p. 75–86° C. $^1$H NMR (CD$_3$OD, 300 MHz) δ 0.75 (t, J=7 Hz, 3H), 0.82 (t, J=7 Hz, 3H), 1.32–1.43 (m, 6H), 1.65–1.77 (m, 2H), 3.0–3.09 (m, 4H), 3.23–3.27 (m, 2H), 3.44 (t, J=6 Hz, 1H), 3.47–3.56 (m, 2H), 3.78 (d, J=9 Hz, 1H), 3.83–3.93 (m, 2H), 3.87 (s, 3H), 3.92 (s, 3H), 4.63 (d, J=13 Hz, 1H), 5.97 (s, 2H), 6.82 (d, J=7 Hz, 1H), 6.93 (d, J=7 Hz, 1H), 7.06 (d, J=7 Hz, 1H), 7.08 (d, J=3 Hz, 1H), 7.16 (dd, J=3 Hz, J=7 Hz, 1H), 7.27 (d, J=3 Hz, 1H). MS (DCI/NH$_3$) m/e 591 (M+H)$^+$.

EXAMPLE 357 trans,trans-2-(3,4-Dimethoxyphenyl)-4-(1,3-benzodioxol-5-yl)-1-[2-(N-propyl-N-n-hexanesulfonylamino)ethyl]pyrrolidine-3-carboxylic acid Using the procedures described in Example 1, the title compound was prepared and isolated as a white solid. m.p. 65–66° C. $^1$H NMR (CDCl$_3$, 300 MHz) δ 0.80 (t, J=7 Hz, 3H), 0.89 (t, J=7 Hz, 3H), 1.23–1.48 (m, 6H), 1.43 (sextet, J=7 Hz, 2H), 1.72 (sextet, J=7 Hz, 2H), 2.25–2.35 (m, 1H), 2.73–3.10 (m, 7H), 3.19–3.32 (m, 2H), 3.45 (dd, J=3 Hz, J=9 Hz, 1H), 3.53–3.59 (m, 1H), 3.68 (d, J=9 Hz, 1H), 3.87 (s, 6H), 5.95 (s, 2H), 6.74 (d, J=8 Hz, 1H), 6.79–6.86 (m, 2H), 6.92–6.97 (m, 2H), 7.02 (s, 1H). MS (DCI/NH$_3$) m/e 605 (M+H)$^+$.

EXAMPLE 358 trans,trans-2-(4-Methoxyphenyl)-4-(1,3-benzodioxol-5-yl)-1-[2-(phthalimido)ethyl]-pyrrolidine-3-carboxylic acid The compound of Example 1C (250 mg), N-bromoethylphthalimide (206 mg), and diisopropylethylamine (175 mg) were dissolved in 1 mL of acetonitrile and heated for 2.5 hours at 95° C. Toluene was added, and the mixture was washed with KHCO$_3$ solution. The solution was dried (Na$_2$SO$_4$) and concentrated. The crude product was purified by chromatography on silica gel eluting with 3:1 EtOAc-hexane to give 216 mg of an intermediate ethyl ester which was hydrolyzed by the method of Example 1D to give 130 mg of the title compound as a white powder. $^1$H NMR (300 MHz, CDCl$_3$) δ 3.12–3.26 (m, 2H), 3.60–3.75 (m, 2H), 3.70 (s, 3H), 3.98–4.12 (m, 2H), 4.45–4.55 (m, 1H), 4.69 (d, J=9 Hz, 1H), 4.76–4.88 (m, 1H), 5.96 (s, 2H), 6.55 (d, J=8 Hz, 1H), 6.60–6.70 (m, 3H), 6.79 (d, J=8 Hz, 1H), 7.05–7.45 (m, 5H), 7.75 (d, J=7 Hz, 1H).

EXAMPLE 359 trans,trans-4-(1,3-Benzodioxol-5-yl)-2-(4-methoxyphenyl)-1-(((N-(2-pentyl)-N-phenylamino)carbonyl)methyl)pyrrolidine-3-carboxylic acid Using the procedures described in Example 1, the title compound was prepared. $^1$H NMR (300 MHz, CD$_3$OD) δ 0.86–0.98 (m, 6H), 1.17–1.22 (m, 1H), 1.23–1.41 (m, 3H), 2.70 (dd, J=11.2, 15.3 Hz, 1H), 2.83 (m, 1H), 3.10–3.21 (m, 2H), 3.45–3.60 (m, 2H), 3.79 (s, 3H), 3.86 (m, 1H), 4.74 (m, 1H), 5.91 (m, 1H), 6.73 (dd, J=1.1, 7.7 Hz, 3H), 6.82 (m, 2H), 7.04–7.14 (m, 3H), 7.36 (m, 3H). MS (DCI) m/e 545 (M+H)$^+$. Anal calcd for C$_{32}$H$_{36}$N$_2$O$_6$·0.25 CH$_3$CO$_2$C$_2$H$_5$: C, 69.95; H, 6.76; N, 4.94. Found: C, 70.03; H, 6.54; N, 4.78.

EXAMPLE 360 trans,trans-4-(1,3-Benzodioxol-5-yl)-2-(4-methoxyphenyl)-1-(N-butyl-N-(2-naphthyl)aminocarbonylmethyl)-pyrrolidine-3-carboxylic acid Using the procedures described in Example 1, the title compound was prepared. $^1$H NMR (300 MHz, CD$_3$OD) δ 0.83 (t, J=7 Hz, 3H), 1.23–1.39 (m, 4H), 1.40–1.55 (m, 3H), 2.60–2.72 (m, 2H), 3.00–3.80 (m, 5H), 3.66 (s, 3H), 5.87 (s, 2H), 6.39 (d, J=9 Hz, 2H), 6.74–6.85 (m, 3H), 7.17 (d, J=2 Hz, 1H), 7.40 (dd, J=8 Hz, 1H), 7.52–7.62 (m, 3H), 7.80–7.90 (m, 1H), 7.90–8.00 (m, 2H). MS (DCI) m/e 581 (M+H)$^+$. Analysis calcd for C$_{35}$H$_{36}$N$_2$O$_6$·0.3H$_2$O: C, 71.73; H, 6.29; N, 4.78. Found: C, 71.74; H, 6.26; N, 4.72.

EXAMPLE 361 trans,trans-2-(4-Propoxyphenyl)-4-(1,3-benzodioxol-5-yl)-1-[2-(N-propyl-N-n-pentanesulfonylamino)ethyl]pyrrolidine-3-carboxylic acid Using the procedures described in Example 66, the title compound was prepared and isolated as a white solid. m.p. 53–54° C. $^1$H NMR (CDCl$_3$, 300 MHz) δ 0.79 (t, J=7 Hz, 3H), 0.89 (t, J=7 Hz, 3H), 1.03 (t, J=7 Hz, 3H), 1.24–1.34 (m, 4H), 1.43 (sextet, J=7 Hz, 2H), 1.67–1.75 (m, 2H), 1.80 (sextet, 2H), 2.23–2.33 (m, 1H), 2.72–2.93 (m, 5H), 3.05 (septet, J=7 Hz, 2H), 3.15–3.35 (m, 2H), 3.42 (d, J=9 Hz, 1H), 3.54–3.62 (m, 1H), 3.67 (d, J=9 Hz, 1H), 4.90 (t, J=7 Hz, 2H), 5.95 (s, 2H), 6.73 (d, J=8 Hz, 1H), 6.85 (d, J=8 Hz, 2H), 7.02 (s, 1H), 7.32 (d, J=8 Hz, 2H). MS (DCI/NH$_3$) m/e 589 (M+H)$^+$.

EXAMPLE 362 trans,trans-4-(1,3-Benzodioxol-5-yl)-2-(4-methoxyphenyl)-1-((2-methylindolin-1-yl)carbonyl)methyl)pyrrolidine-3-carboxylic acid Using the procedures described in Example 1, the title compound was prepared. $^1$H NMR (300 MHz, CD$_3$OD) δ mixture of indole C$_2$ diastereomers, 0.95 (m, 1.5 (CH$_3$)), 1.05 (d, 6.3H, 1.5 (CH$_3$)), 2.62 (m, 1H), 3.01 (m, 2H), 3.14–3.25 (m, 1H), 3.37–3.52 (m, 1.5H), 3.56–3.80 (m, 2H), 3.65 (s, 1.5 (CH$_3$O)), 3.76 (s, 1.5 (CH$_3$O)), 3.93 (m, 0.5H), 4.05–4.13 (m, 0.5H,), 4.42 (m, 0.5H), 4.65–4.74 (m, 1H), 5.91 (m, 2H), 6.72 (d, J=8.1 Hz, 0.5H), 6.75 (m, 0.5H), 6.85 (m, 2H), 6.92 (d, J=8.5 Hz, 1H), 7.00–7.06 (m, 2H), 7.14 (t, J=7.7 Hz, 1H), 7.21 (t, J=6.6 Hz, 1H), 7.38 (m, 2H), 7.99 (m, 1H). MS (DCI) m/e 515 (M+H$^+$). Anal calcd for C$_{30}$H$_{30}$N$_2$O$_6$·0.35H$_2$O·0.3 CH$_3$CO$_2$C$_2$H$_5$: C, 68.47; H, 6.10; N, 5.12. Found: C, 68.46; H, 5.97; N, 5.07.

EXAMPLE 363 trans,trans-4-(1,3-Benzodioxol-5-yl)-2-(4-methoxyphenyl)-1-(2-hydroxy-3-propylhex-1-yl)pyrrolidine-3-carboxylic acid Using the procedures described in Example 1, the title compound was prepared. $^1$H NMR (300 MHz, CD$_3$OD) δ 1.06 (m, 6H), 1.26–1.60 (m, 9H), 3.16 (dd, J=10.9, 12.6 Hz, 1H), 3.18 (d, J=11 Hz, 1H), 3.44 (d, J=2.0 Hz, 1H), 3.61 (t, J=11 Hz, 1H), 3.73 (t, J=11.0 Hz, 1H), 3.85 (m, 1H), 3.96–4.17 (m, 2H), 4.02 (s, 1.5 (CH$_3$O diastereomer)), 4.03 (s, 1.5 (CH$_3$O diastereomer)), 6.15 (s, 2H), 7.01 (d, J=8.1 Hz, 0.5H), 7.00 (d, J=8.1 Hz, 0.5H), 7.10 (m, 1H), 7.23 (m, 3H), 7.77 (m, 2H). MS (DCI.) m/e 484 (M+H$^+$). Anal calcd for C$_{28}$H$_{37}$NO$_6$·0.33H$_3$PO$_4$: C, 65.34; H, 7.44; N, 2.72. Found: C, 65.30; H, 7.40; N, 2.60.

EXAMPLE 364 trans,trans-4-(1,3-Benzodioxol-5-yl)-2-(4-methoxyphenyl)-1-(((N-(4-heptyl)-N-(3,4-dimethoxybenzyl)amino)carbonyl)methyl)pyrrolidine-3-carboxylic acid Using the procedures described in Example 1, the title compound was prepared. $^1$H NMR (300 MHz, CD$_3$OD) δ1:1 mixture of rotamers, 0.61 (t, J=7.1 Hz, 1.5H), 0.72 (7.3, 1.5H), 0.76 (t, J=7.1, 1.5, 0.83, t, 7.3 Hz, 1.5H), 1.05–1.60 (m, 8H), 2.84–3.10 (m, J=2.5, 3.18, t, 9.7 Hz, 0.5H), 3.41–3.52 (m, 2H), 3;47–3.69 (m, 2H), 3.66 (s, 1.5H), 3.73 (s, 1.5H), 3.77 (s, 1.5H), 3.78 (s, 1.5H), 3.79 (s, 1.5H), 3.86 (d, J=9.8 Hz, 0.5H), 4.19 (d, J=17.7 Hz, 0.5H), 4.29 (d, J=15.2 Hz, 0.5H), 4.40–4.49 (m, 0.5H), 4.47 (d, J=15.3 Hz, 0.5H), 4.60 (d, J=17.6 Hz, 0.5H), 5.93 (m, 2H), 6.46 (dd, J=1.7, 8.2 Hz, 0.5H), 6.52 (d, J=2.0 Hz, 0.5H), 6.74 (m, 2.5H), 6.80 (s, 1H), 6.83–6.88 (m, 1H), 6.92 (m, 1.5H), 7.03 (dd, J=1.7, 6.8 Hz, 1H), 7.19 (m, 1H), 7.36 (m, 1H). MS (DCI) m/e 647 (M+H$^+$). Anal calcd for C$_{37}$H$_{46}$N$_2$O$_8$: C, 68.71; H, 7.17; N, 4.33. Found: C, 68.41; H, 7.26; N, 4.11.

EXAMPLE 365 trans,trans-4-(1,3-Benzodioxol-5-yl)-2-(4-methoxyphenyl)-1-((indolin-1-yl)carbonyl)methyl)pyrrolidine-3-carboxylic acid Using the procedures described in Example 1, the title compound was prepared. $^1$H NMR (300 MHz, CD$_3$OD) δ2.97 (dd, J=8.1, 9.5 Hz, 1H), 3.10 (t, J=8.1 Hz, 2H), 3.16–3.22 (m, 2H), 3.51–3.68 (m, 3H), 3.73 (m, 3H), 3.83–4.05 (m, 3H), 5.90 (m, 2H), 6.73 (d, J=8.1 Hz, 1H), 6.86 (m, 3H), 6.99 (dt, J=1.1, 7.4 Hz, 1H), 7.08(d, J=0.7 Hz, 1H), 7.11 (m, 1H), 7.18(d, J=7.1 Hz, 1H), 7.38(d, J=8.5 Hz, 2H), 8.02 (8.1, 1H). MS (C.I.) m/e 501 (M+H$^+$). Anal calcd for C$_{29}$H$_{28}$N$_2$O$_6$.0.5H$_2$O.0.15 CH$_3$CO$_2$C$_2$H$_5$: C, 68.01; H, 5.82; N, 5.36. Found: C, 68.03; H, 5.65; N, 5.25.

EXAMPLE 366 trans,trans-4-(1,3-Benzodioxol-5-yl)-2-(4-methoxyphenyl)-1-(N-butyl-N-(2-chlorophenyl)aminocarbonylmethyl)pyrrolidine-3-carboxylic acid Using the procedures described in Example 1, the title compound was prepared. $^1$H NMR (300 MHz, CD$_3$OD) δ0.89 (dt, J=7 Hz, 3H), 1.23–1.51 (m, 4H), 2.52–4.00 (m, 8H), 3.78 (d, J=6 Hz, 3H), 5.92 (d, J=6 Hz, 2H), 6.70–6.87 (m, 4H), 7.02–7.21 (m, 4H), 7.27–7.52 (m, 3H). MS (DCI) m/e 565 (M+H)$^+$. Analysis calcd for C$_{31}$H$_{32}$N$_2$O$_6$Cl.0.6H$_2$O: C, 64.66; H, 5.99; N, 4.86. Found: C, 64.59; H, 6.00; N, 4.64.

EXAMPLE 367 trans,trans-2-(4-Methoxphenyl)-4-(1,3-benzodioxol-5-yl)-1-(3,4,5-trimethoxybenzyl)pyrrolidine-3-carboxylic acid The compound resulting from Example 1C (0.25 g) was reacted with 0.169 g of 3,4,5-trimethoxybenzyl chloride and 0.175 g of diisopropylethylamine in 1 mL of acetonitrile for 2 hours at room temperature. The resulting ester was isolated and then hydrolyzed by the method of Example 1D to give 0.193 g of the title compound. m.p. 108–110° C. $^1$H NMR (300 MHz, CDCl$_3$) δ2.75 (t, J=9 Hz, 1H), 2.95–3.05 (m, 2H), 3.20 (d, J=11 Hz, 1H), 3.45–3.55 (m, 1H), 3.7–3.8 (m, 2H), 3.84 (s, 3H), 5.95 (dd, J=2 Hz, 6 Hz, 2H), 6.55 (s, 2H), 6.70 (d, J=8 Hz, 1H), 6.30–6.35 (m, 1H), 6.90 (d, J=9 Hz, 2H), 7.13 (d, J=2 Hz, 1H), 7.43 (d, J=9 Hz, 2H).

EXAMPLE 368 trans,trans-4-(1,3-Benzodioxol-5-yl)-2-(4-methoxyphenyl)-1-(N-butyl-N-(3-chlorophenyl)aminocarbonylmethyl)-Pyrrolidine-3-carboxylic acid Using the procedures described in Example 1, the title compound was prepared. $^1$H NMR (300 MHz, CD$_3$OD) δ 0.89 (t, J=7 Hz, 3H), 1.20–1.42 (m, 4H), 3.42–3.87 (m, 9H), 3.9 (s, 3H), 5.96 (s, 2H), 6.75 (7.10, J=m Hz, 7H), 7.33–7.50 (m, 4H). MS (C.I.) m/e 565(M+H). Analysis calcd for C$_{31}$H$_{33}$N$_2$O$_6$Cl.1.0CF$_3$COOH: C, 58.37; H, 5.05; N, 4.13. Found: C, 58.41; H, 4.99; N, 4.08.

EXAMPLE 369 trans,trans-2-(4-Methoxphenyl)-4-(1,3-benzodioxol-5-yl)-1-[2-(di-n-butylamino)pyrimidin-4-yl]pyrrolidine-3-carboxylic acid The compound resulting from Example 1C (0.25 g) was reacted with 0.11 g of 2,4-dichloropyrimidine and 0.175 g of diisopropylethylamine in 1 mL of acetonitrile for 2 hours at room temperature to give 0.218 g of ethyl 2-(4-methoxphenyl)-4-(1,3-benzodioxol-5-yl)-1-(2-chloro-4-pyrimidyl)-pyrrolidine-3-carboxylate. This compound was reacted with 1 mL of dibutylamine in 2 mL of toluene at 125° C. for 17 hours. The resulting ethyl ester was hydrolyzed by the method of Example 1D to give 0.142 g of the title comopund as a white powder. $^1$H NMR (300 MHz, CDCl$_3$) δ0.75–0.90 (broad, 6H), 1.1–1.3 (br, 4H), 1.35–1.55 (br, 4H), 3.05 (m, 1H), 3.3–3.5 (br, 2H), 3.55–3.67 (m, 2H), 3.75 (s, 3H), 4.6 (br, 1H), 5.2 (br, 1H), 5.45 (br, 1H), 5.87 (s, 2H), 6.3 (br, 1H), 6.67 (d, J=8 Hz, 1H), 6.7–6.85 (m, 4H), 7.10 (d, J=9 Hz, 2H).

EXAMPLE 370 trans,trans-4-(1,3-Benzodioxol-5-yl)-2-(4-methoxyphenyl)-1-(((N-(2-methylbut-2-yl)-N-phenylamino)carbonyl)methyl)pyrrolidine-3-carboxylic acid Using the procedures described in Example 1, the title compound was prepared. $^1$H NMR (300 MHz, CD$_3$OD) δ 0.90 (t, J=7.5 Hz, 3H), 1.12 (s, 3H), 1.14 (s, 3H), 2.06 (q, J=7.5 Hz, 2H), 2.73 (d, J=15.3 Hz, 1H), 2.91 (t, J=9.5 Hz, 1H), 3.11 (d, J=15.6 Hz, 1H), 3.21 (t, J=8.8 Hz, 1H), 3.50–3.61 (m, 2H), 3.80 (s, 3H), 4.00 (d, J=10.2 Hz, 1H), 5.91 (s, 2H), 6.74 (d, J=7.8 Hz, 1H), 6.85 (m, 3H), 6.93 (m, 1H), 6.98 (m, 1H), 7.03 (d, J=1.7 Hz, 1H), 7.17 (m, 2H), 7.36 (m, 3H). MS (DCI) m/e 545 (M+H$^+$). Anal calcd for C$_{32}$H$_{36}$N$_2$O$_6$: C, 70.57; H, 6.66; N, 5.14. Found: C, 70.17; H, 6.53; N, 4.97.

EXAMPLE 371 trans,trans-2-(4-Ethylphenyl)-4-(5-indanyl)-1-(N,N-di(n-butyl)aminocarbonylmethyl)-pyrrolidine-3-carboxylic acid Using the procedures described in Example 1, the title compound was prepared. $^1$H (300 MHz, CDCl$_3$) δ 7.25 (3H, m), 7.21 (1H, d, 3 Hz), 7.17 (3H, m), 3.80 (1H, d, 10 Hz), 3.65 (1H, ddd, 6, 5, 3 Hz), 3.4 (4H, m), 3.10 (2H, m), 2.98 (2H, m), 2.88 (5H, m), 2.79 (1H, d, 16 Hz), 2.62 (2H, q, 7 Hz), 2.05 (2H, m), 1.42 (2H, m), 1.32 (1H, m), 1.21 (3H, t, 7 Hz), 1.05 (2H, sext, 7 Hz), 0.87 (3H, t, 7 Hz), 0.79 (3H, t, 7 Hz). MS (DCI, NH$_3$) m/e 505 (M+H$^+$). Anal calcd for C$_{32}$H$_{44}$N$_2$O$_3$: C, 76.15; H, 8.79; N, 5.55. Found: C, 75.96; H, 8.75; N, 5.36.

EXAMPLE 372 trans,rans-2-(3,4-Difluorophenyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as a white solid. m.p. 62–63° C. $^1$H NMR (CDCl$_3$, 300 MHz), δ 0.83 (t, J=7 Hz, 3H), 0.88 (t, J=7 Hz, 3H), 1.13 (sextet, J=7 Hz, 2H), 1.20–1.32 (m,3H), 1.36–1.49 (m,3H), 2.85–2.93 (m,2H), 2.98–3.23 (m, 4H), 3.36–3.45 (m, 3H), 3.58–3.66 (m 1H), 3.94 (d, J=8 Hz, 1H), 5.93 (s, 2H), 6.72 (d, J=7.5 Hz, 1H), 6.84 (dd, J=1 Hz, J=7.5 Hz, 1H), 6.98 (d, J=7.5 Hz, 1H), 7.08–7.15 (m, 2H), 7.22–7.28 (m, 1H). MS (CDI/NH$_3$) m/e517 (M+H)$^+$.

EXAMPLE 373 trans,trans-2-(3,4-Difluorophenyl)-4-(1,3-benzodioxol-5-yl)-1-[2-(N-propyl-N-n-pentanesulfonylamino)ethyl]pyrrolidine-3-carboxylic acid Using the procedures described in Example 1, the title compound was prepared and isolated as a white solid. m.p. 71–72° C. $^1$H NMR (CDCl$_3$, 300 MHz) δ 0.82 (t, J=7 Hz, 3H), 0.90 (t, J=7 Hz, 3H), 1.25–1.38 (m, 4H), 1.46 (sextet, J=7 Hz, 2H), 1.74 (quintett, J=7 Hz, 2H), 2.26–2.36 (m, 1H), 2.72–2.95 (m, 5H), 2.98–3.12 (m, 2H), 3.15–3.34 (m, 2H), 3.45 (dd, J=3 Hz, J=9 Hz, 1H), 3.53–3.60 (m, 1H), 3.71 (d, J=9 Hz, 1H), 5.96 (s, 2H), 6.75 (d, J=9 Hz, 1H), 3.82 (dd, J=2 Hz, J=9 Hz, 1H), 5.96 (d, J=2 Hz, 1H), 7.09–7.18 (m, 2H), 7.23–7.34 (m, 1H). MS (CDI/NH$_3$) m/e567 (M+H)$^+$.

EXAMPLE 374 trans,trans-4-(1,3-Benzodioxol-5-yl)-2-(ethoxymethyl)-1-(((N,N-di(n-butyl)aminocarbonylmethyl)-pyrrolidine-3-carboxylic acid Using the procedures described in Example 1, the title compound was prepared. TLC (10% MeOH—CH$_2$Cl$_2$) R$_f$=0.53. $^1$H NMR (CDCl$_3$, 300 MHz, rotameric forms) δ 0.70 (t, J=7 Hz), 0.80 (t, J=7 Hz) and 0.96–1.04 (m, 6H total), 1.04–1.75 (m, 11H), 1.34–1.53 (br m, 4H), 2.65 (AB) and 2.80–3.08 (m, 2H total), 3.10–3.82 (br m, 12H), 4.03 (m) and 4.22–4.45 (br m, 2H total), 5.90 (s) and 5.91 (s, 2H total), 6.65–6.84 (m) and 6.93 (m) and 6.99 (m, 3H total). MS (FAB) m/e 463 (M+H)$^+$. Anal calcd for C$_{25}$H$_{38}$N$_2$O$_6$.1.5H$_2$O: C, 61.33; H, 8.44; N, 5.72. Found: C, 61.28; H, 7.78; N, 5.62.

EXAMPLE 375 trans,trans-4-(1,3-Benzodioxol-5-yl)-2-(n-butyl)-1-(N,N-di(n-butyl)aminocarbonylmethyl)-pyrrolidine-3-carboxylic acid Using the procedures described in Example 1, the title compound was prepared and isolated as a colorless wax. TLC (10% MeOH—CH$_2$Cl$_2$) R$_f$=0.37. $^1$H NMR (CDCl$_3$, 300 MHz, rotameric forms) δ 0.71 (t, J=7 Hz) and 0.77–1.05 (m, 9H total), 1.05–1.20 (m, 2H), 1.20–1.72 (br m, 13H), 2.48–2.52 (m, 1H), 2.87–3.00 (m, 1H), 3.05–3.60 (m, 5H), 3.60–3.80 (br m, 2H), 3.88–4.05 (br m, 1H), 4.28 (br d, J=15 Hz, 1H total), 5.90 (s) and 5.92 (s, 2H total), 6.67–6.82 (m, 3H total). MS (FAB) m/e 461 (M+H)$^+$. Anal calcd for C$_{26}$H$_{40}$N$_2$O$_5$.1.75H$_2$O: C, 63.45; H, 8.90; N, 5.69. Found: C, 63.18; H, 8.22; N, 5.60.

EXAMPLE 376 trans,trans-4-(1,3-Benzodioxol-5-yl)-2-(2-methylbutyl)-1-(N,N-di(n-butyl)aminocarbonylmethyl)-pyrrolidine-3-carboxylic acid Using the procedures described in Example 1, the title compound was prepared and isolated as a colorless glass. TLC (10% MeOH—CH$_2$Cl$_2$) R$_f$=0.49. $^1$H NMR (CDCl$_3$, 300 MHz, rotameric forms and mixture of diastereomers) δ 0.69 (br t, J=7 Hz) and 0.75–2.15 (several br m, approx. 26H total), 2.48–2.65 (br m, 1H), 2.87–3.01 (br m, 1H), 3.06–3.82 (br m, 7H), 3.90–4.40 (br m, 2H), 5.90 (s) and 5.92 (s, 2H total), 6.67–6.90 (m, 3H total). MS (FAB) m/e 475 (M+H)$^+$.

EXAMPLE 377 trans,trans-4-(1,3-Benzodioxol-5-yl)-2-(3-methylbutyl)-1-(N,N-di(n-butyl)aminocarbonylmethyl)-pyrrolidine-3-carboxylic acid Using the procedures described in Example 1, the title compound was prepared. TLC (10% MeOH—CH$_2$Cl$_2$) R$_f$=0.41. $^1$H NMR (CDCl$_3$, 300 MHz, rotameric forms) δ 0.73 (t, J=7 Hz) and 0.77–1.05 (m, 12H total), 1.07–1.75 (m, approx. 14H plus H$_2$O), 2.48–2.63 (m, 1H), 2.87–3.05 (m, 1H), 3.05–3.60 (several br m, 5H), 3.62–4.02 (br m, 2H), 4.29 (br d, J=15 Hz, 1H), 5.89 (s) and 5.93 (s, 2H total), 6.65–6.90 (m, 3H total). MS (FAB) m/e 475 (M+H)$^+$.

EXAMPLE 378 trans,trans-2-(4-Methoxyphenyl)-4-(1,3-benzodioxol-5-yl)-1-[2-(N-propyl-N-((N-methyl-N-propylamino)sulfonyl)amino)ethyl]pyrrolidine-3-carboxylic acid Using the procedures described in Example 66, the title compound was prepared and isolated as a white solid. m.p. 58–59° C. $^1$H NMR (CDCl$_3$, 300 MHz) δ 0.78 (t, J=7 Hz, 3H), 0.90 (t, J=7 Hz, 3H), 1.27 (sextet, J=7 Hz, 2H), 1.48 (m, 4H), 2.22–2.30 (m, 1H), 2.62 (s, 3H), 2.68–2.78 (m, 1H), 2.84–3.03 (m, 5H), 3.08–3.31 (m, 3H), 3.39 (dd, J=3 Hz, J=9 Hz,1H), 3.50–3.58 (m, 1H), 3.63 (d, J=9 Hz, 1H), 3.79 (s, 3H), 5.95 (s, 2H), 3.73 (d, J=8 Hz, 1H), 6.83 (dd, J=2 Hz, J=8 Hz, 1H), 3.87 (d, J=9 Hz, 2H), 7.01 (d, J=2 Hz, 1H), 7.33 (d, J=9 Hz, 2H). MS (DCI/NH$_3$) m/e 576 (M+H)$^+$.

EXAMPLE 379 trans,trans-2,4-Di(3,4-difluorophenyl)-1-(N,N-di(n-butyl)aminocarbonylmethyl)-pyrrolidine-3-carboxylic acid Using the procedures described in Example 1, the title compound was prepared. $^1$H NMR (300 MHz, CDCl$_3$) δ 7.35 (2H, m), 7.18 (4H, m), 4.87 (1H, d, J=12), 4.00–3.60 (5H, m), 3.60–3.10 (3H, m), 3.10–2.90 (2H, m), 1.45 (2H, m), 1.29 (4H, m), 1.15 (2H, m), 0.91 (3H, t, J=9), 0.83 (3H, t, J=9). MS (DCI/NH$_3$) m/e 509 (M+H$^+$). Anal calcd for C$_{27}$H$_{32}$F$_4$N$_2$O$_3$.0.75 TFA: C, 57.62; H, 5.56; N, 4.72. Found: C, 57.72; H, 5.67; N, 4.66.

EXAMPLE 380 trans,trans-4-(3,4-Dimethylphenyl)-2-(4-methoxyphenyl)-1-(N,N-di(n-butyl)aminocarbonylmethyl)-pyrrolidine-3-carboxylic acid Using the procedures described in Example 1, the title compound was prepared. $^1$H NMR (300 MHz, CDCl$_3$) δ 7.43 (2H, d, J=9), 7.25 (1H, bs), 7.18 (1H, dd, J=8, 3), 7.11 (1H, d, J=9), 6.90 (2H, d, J=10), 5.48 (1H, d, J=12), 4.26 (1H, d, J=18), 4.16 (2H, m), 3.83 (2H, m), 3.81 (3H, s), 3.56 (1H, bd, J=18), 3.37 (1H, m), 3.20 (1H, m), 2.96 (2H, m), 2.24 (3H, s), 2.22 (3H, s), 1.47 (2H, m), 1.27 (4H, m), 1.10 (2H, m), 0.93 (3H, t, J=9), 0.81 (3H, t, J=9). MS (DCI/NH$_3$) m/e 495 (M+H$^+$). Anal calcd for C$_{30}$H$_{42}$N$_2$O$_4$.1.25 TFA: C, 61.26; H, 6.84; N, 4.40. Found: C, 61.16; H, 7.05; N, 4.38.

EXAMPLE 381 trans,trans-2,4-Di(3-fluoro-4-methoxyphenyl)-1-(N,N-di(n-butyl)aminocarbony)methyl)-pyrrolidine-3-carboxylic acid Using the procedures described in Example 1, the title compound was prepared. $^1$H NMR (300 MHz, CDCl$_3$) δ 7.20 (2H, m), 7.17 (2H, m), 6.93 (2H, m), 5.48 (1H, m), 4.26 (1H, m), 4.16 (2H, m), 3.83 (2H, m), 3.87 (6H, s), 3.56 (1H, m), 3.37 (1H, m), 3.20 (1H, m), 2.96 (2H, m), 1.47 (2H, m), 1.27 (4H, m), 1.10 (2H, m), 0.93 (3H, t, J=9), 0.81 (3H, t, J=9). MS (DCI/NH$_3$) m/e 533 (M+H$^+$). Anal calcd for C$_{29}$H$_{38}$F$_2$N$_2$O$_5$.0.75H$_2$O: C, 63.78; H, 7.29; N, 5.13. Found: C, 63.77; H, 7.08; N, 4.99.

EXAMPLE 382 trans,trans-4-(1,3-Benzodioxol-5-yl)-2-(4-methoxyphenyl)-1-(((N-(2-pentyl), N-(3-methylphenyl)amino)carbonyl)methyl)pyrrolidine-3-carboxylic acid Using the procedures described in Example 1, the title compound was prepared. $^1$H NMR (300 MHz, CD$_3$OD) δ 0.90 (m, 3H), 0.95 (t, J=7.3 Hz, 3H), 1.13–1.37 (m, 4H), 2.30 (s, 3H), 2.34 (s (CH$_3$ rotamer)), 2.73–2.91 (m, 2H), 3.17–3.26 (m, 2H), 3.32–3.62 (m, 2H), 3.77–4.08 (m, 1H), 3.80 (s, 3H), 4.71 (m, 1H), 5.92 (m, 2H), 6.61–6.84 (m, 6H), 7.04–7.16 (m, 3H), 7.23–7.29 (m, 2H). MS (DCI) m/e 559 (M+H$^+$). Anal calcd for C$_{33}$H$_{38}$N$_2$O$_6$.0.35H$_2$O.0.05 CH$_3$CO$_2$C$_2$H$_5$: C, 70.03; H, 6.92; N, 4.92. Found: C, 70.08; H, 6.82; N, 4.95.

EXAMPLE 383 trans,trans-4-(1,3-Benzodioxol-5-yl)-2-(4-methoxyphenyl)-1-(N-butyl-N-(1-naphthyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.40 (m, 2H), 1.40–1.60 (m, 2H), 2.42–2.80 (m, 2H), 2.85–4.00 (m, 6H), 3.77 (d, J=1.5 Hz, 3H), 4.05–4.20 (m, 1H), 5.94 (d, J=2 Hz, 2H), 6.6 (dd, J=9, 10 Hz, 1H), 6.70–6.85 (m, 4H), 6.95–7.02 (m, 2H), 7.17 (dd, 8H, 1/2), 7.25 (dd, 8H, 1/2), 7.38–7.60 (m, 4H), 7.87–8.00 (m, 2H). MS (E.S.I.) m/e (M+H) 581. Analysis calcd for C$_{35}$H$_{36}$N$_2$O$_6$.1.4H$_2$O: C, 69.38; H, 6.45; N, 4.62. Found: C, 69.36; H, 6.07; N, 4.41.

EXAMPLE 384 trans,trans-2-(4-Methoxyphenyl)-4-(1,3-benzodioxol-5-yl)-1-[2-(N-phenyl-N-n-hexanesulfonylamino)ethyl]pyrrolidine-3-carboxylic acid Using the procedures described in Example 66, the title compound was prepared and isolated as a tan solid. m.p. 67–68° C. $^1$H NMR (CD$_3$OD, 300 MHz) δ 0.88 (t, J=7 Hz, 3H), 1.25–1.40 (m, 6H), 1.73 (quintet, J=7 Hz, 2H), 2.13–2.23 (m, 1H), 2.64–2.88 (m, 3H), 3.02 (sextet, J=8 Hz, 2H), 3.44–3.53 (m, 2H), 3.58 (d, J=9 Hz, 1H), 3.56–3.75 (m, 1H), 3.78 (s, 3H), 3.88–3.98 (m, 1H), 5.93 (s, 2H), 6.72 (d, J=9 Hz, 1H), 5.78–5.84 (m, 3H), 6.96 (d, J=2 Hz, 1H), 7.20 (d, J=9 Hz, 2H), 7.27–7.36 (m, 5H). MS (DCI/NH$_3$) m/e 609 (M+H)$^+$.

EXAMPLE 385 trans,trans-4-(1,3-Benzodioxol-5-yl)-2-(4-methoxyphenyl)-1-(2-methyl-1,2,3,4-tetrahydroquinolin-1-yl)carbonylmethyl)pyrrolidine-3-carboxylic acid Using the procedures described in Example 1, the title compound was prepared. $^1$H NMR (300 MHz, CD$_3$OD) δ 1.03 (m, 3H), 1.10–1.45 (m, 1H), 2.10–2.85 (m, 4H), 2.90–4.00 (m, 7H), 3.76 (s, 1.5H), 3.77 (s, 1.5H, isomer), 5.90 (m, 2H), 6.70–7.40 (m, 11H). MS (DCI) m/e 529 (M+H)$^+$. Analysis calcd for C$_{31}$H$_{32}$N$_2$O$_6$.0.3H$_2$O: C, 69.73; H, 6.15; N, 5.25. Found: C, 69.74; H, 6.10; N, 5.01.

EXAMPLE 386 trans,trans-4-(1,3-Benzodioxol-5-yl)-2-(4-methoxyphenyl)-1-(3-butyl-hept-2-en-1-yl)pyrrolidine-3-carboxylic acid Using the procedures described in Example 1, the title compound was prepared. $^1$H NMR (300 MHz, CD$_3$OD) δ 0.86 (t, J=7.0 Hz, 3H), 0.90 (t, J=7.0 Hz, 3H), 1.20–1.41 (m, 8H), 1.95–2.06 (m, 4H), 3.24 (d, J=11.0 Hz, 1H), 3.51–3.59 (m, 3H), 3.60–3.71 (m, 1H), 3.77–3.84 (m, 1H), 3.81 (s, 3H), 4.45 (d, J=11.0 Hz, 1H), 5.52 (t, J=7.4 Hz, 1H), 5.93 (s, 2H), 6.77 (d, J=8.1 Hz, 1H), 6.87 (dd, J=1.8, 8.1 Hz, 1H), 6.99 (m, 3H), 7.46 (m, 2H). MS (DCI) m/e 494 (M+H$^+$). Anal calcd for C$_{30}$H$_{39}$NO$_5$: C, 72.99; H, 7.96; N, 2.84. Found: C, 72.73; H, 7.89; N, 2.64.

EXAMPLE 387 trans,trans-2-(3-Fluoro-4-methoxyphenyl)-4-(1,3-benzodioxol-5-yl)-1-[2-(N-propyl-N-n-hexanesulfonylamino)ethyl]pyrrolidine-3-carboxylic acid Using the procedures described in Example 66, the title compound was prepared and isolated as a white solid. m.p. 63–65° C. $^1$H NMR (CDCl$_3$, 300 MHz) δ 0.82 (t, J=7 Hz; 3H), 0.88 (t, J=6 Hz, 3H), 1.23–1.47 (m, 6H), 1.44 (sextet, J=7 Hz, 2H), 1.71 (quintet, J=6 Hz, 2H), 2.24–2.34 (m, 1H), 2.70–2.93 (m, 5H), 2.96–3.12 (m, 2H), 3.15–3.35 (m, 2H), 3.43 (dd, J=3 Hz, J=9 Hz, 1H), 3.52–3.59 (m, 1H), 3.66 (d, J=9 Hz, 1H), 3.87 (s, 3H), 5.95 (s, 2H), 6.74 (d, J=8 Hz, 1H), 6.82 (d, J=8 Hz, 1H), 6.42 (t, J=8 Hz, 1H), 6.96(s, 1H), 7.12 (d, J=9 Hz, 1H), 7.17 (d, J=12 Hz, 1H). MS (DCI/NH$_3$) m/e 593 (M+H)$^+$.

EXAMPLE 388 trans,trans-4-(1,3-Benzodioxol-5-yl)-2-(4-methoxyphenyl)-1-((3-pyridyl)methyl)pyrrolidine-3-carboxylic acid Using the procedures described in Example 1, the title compound was prepared. $^1$H NMR (300 MHz, CD$_3$OD) δ 2.87 (m, 2H), 3.04 (dd, J=3.2, 9.7 Hz, 1H), 3.21 (d, J=13.7 Hz, 1H), 3.51 (m, 1H), 3.76–3.85 (m, 2H), 3.79 (s, 3H), 5.90 (m, 2H), 6.71 (m, 1H), 6.79 (dd, J=1.7 Hz, 7.8H), 6.94 (m, 3H), 7.36–7.45 (m, 3H), 7.81 (m, 1H), 8.39 (m, 1H), 8.46 (dd, J=1.4 Hz, 1H). Anal calcd for C$_{25}$H$_{24}$N$_2$O$_5$0.70H$_2$O. 0.05 CH$_3$CO$_2$C$_2$H$_5$: C, 67.34; H, 5.79; N, 6.23. Found: C, 67.31; H, 5.63; N, 5.90.

EXAMPLE 389 trans,trans-2-(n-Hexyl)-4-(1,3-benzodioxol-5-yl)-1-(N,N-di(n-butyl)aminocarbonylmethyl)-Pyrrolidine-3-carboxylic acid Using the procedures described in Example 1, the title compound was prepared. $^1$H NMR (CDCl$_3$, 300 MHz) δ 0.82–1.00 (m, 9H), 1.20–1.40 (m, 12H), 1.45–1.60 (m, 4H), 1.70–1.90 (br m, 2H), 3.10–3.46 (m, 6H), 3.65 (t, J=10.8 Hz, 1H), 3.76 (t, J=11.0 Hz, 1H), 3.92–4.06 (m, 2H), 4.14–4.34 (m, 2H), 5.94 (s, 2H), 6.73 (d, J=8.1 Hz, 1H), 6.79 (dd, J=8.1, 1.8 Hz, 1H), 6.87 (d, J=1.8 Hz, 1H). MS(DCI/NH$_3$) m/e 489 (M+H)$^+$. Anal calcd for C$_{28}$H$_{44}$N$_2$O$_5$.0.9 TFA: C, 60.53; H, 7.65; N, 4.74. Found: C, 60.62; H, 7.69; N, 4.61.

EXAMPLE 390 trans,trans-4-(1,3-Benzodioxol-5-yl)-2-(4-methoxyphenyl)-1-(((N-(2-pentyl)-N-(4-fluoro-3-methylphenyl)amino)carbonyl)methyl)pyrrolidine-3-carboxylic acid Using the procedures described in Example 1, the title compound was prepared. $^1$H NMR (300 MHz, CD$_3$OD) δ 0.92 (m, 3H), 0.97 (t, J=7.1 Hz, 3H), 1.13–1.40 (m, 4H), 2.22 (m, 3H), 2.58–2.74 (m, 1H), 2.78–2.87 (m, 1H), 3.09–3.25 (m, 2H), 3.39–3.60 (m, 2H), 3.70–3.90 (m, 1H), 3.80 (s, 3H), 4.70 (m, 1H), 5.93 (m, 2H), 6.70–6.76 (m, 1H), 6.75 (d, J=1.4, 8.1 Hz, 1H), 6.80–6.94 (m, 4H), 6.96–7.13 (m, 4H). MS (DCI.) m/e 577 (M+H$^+$). Anal calcd for C$_{33}$H$_{37}$FN$_2$O$_6$.0.25H$_2$O: C, 68.20; H, 6.50; N, 4.82. Found: C, 68.21; H, 6.46; N, 4.74.

EXAMPLE 391 trans,trans-4-(1,3-Benzodioxol-5-yl)-2-(4-methoxyphenyl)-1-((2-pyridyl)methyl)pyrrolidine-3-carboxylic acid Using the procedures described in Example 1, the title compound was prepared. $^1$H NMR (300 MHz, CD$_3$OD) δ 2.97 (dd, J=7.9, 9.7 Hz, 1H), 3.04 (t, J=9.6 Hz, 1H), 3.18 (dd, J=4.4 Hz, 9.9H), 3.47 (d, J=14.0 Hz, 1H), 3.59 (m, 1H), 3.78 (s, 3H), 3.96 (d, J=9.9 Hz, 1H), 3.97 (d, J=13.6 Hz, 1H), 5.90 (m, 2H), 6.73 (d, J=8.1 Hz, 1H), 6.83 (dd, J=1.7, 7.9 Hz, 1H), 6.92 (m, 2H), 6.96 (d, J=1.8 Hz, 1H), 7.28 (m, 1H), 7.44 (m, 2H), 7.53 (d, J=8.1 Hz, 1H), 7.80 (dt, J=1.8, 7.7 Hz, 1H), 8.42 (m, 1H). MS (DCI) m/e 433 (M+H$^+$). Anal calcd for C$_{25}$H$_{24}$N$_2$O$_5$.0.35H$_2$O: C, 68.43; H, 5.67; N, 6.38. Found: C, 68.44; H, 5.61; N, 6.24.

EXAMPLE 392 trans,trans-2-(3-Phenylpropyl)-4-(1,3-benzodioxol-5-yl)-1-(N,N-di(n-butyl)aminocarbonylmethyl)-Pyrrolidine-3-carboxylic acid Using the procedures described in Example 1, the title compound was prepared. $^1$H NMR (CDCl$_3$, 300 MHz) δ 0.89–0.97 (m, 6H), 1.22–1.36 (m, 4H), 1.41–1.55 (m, 4H), 1.63–1.95 (m, 4H), 2.62 (dt, J=7.2, 2.1 Hz, 2H), 3.05–3.44 (m, 7H), 3.53–3.60 (m, 2H), 3.65–3.76 (m, 1H), 3.82–3.90 (m, 1H), 3.96–4.10 (m, 1H), 5.92 (s, 2H), 6.71 (d, J=8.1 Hz, 1H), 6.77 (dd, J=8.1, 1.5 Hz, 1H), 6.86(d, J=1.2 Hz, 1H), 7.10–7.28 (m, 5H). MS(DCI/NH$_3$) m/e 523 (M+H)$^+$. Anal calcd for C$_{31}$H$_{42}$N$_2$O$_5$.0.6 TFA: C, 65.43; H, 7.26; N, 4.74. Found: C, 65.28; H, 7.29; N, 4.50.

EXAMPLE 393 trans—trans-2-(4-Methoxy-3-fluorophenyl)-4-(7-methoxy-1,3-benzodioxol-5-yl)-1-(N,N-di(n-butyl)aminocarbonylmethyl)-pyrrolidine-3-carboxylic acid Using the procedures described in Example 1, the title compound was prepared and isolated as a white solid. m.p. 115–117° C. $^1$H NMR (300 MHz, CDCl$_3$) δ 0.82 (t, J=7 Hz, 3H), 0.88 (t, J=7 Hz, 3H), 1.05–1.5 (m, 8H), 2.85 (d, J=13 Hz, 1H), 2.90–3.17 (m, 5H), 3.20–3.35 (m, 1H), 3.35–3.50 (m, 3H), 3.55–3.65 (m, 1H), 3.84 (d, J=10 Hz, 1H), 3.87 (s, 3H), 3.92 (s, 3H), 5.94 (dd, J=4 Hz, 2 Hz, 2H), 6.62 (s, 1H), 6.70 (s, 1H), 6.90 (t, J=8 Hz, 1H), 7.05–7.20 (m, 2H).

EXAMPLE 394 trans—trans-2-(1,4-Benzodioxan-6-yl)-4-(7-methoxy-1,3-benzodioxol-5-yl)-1-(N,N-di(n-butyl)aminocarbonylmethyl)-pyrrolidine-3-carboxylic acid Using the procedures described in Example 1, the title compound was prepared and isolated as a white solid. m.p. 107–110° C. $^1$H NMR (300 MHz, CDCl$_3$) δ 0.82 (t, J=7 Hz, 3H), 0.88 (t, J=7 Hz, 3H), 1.05–1.50 (m, 8H), 2.75 (d, J=13 Hz, 1H), 2.90–3.12 (m, 4H), 3.32–3.60 (m, 5H), 3.69 (d, J=8 Hz, 1H), 3.90 (s, 3H), 4.23 (s, 4H), 5.95 (dd, J=4 Hz, 2 Hz, 2H), 6.62 (s, 1H), 6.70 (s, 1H), 6.78–6.93 (m, 3H).

EXAMPLE 395 trans,trans-4-(1,3-Benzodioxol-5-yl)-2-(4-methoxyphenyl)-1-(3-butyl-2-fluoro-hept-2-en-1-yl)pyrrolidine-3-carboxylic acid Using the procedures described in Example 1, the title compound was prepared. $^1$H NMR (300 MHz, CD$_3$OD) δ 0.84 (t, J=7.0 Hz, 3H), 0.88 (t, J=7.0 Hz, 3H), 1.16–1.37 (m, 8H), 1.83 (t, J=8.5 Hz, 2H), 2.03–2.08 (m, 2H), 2.76–2.92 (m, 2H), 3.02 (t, J=9.3 Hz, 1H), 3.32–3.42 (m, 2H), 3.50 (m, 1H), 3.71 (d, J=9.2 Hz, 1H), 3.78 (s, 3H), 5.91 (m, 2H), 6.72 (d, J=7.8 Hz, 1H), 6.83 (dd, J=1.7, 8.1 Hz, 1H), 6.90 (m, 2H), 7.02 (d, J=1.7 Hz, 1H), 7.34 (m, 2H). MS (DCI) m/e 512 (M+H$^+$). Anal calcd for C$_{30}$H$_{38}$FNO$_5$: C, 70.43; H, 7.49; N, 2.74. Found: C, 70.58; H, 7.54; N, 2.66.

EXAMPLE 396 trans,trans-2-(3-Fluoro-4-ethoxyphenyl)-4-(1,3-benzodioxol-5-yl)-1-[2-(N-propyl-N-n-pentanesulfonylamino)ethyl]pyrrolidine-3-carboxylic acid Using the procedures described in Example 66, the title compound was prepared and isolated as a white solid. m.p. 65–66° C. $^1$H NMR (CDCl$_3$, 300 MHz) δ 0.82 (t, J=7 Hz, 3H), 0.90 (t, J=7 Hz, 3H), 1.26–1.36 (m, 4H), 1.41–1.52 (m, 5H), 1.73 (quintet, J=7 Hz, 2H), 2.23–2.33 (m, 1H), 2.69–2.96 (m, 5H), 2.97–3.12 (m, 2H), 3.16–3.37 (m, 2H), 3.43 (d, J=9 Hz, 1H), 3.52–3.59 (m, 1H), 3.66 (d, J=9 Hz, 1H), 4.08 (q, J=7 Hz, 2H), 5.95 (s, 2H), 6.74 (d, J=8 Hz, 1H), 6.82 (d, J=8 Hz, 1H), 6.92 (t, J=8 Hz, 1H), 6.97 (s, 1H), 7.07 (d, J=8 Hz, 1H), 7.15 (d, J=12 Hz, 1H). MS (DCI/NH$_3$) m/e 593 (M+H)$^+$.

EXAMPLE 397 trans,trans-2-(4-Methoxy-3-fluorophenyl)-4-(7-methoxy-1,3-benzodioxol-5-yl)-1-((N-butyl-N-propylamino)carbonylmethyl)pyrrolidine-3-carboxylic acid Using the procedures described in Example 1, the title compound was prepared and isolated as a white solid. m.p. 118–120° C. $^1$H NMR (300 MHz, CDCl$_3$) δ 0.70–0.90 (4 triplets, J=7 Hz), 1.05–1.55 (m, 8H), 2.80–3.50 (m, 9H), 3.55–3.65 (m, 1H), 3.82 (d, J=10 Hz, 1H), 3.85 (s, 3H), 3.92 (s, 3H), 5.96 (s, 2H), 6.62 (s, 1H), 6.70 (s, 1H), 6.90 (t, J=8 Hz, 1H), 7.08–7.22 (m, 2H).

EXAMPLE 398 trans,trans-4-(1,3-benzodioxol-5-yl)-2-(4-methoxyphenyl)-1-(N-butyl-N-(4-chlorophenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.50 (m, 4H), 2.66–4.00 (m, 9H), 3.81 (s, 3H), 5.95 (s, 2H), 6.77 (d, J=7 Hz, 1H), 6.85 (d, J=8 Hz, 3H), 7.05 (m, 5H), 7.33–7.42 (m, 2H). MS (C.I,) m/e 565 (M+H). Analysis calcd for C$_{31}$H$_{33}$N$_2$O$_6$Cl.0.25H$_3$PO$_4$: C, 63.16; H, 5.77; N, 4.75. Found: C, 63.14; H, 5.59; N, 4.53.

EXAMPLE 399 trans,trans-4-(1,3-Benzodioxol-5-yl)-2-(4-methoxyphenyl)-1-(4-methyl-1,2,3,4-tetrahydroquinolin-1-yl)carbonylmethyl)pyrrolidine-3-carboxylic acid Using the procedures described in Example 1, the title compound was prepared. $^1$H NMR (300 MHz, CD$_3$OD) δ 1.27 (d, J=7 Hz, 1.5H), 1.28 (d, 7H, 1.5-diastereomer), 1.39–1.55 (m, 1H), 2.02–2.15 (m, 1H), 2.60–3.25 (m, 5H), 3.33–4.00 (m, 5H), 3.78 (s, 3H), 5.92 (d, J=3 Hz, 2H), 6.73 (dd, J=8 Hz, 1H), 6.75–6.90 (m, 3H), 6.91–7.35 (m, 7H). MS (DCI) m/e 529 (M+H)$^+$. Analysis calcd for C$_{31}$H$_{32}$N$_2$O$_6$: C, 70.44; H, 6.10; N, 5.30. Found: C, 70.16; H, 6.04; N, 5.04.

EXAMPLE 400 trans,trans-2-(3-Fluoro-4-methoxyphenyl)-4-(1,3-benzodioxol-5-yl)-1-[2-(N-propyl-N-(2-(piperidin-1-yl)ethanesulfonylamino)ethyl]pyrrolidine-3-carboxylic acid Using the procedures described in Example 66, the title compound was prepared and isolated as a white solid. m.p. 95–96° C. $^1$H NMR (CDCl$_3$, 300 MHz) δ 0.82 (t, J=7 Hz, 3H), 1.43–1.55 (m, 4H), 1.63–1.72 (m, 4H), 2.29–2.38 (m, 1H), 2.64–2.78 (m, 5H), 2.87 (t, J=8 Hz, 1H), 2.95–3.04 (m, 5H), 3.20–3.30 (m, 1H), 3.32–3.43 (m, 4H), 3.54–3.63 (m, 1H), 3.78 (d, J=8 Hz, 1H), 3.87 (s, 3H), 5.92 (s, 2H), 6.72 (d, J=8 Hz, 1H), 6.78 (dd, J=2 Hz, J=8 Hz, 1H), 6.88 (t, J=8 Hz, 1H), 6.94 (d, J=2 Hz, 1H), 7.08–7.20 (m, 2H). MS (DCI/NH$_3$) m/e 620 (M+H)$^+$.

EXAMPLE 401 trans,trans-2-(n-Heptyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared. $^1$H NMR (CDCl$_3$, 300 MHz) δ 0.83–0.98 (s, 9H), 1.18–1.40 (m, 14H), 1.44–1.60 (m, 4H), 1.72–1.96 (br m, 2H), 3.12–3.45 (m, 6H), 3.65 (t, J=10.5 Hz, 1H), 3.76 (t, J=11.2 1H), 3.90–4.06 (m, 2H), 4.13–4.33 (m, 2H), 5.93 (s, 2H), 6.73 (d, J=7.8 Hz, 1H), 6.79 (dd, J=7.8, 1.7 Hz, 1H), 6.87 (d, J=1.7 Hz, 1H). MS(DCI/NH$_3$) m/e 503 (M+H)$^+$. Anal calcd for C$_{29}$H$_{46}$N$_2$O$_5$.0.75 TFA: C, 62.28; H, 8.01; N, 4.76. Found: C, 62.20; H, 7.99; N, 4.50.

EXAMPLE 402 trans,trans-4-(1,3-Benzodioxol-5-yl)-2-(4-methoxyphenyl)-1-(3-methyl-1,2,3,4-tetrahydroquinolin-1-yl)carbonylmethyl)pyrrolidine-3-carboxylic acid Using the procedures described in Example 1, the title compound was prepared. $^1$H NMR (300 MHz, CD$_3$OD) δ 0.99 (d, 1.5H), 1.03 (d, J=6 Hz, 1.5H, second diastereomer), 2.60–4.00 m (12), 3.78 (s, 1.5H), 3.79 (s, 1.5H, second diastereomer), 5.92 (s, 1H), 5.93 (s, 1H, diastereomer), 6.65–7.40 (m, 11H). MS (DCI) m/e 529 (M+H)$^+$. Analysis calcd for C$_{31}$H$_{32}$N$_2$O$_6$.0.8H$_2$O: C, 68.57; H, 6.24; N, 5.16. Found: C, 70.44; H, 6.10; N, 5.30.

EXAMPLE 403 trans,trans-4-(1,3-Benzodioxol-5-yl)-2-(4-methoxyphenyl)-1-((N-butyl-N-(4-fluorophenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.2–1.47 (m, 4H), 2.7 (d, J=12 Hz, 1H), 2.80 (t, J=9 Hz, 1H), 3.09 (t, J=9 Hz, 1H), 3.25 (d, J=15 Hz, 1H), 3.40–3.47 (m, 1H), 3.49–3.65 (m, 3H), 3.75 (d, J=12 Hz, 1H), 3.80 (s, 3H), 5.94 (s, 2H), 6.72–6.86 (m, 4H), 7.00–7.15 (m, 7H). MS (DCI) m/e 549 (M+H)$^+$. Analysis calcd for C$_{31}$H$_{33}$N$_2$O$_6$F.0.4H$_2$O: C, 66.99; H, 6.13; N, 5.04. Found: C, 66.99; H, 5.94; N, 4.99.

EXAMPLE 404 trans,trans-1-(N-Butyl-N-(3-methylphenyl)aminocarbonylmethyl)-2-(4-methoxyphenyl)-4-(5-benzofuranyl)pyrrolidine-3-carboxylic acid Using the procedures described in Example 1, the title compound was prepared. $^1$H NMR (300 MHz, CDCl$_3$) δ 7.66 (1H, bs), 7.60 (1H, d, J=3 Hz), 7.45 (2H, s), 7.15 (4H, m), 6.75 (5H, m), 3.96 (1H, d, J=10 Hz), 3.78 (3H, s), 3.74 (1H, m), 3.59 (3H, m), 3.21 (1H, t, J=9 Hz), 3.19 (1H, d, J=16 Hz), 2.92 (1H, t, J=9 Hz), 2.70 (1H, d, J=16 Hz), 2.29 (3H, s), 1.41 (2H, m), 1.24 (2H, m), 0.85 (3H, t, J=7 Hz). MS (DCI, NH$_3$) m/e 541 (M+H)$^+$. Anal. calcd for C$_{33}$H$_{34}$N$_2$O.1H$_2$O: C, 71.21; H, 6.52; N, 5.03. Found: C, 71.31; H, 6.30; N, 4.98.

EXAMPLE 405 trans,trans-1-(N-Butyl-N-(3-methylphenyl)aminocarbonylmethyl)-2-(4-fluorophenyl)-4-(5-benzofuranyl)pyrrolidine-3-carboxylic acid Using the procedures described in Example 1, the title compound was prepared. $^1$H NMR (300 MHz, CDCl$_3$) δ 7.67 (1H, bs), 7.60 (1H, d, J=3 Hz), 7.45 (2H, m), 7.18 (3H, m), 7.12 (1H, d, J=7 Hz), 6.93 (2H, m), 6.76 (1H, d, J=3 Hz), 6.70(2H, bd), 4.02(1H, m), 3.77(1H, m), 3.59(3H, m), 3.29(1H, m), 3.19(1H, m), 2.94 (1H, m), 2.71 (1H, m), 2.30 (3H, s), 1.45 (2H, m), 1.26 (2H, sext, J=7 Hz), 0.84 (3H, t, J=7 Hz). MS (DCI, NH$_3$) m/e 529 (M+H)$^+$. Anal. calcd for C$_{33}$H$_{34}$N$_2$O$_5$.0.2 HOAc: C, 71.98: H, 6.30; N, 5.18. Found: C, 71.68; H, 5.89; N, 5.25.

EXAMPLE 406 trans,trans-4-(1,3-Benzodioxol-5-yl)-2-(4-methoxyphenyl)-1-((N,N-di-(3-methylphenyl)amino)carbonyl)methyl)pyrrolidine-3-carboxylic acid Using the procedures described in Example 1, the title compound was prepared. $^1$H NMR (300 MHz, CD$_3$OD) δ 2.27 (s, 6H), 2.81 (dd, J=8.1, 9.5 Hz, 1H), 2.98 (d, J=15.3 Hz, 1H), 3.20 (t, J=16.6 Hz, 1H), 3.47–3.60 (m, 3H), 3.80 (s, 3H), 3.85 (d, J=9.5 Hz, 1H), 5.91 (s, 2H), 6.73 (d, J=7.8 Hz, 1H), 6.85 (m, 3H), 6.95 (m, 4H), 7.05 (d, J=1.7 Hz, 1H), 7.06–7.24 (m, 6H). MS (DCI) m/e 579 (M+H)$^+$. Anal calcd for C$_{35}$H$_{34}$N$_2$O$_6$.0.15H$_2$O.0.20 CH$_3$CO$_2$C$_2$H$_5$: C, 71.79; H, 6.04; N, 4.68. Found: C, 71.81; H, 5.79; N, 4.51.

EXAMPLE 407 trans,trans-4-(1,2-Dihydrobenzofuran-5-yl)-2-(4-methoxyphenyl)-1-(((N-butyl-N-(3-methylphenyl)amino)carbonyl)methyl)pyrrolidine-3-carboxylic acid Using the procedures described in Example 1, the title compound was prepared. $^1$H (300 MHz, CDCl$_3$) δ 7.73 (2H, m), 7.40–7.10 (4H, m), 6.92 (2H, m), 6.72 (2H, d, J=9), 6.63 (1H, m), 5.40 (1H, m), 4.55 (2H, t, J=9), 4.30–4.10 (3H, m), 3.84 (3H, s), 3.82 (1H, m), 3.65 (1H, m), 3.39 (1H, m), 3.21 (2H, t, J=9), 3.10–2.90 (2H, m), 2.26 (3H, s), 1.55 (2H, m), 1.45 (2H, m), 0.92 (3H, t, J=9). MS (DCI/NH$_3$) m/e 543 (M+H)$^+$). Anal calcd for C$_{33}$H$_{38}$N$_2$O$_5$.0.65H$_2$O: C, 71.50; H, 7.15; N, 5.05. Found: C, 71.47; H, 6.96; N, 4.83.

EXAMPLE 408 trans,trans-2-(3-Fluoro-4-methoxyphenyl)-4-(1,3-benzodioxol-5-yl)-1-{2-(N-propyl-N-[2-(N,N-dimethylamino)]ethanesulfonylamino)ethyl}pyrrolidine-3-carboxylic acid Using the procedures described in Example 66, the title compound was prepared and isolated as a white solid. m.p. 81–82° C. $^1$H NMR (CDCl$_3$, 300 MHz) δ 0.80 (t, J=7 Hz, 3H), 1.43 (sextet, J=7 Hz, 2H), 2.15–2.24 (m, 1H), 2.36 (s, 6H), 2.66–2.76 (m, 1H), 2.83–3.04 (m, 6H), 3.18–3.41 (m, 5H), 3.55–3.63 (m, 1H), 3.72 (d, J=8 Hz, 1H), 3.85 (s, 3H), 5.90 (d, J=6 Hz, 2H), 6.67 (d, J=8 Hz, 1H), 6.78 (dd, J=2 Hz, J=8 Hz, 1H), 6.84 (t, J=8 Hz, 1H), 7.94 (d, J=2 Hz, 1H), 7.09 (d, J=8 Hz, 1H), 7.20 (dd, J=2 Hz, J=12 Hz, 1H). MS (DCI/NH$_3$) m/e 580 (M+H)$^+$.

EXAMPLE 409 trans,trans-1-(N,N-Dibutylaminocarbonylmethyl)-2-(4-fluorophenyl)-4-(5-benzofuranyl)pyrrolidine-3-carboxylic acid Using the procedures described in Example 1, the title compound was prepared. $^1$H NMR (300 MHz, CDCl$_3$) δ 7.88 (1H, bs), 7.80 (2H, m), 7.61 (1H, d, J=3 Hz), 7.55 (1H, bd, J=8 Hz), 7.46 (1H, d, J=8 Hz), 7.07 (2H, t, J=8 Hz), 6.76 (1H, d, J=3 Hz), 5.53 (1H, bd, J=1 Hz), 4.18 (2H, m), 3.91 (3H, m), 3.55 (1H, d, J=16 Hz), 3.30 (3H, m), 3.12 (1H, dd, J=10&9 Hz), 2.95 (1H, m), 1.51 (2H, m), 1.31 (4H, m), 1.12 (2H, m), 0.92 (3H, m), 0.83 (3H, t, J=7 Hz). MS m/e (DCI, NH$_3$) 595 (M+H$^+$).

EXAMPLE 410 trans,trans-4-(1,2-Dihydrobenzofuran-5-yl)-2-(4-ethylphenyl)-1-(((N-butyl-N-(3-methylphenyl)amino)carbonyl)methyl)pyrrolidine-3-carboxylic acid Using the procedures described in Example 1, the title compound was prepared. $^1$H NMR (300 MHz, CDCl$_3$) δ 7.35 (2H, m), 7.20–7.00 (7H, m), 6.70 (2H, d, J=9), 5.38 (1H, m), 4.55 (2H, t, J=9), 4.05 (1H, m), 3.64 (2H, m), 3.45 (1H, m), 3.21 (2H, t, J=9), 2.95 (1H, m), 2.75 (1H, m), 2.63 (2H, q, J=8), 2.38 (2H, m), 2.27 (3H, s), 1.43 (2H, m), 1.30 (2H, m), 1.22 (3H, t, J=9), 0.89 (3H, t, J=9). MS (DCI/NH$_3$) m/e 541 (M+H$^+$). Anal calcd for C$_{34}$H$_{40}$N$_2$O$_4$.1.6 AcOH: C, 70.17; H, 7.34; N, 4.40. Found: C, 70.11; H, 7.06; N, 4.80.

EXAMPLE 411 trans,trans-4-(1,2-Dihydrobenzofuran-5-yl)-2-(4-fluorophenyl)-1-(N,N-di(n-butyl)aminocarbonylmethyl)-pyrrolidine-3-carboxylic acid Using the procedures described in Example 1, the title compound was prepared. $^1$H NMR (300 MHz, CDCl$_3$) δ 7.40 (2H, m), 7.28 (1H, bs), 7.18 (1H, dd, J=8, 3), 7.00 (2H, t, J=9), 6.72 (1H, d, J=9), 4.53 (2H, t, J=9), 3.92 (1H, m), 3.65 (1H, m), 3.42 (3H, m), 3.19 (2H, t, J=9), 3.15–2.90 (6H, m), 1.43 (3H, m), 1.25 (3H, m), 1.10 (2H, m), 0.90 (3H, t, J=8), 0.83 (3H, t, J=8). MS (DCI/NH$_3$) m/e 497 (M+H$^+$). Anal calcd for C$_{29}$H$_{37}$FN$_2$O$_4$.0.25H$_2$O: C, 69.51; H, 7.54; N, 5.59. Found: C, 69.45; H, 7.60; N, 5.44.

EXAMPLE 412 trans,trans-4-(1,2-Dihydrobenzofuran-5-yl)-2-(4-fluorophenyl)-1-(((N-butyl-N-(3-methylphenyl)amino)carbonyl)methyl)pyrrolidine-3-carboxylic acid Using the procedures described in Example 1, the title compound was prepared. $^1$H NMR (300 MHz, CDCl$_3$) δ 7.28 (1H, bs), 7.25–7.00 (5H, m), 6.91 (2H, m), 6.72 (3H, d, J=9), 4.54 (2H, t, J=9), 4.00 (1H, m), 3.60 (3H, m), 3.45 (1H, m), 3.19 (2H, t, J=9), 3.11 (2H, m), 2.84 (1H, m), 2.67 (1H, bd, J=18), 2.26 (3H,s), 1.42 (2H, m), 1.25 (2H, m), 0.88 (3H, t, J=8). MS (DCI/NH$_3$) m/e 531 (M+H$^+$). Anal calcd for C$_{32}$H$_{35}$FN$_2$O$_4$.0.25H$_2$O: C, 71.82; H, 6.69; N, 5.23. Found: C, 71.66; H, 6.55; N, 5.03.

EXAMPLE 413 trans,trans-4-(Indan-5-yl)-2-(4-methoxyphenyl)-1-(N,N-di(n-butyl)aminocarbonylmethyl)-pyrrolidine-3-carboxylic acid Using the procedures described in Example 1, the title compound was prepared. $^1$H NMR (300 MHz, CDCl$_3$) δ 7.32 (3H, m), 7.18 (2H, m), 6.85 (2H, d, J=9), 3.83 (1H, m), 3.79 (3H, s), 3.67 (1H, m), 3.50–3.20 (4H, m), 3.20–2.92 (4H, m), 2.87 (5H, m), 2.79 (1H, bd, J=15), 2.06 (2H, m), 1.43 (2H, m), 1.27 (4H, m), 1.08 (2H, m), 0.88 (3H, t, J=8), 0.82 (3H, t, J=8). MS (DCI/NH$_3$) m/e 507 (M+H$^+$). Anal calcd for C$_{31}$H$_{42}$N$_2$O$_4$: C, 73.49; H, 8.36; N, 5.53. Found: C, 73.18; H, 8.29; N, 5.17.

EXAMPLE 414 trans,trans-2-(4-Methoxyphenyl)-4-(3,4-difluorophenyl)-1-((N-butyl-N-(3-methylphenyl)amino)carbonylmethyl)pyrrolidine-3-carboxylic acid Using the procedures described in Example 1, the title compound was prepared. $^1$H NMR (300 MHz, CDCl$_3$) δ 0.86 (t, J=7 Hz, 3H), 1.10–1.35 (m, 2H), 1.35–1.52 (m, 2H), 2.29 (s, 3H), 2.63 (d, J=13 Hz, 1H), 2.76 (t, J=7 Hz, 1H), 3.06–3.20 (m, 2H), 3.42–3.53 (m, 1H), 3.50–3.64 (m, 3H), 3.80 (s, 3H), 3.86 (d, J=9 Hz, 1H), 6.66–6.82 (m, 4H), 7.02–7.22 (m, 6H), 7.30–7.40 (m, 1H).

EXAMPLE 415 trans,trans-1-(N-Butyl-N-(3-chlorophenyl)aminocarbonylmethyl)-2-(4-fluorophenyl)-4-(5-benzofuranyl)pyrrolidine-3-carboxylic acid Using the procedures described in Example 1, the title compound was prepared. $^1$H NMR (300 MHz, CDCl$_3$) δ 7.64 (1H, d, J=2 Hz), 7.61 (1H, d, J=3 Hz), 7.47 (1H, d, J=8 Hz), 7.41 (1H, dd, J=8&3 Hz), 7.30 (1H, dt, J=8&2 Hz), 7.21 (1H, d, J=8 Hz), 7.19 (2H, m), 7.00 (1H, bs), 6.94 (2H, t, J=8 Hz), 6.83 (1H, bd, J=8 Hz), 6.74 (1H, dd, J=2&1 Hz), 3.96 (1H, d, J=10 Hz), 3.75 (1H, ddd, 6, 5&3 Hz), 3.59 (3H, m), 3.23 (1H, t, J=10 Hz), 3.18 (1H, d, J=16 Hz), 2.92 (1H, dd, J=10&9 Hz), 2.69 (1H, d, J=16 Hz), 1.41 (2H, m), 1.23 (2H, m), 0.87 (3H, t, J=7 Hz). MS (DCI, NH$_3$) 549, 551 (M+H$^+$). Anal. calcd for C$_{31}$H$_{30}$ClFN$_2$O: C, 67.82; H, 5.51; N, 5.10. Found: C, 67.43; H, 5.33; N, 4.78.

EXAMPLE 416 trans,trans-4-(1,3-Benzodioxol-5-yl)-2-(4-methoxyphenyl)-1-(((N-propyl-N-(4-phenoxybenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 7.40–7.20 (5H, m), 7.13 (2H, m), 6.98 (2H, m), 6.93–6.60 (7H, m), 5.93 (1H, d, J=2), 5.88 (5.85) (1H, d, J=2), 4.90 (4.50) (1H, d, J=15), 4.10 (4.25) (1H, d, J=15), 3.77 (3.73) (3H, s), 3.72 (1H, m), 3.60 (1H, m), 3.53–3.20 (3H, m), 3.15–2.75 (4H, m), 1.60–1.20 (2H, m), 0.83 (0.64) (3H, t, J=8). MS (DCI/NH$_3$) m/e 623 (M+H$^+$). Anal calcd for C$_{37}$H$_{38}$N$_2$O$_7$.0.25H$_2$O: C, 70.85; H, 6.19; N, 4.47. Found: C, 70.68; H, 6.10; N, 4.42.

EXAMPLE 417 trans,trans-4-(1,2-Dihydrobenzofuran-5-yl)-2-(4-ethylphenyl)-1-(((N-(2-pentyl)-N-(4-fluoro-3-methylphenyl)amino)carbonyl)methyl)pyrrolidine-3-carboxylic acid Using the procedures described in Example 1, the title compound was prepared. $^1$H NMR (300 MHz, CDCl$_3$) δ 7.30 (1H, bs), 7.20–7.00 (5H, m), 6.87 (1H, m), 6.73 (2H, d, J=9), 6.57 (1H, m), 4.81 (1H, m), 4.55 (2H, t, J=9), 3.92 (1H, bd, J=11), 3.60 (1H, m), 3.43 (1H, m), 3.18 (2H, t, J=9), 3.17 (1H, m), 3.06 (1H, dd, J=15, 6), 2.88 (1H, dd, J=11, 9), 2.61 (2H, q, J=8), 2.59 (1H, m), 2.18 (3H, m), 1.40–1.10 (4H,m), 1.22 (3H, t, J=9), 1.00–0.80 (6H, m). MS (DCI/NH$_3$) m/e 573 (M+H$^+$). Anal calcd for C$_{35}$H$_{41}$FN$_2$O$_4$.0.75H$_2$O: C, 71.71; H, 7.31; N, 4.78. Found: C, 71.56; H, 7.33; N, 4.56.

EXAMPLE 418 trans,trans-2-(4-Methoxphenyl)-4-(1,3-benzodioxol-5-yl)-1-[2-(N-propyl-N-[2-pyrimidinyl]amino)ethyl]pyrrolidine-3-carboxylic acid Ethyl 2-(4-methoxyphenyl)-4-(1,3-benzodioxol-5-yl)-1-[2-(N-propylamino)propyl]pyrrolidine-3-carboxylate, prepared by the procedures of Example 61B (300 mg), 138 mg of 2-bromopyrimidine, and 150 mg of diisopropylethylamine were heated at 95° C. for 15 hours in 2 mL of acetonitrile. The resulting intermediate trans—trans ethyl ester was isolated by chromatography on silica gel eluting with 5–10% ETOAc in $CH_2Cl_2$ and hydrolyzed with NaOH in ethanol/water to give 95 mg of the title compound. $^1H$ NMR (300 MHz, $CDCl_3$) δ 0.82 (t, J=7 Hz, 3H), 1.50 (sextet, J=7 Hz, 2H), 2.15–2.30 (m, 1H), 2.75–2.97 (m, 3H), 3.40–3.55 (m,4H), 3.60–3.70 (m, 3H), 3.75 (s, 3H), 5.95 (s, 2H), 6.34 (t, J=4 Hz, 1H), 6.65 (d, J=8 Hz, 1H), 6.75–6.82 (m, 1H), 6.78 (d, J=9 Hz, 2H), 6.96 (d, J=2 Hz, 1H), 7.27 (d, J=9 Hz, 2H), 8.20 (d, J=4 Hz, 2H).

EXAMPLE 419 trans,trans-4-(1,3-Benzodioxol-5-yl)-2-(4-methoxyphenyl)-1-(3-butyl-2-chloro-hept-2-en-1-yl)pyrrolidine-3-carboxylic acid Using the procedures described in Example 1, the title compound was prepared. $^1H$ NMR (300 MHz, $CD_3OD$) δ 0.84 (t, J=6.8 Hz, 3H), 0.88 (t, J=6.7 Hz, 3H), 1.19–1.39 (m, 8H), 2.05–2.09 (m, 2H), 2.17–2.23 (m, 2H), 2.78 (dd, J=6.6, 9.2 Hz, 1H), 2.95 (t, J=9.2 Hz, 1H), 3.32–3.37 (m, 2H), 3.49 (m, 1H), 3.70 (d, J=9.2 Hz, 1H), 3.77 (s, 3H), 5.91 (m, 2H), 6.72 (d, J=8.1 Hz, 1H), 6.85 (dd, J=1.9, 8.1 Hz, 1H), 6.89 (m, 2H), 7.08 (d, J=1.5 Hz, 1H), 7.36 (m, 2H). MS (DCI) m/e 528 (M+H$^+$). Anal calcd for $C_{30}H_{38}ClNO_5.0.25H_2O$: C, 67.66; H, 7.29; N, 2.63. Found: C, 67.62; H, 7.18; N, 2.40.

EXAMPLE 420 trans,trans-4-(1,2-Dihydrobenzofuran-5-yl)-2-(4-methoxyphenyl)-1-(((N-(2-pentyl)-N-(4-fluoro-3-methylphenyl)amino)carbonyl)methyl)pyrrolidine-3-carboxylic acid Using the procedures described in Example 1, the title compound was prepared. $^1H$ NMR (300 MHz, $CDCl_3$) δ 7.28 (1H, bs), 7.15 (3H, m), 6.90 (1H, m), 6.77 (2H, dd, J=9, 3), 6.71 (2H, d, J=9), 6.56 (1H, m), 4.80 (1H, m), 4.53 (2H, t, J=9), 3.92 (1H, m), 3.79 (3H, s), 3.60 (1H, m), 3.45 (1H, m), 3.19 (2H, t, J=9), 3.18 (1H, m), 3.03 (1H, dd, J=15, 6), 2.85 (1H, m), 2.55 (1H, m), 2.18 (3H, m), 1.40–1.05 (4H, m), 1.00–0.80 (6H, m). MS (DCI/$NH_3$) m/e 575 (M+H$^+$). Anal calcd for $C_{34}H_{39}FN_2O_5.0.35H_2O$: C, 70.29; H, 6.89; N, 4.82. Found: C, 70.37; H, 6.92; N, 4.30.

EXAMPLE 421 trans,trans-4-(1,2-Dihydrobenzofuran-5-yl)-2-(4-methoxyphenyl)-1-(((N-butyl-N-(3-chlorophenyl)amino)carbonyl)methyl)pyrrolidine-3-carboxylic acid Using the procedures described in Example 1, the title compound was prepared. $^1H$ NMR (300 MHz, $CDCl_3$) δ 7.29 (1H, d, J=3), 7.25–7.05 (5H, m), 6.98 (1H, bs), 6.80 (2H, m), 6.72 (2H, d, J=9), 4.53 (2H, t, J=9), 3.85 (1H, d, J=10), 3.79 (3H, s), 3.58 (3H, m), 3.42 (1H, dd, J=10, 6), 3.18 (4H, m), 2.87 (1H, m), 2.66 (1H, m), 1.40 (2H, m), 1.25 (2H, m), 0.86 (3H, t, J=9). MS (DCI/$NH_3$) m/e 563 (M+H$^+$). Anal calcd for $C_{32}H_{35}ClN_2O_5.0.25H_2O$: C, 67.72; H, 6.30; N, 4.94. Found: C, 67.72; H, 6.21; N, 4.55.

EXAMPLE 422 trans,trans-4-(1,3-Benzodioxol-5-yl)-2-(5-ethylfuran-2-yl)-1-(N,N-di(n-butyl)aminocarbonylmethyl)-pyrrolidine-3-carboxylic acid Using the procedures described in Example 1, the title compound was prepared. $^1H$ NMR (300 MHz, $CDCl_3$) δ 7.77 (1H, bs), 7.11 (1H, d, J=3), 7.02 (1H, dd, J=9, 3), 6.82 (1H, d, J=9), 6.52 (1H, d, J=4), 6.08 (1H, d, J=4), 5.98 (2H, s), 5.80 (1H, d, J=6), 4.70 (1H, bd, J=15), 4.37 (2H, m), 3.70 (2H, m), 3.39 (2H, m), 3.20 (1H, m), 3.10–2.82 (2H, m), 2.76 (2H, q, J=8), 1.45 (2H, m), 1.32 (3H, t, J=9), 1.30–1.10 (6H, m), 0.87 (3H, t, J=9), 0.85 (3H, t, J=9). MS (DCI/$NH_3$) m/e 499 (M+H$^+$). Anal calcd for $C_{28}H_{38}N_2O_6.1.75$ HCl: C, 59.80; H, 7.12; N, 4.98. Found: C, 59.51; H, 6.96; N, 4.88.

EXAMPLE 423 trans,trans-4-(1,2-Dihydrobenzofuran-5-yl)-2-(4-fluorophenyl)-1-(((N-(2-pentyl)-N-(4-fluoro-3-methylphenyl)amino)carbonyl)methyl)pyrrolidine-3-carboxylic acid Using the procedures described in Example 1, the title compound was prepared. $^1H$ NMR (300 MHz, $CDCl_3$) δ 7.30–7.10 (4H, m), 6.92 (3H, m), 6.73 (2H, d, J=9), 6.59 (1H, m), 4.80 (1H, m), 4.53 (2H, t, J=9), 4.00 (1H, bd, J=10), 3.62 (1H, m), 3.45 (1H, m), 3.22 (1H, m), 3.21 (2H, t, J=9), 3.02 (1H, dd, J=15, 6), 3.85 (1H, t, J=10), 2.58 (1H, bd, J=18), 2.20 (3H, bs), 1.40–1.30 (3H, m), 1.15 (1H, m), 1.00–0.80 (6H, m). MS (DCI/$NH_3$) m/e 563 (M+H$^+$). Anal calcd for $C_{33}H_{36}F_2N_2O_4$: C, 70.44; H, 6.45; N, 4.98. Found: C, 70.06; H, 6.47; N, 4.71.

EXAMPLE 424 trans,trans-4-(1,2-Dihydrobenzofuran-5-yl)-2-(4-fluorophenyl)-1-(((N-butyl-N-(3-chlorophenyl)amino)carbonyl)methyl)pyrrolidine-3-carboxylic acid Using the procedures described in Example 1, the title compound was prepared. $^1H$ NMR (300 MHz, $CDCl_3$) δ 7.30 (2H, m), 7.25–7.10 (4H, m), 6.95 (3H, m), 6.82 (1H, bd, J=9), 6.73 (1H, d, J=9), 4.55 (2H, t, J=9), 3.92 (1H, bd, J=11), 3.60(3H, m), 3.43(1H, dd, J=9, 6), 3.21 (2H, t, J=9), 3.16(2H, m), 2.87(1H, m), 2.69 (1H, m), 1.42 (2H, m), 1.26 (2H, m), 0.87 (3H, t, J=9). MS (DCI/$NH_3$) m/e 551 (M+H$^+$). Anal calcd for $C_{31}H_{32}ClFN_2O_4.0.25H_2O$: C, 67.02; H, 5.90; N, 5.04. Found: C, 66.98; H, 5.71; N, 4.76.

EXAMPLE 425 trans,trans-4-(1,2-Dihydrobenzofuran-5-yl)-2-(4-ethylphenyl)-1-(((N-butyl-N-(3-chlorophenyl)amino)carbonyl)methyl)pyrrolidine-3-carboxylic acid Using the procedures described in Example 1, the title compound was prepared. $^1H$ NMR (300 MHz, $CDCl_3$) δ 7.30 (1H, m), 7.21 (1H, d, J=9), 7.15 (2H, m), 7.09 (4H, bs), 6.96 (1H, bs), 6.80 (1H, bd, J=9), 6.73 (1H, d, J=9), 4.54 (2H, t, J=9), 3.89 (1H, bd, J=11), 3.60 (3H, m), 3.43 (1H, m), 3.22 (2H, t, J=9), 3.18 (2H, m), 2.92 (1H, m), 2.72 (1H, m), 2.62 (2H, q, J=8), 1.41 (2H, m), 1.26 (2H, m), 1.23 (3H, t, J=9), 0.87 (3H, t, J=9). MS (DCI/$NH_3$) m/e 561 (M+H$^+$).

Anal calcd for $C_{33}H_{37}ClN_2O_4 \cdot 0.25H_2O$: C, 70.08; H, 6.68; N, 4.95. Found: C, 70.13; H, 6.59; N, 4.65.

EXAMPLE 426 trans,trans-1-(N-Butyl-N-(3-chlorophenyl)carboxamidomethyl)-2-(4-methoxyphenyl)-4-(5-benzofuranyl)pyrrolidine-3-carboxylic acid Using the procedures described in Example 1, the title compound was prepared. $^1$H NMR (300 MHz, CDCl$_3$) δ 7.67 (1H, bs), 7.60 (1H, d, J=3 Hz), 7.48 (1H, d, J=8 Hz), 7.42 (1H, dd, J=8&3 Hz), 7.29 (1H, dt, J=8&3 Hz), 7.21 (1H, d, J=8 Hz), 7.14 (2H, m), 6.99 (1H, bs), 6.76 (4H, m), 3.88 (1H, d, J=10 Hz), 3.75 (1H, ddd, J=6, 5&3 Hz), 3.59 (2H, m), 3.53 (1H, dd, J=10&3 Hz), 3.22 (1H, t, J=9 Hz), 3.19 (1H, m), 2.96(1H, m), 2.70 (1H, d, J=16 Hz), 1.42 (2H, m), 1.26 (2H, m), 0.87 (3H, t, J=7 Hz). MS (DCI, NH$_3$) m/e 563, 561 (M+H$^+$). Anal. calcd for $C_{32}H_{33}ClN_2O_5 \cdot 0.5H_2O$: C, 67.42; H, 6.01; N, 4.91. Found: C, 67.45; H, 5.82; N, 4.68.

EXAMPLE 427 trans,trans-4-(1,3-Benzodioxol-5-yl)-2-(4-methoxyphenyl)-1-(((N-cyclohexyl-N-butylamino)carbonyl)methyl)pyrrolidine-3-carboxylic acid Using the procedures described in Example 1, the title compound was prepared. $^1$H NMR (300 MHz, CDCl$_3$) (rotamer) δ 0.78 (0.86) (t, 3H, J=7 Hz), 0.90–1.90 (envelope, 14H), 2.69 (2.80) (d, 1H, J=12 Hz), 2.9–3.8 (envelope, 10H), 3.78 (3.80) (s, 3H), 5.92 (s, 2H), 6.72 (d, 1H, J=9 Hz) 6.86 (m, 3H) 7.03 (d, 1H, J=6 Hz), 7.34 (m, 2H). MS (DCI/NH$_3$) m/e 537 (M+H$^+$). Anal. calc'd for $C_{31}H_{40}N_2O_6 \cdot 1H_2O$: C, 67.13; H, 7.63; N, 5.05. Found: C, 67.09; H, 7.34; N, 4.92.

EXAMPLE 428 trans,trans-4-(1,3-Benzodioxol-5-yl)-2-(4-ethylphenyl)-1-(((N-(3-methylphenyl)-N-butylamino)carbonyl)methyl)pyrrolidine-3-carboxylic acid Using the procedures described in Example 1, the title compound was prepared. $^1$H NMR (300 MHz, CDCl$_3$) δ 0.86 (t, 3H, J=7 Hz), 1.22 (t, 3H, J=7 Hz), 1.25 (m, 2H), 1.43 (m, 2H), 2.26 (s, 3H), 2.6 (q, 2H, J=7 Hz), 2.68 (d, 1H, J=12 Hz), 2.86 (t, 1H, J=8 Hz), 3.19 (q, 2H, J=7 Hz), 3.44 (dd, 1H, J=3 Hz, 10 Hz), 3.59 (m, 3H), 3.94 (d, 1H, 9 Hz), 5.92 (s, 2H), 6.75 (m, 3H), 6.86 (dd, 1H, J=2 Hz, 8 Hz), 7.08 (m, 6H), 7.17 (t, 1H, J=8 Hz). MS (DCI/NH$_3$) m/e 543 (M+H$^+$). Anal. calc'd for $C_{33}H_{38}N_2O_5 \cdot 0.60H_2O$: C, 71.61; H, 7.14; N, 5.06. Found: C, 71.57; H, 6.80; N, 4.87.

EXAMPLE 429 trans,trans-4-(Benzofuran-5-yl)-2-(4-ethylphenyl)-1-(((N-(3-methylphenyl)-N-butylamino)carbonyl)methyl)pyrrolidine-3-carboxylic acid Using the procedures described in Example 1, the title compound was prepared. $^1$H NMR (300 MHz, CDCl$_3$) δ 0.90 (t, 3H, J=7 Hz), 1.30 (t, 3H, J=7 Hz), 1.31 (m, 2H), 1.43 (m, 2H), 2.27 (s, 3H), 2.73 (q, 2H, J=7 Hz), 3.15 (d, 2H, J=17 Hz), 3.61 (t, 2H, J=8 Hz), 3.82 (m, 2H), 4.00 (t, 1H, 12 Hz), 4.26 (m, 2H), 5.53 (br d, 1H), 6.54 (br s, 2H), 6.76 (d, 1H, J=2 Hz), 7.14 (m, 3H), 7.28 (s, 1H), 7.40 (m, 3H), 7.48 (d, 1H, J=8 Hz), 7.63 (d, 1H, J=2 Hz), 7.73 (s, 1H). HRMS. calc'd for $C_{34}H_{39}N_2O_4$ (M+H)$^+$: 539.2910. Found: 539.2891

EXAMPLE 430 trans,trans-4-(1,4-Benzodioxan-6-yl)-2-(4-ethylphenyl)-1-(((N-(3-methylphenyl)-N-butylamino)carbonyl)methyl)pyrrolidine-3-carboxylic acid Using the procedures described in Example 1, the title compound was prepared. $^1$H NMR (300 MHz, CDCl$_3$) δ 0.87 (t, 3H, J=7 Hz), 1.22 (t, 3H, J=7 Hz), 1.24 (m, 2H), 1.42 (m, 2H), 2.30 (s, 3H), 2.61 (q, 2H, J=7 Hz), 2.67 (d, 1H, J=14 Hz), 2.86 (t, 1H, J=8 Hz), 3.18 (q, 2H, J=7 Hz), 3.41 (dd, 1H, J=4, 10 Hz), 3.59 (m, 3H), 3.93 (d, 1H, J=10 Hz), 4.25 (m, 4H), 6.74 (br s, 2H), 6.80 (d, 1H, J=8 Hz), 6.93 (dd, 1H, J=2 Hz,8 Hz), 6.99 (d, 1H, J=2 Hz), 7.07 (m, 5H), 7.17 (t, 1H, J=8 Hz). MS (DCI/NH$_3$) m/e 557 (M+H)$^+$. Anal. calc'd for $C_{34}H_{40}N_2O_5 \cdot 0.40H_2O$: C, 72.42; H, 7.29: N, 4.97. Found: C, 72.49; H, 7.16; N, 4.62.

EXAMPLE 431 trans,trans-2-(3-Fluoro-4-methoxyphenyl)-4-(1,3-benzodioxol-5-yl)-1-[2-(N-propyl-N-2-mesitylenesulfonylamino)ethyl]pyrrolidine-3-carboxylic acid Using the procedures described in Example 66, the title compound was prepared and isolated as a white solid. m.p. 80–82° C. $^1$H NMR (CDCl$_3$, 300 MHz) δ 0.69 (t, J=7 Hz, 3H), 1.37 (sextet, J=7 Hz, 2H), 2.09–2.17 (m, 1H), 2.24 (s, 3H), 2.53 (s, 6H), 2.54–2.64 (m, 1H), 2.73–2.86 (m, 2H), 3.02 (sextet, J=7 Hz, 2H), 3.13–3.28 (m, 3H)), 3.44–3.53 (m, 1H), 3.57 (d, J=9 Hz, 1H), 3.89 (s, 3H), 5.94 (s, 2H), 6.74 (d, J=8 Hz, 1H), 6.78 (dd, J=2 Hz, J=8 Hz, 1H), 6.85 (s, 2H), 6.92 (d, J=8 Hz, 1H), 9.94 (d, J=2 Hz, 1H), 7.06 (d, J=8 Hz, 1H), 7.13 (dd, J=2 Hz, J=12 Hz, 1H). MS (DCI/NH$_3$) m/e 627 (M+H)$^+$.

EXAMPLE 432 trans,trans-2-(4-Methoxyphenyl)-4-(3,4-difluorophenyl)-1-((N-butyl-N-(3-chlorophenyl)amino)carbonylmethyl)pyrrolidine-3-carboxylic acid Using the procedures described in Example 1, the title compound was prepared. $^1$H NMR (300 MHz, CDCl$_3$) δ 0.86 (t, J=7 Hz, 3H), 1.18–1.32 (m, 2H), 1.35–1.48 (m, 2H), 2.64 (d, J=13 Hz, 1H), 2.71 (t, J=7 Hz, 1H), 3.08–3.18 (m, 2H), 3.42–3.48 (m, 1H), 3.53–3.64 (m, 3H), 3.77 (s, 3H), 3.80 (d, J=9 Hz, 1H), 6.73–6.85 (m, 3H), 6.94 (s, 1H), 7.04–7.40 (m, 7H).

EXAMPLE 433 trans,trans-2-(3-Fluoro-4-methoxyphenyl)-4-(1,3-benzodioxol-5-yl)-1-(2-(N-propyl-N-(3-chloropropanesulfonyl)amino)ethyl)pyrrolidine-3-carboxylic acid Using the procedures described in Example 1, the title compound was prepared. $^1$H NMR (CD$_3$OD, 300 MHz) δ 0.80 (t, 3H, J=7), 1.47 (bd hex, 2H, J=8), 2.15 (pen, 2H, J=7), 2.32 (m, 1H), 2.7–3.2 (m, 9H), 3.46 (dd, 1H, J=4, 10), 3.57 (m, 1H), 3.64 (t, 2H, J=6), 3.67 (d, 1H, J=9), 3.86 (s, 3H), 5.92 (s, 2H), 6.74 (d, 1H, J=8), 6.84 (dd, 1H, J=2, 8), 6.96 (d, 1H, J=2), 7.06 (t, 1H, J=9), 7.18 (m, 2H). MS (DCI/NH$_3$) m/e 585 (M+H; $^{35}$Cl)$^+$; 587 (M+H; $^{37}$Cl)$^+$. Anal calcd for C$_{27}$H$_{34}$N$_2$O$_7$ClFS: C, 55.43; H, 5.86; N, 4.79. Found: C, 55.65; H, 5.81; N, 4.70.

EXAMPLE 434 trans,trans-2-(3-Fluoro-4-methoxyphenyl)-4-(1,3-benzodioxol-5-yl)-1-(2-(N-isobutyl-N-(3-chloropropanesulfonyl)amino)ethyl)pyrrolidine-3-carboxylic acid Using the procedures described in Example 66, the title compound was prepared. $^1$H NMR (CD$_3$OD, 300 MHz) δ 0.79 (d, 3H, J=7), 0.84 (d, 3H, J=7), 1.68 (hept, 1H, J=7), 2.18 (pen, 2H, J=7), 2.8–3.4 (m, 10H), 3.5–3.8 (m, 3H), 3.65 (t, 2H, J=6), 3.90 (s, 3H), 5.94 (s, 2H), 6.77 (d, 1H, J=8), 6.87 (dd, 1H, J=2, 8), 6.99 (d, 1H, J=2), 7.13 (t, 1H, J=9), 7.27 (m, 2H). MS (DCI/NH$_3$) m/e 599 (M+H)$^+$. Anal calcd for C$_{28}$H$_{36}$N$_2$O$_7$ClFS.0.3 TFA: C, 54.24; H, 5.78; N, 4.42. Found: C, 54.19; H, 5.71; N, 4.01.

EXAMPLE 435 trans,trans-2-Propoxymethyl-4-(1,3-benzodioxol-5-yl)-1-(N,N-di(n-butyl)aminocarbonylmethyl)-pyrrolidine-3-carboxylic acid Using the procedures described in Example 1, the title compound was prepared. $^1$H NMR (CDCl$_3$, 300 MHz) δ 0.87–0.98 (m, 9H), 1.21–1.39 (m, 4H), 1.43–1.57 (m, 4H), 1.58–1.70 (m, 2H), 3.13–3.29 (m, 4H), 3.34–3.43 (m, 3H), 3.45–3.55 (m, 3H), 3.69 (dd, J=10.2, 4.5 Hz, 1H), 3.80–4.20 (m, 4H), 5.93 (s, 2H), 6.73 (d, J=7.8 Hz, 1H), 6.84 (dd, J=8.2, 1.7 Hz, 1H), 6.93 (d, J=1.7 Hz, 1H). MS(DCI/NH$_3$) m/e 477 (M+H)$^+$. Anal calcd for C$_{26}$H$_{40}$N$_2$O$_6$.0.50 TFA: C, 60.77; H, 7.65; N, 5.25. Found: C, 60.73; H, 7.74; N, 5.22.

EXAMPLE 436 trans,trans-2-(3-Fluoro-4-methoxyphenyl)-4-(1,3-benzodioxol-5-yl)-1-[2-(N-propyl-N-(4-methylbutanesulfonylamino)ethyl]pyrrolidine-3-carboxylic acid Using the procedures described in Example 66, the title compound was prepared and isolated as a white solid. m.p. 65–67° C. $^1$H NMR (CDCl$_3$, 300 MHz) δ 0.82 (t, J=7 Hz, 3H), 0.88 (d, J=5 Hz, 6H), 1.46 (sextet, J=7 Hz, 2H), 1.56–1.64 (m, 3H), 2.24–2.33 (m, 1H), 2.68–2.93 (m, 5H), 2.98–3.12 (m, 2H), 3.15–3.35 (m, 2H), 3.43 (dd, J=3 Hz, J=9 Hz, 1H), 3.52–3.58 (, 1H), 3.65 (d, J=12 Hz, 1H), 3.87 (s, 3H), 5.95 (s, 2H), 6.73 (d, J=8 Hz, 1H), 6.82 (dd, J=2 Hz, J=8 Hz, 1H), 6.92 (t, J=8 Hz, 1H), 6.97 (d, J=2 Hz, 1H), 7.10 (d, J=9 Hz, 1 Hz), 7.16 (dd, J=2 Hz, J=12 Hz, 1H). MS (DCI/NH$_3$) m/e 579 (M+H)$^+$.

EXAMPLE 437 trans,trans-2-(4-Methoxy-3-fluorophenyl)-4-(7-methoxy-1,3-benzodioxol-5-yl)-1-[2-(N-propyl-N-(n-pentanesulfonyl)amino)ethyl]pyrrolidine-3-carboxylic acid Using the procedures described in Example 66, the title compound was prepared. $^1$H NMR (300 MHz, CDCl$_3$) δ 0.81 (t, J=7 Hz, 3H), 0.90 (t, J=9 Hz, 3H), 1.25–1.35 (m, 4H), 1.44 (sextet, J=7 Hz, 2H), 1.67–1.78 (m, 2H), 2.22–2.34 (m, 1H), 2.30–2.95 (m, 5H), 2.95–3.10 (m, 2H), 3.15–3.33 (m, 2H), 3.45 (dd, J=3 Hz, 9 Hz, 1H), 3.47–3.56 (m, 1H), 3.65 (d, J=9 Hz, 3H), 3.88 (s, 3H), 3.94 (s, 3H), 5.95 (s, 2H), 6.55 (s, 1H), 6.65 (s, 1H), 6.92 (t, J=7H, 1H), 7.11 (d, J=9 Hz,1H), 7.17 (d, J=12 Hz, 1H).

EXAMPLE 438 trans,trans-2-(3-Fluoro-4-methoxyphenyl)-4-(1,3-benzodioxol-5-yl)-1-[2-(N-propyl-N-(2,2,3,3,3-pentafluoropropoxyethanesulfonyl)amino)ethyl]pyrrolidine-3-carboxylic acid Using the procedures described in Example 66, the title compound was prepared and isolated as a white solid. m.p. 63–64° C. $^1$H NMR (CDCl$_3$, 300 MHz) δ 0.82 (t, J=7 Hz, 3H), 1.45 (sextet, J=7 Hz, 2H), 2.24–2.33 (m, 1H), 2.70–2.82 (m, 1H), 2.85–3.09 (m, 5H), 3.14–3.28 (m, 4H), 3.43 (dd, J=3 Hz, J=9 Hz, 1H), 3.52–3.58 (m, 1H), 3.65 (d, J=9 Hz, 1H), 3.87 (s, 3H), 3.92–3.98 (m, 3H), 5.94 (s, 2H), 6.74 (d, J=8 Hz, 1H), 6.82 (dd, J=2 Hz, J=8 Hz, 1H), 6.92 (t, J=8 Hz, 1H), 6.97 (d, J=2 Hz, 1H), 7.10 (d, J=9 Hz, 1H), 7.17 (dd, J=2 Hz, J=12 Hz, 1H). MS (DCI/NH$_3$) m/e 685 (M+H)$^+$.

EXAMPLE 439 trans,trans-2-(1,4-Benzodioxan-6-yl)-4-(7-methoxy-1,3-benzodioxol-5-yl)-1-[2-(N-propyl-N-(n-pentanesulfonyl)amino)ethyl]pyrrolidine-3-carboxylic acid Using the procedures described in Example 66, the title compound was prepared. $^1$H NMR (CDCl$_3$) δ 0.81 (t, J=7 Hz, 3H), 0.90 (t, J=7 Hz, 3H), 1.23–1.36 (m, 4H), 1.45 (sextet, J=7 Hz, 2H), 1.65–1.78 (m, 2H), 2.20–2.30 (m, 1H), 2.30–2.95 (m, 5H), 2.95–3.10 (m, 2H), 3.15–3.35 (m, 2H), 3.42 (dd, J=3 Hz, 9 Hz, 1H), 3.46–3.56 (m, 1H), 3.59 (d, J=9 Hz, 1H), 3.91 (s, 3H), 4.24 (s, 4H), 5.95 (s, 2H), 6.57 (s, 1H), 6.68 (s, 1H), 6.82 (d, J=8 Hz, 1H), 6.88 (dd, J=2 Hz, 8 Hz, 1H), 6.95 (d, J=2 Hz, 1H).

EXAMPLE 440 trans,trans-4-(1,3-Benzodioxol-5-yl)-2-(4-methoxyphenyl)-1-(((N-butyl-N-(4-methoxybenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 7.32 (1H, d, J=10), 7.22 (1H, m), 7.10 (1H, d, J=9), 7.03 (6.98) (1H, d, J=3), 6.90–6.80 (4H, m), 6.79 (2H, d, J=9), 6.77 (1H, t, J=8), 5.85 (2H, s), 4.92 (4.10) (1H, d, J=15), 4.42 (4.22) (1H, d, J=15), 3.81 (1H, m), 3.79 (3.78) (3H, s), 3.76 (3H, s), 3.62 (1H, m), 3.43 (2H, m), 3.30–2.70 (5H, m), 1.42 (1H, m), 1.23 (2H, m), 1.01 (1H, m), 0.83 (0.75) (3H, t, J=8). MS (DCI/NH$_3$) m/e 575 (M+H$^+$). Anal calcd for C$_{33}$H$_{38}$N$_2$O$_7$.0.5H$_2$O: C, 67.91; H, 6.73; N, 4.80. Found: C, 67.78; H, 6.44; N, 4.55.

EXAMPLE 441 trans,trans-2-(3-Fluoro-4-methoxyphenyl)-4-(1,3-benzodioxol-5-yl)-1-(2-(N-isobutyl-N-(pentanesulfonylamino)ethyl)pyrrolidine-3-carboxylic acid Using the procedures described in Example 66, the title compound was prepared. $^1$H NMR (CD$_3$OD, 300 MHz) δ

0.76 (d, 3H, J=7), 0.84 (d, 3H, J=7), 0.92 (t, 3H, J=7), 1.36 (m, 4H), 1.70 (m, 3H), 2.90 (m, 2H), 3.02 (m, 2H), 3.1–3.8 (m, 7H), 3.84 (d, 2H, J=8), 3.91 (s, 3H), 5.96 (s, 2H), 6.80 (d, 1H, J=8), 6.88 (dd, 1H, J=2, 8), 7.00 (d, 1H, J=2), 7.19 (t, 1H, J=9), 7.35 (m, 2H). MS (DCI/NH$_3$) m/e 593 (M+H)$^+$. Anal calcd for C$_{30}$H$_{41}$N$_2$O$_7$F.0.5 TFA: C, 57.31; H, 6.44; N, 4.31. Found: C, 57.08; H, 6.15; N, 3.95.

EXAMPLE 442 trans,trans-4-(1,3-Benzodioxol-5-yl)-2-(4-methoxyphenyl)-1-(N-butyl-N-(3-fluorophenylamino)carbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.10–1.30 (m, 4H), 2.70–2.90 (m, 2H), 3.13 (t, J=8 Hz, 1H), 3.40–3.90 (m, 6H), 3.79 (s, 3H), 5.93 (s, 2H), 6.75 (d, J=8 Hz, 1H), 6.80–7.20 (m, 9H), 7.40 (m, 1H). MS (DCI) m/e 549 (M+H)$^+$. Anal calcd for C$_{31}$H$_{33}$N$_2$O$_6$F.0.8H$_2$O: C, 66.13; H, 6.19; N, 4.98. Found: C, 66.21; H, 5.83; N. 4.84.

EXAMPLE 443 trans,trans-4-(1,3-Benzodioxol-5-yl)-2-(4-fluorophenyl)-1-(N-butyl-N-(3-chlorophenylamino)carbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.50 (m, 4H), 2.65–2.85 (m, 2H), 3.05–3.85 (m, 7H), 5.93 (s, 2H), 6.75 (d, J=8 Hz, 1H), 6.85 (dd, J=8 Hz, 1H), 6.90–7.10 (m, 4H), 7.10–7.25 (m, 3H), 7.33–7.45 (m, 2H). MS (DCI) m/e 553 (M+H)$^+$. Anal calcd for C$_{30}$H$_{30}$N$_2$O$_5$FCl: C, 65.16; H, 5.47; N, 5.07. Found: C, 65.37; H, 5.41; N, 4.98.

EXAMPLE 444 trans,trans-4-(1,3-Benzodioxol-5-yl)-2-(4-methoxyphenyl)-1-(((N-butyl-N-(3,4-dimethoxybenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 7.33 (1H, d, J=10), 7.23 (1H, m), 7.03 (6.97) (1H, d, J=3), 6.90–6.60 (6H, m), 6.47 (1H, m), 5.93 (2H, m), 4.83 (4.09) (1H, d, J=15), 4.45 (4.22) (1H, d, J=15), 3.83 (3.86) (3H, s), 3.79 (1H, m), 3.77 (3.76) (3H, s), 3.75 (3.65) (3H, s), 3.60 (1H, m), 3.43 (2H, m), 3.28 (1H, m), 3.20–2.70 (4H, m), 1.43 (1H, m), 1.23 (2H, m), 1.02 (1H, m), 0.84 (0.77) (3H, t, J=8). MS (DCI/NH$_3$) m/e 605 (M+H$^+$). Anal calcd for C$_{34}$H$_{40}$N$_2$O$_8$: C, 67.53; H, 6.67; N, 4.63. Found: C, 67.28; H, 6.63; N, 4.38.

EXAMPLE 445 trans,trans-4-(1,3-Benzodioxol-5-yl)-2-(4-methoxyphenyl)-1-(((N-butyl-N-(2-methoxybenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 7.33 (1H, d, J=10), 7.11 (2H, m), 7.03 (1H, dd, J=8, 3), 6.90–6.60 (7H, m), 5.93 (2H, m), 4.83 (4.15) (1H, d, J=15), 4.47 (4.30) (1H, d, J=15), 3.81 (1H, m), 3.78 (3.73) (3H, s), 3.72 (3H, s), 3.59 (1H, m), 3.43 (2H, m), 3.30 (1H, m), 3.20–2.70 (4H, m), 1.42 (1H, m), 1.23 (2H, m), 1.01 (1H, m), 0.83 (0.77) (3H, t, J=8). MS (DCI/NH$_3$) m/e 575 (M+H$^+$). Anal calcd for C$_{33}$H$_{38}$N$_2$O$_7$: C, 68.97; H, 6.66; N, 4.87. Found: C, 68;70; H, 6.56; N, 4.61.

EXAMPLE 446 trans,trans-4-(1,3-Benzodioxol-5-yl)-2-(4-methoxyphenyl)-1-(((N-butyl-N-(3-methoxybenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 7.31 (1H, d, J=10), 7.13 (1H, d, J=9), 7.16 (1H, dt, J=8, 3), 7.03 (1H, dd, J=10, 2), 6.90–6.60 (6H, m), 6.50 (1H, m), 5.94 (2H, m), 4.82 (4.19) (1H, d, J=15), 4.50 (4.23) (1H, d, J=15), 3.78 (3.76) (3H, s), 3.77 (1H, m), 3.75 (3.67) (3H, s), 3.59 (1H, m), 3.57–3.35 (2H, m), 3.25 (1H, m), 3.20–2.70 (4H, m), 1.43 (1H, m), 1.23 (2H, m), 1.02 (1H, m), 0.84 (0.77) (3H, t, J=8). MS (DCI/NH$_3$) m/e 575 (M+H$^+$). Anal calcd for C$_{33}$H$_{38}$N$_2$O$_7$: C, 68.97; H, 6.66; N, 4.87. Found: C, 68.72; H, 6.55; N, 4.60.

EXAMPLE 447 trans,trans-2-(3-Fluoro-4-methoxyphenyl)-4-(1,3-benzodioxol-5-yl)-1-(2-(N-(2-methoxyethyl)-N-(3-chloropropanesulfonyl)amino)ethyl)pyrrolidine-3-carboxylic acid Using the procedures described in Example 66, the title compound was prepared. $^1$H NMR (CD$_3$OD, 300 MHz) δ 2.15 (pen, 2H, J=7), 2.33 (m, 1H), 2.81 (m, 2H); 2.93 (t, 1H, J=9); 3.1–3.6 (m, 10H), 3.24 (s, 3H); 3.65 (t, 2H, J=6), 3.70 (d, 1H, J=9), 3.87 (s, 3H), 5.92 (s, 2H), 6.74 (d, 1H, J=8), 6.84 (dd, 1H, J=2, 8), 6.97 (d, 1H, J=2), 7.07 (t, 1H, J=9), 7.17 (m, 2H). MS (DCI/NH$_3$) m/e 601 (M+H)$^+$. Anal calcd for C$_{27}$H$_{34}$N$_2$O$_8$ClFS: C, 53.95; H, 5.70; N, 4.66. Found: C, 53.65; H, 5.49; N, 4.26.

EXAMPLE 448 trans,trans-2-(3-Fluoro-4-methoxyphenyl)-4-(1,3-benzodioxol-5-yl)-1-(2-(N-(2-methoxyethyl)-N-(pentanesulfonyl)amino)ethyl)pyrrolidine-3-carboxylic acid Using the procedures described in Example 66, the title compound was prepared. $^1$H NMR (CD$_3$OD, 300 MHz) δ 0.93 (m, 3H), 1.34 (m, 4H), 1.69 (m, 2H), 2.33 (m, 1H), 2.75–3.1 (m, 7H), 3.23 (s, 3H), 3.3–3.6 (m, 6H), 3.70 (d, 1H, J=9), 3.86 (s, 3H), 5.92 (s, 2H), 6.74 (d, 1H, J=8), 6.84 (dd, 1H, J=2, 8), 6.97 (d, 1H, J=2), 7.07 (t, 1H, J=9), 7.18 (m, 2H). MS (DCI/NH$_3$) m/e 595 (M+H)$^+$. Anal calcd for C$_{29}$H$_{39}$N$_2$O$_8$FS: C, 58.57; H, 6.61; N, 4.71. Found: C, 58.21; H, 6.29; N, 4.29.

EXAMPLE 449 trans,trans-4-(1,3-Benzodioxol-5-yl)-2-(4-methoxyphenyl)-1-(((N-4-heptyl)-N-(4-fluoro-3-methylphenylamino)carbonyl)methyl)pyrrolidine-3-carboxylic acid Using the procedures described in Example 1, the title compound was prepared. $^1$H NMR (300 MHz, CD$_3$OD) δ

0.89 (m, 6H), 1.18–1.36 (m, 8H), 2.15 (bs, 1.5 (CH$_3$ rotamer)), 2.28 (bs, 1.5 (CH$_3$ rotamer)), 2.64 (t, J=14.9 Hz, 1H), 2.82 (m, 1H), 3.07–3.29 (m, 2H), 3.32–3.41 (m, 1H), 3.53–3.60 (m, 1H), 3.70–3.79 (m, 1H), 3.79 (s, 3H), 4.68 (m, 1H), 5.92 (m, 2H), 6.69–6.90 (m, 6H), 6.93–7.07 (m, 4H). MS (DCI) m/e 605 (M+H$^+$). Anal calcd for C$_{35}$H$_{41}$FN$_2$O$_6$: C, 69.52; H, 6.83; N, 4.63. Found: C, 69.31; H, 6.78; N, 4.35.

EXAMPLE 450 trans,trans-4-(1,3-Benzodioxol-5-yl)-2-(4-methoxyphenyl)-1-(((N-(5-nonyl)-N-(4-fluoro-3-methylphenyl)amino)carbonyl)methyl)pyrrolidine-3-carboxylic acid Using the procedures described in Example 1, the title compound was prepared. $^1$H NMR (300 MHz, CD$_3$OD) δ 0.81–0.90 (m, 6H), 1.30 (m, 12H), 2.14 (s, 1.5 (CH$_3$ rotamer)), 2.30 (s, 1.5 (CH$_3$ rotamer)), 2.60 (t, J=14.8 Hz, 1H), 2.80 (m, 1H), 3.09–3.24 (m, 2H), 3.33–3.42 (m, 1H), 3.50–3.55 (m, 1H), 3.65–3.77 (m, 1H), 3.79 (s, 3H), 4.64 (m, 1H), 5.93 (m, 2H), 6.70–6.84 (m, 5H), 6.91–7.13 (m, 5H). MS (DCI) m/e 633 (M+H$^+$). Anal calcd for C$_{37}$H$_{45}$FN$_2$O$_6$: C, 70.23; H, 7.17; N, 4.43. Found: C, 70.14; H. 7.13; N, 4.19.

EXAMPLE 451 trans,trans-4-(1,3-Benzodioxol-5-yl)-2-(4-methoxyphenyl)-1-((N-(5-nonylamino)carbonyl)methyl)pyrrolidine-3-carboxylic acid Using the procedures described in Example 1, the title compound was prepared. $^1$H NMR (300 MHz, CD$_3$OD) δ 0.80 (t, J=7.0 Hz, 3H), 0.84 (t, J=7.1 Hz, 3H), 1.15–1.55 (m, 12H), 2.88 (d, J=15.9 Hz, 1H), 3.07 (m, 2H), 3.26 (d, J=16.3 Hz, 1H), 3.36 (dd, J=4.4, 9.8 Hz, 1H), 3.64 (m, 1H), 3.76 (m, 1H), 3.79 (s, 3H), 3.98 (d, J=9.5 Hz, 1H), 5.93 (m, 2H), 6.77 (d, J=7.8 Hz, 1H), 6.85 (dd, J=1.7, 8.1 Hz, 1H), 6.93 (m, 2H), 6.99 (d, J=1.7 Hz, 1H), 7.39 (m, 2H). MS (DCI) m/e 525 (M+H$^+$). Anal calcd for C$_{30}$H$_{46}$N$_2$O$_6$.0.35H$_2$O: C, 67.86; H, 7.73; N, 5.28. Found: C, 67.87;H, 7.63;N, 5.11.

EXAMPLE 452 trans,trans-4-(1,3-Benzodioxol-5-yl)-2-(4-methoxyphenyl)-1-((N-butyl-N-(2-fluorophenyl)amino)carbonylmethyl)pyrrolidine-3-carboxylic acid Using the procedures described in Example 1, the title compound was prepared. $^1$H NMR (300 MHz, CD$_3$OD) δ 0.87 (dt, J=7 Hz, 3H), 1.15–1.32 (m, 4H), 3.77 (d, J=2 Hz, 3H), 2.65–5.92 (m, 9H), 5.93 (d, J=4 Hz, 2H), 6.70–6.90 (m, 4H), 7.00–7.45 (m, 7H). MS (DCI) m/e 549 (M+H)$^+$. Anal calcd for C$_{31}$H$_{33}$N$_2$O$_6$.0.4H$_2$O: C, 66.99; H, 6.13; N, 5.04. Found: C, 67.01; H, 6.23; N, 4.68.

EXAMPLE 453 trans,trans-2-(4-Methoxphenyl)-4-(1,3-benzodioxol-5-yl)-1-[2-(N-propyl-N-(2-benzothiazolyl)amino)ethyl]pyrrolidine-3-carboxylic acid The title compound was prepared by the method of Example 418, substituting 2-chlorobenzothiazole for 2-bromopyrimidine. $^1$H NMR (300 MHz, CDCl$_3$) δ 0.88 (t, J=7 Hz, 3H), 1.59 (sextet, J=7 Hz, 2H), 2.25–2.37 (m, 1H), 2.85–2.97 (m, 3H), 3.28–3.36 (m, 2H), 3.50–3.58 (m, 3H), 3.60–3.65 (m, 1H), 3.67 (d, J=9 Hz, 1H), 3.71 (s, 3H), 5.87 (d, J=2 Hz, 1H), 5.91 (d, J=2 Hz, 1H), 6.57 (d, J=8 Hz, 1H), 6.73 (dd, J=2 Hz, 9 Hz, 1H), 6.76 (d, J=8 Hz, 2H), 6.91 (d, J=2 Hz, 1H), 7.01 (t, J=8 Hz, 1H), 7.22 (t, J=8 Hz, 1H), 7.29 (d, J=8 Hz, 2H), 7.40 (d, J=7 Hz, 1H), 7.55 (d, J=7 Hz, 1H).

EXAMPLE 454 trans,trans-2-(2-Ethoxyethyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared. $^1$H NMR (CDCl$_3$, 300 MHz) δ 0.91 (t, J=7.4 Hz, 3H), 0.94 (t, J=7.4 Hz, 3H), 1.19 (t, J=7.0 Hz, 3H), 1.24–1.38 (m, 5H), 1.46–1.60 (m, 4H), 2.03–2.12 (m, 2H), 3.07 (t, J=8.0 Hz, 1H), 3.07–3.34 (m, 6H), 3.43–3.52 (m, 3H), 3.59–3.74 (m, 3H), 3.80–4.01 (m, 2H), 5.93 (s, 2H), 6.72 (d, J=8.1 Hz, 1H), 6.79 (dd, J=8.2 Hz, 1.7 Hz, 1H), 6.87 (d, J=1.7 Hz, 1H). MS(DCI/NH$_3$) m/e 477 (M+H)$^+$. Anal calcd for C$_{26}$H$_{40}$N$_2$O$_6$.0.4 TFA: C, 61.64; H, 7.80; N, 5.36. Found: C, 61.63; H, 7.84; N, 5.29.

EXAMPLE 455 trans,trans-2-(4-Methoxy-3-fluorophenyl)-4-(1,3-benzodioxol-5-yl)-1-[2-(N-propyl-N-(2-(morpholin-4-ylethyl)sulfonylamino)ethyl]pyrrolidine-3-carboxylic acid Ethyl 2-(4-methoxy-3-fluorophenyl)-4-(1,3-benzodioxol-5-yl)-1-[2-(N-propyl-N-(2-vinylsulfonyl)amino)ethyl]pyrrolidine-3-carboxylic acid, prepared by the procedures of Example 125, was reacted with excess morpholine for 4 hours at room temperature. Chromatography on silica gel eluting with EtOAc gave a 65% yield of an intermediate ethyl ester which was hydrolyzed to the title compound with NaOH in ethanol/water. $^1$H NMR (300 MHz, CDCl$_3$) δ 0.81 (t, J=7 Hz, 3H), 1.46 (sextet, J=7 Hz, 2H), 2.43–2.52 (m, 4H), 2.70–2.92 (m, 5H), 2.97–3.33 (m, 6H), 3.60 (dd, J=3 Hz, 9 Hz, 1H), 3.51–3.59 (m, 1H), 3.62–3.70 (m, 5H), 3.88 (s, 3H), 5.95 (s, 2H), 6.72 (d, J=8 Hz, 1H), 6.70 (dd, J=2 Hz, 8 Hz, 1H), 6.90 (t, J=9 Hz, 1H), 6.96 (d, J=2 Hz, 1H), 7.10 (d, J=8 Hz, 1H), 7.18 (dd, J=2 Hz, 12 Hz, 1H).

EXAMPLE 456 trans,trans-2-(3-Fluoro-4-methoxyphenyl)-4-(1,3-benzodioxol-5-yl)-1-[2-(N-propyl-N-((2,2,2-trifluoroethoxyethane)sulfonyl)amino)ethyl]pyrrolidine-3-carboxylic acid Using the procedures described in Example 66, the title compound was prepared and isolated as a white solid. m.p. 95–96° C. $^1$H NMR (CD$_3$OD, 300 MHz) δ 0.80 (t, J=7 Hz, 3H), 1.35–1.48 (m, 2H), 3.07 (sextet, J=7 Hz, 2H), 3.23–3.55 (m, 8H), 3.80–3.87 (m, 2H), 3.93 (s, 3H), 3.94–4.02 (m, 4H), 4.66 (d, J=12 Hz, 1H), 5.96 (s, 2H), 6.83 (d, J=8 Hz, 1H), 6.94 (d, J=8 Hz, 1H), 7.06 (d, J=2 Hz, 1H), 7.23 (t, J=9 Hz, 1H), 7.43 (d, J=9 Hz, 1H), 7.49 (dd, J=2 Hz,J=12 Hz, 1H). MS (DCI/NH$_3$) m/e 635 (M+H)$^+$.

EXAMPLE 457 trans,trans-4-(1,3-Benzodioxol-5-yl)-2-(4-fluorophenyl)-1-(N-butyl-N-(3-methylphenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.50 (m, 4H), 2.31 (s, 3H), 2.65–2.80 (m, 2H), 3.19 (t, J=7 Hz, 1H), 3.25 (d, J=10 Hz, 1H), 3.35–3.65 (m, 4H), 3.79 (d, J=10 Hz, 1H), 5.93 (s, 2H), 6.74 (d, J=7 Hz, 1H), 6.80–6.90 (m, 3H), 6.91–7.09 (m, 3H), 7.10–7.35 (m, 4H). MS (DCI) m/e 533 (M+H)$^+$. Anal calcd for C$_{31}$H$_{33}$N$_2$O$_5$F: C, 69.91; H, 6.25; N, 5.26. Found: C, 69.56; H, 6.26; N, 5.23.

EXAMPLE 458 trans,trans-2-(3-Fluoro-4-methoxyphenyl)-4-(1,3-benzodioxol-5-yl)-1-(2-(N-(2-methoxyethyl)-N-(butanesulfonylamino)ethyl)pyrrolidine-3-carboxylic acid Using the procedures described in Example 66, the title compound was prepared. $^1$H NMR (CD$_3$OD, 300 MHz) δ 0.94 (m, 3H), 1.23 (hex, 2H, J=8), 1.69 (m, 2H), 3.08 (m, 2H), 3.20 (s, 3H), 3.3–3.5 (m, 10H), 3.77 (m, 2H), 3.92 (s, 3H), 4.60 (m, 1H), 5.96 (s, 2H), 6.81 (d, 1H, J=8), 6.88 (dd, 1H, J=2, 8), 6.99 (d, 1H, J=2), 7.22 (t, 1H, J=9), 7.38 (m, 2H). MS (APCI) m/e 581 (M+H)$^+$. Anal calcd for C$_{28}$H$_{37}$N$_2$O$_8$FS.1.1 TFA: C, 51.37; H, 5.44; N, 3.97. Found: C, 51.27; H, 5.35; N, 4.11.

EXAMPLE 459 trans,trans-2-(3-Fluoro-4-methoxyphenyl)-4-(1,3-benzodioxol-5-yl)-1-[2-(N-propyl-N-(2-methylpropanesulfonyl)amino)ethyl]pyrrolidine-3-carboxylic acid Using the procedures described in Example 66, the title compound was prepared and isolated as a white solid. m.p. 77–78° C. $^1$H NMR (CDCl$_3$, 300 MHz) δ 0.83 (t, J=7 Hz, 3H), 1.06 (d, J=6 Hz, 6H), 1.45 (q, J=7 Hz, 2H), 2.20 (septet, J=6 Hz, 1H), 2.26–2.36 (m, 1H), 2.62–2.78 (m, 3H), 2.85–2.95 (m, 2H), 2.97–3.10 (m, 2H), 3.15–3.35 (m, 2H), 3.43 (dd, J=3 Hz, J=9 Hz, 1H), 3.53–3.62 (m, 1H), 3.66 (d, J=9 Hz, 1H), 3.88 (s, 3H), 5.95 (s, 2H), 6.74 (d, J=8 Hz, 1H), 6.82 (dd, J=2 Hz, J=8 Hz, 1H), 6.92 (t, J=8 Hz, 1H), 6.97 (d, J=2 Hz, 1H), 7.12 (d, J=9 Hz, 1H), 7.18 (dd, J=2 Hz, J=12 Hz, 1H). MS (DCI/NH$_3$) m/e 565 (M+H)$^+$.

EXAMPLE 460 trans,trans-4-(1,3-Benzodioxol-5-yl)-2-(4-methoxyphenyl)-1-(((N-butyl-N-(4-nitrobenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 8.11 (2H, m), 7.32 (3H, dd, J=9, 2), 7.16 (7.07) (1H, bd, J=10), 6.98 (6.94) (1H, d, J=2), 6.85 (2H, d, J=9), 6.83–6.70 (2H, m), 5.99 (5.97) (2H, d, J=2), 5.02 (4.18) (1H, d, J=15), 4.63 (4.38) (1H, d, J=15), 3.79 (3.77) (3H, s), 3.72 (1H, d, J=10), 3.61 (1H, m), 3.48 (1H, bd, J=15), 3.43–3.20 (2H, m), 3.06 (2H, m), 2.90 (1H, m), 3.79 (1H, bd, J=14), 1.43 (1H, m), 1.23 (2H, m), 1.02 (1H, m), 0.84 (0.78) (3H, t, J=8).

MS (DCI/NH$_3$) m/e 590 (M+H)$^+$. Anal calcd for C$_{32}$H$_{35}$N$_3$O$_8$: C, 65.18; H, 5.98; N, 7.13. Found: C, 65.89; H, 5.85; N, 6.85.

EXAMPLE 461 trans,trans-2-(4-Ethylphenyl)-4-(3,4-difluorophenyl)-1-(N,N-di(n-butyl)aminocarbonylmethyl)-pyrrolidine-3-carboxylic acid Using the procedures described in Example 1, the title compound was prepared. $^1$H NMR (CD$_3$OD, 300 MHz) δ 0.78 (t, 3H, J=7), 0.87 (t, 3H, J=7), 1.02 (hex, 2H, J=7), 1.22 (t, 3H, J=7), 1.27 (m, 2H), 1.45 (m, 2H, J=7), 2.63 (q, 2H, J=7), 2.77 (d, 1H, J=14), 2.94 (dd, 1H, J=7, 9), 3.05 (m, 3H), 3.3–3.5 m, 3H), 3.44 (d, 1H, J=14), 3.66 (m, 1H), 3.75 (d, 1H, J=10), 7.20 (td, 2H, J=1,8), 7.22 (m, 2H), 7.32 (td, 2H, J=1,8), 7.43 (ddd, 1H, J=2,8,12). MS (DCI/NH$_3$) m/e 501 (M+H)$^+$. Anal calcd for C$_{29}$H$_{38}$N$_2$O$_3$F$_2$.0.6H$_2$O: C, 68.11; H, 7.73; N, 5.48. Found: C, 68.03; H, 7.53; N, 5.37.

EXAMPLE 462 trans,trans-4-(1,3-Benzodioxol-5-yl)-2-(4-methoxyphenyl)-1-(N-butyl-N-(4-fluoro-3-methylphenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.50 (m, 4H), 2.21 (d, J=2 Hz, 3H), 2.64 (d, J=14 Hz, 1H), 2.75 (dd, J=10 Hz, 1H), 3.05 (t, J=7 Hz, 1H), 3.25 (d, J=15 Hz, 1H), 3.35–3.70 (m, 5H), 3.77 (s, 3H), 5.92 (s, 2H), 6.70–6.92 (m, 6H), 6.96–7.10 (m, 4H). MS (DCI) m/e 563 (M+H)$^+$. Anal calcd for C$_{32}$H$_{35}$N$_2$O$_6$F.0.5H$_2$O: C, 67.24; H, 6.35; N, 4.90. Found: C, 67.16; H, 6.06; N, 4.81.

EXAMPLE 463 trans,trans-4-(1,3-Benzodioxol-5-yl)-2-(4-methoxyphenyl)-1-(N-butyl-N-((3-isopropyl)phenyl)amino)carbonylmethyl)-pyrrolidine-3-carboxylic acid Using the procedures described in Example 1, the title compound was prepared. $^1$H NMR (300 MHz, CD$_3$OD) δ 0.87 (t, 3H), 1.17 (d, J=7 Hz, 6H), 1.20–1.50 (m, 4H), 2.63 (d, J=15 Hz, 1H), 2.75 (t, J=7 Hz, 1H), 2.85 (m, 1H), 3.00 (t, J=7 Hz, 1H), 3.25 (d, J=15 Hz, 1H), 3.40–3.70 (m, 5H), 3.75 (s, 3H), 5.90 (s, 2H), 6.65–6.80 (m, 3H), 6.71 (dt, J=7 Hz, 3H), 7.07 (m, 3H), 7.20–7.35 (m, 2H). MS (DCI) m/e 573 (M+H)$^+$. Anal calcd for C$_{34}$H$_{40}$N$_2$O$_6$.0.15H$_3$PO$_4$: C, 69.52; H, 6:94; N, 4.77. Found: C, 63.31; H, 6.72; N, 4.43.

EXAMPLE 464 trans,trans-4-(1,3-Benzodioxol-5-yl)-2-(4-methoxyphenyl)-1-(N-butyl-N-(3-ethylphenyl)aminocarbonylmethyl)pyrrolidine-3-carboxylic acid Using the procedures described in Example 1, the title compound was prepared. $^1$H NMR (300 MHz, CD$_3$OD) δ 0.87 (m, J=7 Hz, 3H), 1.16 (t, J=7 Hz, 3H), 1.20–1.47 (m, 4H), 2.50 (q, J=7 Hz, 2H), 2.70–2.85 (m, 2H), 3.13 (t, J=7 Hz, 1H), 3.20–4.5 (m, 6H), 3.78 (s, 3H), 3.83 (d, J=8 Hz, 1H), 5.92 (s, 2H), 6.72 (d, J=8 Hz, 1H), 6.80–6.90 (m, 5H), 7.02–7.13 (m, 3H), 7.15–7.25 (m, 2H). MS (DCI) m/e 559

(M+H)⁺. Anal calcd for C₃₃H₃₈N₂O₆·0.3H₂O: C, 70.27; H, 6.90; N, 4.97. Found: C, 70.31; H, 6.63; N, 4.60.

EXAMPLE 465 trans,trans-4-(1,3-Benzodioxol-5-yl)-2-(4-ethylphenyl)-1-(((N-(3-chlorophenyl)-N-butylamino)carbonyl)methyl)pyrrolidine-3-carboxylic acid Using the procedures described in Example 1, the title compound was prepared. $^1$H NMR (300 MHz, CDCl₃) δ 0.87 (t, 3H, J=7 Hz), 1.23 (t, 3H, J=7 Hz), 1.28 (m, 2H), 1.41 (m, 2H), 2.63 (q, 2H, J=7 Hz), 2.67 (m, 1H), 2.92 (m, 1H), 3.20 (m, 2H), 3.42 (m, 1H), 3.60 (q, 2H, J=7 Hz), 3.93 (m, 1H), 5.92 (s, 2H), 6.75 (d, 1H, J=8 Hz), 6.84 (m, 3H), 6.95 (br s, 1H), 7.02 (s, 1H), 7.10 (br s, 3H), 7.25 (m, 2H). MS (APCI) m/e 563 (M+H)⁺. Anal. calc'd for C₃₂H₃₅N₂O₅Cl·0.80H₃PO₄: C, 59.92; H, 5.88; N, 4.37. Found: C, 59.90; H, 5.83; N, 4.07.

EXAMPLE 466 trans,trans-4-(1,4-Benzodioxan-6-yl)-2-(4-ethylphenyl)-1-(((N-(3-chlorophenyl)-N-butylamino)carbonyl)methyl)pyrrolidine-3-carboxylic acid Using the procedures described in Example 1, the title compound was prepared. $^1$H NMR (300 MHz, CDCl₃) δ 0.86 (t, 3H, J=7 Hz), 1.23 (t, 3H, J=7 Hz), 1.25 (m, 2H), 1.40 (m, 2H), 2.64 (q, 2H, J=7 Hz), 2.70 (m, 1H), 2.95 (m, 1H), 3.20 (m, 2H), 3.40 (m, 1H), 3.57 (m, 3H), 3.90 (m, 1H), 4.25 (s, 4H), 6.80 (d, 1H, J=8 Hz), 6.95 (d, 1H, J=2 Hz), 6.95 (m, 2H), 7.07 (br s, 3H), 7.22 (m, 3H). MS (APCI) m/e 577. (M+H)⁺. Anal. calc'd for C₃₃H₃₇N₂O₅Cl·0.85H₂O: C, 66.90; H, 6.58; N, 4.73. Found: C, 66.92; H, 6.25; N, 4.36.

EXAMPLE 467 trans,trans-4-(Benzofuran-5-yl)-2-(4-ethylphenyl)-1-(((N-(3-chlorophenyl)-N-butylamino)carbonyl)methyl)pyrrolidine-3-carboxylic acid Using the procedures described in Example 1, the title compound was prepared. $^1$H NMR (300 MHz, CDCl₃) δ 0.85 (t, 3H, J=7 Hz), 1.26 (t, 3H, J=7 Hz), 1.30 (m, 2H), 1.40 (m, 2H), 2.60 (q, 2H, J=7 Hz), 2.72 (m, 1H), 2.93 (m, 1H), 3.22 (m, 2H), 3.50 (m, 1H), 3.55 (m, 2H), 3.75 (m, 1H), 3.90 (br d, 1H), 6.75 (d, 1H, J=1 Hz), 6.80 (br d, 1H), 6.95 (br s, 1H), 7.08 (m, 4H), 7.20 (t, 1H, J=8 Hz), 7.28 (t, 1H, J=8 Hz), 7.42 (m, 2H), 7.58 (d, 1H, J=1 Hz), 7.63 (s, 1H). MS (APCI) m/e 559 (M+H)⁺. Anal. calc'd for C₃₃H₃₅N₂O₄Cl·0.45H₂O: C, 69.88; H, 6.38; N, 4.94. Found: C, 69.83; H, 6.04; N, 4.87.

EXAMPLE 468 trans,trans-2-(4-Methoxy-3-fluorophenyl)-4-(7-methoxy-1,3-benzodioxol-5-yl)-1-[2-(N-butyl-N-phenylamino)ethyl]pyrrolidine-3-carboxylic acid Ethyl 2-(4-methoxy-3-fluorophenyl)-4-(7-methoxy-1,3-benzodioxol-5-yl)-1-[2-(bromoethyl]-pyrrolidine-3-carboxylate, prepared using the procedures of Example 61A (300 mg), was reacted with N-butyl aniline (190 mg) in 1 mL of dioxane containing 130 mg of diisopropylethylamine to give the ethyl ester. The ester was hydroyzed with sodium hydroxide to give 148 mg of the title compound as a white powder. $^1$H NMR (300 MHz, CDCl₃) δ 0.90 (t, J=9 Hz, 3H), 1.28 (sextet, J=7 Hz, 2H), 1.46 (quintet, J=7 Hz, 2H), 2.20–2.32 (m, 1H), 2.68–2.77 (m, 1H), 2.82–2.95 (m, 2H), 3.12–3.22 (m, 2H), 3.30–3.44 (m, 3H), 3.45–3.55 (m, 1H), 3.62 (d, J=9 Hz, 1H), 3.83 (s, 3H), 3.90 (s, 3H), 5.95 (s, 2H), 6.51 (d, J=7 Hz, 2H), 6.55–6.62 (m, 2H), 6.69 (d, J=2 Hz, 1H), 6.84 (t, J=8 Hz, 1H), 7.02–7.15 (m, 3H), 7.19 (dd, J=2 Hz, 12 Hz, 1H).

EXAMPLE 469 trans,trans-4-(1,4-Benzodioxan-6-yl)-2-(4-ethylphenyl)-1-(((N,N-di(n-butyl)aminocarbonylmethyl)-Pyrrolidine-3-carboxylic acid Using the procedures described in Example 1, the title compound was prepared. $^1$H NMR (300 MHz, CDCl₃) δ 0.78 (t, 3H, J=7 Hz), 0.88 (t, 3H, J=7 Hz), 1.05 (q, 2H, J=7 Hz), 1.23 (t, 3H, J=7 Hz), 1.28 (m, 2H), 1.45 (m, 2H), 2.64 (q, 2H, J=7 Hz), 2.78 (m, 1H), 2.9–3.2 (envelope, 4H), 3.30 (m, 1H), 3.40 (m, 3H), 3.60 (m, 1H), 3.80 (m, 1H), 4.25 (s, 4H), 6.80 (d, 1H, J=8 Hz), 6.90 (m, 1H), 6.98 (d, 1H, J=2 Hz), 7.17 (d, 2H, J=8 Hz), 7.30 (m, 2H). MS (APCI) m/e 523 (M+H)⁺. Anal. calc'd for C₃₁H₄₂N₂O₅·1.1 HOAc: C, 67.73; H, 7.94; N, 4.76. Found: C, 67.81; H, 7.55; N, 4.48.

EXAMPLE 470 trans,trans-4-(1,4-Benzodioxan-6-yl)-2-(4-methoxyphenyl)-1-((N-butyl-N-(3-methylphenylamino)carbonyl)methyl)pyrrolidine-3-carboxylic acid Using the procedures described in Example 1, the title compound was prepared. $^1$H NMR (300 MHz, CD₃OD) δ 0.87 (t, J=7.1 Hz, 3H), 1.30 (m, 2H), 1.44 (m, 2H), 2.30 (s, 3H), 2.80 (d, J=15.2 Hz, 1H), 2.85 (t, J=9.3 Hz, 1H), 3.19 (t, J=9.3 Hz, 1H), 3.33 (d, J=10.2 Hz, 1H), 3.42–3.61 (m, 3H), 3.79 (s, 3H), 3.91 (d, J=9.8 Hz, 1H), 4.22 (m, 4H), 6.75–6.86 (m, 6H), 6.95 (d, J=2.0 Hz, 1H), 7.09 (d, J=8.8 Hz, 2H), 7.22 (d, J=10.2 Hz, 1H), 7.26 (t, J=7.6 Hz, 1H). MS (DCI) m/e 559 (M+H)⁺. Anal calcd for C₃₃H₃₈N₂O₆·0.4 CH₃CO₂C₂H₅: C, 69.97; H, 6.99; N, 4.72. Found: C, 0.06; H, 6.66; N, 4.48.

EXAMPLE 471 trans,trans-4-(1,4-Benzodioxan-6-yl)-2-(4-methoxyphenyl)-1-((N-butyl-N-(3-chlorophenylamino)carbonyl)methyl)pyrrolidine-3-carboxylic acid Using the procedures described in Example 1, the title compound was prepared. $^1$H NMR (300 MHz, CD₃OD) δ 0.87 (t, J=7.0 Hz, 3H), 1.25 (m, 2H), 1.40 (m, 2H), 2.78 (d, J=14.6 Hz, 1H), 2.86 (t, J=9.0 Hz, 1H), 3.16 (t, J=9.5 Hz, 1H), 3.34–3.43 (m, 2H), 3.48–3.62 (m, 3H), 3.79 (s, 3H), 3.85 (d, J=9.5 Hz, 1H), 4.22 (m, 4H), 6.78 (d, J=8.5 Hz, 1H), 6.81–6.86 (m, 3H), 6.93–7.09 (m, 5H), 7.33–7.38 (m, 2H). MS (DCI) m/e 579 (M+H)⁺. Anal calcd for C₃₂H₃₅ClN₂O₆·1.1CH₃CO₂C₂H₅·0.15H₃PO₄: C, 63.30; H, 6.46; N, 4.06. Found: C, 63.54; H, 6.09; N, 3.98.

EXAMPLE 472 trans,trans-4-(1,3-Benzodioxol-5-yl)-2-(4-methoxyphenyl)-1-(4-pridylmethyl)pyrrolidine-3-carboxylic acid Using the procedures described in Example 1, the title compound was prepared. $^1$H NMR (300 MHz, CD$_3$OD) δ 2.84 (t, J=9.6 Hz, 1H), 2.88 (dd, J=9.6, 7.3 Hz, 1H), 3.09 (dd, J=3.3, 9.6 Hz, 1H), 3.21 (d, J=14.3 Hz, 1H), 3.53 (m, 1H), 3.78 (s, 3H), 3.81 (m, 2H), 5.92 (m, 2H), 6.73 (d, J=8.1 Hz, 1H), 6.82 (dd, J=1.8, 8.1 Hz, 1H), 6.93 (m, 2H), 6.95 (d, J=1.5 Hz, 1H), 7.43 (m, 4H), 8.44 (d, J=5.2 Hz, 2H). MS (DCI) m/e 433 (M+H$^+$). Anal calcd for C$_{25}$H$_{24}$N$_2$O$_5$.0.3 CH$_3$CO$_2$C$_2$H$_5$: C, 68.57; H, 5.80; N, 6.10. Found: C, 68.68; H, 5.60; N, 5.81.

EXAMPLE 473 trans,trans-4-(1,3-Benzodioxol-5-yl)-2-(4-methoxyphenyl)-1-((N-butyl-N-(3-tert-butylphenylamino)carbonyl)methyl)pyrrolidine-3-carboxylic acid Using the procedures described in Example 1, the title compound was prepared. $^1$H NMR (300 MHz, CD$_3$OD) δ 0.88 (t, J=7.2 Hz, 3H), 1.23 (s, 9H), 1.26–1.45 (m, 4H), 2.74 (dd, J=15.1 Hz, 1H), 2.84 (m, 1H), 3.13 (t, J=9.0 Hz, 1H), 3.29 (d, J=15.1 Hz, 1H), 3.50–3.66 (m, 4H), 3.77 (s, 3H), 3.84 (d, J=9.6 Hz, 1H), 5.92 (s, 2H), 6.74 (d, J=7.7 Hz, 1H), 6.79–6.85 (m, 4H), 6.86–6.90 (m, 1H), 6.99 (t, J=1.8 Hz, 1H), 7.06 (d, J=1.8 Hz, 1H), 7.13 (m, 2H), 7.33 (t, J=7.7 Hz, 1H), 7.42 (m, 1H). MS (DCI) m/e 587 (M+H$^+$). Anal calcd for C$_{35}$H$_{42}$N$_2$O$_6$: C, 71.65; H, 7.22; N, 4.77. Found: C, 71.56; H, 7.33; N, 4.69.

EXAMPLE 474 trans,trans-4-(1,3-Benzodioxol-5-yl)-2-(4-methoxyphenyl)-1-((N-butyl-N-(3-n-butylphenylamino)carbonyl)methyl)pyrrolidine-3-carboxylic acid Using the procedures described in Example 1, the title compound was prepared. $^1$H NMR (300 MHz, CD$_3$OD) δ 0.88 (t, J=7.3 Hz, 3H), 0.92 (t, J=7.3 Hz, 3H), 1.23–1.59 (m, 8H), 2.58 (t, J=7.6 Hz, 2H), 2.75 (d, J=15.3 Hz, 1H), 2.80 (dd, J=8.5, 9.5 Hz, 1H), 3.12 (t, J=9.3 Hz, 1H), 3.29 (d, J=15.6 Hz, 1H), 3.46 (dd, J=4.9, 9.7 Hz, 1H), 3.52–3.64 (m, 3H), 3.78 (s, 3H), 3.83 (d, J=9.8 Hz, 1H), 5.92 (s, 2H), 6.74 (d, J=8.1 Hz, 1H), 6.79–6.87 (m, 4H), 7.05 (d, J=1.7 Hz, 1H), 7.10 (d, J=8.8 Hz, 2H), 7.20 (d, 7.8H), 7.29 (t, J=7.6 Hz, 1H). MS (DCI) m/e 587 (M+H$^+$). Anal calcd for C$_{35}$H$_{42}$N$_2$O$_6$: C, 71.65; H, 7.22; N, 4.77. Found: C, 71.33; H, 7.28; N, 4.74.

EXAMPLE 475 trans,trans-4-(3,4-Difluorophenyl)-2-(4-ethylphenyl)-1-(N-(n-butyl)-N-(3-methylphenyl)aminocarbonylmethyl)pyrrolidine-3-carboxylic acid Using the procedures described in Example 1, the title compound was prepared. $^1$H NMR (CD$_3$OD, 300 MHz) δ 0.87 (t, 3H, J=7), 1.19 (t, 3H, J=7), 1.28 (m, 2H), 1.43 (m, 2H), 2.28 (s, 3H), 2.60 (q, 2H, J=7), 2.66 (m, 2H), 3.06 (m, 1H), 3.21 (d, 1H, J=15), 3.42 (dd, 1H, J=4,9), 3.58 (m, 3H), 3.71 (d, 1H, J=9), 6.80 (s, 2H), 7.06 (s, 4H), 7.18 (m, 4H), 7.45 (m, 1H). MS (APCI) m/e 535 (M+H)$^+$. Anal calcd for C$_{32}$H$_{36}$N$_2$O$_3$F$_2$.1.3 HOAc: C, 67.83; H, 6.78; N, 4.57. Found: C, 67.83; H, 6.46; N, 4.70.

EXAMPLE 476 trans,trans-2-(4-Ethylphenyl)-4-(3,4-difluorophenyl)-1-(N-(n-butyl)-N-(3-chlorophenyl)aminocarbonylmethyl)pyrrolidine-3-carboxylic acid Using the procedures described in Example 1, the title compound was prepared. $^1$H NMR (CD$_3$OD, 300 MHz) δ 0.82 (t, 3H, J=7), 1.16 (t, 3H, J=7), 1.23 (m, 2H), 1.35 (m, 2H), 2.55 (q, 2H, J=7), 2.66 (m, 2H), 3.01 (t, 1H, J=9), 3.16 (d, 1H, J=15), 3.32 (dd, 1H, J=4,9), 3.56 (m, 3H), 3.67 (d, 1H, J=9), 6.94 (d, 1H, J=7), 7.02 (m, 5H), 7.14 (m, 2H), 7.32 (m, 3H). MS (APCI) m/e 555 (M+H)$^+$. Anal calcd for C$_{31}$H$_{33}$N$_2$O$_3$ClF$_2$.0.6 TFA: C, 61.88; H, 5.42; N, 4.48. Found: C, 61.90; H, 5.62; N, 3.98.

EXAMPLE 477 trans,trans-4-(1,4-Benzodioxan-6-yl)-2-(4-fluorophenyl)-1-(N-butyl-N-(3-chlorophenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.10–1.30 (m, 4H), 2.60–2.75 (m; 2H), 3.03 (t, J=7 Hz, 1H), 3.15–3.75 (m, 6H), 4.02 (m, 4H), 6.75 (d, J=6 Hz, 1H), 6.85 (dd, J=7 Hz, 1H), 6.90 (7.19, J=m Hz, 6H), 7.32–7.43 (m, 3H). MS (DCI) m/e 567 (M+H)$^+$. Anal calcd for C$_{31}$H$_{32}$N$_2$O$_5$FCl.1.6H$_2$O: C, 62.49; H, 5.95; N, 4.70. Found: C, 62.20; H, 5.54; N, 4.42.

EXAMPLE 478 trans,trans-4-(Benzofuran-5-yl)-2-(4-ethylphenyl)-1-(N,N-di(n-butyl)aminocarbonylmethyl)-pyrrolidine-3-carboxylic acid Using the procedures described in Example 1, the title compound was prepared. $^1$H NMR (300 MHz, CDCl$_3$) δ 0.78 (t, 3H, J=7 Hz), 0.84 (t, 3H, J=7 Hz), 1.05 (q, 2H, J=7 Hz), 1.21 (t, 1H, J=7 Hz), 1.25 (m, 2H), 1.45 (m, 2H), 2.62 (q, 2H, J=7 Hz), 2.80 (d, 1H, J=13 Hz), 3.0 (m, 2H), 3.15 (m, 2H), 3.35 (m, 1H), 3.43 (m, 2H), 3.52 (m, 1H), 4.40 (m, 2H), 6.73 (d, 1H, J=1 Hz), 7.14 (d, 2H, J=8 Hz), 7.26 (s, 1H), 7.31 (d, 2H, J=8 Hz), 7.44 (s, 2H), 7.60 (d, 1H, J=1 Hz), 7.65 (s, 1H). MS (APCI) m/e 505 (M+H)$^+$. Anal. calc'd for C$_{31}$H$_{40}$N$_2$O$_4$: C, 73.78; H, 7.99; N, 5.55. Found: C, 73.69; H, 7.97; N, 5.21.

EXAMPLE 479 trans,trans-2-(4-Methoxy-3-fluorophenyl)-4-(7-methoxy-1,3-benzodioxol-5-yl)-1-[2-(N-propyl-N-(pyrrolidine-1-carbonylmethyl)amino)ethyl]pyrrolidine-3-carboxylic acid Ethyl 2-(4-methoxy-3-fluorophenyl)-4-(7-methoxy-1,3-benzodioxol-5-yl)-1-[2-(N-propyl-aminoethyl]-pyrrolidine-3-carboxylate, prepared according to the procedures of Example 61B (300 mg), N-bromoacetyl pyrrrolidine (132 mg) and diisopropylethylamine (154 mg) were heated for 1 hour at 50° C. in 1 mL of acetonitrile to give the intermediate ethyl ester. The ester was hydrolyzed to the title compound by the method of Example 1D. $^1$H NMR (300 MHz, CDCl$_3$)

δ 0.88 (t, J=7 Hz, 3H), 1.30–1.45 (m, 2H), 1.75–1.92 (m, 4H), 2.30–2.40 (m, 1H), 2.47–2.58 (m, 2H), 2.70–3.00 (m, 5H), 3.24–3.45 (m, 6H), 3.50–3.70 (m, 2H), 3.83 (s, 3H), 3.86 (d, J=9 Hz, 1H), 3.88 (s, 3H), 5.93 (s, 2H), 6.58 (d, J=2 Hz, 1H), 6.70 (d, J=2 Hz, 1H), 6.87 (t, J=8 Hz, 1H), 7.10 (d, J=9 Hz, 1H), 7.21 (dd, J=2 Hz, 12 Hz, 1H).

EXAMPLE 480 trans,trans-2-(4-Methoxyphenyl)-4-(1,3-benzo-dioxol-5-yl)-1-(2-((N-(perhydroazepinylcarbonyl)-(D)-leucyl)amino)ethyl)pyrrolidine-3-carboxylic acid

EXAMPLE 480A

D-Leucine O-benzyl ester Tosylate salt

To benzyl alcohol (8.2 g) dissolved in benzene (30 mL) was added D-leucine (5.0 g) and p-toluenesulfonic acid monohydrate (8.0 g). The reaction was warmed to reflux with removal of water overnight. Once TLC indicated consumption of starting material, the reaction was cooled, and the resulting solid was filtered and washed with EtOAc to give the title compound as a white powder (14.26 g, 99%).

EXAMPLE 480B

N-Perhydroazepinylcarbonyl-D-Leucine O-Benzyl ester

To the compound resulting from Example 480A (1.0 g) dissolved in chloroform (20 mL) was added triethylamine (0.4 mL). The solution was cooled to 0° C., and carbonyldiimidazole was added. After 1.5 hours, TLC indicated complete consumption of starting material, so hexamethylene imine (0.327 mL) was added. After 1 hour, an additional amount of hexamethylene imine (0.330 mL) was added, and the reaction was stirred at ambient temperature overnight. The solution was washed with sodium bicarbonate (2×20 mL), 1 $\underline{N}$ $H_3PO_4$ (2×20 mL), and brine (20 mL), dried over $Na_2SO_4$, decanted and evaporated. The residue was purified by flash chromatography on silica gel eluting with 25–50% EtOAc in hexanes to give the title compound as a crystalline solid (0.835 g, 89%).

EXAMPLE 480C

N-Perhydroazepinylcarbonyl-D-Leucine

To the compound resulting from Example 480B (200 mg) dissolved in dry ethanol (1.0 mL) was added 10% palladium on carbon (10 mg). After flushing the flask with nitrogen, the reaction was stirred vigorously under an atmosphere of hydrogen for 1 hour. The reaction was filtered through infusorial earth and evaporated to give the title compound (140 mg).

EXAMPLE 480D trans,trans-2-(4-Methoxyphenyl)-4-(1,3-benzo-dioxol-5-yl)-1-(cyanomethyl)-pyrrolidine-3-carboxylic acid ethyl ester To the compound resulting from Example 1C (510 mg of a 50% wt. solution in toluene) dissolved in acetonitrile (2.0 mL) was added diisopropylethylamine (0.24 mL), followed by bromoacetonitrile (0.072 mL). After 2 hours, TLC indicated complete comsumption of starting material. The solvent was evaporated, and the residue was purified by flash chromatography on silica gel eluting with 20–40% EtOAc in hexanes to give the title compound as a colorless oil (0.28 g, 99%).

EXAMPLE 480E trans,trans-2-(4-Methoxyphenyl)-4-(1,3-benzo-dioxol-5-yl)-1-(2-aminoethyl)-Pyrrolidine-3-carboxylic acid ethyl ester To the compound resulting from Example 480D (275 mg) dissolved in 10 mL each of triethylamine and ethanol was added Raney nickel catalyst (0.2 g), and the reaction was placed under a hydrogen atmosphere (4 atmospheres) for 3 days. The reaction was filtered and evaporated. The residue was dissolved in methylene chloride (10 mL) and extracted with 1 $\underline{M}$ HCl (5×1 mL). The combined aqueous extracts were basified and then extracted with methylene chloride (5×2 mL). The combined organic extracts were dried with $MgSO_4$, filtered and evaporated to give the title compound as an unstable oil (0.14 g).

EXAMPLE 480F trans,trans-2-(4-Methoxyphenyl)-4-(1,3-benzo-dioxol-5-yl)-1-(2-((N-(perhydroazepinylcarbonyl) leucyl)amino)ethyl)pyrrolidine-3-carboxylic acid, ethyl ester The compound resulting from Example 480E (0.10 g) was dissolved in methylene chloride (3.0 mL), and the compound resulting from Example 480C (0.07 g) was added. The solution was cooled to 0° C., and EDCI (0.052 g) was added. After 4 hours, the reaction was evaporated and partitioned between water (1 mL), and EtOAc (10 mL). The orgainc solution was washed with water (1 mL) and brine (1 mL), dried over $MgSO_4$, filtered and evaporated. The residue was purified by flash chromatography on silica gel eluting with 50–60% EtOAc in hexanes to give the title compound as a colorless oil (0.075 g, 48%).

EXAMPLE 480G trans,trans-2-(4-Methoxyphenyl)-4-(1,3-benzo-dioxol-5-yl)-1-(2-((N-(perhydroazepinylcarbonyl) leucyl)amino)ethyl)pyrrolidine-3-carboxylic acid The compound resulting from Example 480F (0.75 g) was dissolved in ethanol (1.0 mL) and 5 $\underline{M}$ NaOH (0.050 mL) was added. After 2 hours, additional 5 $\underline{M}$ NaOH (0.090 mL) was added. After an additional 3.5 hours, the reaction was evaporated. The residue was dissolved in water (5 mL) and washed with diethyl ether (2×2 mL). The aqueous solution was acidified with 1 $\underline{N}$ $H_3PO_4$ to pH·3. The solid which precipitated dissolved when the mixture was extracted with chloroform (3×3 mL). The chloroform extracts were washed with brine (2 mL), dried with $MgSO_4$, filtered and evaporated to give the title compound as a tan solid (0.053 g). Purification by HPLC (Vydac mC18) eluting with a 10–70% gradient of $CH_3CN$ in 0.1% TFA provided suitable material (0.049 g) after lyophilization of the desired fractions. $^1$H NMR ($CDCl_3$, 300 MHz) δ 0.82 (dd, 6.4, 4.4 Hz, 6H), 0.87 (dd, J=5.7, 5.7 Hz, 6H), 1.04–1.28 (m, 3H), 1.34–1.65 (m, 19H), 2.95 (br m, 2H), 3.15–3.40 (m, 14H), 3.40–3.55 (m, 4H), 3.58–3.68 (m, 2H), 3.70–3.76 (br m, 2H), 3.80 (s, 3H), 3.81 (s, 3H), 4.15 (br m, 2H), 5.10 (br m, 2H), 5.93 (s, 3H), 5.95 (s, 3H), 6.70–6.97 (m, 13H), 7.43–7.56 (br m, 3H), 8.2 (br s, 1H), 8.5 (br s, 1H). MS(DCI/NH$_3$) m/e 623 (M+H)$^+$. Anal calcd for C$_{34}$H$_{46}$N$_4$O$_7$ 2.00 TFA: C, 53.65; H, 5.69; N, 6.58. Found: C, 53.66; H, 5.66; N, 6.54.

EXAMPLE 481 trans,trans-4-(1,3-Benzodioxol-5-yl)-2-(4-methoxyphenyl)-1-(N,N-di(n-hexyl)aminocarbonylmethyl)pyrrolidine-3-carboxylic acid Using the procedures described in Example 1, the title compound was prepared. $^1$H NMR (300 MHz, CD$_3$OD) δ 0.80–0.95 (m, 6H), 1.0 (m, 2H), 1.07 (1.55, J=m Hz, 14H), 2.70 (d, J=13 Hz, 1H), 2.85–3.15 (m, 4H), 3.20–3.60 (m, 9H), 3.64 (d, J=10 Hz, 1H), 3.79 (s, 3H), 5.90 (m, 2H), 6.70 (d, 8H), 1, 6.80–6.93 (m, 3H), 7.05 (2, 1H), 7.35 (d, J=10 Hz, 2H). Anal calcd for C$_{33}$H$_{46}$N$_2$O$_6$.1.7H$_2$O: C, 66.35; H, 8.34; N, 4.69. Found: C, 66.32; H, 8.04; N, 4.52.

EXAMPLE 482 trans,trans-4-(1,4-Benzodioxan-6-yl)-2-(4-fluorophenyl)-1-(N-butyl-N-(3-methylphenyl)aminocarbonylmethyl)pyrrolidine-3-carboxylic acid Using the procedures described in Example 1, the title compound was prepared. $^1$H NMR (300 MHz, CD$_3$OD) δ 0.87 (t, J=7 Hz, 3H), 1.20–1.35 (m, 2H), 1.35–1.40 (m, 2H), 2.32 (s, 3H), 2.55–2.70 (m, 2H), 2.97 (t, J=7 Hz, 1H), 3.22 (d, J=14 Hz, 1H), 3.25–3.70 (m, 5H), 4.20 (m, 4H), 6.97 (d, J=2 Hz, 1H), 7.09 (m, 2H), 7.15–7.35 (m, 2H). MS (DCI) m/e 547 (M+H)$^+$. Anal calcd for C$_{32}$H$_{35}$N$_2$O$_5$F.1.2H$_2$O: C, 67.64; H, 6.63; N, 4.93. Found: C, 67.73; H, 6.37; N, 4.70.

EXAMPLE 483 trans,trans-4-(1,3-Benzodioxol-5-yl)-2-(4-methoxyphenyl)-1-(((N-butyl-N-(3-nitrobenzyl)amino)carbonyl)methyl)pyrrolidine-3-carboxylic acid Using the procedures described in Example 1, the title compound was prepared. $^1$H NMR (300 MHz, CDCl$_3$) δ (rotamer) 8.14 (2H, m), 8.05 (7.83) (1H, m), 7.60–7.30 (3H, m), 7.13 (1H, m), 7.10–6.70 (5H, m), 5.94 (2H, m), 5.43 (5.33) (1H, d, J=12), 4.75 (1H, bd, J=15), 4.60–4.20 (2H, m), 4.10 (2H, m), 3.80 (3.76) (3H, s), 3.75–3.40 (3H, m), 3.20–2.80 (2H, m), 1.50 (1H, m), 1.30 (1H, m), 1.20–1.00 (2H, m), 0.91 (0.78) (3H, t, J=8). MS (DCI/NH$_3$) m/e 590 (M+H)$^+$. Anal calcd for C$_{32}$H$_{35}$N$_3$O$_8$.2.1 TFA: C, 52.44; H, 4.51; N, 5.07. Found: C, 52.25; H, 4.83; N, 5.71.

EXAMPLE 484 trans,trans-4-(1,2-Dihydrobenzofuran-5-yl)-2-(4-ethylphenyl)-1-(((N-butyl-N-(3,4-dimethoxybenzyl)amino)carbonyl)methyl)pyrrolidine-3-carboxylic acid Using the procedures described in Example 1, the title compound was prepared. $^1$H (300 MHz, CDCl$_3$) δ (rotamer) 7.40 (2H, m), 7.30–7.10 (4H, m), 6.90–6.70 (3H, m), 6.48 (1H, m), 5.45 (1H, m), 4.65 (1H, d, J=15), 4.57 (2H, dt, J=9, 3), 4.40–4.00 (5H, m), 3.87 (3.85) (3H, s), 3.84 (1H, m), 3.83 (3.79) (3H, s), 3.56 (2H, m), 3.20 (2H, t, J=10), 2.90 (1H, m), 2.64 (2H, q, J=8), 1.52 (1H, m), 1.31 (2H, m), 1.22 (3H, dt, J=9, 2), 1.07 (1H, m), 0.92 (0.78) (3H, t, J=8). MS (DCI/NH$_3$) m/e 601 (M+H)$^+$. Anal calcd for C$_{36}$H$_{44}$N$_2$O$_6$.1.35 TFA: C, 61.59; H, 6.06; N, 3.71. Found: C, 61.69; H, 6.04; N, 3.63.

EXAMPLE 485 trans,trans-4-(1,3-Benzodioxol-5-yl)-2-(4-methoxyphenyl)-1-(((N-butyl-N-(4-heptyl)amino)carbonyl)methyl)pyrrolidine-3-carboxylic acid Using the procedures described in Example 1, the title compound was prepared. $^1$H NMR (300 MHz, CD$_3$OD) δ 0.71–1.04 (m, 11H), 1.07–1.35 (m, 6H), 1.73–1.53 (m, 4H), 2.79–3.25 (m, 5H), 3.35–3.44 (m, 1H), 3.51–3.68 (m, 3H), 3.78–3.89 (m, 1H), 3.79 (s, 3H), 5.92 (m, 2H), 6.74 (dd, J=1.7, 8.1 Hz, 1H), 6.85 (td, J=1.7, 8.1 Hz, 1H), 6.93 (m, 2H), 7.02 (dd, J=1.7, 9.5 Hz, 1H), 7.36 (m, 2H). MS (C.I.) m/e 553 (M+H$^+$). Anal calcd for C$_{32}$H$_{44}$N$_2$O$_6$: C, 69.54; H, 8.02; N, 5.07. Found: C, 69.31; H, 7.89; N, 5.06.

EXAMPLE 486 trans,trans-2-(4-Methylcyclohexyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as an amorphous solid. $^1$H NMR (CDCl$_3$, 300 MHz) δ 0.88 (3H, d, J=7 Hz), 0.92 (3H, t, J=7 Hz), 0.96 (3H, t, J=7 Hz), 1.05 (1H, m), 1.22–1.40 (7H, m), 1.45–1.65 (6H, m), 1.67–1.84 (4H, m), 3.17–3.45 (6H, m), 3.70 (1H, brm), 3.82 (1H, dd, J=9 Hz, 15 Hz), 3.86 (1H, d, J=15 Hz), 5.93 (2H, s), 6.73 (1H, d, J=8 Hz), 6.78 (1H, dd, J=2 Hz, 8 Hz), 6.88 (1H, d, J=2 Hz). MS (DCI/NH$_3$) m/e 501 (M+H)$^+$. Anal calcd for C$_{29}$H$_{44}$N$_2$O$_5$.0.25 CF$_3$CO$_2$H: C, 66.96; H, 8.43; N, 5.29. Found: C, 66.79; H, 8.60; N, 4.87.

EXAMPLE 487 trans,trans-2-(2-Propylpentyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as an amorphous solid. $^1$H NMR (CDCl$_3$, 300 MHz) δ 0.85 (6H, m), 0.92 (3H, t, J=7 Hz), 0.97 (3H, t, J=7 Hz), 1.12–1.40 (13H, m), 1.42–1.68 (6H, m), 2.90 (1H, m), 3.14–3.30 (2H, m), 3.33 (4H, m), 3.72 (1H, brm), 3.90 (1H, brm), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCI/NH$_3$) m/e 517 (M+H)$^+$. Anal calcd for C$_{30}$H$_{48}$N$_2$O$_5$.0.35 CF$_3$CO$_2$H: C, 66.24; H, 8.76; N, 5.03. Found: C, 66.26; H, 8.82; N, 4.98.

EXAMPLE 488 trans,trans-4-(1,4-Benzodioxan-6-yl)-2-(4-fluorophenyl)-1-(N,N-di(n-butyl)aminocarbonylmethyl)-pyrrolidine-3-carboxylic acid Using the procedures described in Example 1, the title compound was prepared. $^1$H NMR (300 MHz, CD$_3$OD) δ 0.83 (t, J=7 Hz, 3H), 0.89 (t, J=7 Hz, 3H), 0.90–1.17 (m, 4H), 1.20–1.65 (m, 5H), 2.77d (13, 1H), 2.87 (dd, J=8, 2 Hz, 1H), 2.95–3.60 (m, 7H), 3.71 (d, J=9 Hz, 1H), 4.21 (s, 4H), 6.72 (d, 1H), 6.91 (dd, J=8 Hz, 1H), 6.97 (d, J=2 Hz, 1H), 7.05 (t, J=7 Hz, 2H), 7.40–7.50 (m, 2H). MS (DCI) m/e 513 (M+H)⁺. Anal calcd for $C_{29}H_{37}N_2O_5F.1.2C\ F_3COOH$: C, 58.07; H, 5.93; N, 4.31. Found: C, 57.94; H, 5.81; N, 4.56.

EXAMPLE 489 trans,trans-2-(3-Methylpentyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as an amorphous solid. ¹H NMR (CDCl₃, 300 MHz) δ 0.83 (3H, t, J=7 Hz), 0.85 (3H, d, J=7 Hz), 0.91 (3H, t, J=7 Hz), 0.97 (3H, t, J=7 Hz), 1.05–1.22 (2H, m), 1.22–1.41 (7H, m), 1.43–1.68 (5H, m), 1.89 (1H, m), 2.94 (1H, t, J=6 Hz), 3.15–3.27 (3H, m), 3.29–3.60 (5H, m), 3.72 (1H, brd, J=6 Hz), 3.92 (1H, brd, J=13.5 Hz), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCI/NH₃) m/e 489 (M+H)⁺. Anal calcd for $C_{28}H_{44}N_2O_5.0.30\ CF_3CO_2H$: C, 65.70; H, 8.54; N, 5.36. Found: C, 65.93; H, 8.81; N, 4.84.

EXAMPLE 490 trans,trans-2-(2-Ethylbutyl)-4-(1,3-benzodioxol-5-yl)-1-(N,N-di(n-butyl)aminocarbonylmethyl)-pyrrolidine-3-carboxylic acid Using the procedures described in Example 1, the title compound was prepared and isolated as an amorphous solid. ¹H NMR (CDCl₃, 300 MHz) δ 0.85 (6H, m), 0.92 (3H, t, J=7 Hz), 0.97 (3H, t, J=7 Hz), 1.13–1.41 (13H, m), 1.43–1.72 (6H, m), 2.96 (1H, brm), 3.12–3.52 (6H, m), 3.55–3.70 (1H, m), 3.70–3.86 (2H, m), 3.99 (1H, brm), 5.93 (2H, dd, J=2 Hz, 4 Hz), 6.73 (1H, d, J=8 Hz), 6.78 (1H, dd, J=2 Hz, 8 Hz), 6.88 (1H, d, J=2 Hz). MS (DCI/NH₃) m/e 489 (M+H)⁺. Anal calcd for $C_{28}H_{44}N_2O_5.0.45\ CF_3CO_2H$: C, 64.28; H, 8.30; N, 5.19. Found: C, 64.16; H, 8.38; N, 5.08.

EXAMPLE 491 trans,trans-2-(3-Fluoro-4-methoxyphenyl)-4-(1,3-benzodioxol-5-yl)-1-(2-(N-isobutyl-N-(butonesulfonylamino))ethyl)pyrrolidine-3-carboxylic acid Using the procedures described in Example 66, the title compound was prepared. ¹H NMR (CD₃OD, 300 MHz) δ 0.74 (d, 3H, J=7), 0.83 (d, 3H, J=7), 0.94 (t, 3H, J=7), 1.44 (hex, 2H), 1.67 (m, 4H), 2.91 (d, 2H, J=8), 3.04 (dd, 2H, J=8,10), 3.1–3.6 (m, 5H), 3.78 (m, 2H), 3.92 (s, 3H), 4.60 (m, 1H), 5.97 (s, 2H), 6.82 (d, 1H, J=8), 6.89 (dd, 1H, J=2, 8), 7.01 (d, 1H, J=2), 7.22 (t, 1H, J=9), 7.39 (m, 2H). MS (ESI) m/e 579 (M+H)⁺.

EXAMPLE 492 trans,trans-2-(4-Methoxy-3-fluorophenyl)-4-(1,3-benzodioxol-5-yl)-1-[2-(N-propyl-N-(4-ethylpyrimidin-2-yl)amino)ethyl]pyrrolidine-3-carboxylic acid 1-Dimethylamino-1-pentene-3-one, prepared by the method described in Syn. Comm. 12 (1), 35 (1982), was converted to 2-amino-4-ethylpyrimidine with guanidine by the method of Chem. Ber. 97, 3397 (1964). This material was converted to 2-bromo-4-ethyl-pyrimidine with NaNO₂ and HBr, using the method of Helv. Chim. Acta 75, 1629 (1992). This bromopyrimidine was reacted with ethyl 2-(4-methoxphenyl)-4-(1,3-benzodioxol-5-yl)-1-[2-(N-propylamino)propyl]-pyrrolidine-3-carboxylate, prepared using the procedures of Example 61B, using the procedure for Example 418, to give the title compound as a white powder. ¹H NMR (300 MHz, CDCl₃) δ 0.83 (t, J=7 Hz, 3H), 1.11 (t, J=7 Hz, 3H), 1.45 (sextet, J=7 Hz, 2H), 2.18–2.27 (m, 1H), 2.45 (q, J=7 Hz, 2H), 2.80–2.97 (m, 3H), 3.40–3.75 (m, 7H), 3.83 (s, 3H), 5.95 (s, 2H), 6.25 (d, J=4 Hz, 1H), 6.68 (d, J=8 Hz, 1H), 6.79 (dd, J=2 Hz, 8 Hz, 1H), 6.82 (t, J=9 Hz, 1H), 6.92 (d, J=2 Hz, 1H), 7.05 (d, J=9 Hz, 1H), 7.15 (dd, J=2 Hz, 12 Hz, 1H), 8.10 (d, J=4 Hz, 1H).

EXAMPLE 493 trans,trans-4-(1,3-Benzodioxol-5-yl)-2-(4-methoxyphenyl)-1-((N-butyl-N-(3,4-dimethylphenyl)aminocarbonyl)methyl)pyrrolidine-3-carboxylic acid Using the procedures described in Example 1, the title compound was prepared. ¹H NMR (300 MHz, CD₃OD) δ 0.87 (t, J=7.3 Hz, 3H), 1.23–1.36 (m, 2H), 1.38–1.43 (m, 2H), 2.22 (s, 3H), 2.29 (s, 3H), 2.79 (d, J=14.9 Hz, 1H), 2.84 (dd, J=8.6, 9.7 Hz, 1H), 3.16 (t, J=9.5 Hz, 1H), 3.32 (d, J=15.3 Hz, 1H), 3.43–3.61 (m, 4H), 3.79 (s, 3H), 3.88 (d, J=9.8 Hz, 1H), 5.93 (s, 2H), 6.74 (m, 3H), 6.83 (m, 3H), 7.04 (d, J=1.7 Hz, 1H), 7.11 (m, 3H). MS (C.I.) m/e 559(MH⁺). Anal calcd for $C_{33}H_{38}N_2O_6.0.3H_2O$: C, 70.27; H, 6.90; N, 4.97. Found: C, 70.24; H, 6.62; N, 4.58.

EXAMPLE 494 trans,trans-2-(3-Methylpent-3-en-1-yl)-4-(1,3-benzodioxol-5-yl)-1-(N,N-di(n-butyl)aminocarbonylmethyl)-pyrrolidine-3-carboxylic acid Using the procedure described in Example 1, the title compound was prepared and isolated as an amorphous solid. ¹H NMR (CDCl₃, 300 MHz) δ 0.92 (3H, t, J=7 Hz), 0.97 (3H, t, J=7 Hz), 1.22–1.40 (5H, m), 1.44–1.61 (8H, m), 1.82 (1H, brm), 2.02 (2H, m), 3.05–3.30 (4H, m), 3.3.8 (1H, m), 3.55 (1H, brm), 3.85 (2H, m), 4.12 (1H, brd, J=15 Hz), 5.11 (1H, dd, J=6 Hz, 12 Hz), 5.93 (2H, s), 6.73 (1H, d, J=8 Hz), 6.78 (TH, dd, J=2 Hz, 8 Hz), 6.88 (1H, d, J=2 Hz). MS (DCI/NH₃) m/e 487 (M+H)⁺. Anal calcd for $C_{28}H_{42}N_2O_5.0.7\ CF_3CO_2H$: C, 62.34; H, 7.60; N, 4.95. Found: C, 62.49; H, 7.43; N, 4.73.

EXAMPLE 495

1-(N-Phenylaminocarbonylmethyl)-2-(4-methoxyphenyl)-4-(1,3-benzodioxol-5-yl)pyrrolidine-3-carboxylic acid

EXAMPLE 495A

N-Phenylbromoacetamide

To a stirred solution of aniline (7.40 mmol) in methylene chloride (25 mL) at −50° C. was added successively N,N-diisopropylethylamine (1.58 mL, 8.14 mmol, 1.1 eq) and bromoacetyl bromide (0.72 mL, 7.40 mmol, 1 eq) such that the temperature did not exceed −40° C. On completion of the addition, the cooling bath was removed, and the reaction mixture was allowed to warm to room temperature. After stirring for a further 30 minutes, the mixture was diluted with ether (70 mL) and poured into 1 N sodium bisulfate solution. The phases were separated, and the upper layer was washed successively with water and brine. The organic phase was dried ($Na_2SO_4$) and the solvent evaporated to half volume, at which point the product crystallized. The crystals were removed by vacuum filtration to afford the title compound.

EXAMPLE 495B trans,trans-1-(N-Phenylaminocarbonylmethyl)-2-(4-methoxyphenyl)-4-(1,3-benzodioxol-5-yl)pyrrolidine-3-carboxylic acid Using the procedures described in Example 1 and the compound resulting from Exampe 495A, the title compound was prepared. $^1$H NMR (300 MHz, $CDCl_3$) δ 8.8 (bs, 1H) 7.49 (2H, d, J=8 Hz), 7.38 (4H, m), 7.11 (1H, tt, J=8&2 Hz), 6.99 (1H, d, J=2 Hz), 6.91 (2H, d, J=8 Hz), 6.86 (1H, d, J=2 Hz), 6.81 (1H, d, J=8 Hz), 5.99 (1H, d, J=2 Hz), 5.98 (1H, d, J=2 Hz), 3.94 (1H, d, J=10 Hz), 3.78 (3H, s), 3.70 (1H, ddd, J=6, 5&3 Hz), 3.42 (1H, dd, J=10&3 Hz), 3.41 (1H, d, J=16 Hz), 3.18 (1H, dd, J=11 &9 Hz), 3.01 (1H, t, J=10 Hz), 2.93 (1H, d, J=16 Hz). MS (DCI, $NH_3$) m/e 475 (M+H$^+$). Anal. Calc for $C_{27}H_{26}N_2O_6 \cdot 1H_2O$: C, 65.85, H, 5.73, N 5.69, Found: C, 65.95, H, 5.52, N, 5.38.

EXAMPLE 496 trans,trans-1-(N-(2,3-Dimethylphenyl)aminocarbonylmethyl)-2-(4-methoxyphenyl)-4-(1,3-benzodioxol-5-yl)pyrrolidine-3-carboxylic acid Using the procedures described in Example 1, the title compound was prepared. $^1$H NMR (300 MHz, $CDCl_3$) δ 8.68 (1H, bs), 7.64 (d, J=8 Hz), 7.38, (2H, d, J=8 Hz), 7.09 (1H, t, J=8 Hz), 6.97, (1H, d, J=8 Hz), 6.90 (1H, d, J=2 Hz), 6.88 (2H, d, J=8 Hz), 6.82 (1H, dd, J=8&3 Hz), 6.76 (1H, d, J=8 Hz), 5.97 (1H, d, J=2 Hz), 5.96 (1H, d, J=2 Hz), 3.95 (1H, d, J=10 Hz), 3.80 (3H, s), 3.70 (1H, ddd, J=6, 5&3 Hz), 3.48 (1H, dd, J=10&3 Hz), 3.44 (1H, d, J=16 Hz), 3.18 (1H, dd, J=11 &9 Hz), 3.06 (1H, t, J=10 Hz), 2.96 (1H, d, J=16 Hz), 2.31 (3H, s), 2.16 (3H, s). MS (DCI, $NH_3$) m/e 503 (M+H$^+$). Anal. Calc for $C_{29}H_{30}N_2O_6 \cdot 0.5H_2O$: C, 68.09, H, 6.11, N, 5.48. Found: C, 68.13, H, 5.91, N, 5.29.

EXAMPLE 497 trans,trans-1-(N-(2,4-Dimethylphenyl)aminocarbonylmethyl)-2-(4-methoxyphenyl)-4-(1,3-benzodioxol-5-yl)pyrrolidine-3-carboxylic acid Using the procedures described in Example 1, the title compound was prepared. $^1$H NMR (300 MHz, $CDCl_3$) δ 8.60 (1H, bs), 7.78 (d, J=8 Hz), 7.38, (2H, d, J=8 Hz), 6.99 (1H, m), 6.95, (1H, d, J=8 Hz), 6.94 (1H, d, J=2 Hz), 6.88 (2H, d, J=8 Hz), 6.82 (1H, dd, J=8&3 Hz), 6.77 (1H, d, J=8 Hz), 5.97 (1H, d, J=2 Hz), 5.96 (1H, d, J=2 Hz), 3.92 (1H, d, J=10 Hz), 3.79 (3H, s), 3.68 (1H, ddd, J=6, 5&3 Hz), 3.43 (1H, dd, J=10&3 Hz), 3.42 (1H, d, J=16 Hz), 3.18 (1H, dd, J=11 &9 Hz), 3.04 (1H, t, J=-10 Hz), 2.95 (1H, d, J=16 Hz), 2.29 (3H, s), 2.24 (3H, s). MS (DCI, $NH_3$) m/e 503 (M+H$^+$). Anal. Calc for $C_{29}H_{30}N_2O_6 \cdot 0.75H_2O$: C, 67.50, H, 6.15, N 5.43. Found: C, 67.42; H, 5.95; N, 5.13.

EXAMPLE 498 trans,trans-1-(N-(2,5-Dimethylphenyl)aminocarbonylmethyl)-2-(4-methoxyphenyl)-4-(1,3-benzodioxol-5-yl)pyrrolidine-3-carboxylic acid Using the procedures described in Example 1, the title compound was prepared. $^1$H NMR (300 MHz, $CDCl_3$) δ 8.62 (1H, bs), 7.79 (1H, bs), 7.38, (2H, d, J=8 Hz), 7.03 (1H, d, J=8 Hz), 6.95, (1H, d, J=8 Hz), 6.94 (1H, d, J=2 Hz), 6.88 (2H, d, J=8 Hz), 6.82 (1H, dd, J=8&3 Hz), 6.77 (1H, d, J=8 Hz), 5.97 (2H, s), 3.92 (1H, d, J=10 Hz), 3.78 (3H, s), 3.70 (1H, ddd, J=6, 5&3 Hz), 3.48 (1H, dd, J=10&3 Hz), 3.42 (1H, d, J=16 Hz), 3.18 (1H, dd, J=11 &9 Hz), 3.04 (1H, t, J=10 Hz), 2.95 (1H, d, J=16 Hz), 2.29 (3H, s), 2.24 (3H, s). MS (DCI, $NH_3$) m/e 503 (M+H$^+$). Anal. Calc for $C_{29}H_{30}N_2O_6 \cdot 0.5H_2O$: C, 68.09; H, 6.11; N, 5.48. Found: C, 67.72; H, 5.89; N, 5.25.

EXAMPLE 499 trans,trans-1-(N-(3,4-Dimethylphenyl)aminocarbonylmethyl)-2-(4-methoxyphenyl)-4-(1,3-benzodioxol-5-yl)pyrrolidine-3-carboxylic acid Using the procedures described in Example 1, the title compound was prepared. $^1$H NMR (300 MHz, $CDCl_3$) δ 8.73 (1H, bs), 7.38 (2H, bd, J=8 Hz), 7.30, (1H, d, J=3 Hz), 7.20 (1H, bs), 7.08, (1H, d, J=8 Hz), 7.01 (1H, bs), 6.90 (2H, d, J=8 Hz), 6.85 (1H, bs), 6.80 (1H, d, J=8 Hz), 5.99 (1H, d, J=3 Hz), 5.98 (1H, d, J=3 Hz), 3.92 (1H, d, J=10 Hz), 3.78 (3H, s), 3.70 (1H, ddd, J=6, 5&3 Hz), 3.48 (1H, dd, J=10&3 Hz), 3.42 (1H, d, J=16 Hz), 3.18 (1H, dd, J=11 &9 Hz), 3.04 (1H, t, J=10 Hz), 2.95 (1H, d, J=16 Hz), 2.25 (3H, s), 2.21 (3H, s). MS (DCI, $NH_3$) m/e 503 (M+H$^+$). Anal. Calc for $C_{29}H_{30}N_2O_6 \cdot 0.75H_2O$: C, 67.50; H, 6.15; N, 5.43. Found: C, 67.24; H, 5.94; N, 5.20.

EXAMPLE 500 trans,trans-1-(N-(3,5-Dimethylphenyl)aminocarbonylmethyl)-2-(4-methoxyphenyl)-4-(1,3-benzodioxol-5-yl)pyrrolidine-3-carboxylic acid Using the procedures described in Example 1, the title compound was prepared. $^1$H NMR (300 MHz, $CDCl_3$) δ 8.75 (1H, bs), 7.35, (2H, d, J=8 Hz), 7.10 (2H, s), 7.02 (1H, d, J=3 Hz), 6.90 (2H, d, J=8 Hz), 6.84 (1H, d, J=2 Hz), 6.80, (1H, d, J=8 Hz), 6.76 (1H, bs), 5.99 (1H, d, J=3 Hz), 5.98 (1H, d, J=3 Hz), 3.92 (1H, d, J=10 Hz), 3.79 (3H, s), 3.68 (1H, ddd, J=6, 5&3 Hz), 3.40 (2H, m), 3.18 (1H, dd, J=11 &9 Hz), 2.98 (1H, t, J=10 Hz), 2.88 (1H, d, J=16 Hz), 2.3 (6H, s). MS (DCI, $NH_3$) m/e 503 (M+H$^+$). Anal. Calc for $C_{29}H_{30}N_2O_6 \cdot 0.5H_2O$: C, 68.09; H, 6.11; N, 5.48. Found: C, 67.93; H, 6.01; N, 5.19.

EXAMPLE 501

Alternate Preparation of (+)-trans,trans-1-(N,N-Di (n-butyl)aminocarbonylmethyl)-2-(4-methoxyphenyl)-4-(1,3-benzodioxol-5-yl)pyrrolidine-3-carboxylic acid Hydrochloride Salt

EXAMPLE 501A

N,N-Dibutyl bromoacetamide

To a solution of bromoacetyl bromide (72.3 mL, 830 mmol) in toluene (500 mL) cooled to 0° C. was added a solution of dibutylamine (280.0 mL, 1.66 mol) in toluene (220 mL) via an addition funnel maintaining the reaction temperature below 10° C. Upon completion of the addition, the reaction mixture was stirred at 0° C. for 15 minutes. A solution of 2.5% aqueous $H_3PO_4$ (500 mL) was slowly introduced, and the reaction mixture was allowed to warm to room temperature with vigorous stirring. The solution is 2.5% phosphoric acid by weight. The layers were separated and the organic phase washed with water (500 mL) and concentrated to provide the bromoacetamide as a solution in toluene.

EXAMPLE 501B 5-(2-Nitrovinyl)-1,3-benzodioxole

To piperonal (15.55 kg, 103.5 mol) under mechanical stirring and under nitrogen was added ammonium acetate (13.4 kg, 173.8 mol), acetic acid (45.2 kg), and nitromethane (18.4 kg, 301.4 mol) sequentially. The mixture was warmed to 70° C. After about 30 minutes, the yellow product began to crystallize. The reaction temperature was raised to 80° C. and stirred for about 10 hours until minimal piperonal remains. The somewhat thick reaction mixture was cooled to 10° C. and filtered. The precipitate was washed with acetic acid (2×8 kg) and then water (2×90 kg). The product was dried under a nitrogen purge and then in a vacuum oven at 50° C. for 2 days to afford 15.94 kg (80%) of the title compound as a bright yellow solid.

EXAMPLE 501C

4-Methoxybenzoyl acetate

To potassium t-amylate (25 wt %, 50.8 kg, 99.26 mol) in toluene (15.2 kg) cooled to 5° C. under mechanical stirring and under nitrogen was added a mixture of 4-methoxyacetophenone (6.755 kg, 44.98 mol) and diethyl carbonate (6.40 kg, 54.18 mol) in toluene over 1 hour maintaining the temperature below 10° C. The reaction mixture was heated to 60° C. for 8 hours until no 4-methoxyacetophenone was detected by HPLC. The mixture was cooled to 20° C. and quenched by adding to a mixture of acetic acid (8 kg) and water (90 kg) over 30 minutes while maintaining the temperature at <20° C. The layers were separated, and the organic layer was washed with 5% sodium bicarbonate solution (41 kg) and concentrated to 14.65 kg. The temperature is maintained below 50° C. during the distillation. The yellow product concentrate was assayed by HPLC against an external standard and the yield was found to be 9.40 kg (94%).

EXAMPLE 501D

Ethyl 2-(4-methoxybenzoyl)-4-nitromethyl-3-(1,3-benzodioxol-5-yl)butyrate

To the compound resulting from Example 501B (7.5 kg, 37.9 mol) suspended in THF (56 kg) with mechanical stirring under nitrogen was added the compound resulting from Example C (8.4 kg, 37.9 mol). The mixture was cooled to 17° C., sodium ethoxide (6.4 g, 0.095 mol) was added, and the reaction was stirred for 30 minutes. After about 15 minutes, the nitrostyrene was completely dissolved. Sodium ethoxide (6.4 g, 0.095 mol) was added, and the mixture was stirred at 25° C. until HPLC shows less than 1 area % ketoester remaining. The reaction was concentrated to 32.2 kg which was determined by HPLC assay to be ~14.9 kg (95%).

EXAMPLE 501E

Ethyl cis, cis-2-(4-methoxyphenyl)-4-(1,3-benzodioxol-5-yl)pyrrolidine-3-carboxylate Raney nickel (20.0 g), from which the water had been decanted, was charged to a stirred hydrogenator equipped with a thermocouple. THF (20 mL), the crude compound resulting from Example 501 D (40.82 g, 0.0482 mol), and acetic acid (2.75 mL, 0.0482 mol) were added sequentially. The mixture was put under a hydrogen atmosphere at 60 psi until the hydrogen uptake slowed dramatically. TFA was added, and the mixture was hydrogenated at 200 psi until HPLC shows no residual imine and <2 area % nitrone. The catalyst was filtered away and washed with 100 mL of methanol. The filtrate was assayed by HPLC and found to contain 13.3 g (75% yield) of the cis, cis-pyrrolidine compound. The filtrate was concentrated and chased with additional THF (200 mL) to give a final volume of 100 mL. The mixture was neutralized with 2 N NaOH solution (50 mL), diluted with water (200 mL), and extracted with ethyl acetate (2×100 mL). The combined nearly colorless ethyl acetate layers were assayed against an external standard by HPLC to be 13.0 g (73%) of the title compound.

EXAMPLE 501F

Ethyl trans,trans-2-(4-methoxyphenyl)-4-(1,3-benzodioxol-5-yl)pyrrolidine-3-carboxylate The solution of the compound resulting from Example 501E (38.1 g, 0.103 mol) was chased with ethanol (200 mL) to a final volume of 100 mL and sodium ethoxide (3.40 g, 0.050 mol) was added. The mixture was heated to 75° C. When HPLC shows <3% of the cis,cis isomer remaining, the mixture was cooled to room temperature. The product was assayed by HPLC against an external standard and found to contain 34.4 g (90% yield) of the title compound. The crude compound solution was concentrated and the residue taken up in isopropyl acetate (400 mL). The organic layer was washed with water (2×150 mL) and then extracted with 0.25 M phosphoric acid solution (2×400 mL). The combined phosphate layers were stirred with ethyl acetate (200 mL) and neutralized to pH 7 with solid sodium bicarbonate (21 g). The organic layer was separated and found to contain 32.9 g (87%) of the title compound.

EXAMPLE 501G

Ethyl (2R,3R,4S)-(+)-2-(4-methoxyphenyl)-4-(1,3-benzodioxol-5-yl)pyrrolidine-3-carboxylate, (S)-(+) mandelate salt The solution resulting from Example 501F was chased with acetonitrile (100 mL) to give a final volume of 50 mL. (S)-(+)-Mandelic acid (2.06 g, 0.0136 mmol) was added and allowed to dissolve. The mixture was seeded with the product and allowed to stir at room temperature for 16 hours. The reaction mixture was cooled to 0° C. and stirred for 5 hours. The product was filtered and dried in a vacuum oven with a nitrogen purge for 1 day at 50° C. to give 5.65 g (40%) of the title compound. The purity of the product can be determined by chiral HPLC using Chiralpak AS, isocratic elution with 95:5:0.05 hexane-ethanol-diethylamine; flow –1 mL/min.; UV detection at 227 nm. Retention times: (+)-enantiomer: 15.5 min.; (–)-enantiomer: 21.0 min.

EXAMPLE 501H (2R,3R,4S)-(+)-2-(4-methoxyphenyl)-4-(1,3-benzo-dioxol-5-yl)-1-(N,N-di(n-butyl)aminocarbonylm-ethyl)-pyrrolidine-3-carboxylic acid The compound resulting from Example 501G (20.0 g, 0.0383 mol) was suspended in ethyl acetate (150 mL) and 5% sodium bicarbonate solution (150 mL). The mixture was stirred at room temperature until the salt dissolved and carbon dioxide evolution had ceased. The organic layer was separated and concentrated. The residue was chased with acetonitrile (200 mL) to a final volume of 100 mL and cooled to 10° C. Diisopropylethylamine (11.8 mL, 0.0574 mol) and the compound resulting from Example A (10.5 g, 0.0421 mol) were added, and the mixture was stirred for 12 hours at room temperature. The reaction mixture was concentrated and chased with ethanol (200 mL) to a final volume of 100 mL. Sodium hydroxide solution (40%, 20 mL, 0.200 mol) was added, and the mixture was heated at 60° C. for 4 hours until HPLC showed no starting material remaining. The reaction mixture was poured into water (400 mL) and washed with hexanes (2×50 mL). The aqueous layer was washed with hexane (2×20 mL). A stirred mixture of the aqueous layer and ethyl acetate (400 mL) was neutralized to pH 5 with concentrated HCl (12 mL). The organic layer was separated and found to contain 18.3 g (94% yield) of the title compound.

EXAMPLE 501I (2R,3R,4S)-(+)-2-(4-methoxyphenyl)-4-(1,3-benzo-dioxol-5-yl)-1-(N,N-di(n-butyl)aminocarbonylm-ethyl)-pyrrolidine-3-carboxylic acid hydrochloride salt To a solution of the compound of Example 501H in ethyl acetate at room temperature in a mechanically stirred vessel equipped with a thermocouple, was added 39.4 mL of 1 N HCl in ethanol (0.0394 mol) The resultant solution was filtered to remove foreign matter, concentrated in vacuo, and chased with ethyl acetate (400 mL). The solution was seeded repeatedly, as the solvent was removed, until crystallization was initiated. The mixture was concentrated to a volume of 100 mL, and the product was filtered and washed with ethyl acetate (25 mL). The resultant white solid was dried in a vacuum oven under a nitrogen purge at 50° C. to afford 17.6 g (90%) of the title compound.

EXAMPLE 502 trans,trans-2-(2-Methylpentyl)-4-(1,3-benzodioxol-5-yl)-1-(N,N-di(n-butyl)aminocarbonylmethyl)-Pyr-rolidine-3-carboxylic acid

EXAMPLE 502A (±)-Ethyl 3-methylhexanoate

To a slurry of 60% sodium hydride (2.26 g, 57 mmol) in 10 mL of hexanes and 100 mL of diethyl ether was added triethylphosphonoacetate (10.3 mL, 52 mmol). Once gas evolution ceased, 2-pentanone (6.0 mL 64 mmol) was added. After 3 hours at room temperature, the reaction was quenched with water, and partitioned into ether. The organic layer was washed with water and brine, dried with anhydrous sodium sulfate, filtered, and the solvent was removed under reduced pressure. The residue was dissolved in 50 mL of ethanol and 10% palladium on carbon (6.0 g) was added. The vessel was pressurized to 4 atmosphere of hydrogen, and was shaken at room temperature for 3 hours. The reaction was filtered and the solvent was removed under reduced pressure to give 3.0 g of the title compound.

EXAMPLE 502B (±)-Ethyl 5-methyl-3-oxooctanoate

To a solution of ethyl 3-methylhexanoate in 150 mL of ethanol was added sodium hydroxide (2.3 g, 57.6 mmol). After 48 hours at room temperature, solvent was removed under reduced pressure, and the residue was dissolved in 150 mL of water. The solution was washed with ether, then acidified with concentrated hydrochloric acid and washed with methylene chloride. The organic layer was dried with anhydrous magnesium sulfate, filtered, and the solvent was removed under reduced pressure to give 2.7 g of the corresponding acid from which 3.9 g of the title compound was prepared by the method of Bram and Vilkas, *Bul. Chem. Soc. Fr.*, 945 (1964).

EXAMPLE 502C trans,trans-2-(2-Methylpentyl)-4-(1,3-benzodioxol-5-yl)-1-(N,N-di(n-butyl)aminocarbonylmethyl)-pyr-rolidine-3-carboxylic acid Using the procedures described in Example 1 and substituting ethyl 5-methyl-3-oxooctanoate for ethyl (4-methoxy-benzoyl)acetate afforded the title compound, which was isolated by lyophilization from dilute aqueous TFA/CH$_3$CN. Note that the multiplicity of the signals in the aryl region of the NMR spectrum reflects a 1:1 mixture of diastereomers on the alkyl chain. $^1$H NMR (CDCl$_3$, 300 MHz) δ 0.8–1.0 (m, 12H), 1.2–1.4 (m, 7H), 1.45–1.6 (m, 6H), 1.6–1.74 (m, 1H), 1.8–2.0 (m, 1H), 3.1–3.4 (m, 5H), 3.67–3.78 (m, 1H), 3.8–3.91 (m, 1H), 4.0–4.2 (m, 2H), 4.3–4.5 (m, 2H), 5.93 (d, J=1.5 Hz, 2H), 6.73 (dd, J=8.1, 1.2 Hz, 1H), 6.79 (ddd, J=7.8, 1.8, 1.8 Hz, 1H), 6.86 (dd, J=3.9, 1.5 Hz, 1H). MS (DCI/NH$_3$) m/e 489 (M+H)$^+$. Anal calcd for C$_{28}$H$_{44}$N$_2$O$_5$.1.0 TFA.0.5H$_2$O: C, 58.91; H, 7.58; N, 4.58. Found: C, 58.91; H, 7.58; N, 4.45.

EXAMPLE 503 trans,trans-2-(2,2-Dimethylpentyl)-4-(1,3-benzo-dioxol-5-yl)-1-(N,N-di(n-butyl)aminocarbonylm-ethyl)-pyrrolidine-3-carboxylic acid Ethyl 3,3-dimethylhexanoate was prepared using the general procedure of Cahiez et al., *Tetrahedron Lett.*, 31, 7425 (1990). Using the procedures described in Example 502 and substituting ethyl 3,3-dimethylhexanoate for ethyl 3-methylhexanoate afforded the title compound, which was isolated by lyophilization from dilute aqueous TFA/CH$_3$CN. $^1$H NMR (CDCl$_3$, 300 MHz) δ 0.80–0.99 (m, 15H), 1.10–1.37 (m, 8H), 1.43–1.58 (m, 4H), 1.77–1.97 (m, 2H), 3.48–3.12 (m, 5H), 3.60–3.69 (m, 1H), 3.75–3.86 (m, 1H), 3.95–4.16 (m, 2H), 4.28–4.4 (m, 2H), 5.94 (s, 2H), 6.74 (d, J=7.8 Hz, 1H), 6.8 (dd, J=8.1, 1.5 Hz, 1H), 6.87 (d, J=1.8 Hz, 1H). MS (DCI/NH₃) m/e 503 (M+H)⁺. Anal calcd for $C_{29}H_{46}N_2O_5 \cdot 1.05$ TFA: C, 60.01; H, 7.62; N, 4.50. Found: C, 60.21; H, 7.37; N, 4.33.

EXAMPLE 504 trans,trans-2-(2-(1,3-Dioxo-2-yl)ethyl)-4-(1,3-benzodioxol-5-yl)-1-(N,N-di(n-butyl)aminocarbonylmethyl)-pyrrolidine-3-carboxylic acid

EXAMPLE 504A

Ethyl 5-(1,3-dioxolyl)-3-oxopentanoate

The title compound was synthesized from ethyl acetoacetate and 2-bromomethyl-1,3-dioxane, according to the procedure of Huckin and Weiler, Tetrahedron Lett. 3927, (1971).

Sodium hydride 4.97 g (0.124 mol), as a 60% mineral oil dispersion, was weighed into a 250 mL flask, into which 80 ml of tetrahydrofuran was directly added. The flask was capped with septum cap, flushed with nitrogen, and cooled in an ice bath. To above stirred slurry was added dropwise 15.0 mL (0.118 mol) ethyl acetoacetate. After the addition was complete, the resulting mixture was stirred at 0° C. for additional 10 min. To above mixture was then added 48.4 mL (0.121 mol) n-butyl lithium, a 2.50 M solution in hexane, in a dropwise manner. The resulting orange color solution was stirred for 10 min before 13.5 mL (0.130 mol) bromomethyl-1,3-dioxane was added in one portion. The reaction mixture was then allowed to warm to room temperature and stirred for additional 120 min before it was then quenched by slow addition of 9.8 ml (ca. 0.12 mol) concentrated hydrochloric acid. The biphasic mixture was poured to 50 ml of water and extracted with 150 ml of ethyl ether. The aqueous layer was extracted thoroughly with additional ethyl ether. The ethereal extracts were combined, washed with 2×50 ml of saturated brine, dried over anhydrous magnesium sulfate, filtered and evaporated under reduced pressure to give an brown oily residue. The crude product was purified using silica gel flash chromatography eluting with 20% ether/hexane to give 5.40 g (20%) of b-keto ester as a light yellow oil.

EXAMPLE 504C trans,trans-2-(2-(1,3-Dioxo-2-yl)ethyl)-4-(1,3-benzodioxol-5-yl)-1-(N,N-di(h-butyl)aminocarbonylmethyl)-pyrrolidine-3-carboxylic acid Using the procedures described in Example 502 and substituting ethyl 5-(1,3-dioxolyl)-2-oxopentanoate for ethyl 3-methylhexanoate afforded the title compound. ¹H NMR (CDCl₃, 300 MHz) δ 0.93 (t, J=7.2 Hz, 3H), 0.95 (t, J=7.2 Hz, 3H), 1.23–1.38 (m, 4H), 1.52 (sextet, J=7.9 Hz, 4H), 1.85–1.95 (m, 2H), 2.02–2.17 (m, 2H), 3.18 (dd, J=6.0 Hz, 9.0 Hz, 2H), 3.30 (dd, J=9.0 Hz, 18.0 Hz, 2H), 3.35 (m, 1H), 3.79 (dd, J=3.6 Hz, 6.9 Hz, 1H), 3.83–3.88 (m, 3H), 3.97 (dd, J=4.8 Hz, 6.0 Hz, 1H), 4.05 (q, J=9.6 Hz, 2H), 4.30–4.40 (m, 1H), 4.37 (s, 2H), 4.87 (t, J=3.6 Hz, 1H), 5.94 (s, 2H), 6.73 (d, J=8.1 Hz, 1H), 6.79 (dd, J=1.8 Hz, 8.1 Hz, 1H), 6.87 (d, J=1.8 Hz, 1H). MS (APCI) (M+H)+at m/e 505. Anal calcd for $C_{27}H_{40}N_2O_7 \cdot 1.2$ TFA: C, 55.05; H, 6.47; N, 4.37. Found: C, 55.12; H, 6.44; N, 4.27.

EXAMPLE 505 trans,trans-2-(2-(2-Tetrahydro-2H-pyran)ethyl)-4-(1,3-benzodioxol-5-yl)-1-(N,N-di(n-butyl)aminocarbonylmethyl)-pyrrolidine-3-carboxylic acid

EXAMPLE 505A

Ethyl 5-(2-tetrahydro-2H-pyran)-3-oxopentanoate

Using the procedure of Huckin and Weiler, Tetrahedron Lett. 3927, (1971), the title compound was prepared from ethyl acetoacetate and 2-(bromomethyl)tetrahydro-2H-pyran as a light yellow oil.

EXAMPLE 505B trans,trans-2-(2-(2-Tetrahydro-2H-pyran)ethyl)-4-(1,3-benzodioxol-5-yl)-1-(N,N-di(n-butyl)aminocarbonylmethyl)-pyrrolidine-3-carboxylic acid Using the procedures described in Example 502 and substituting ethyl 5-(2-tetrahydro-2H-pyran)-2-oxopentanoate for ethyl 3-methylhexanoate afforded the title compound as an amorphous solid. ¹H NMR (CDCl₃, 300 MHz) as a mixture of two diastereoisomers: δ 0.89 (t, J=8.1 Hz, 3H), 0.89 (t, J=8.1 Hz, 3H), 0.91 (t, J=8.1 Hz, 3H), 0.91 (t, J=8.1 Hz, 3H), 1.20–1.40 (m, 10H), 1.42–1.66 (m, 18H), 1.71 (brm, 2H), 1.85 (brm, 2H), 1.96–2.23 (brm, 4H), 3.10–3.29 (m. 8H), 3.29–3.52 (m, 6H), 3.54–3.81 (m, 6H), 4.01 (q, J=9 Hz, 2H), 4.12–4.25 (m, 4H), 4.43 (d, J=9 Hz, 2H), 4.50 (d, J=2.7 Hz, 2H), 5.94 (s, 2H), 5.95 (s, 2H), 6.76 (s, 2H), 6.76 (s, 2H), 6.81 (s, 1H), 6.81 (s, 1H). MS (APCI) (M+H)+at m/e 517. Anal calcd for $C_{29}H_{44}N_2O_6 \cdot 1.4$ TFA: C, 56.48; H, 6.77; N, 4.14. Found: C, 56.46; H, 6.99; N, 3.83.

EXAMPLE 506 trans,trans-2-(2,2,4-Trimethyl-3-pentenyl)-4-(1,3-benzodioxol-5-yl)-1-(N,N-di(n-butyl)aminocarbonylmethyl)-pyrrolidine-3-carboxylic acid

EXAMPLE 506A

Methyl 3,3,5-trimethyl-4-hexenoate

To a slurry of isopropyltripenylphosphonium iodide (20.5 g, 47 mmol) in 200 mL of tetrahydrofuran was added n-butyllithium (27 mL of a 1.6M solution in hexane, 43 mmol), and the solution was briefly warmed to 0° C. After recooling, a solution of methyl 3,3-dimethyl-4-oxobutenoate (5.7 g, 40 mmol), prepared according to the procedure of Hudlicky et al., Synth. Commun., 16 169 (1986) in 10 mL of tetrahydrofuran was added, and the reaction was warmed to 0° C. for 30 min. The reaction was quenched with dilute hydrochloric acid, and partitioned with ethyl acetate. The organic layer was washed with water, and brine, dried with anhydrous magnesium sulfate, filtered, and the solvent was removed under reduced pressure. The residue was purified by flash chromatography on silica gel eluting with 10% ethyl acetate in hexanes to give 2.1 g (30%) of the title compound.

EXAMPLE 506B trans,trans-2-(2,2,4-Trimethyl-3-Pentenyl)-4-(1,3-benzodioxol-5-yl)-1-(N,N-di(n-butyl)aminocarbonylmethyl)-pyrrolidine-3-carboxylic acid Using the procedures described in Example 502 and substituting methyl 3,3,5-trimethyl-4-hexenoate for ethyl 3-methylhexanoate afforded the title compound, which was isolated by lyophilization from dilute aqueous TFA/CH$_3$CN. $^1$H NMR (CDCl$_3$, 300 MHz) δ 0.92 (t, J=7.2 Hz, 3H), 0.94 (t, J=7.2 Hz, 3H), 1.11 (s, 3H), 1.13 (s, 3H), 1.24–1.37 (m, 4H), 1.46–1.59 (m, 4H), 1.61 (d, J=1.2 Hz, 3H), 1.69 (d, J=1.2 Hz, 3H), 2.04–2.11 (m, 2H), 3.10–3.20 (m, 2H), 3.30–3.39 (m, 3H), 3.67–3.82 (m, 2H), 3.95–4.08 (m, 1H), 4.32 (m, 2H), 4.37–4.47 (m, 1H), 4.99 (s, 1H), 5.95 (s, 2H), 6.73 (d, J=7.8 Hz, 1H), 6.78 (dd, J=8.4, 1.2 Hz, 1H), 6.84 (d, J=1.2 Hz, 1H). MS (DCI/NH$_3$) m/e 515 (M+H)$^+$. Anal calcd for C$_{30}$H$_{46}$N$_2$O$_5$.1.05 TFA: C, 60.77; H, 7.48: N, 4.42. Found: C, 60.83; H, 7.20; N, 4.43.

EXAMPLE 507 trans,trans-2-(2,2,-Dimethyl-2-(1,3-dioxolan-2-yl) ethyl)-4-(1,3-benzodioxol-5-yl)-1-(N,N-di(n-butyl) aminocarbonylmethyl)-pyrrolidine-3-carboxylic acid

EXAMPLE 507A

Methyl 3,3-dimethyl-3-(1,3-dioxolan-2-yl)propanoate

Methyl 3,3-dimethyl-4-oxobutanoate (10 g, 70 mmol), prepared according to the procedure of Hudlicky et al., Synth. Commun., 16 169 (1986), was dissolved in 40 mL of benzene, followed by addition of ethylene glycol (20 mL), and p-toluenesulfonic acid monohydrate (1.3 g). The reaction was refluxed with azeotropic removal of water for 1 hour. The reaction was poured into 200 mL of ether, washed with saturated sodium bicarbonate, water and brine, dried with anhydrous magnesium sulfate, filtered, and the solvent was removed under reduced pressure to give 12.4 g (94%) of the title compound.

EXAMPLE 507B trans,trans-2-(2,2,-Dimethyl-2-(1,3-dioxolan-2-yl) ethyl)-4-(1,3-benzodioxol-5-yl)-1-(N,N-di(n-butyl) aminocarbonylmethyl)-pyrrolidine-3-carboxylic acid Using the procedures described in Example 502 and substituting methyl 3,3-dimethyl-3-(1,3-dioxolan-2-yl)propanoate for ethyl 3-methylhexanoate afforded the title compound, which was isolated by lyophilization from dilute aqueous TFA/CH$_3$CN. $^1$H NMR (CDCl$_3$, 300 MHz) δ 0.82–1.00 (m, 12H), 1.24–1.40 (m, 4H), 1.43–1.64 (m, 5H), 1.76–1.84 (m, 1H), 2.93–3.00 (m, 1H), 3.15–3.47 (m, 6H), 3.60–3.70 (m, 3H), 3.74–3.95 (m, 5H), 4.48 (s, 1H), 5.94 (m, 2H), 6.72 (d, J=8.0 Hz, 1H), 6.83 (dd, J=8.0, 1.2 Hz, 1H), 6.94 (d, J=1.2 Hz, 1H). MS (DCI/NH$_3$) m/e 533 (M+H)$^+$. Anal calcd for C$_{29}$H$_{44}$N$_2$O$_7$.1.1 TFA.0.2H$_2$O: C, 56.63; H, 6.93; N, 4.23. Found: C, 56.60; H, 6.96; N, 4.25.

EXAMPLE 508 trans,trans-2-(2-(1,3-Dioxo-2-yl)ethyl)-4-(1,3-benzodioxol-5-yl)-1-[[N-4-heptyl-N-(2-methyl-3-fluorophenyl)]amino carbonylmethyl]-pyrrolidine-3-carboxylic acid

EXAMPLE 508A

4-Heptanol

To an ice cooled solution of 1.14 g (10.0 mmol) of 4-heptanone in 20 mL of diethyl ether was added 370 mg (10.0 mmol) of LiAlH$_4$, in portions to keep ether reflux at a minimum. After 45 minutes, the reaction was quenched by sequential dropwise addition of 0.4 mL H$_2$O, 0.4 mL 15% (w/v) NaOH$_{(aq)}$, and 1.2 mL H$_2$O. After stirring another 45 minutes, MgSO$_4$ was added until the salts were free flowing, then the reaction was filtered. The salts were washed with diethyl ether (3×5 mL), then the filtrate and washings were concentrated to a colorless oil. Yield 1.16 g (100%).

EXAMPLE 508B

4-Methanesulfonyloxyheptane

To an ice cooled solution of 834 mg (7.19 mmol) of 4-heptanol in 35 mL of CH$_2$Cl$_2$ was added 1.5 mL of triethylamine. Next, 0.7 mL (9 mmol) of methanesulfonyl chloride was added, dropwise, over 1 minute. The mixture was stirred at 0° C. for 30 minutes, then extracted with H$_2$O (1×15 mL), 5% NH$_4$OH (2×15 mL), 1M HCl (2×15 mL), and brine (1×15 mL), dried over MgSO$_4$, filtered, and concentrated to an oil. Yield 1.31 g (94%). $^1$H NMR (300 MHz, CDCl$_3$) d 0.96 (t, 6, J=9), 1.43 (m, 4), 1.64 (m, 4), 3.00 (s, 3), 4.73 (quintet, 1 J=5).

EXAMPLE 508C

4-Fluoro-3-methylaniline

To a solution of 20 g (129 mmol) of 2-fluoro-5-nitrotoluene in 400 mL of ethanol was added 2 g of 10% Pd—C. The mixture was shaken under 45 P.S.I. H$_2$ until hydrogen uptake ceased. The catalyst was filtered away and washed with ethanol, then the combined filtrate and washings were concentrated to 15.2 g (94%) of a colorless oil.

EXAMPLE 508D

N-Heptyl-4-fluoro-3-methylaniline

To a solution of 4.10 g (3.28 mmol) of 4-fluoro-3-methylaniline in 30 mL of acetonitrile was added 7.64 g (3.93 mmol) of 4-methanesulfonyloxyheptane, and 3.4 g (4.1 mmol) of NaHCO$_3$(s). The mixture was stirred at reflux for 24 hours, then poured into 150 mL of H$_2$O and extracted with diethyl ether (2×30 mL). The combined ether layers were back extracted with brine (1×30 mL), dried over MgSO$_4$, filtered, and concentrated to an oil. This was purified via silica gel chromatography, eluting with 97.5:2.5 hexanes:ethyl acetate, to give 2.56 g (35%) of a pale yellow oil.

EXAMPLE 508E

N,N-(4-Heptyl)-(4-fluoro-3-methyl)phenylbromoacetamide

To an ice cooled solution of 4.88 g (21.9 mmol) of N-(4-heptyl)-4-fluoro-3-methylaniline and 4.9 mL (61 mmol) of pyridine in 100 mL of toluene was added a solution of 4.90 mL (56.2 mmol) of bromoacetyl bromide in 7 mL of toluene. The solution was stirred for 24 hours, gradually warming to 25° C., then extracted with 1M HCl (1×100 mL). The aqueous layer was back extracted with diethyl ether (1×50 mL), then the combined organic layers were washed with H$_2$O (2×50 mL), saturated NaHCO$_{3(aq)}$ (2×50 mL), and brine (1×50 mL), dried over MgSO$_4$, filtered, and concentrated in vacuo to an oil. This was purified via silica gel chromatography, eluting with 90:10 hexanes:ethyl acetate to give 7.48 g (99%) of a light yellow oil. $^1$H NMR (300 MHz, CDCl$_3$) δ 0.94 (t, 6, J=5), 1.33 (m, 4), 1.43 (m, 4), 2.30 (s, 1.5), 2.31 (s, 1.5), 3.54 (s, 2), 4.72 (quintet, 1, J=5), 6.96–7.04 (m, 2), 7.07(d, 1, J=7).

EXAMPLE 508F trans,trans-2-(2-(1,3-Dioxol-2-yl)ethyl)-4-(1,3-benzodioxol-5-yl)-1-[[N-4-heptyl-N-(2-methyl-3-fluorophenyl)]amino carbonylmethyl]-pyrrolidine-3-carboxylic acid Using the procedures described in Example 502, substituting ethyl 5-(1,3-dioxolyl)-2-oxopentanoate for ethyl 3-methylhexanoate and N,N-(4-heptyl)-(4-fluoro-3-methyl)phenyl-bromoacetamide for N,N-dibutylbromoacetamide afforded the title compound as an amorphous solid. $^1$H NMR (CDCl$_3$, 300 MHz) δ 0.93 (brt, 6H), 1.23–1.47 (m, 8H), 1.67–2.10 (m, 4H), 2.32 (s, 3H), 3.16 (t, J=9.0 Hz, 1H), 3.52–3.67 (brm, 2H), 3.73 (t, J=9.0 Hz, 1H), 3.81–4.02 (m, 6H), 4.13 (brm, 1H), 4.72 (quintet, J=6.9 Hz, 1H), 4.86 (t, J=4.0 Hz, 1H), 5.93 (s, 2H), 6.72 (d, J=8.1 Hz, 1H), 6.78 (dd, J=1.8, 8.1 Hz, 1H), 6.85 (d, J=1.8 Hz, 1H), 6.96 (m, 2H), 7.08 (t, J=9.0 Hz, 1H). MS (DCI/NH$_3$) (M+H)$^+$ at m/e 599. Anal Calcd for C$_{33}$H$_{43}$N$_2$O$_7$F.0.8 TFA: C, 60.24; H, 6.40; N, 4.06. Found: C, 60.21; H, 6.14; N, 3.86.

EXAMPLE 509 trans,trans-2-(2-(1,3-Dioxol-2-yl)ethyl)-4-(1,3-benzodioxol-5-yl)-1-(N,N-di(n-butyl)aminocarbonylmethyl)-pyrrolidine-3-carboxylic acid Using the procedures described in Example 502, substituting ethyl 5-(1,3-dioxolyl)-2-oxopentanoate for ethyl 3-methylhexanoate and 6-methoxypiperonal for piperonal afforded the title compound as an amorphous solid. $^1$H NMR (CDCl$_3$, 300 MHz) δ 0.93 (t, J=7.8 Hz, 3H), 0.95 (t, J=7.8 Hz, 3H), 1.31 (m, 4H), 1.53 (m, 4H), 1.90 (m, 2H), 2.09 (m, 2H), 3.19 (dd, J=8.4 Hz, 8.4 Hz, 2H), 3.30 (q, J=9.6 Hz, 2H), 3.25–3.42 (m, 1H), 3.73 (q, J=10.5 Hz, 1H), 3.78–3.94 (m, 4H), 3.88 (s, 3H), 3.96 (dd, J=5.1 Hz, 6.0 Hz, 1H), 4.03 (dd, J=3.0 Hz, 6.3 Hz, 2H), 4.33 (m, 3H), 4.87 (t, J=3.6 Hz, 1H), 5.94 (s, 2H), 6.53 (d, J=1.8 Hz, 1H), 6.63 (d, J=1.8 Hz, 1H). MS (DCI/NH$_3$) (M+H)+at m/e 535. Anal calcd for C$_{28}$H$_{42}$N$_2$O$_8$.1.05 TFA: C, 55.25; H, 6.63; N, 4.28. Found: C, 55.39; H, 6.66; N, 4.26.

EXAMPLE 510 trans,trans-2-((2-Methoxyphenoxy)-methyl)-4-(1,3-benzodioxol-5-yl)-1-(N,N-di(n-butyl)aminocarbonylmethyl)-pyrrolidine-3-carboxylic acid Using the procedures described in Example 502, substituting o-methoxyphenoxyacetic acid for 3-methylhexanoic acid, the above compound was prepared as an amorphous solid. $^1$H NMR (CDCl$_3$, 300 MHz) δ 0.85 (t, J=7 Hz, 3H), 0.90 (t, J=7 Hz, 3H), 1.15–1.35 (m, 4H), 1.40–1.55 (m, 4H), 3.05–3.25 (m, 4H), 3.28–3.55 (m, 4H), 3.58–3.68 (m, 1H), 3.75–3.80 (m, 1H), 3.82 (s, 3H), 3.91 (d, J=14 Hz, 1H), 4.05–4.15 (m, 1H), 4.23–4.33 (m, 1H), 5.91 (s, 2H), 6.70 (d, J=8 Hz, 1H), 6.82–6.95 (m, 5H), 7.03 (s, 1H). MS (DCI/NH$_3$) (M+H)$^+$ at m/e 541. Anal calcd for C$_{30}$H$_{40}$N$_2$O$_7$: C, 66.65; H, 7.46; N, 5.18. Found: C, 66.37; H, 7.61; N, 5.09.

EXAMPLE 511

(2S,3R,4S)-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylic acid

EXAMPLE 511A trans,trans-N-tert-Butoxycarbonyl-2-(2,2-dimethylpentyl)-4-(1,3-benzodioxol-5-yl)-pyrrolidine-3-carboxylic acid Ethyl trans,trans-2-(2,2-dimethylpentyl)-4-(1,3-benzodioxol-5-yl)-pyrrolidine-3-carboxylate (2.5 g, 6.9 mmol), prepared according to Example 503, was dissolved in 50 mL of methylene chloride and di-tert-butyldicarbonate (1.5 g) was added. After stirring overnight at room temperature, the solvent was removed under reduced pressure and the residue was purified by flash chromatography on silica gel eluting with 10% ethyl acetate/hexanes to give the ethyl ester of the title compound (2.8 g) as a colorless oil. The ester was dissolved in 50 mL of ethanol followed by addition of sodium hydroxide (10 mL of a 5M aqueous solution). After stirring for 20 hours at room temperature, the solvent was removed under reduced pressure, and the residue was dissolved in 150 mL of water, and acidified with concentrated phosphoric acid. The mixture was extracted with chloroform (3×50 mL), and the organic layers were washed wiith brine, dried over anhydrous magnesium sulfate, filtered, and the solvent was removed under reduced pressure to give the title compound (2.4 g) as a white foam.

EXAMPLE 511B

Methyl trans,trans-2-(2,2-dimethylpentyl)-4-(1,3-benzodioxol-5-yl)-1-(N-4-heptyl-N-(4-fluoro-3-methylphenyl))aminocarbonylmethyl)-pyrrolidine-3-carboxylate: As a single enantiomer The product from Example 510A (1.97 g, 4.5 mmol) was dissolved in 20 mL of THF and cooled to 0° C., followed by addition of DMF (0.017 mL, 5%), and oxalyl chloride (0.437 mL, 5.00 mmol). After 1 hour, solvent was removed at 0° C. under a stream of nitrogen. The residue was dissolved in 5 mL of benzene and evaporated. In a separate flask, (S)-4-benzyl-2-oxazolidinone (1.2 g, 6.8 mmol) was dissolved in 30 mL of THF followed by addition of n-butyllithium (4.0 mL of a 1.6M solution in hexanes) at 0° C., and the slurry was stirred for 15 min. The acid chloride was dissolved in 20 mL of THF and cooled to 0° C., followed by dropwise addition of the lithium oxazolide suspension via cannula. After 30 min, the reaction was partitioned between ether and saturated bicarbonate. The organic phase was washed with water then brine, dried over anhydrous magnesium sulfate, filtered, and the solvent was removed under reduced pressure. The residue was purified by flash chromatography on silica gel eluting with 15% ethyl acetate/hexanes to give the undesired diastereomer (1.17 g, 43%), then elution with 20% ethyl acetate/hexanes gave the desired diastereomer (1.04 g, 38%).

The desired diastereomer of the N-acyloxazolidinone (0.84 g, 1.42 mmol) was dissolved in 2.5 mL of dichloromethane, and 2.5 mL of trifluoroacetic acid was added. After 30 min, the volatiles were removed under a stream of nitrogen, and the residue was twice dissolved in 5 mL of toluene and evaporated under reduced pressure.

The TFA salt was stirred with 4 mL of acetonitrile followed by addition of diisopropylethyl amine (1.0 mL, 5.7 mmol), and N-4-heptyl-N-(4-fluoro-3-methylphenyl)bromoacetamide (589 mg, 1.7 mmol) as a solution in 2 mL of acetonitrile. After 21 hours, the reaction was warmed to 50° C. for 3.5 hours. The reaction was cooled, the solvent removed under reduced pressure, and the residue was purified by flash chromatography on silica gel eluting with 20–30% ethyl acetate/hexanes to give 0.939 g of amide as a colorless oil.

The above amide (200 mg, 0.26 mmol) was dissolved in 2.0 mL of THF and 0.7 mL of water. Solid lithium hydroxide monohydrate (22 mg, 0.53 mmol) was added at 0° C., followed by 30% hydrogen peroxide (0.050 mL, 0.55 mmol). After 1 hour, the reaction was warmed to room temperature. After an additional hour, the reaction was partitioned between 1:1 ethyl acetate:hexanes and water, 0.15 g of sodium thiosulfate was added and the mixture was mixed thoroughly. The organic layer was washed with water and brine, dried over anhydrous magnesium sulfate, filtered, and the solvent was removed under reduced pressure. The crude residue was dissolved in 2 mL of ether, and 1 mL of methanol. A solution of (trimethylsilyl)diazomethane in hexanes was added dropwise until the yellow color remained. The reaction was quenched by addition of 2 drops of glacial acetic acid, and the solvent was removed under reduced pressure. The residue was purified by flash chromatography on 10 g of silica gel eluting with 15–20% ethyl acetate/hexanes to give 70 mg of the title compound as a crystalline solid (mp 137.5° C.).

EXAMPLE 511C (2S,3R,4S)-trans,trans-2-(2,2-Dimethylpentyl)-4-(1,3-benzodioxol-5-yl)-1-(N-4-heptyl-N-(4-fluoro-3-methylphenyl))aminocarbonylmethyl)-pyrrolidine-3-carboxylate The product from Example 510B (65 mg, 0.10 mmol) was dissolved in 1.0 mL of methanol and sodium hydroxide (0.1 mL of a 5M aqueous solution) was added. After 2 hours, the reaction was warmed to reflux. After 6 hours, the reaction was cooled, and the solvent was removed under reduced pressure. The residue was dissolved in water and acidified with concentrated phosphoric acid. The aqueous solution was washed with chloroform (3×5 mL), which was then washed with brine, dried with anhydrous magnesium sulfate, filtered and evaporated under reduced pressure. The title compound was isolated by lyophilization from dilute aqueous TFA/CH$_3$CN. $^1$H NMR (CDCl$_3$, 300 MHz) d 0.78–0.95 (m, 15H), 1.04–1.46 (m, 12H), 1.76–2.95 (m, 2H), 2.31 (s, 3H), 3.23–3.33 (m, 1H), 3.47–3.58 (m, 1H), 3.6–3.75 (m, 2H), 3.80–3.95 (m, 2H), 4.05–4.15 (m, 1H), 4.73 (m, 1H), 5.94 (s, 2H), 6.70–6.80 (m, 2H), 6.82–6.93 (m, 2H), 6.96–7.14 (m, 2H). MS (DCI/NH$_3$) m/e 597 (M+H)$^+$. Anal calcd for C$_{35}$H$_{49}$N$_2$FO$_5$.0.05H$_2$O.0.8TFA: C, 63.81; H, 7.30; N, 4.07. Found: C, 63.84; H, 7.18; N, 3.94. [a]$_D^{21}$=+46° (c 2.7 g/L, CHCl$_3$)

EXAMPLE 512 trans,trans-2-(2-(2-Oxopyrrolidin-1-yl)ethyl)-4-(1,3-benzodioxol-5-yl)-1-(N,N-di(n-butyl)aminocarbonylmethyl)-pyrrolidine-3-carboxylic acid

EXAMPLE 512A

2-Oxopyrrolidin-1-ylpropionic acid

To a stirred solution of 5.0 mL (40.5 mmol) 2-oxopyrrolidin-1-ylpropionitrile in 15 mL of dioxane was added 8.1 mL of hydrochloric acid, a 6.0 M aqueous solution. The resulting mixture was then refluxed at 110° C. over night. The reaction mixture was then allowed to cool to room temperature, extracted with methylene chloride three times. The extracts were combined and washed with saturated brine solution once, dried over anhydrous sodium sulfate, filtered and evaporated under reduced pressure to give 1.60 g (25%) of acid as a brown oil.

EXAMPLE 512B

Ethyl 5-(2-oxopyrrolidin-1-yl-3-oxopentanoate

The title compound was prepared from the above acid by adapting the method of Bram and Vilkas, Bul. Chem. Soc. Fr., 945 (1964).

EXAMPLE 512C trans,trans-2-(2-(2-Oxopyrrolidin-1-yl)ethyl)-4-(1,3-benzodioxol-5-yl)-1-(N,N-di(n-butyl)aminocarbonylmethyl)-pyrrolidine-3-carboxylic acid Using the procedures described in Example 502, substituting ethyl 5-(2-oxopyrrolidin-1-yl)-3-oxopentanoate for ethyl 3-methylhexanoate afforded the title compound as an amorphous solid. $^1$H NMR (CDCl$_3$, 300 MHz) δ 0.91 (t, J=7.5 Hz, 3H), 0.94 (t, J=7.5 Hz, 3H), 1.23–1.38 (m, 4H), 1.44–1.60 (m,4H), 2.05 (t, J=6.9 Hz, 2H), 2.12–2.25 (m, 1H), 2.38 (td, J=4.2 Hz, 8.4 Hz, 2H), 2.47–2.61 (m, 1H), 3.17 (dd, J=6.0 Hz, 8.7 Hz, 2H), 3.24 (t, J=9 Hz, 1H), 3.32 (t, J=7.8 Hz, 2H), 3.38–3.48 (m, 3H), 3.52 (t, J=9 Hz, 1H), 3.66 (t, J=6.9 Hz, 1H), 3.96 (m, 2H), 4.14 (m, 1H), 4.38 (brs, 2H), 5.93 (s, 2H), 6.74 (d, J=8.1 Hz, 1H), 6.89 (dd, J=1.8 Hz, 8.1 Hz, 1H), 6.87 (d, J=1.8 Hz, 1H). MS (DCI/NH$_3$) (M+H)+at m/e 516. Anal calcd for C$_{28}$H$_{41}$N$_3$O$_6$.1.4 TFA: C, 54.78; H, 6.33; N, 6.22. Found: C, 54.69; H, 6.33; N, 6.14.

EXAMPLE 513 trans,trans-2-(2-(1,3-Dioxol-2-yl)ethyl)-4-(7-methoxy-1,3-benzodioxol-5-yl)-1-(N-4-heptyl-N-(4-fluoro-3-methylphenyl))aminocarbonylmethyl)-pyrrolidine-3-carboxylic acid Using the procedures described in Example 502, substituting ethyl 5-(1,3-dioxolyl)-2-oxopentanoate for ethyl 3-methylhexanoate, N-4-heptyl-N-(4-fluoro-3-methylphenyl) bromoacetamide for N,N-dibutyl bromoacetamide and 6-methoxypiperonal for piperonal afforded the title compound as an amorphous solid. $^1$H NMR (CDCl$_3$, 300 MHz) δ 0.93 (br t, 6H), 1.23–1.47 (m, 8H), 1.67–2.10 (m, 4H), 2.32 (s, 3H), 3.16 (t, J=9 Hz, 1H), 3.60–4.03 (m, 8H), 3.88 (s, 3H), 4.21 (brs, 1H), 4.72 (quintet, J=6.6 Hz, 1H), 4.86 (t, J=3.6 Hz, 1H), 5.93 (s, 2H), 6.49 (s, 1H), 6.61 (s, 1H), 6.96

(m, 2H), 7.08 (t, J=9 Hz, 1H). MS (DCI/NH$_3$) (M+H)+at m/e 629. Anal calcd for C$_{34}$H$_{45}$N$_2$O$_8$F.1.0 TFA: C, 58.21; H, 6.24; N, 3.77. Found: C, 58.11; H, 6.11; N, 3.58.

EXAMPLE 514 trans,trans-2-(2,2-Dimethylpentyl)-4-(7-methoxy-1,3-benzodioxol-5-yl)-1-(N,N-di(n-butyl)aminocarbonylmethyl)-pyrrolidine-3-carboxylic acid Using the procedures described in Example 502, substituting ethyl 5-methyl-3-oxooctanoate for ethyl 3-methylhexanoate and 6-methoxypiperonal for piperonal afforded the title compound as an amorphous solid. $^1$H NMR (CDCl$_3$, 300 MHz) δ 0.81 (s, 3H), 0.84 (s, 3H), 0.86 (t, J=6.9 Hz, 3H), 0.93 (t, J=6.9 Hz, 3H), 0.96 (t, J=6.9 Hz, 3H), 1.09–1.38 (m, 8H), 1.45–1.59 (m, 4H), 1.84–2.00 (m, 2H), 3.15 (dd, J=6.9 Hz, 10.0 Hz, 2H), 3.30–3.42 (m, 3H), 3.72 (t, J=10.5 Hz, 1H), 3.86 (t, J=10.5 Hz, 1H), 3.88 (s, 3H), 4.02 (q, J=10.0 Hz, 1H), 4.12 (d, J=16.8 Hz, 1H), 4.29 (d, J=16.8 Hz, 1H), 4.41 (brm, 1H), 5.94 (s, 1H), 6.52 (d, J=1.8 Hz, 1H), 6.67 (d, J=1.8 Hz, 1H). MS (DCI/NH$_3$) (M+H)+ at m/e 533. Anal calcd for C$_{30}$H$_{48}$N$_2$O$_6$.0.9 TFA: C, 60.12; H, 7.76; N, 4.41. Found: C, 60.18; H, 7.62; N, 4.33.

EXAMPLE 515 trans,trans-2-(2,2-dimethylpentyl)-4-(2,3-dihydro-benzofuran-5-yl)-1-(N,N-di(n-butyl)aminocarbonylmethyl)-pyrrolidine-3-carboxylic acid Using the procedures described in Example 502, substituting ethyl 3,3-dimethylhexanoate for ethyl 3-methylhexanoate and 2,3-dihydro-benzofuran-5-carbaldehyde for piperonal afforded the title compound as an amorphous solid by lyophylization with CH$_3$CN/TFA/H$_2$O. $^1$H NMR (300 MHz, CDCl$_3$) δ 0.83 (s, 3H), 0.85 (s, 3H), 0.86 (t, J=7.2 Hz, 3H), 0.92 (t, J=7.2 Hz, 3H), 0.95 (t, J=7.2 Hz, 3H), 1.09–1.39 (m, 8H), 1.44–1.59 (m, 4H), 1.88 (dd, J=15.0, 7.2 Hz, 1H), 2.00 (d, J=15.0 Hz, 1H), 3.09 (m, 2H), 3.18 (t, J=9.0 Hz, 2H), 3.27–3.38 (m, 3H), 3.65–3.95 (m, 2H), 4.05 (q, J=10.0 Hz, 1H), 4.18 (d, J=16.8 Hz, 1H), 4.30–4.45 (m, 2H), 4.55 (t, J=9.0 Hz, 2H), 6.70 (d, J=8.4 Hz, 1H), 7.04 (dd, J=8.4, 2.1 Hz, 1H), 7.23 (brs, 1H). MS (DCI/NH$_3$) at m/e 501 (M+H)+. Anal calc'd for C$_{30}$H$_{48}$N$_2$O$_4$.1.05TFA: C, 62.14; H, 7.97; N, 4.51. Found: C, 62.19; H, 8.00; N, 4.43.

EXAMPLE 516 trans,trans-2-(2,2,-Dimethyl-2-(1,3-dioxolan-2-yl)ethyl)-4-(1-methoxy-1,3-benzodioxol-5-yl)-1-(N,N-di(n-butyl)aminocarbonylmethyl)-pyrrolidine-3-carboxylic acid Using the procedures described in Example 502, substituting methyl 3,3-dimethyl-3-(1,3-dioxolan-2-yl)propanoate for ethyl 3-methylhexanoate and 6-methoxypiperonal for piperonal afforded the title compound as an amorphous solid by lyophylization with CH$_3$CN/TFA/H$_2$O. $^1$H NMR (CDCl$_3$, 300 MHz) δ 0.93 (t, J=7.2 Hz, 3H), 0.94 (t, J=7.2 Hz, 3H), 0.95 (s, 3H), 0.96 (s, 3H), 1.31 (sextet, J=7.2 Hz, 4H), 1.45 (m, 4H), 1.93 (dd, J=15.9, 6.0 Hz, 1H), 2.13 (d, J=15.9 Hz, 1H), 3.20 (dd, J=7.7, 7.7 Hz, 1H), 3.26–3.40 (m, 3H), 3.60 (m, 1H), 3.75–3.86 (m, 3H), 3.88 (s, 3H), 3.93–4.01 (m, 3H), 4.00–4.11 (m, 3H), 4.23 (d, J=15.9 Hz, 1H), 4.37–4.48 (m, 2H), 4.49 (s, 1H), 5.94 (s, 2H), 6.51 (d, J=2.1 Hz, 1H), 6.64 (d, J=2.1 Hz, 1H). MS (DCI/NH$_3$) at m/e 563 (M+H)+. Anal calcd for C$_{30}$H$_{46}$N$_2$O$_8$.0.9 TFA: C, 57.41; H, 7.11: N, 4.21; found: C, 57.35; H, 6.86; N, 4.05.

EXAMPLE 517 trans,trans-2-(2-(2-Methoxyphenyl)-ethyl)-4-(1,3-benzodioxol-5-yl)-1-(N,N-di(n-butyl)aminocarbonylmethyl)-Pyrrolidine-3-carboxylic acid Using the procedures described in Example 502, substituting o-methoxyphenylpropionic acid for 3-methylhexanoic acid, the above compound was prepared as an amorphous solid. $^1$H NMR (CDCl$_3$, 300 MHz) δ 0.85 (t, J=7 Hz, 3H), 0.91 (t, J=7 Hz, 3H), 1.10–1.27 (m, 4H), 1.42–1.60 (m, 4H), 1.72–1.89 (m, 1H), 1.91–2.02 (m, 1H), 2.55–2.77 (m, 2H), 2.94 (t, J=6 Hz, 1H), 3.05–330 (m, 6H), 3.59–3.82 (m, 3H), 3.73 (d, J=14 Hz, 1H), 3.77 (s, 3H), 5.91 (s, 2H), 6.70 (d, J=8 Hz, 1H), 6.78–6.88 (m, 3H), 6.92 (d, J=2 Hz, 1H), 7.08–7.19 (m, 2H). MS (DCI/NH$_3$) (M+H)+at m/e 539. Anal calcd for C$_{31}$H$_{42}$N$_2$O$_6$: C, 69.12; H, 7.86; N, 5.20. Found: C, 68.89; H, 7.70; N, 4.99.

EXAMPLE 518 trans,trans-2-(2,2-Dimethyl-3-(E)-pentenyl)-4-(1-methoxy-1,3-benzodioxol-5-yl)-1-(N,N-di(n-butyl)aminocarbonylmethyl)-pyrrolidine-3-carboxylic acid

EXAMPLE 518A

4-Methyl-3-penten-2-ol

To a stirred solution of 3-methyl-2-butenal (8.7 g, 103 mmol) in 100 mL of tetrahydrofuran under N$_2$ at 0° C. was added methylmagnesium bromide (38 mL of a 3.0M solution in ethyl ether, 114 mmol) dropwise. The resulting mixture was allowed to warm to room temperature slowly and stirred at room temperature for 1 hour before it was quenched with 25 mL of saturated NH$_4$Cl. The resulting biphasic mixture was partitioned between ethyl ether and water. The organic layer was washed with brine, dried with anhydrous magnesium sulfate, filtered, and the solvent was removed under reduced pressure to give 8.4 g (81%) of alcohol as a colorless oil.

EXAMPLE 518B trans-Ethyl 3,3-dimethyl-4-pentenoate

A mixture of 4-methyl-3-penten-2-ol (7.4 g, 74 mmol), triethyl orthoacetate (13.6 mL, 74 mmol) and propionic acid (0.28 mL, 3.7 mmol) was heated at 150° C. for 7 hours. The product was then distilled under normal pressure (200–220° C.) to give 5.0 g of crude ester as a colorless oil.

EXAMPLE 518C trans,trans-2-(2,2-Dimethyl-3-(E)-pentenyl)-4-(1-methoxy-1,3-benzodioxol-5-yl)-1-(N,N-di(n-butyl)aminocarbonylmethyl)-pyrrolidine-3-carboxylic acid Using the procedures described in Example 502, substituting trans-ethyl 3,3-dimethyl-4-pentenoate for ethyl 3-methylhexanoate and 6-methoxypiperonal for piperonal afforded the title compound as an amorphous solid by lyophilization from dilute aqueous TFA/CH$_3$CN. $^1$H NMR (CDCl$_3$, 300 MHz) δ 0.92 (t, J=7.2 Hz, 3H), 0.95 (t, J=7.2

Hz, 3H), 0.97 (s, 3H), 0.99 (s, 3H), 1.31 (sextet, J=7.2 Hz, 4H), 1.52 (quintet, J=7.2 Hz, 4H), 1.58 (d, J=5.4 Hz, 3H), 1.92(dd, J=15.0, 6.6 Hz, 1H), 2.04(d, J=15.0 Hz, 1H), 3.15(dd, J=7.8, 7.8 Hz, 1H), 3.30–3.40 (m, 3H), 3;75 (m, 2H), 3.87 (s, 3H), 3.99 (q, J=9 Hz, 2H), 4.11–4.30 (m, 3H), 5.29 (d, J=15.6 Hz, 1H), 5.38 (dd, J=15.6, 6 Hz, 1H), 5.94 (s, 2H), 6.50 (d, J=1.8 Hz, 1H), 6.63 (d, J=1.8 Hz, 1H). MS (DCI/NH$_3$) at m/e 531 (M+H)$^+$. Analysis calc'd for $C_{30}H_{46}N_2O_6$.0.95 TFA: C, 59.95; H, 7.41; N, 4.38; found: C, 60.00; H, 7.33; N, 4.35.

EXAMPLE 519 trans,trans-2-(3-(2-pyridyl)ethyl)-4-(1,3-benzo-dioxol-5-yl)-1-(N,N-di(n-butyl)aminocarbonylm-ethyl)-pyrrolidine-3-carboxylic acid

EXAMPLE 519A 3-(2-Pyridyl)-propionic Acid

In a 50 mL round-bottomed flask equipped with a stirring bar was placed 3-(2-pyridyl)-propanol (1 g, 7.6 mmol), water (13 mL) and concentrated sulfuric acid (0.5 g, 5.1 mmol). To this stirred solution was added over a period of 30 min potassium permanganate (1.8 g, 11.3 mmol) while the reaction temperature was maintained at 50° C. After the addition was completed, the mixture was held at 50° C. until the color of the reaction mixture turned brown, then heated at 80° C. for 1 hour and filtered. The filtrate was evaporated to dryness to yield quantitatively the desired acid (1.14 g) suitable for next step without further purification. To prepare a pure acid, the residue thus obtained was boiled in ethanol (10 mL) in the presence of charcoal (0.1 g) for 5 min, filtered and cooled to give crystalline 3-(2-pyridyl)-propionic acid (0.88 g, 78%).

EXAMPLE 519B trans,trans-2-(3-(2-pyridyl)ethyl)-4-(1,3-benzo-dioxol-5-yl)-1-(N,N-di(n-butyl)aminocarbonylm-ethyl)-pyrrolidine-3-carboxylic acid Using the procedure described in Example 502, the title compound was isolated by lyophilization from dilute aqueous TFA/CH$_3$CN as an amorphous solid. $^1$H NMR (CDCl$_3$, 300 MHz) δ 8.65 (d, J=6.0 Hz, 1H), 8.06 (t, J=6.91 Hz, 1H), 7.70 (d, J=9.0 Hz, 1H), 7.51 (t, J=6.91 Hz, 1H), 6.82–6.66 (m, 3H), 5.91 (s, 2H), 4.45 (s, 2H), 4.29–4.18 (m, 1H), 4.04 (dd, J=20.1, 10.5 Hz, 1H), 3.84 (t, J=12.6 Hz, 1H), 3.62 (dd, J=13.8, 9.6 Hz, 1H), 3.46–3.13 (m, 7H), 2.51 (broad s, 2H), 1.60–1.43 (m, 4H), 1.37–1.22 (m, 4H), 0.91 (t, J=8.4 Hz, 6H). MS (DCI/NH$_3$) m/e 510 (M+H)$^+$. Anal calcd for $C_{29}H_{39}N_3O_5$.1.75 TFA: C, 55.04; H, 5.79; N, 5.92. Found: C, 55.08; H, 5.64; N, 5.81.

EXAMPLE 520

(2S,3R,4S)-2-(2-(2-oxopyrrolidin-1-yl)ethyl)-4-(1,3-benzodioxol-5-yl)-1-(N,N-di(n-butyl)aminocarbon-ylmethyl)-pyrrolidine-3-carboxylic acid

EXAMPLE 520A (2S,3R,4S)-Ethyl-2-(2-(2-oxopyrrolidin-1-yl)ethyl)-4-(1,3-benzodioxol-5-yl)pyrrolidine-3-carboxylate-(S)-Mandelate The racemic amino ester from Example 512 (3.45 g, 8.98 mmol) in 10 mL of ethyl acetate was treated with (S)-(+)-mandelic acid (0.75 g, 4.93 mmol). Upon the formation of the clear solution, hexane was dropped in slowly with stirring till the solution became light cloudy. The solution was left stirred at room temperature over night. The crystals was then collected by filtration, recrystalized from ethyl acetate/hexane twice to give a yield of 800 mg (17%) of pure salt.

EXAMPLE 520B (2S,3R,4S)-Ethyl-2-(2-(2-oxopyrrolidin-1-yl)ethyl)-4-(1,3-benzodioxol-5-yl)-1-(N,N-di(n-butyl)ami-nocarbonylmethyl)-pyrrolidine-3-carboxylate To a stirred solution of pure mandelate (150 mg, 0.28 mmol) in CH$_3$CN was added N,N-dibutylbromoacetamide (84 mg, 0.34 mmol) and diisopropylethylamine (98 uL, 0.56 mmol). The resulting mixture was stirred at room temperature over night. Solvent was then removed under reduced pressure and the crude product was purified by silica gel flash chromatography to give 140 mg (90% yield) of the title compound.

EXAMPLE 520C (2S,3R,4S)-2-(2-(2-oxopyrrolidin-1-yl)ethyl)-4-(1,3-benzodioxol-5-yl)-1-(N,N-di(n-butyl)aminocarbon-ylmethyl)-pyrrolidine-3-carboxylic acid Using the procedures described in Example 502, the title compound was prepared as an amorphous solid by lyophyl-ization with CH$_3$CN/TFA/H$_2$O. $^1$H NMR (CDCl$_3$, 300 MHz) δ 0.91 (t, J=7.5 Hz, 3H), 0.94 (t, J=7.5 Hz, 3H), 1.23–1.38 (m, 4H), 1.44–1.60 (m,4H), 2.05 (t, J=6.9 Hz, 2H), 2.12–2.25 (m, 1H), 2.38 (td, J=4.2 Hz, 8,4 Hz, 2H), 2.47–2.61 (m, 1H), 3.17 (dd, J=6.0 Hz, 8.7 Hz, 2H), 3.24 (t, J=9 Hz, 1H), 3.32 (t, J=7.8 Hz, 2H), 3.38–3.48 (m, 3H), 3.52 (t, J=9 Hz, 1H), 3.66 (t, J=6.9 Hz, 1H), 3.96 (m, 2H), 4.14 (m, 1H), 4.38 (brs, 2H), 5.93 (s, 2H), 6.74 (d, J=8.1 Hz, 1H), 6.89 (dd, J=1.8 Hz, 8.1 Hz, 1H), 6.87 (d, J=1.8 Hz, 1H). MS (DCI/NH$_3$) (M+H)+at m/e 516. Anal calcd for $C_{28}H_{41}N_3O_6$.0.85 TFA: C, 58.23; H, 6.89; N, 6.86. Found: C, 58.37; H, 6.90; N, 6.84.

EXAMPLE 521

(2S,3R,4S)-2-(2-(2-oxopyrrolidin-1-yl)ethyl)-4-(1,3-benzodioxol-5-yl)-1-(N-4-heptyl-N-(4-fluoro-3-me-thylphenyl))aminocarbonylmethyl)-pyrrolidine-3 carboxylic acid Using the procedures described in Example 520, substituting N,N-(4-heptyl)-(4-fluoro-3-methyl)phenyl-bromoac-etamide for N,N-dibutylbromoacetamide afforded the title compound as an amorphous solid by lyophylization with CH$_3$CN/TFA/H$_2$O. $^1$H NMR (CDCl$_3$, 300 MHz) δ 0.85–0.98 (m, 6H), 1.22–1.55 (m, 8H), 2.04 (quintet, J=7.9 Hz, 4H), 2.32 (s, 3H), 2.36 (t, J=7.9 Hz, 2H), 2.61 (m, 1H), 3.14 (m, 1H), 3.25–3.61 (m, 5H), 3.66–3.77 (m, 1H), 3.79–3.90 (m, 2H), 3.92–4.03 (m, 1H), 4.69 (quintet, J=6.8 Hz, 1H), 5.95 (s, 2H), 6.71 (s, 2H), 6.78 (s, 1H), 6.93–7.13 (m, 3H); MS (DCI/NH$_3$) at m/e 610 (M+H)$^+$. Anal calc'd for $C_{34}H_{44}N_3O_6F_1$.1.45 TFA: C, 57.18; H, 5.91; N, 5.42. Found: C, 57.20; H, 5.62; N, 5.52.

EXAMPLE 522 trans,trans-2-(2-(1-pyrazolyl)ethyl)-4-(1,3-benzo-dioxol-5-yl)-1-(N,N-di(n-butyl)aminocarbonylmethyl)-pyrrolidine-3-carboxylic acid

EXAMPLE 522A 3-(1-Pyrazolyl)-propionic Acid

In a 10 mL round-bottomed flask equipped with a condenser and a stirring bar was placed pyrazole (0.50 g, 7.3 mmol), acrylic acid (0.50 mL, 7.3 mmol) and triethylamine (3 mL). The reaction mixture was refluxed for 6 hours. After removing triethylamine, the viscous oil was dried on high vacuo during 12 hours to yield quantitatively the desired acid (1.0 g) suitable for the next step without further purification.

EXAMPLE 522B trans,trans-2-(2-(1-pyrazolyl)ethyl)-4-(1,3-benzo-dioxol-5-yl)-1-(N,N-di(n-butyl)aminocarbonylmethyl)-pyrrolidine-3-carboxylic acid Using the procedure described in Example 502, the title compound was isolated by lyophilization from dilute aqueous TFA/CH$_3$CN as an amorphous solid $^1$H NMR (CDCl$_3$, 300 MHz) δ 7.56 (d, J=3.0 Hz, 1H), 7.50 (d, J=3 Hz, 1H), 6.83–6.66 (m, 3H), 6.28 (t, J=3 Hz, 1H), 5.91 (s, 2H), 4.55–3.98 (m, 6H), 3.83–3.72 (t, J=10.5 Hz, 1H), 3.61–3.40 (t, J=10.5 Hz, 1H), 3.36–3.12 (m, 5H), 2.69–2.43 (m, 2H), 1.59–1.42 (m, 4H), 1.38–1.21 (m, 4H), 0.91 (t, J=7.5 Hz, 6H). MS (DCI/NH$_3$) at m/e 499 (M+H)$^+$. Anal calcd for C$_{27}$H$_{38}$N$_4$O$_5$.0.75 TFA: C, 58.60; H, 6.69; N, 9.59. Found: C, 58.53; H, 6.45; N, 9.67.

EXAMPLE 523 trans,trans-2-(4-Methoxyphenyl)-4-(1,3-benzo-dioxol-5-yl)-1-((N-butyl-N-(3-hydroxypropyl)amino)carbonylmethyl)-pyrrolidine-3-carboxylic acid

EXAMPLE 523A

N-Butyl-N-(3-hydroxypropyl)-amine

To a solution of 15.9 g (100 mmol) of methyl 3-N-(n-butyl)aminopropionate in 150 mL of diethyl ether at 0.C was added 50 mL (0.35 mmol) of 1.0M LiAlH$_4$ in diethyl ether, keeping reflux at a minimum. The mixture was stirred at 0.C for 2.25 hours, the quenched by sequential dropwise addition of 1.9 mL H$_2$O, 1.9 mL 15% w/v NaOH$_{(aq)}$, and 5.7 mL H$_2$O. After stirring for 30 min, the salts were filtered and washed with diethyl ether, then the filtrate was concentrated to 11.3 g (86%) of a light yellow oil.

EXAMPLE 523B

N-Butyl-N-(3-hydroxypropyl)-chloroacetamide

To an ice cooled solution of 1.31 g (10.0 mmol) of N-butyl,N-(3-hydroxypropyl)amine in 20 mL of ethyl acetate was added a solution of 1.71 g (10.0 mmol) of chloroacetic anhydride in 10 mL of ethyl acetate. The mixture was stirred, and gradually warmed to room temperature over 18 hours. The reaction was extracted with H$_2$O (1×50 mL), saturated NaHCO$_{3(aq)}$ (2×50 mL), and brine (1×50 mL), dried over MgSO$_4$, filtered, and concentrated to an oil. The product was purified via silica gel chromatography, eluting with 80:20 hexanes:ethyl acetate to give 723 mg (35%) of a light yellow oil.

EXAMPLE 523C trans,trans-2-(4-Methoxyphenyl)-4-(1,3-benzo-dioxol-5-yl)-1-((N-butyl-N-(3-hydroxypropyl)amino)carbonylmethyl)-pyrrolidine-3-carboxylic acid Using the procedures described in Example 1D, substituting N-butyl-N-(3-hydroxypropyl)-chloroacetamide for N-propyl bromoacetamide and adding DMSO as cosolvent, afforded the title compound, which was isolated by lyophilization from dilute aqueous TFA/CH$_3$CN. $^1$H NMR (CD$_3$OD, 300 MHz) δ 0.78–0.95 (m, 3H), 1.00–1.80 (m, 4H), 2.80–3.65 (m, 15H), 3.80 (d, J=1.5 Hz, 2H), 5.93 (s, 2H), 6.72–7.05 (m, 5H), 7.33–7.40 (m, 2H). MS (DCI/NH$_3$) at m/e 513 (M+H)$^+$. Anal calc'd for C$_{28}$H$_{36}$N$_2$O$_7$.1.6H$_2$O: C, 62.12: H, 7.30; N, 5.17. Found: C, 62.04; H, 7.21; N, 4.88.

EXAMPLE 524 trans,trans-2-(4-Methoxyphenyl)-4-(1,3-benzo-dioxol-5-yl)-1-[(N-propyl-N-propoxyamino)carbonylmethyl]-pyrrolidine-3-carboxylic acid

EXAMPLE 524A

N-Boc-O-allylhydroxylamine

O-Allylhydroxylamine hydrochloride hydrate (5.0 g) was dissolved in THF (15 mL). The solution was cooled to 0° C. in an ice bath. Diisopropylethylamine (8 mL) and di-t-butyldicarbonate (10.0 g) were added. The mixture was stirred at 0° C. for 1 hour at which point the bath was removed and the reaction allowed to warm to room temperature and stirred overnight. The THF was removed in vacuo and the residue taken up in EtOAc (25 mL) and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil (6.5 g) which was used without any further purification.

EXAMPLE 524B

N-Boc-N-propyl-O-allylhydroxylamine

N-Boc-O-allylhydroxylamine (6.5 g) from the above procedure was dissolved in dry THF (25 mL) and the solution cooled to 0° C. in an ice bath. Sodium hydride (1.5 g, 60% dispersion in oil) was added portionwise over 5 min. The resulting mixture was stirred for 30 min at 0° C. 1-Iodopropane (3.8 mL) was added dropwise to the mixture. The reaction was stirred at 0° C. for 1 hour, then stirred overnight at room temperature. The THF was removed in vocuo and the residue taken up in EtOAc (50 mL) and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil, which was purified by flash chromatography on silica gel eluting with 5% EtOAc/hexanes to give the title compound as a colorless oil (6.0 g).

EXAMPLE 524C

N-Boc-N-propyl-N-propoxyamine

N-Boc-N-propyl-O-allylhydroxylamine (6.0 g) was dissolved in EtOAc (100 mL). 10% Palladium-on-carbon (0.5 g) was added, and the mixture was purged with nitrogen. The nitrogen line was exchanged for a balloon of hydrogen, and the mixture was stirred at room temperature for 6 hours. The catalyst was removed by filtration through a pad of Celite and the solvents were removed in vocuo to give a yellow oil which was purified by flash chromatography on silica gel eluting with 5% EtOAc/hexanes to give the title compound as a colorless oil (5.8 g).

EXAMPLE 524D

N-Propyl-N-propoxyamine hydrochloride

N-Boc-N-propyl-N-propoxyamine (5.8 g) was dissolved in 4N HCl/dioxane (10 mL) and stirred at room temperature for 7 hours. The solvent was removed in vacuo and the residue triturated with diethyl ether. The resulting yellow solid (2.1 g) was collected by filtration and washed with diethyl ether.

EXAMPLE 524E

N-propyl-N-propoxy-bromoacetamide

N-Propyl-N-propoxyamine hydrochloride (0.30 g) was dissolved in acetonitrile and cooled to −20° C. Pyridine (0.2 mL) was added. Bromoacetyl bromide (0.15 g) was added dropwise over 5 min. The solution was stirred at −20° C. for 30 min. The bath was removed and the solution was stirred for 6 hours at room temperature. The solvent was removed in vocuo and the residue taken up in EtOAc (50 mL) and washed with water (1×25 mL), 1N phosphoric acid (3×25 mL), and brine (1×25 mL). The organic layer was dried with sodium sulfate and evaporated to give a dark orange oil (0.35 g). The product is a mixture of chloro- and bromoacetamides in a ratio of ~3:1.

EXAMPLE 524F trans,trans-2-(4-Methoxyphenyl)-4-(1,3-benzo-dioxol-5-yl)-1-((N-butyl-N-(3-hydroxypropyl)amino)carbonylmethyl)-pyrrolidine-3-carboxylic acid Prepared according to the procedure of Example 523C, employing N-propyl-N-propoxy-bromoacetamide and ethyl 2-(4-methoxyphenyl)-4-(1,3-benzodioxol-5-yl)-pyrrolidine-3-carboxylate. The crude product was purified by preparative HPLC (Vydac mC18) eluting with a 10–70% gradient of $CH_3CN$ in 0.1% TFA. The appropriate fraction was lyophilized to give the product as a white solid. $^1H$ NMR ($CDCl_3$, 300 MHz) δ 0.87 (m, 6H, J=8 Hz), 1.49 (m, 2H, J=8 Hz), 1.61 (m, 2H, J=8 Hz), 3.55 (m, 6H), 3.80 (m, 2H), 3.81 (s, 3H), 4.00 (m, 2H), 4.13 (d, 2H, J=17 Hz), 5.96 (s, 2H), 6.77 (d, 1H, J=9 Hz), 6.90 (m, 3H), 7.05 (d, 1H, J=1 Hz), 7.44 (d, 2H, J=9 Hz). MS ($DCI/NH_3$) m/e 499 (M+H)$^+$. Anal calcd for $C_{27}H_{34}N_2O_7$·1.20 TFA: C, 55.57; H, 5.58; N, 4.41. Found: C, 55.59; H, 5.58; N, 4.55.

EXAMPLE 525 trans,trans-2-(4-Methoxyphenyl)-4-(1,3-benzo-dioxol-5-yl)-1-[(N-butyl-N-propoxyamino)carbonyl-methyl]-pyrrolidine-3-carboxylic acid

EXAMPLE 525A

N-butyl-N-(2-hydroxyethyl)-amine

In a thick walled glass tube 5 ml (100 mmol) of ethylene oxide was condensed at −78.C. To this 12.5 ml (120 mmol) of butylamine was added and the tube was sealed. The resultant solution was allowed to heat in an oil bath at 50.C for 18 hours. Unreacted reagents were removed by evaporation to give the title compound.

EXAMPLE 525B

N-Butyl-N-(2-azidoethyl)-chloroacetamide

To 500 mg of N-butyl,N-2-hydroxyethylamine was added 2 mL of thinoyl chloride, dropwise. After the initial reaction had ceased, the reaction was stirred for 10 min, then concentrated to an oil. Diethyl ether was added and evaporated to aid in removal of the thionyl chloride. The residue was taken up in 10 mL of DMF, and 1.0 g (16 mmol) of sodium azide was added. The reaction was stirred at 75.C for 2 hours, then poured into 50 mL of 0.6M $NaHCO_{3(aq.)}$ and extracted with diethyl ether (3×15 mL). The combined ether layers were back extracted with brine (1×15 mL), dried over $MgSO_4$, and filtered. To the ether solution was added 850 mg (4.97 mmol) of chloroacetic anhydride. The reaction was stirred for 10 min, then concentrated to an oil. This was taken up in 10 mL of saturated $NaHCO_{3(aq.)}$ and extracted with diethyl ether (3×5 mL). The combined ether layers were back extracted with brine (1×5 mL), dried over $MgSO_4$, filtered, and concentrated to an oil. This was purified via silica gel chromatography, eluting with 30% ethyl acetate:hexanes, to give 161 mg (17%) of an oil.

EXAMPLE 525C trans,trans-2-(4-Methoxyphenyl)-4-(1,3-benzo-dioxol-5-yl)-1-[(N-butyl-N-(2-aminoethyl)amino)carbonylmethyl]-pyrrolidine-3-carboxylic acid According to the procedure of Example 523C, N-butyl-N-(2-azidoethyl)-chloroacetamide was coupled with ethyl 2-(4-Methoxyphenyl)-4-(1,3-benzodioxol-5-yl)-pyrrolidine-3-carboxylate. The crude product was chromatographed on silica, using 40% EtOAc in hexanes to elute. The product was dissolved in a solution of ethanol and aqueous 2.5 N sodium hydroxide and stirred for 3 hours at room temperature. The solution was concentrated in vacuo and water added. The mixture was extracted with ether: the aqueous layer was acidified to pH 4 with 1N $H_3PO_4$ and extracted with EtOAc. The latter organic extract was washed with brine and dried over $Na_2SO_4$. To 100 mg (0.10 mmol) of the azide was added 1 mL of 1M $HCl_{(aq.)}$, 0.5 mL of dioxane, and 5 mg of 10% Pd—C. The suspension was stirred under 1 atm. of $H_2$ for 5 hours, then filtered and concentrated to a white solid. The product was purified via HPLC, eluting with a 0 to 70 $CH_3CN$ in 0.1% aqueous TFA gradient to give the title compound as its TFA salt. $^1H$ NMR ($CD_3OD$, 300 MHz) δ 0.92 (t, J=7.0 Hz, 3H), 0.96 (t, rotamer), 1.23 (m, 2H), 1.41 (m, 2H), 3.06 (m, 4H), 3.39 (m, 2H), 3.69 (m, 2H), 3.84 (s, 3H), 3.94 (m, 3H), 4.18 (m, 2H), 5.05 (bd, J=10.7 Hz, 1H), 5.98 (s, 2H), 6.84 (d, J=7.7 Hz, 1H), 6.93 (dd, J=1.8, 8.1 Hz, 1H), 7.05 (m, 3H), 7.56 (m, 2H). MS (DCI/NH$_3$) at m/e 498 (M+H)$^+$. Anal calcd for C$_{27}$H$_{35}$N$_3$O$_6$.3.15 TFA: C, 46.68. H, 4.49. N, 4.90. Found: C, 46.61; H, 4.73; N, 4.79.

EXAMPLE 526 trans,trans-2-(4-Methoxyphenyl)-4-(1,3-benzo-dioxol-5-yl)-1-((N-butyl-N-(3-aminopropyl)amino)carbonylmethyl)-pyrrolidine-3-carboxylic acid To and ice-cold solution of the compound of Example 523C (100 mg, 0.19 mmol) in 1 mL of dichloromethane was added 17 mL of methanesulfonyl chloride, and 39 mL of triethylamine. The mixture was stirred for 20 min, then diluted with 1.5 mL of dichloromethane and extracted once with 5 mL of water to which had been added 1 drop of 85% H$_3$PO$_4$, then 5% ammonium hydroxide (1×2.5 mL), and brine (1×2.5 mL), dried over MgSO$_4$, filtered, and concentrated to an oil. To a solution of 81 mg (0.13 mmol) of the mesylate in 1 mL of DMF was added 65 mg (10 mmol) of sodium azide. The mixture was stirred for 1 hour at 50.C, then poured into 10 mL of water and extracted with diethyl ether (3×5 mL). The combined ether layers were back extracted with brine (1×5 mL), dried over MgSO$_4$, filtered, and concentrated to an oil. This was purified via silica gel chromatography, eluting with 60:40 hexanes:ethyl acetate to give 57 mg of a colorless oil. The product was dissolved in a solution of ethanol and aqueous 2.5 N sodium hydroxide and stirred for 3 hours at room temperature. The solution was concentrated in vacuo and water added. The mixture was extracted with ether; the aqueous layer was acidified to pH 4 with 1N H$_3$PO$_4$ and extracted with EtOAc. The latter organic extract was washed with brine and dried over Na$_2$SO$_4$. To this azide was added 1 mL of 1M HCl$_{(aq.)}$, 0.5 mL of dioxane, and 5 mg of 10% Pd—C. The suspension was stirred under 1 atm. of H$_2$ for 5 hours, then filtered and concentrated to a white solid. The product was purified via HPLC, eluting with a 0 to 70 CH$_3$CN in 0.1% aqueous TFA gradient to give the title compound as its TFA salt. $^1$H NMR (D$_6$-DMSO, 300 MHz) δ 0.85 (apparent q, J=6.8 Hz, 3H), 1.17 (m, 2H), 1.30 (m, 2H), 1.67 (m, 2H), 2.71 (m, 2H), 3.04 (m, 1H), 3.21 (m, 3H), 3.45 (m, 1H), 3.75 (m, 3H), 3.97 (s, 3H), 3.85–4.80 (broad m, 3H), 6.03 (m, 2H), 6.87 (dd, J=1.4, 8.1 Hz, 1H), 6.92 (d, J=7.8 Hz, 1H), 7.01 (m, 2H), 7.16 (m, 1H), 7.55 (m, 2H), 7.72 (m, 2H), 7.85 (m, 1H); MS (DCI/NH$_3$) (M+H)$^+$ at m/e 512. Anal calcd for C$_{28}$H$_{37}$N$_3$O$_6$.3.0 TFA: C, 47.84. H, 4.72. N, 4.92. Found: C, 47.86; H, 4.75; N, 4.97.

EXAMPLE 527 trans,trans-2-(4-Methoxyphenyl)-4-(1,3-benzo-dioxol-5-yl)-1-((N-butyl-N-(3-dimethylaminopropyl)amino)carbonylmethyl)-pyrrolidine-3-carboxylic acid

EXAMPLE 527A

N-butyl-N-(3-bromopropyl)bromoacetamide

To 1.50 g (11.4 mmol) of N-butyl-N-(3-hydroxy)propylamine was added 3 mL of 48% HBr$_{(aq.)}$, and 1.5 mL of conc. H$_2$SO$_4$. The reaction was stirred at reflux for 3 hours, then cooled to room temperature and stirred for 22 hours. The mixture was poured over 50 mL of ice, and the solution was treated with 50 mL of 2M NaOH$_{(aq.)}$. The basic solution was extracted with ethyl acetate (3×25 mL), then the combined ethyl acetate layers were back extracted with brine (1×25 mL), dried, and filtered. To the ice cooled ethyl acetate solution was added 3 mL of triethylamine, then 1.5 mL of bromoacetyl bromide as a solution in 3.5 mL of ethyl acetate. The reaction was stirred at 0° C. for 30 min, then extracted with 1M HCl$_{(aq.)}$ (2×25 mL) saturated NaHCO$_3$ $_{(aq.)}$ (1×25 mL) and brine (1×25 mL). The organic layer was dried over MgSO$_4$, filtered, and concentrated to an oil. This was purified via silica gel chromatography, eluting with 30% ethyl acetate in hexanes to give 1.47 g of a colorless oil.

EXAMPLE 527B

Ethyl trans,trans-2-(4-Methoxyphenyl)-4-(1,3-benzodioxol-5-yl)-1-((N-butyl-N-(3-bromopropyl)amino)carbonylmethyl)-pyrrolidine-3-carboxylate According to the procedure of Example 523C, N-butyl-N-(3-bromopropyl-bromoacetamide was coupled with ethyl 2-(4-Methoxyphenyl)-4-(1,3-benzodioxol-5-yl)-pyrrolidine-3-carboxylate. The crude product was chromatographed on silica, using 40% EtOAc in hexanes to elute.

EXAMPLE 527C trans,trans-2-(4-Methoxyphenyl)-4-(1,3-benzo-dioxol-5-yl)-1-((N-butyl-N-(3-dimethylaminopropyl)amino)carbonylmethyl)-Pyrrolidine-3-carboxylic acid To 400 mg (0.663 mmol) of the compound of Example 527B in 4 mL of absolute EtOH was added 1.2 mL of 2.0 M Me$_2$NH in THF. The reaction was heated at 50.C for 3 h, then stirred at room temperature for 18 hours. The mixture was concentrated, then reconcentrated from CH$_3$CN to remove most of the trimethylamine. The product was purified via silica gel chromatography, eluting with 9:1 CH$_2$Cl$_2$:MeOH over about 20 mL of silica gel to give the ethyl ester. The product was dissolved in a solution of ethanol and aqueous 2.5 N sodium hydroxide and stirred for 3 hours at room temperature. The solution was concentrated in vacuo and water added. The mixture was extracted with ether; the aqueous layer was acidified to pH 4 with 1N H$_3$PO$_4$, and the product was purified by preparative HPLC. $^1$H NMR (CD$_3$OD, 300 MHz) δ 0.92 (t, J=7.0 Hz, 3H), 1.22 (m, 2H), 1.39 (m, 2H), 1.90 (m, 2H), 2.87 (s, 6H), 3.07 (m, 4H), 3.24 (m, 1H), 3.43 (m, 1H), 3.62 (m, 1H), 3.84 (s, 3H), 3.88 (m, 3H), 4.07 (m, 1H), 4.17 (m, 1H), 4.97 (m, 1H), 5.97 (s, 2H), 6.83 (d, J=8.1 Hz, 1H), 6.93 (dd, J=1.7, 8.1 Hz, 1H), 7.05 (m, 3H), 7.53 (m, 2H). MS (DCI/NH$_3$) at m/e 540 (M+H)$^+$. Anal calcd for C$_{30}$H$_{41}$N$_3$O$_6$.2.95 TFA: C, 49.22. H, 5.06. N, 4.80. Found: C, 49.16; H, 5.11; N, 4.62.

EXAMPLE 528 trans,trans-2-(4-Methoxyphenyl)-4-(1,3-benzo-dioxol-5-yl)-1-[(N-butyl-N-(3-trimethylammoniopropyl)amino)carbonylmethyl]-pyrrolidine-3-carboxylic acid Prepared according to the procedures of Example 527C, substituting aqueous Me$_3$N for Me$_2$NH. $^1$H NMR (CD$_3$OD, 300 MHz) δ 0.91 (m, 3H), 1.24 (m, 2H), 1.40 (m, 2H), 1.99 (m, 2H), 3.13 (s, 9H), 3.18 (s, rotamer), 3.20 (m, 3H), 3.39

(m, 4H), 3.72 (m, 1H), 3.84 (s, 3H), 4.03 (m, 3H), 4.35 (m, 1H), 5.19 (m, 1H), 5.97 (s, 2H), 6.84 (d, J=8.1 Hz, 1H), 6.96 (dd, J=1.7, 7.9 Hz, 1H), 7.10 (m, 3H), 7.62 (m, 2H). MS (DCI/NH$_3$) at m/e 554 (M+H)$^+$. Anal calcd for C$_{31}$H$_{44}$N$_3$O$_6$.0.1H$_2$O.1.65 TFA: C, 47.25. H, 4.96. N, 4.32. Found: C, 47.25; H, 4.74; N, 4.75.

EXAMPLE 529 trans,trans-2-(4-Methoxyphenyl)-4-(1,3-benzo-dioxol-5-yl)-1-((N-butyl-N-(4-aminobutyl)amino) carbonylmethyl)-pyrrolidine-3-carboxylic acid

EXAMPLE 529A

N-butyl-N-(4-hydroxybutyl)-amine

A solution of 8.1 g (110 mmol) of n-butylamine and 8.6 g of butyrolactone in 50 ml toluene was allowed to reflux under nitrogen atmosphere for 50 hours. Volatile solvents were removed in vocuo. To a solution of 3.18 gm (20 mmol) of the resultant N-butyl-4-hydroxybutyramide in 50 ml of toluene were added 120 ml (120 mmol) DIBAL (25% W). The solution was heated with stirring at 70.C for 18 hours. After cooling to 0.C, the reaction was quenched with methanol (⅓ amount of DIBAL solution was used) followed by addition of saturated solution of Rochelle's salt. The mixture was extracted twice with EtOAc; the organic extracts were washed with brine and dried over Na$_2$SO$_4$.

EXAMPLE 529B

N-butyl-N-(4-hydroxybutyl)-chloroacetamide

Pyridine (2 ml) was added to an ice cold solution of 0.58 gm (4 mmol) of N-butyl-N-(4-hydroxybutyl)-amine in 10 ml of EtOAc. To this solution 0.769 gm (4.5 mmol) chloroacetic anhydride was added in small portions. The reaction mixture was allowed to stir for 5 hours at 0.C, and then was allowed to warm to room temperature. Bicarbonate was added, and the resultant mixture was extracted with EtOAc. The organic layer was washed with water and brine. The crude material was purified by column chromatography.

EXAMPLE 529C

Ethyl trans,trans-2-(4-Methoxyphenyl)-4-(1,3-benzodioxol-5-yl)-1-((N-butyl-N-(4-hydroxybutyl) amino)carbonylmethyl)-pyrrolidine-3-carboxylate According to the procedure of Example 523C, N-butyl-N-(4-hydroxybutyl-chloroacetamide was coupled with ethyl 2-(4-Methoxyphenyl)-4-(1,3-benzodioxol-5-yl)-pyrrolidine-3-carboxylate. The crude product was chromatographed on silica gel.

EXAMPLE 529D

Ethyl trans,trans-2-(4-Methoxyphenyl)-4-(1,3-benzodioxol-5-yl)-1-[(N-butyl-N-(4-bromobutyl)amino) carbonylmethyl]-pyrrolidine-3-carboxylate To the solution of 0.180 gm (0.33 mmol) of the compound of Example 529C in 2 ml DMF 0.086 gm (1 mmol) of lithium bromide and 0.120 ml (0.66 mmol) of PBr$_3$ was added. The reaction mixture was allowed to stir at 0.C for 2 hours and was slowly warmed to room temperature. Bicarbonate was added, and the resultant mixture was extracted with EtOAc. The organic layer was washed with water and brine. The crude material was purified by column chromatography.

EXAMPLE 529E trans,trans-2-(4-Methoxyphenyl)-4-(1,3-benzo-dioxol-5-yl)-1-[(N-butyl-N-(4-aminobutyl)amino) carbonylmethyl]-Pyrrolidine-3-carboxylic acid To a solution of 0.135 gm (0.21 mmol) of the compound of Example 529D in 2 ml DMF was added 0.1 gm of sodium azide. Reaction was allowed to stir at room temperature for 18 hours under nitrogen atmosphere. After addition of water, the product was extracted into EtOAc. The crude product (117 mg) was dissolved in 10 ml ethanol under nitrogen atmosphere. To this 45 mgs of 10% Pd/C catalyst was added, the nitrogen from the reaction flask was evacuated and was flushed with hydrogen by placing a balloon filled with hydrogen.

The reaction was allowed to stir for 4 hours under hydrogen atmosphere, and was worked up by filtering through a Celite pad. The product was dissolved in a solution of ethanol and aqueous 2.5 N sodium hydroxide and stirred for 8 hours at room temperature. The solution was concentrated in vacuo and water added. The mixture was extracted with ether: the aqueous layer was acidified to pH 4 with 1N H$_3$PO$_4$, and the product was purified by preparative HPLC. $^1$H NMR (CD$_3$OD, 300 MHz) δ 0.90 (t, J=7 Hz, 3H), 1.10–1.65 (m, 6H), 2.85–2.95 (m, 2H), 3.00–4.10 (m, 14H), 5.50 (d, J=3 Hz, 2H), 5.97 (s, 2H), 6.82 (d, J=8 Hz, 1H), 6.91 (dd, J=7 Hz, 1H), 7.00–7.06 (m, 3H), 7.45–7.55 (m, 2H). MS (DCI/NH$_3$) at m/e 526 (M+H)$^+$. Anal calc'd for C$_{29}$H$_{39}$N$_3$O$_6$.2.2 TFA: C, 51.75: H, 5.35; N, 5.41. Found: C, 51.75: H, 5.31; N, 5.30.

EXAMPLE 530 trans,trans-2-(4-Methoxyphenyl)-4-(1,3-benzo-dioxol-5-yl)-1-((N-butyl-N-(4-dimethylaminobutyl) amino)carbonylmethyl)-pyrrolidine-3-carboxylic acid The title compound was prepared from the compound of Example 529D, employing the procedures of Example 527C. $^1$H NMR (CD$_3$OD, 300 MHz) δ 0.90 (dt, J=7 Hz, 3H), 1.1–1.75 (m, 8H), 2.75 (d, J=7 Hz, 6H), 3.0–4.25 (m, 16H), 5.97 (s, 2H), 6.83 (d, J=8 Hz, 1H), 6.93 (dd, J=8 Hz, 1H), 7.02–7.08 (m, 3H), 7.49–7.56 (m, 2H). MS (DCI/NH$_3$) at m/e 554 (M+H)$^+$. Anal calc'd for C$_{31}$H$_{43}$N$_3$O$_6$.2.1 TFA: C, 53.31; H, 5.73; N, 5.30. Found: C, 53.50; H. 5.38; N, 5.34.

EXAMPLE 531 trans,trans-2-(4-Methoxyphenyl)-4-(1,3-benzo-dioxol-5-yl)-1-((N-butyl-N-(3-pyridyl)amino)carbo-nylmethyl)-pyrrolidine-3-carboxylic acid

EXAMPLE 531A

N-butyl-N-(3-pyridyl)-amine

To a solution of 941 mg (10 mmol) of 3-aminopyridine and 0.9 mL of butyraldehyde in 30 mL of CH$_3$OH was added 10 mL of glacial acetic acid. The mixture was stirred at room temperature for 1 hour, then the reaction was cooled with an ice bath, and 650 mg (10.3 mmol) of sodium cyanoborohydride was added. The ice bath was removed, and the reaction was stirred for 4.5 hours at room temperature. The mixture was poured into 300 mL of 0.67M NaOH$_{(aq.)}$, and extracted with ethyl acetate (3×50 mL). The combined organic layers were back extracted with brine (1×50 mL), dried over MgSO$_4$, filtered, and concentrated to an oil. The product was isolated via silica gel chromatography, eluting with 3:1 ethyl acetate:hexanes to give 1.18 g (79%) of a colorless solid.

EXAMPLE 531B trans,trans-2-(4-Methoxyphenyl)-4-(1,3-benzo-dioxol-5-yl)-1-((N-butyl-N-(3-pyridyl)amino)carbonylmethyl)-pyrrolidine-3-carboxylic acid The compound of Example 531A was reacted according to the procedures of Example 523, to give the title compound. $^1$H NMR (D6-DMSO, 300 MHz) δ 0.80 (t, J=6.4 Hz, 3H), 1.15–1.99 (m, 4H), 2.59 (m, 1H), 3.05 (m, 2H), 3.26 (m, 2H), 3.49 (m, 2H), 3.56 (t, J=7.1 Hz, 2H), 3.73 (s, 3H), 6.00 (s, 2H), 6.80 (m, 3H), 6.85 (d, J=8.1 Hz, 1H), 6.98 (m, 2H), 7.04 (m, 1H), 7.41 (dd, J=1, 4.7 Hz, 8.1H), 7.58 (m, 1H), 8.36 (bs, 1H), 8.54 (bs, 1H), 12.24 (bs, 1H). MS (DCI/NH$_3$) at m/e 532 (M+H)$^+$. Anal calcd for C$_{30}$H$_{33}$N$_3$O$_6$.0.1H$_3$PO$_4$: C, 66.55. H, 6.20. N, 7.76. Found: C, 66.59; H, 6.06; N, 7.60.

EXAMPLE 532 trans,trans-2-(4-Methoxyphenyl)-4-(1,3-benzo-dioxol-5-yl)-1-[(N-butyl-N-(3-aminomethylphenyl)amino)carbonylmethyl]-pyrrolidine-3-carboxylic acid

EXAMPLE 532A

N-butyl-N-(3-hydroxymethylphenyl)-amine

To a solution of 3.69 g (30 mmol) of 3-amino benzyl alcohol in 20 ml DMSO was added 3.78 g (45 mmol) solid NaHCO$_3$ and 2.91 ml (27 mmol) 1-bromobutane. The reaction was allowed to stir at 50.C for 18 hours (overnight). Reaction was worked up by adding 250 ml water and product was extracted in ethyl acetate. Water was added, and the resultant mixture was extracted with EtOAc. The organic layer was washed with water and brine.

EXAMPLE 532B

N-butyl-N-(3-hydroxymethylphenyl)-bromoacetamide

To a solution of 3.42 g (19.2 mmol) of the compound of Example 532A in 20 ml toluene, was added 2.42 ml (30 mmol) pyridine. The mixture was cooled to 0.C, 4.025 gm (20.0 mmol) of bromoacetyl bromide (diluted with 5 ml toluene) was added in a dropwise fashion.

The reaction mixture was allowed to stir for 5 hours at 0.C and then was allowed to warm to room temperature. Saturated potassium carbonate solution was added, and the mixture was stirred vigorously for 2 hours. The mixture was extracted with EtOAc; the organic layer was washed with 1N H$_3$PO$_4$, water, and brine.

EXAMPLE 532C

Ethyl trans,trans-2-(4-Methoxyphenyl)-4-(1,3-benzodioxol-5-yl)-1-[(N-butyl-N-(3-chloromethylphenyl)amino)carbonylmethyl]-pyrrolidine-3-carboxylate According to the procedure of Example 523C, N-butyl-N-(3-hydroxymethylphenyl)-bromoacetamide was coupled with ethyl 2-(4-Methoxyphenyl)-4-(1,3-benzodioxol-5-yl)-pyrrolidine-3-carboxylate. The crude product (129 mg) was dissolved in 0.5 ml of DMF and cooled to 0° C.; 19 mg of LiCl was added, followed by 85 µl of thionyl chloride. The mixture was allowed to stir for 30 min; water was added, and the mixture was extracted with EtOAc. The organic extracts were washed with water and brine, and dried over Na$_2$SO$_4$.

EXAMPLE 532D trans,trans-2-(4-Methoxyphenyl)-4-(1,3-benzo-dioxol-5-yl)-1-((N-butyl-N-(3-aminomethylphenyl)amino)carbonylmethyl)-pyrrolidine-3-carboxylic acid The compound of Example 532C (182 mg) was dissolved in 1 mL of DMF. Two drops of water were added, followed by 126 mg (2.0 mmol, 6.5 eq) of sodium azide. The resultant solution was heated at 115° C. for 3 hours. Water was added, and the mixture was extracted with EtOAc. The organic extracts were washed with water and brine, and dried over Na$_2$SO$_4$.

EXAMPLE 532E trans,trans-2-(4-Methoxyphenyl)-4-(1,3-benzo-dioxol-5-yl)-1-((N-butyl-N-(3-aminomethylphenyl)amino)carbonylmethyl)pyrrolidine-3-carboxylic acid In a 50 ml round bottom flask 0.090 gm Tin (II) chloride was suspended in 1 ml acetonitrile. Triethylamine (0.2 mL) was added, followed by 0.19 ml of thiophenol; the reaction mixture turned yellow. Reaction flask was cooled to 0.C in ice bath; a solution of 0.185 gm of the compound of Example 532D in 2 ml acetonitrile was added. The mixture was allowed to stir for 30 min. Ether (10 ml) was added, followed by addition of 10 ml 2N HCl. The aqueous extract was basified with 4N NaOH and extracted with dichloromethane. The organic layer was washed with water and brine. The crude product was dissolved in a solution of ethanol and aqueous 2.5 N sodium hydroxide and stirred for 8 hours at room temperature. The solution was concentrated in vacuo and water added. The mixture was extracted with ether; the aqueous layer was acidified to pH 4 with 1N H$_3$PO$_4$, and the product was purified by preparative HPLC. $^1$H NMR (CD$_3$OD, 300 MHz) δ 0.88 (t, J=7 Hz, 3H), 1.15–1.45 (m, 4H), 3.40–4.20 (m, 14H), 5.97 (s, 2H), 6.82 (d, J=8 Hz, 1H), 6.88 (dd, J=8 Hz, 1H), 6.97–7.20 (m, 5H), 7.40 (d, J=9 Hz, 2H), 7.56 (d, J=5 Hz, 2H). MS (DCI/NH$_3$) at m/e 560 (M+H)$^+$. Anal calcd for C$_{32}$H$_{37}$N$_3$O$_6$.4.2 TFA: C, 46.72; H, 4.00; N, 4.05. Found: C, 46.66; H, 4.06; N, 4.00.

EXAMPLE 533 trans,trans-2-(4-Methoxyphenyl)-4-(1,3-benzo-dioxol-5-yl)-1-((N-butyl-N-(3-trimethylammoniom-ethylphenyl)amino)carbonylmethyl)-pyrrolidine-3-carboxylic acid To a stirred solution of 0.128 gm of the compound of Example 532C in 0.5 ml methanol, 0.25 ml of an aqueous solution of trimethylamine was added. The mixture was allowed to stir at room temperature under nitrogen atmosphere for 4 hours. 1N HCl was added; the aqueous was washed with ether to extract organic impurities. The aqueous layer was dried azeotropically with toluene, and the residue was dried under high vacuum. Yield 0.115 gm. $^1$H NMR (300 MHz, D6-DMSO) δ 0.83 (t, J=7 Hz, 3H), 1.15–1.40 (m, 4H), 2.62 (s, 2H), 3.35 (s, 9H), 3.40–3.80 (m, 10H), 4.47 (s, 2H), 6.00 (s, J=3 Hz, 2H), 6.75–6.90 (m, 3H), 7.25–7.37 (m, 2H), 7.45–7.60 (m, 3H). MS (DCI/NH$_3$) at m/e 602 (M+H)$^+$.

EXAMPLE 534

(2R,3R,4S)$_2$-(3-Fluoro-4-methoxyphenyl)-4-(1,3-benzodioxol-5-yl) 1-(2-(N-propyl-N-pentanesulfonylamino)ethyl)-pyrrolidine-3-carboxylic acid

EXAMPLE 534A

Ethyl (3-fluoro-4-methoxy)benzoylacetate

Sodium hydride (17 g of a 60% suspension in mineral oil) is washed three times with toluene. The powder is suspended in 138 mL of toluene, and 35 mL of diethyl carbonate is added. The mixture is heated to 90° C., and a solution of 25 g of 3-fluoro-4-methoxyacetophenone and 50 ml of diethyl carbonate in 50 ml of toluene was added portionwise. Heating is continued for 30 min, then the reaction is cooled to room temperature. A solution of 50 ml of concentrated HCl in 75 ml of ice water is added slowly, and the mixture is stirred. The mixture is extracted with toluene; the combined organic extracts are washed with brine and bicarbonate solutions. The product is dried over Na$_2$SO$_4$ and decolorized with charcoal to give 34.5 g (97%) of the title compound.

EXAMPLE 534B

Ethyl 2-(3-Fluoro-4-methoxyphenyl)-4-(1,3-benzodioxol-5-yl)-pyrrolidine-3-carboxylate The compound of Example 534A (12.5 g) and 5-(nitrovinyl)-1,3-benzodioxole (13.1 g, 20% excess) were suspended in a mixture of 75 ml of THF and 13 ml of IPrOH. DBU (0.25 g) was added, and the mixture was stirred at room temperature for 30 min. An additional 0.1 g of DBU was added, and the solution was stirred for 1 hour. The solvents were removed in vacuo; toluene was added, along with brine containing 3 ml of concentrated HCl. The mixture was extracted twice with toluene; the organics were dried over MgSO$_4$. The residue was flashed on silica, using CH$_2$Cl$_2$ to elute. Yield 75%. This material (17.4 g) is combined with 35 g of Raney Nickel (washed) in 250 mL of EtOAc. The mixture is shaken under 4 atm of hydrogen for 18 hours. The solution is concentrated in vacuo; the residue is chromatographed on silica, eluting with 4% EtOAc in CH$_2$Cl$_2$. Yield 10.13 g=66%. The product is combined with 26 ml of THF and 50 ml of EtOH; 2.18 g of NaBH$_3$CN are added, along with a trace of bromcresol green as indicator. A solution of 1:2 concentrated HCl/EtOH is added dropwise to maintain pH at green-yellow; after color persists, the reaction mixture is stirred for an additional 20 min. The solvents are removed in vacuo; the residue is stirred with mixture of toluene and KHCO$_3$ solution. The organic phase is washed with water and brine, and dried over MgSO$_4$. The crude product is purified by flash chromatography on silica, eluting with 2:1 EtOAc/hexanes. Yield 5.92 g (58%) of a 2:1 mixture of trans—trans and cis-trans isomers.

EXAMPLE 534C

Ethyl (2R,3R,4S)-2-(3-Fluoro-4-methoxyphenyl)-4-(1,3-benzodioxol-5-yl)-pyrrolidine-3-carboxylate To the racemic amino ester above (15.0 g, 38.8 mmol), dissolved in 75 ml methylene chloride and cooled in an ice bath, was added Boc anhydride (9.30 g, 42.7 mmol). After stirring 2 hours at room temperature, the solution was concentrated in vacuo; the residue was dissolved in 50 ml ethanol and treated with a solution of 3.75 g sodium hyroxide in 19 ml water. The solution was warmed until all was soluble. After stirring for 2 hours at room temperature, the solution was concentrated and redissolved in 200 ml of water. This was extracted with 75 ml of diethyl ether. The ether layer was extracted with 40 ml of water. The combined aqueous phases were acidified with 7.5 g acetic acid; the mixture was stirred until a solid formed. The solid was filtered, washed with water and dissolved in methylene chloride. After drying with sodium sulfate, the solution was concentrated and the residue crystallized from 1:1 ether: hexane to get 15.99 g of product, m.p. 200–203 (90% yield). The crude acid was suspended in 80 ml ethyl acetate and treated with 4.00 g (33.1 mmol) of (S)-(–)-a-methylbenzylamine. After heating to dissolve the acid, 80 ml of ether was added. Scratching with a glass rod caused the product to crystallize. The solids were filtered and washed with ether-ethyl acetate solution to give 8.22 g (81% yield based on 50% maximum recovery) of salt, m.p. 165–168° C. After one recrystallization, chiral HPLC analysis, using a Regis Whelk-O column, indicated >99.5% e.e. The salt was dissolved in 500 ml of 36% HCl in ethanol; a white solid forms. The resultant suspension was heated for 16 hours at 52° C. After concentrating in vacuo, the residue was combined with toluene and stirred with potassium bicarbonate in water for 30 minutes. The toluene was separated, dried (Na$_2$SO$_4$) and concentrated. The residue was chromatographed on silica gel, eluting with 33% hexane-67% ethyl acetate to get 6.9 g (99%) of the resolved amino ester.

EXAMPLE 534D

Ethyl (2R,3R,4S)-2-(3-Fluoro-4-methoxyphenyl)-4-(1,3-benzodioxol-5-Yl) 1-(2-(N-propylamino)ethyl)-pyrrolidine-3-carboxylate The compound of Example 534C was dissolved in 1,2-dibromoethane (10 mL per 1 g of starting material); diisopropylethylamine (1 mL per 1 g of starting material) and NaI (100 mg per 1 g of starting material) were added, and the mixture was stirred at 100° C. for 1 hour. Toluene was added, and the mixture was washed with bicarbonate. The solvents were concentrated, and the resultant black residue was chromatographed on silica gel, eluting with 4:1 hexane-EtOAc to give the N-(2-bromoethyl)pyrrolidine (85–92%). This compound was combined with n-propylamine (3.5 eq.) and NaI (10% by weight of bromide) in ethanol (5 mL per 1 g of bromide), and was heated at 80° C. for 2 hours. Toluene was added, and the mixture was washed with bicarbonate, dried (Na₂SO₄), and concentrated. More toluene was added, and removed in vacuo, to get rid of the primary amine. The residue was dissolved in heptane and filtered to remove a small amount of insoluble material. Evaporation of the solvent gave the desired product (86–93% yield), which was used for the next step without further purification.

EXAMPLE 534E

1-Pentanesulfonyl chloride

1-Pentanesulfonic acid, sodium salt (10 g, 57.5 mmol) was charged into a 250 ml round bottom flask (allow headroom). Thionyl chloride (20 mL) is added; gas evolves, and a while solid forms. The mixture is heated at 60° C. for 3 hours. The solvents are removed in vacuo; toluene is added and removed in vacuo to remove residue of SOCl₂. The residue is partitioned between CH₂Cl₂ and ice water; the organic layer is dried over Na₂SO₄. The crude product is purified by distillation (bp 54–56° C. @ 0.5 mm Hg) to give a clear oil, 61% yield.

EXAMPLE 534F (2R,3R,4S)-2-(3-Fluoro-4-methoxyphenyl)-4-(1,3-benzodioxol-5-yl) 1-(2-(N-propyl-N-pentanesulfonylamino)ethyl)-pyrrolidine-3-carboxylic acid The compound of Example 534D (200 mg, 0.43 mmol) was dissolved in 5 mL of CH₃CN; 110 mg (2 eq) of N,N-diisopropylethylamine and 72.8 mg (1.2 eq) of 1-pentanesulfonyl chloride were added sequentially, the resultant solution was allowed to stir at room temperature for 30 min. The solvent was evaporated under reduced pressure and the residue was dissolved in EtOAc. The solution was washed with saturated NaHCO₃ solution, 1N H₃PO₄, and brine, dried over Na₂SO₄ and evaporated to give a yellowish oil which was purified by flash chromatography on silica gel eluting with 40% EtOAc/hexane to give 220 mg of product (85%). This ester was dissolved in 5 mL of EtOH, to which was added NaOH (46 mg, 3 eq) solution in 2 mL of H₂O. This mixture was stirred for 3 hours at room temperature. The solution was concentrated in vacuo using low (<40° C.) heat. Water (10 mL) and ether (50 mL) were added; the ether layer was extracted with 5 mL of water. The combined aqueous mixture was back-extracted with ether and then neutralized with acetic acid. This solution was extracted twice with ether. The ether was dried (Na₂SO₄) and concentrated in vacuo. EtOAc (1 mL) and ether (1 mL) were added to dissolve the product, and hexane was added dropwise to produce a white solid. The solid was collected and dried in vacuo to give 125 mg of the title compound.

EXAMPLE 534H (2R,3R,4S)-2-(3-Fluoro-4-methoxyphenyl)-4-(1,3-benzodioxol-5-yl) 1-(2-(N-propyl-N-pentanesulfonylamino)ethyl)-pyrrolidine-3-carboxylic acid, hydrochloride salt The free amine is dissolved in iPrOH; a slight excess of HCl in iPrOH is added, and the solution is concentrated in vacuo. More IPA is added, and the solution is reconcentrated. The resultant sticky material is stirred with ether overnight to give a white powder, which is collected by filtration and dried overnight in vacuo at 60° C. Yield 95%.

EXAMPLE 535

The compounds in Table 3C may be prepared using methods presented in the above Examples.

TABLE 3C

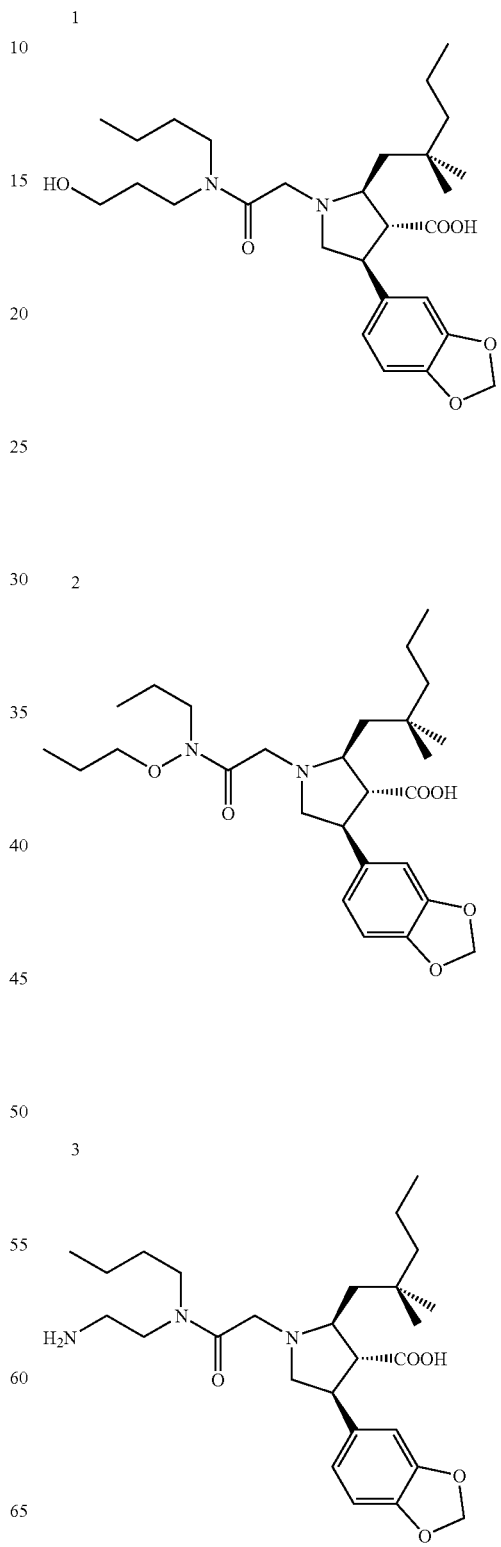

TABLE 3C-continued
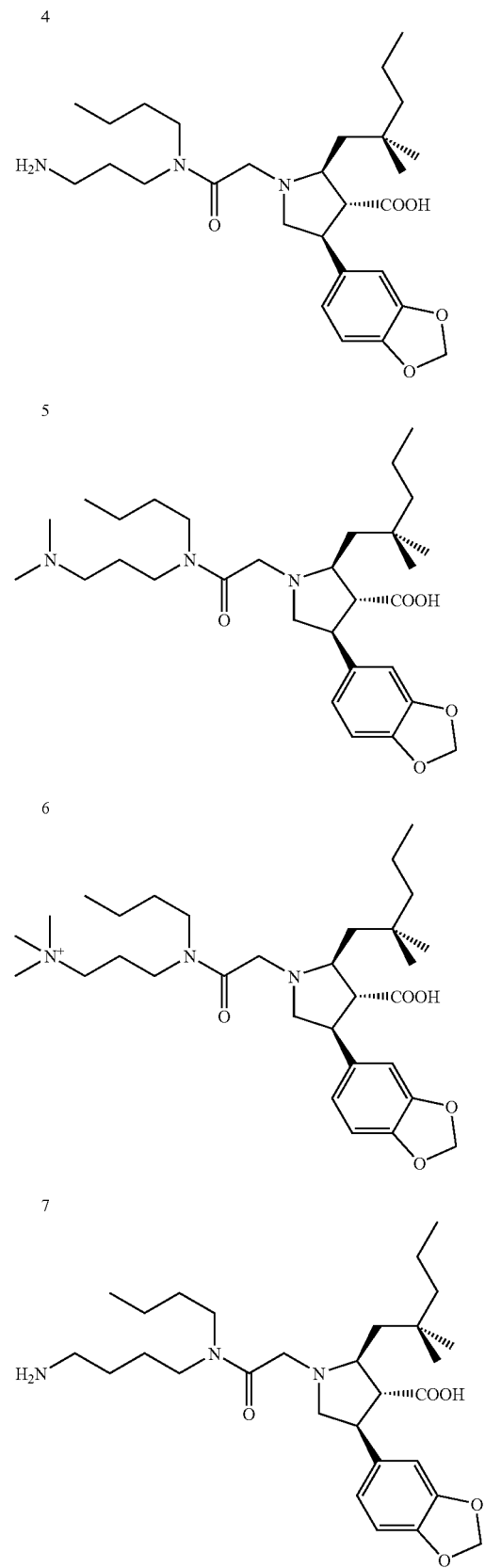
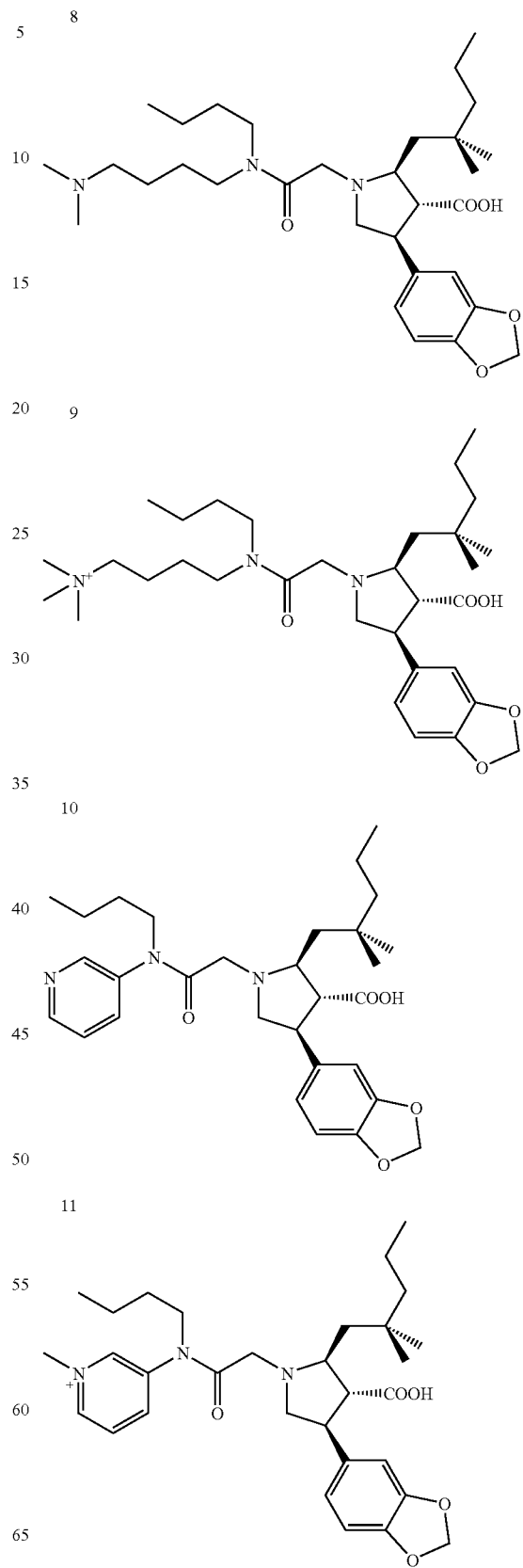

TABLE 3C-continued
12
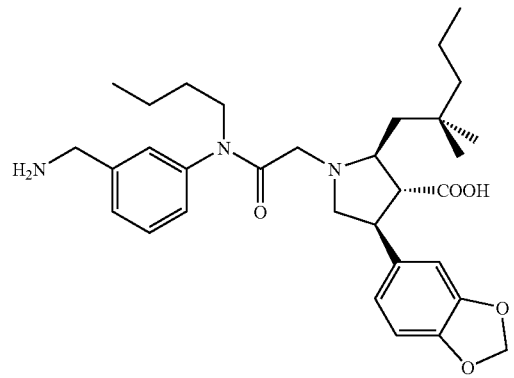
13
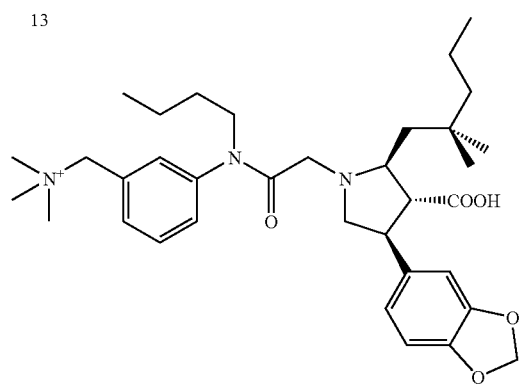
14
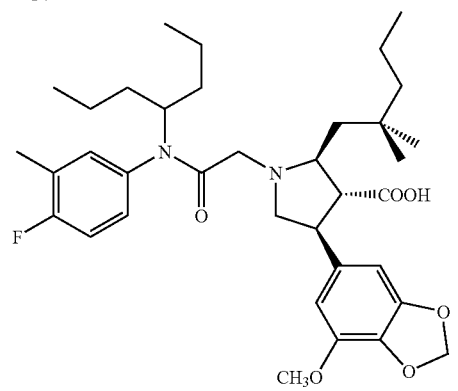
15
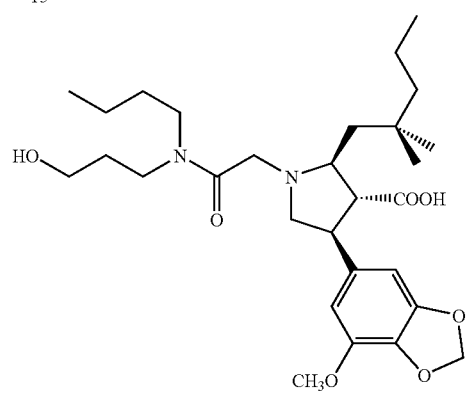
TABLE 3C-continued
16
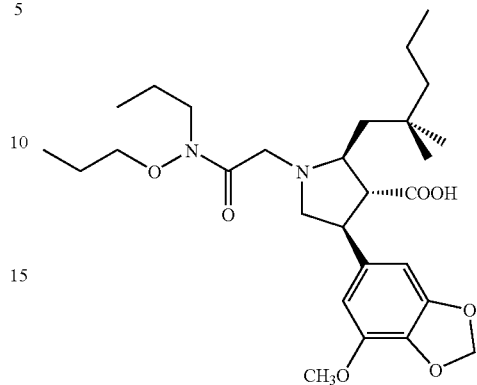
17
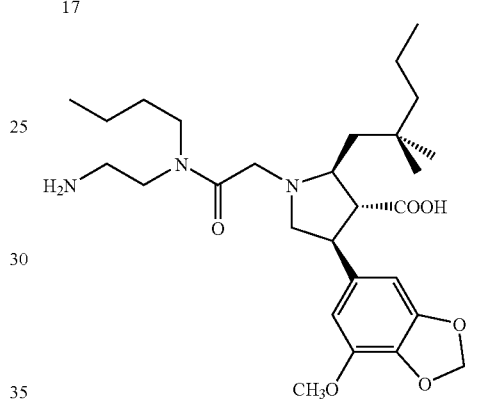
18
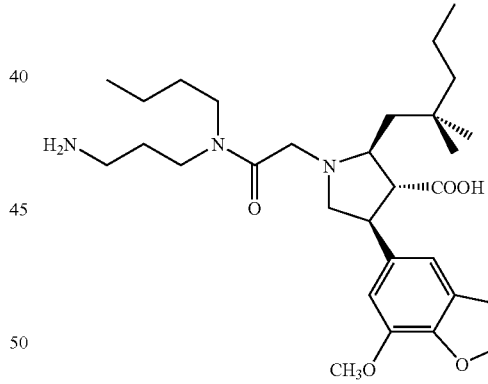
19
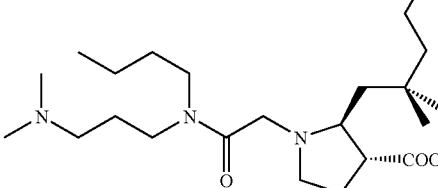

TABLE 3C-continued
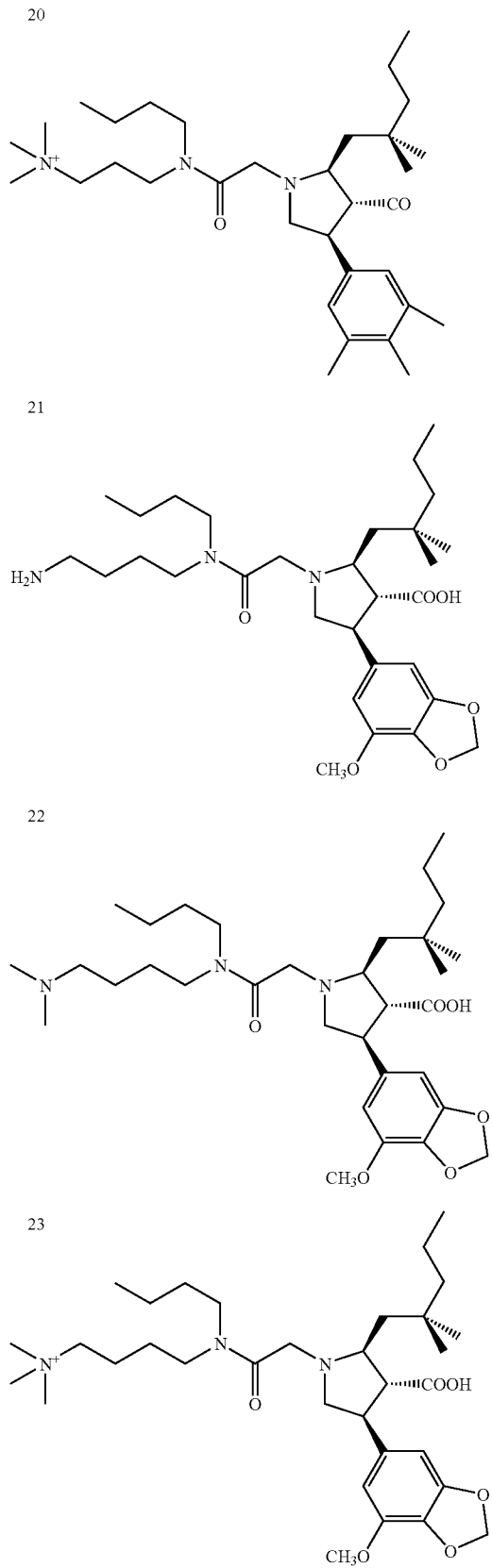
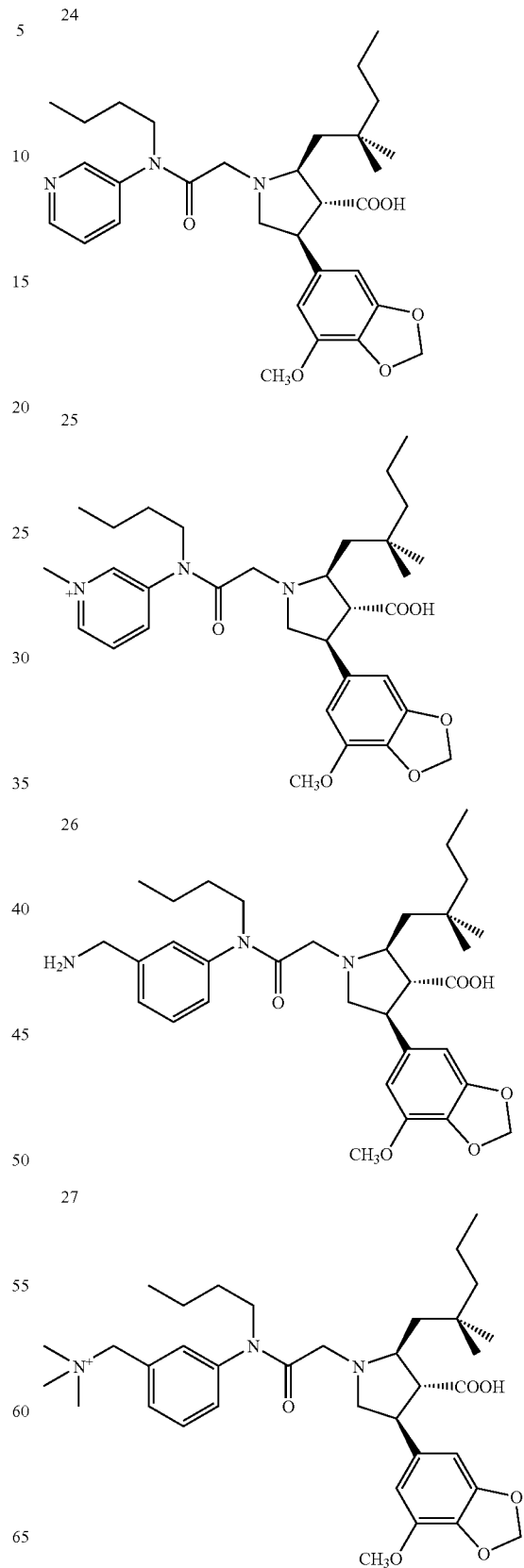

TABLE 3C-continued
28
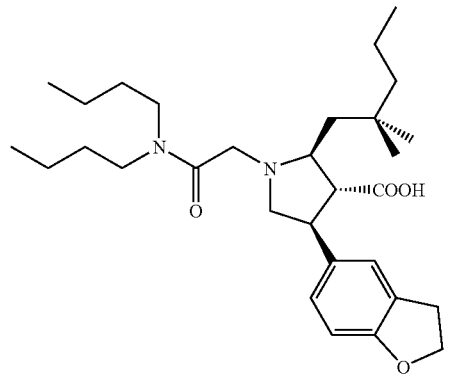
29
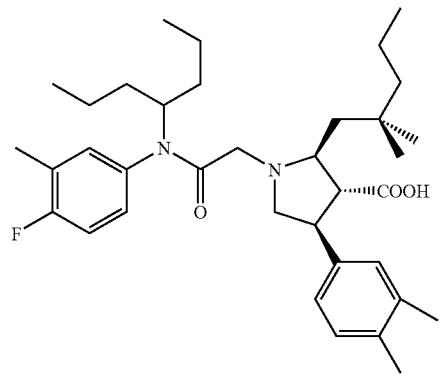
30
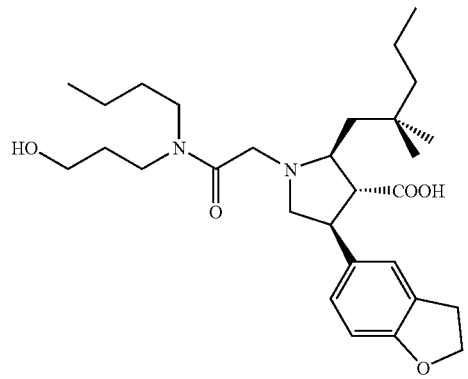
31
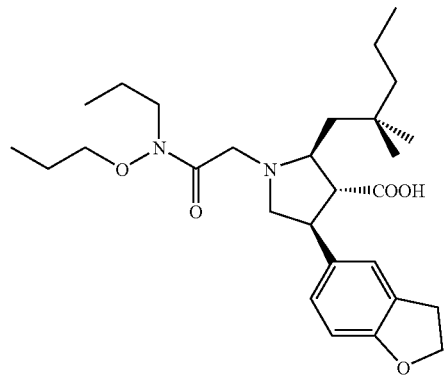
TABLE 3C-continued
32
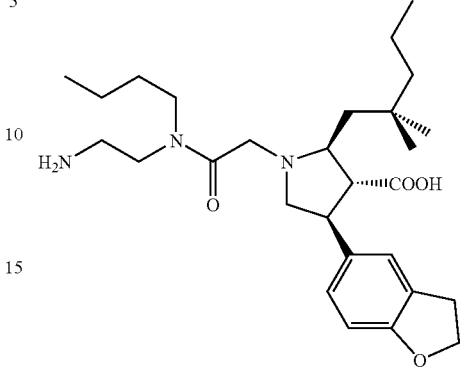
33
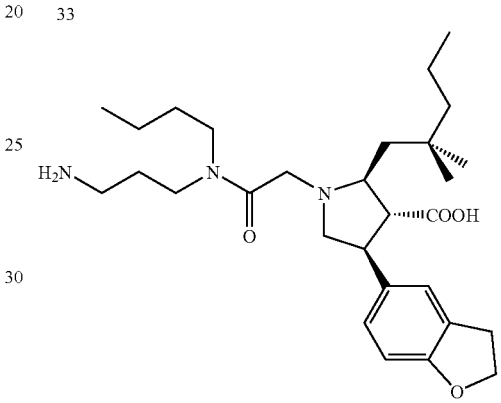
34
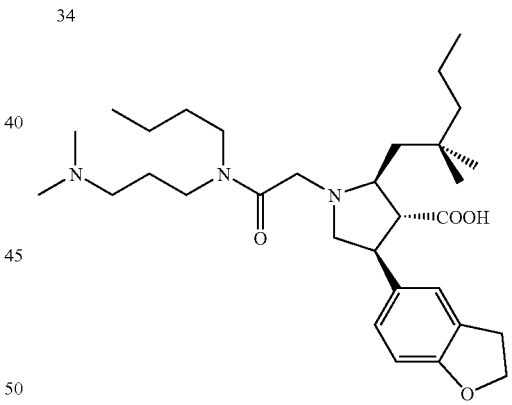
35
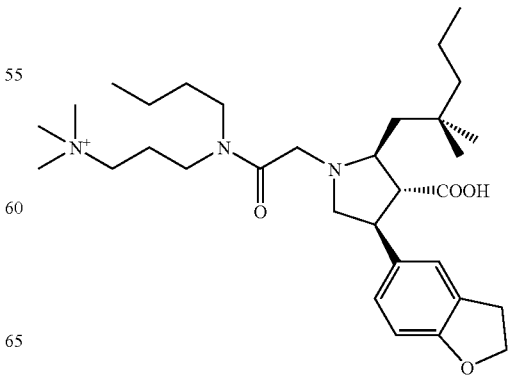

TABLE 3C-continued
36
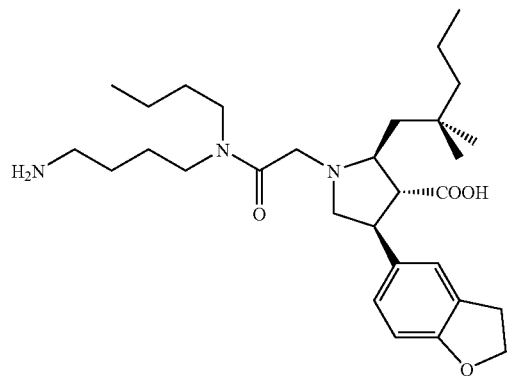
37
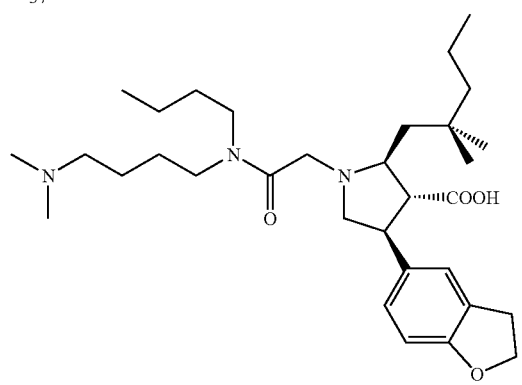
38
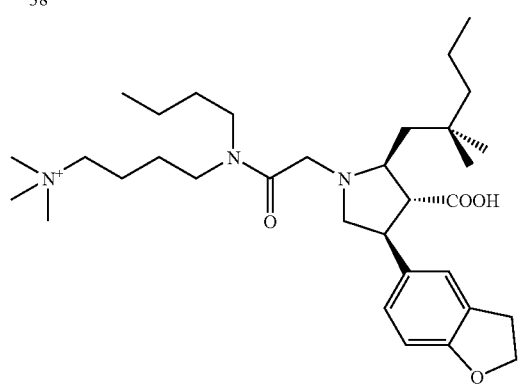
39
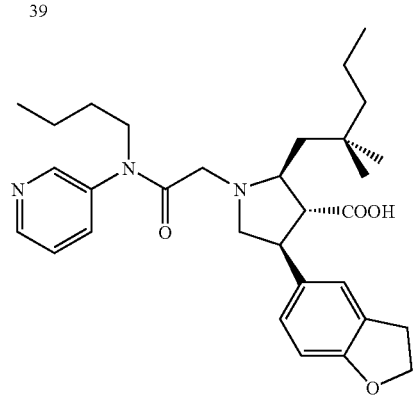
TABLE 3C-continued
40
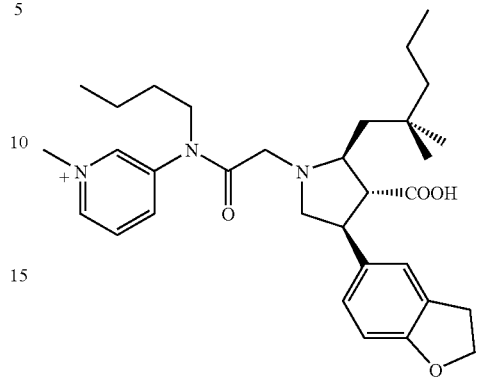
41
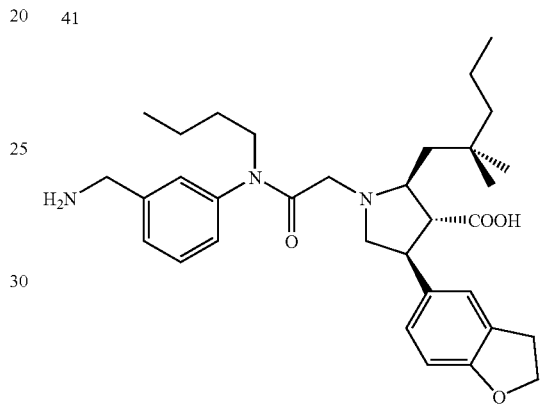
42
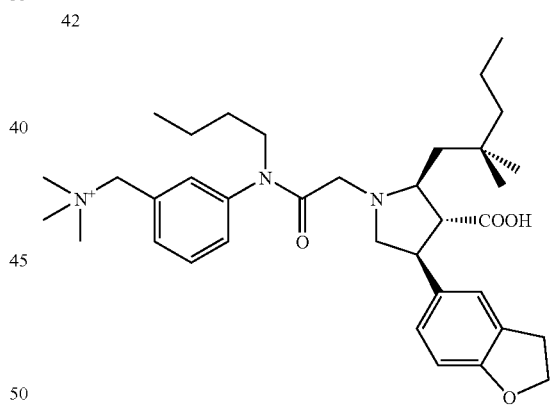
43
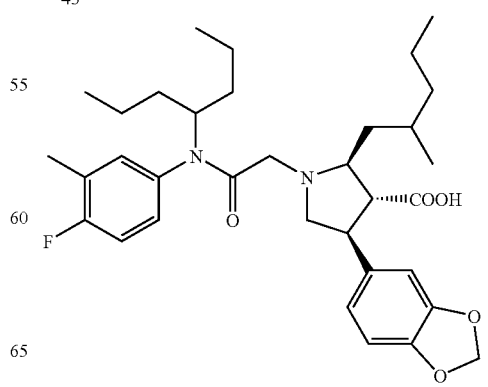

TABLE 3C-continued
44
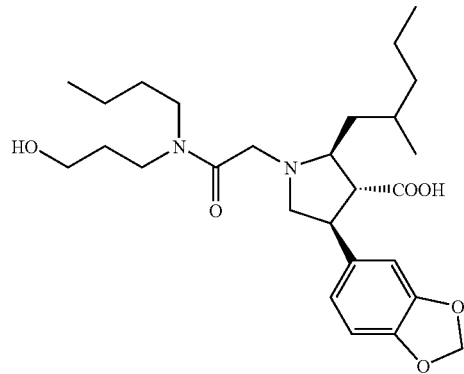
45
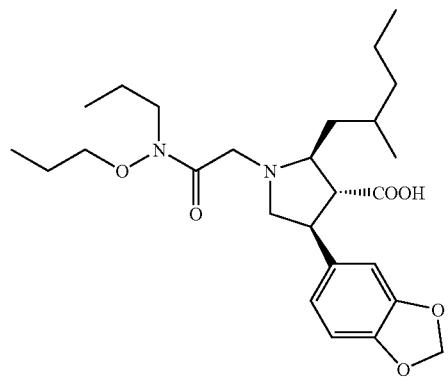
46
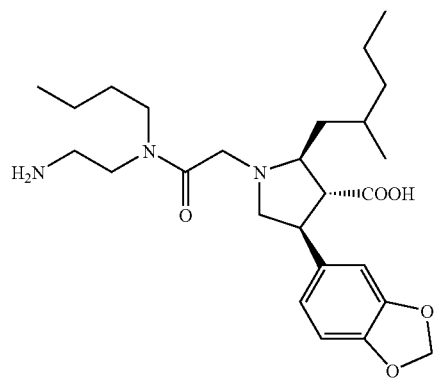
47
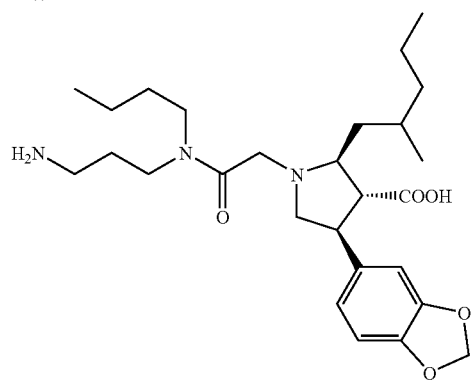
TABLE 3C-continued
48
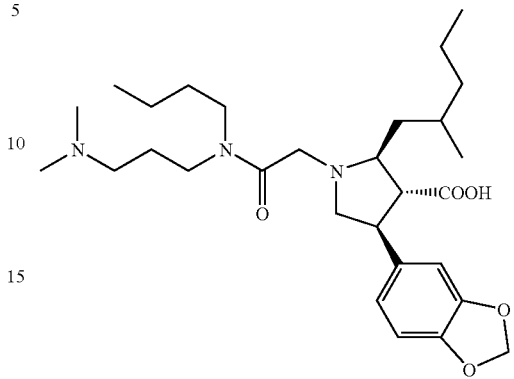
49
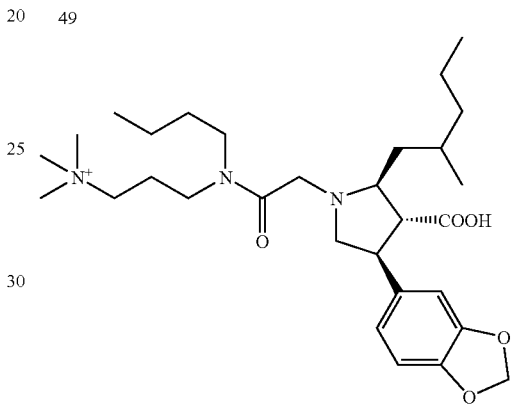
50
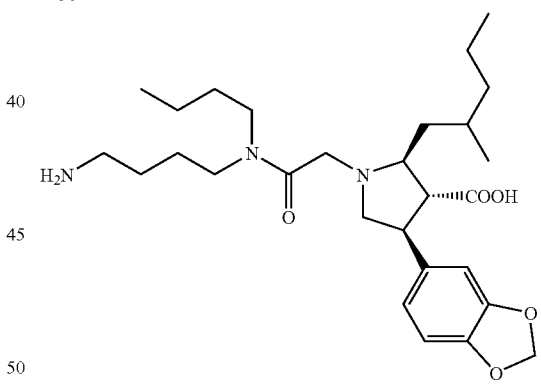
51
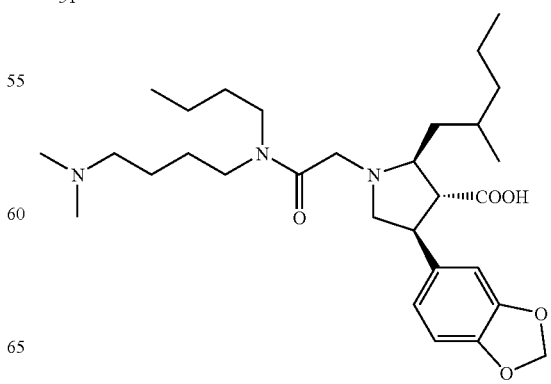

TABLE 3C-continued
52
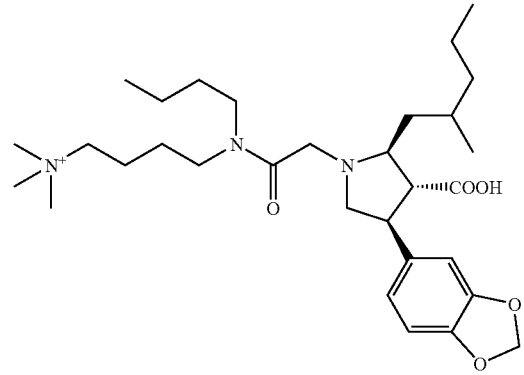
53
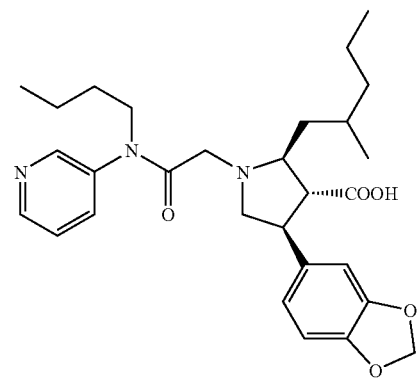
54
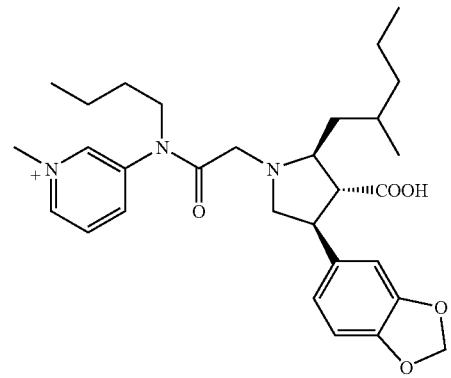
55
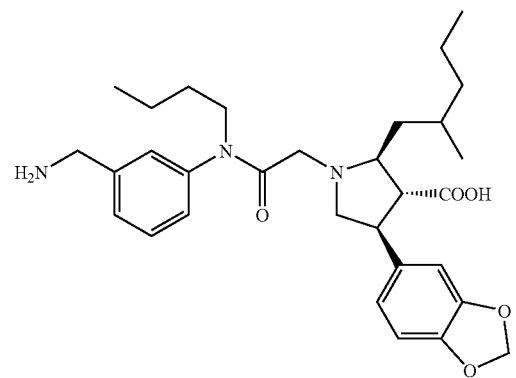
TABLE 3C-continued
56
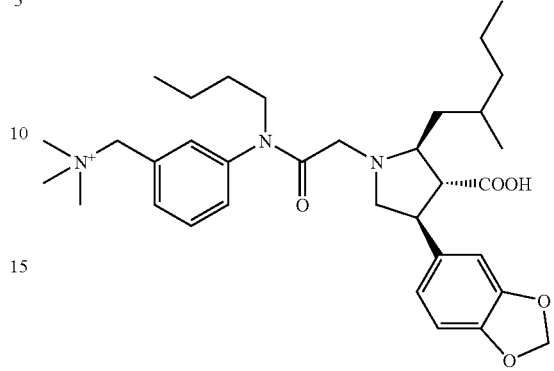
57
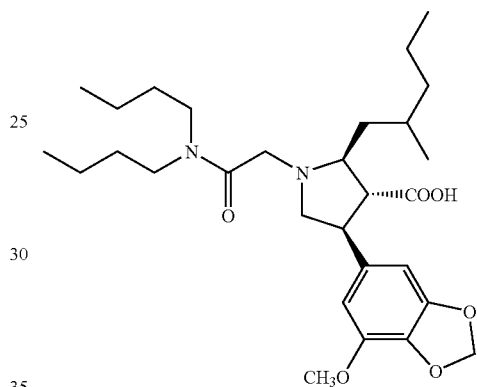
58
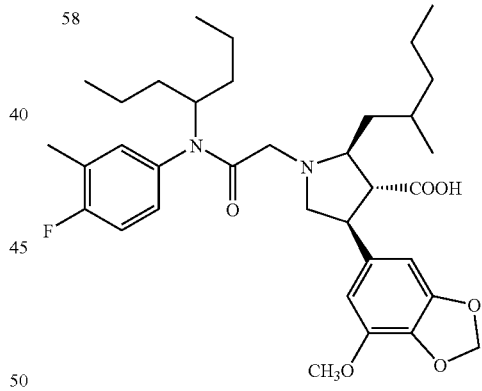
59
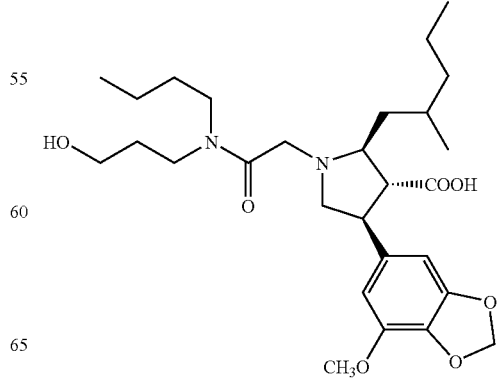

TABLE 3C-continued
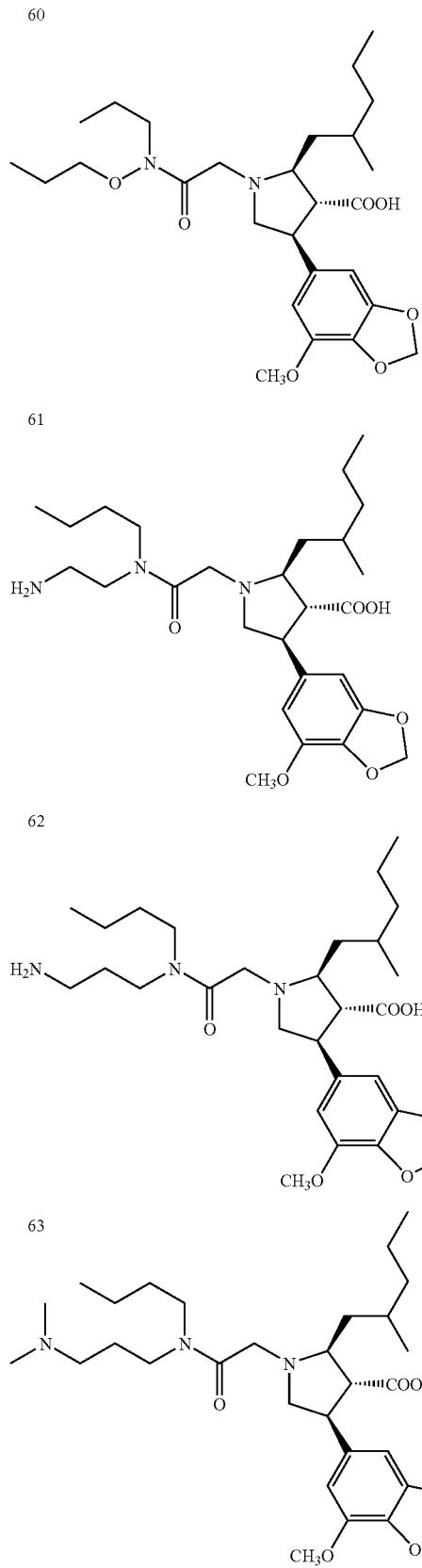
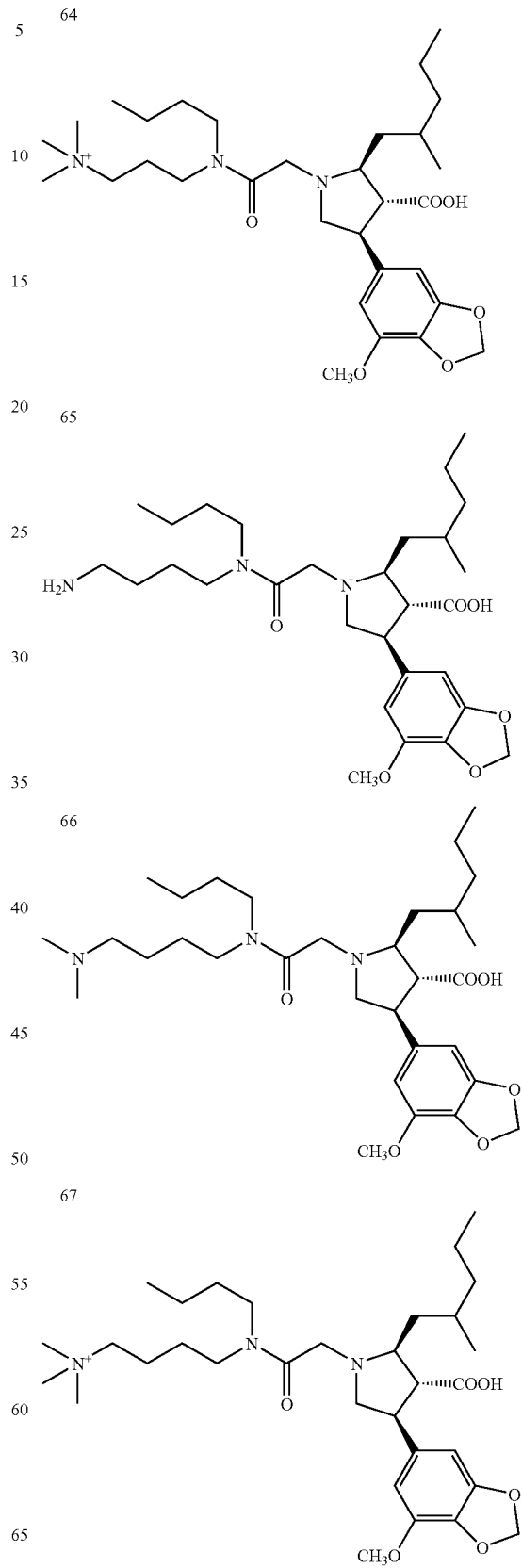

TABLE 3C-continued
68
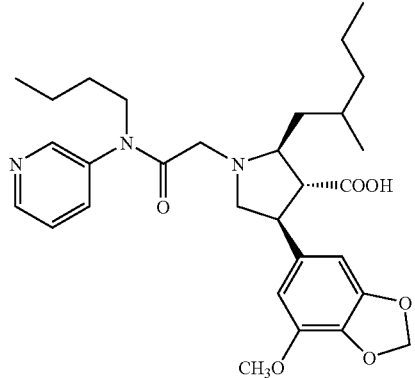
69
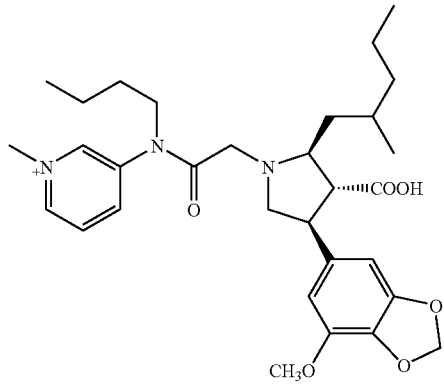
70
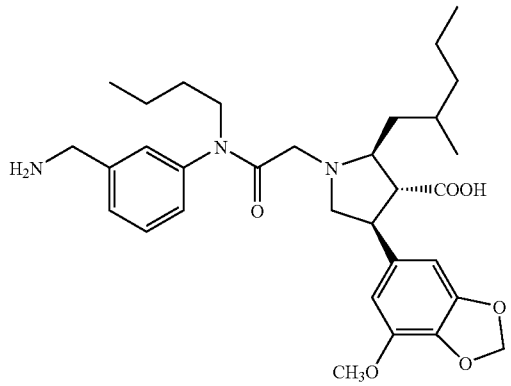
71
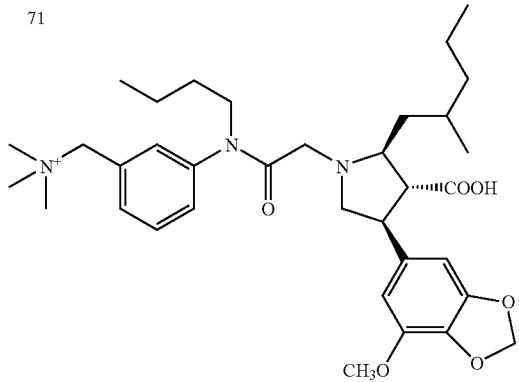
TABLE 3C-continued
72
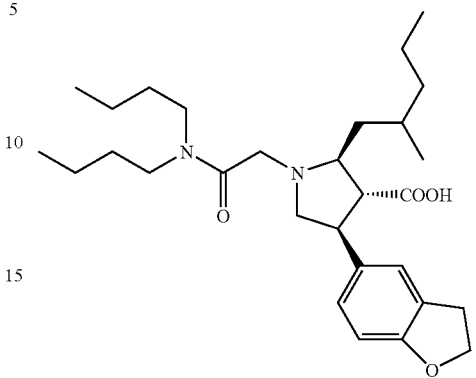
73
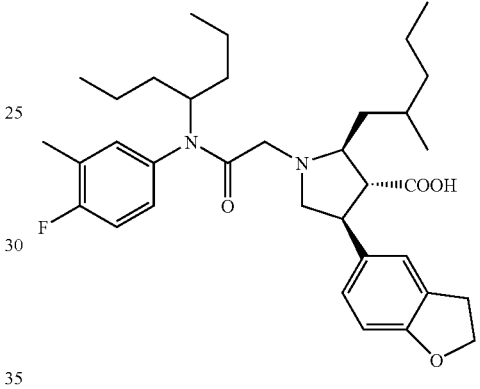
74
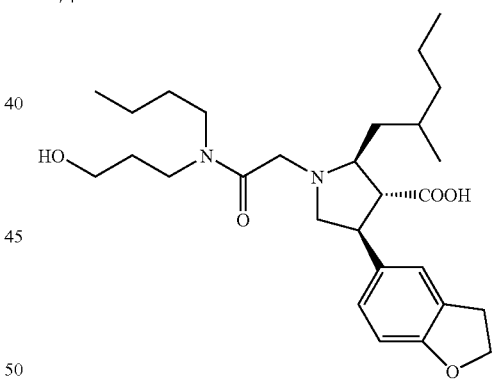
75
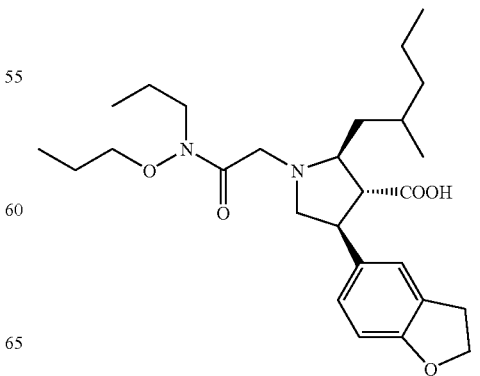

TABLE 3C-continued
76
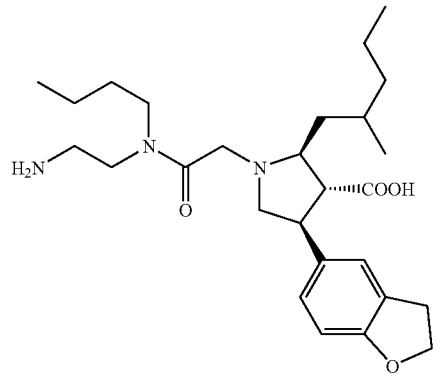
77
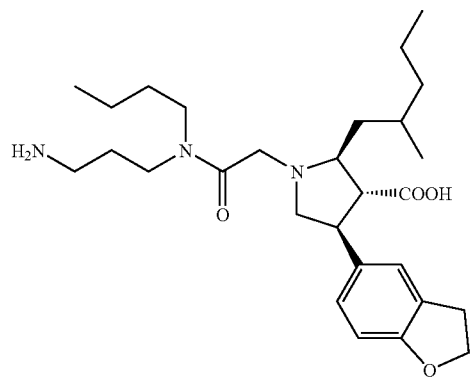
78
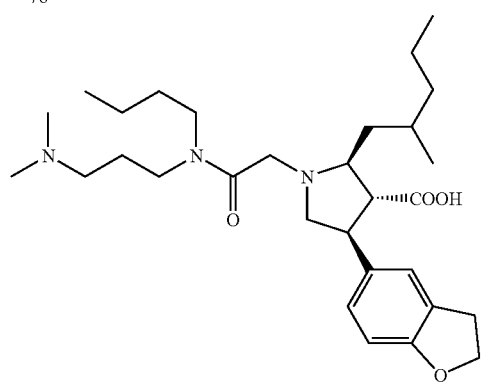
79
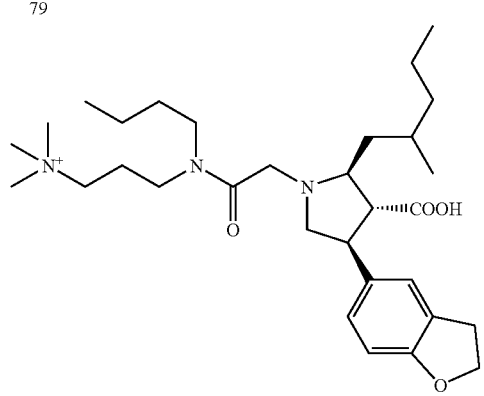
TABLE 3C-continued
80

81

82
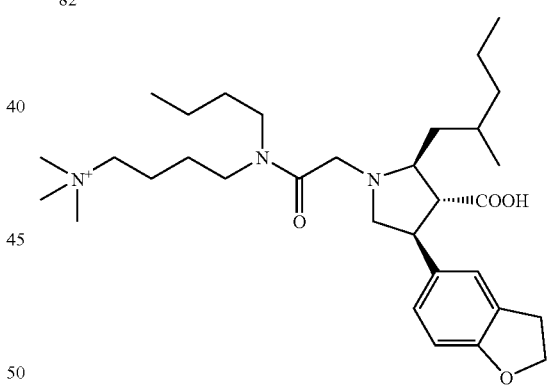
83
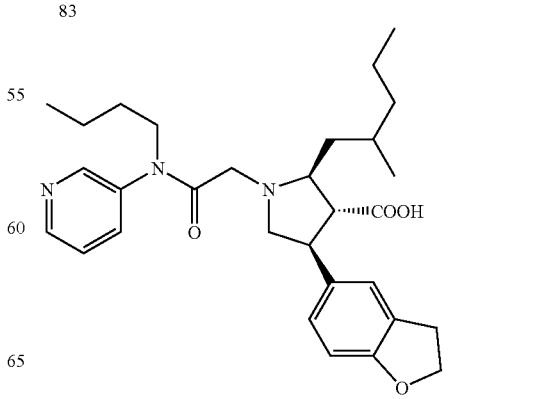

TABLE 3C-continued
84
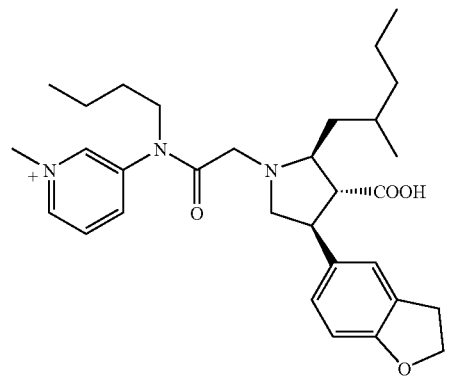
85
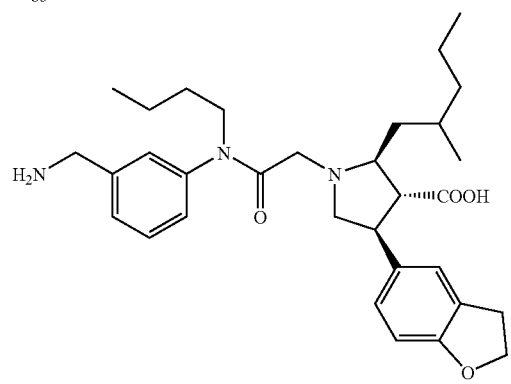
86
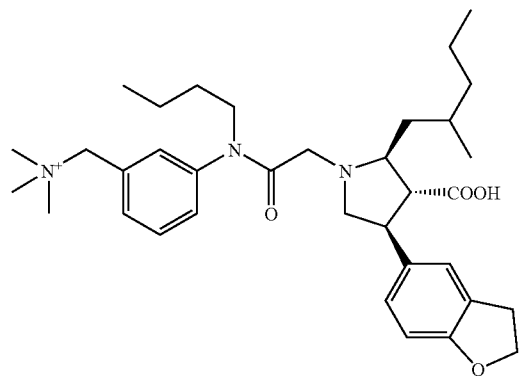
87
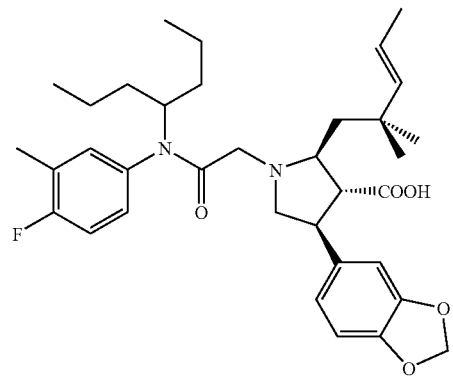
TABLE 3C-continued
88
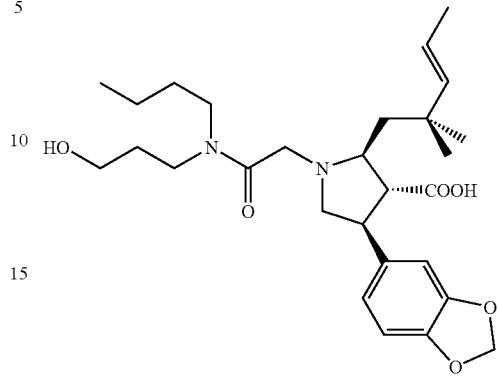
89
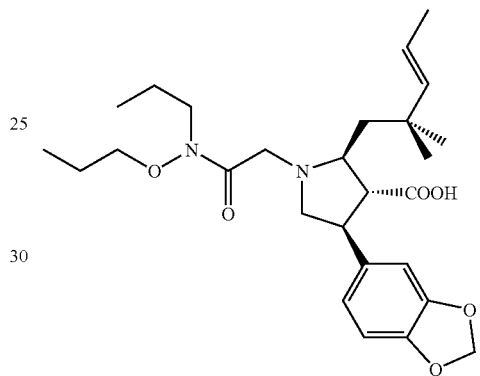
90
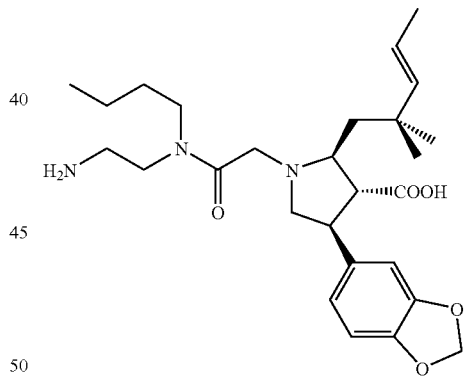
91
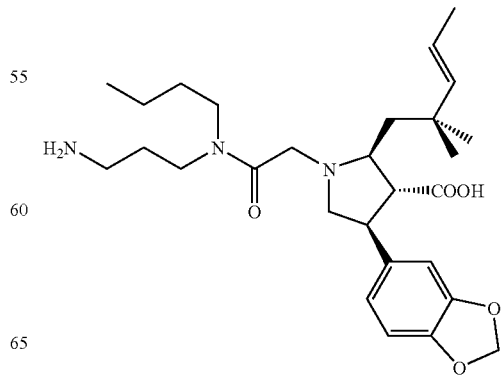

TABLE 3C-continued
92
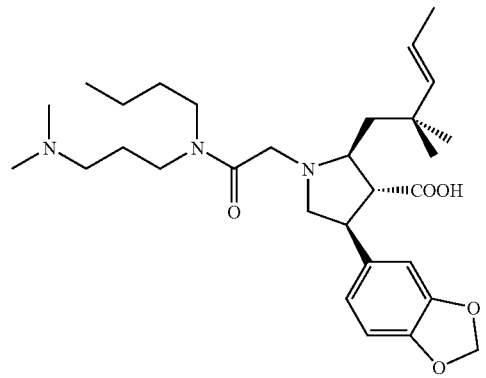
93
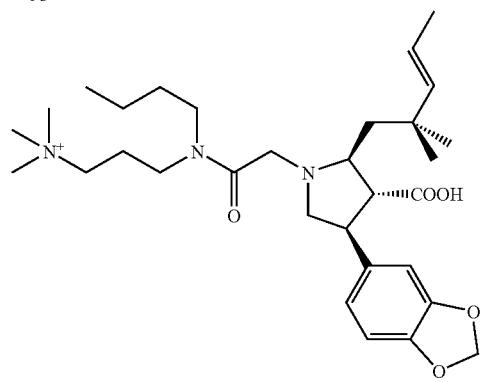
94
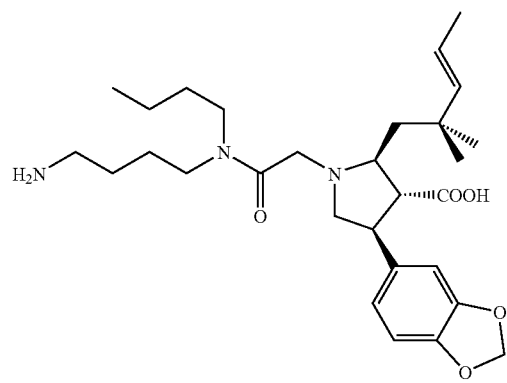
95
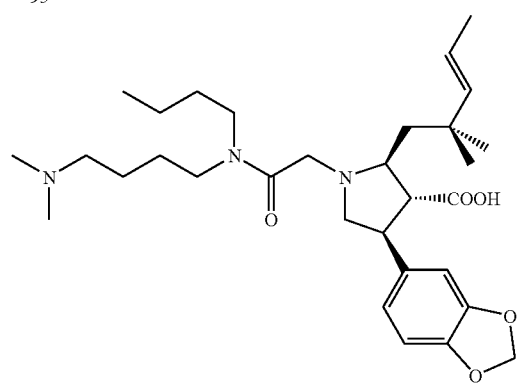
TABLE 3C-continued
96
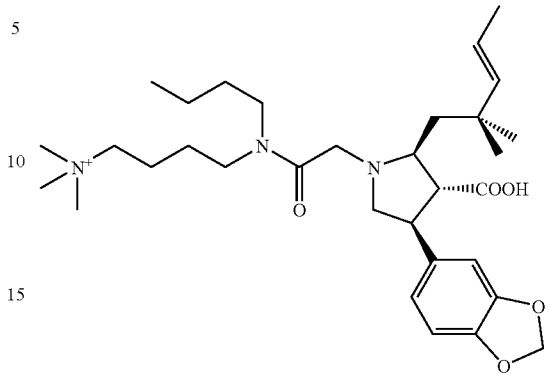
97
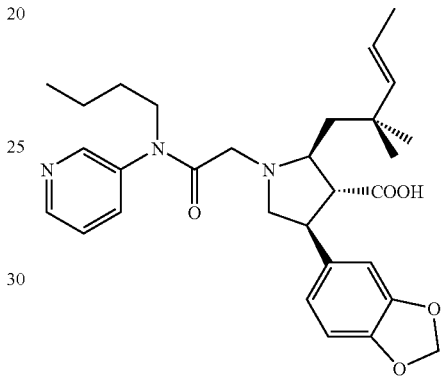
98
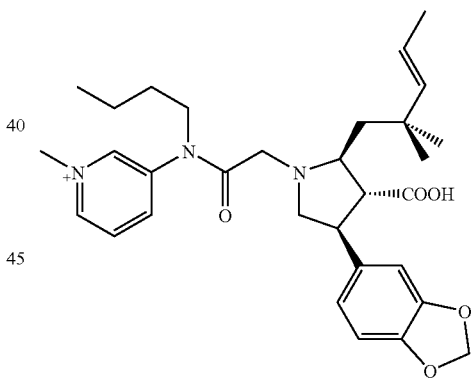
99
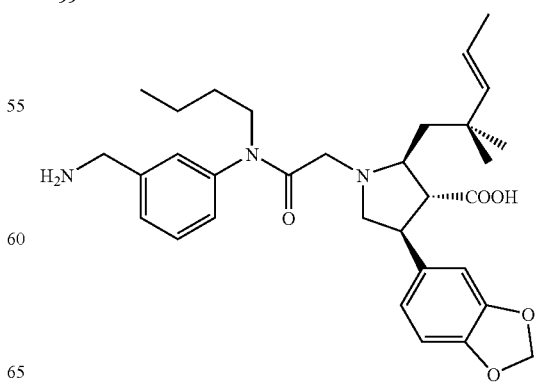

TABLE 3C-continued
100
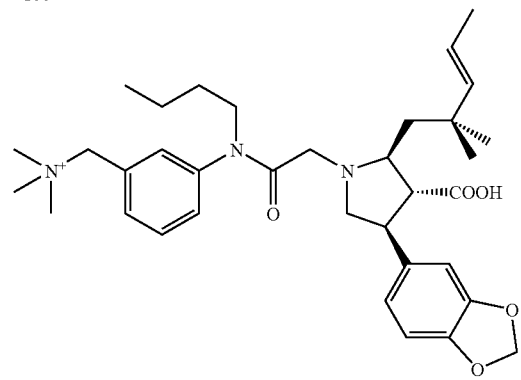
101
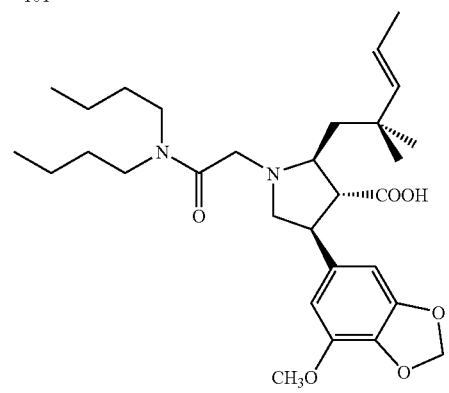
102
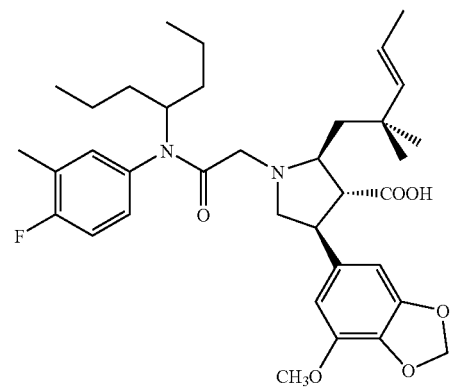
103
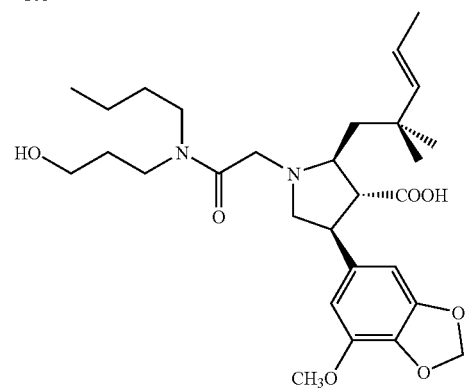
TABLE 3C-continued
104
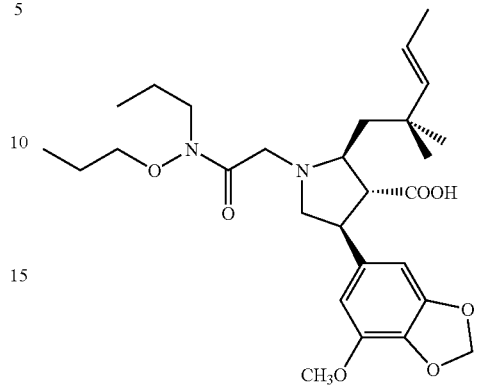
105
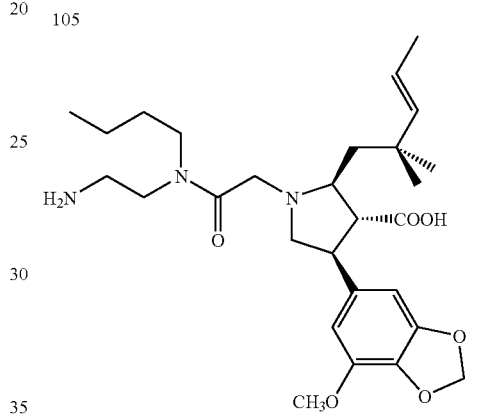
106
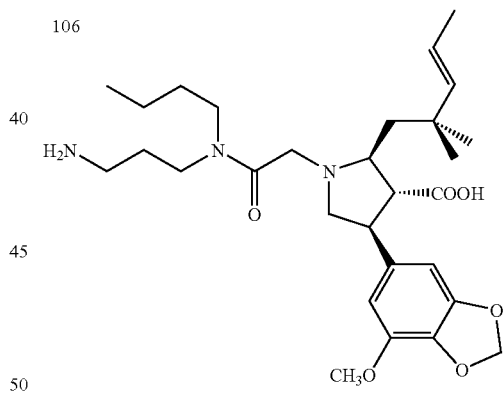
107
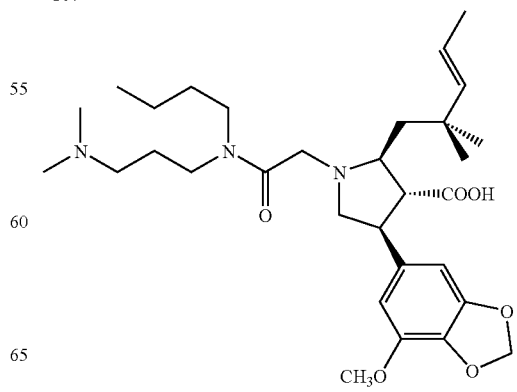

TABLE 3C-continued
108
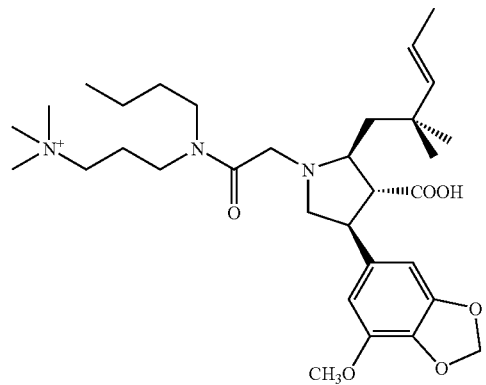
109
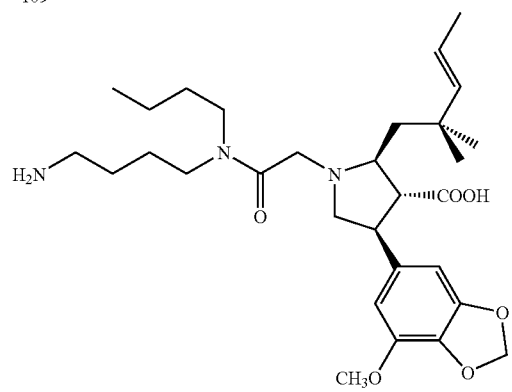
110
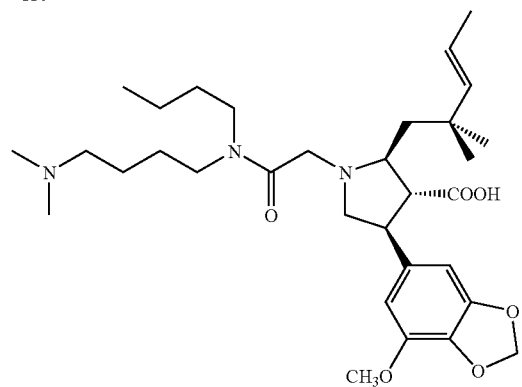
111
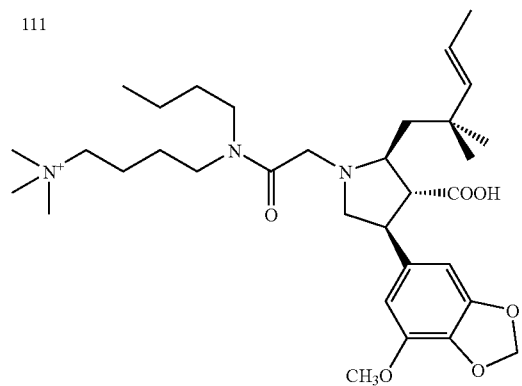
TABLE 3C-continued
112
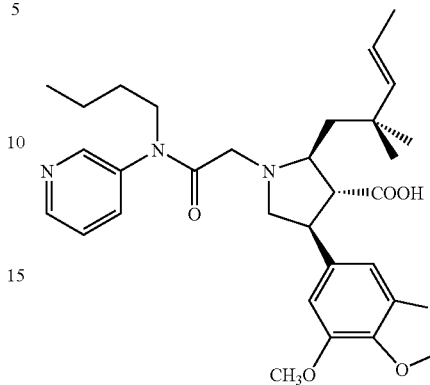
113
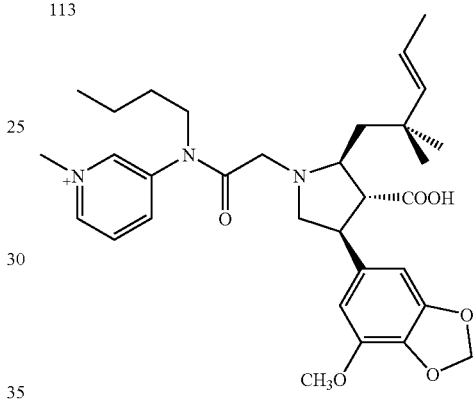
114
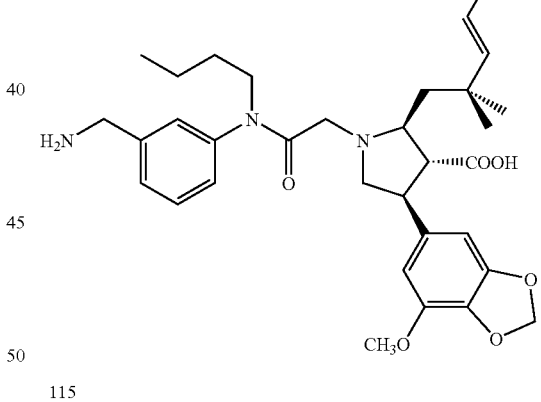
115
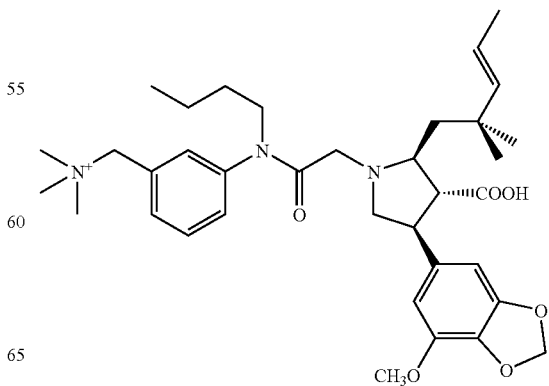

TABLE 3C-continued
116
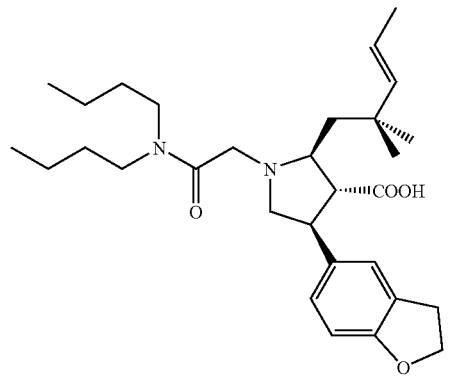
117
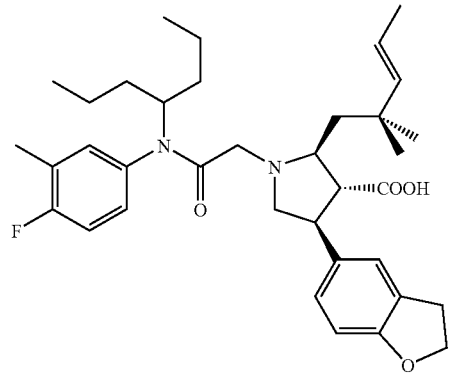
118
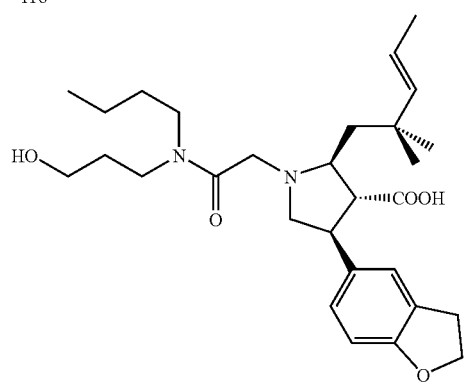
119
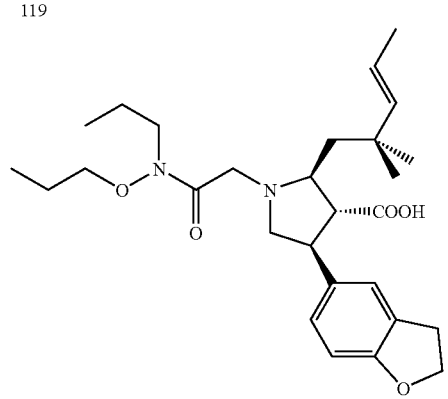
TABLE 3C-continued
120
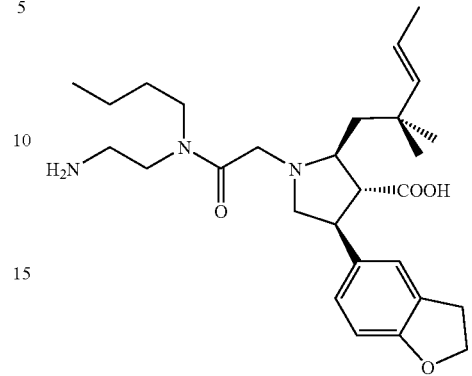
121
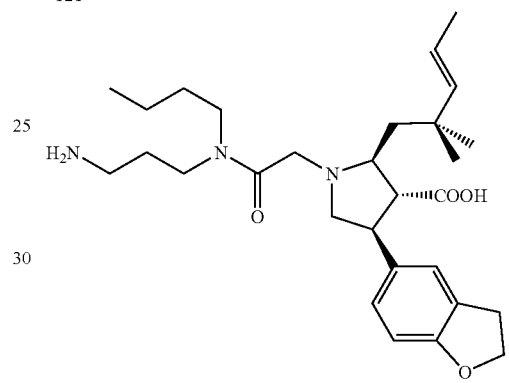
122
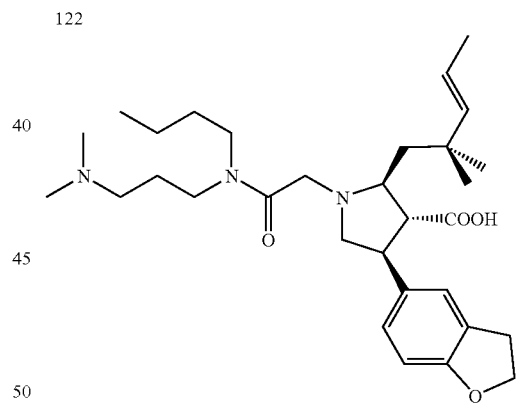
123
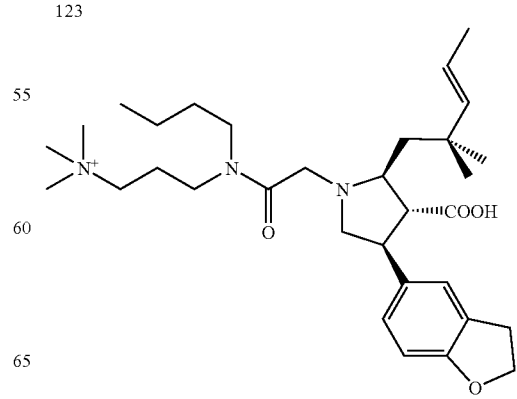

TABLE 3C-continued
124
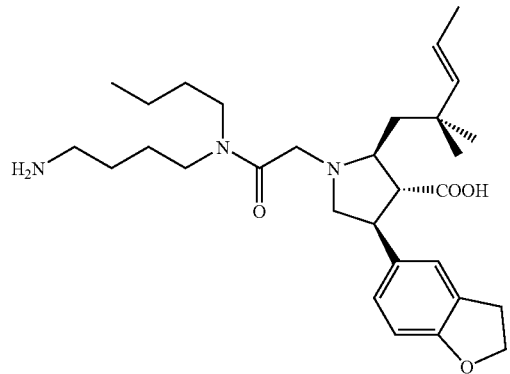
125
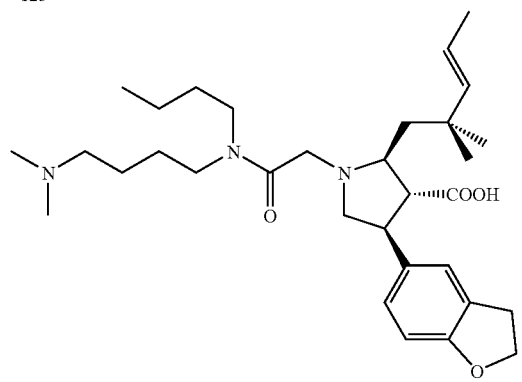
126
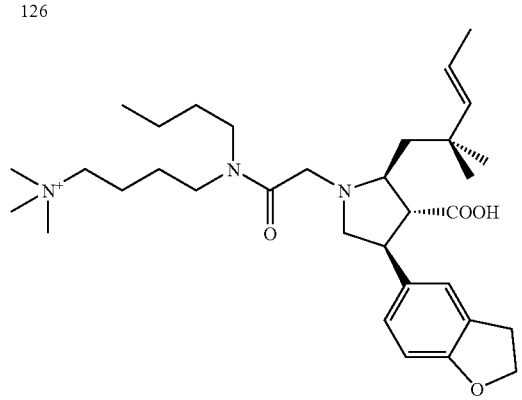
127
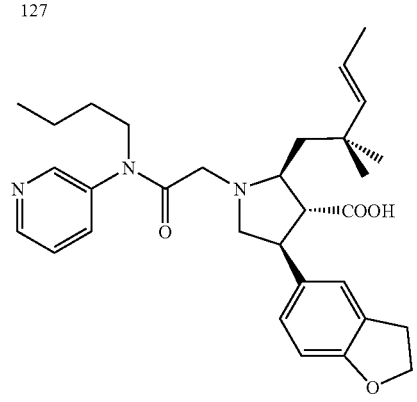
TABLE 3C-continued
128
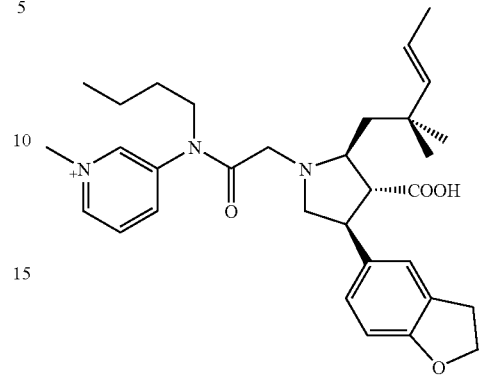
129
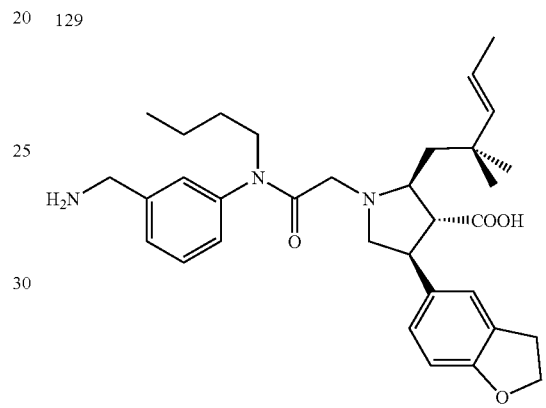
130
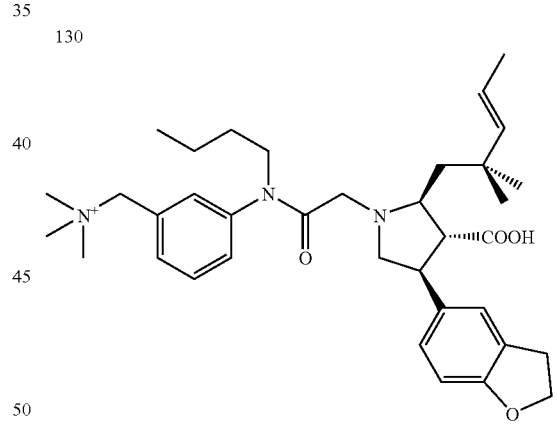
131
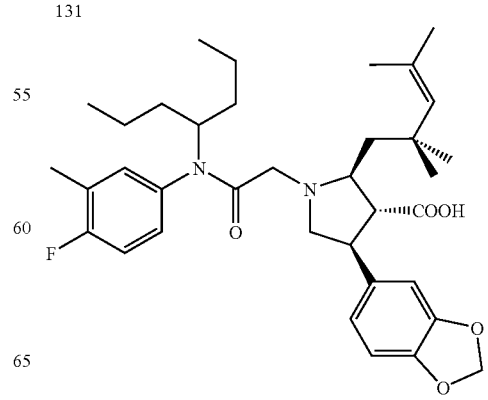

TABLE 3C-continued
132
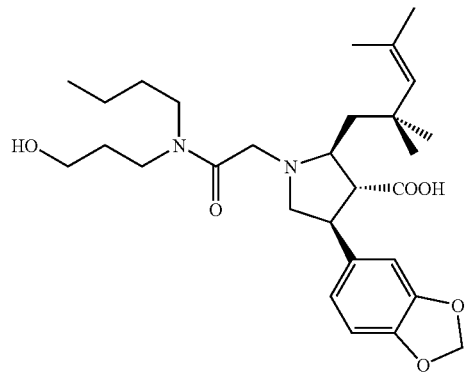
133
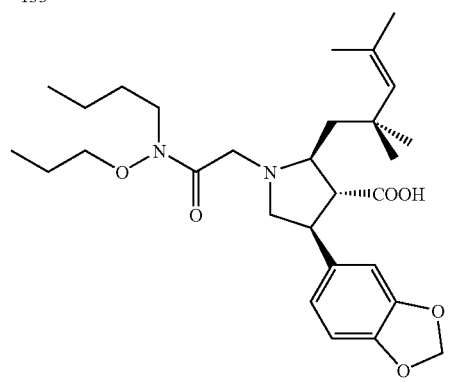
134
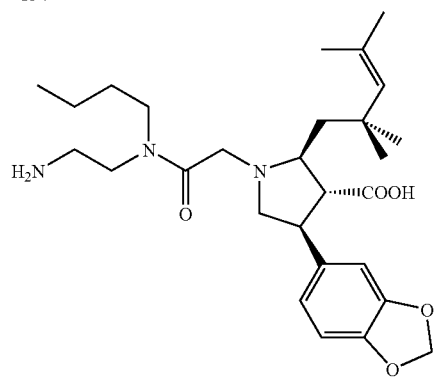
135
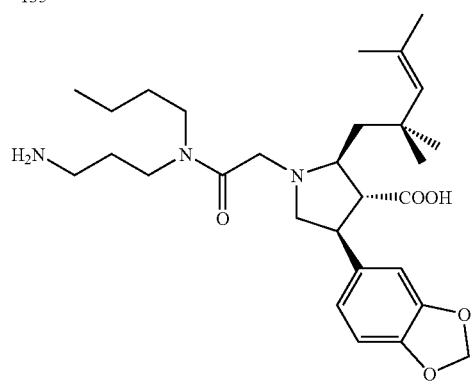
TABLE 3C-continued
136
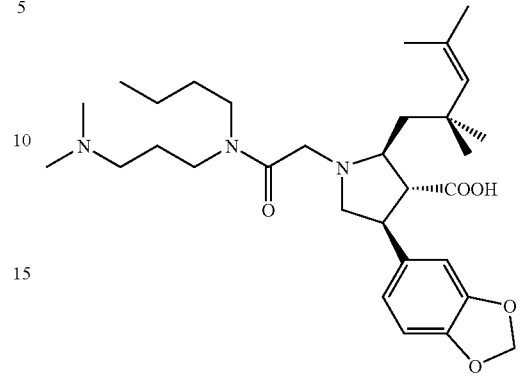
137
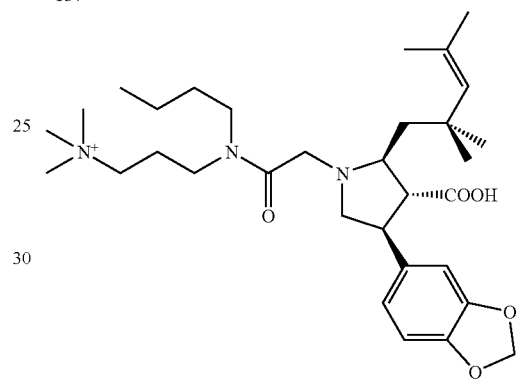
138
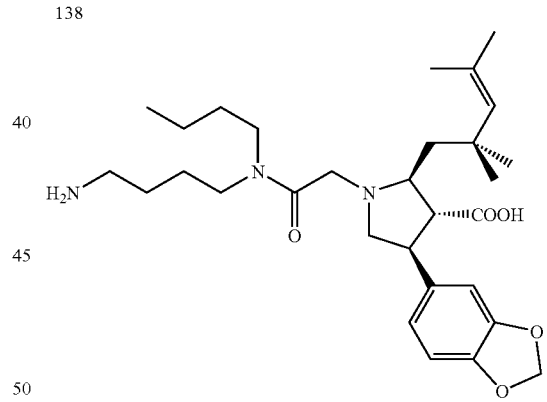
139
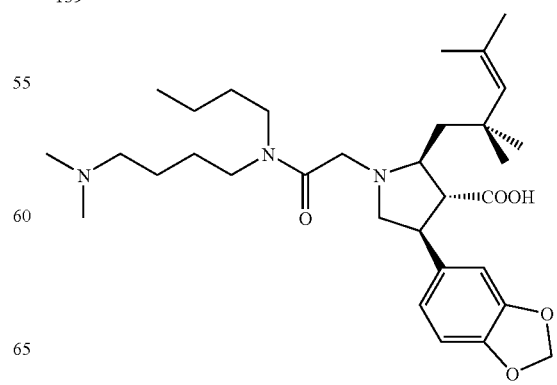

TABLE 3C-continued
140
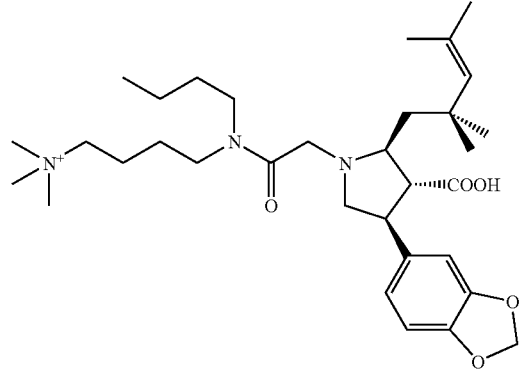
141
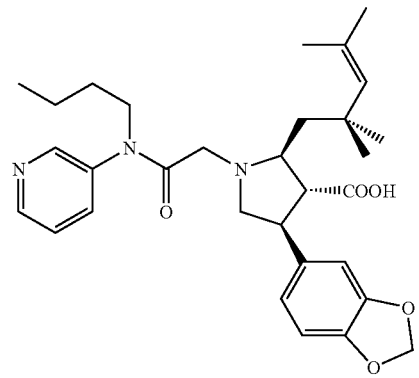
142
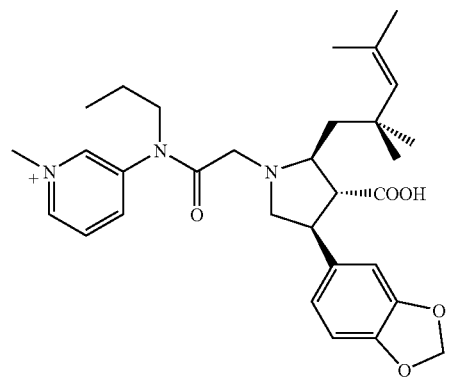
143
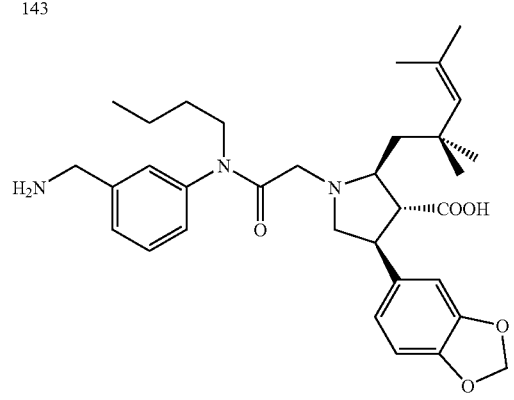
TABLE 3C-continued
144
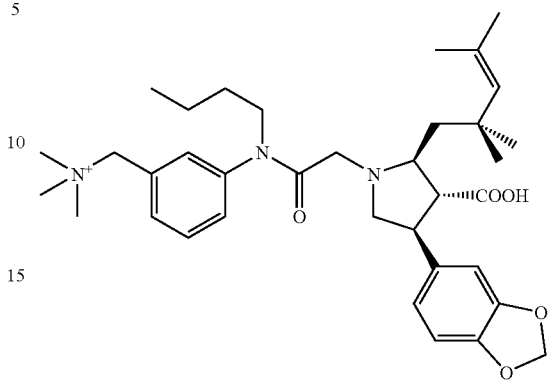
145
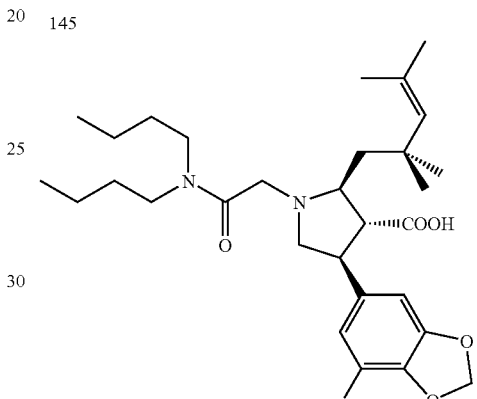
146
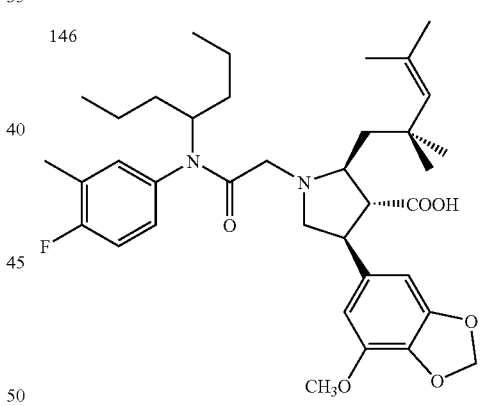
147
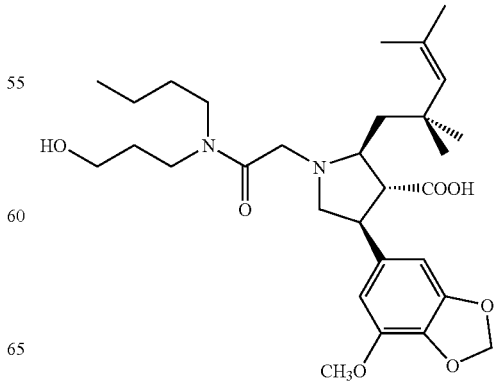

TABLE 3C-continued
148
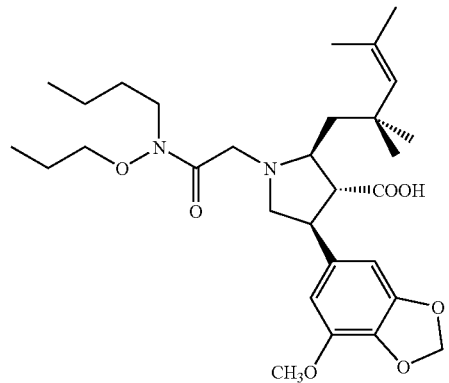
149
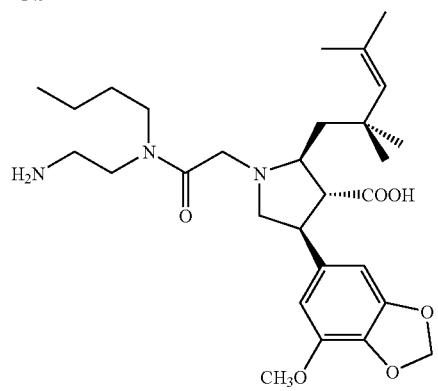
150
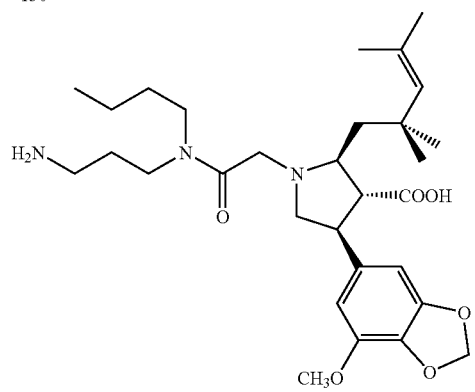
151
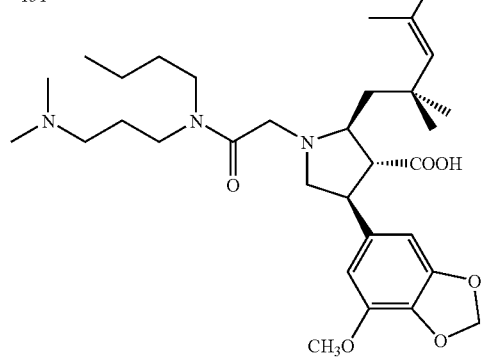
TABLE 3C-continued
152
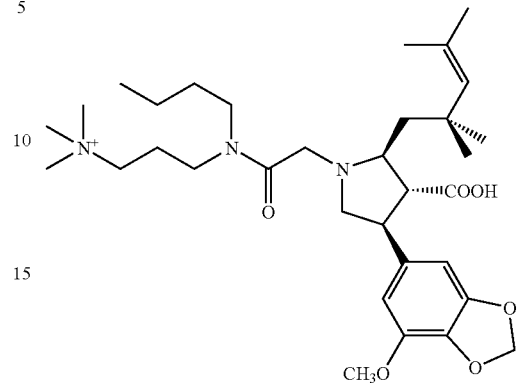
153
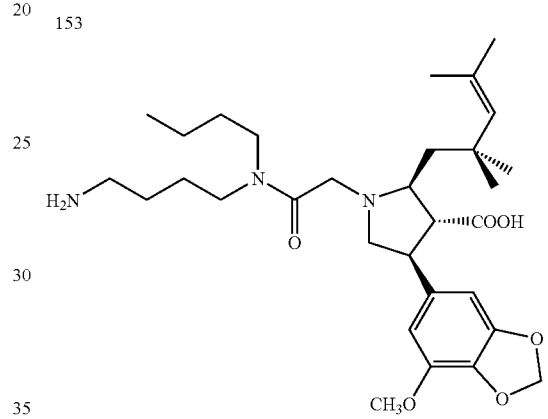
154
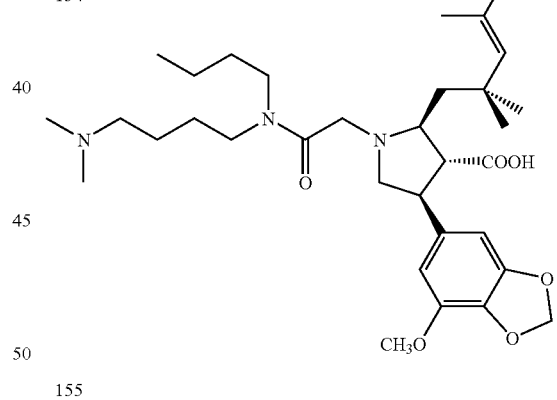
155
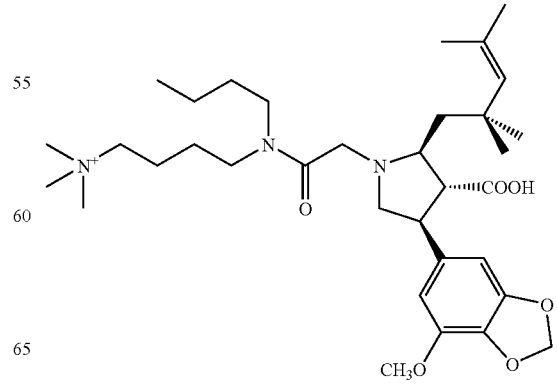

TABLE 3C-continued
156
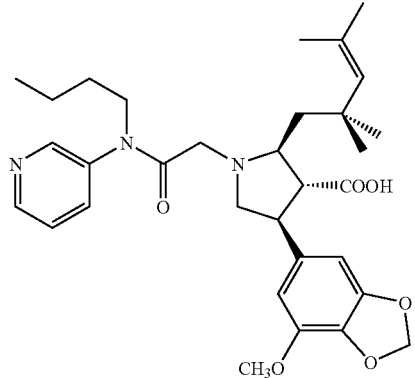
157
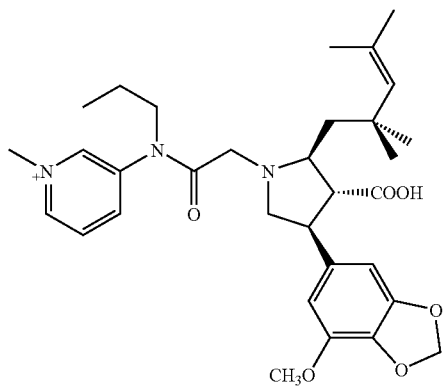
158
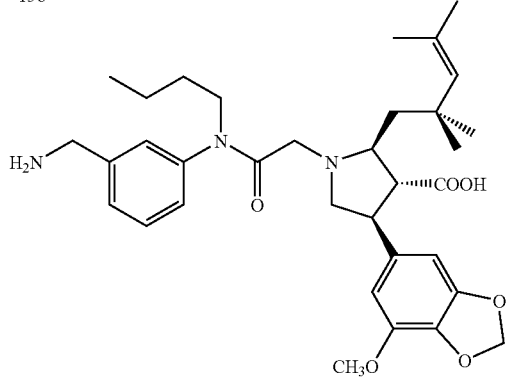
159
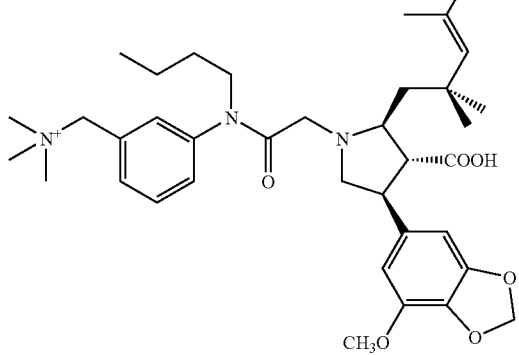
TABLE 3C-continued
160
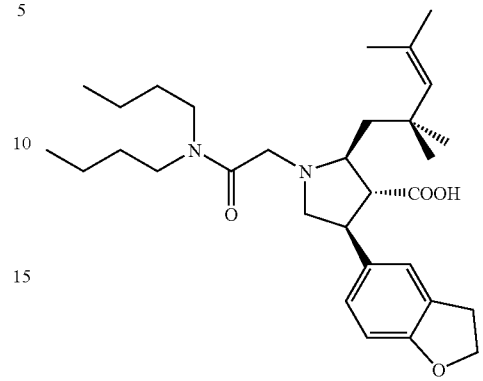
161
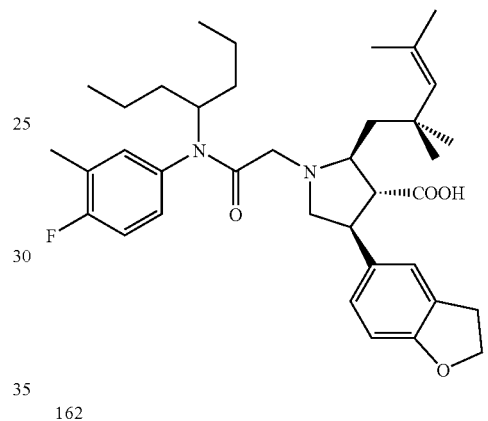
162
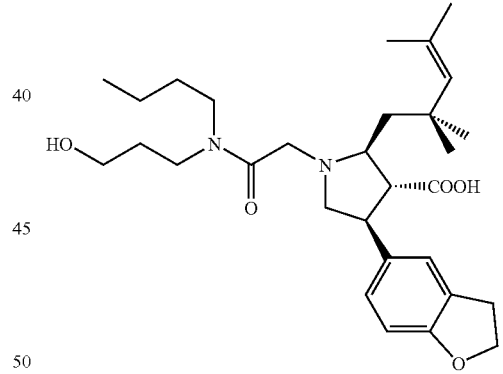
163
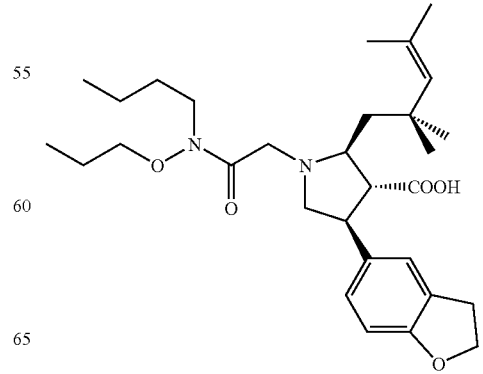

TABLE 3C-continued
164
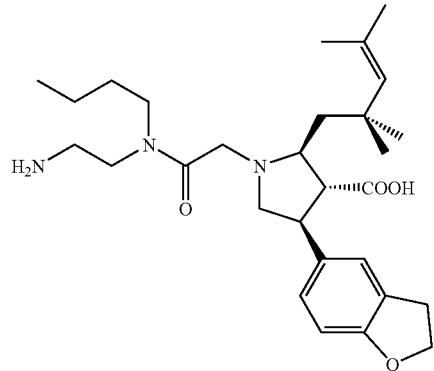
165
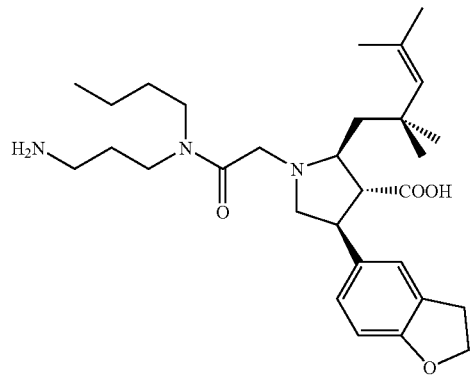
166
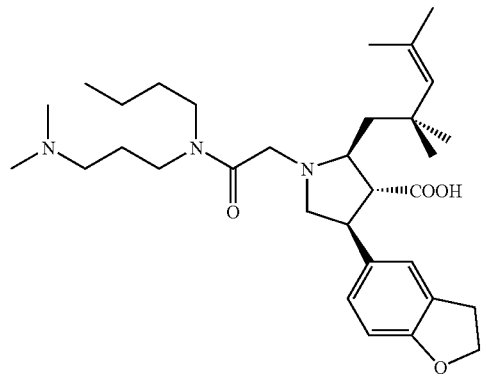
167
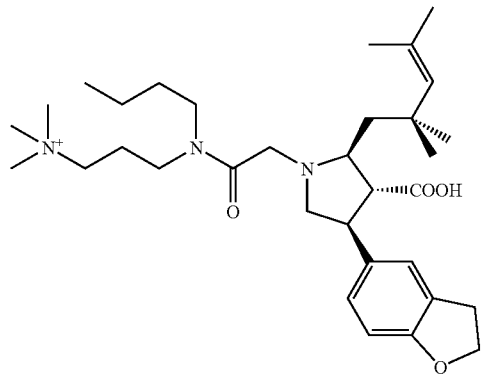
TABLE 3C-continued
168
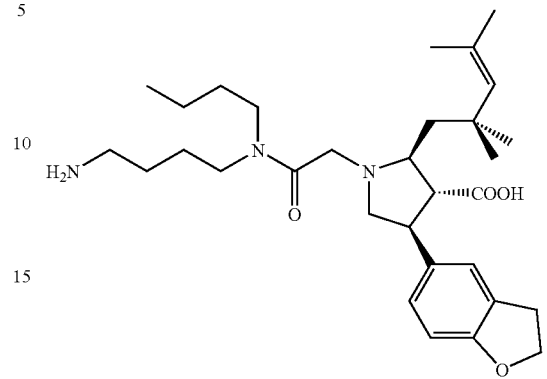
169
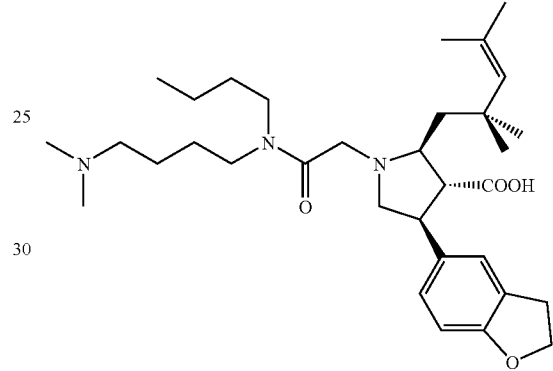
170
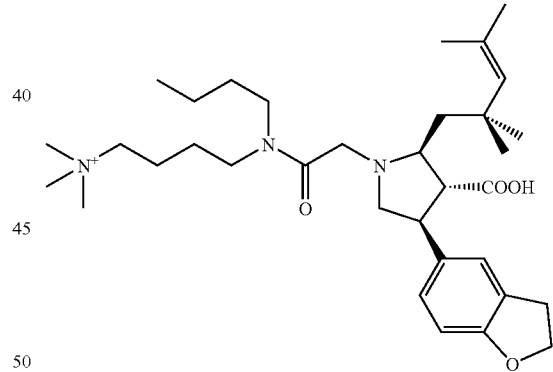
171
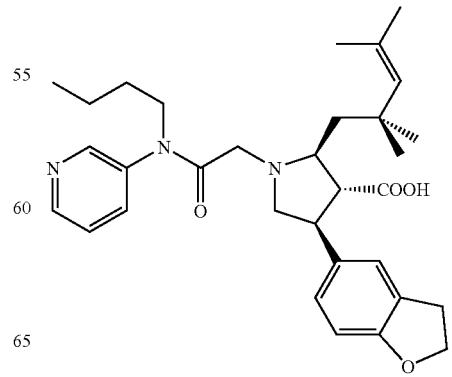

TABLE 3C-continued
172
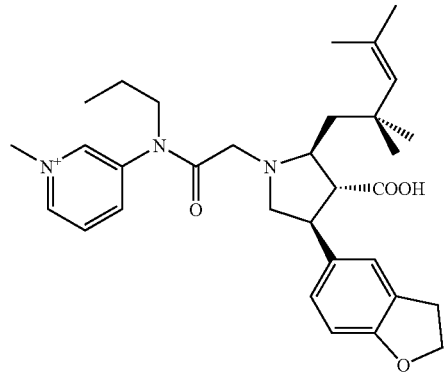
173
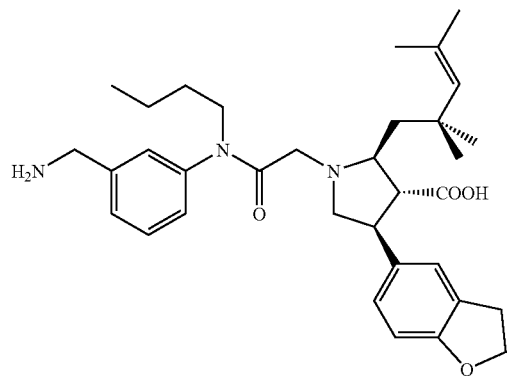
174
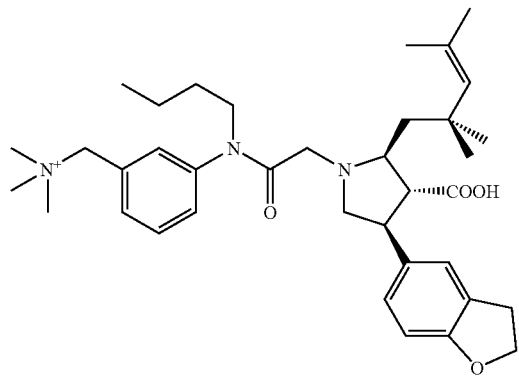
175
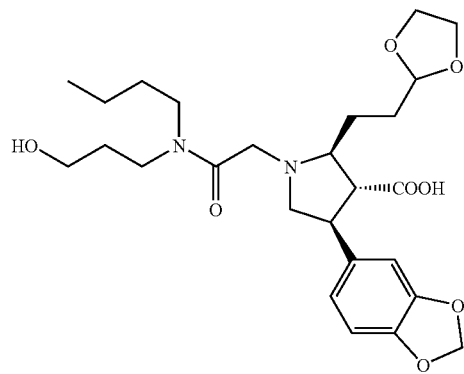
TABLE 3C-continued
176
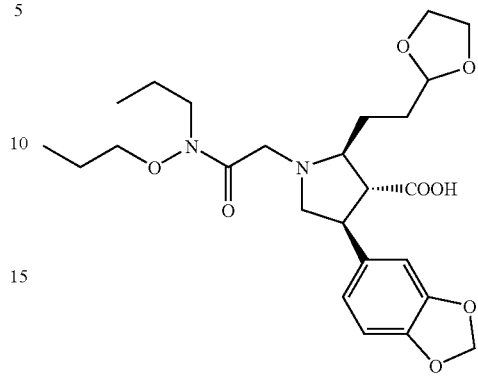
177
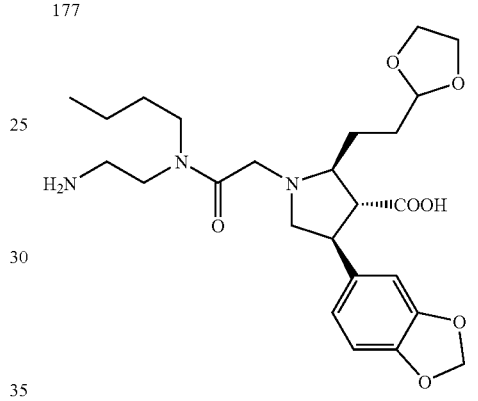
178
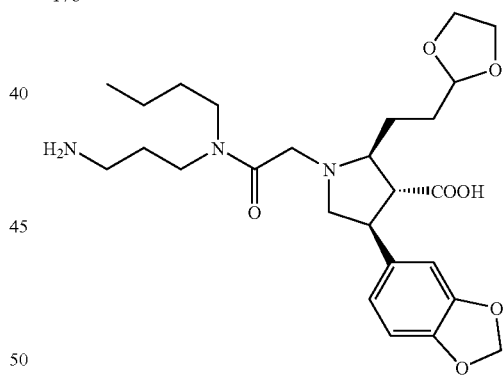
179
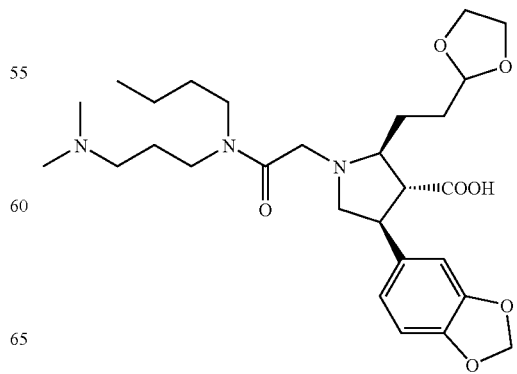

TABLE 3C-continued
181
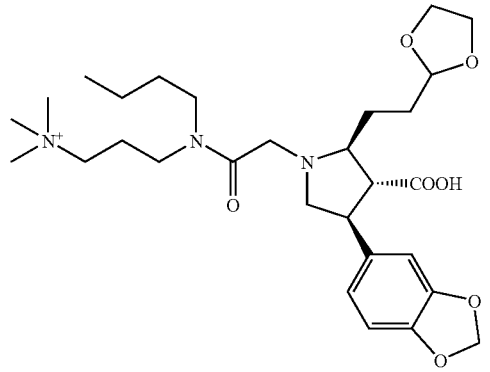
180
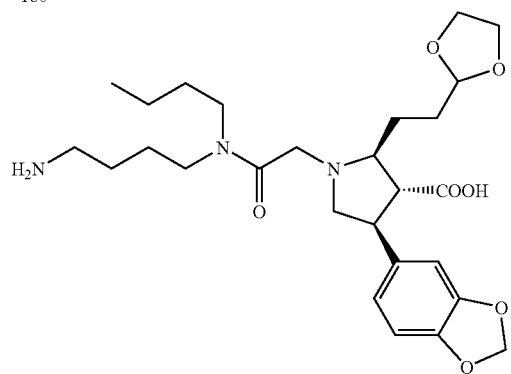
182
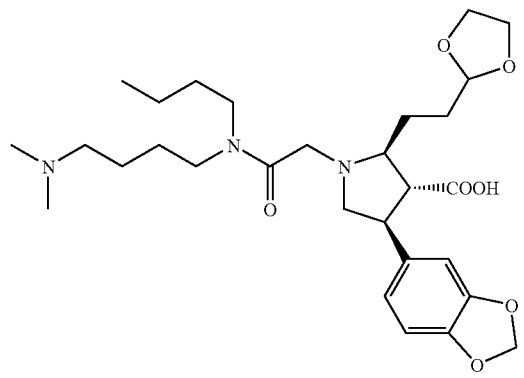
183
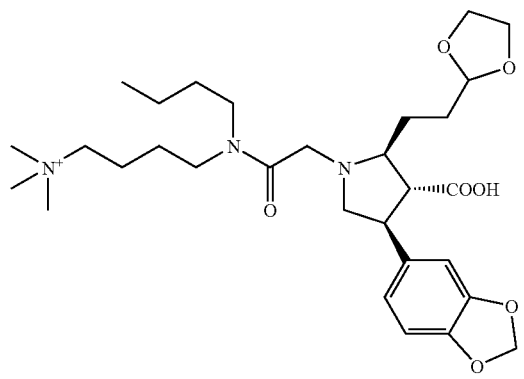
TABLE 3C-continued
184
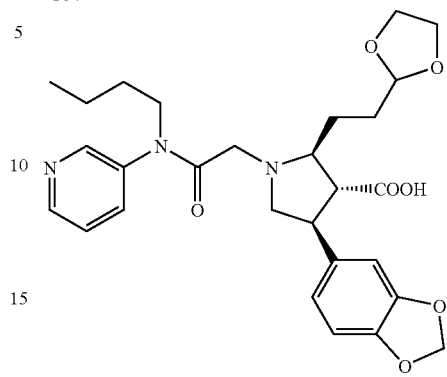
185
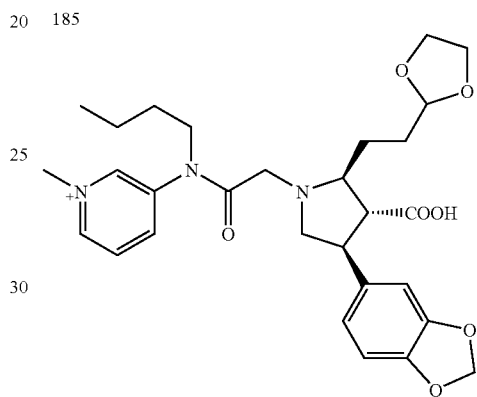
186
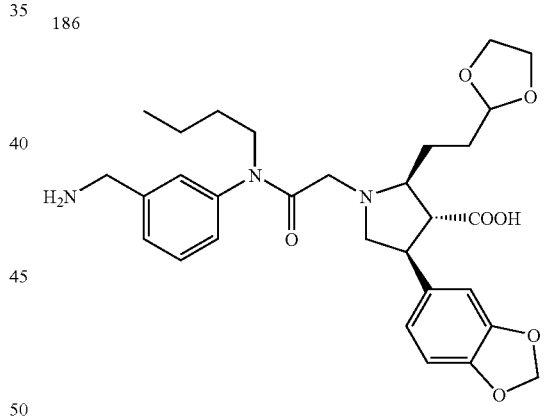
187
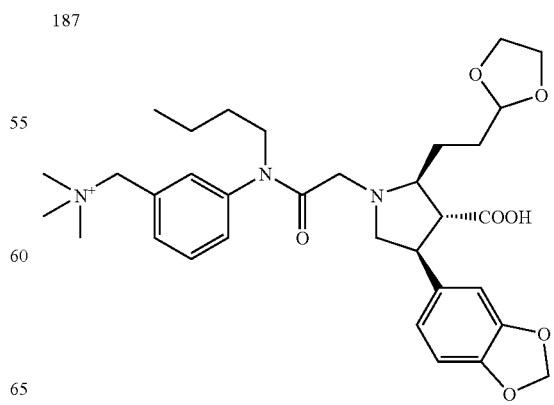

TABLE 3C-continued
188
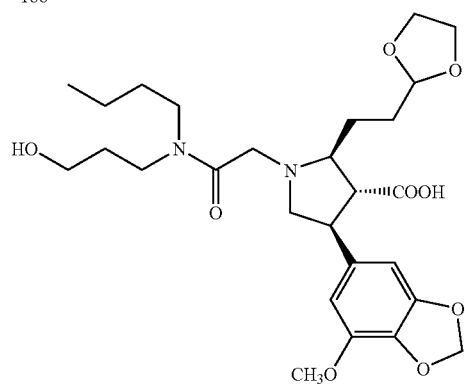
189
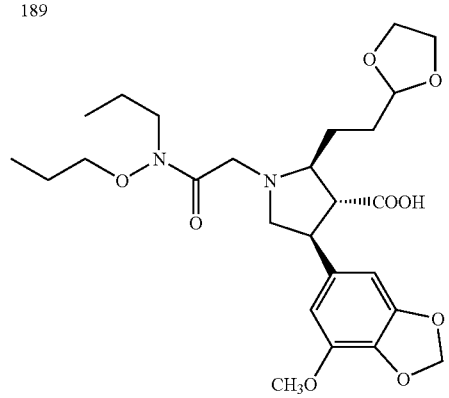
190
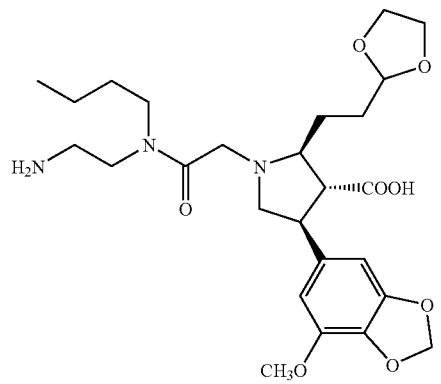
191
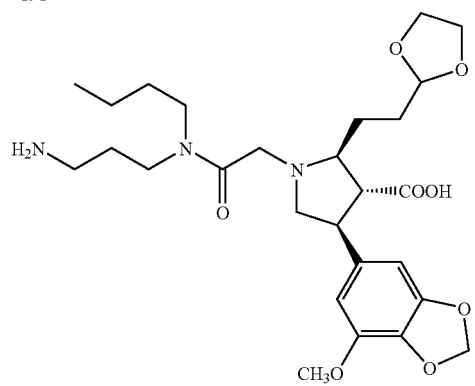
TABLE 3C-continued
192

193

194
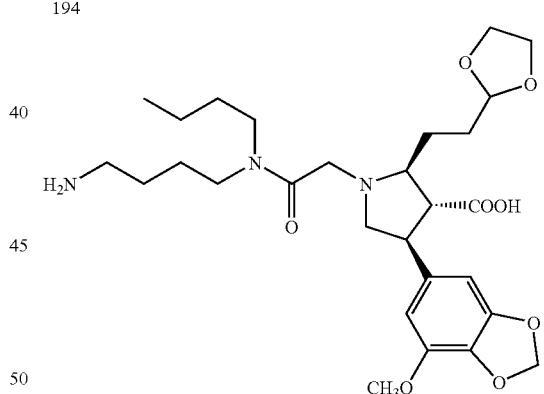
195
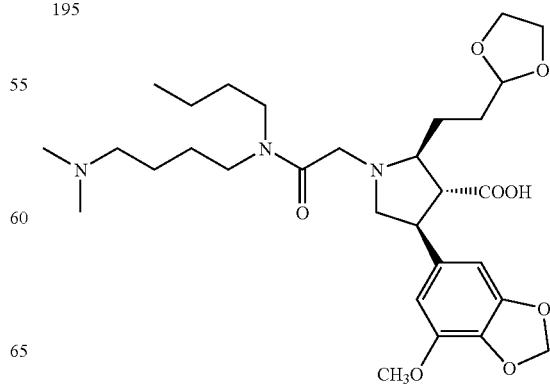

TABLE 3C-continued
196
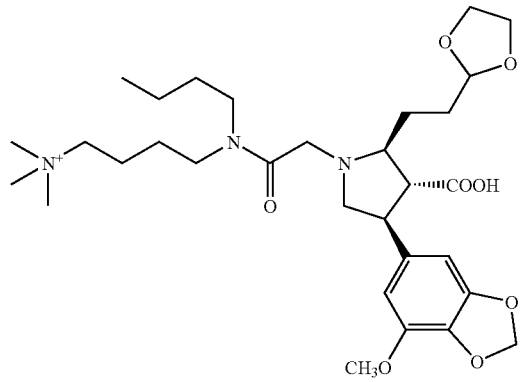
197
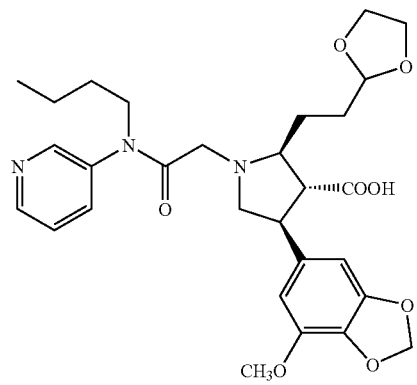
198
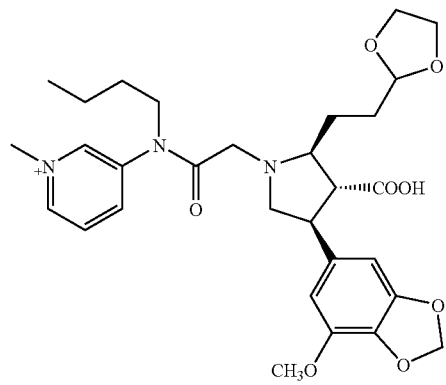
199
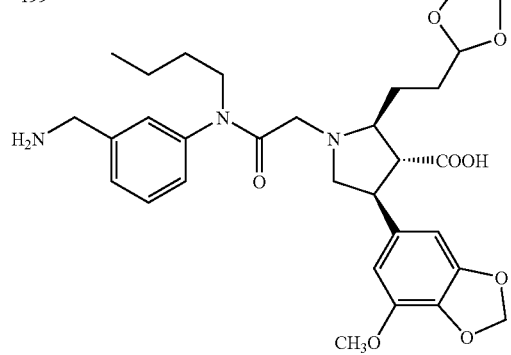
TABLE 3C-continued
200
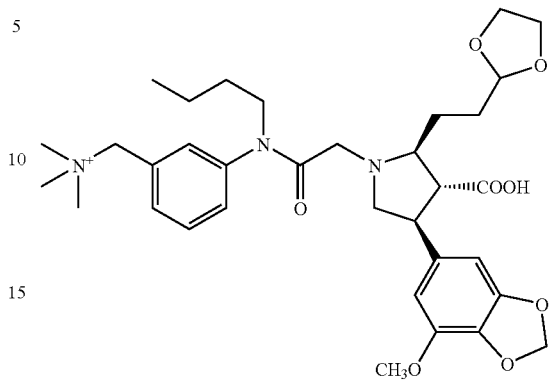
201
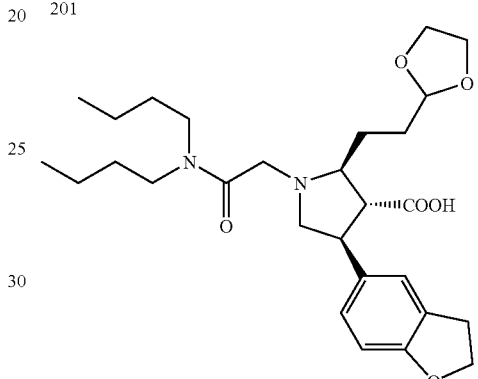
202
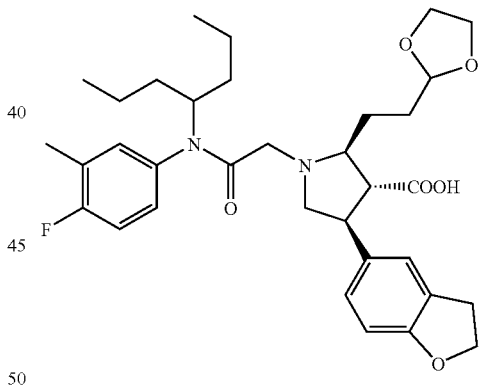
203
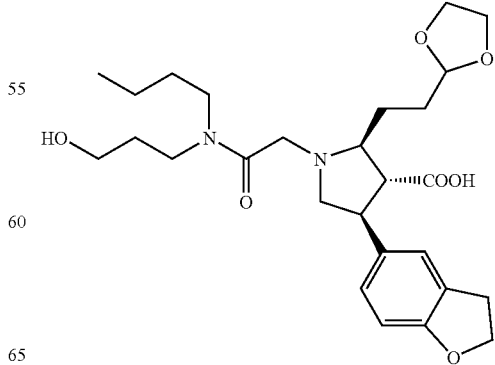

TABLE 3C-continued
204
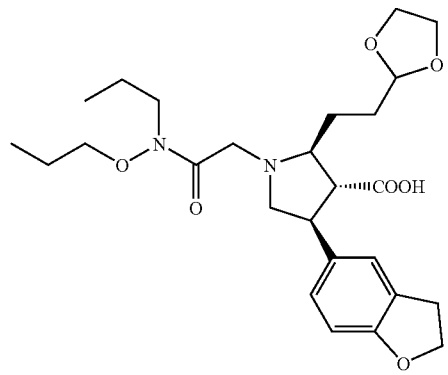
205
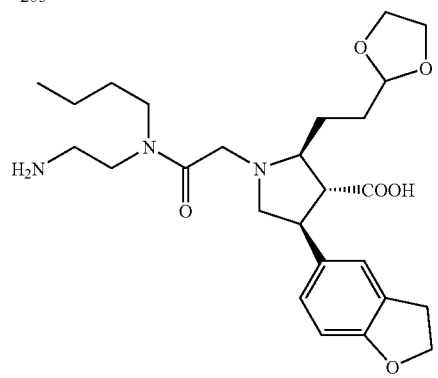
206
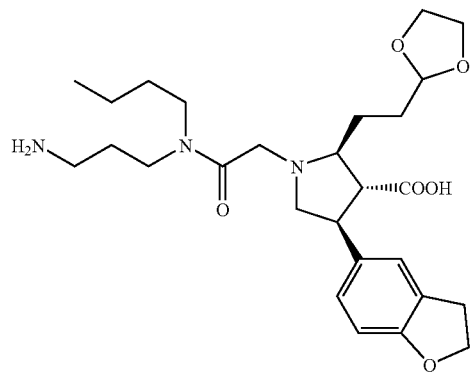
207
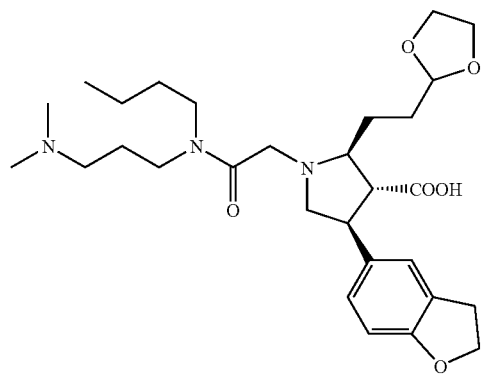
TABLE 3C-continued
208
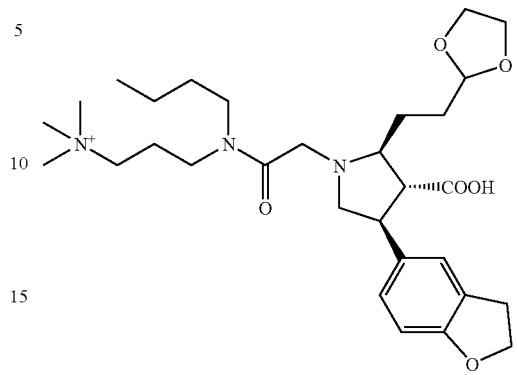
209
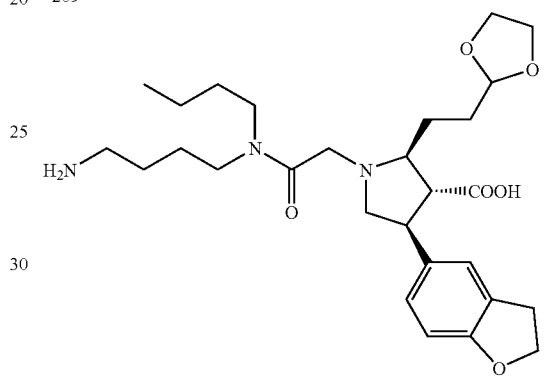
210

211

TABLE 3C-continued
212
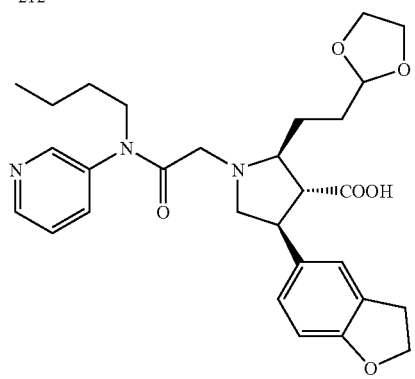
213
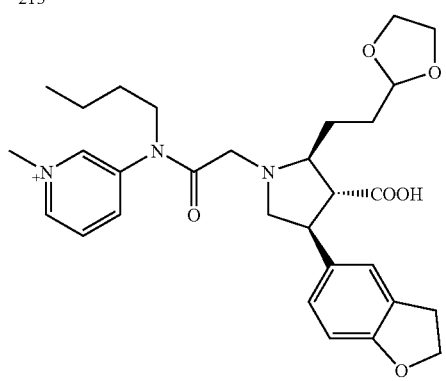
214
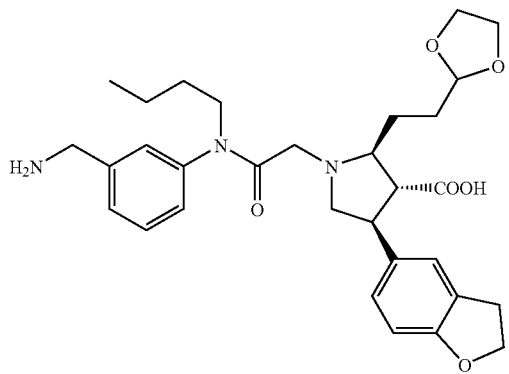
215
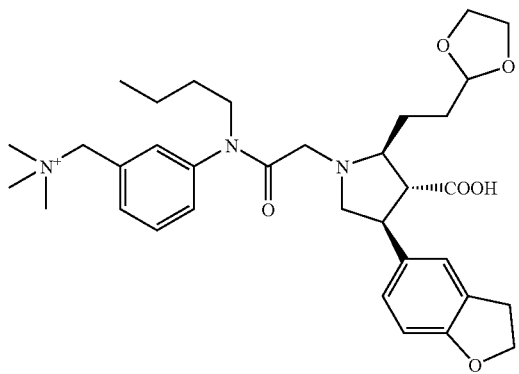
TABLE 3C-continued
216
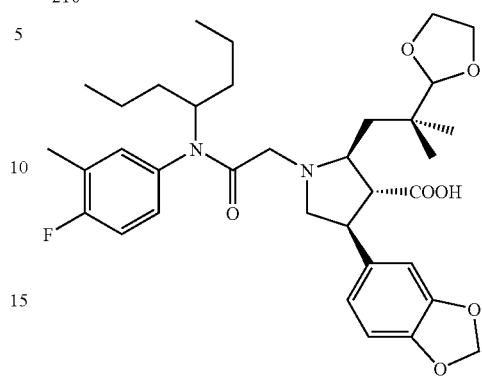
217
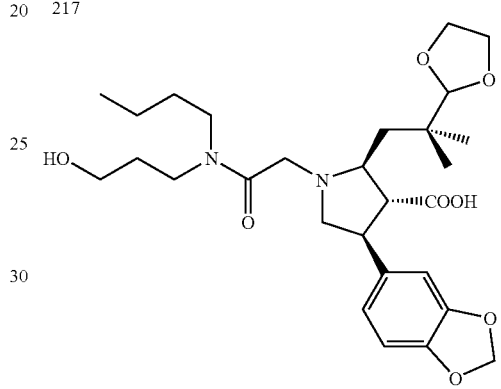
218
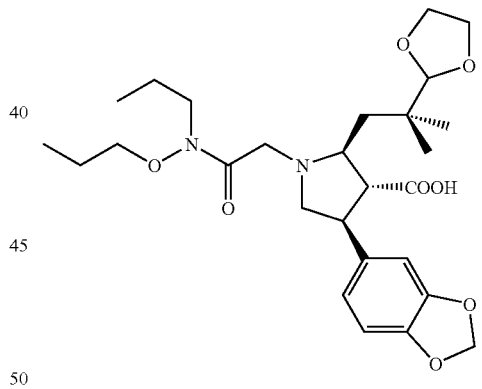
219
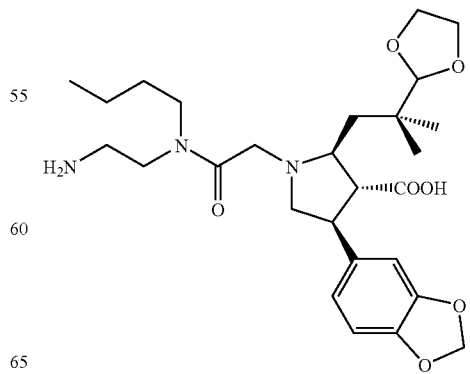

TABLE 3C-continued
220
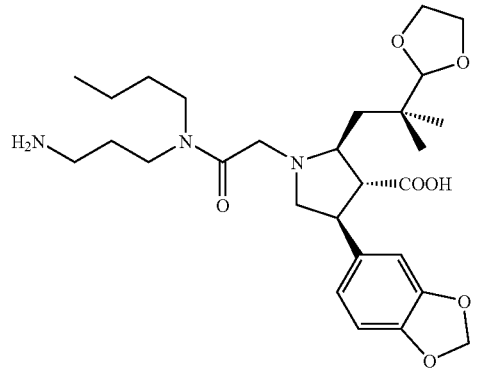
221
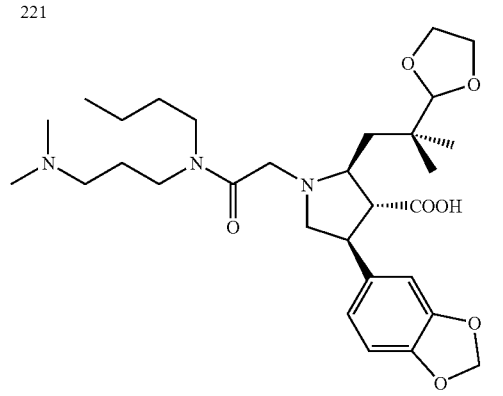
222
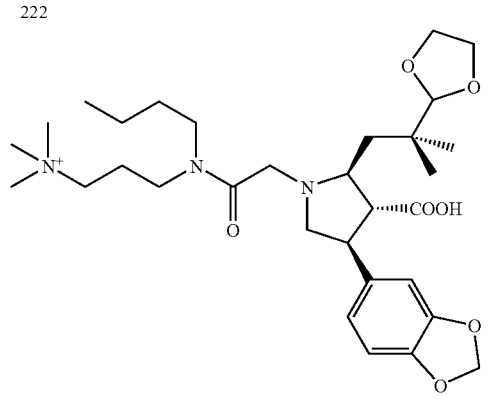
223
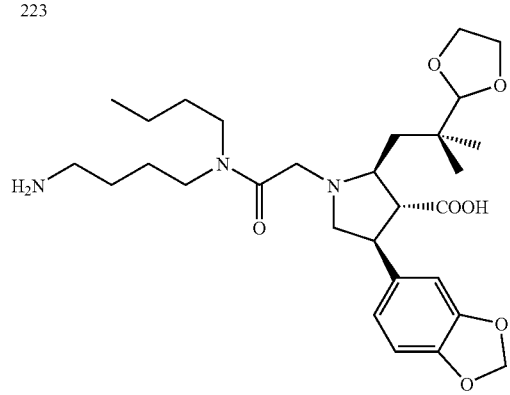
TABLE 3C-continued
224

225

226
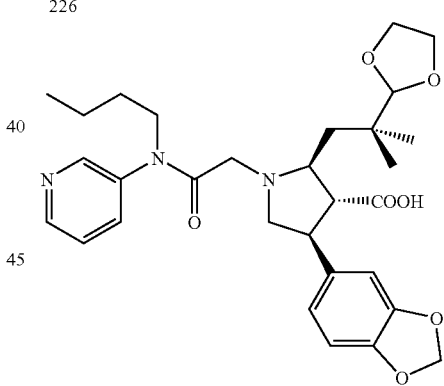
227
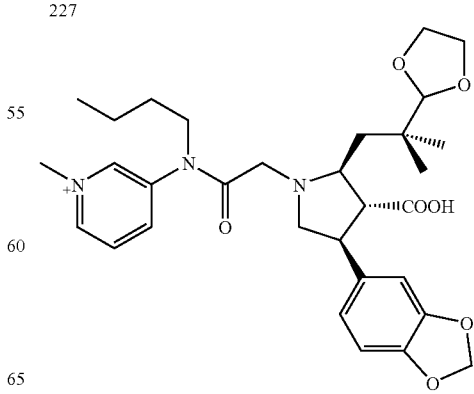

TABLE 3C-continued
228
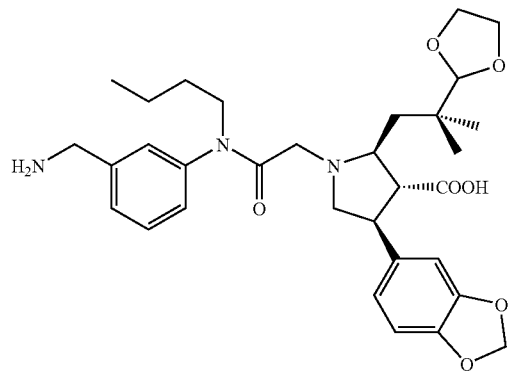
229
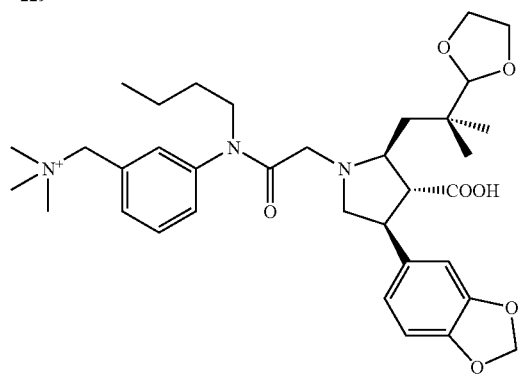
230
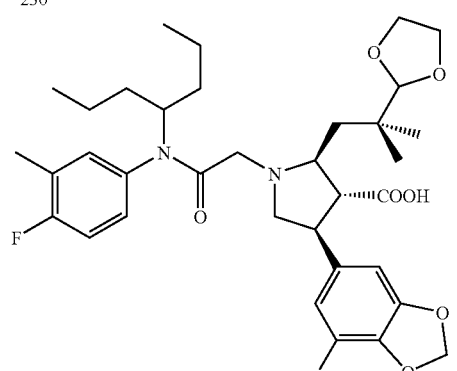
231
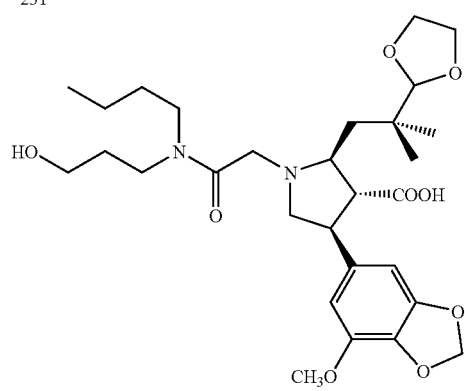
TABLE 3C-continued
232
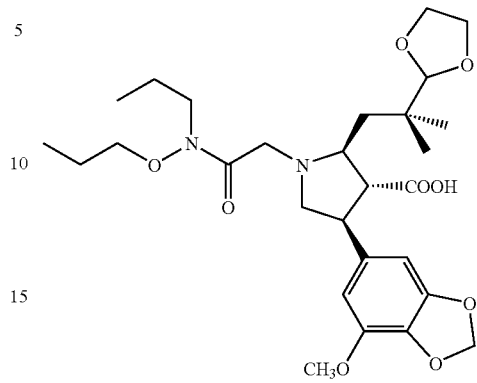
233
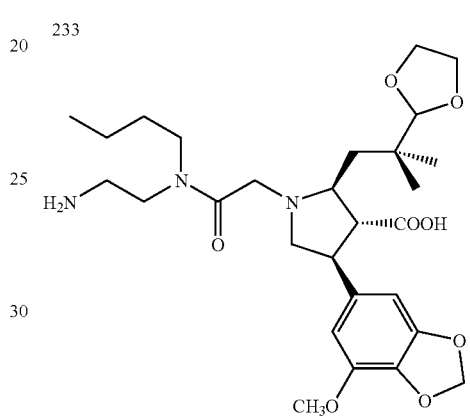
234
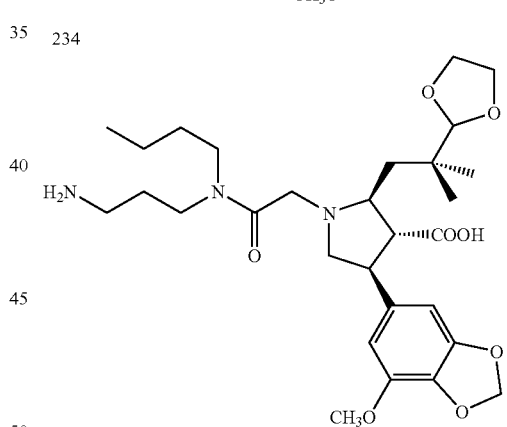
235
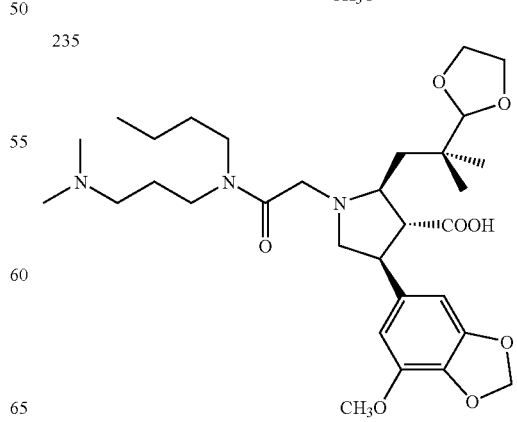

711
TABLE 3C-continued
236
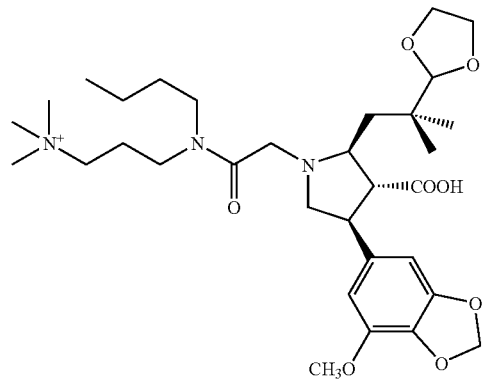
237
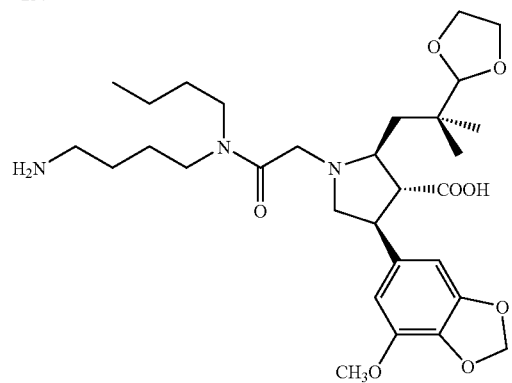
238
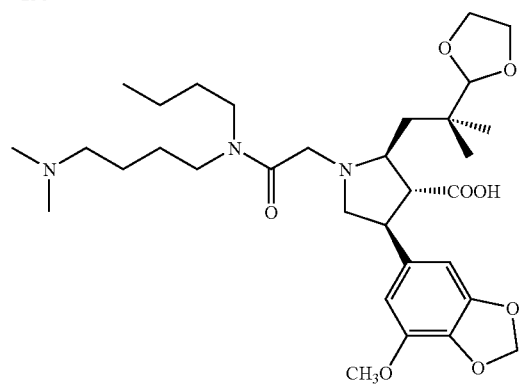
239
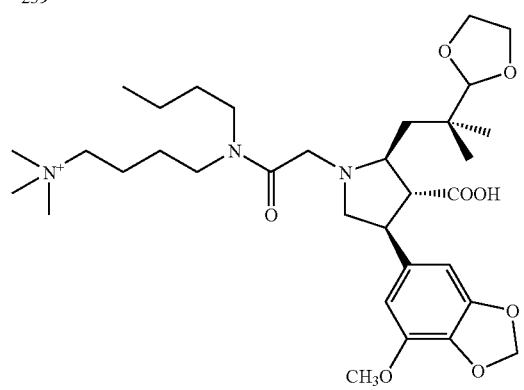
712
TABLE 3C-continued
240
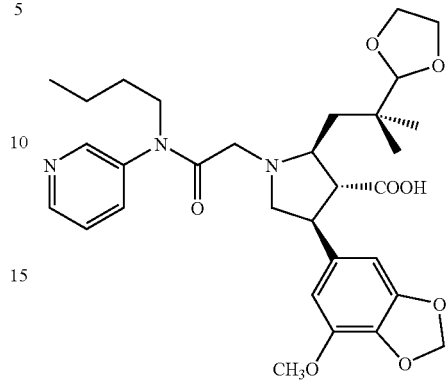
241
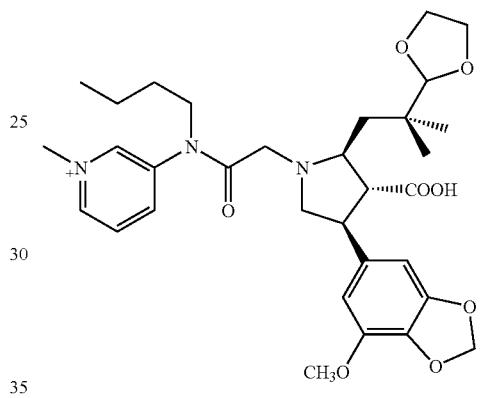
242
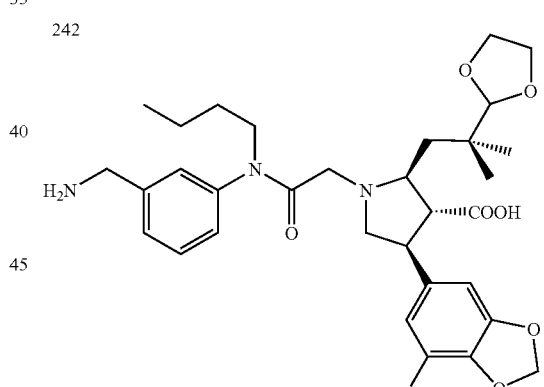
243
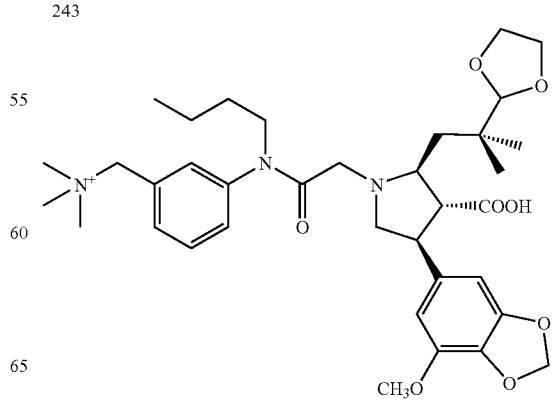

TABLE 3C-continued
244
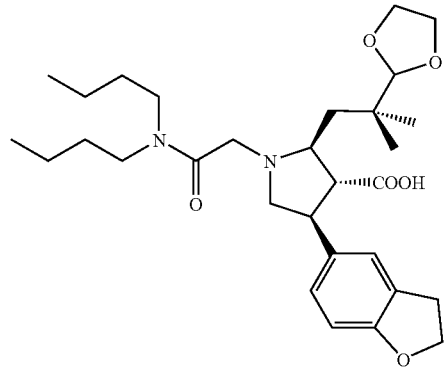
245
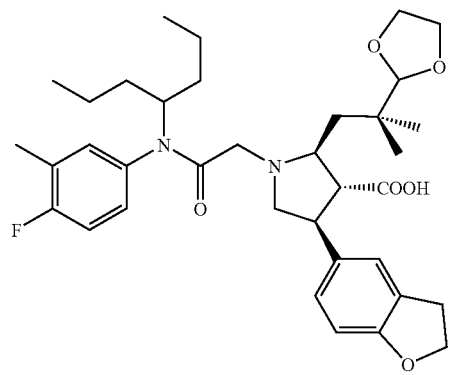
246
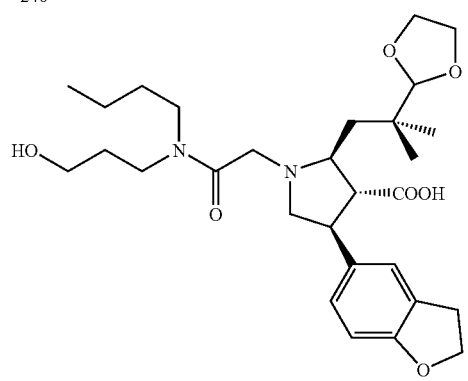
247
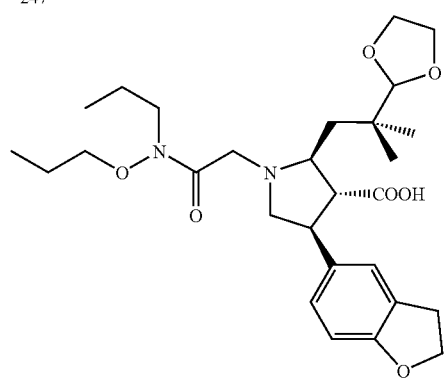
TABLE 3C-continued
248
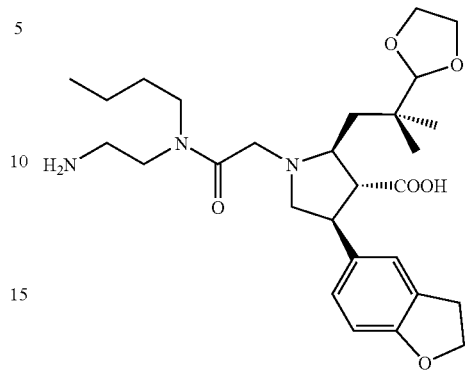
249
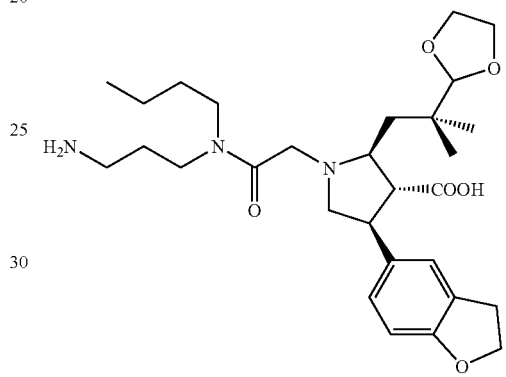
250
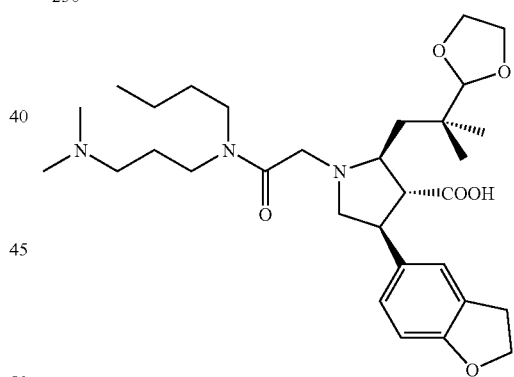
251
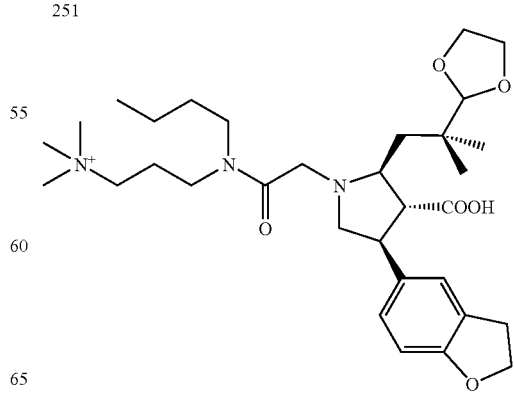

TABLE 3C-continued
252
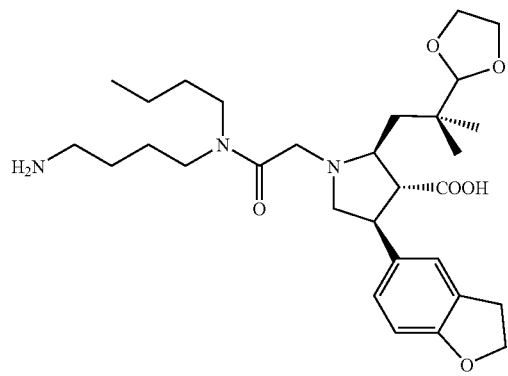
253
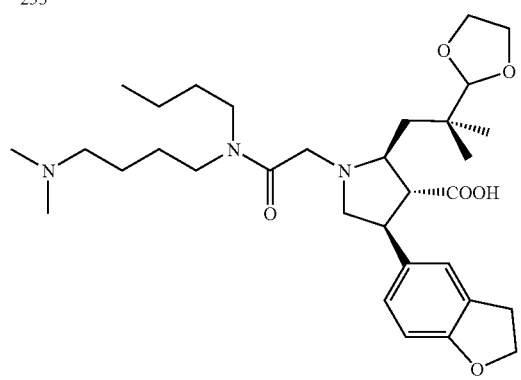
254
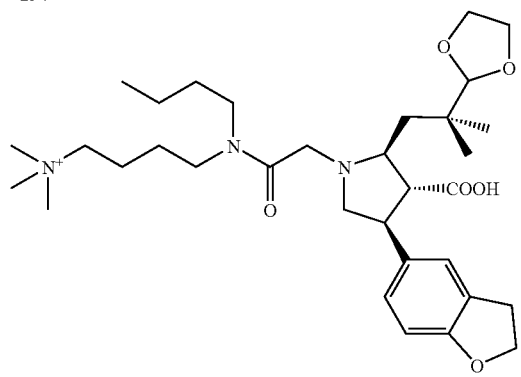
255
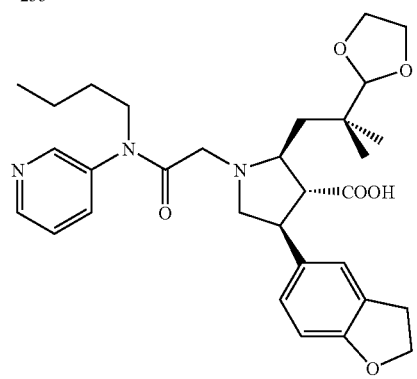
TABLE 3C-continued
256
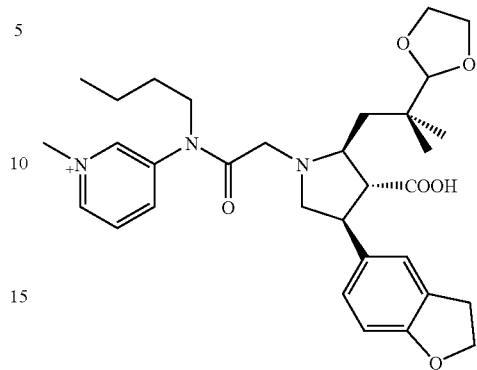
257
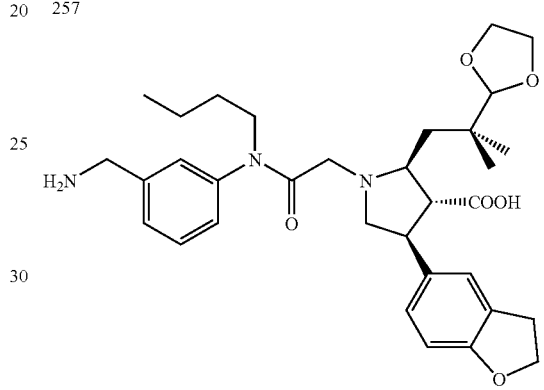
258
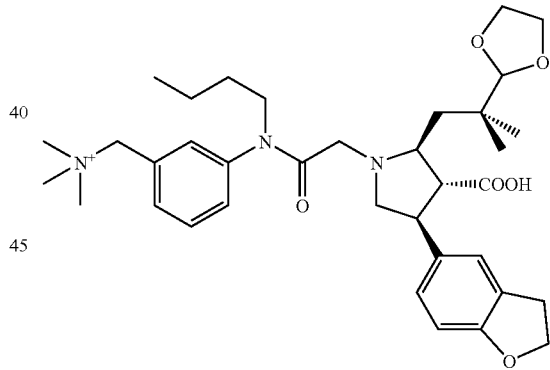
259
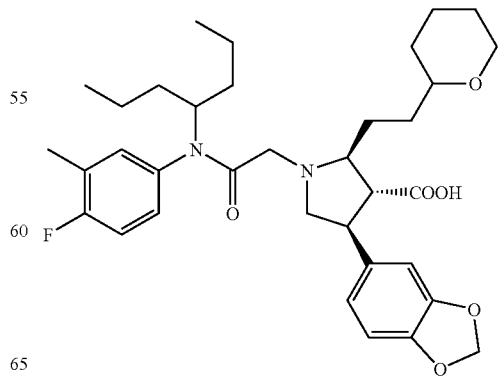

TABLE 3C-continued
260
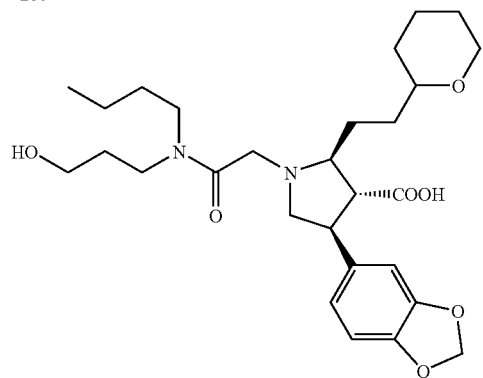
261
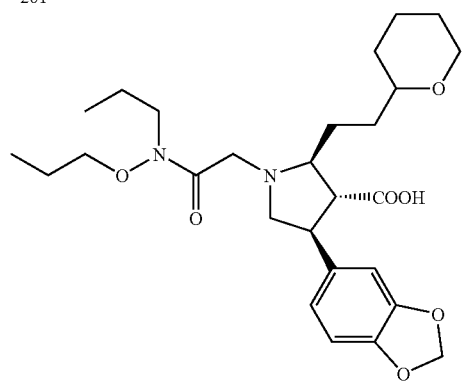
262
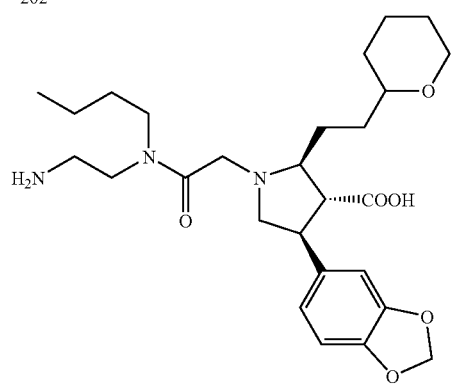
263
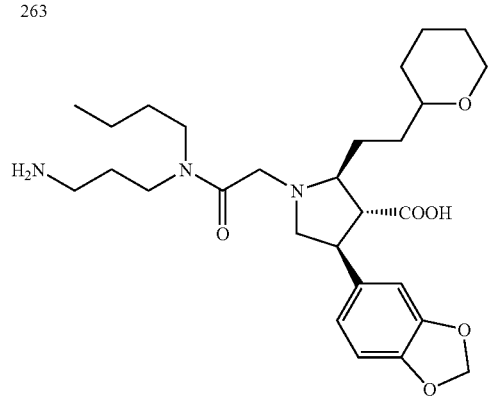
TABLE 3C-continued
264

265
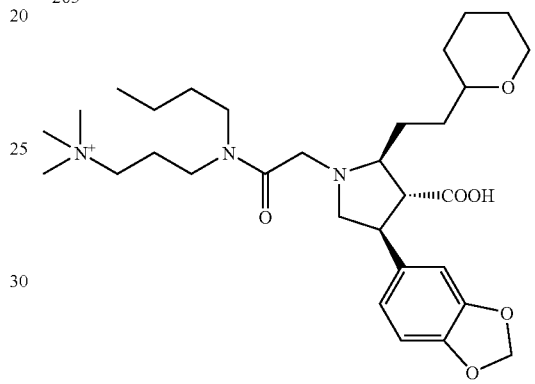
266
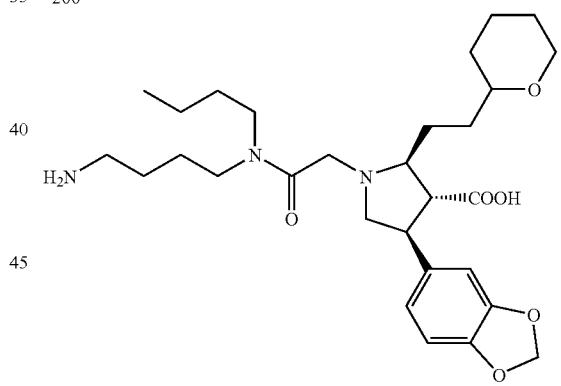
267
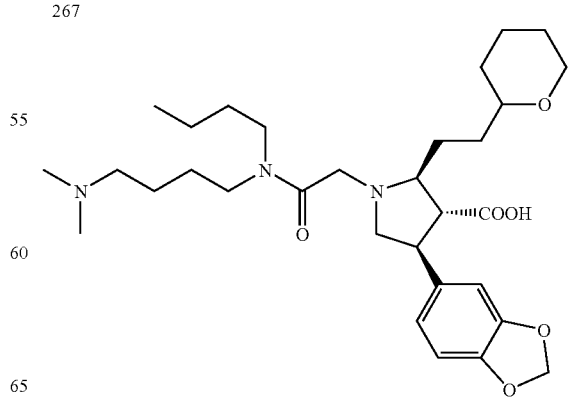

TABLE 3C-continued
268
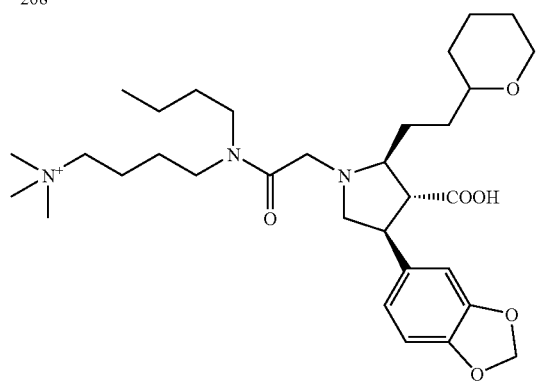
269
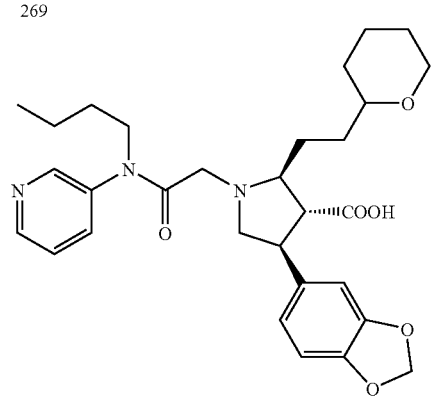
270
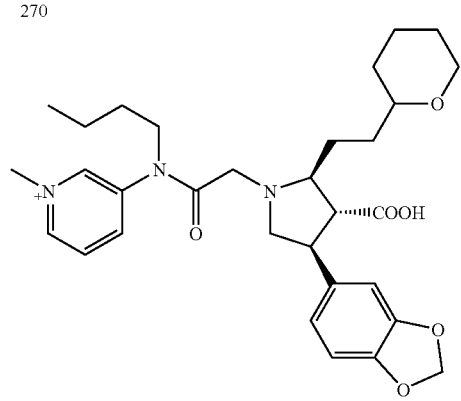
271
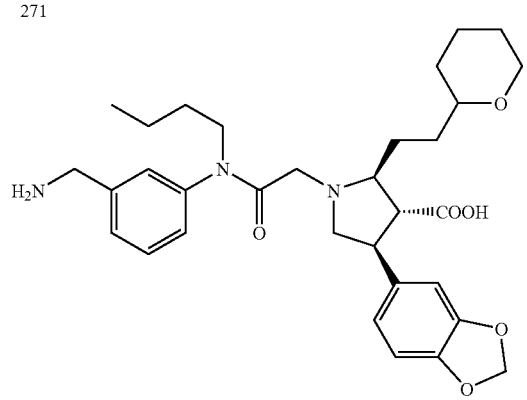
TABLE 3C-continued
272
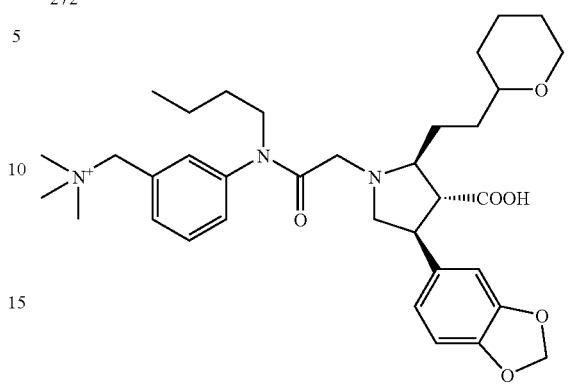
273

274
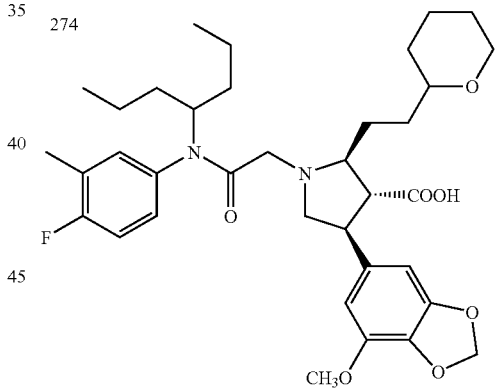
275
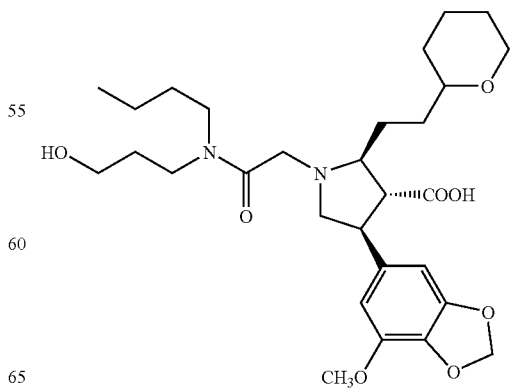

721
TABLE 3C-continued
276
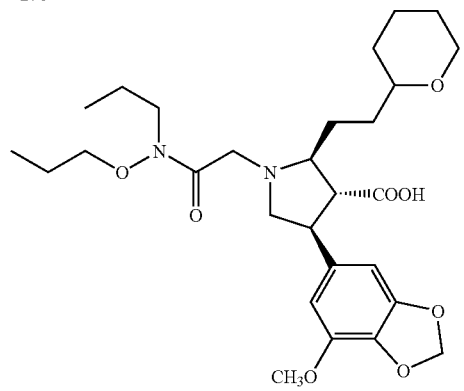
277
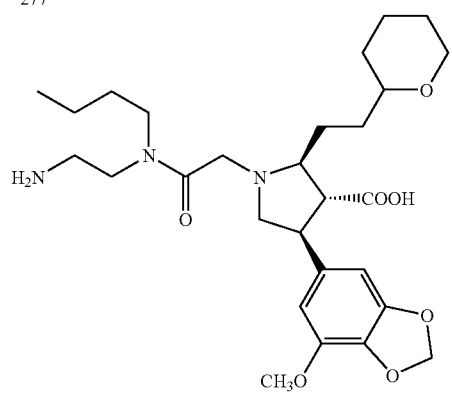
278
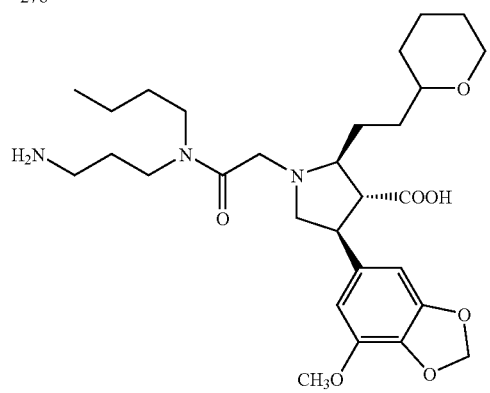
279
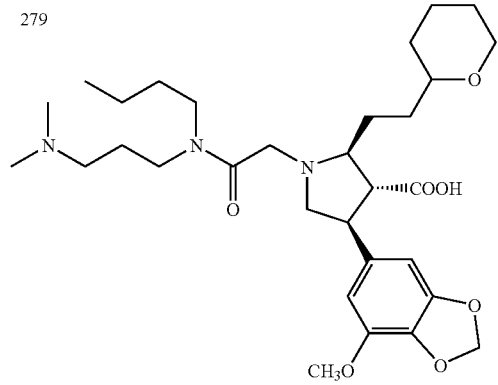
722
TABLE 3C-continued
280
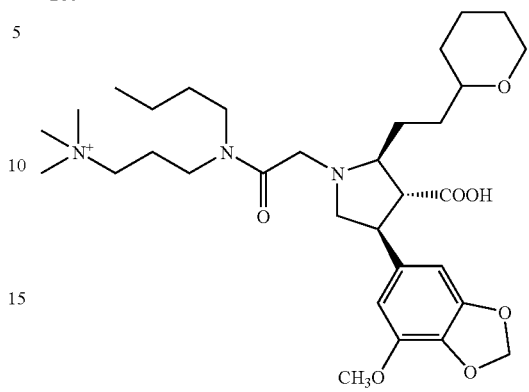
281
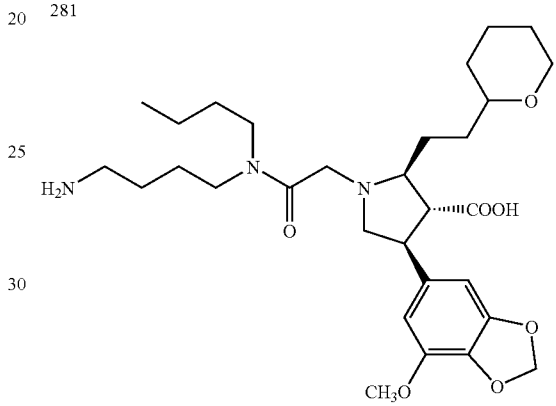
282
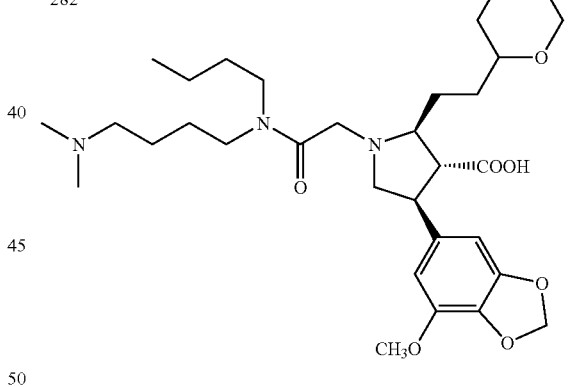
283
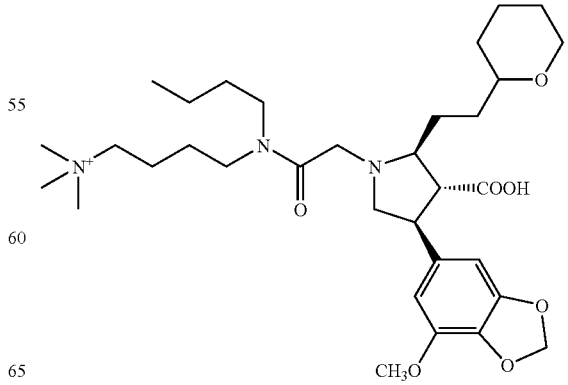

TABLE 3C-continued
284
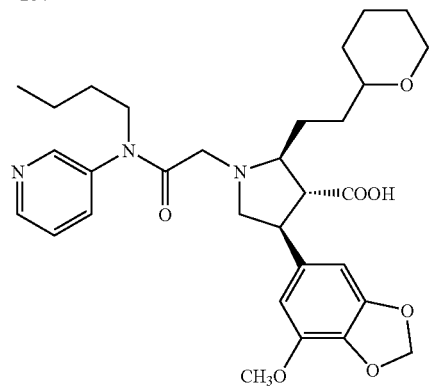
285
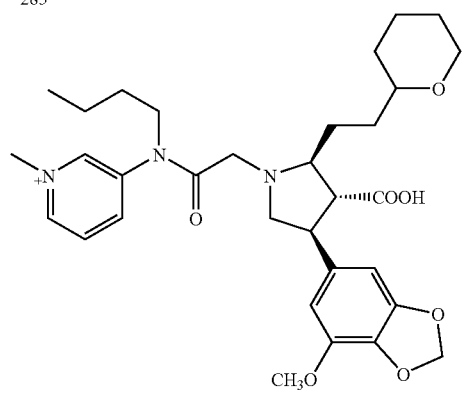
286
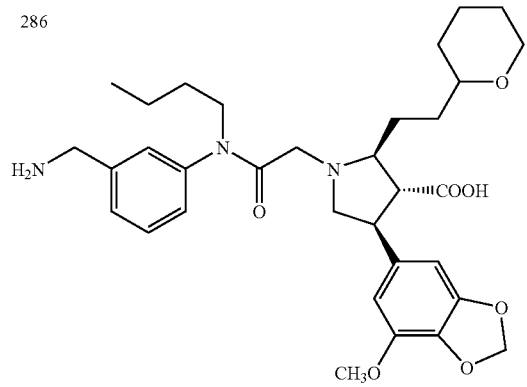
287
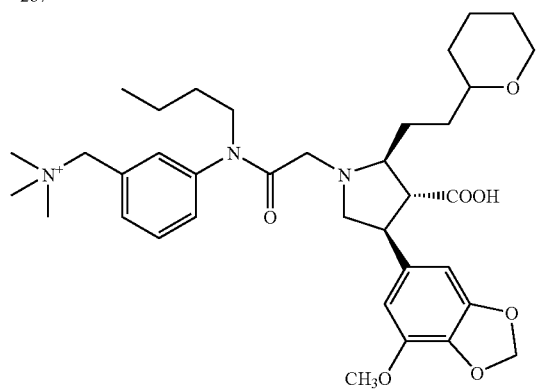
TABLE 3C-continued
288
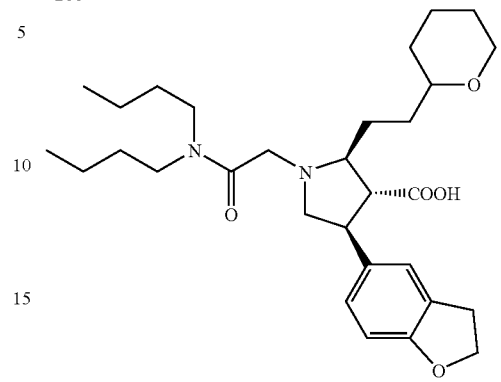
289
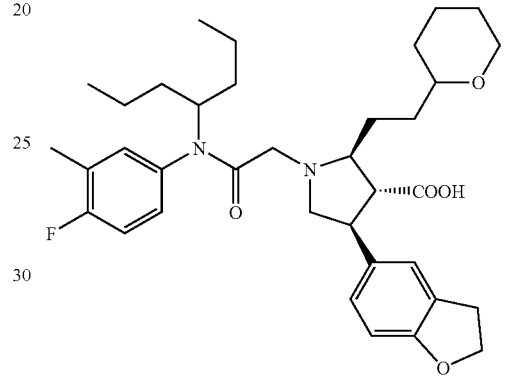
290
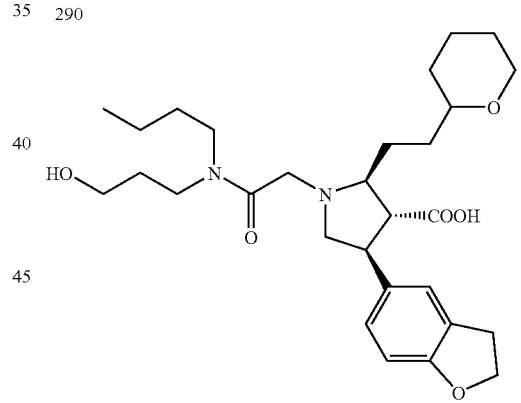
291
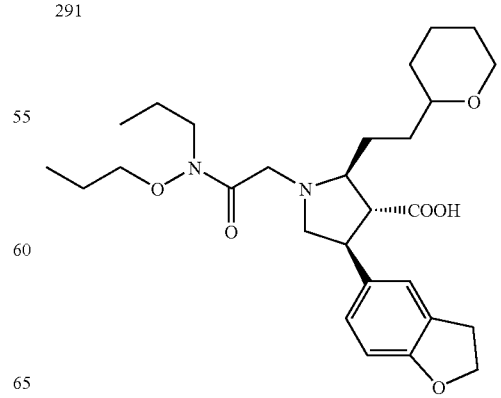

TABLE 3C-continued
292
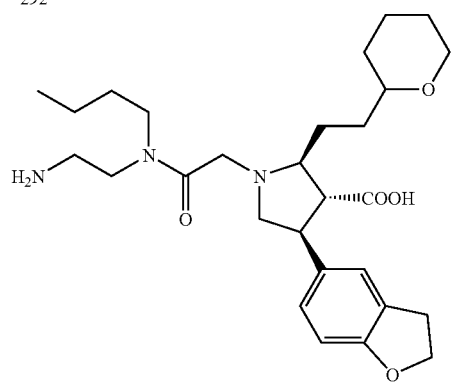
293
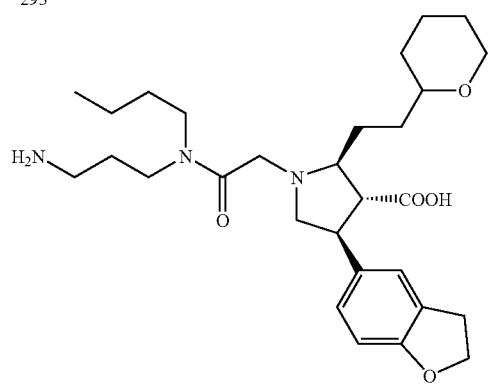
294
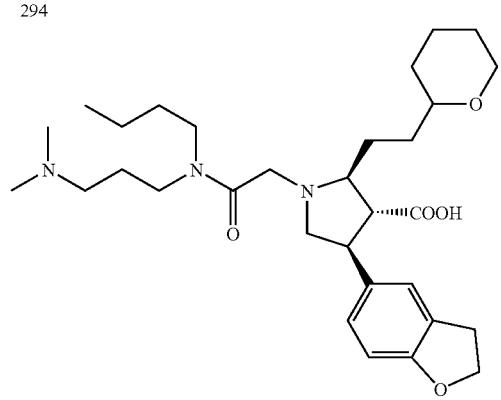
295
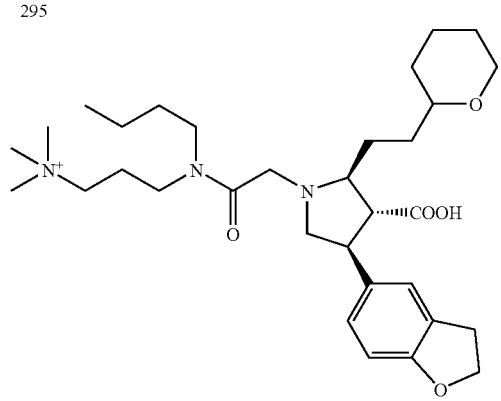
TABLE 3C-continued
296

297
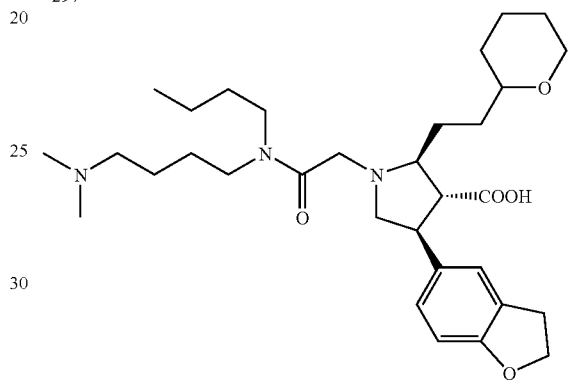
298

299
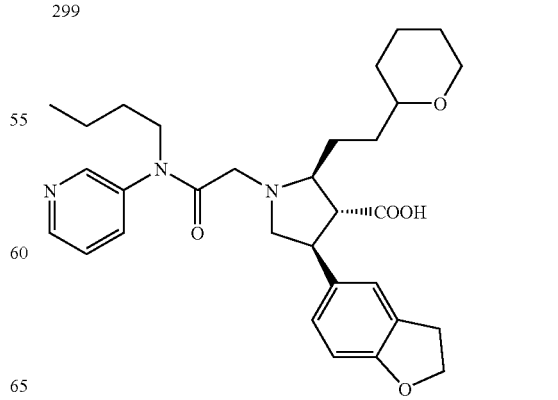

TABLE 3C-continued
300
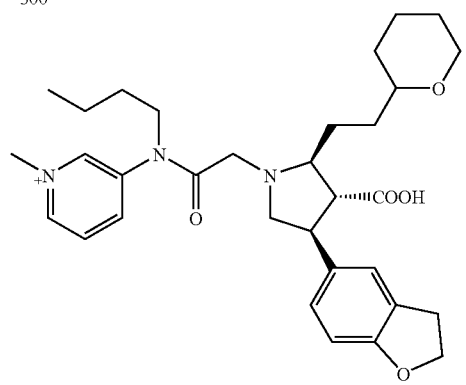
301
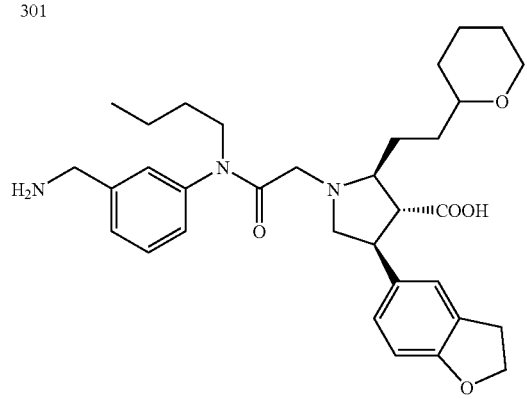
302
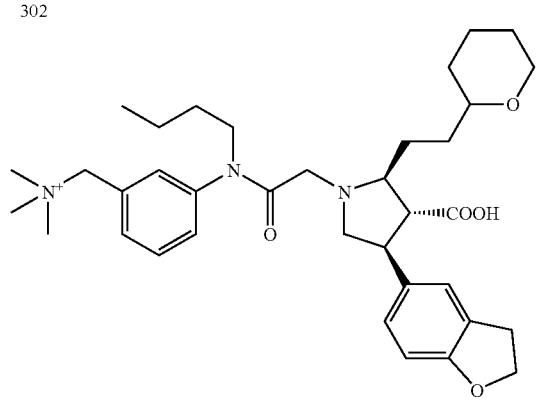
303
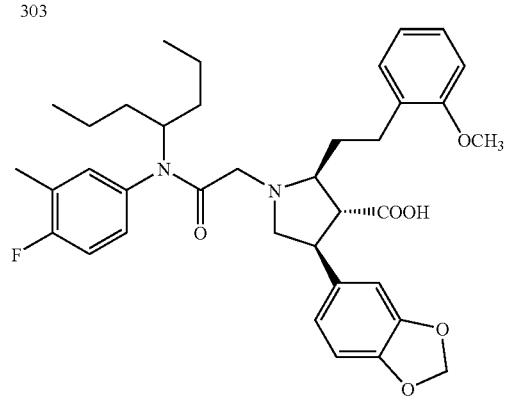
TABLE 3C-continued
304
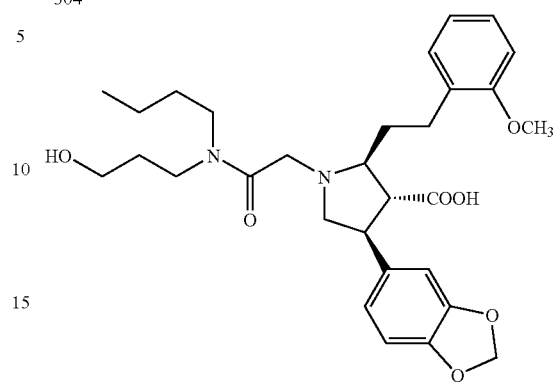
305
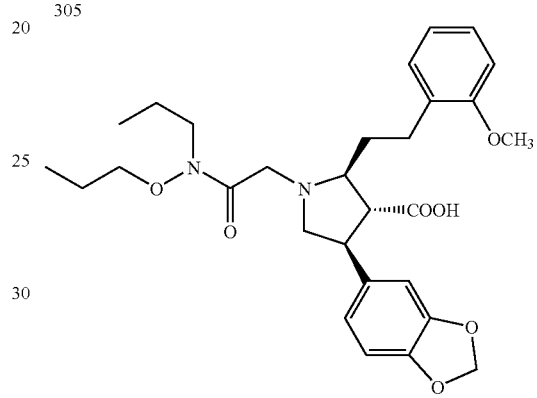
306
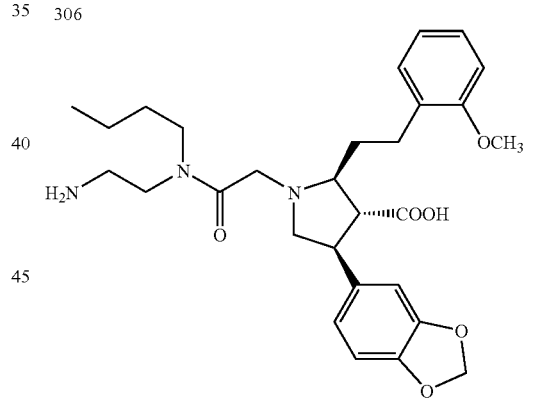
307
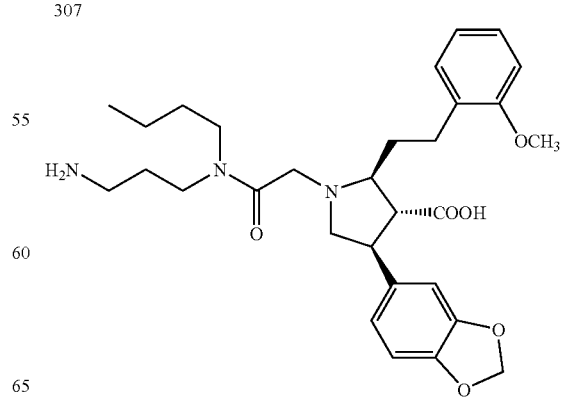

TABLE 3C-continued
308
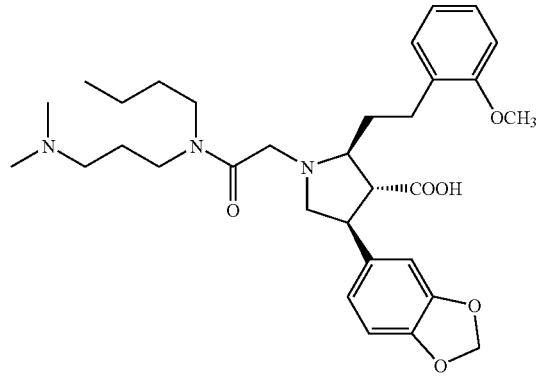
309
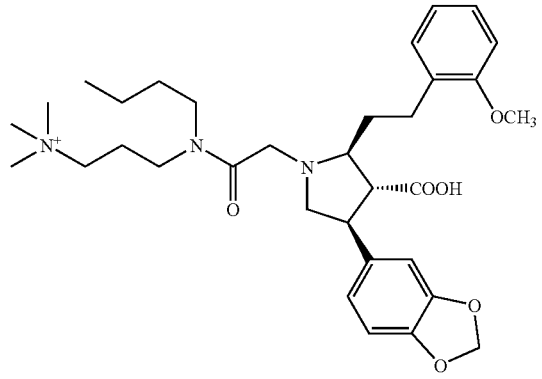
310
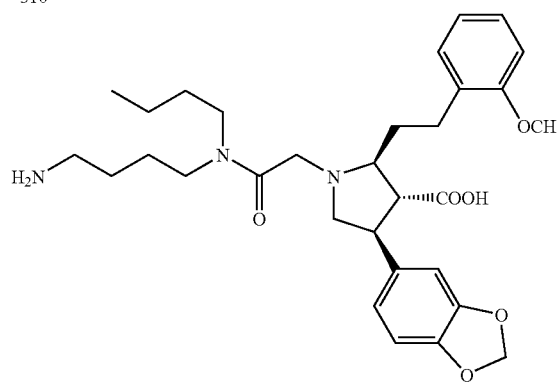
311
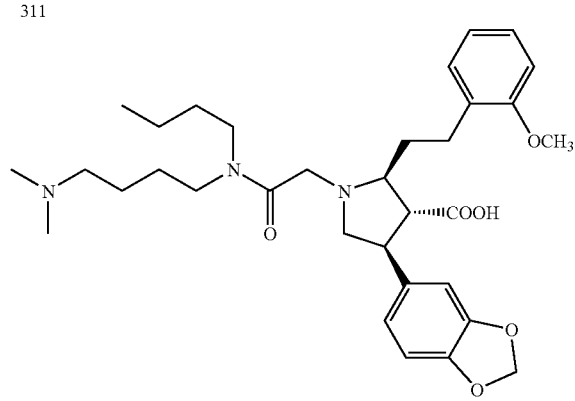
TABLE 3C-continued
312
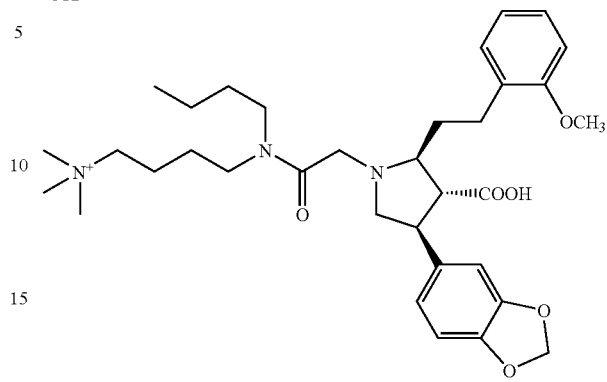
313
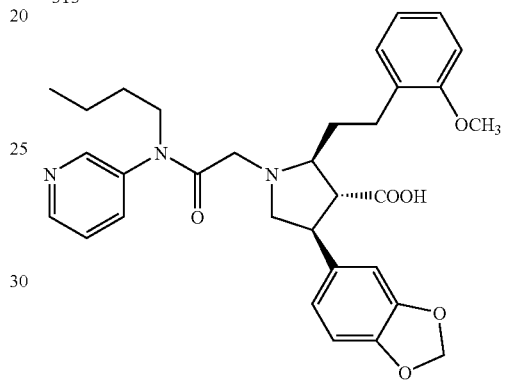
314
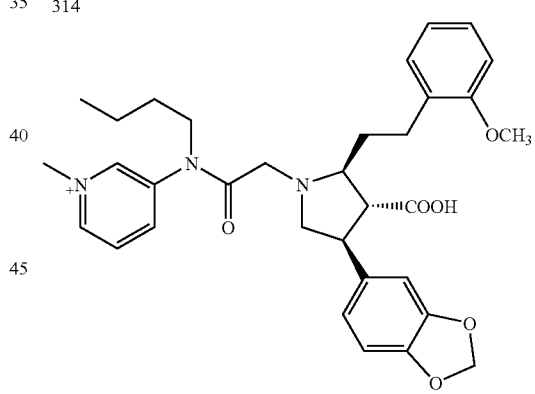
315
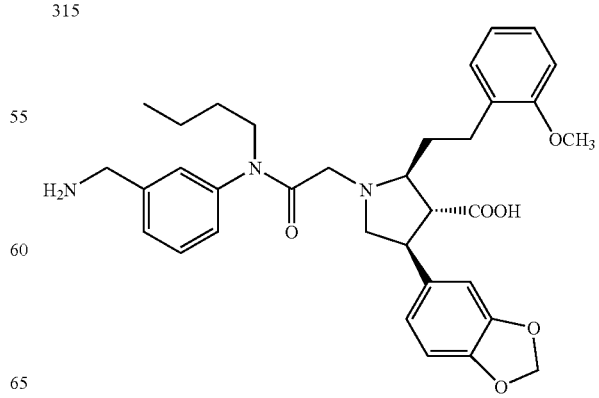

316
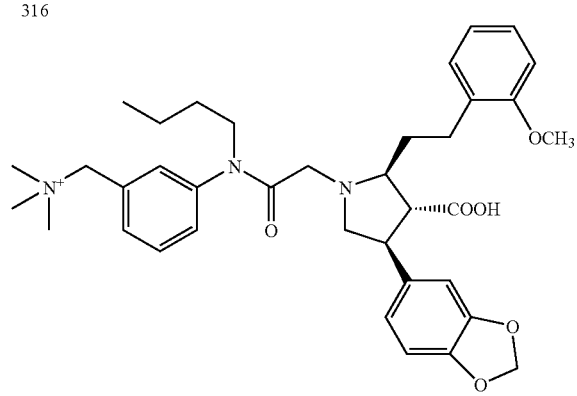
317
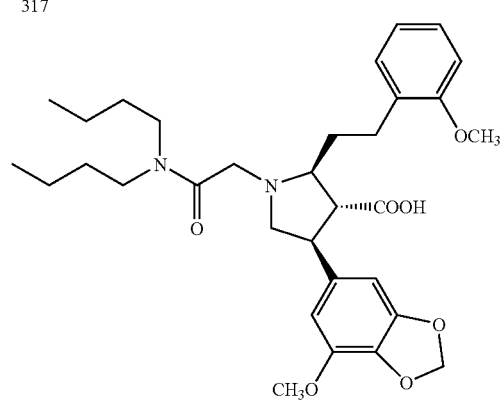
318
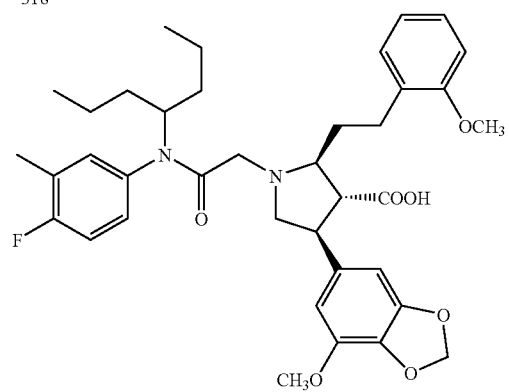
319
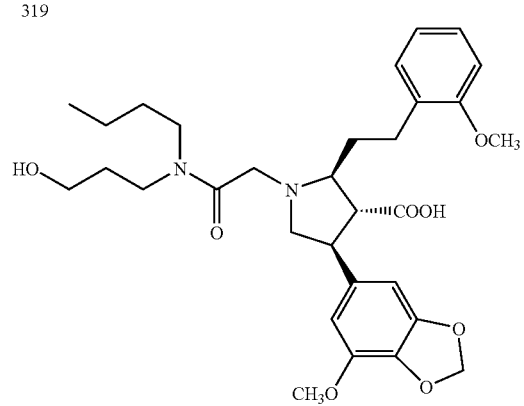
320
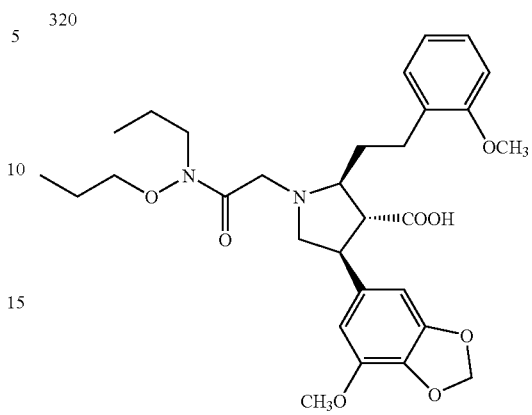
321
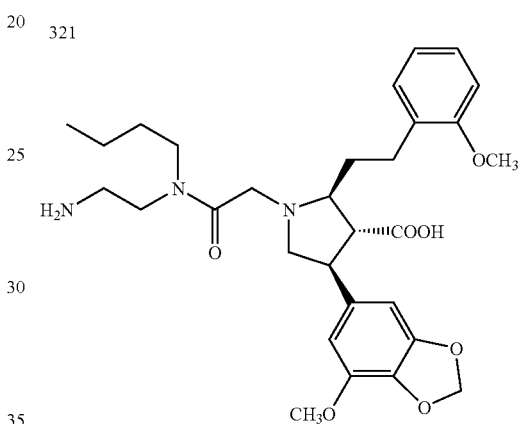
322
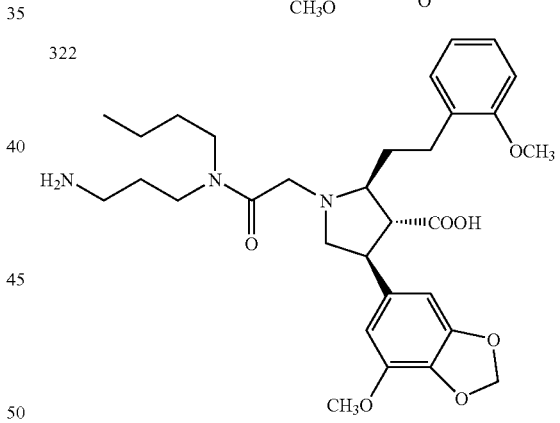
323
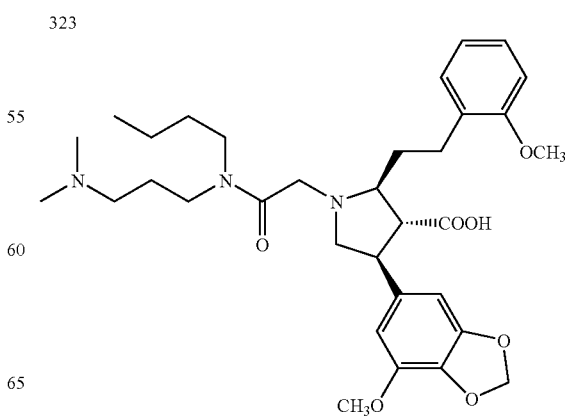

TABLE 3C-continued
324
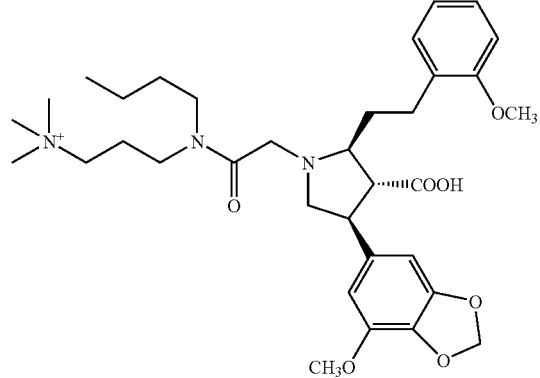
325
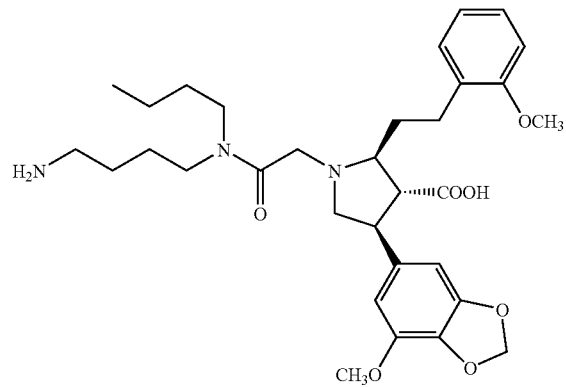
326
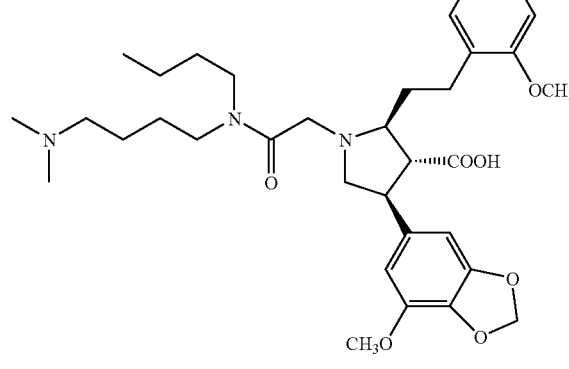
327
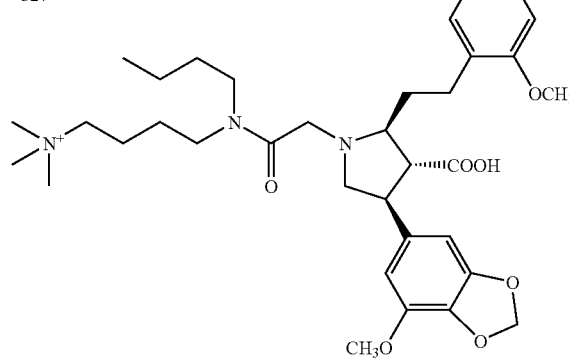
TABLE 3C-continued
328
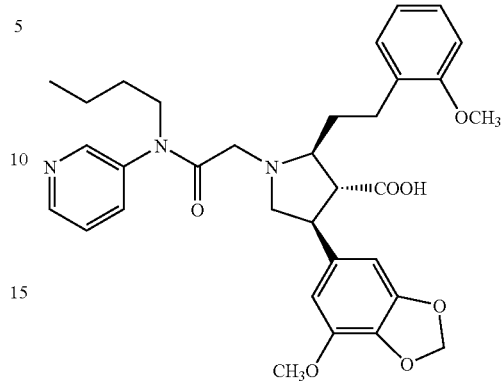
329
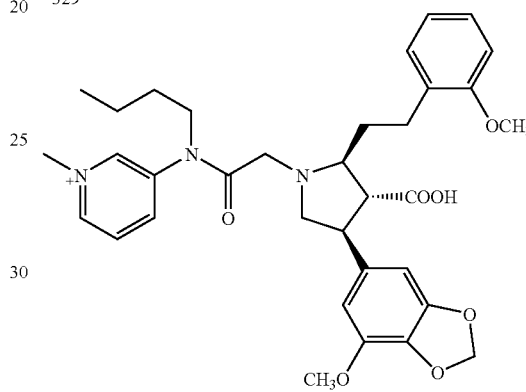
330
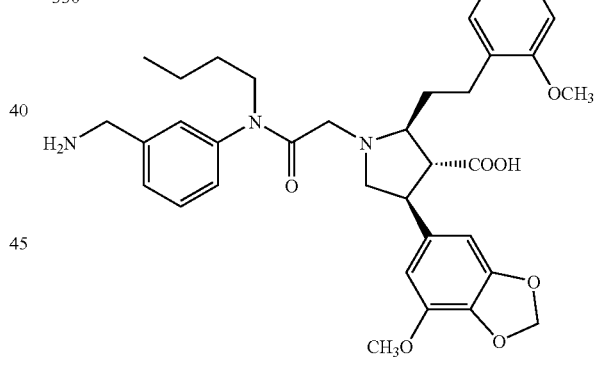
331
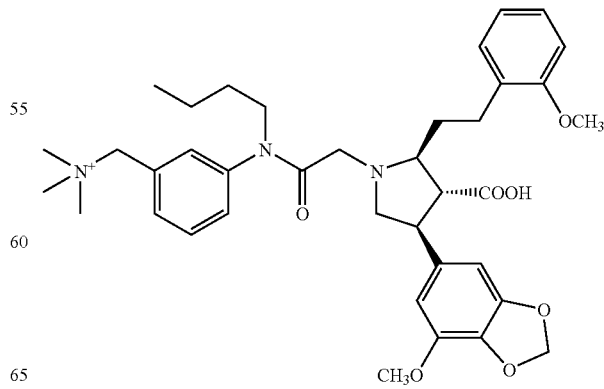

TABLE 3C-continued
332
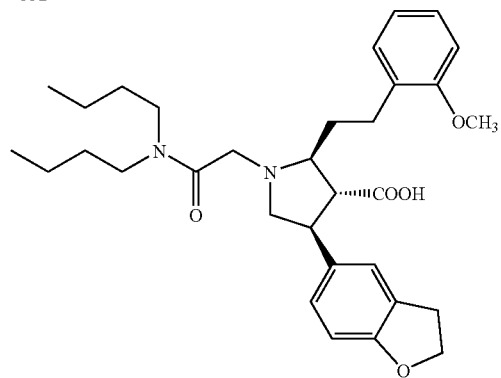
333
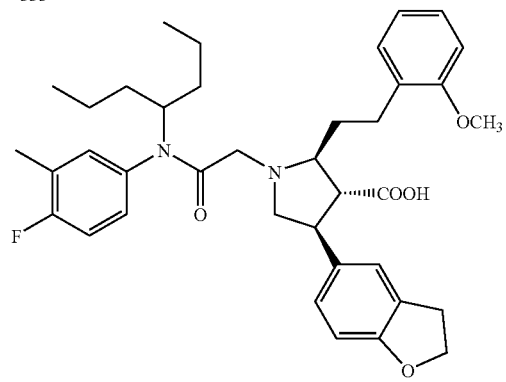
334
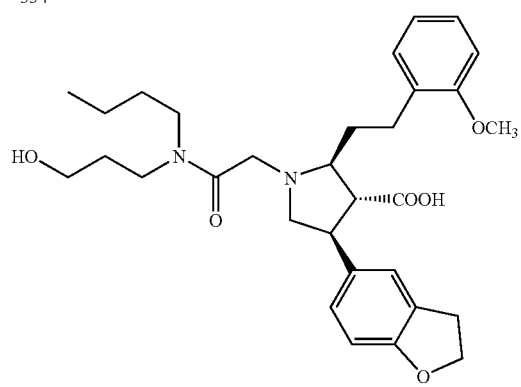
335
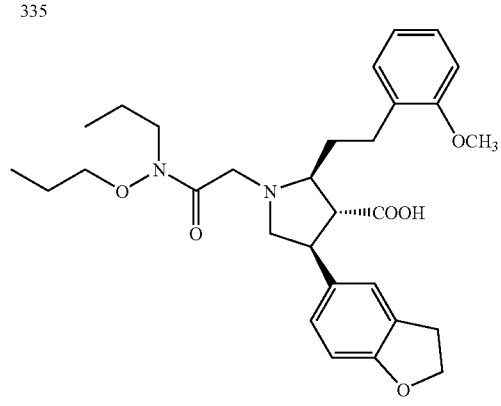
TABLE 3C-continued
336
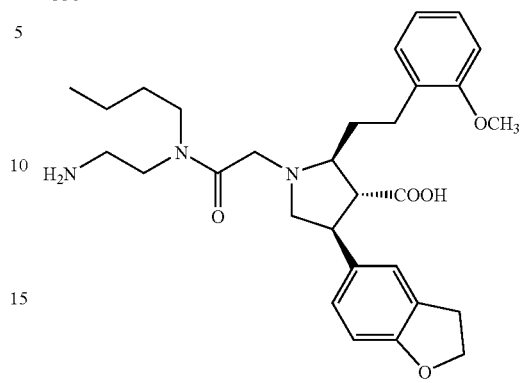
337
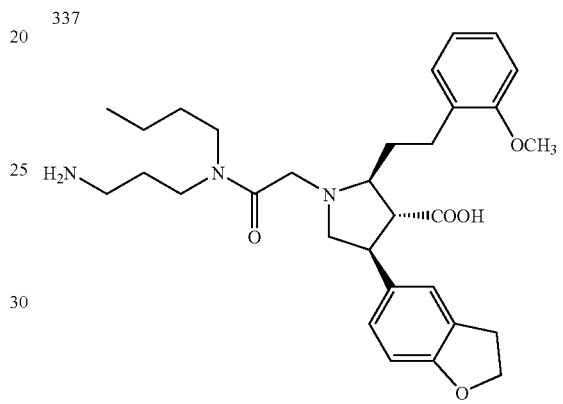
338
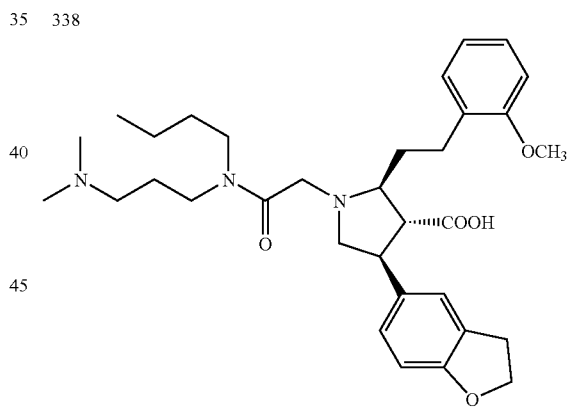
339

TABLE 3C-continued
340
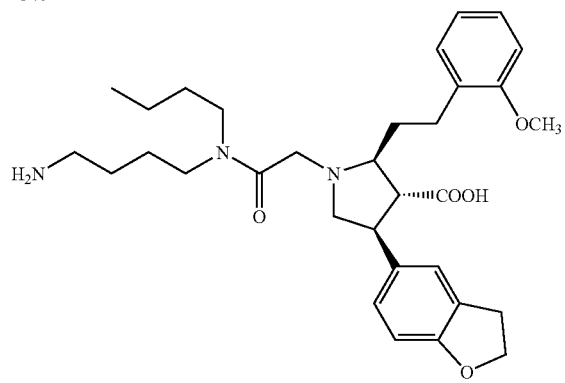
341
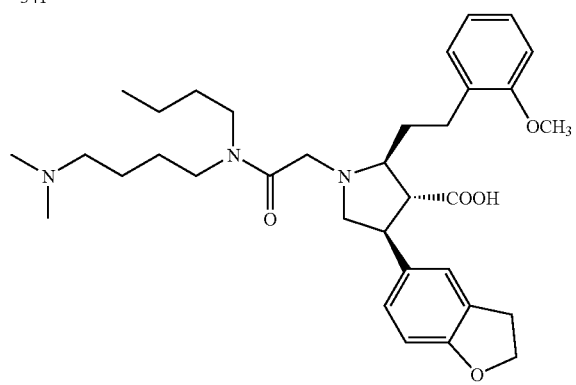
342
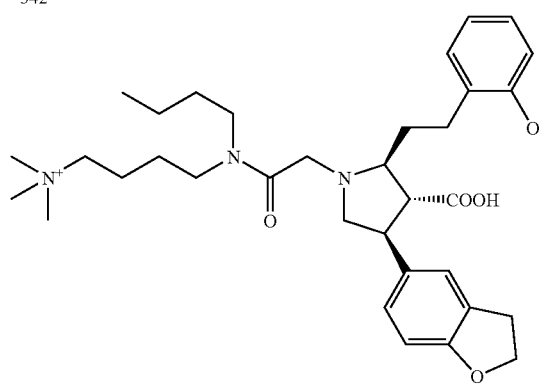
343
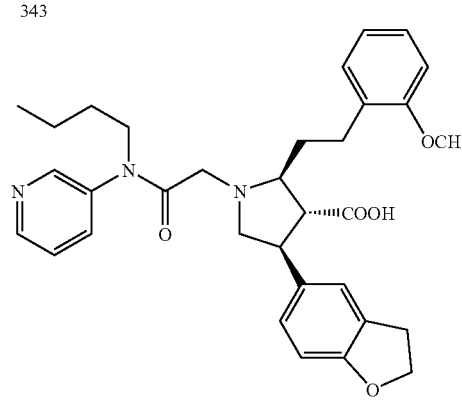
TABLE 3C-continued
344
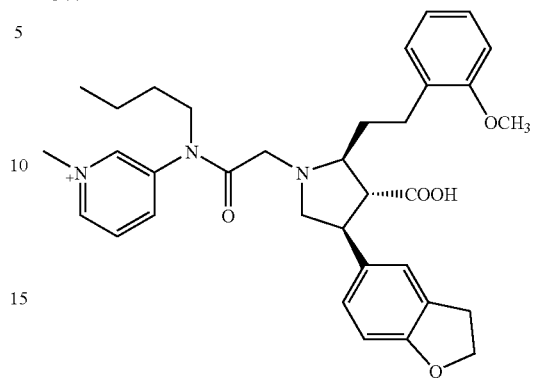
345
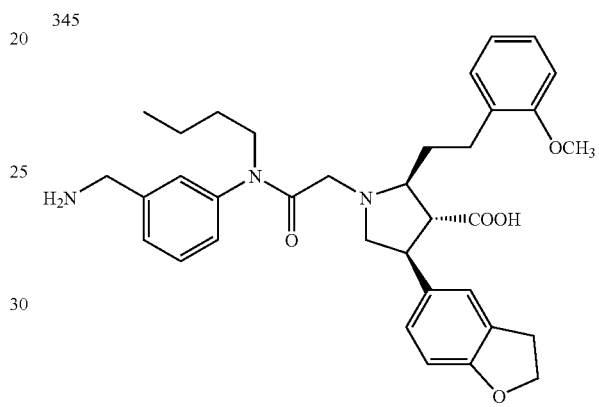
346
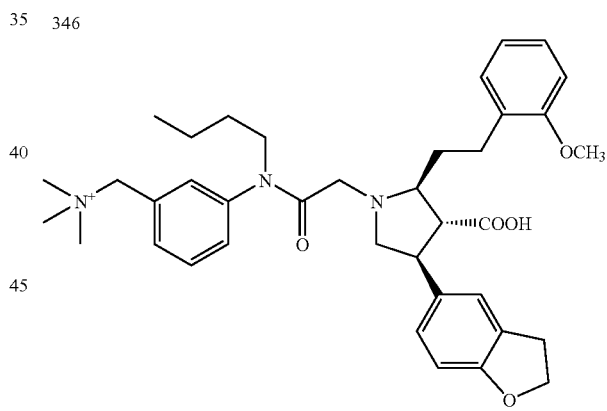
347
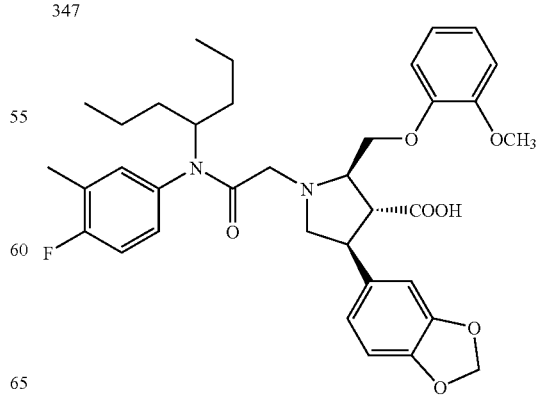

TABLE 3C-continued
348
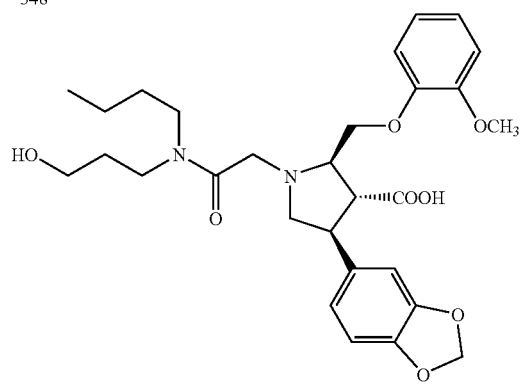
349
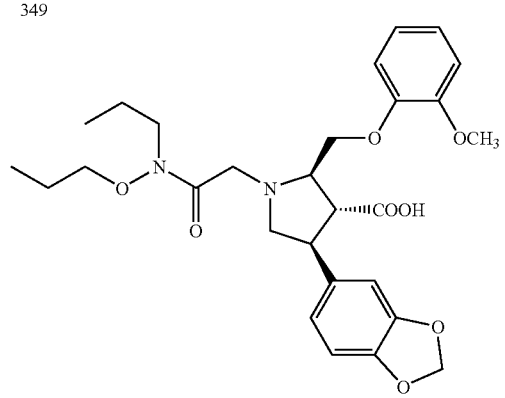
350
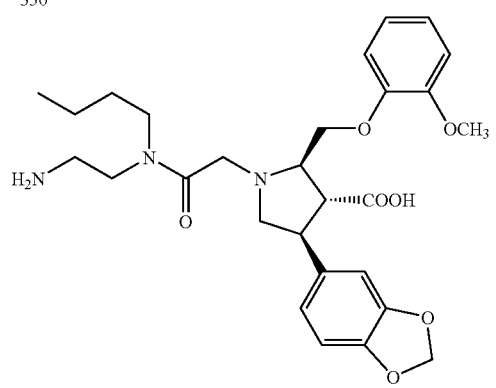
351
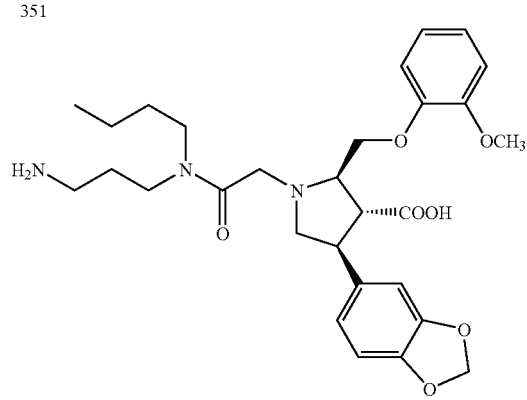
TABLE 3C-continued
352
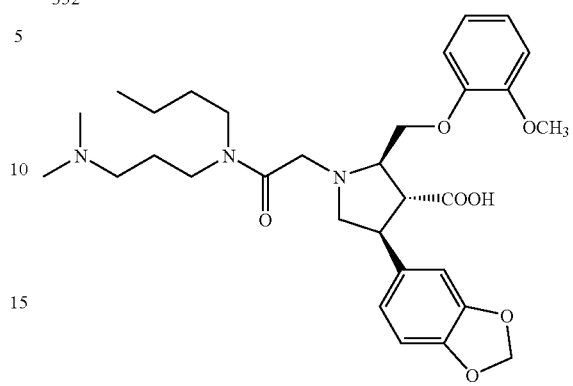
353
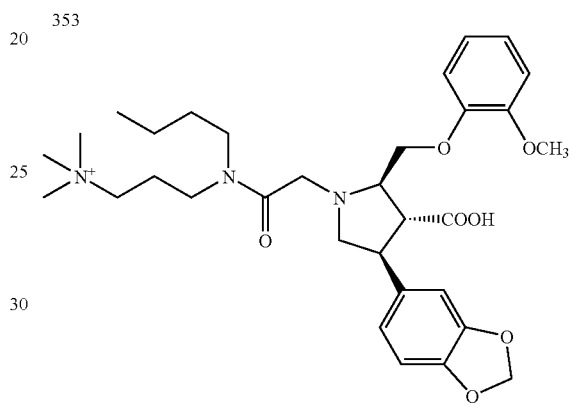
354
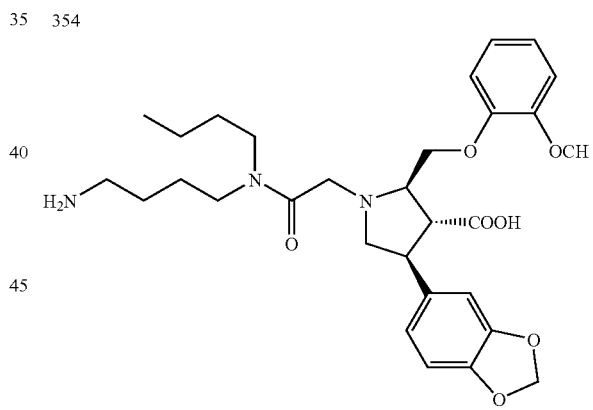
355
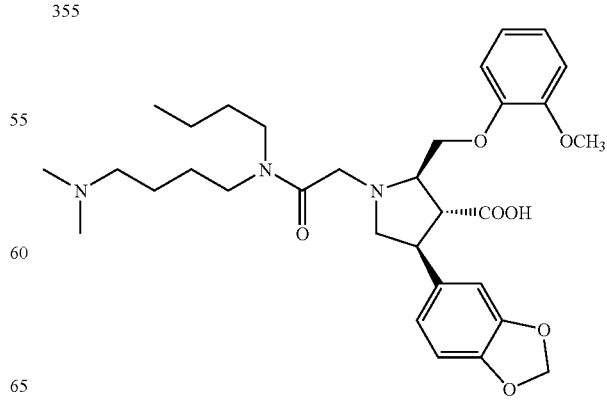

TABLE 3C-continued
356
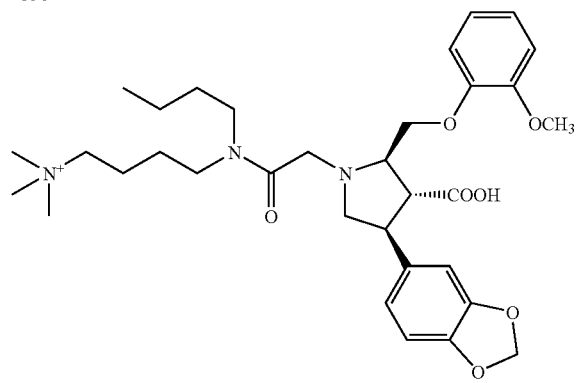
357
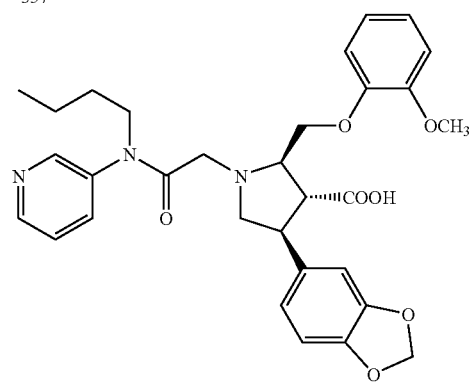
358
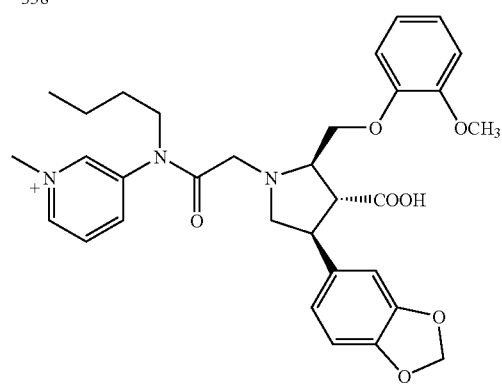
359
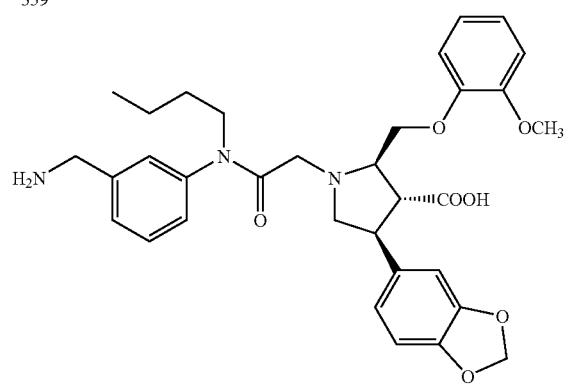
TABLE 3C-continued
360
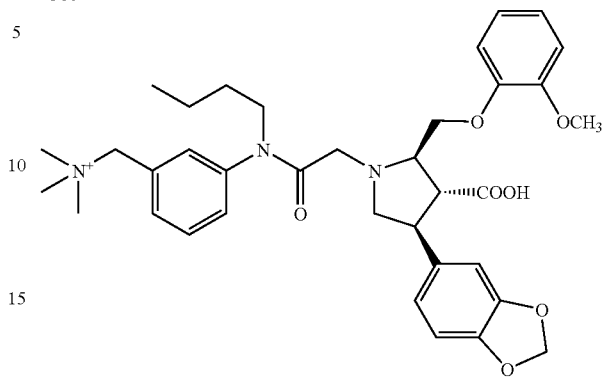
361
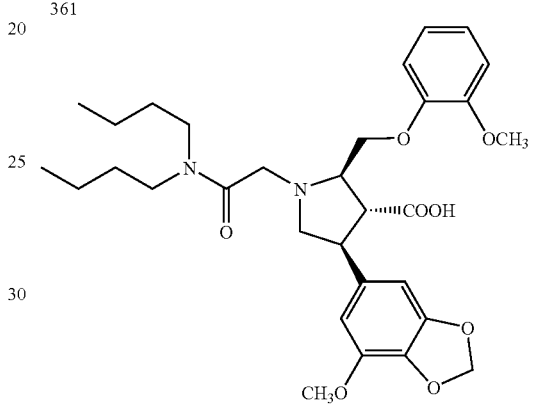
362
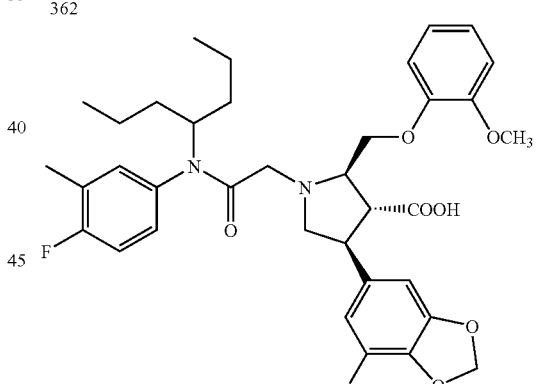
363
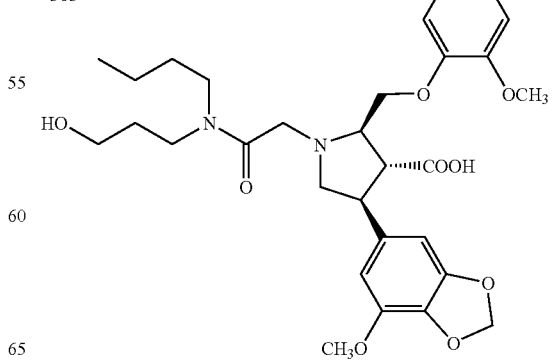

TABLE 3C-continued
364
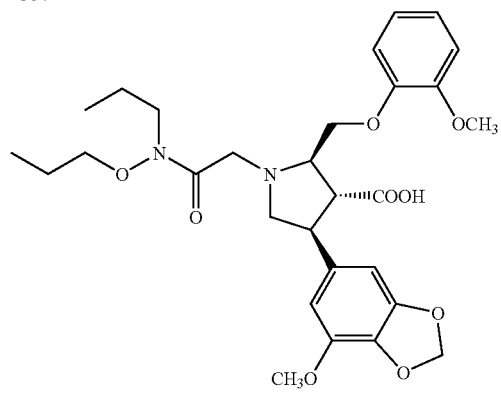
365
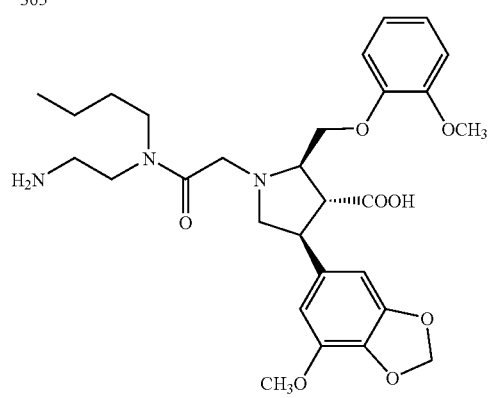
366
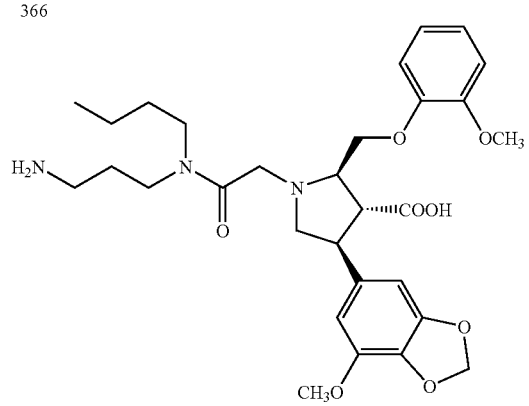
367
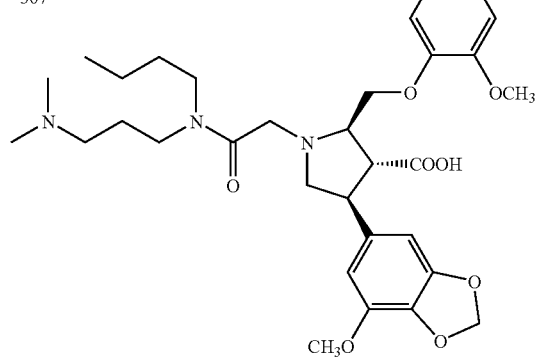
TABLE 3C-continued
368
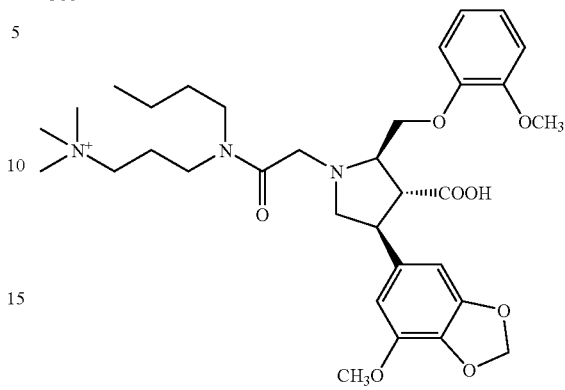
369
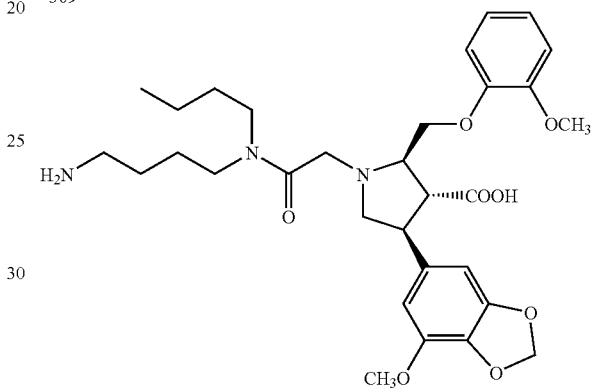
370
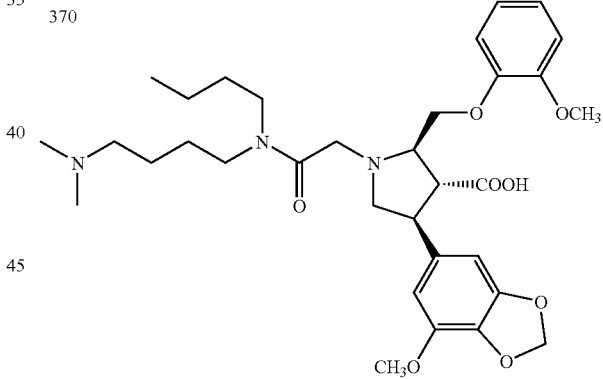
371
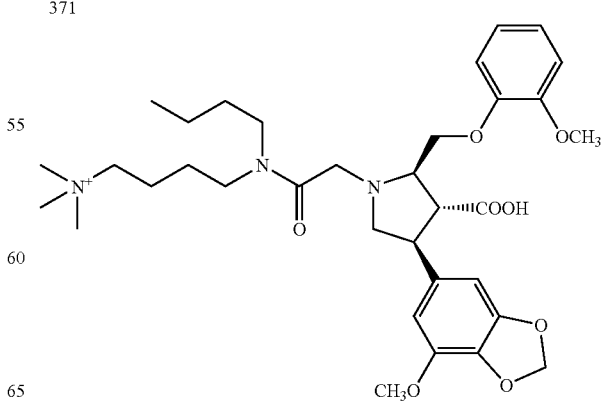

TABLE 3C-continued
372
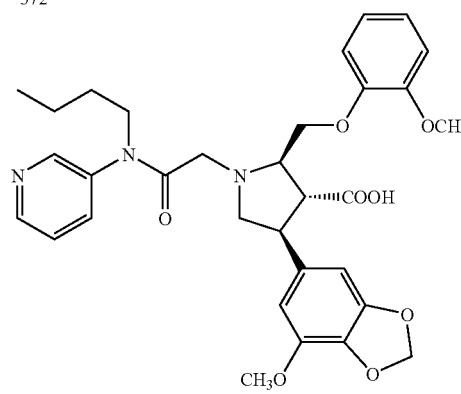
373
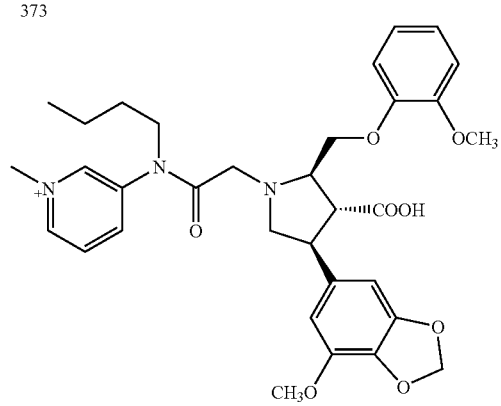
374
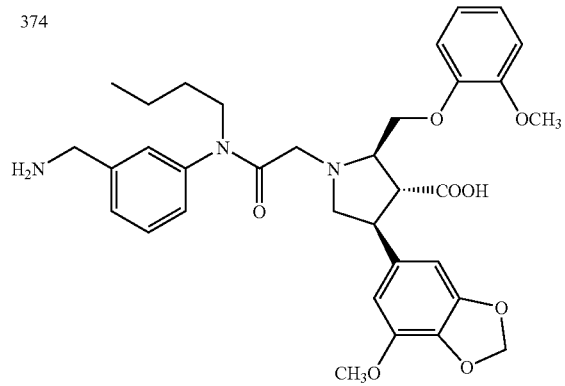
375
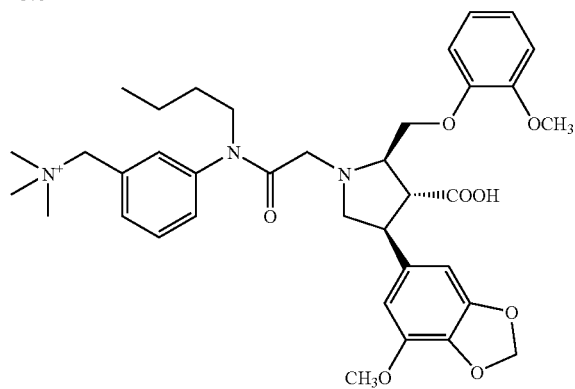
TABLE 3C-continued
376
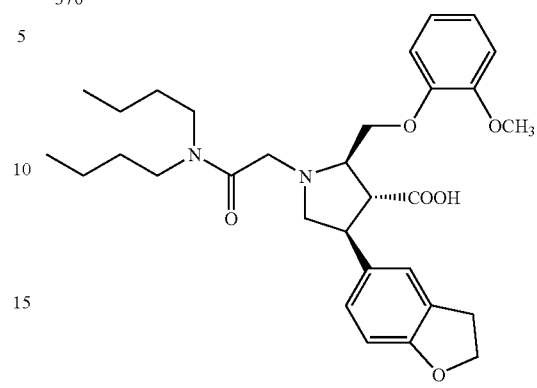
377
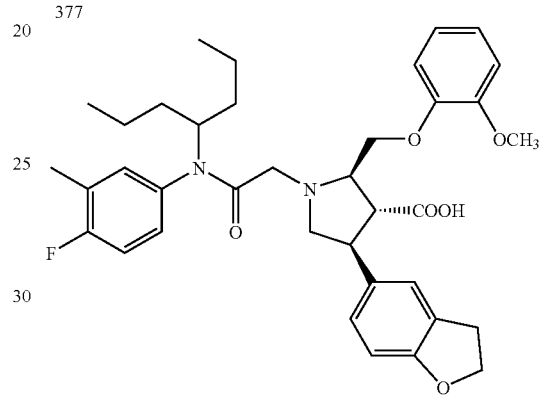
378
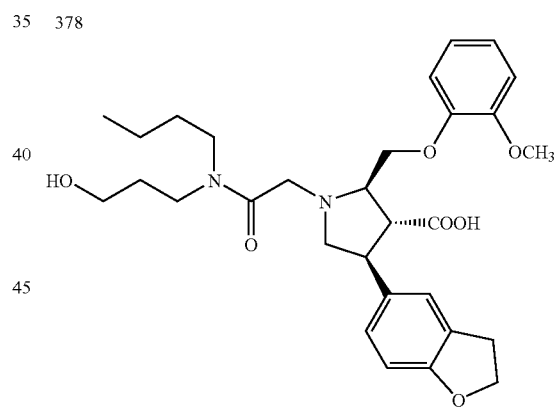
379
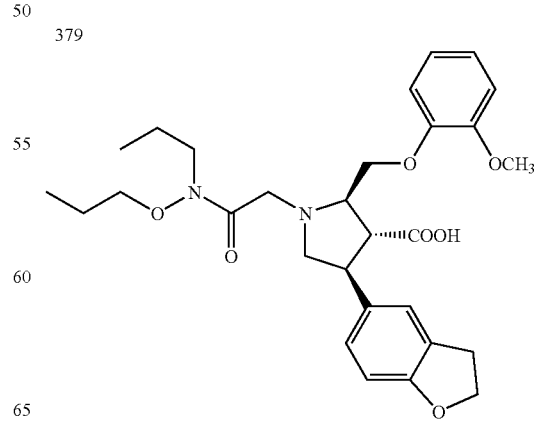

TABLE 3C-continued
380
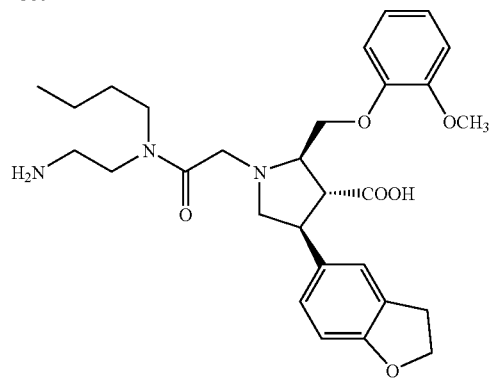
381
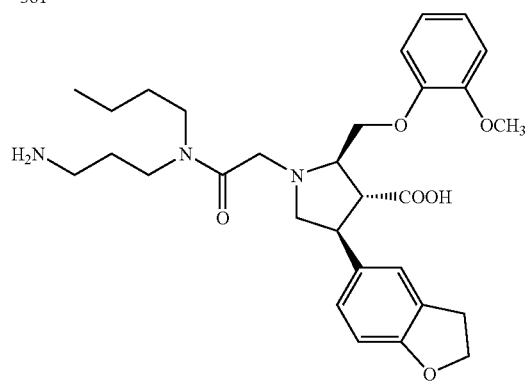
382
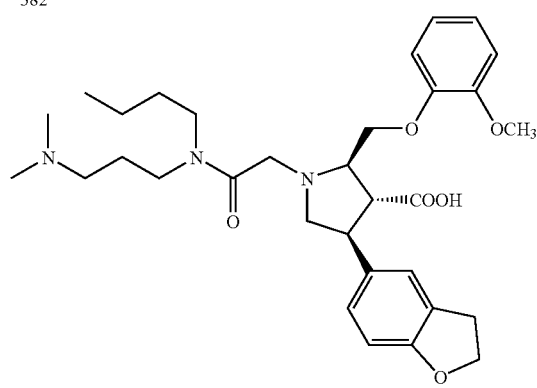
383
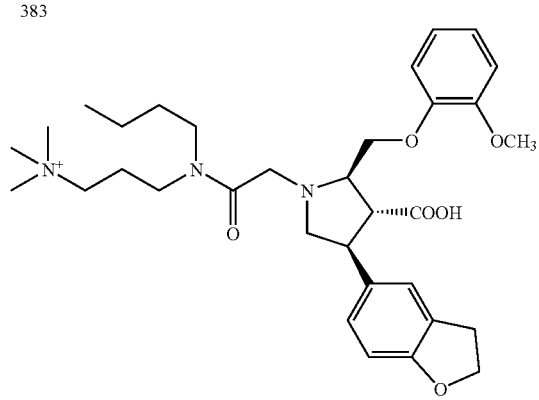
TABLE 3C-continued
384
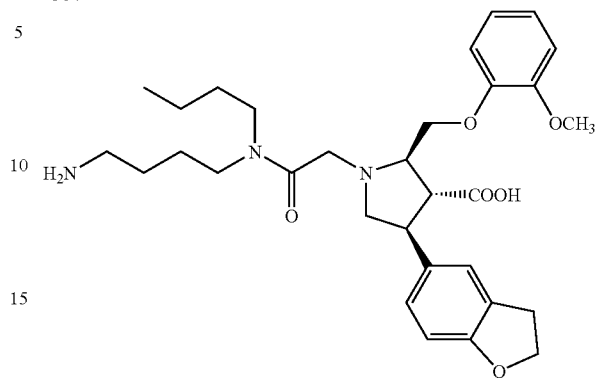
385

386

387
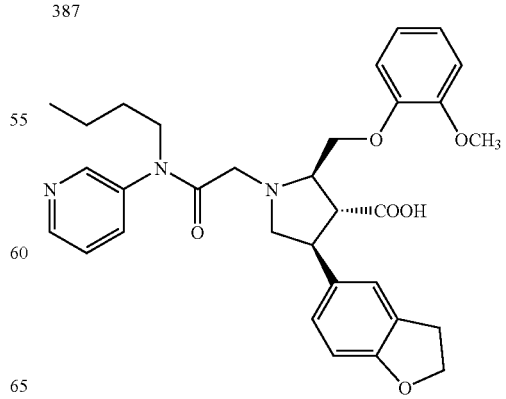

TABLE 3C-continued
388
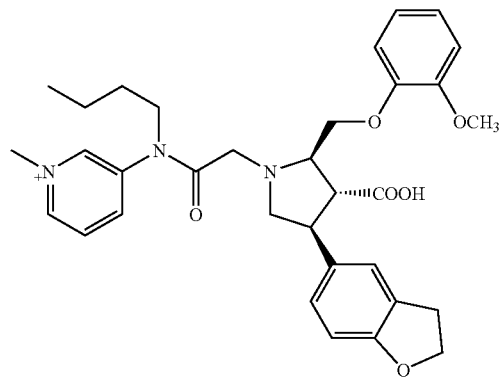
389
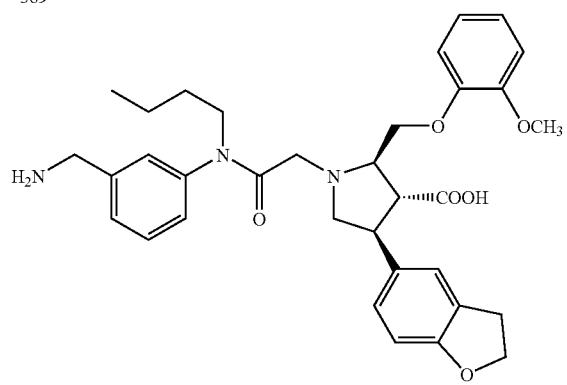
390
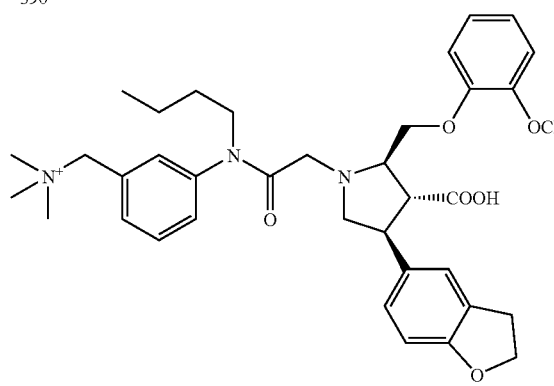
391
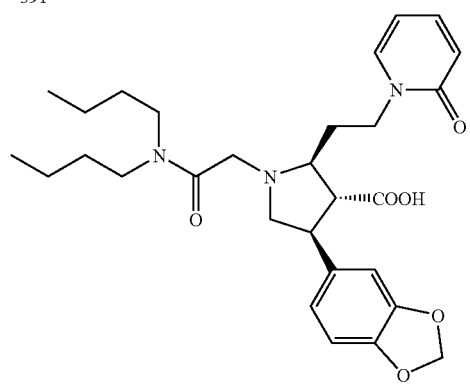
TABLE 3C-continued
392
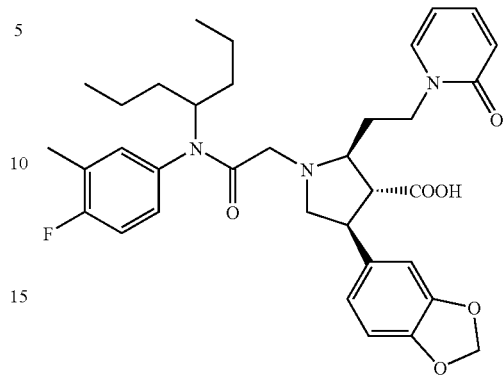
393
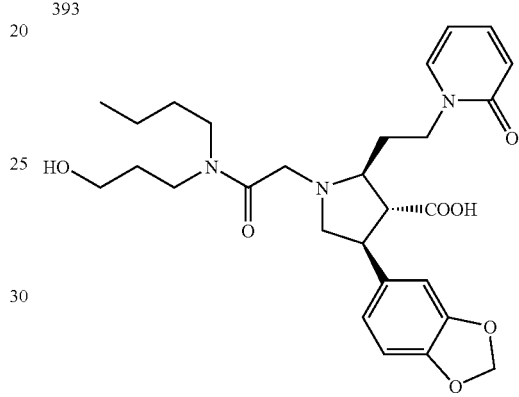
394
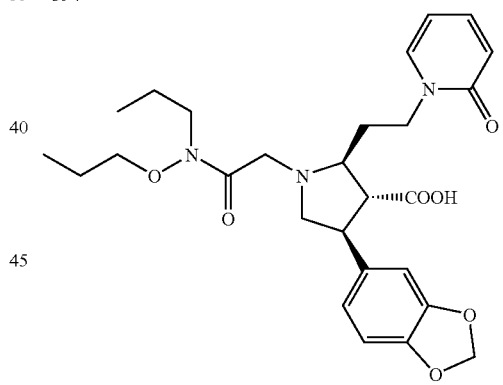
395
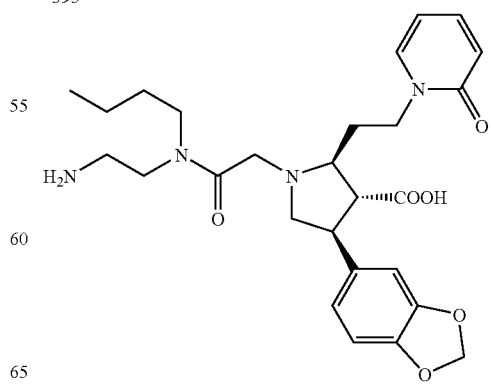

TABLE 3C-continued
396
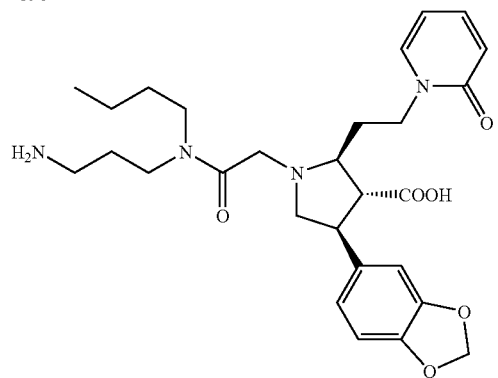
397
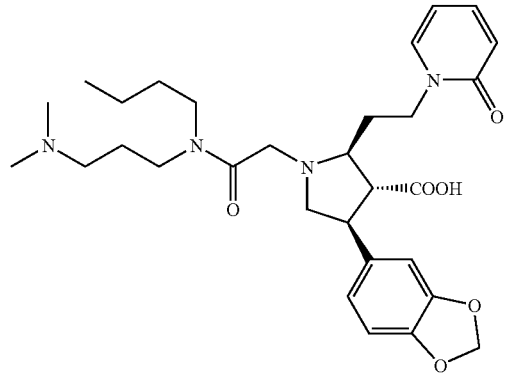
398
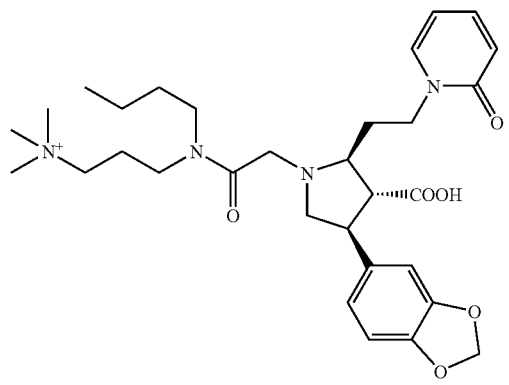
399
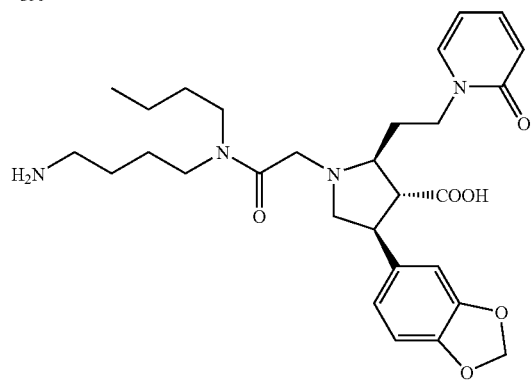
TABLE 3C-continued
400
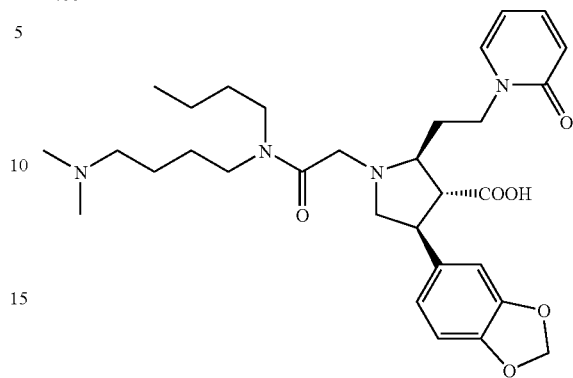
401
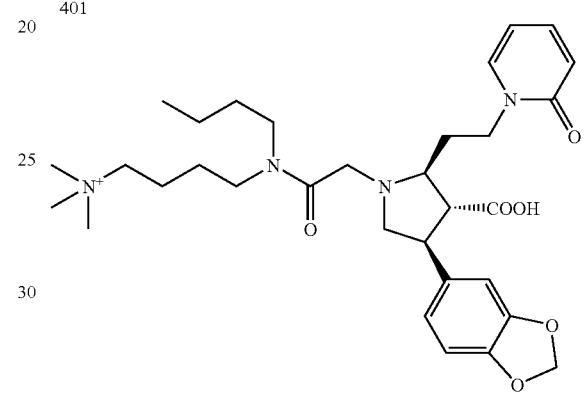
402
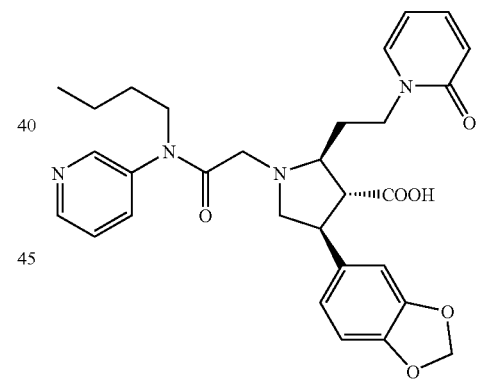
403
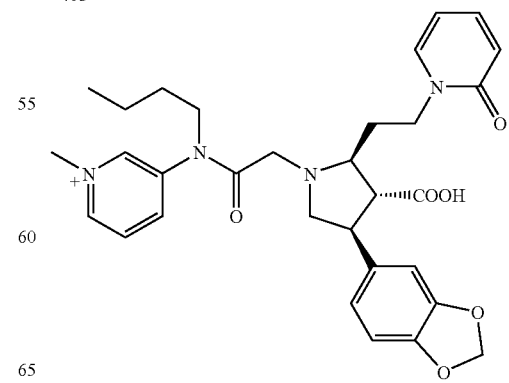

TABLE 3C-continued
404
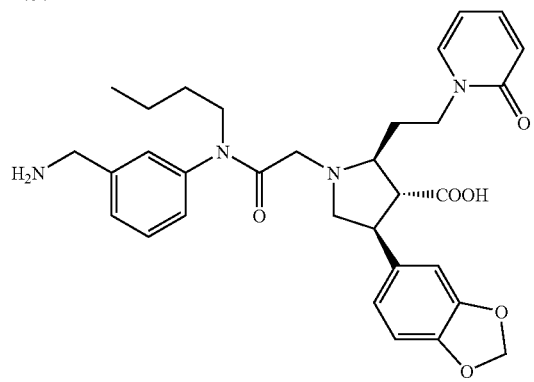
405
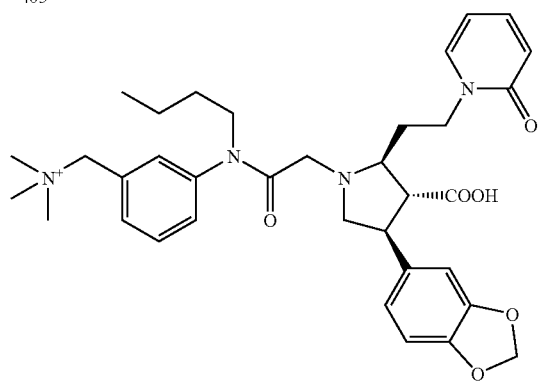
406
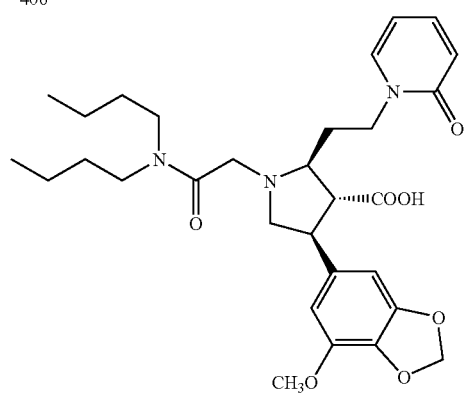
407
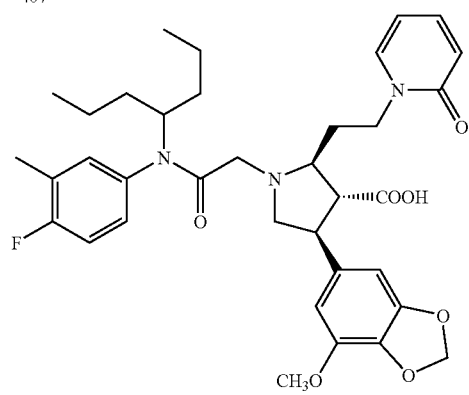
TABLE 3C-continued
408
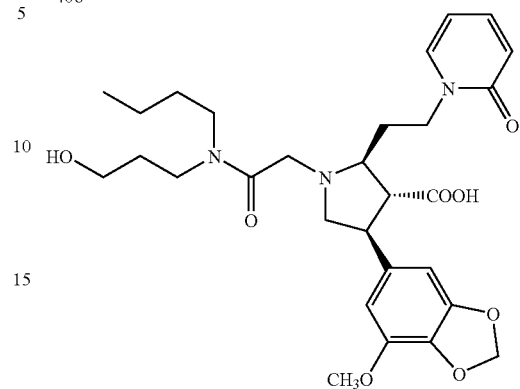
409
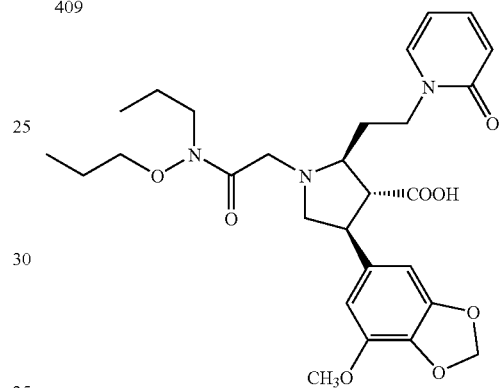
410
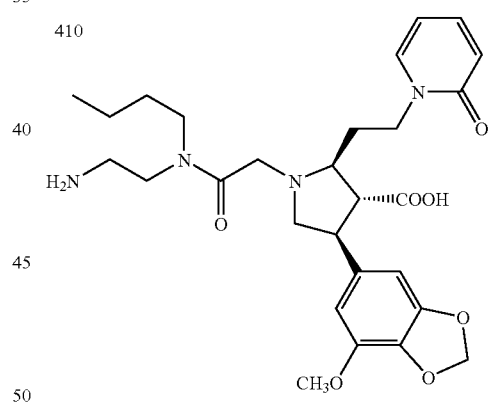
411
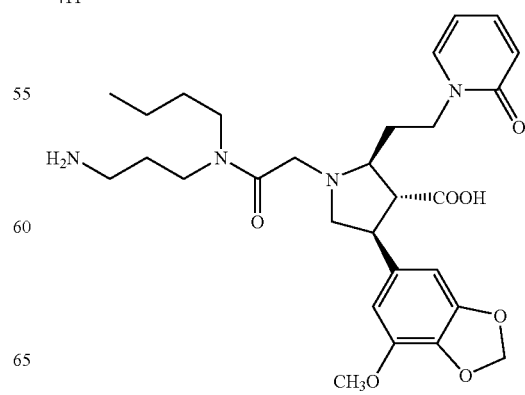

TABLE 3C-continued
412
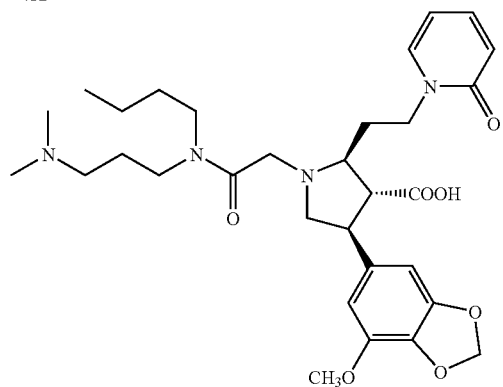
413
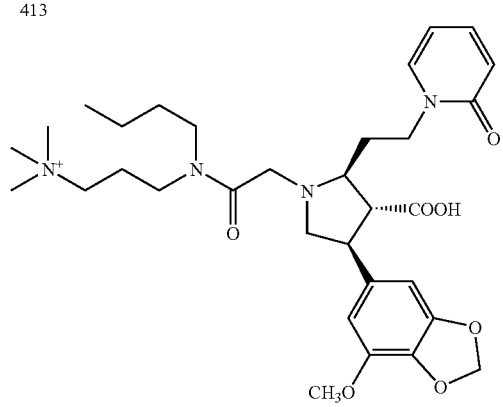
414
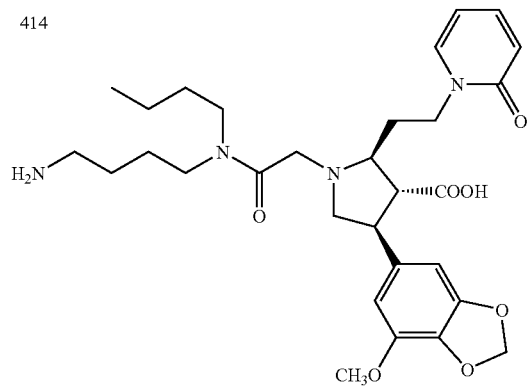
415
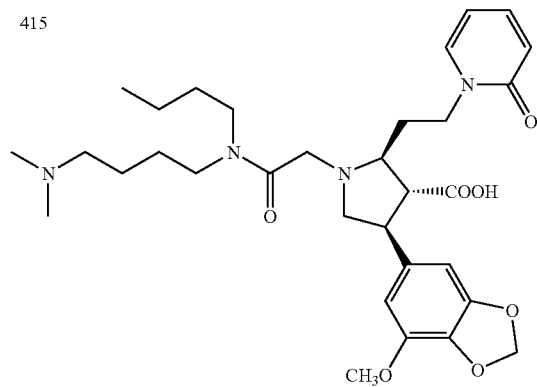
TABLE 3C-continued
416
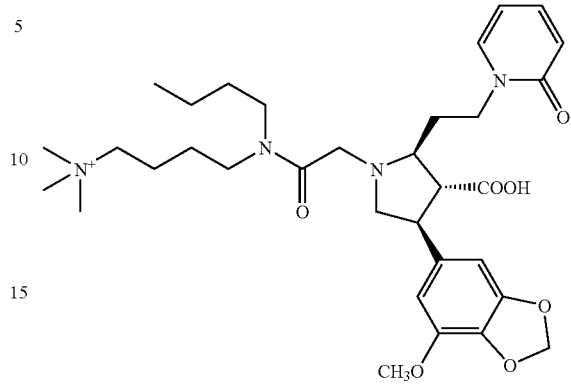
417
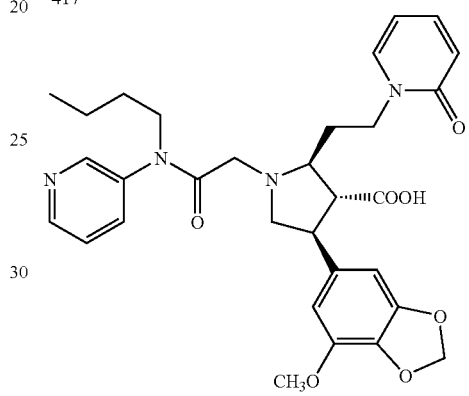
418
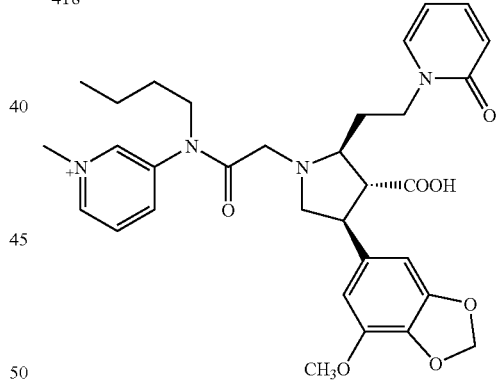
419
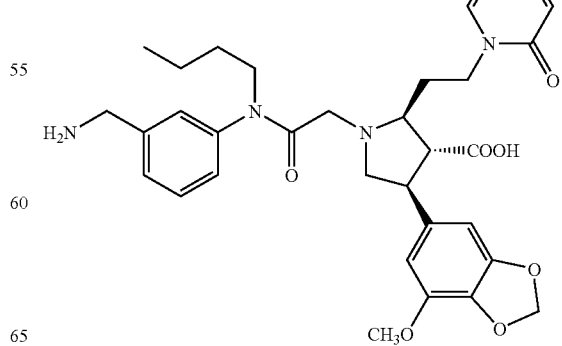

TABLE 3C-continued
420
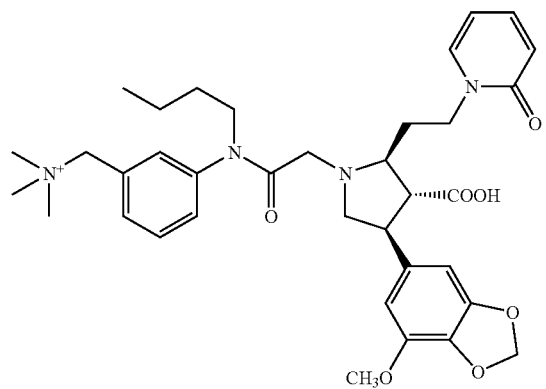
421
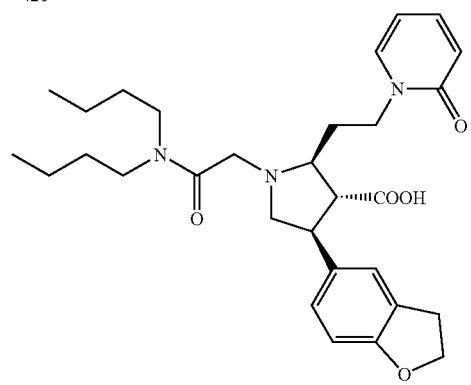
422
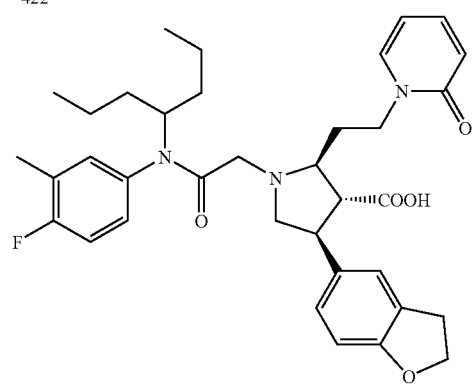
423
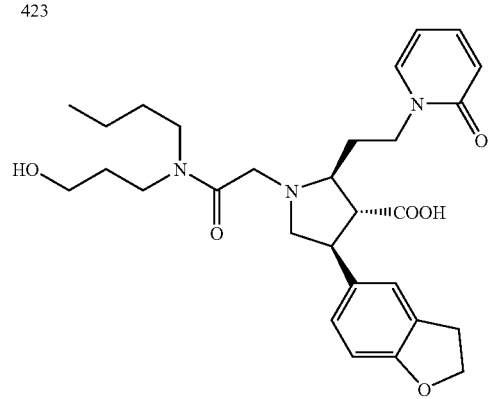
TABLE 3C-continued
424
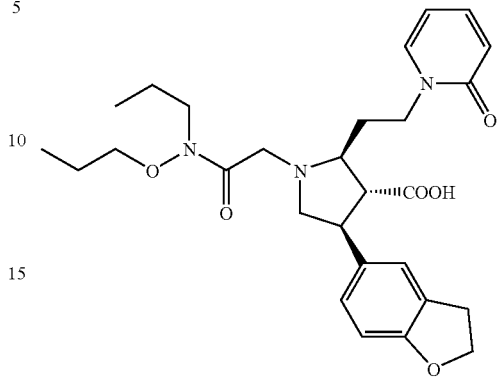
425
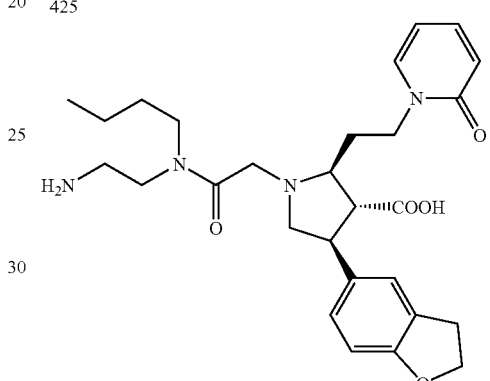
426
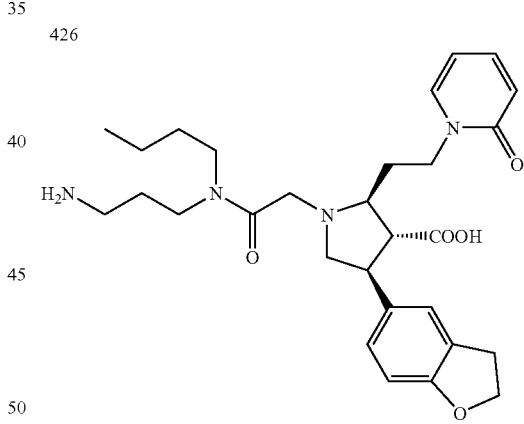
427
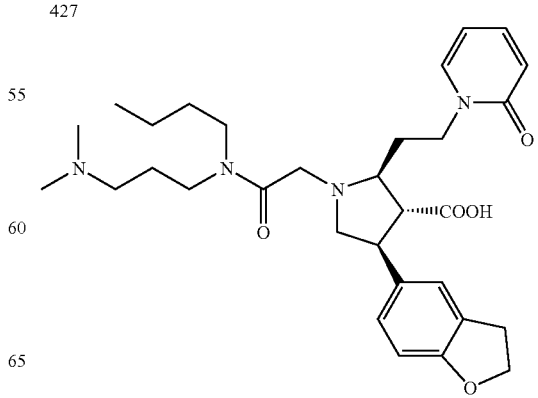

TABLE 3C-continued
428
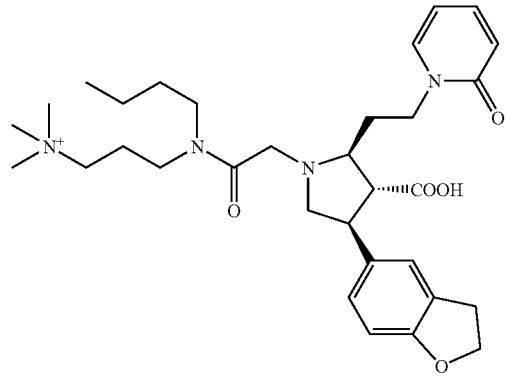
429
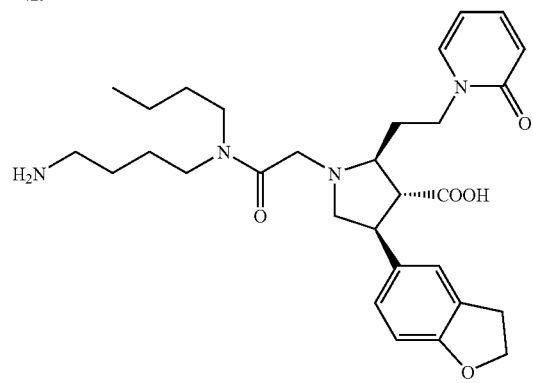
430
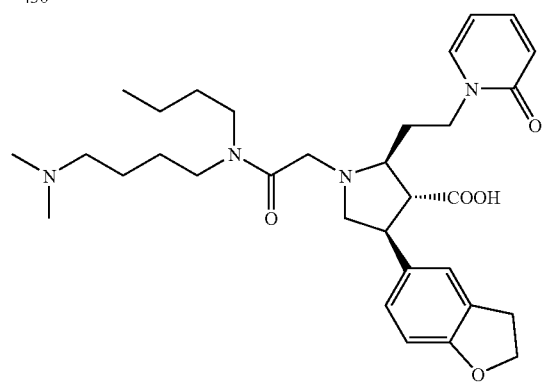
431
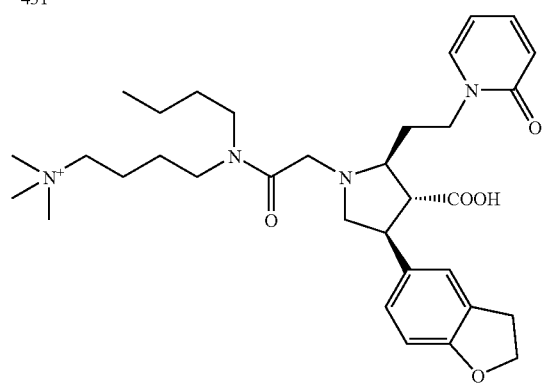
TABLE 3C-continued
432
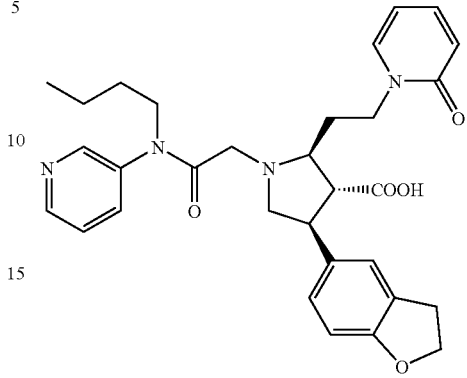
433
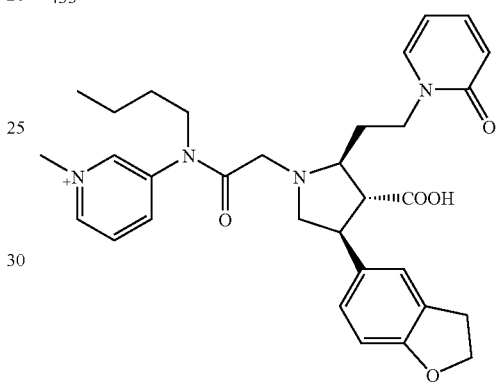
434
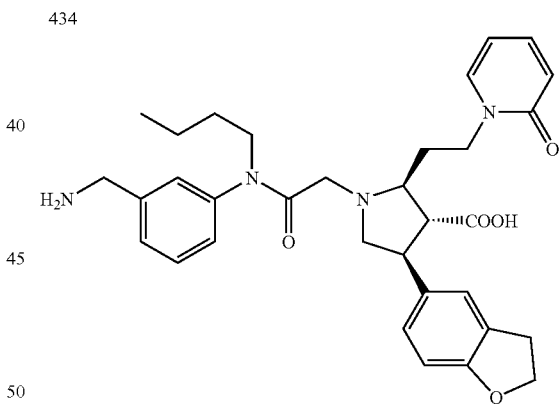
435
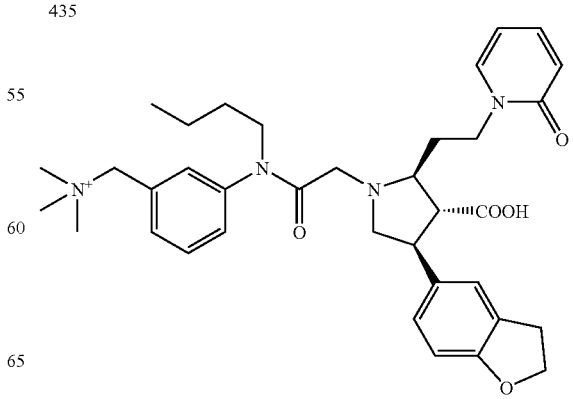

TABLE 3C-continued
436
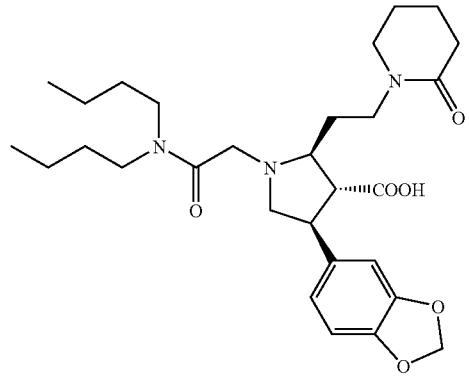
437
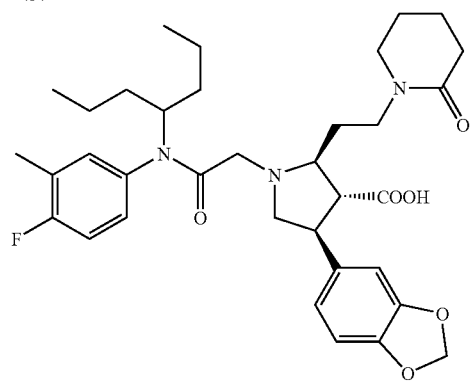
438
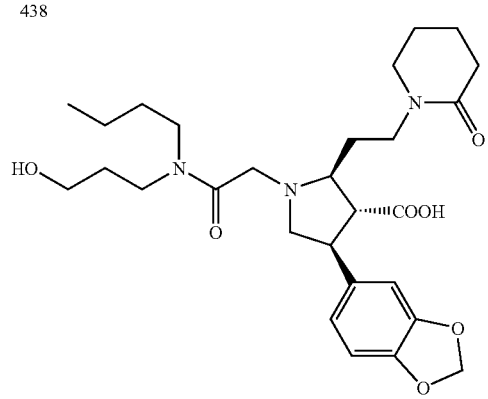
439
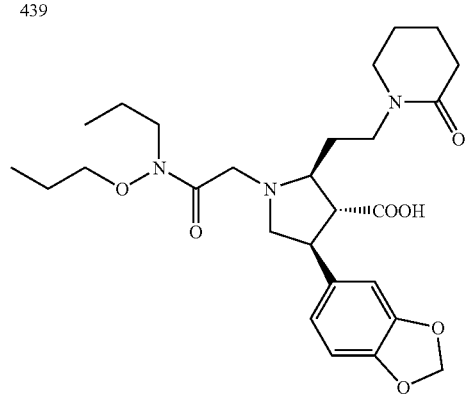
TABLE 3C-continued
440
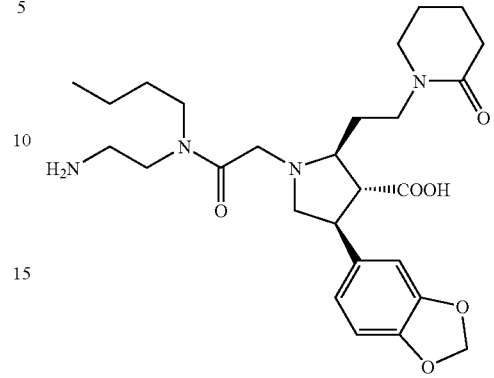
441
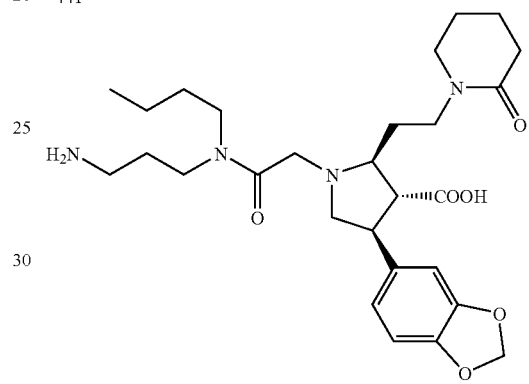
442
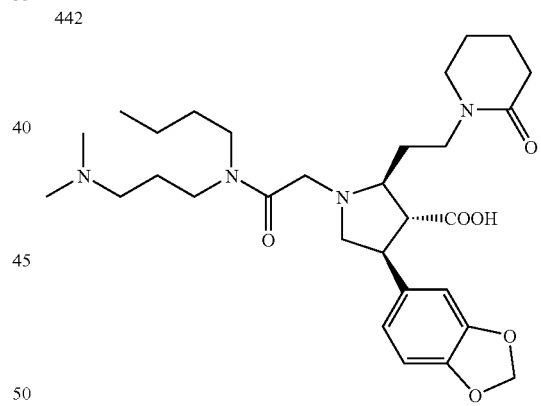
443
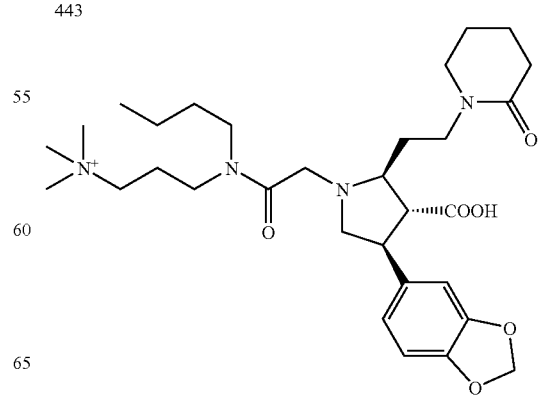

TABLE 3C-continued
444
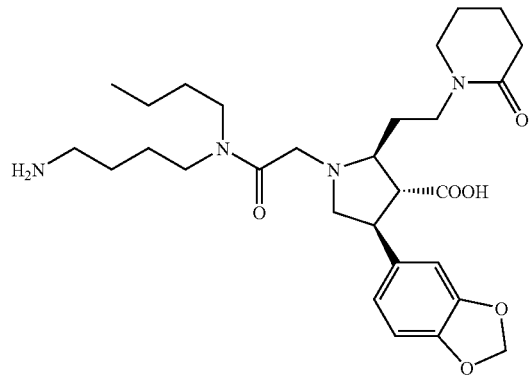
445
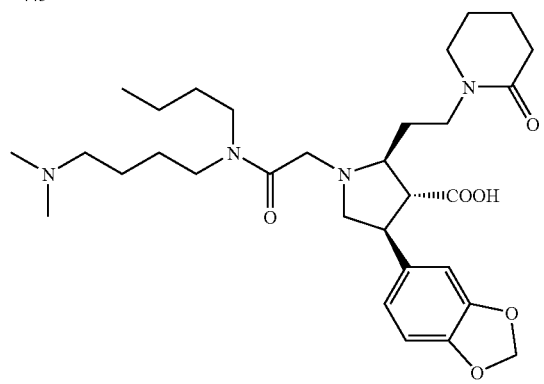
446
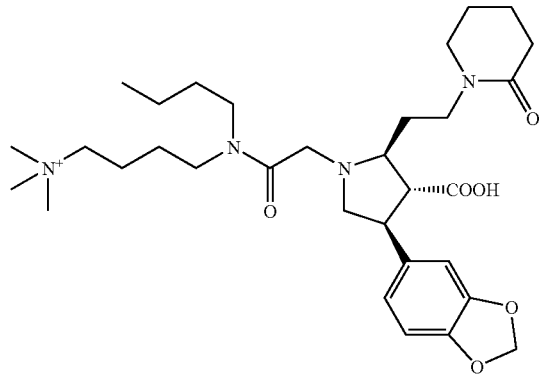
447
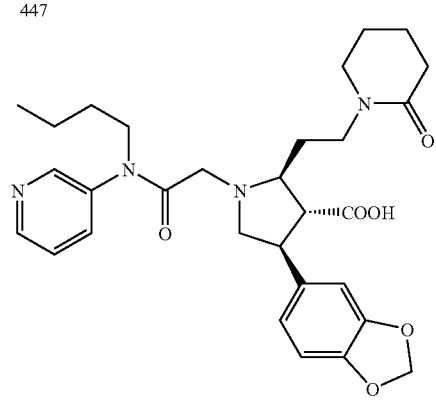
TABLE 3C-continued
448
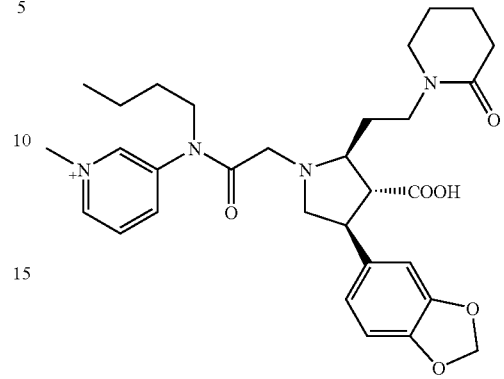
449
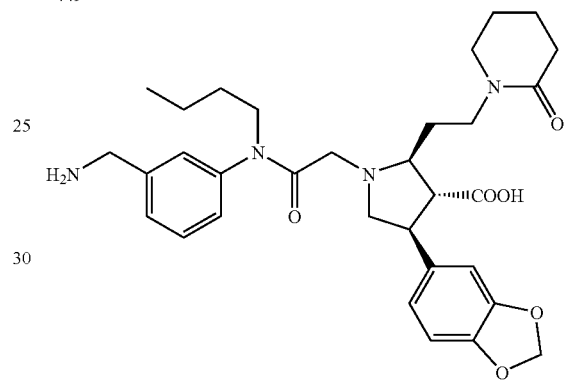
450
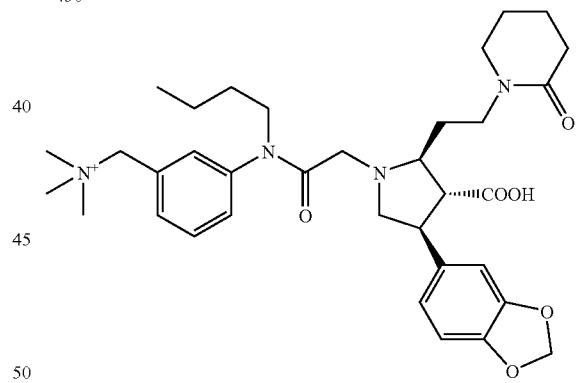
451
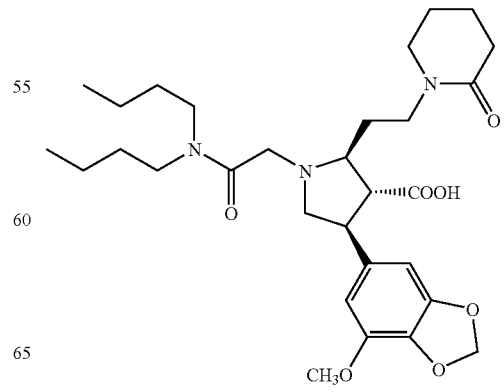

TABLE 3C-continued
452 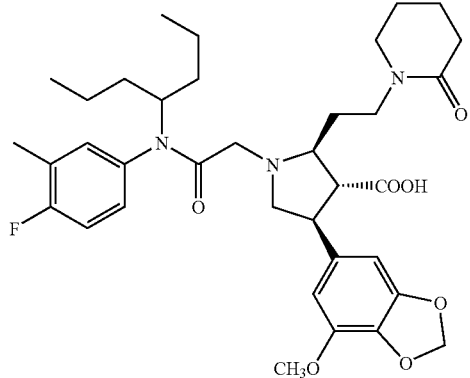
453 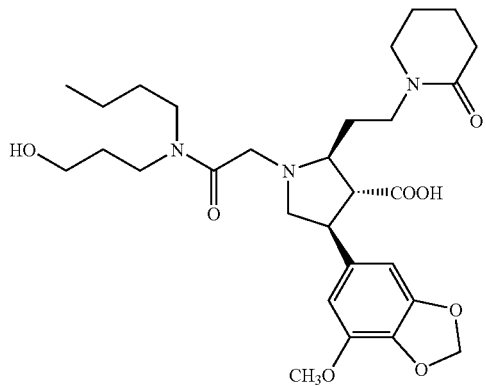
454 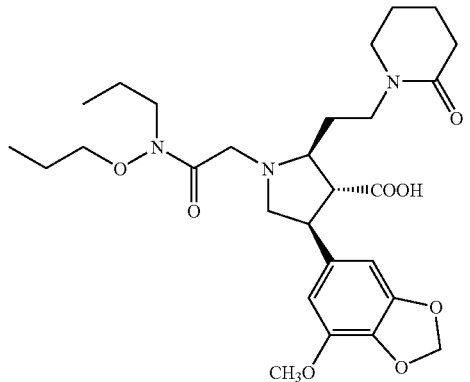
455 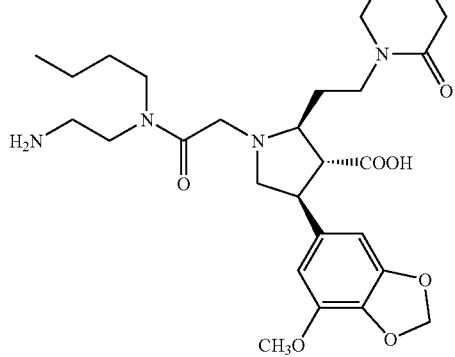
456 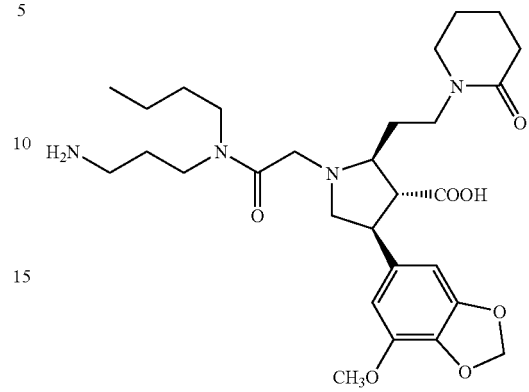
457 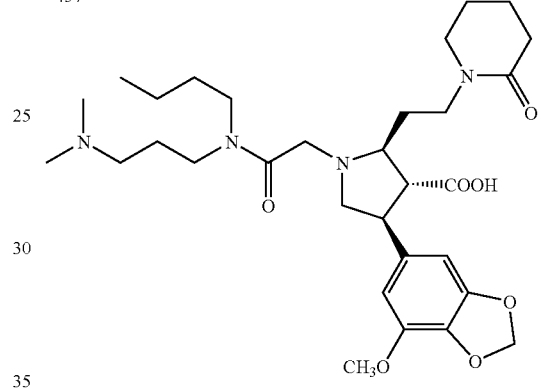
458 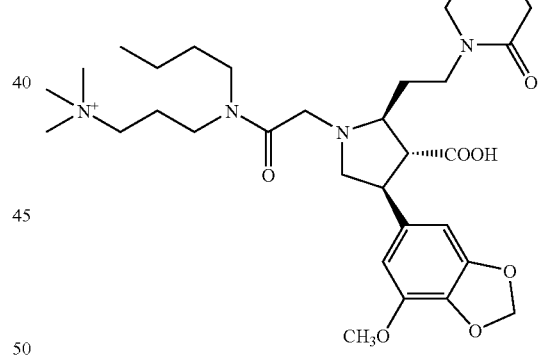
459 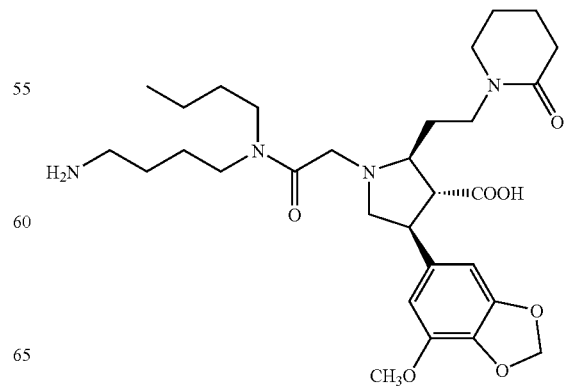

TABLE 3C-continued
460
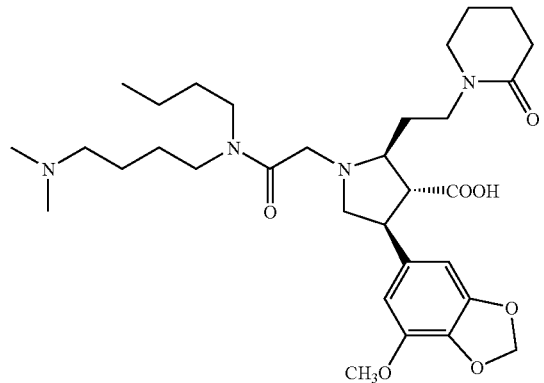
461
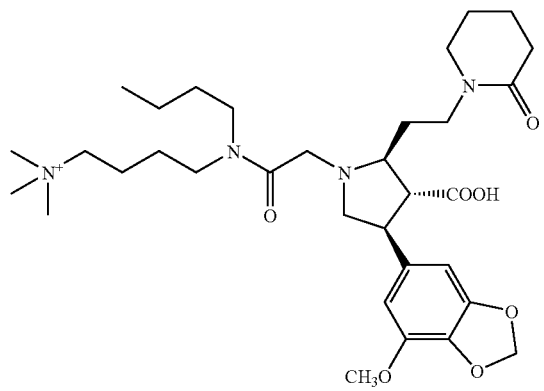
462
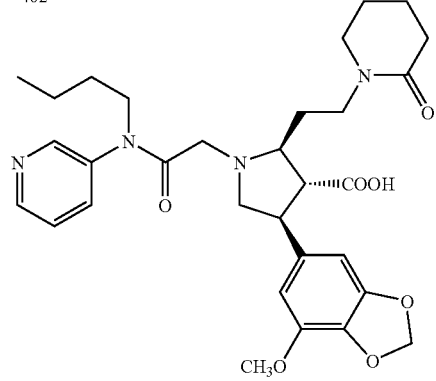
463
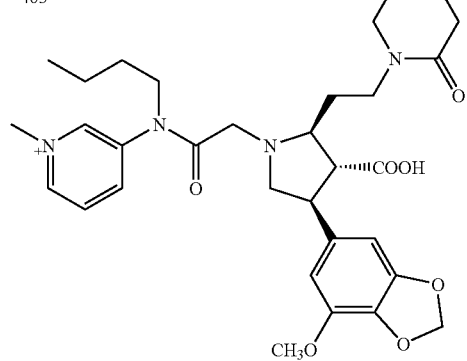
TABLE 3C-continued
464
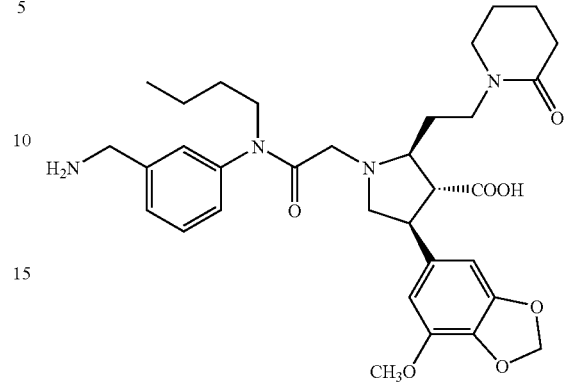
465
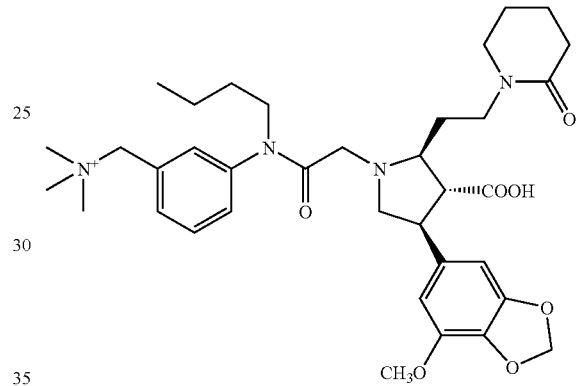
466
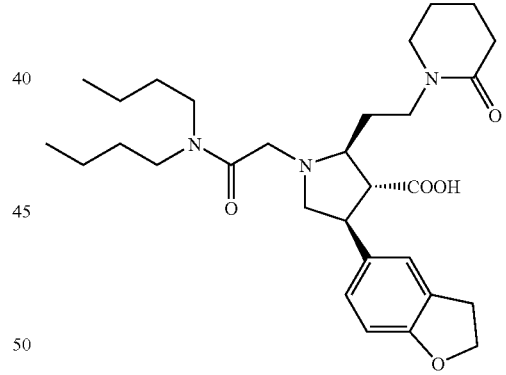
467
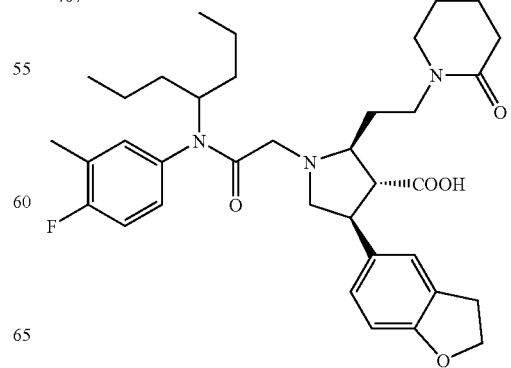

TABLE 3C-continued
468
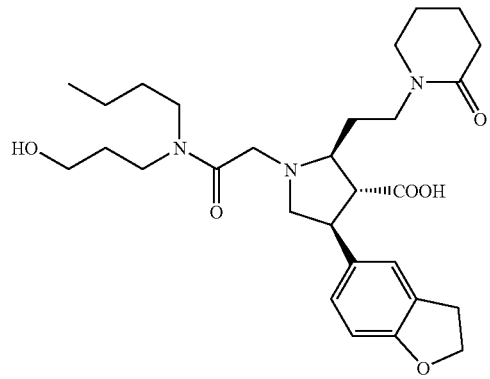
469
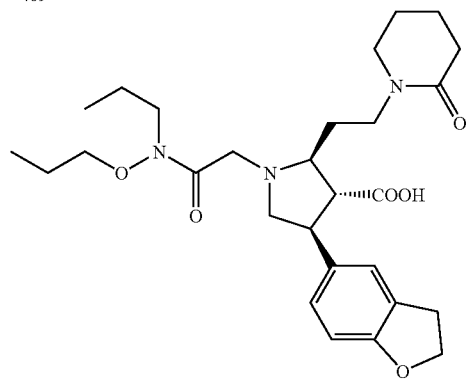
470
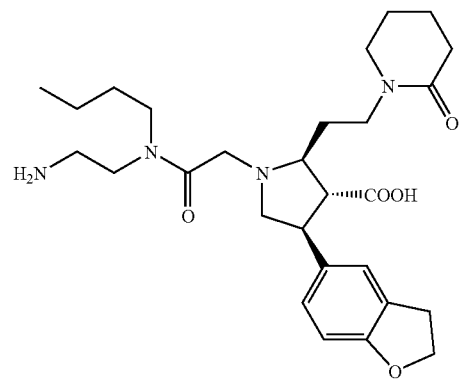
471
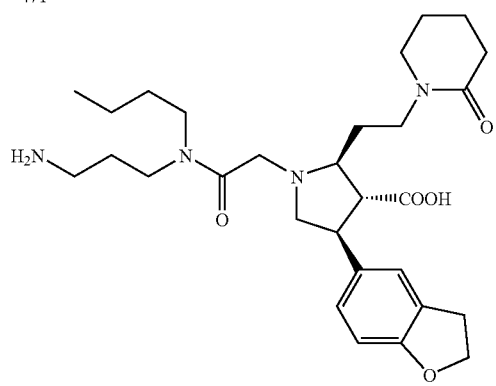
TABLE 3C-continued
472

473

474
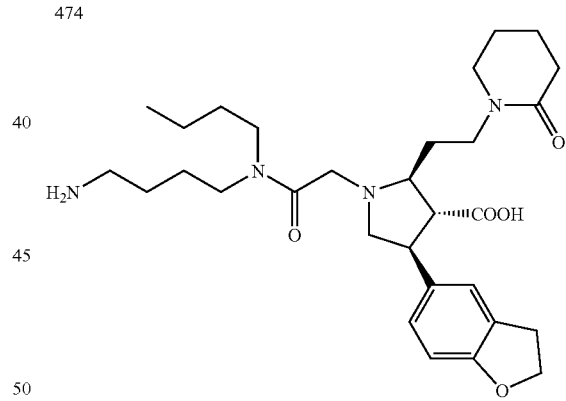
475
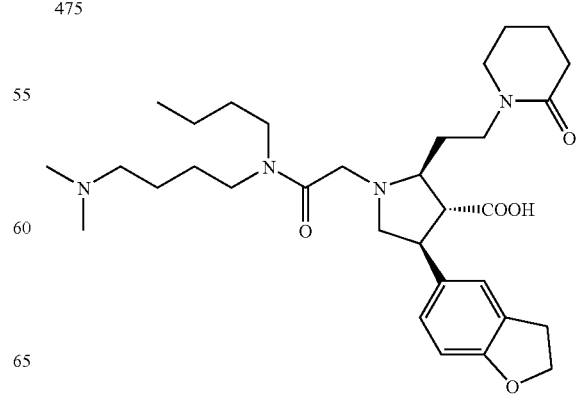

TABLE 3C-continued
476
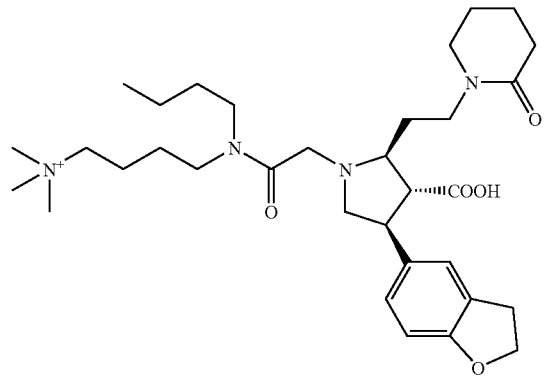
477
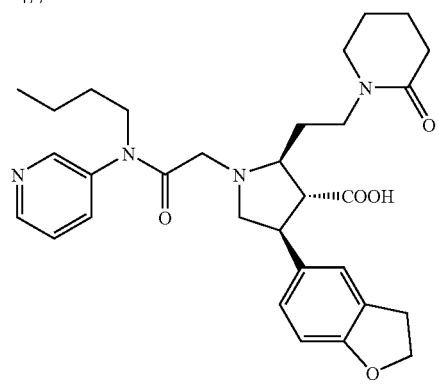
478
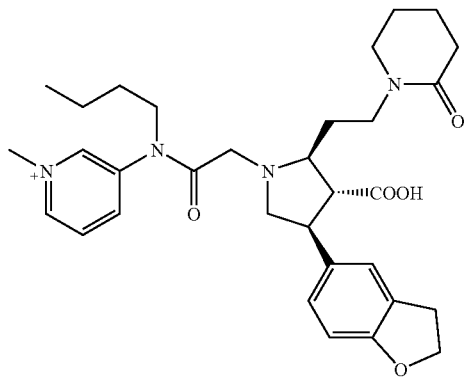
479
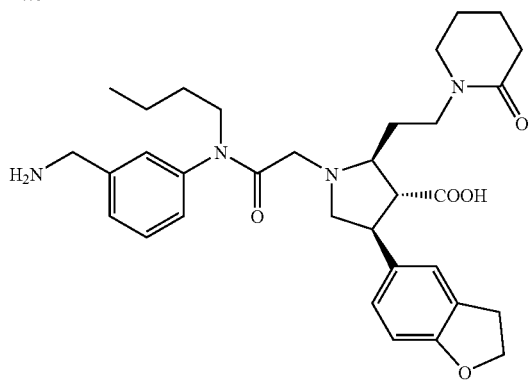
TABLE 3C-continued
480
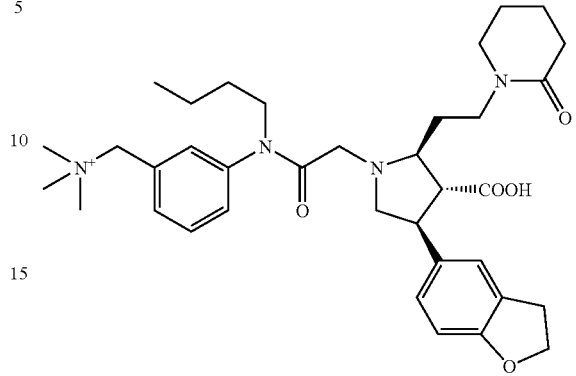
481
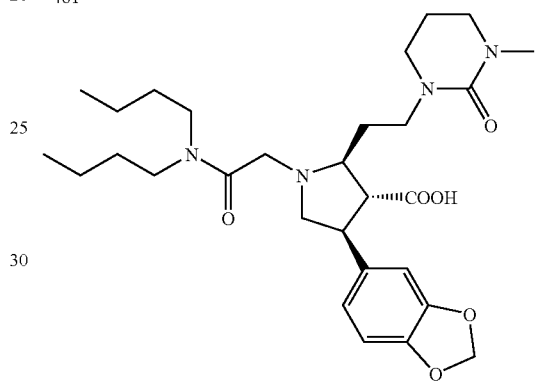
482
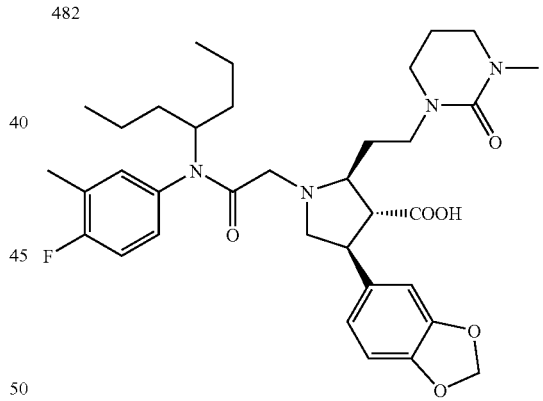
483
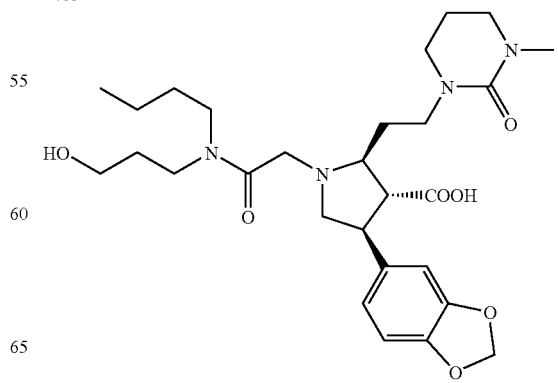

TABLE 3C-continued
484
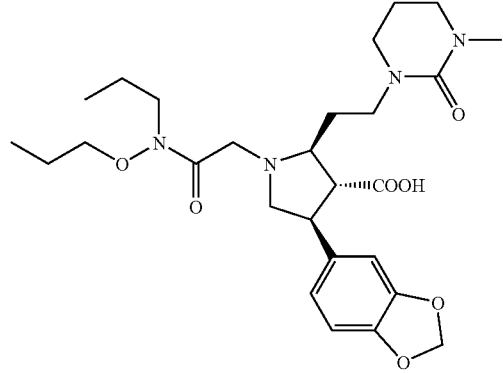
485
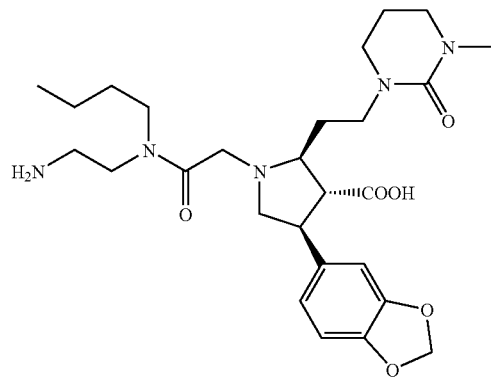
486
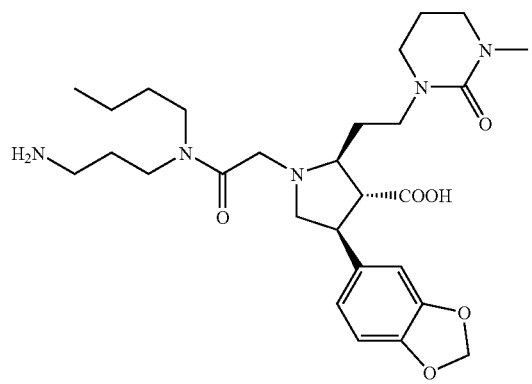
487
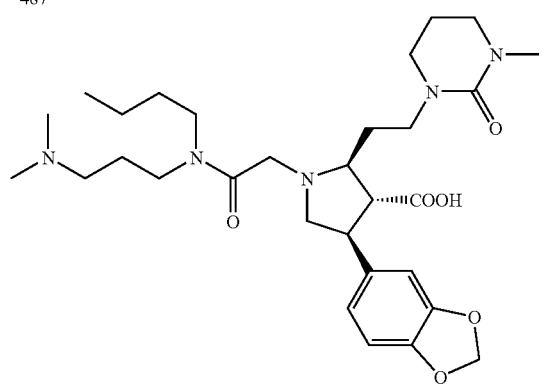
TABLE 3C-continued
488
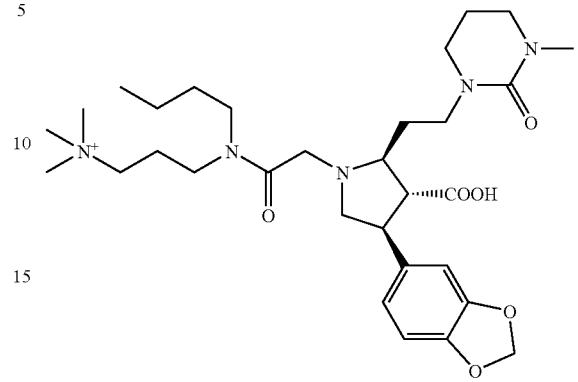
489
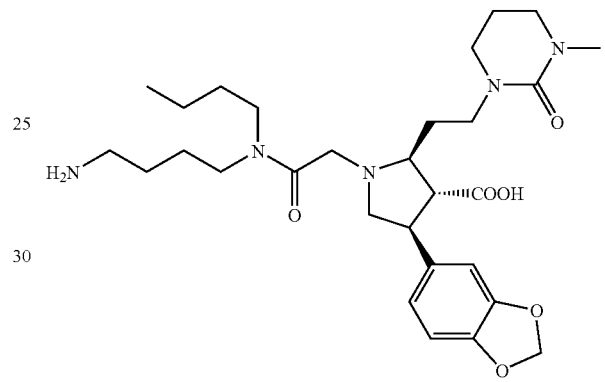
490
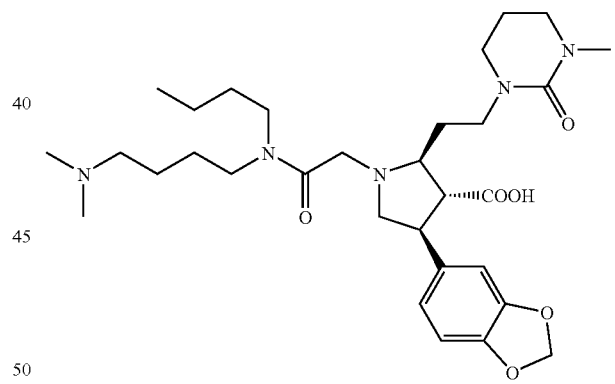
491
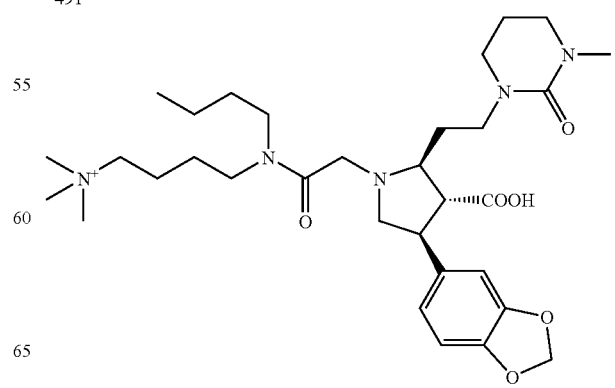

TABLE 3C-continued
492
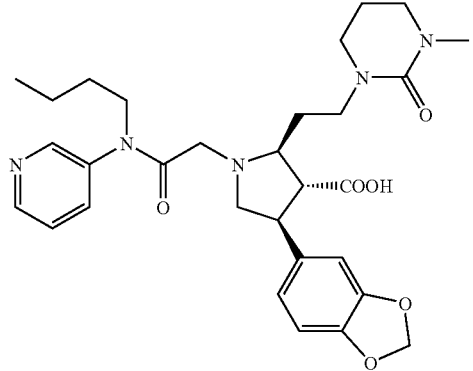
493
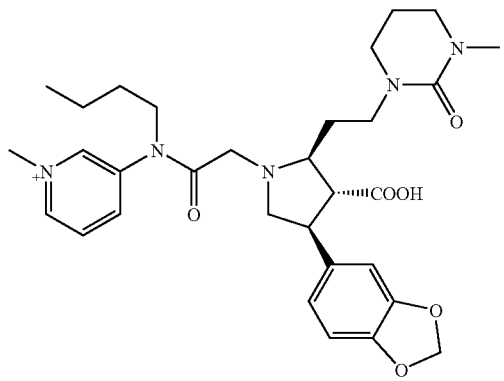
494
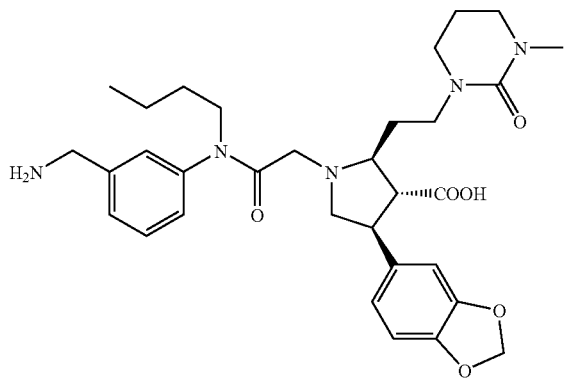
495
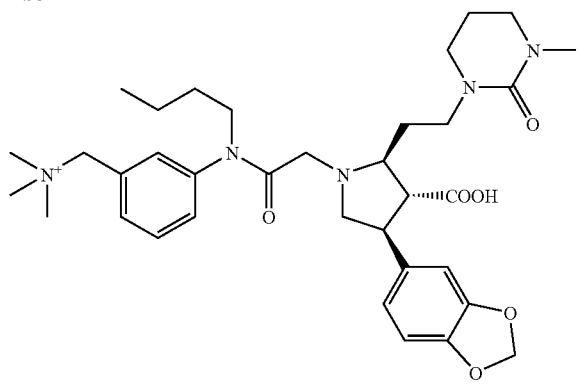
496
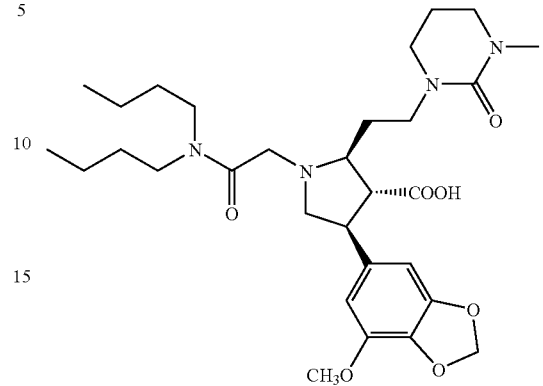
497
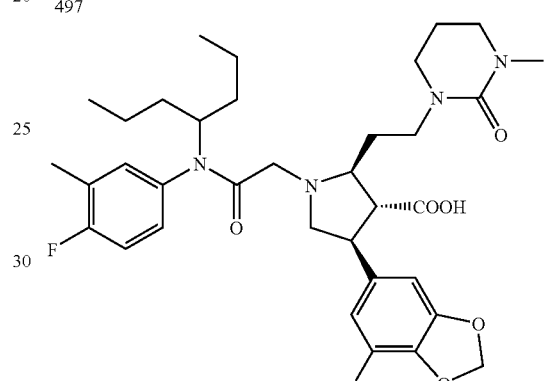
498
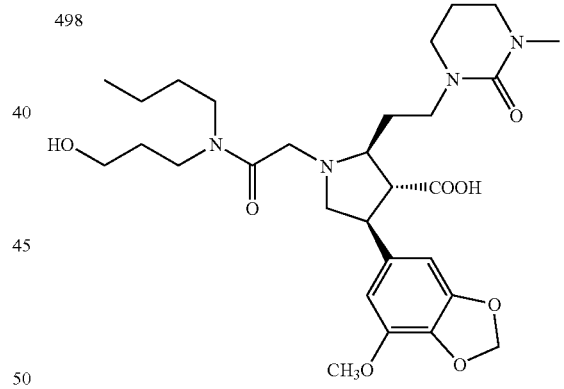
499
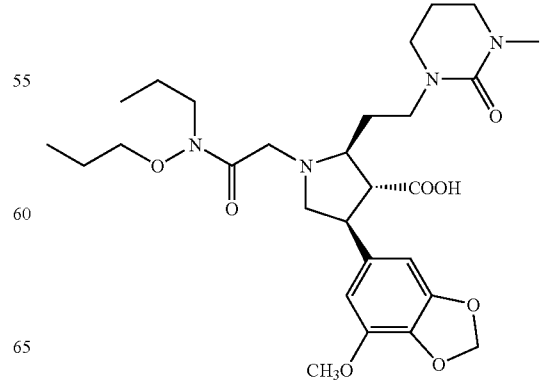

TABLE 3C-continued
500
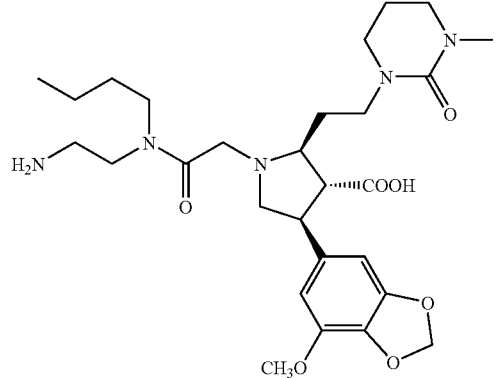
501
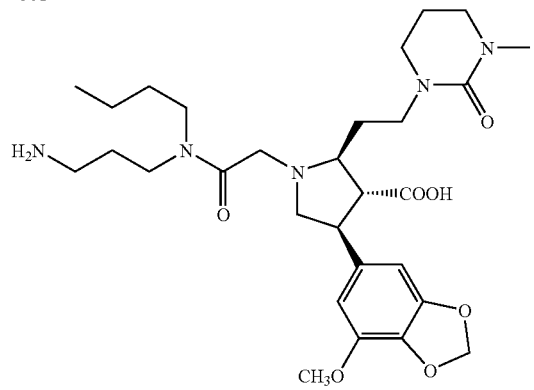
502
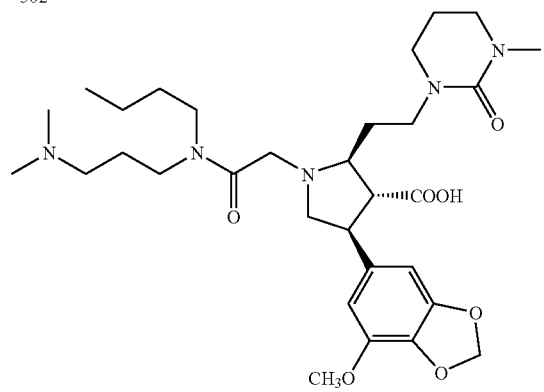
503
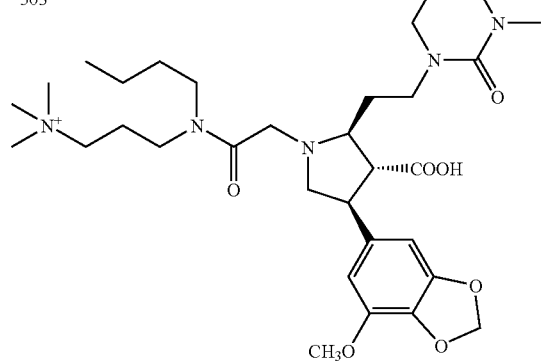
TABLE 3C-continued
504
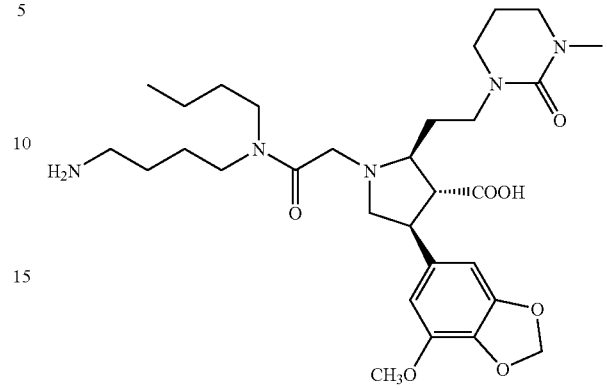
505
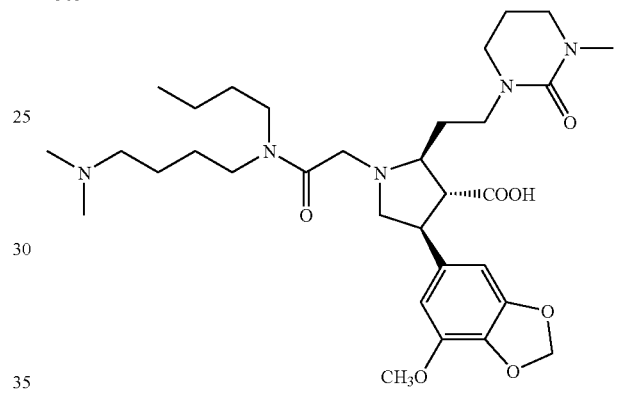
506
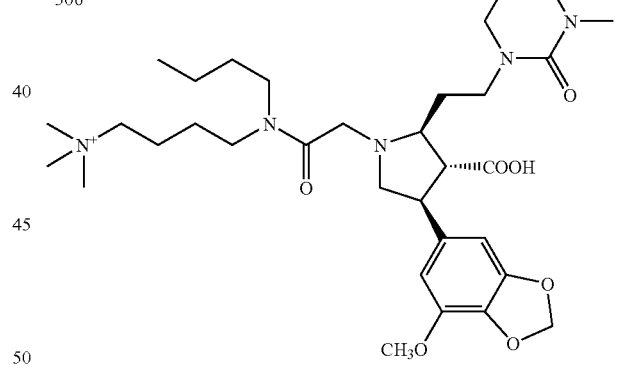
507
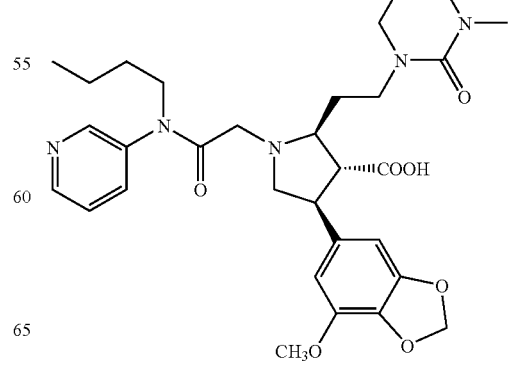

TABLE 3C-continued
508
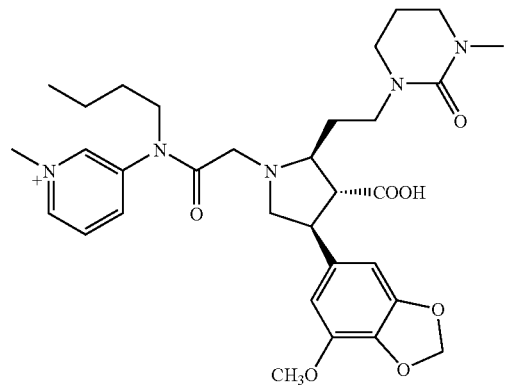
509
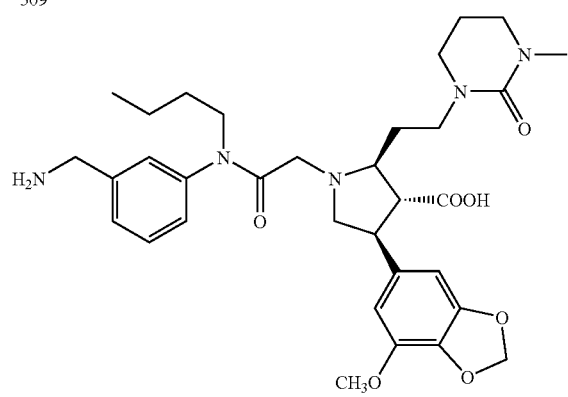
510
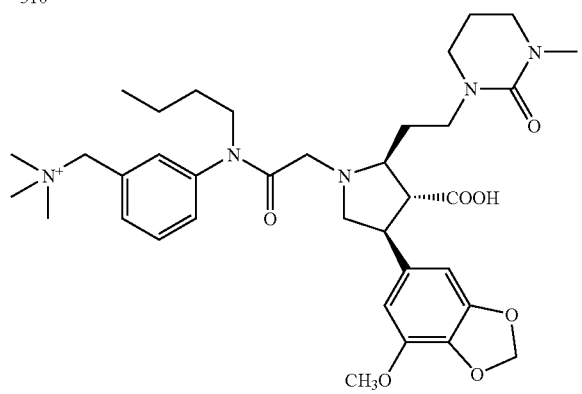
511
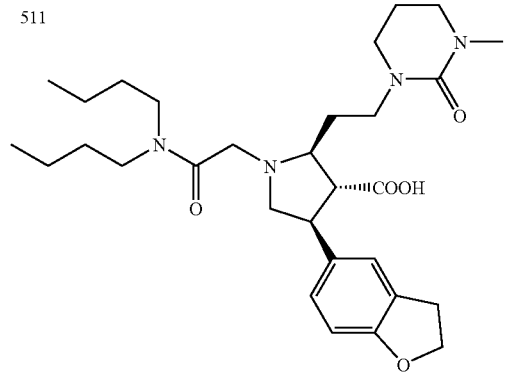
TABLE 3C-continued
512
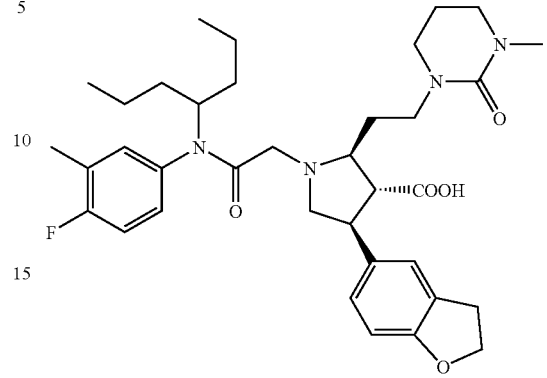
513
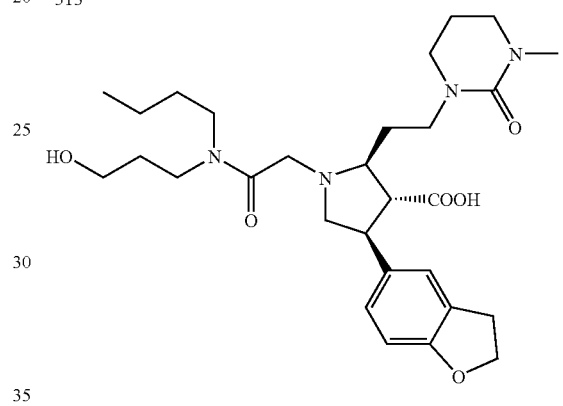
514
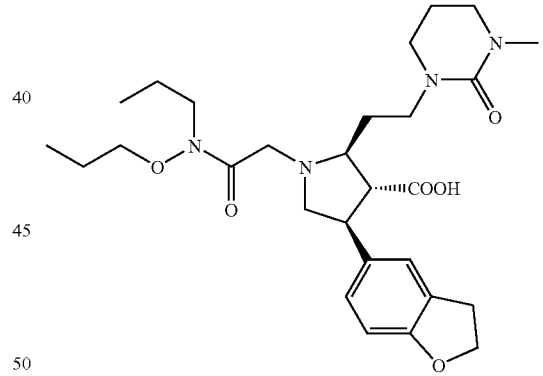
515
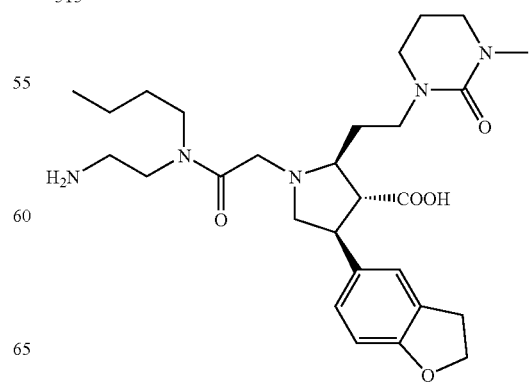

TABLE 3C-continued
516
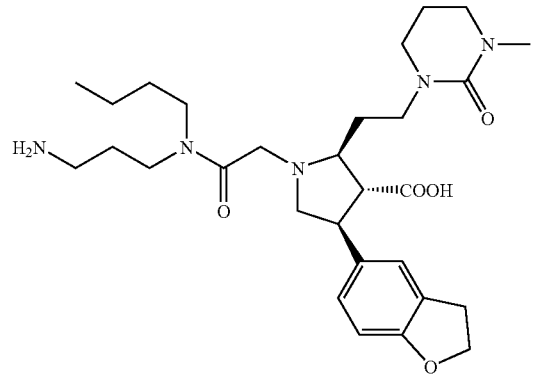
517
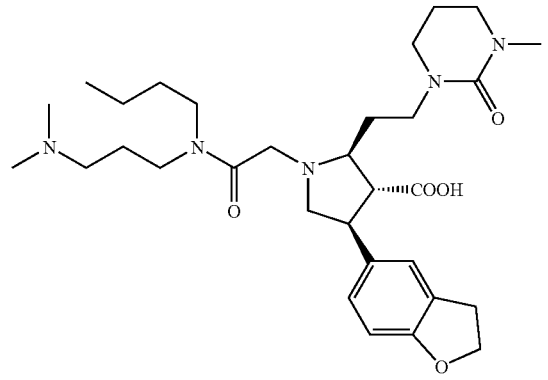
518
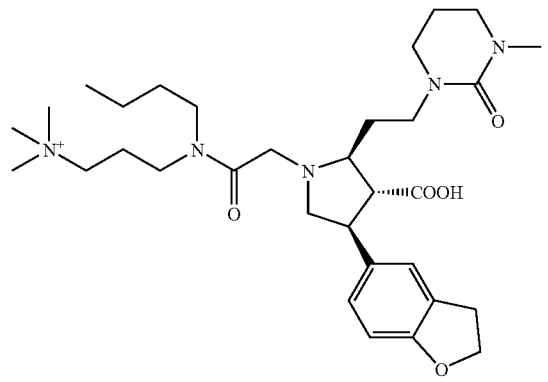
519
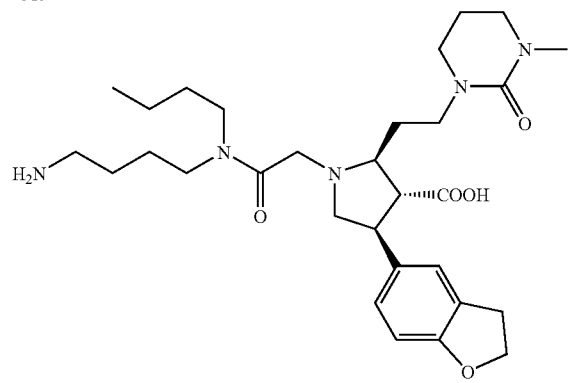
TABLE 3C-continued
520

521

522
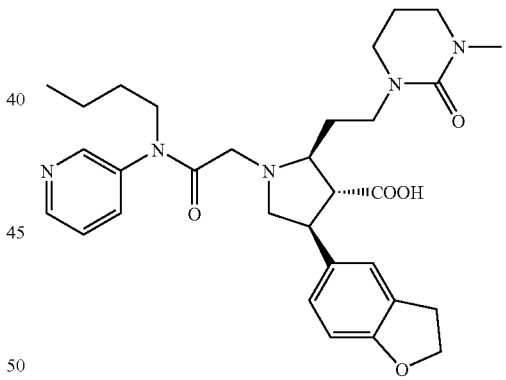
523
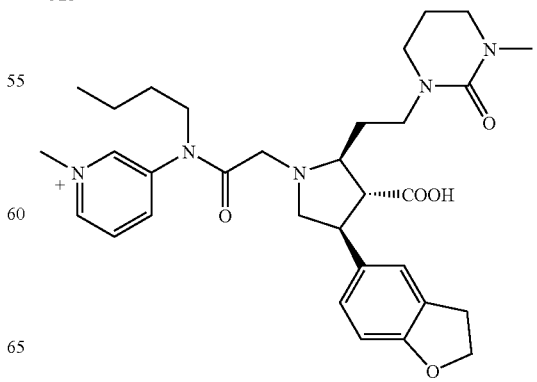

TABLE 3C-continued
524
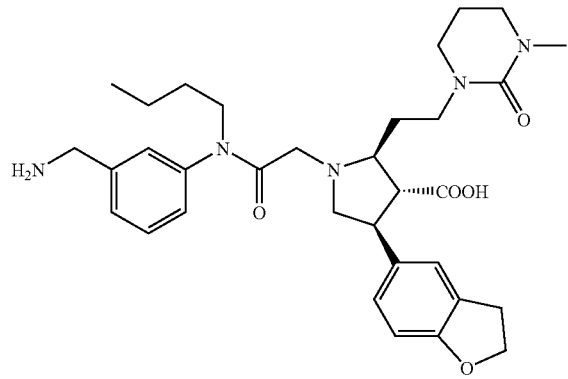
525
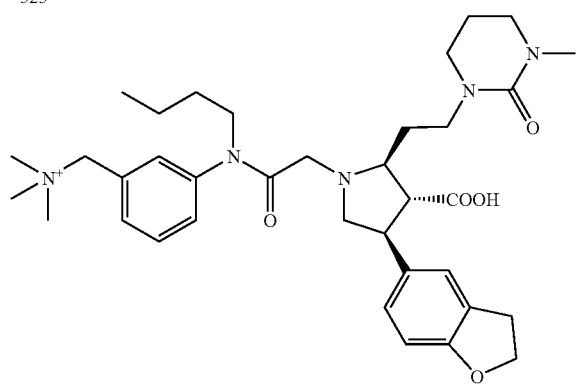
526
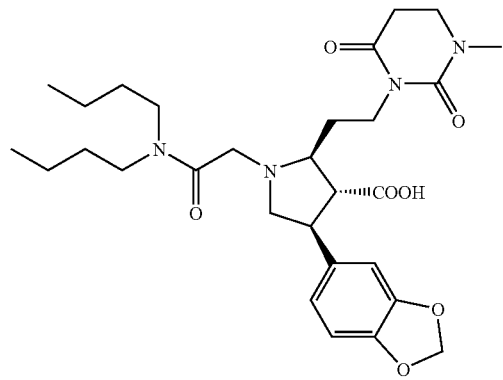
527
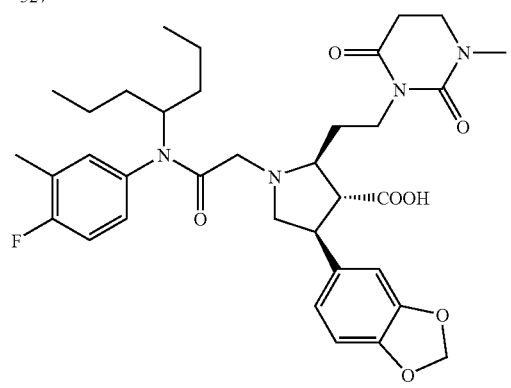
TABLE 3C-continued
528
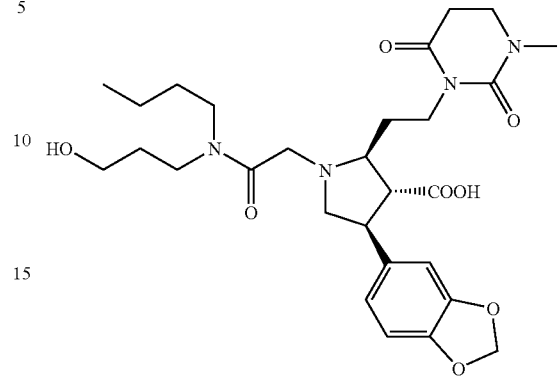
529
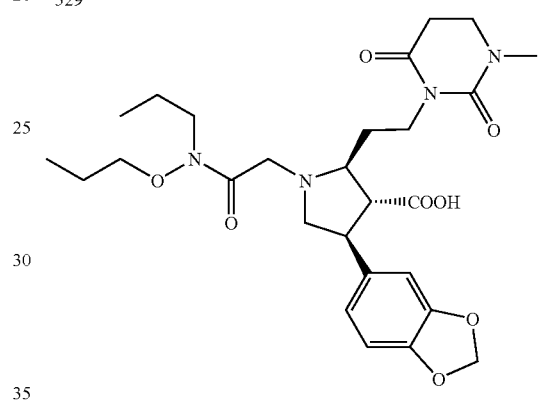
530
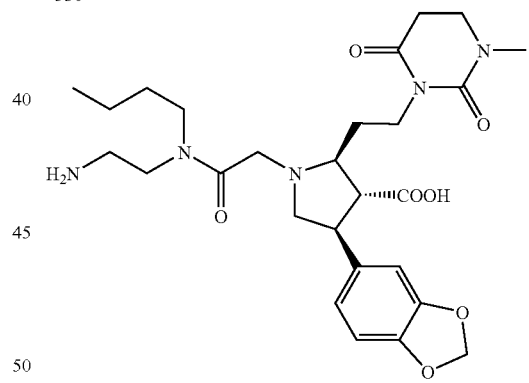
531
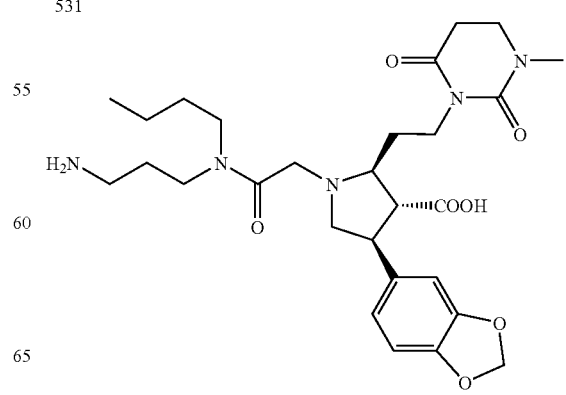

TABLE 3C-continued
532
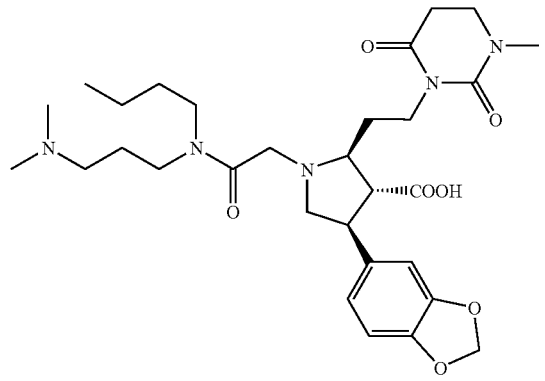
533
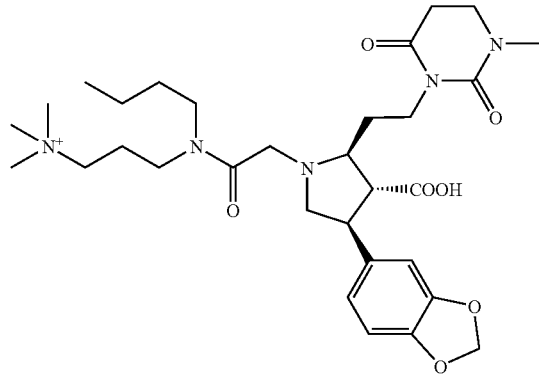
534
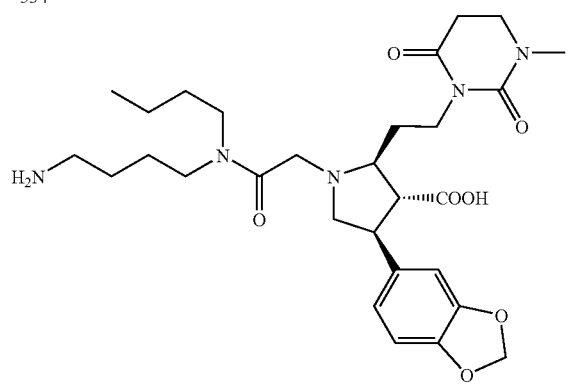
535
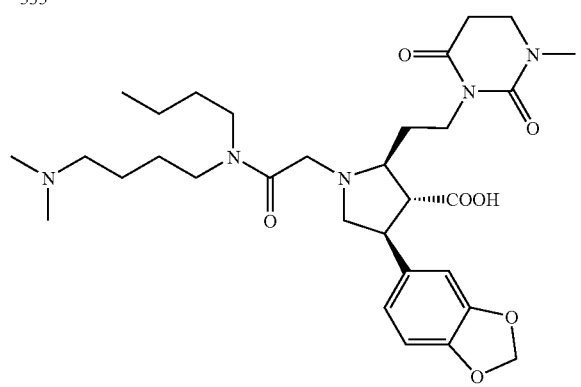
TABLE 3C-continued
536
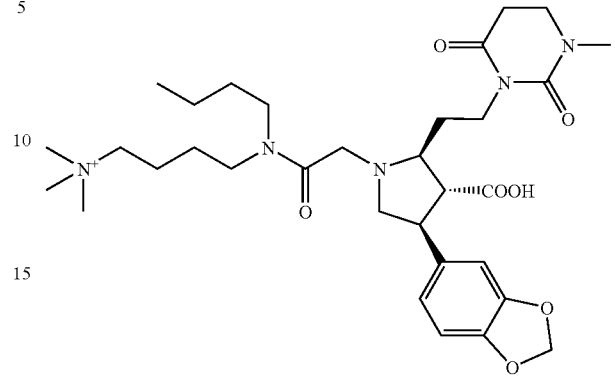
537
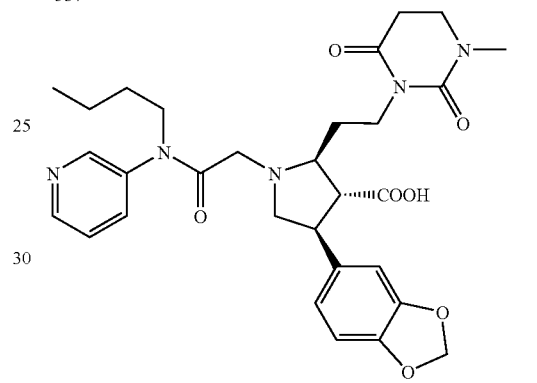
538
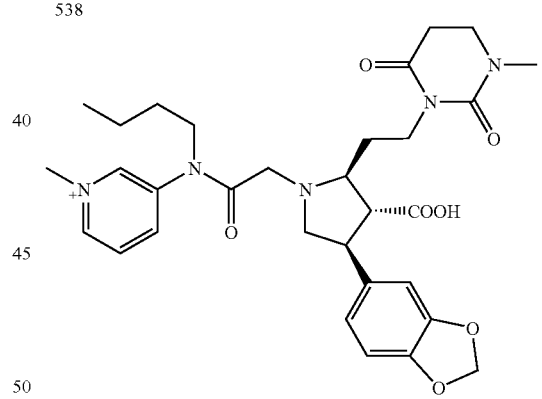
539
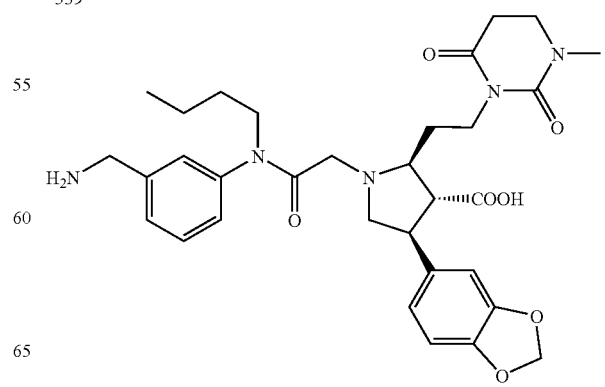

TABLE 3C-continued
540
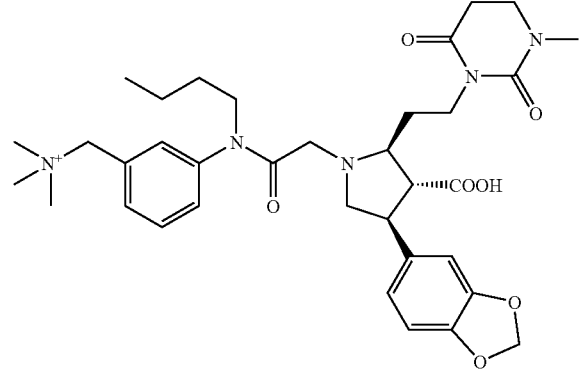
541
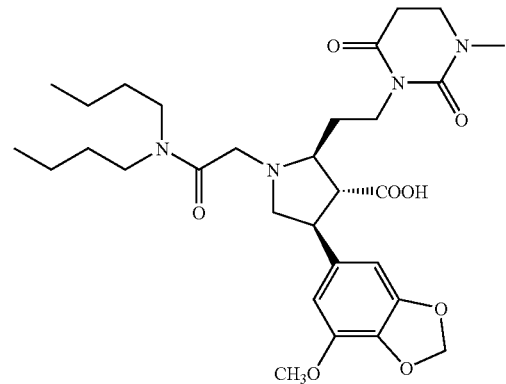
542
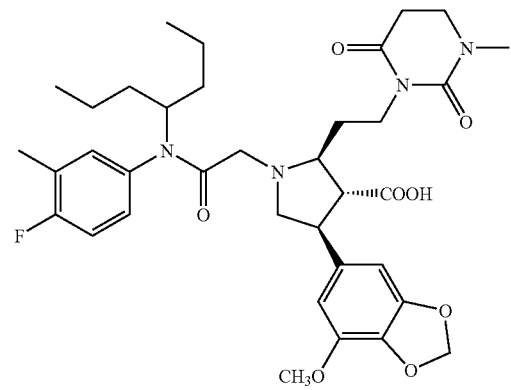
543
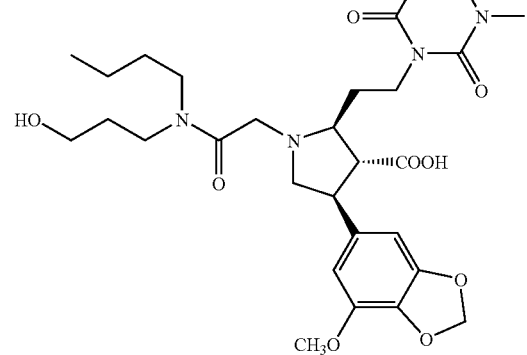
TABLE 3C-continued
544
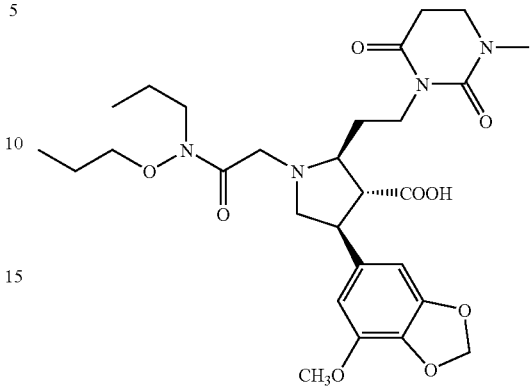
545
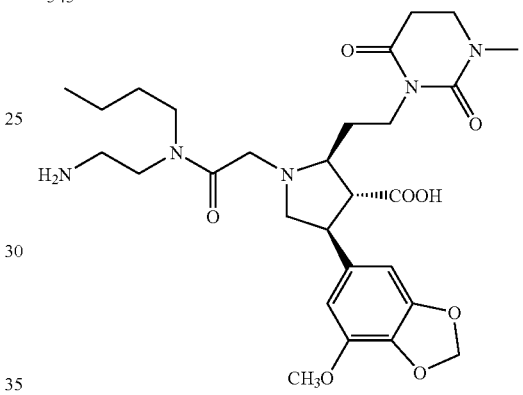
546
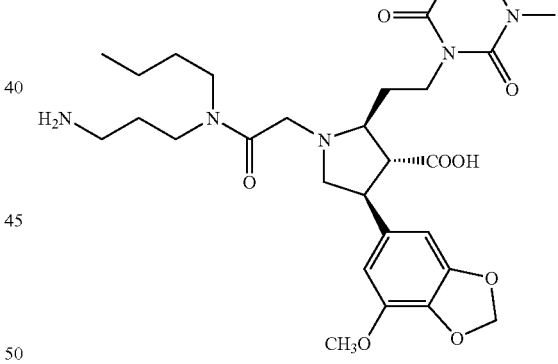
547
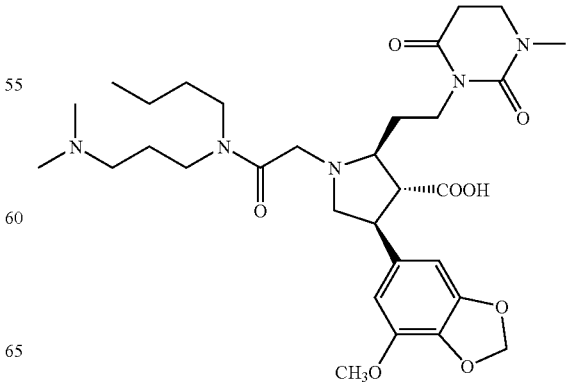

TABLE 3C-continued | TABLE 3C-continued
548
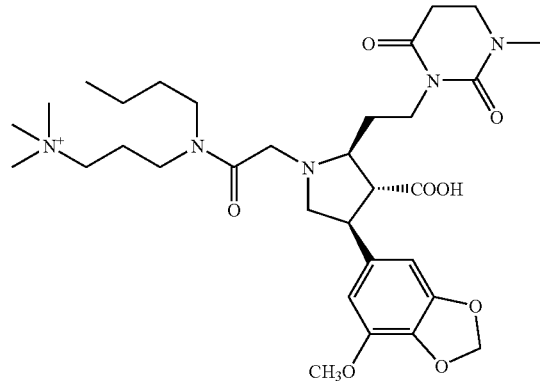
552
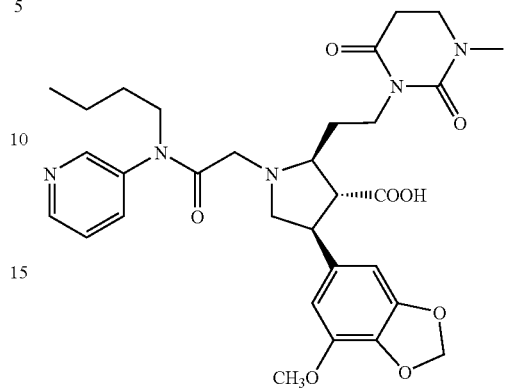
549
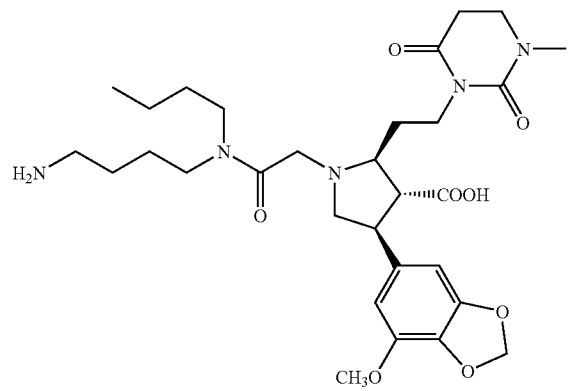
553
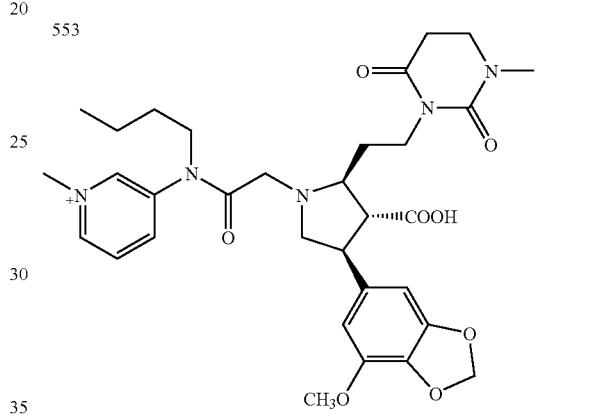
550
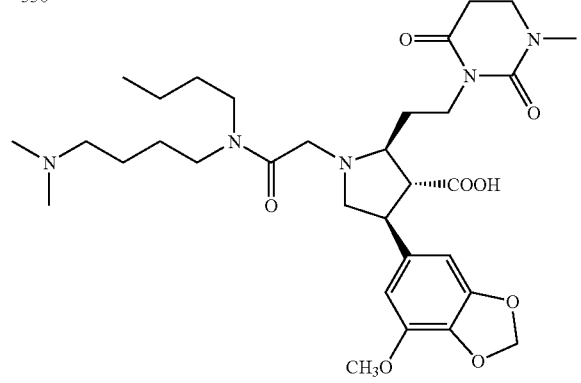
554
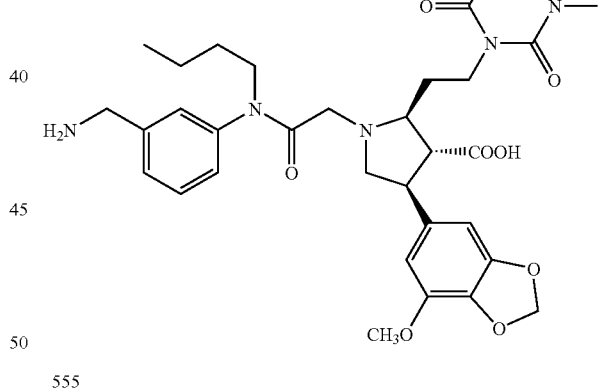
551
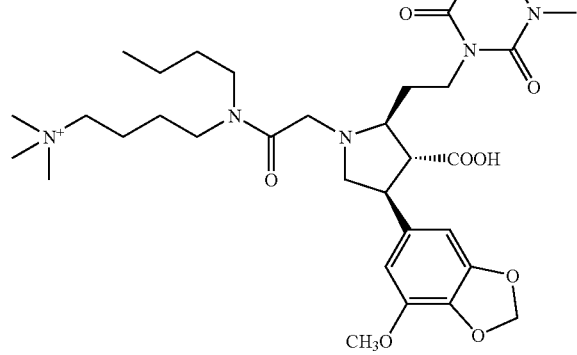
555
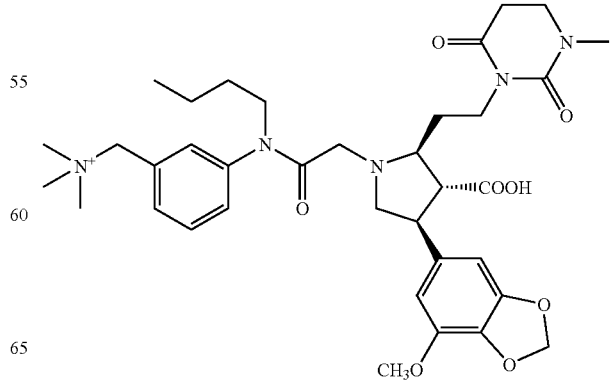

TABLE 3C-continued
556
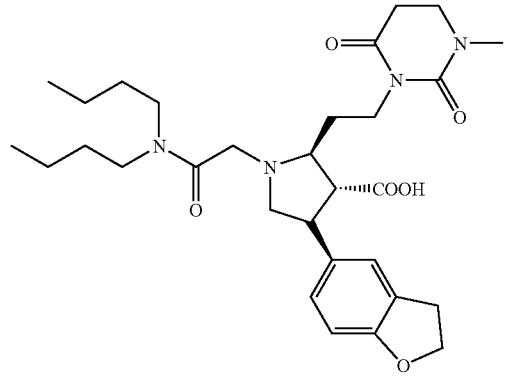
557
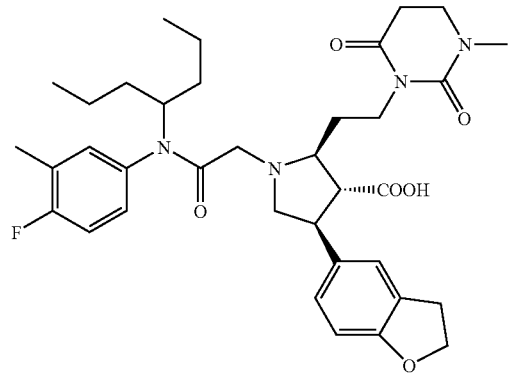
558
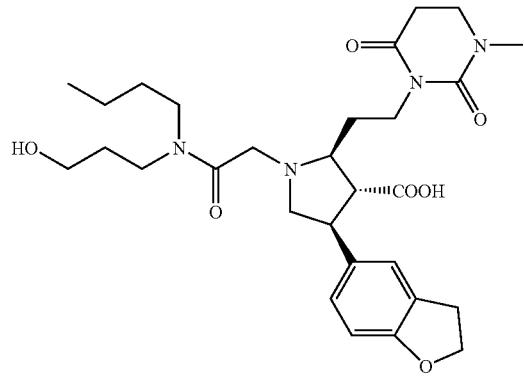
559
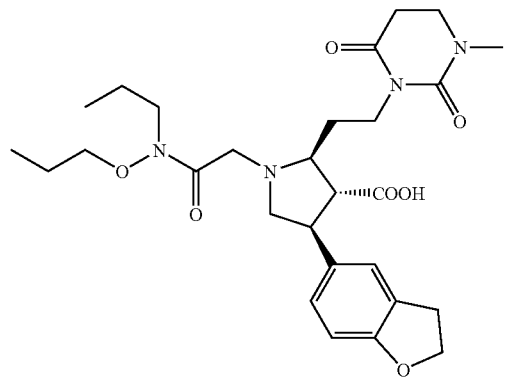
TABLE 3C-continued
560
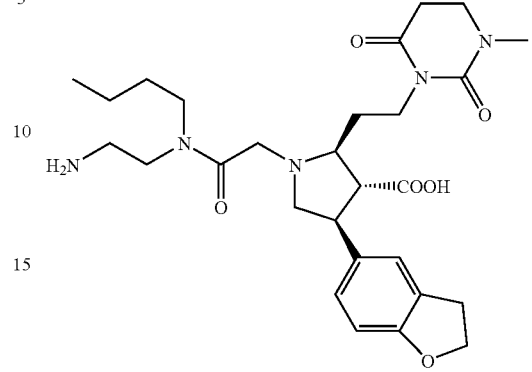
561
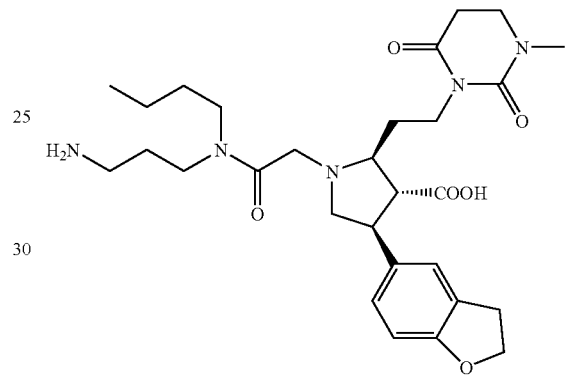
562
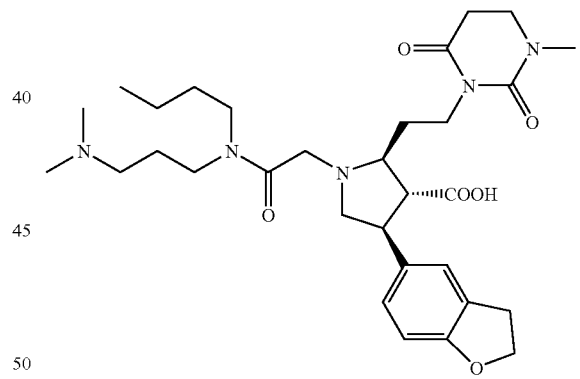
563
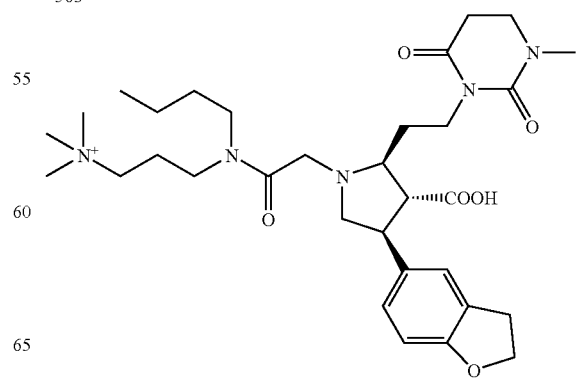

TABLE 3C-continued
564
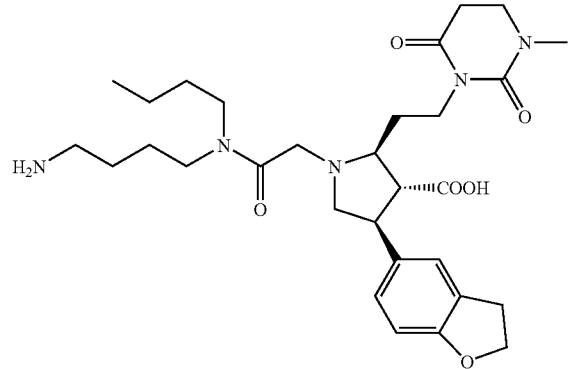
565
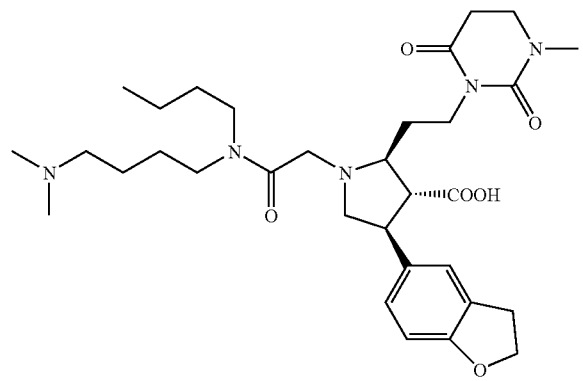
566
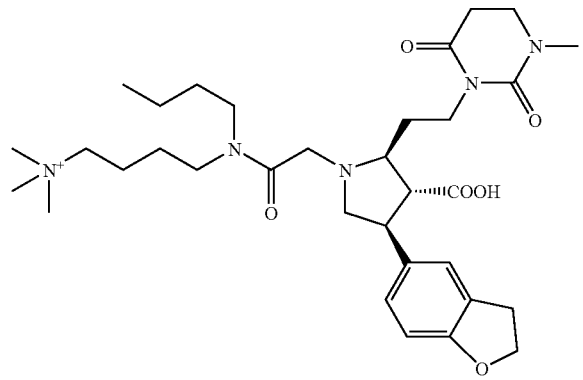
567
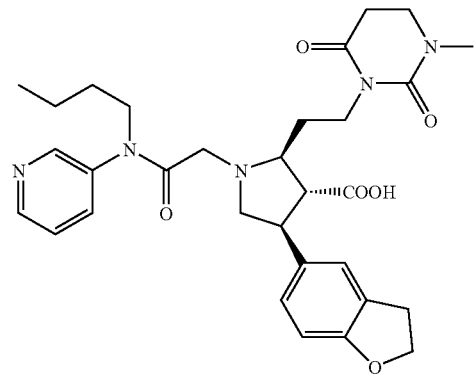
TABLE 3C-continued
568
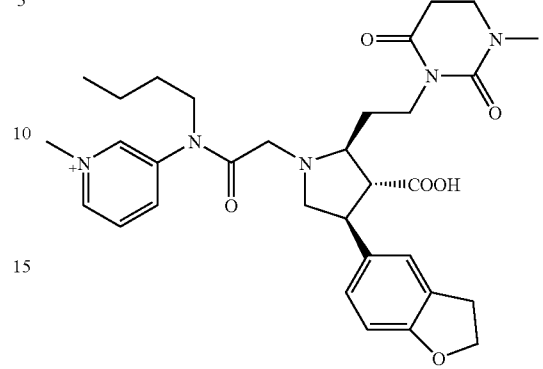
569
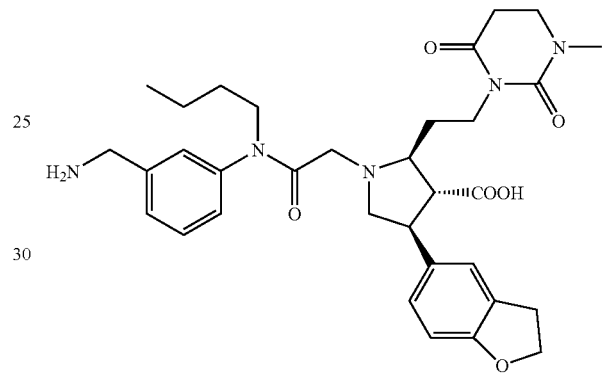
570
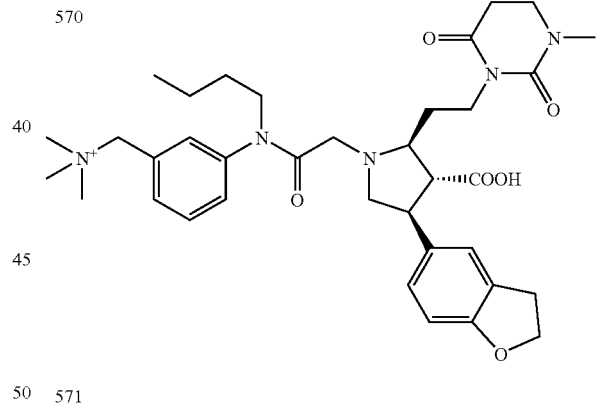
571
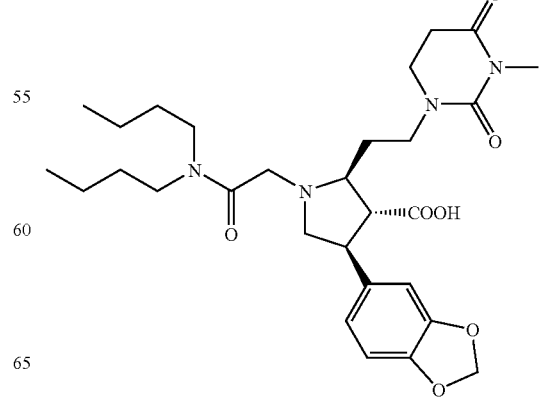

TABLE 3C-continued
572
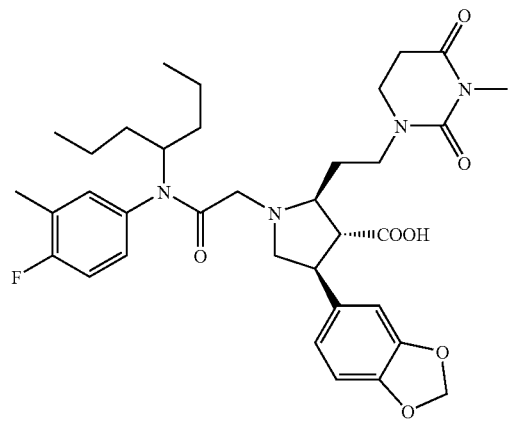
573
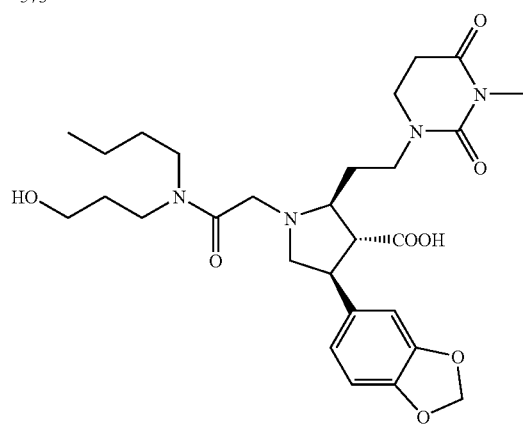
574
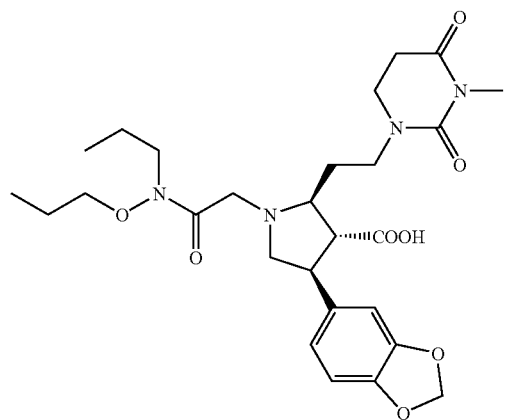
575
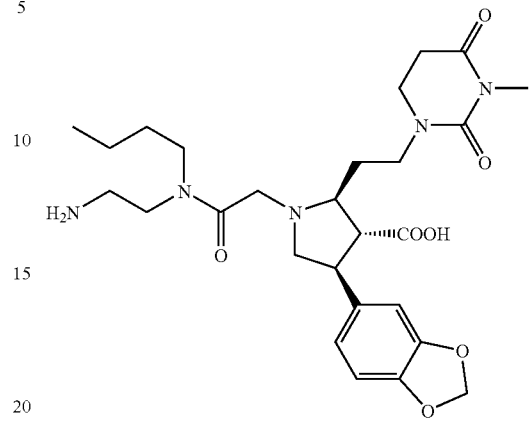
576
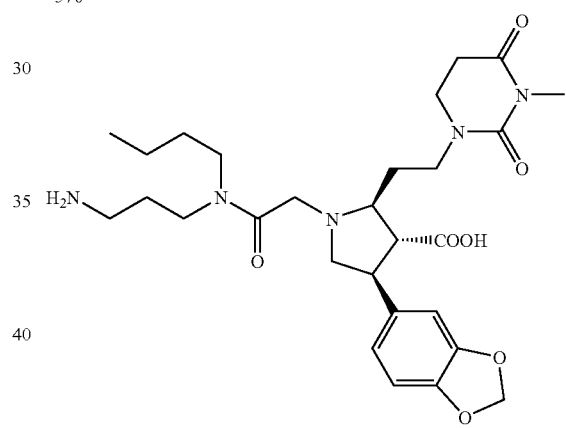
577
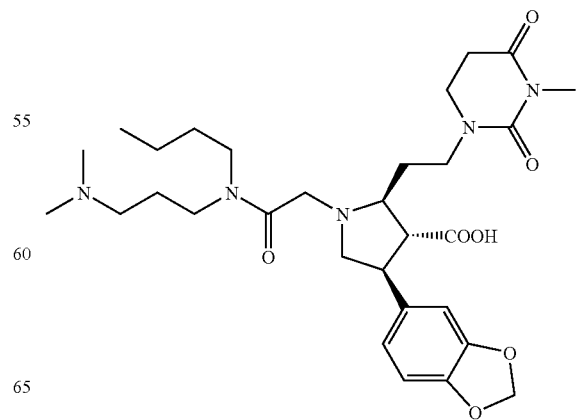

797
TABLE 3C-continued
578
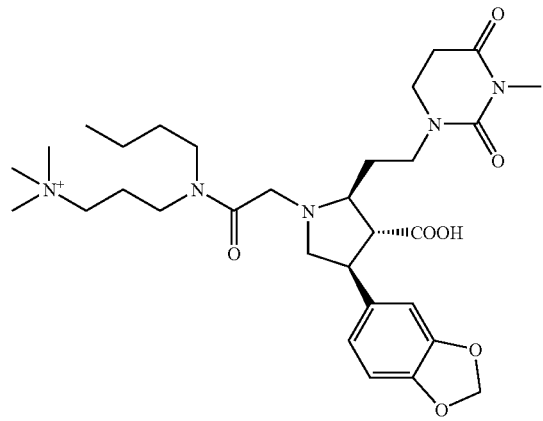
579
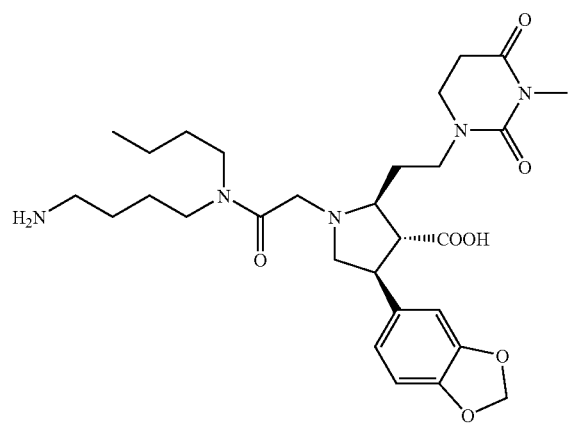
580
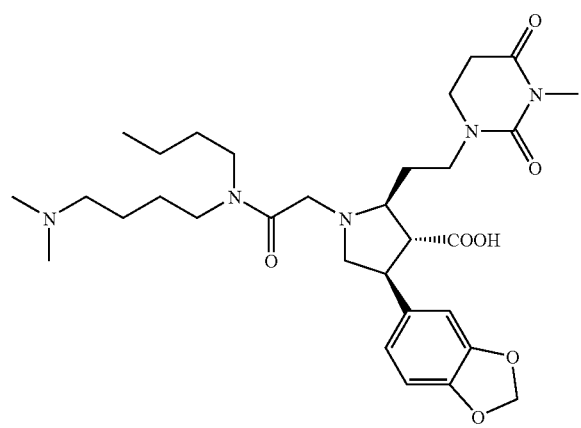
798
TABLE 3C-continued
581
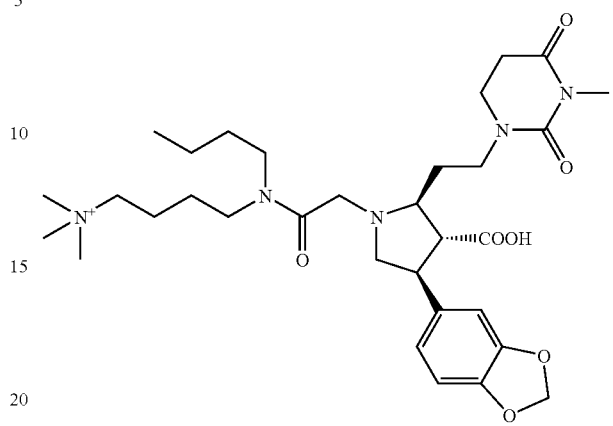
582
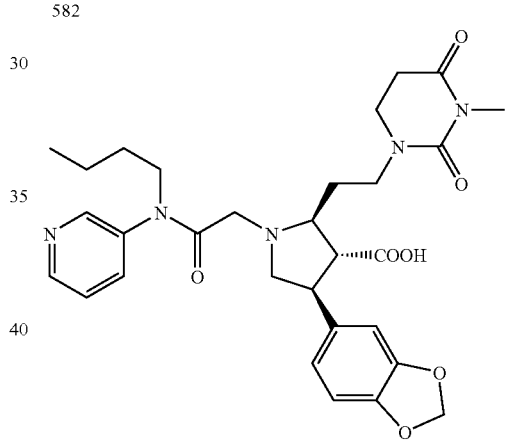
583
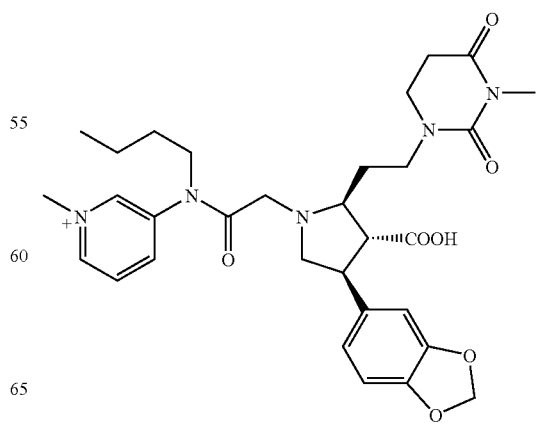

TABLE 3C-continued
584
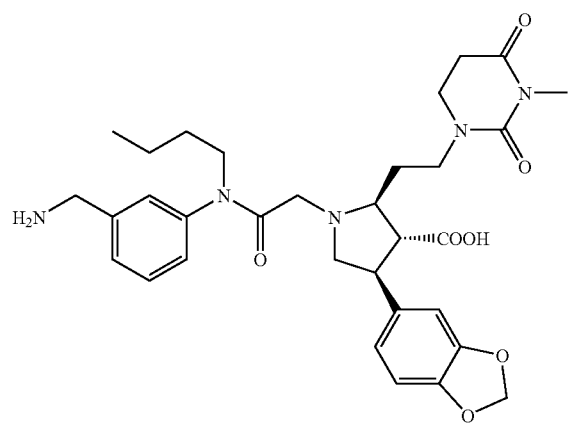
585
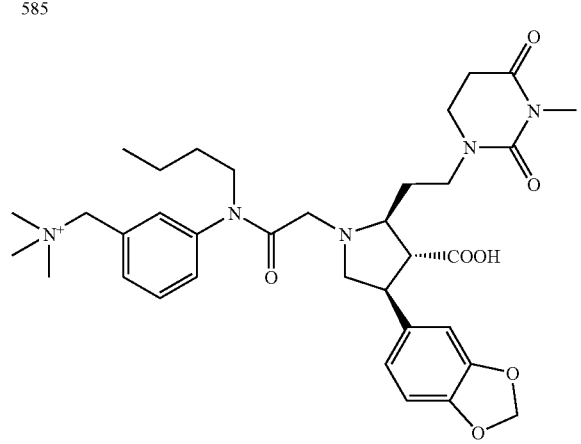
586
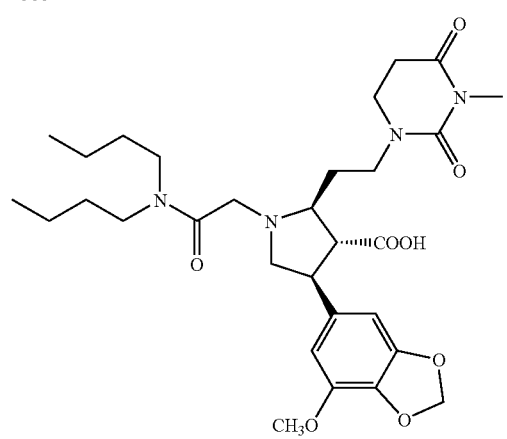
TABLE 3C-continued
587
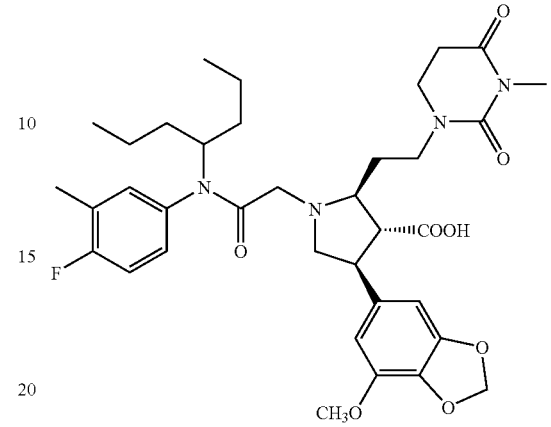
588
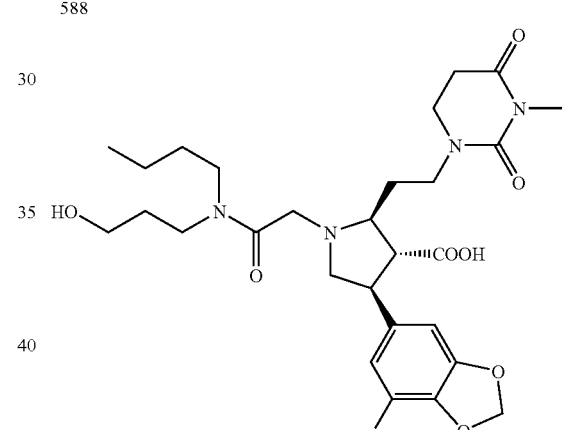
589
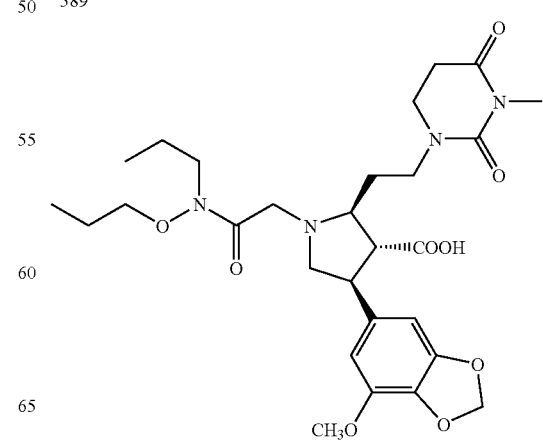

TABLE 3C-continued
590
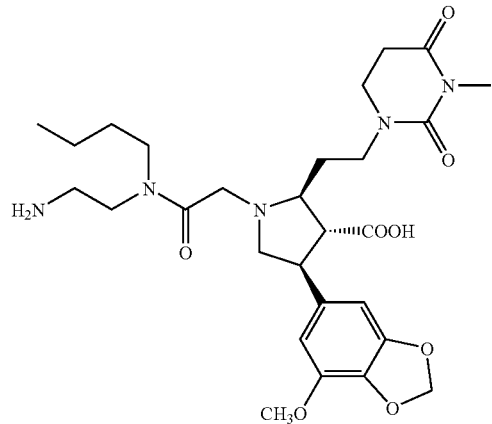
591
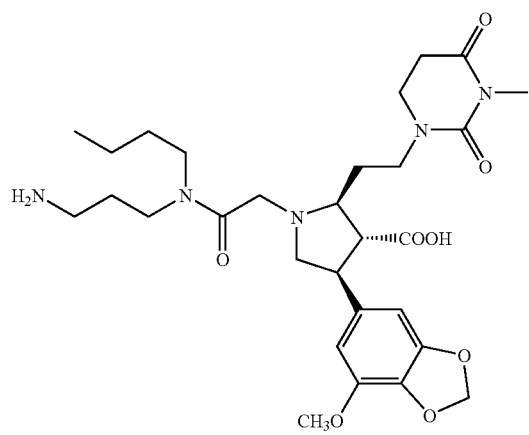
592
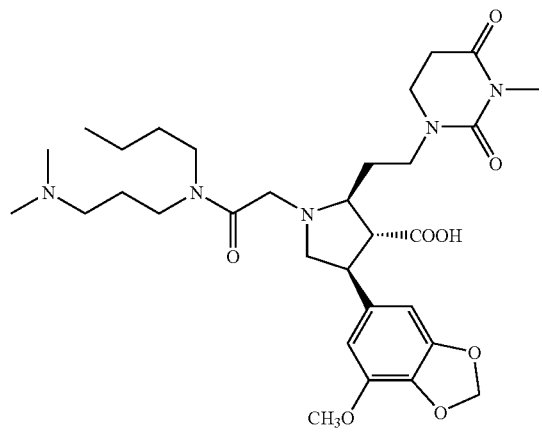
593
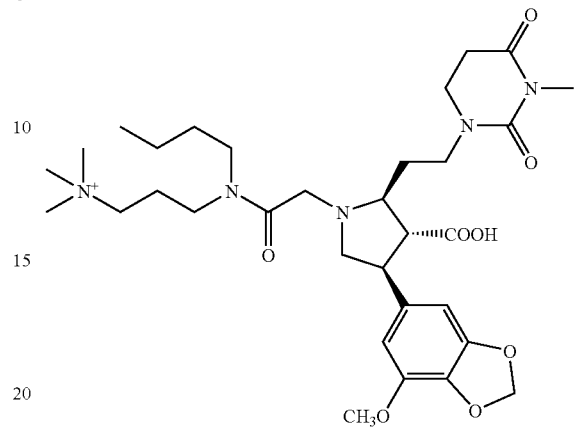
594
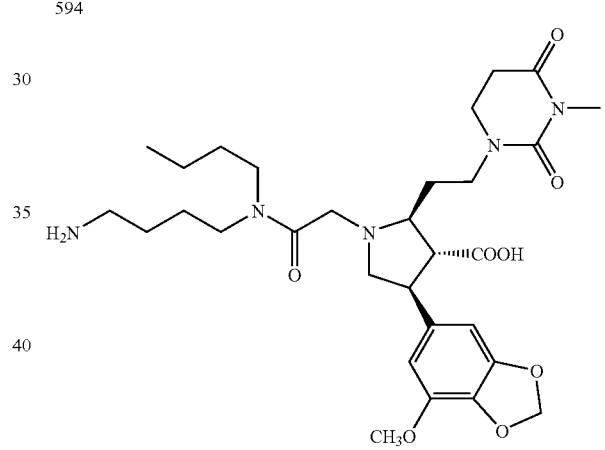
595
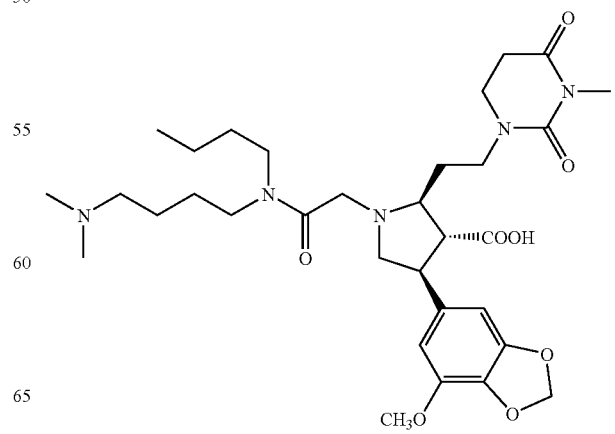

TABLE 3C-continued
596
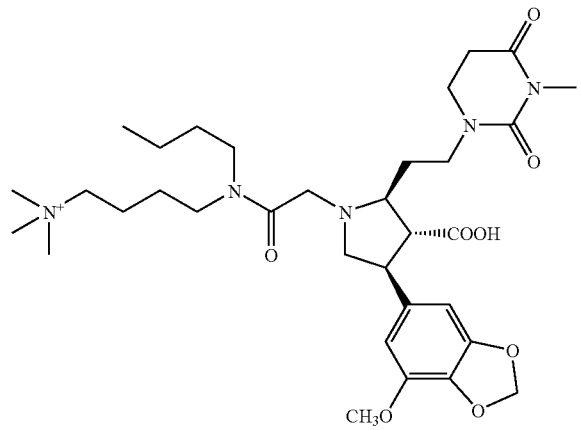
597
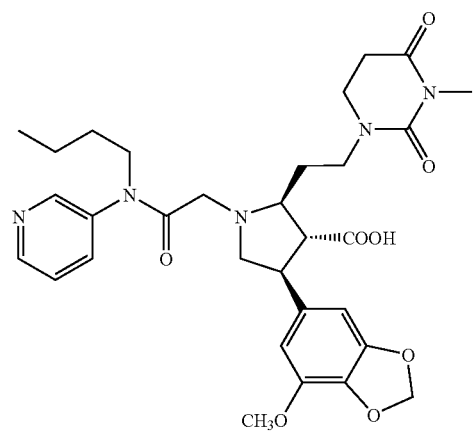
598
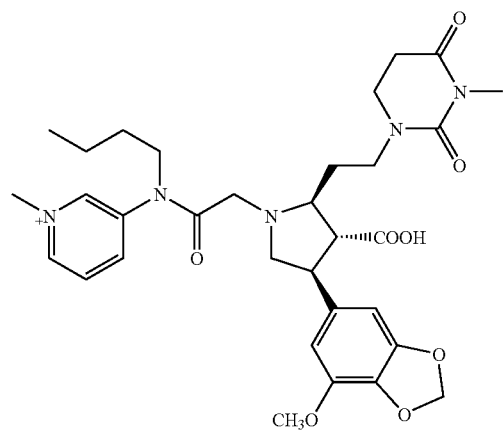
TABLE 3C-continued
599
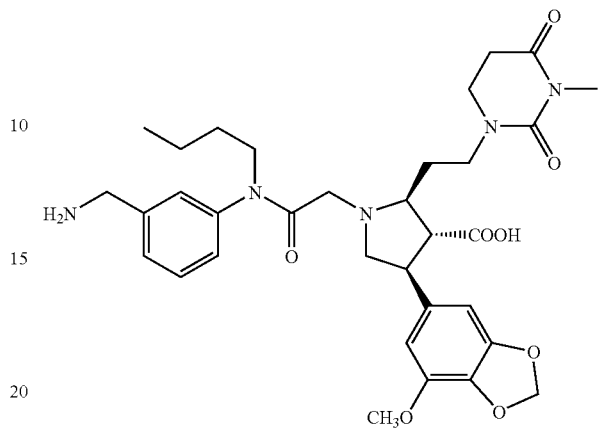
600
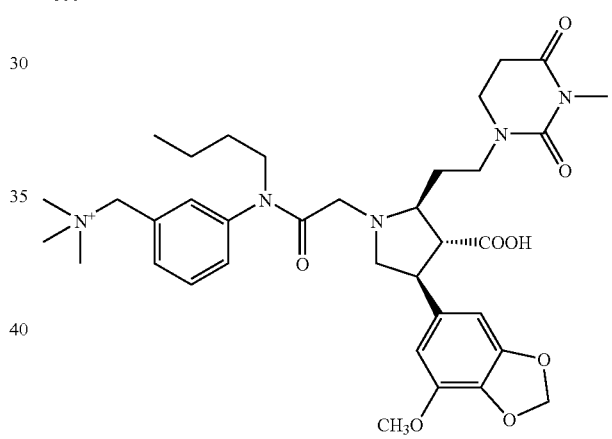
601
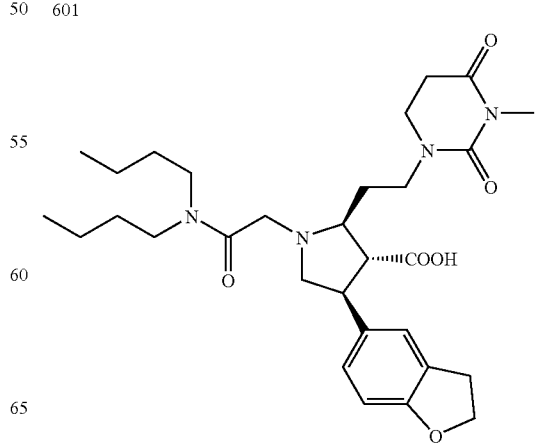

| 805 | 806 |
|---|---|
| TABLE 3C-continued | TABLE 3C-continued |
| 602 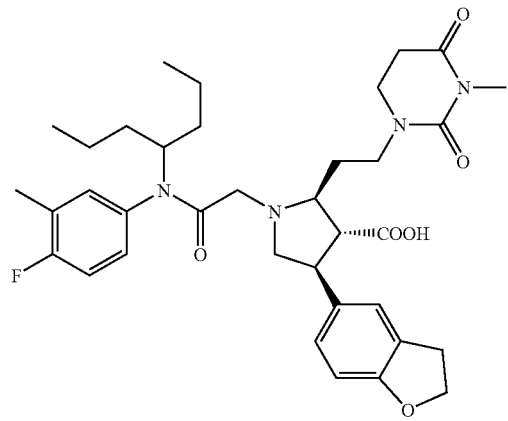 | 605 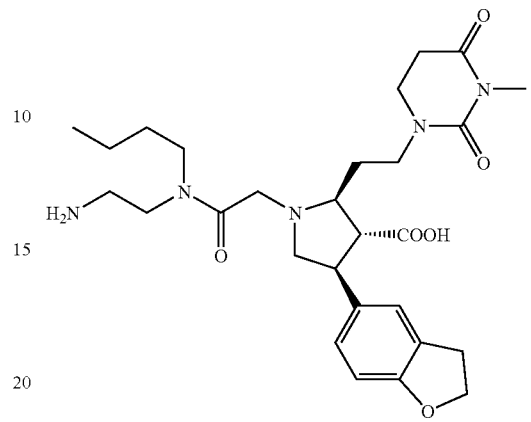 |
| 603 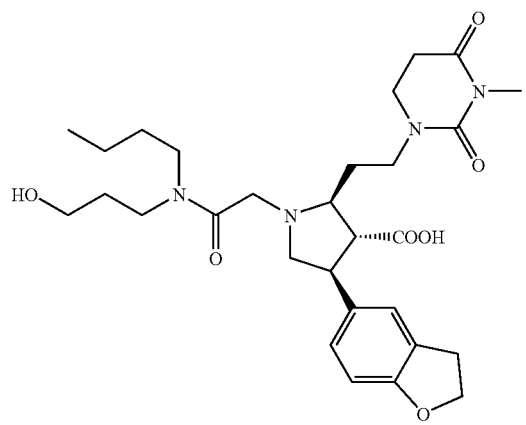 | 606 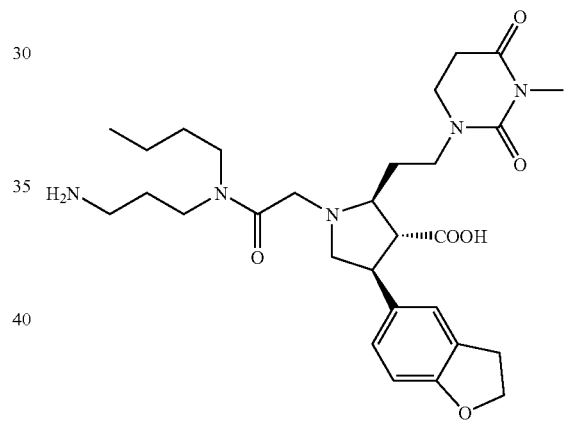 |
| 604 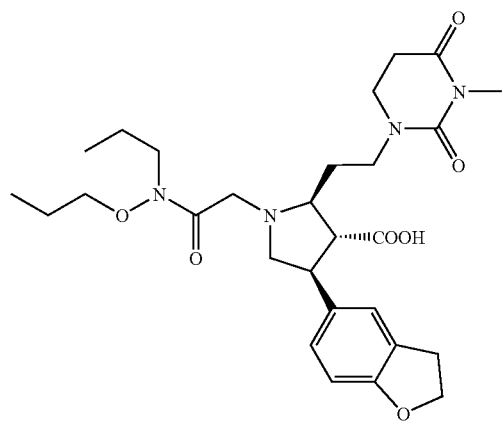 | 607 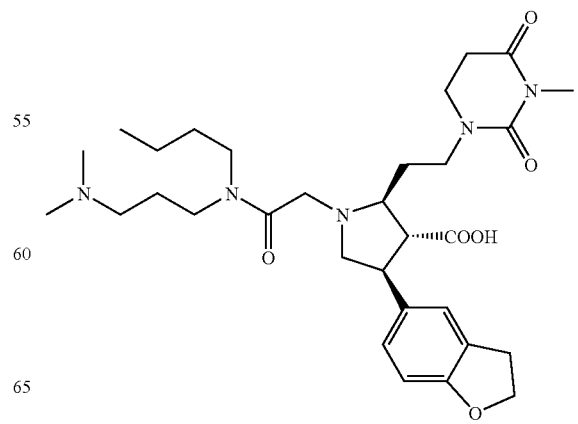 |

TABLE 3C-continued
608
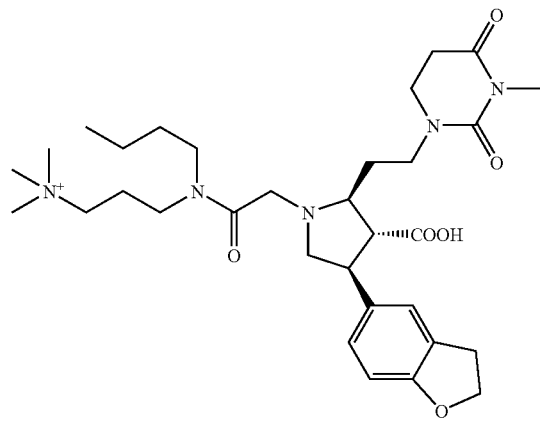
609
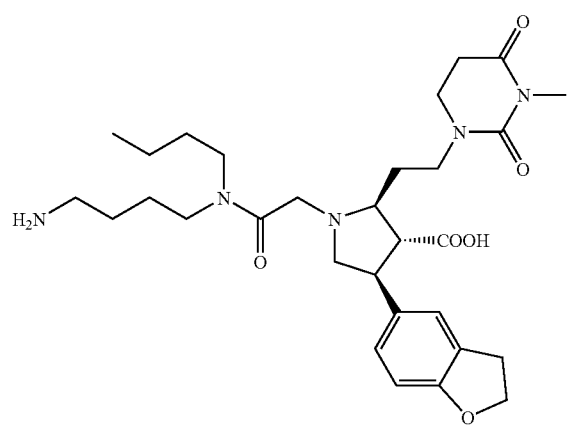
610
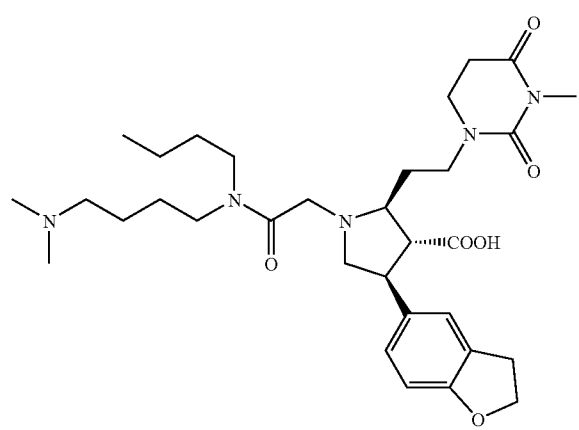
TABLE 3C-continued
611
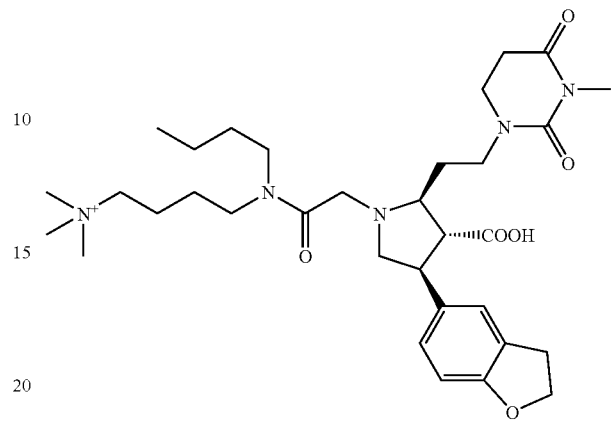
612
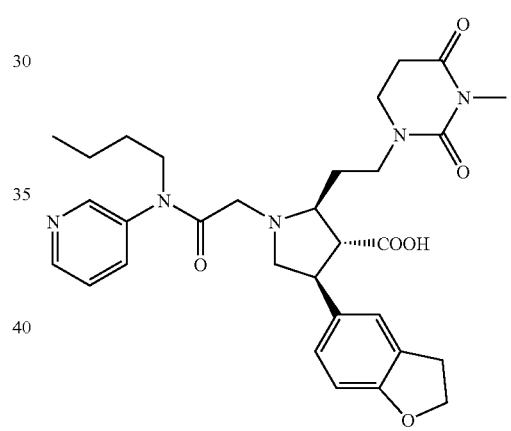
613
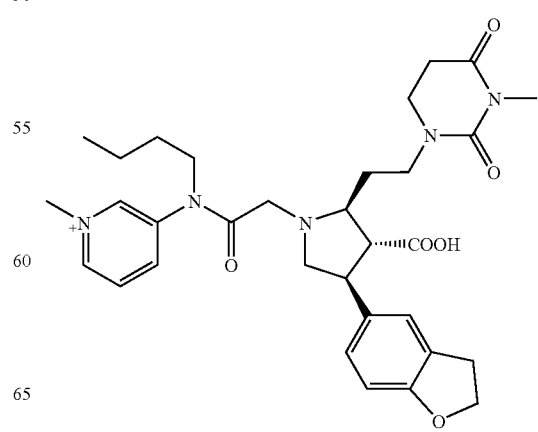

TABLE 3C-continued
614
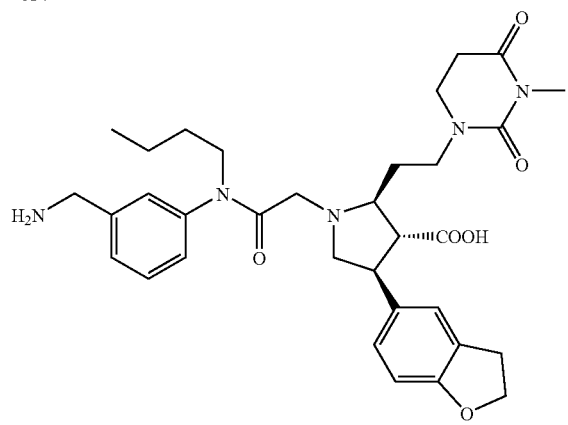
615
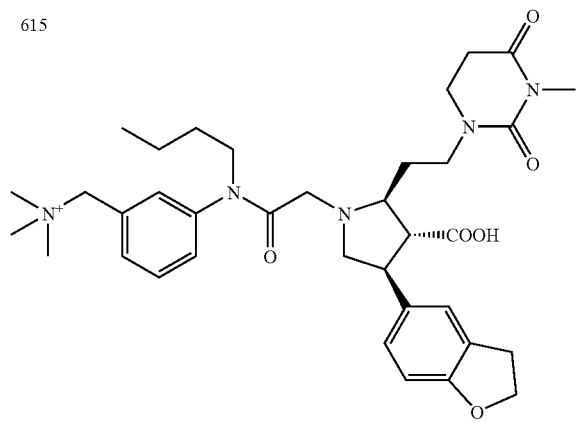
616
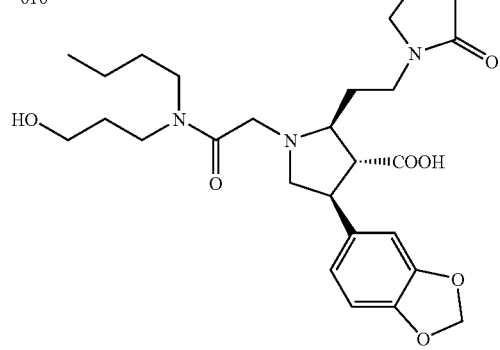
617
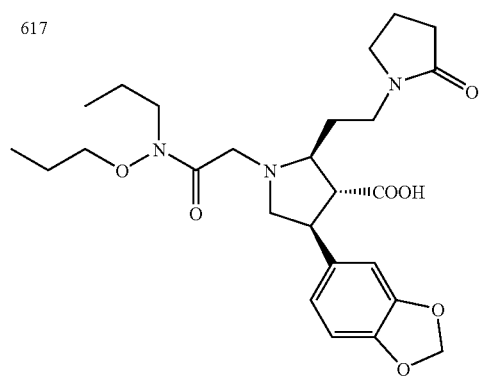
TABLE 3C-continued
618
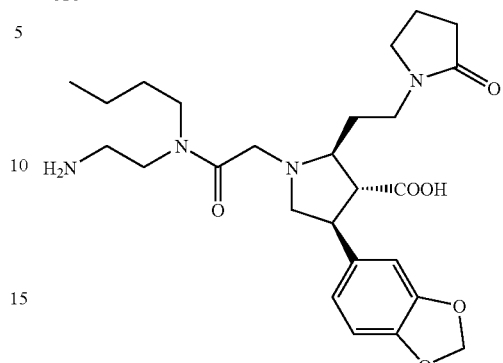
619
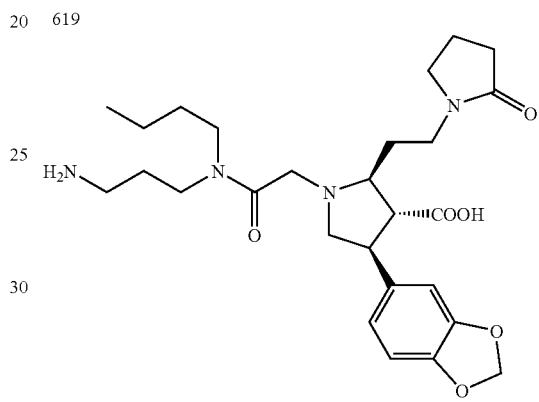
620
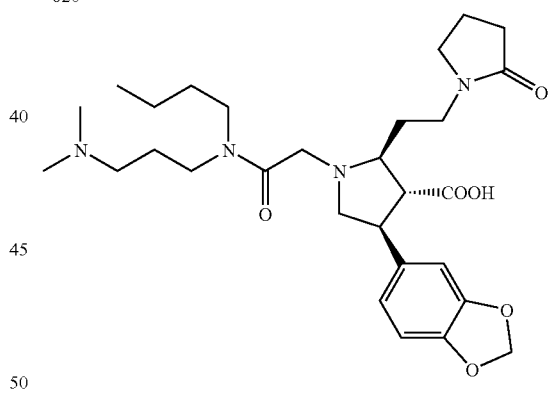
621
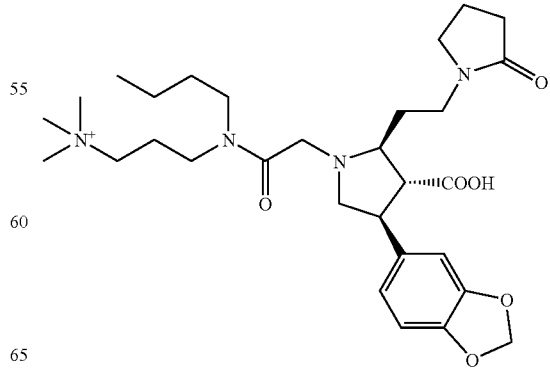

TABLE 3C-continued
622
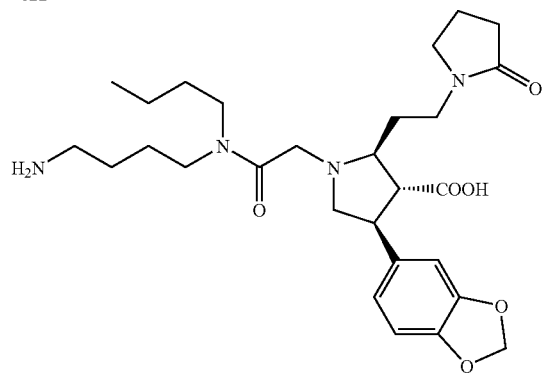
623
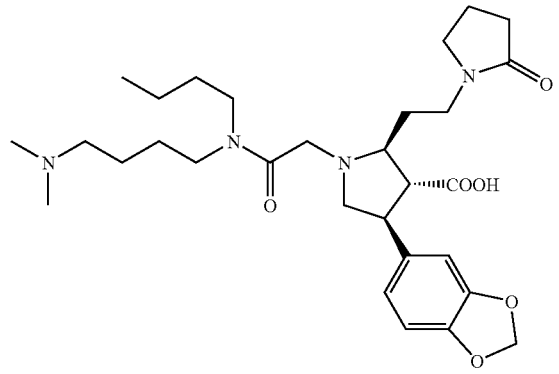
624
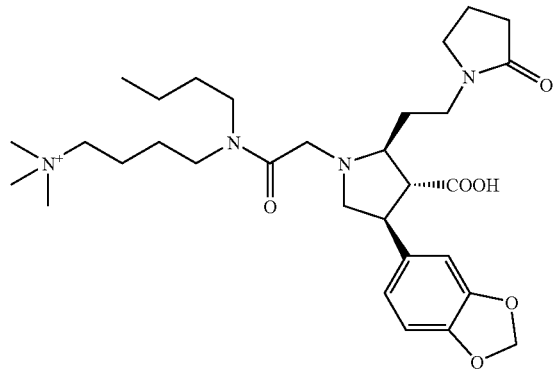
625
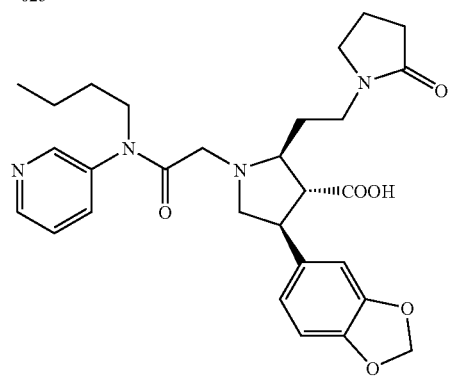
TABLE 3C-continued
626
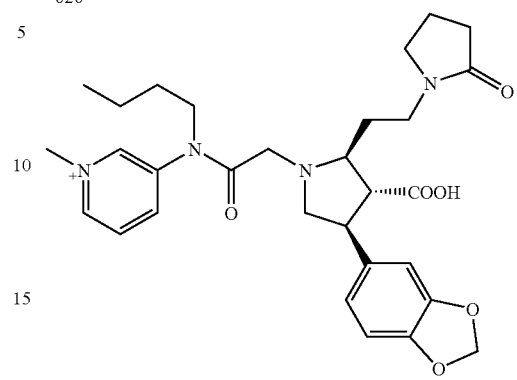
627
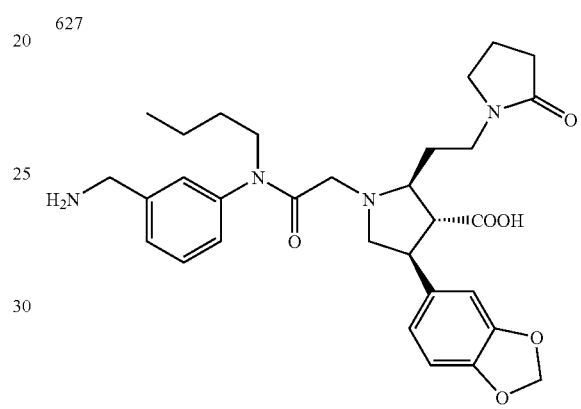
628
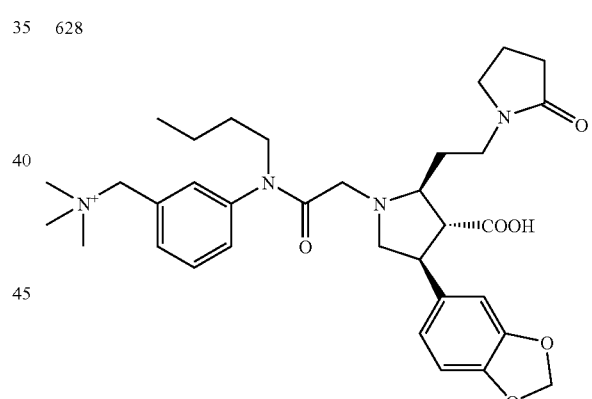
629
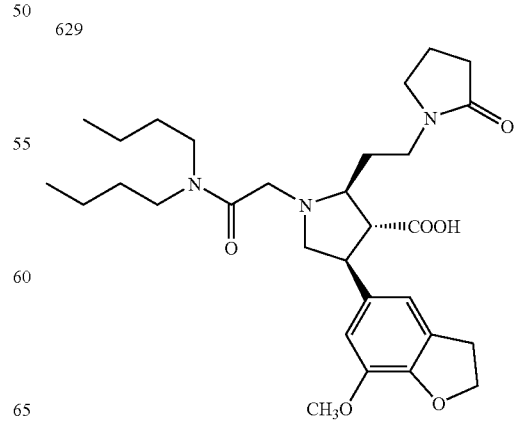

| 813 | 814 |
|---|---|
| TABLE 3C-continued | TABLE 3C-continued |
| 630 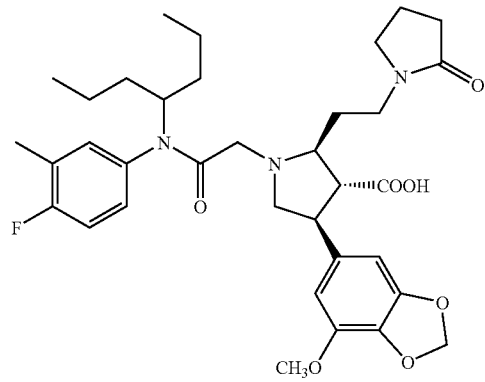 | 634 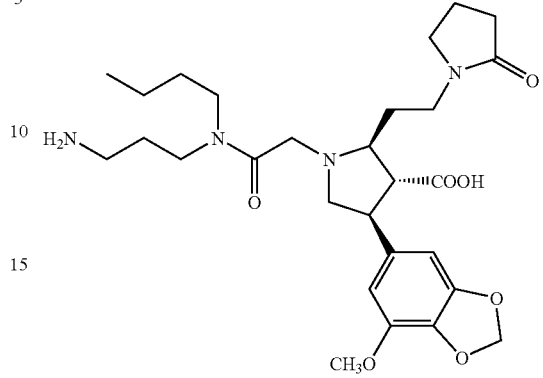 |
| 631 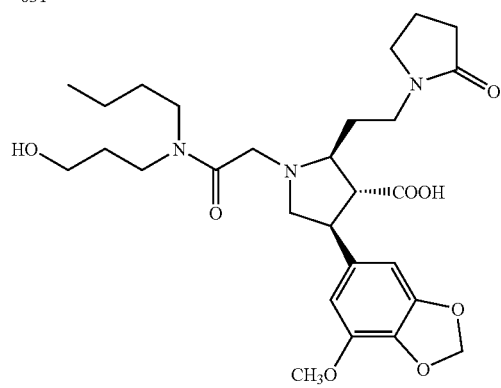 | 635 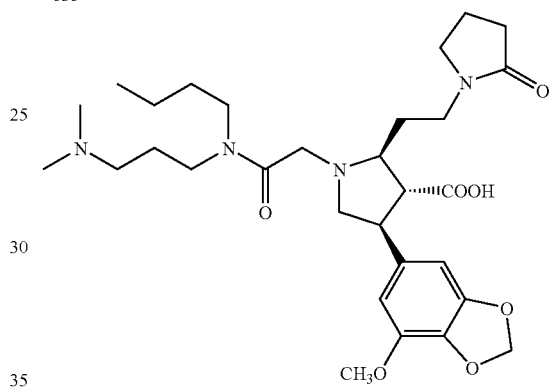 |
| 632 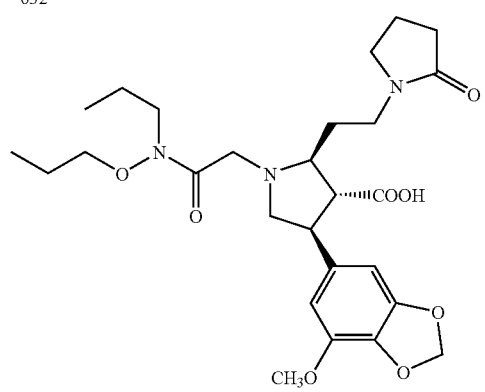 | 636 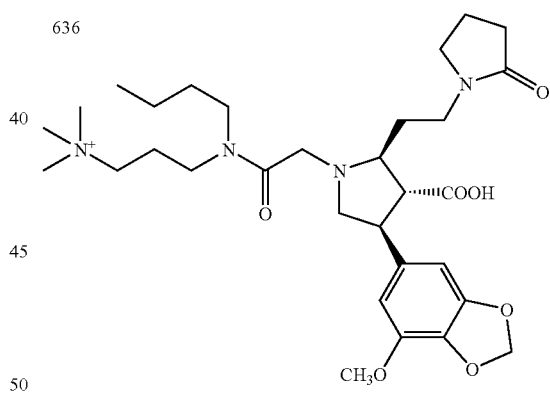 |
| 633 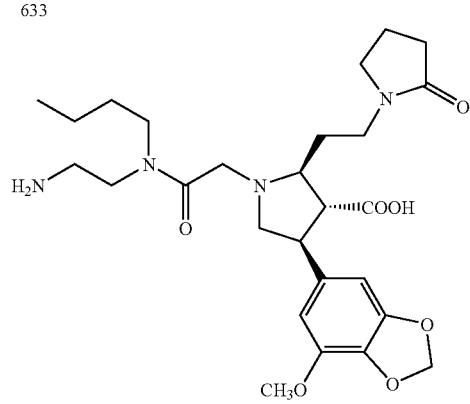 | 637 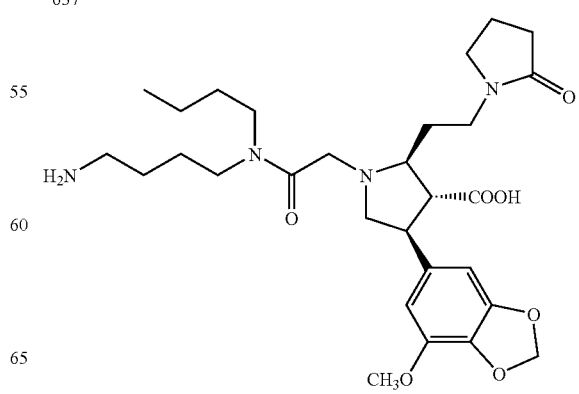 |

TABLE 3C-continued
638
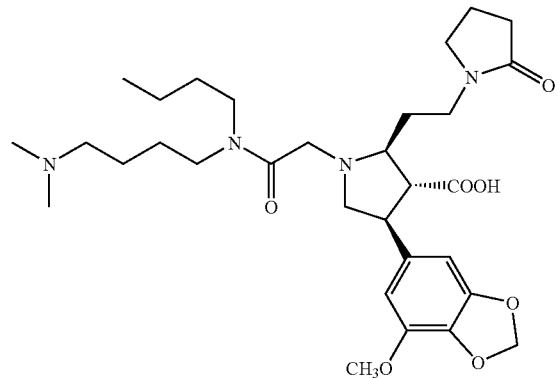
639
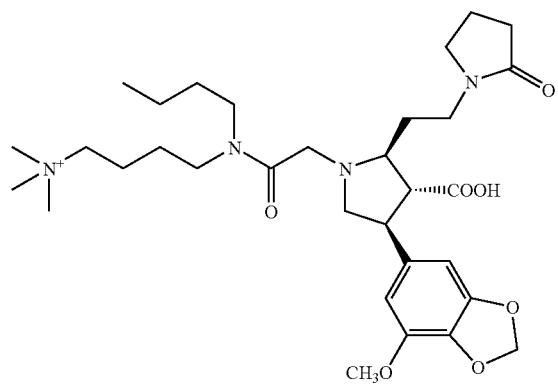
640
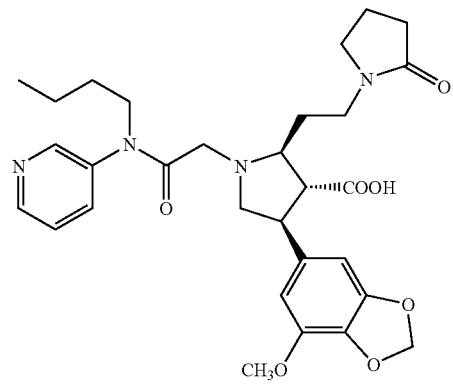
641
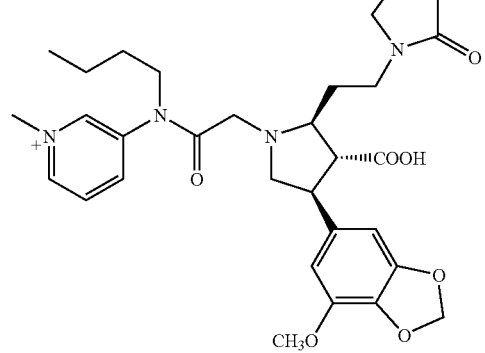
TABLE 3C-continued
642
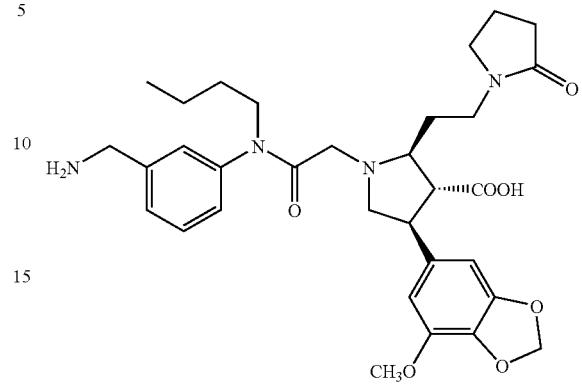
643
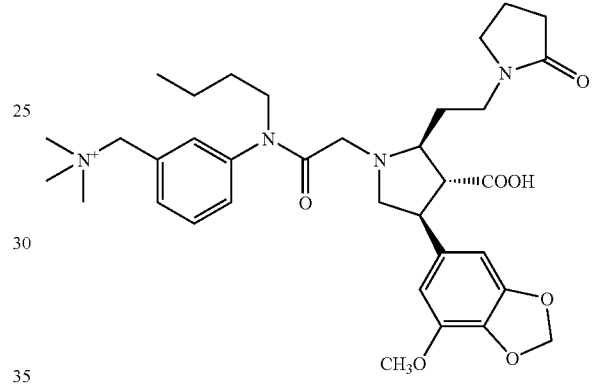
644
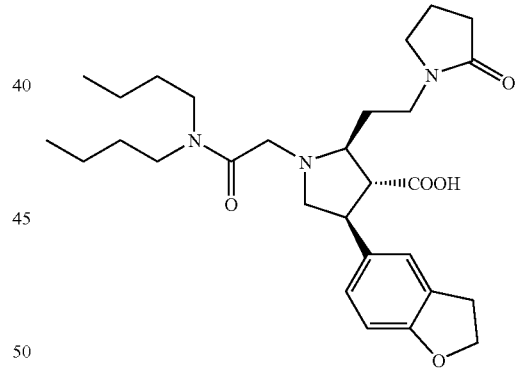
645
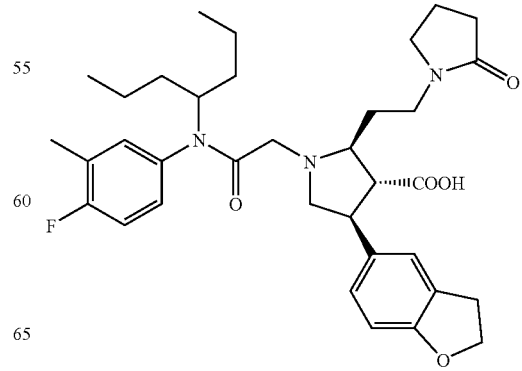

TABLE 3C-continued
646
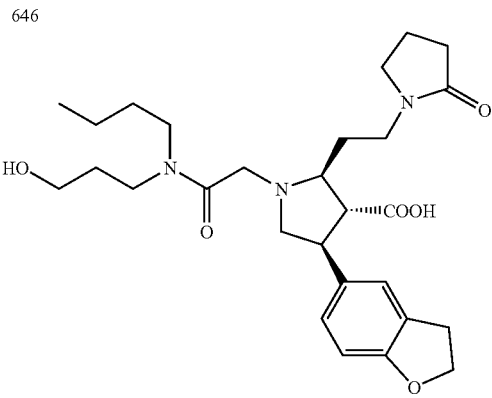
647
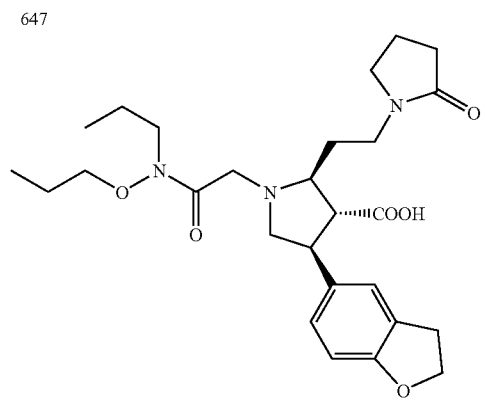
648
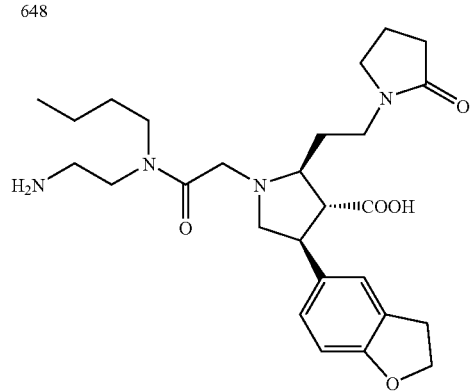
649
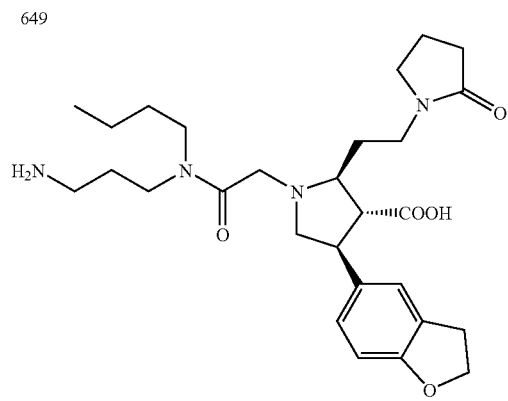
TABLE 3C-continued
650
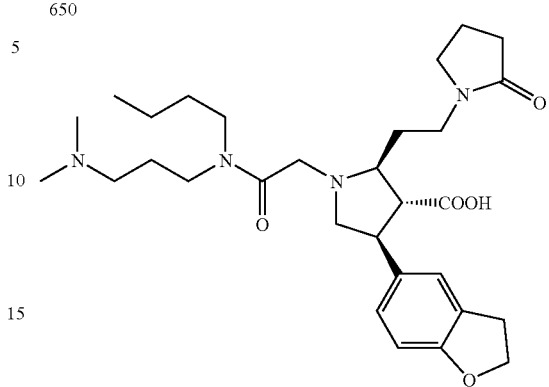
651
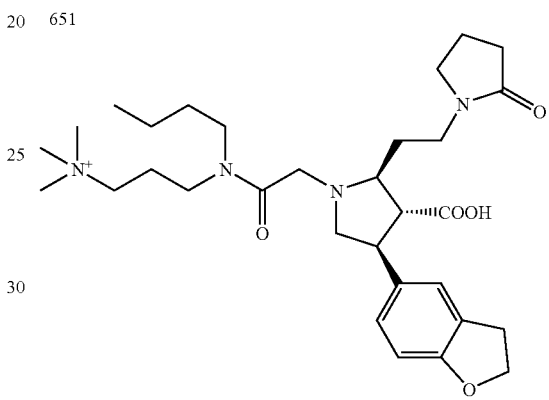
652
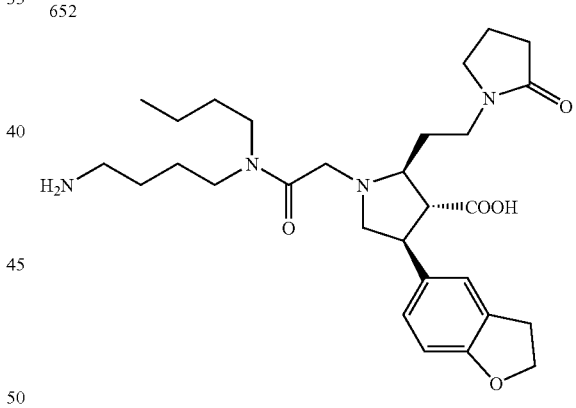
653
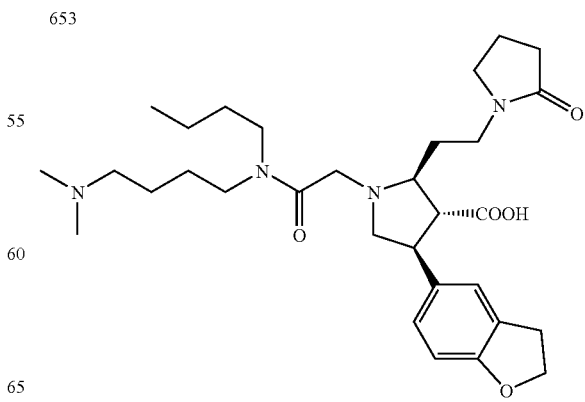

TABLE 3C-continued
654
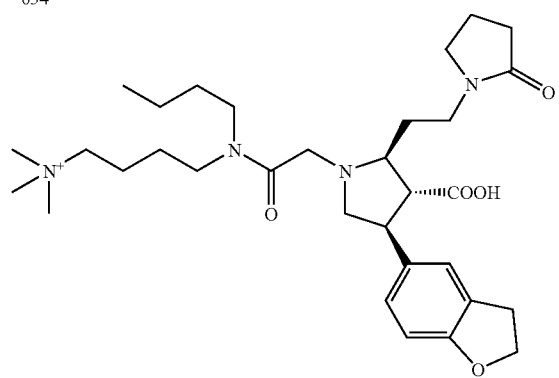
655
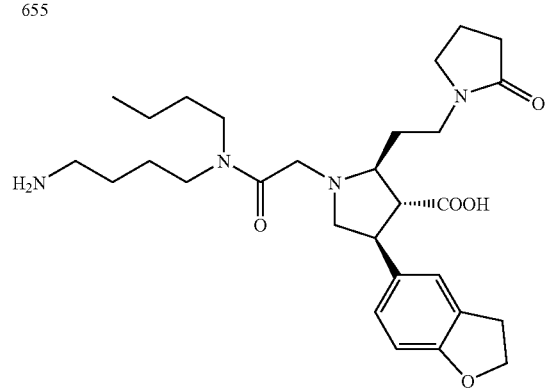
656
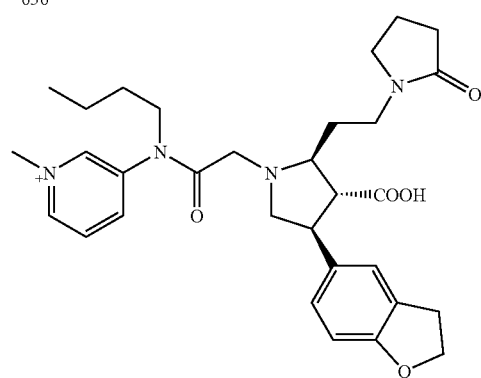
657
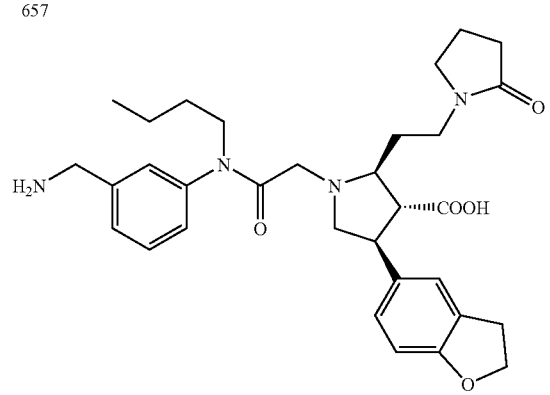
TABLE 3C-continued
658
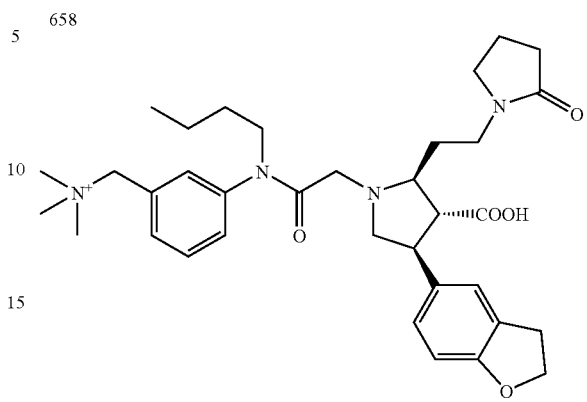
659
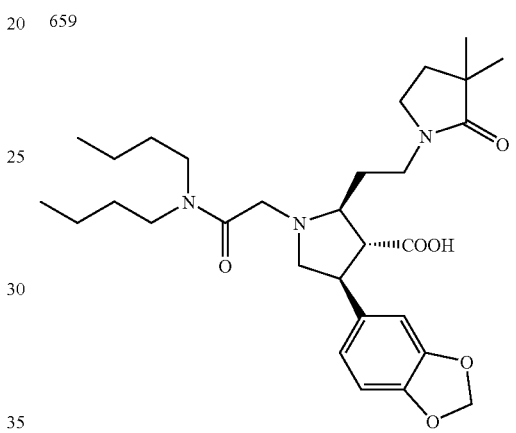
660
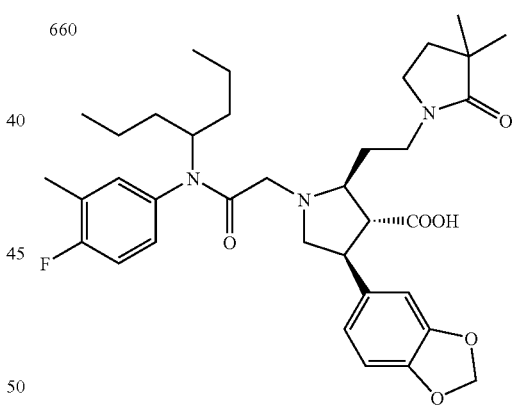
661
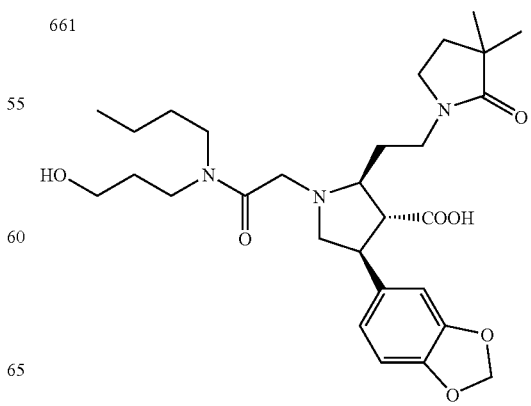

TABLE 3C-continued
662
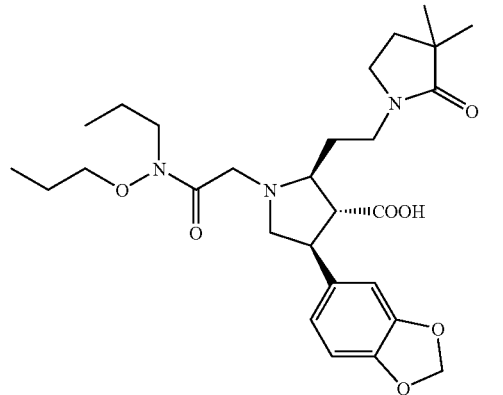
663
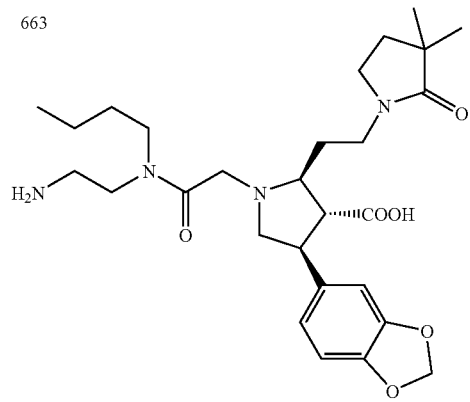
664
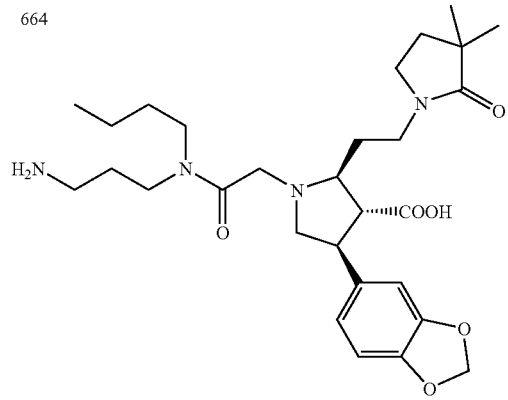
665
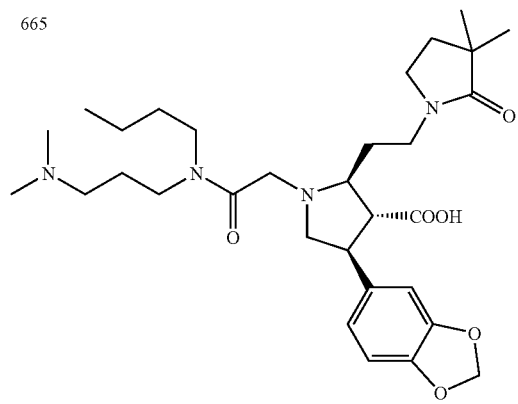
TABLE 3C-continued
666
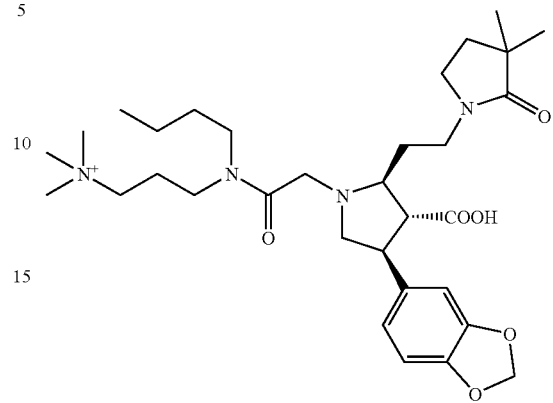
667
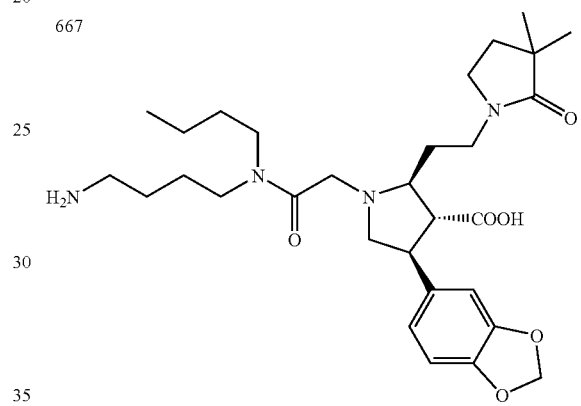
668
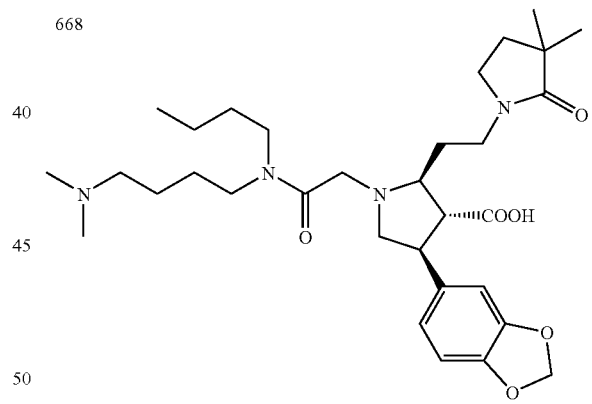
669
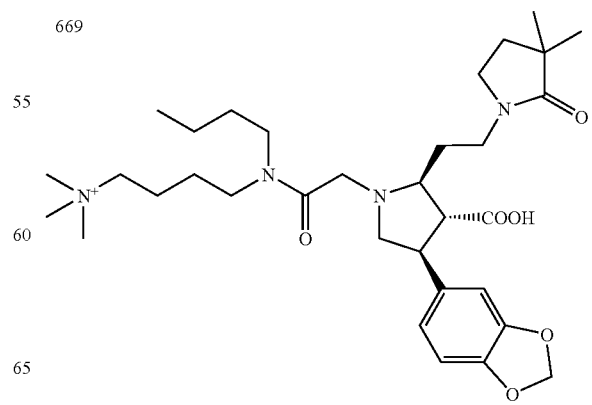

TABLE 3C-continued
670
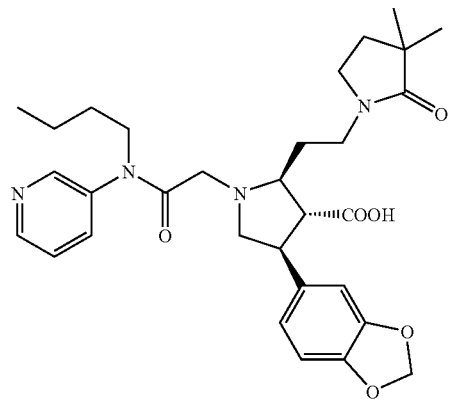
671
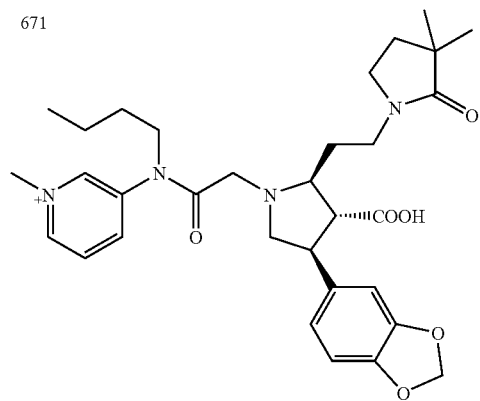
672
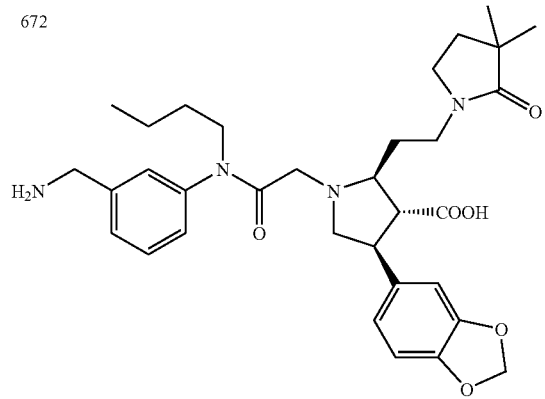
673
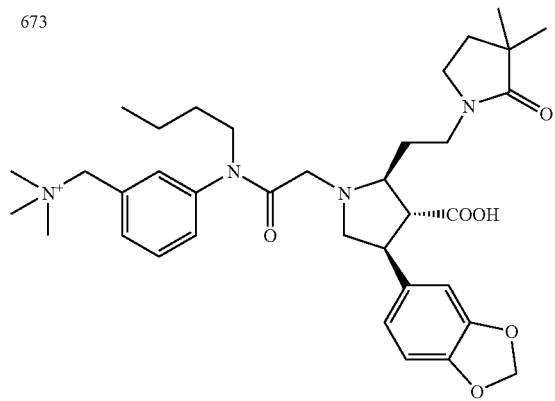
TABLE 3C-continued
674
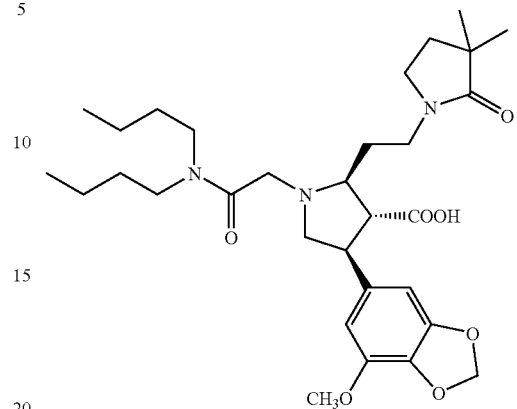
675
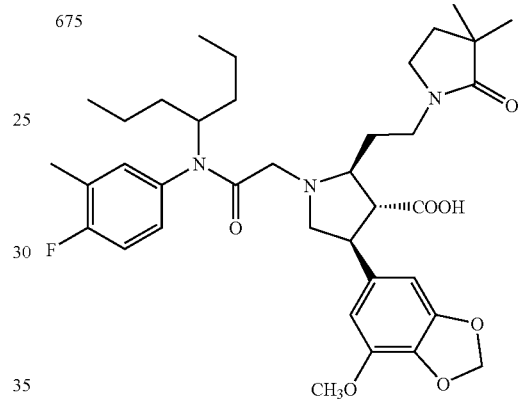
676
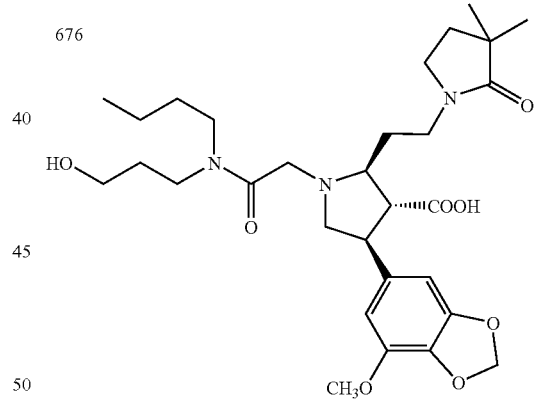
677
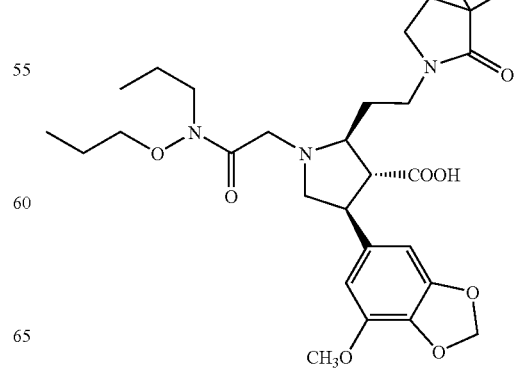

| 825 | 826 |
|---|---|
| TABLE 3C-continued | TABLE 3C-continued |
| 678 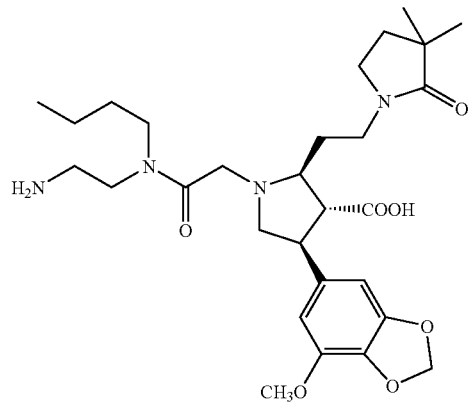 | 681 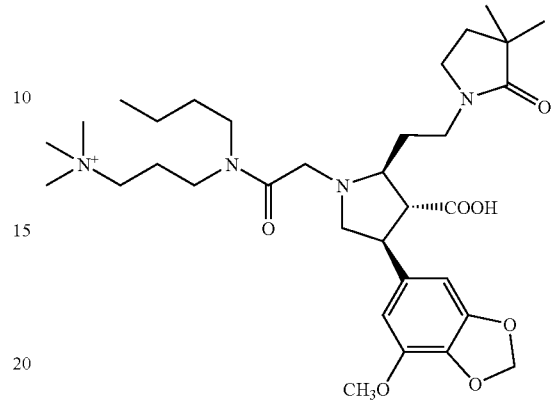 |
| 679 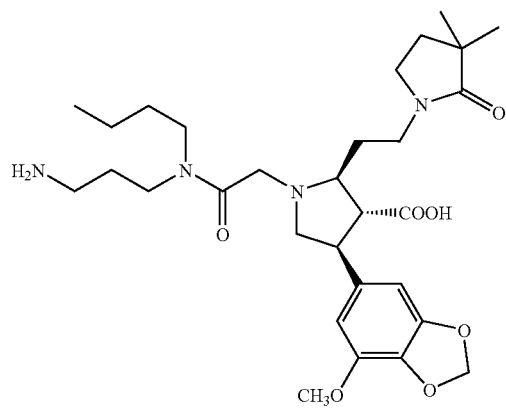 | 682 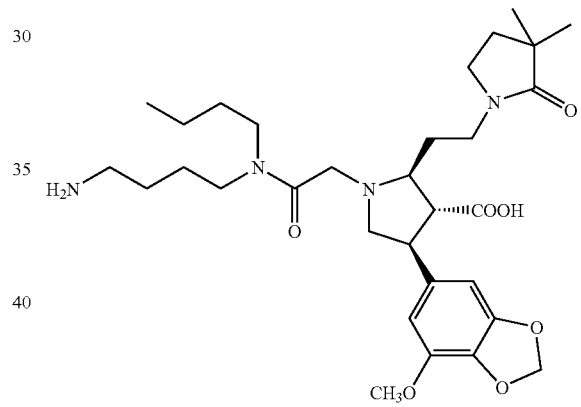 |
| 680 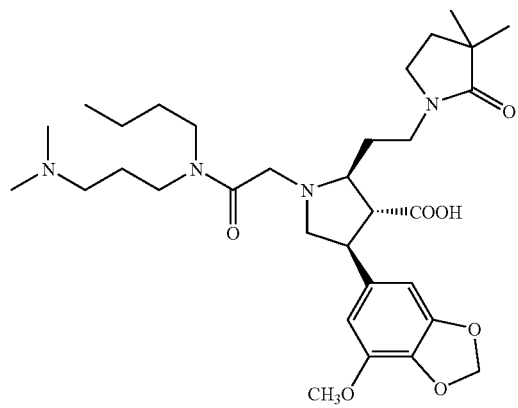 | 683 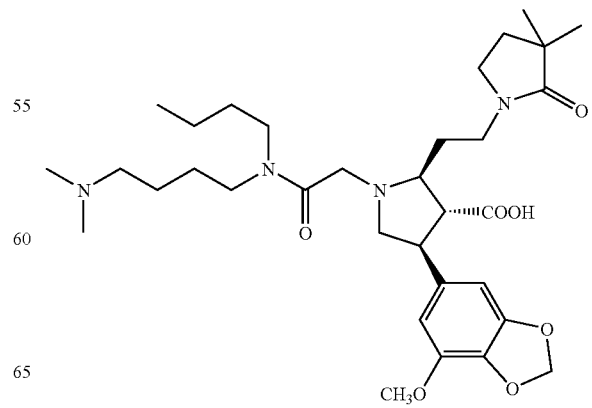 |

TABLE 3C-continued
684
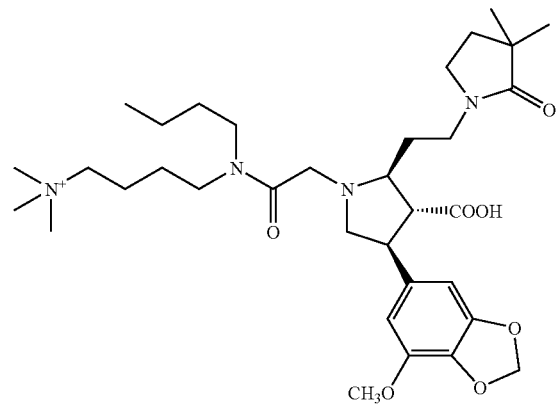
685
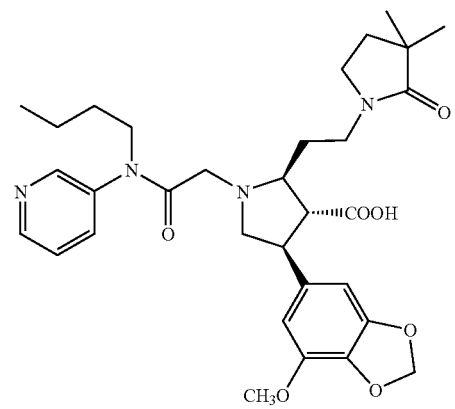
686
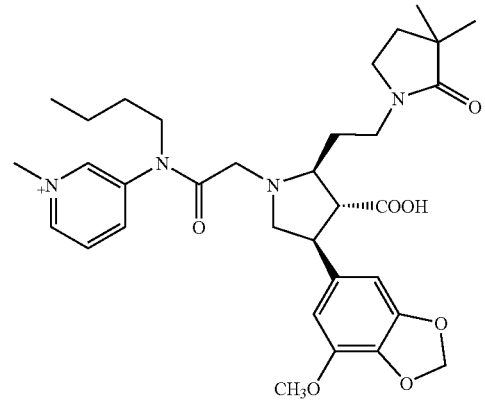
TABLE 3C-continued
687
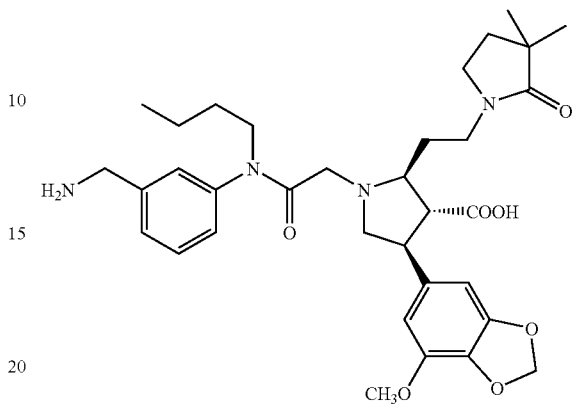
688
689

TABLE 3C-continued
690
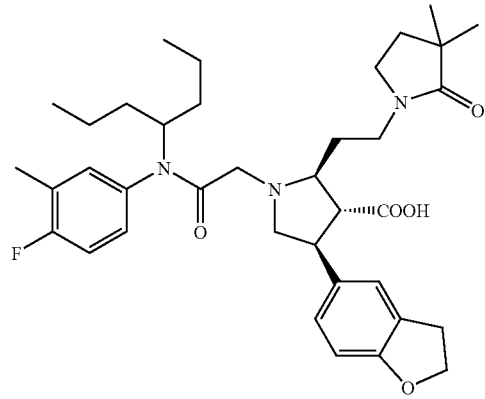
691
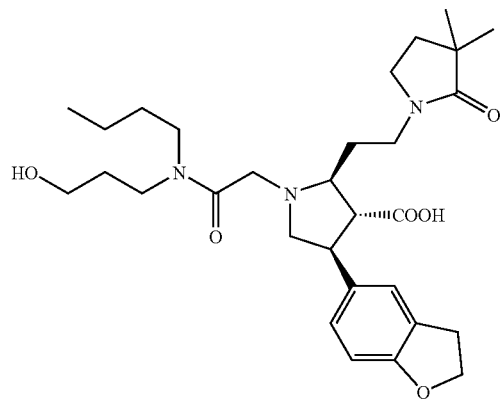
692
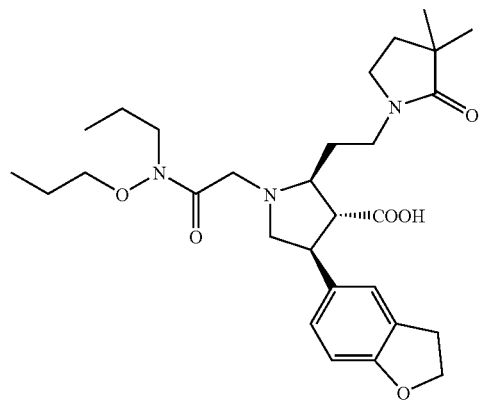
693
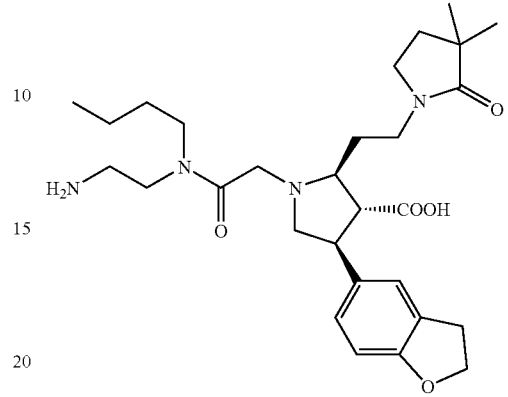
694
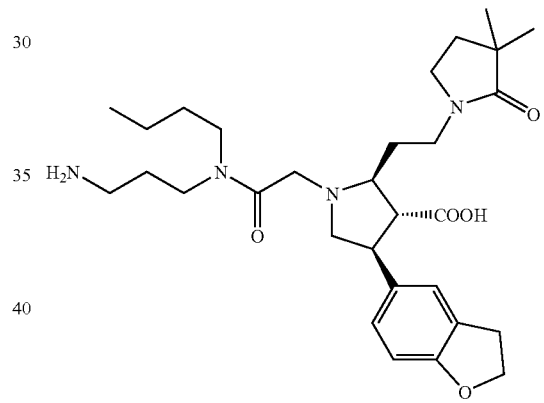
695
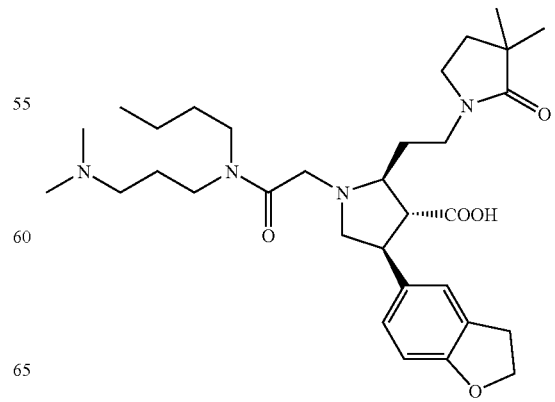

TABLE 3C-continued
696
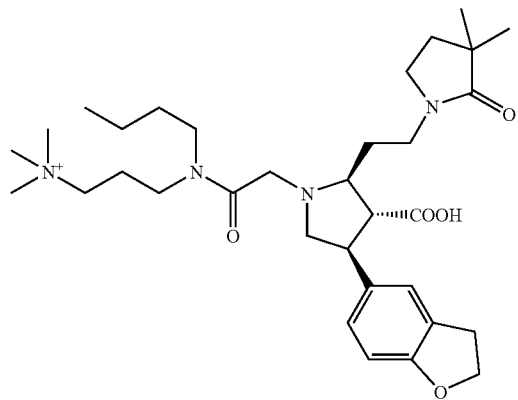
699
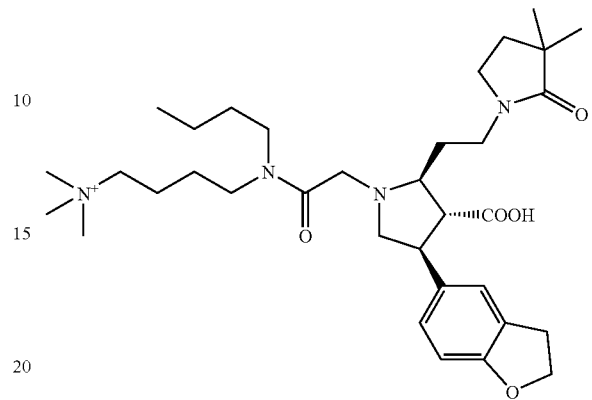
697
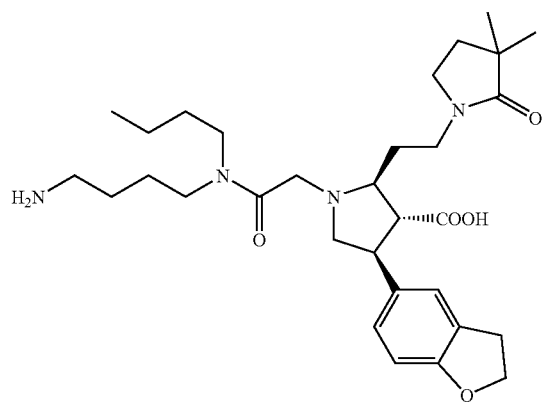
700
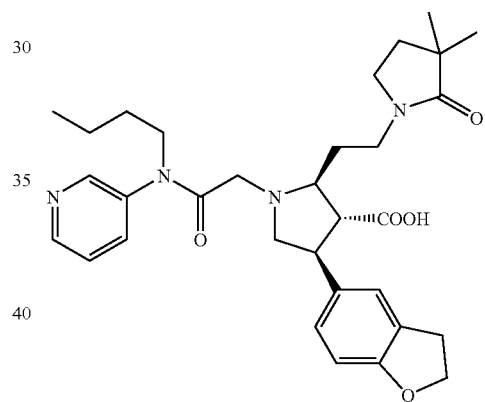
698
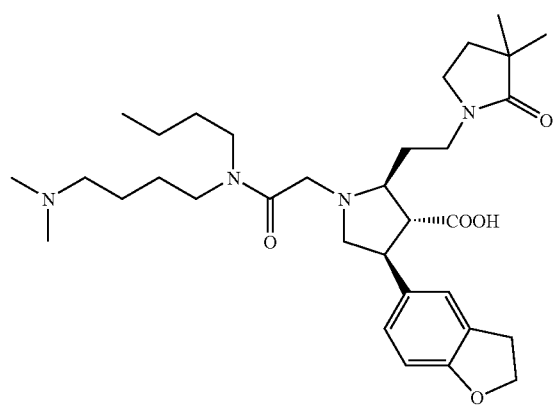
701
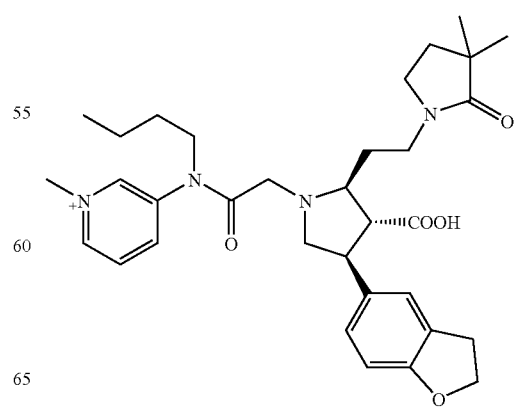

TABLE 3C-continued
702
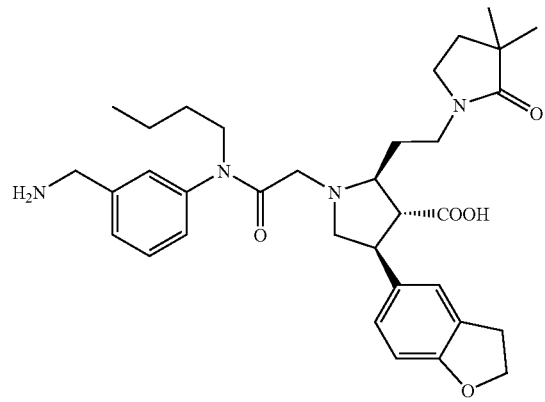
705
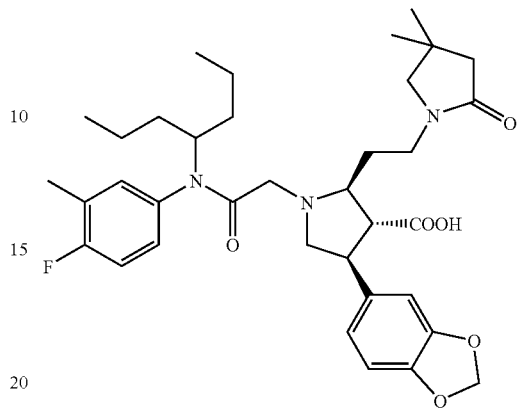
703
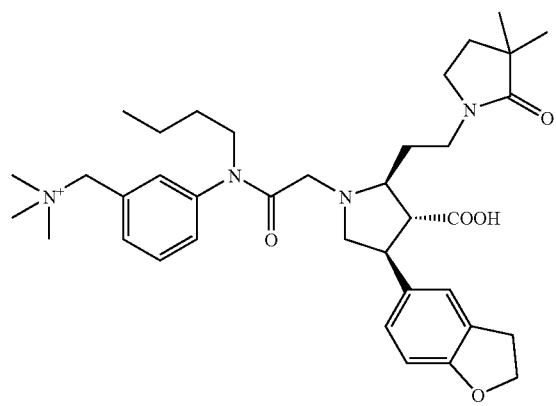
706
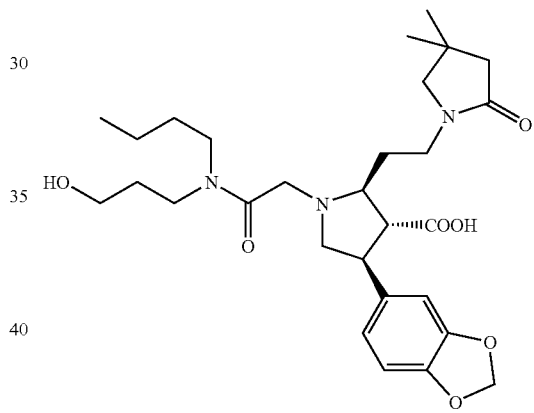
704
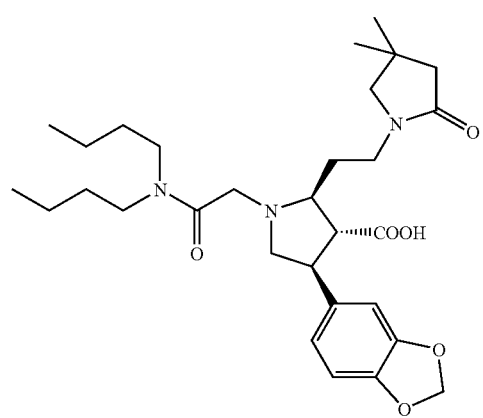
707
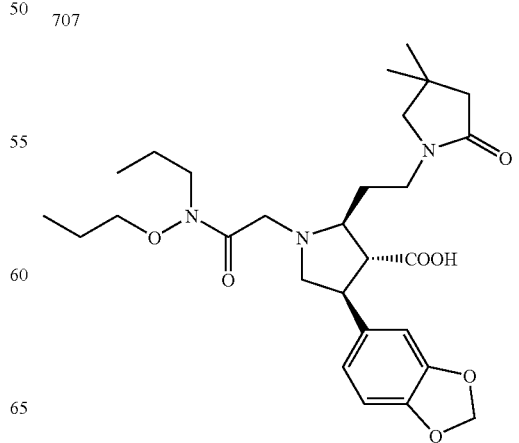

TABLE 3C-continued
708
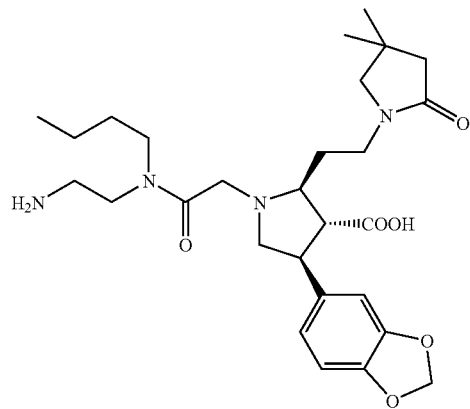
711
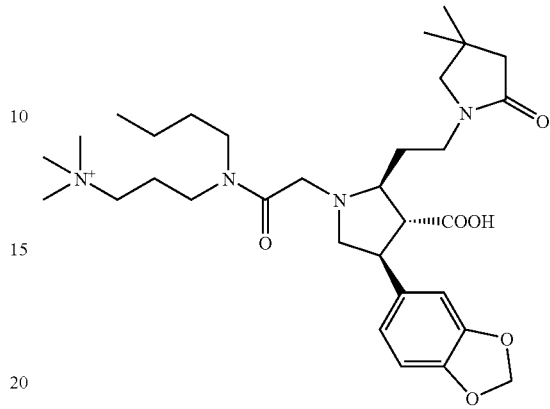
709
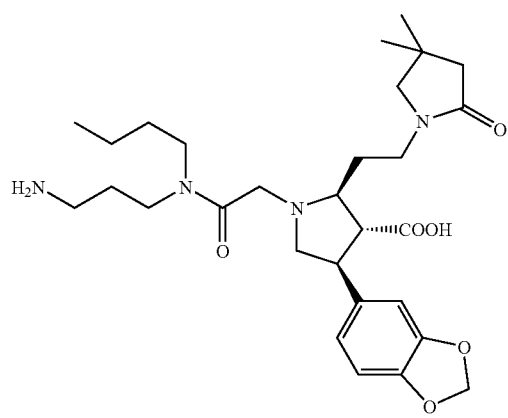
712
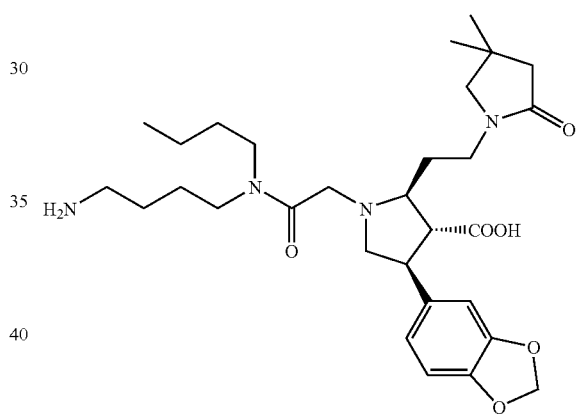
710
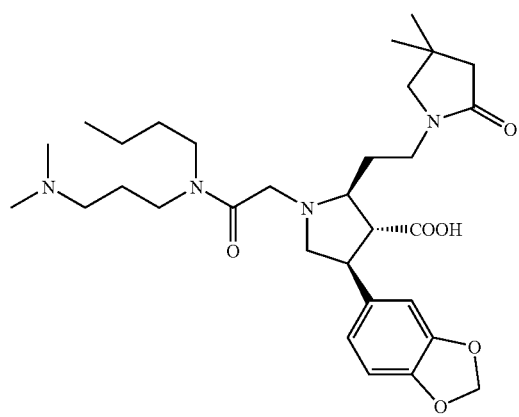
713
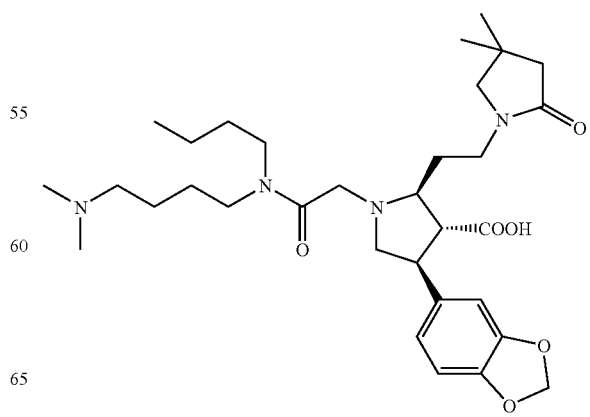

TABLE 3C-continued
714
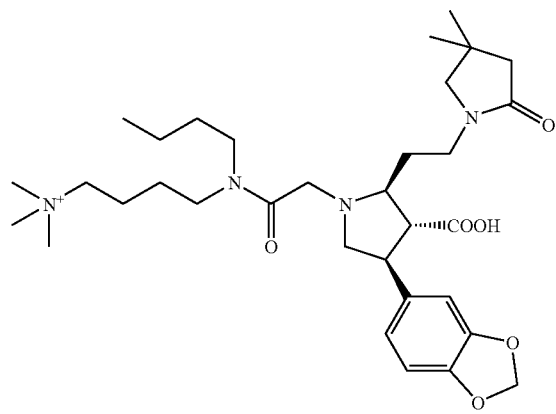
715
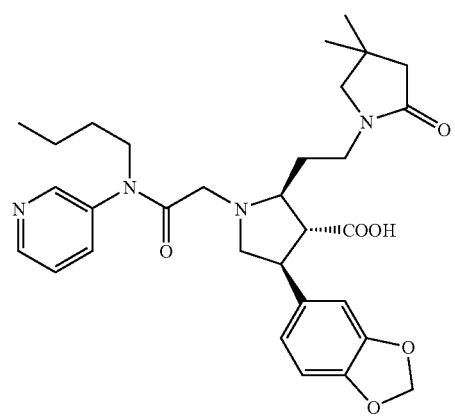
716
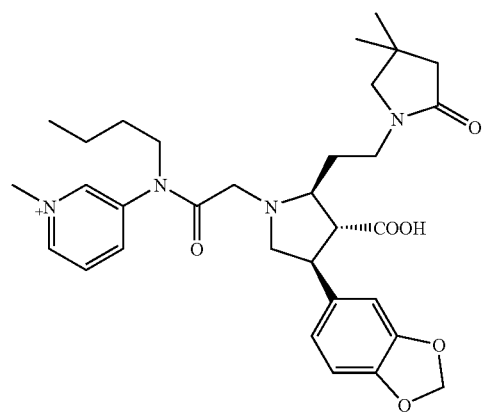
TABLE 3C-continued
717
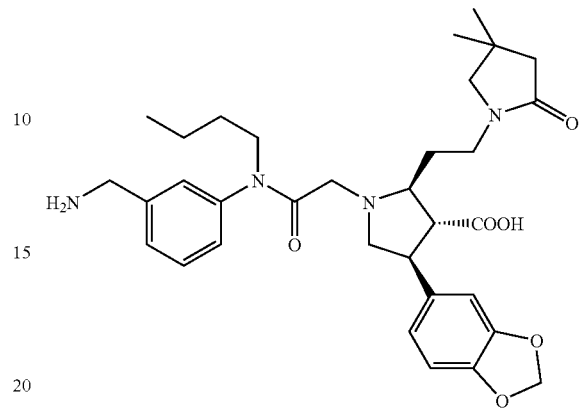
718
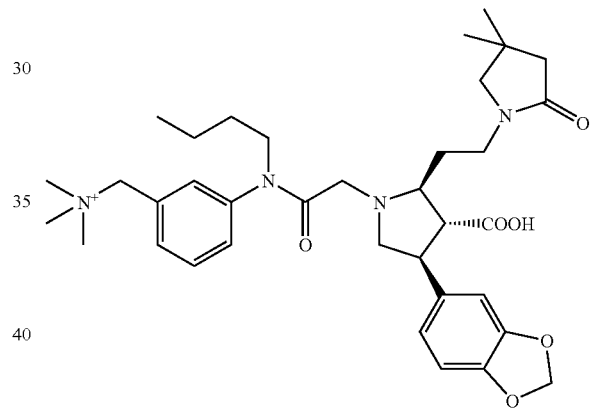
719
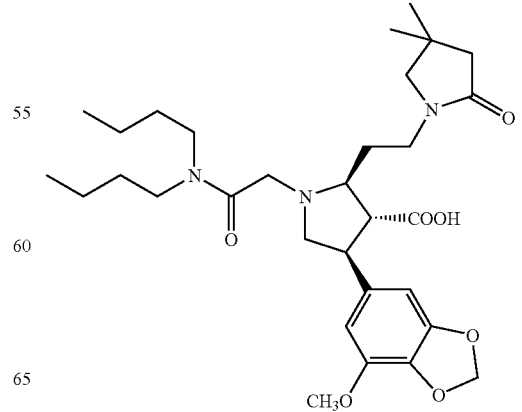

TABLE 3C-continued
720
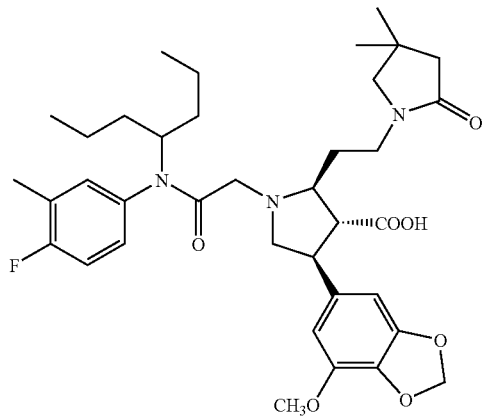
721
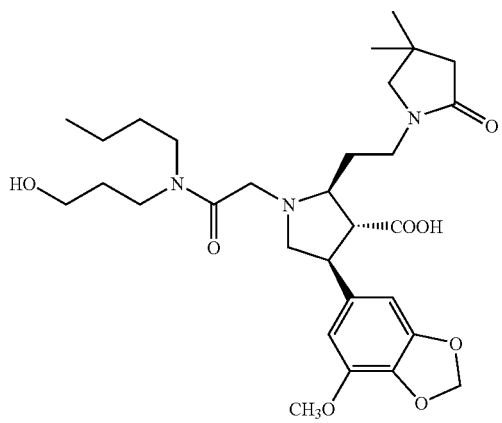
722
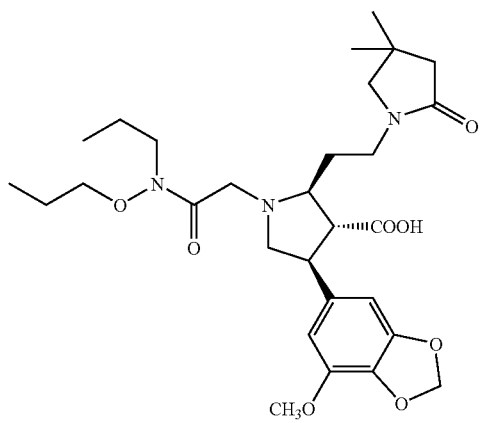
TABLE 3C-continued
723
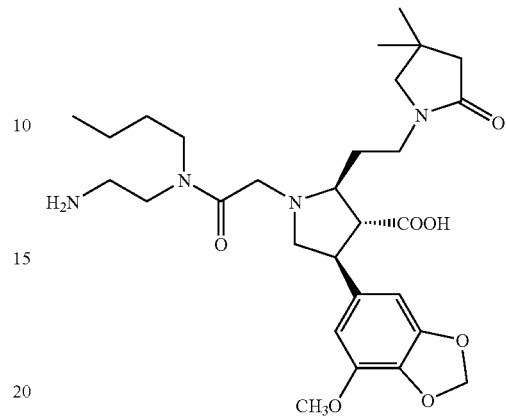
724
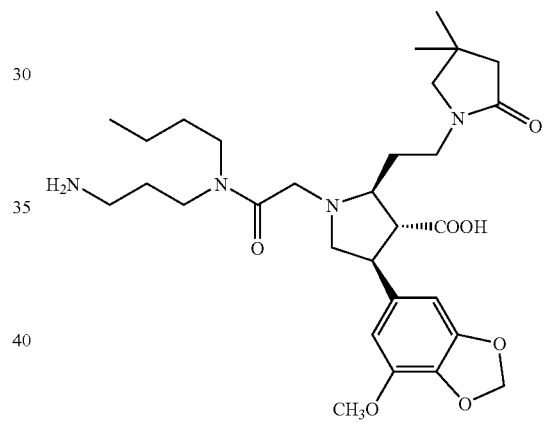
725
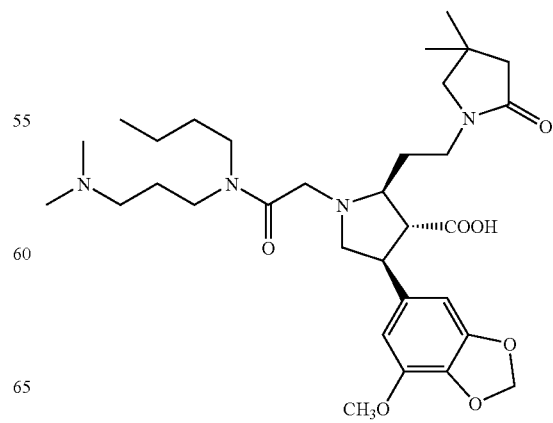

841
TABLE 3C-continued
726
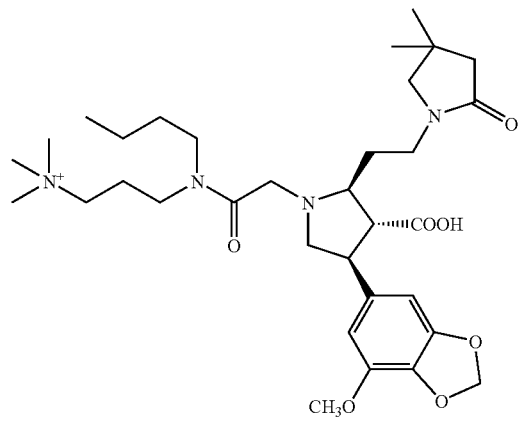
727
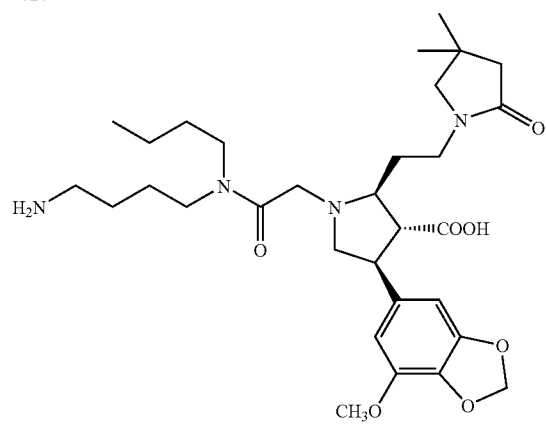
728
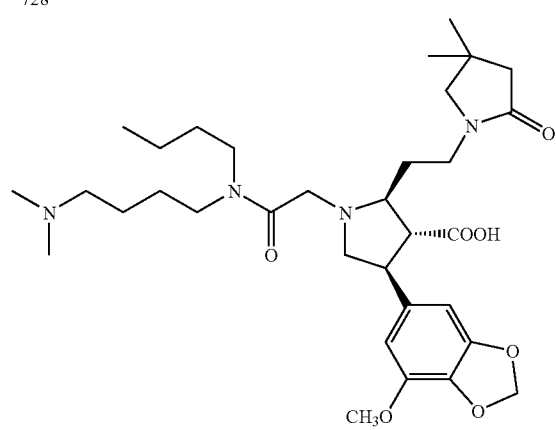
842
TABLE 3C-continued
729
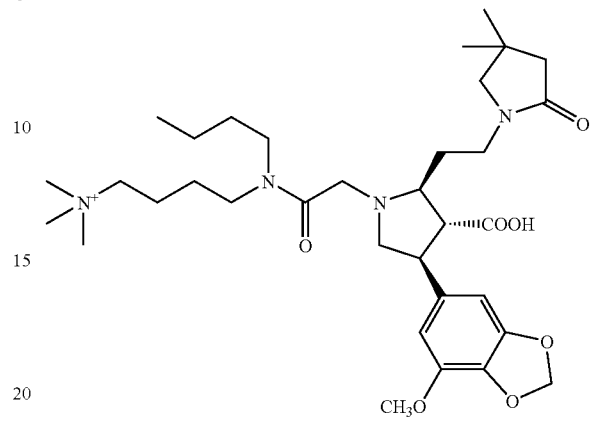
730
731

732
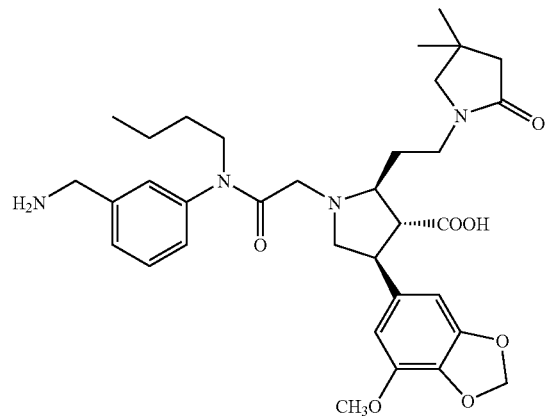
733
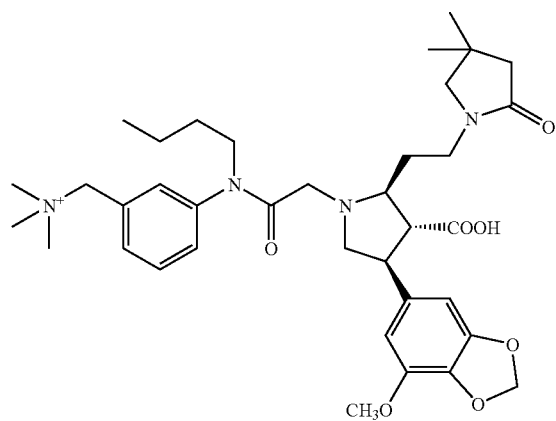
734
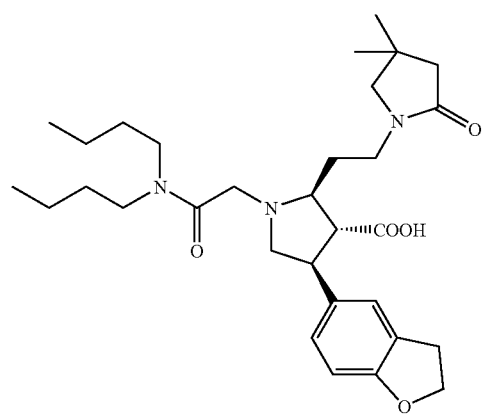
735
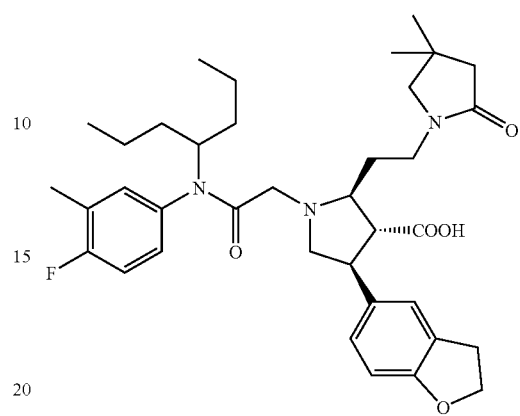
736
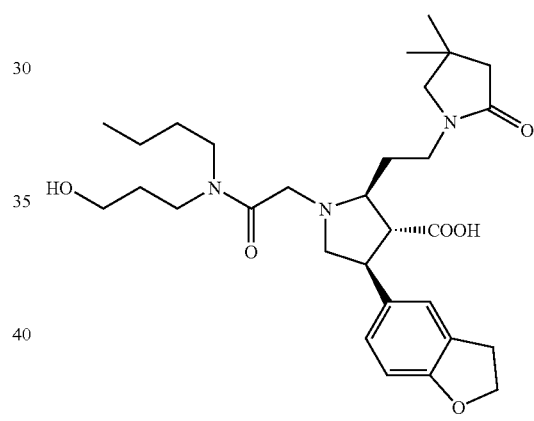
737
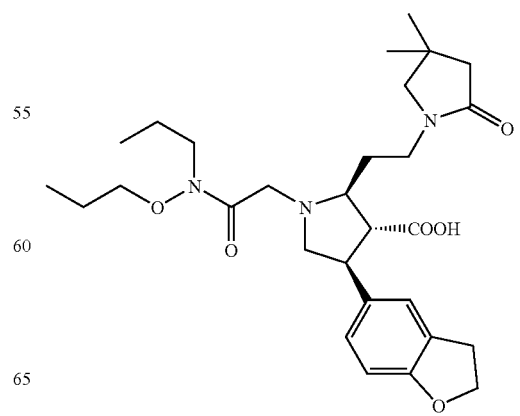

TABLE 3C-continued
738
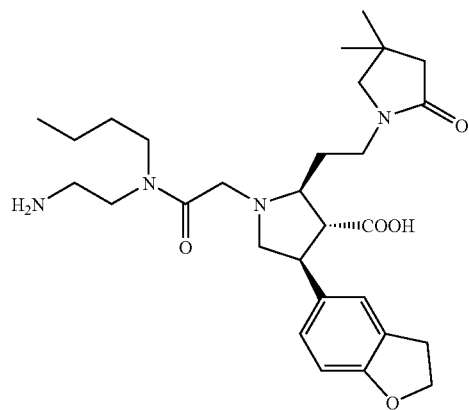
739
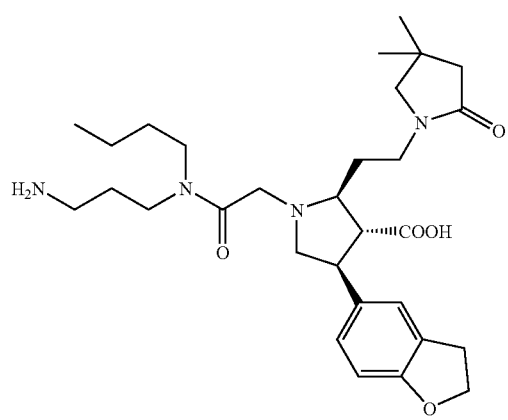
740
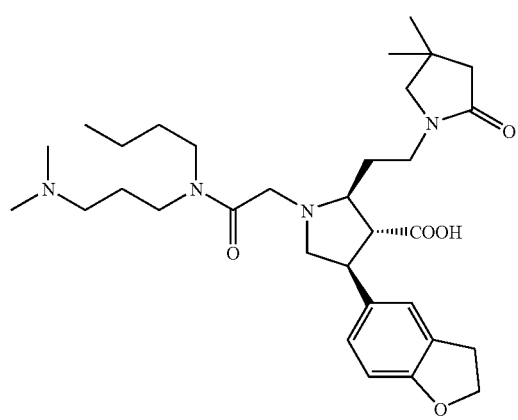
TABLE 3C-continued
741
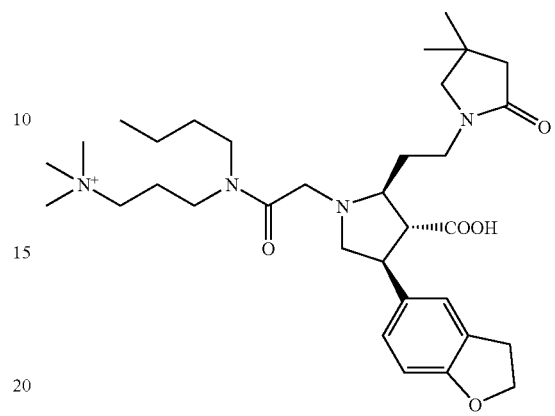
742
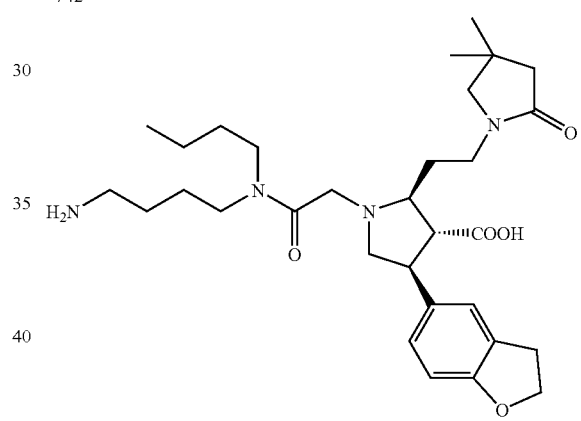
743
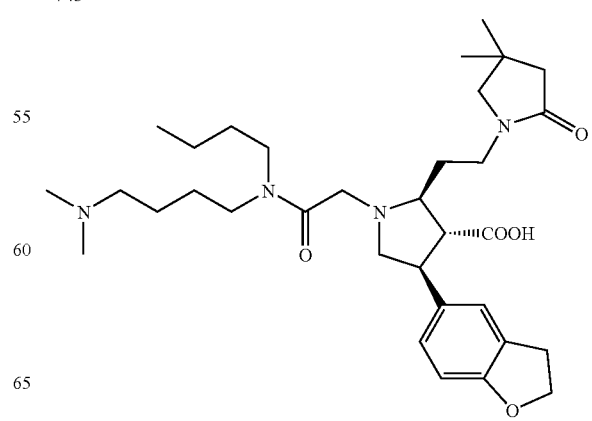

847 848
TABLE 3C-continued | TABLE 3C-continued
744
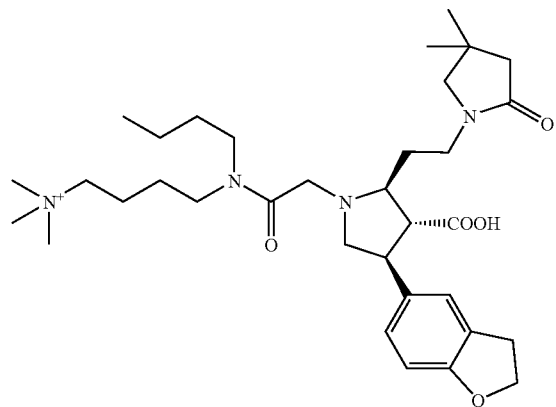
747
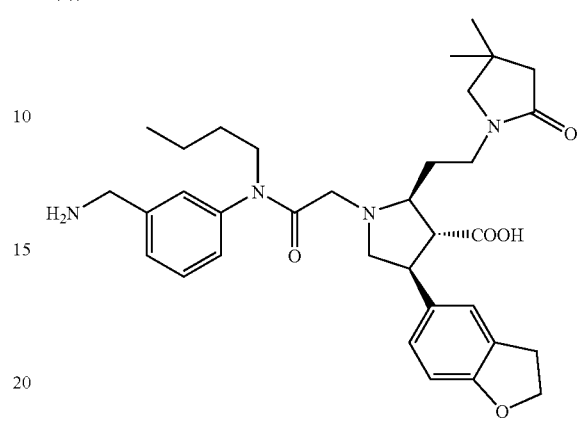
745
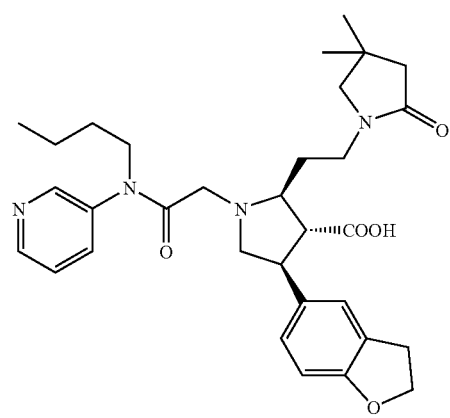
748
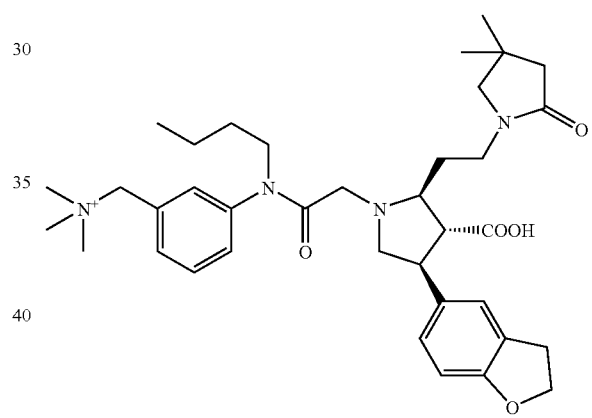
746
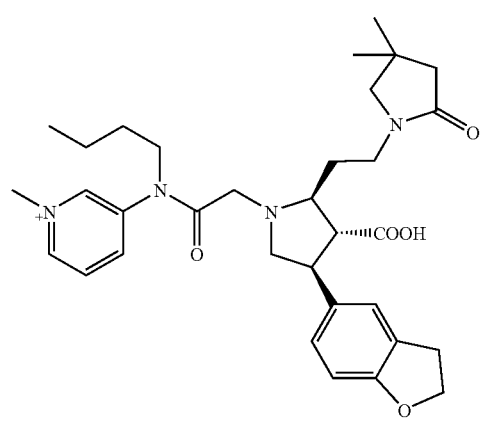
749
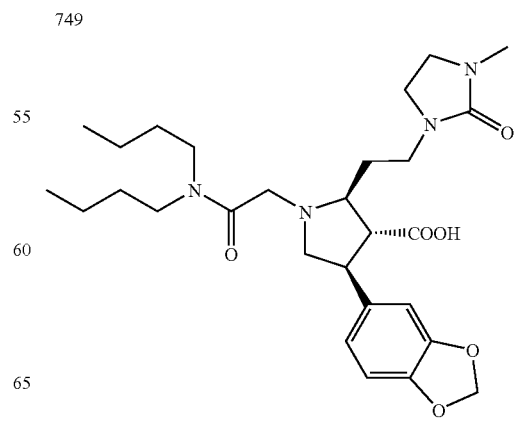

TABLE 3C-continued
750
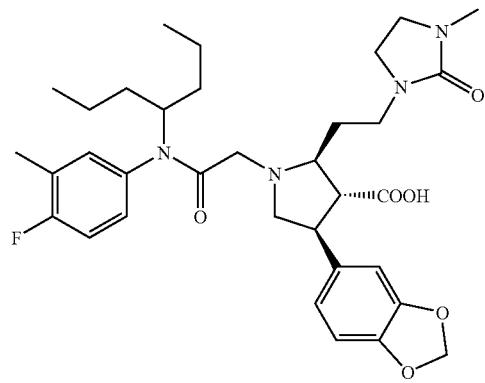
751
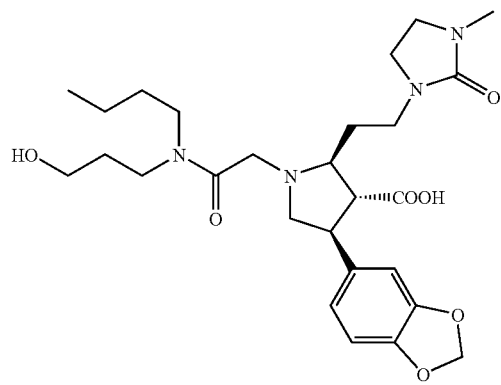
752
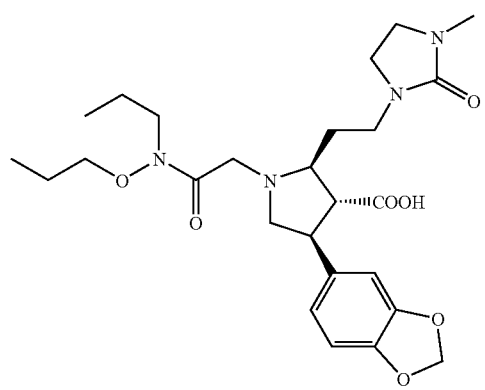
TABLE 3C-continued
753
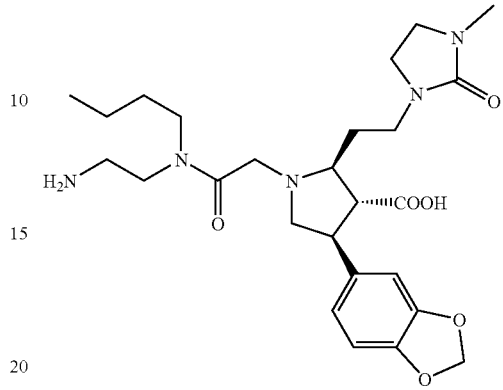
754
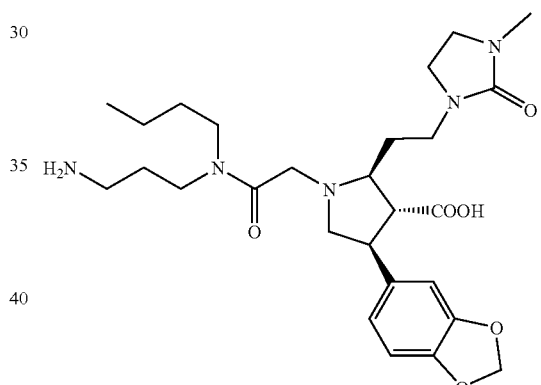
755
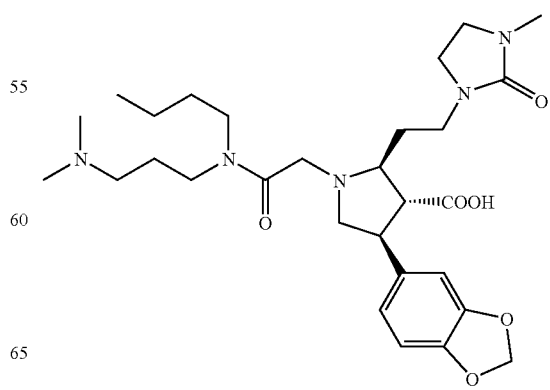

TABLE 3C-continued
756
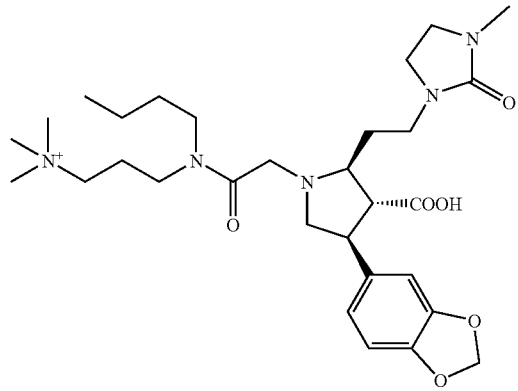
757
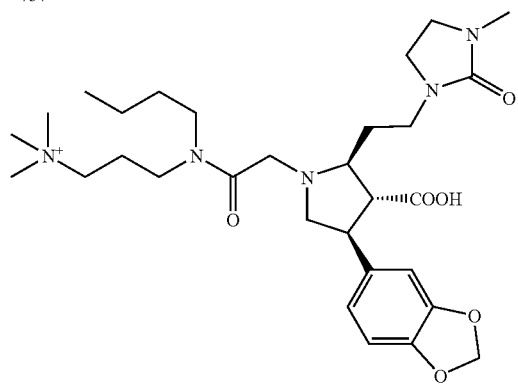
758
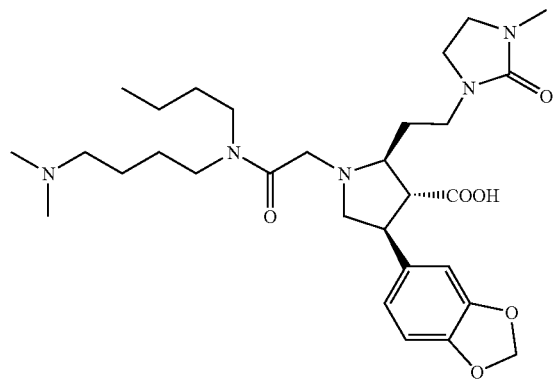
759
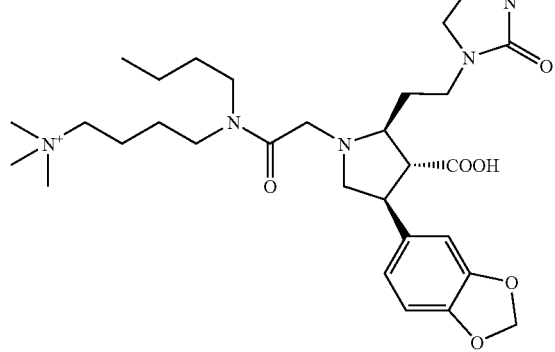
TABLE 3C-continued
760
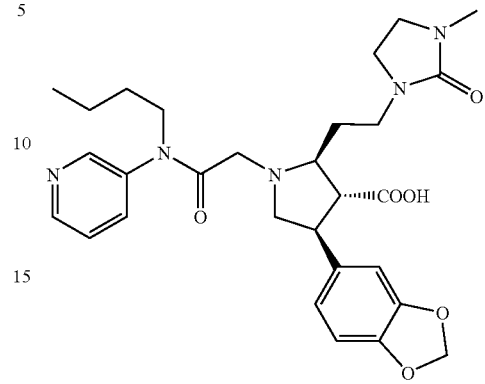
761
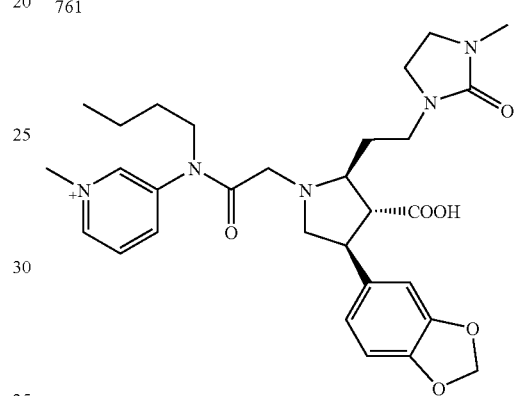
762
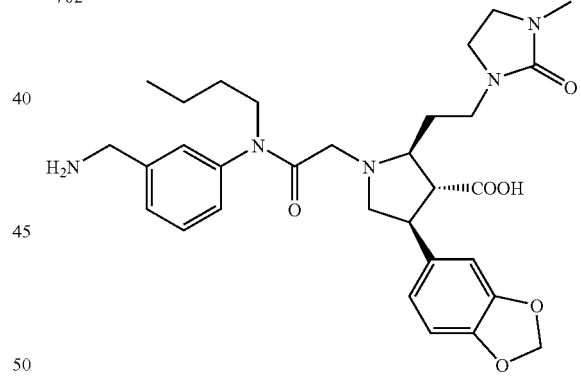
763
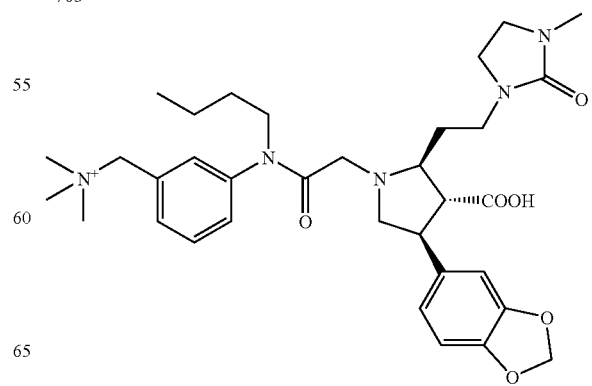

TABLE 3C-continued
764
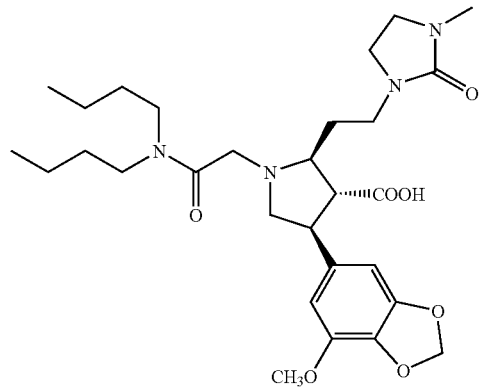
765
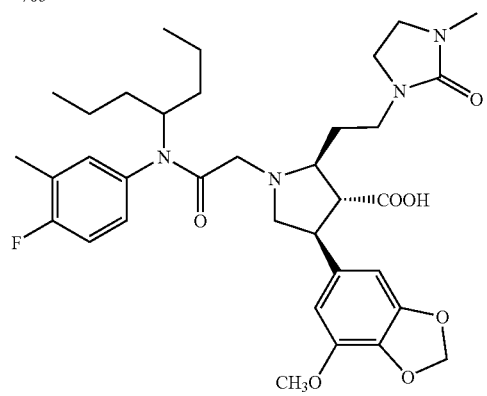
766
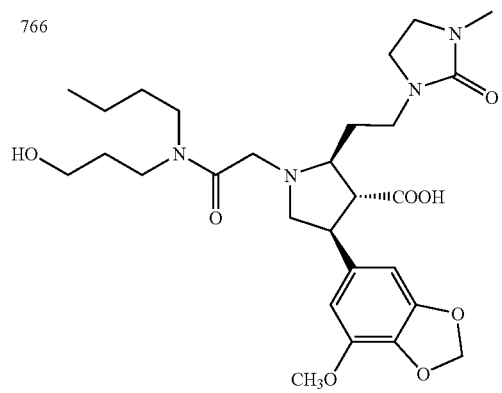
767
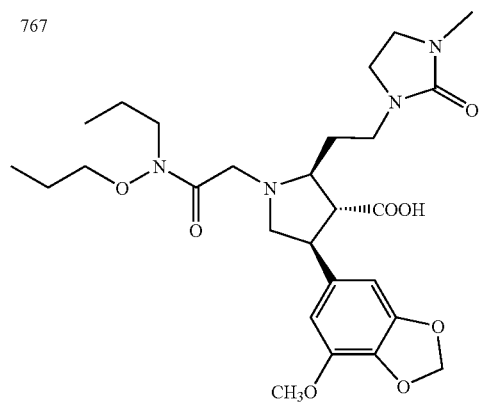
TABLE 3C-continued
768
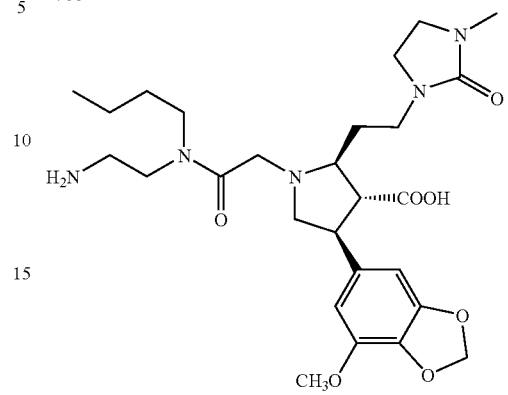
769
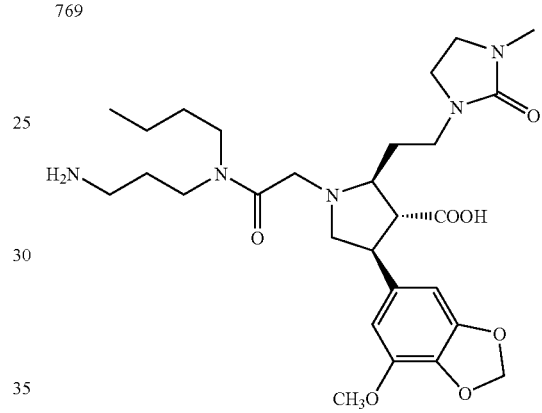
770
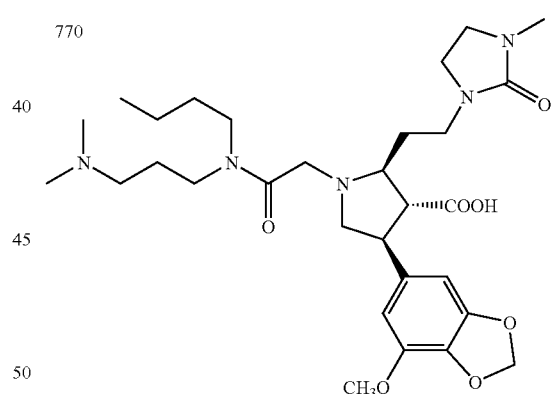
771
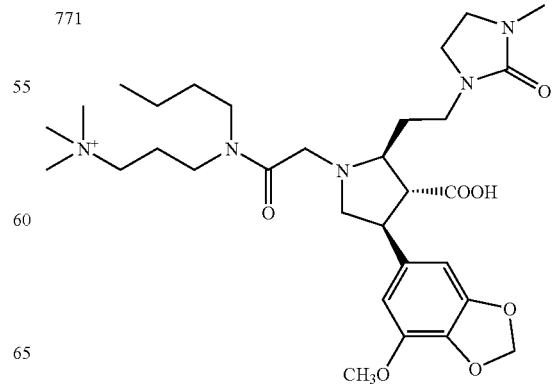

TABLE 3C-continued
772
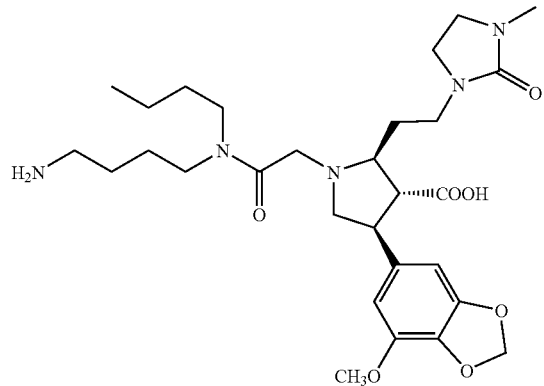
773
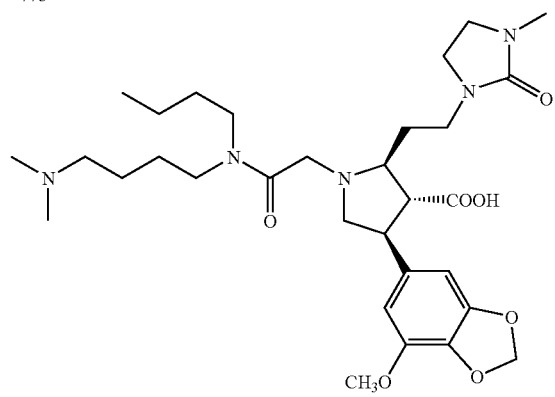
774
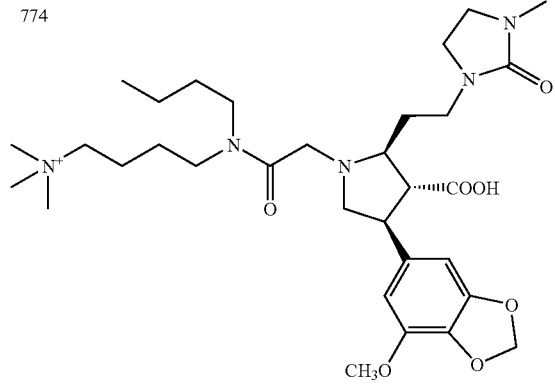
775
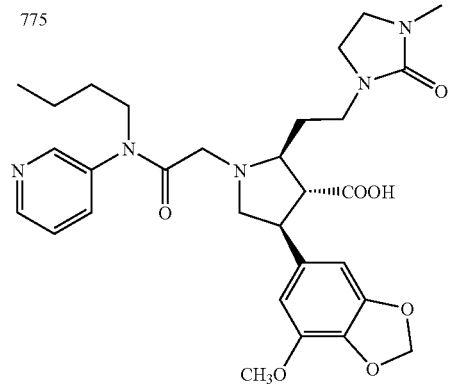
TABLE 3C-continued
776
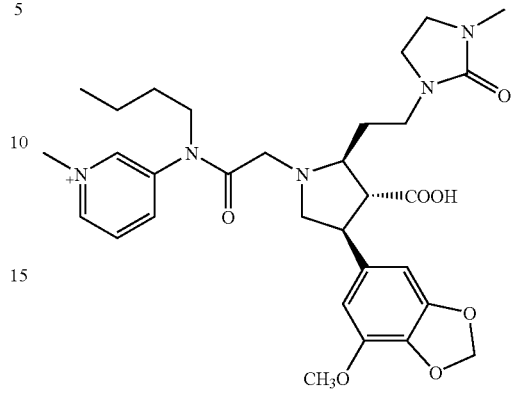
777
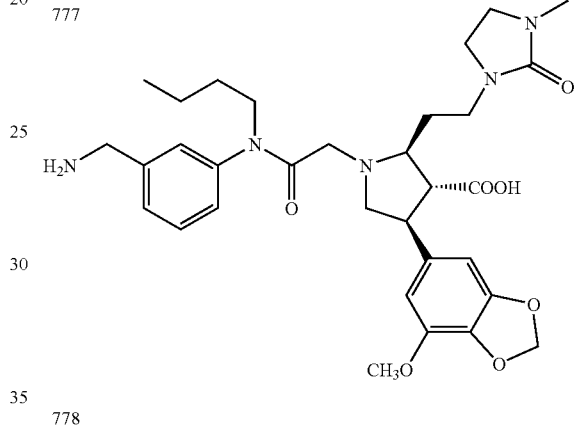
778
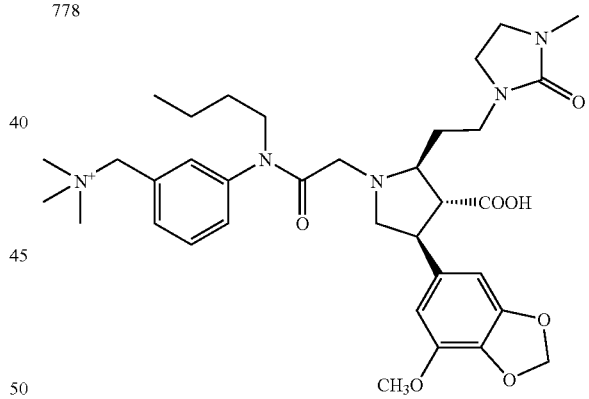
779
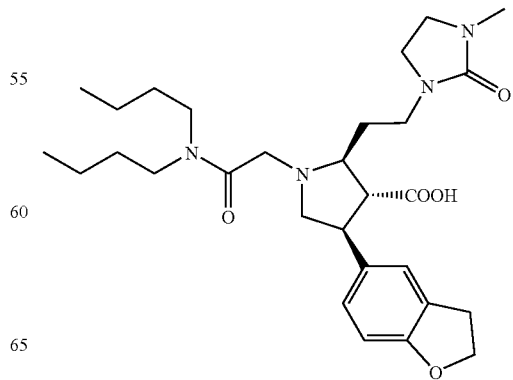

TABLE 3C-continued
780
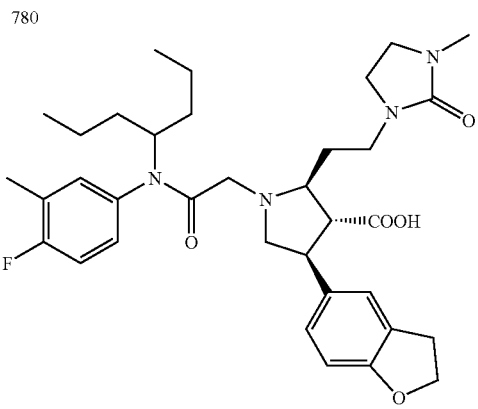
781
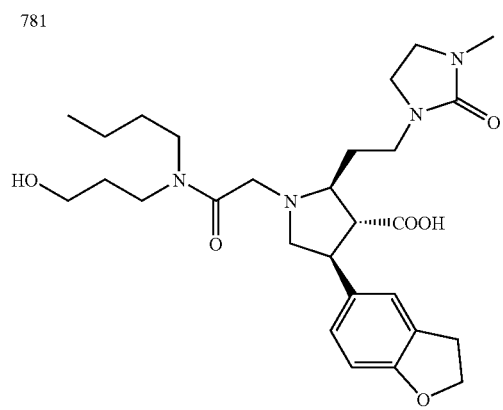
782
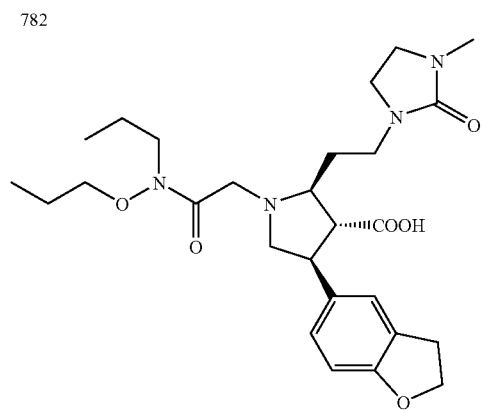
783
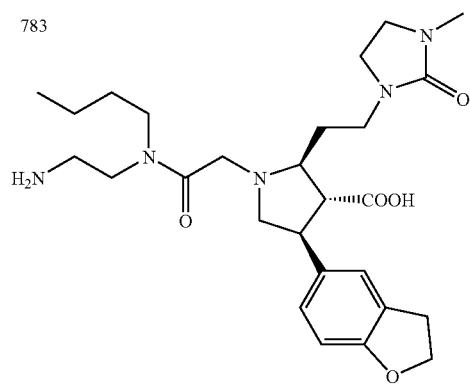
TABLE 3C-continued
784
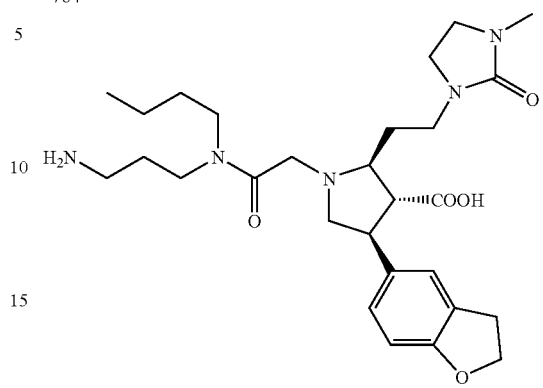
785
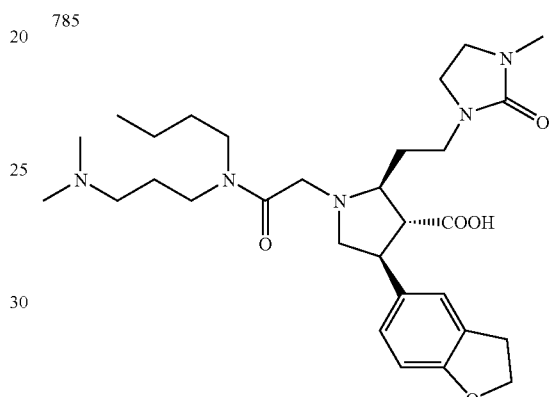
786
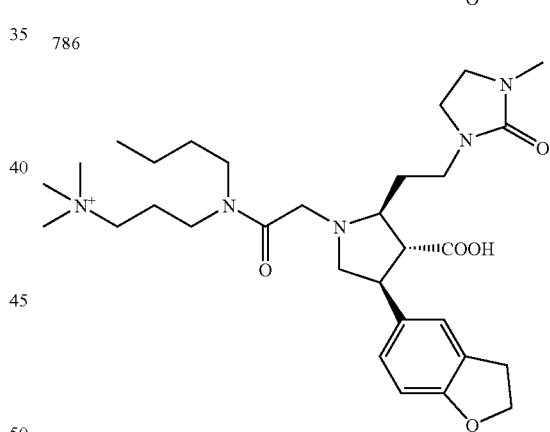
787
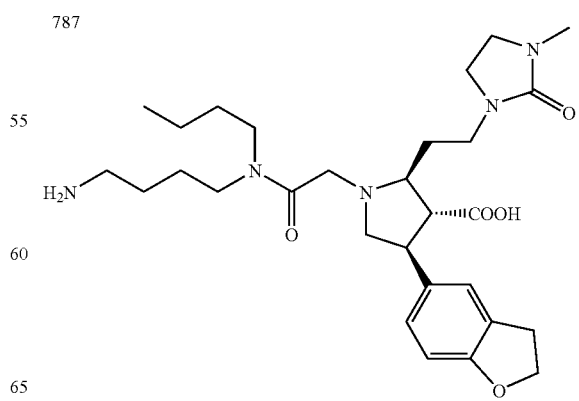

TABLE 3C-continued
788
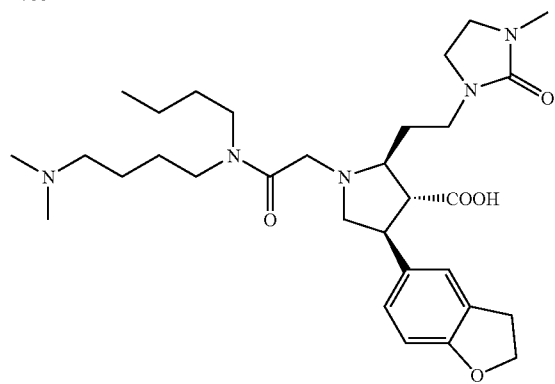
789
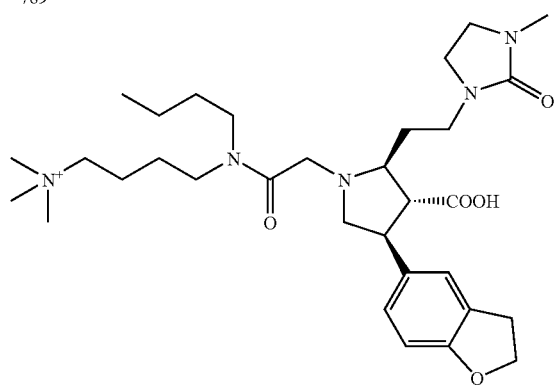
790
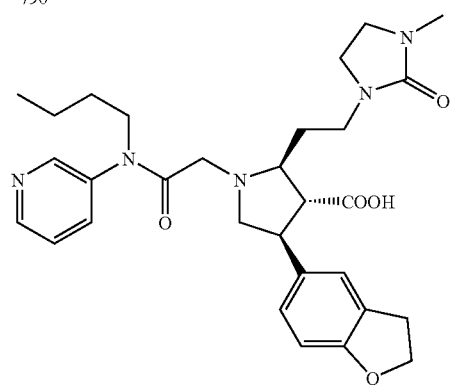
791
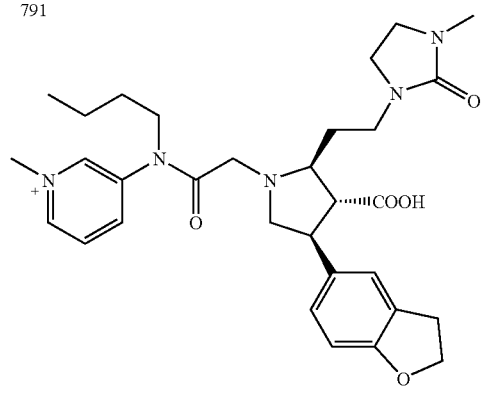
TABLE 3C-continued
792
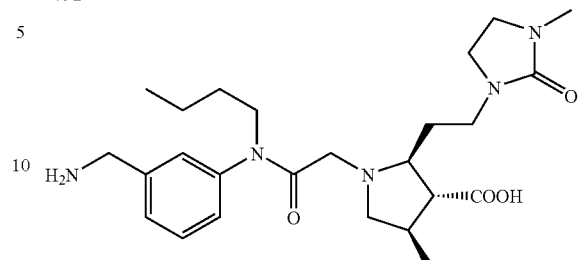
793
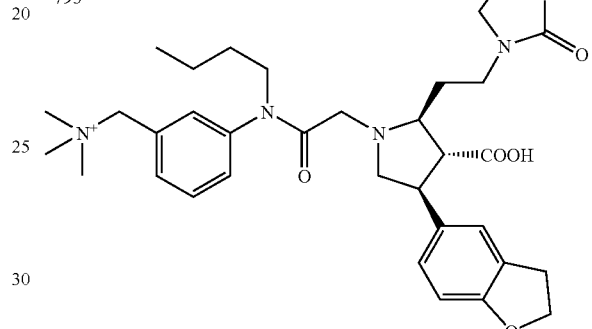
794
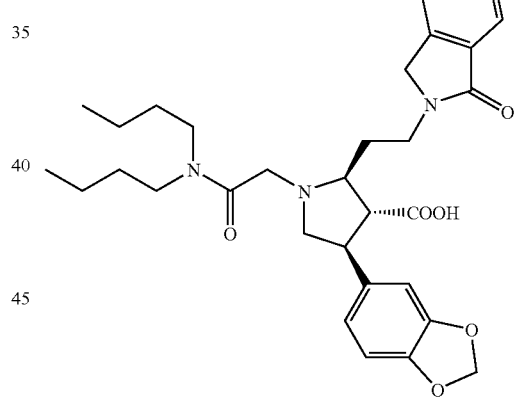
795
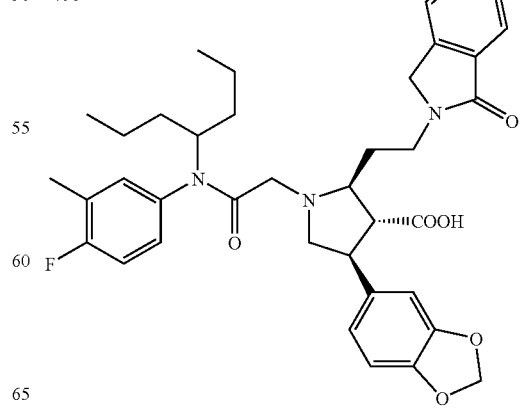

TABLE 3C-continued
796
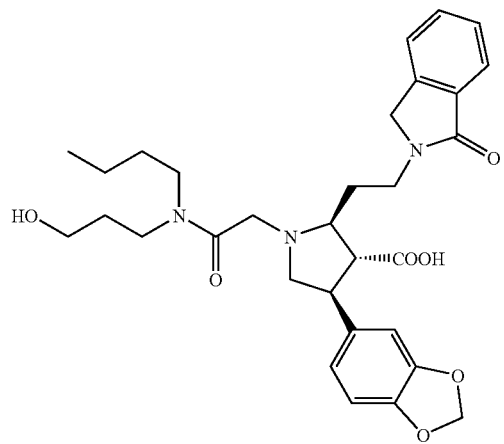
797
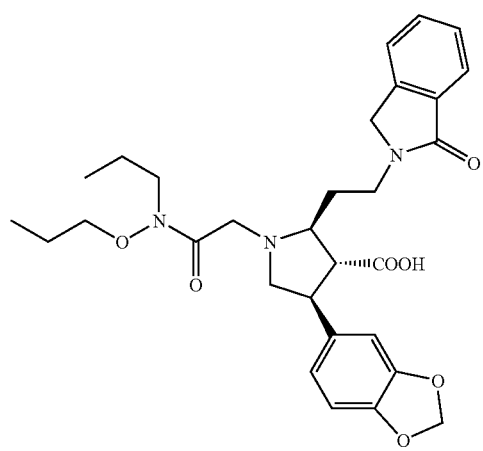
798
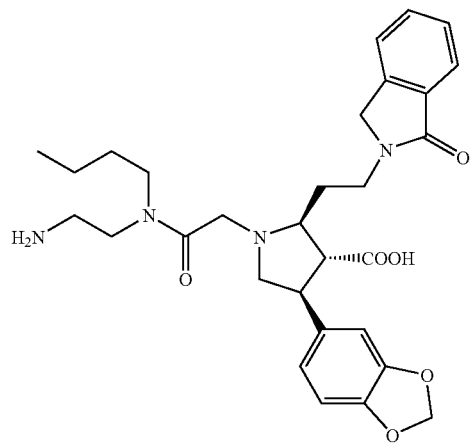
TABLE 3C-continued
799
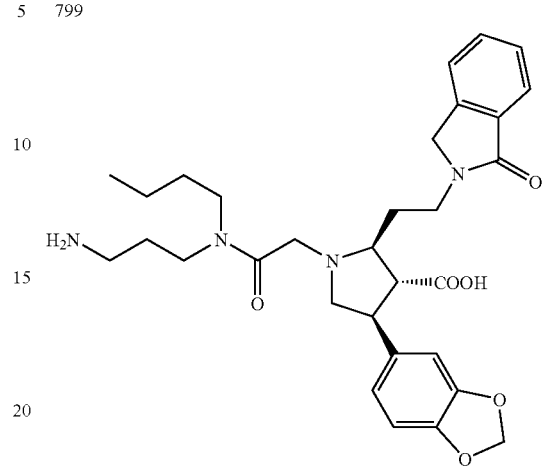
800
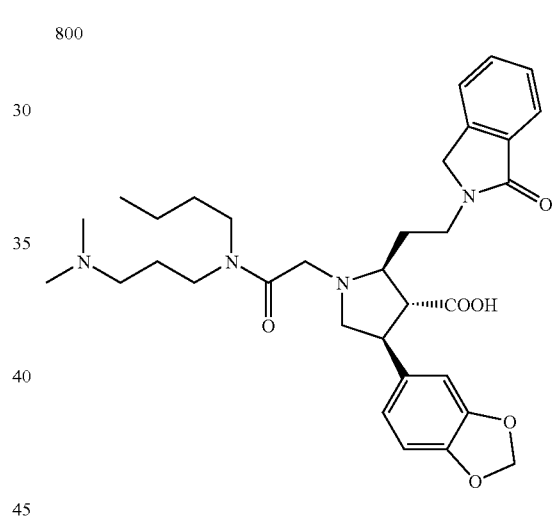
801
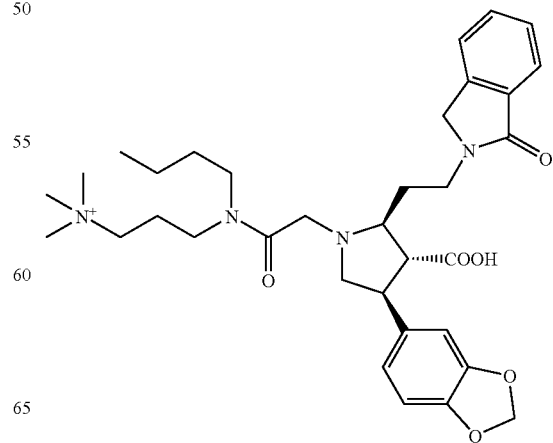

TABLE 3C-continued
802
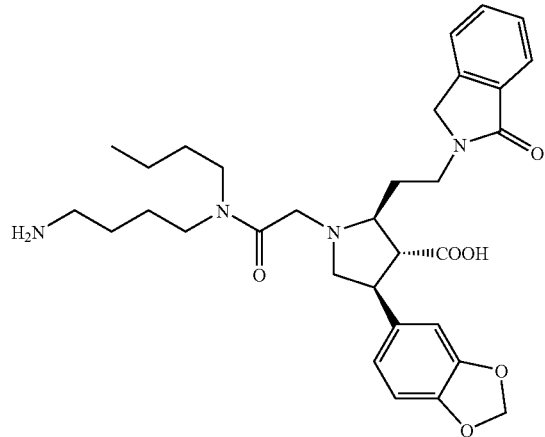
803
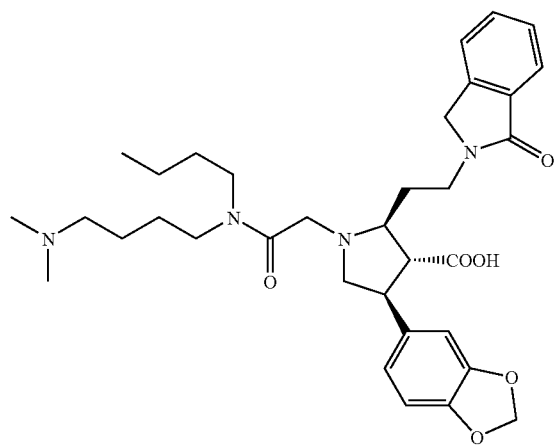
804
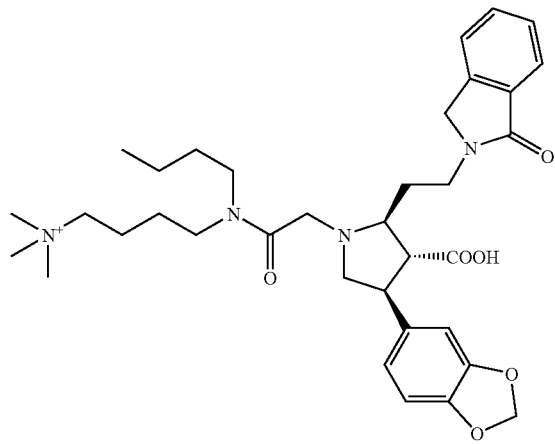
TABLE 3C-continued
805
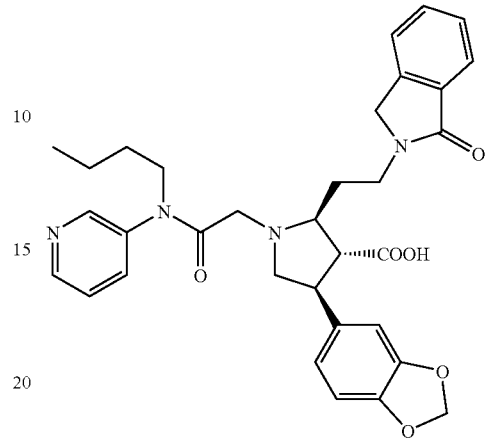
806
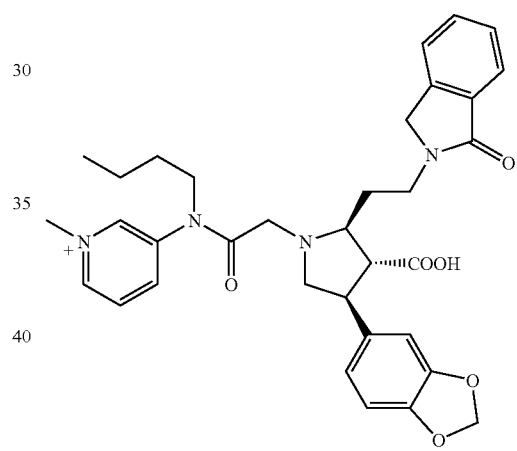
807
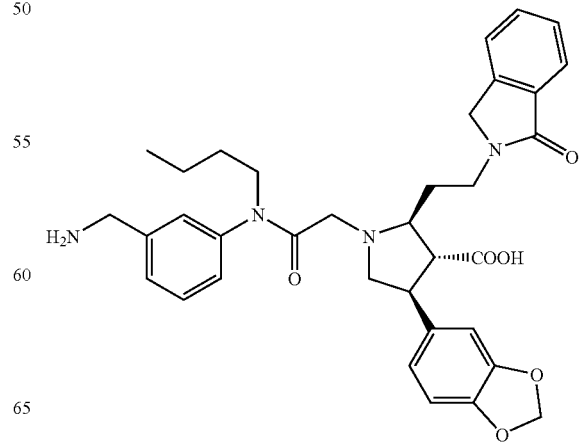

TABLE 3C-continued
808
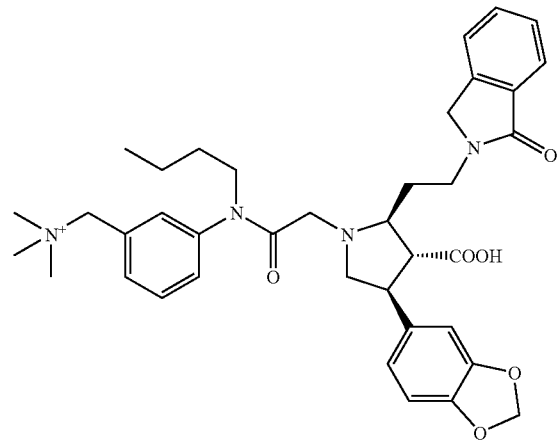
809
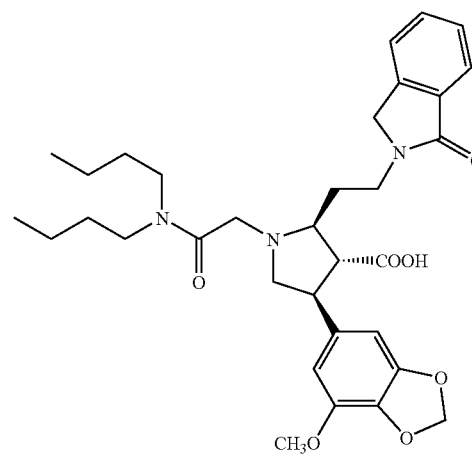
810
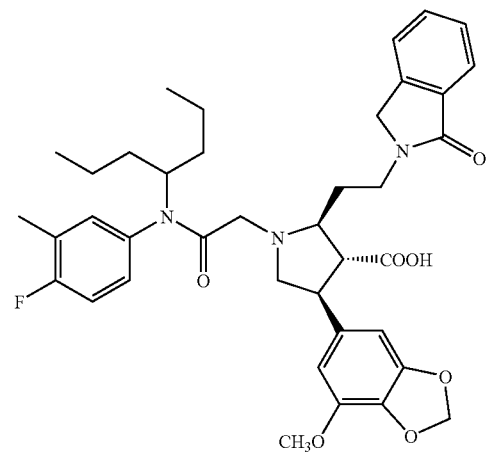
811
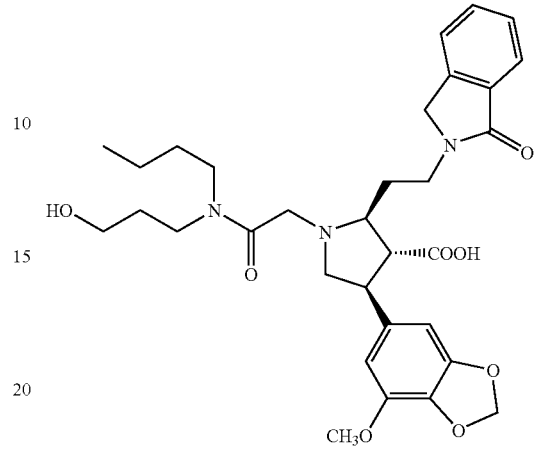
812
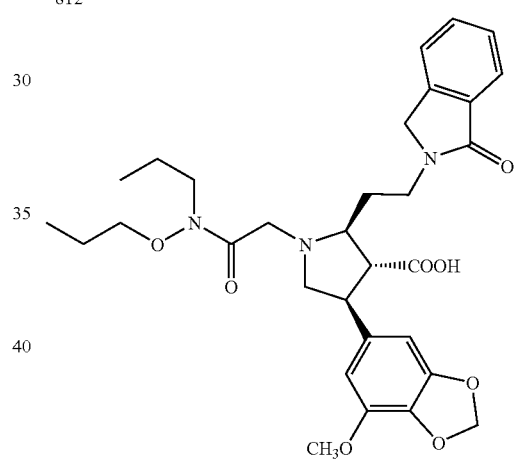
813
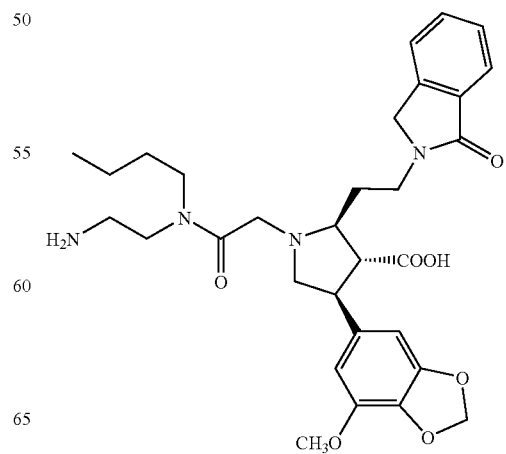

TABLE 3C-continued
814
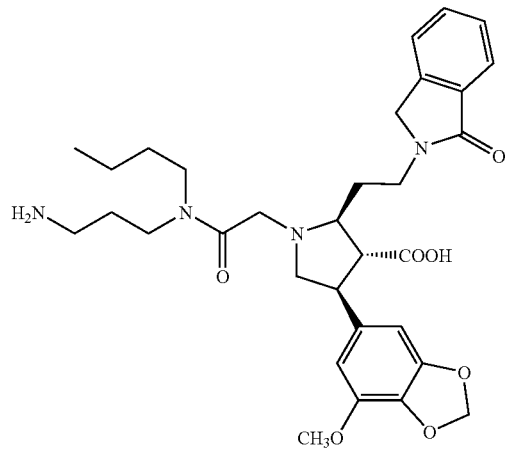
815
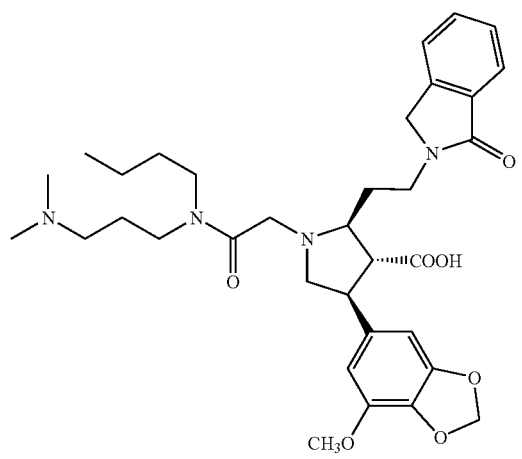
816
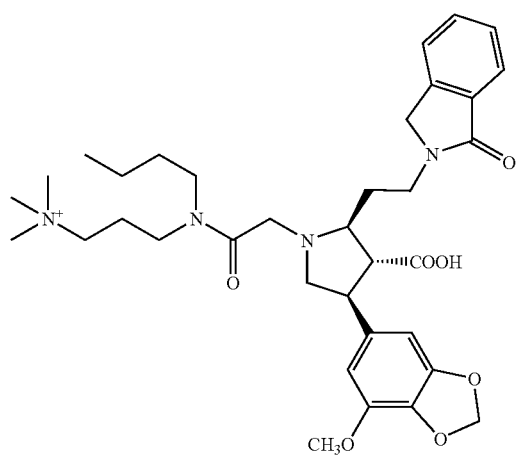
TABLE 3C-continued
817
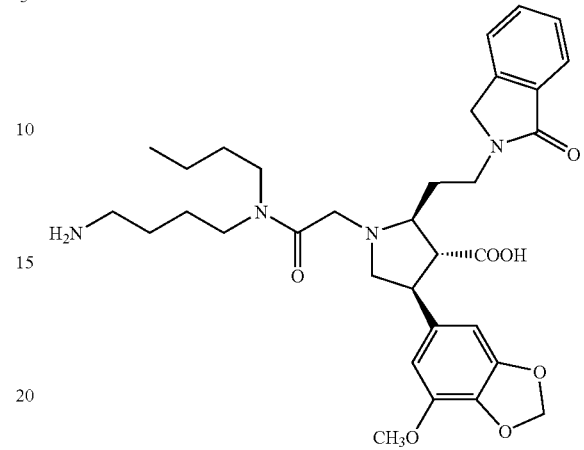
818

819
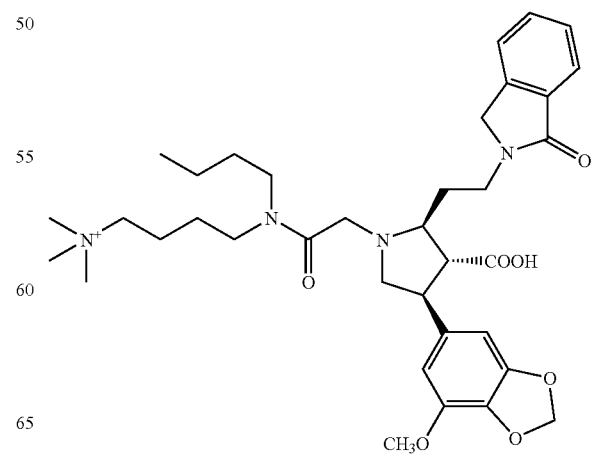

TABLE 3C-continued
820
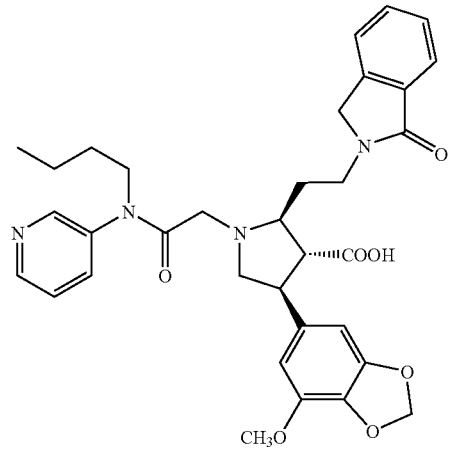
821
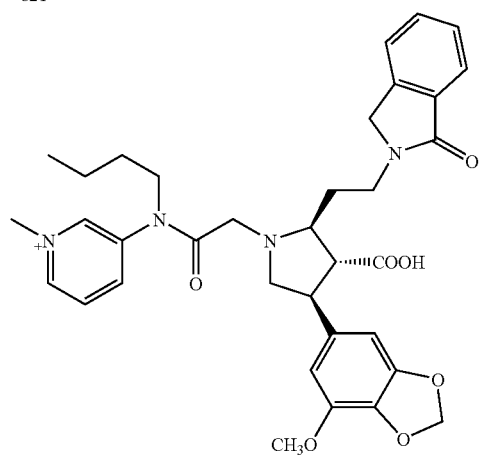
822
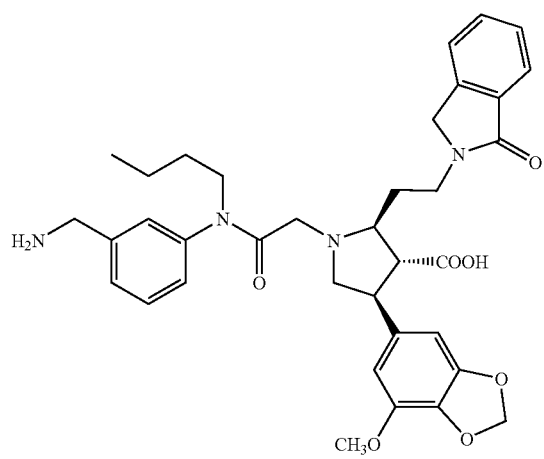
TABLE 3C-continued
823
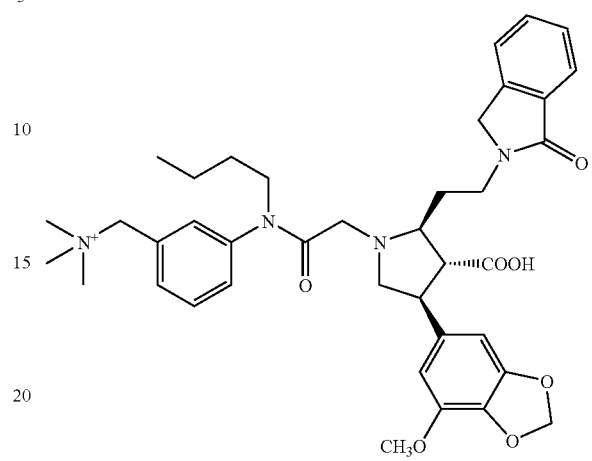
824
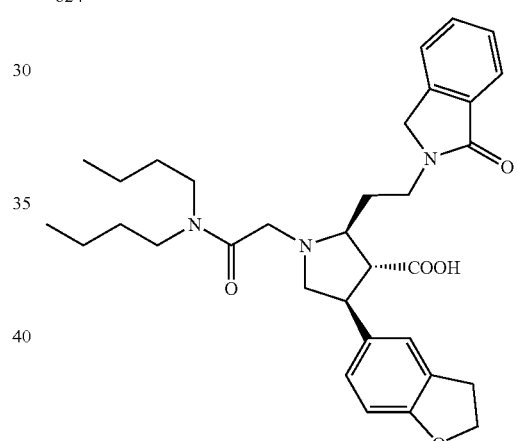
825
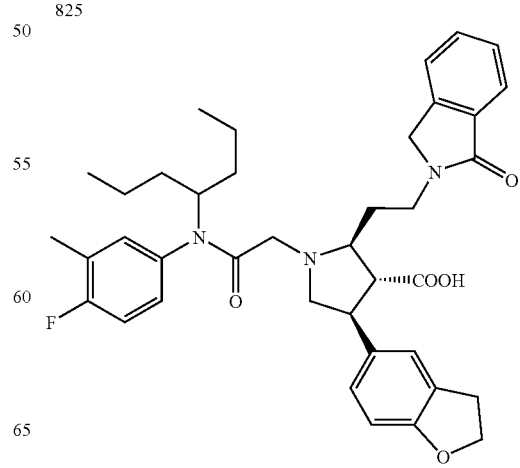

TABLE 3C-continued
826
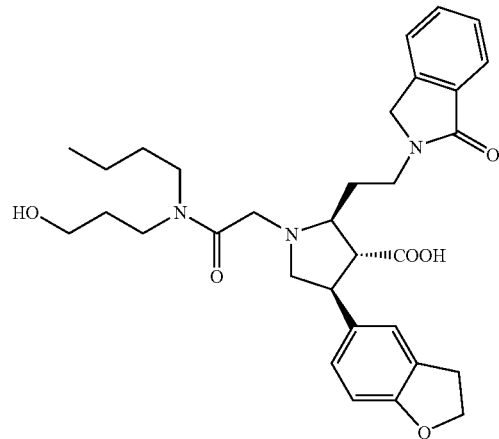
827
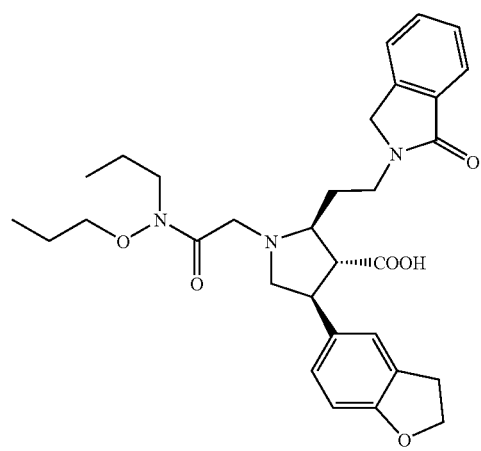
828
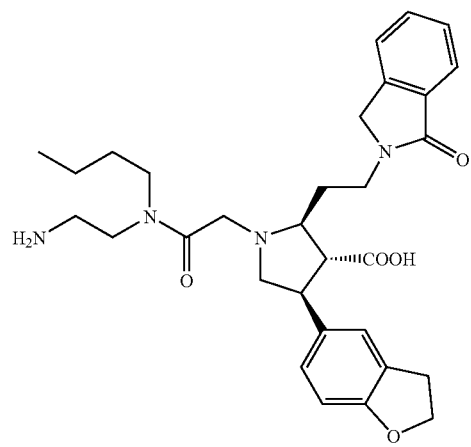
TABLE 3C-continued
829
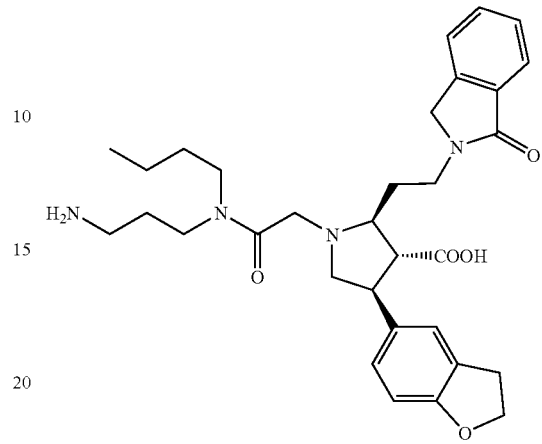
830
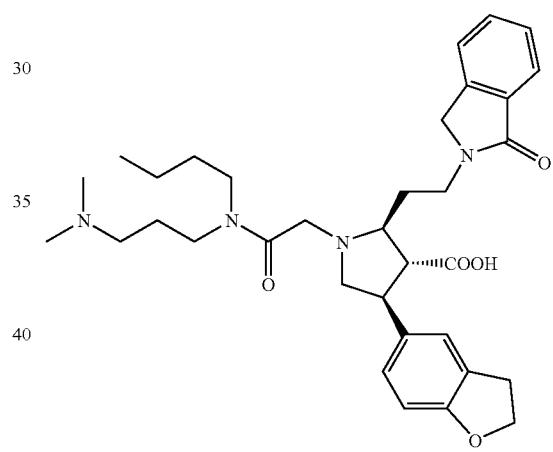
831
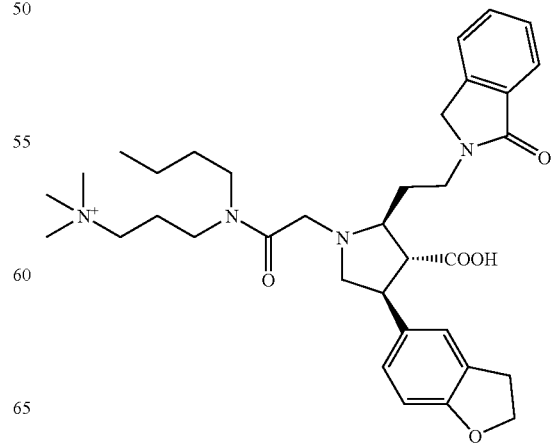

TABLE 3C-continued
832
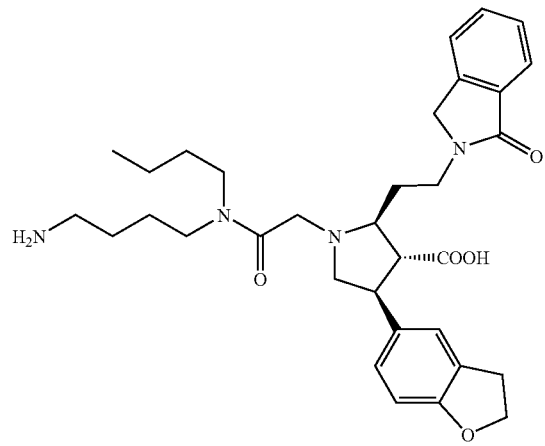
833
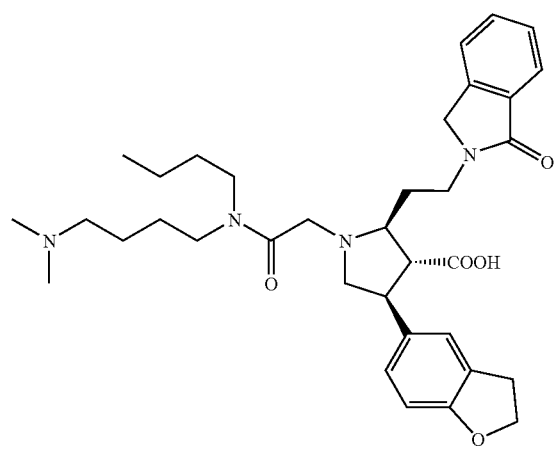
834
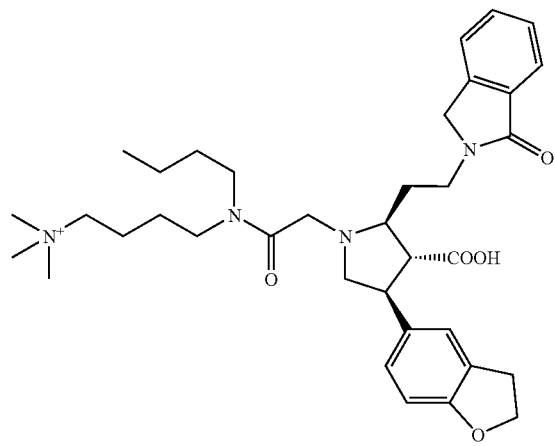
TABLE 3C-continued
835
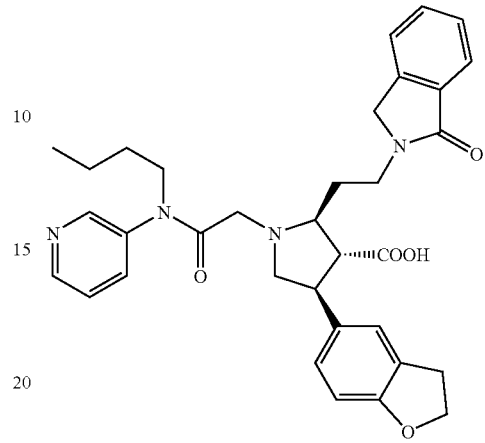
836
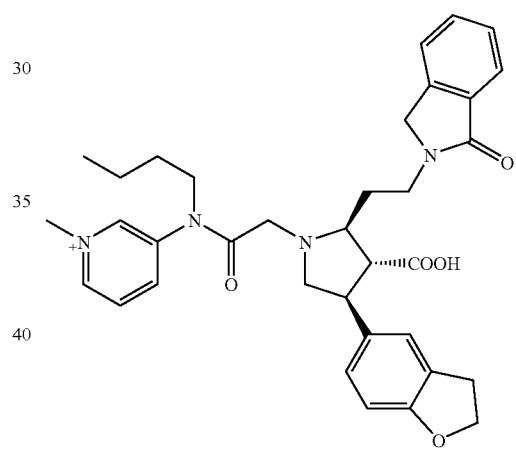
837
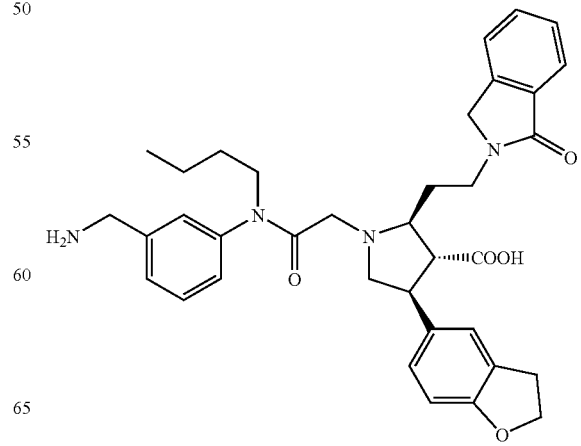

TABLE 3C-continued
838
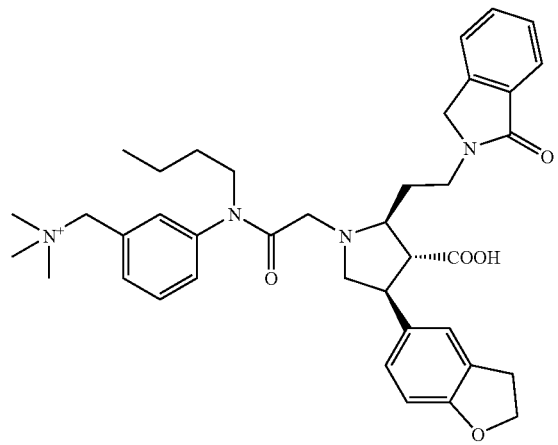
839
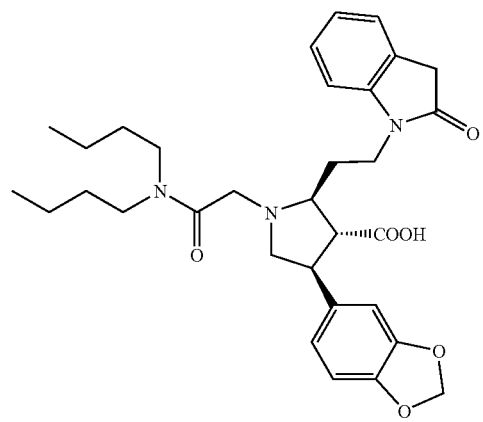
840
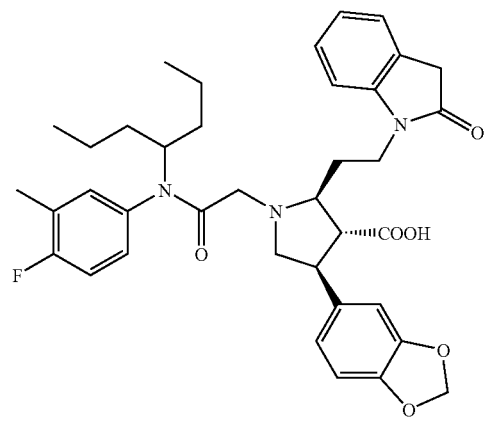
TABLE 3C-continued
841
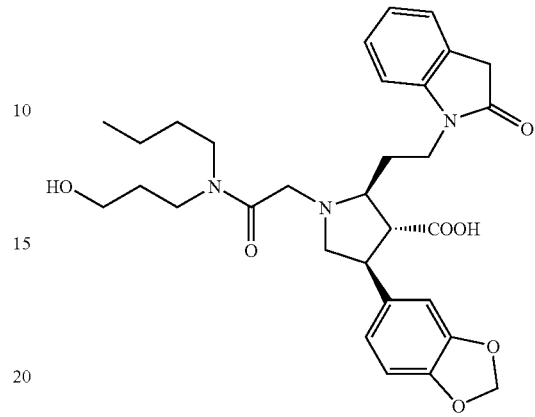
842
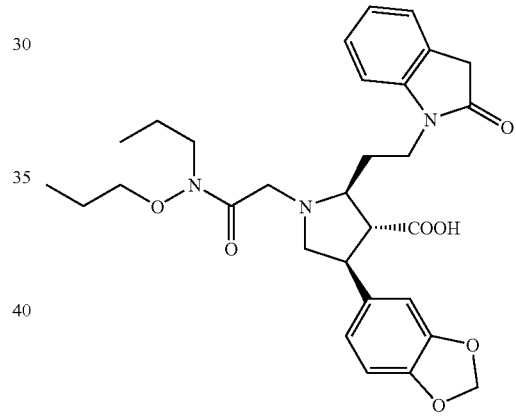
843
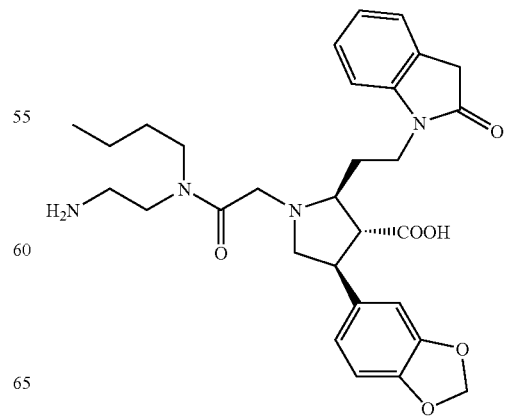

TABLE 3C-continued
844
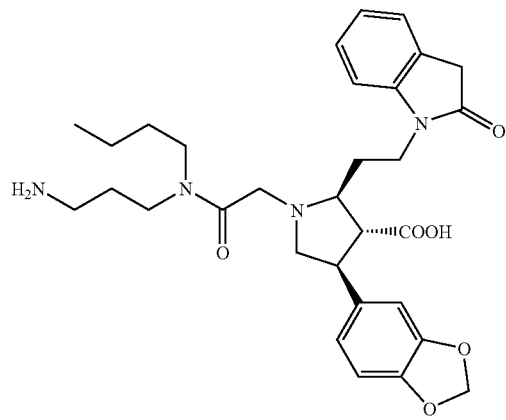
845
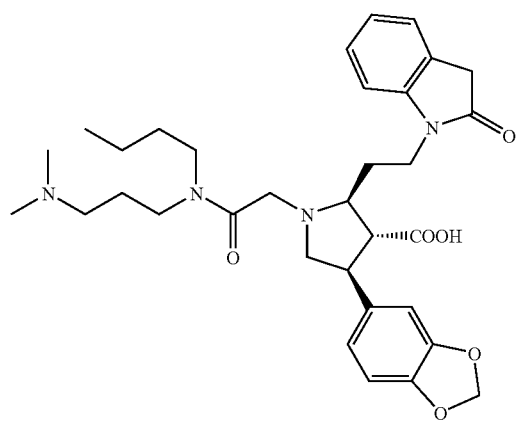
846
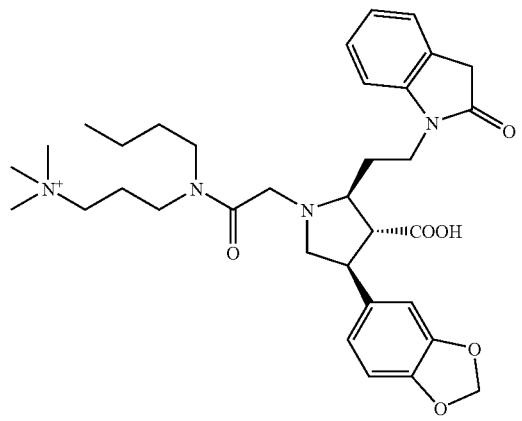
TABLE 3C-continued
847
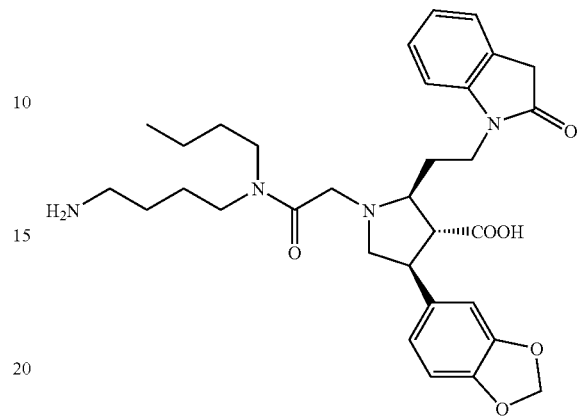
848

849

TABLE 3C-continued
850
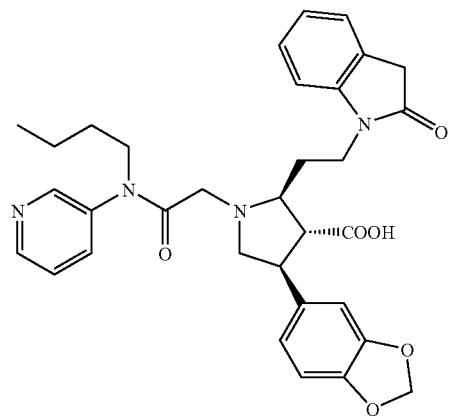
851
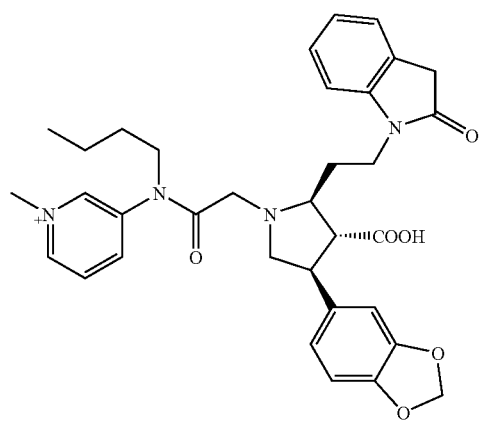
852
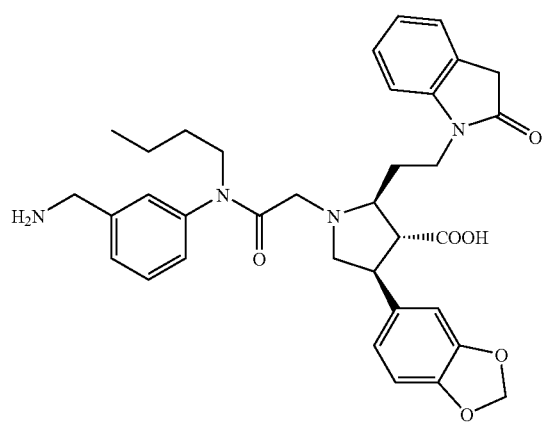
TABLE 3C-continued
853
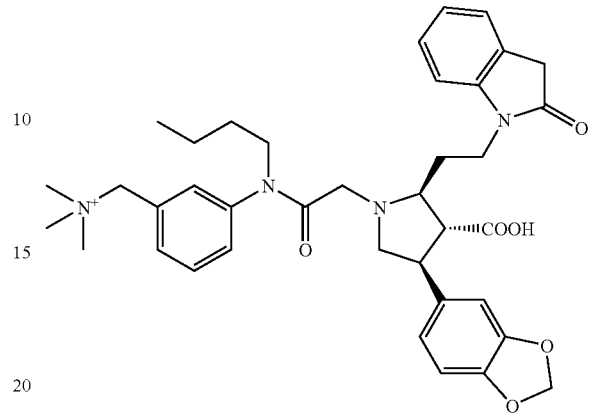
854
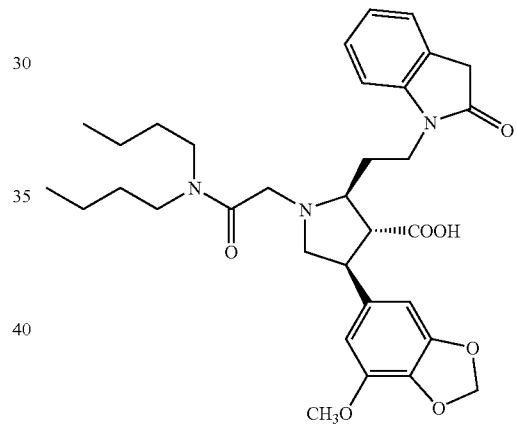
855
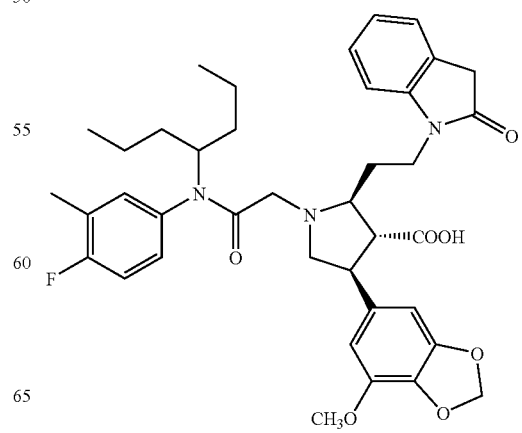

TABLE 3C-continued
856
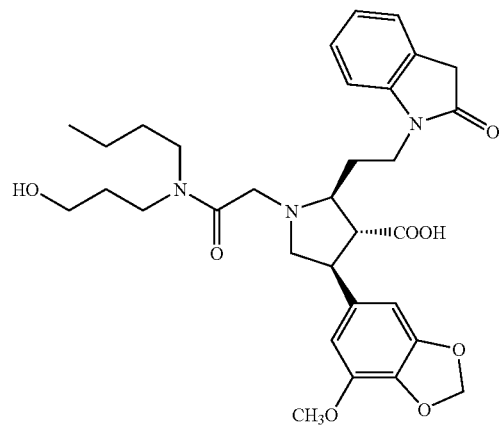
857
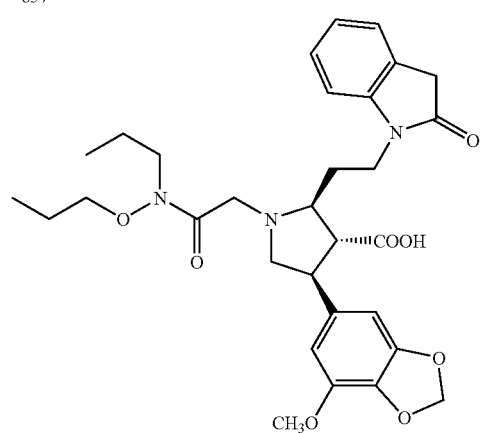
858
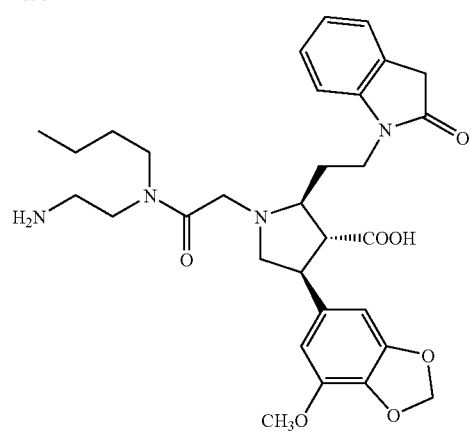
TABLE 3C-continued
859
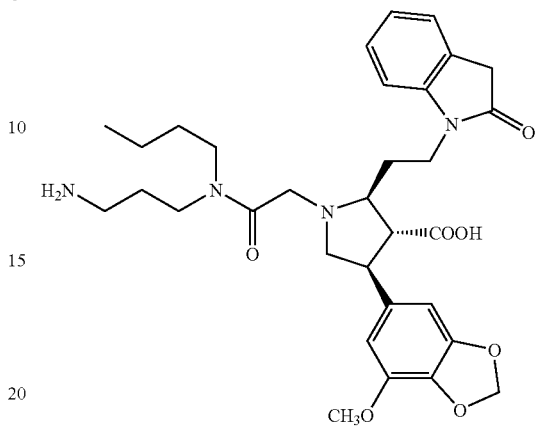
860
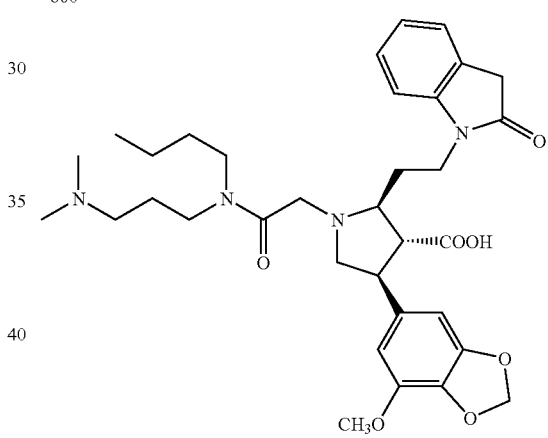
861
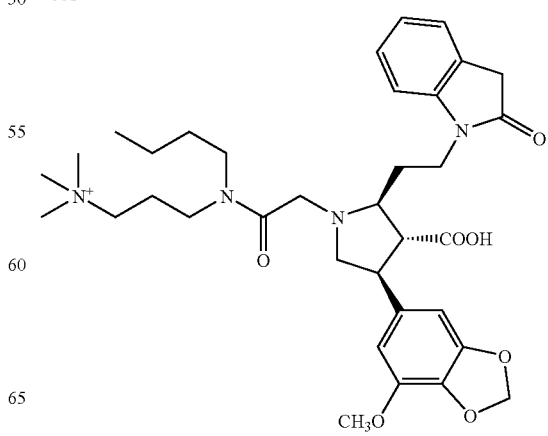

TABLE 3C-continued
862
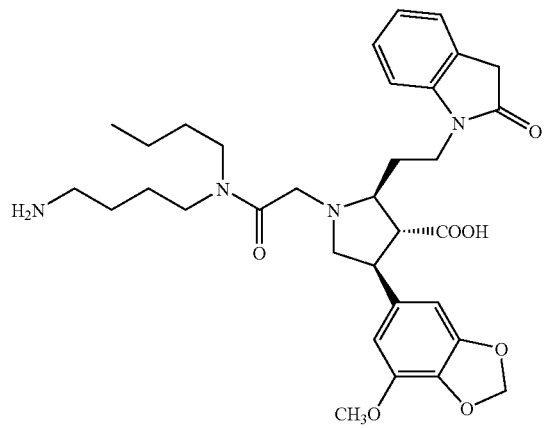
863
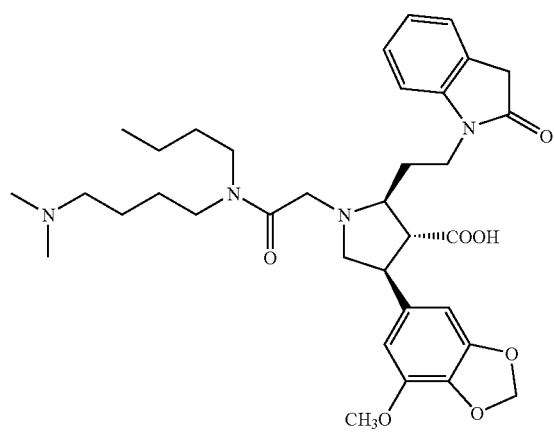
864
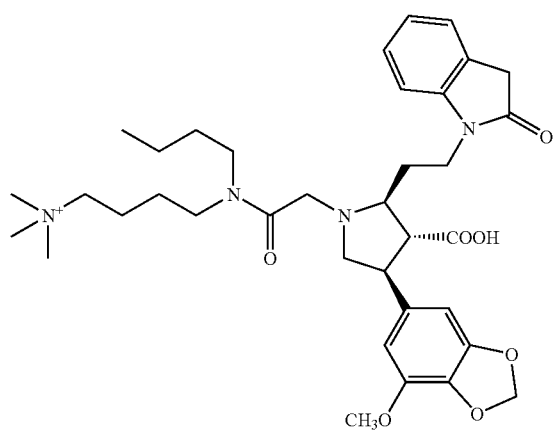
TABLE 3C-continued
865
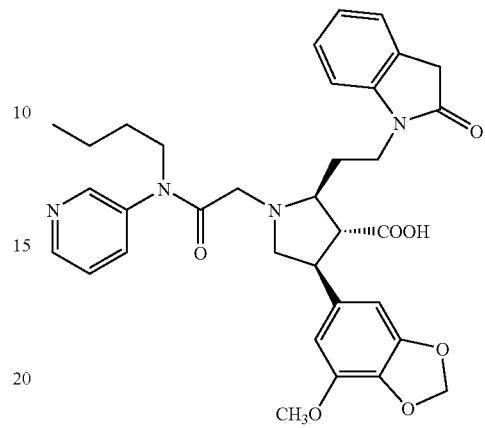
866
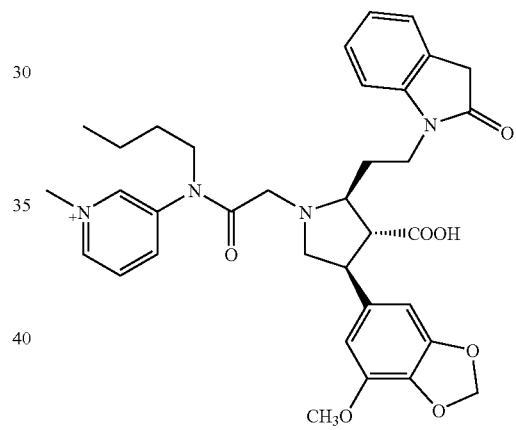
867
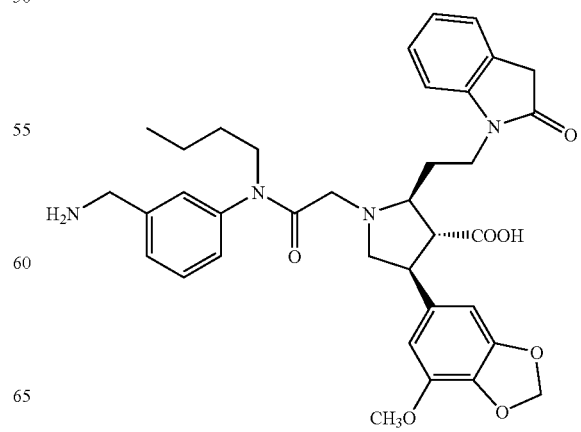

TABLE 3C-continued
868
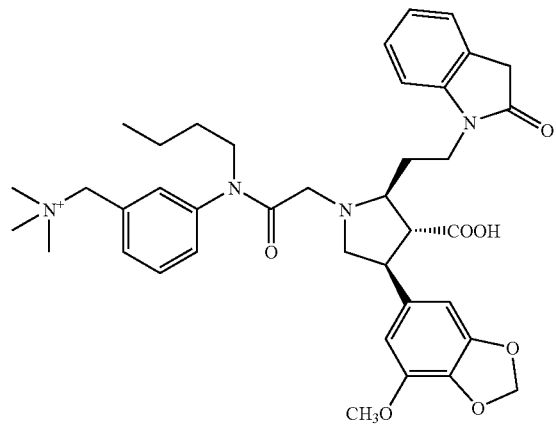
869
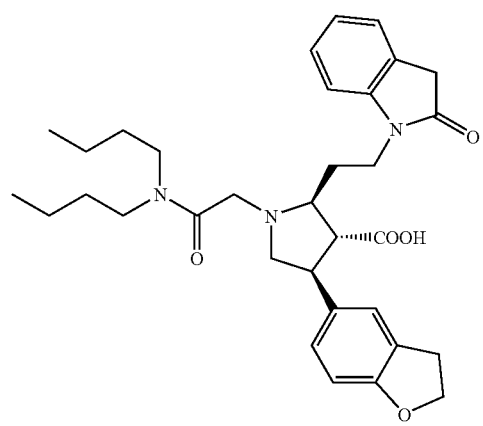
870
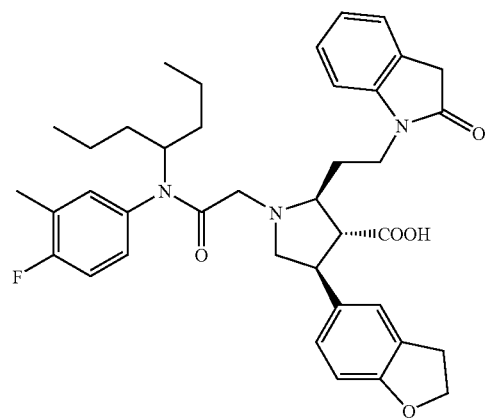
TABLE 3C-continued
871
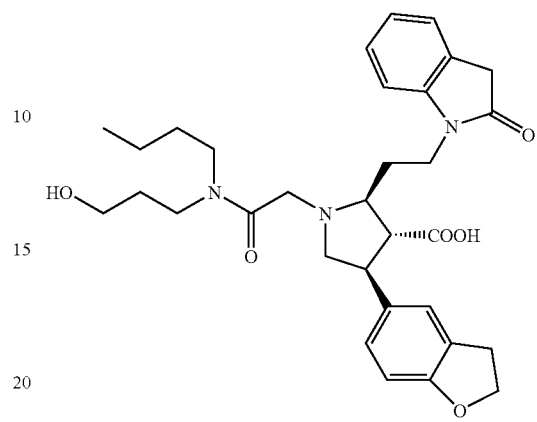
872
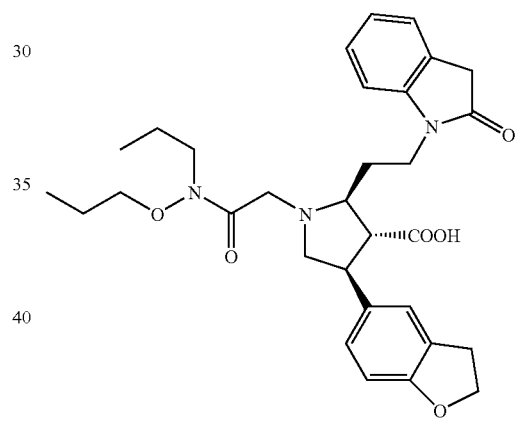
873
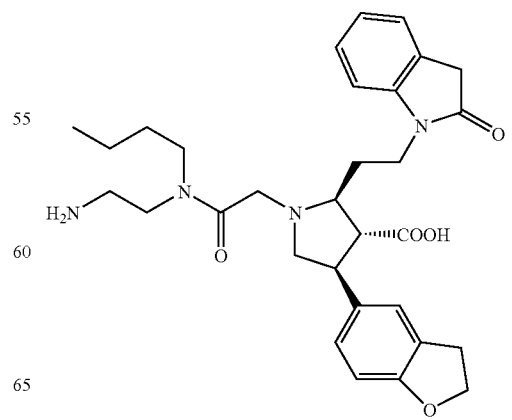

887 888
TABLE 3C-continued | TABLE 3C-continued
874
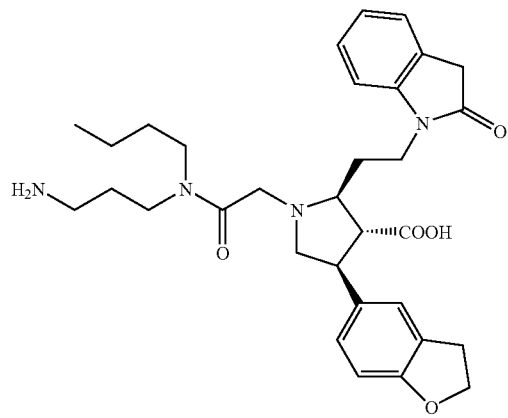
877
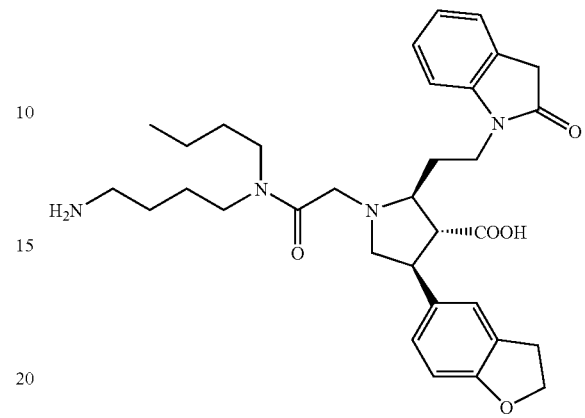
875
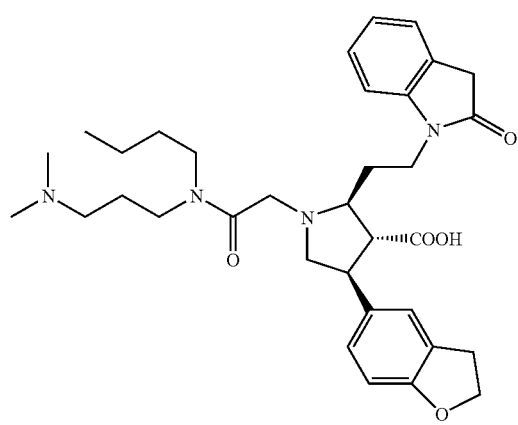
878
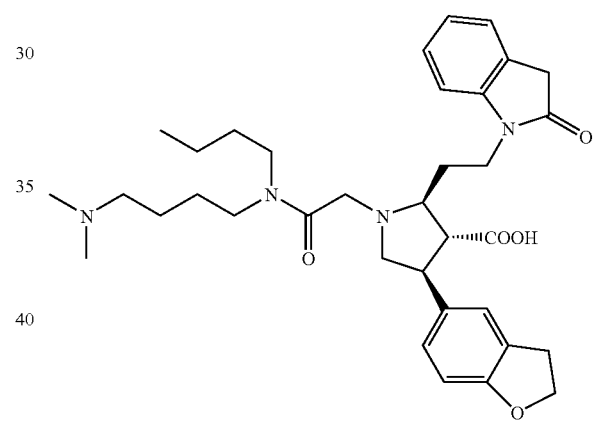
876
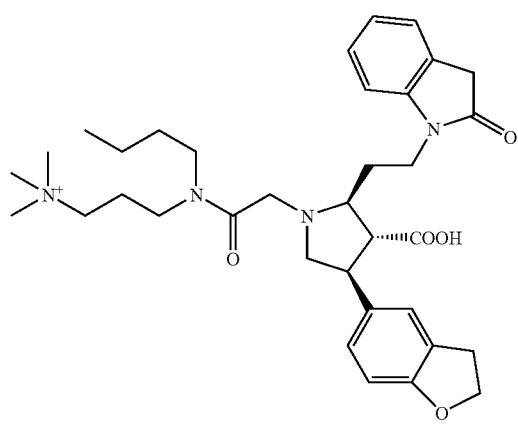
879
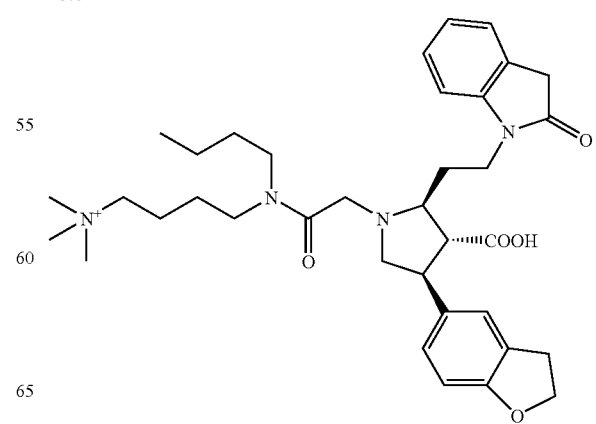

TABLE 3C-continued
880
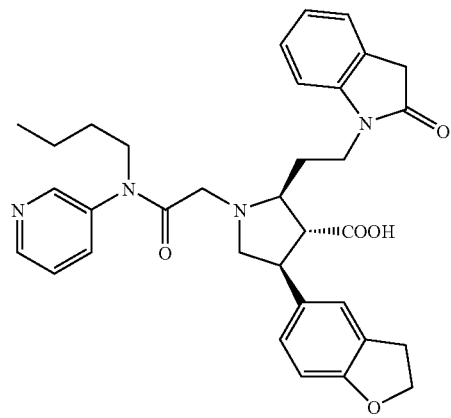
881
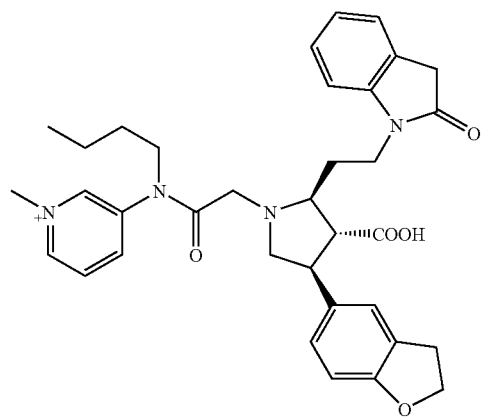
882
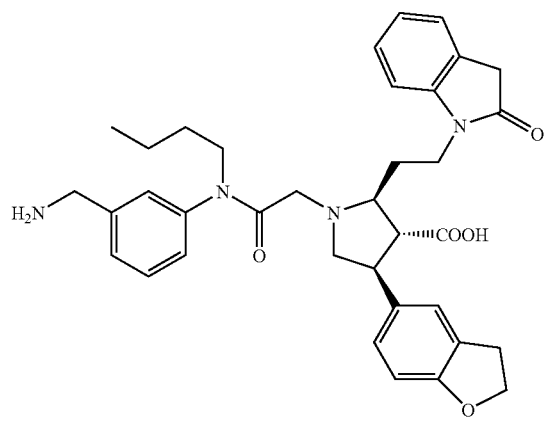
TABLE 3C-continued
883
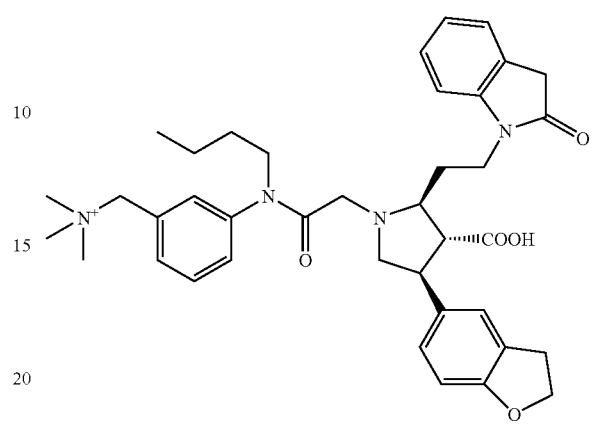
884
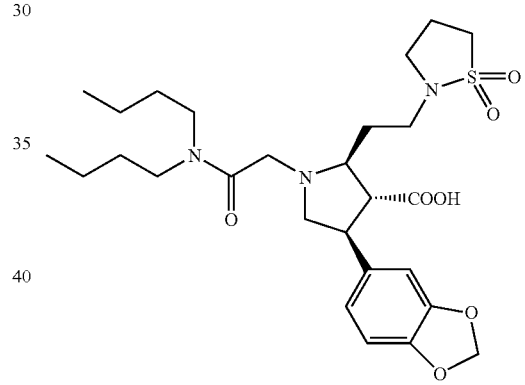
885
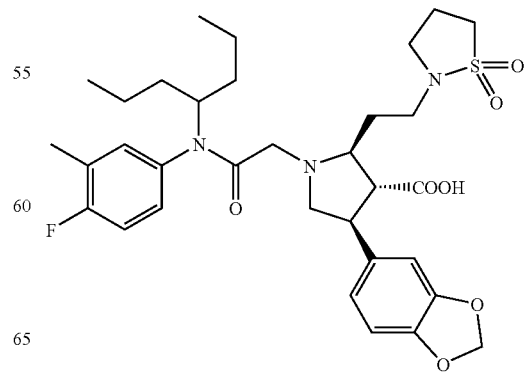

TABLE 3C-continued
886
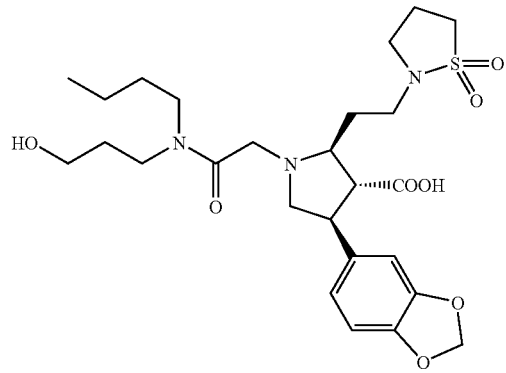
887
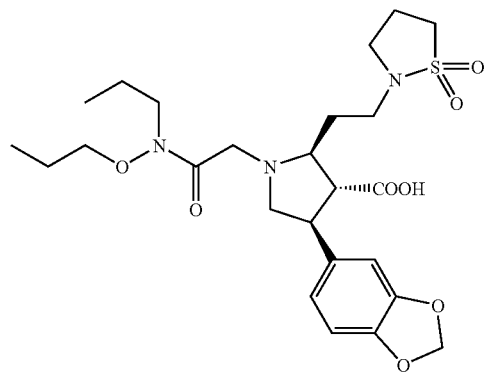
888
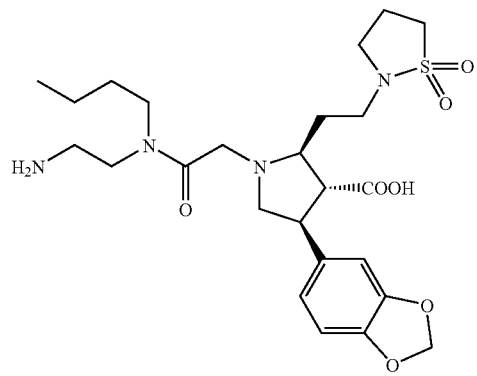
889
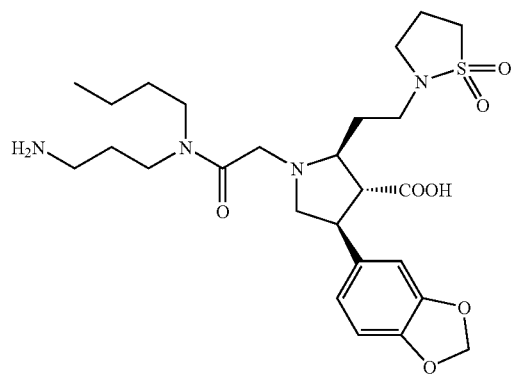
TABLE 3C-continued
890
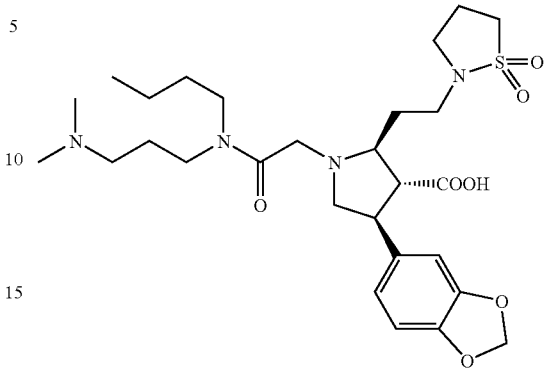
891
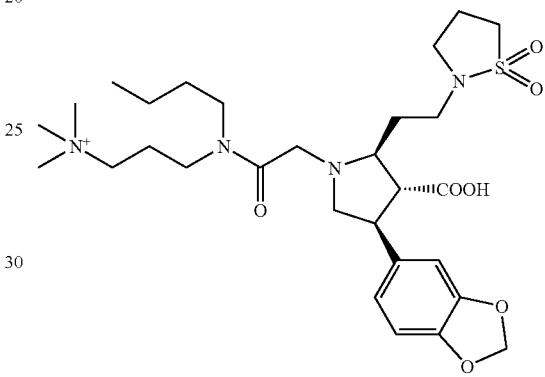
892
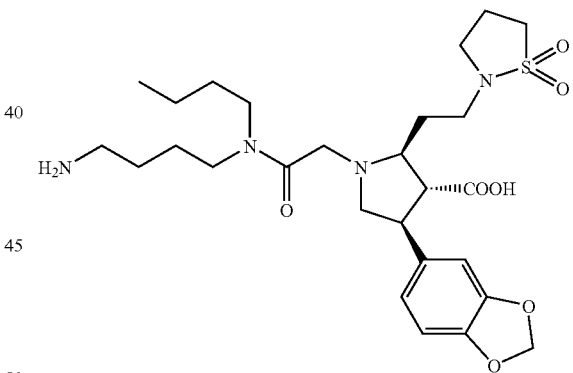
893
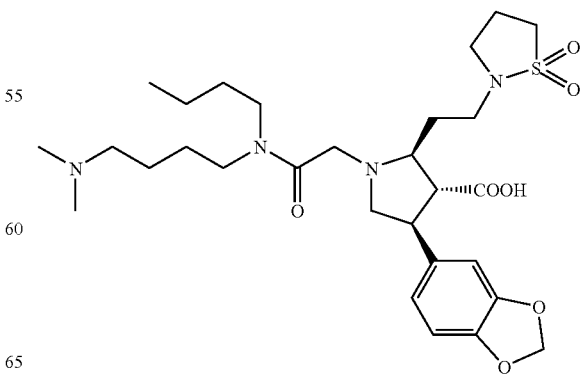

TABLE 3C-continued
894
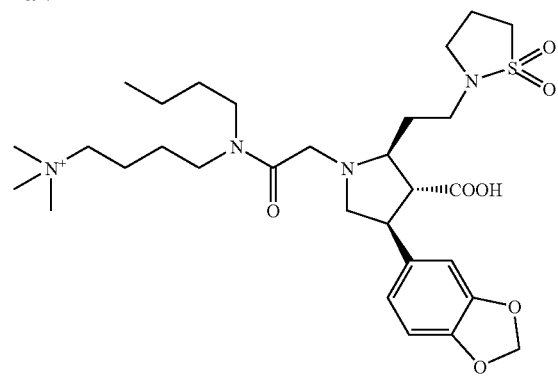
895
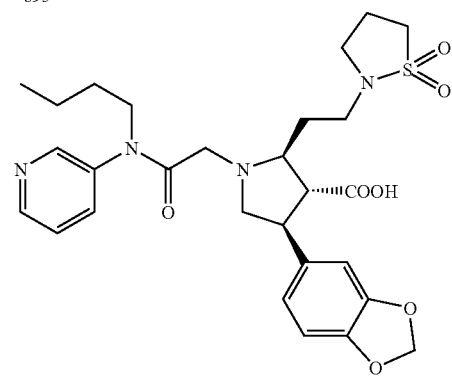
896
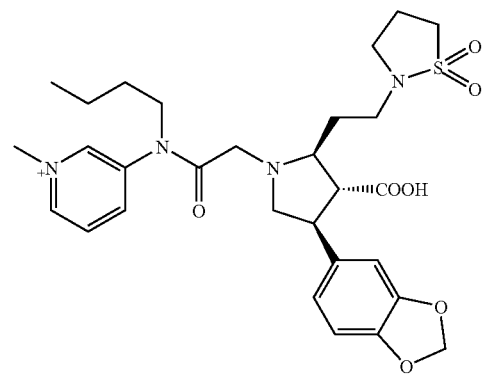
897
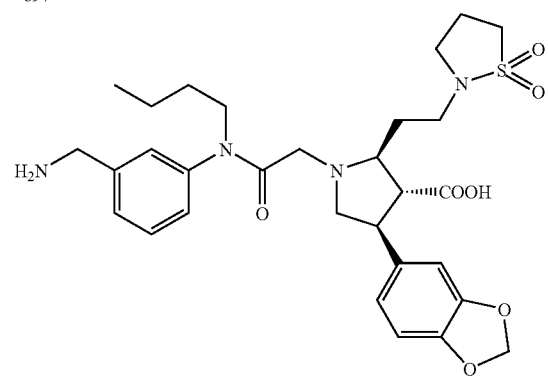
TABLE 3C-continued
898
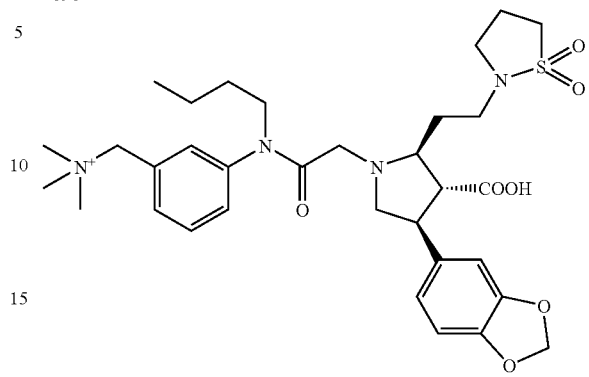
899
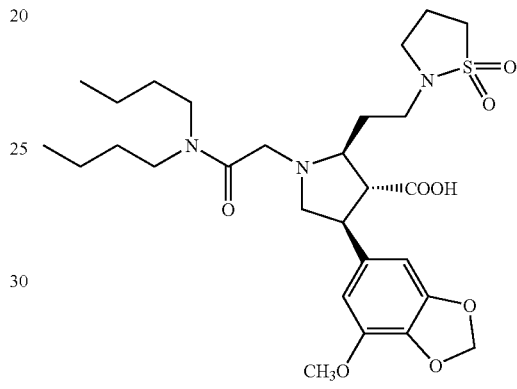
900
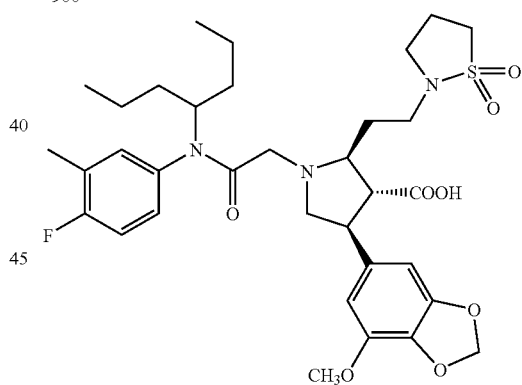
901
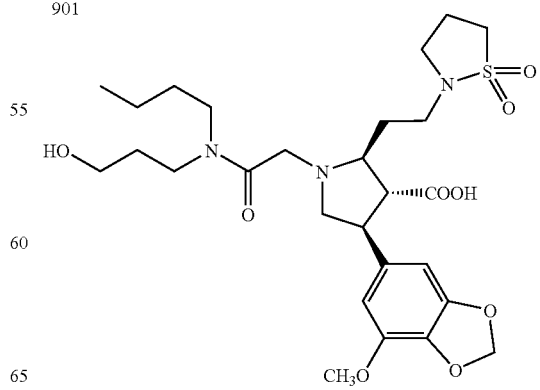

TABLE 3C-continued
902
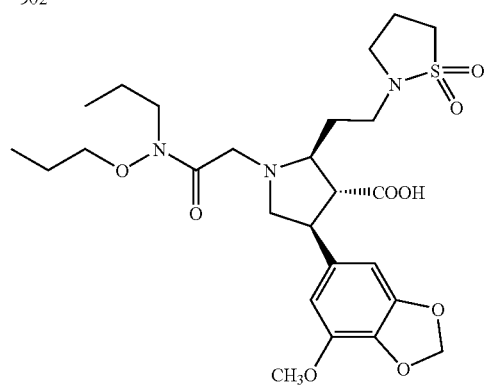
903
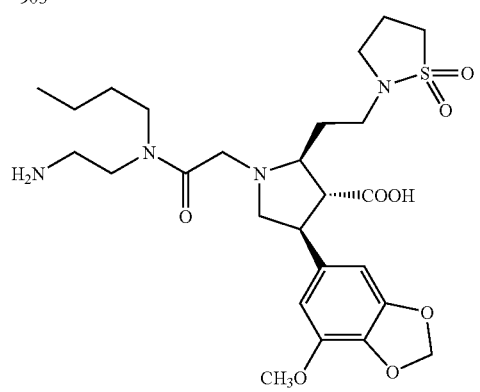
904
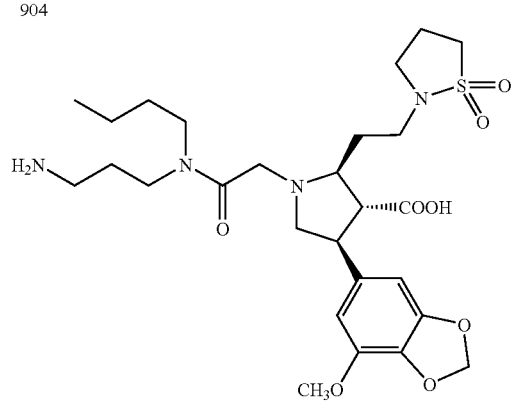
905
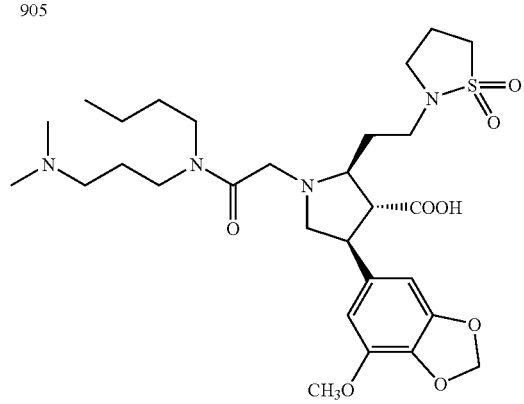
TABLE 3C-continued
906
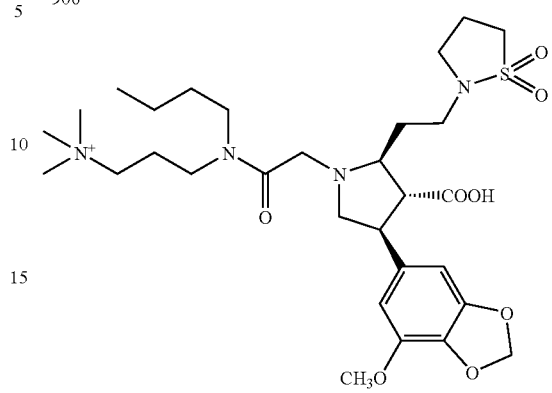
907
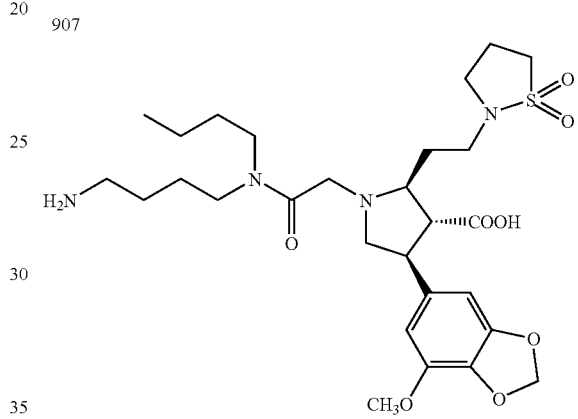
908
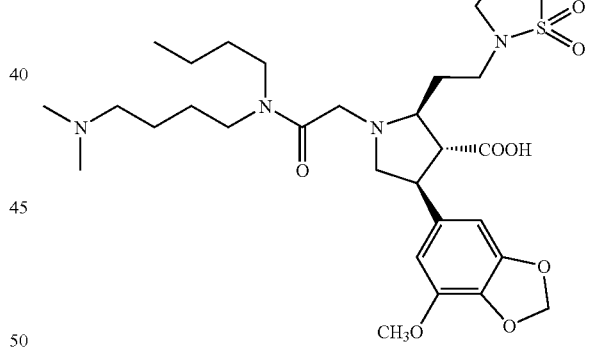
909
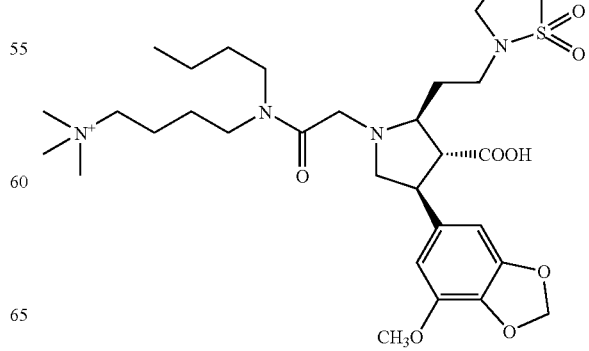

TABLE 3C-continued
910
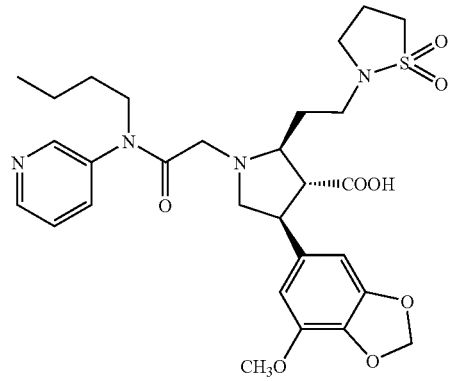
911
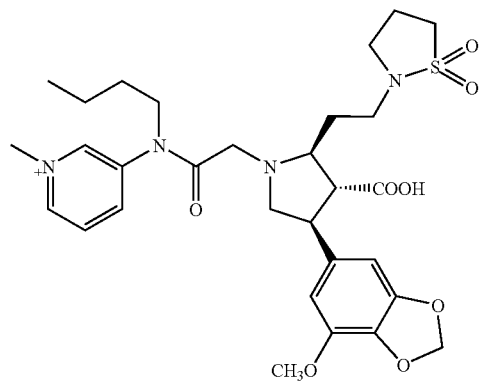
912
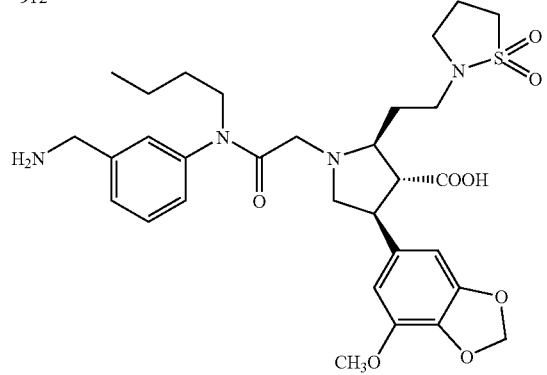
913
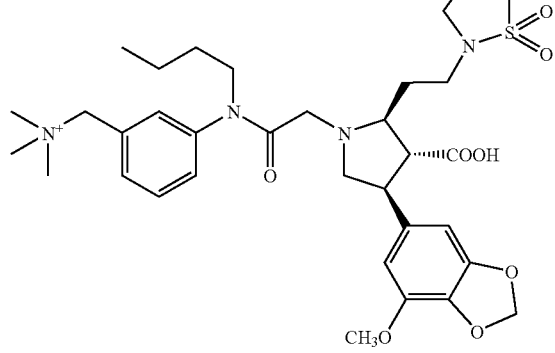
TABLE 3C-continued
914
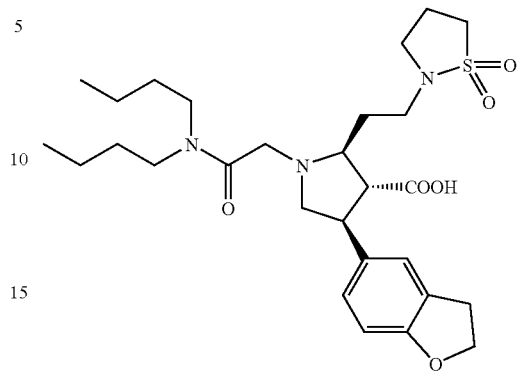
915
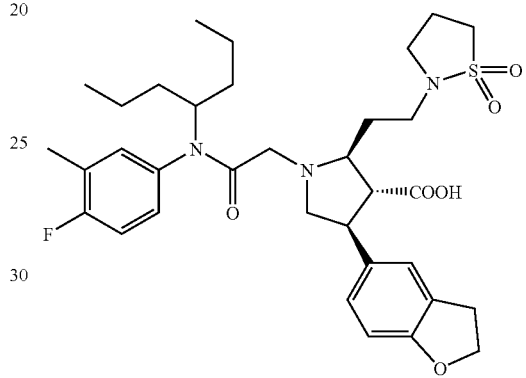
916
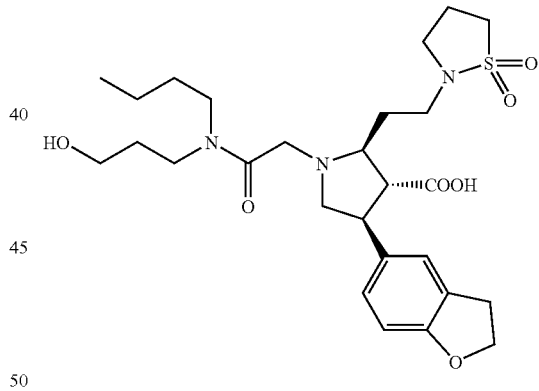
917
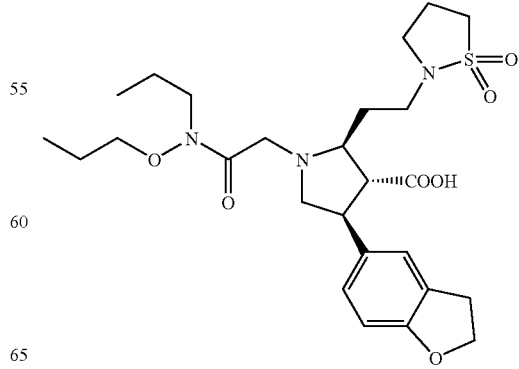

US 7,208,517 B1
| 899 | 900 |
|---|---|
| TABLE 3C-continued | TABLE 3C-continued |
918
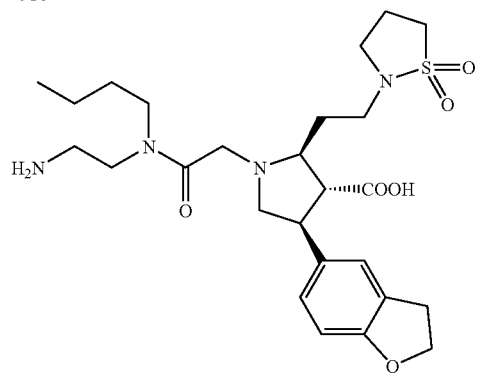
919
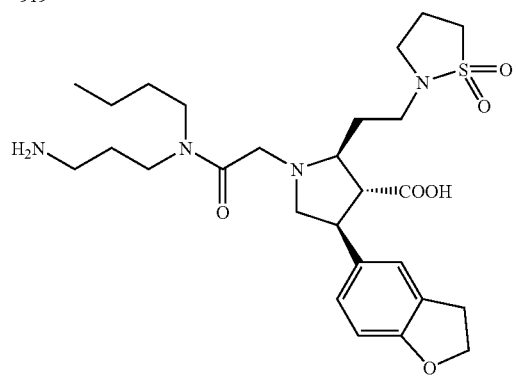
920
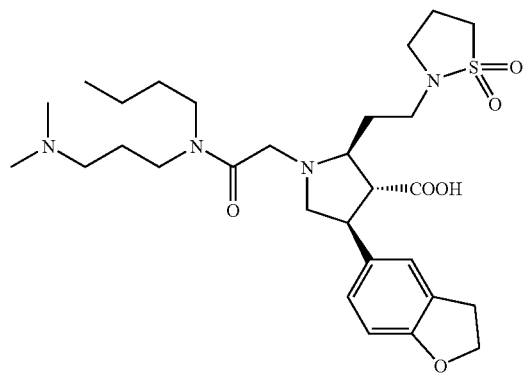
921
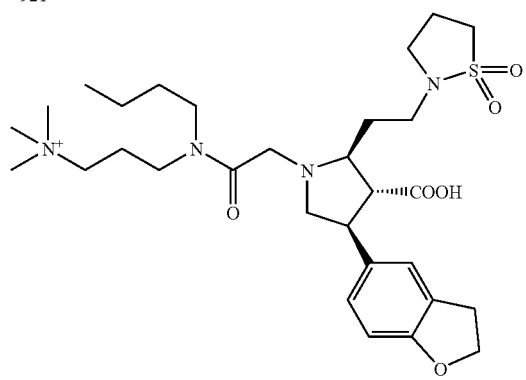
922
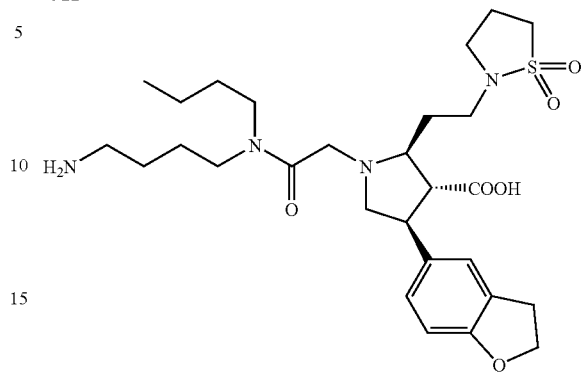
923
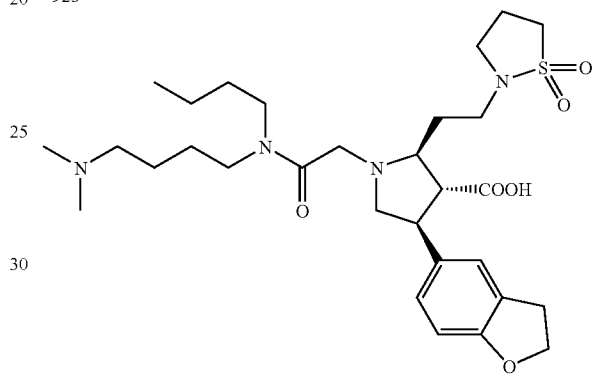
924
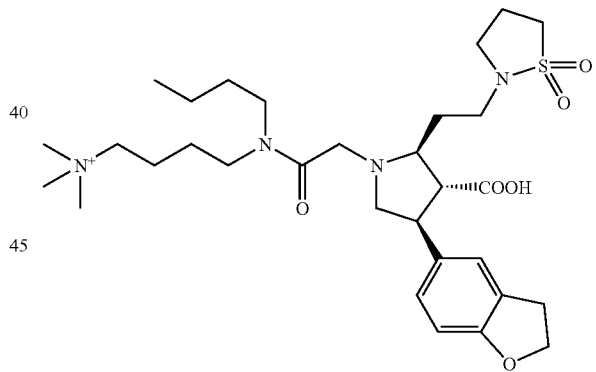
925
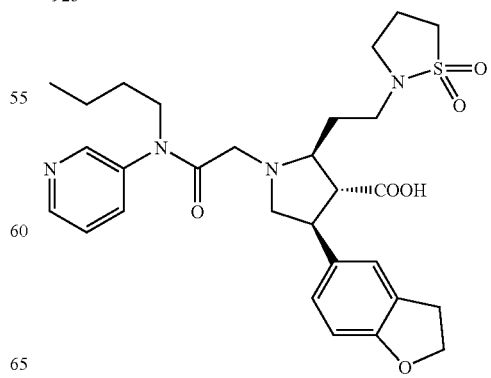

TABLE 3C-continued
926 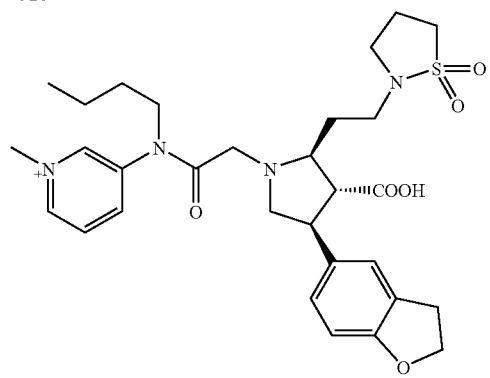
927 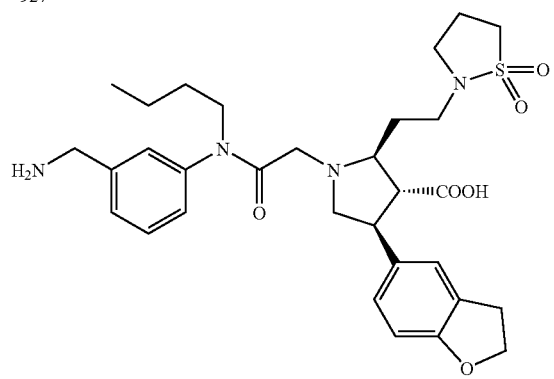
928 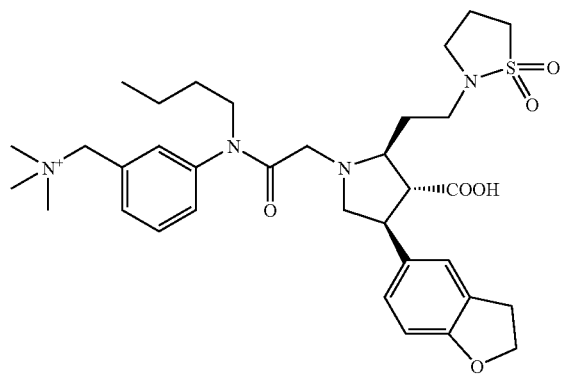
929 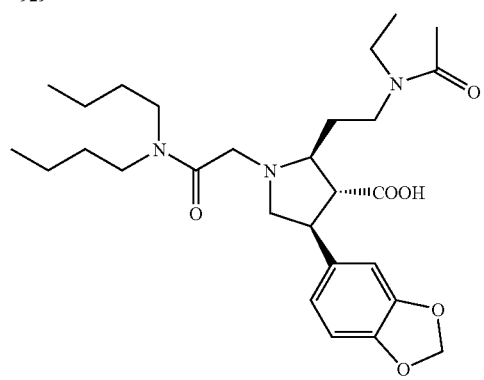
TABLE 3C-continued
930 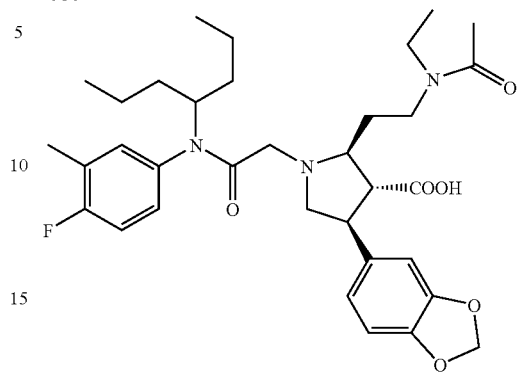
931 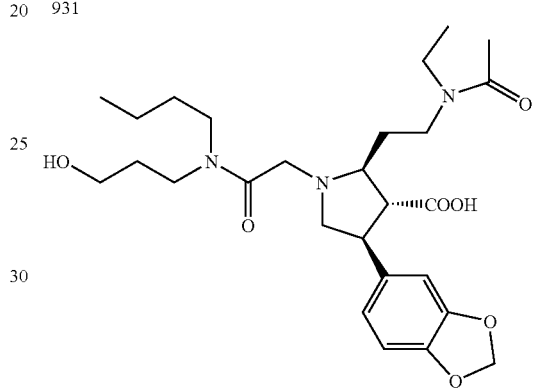
932 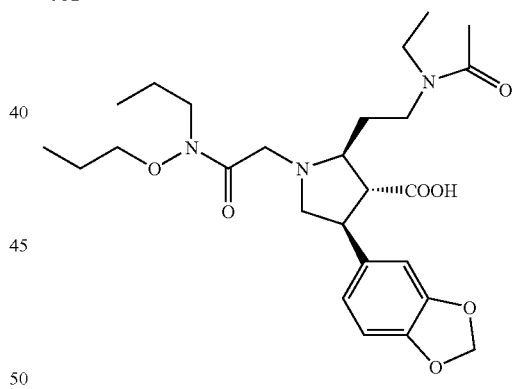
933 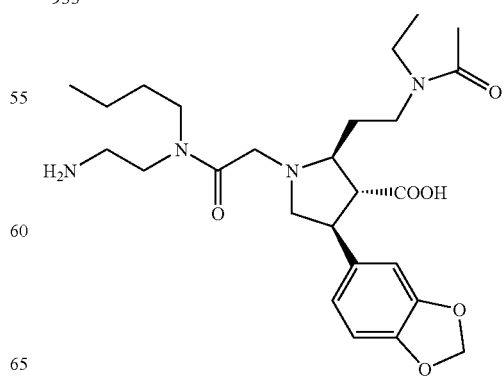

TABLE 3C-continued
934
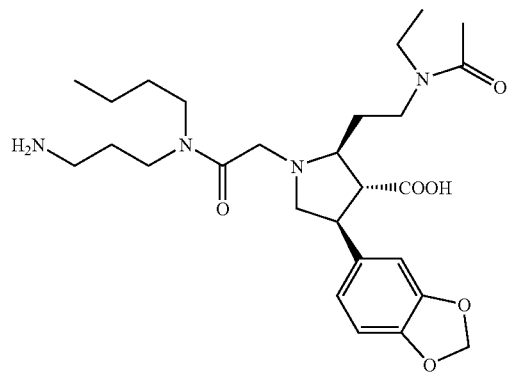
935
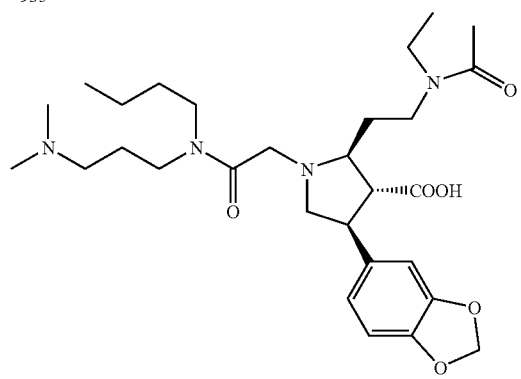
936
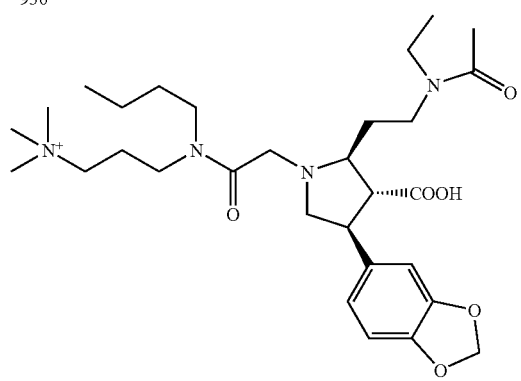
937
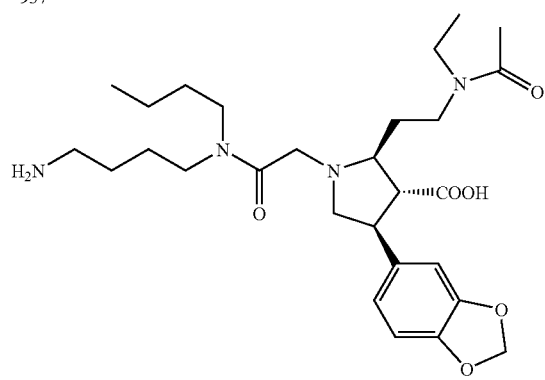
TABLE 3C-continued
938
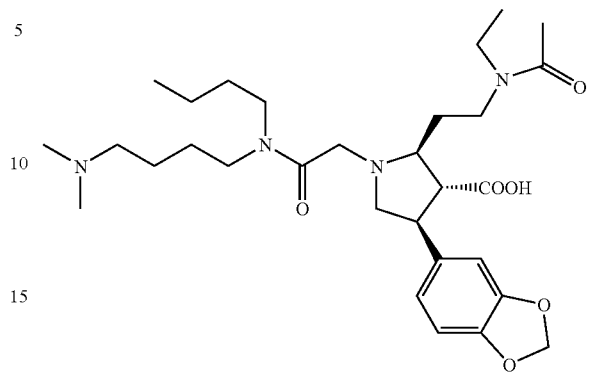
939
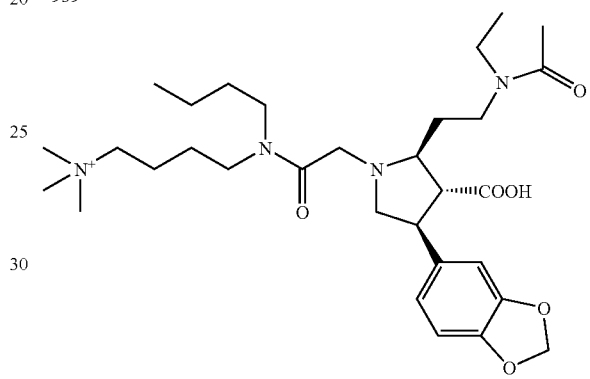
940
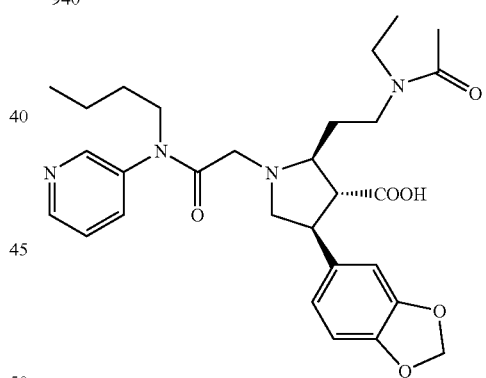
941
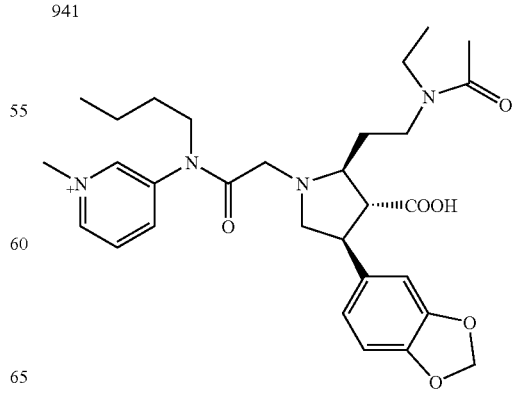

TABLE 3C-continued
942
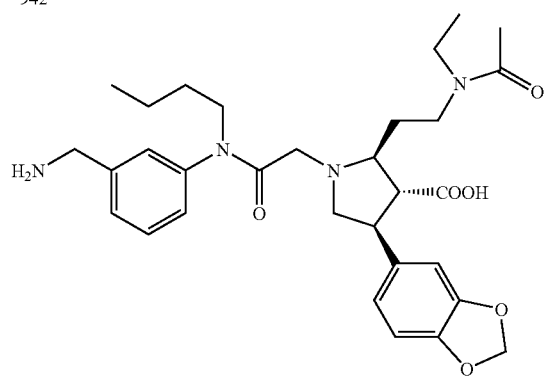
943
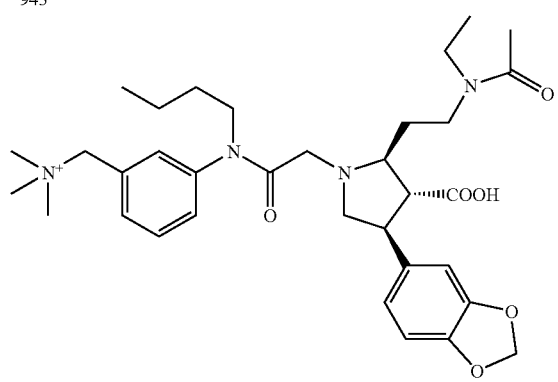
944
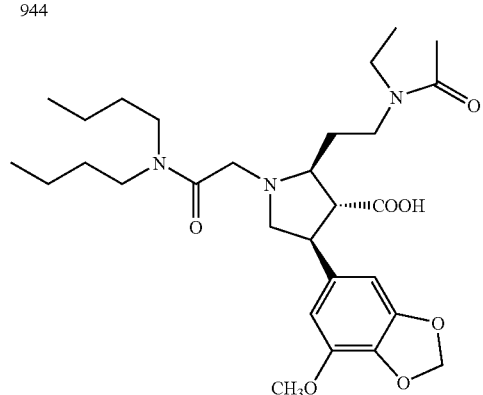
945
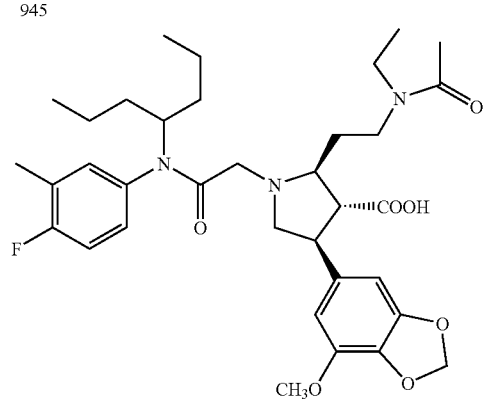
TABLE 3C-continued
946
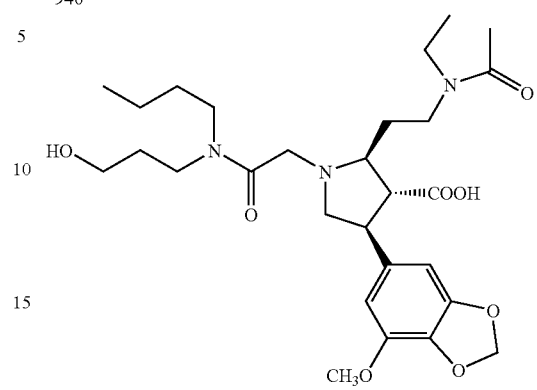
947
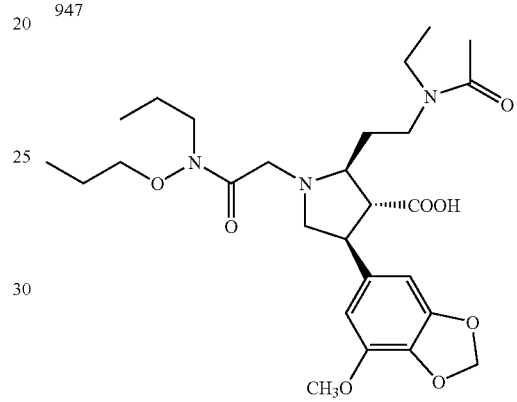
948
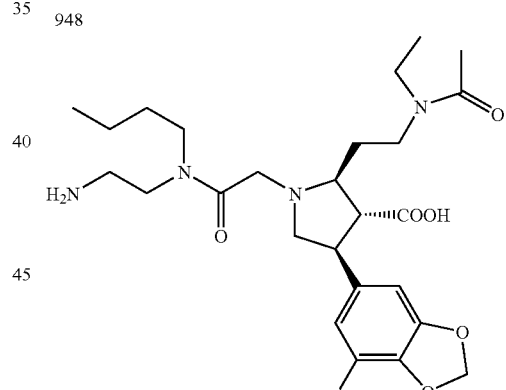
949
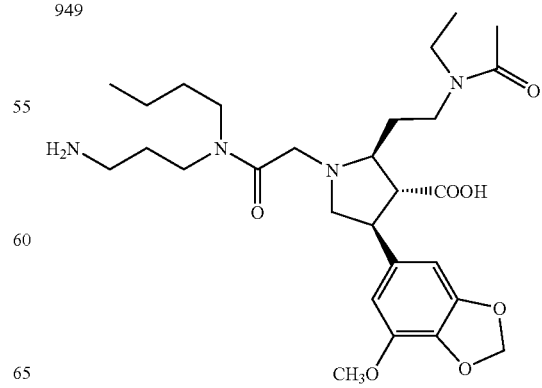

US 7,208,517 B1
TABLE 3C-continued
950
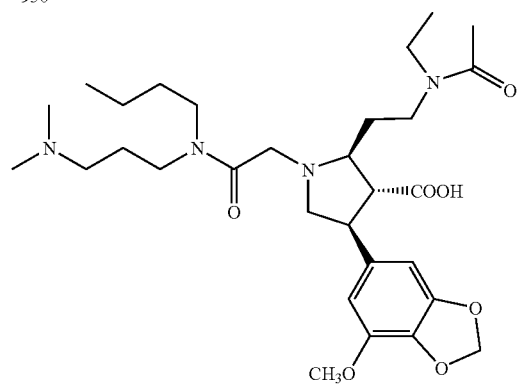
951
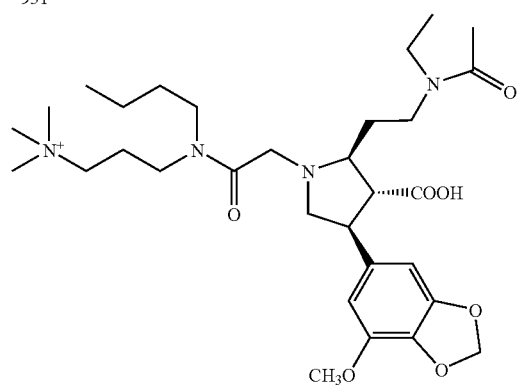
952
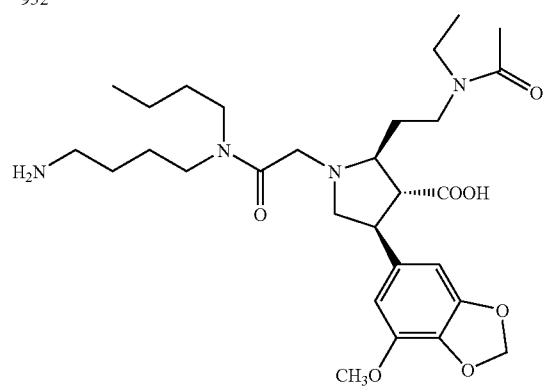
953
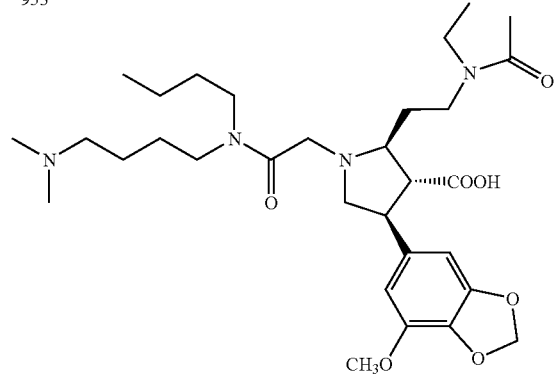
TABLE 3C-continued
954
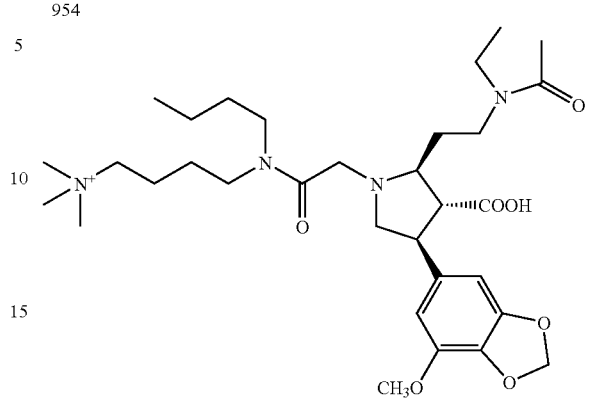
955
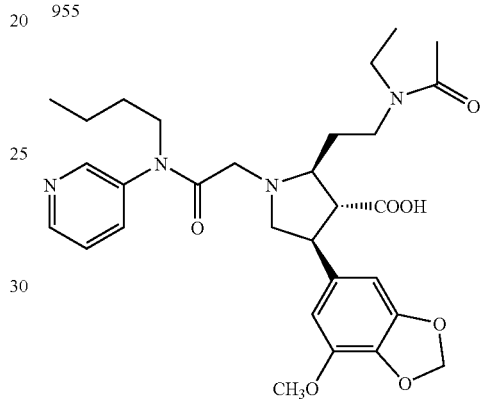
956
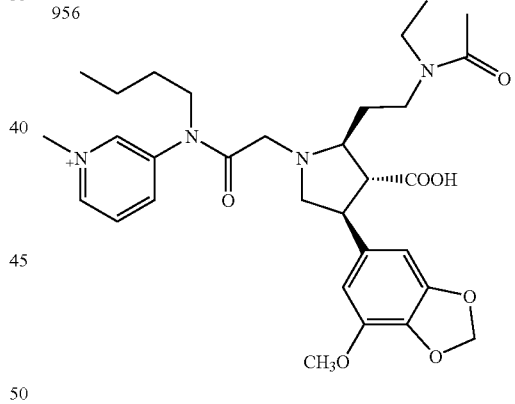
957
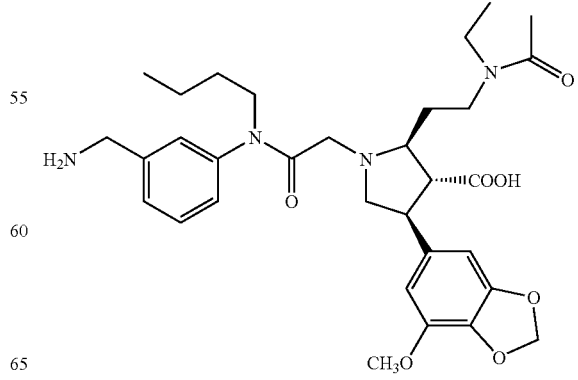

TABLE 3C-continued
958
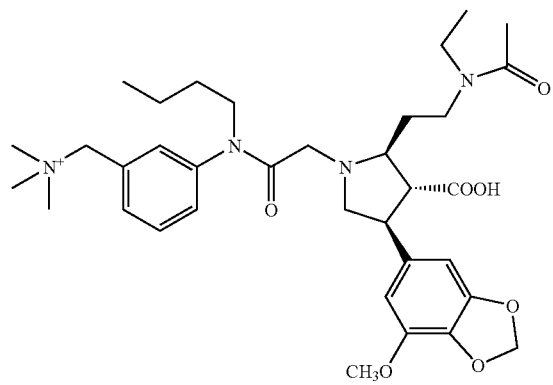
959
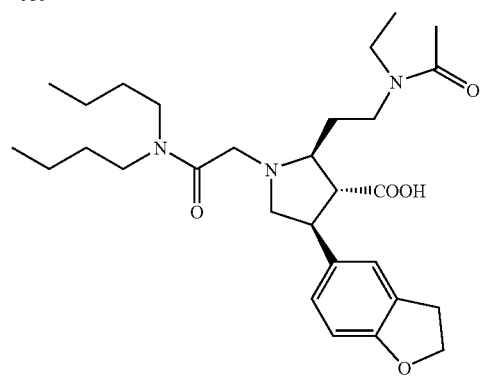
960
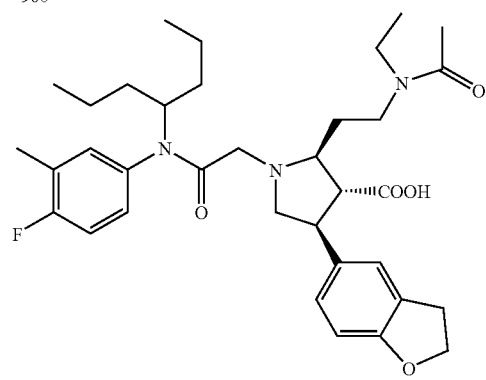
961
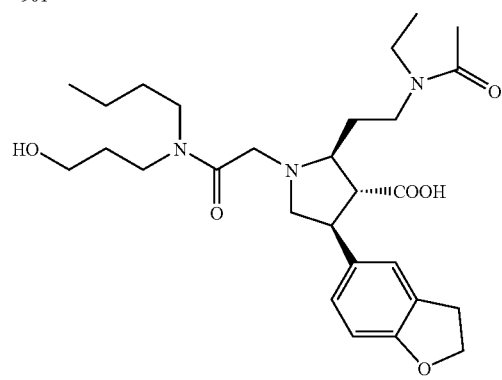
TABLE 3C-continued
962
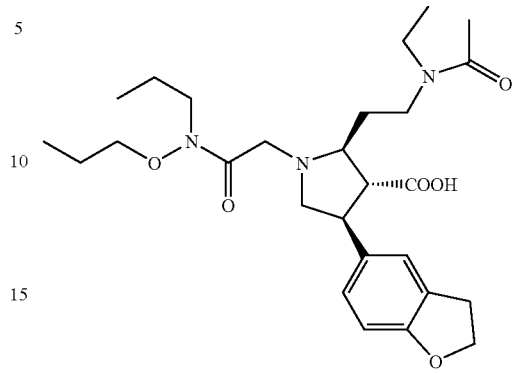
963
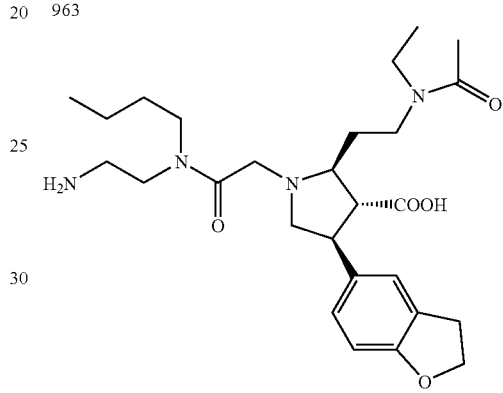
964
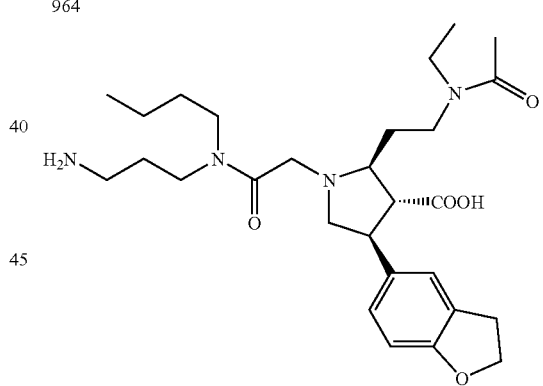
965
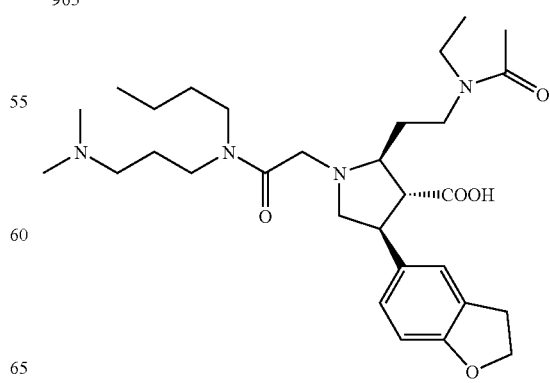

| 911 | 912 |
|---|---|
| TABLE 3C-continued | TABLE 3C-continued |
| 966 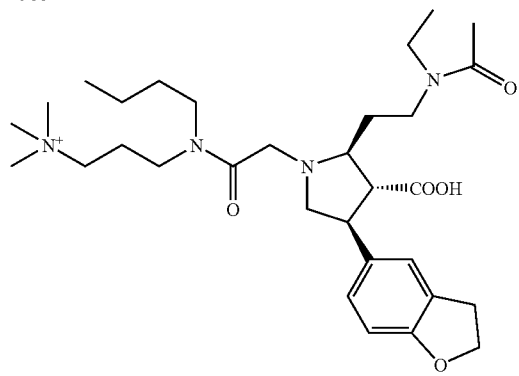 | 970 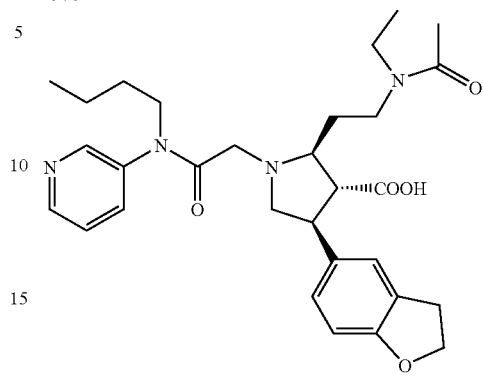 |
| 967 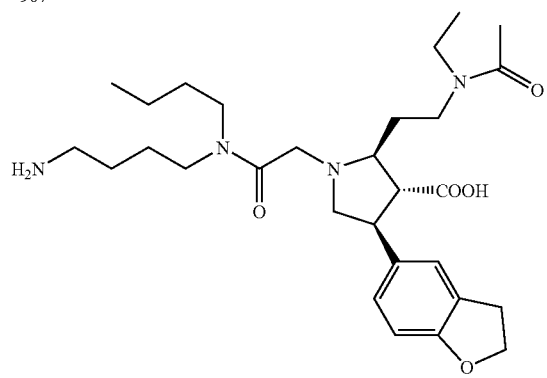 | 971 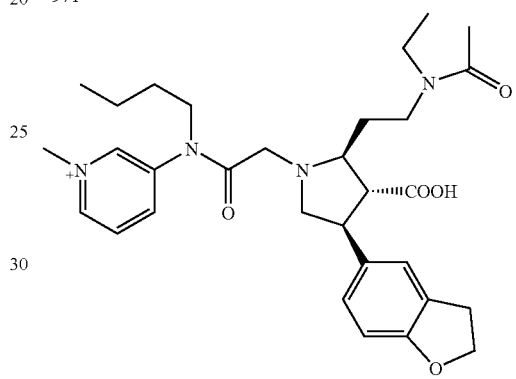 |
| 968 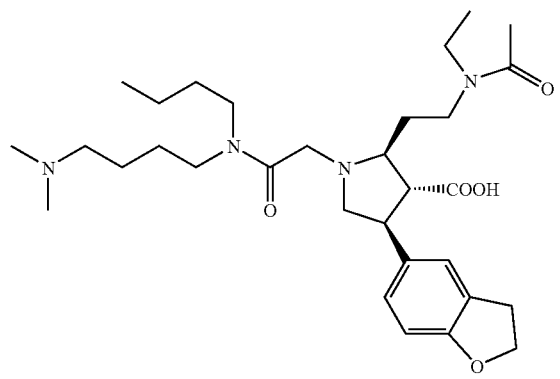 | 972 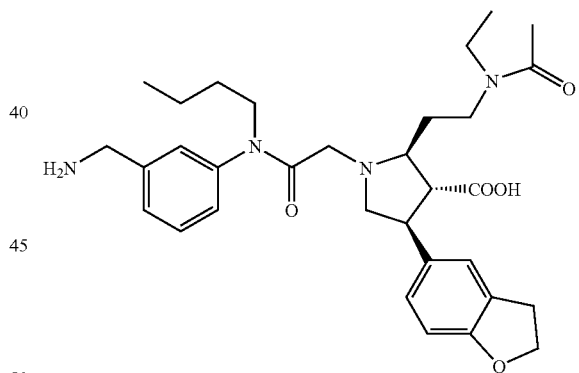 |
| 969 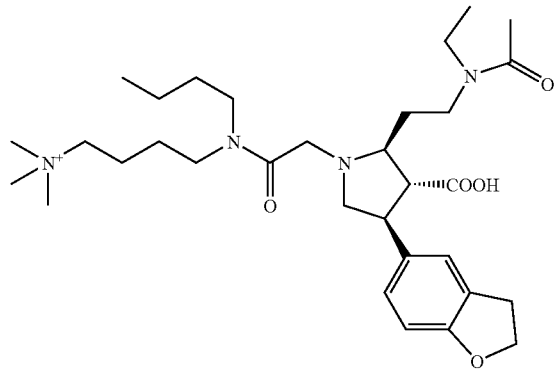 | 973 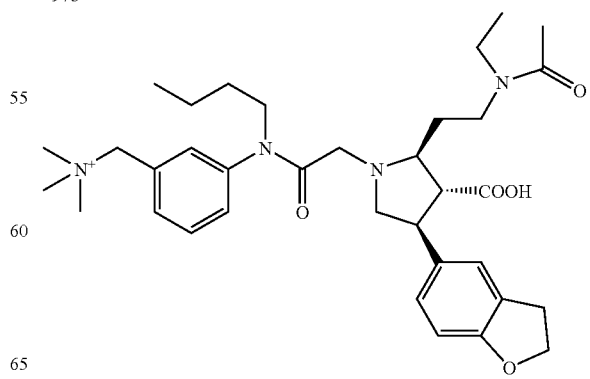 |

TABLE 3C-continued
974
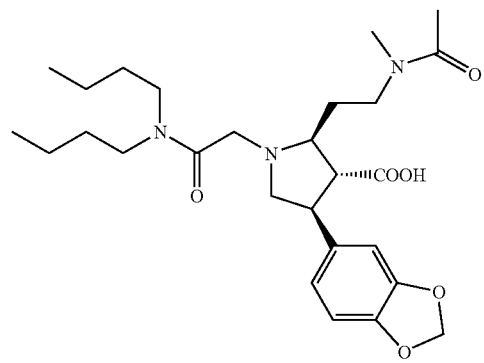
975
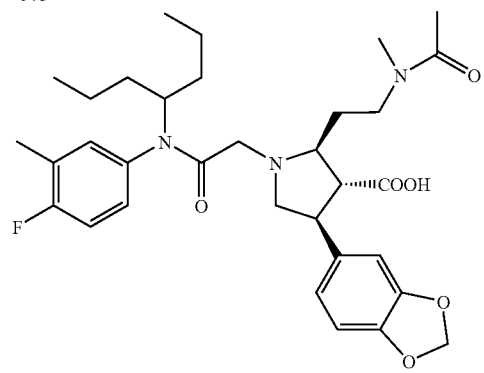
976
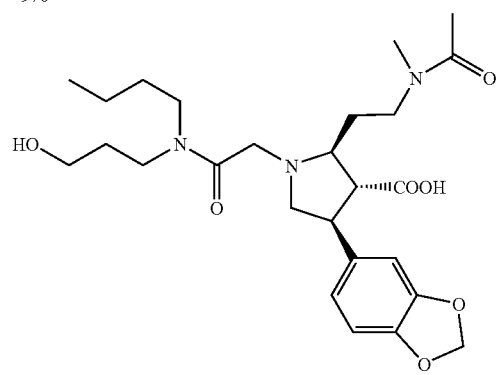
977
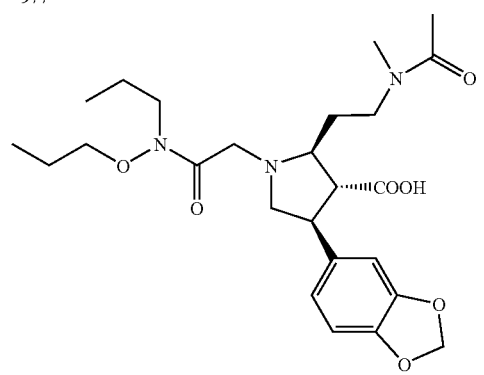
TABLE 3C-continued
978
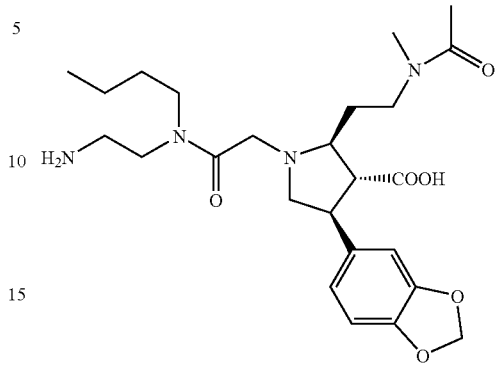
979
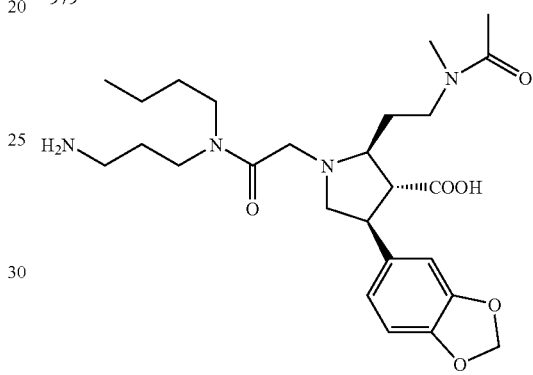
980
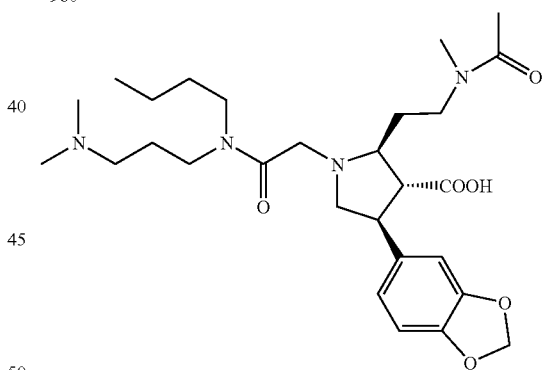
981
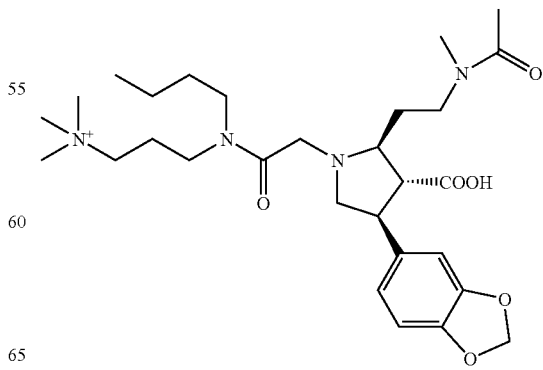

| 915 | 916 |
|---|---|
| TABLE 3C-continued | TABLE 3C-continued |
| 982 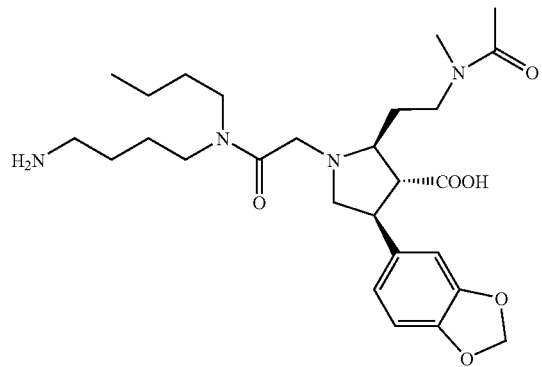 | 986 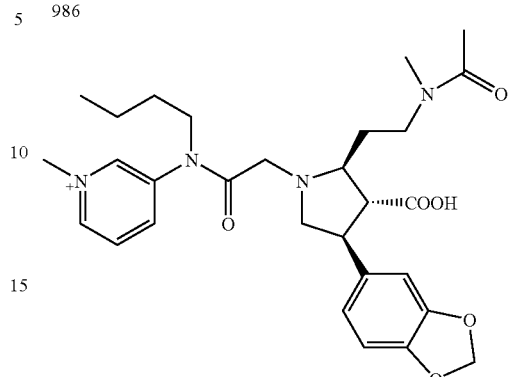 |
| 983 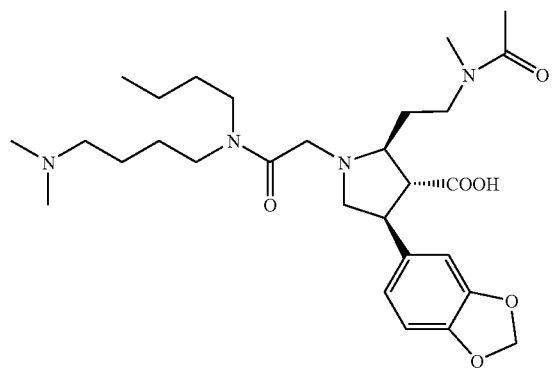 | 987 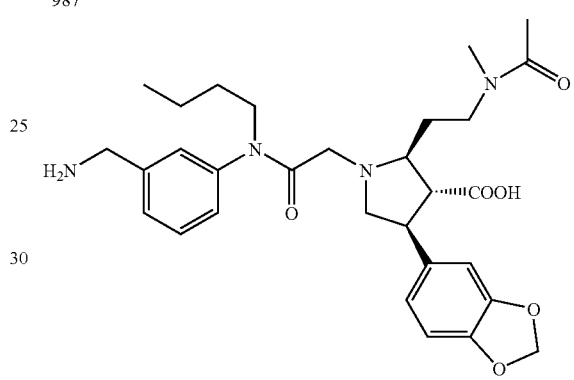 |
| 984 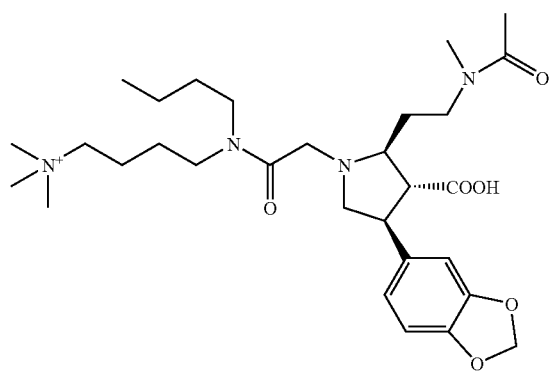 | 988 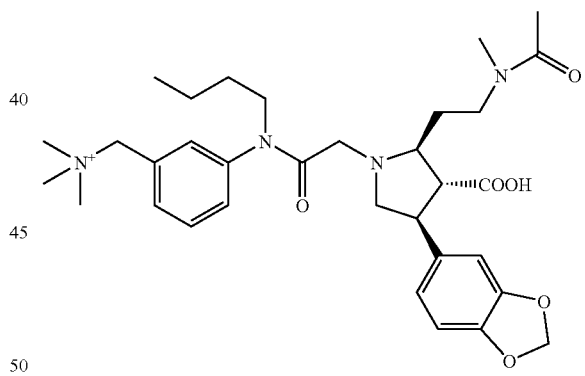 |
| 985 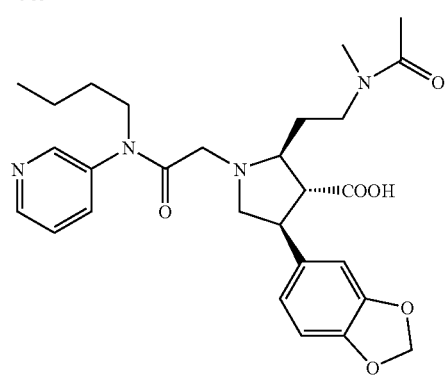 | 989 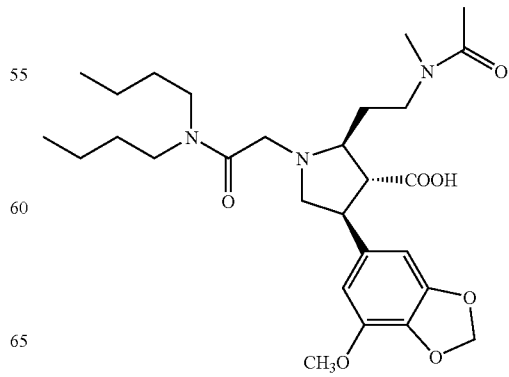 |

TABLE 3C-continued
990
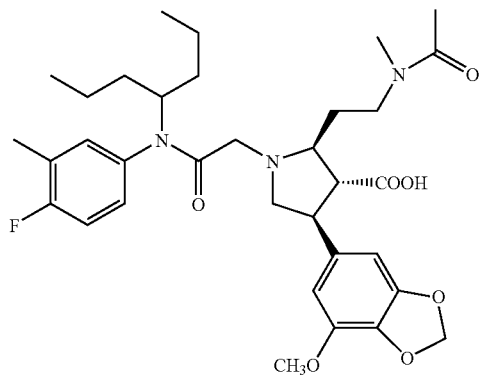
991
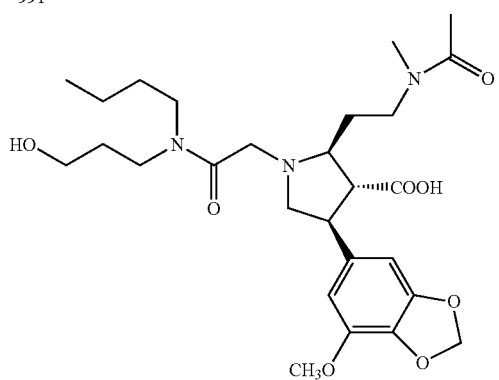
992
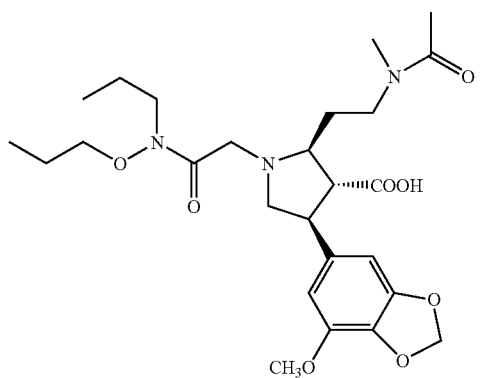
993
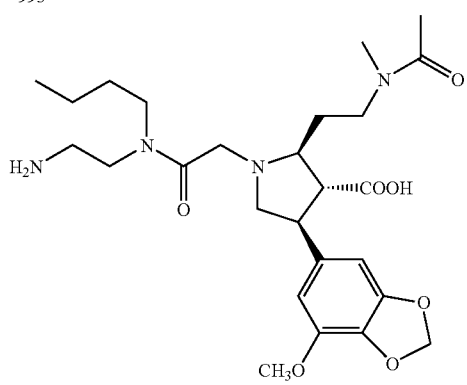
TABLE 3C-continued
994
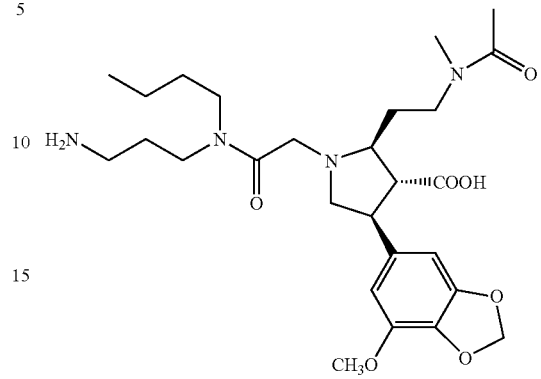
995
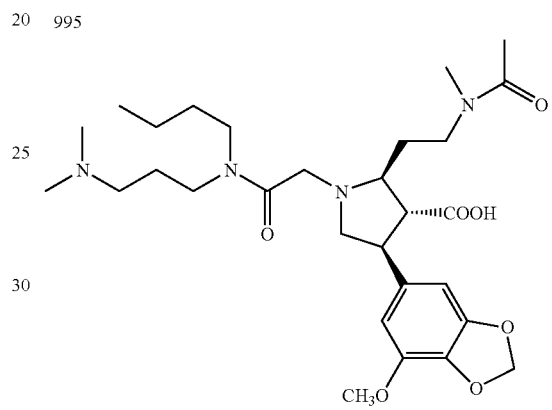
996
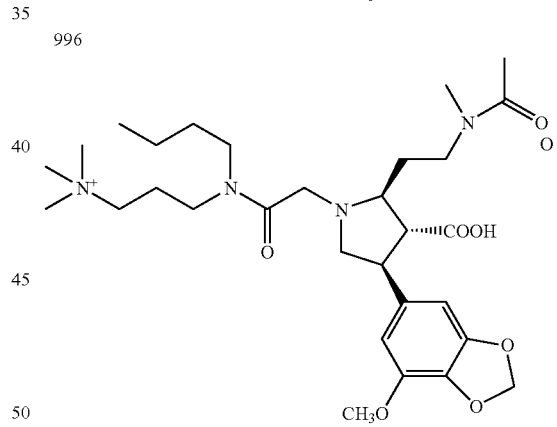
997
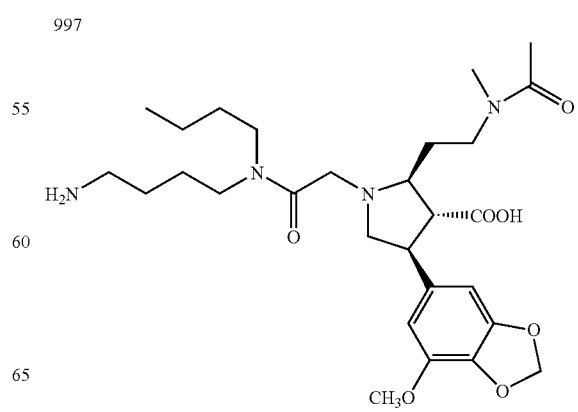

TABLE 3C-continued
998
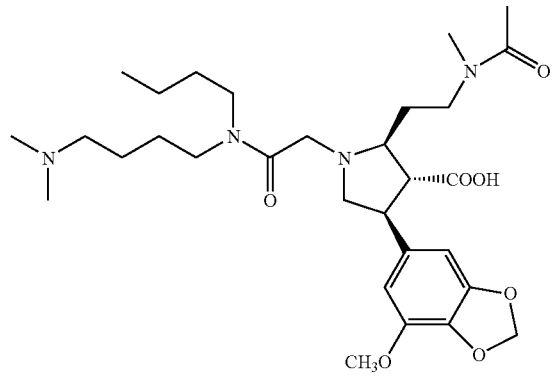
999
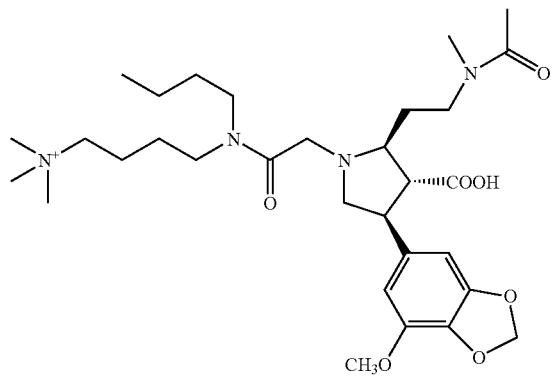
1000
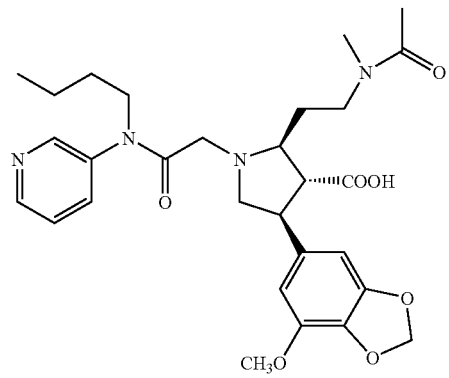
1001
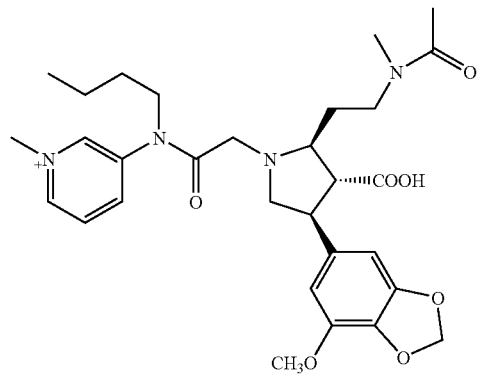
TABLE 3C-continued
1002
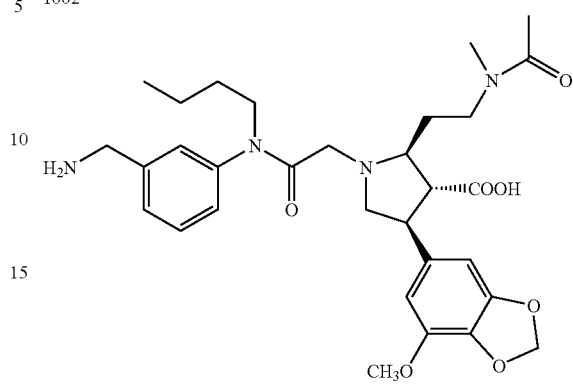
1003
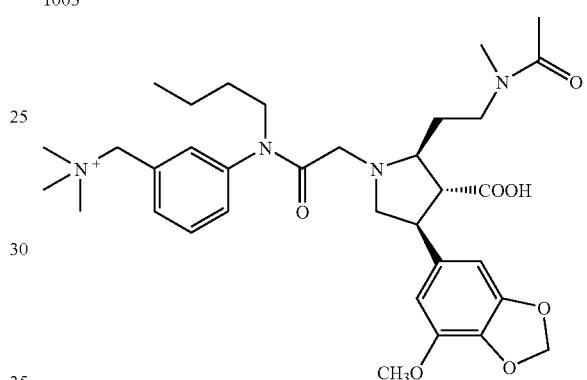
1004
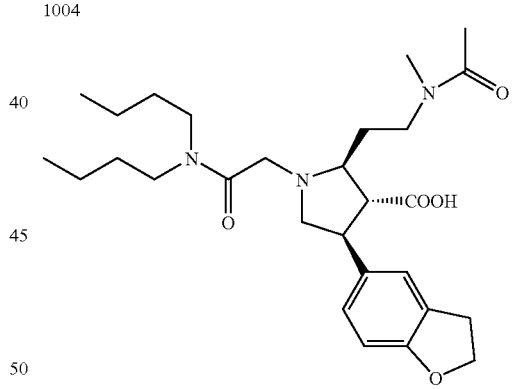
1005
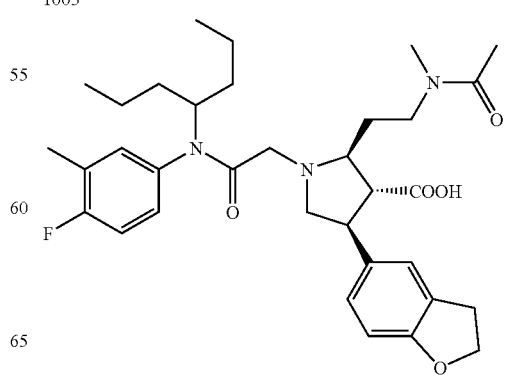

| 921 | 922 |
|---|---|
| TABLE 3C-continued | TABLE 3C-continued |
| 1006 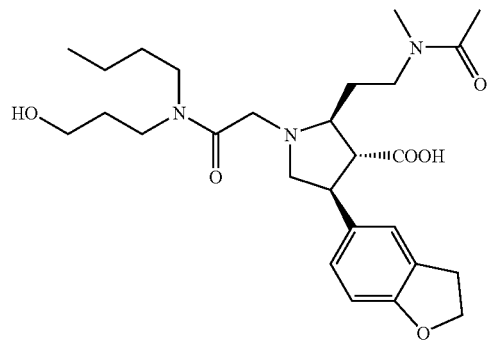 | 1010 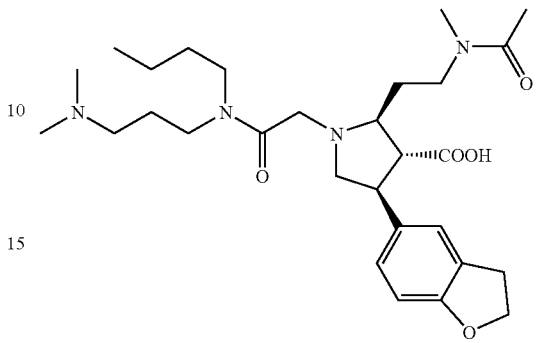 |
| 1007 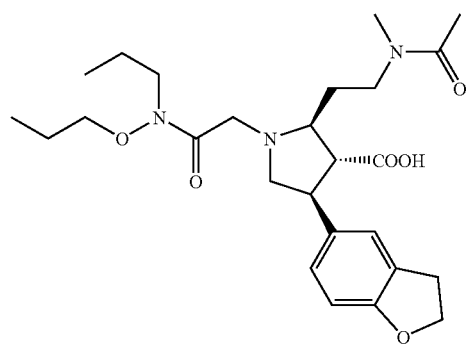 | 1011 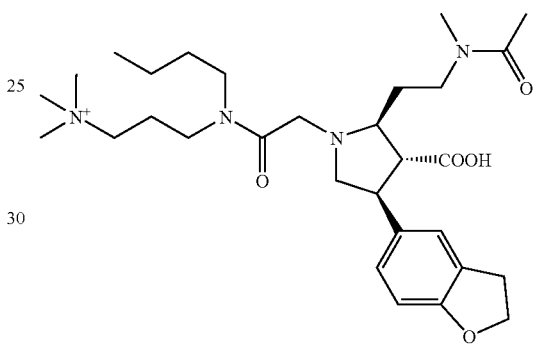 |
| 1008 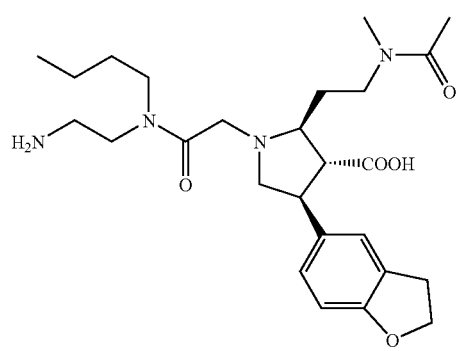 | 1012 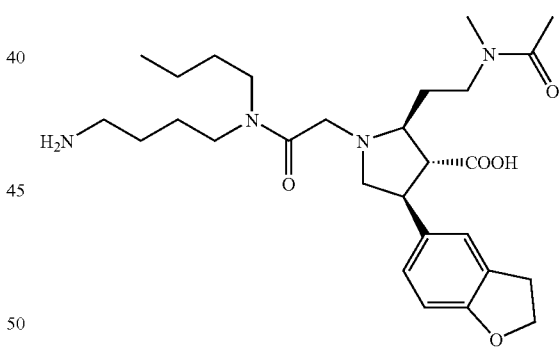 |
| 1009 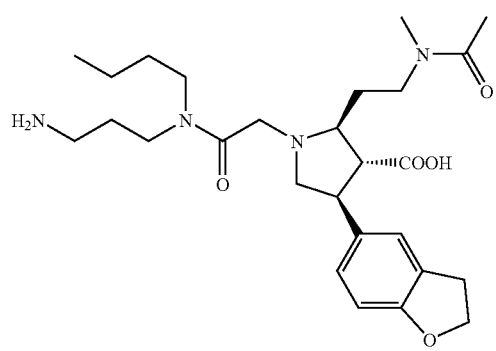 | 1013 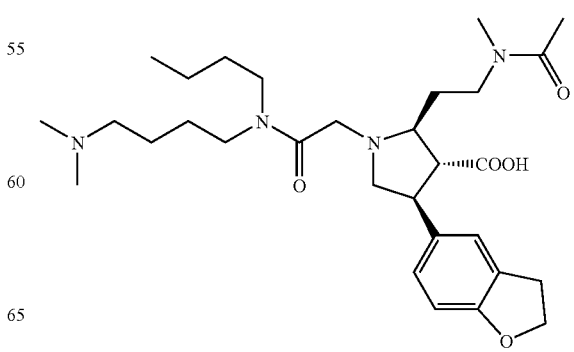 |

TABLE 3C-continued
1014
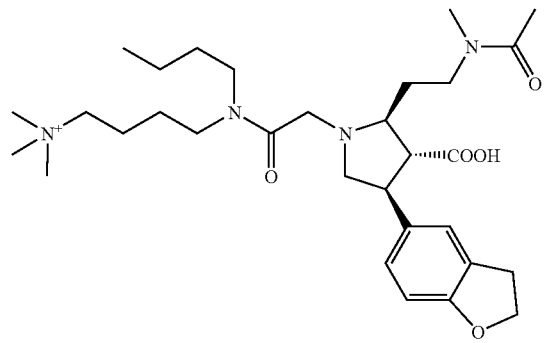
1015
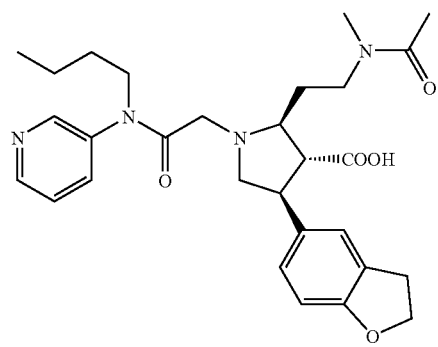
1016
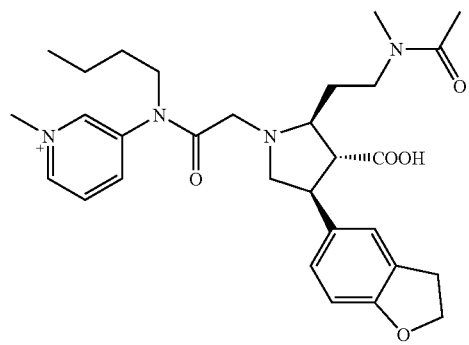
1017
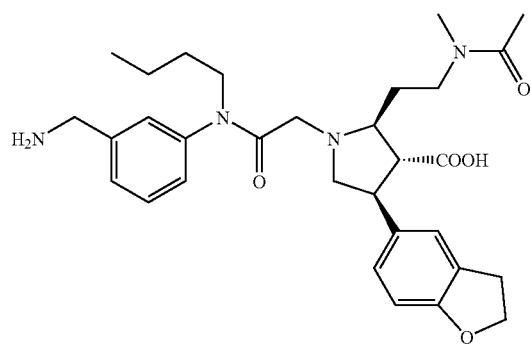
TABLE 3C-continued
1018
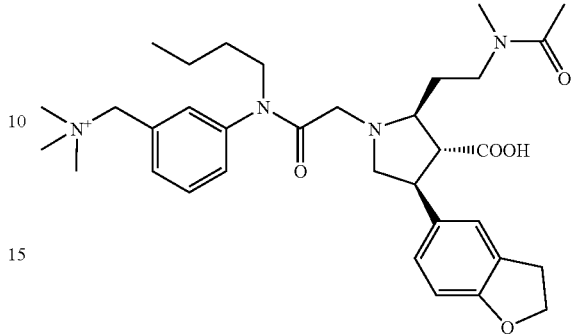
1019
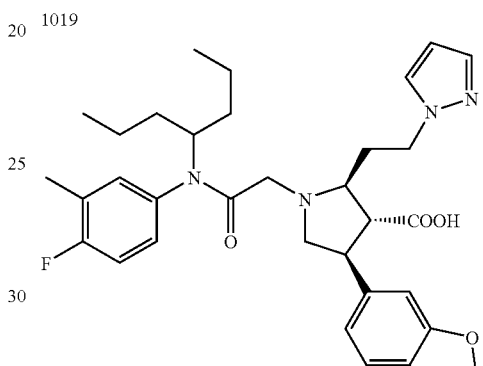
1020
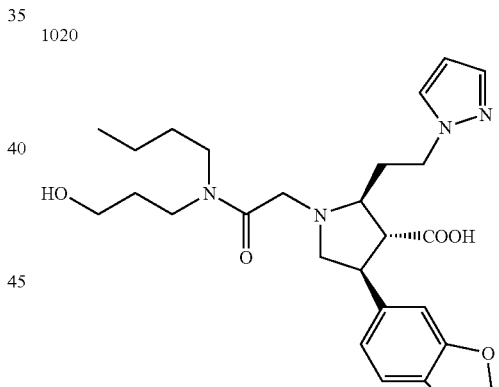
1021
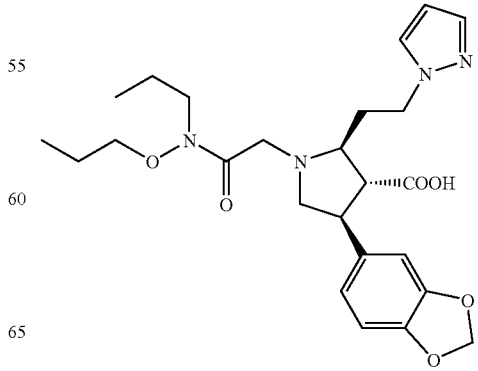

TABLE 3C-continued
1022
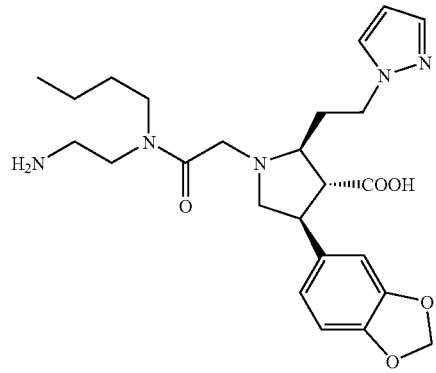
1023
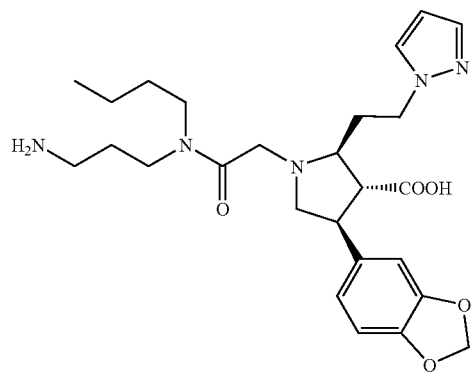
1024
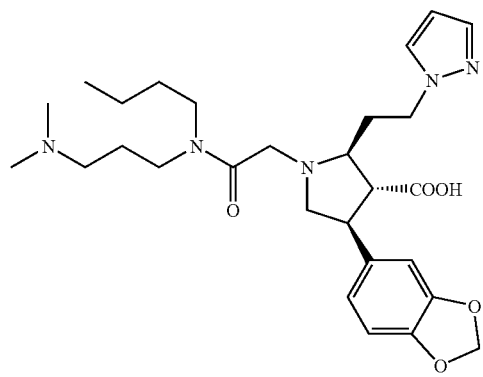
1025
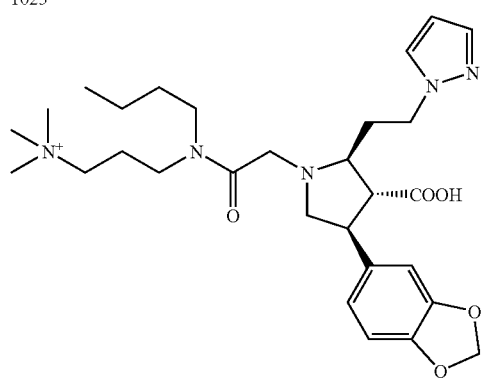
TABLE 3C-continued
1026
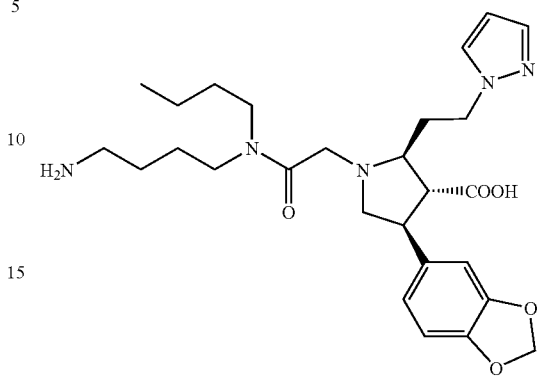
1027

1028

1029
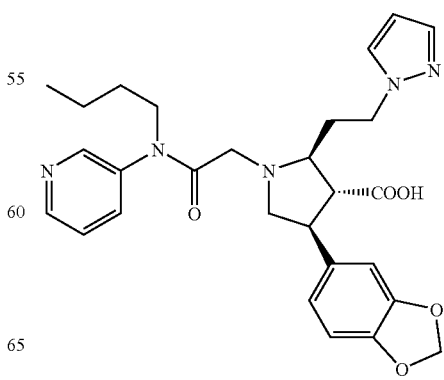

TABLE 3C-continued
1030
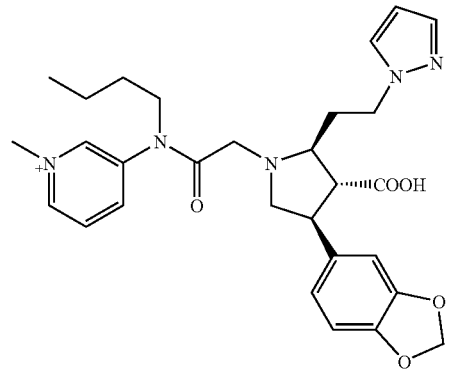
1031
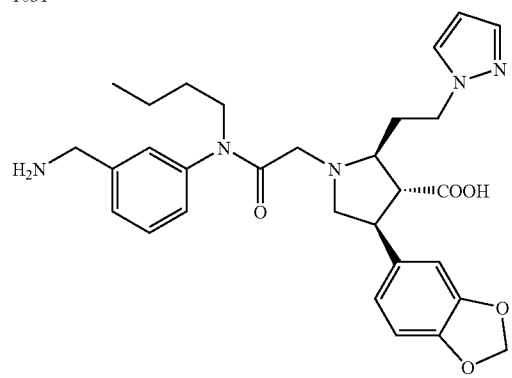
1032
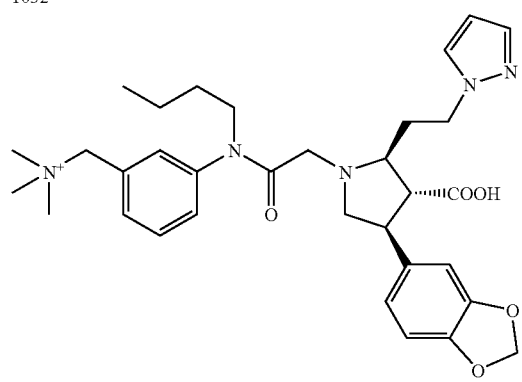
1033
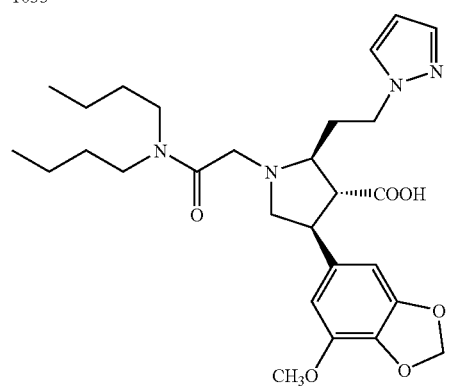
TABLE 3C-continued
1034
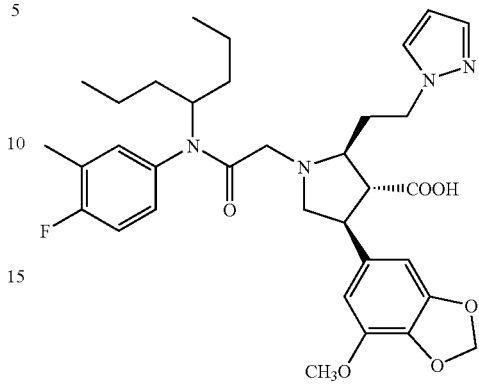
1035
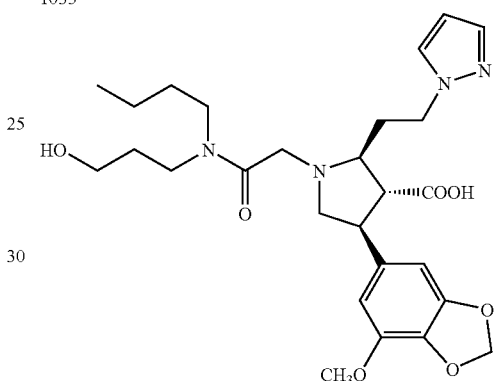
1036
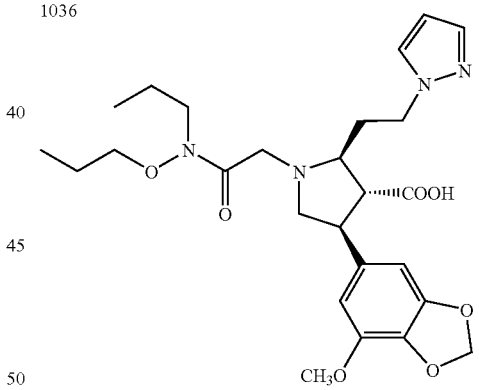
1037
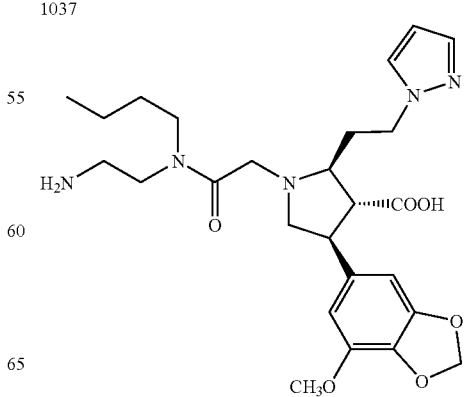

TABLE 3C-continued
1038
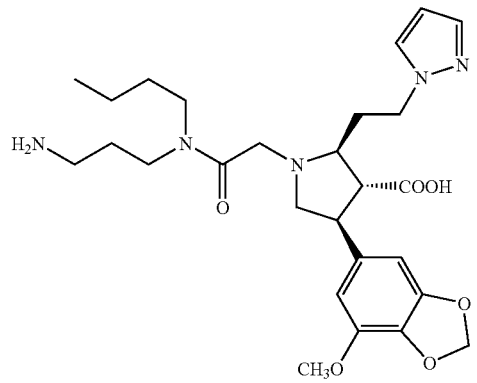
1039
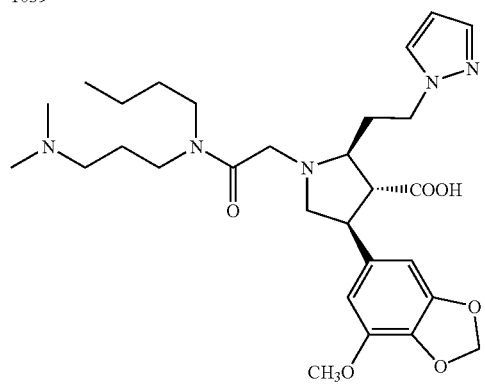
1040
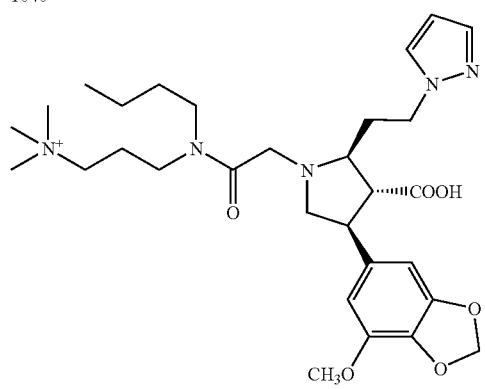
1041
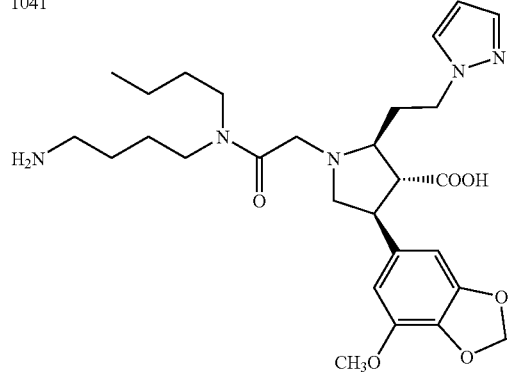
TABLE 3C-continued
1042
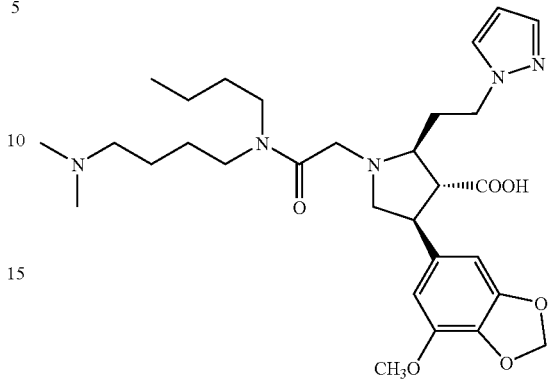
1043
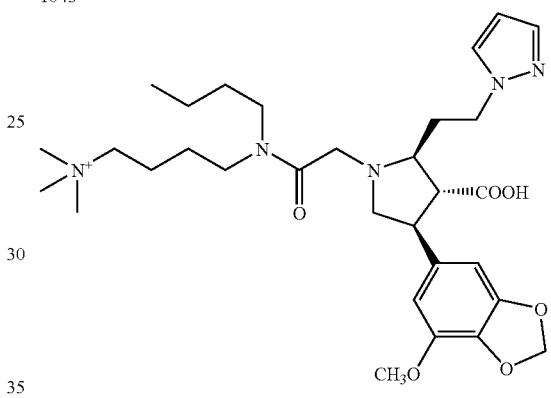
1044
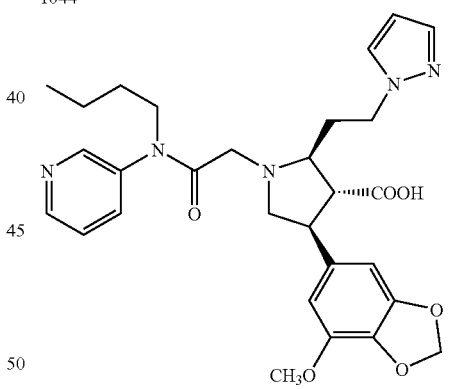
1045
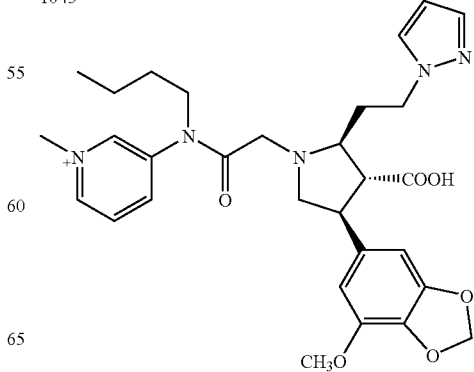

TABLE 3C-continued | TABLE 3C-continued
1046
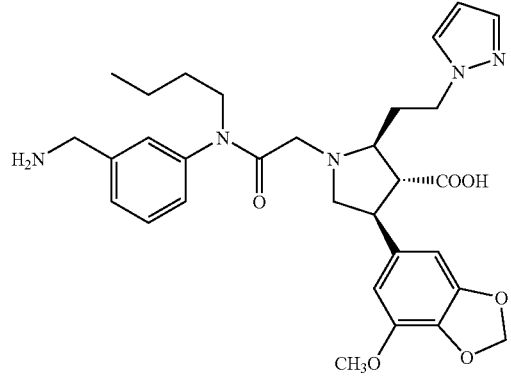
1047
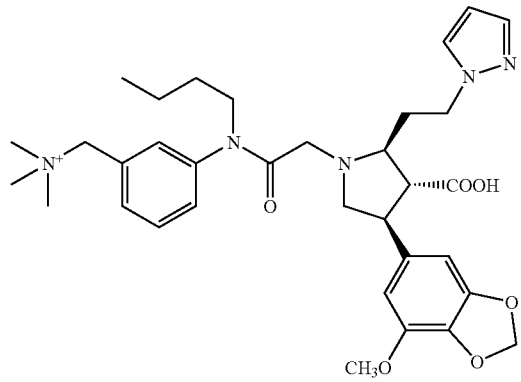
1048
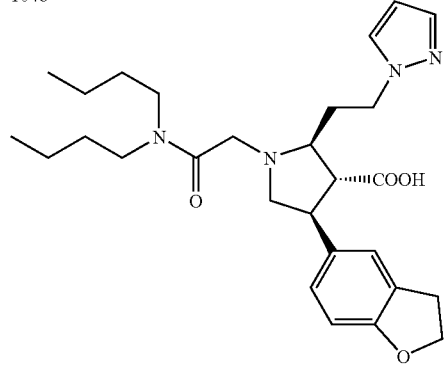
1049
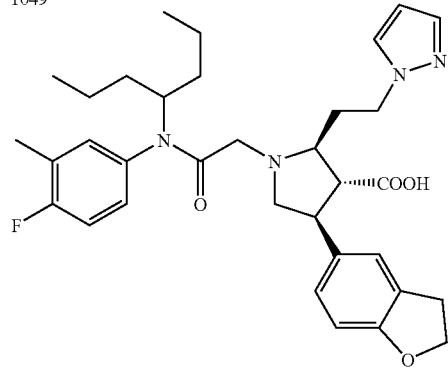
1050
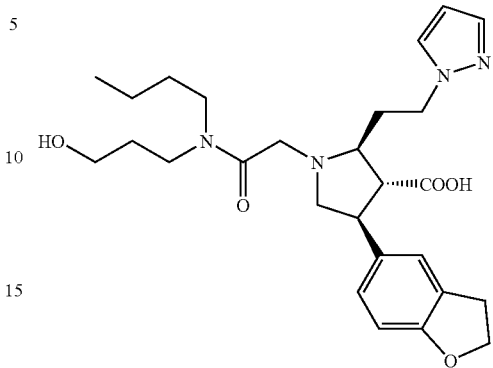
1051
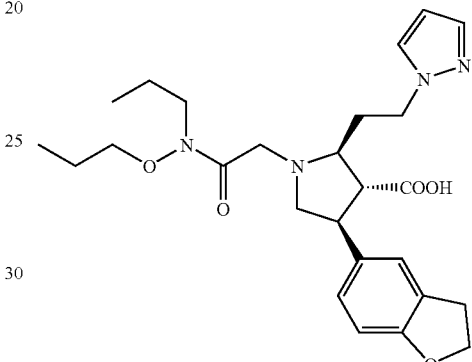
1052
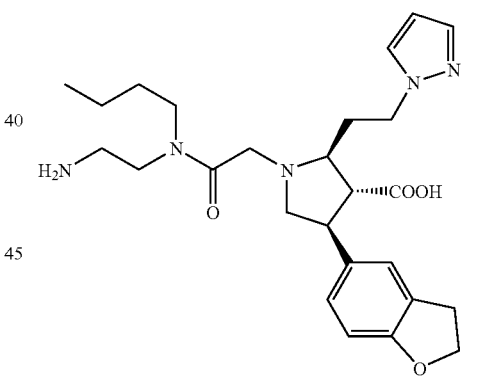
1053
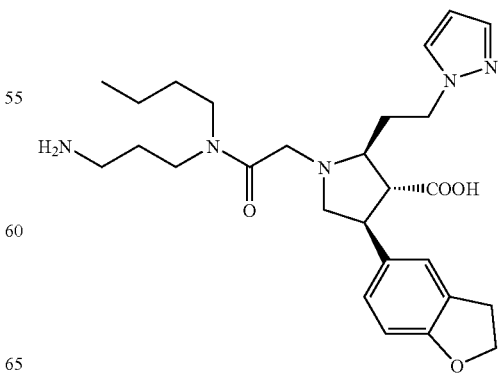

933 934
TABLE 3C-continued | TABLE 3C-continued
1054
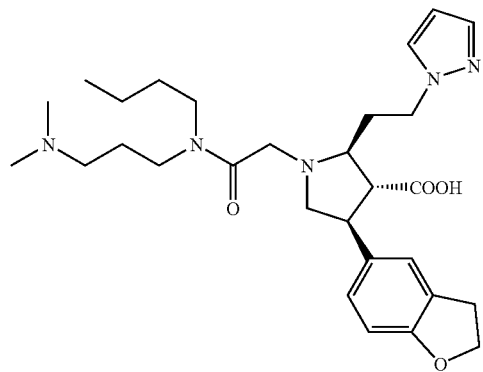
1058
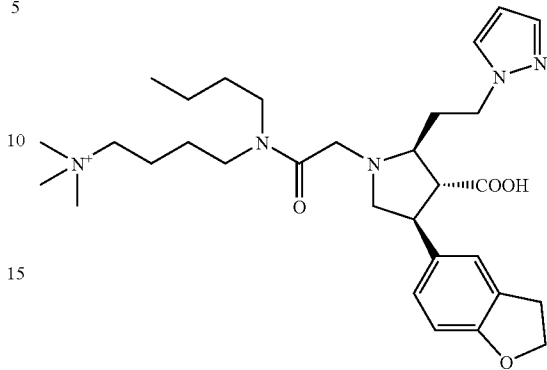
1055
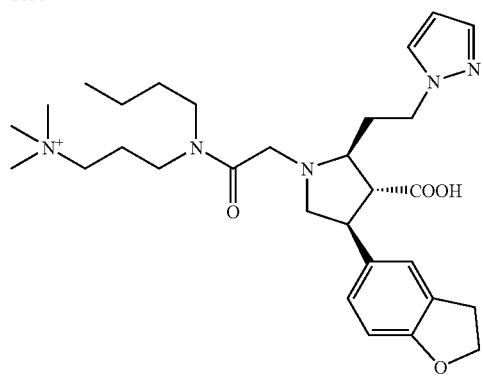
1059
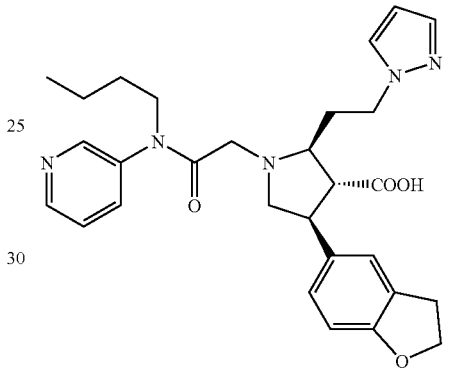
1056
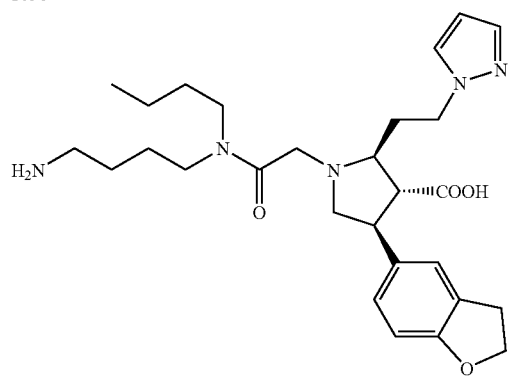
1060
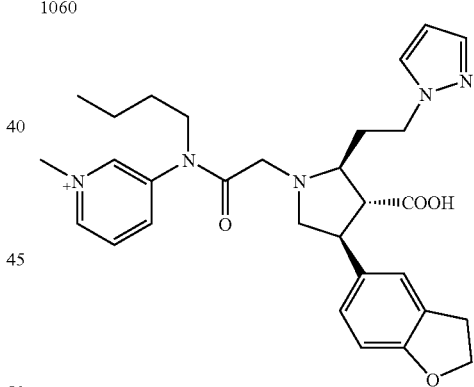
1057
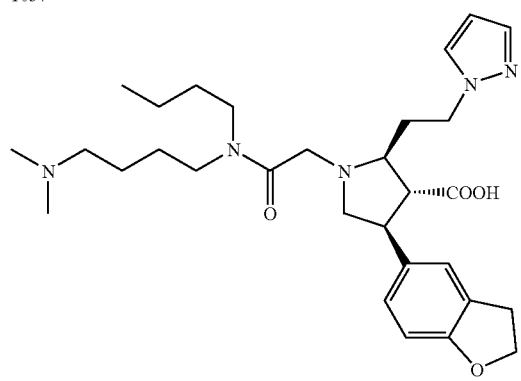
1061
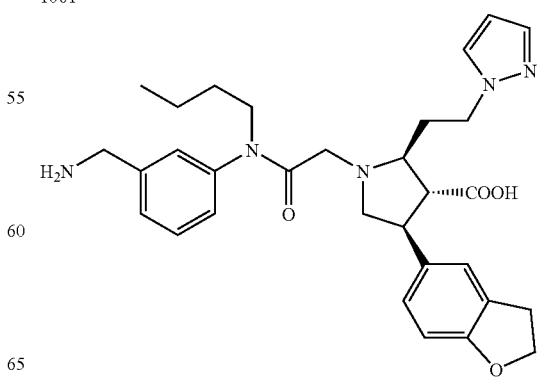

TABLE 3C-continued
1062
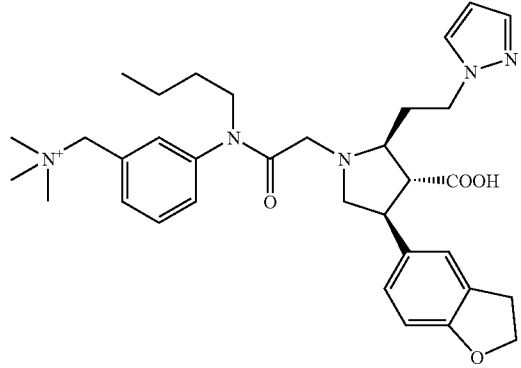
1063
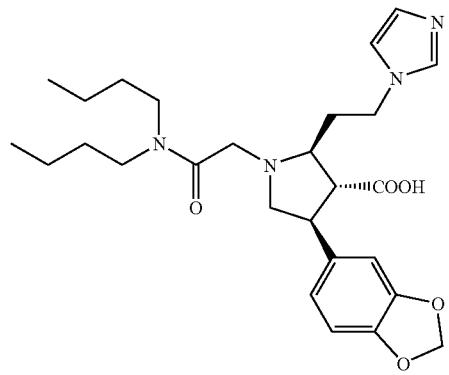
1064
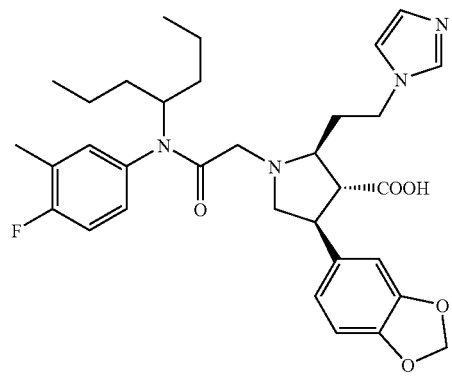
1065
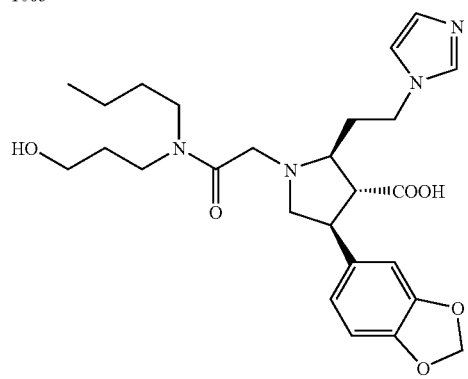
TABLE 3C-continued
1066
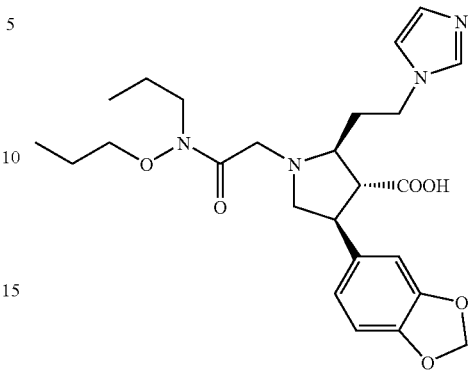
1067
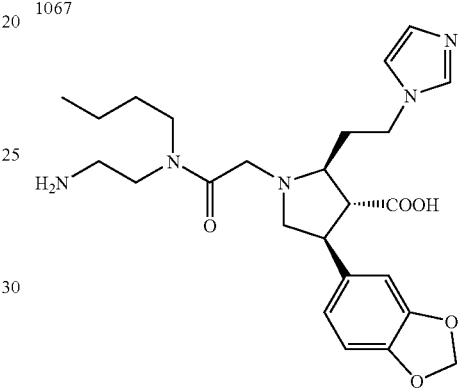
1068
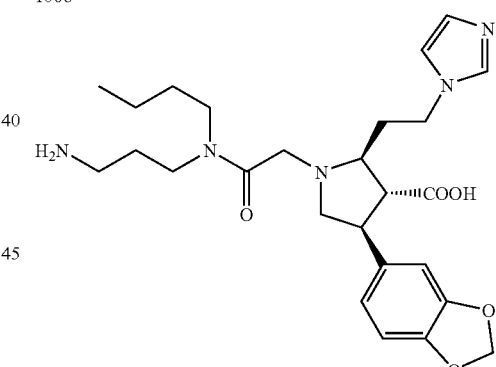
1069
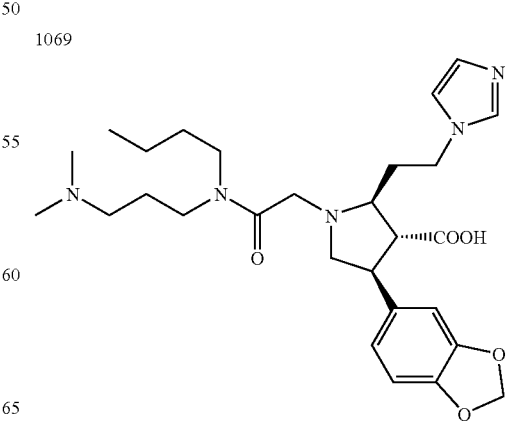

TABLE 3C-continued
1070
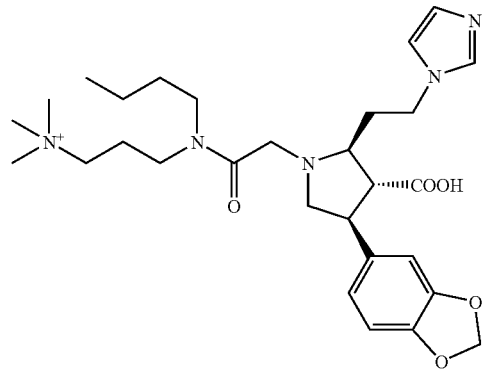
1071
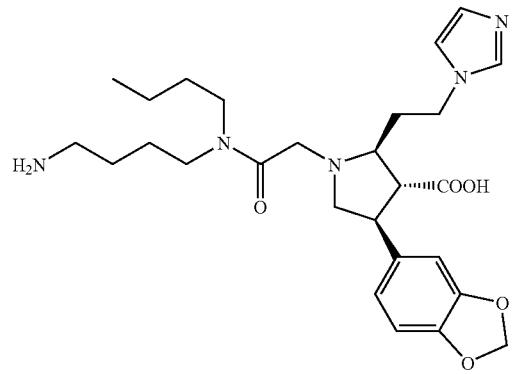
1072
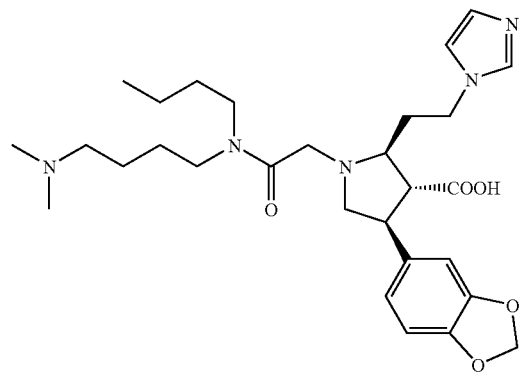
1073
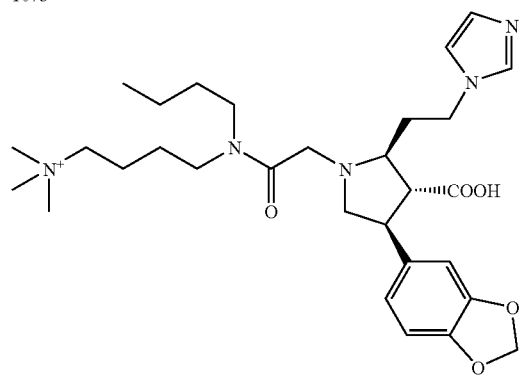
TABLE 3C-continued
1074
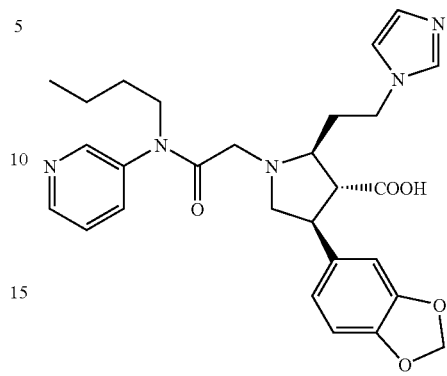
1075
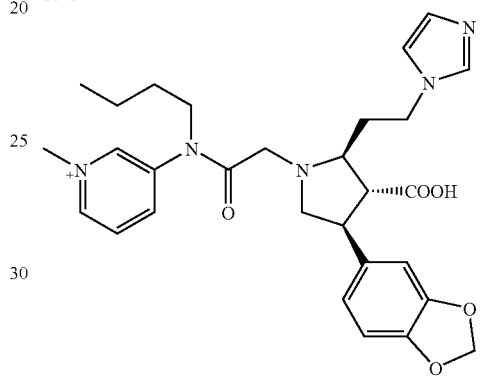
1076
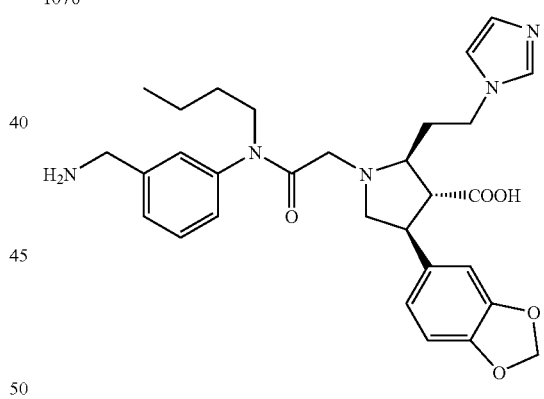
1077
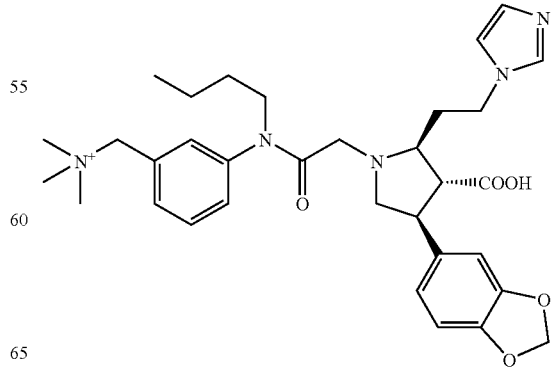

TABLE 3C-continued
1078
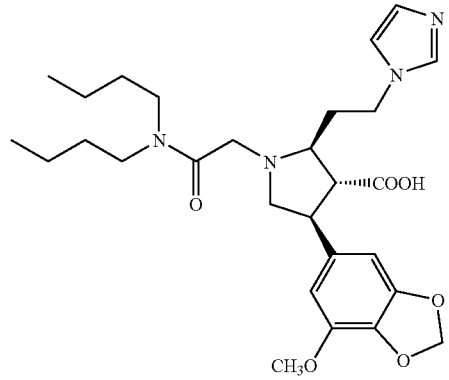
1079
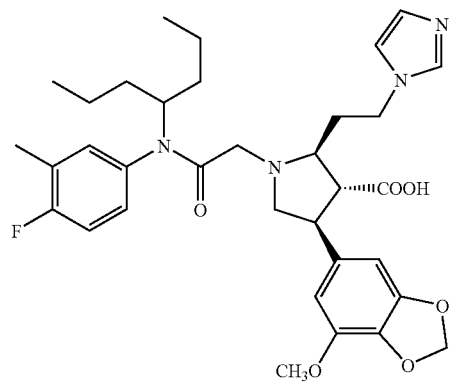
1080
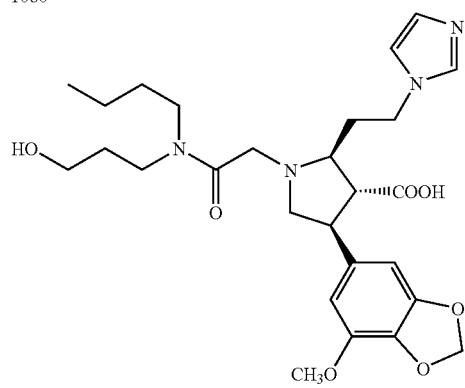
1081
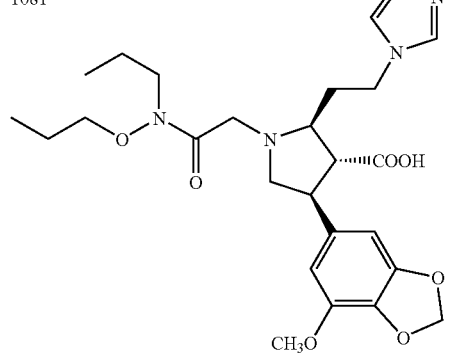
TABLE 3C-continued
1082
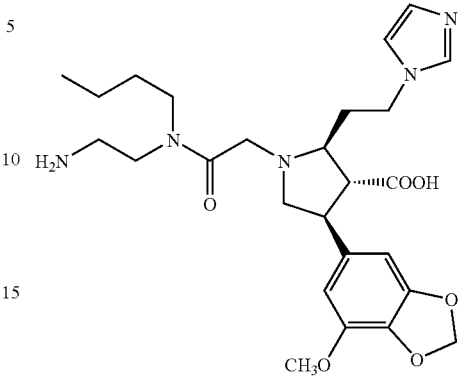
1083
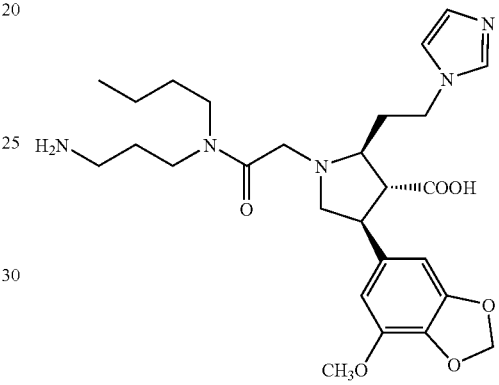
1084
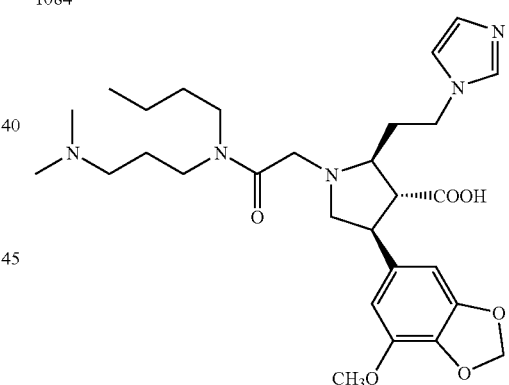
1085
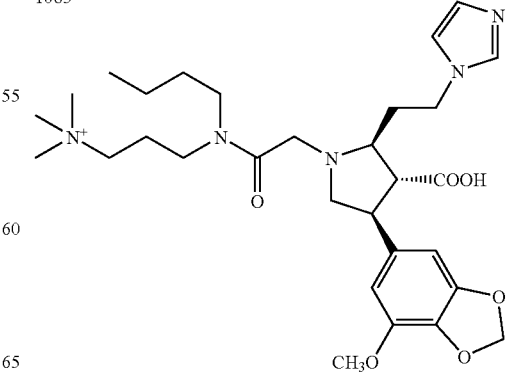

TABLE 3C-continued
1086
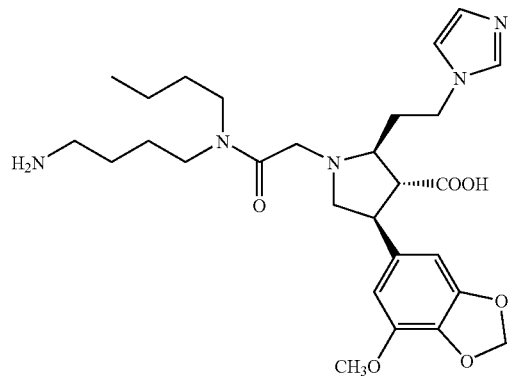
1087
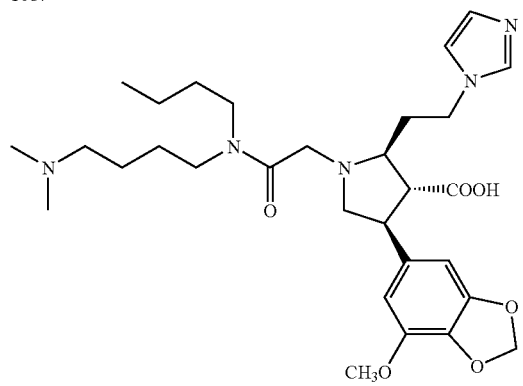
1088
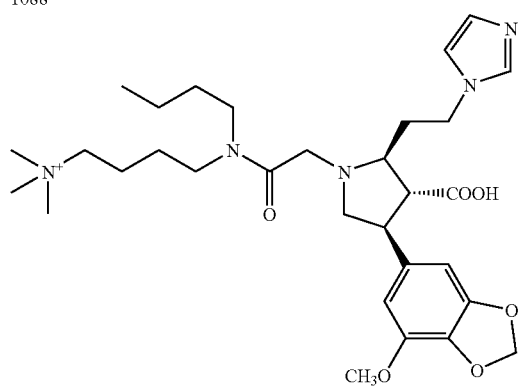
1089
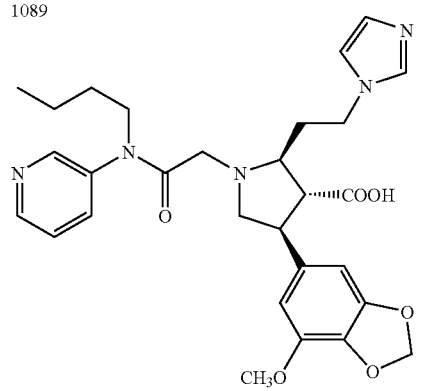
TABLE 3C-continued
1090
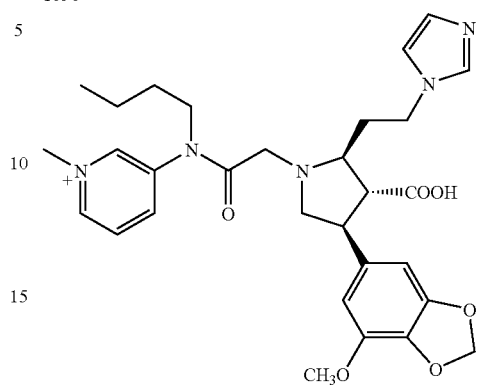
1091
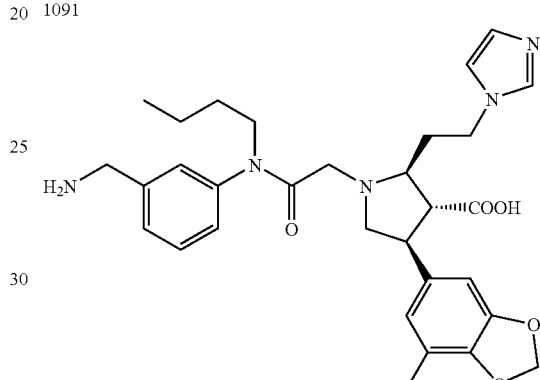
1092
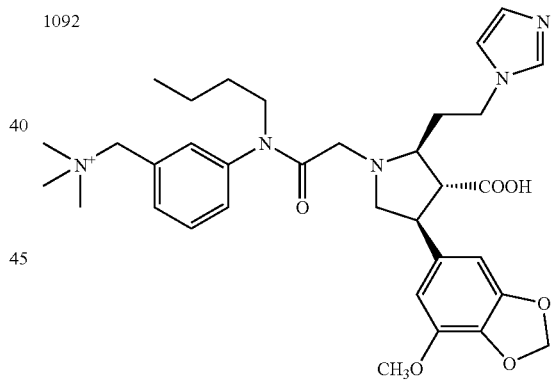
1093
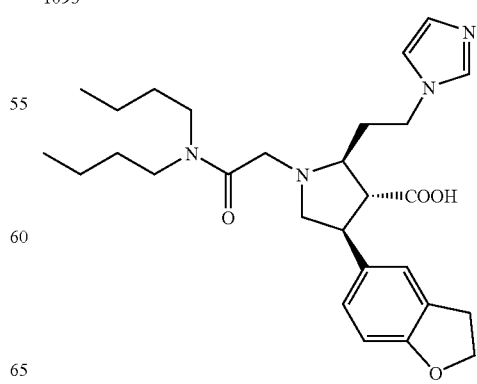

TABLE 3C-continued
1094
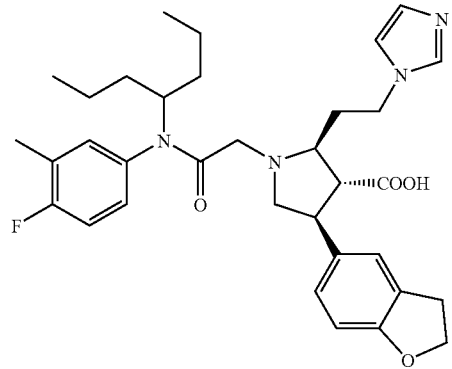
1095
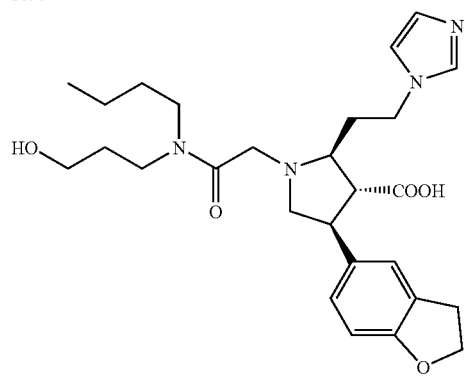
1096
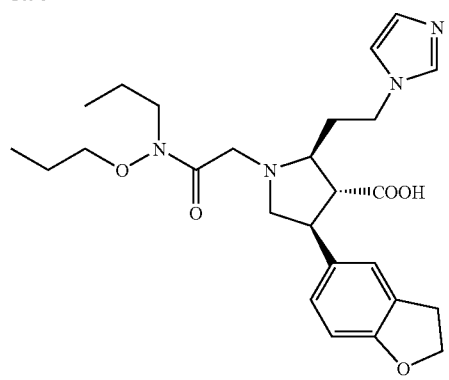
1097
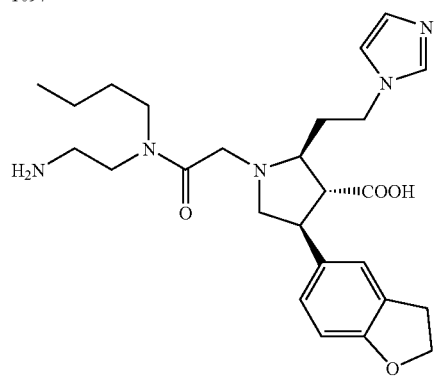
TABLE 3C-continued
1098
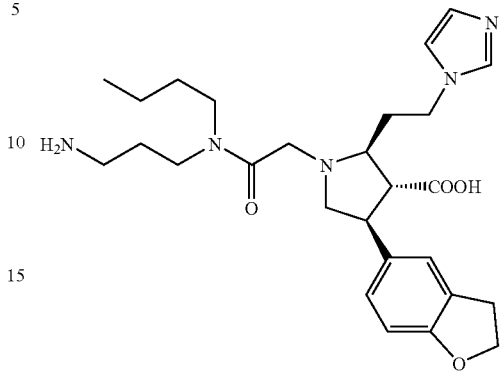
1099
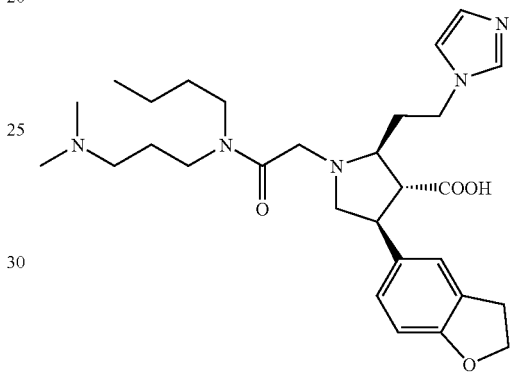
1100
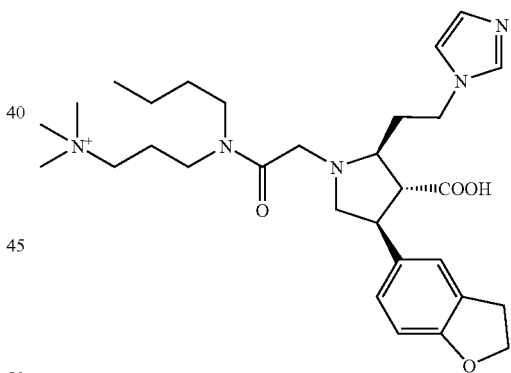
1101
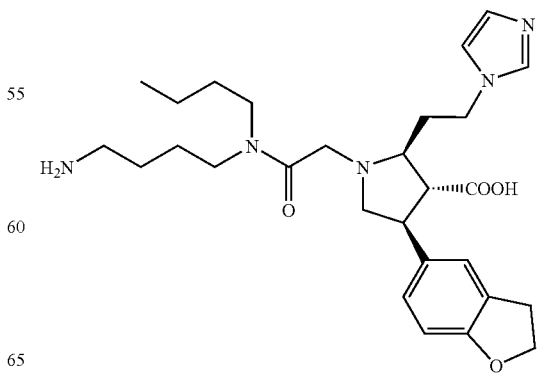

TABLE 3C-continued
1102
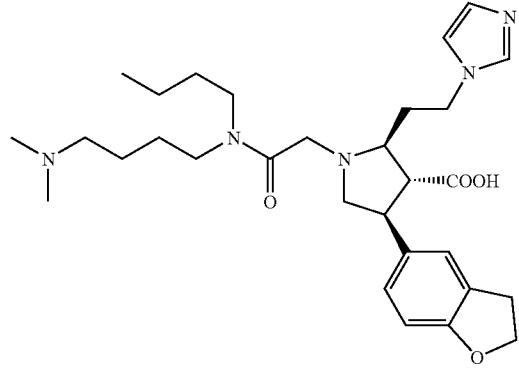
1103
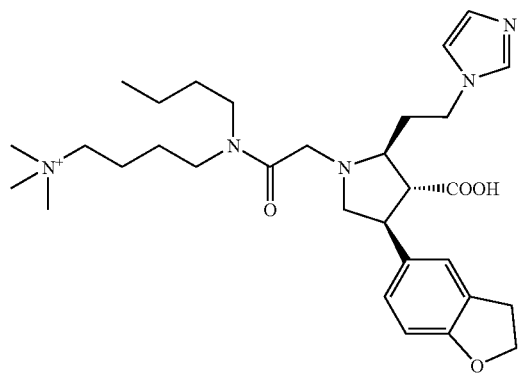
1104
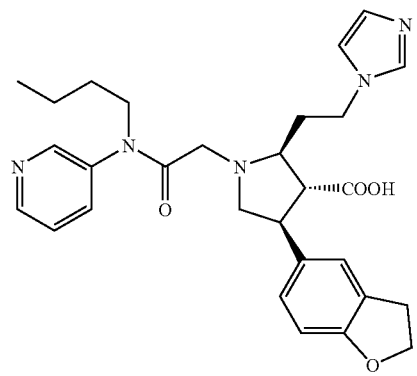
1105
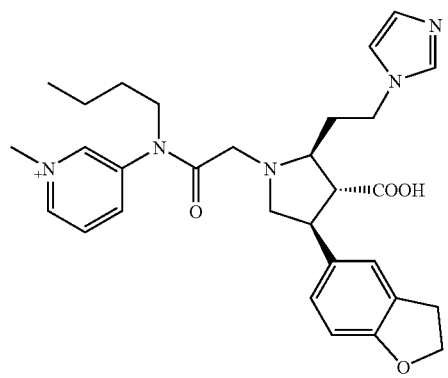
TABLE 3C-continued
1106
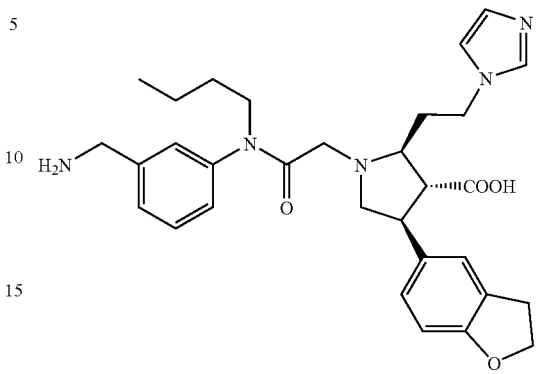
1107
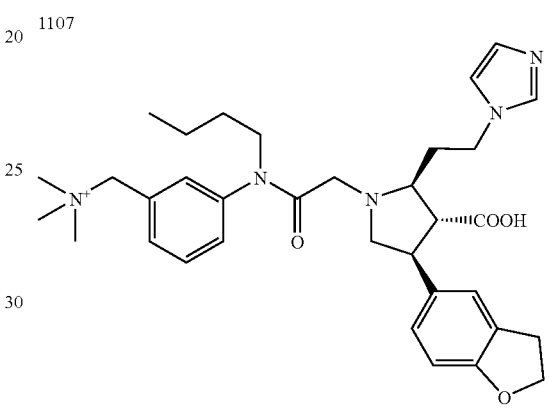
1108
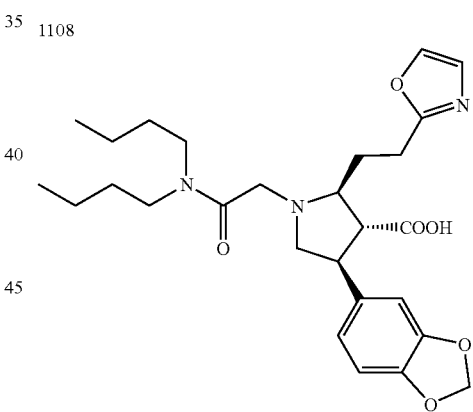
1109
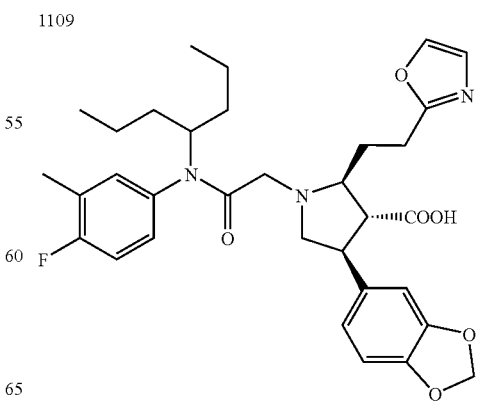

947 948
TABLE 3C-continued | TABLE 3C-continued
1110
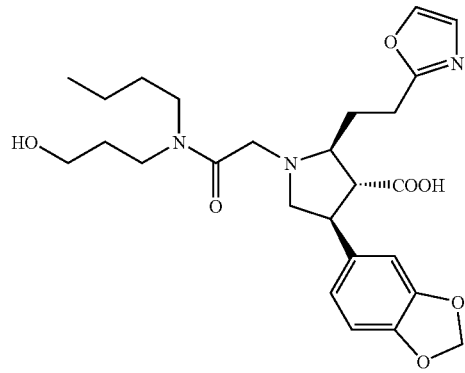
1111
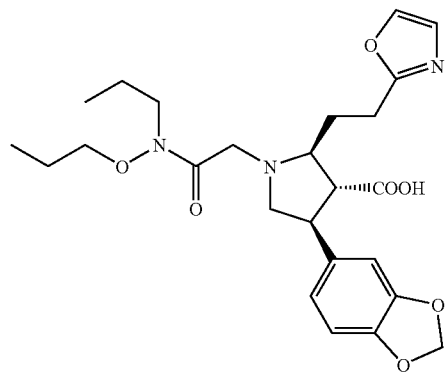
1112
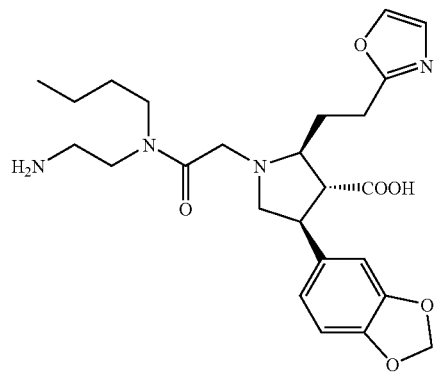
1113
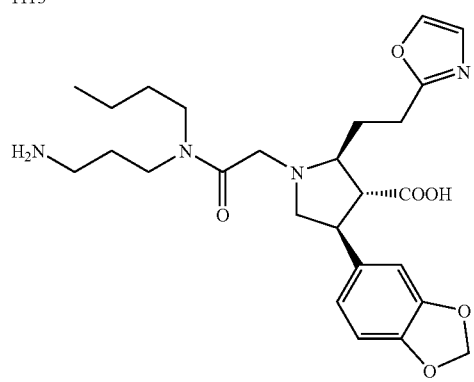
1114
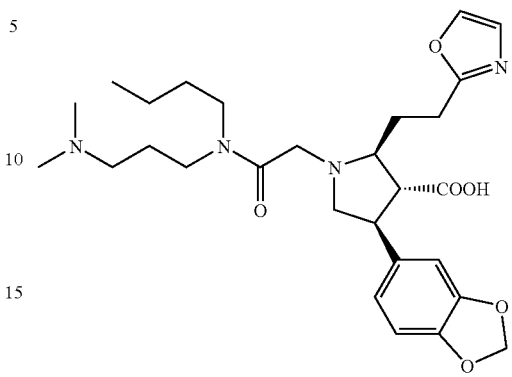
1115
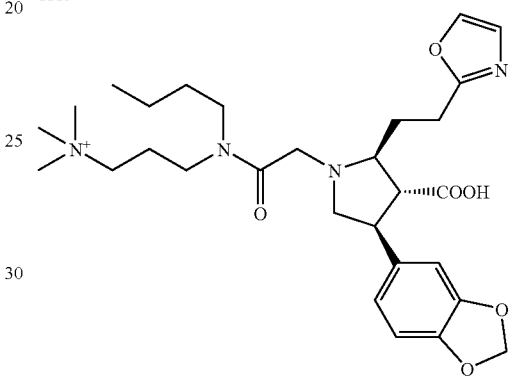
1116
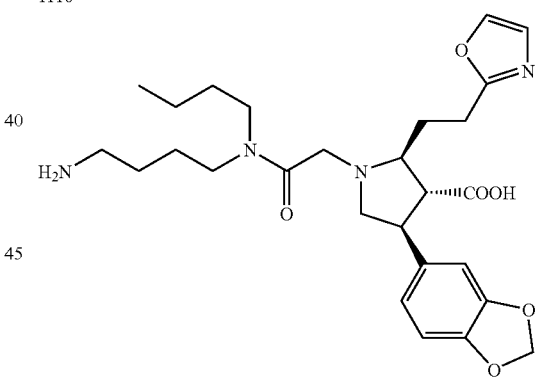
1117
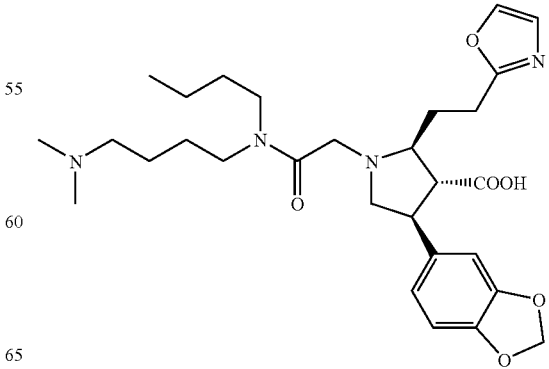

TABLE 3C-continued
1118
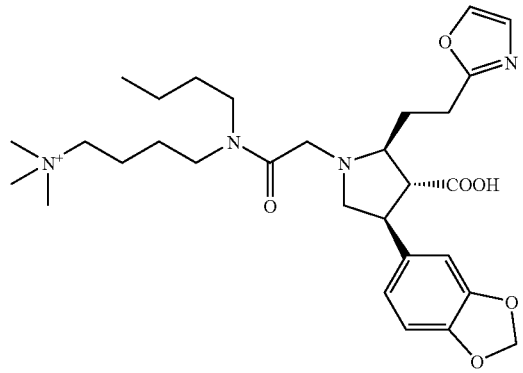
1119
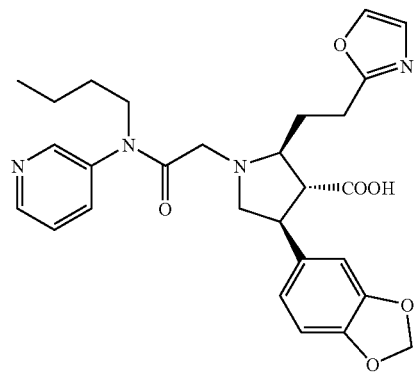
1120
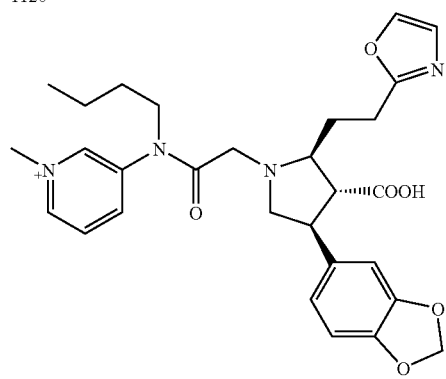
1121
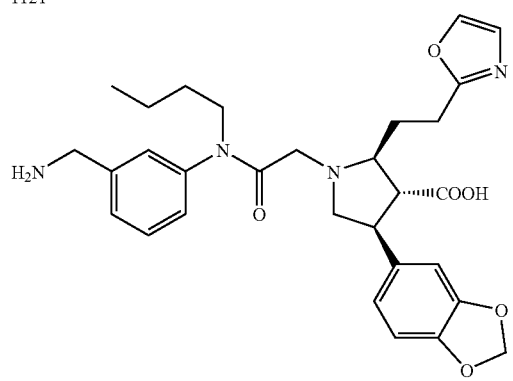
TABLE 3C-continued
1122
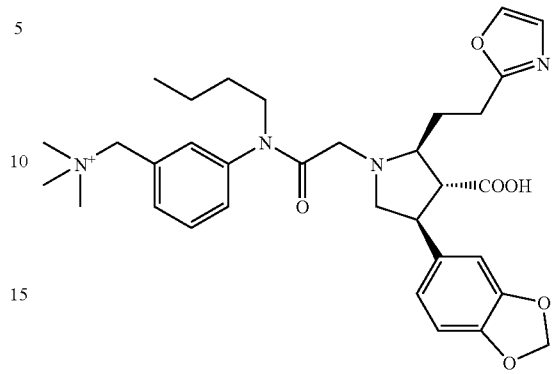
1123
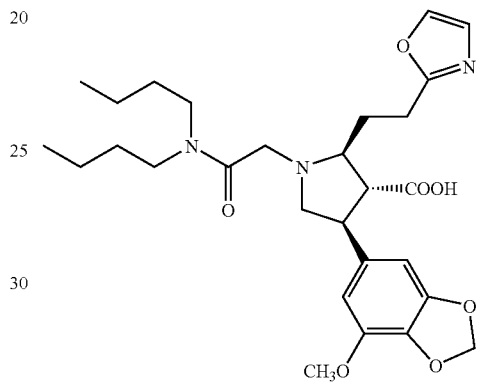
1124
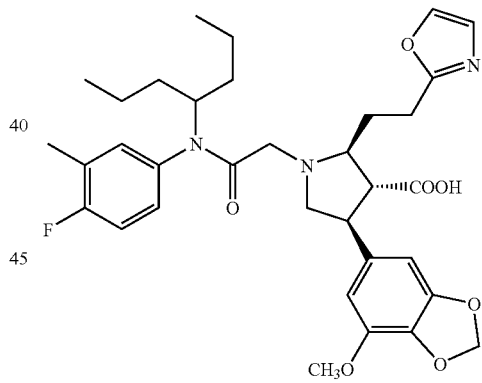
1125
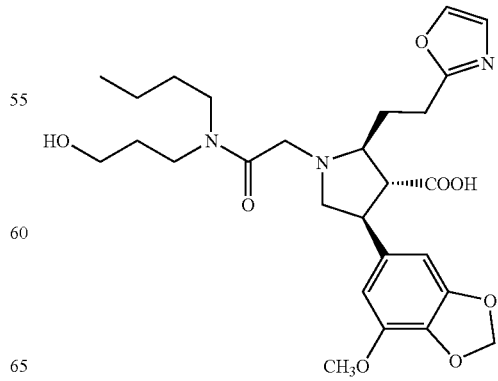

TABLE 3C-continued
1126
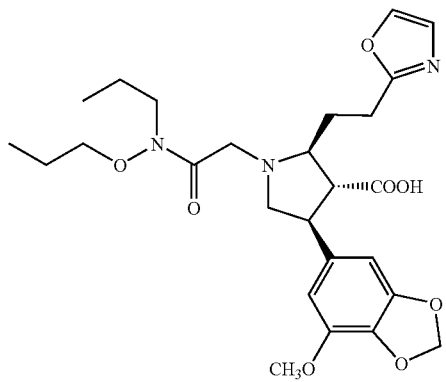
1127
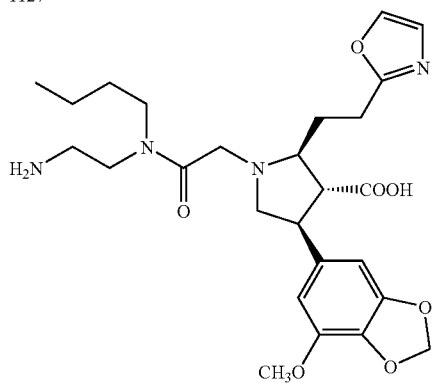
1128
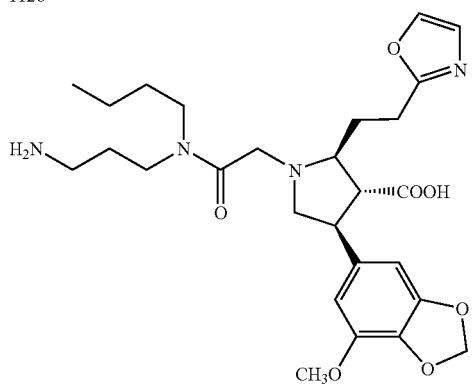
1129
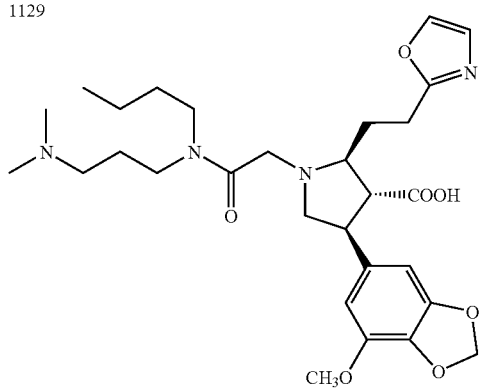
TABLE 3C-continued
1130
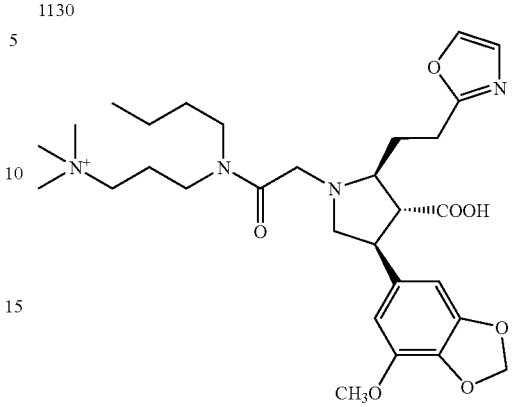
1131
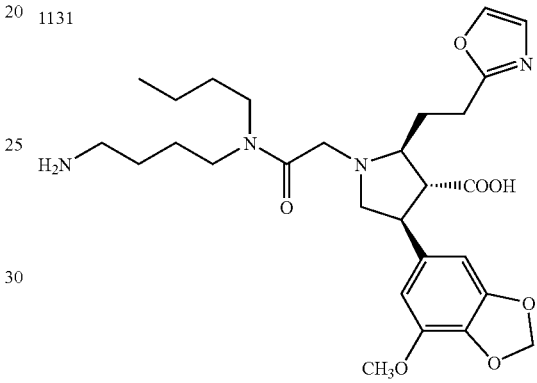
1132
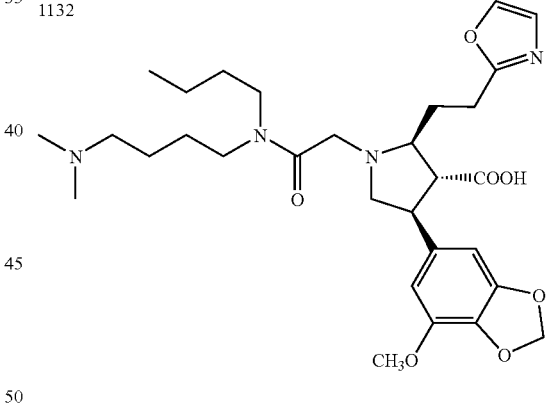
1133
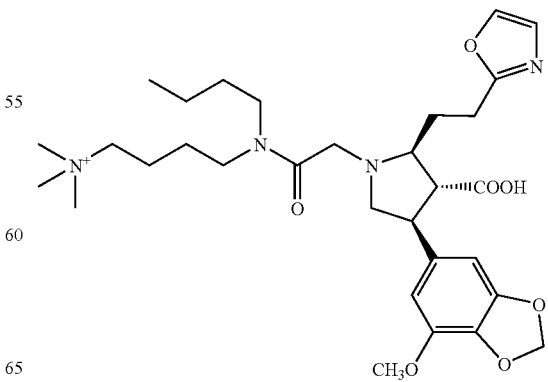

TABLE 3C-continued
1134
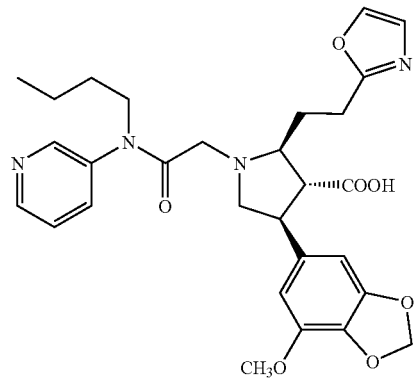
1135
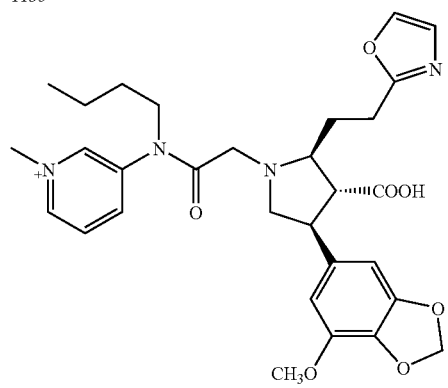
1136
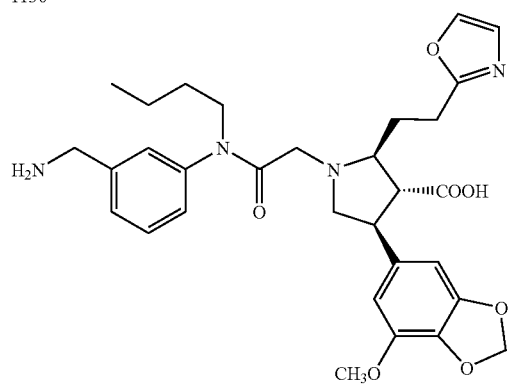
1137
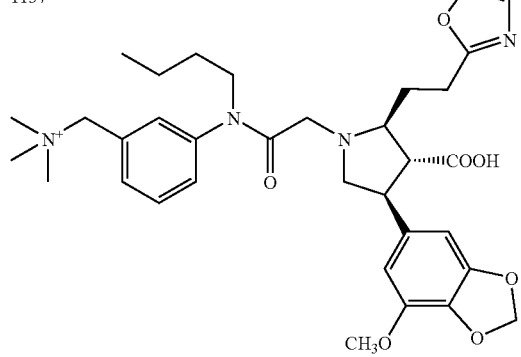
TABLE 3C-continued
1138
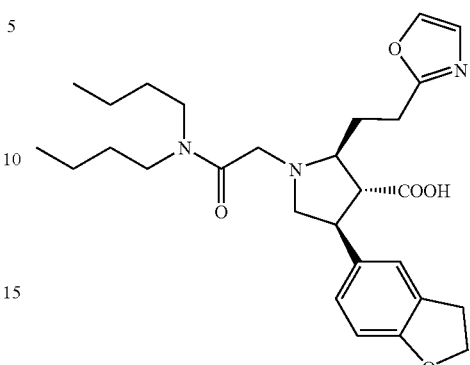
1139
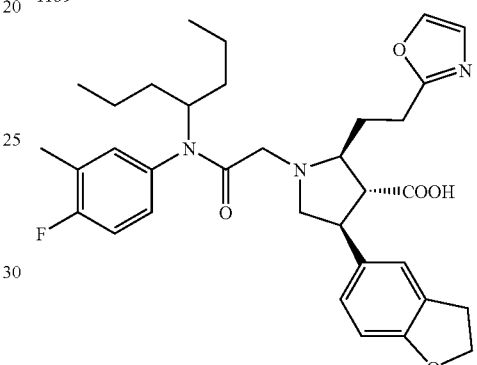
1140
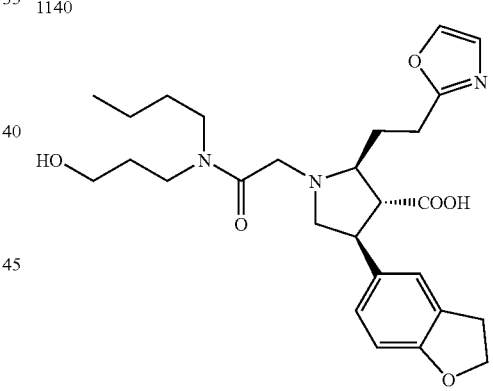
1141
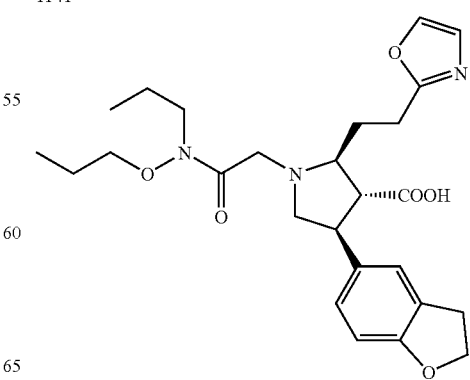

TABLE 3C-continued
1142
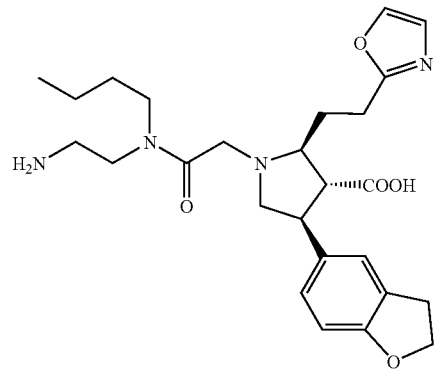
1143
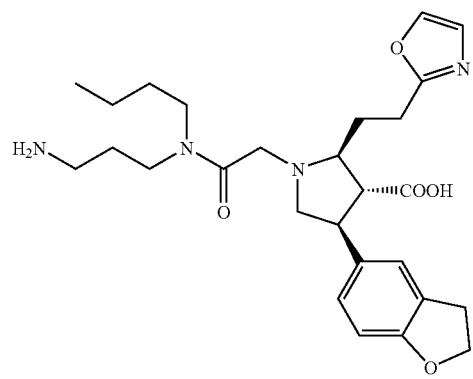
1144
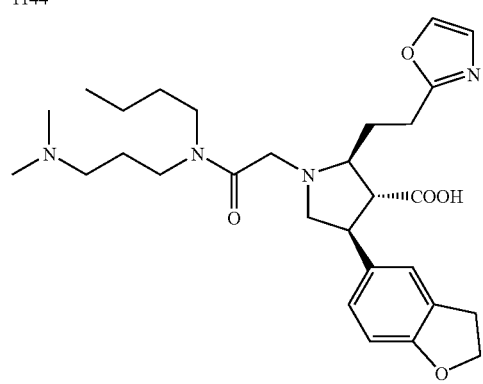
1145
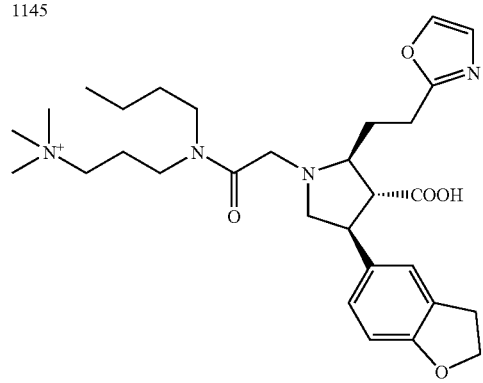
TABLE 3C-continued
1146
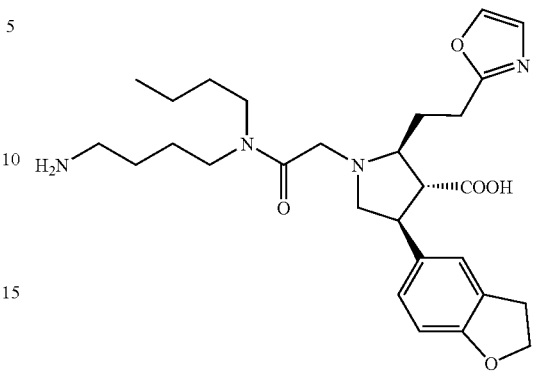
1147
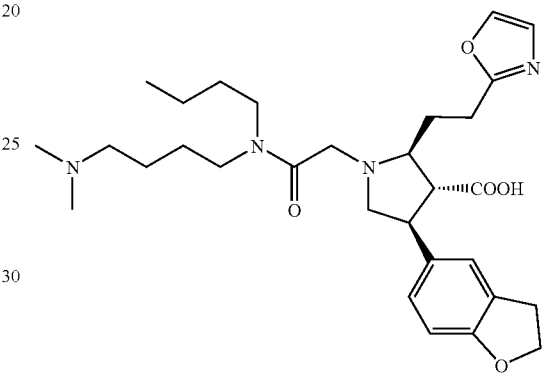
1148
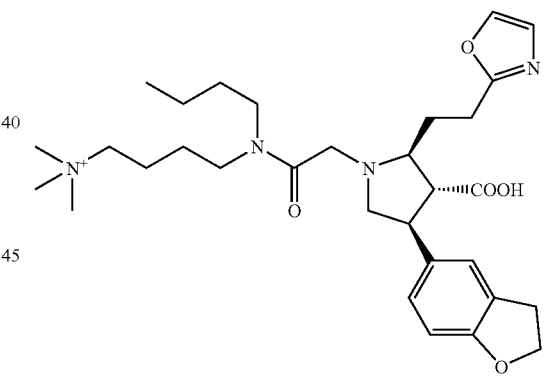
1149
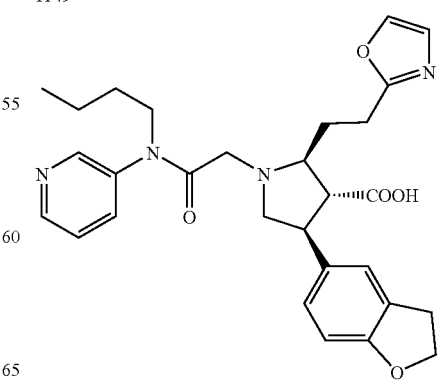

TABLE 3C-continued
1150
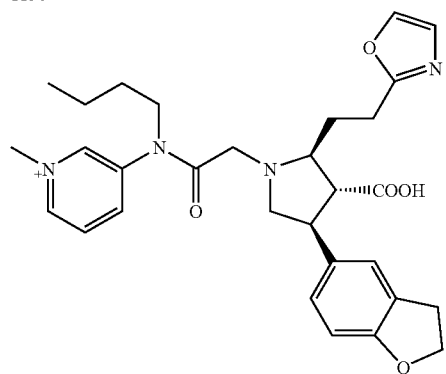
1151
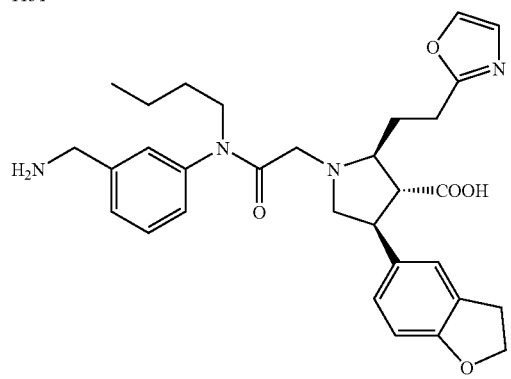
1152
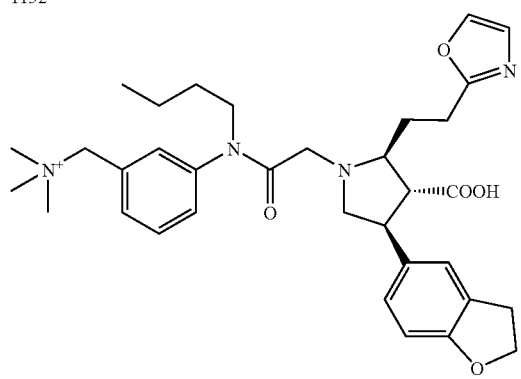
1153
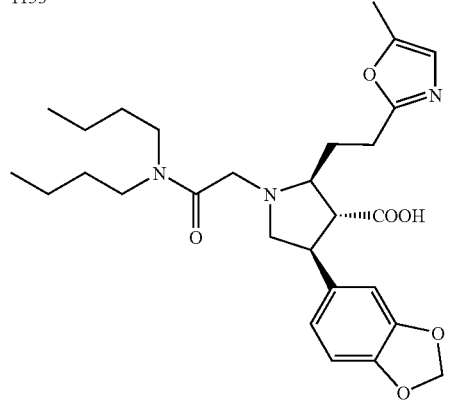
TABLE 3C-continued
1154
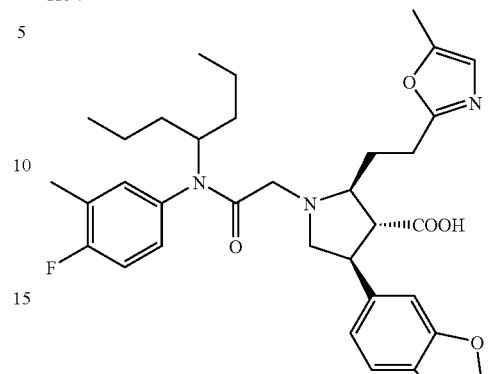
1155
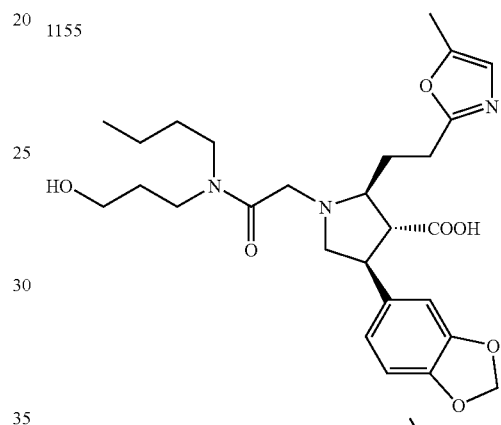
1156
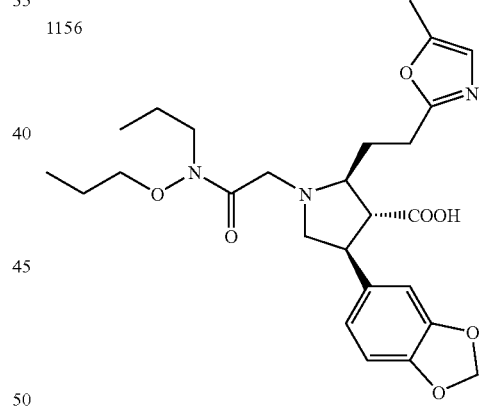
1157
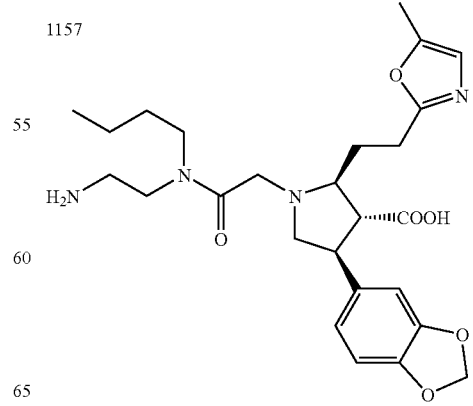

TABLE 3C-continued
1158
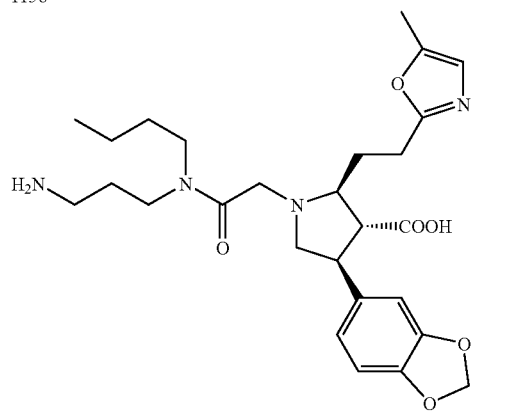
1159
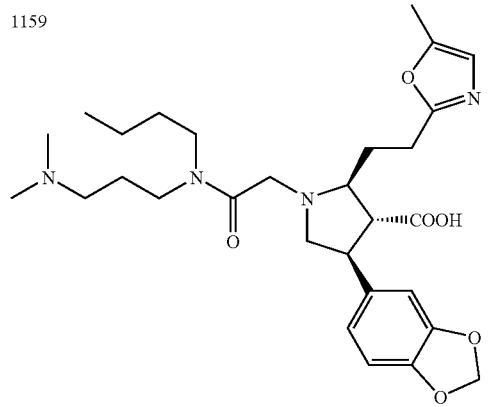
1160
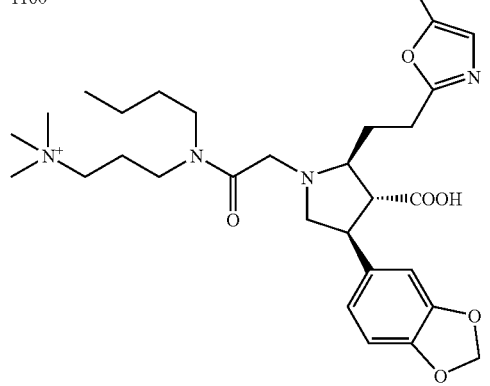
1161
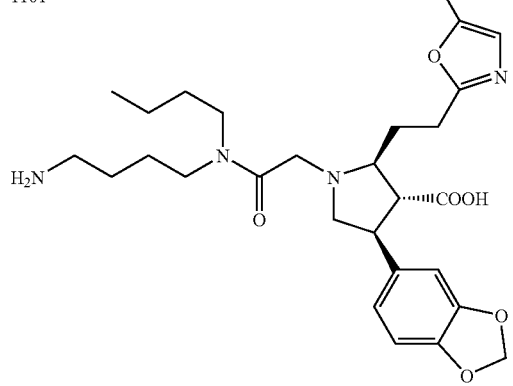
TABLE 3C-continued
1162
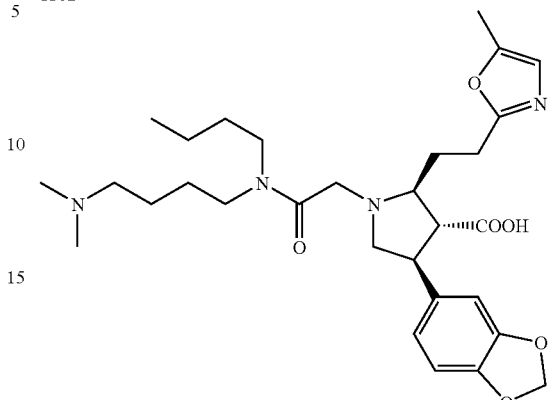
1163
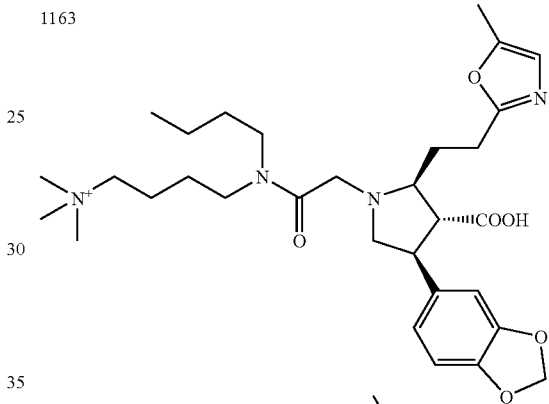
1164
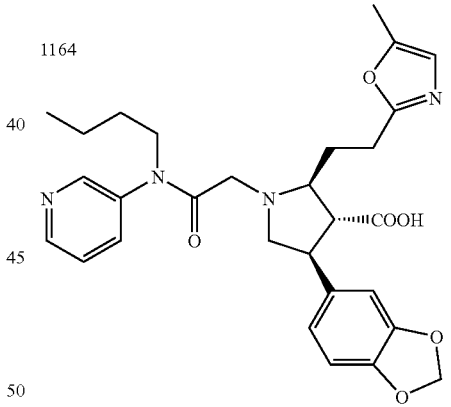
1165
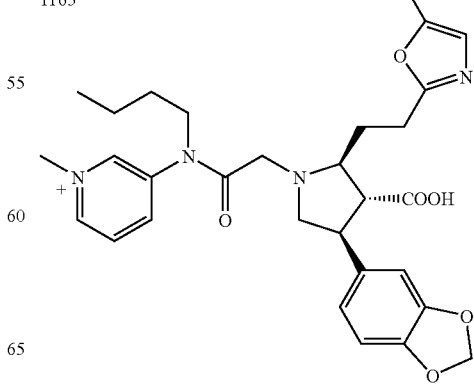

TABLE 3C-continued
1166
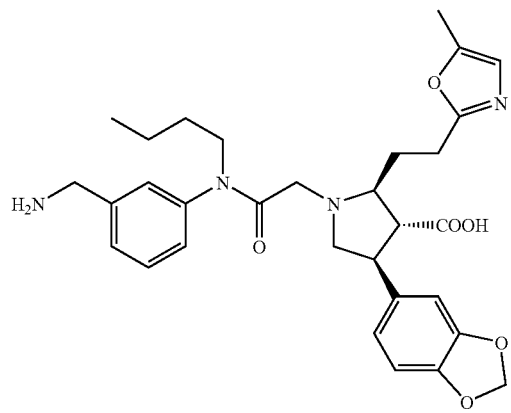
1167
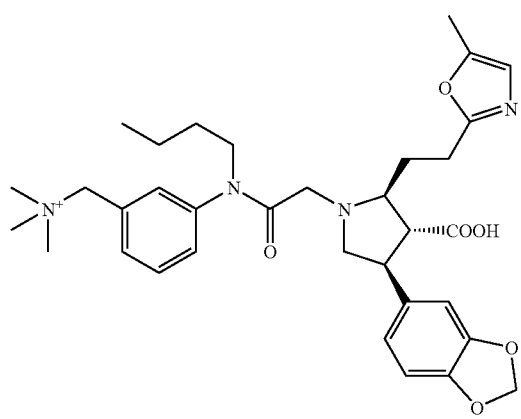
1168
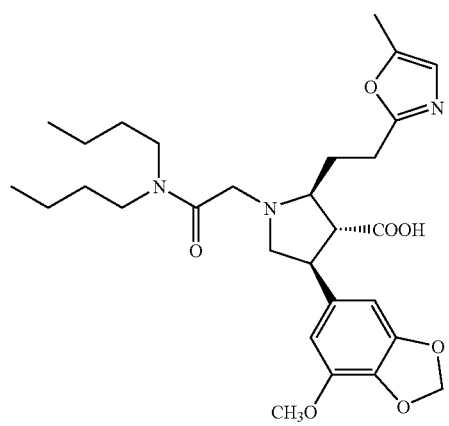
TABLE 3C-continued
1169
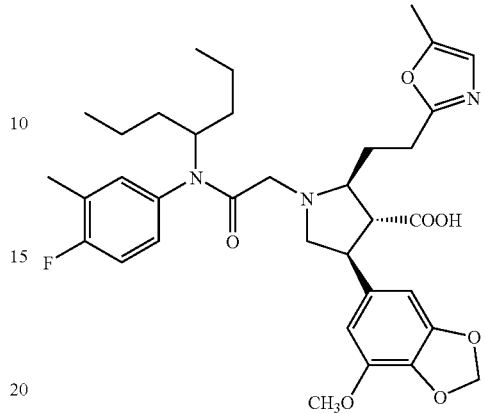
1170
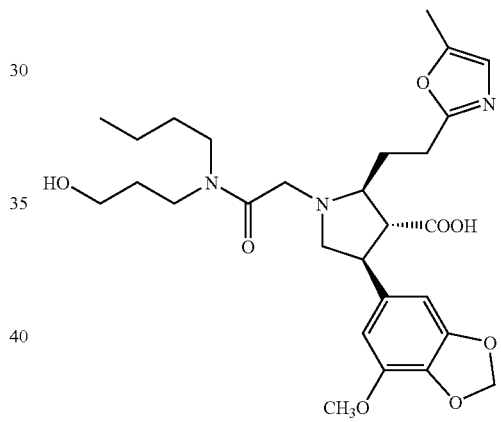
1171
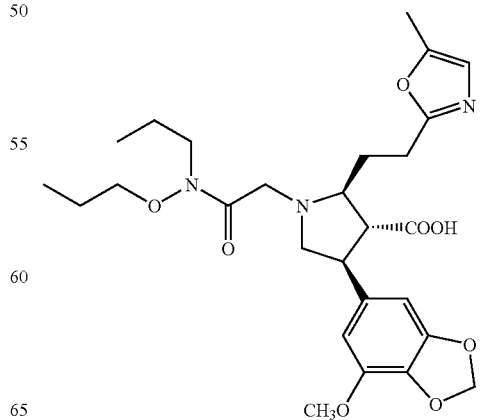

| 1172 | 1175 |
|---|---|
| 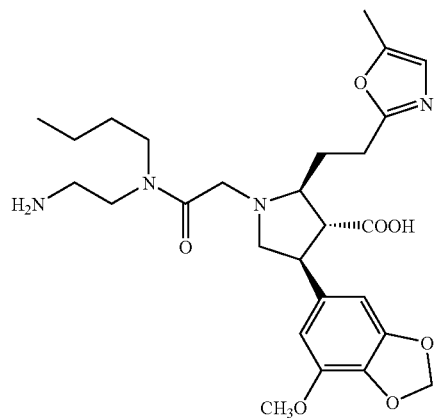 | 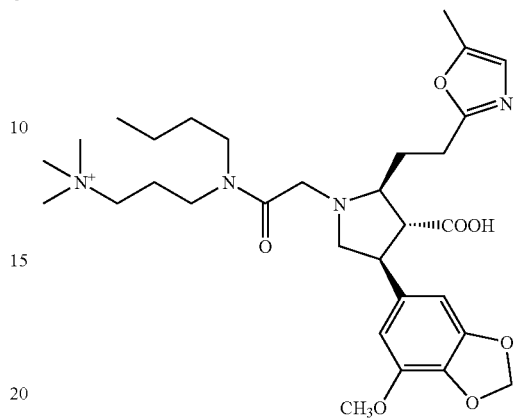 |
| 1173 | 1176 |
| 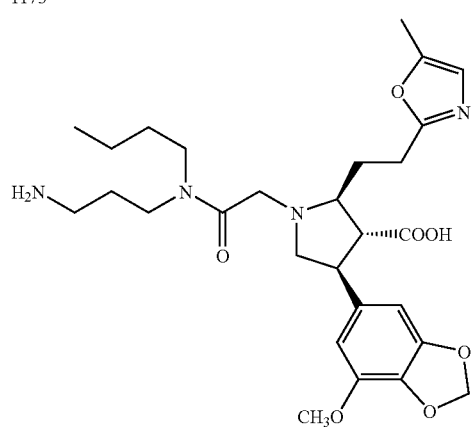 | 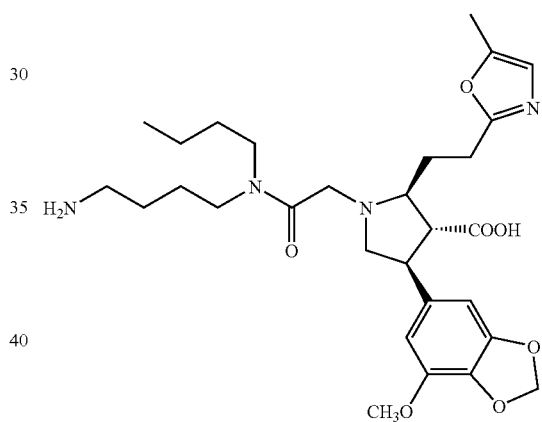 |
| 1174 | 1177 |
| 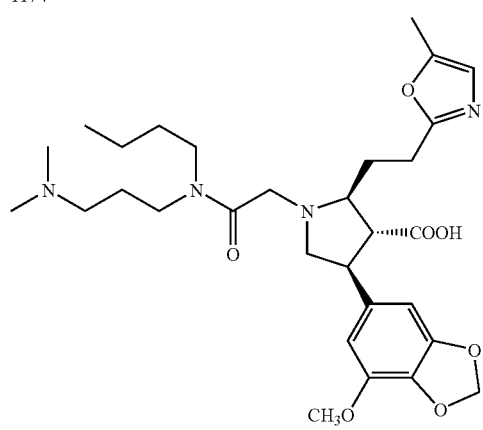 | 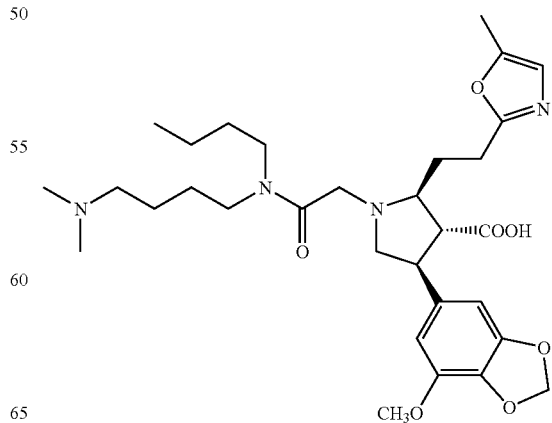 |

TABLE 3C-continued
1178
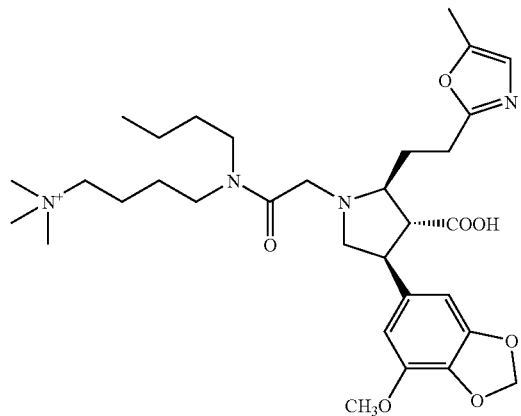
1181
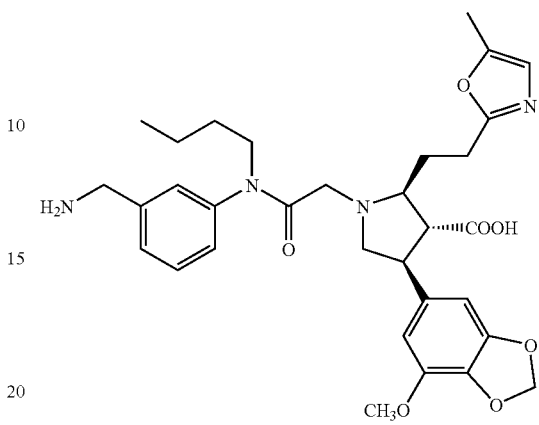
1179
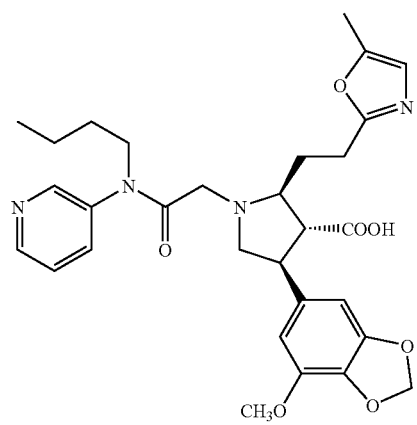
1182
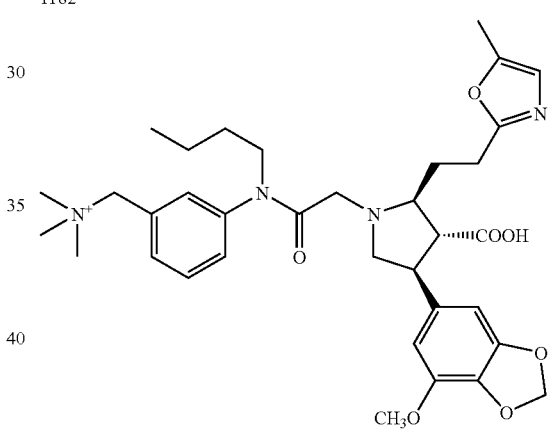
1180
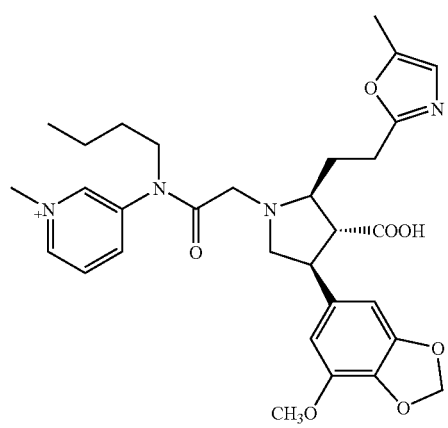
1183
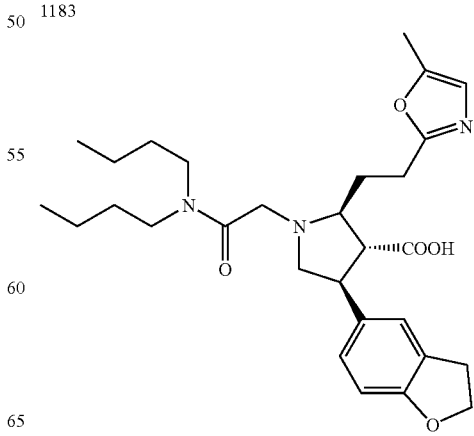

TABLE 3C-continued | TABLE 3C-continued
---|---
1184
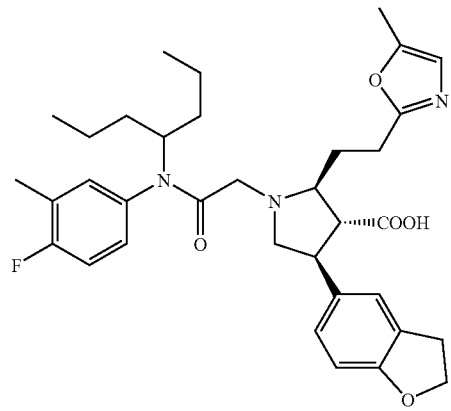
1185
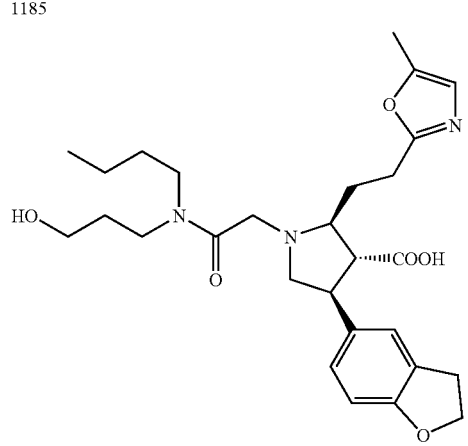
1186
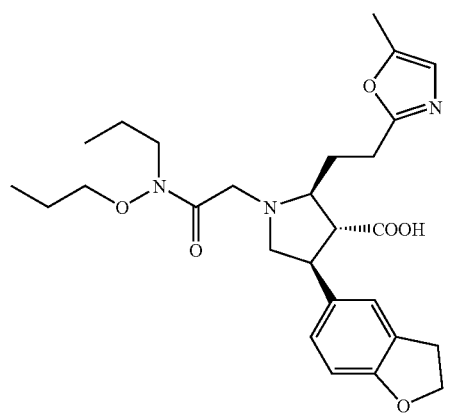
1187
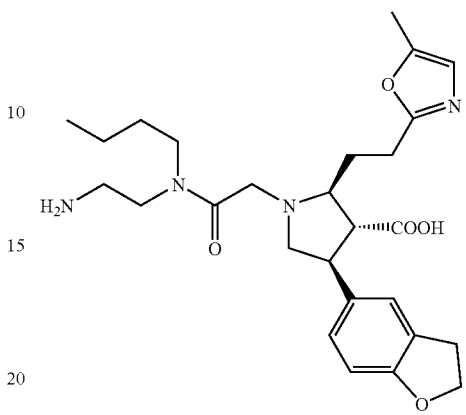
1188
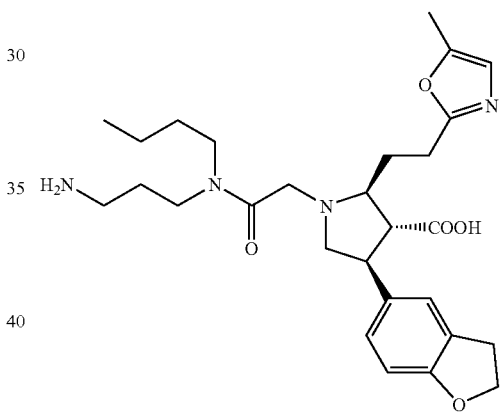
1189
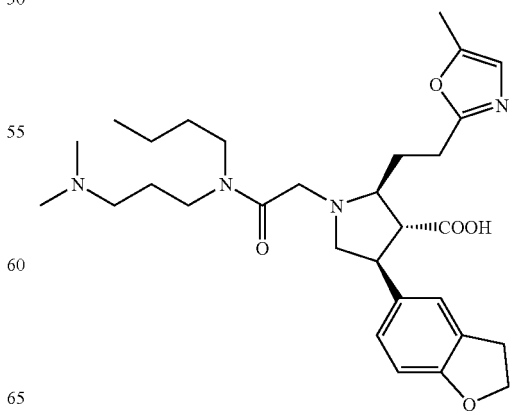

TABLE 3C-continued
1190
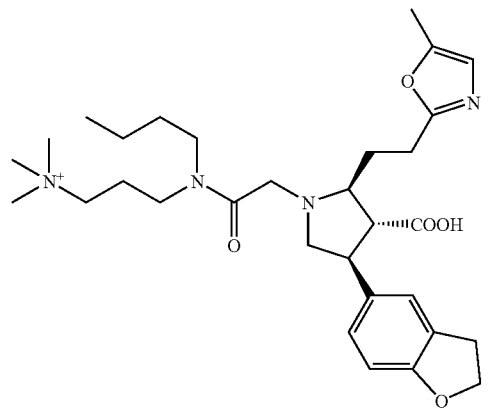
1191
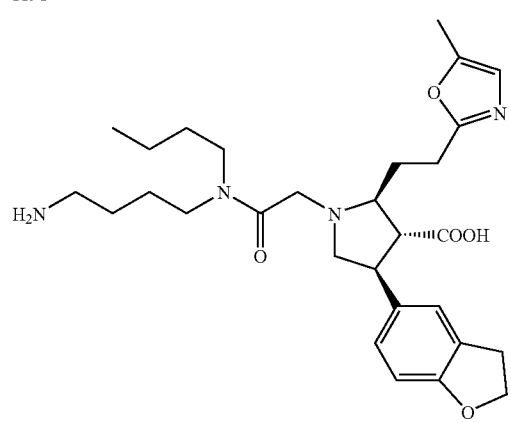
1192
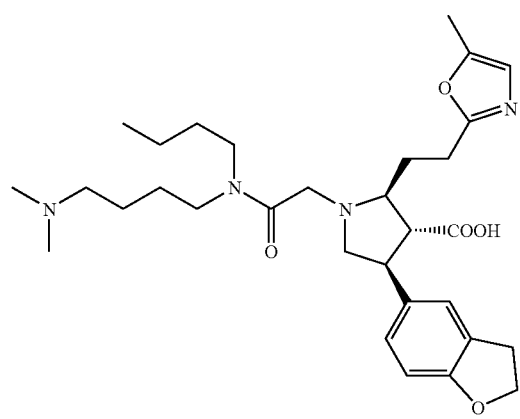
TABLE 3C-continued
1193
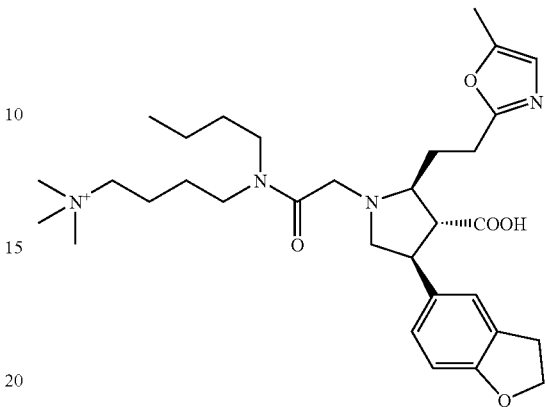
1194
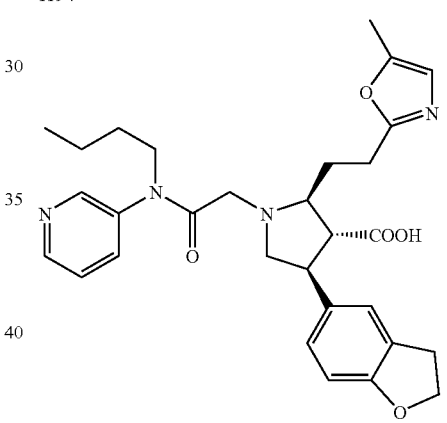
1195
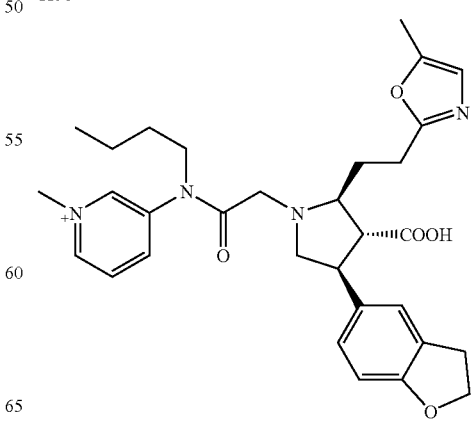

TABLE 3C-continued
1196
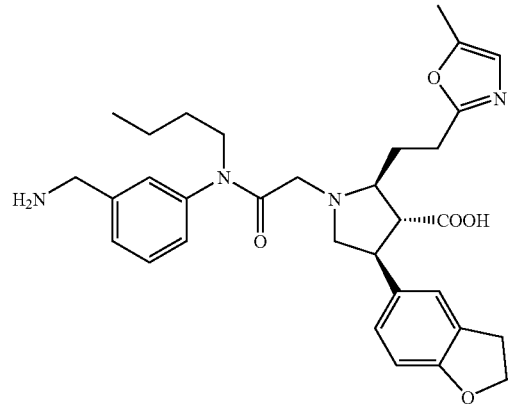
1197
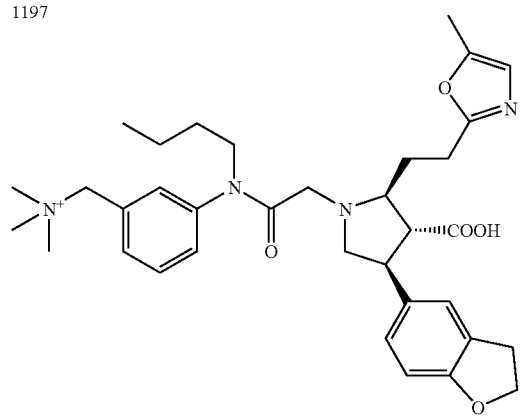
1198
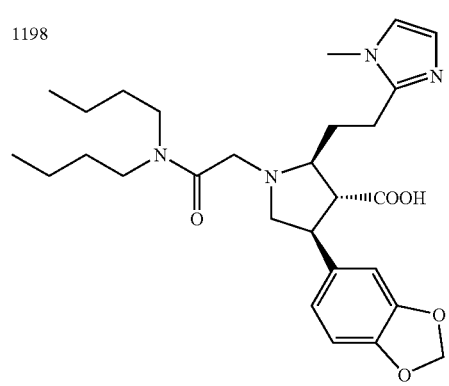
1199
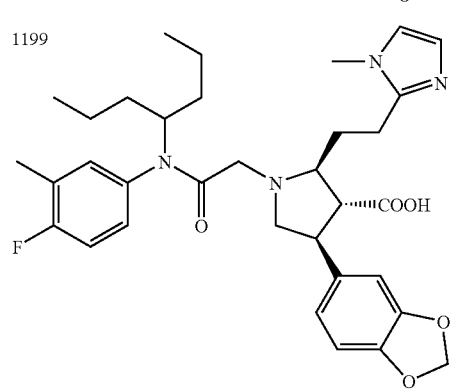
TABLE 3C-continued
1200
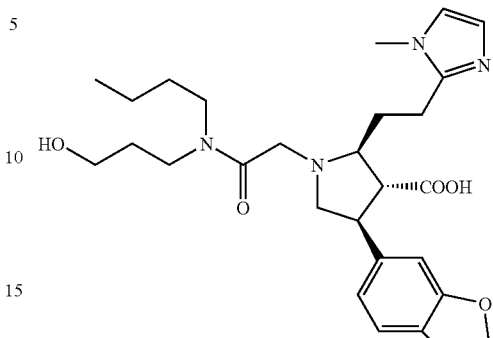
1201
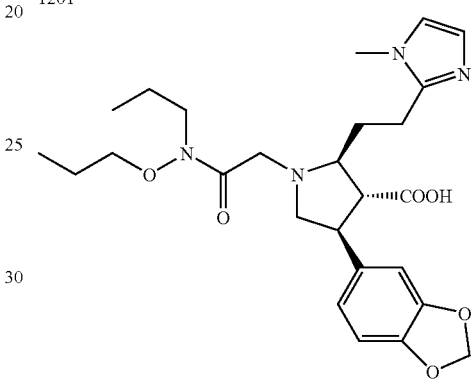
1202
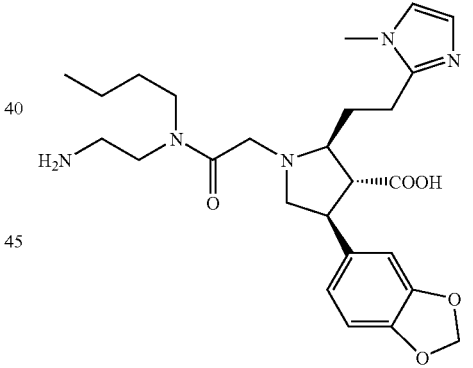
1203
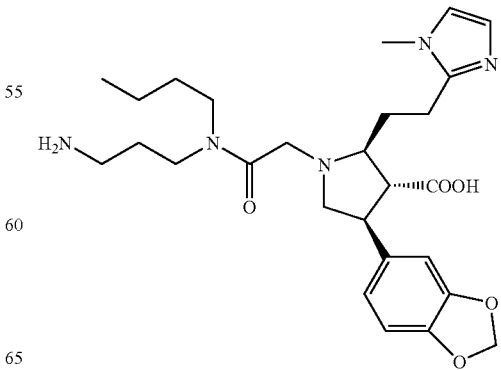

TABLE 3C-continued
1204
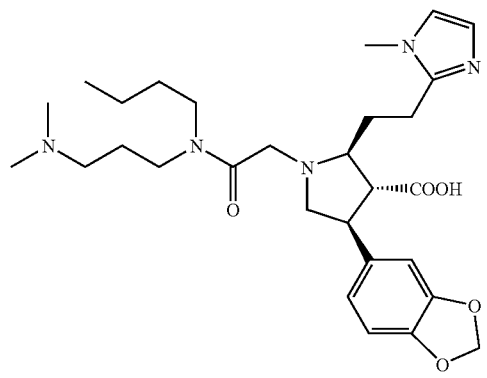
1205
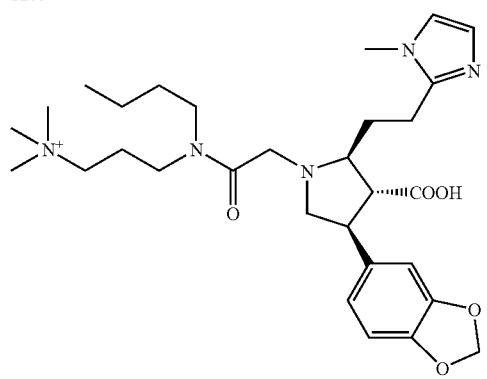
1206
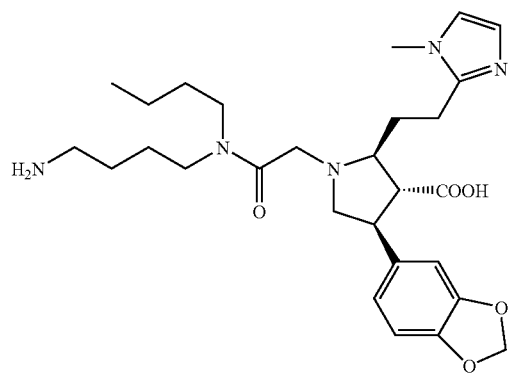
1207
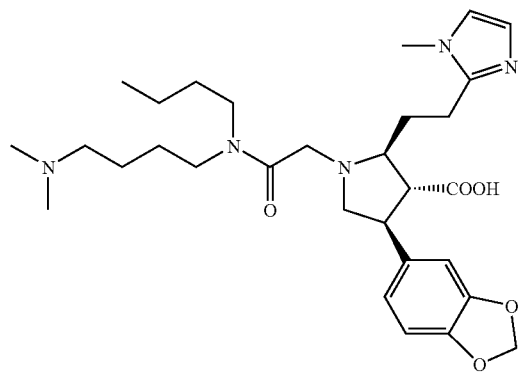
TABLE 3C-continued
1208
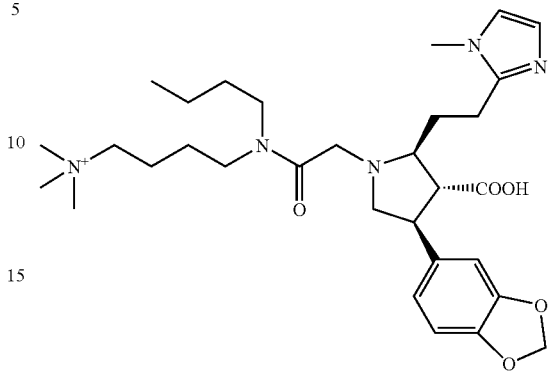
1209
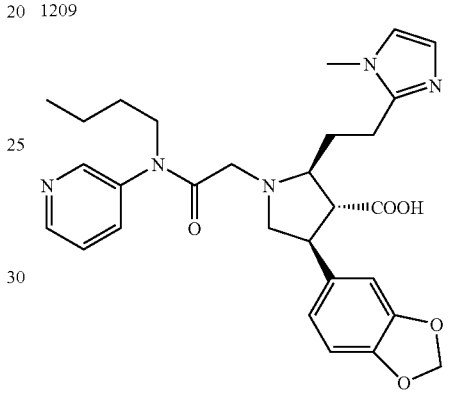
1210
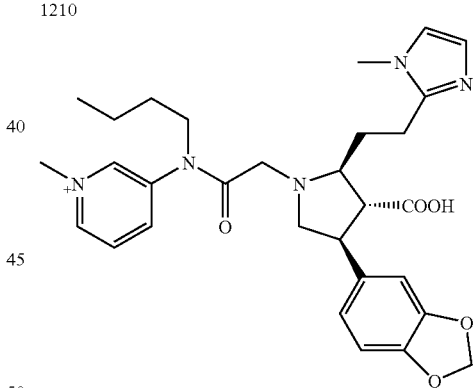
1211
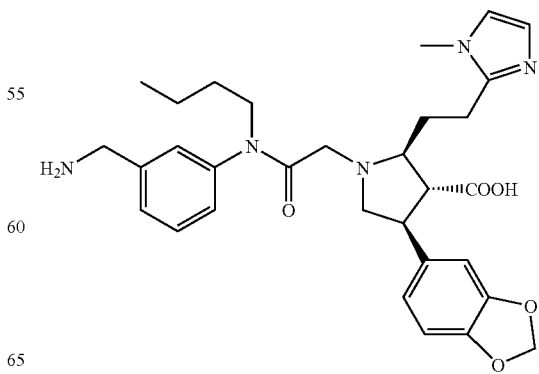

TABLE 3C-continued
1212
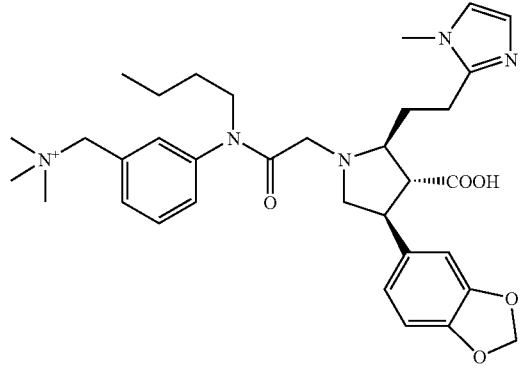
1213
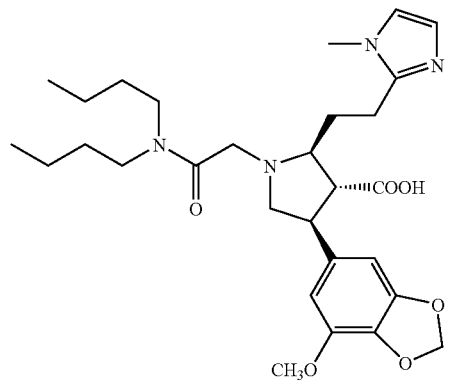
1214
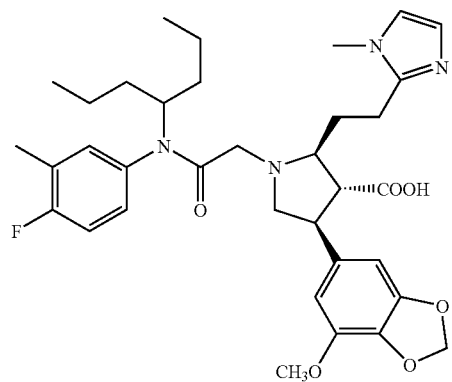
1215
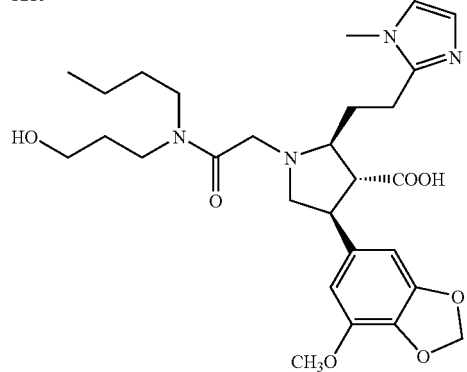
TABLE 3C-continued
1216
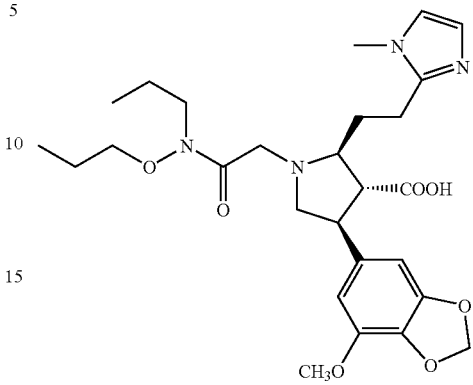
1217
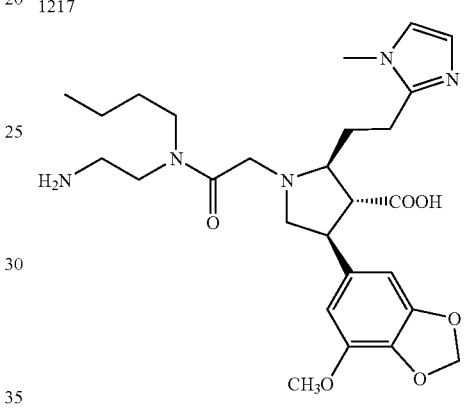
1218
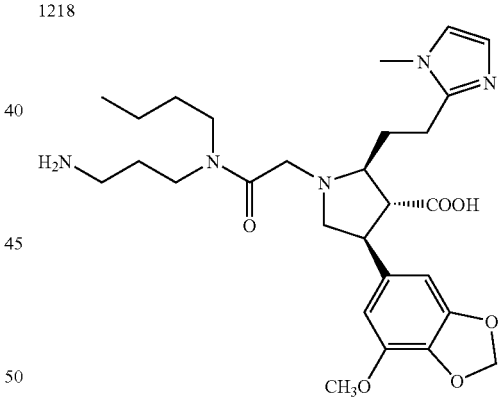
1219
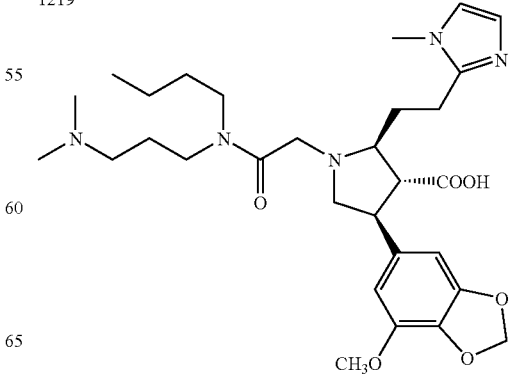

TABLE 3C-continued
1220
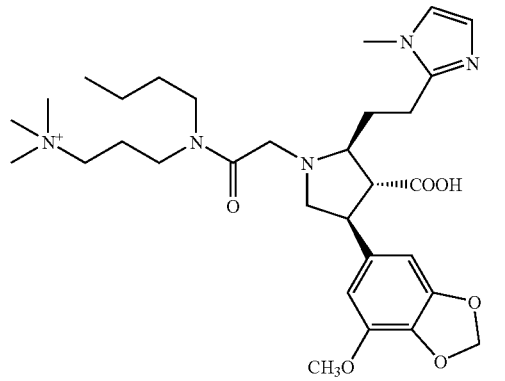
1221
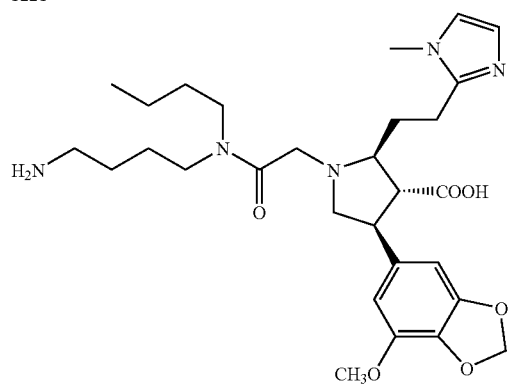
1222
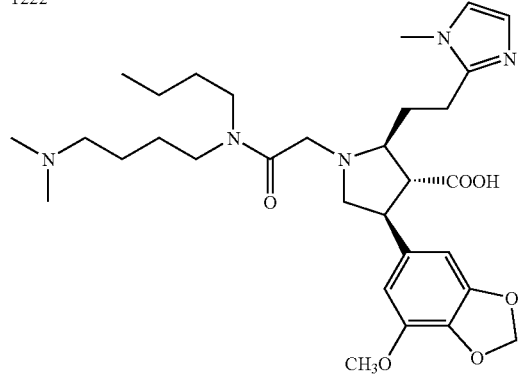
1223
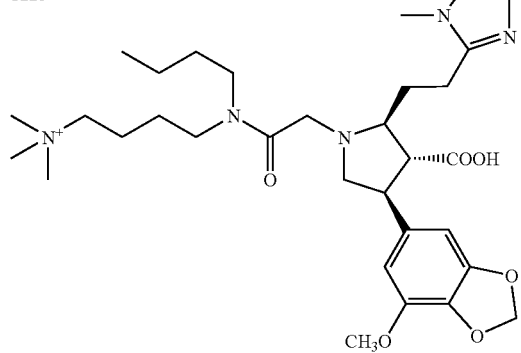
TABLE 3C-continued
1224
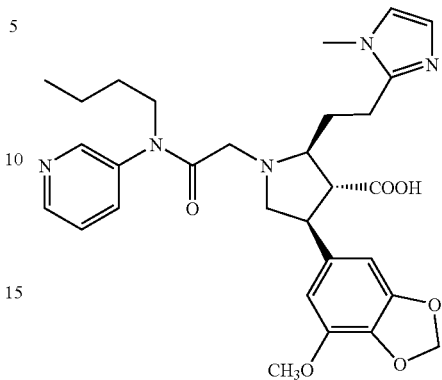
1225
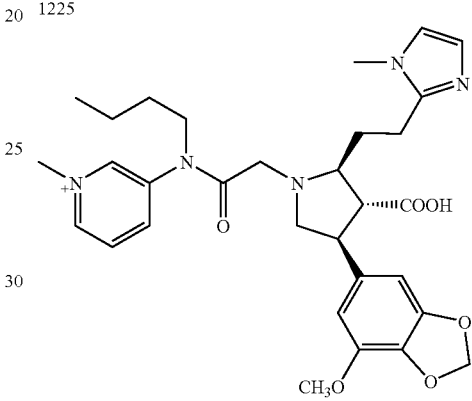
1226
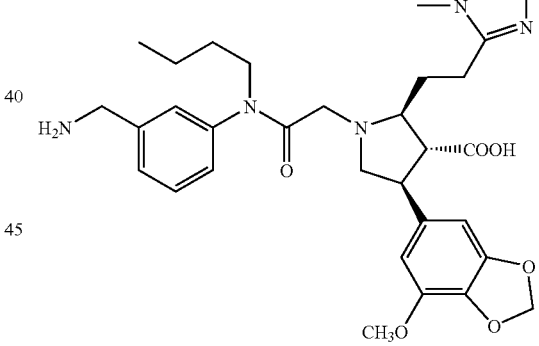
1227
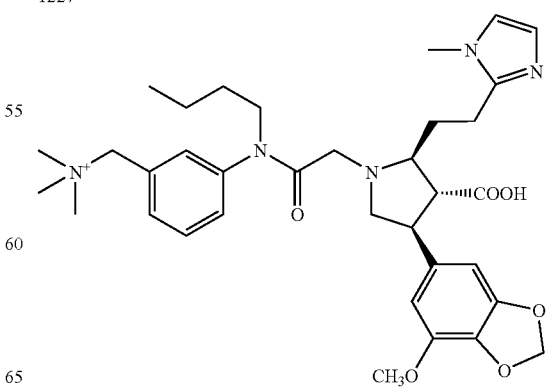

TABLE 3C-continued
1228
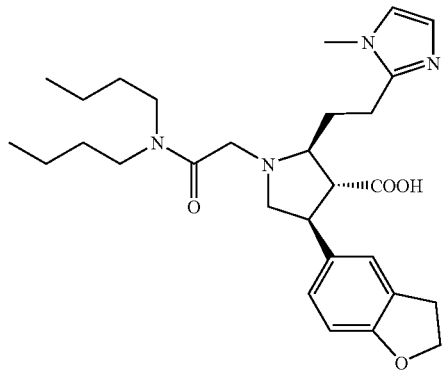
1229
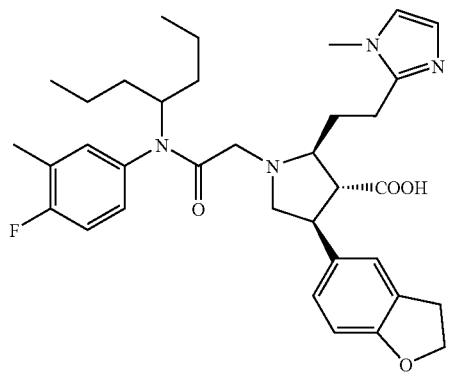
1230
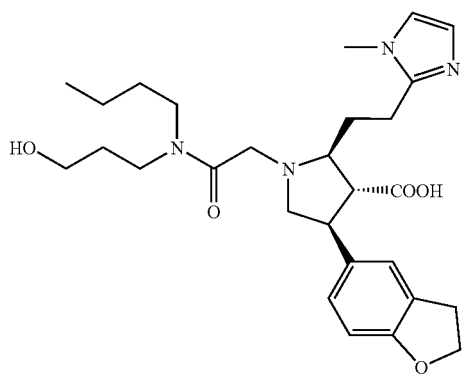
1231
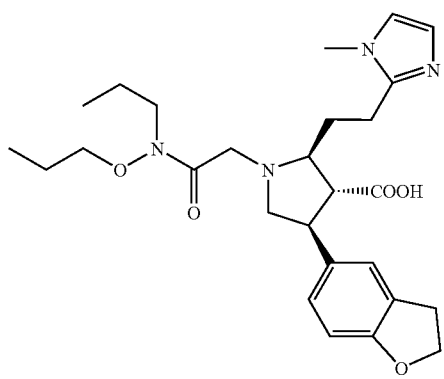
TABLE 3C-continued
1232
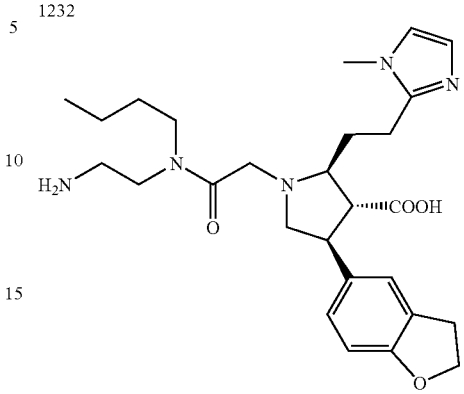
1233
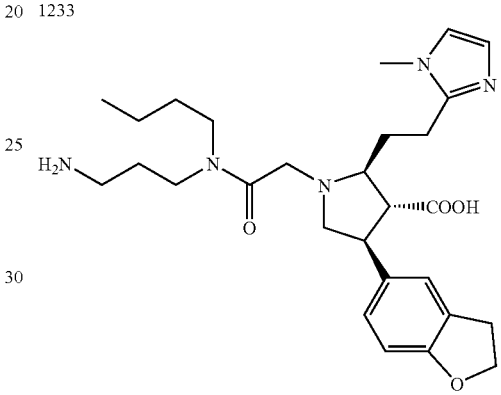
1234
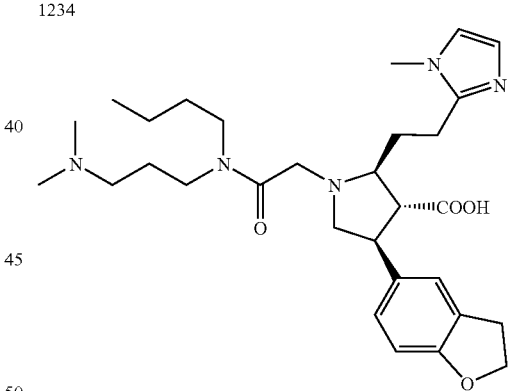
1235
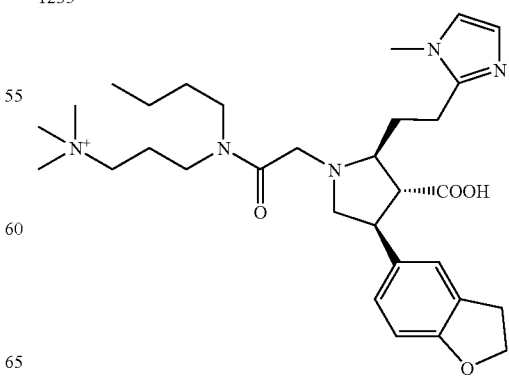

TABLE 3C-continued
1236
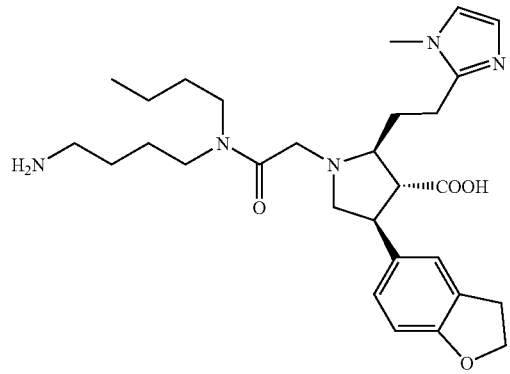
1237
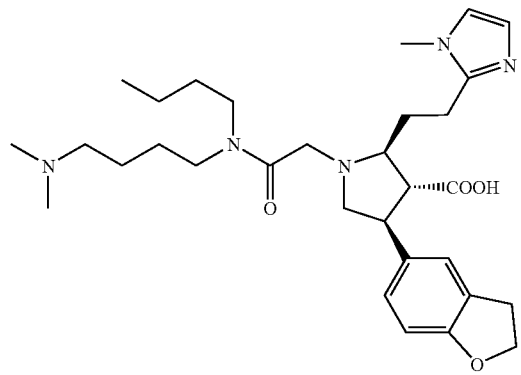
1238
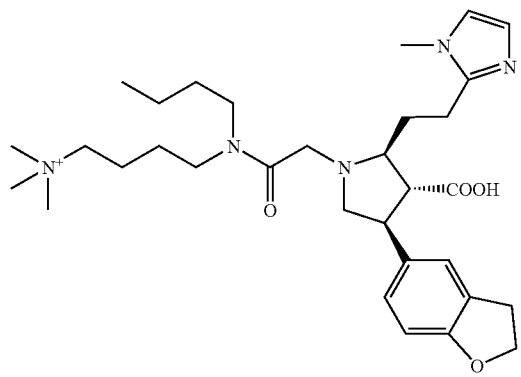
1239
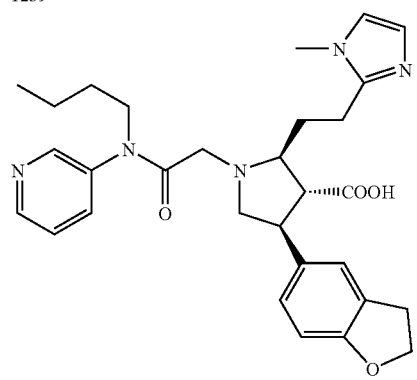
TABLE 3C-continued
1240
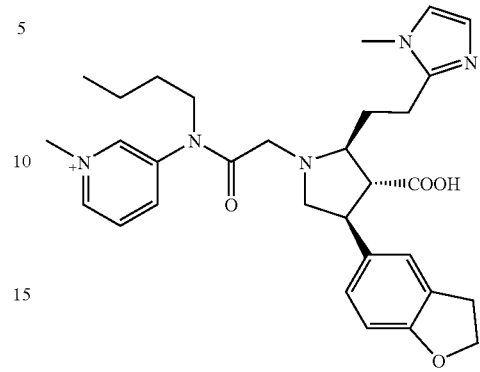
1241
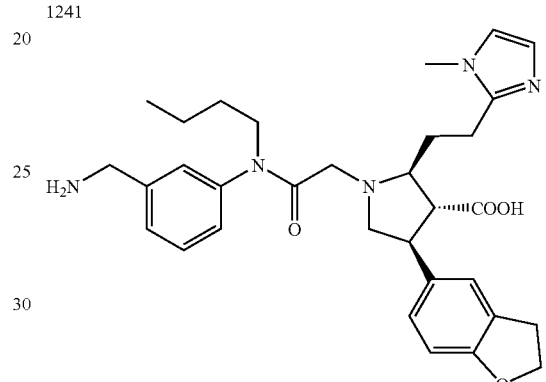
1242
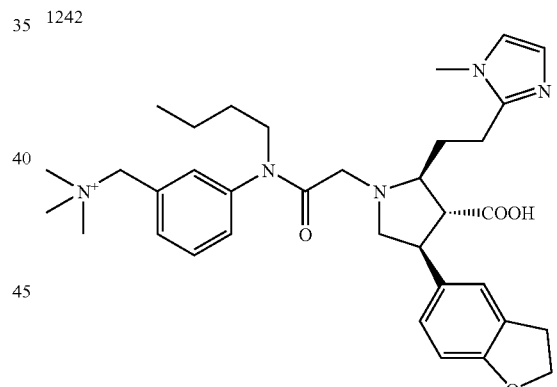
1243
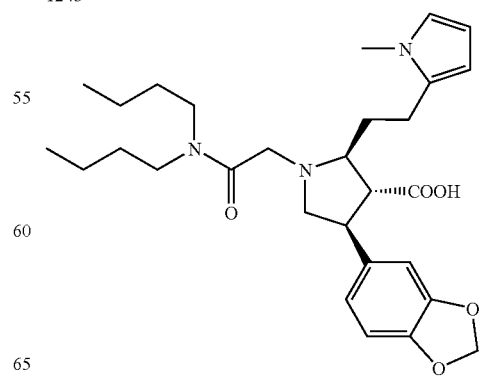

TABLE 3C-continued
1244
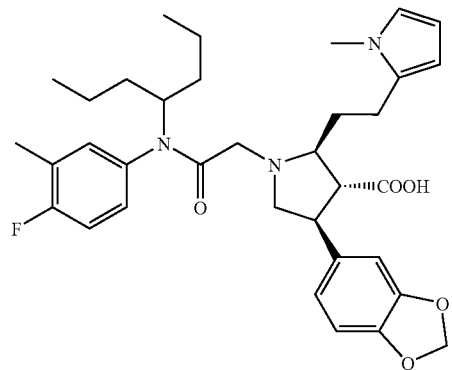
1245
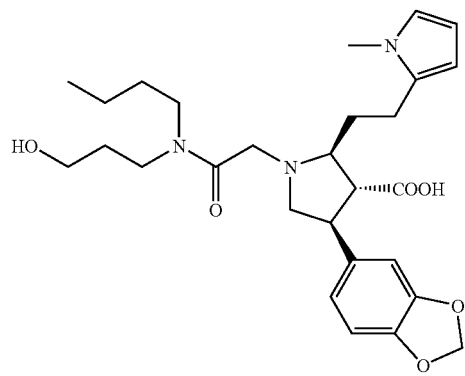
1246
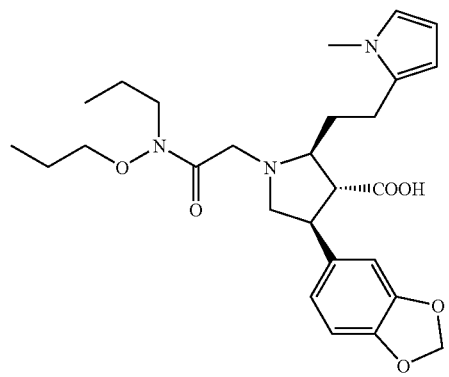
1247
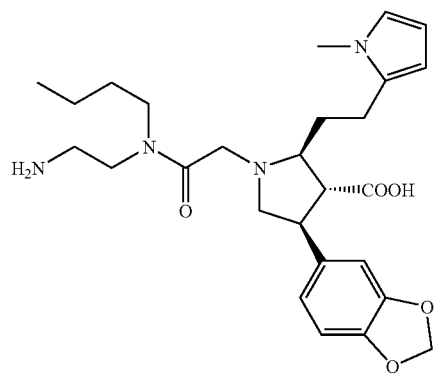
TABLE 3C-continued
1248
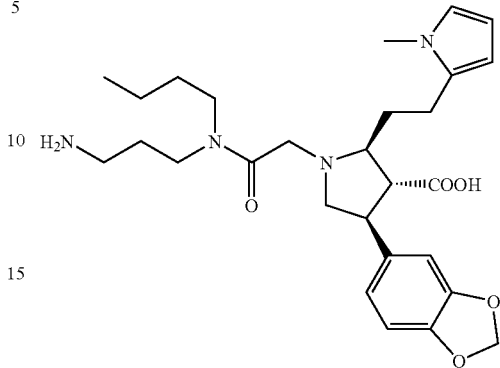
1249
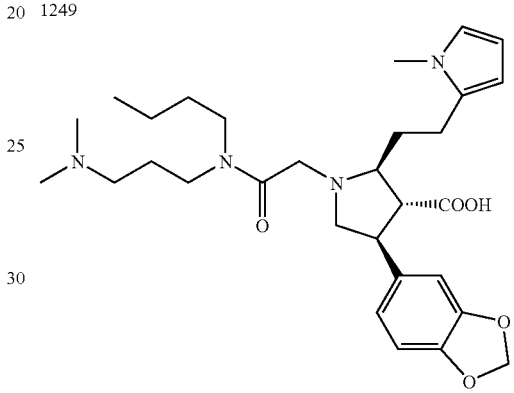
1250
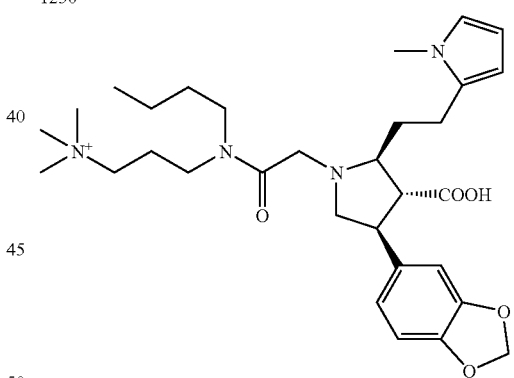
1251
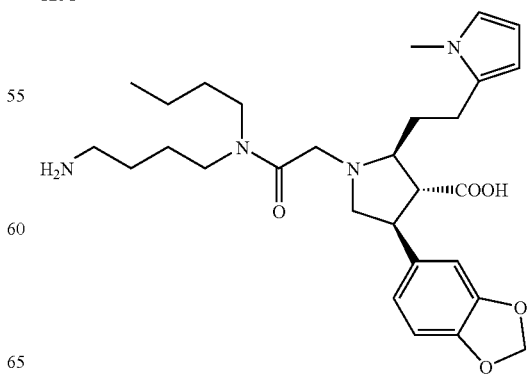

TABLE 3C-continued
1252
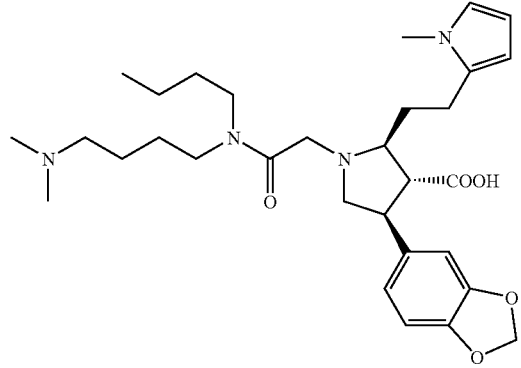
1253
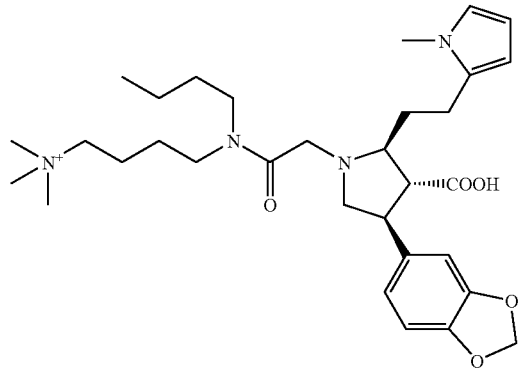
1254
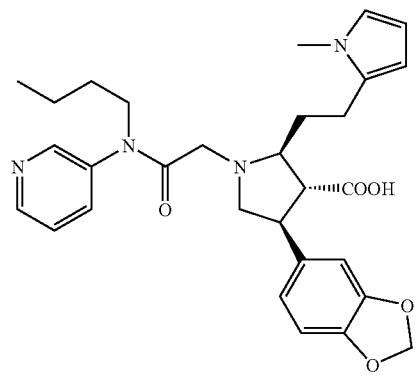
1255
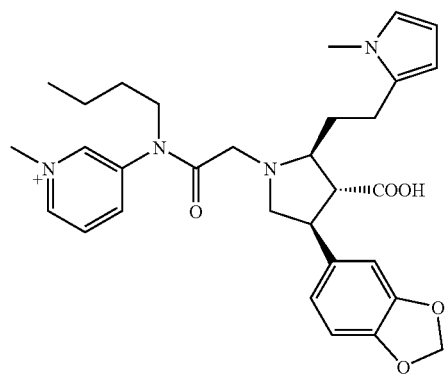
TABLE 3C-continued
1256
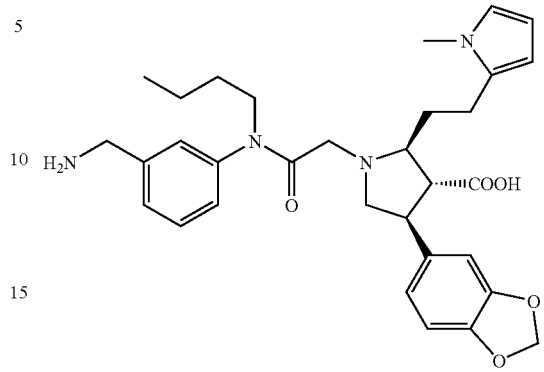
1257
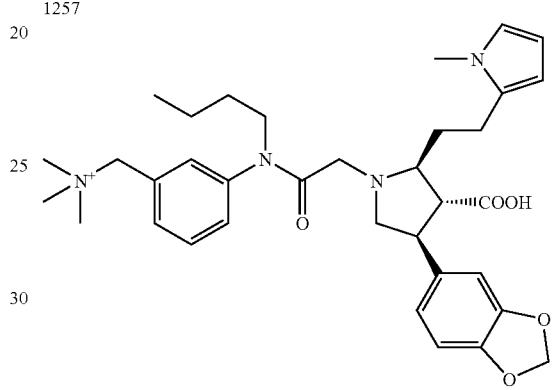
1258
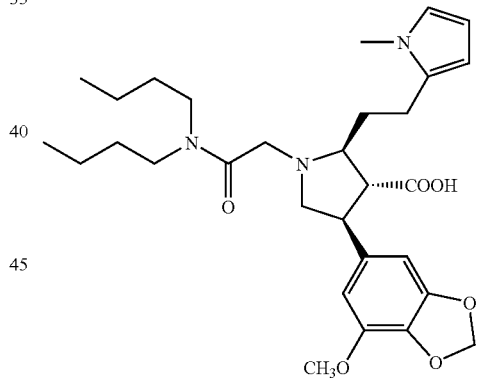
1259
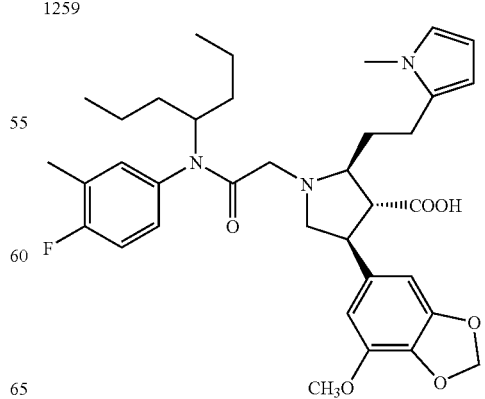

TABLE 3C-continued
1260
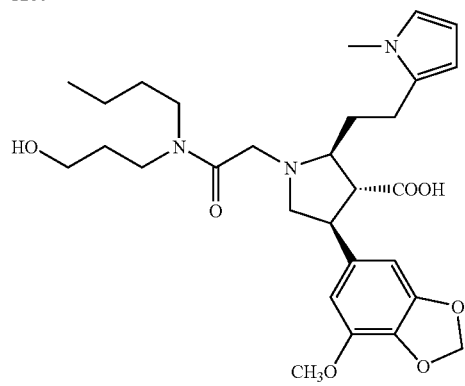
1261
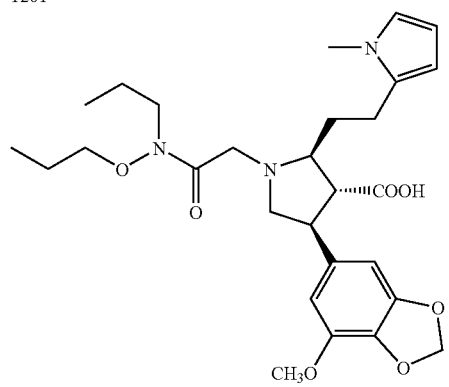
1262
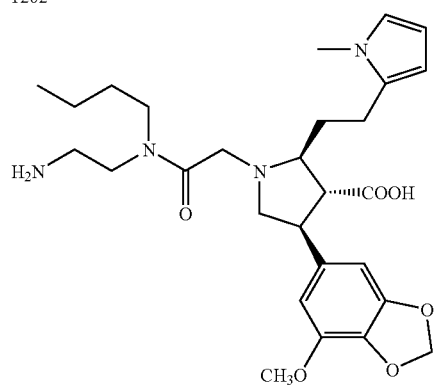
1263
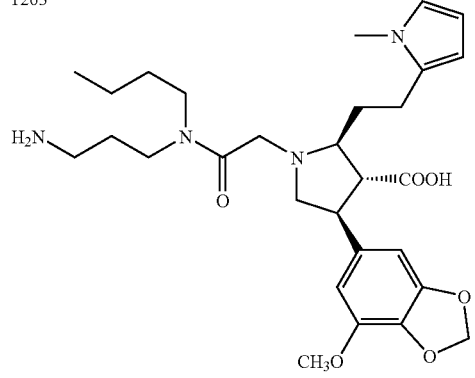
TABLE 3C-continued
1264
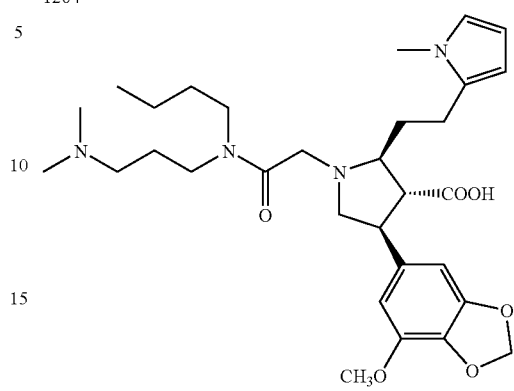
1265
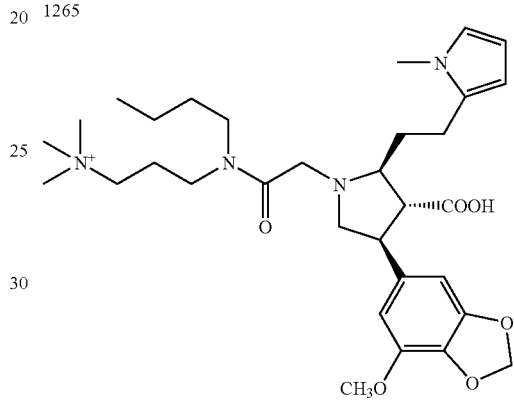
1266
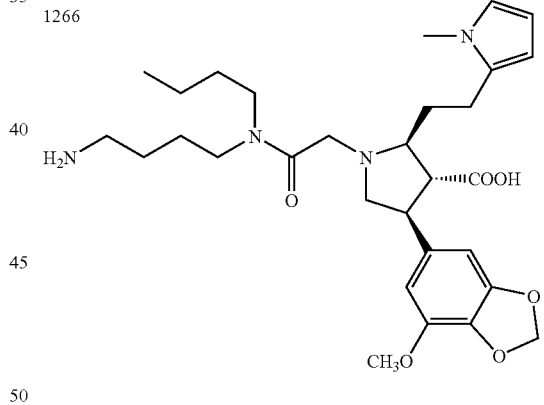
1267
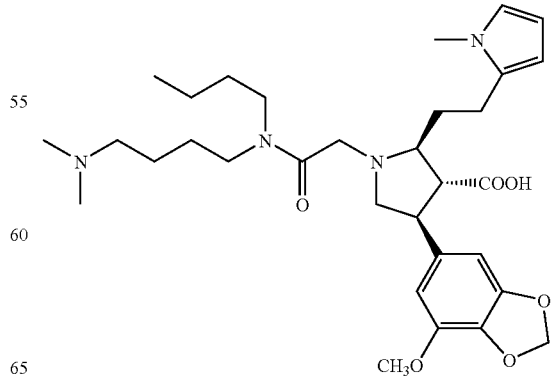

TABLE 3C-continued
1268
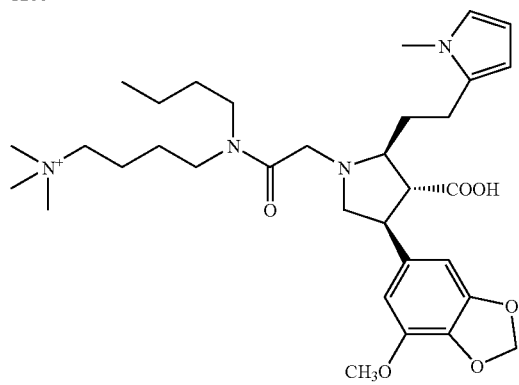
1269
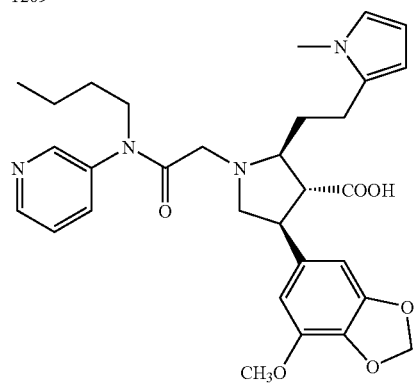
1270
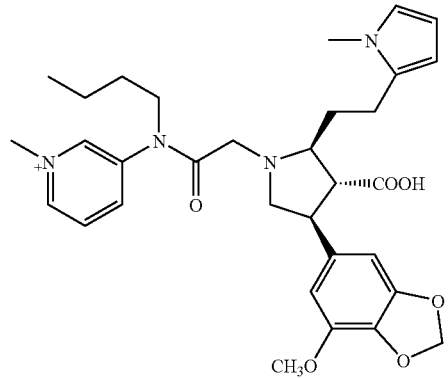
1271
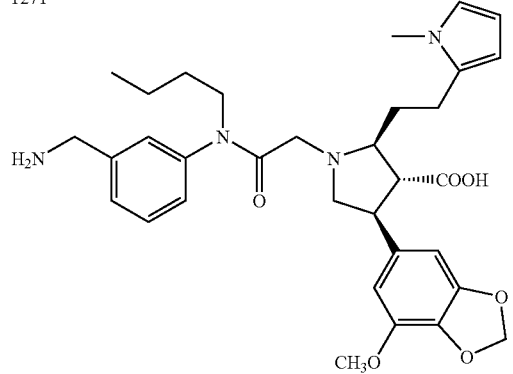
TABLE 3C-continued
1272
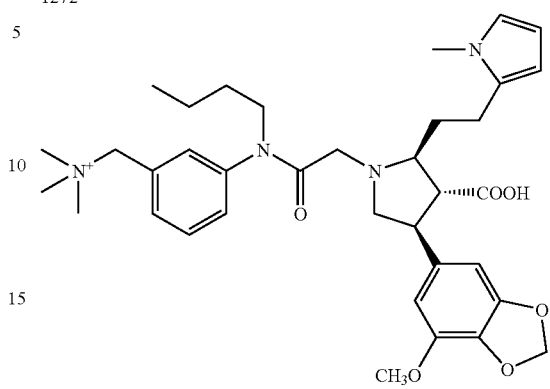
1273
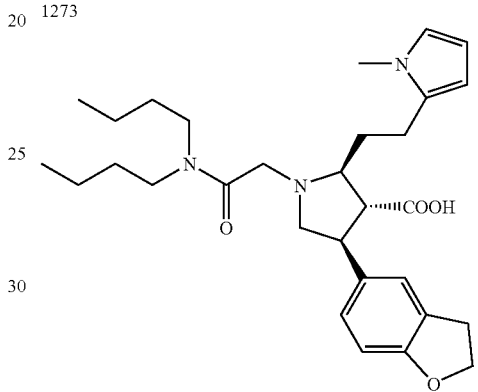
1274
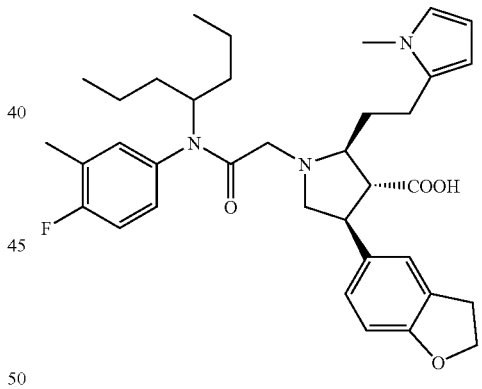
1275
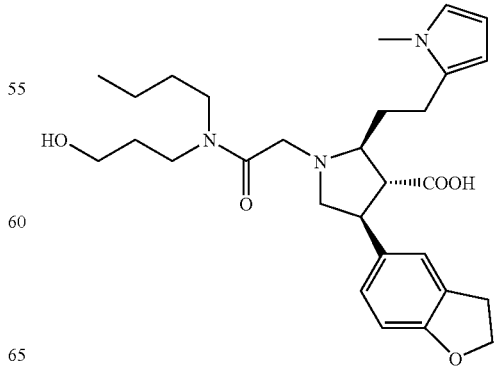

TABLE 3C-continued
1276
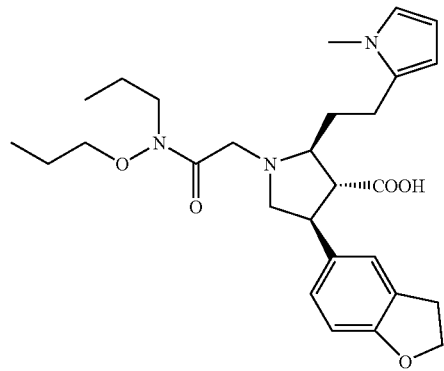
1277
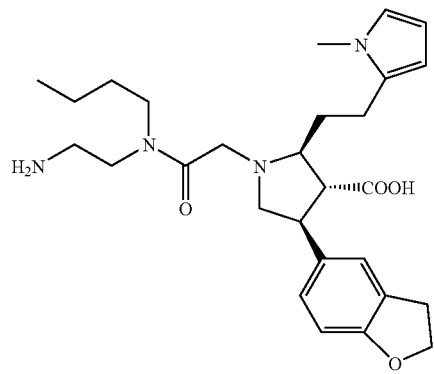
1278
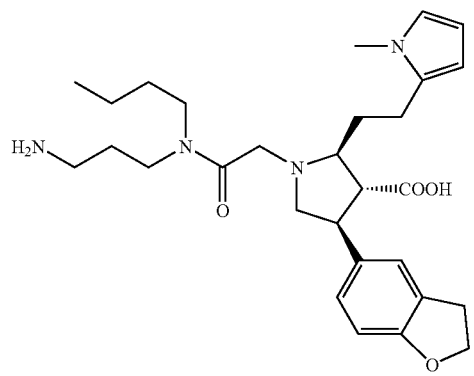
1279
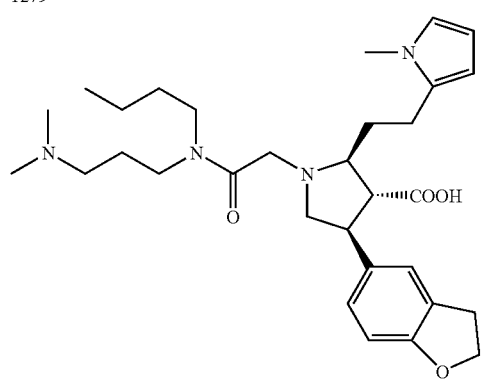
TABLE 3C-continued
1280
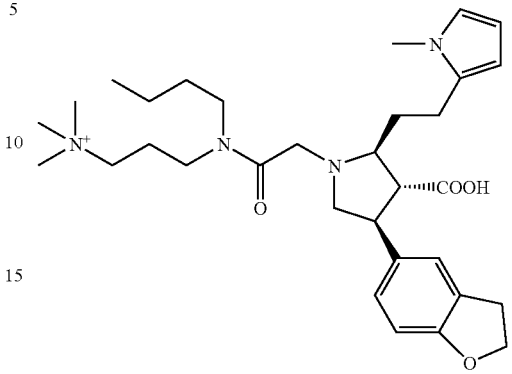
1281
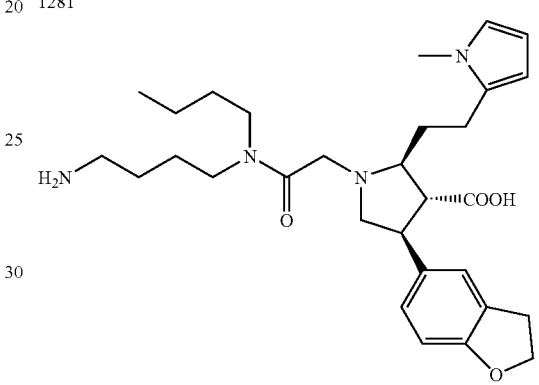
1282
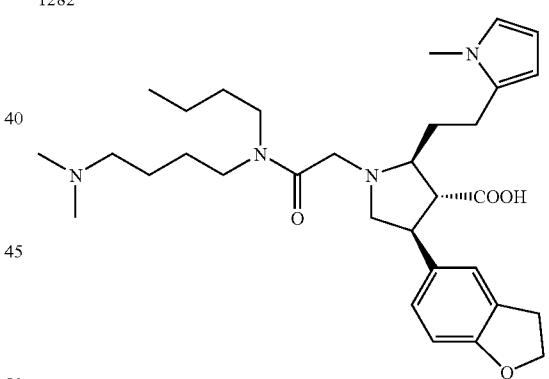
1283
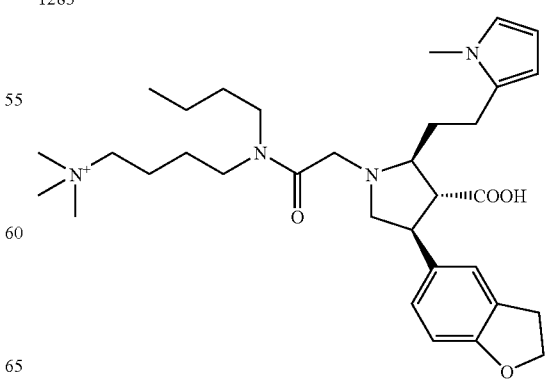

TABLE 3C-continued
1284
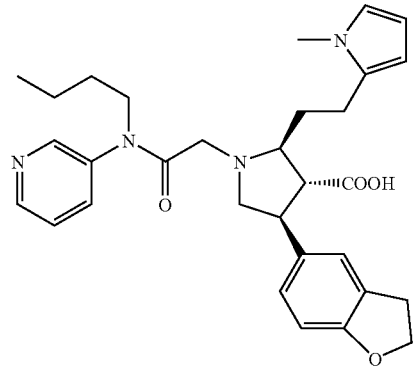
1285
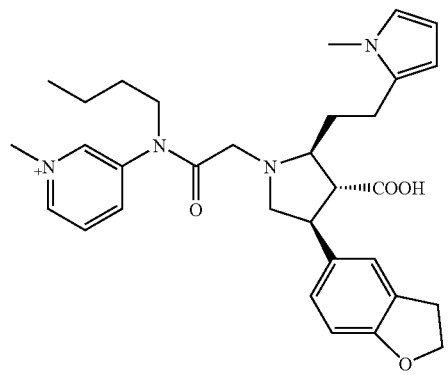
1286
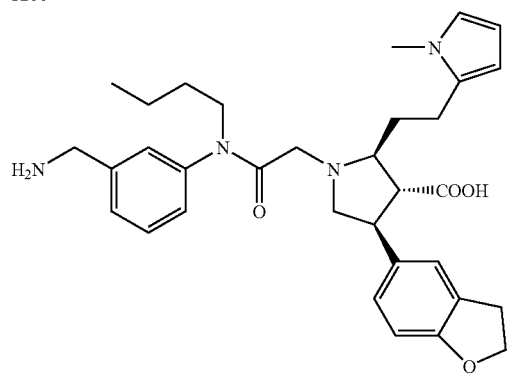
1287
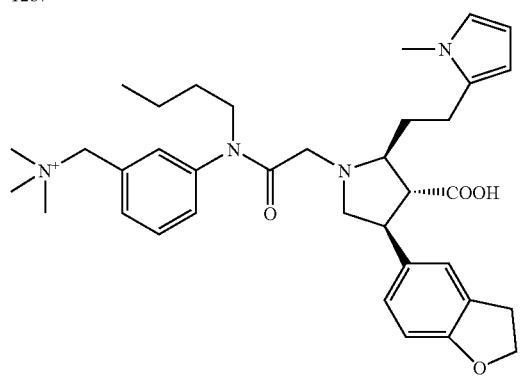
TABLE 3C-continued
1288
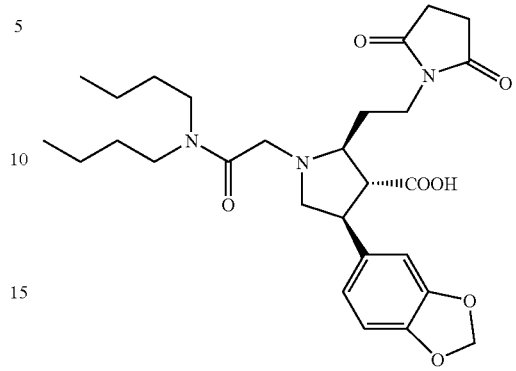
1289
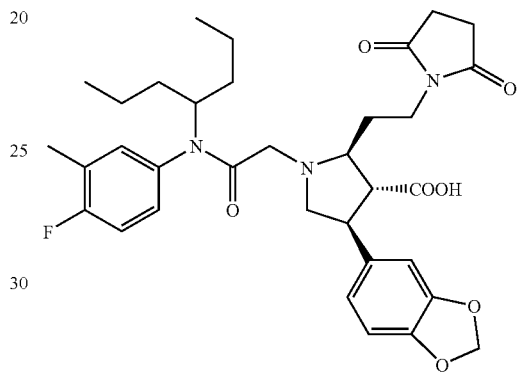
1290
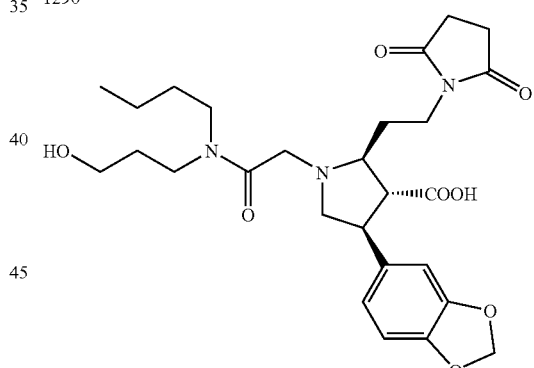
1291
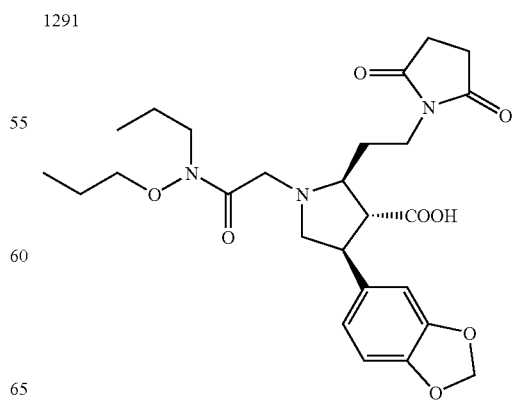

TABLE 3C-continued
1292
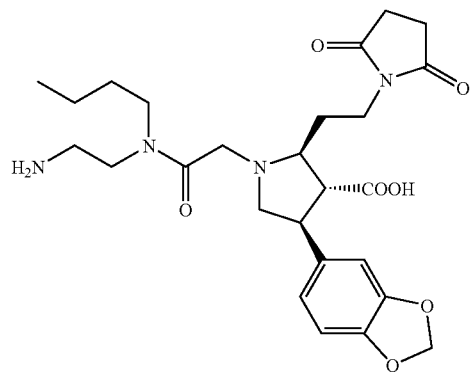
1293
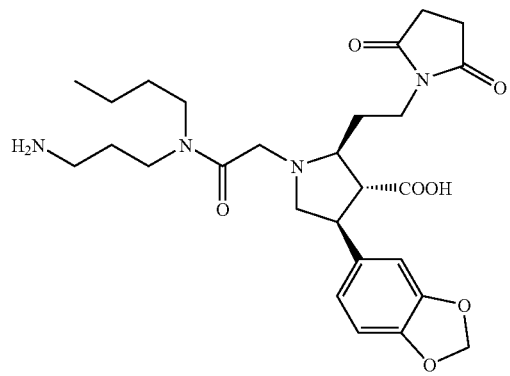
1294
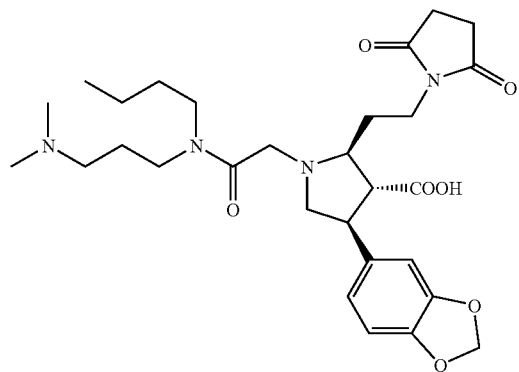
1295
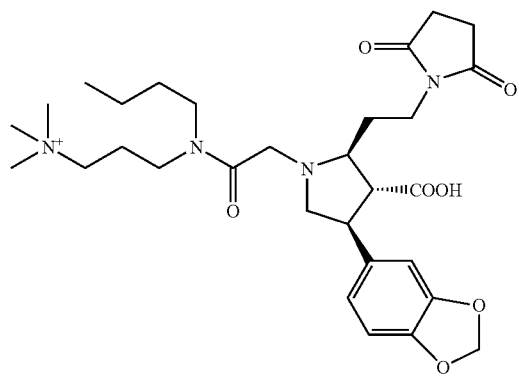
TABLE 3C-continued
1296
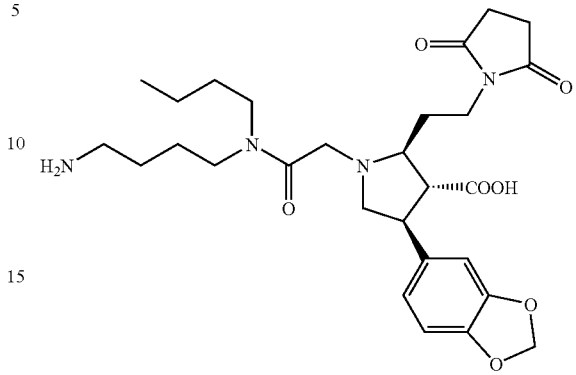
1297
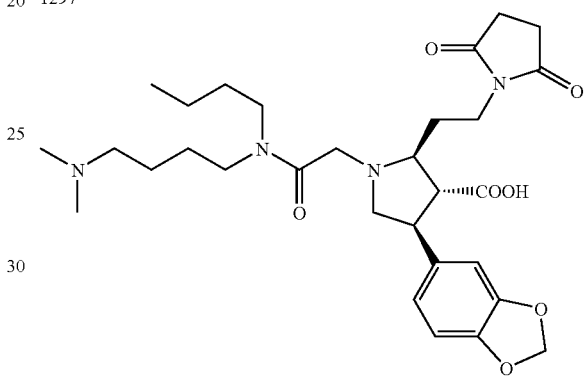
1298
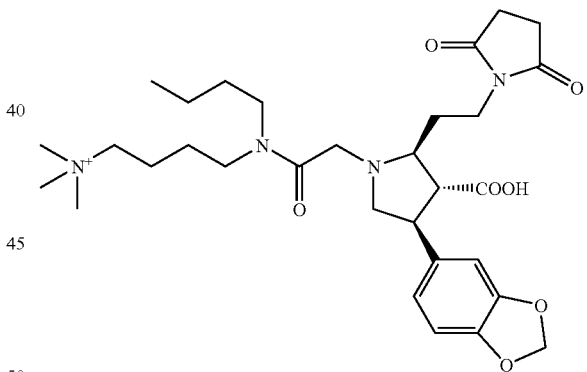
1299
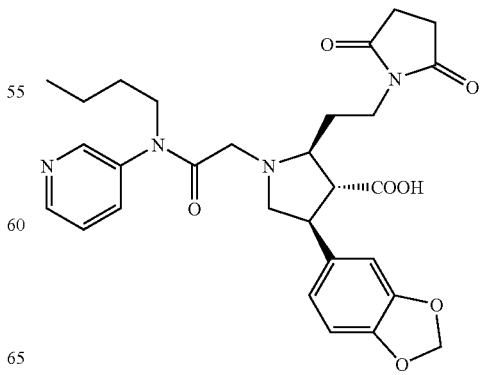

TABLE 3C-continued
1300
1301
1302
1303
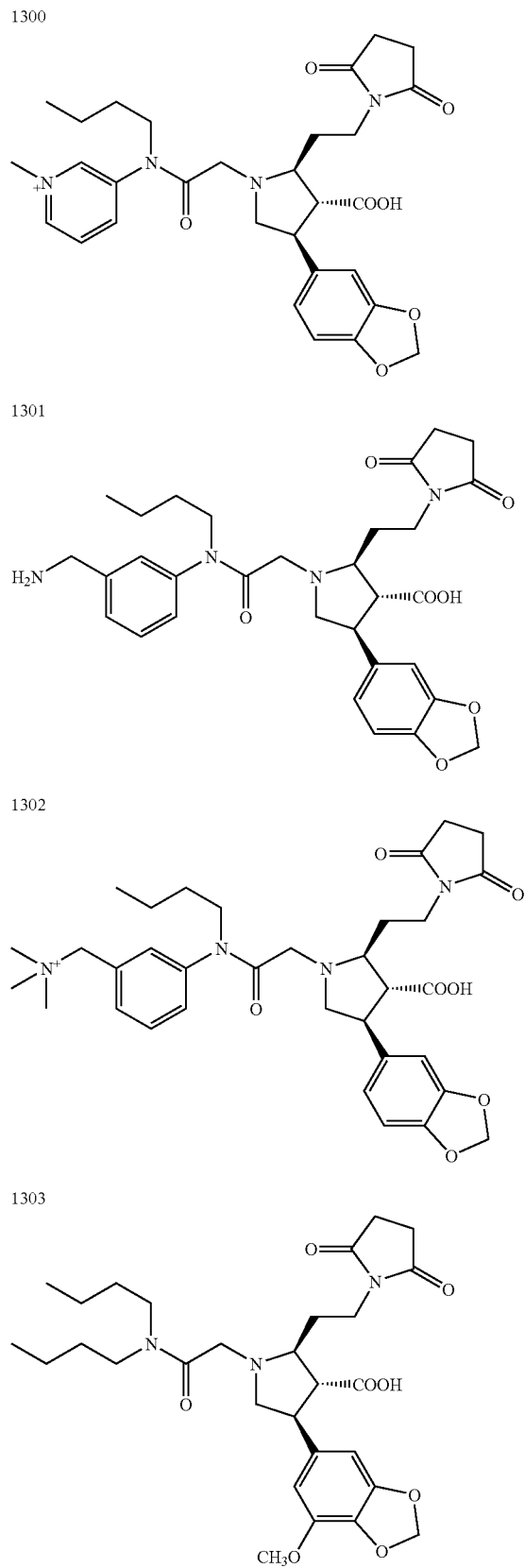
1304
1305
1306
1307
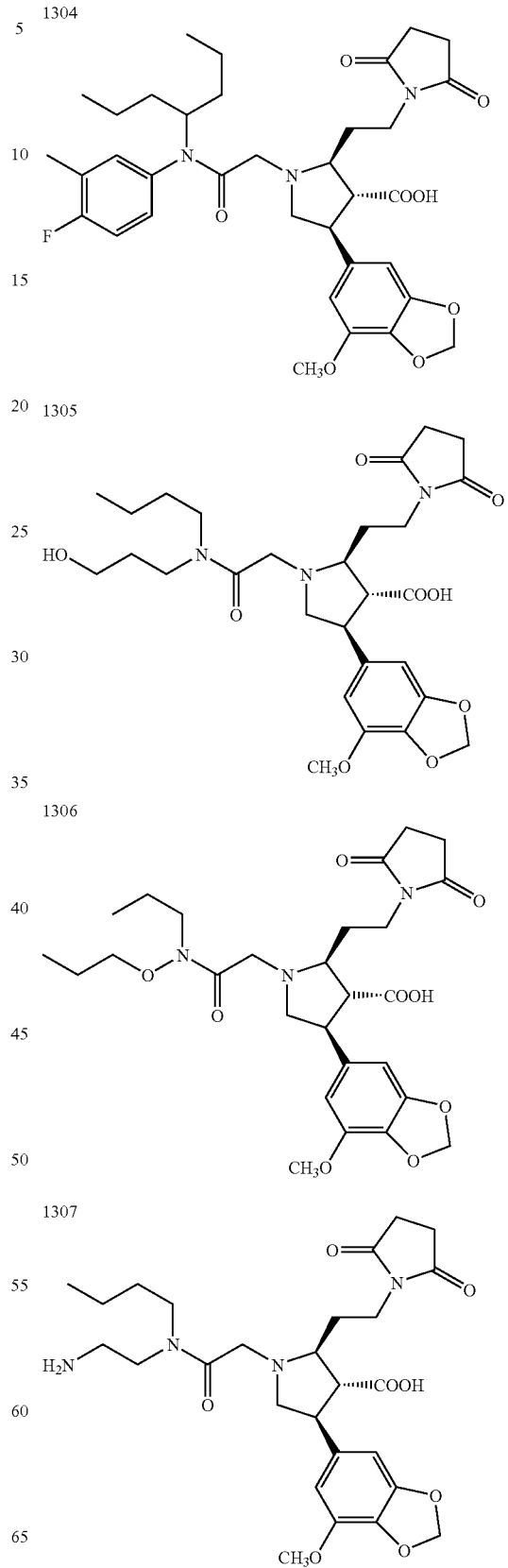

TABLE 3C-continued
1308
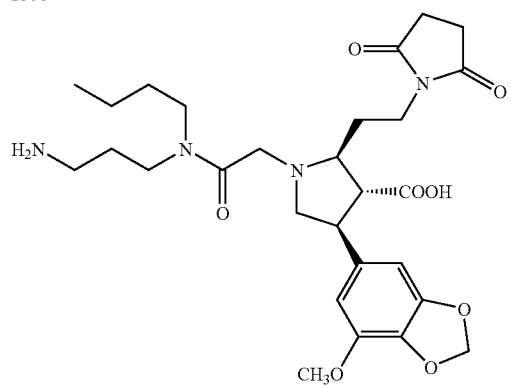
1309
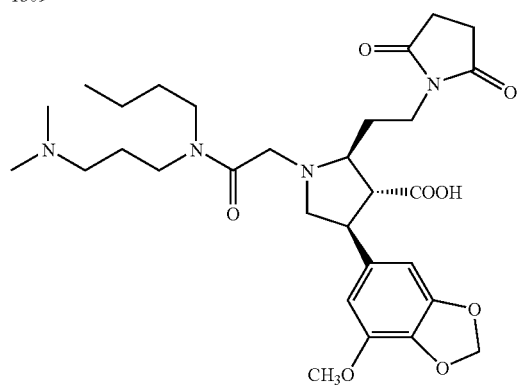
1310
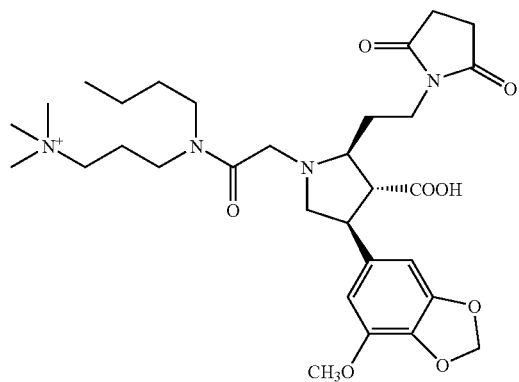
1311
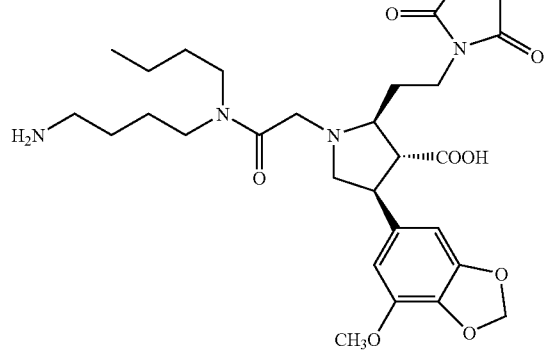
TABLE 3C-continued
1312
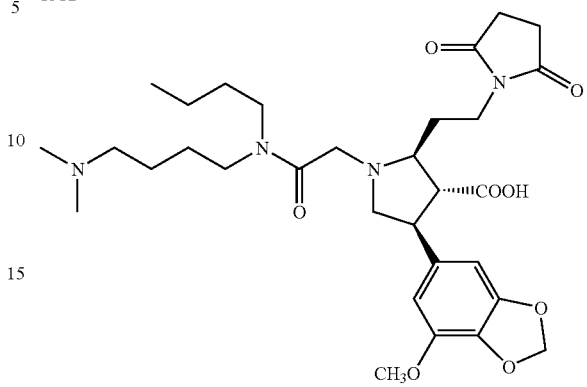
1313
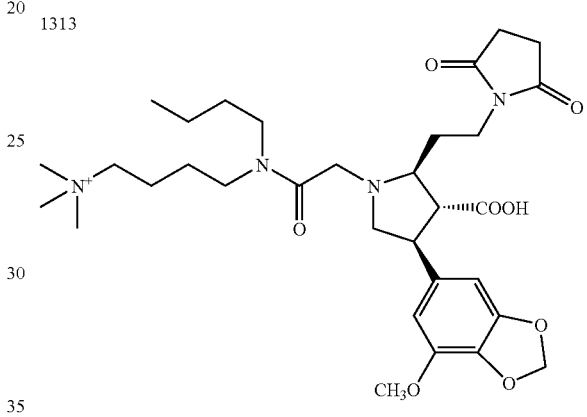
1314
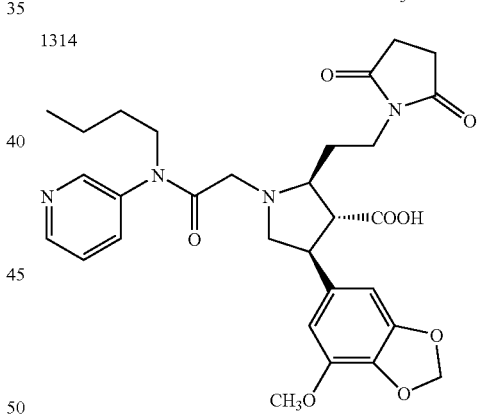
1315
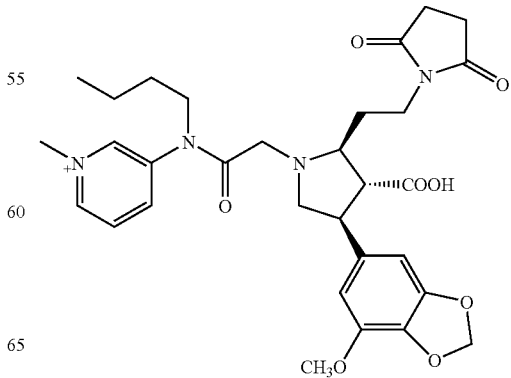

TABLE 3C-continued
1316
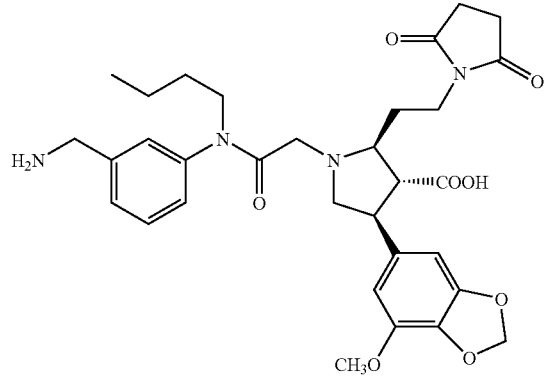
1317
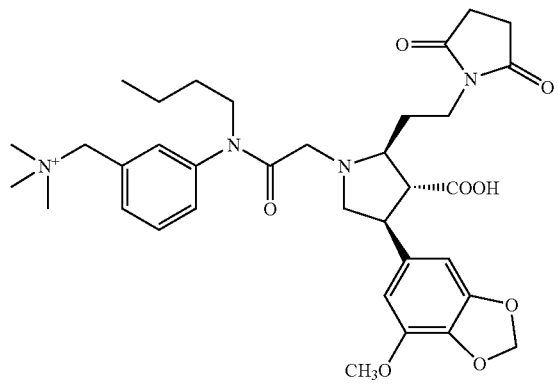
1318
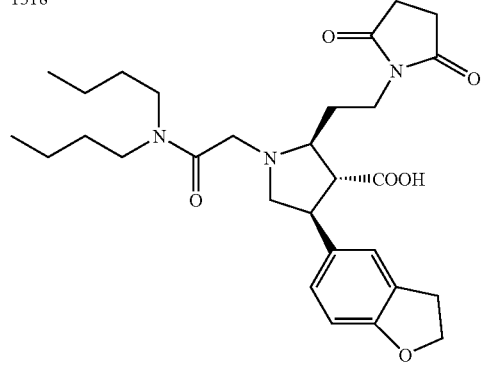
1319
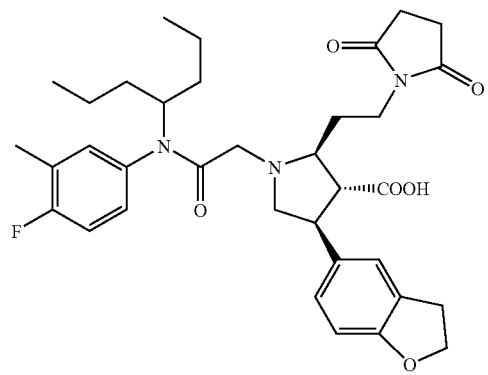
TABLE 3C-continued
1320
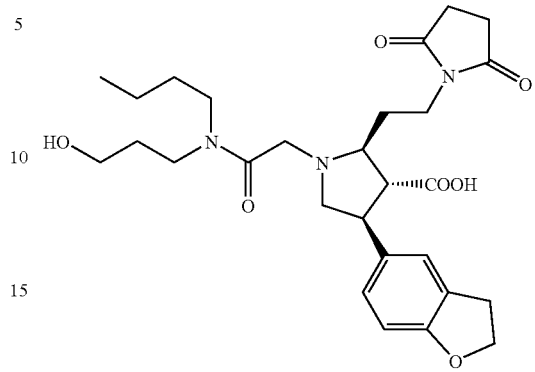
1321
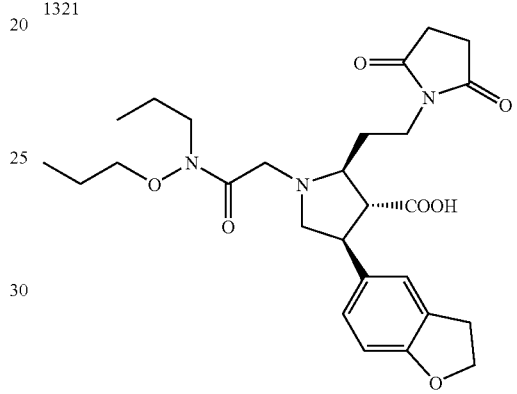
1322
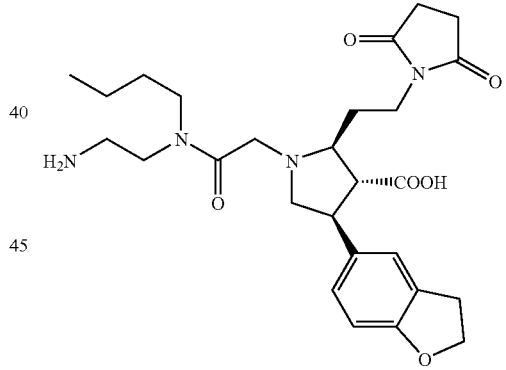
1323
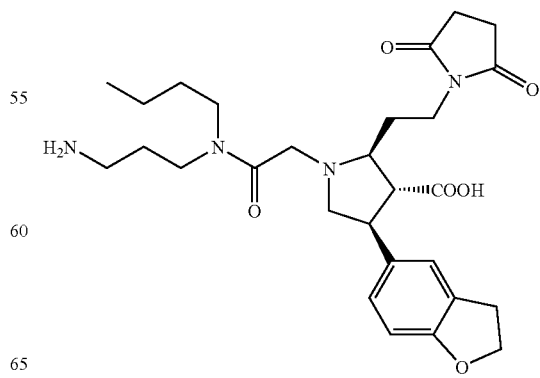

TABLE 3C-continued
1324
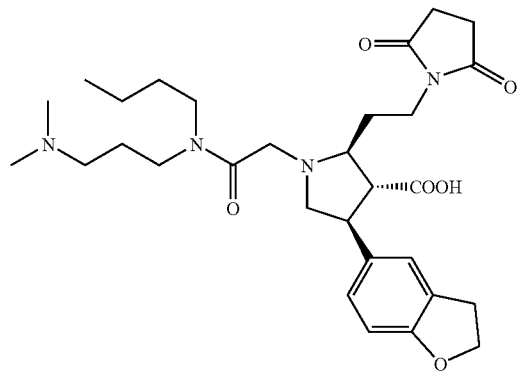
1325
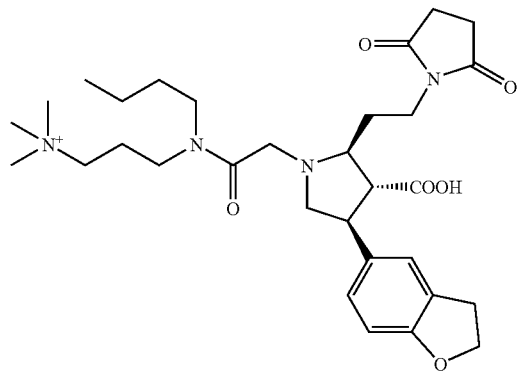
1326
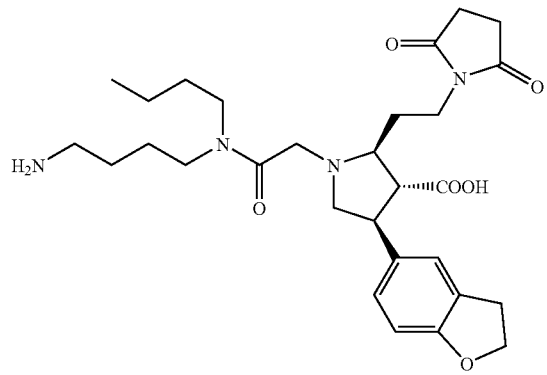
1327
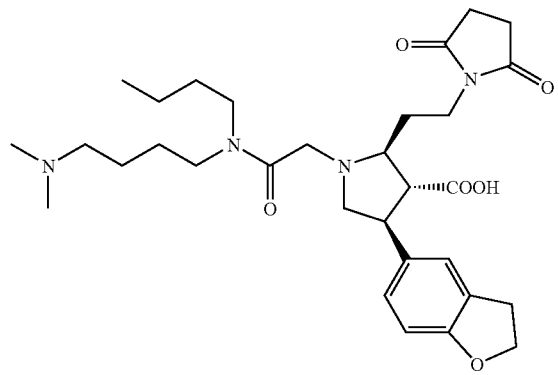
TABLE 3C-continued
1328
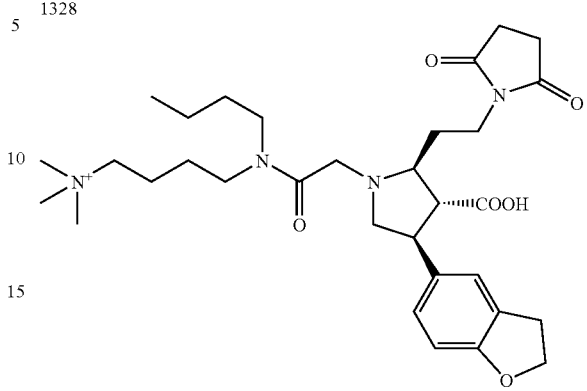
1329
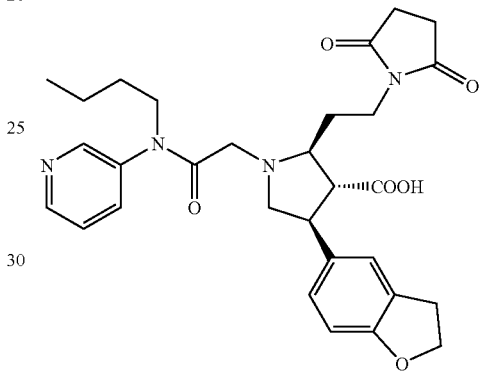
1330
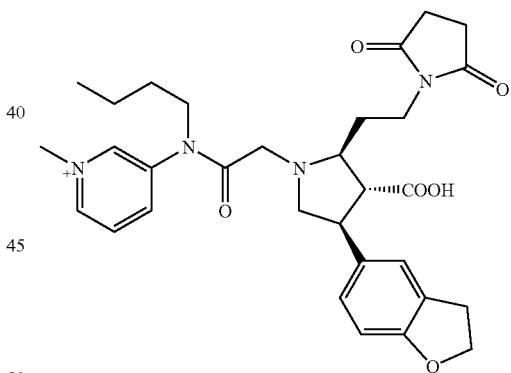
1331
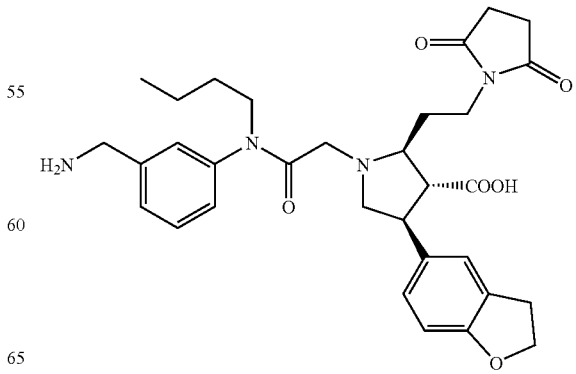

| 1005 | 1006 |
|---|---|
| TABLE 3C-continued | TABLE 3C-continued |
| 1332 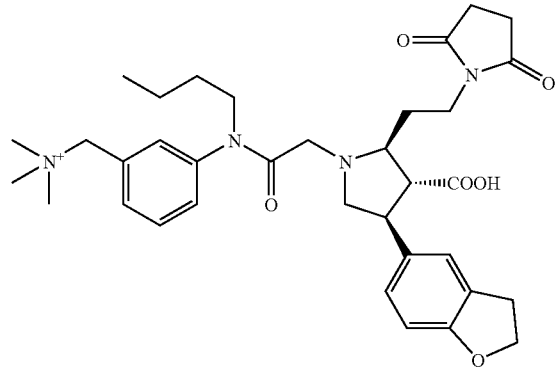 | 1336 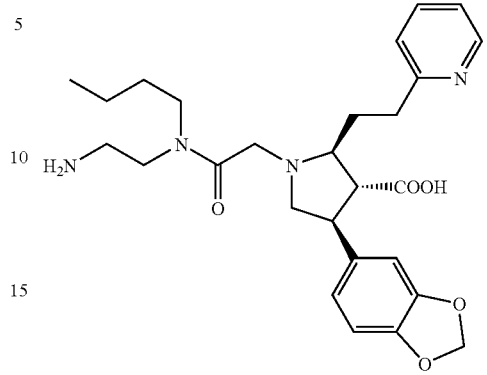 |
| 1333 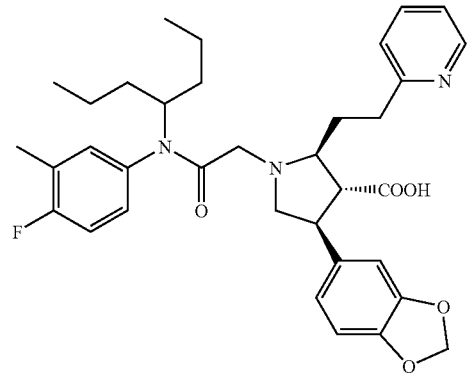 | 1337 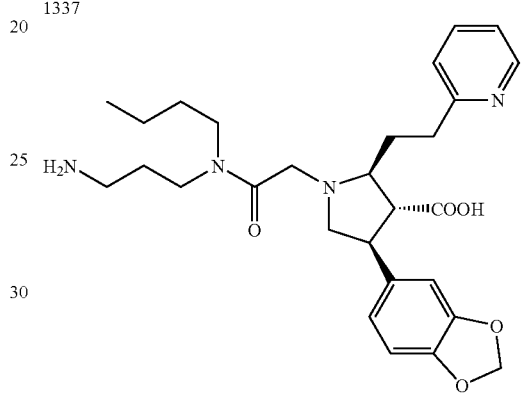 |
| 1334 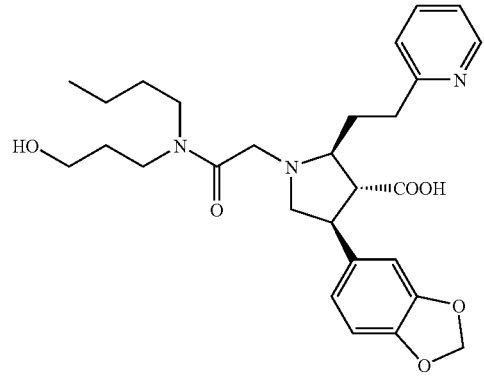 | 1338 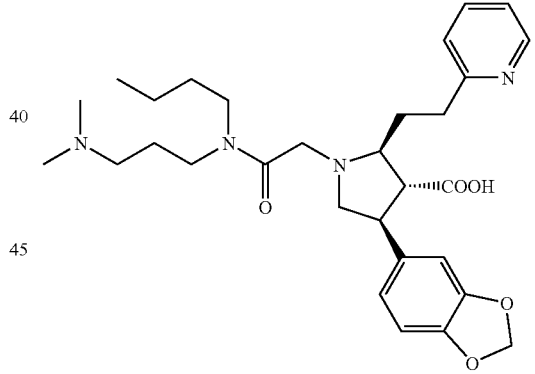 |
| 1335 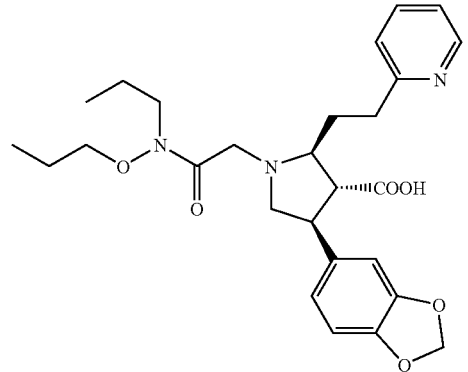 | 1339 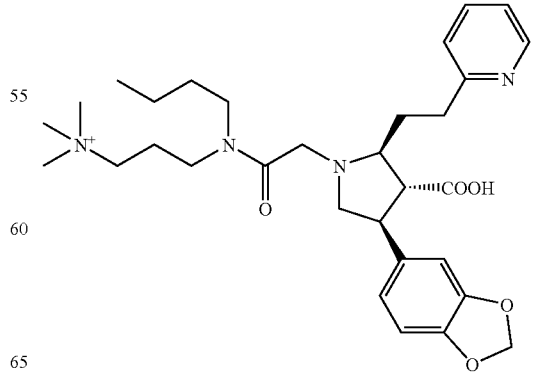 |

TABLE 3C-continued
1340
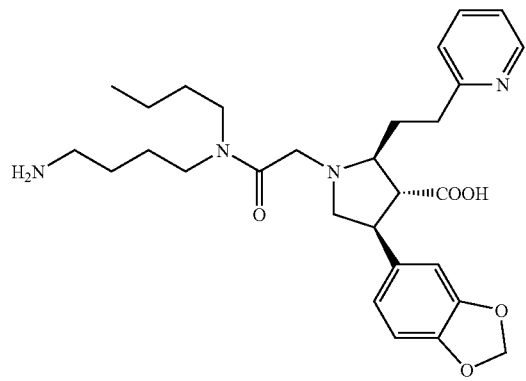
1341
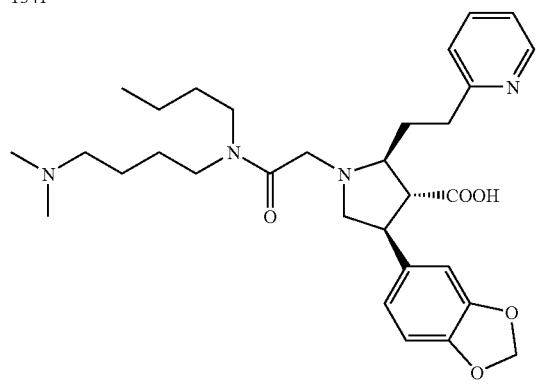
1342
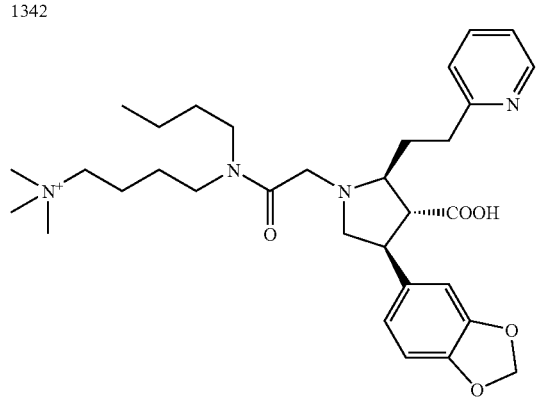
1343
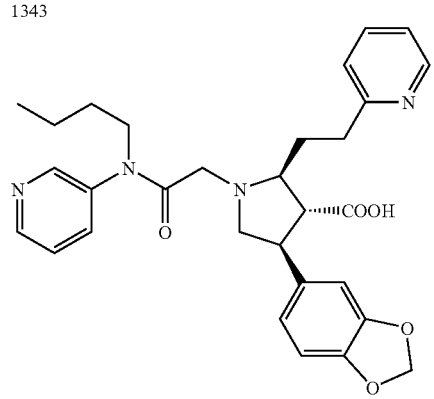
TABLE 3C-continued
1344
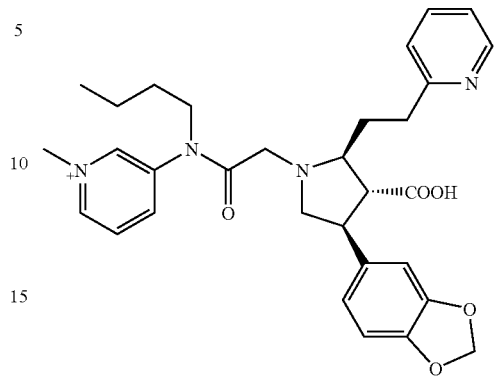
1345
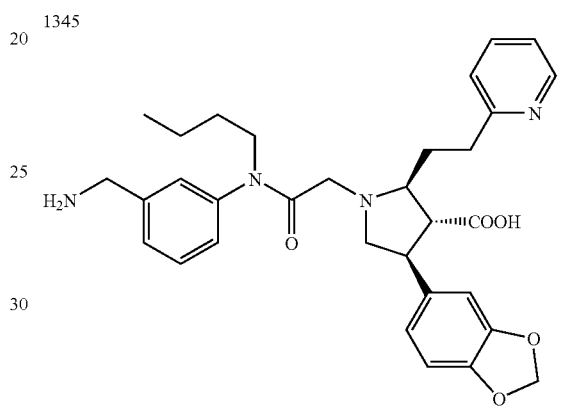
1346
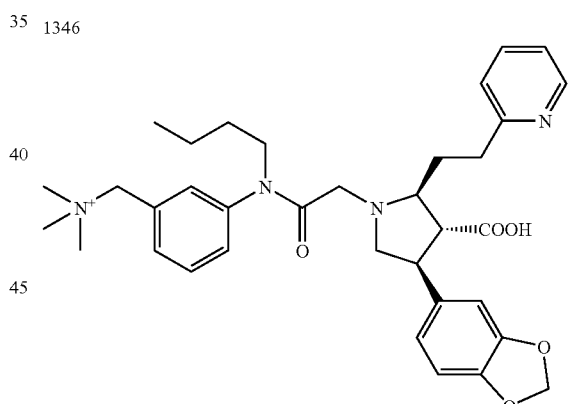
1347
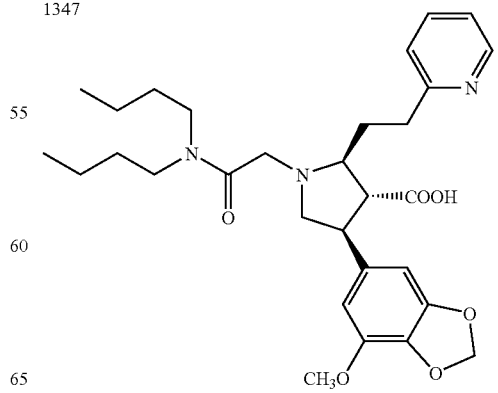

TABLE 3C-continued
1348
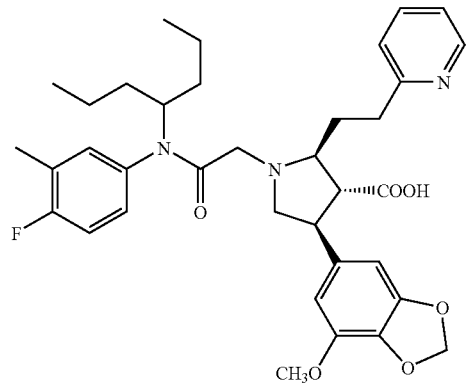
1349
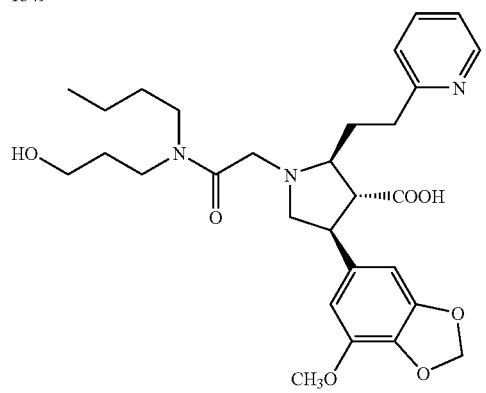
1350
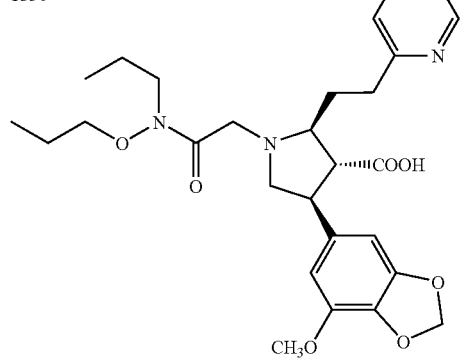
1351
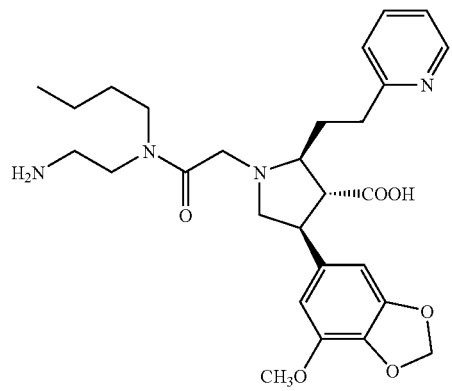
TABLE 3C-continued
1352
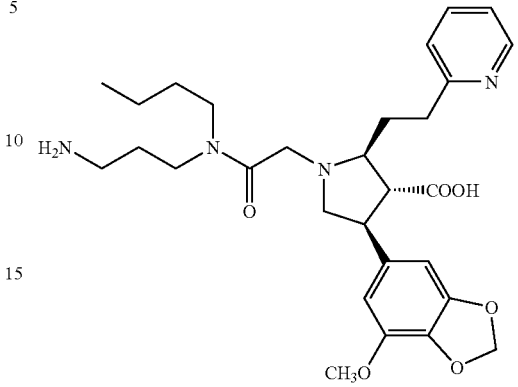
1353
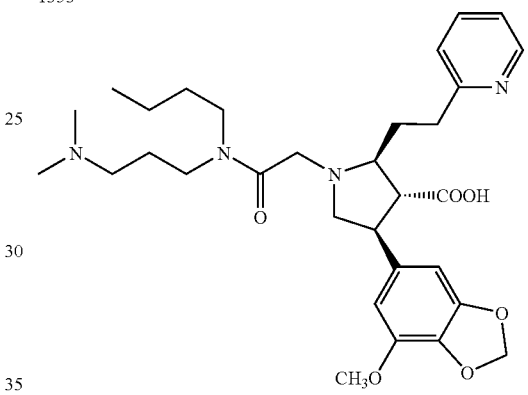
1354
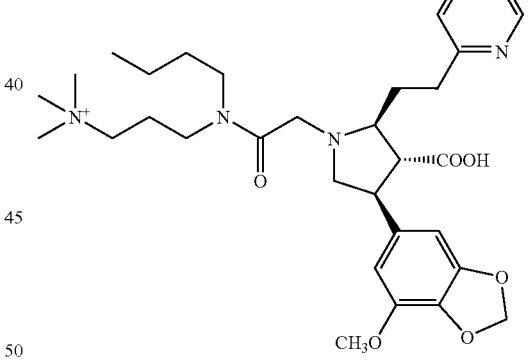
1355
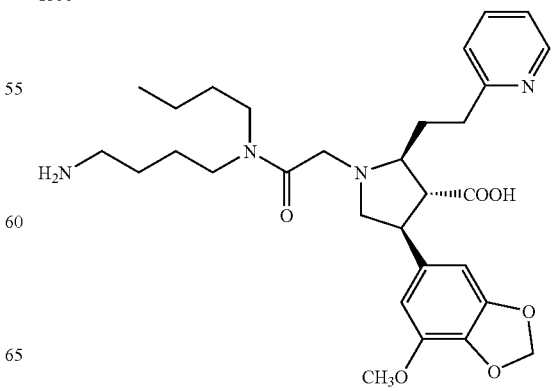

TABLE 3C-continued
1356
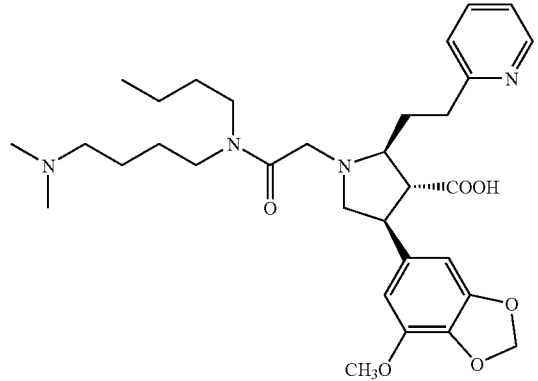
1357
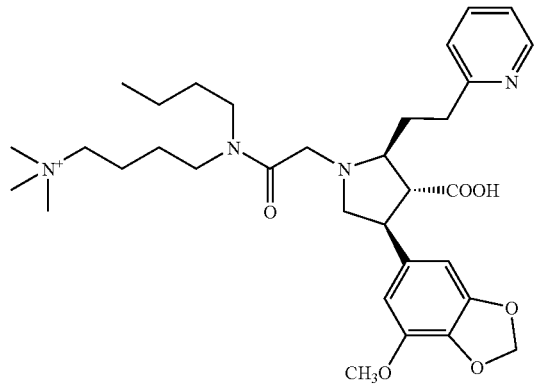
1358
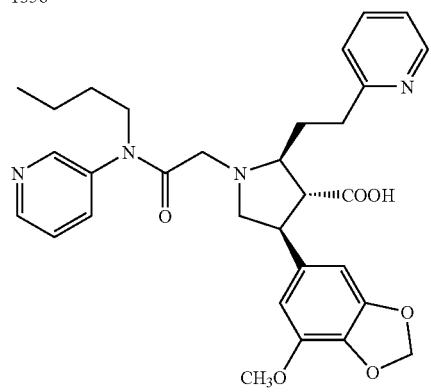
1359
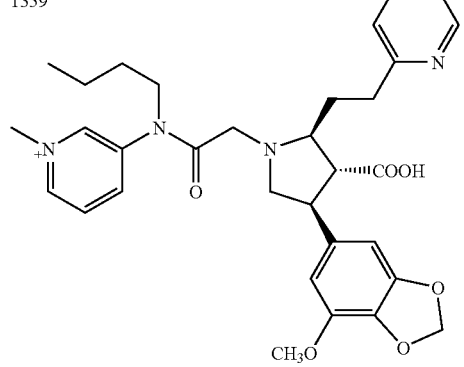
TABLE 3C-continued
1360
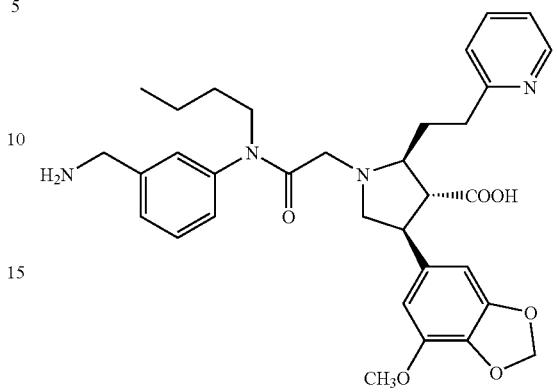
1361
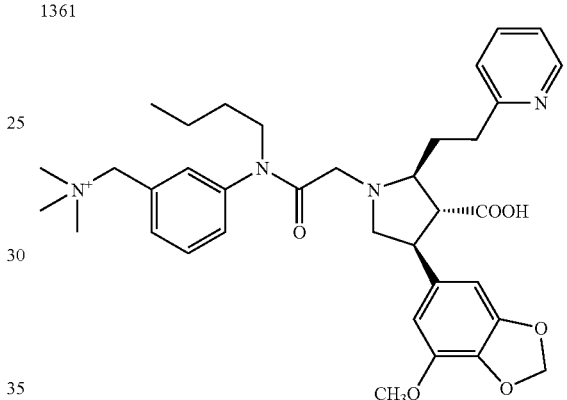
1362
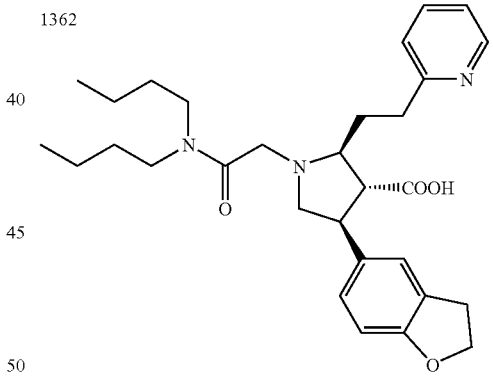
1363
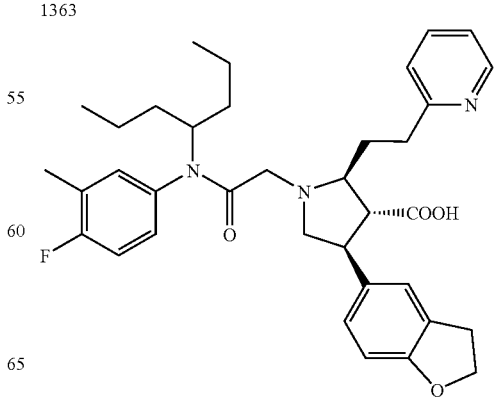

TABLE 3C-continued
1364
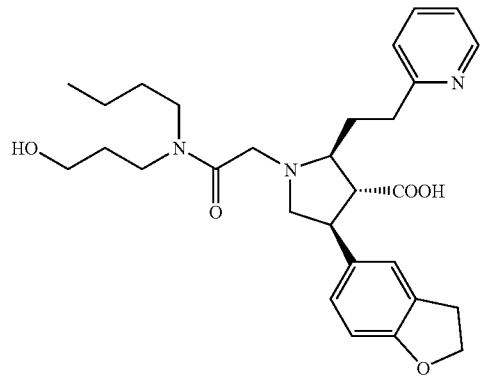
1365
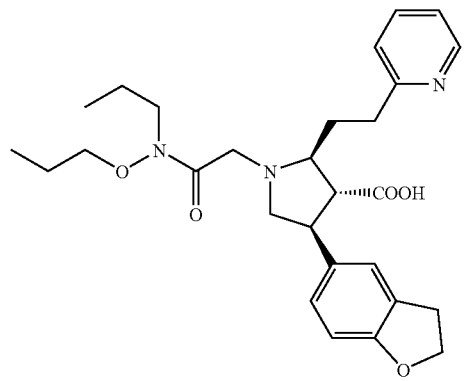
1366
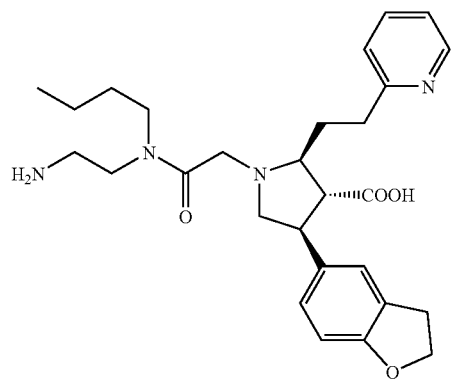
1367
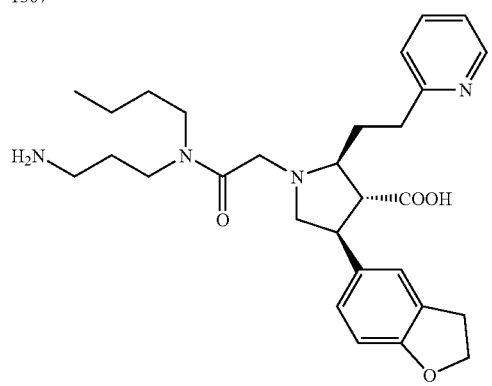
TABLE 3C-continued
1368
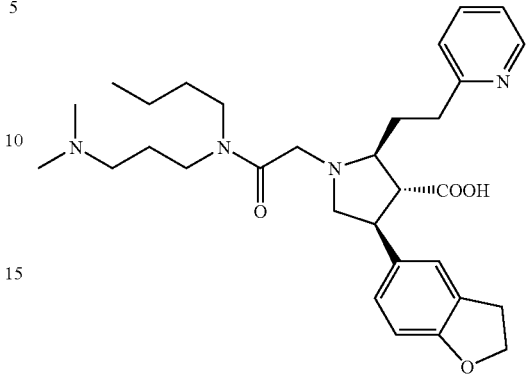
1369
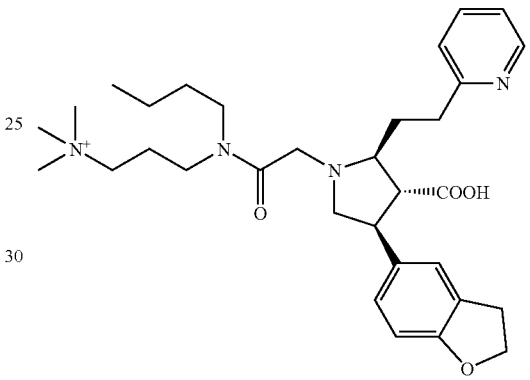
1370
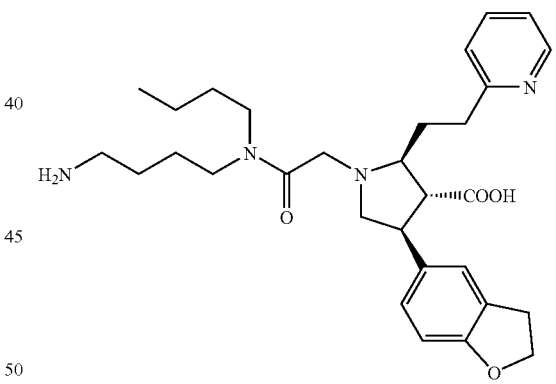
1371
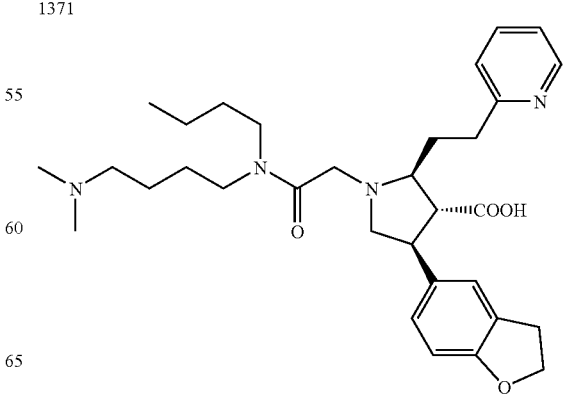

TABLE 3C-continued
1372
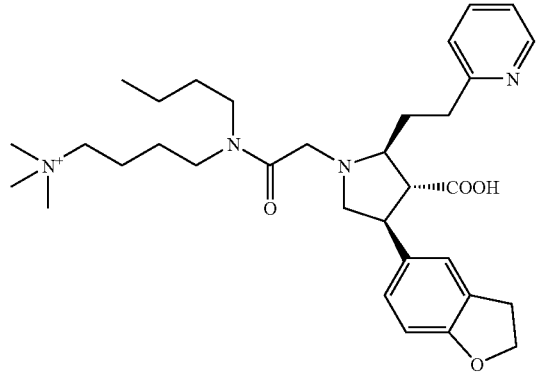
1373
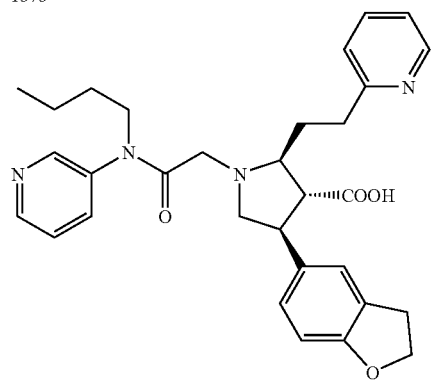
1374
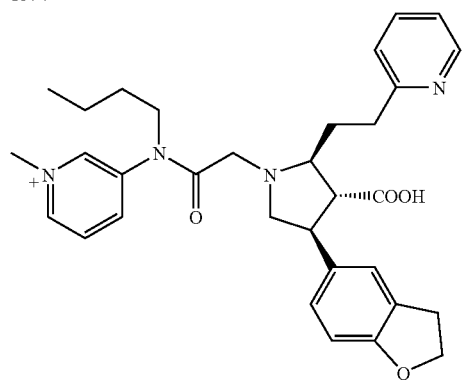
1375
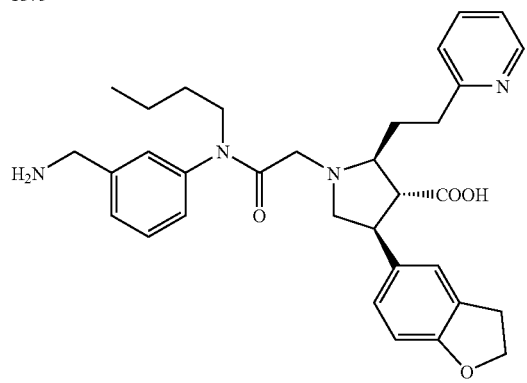
TABLE 3C-continued
1376
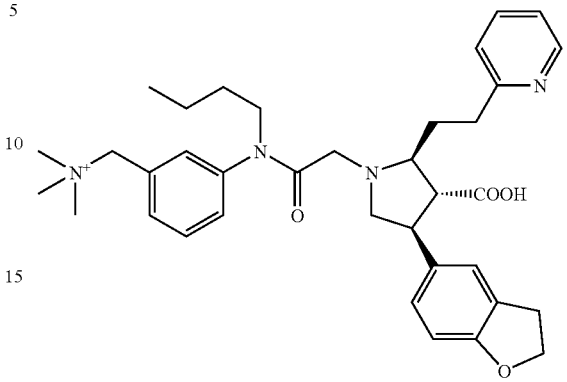
1377
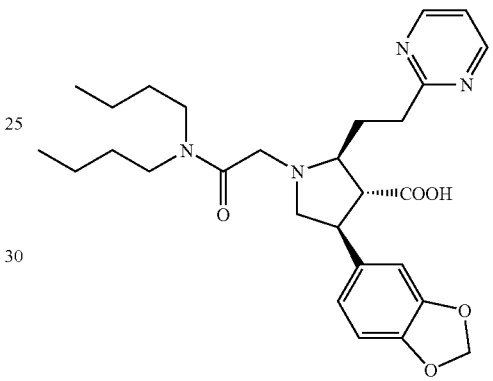
1378
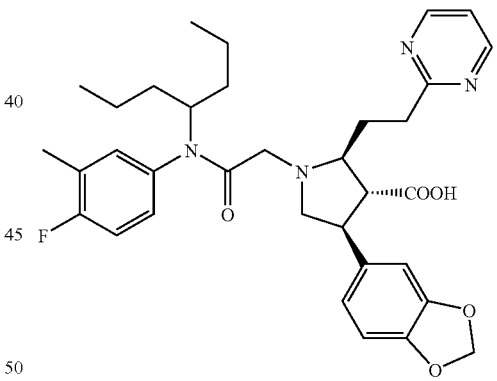
1379
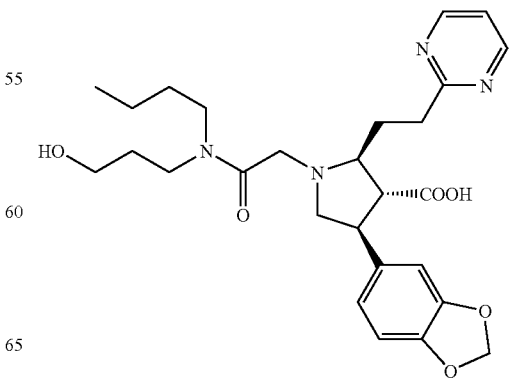

TABLE 3C-continued
1380
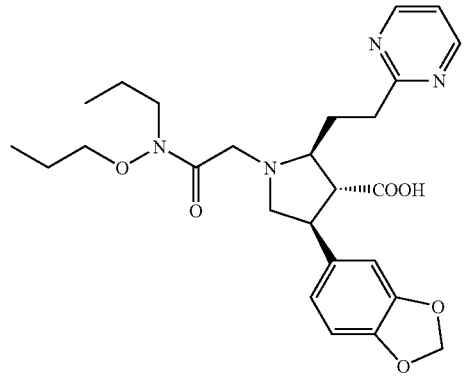
1381
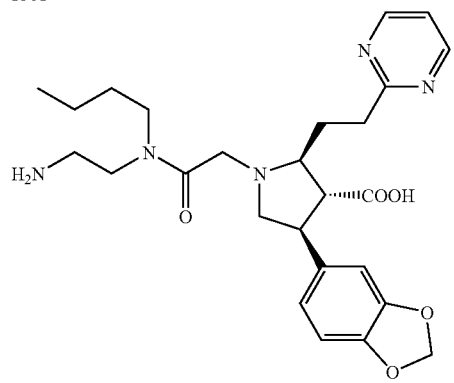
1382
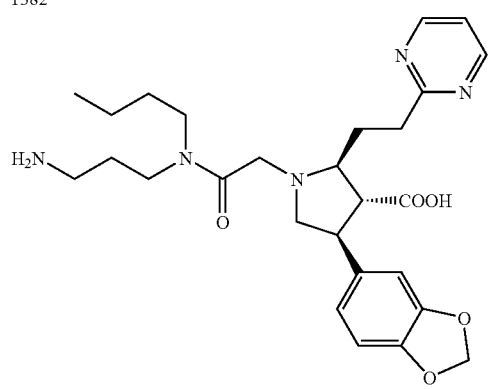
1383
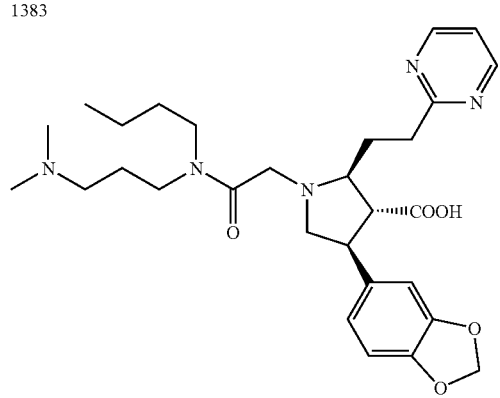
TABLE 3C-continued
1384
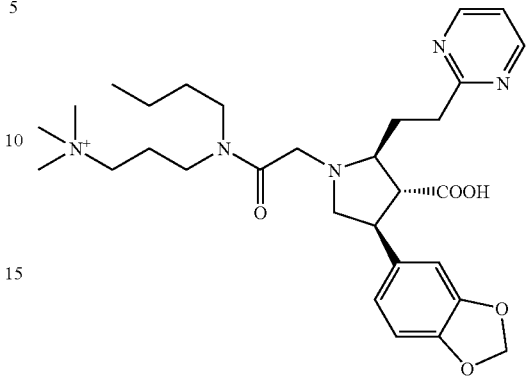
1385
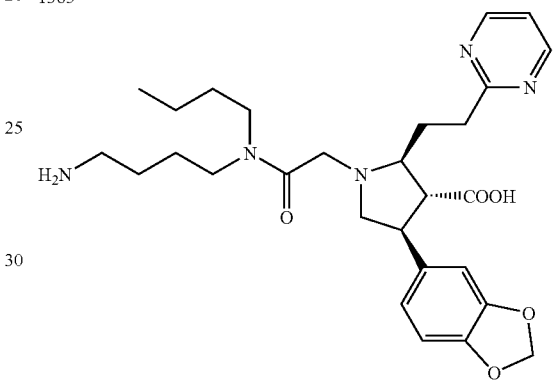
1386
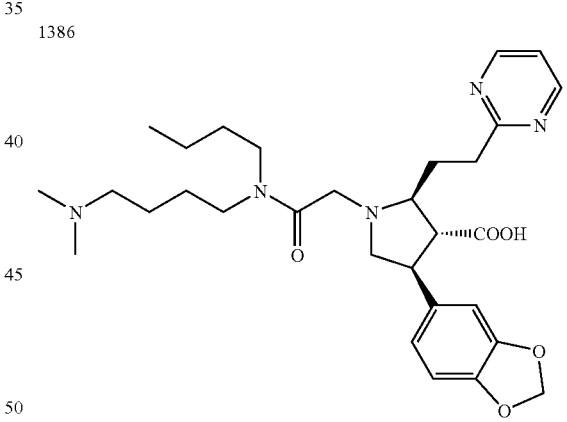
1387
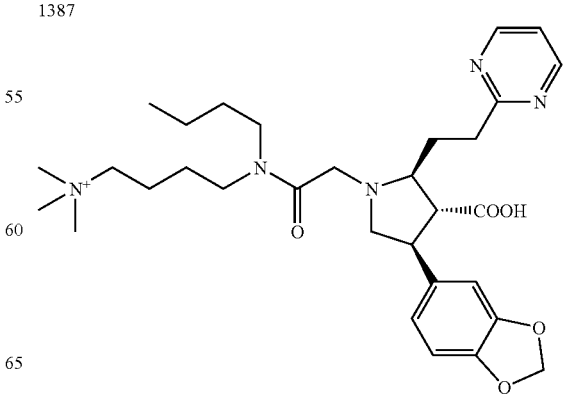

US 7,208,517 B1
| 1388 | 1392 |
|---|---|
| 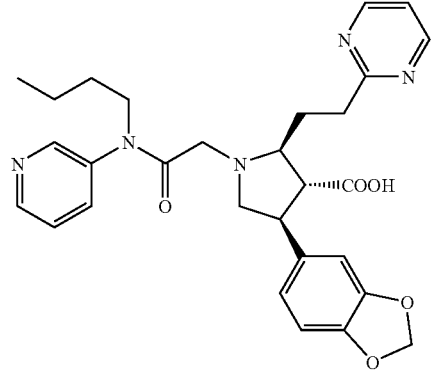 | 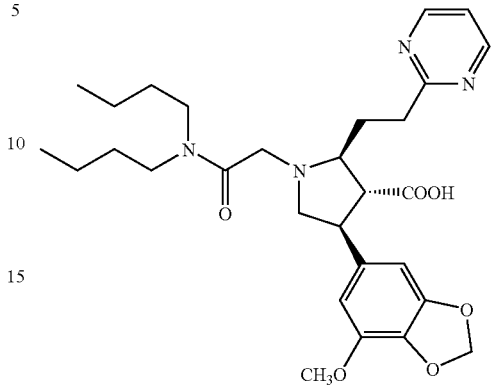 |
| 1389 | 1393 |
| 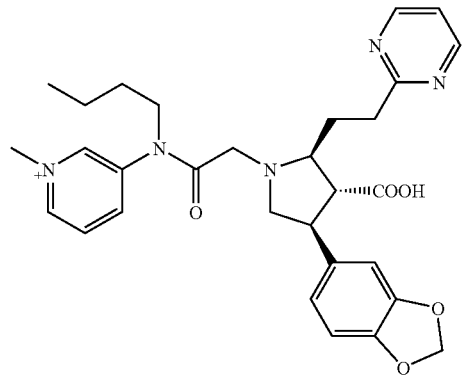 | 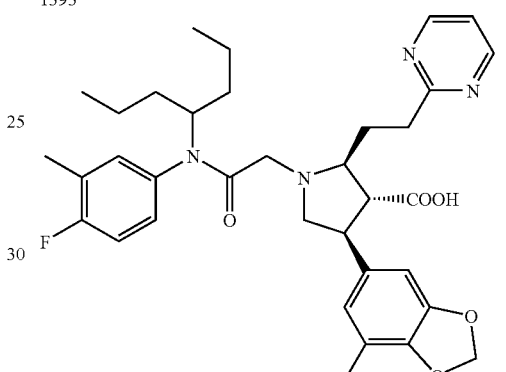 |
| 1390 | 1394 |
| 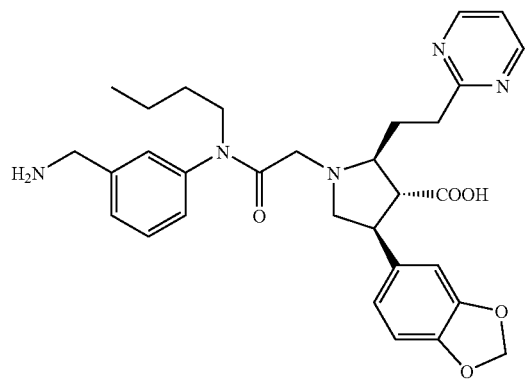 | 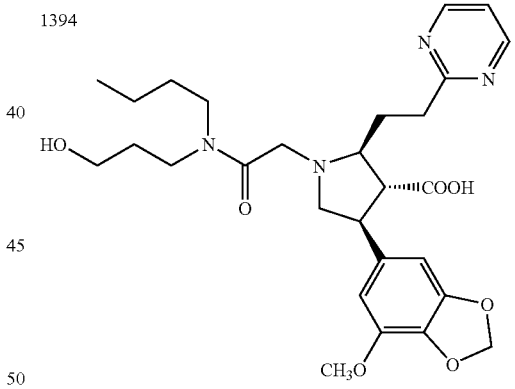 |
| 1391 | 1395 |
| 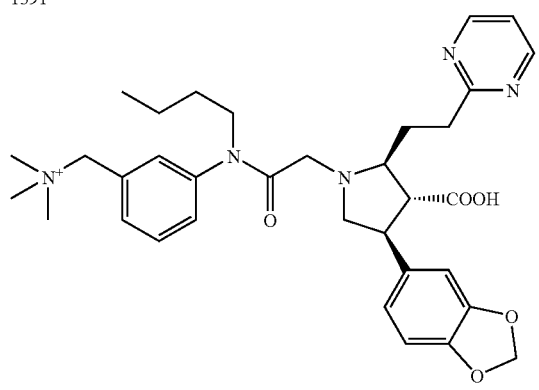 | 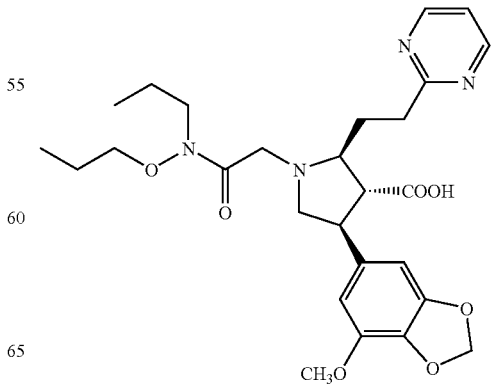 |

TABLE 3C-continued
1396
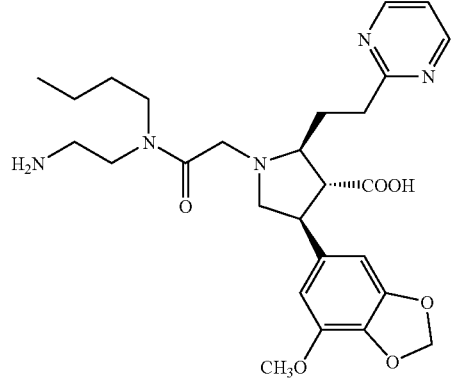
1397
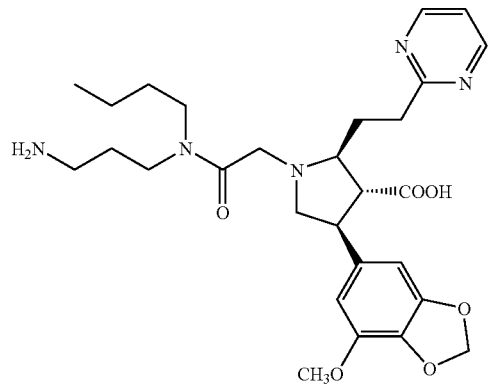
1398
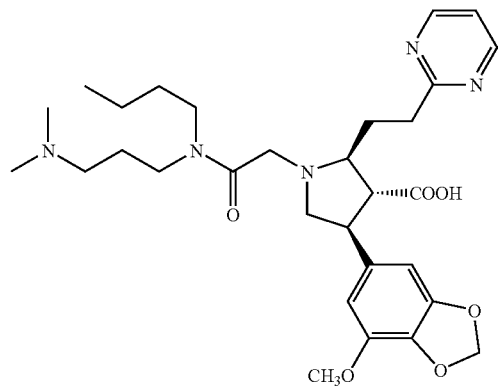
1399
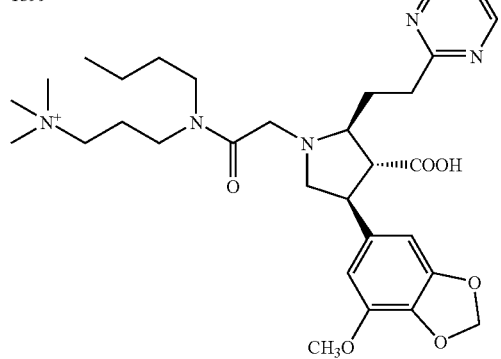
TABLE 3C-continued
1400
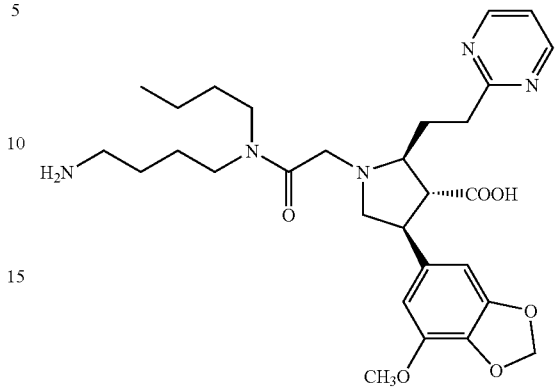
1401
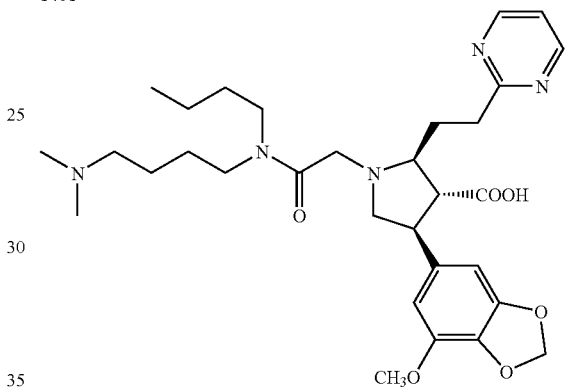
1402
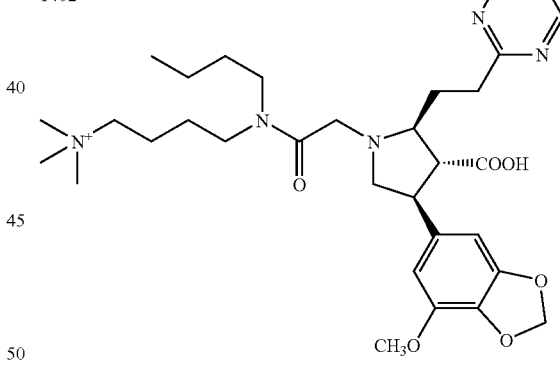
1403
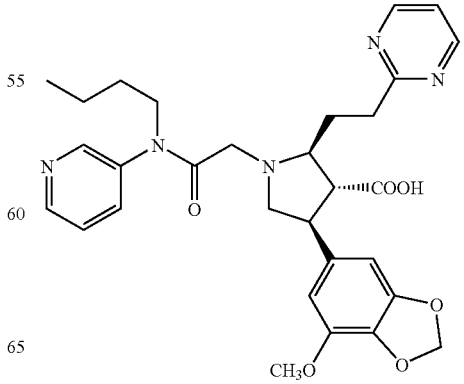

TABLE 3C-continued
1404
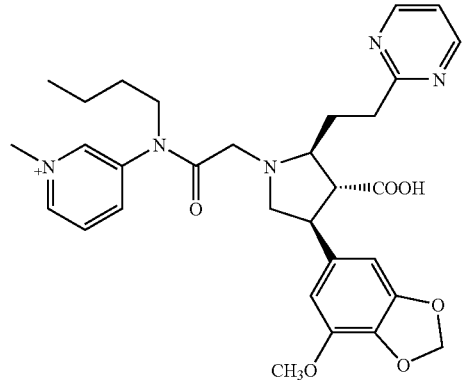
1405
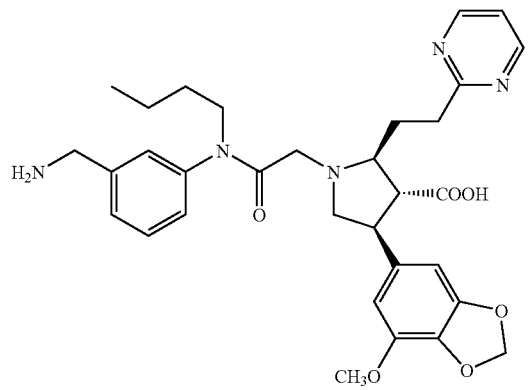
1406
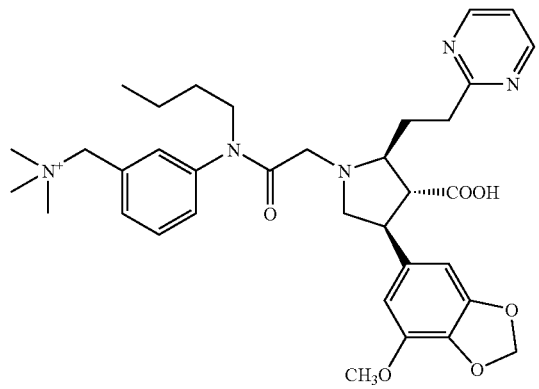
1407
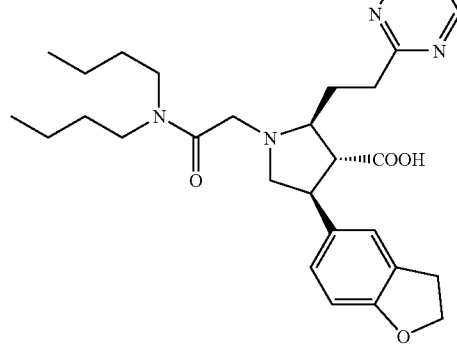
TABLE 3C-continued
1408
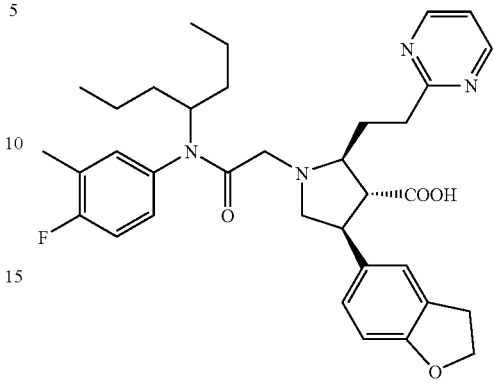
1409
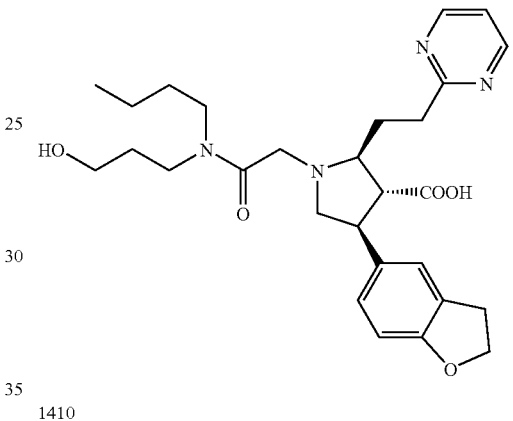
1410
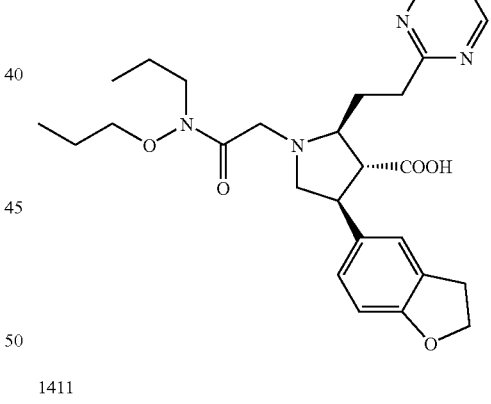
1411
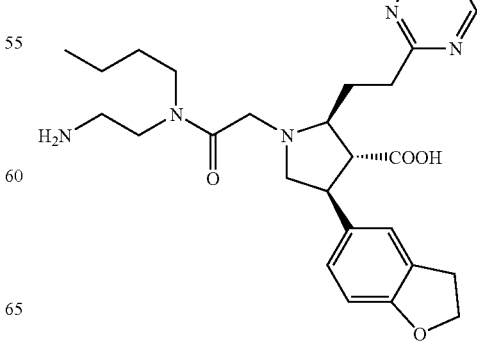

TABLE 3C-continued
1412
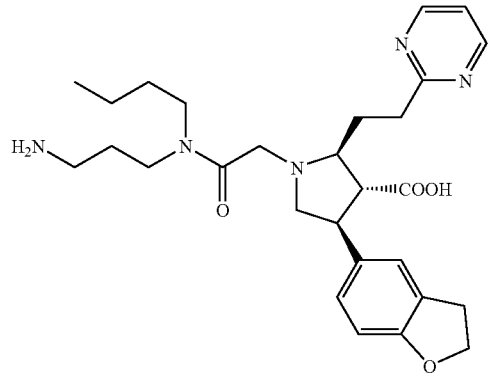
1413
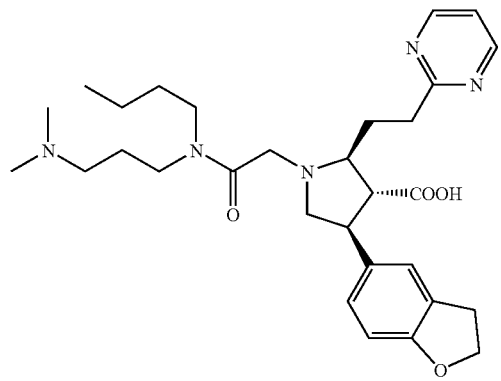
1414
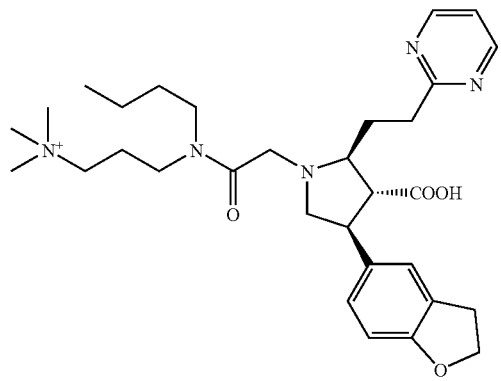
1415
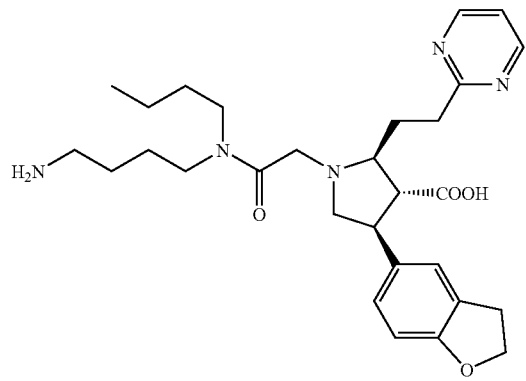
TABLE 3C-continued
1416
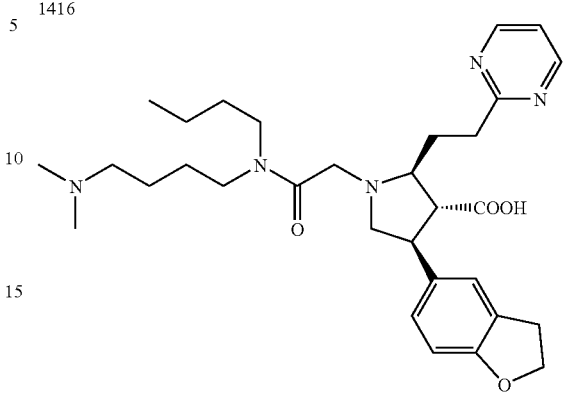
1417
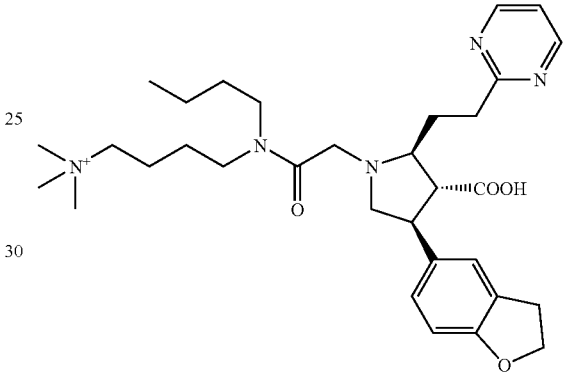
1418
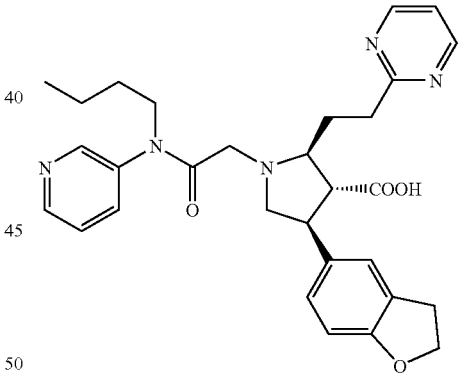
1419
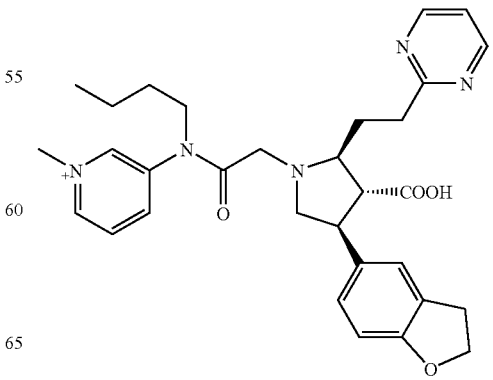

TABLE 3C-continued
1420
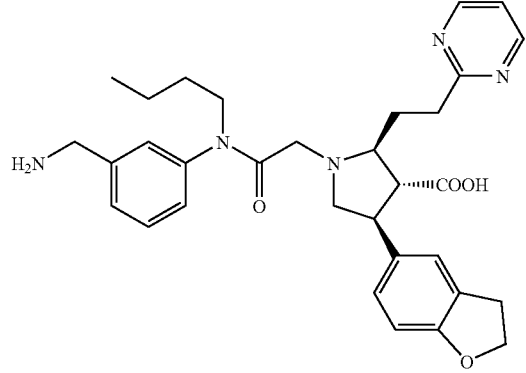
1421
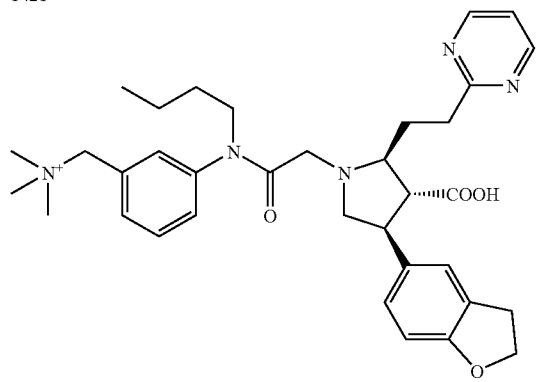
1422
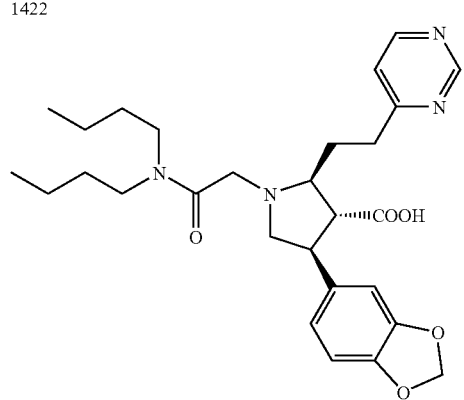
1423
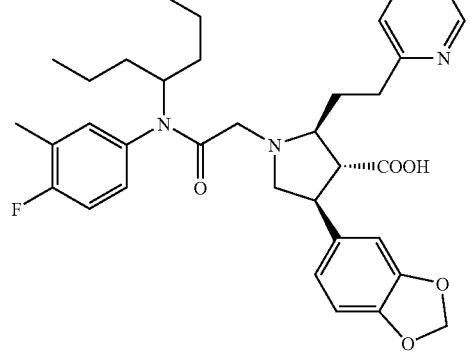
TABLE 3C-continued
1424
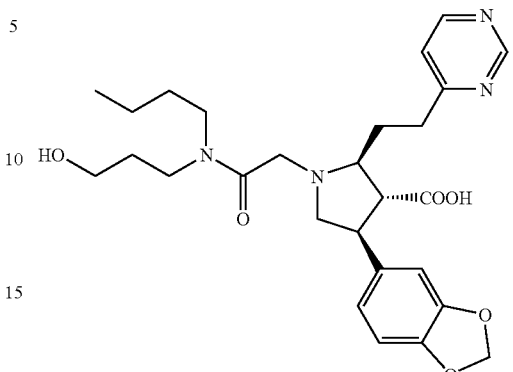
1425
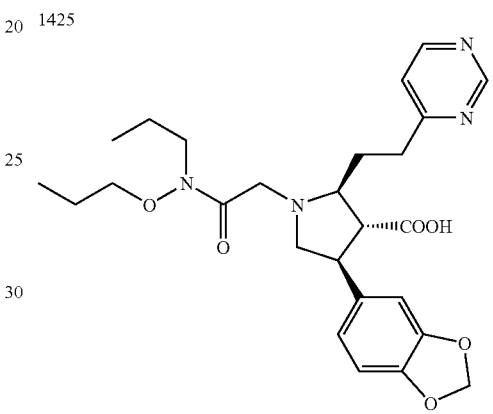
1426
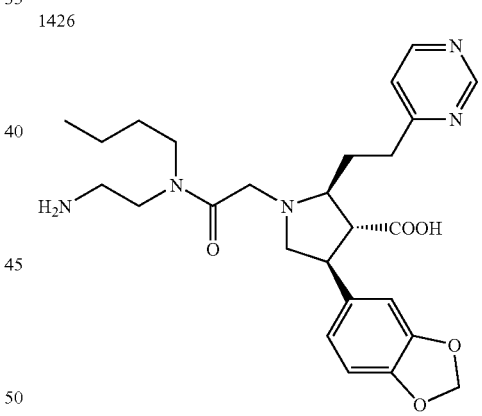
1427
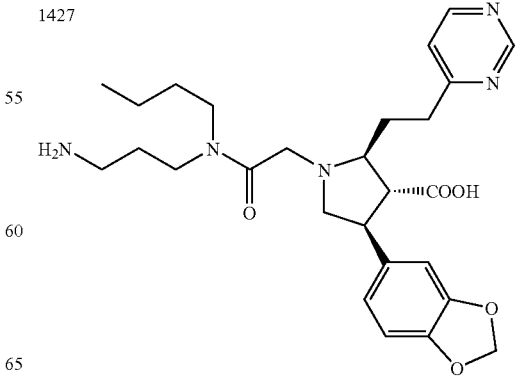

1029
TABLE 3C-continued
1428
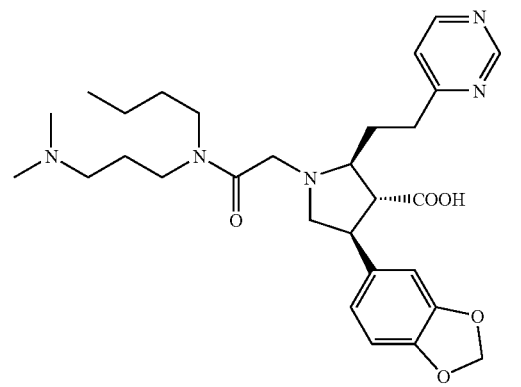
1429
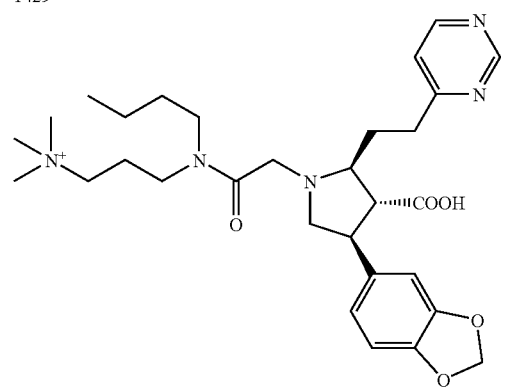
1430
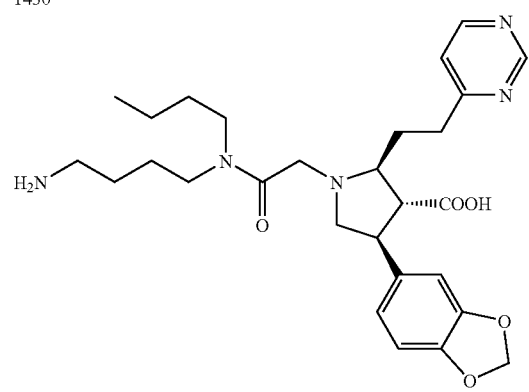
1431
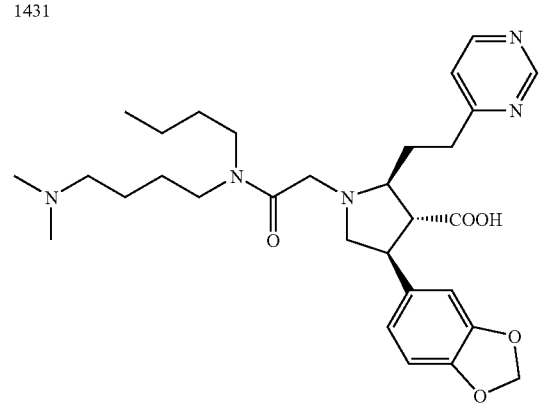
1030
TABLE 3C-continued
1432
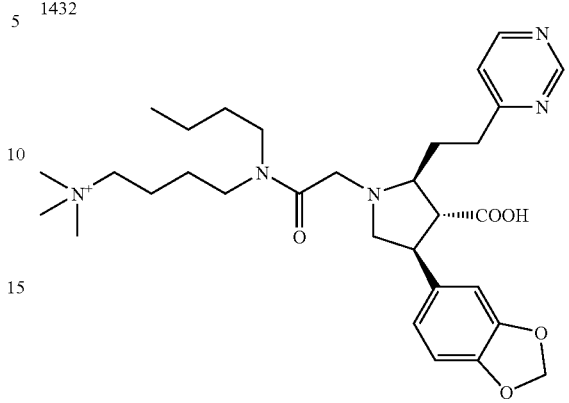
1433
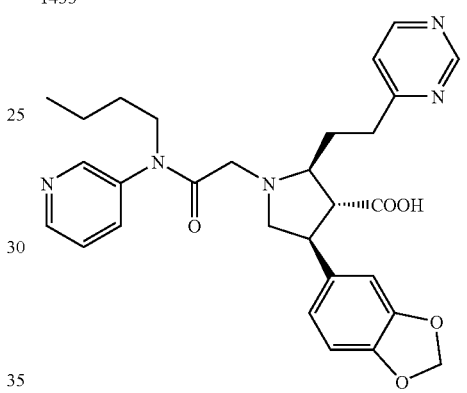
1434
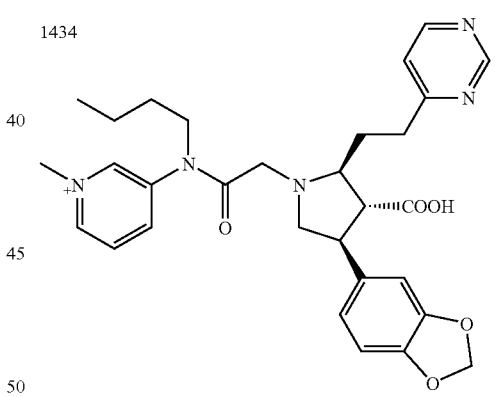
1435
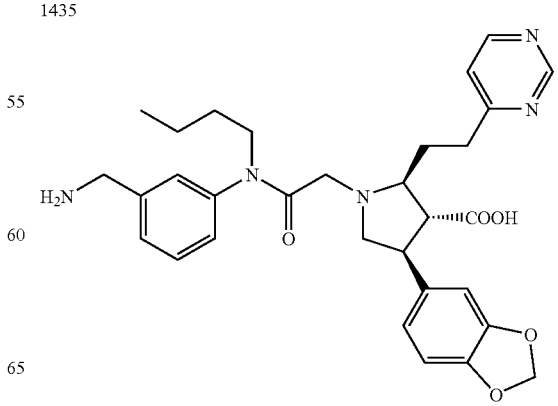

1031
TABLE 3C-continued
1436
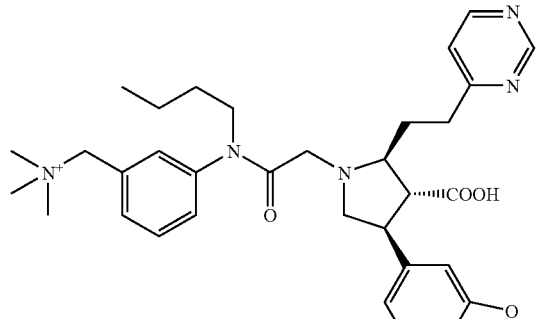
1437
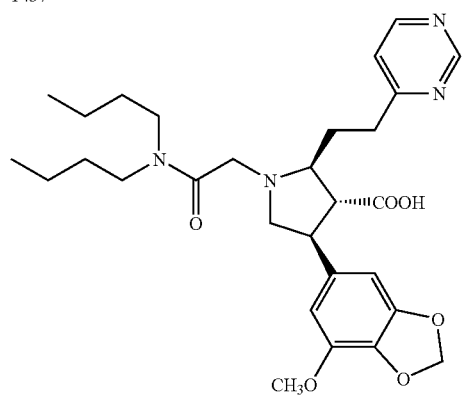
1438
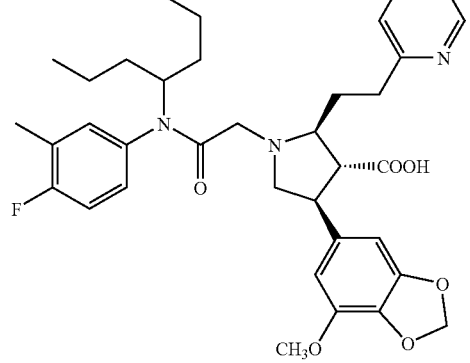
1439
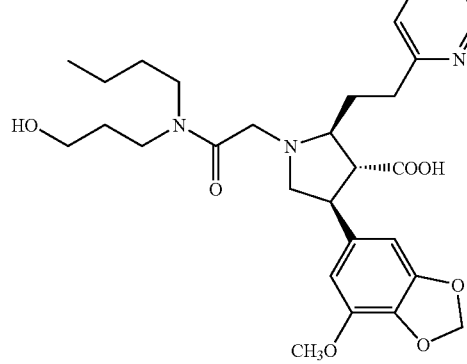
1032
TABLE 3C-continued
1440
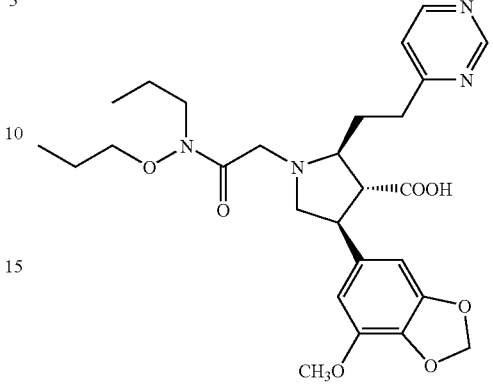
1441
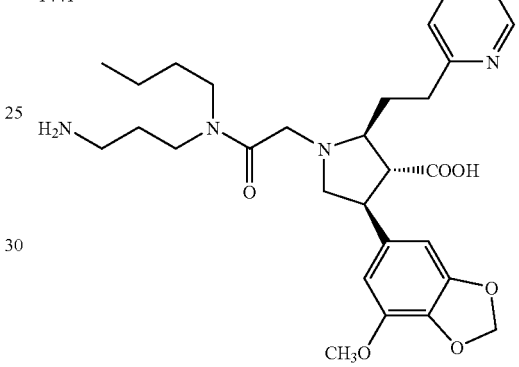
1442
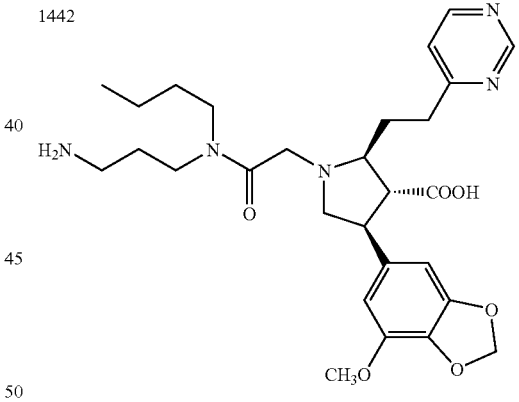
1443
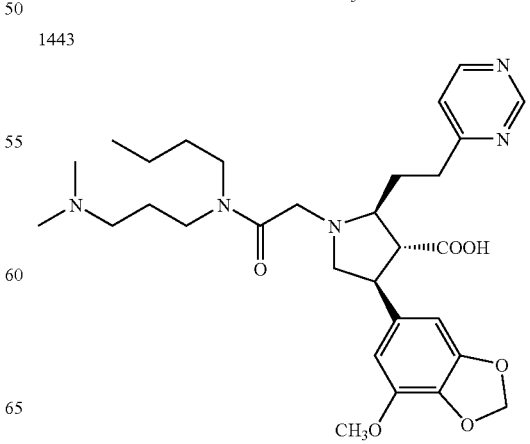

TABLE 3C-continued
1444
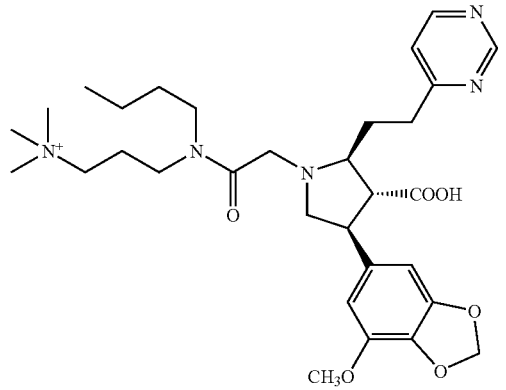
1445
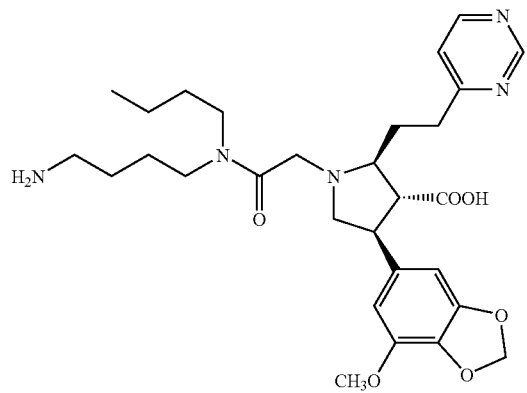
1446
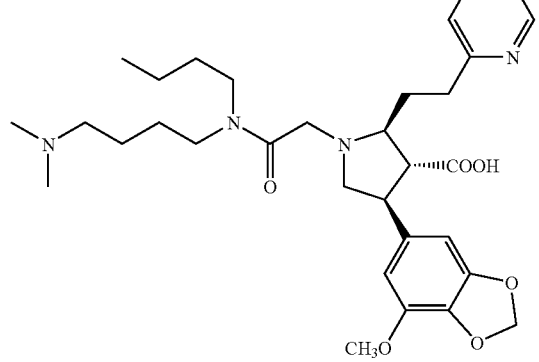
1447
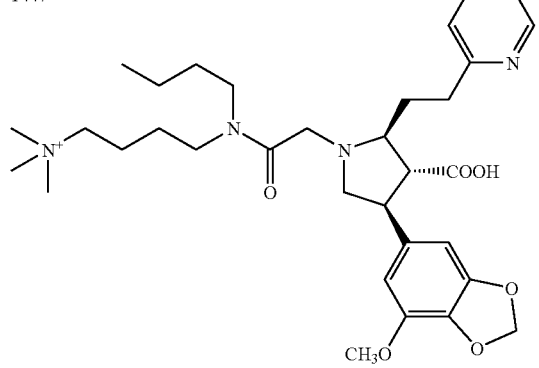
TABLE 3C-continued
1448
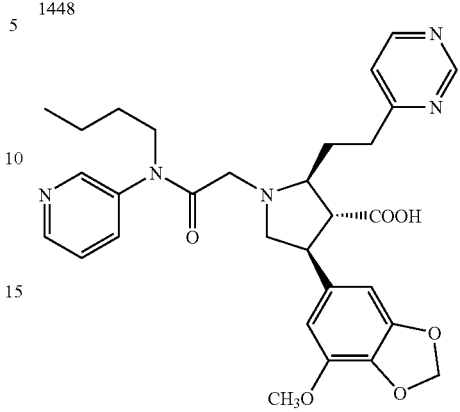
1449
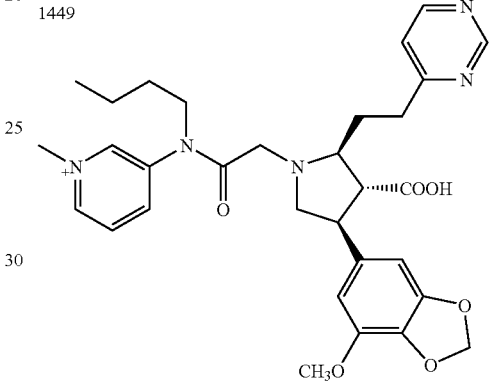
1450
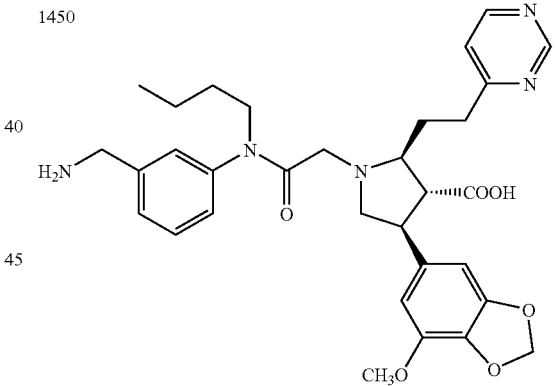
1451
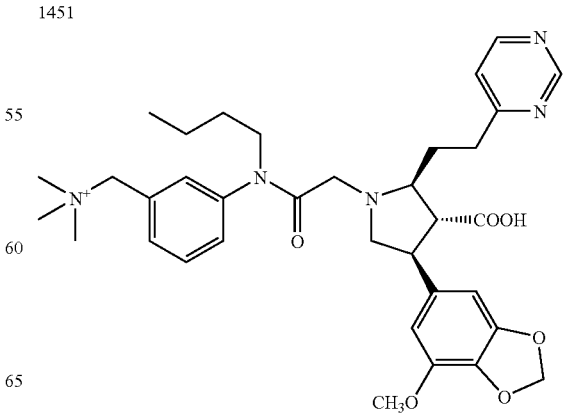

TABLE 3C-continued
1452 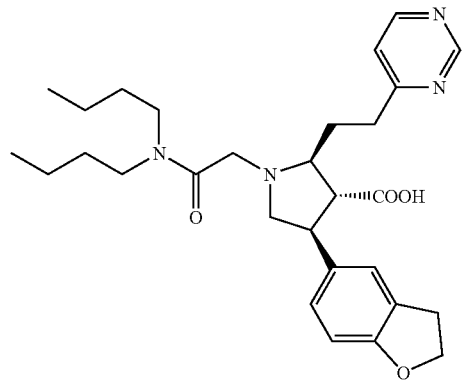
1453 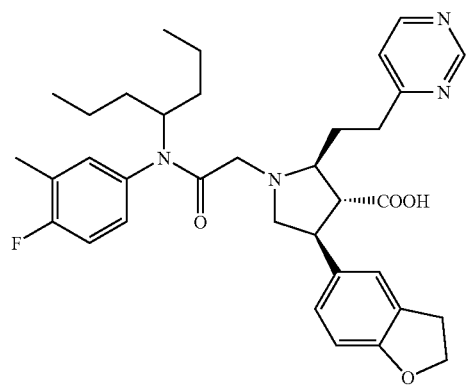
1454 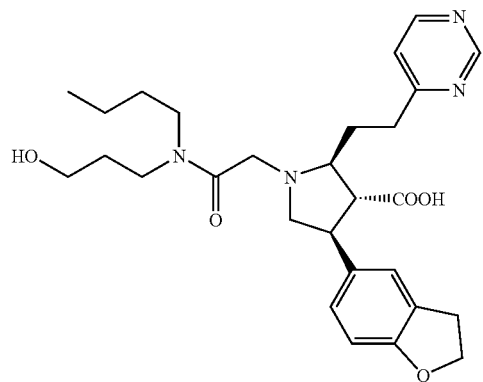
1455 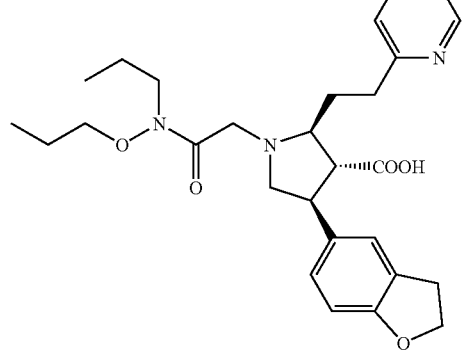
TABLE 3C-continued
1456 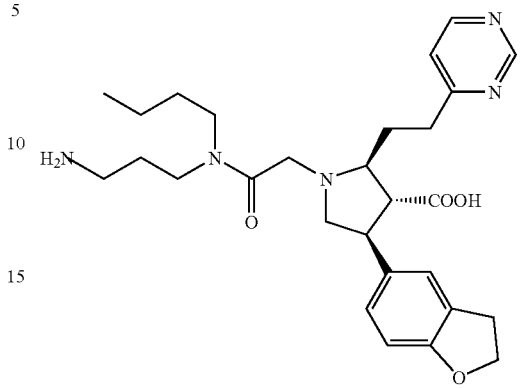
1457 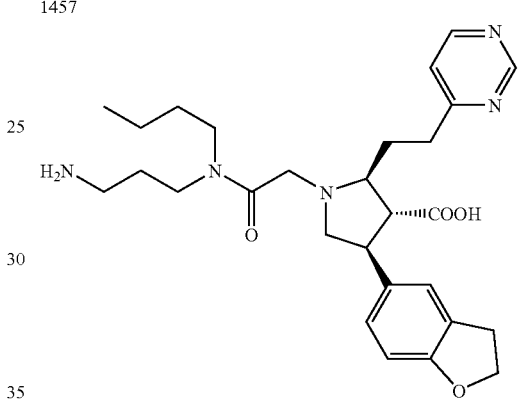
1458 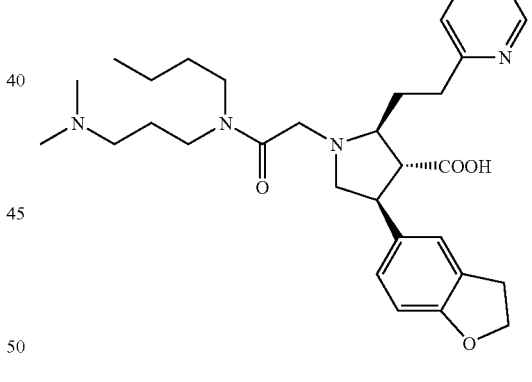
1459 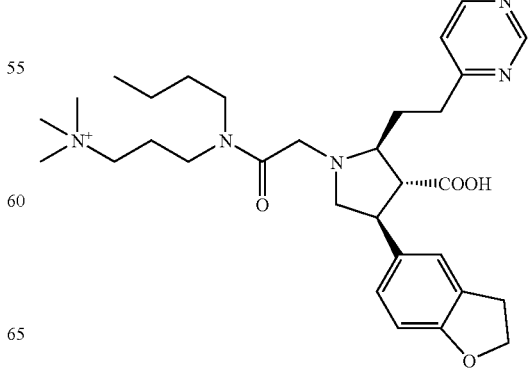

| 1460 | 1464 |
|---|---|
| 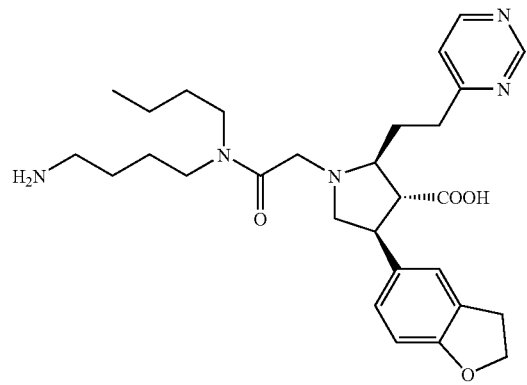 | 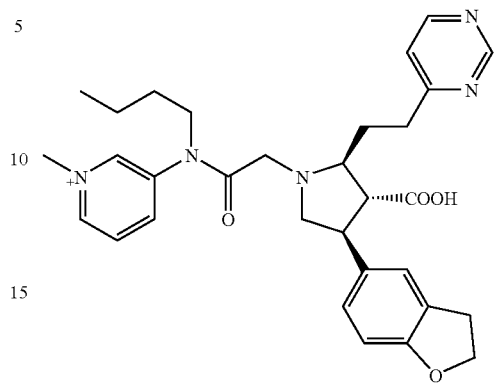 |
| 1461 | 1465 |
| 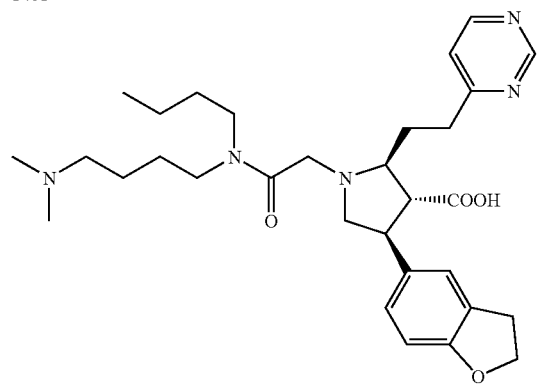 | 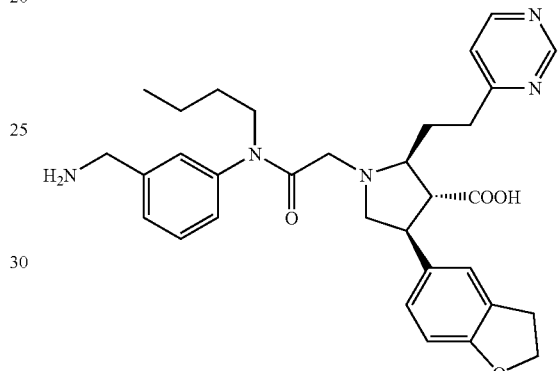 |
| 1462 | 1466 |
| 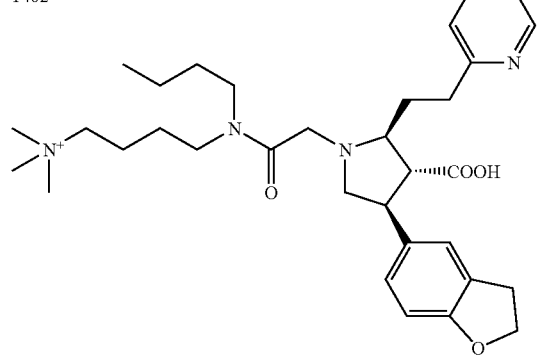 | 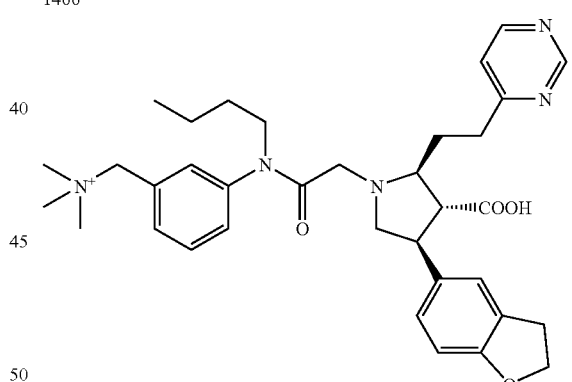 |
| 1463 | 1467 |
| 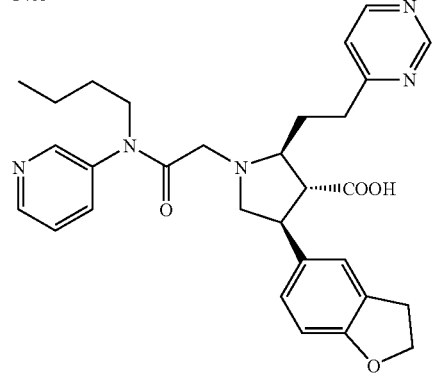 | 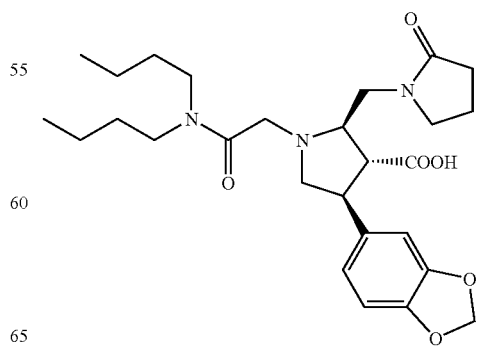 |

TABLE 3C-continued
1468
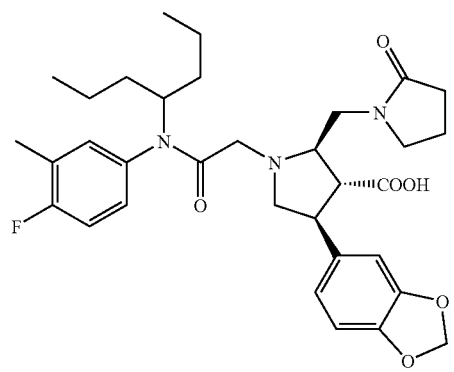
1469
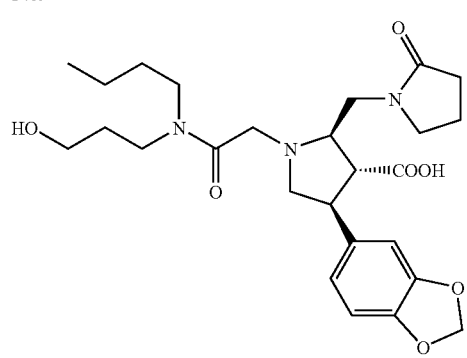
1470
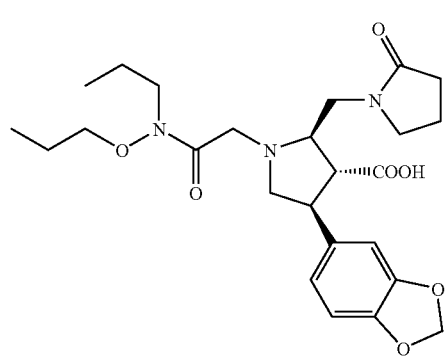
1471
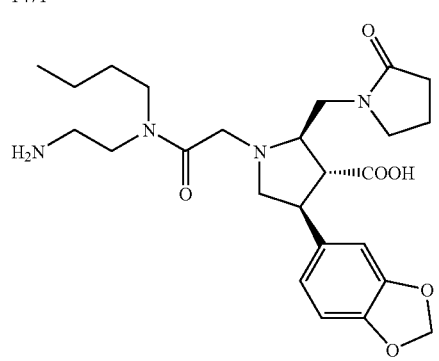
TABLE 3C-continued
1472
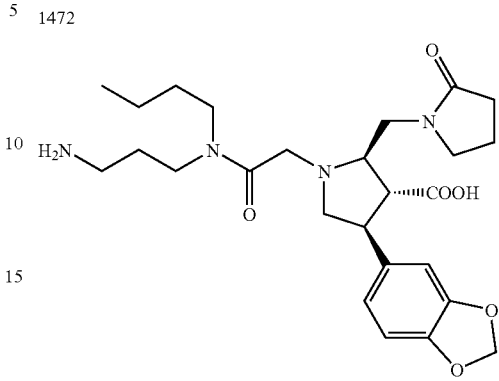
1473
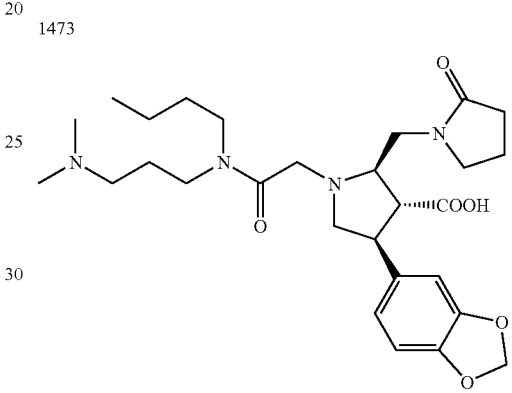
1474
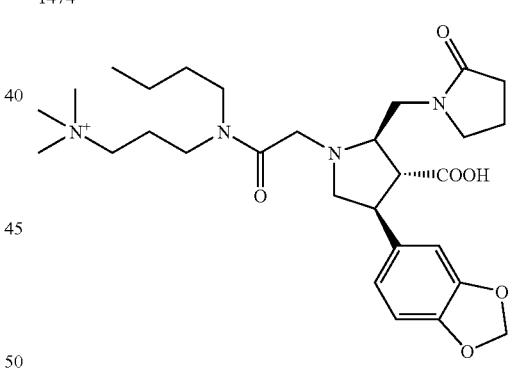
1475
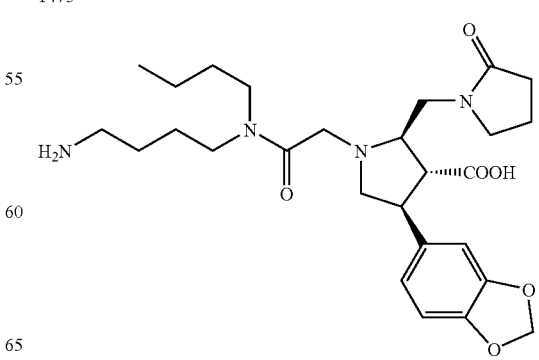

TABLE 3C-continued
1476
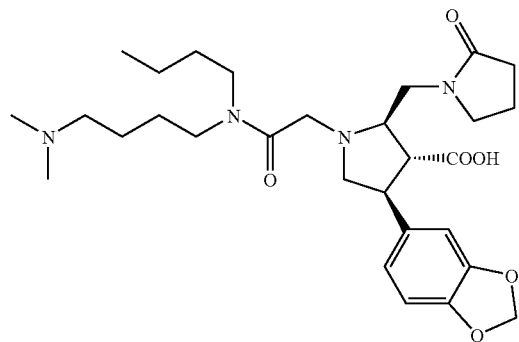
1477
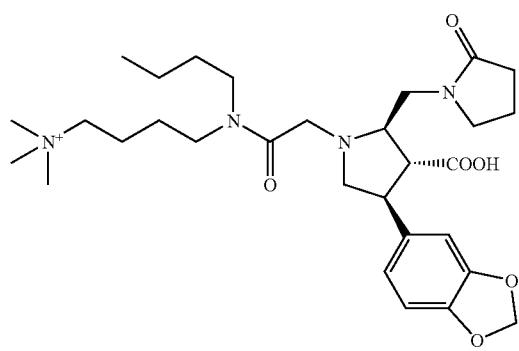
1478
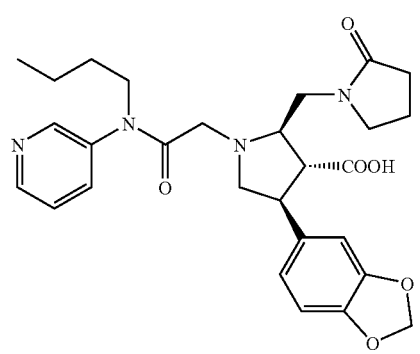
1479
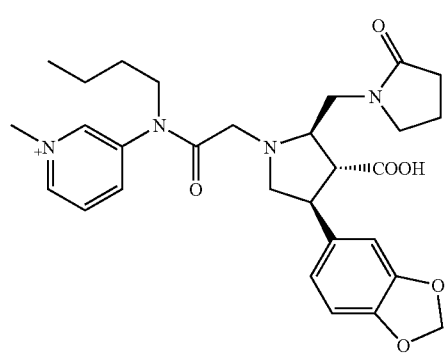
TABLE 3C-continued
1480
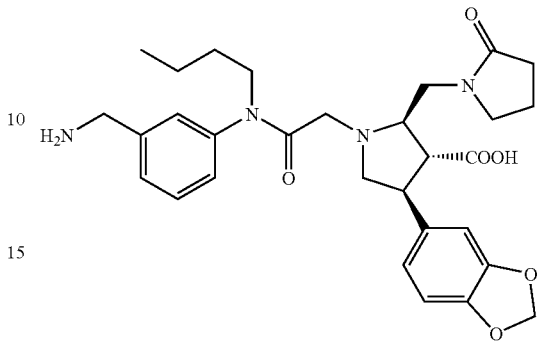
1481
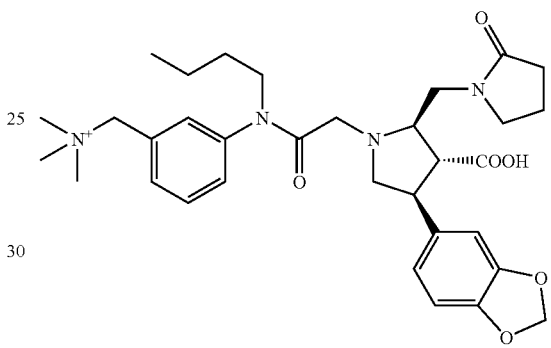
1482
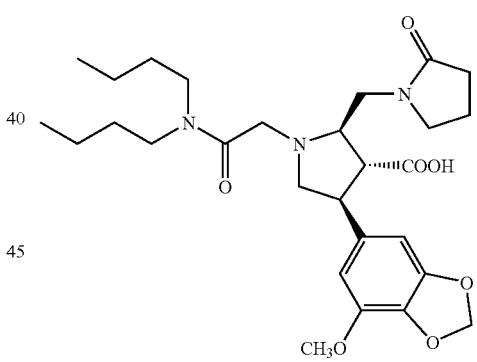
1483
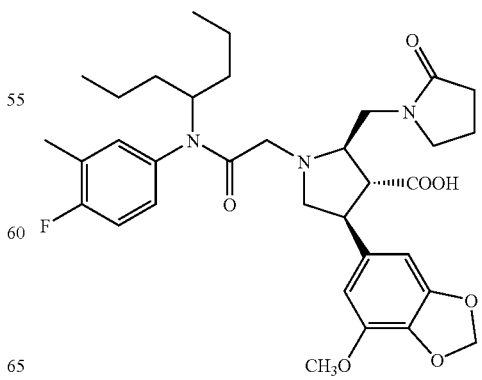

TABLE 3C-continued
1484
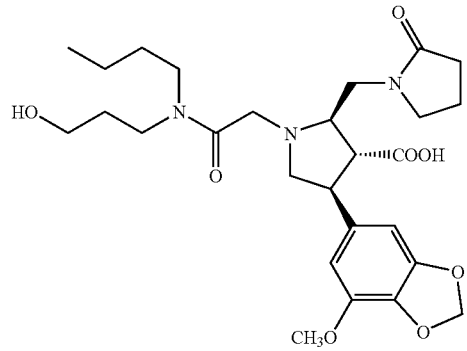
1485
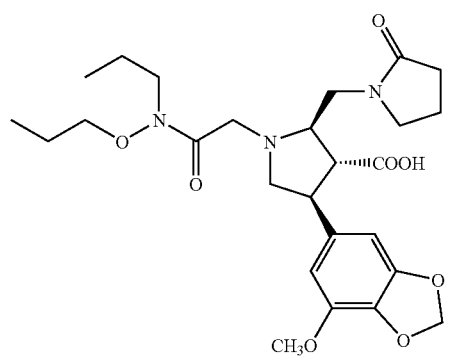
1486
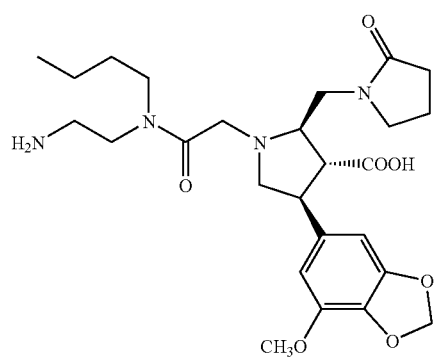
1487
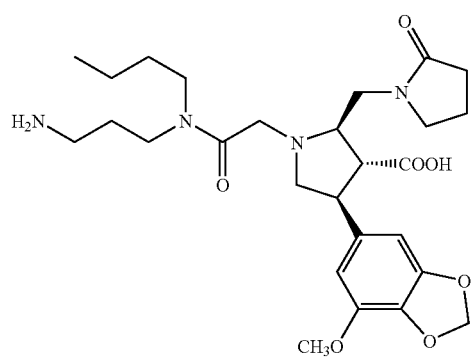
TABLE 3C-continued
1488
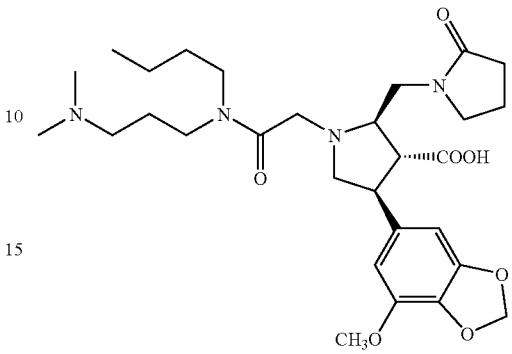
1489
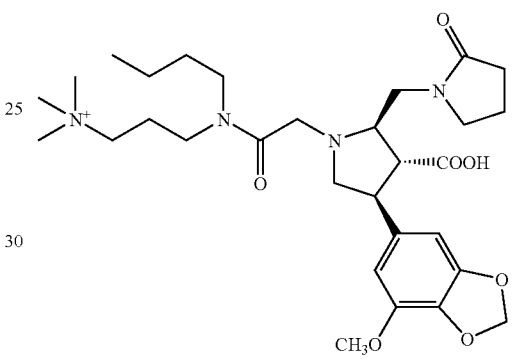
1490
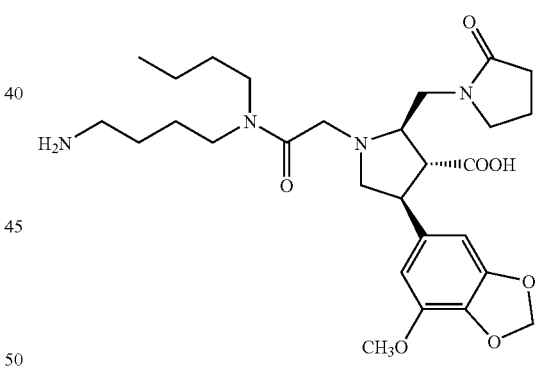
1491
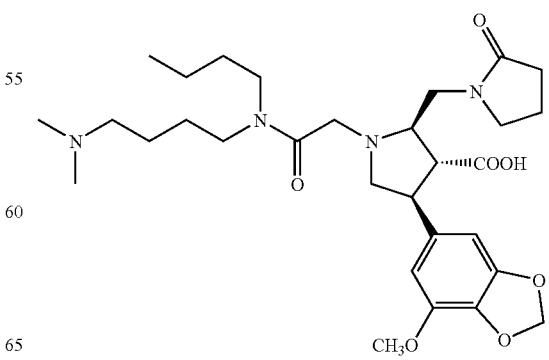

TABLE 3C-continued
1492
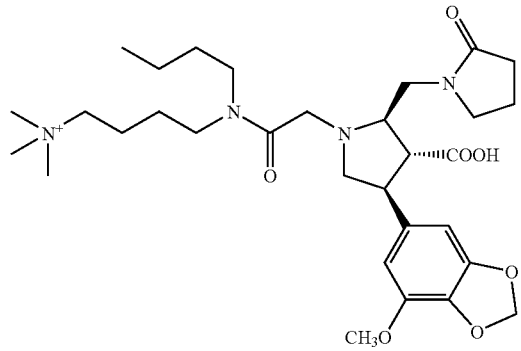
1493
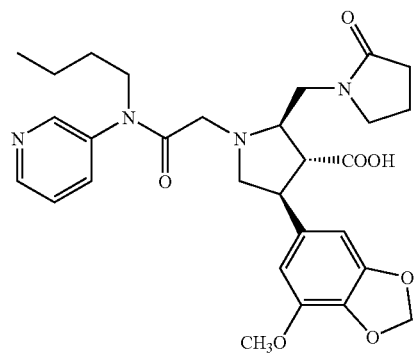
1494
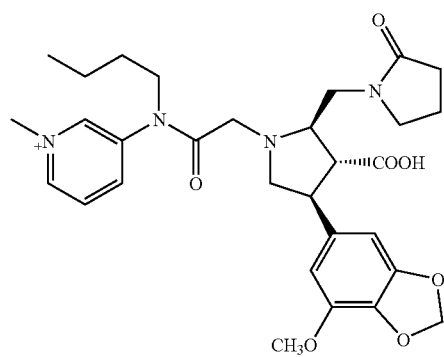
1495
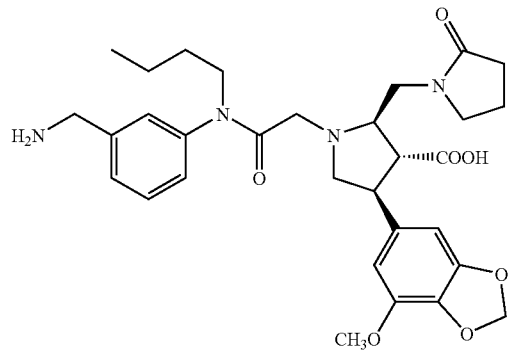
TABLE 3C-continued
1496
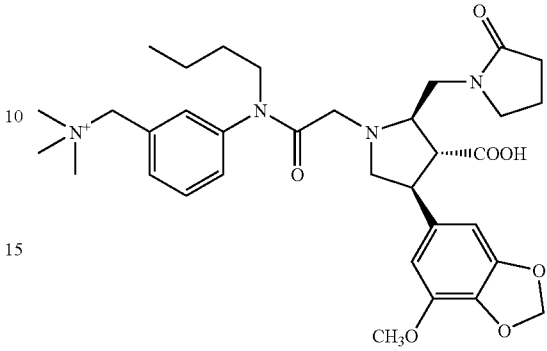
1497
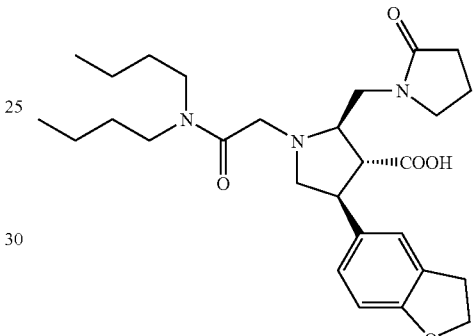
1498
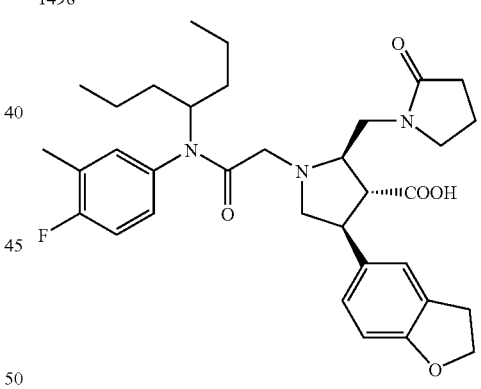
1499
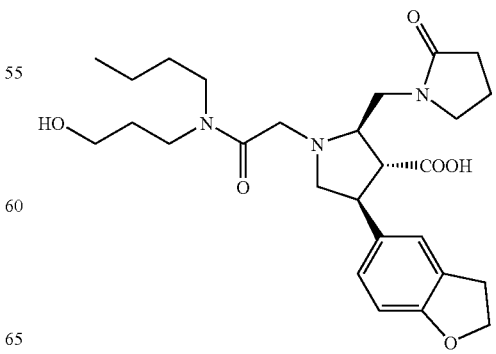

1047
TABLE 3C-continued
1500
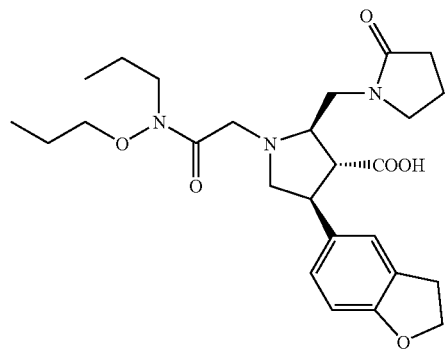
1501
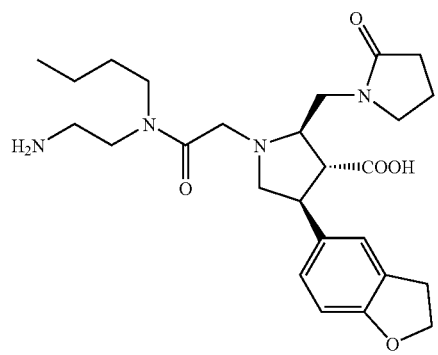
1502
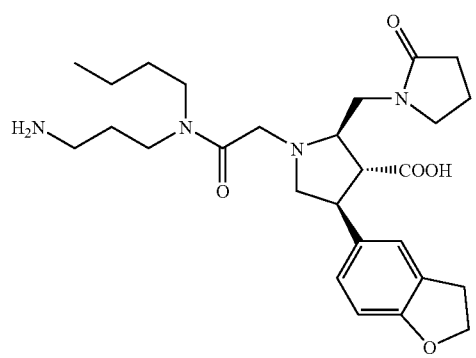
1503
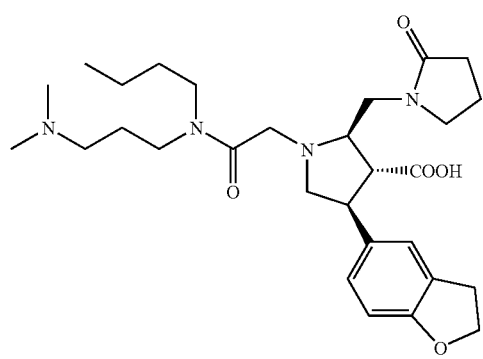
1048
TABLE 3C-continued
1504
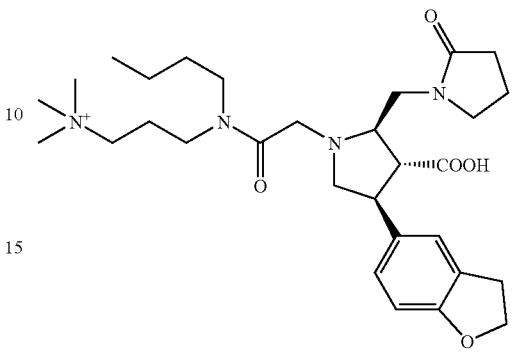
1505
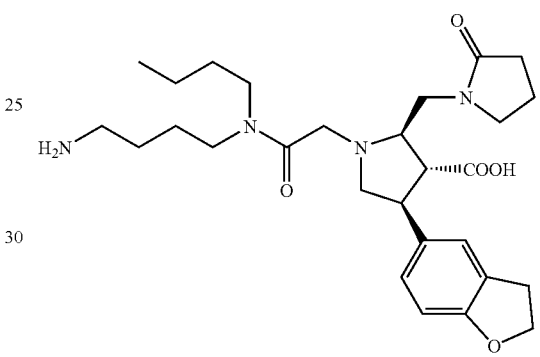
1506
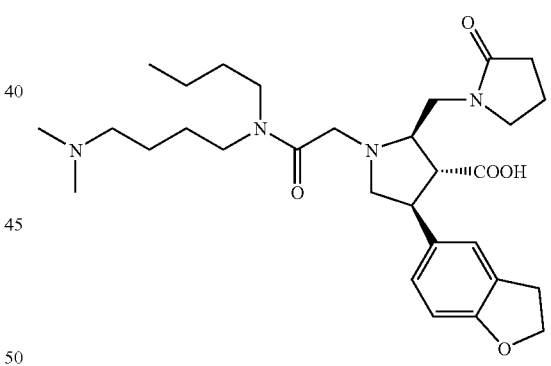
1507
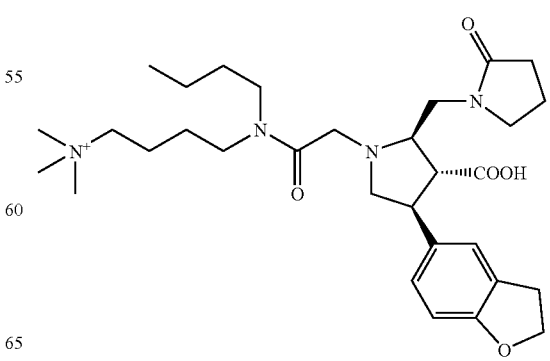

1049 1050
TABLE 3C-continued | TABLE 3C-continued
1508
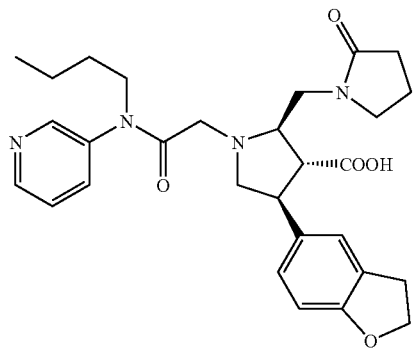
1512
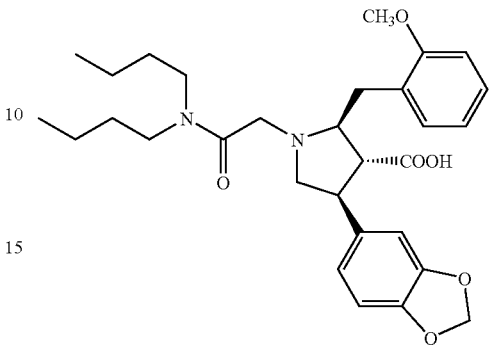
1509
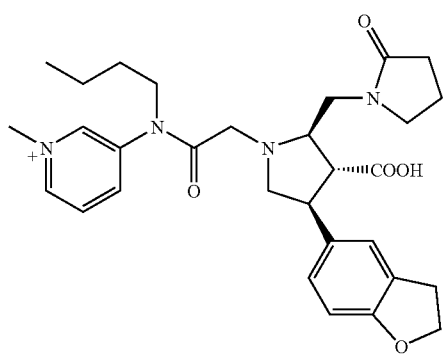
1513
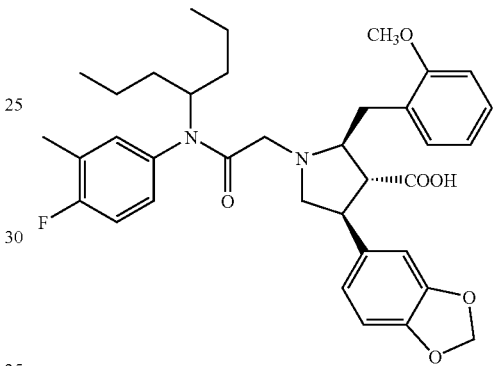
1510
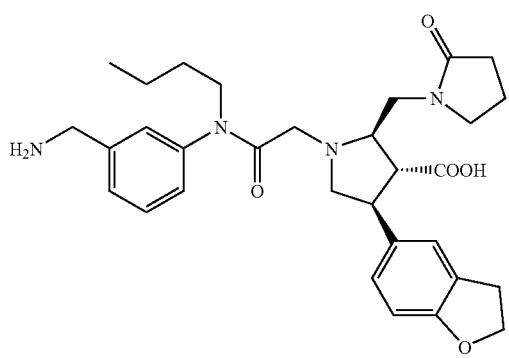
1514
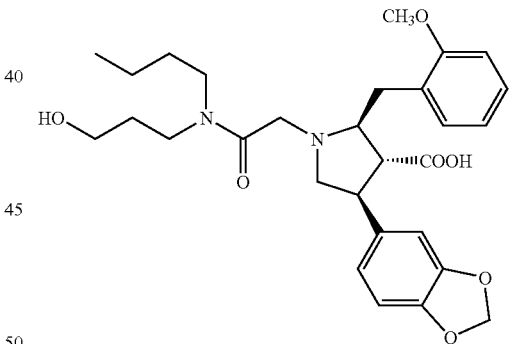
1511
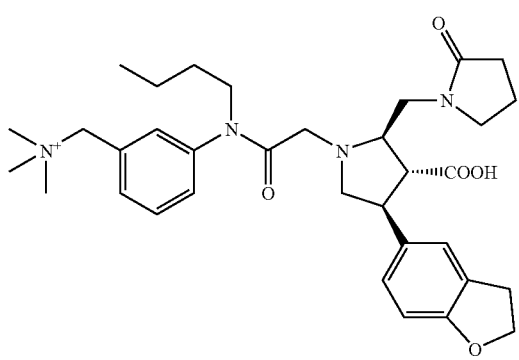
1515
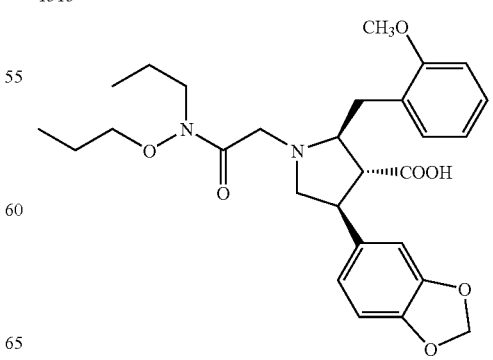

TABLE 3C-continued
1516
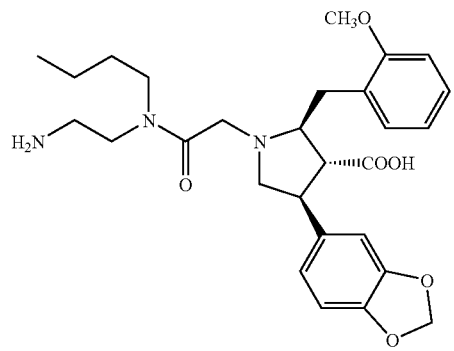
1517
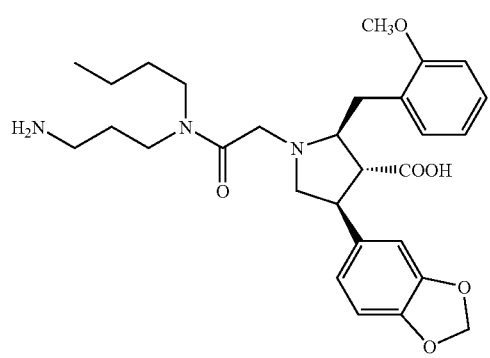
1518
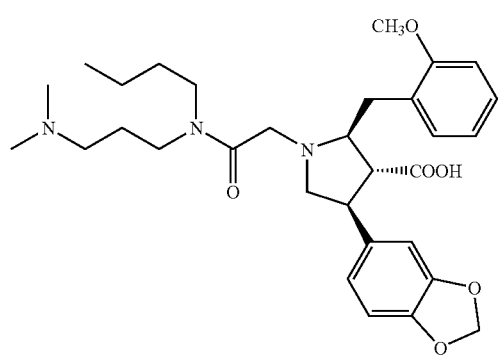
1519
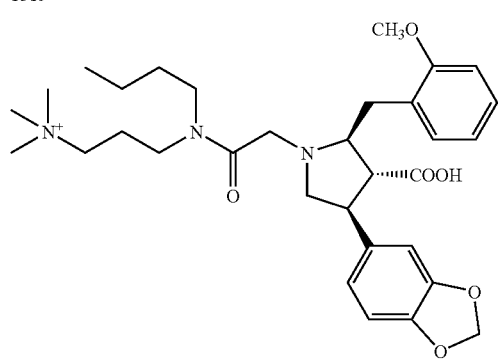
TABLE 3C-continued
1520
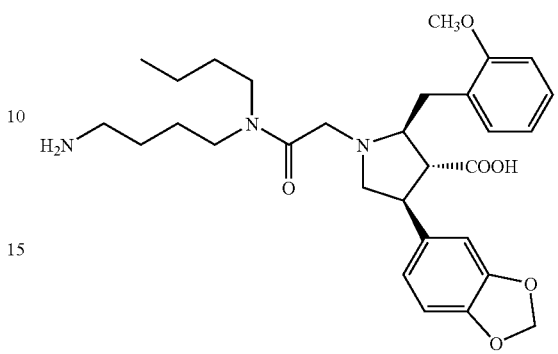
1521
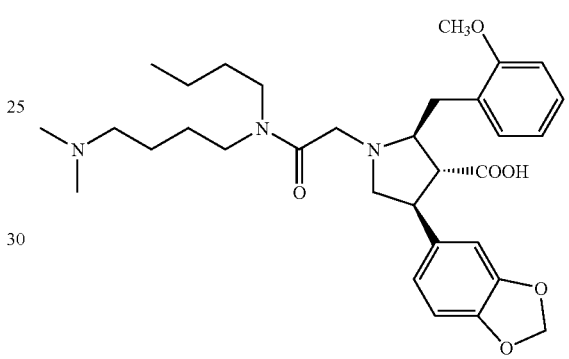
1522
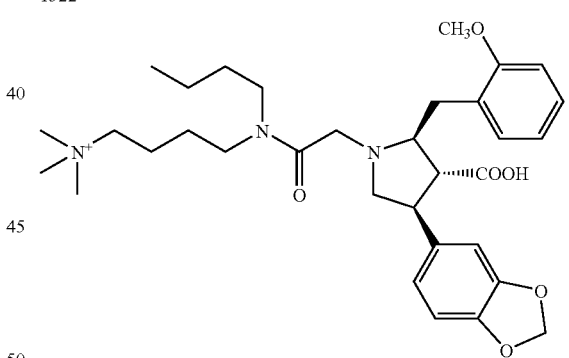
1523
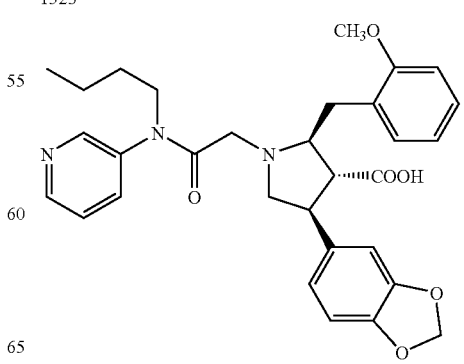

TABLE 3C-continued
1524
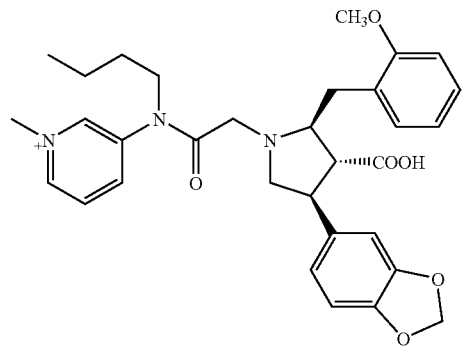
1525
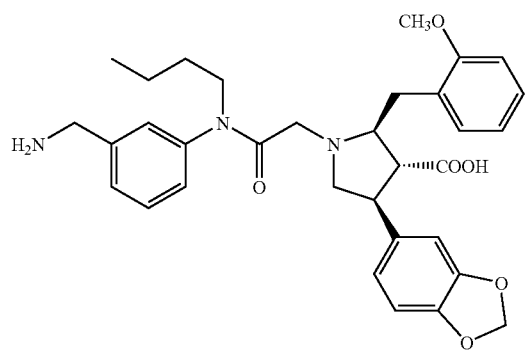
1526
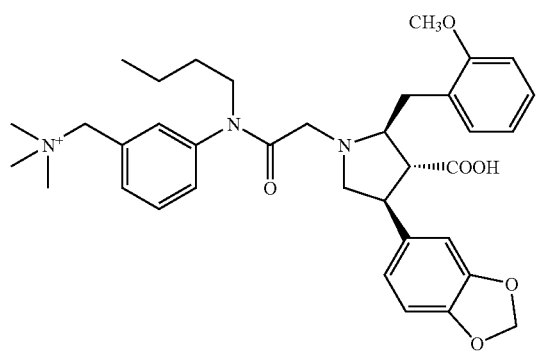
1527
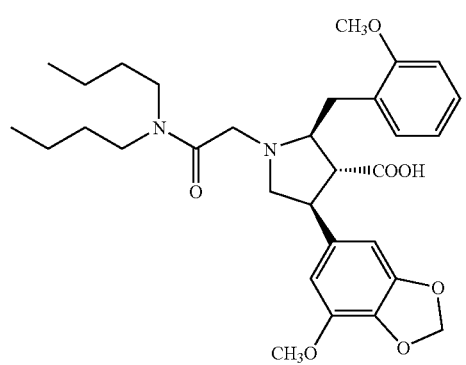
TABLE 3C-continued
1528
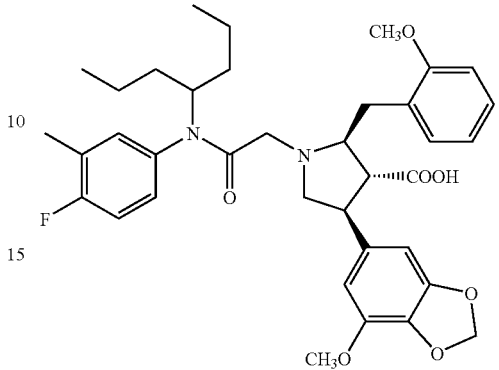
1529
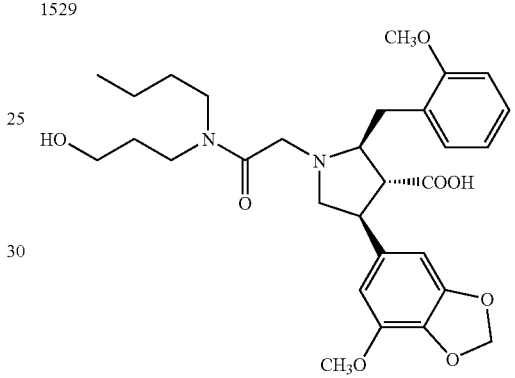
1530
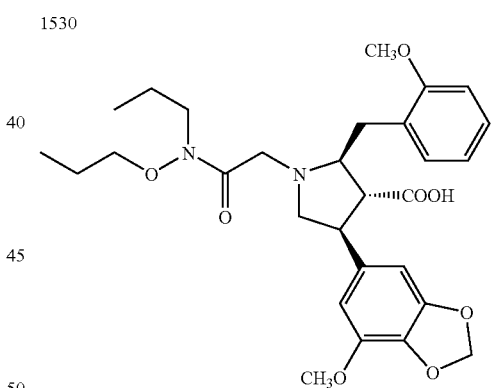
1531
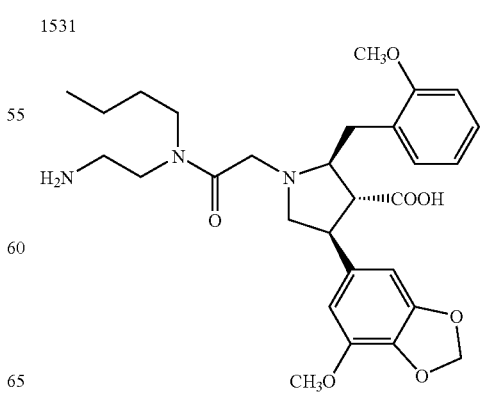

TABLE 3C-continued
1532
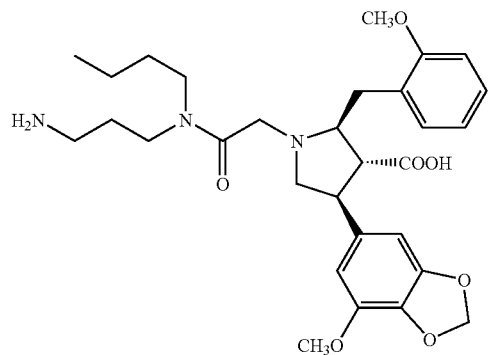
1533
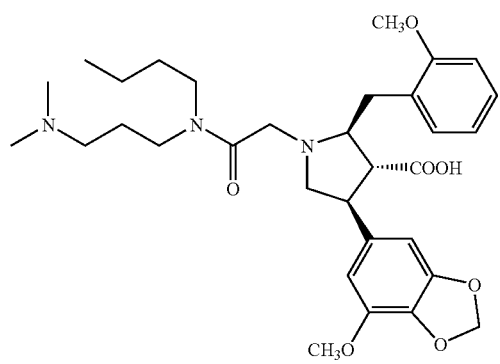
1534
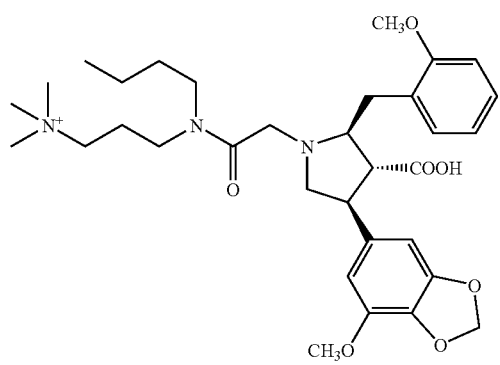
1535
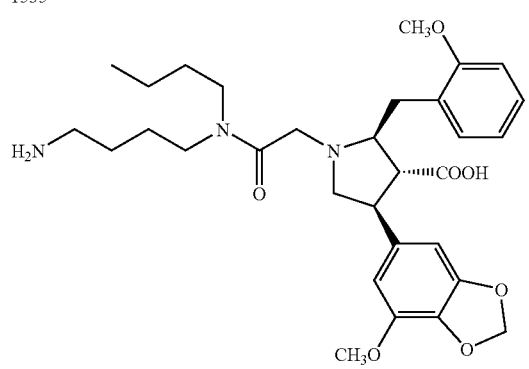
TABLE 3C-continued
1536
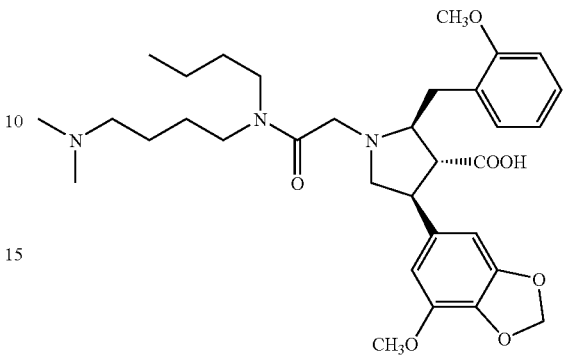
1537
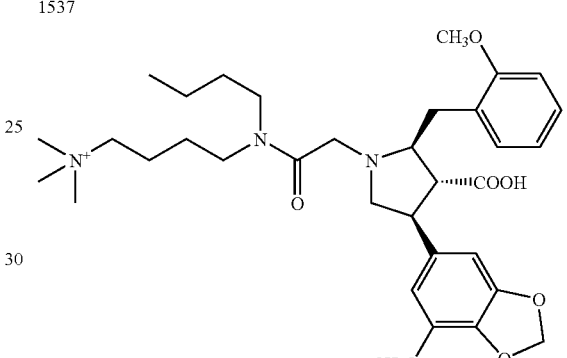
1538
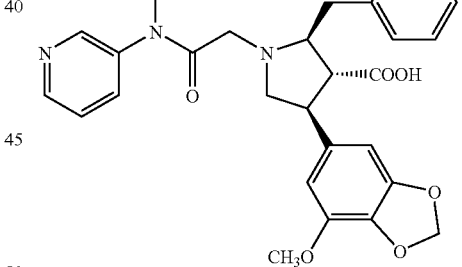
1539
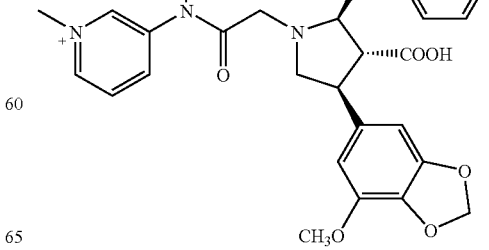

TABLE 3C-continued
1540
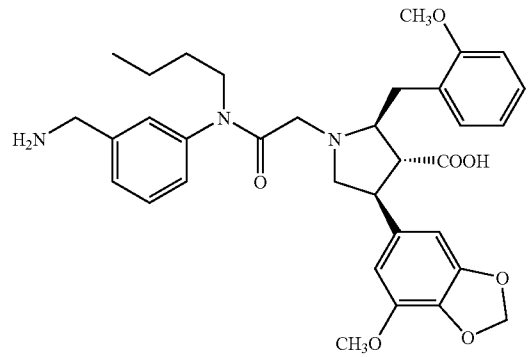
1541
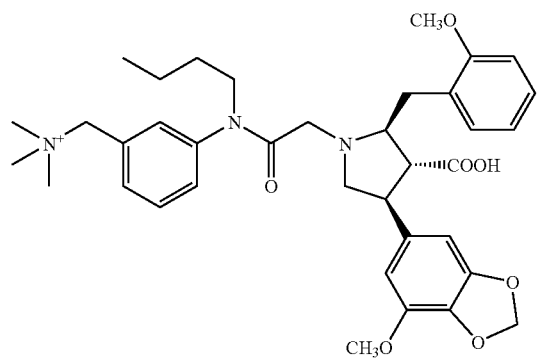
1542
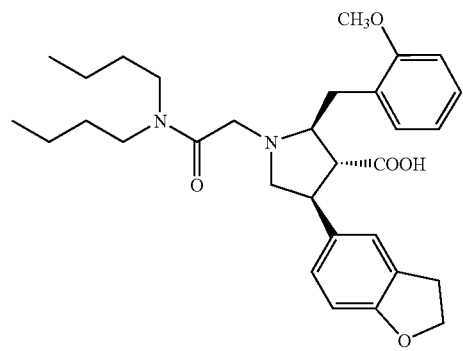
1543
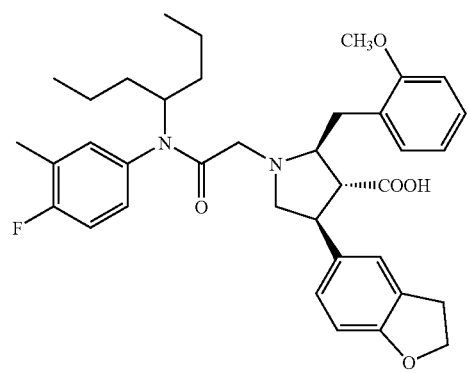
TABLE 3C-continued
1544
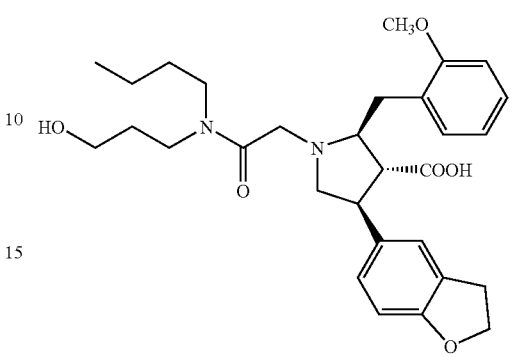
1545
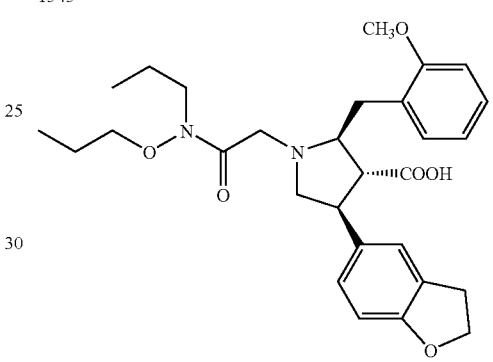
1546
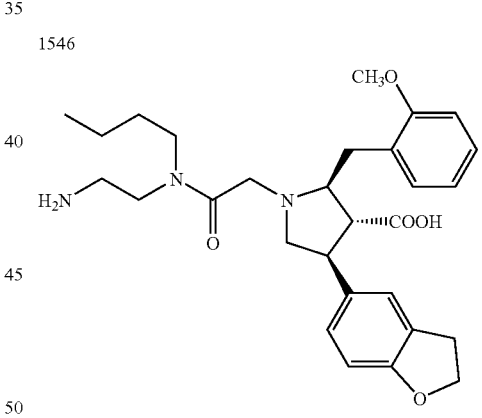
1547
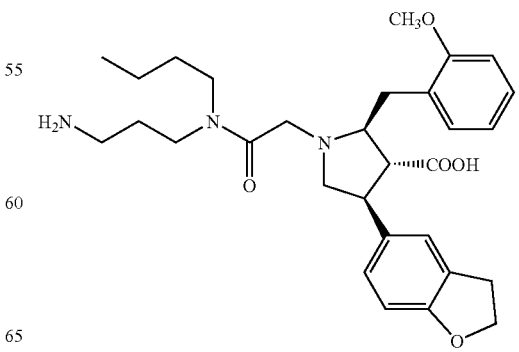

TABLE 3C-continued
1548
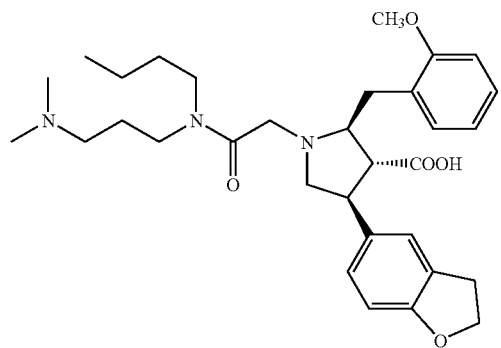
1549
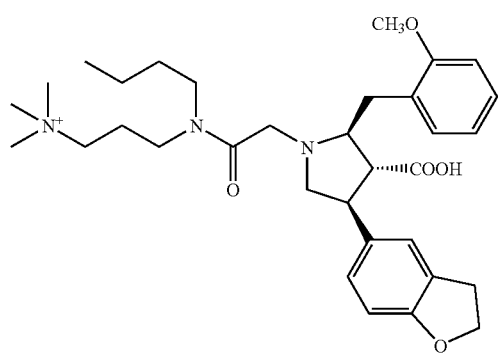
1550
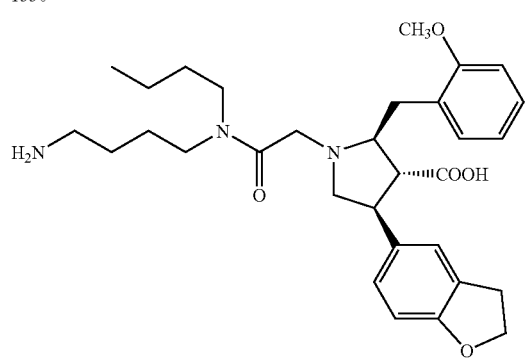
1551
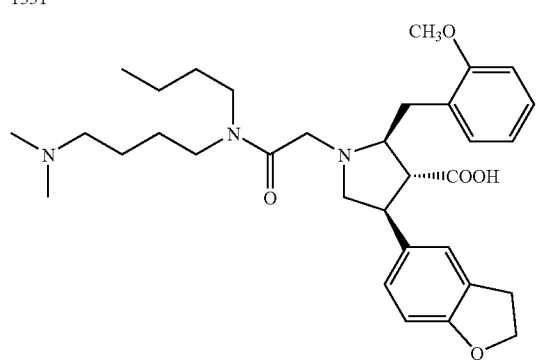
TABLE 3C-continued
1552
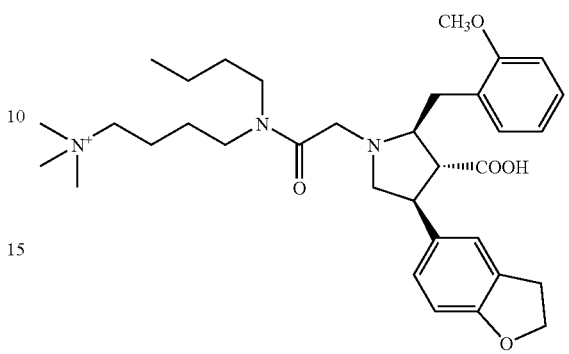
1553
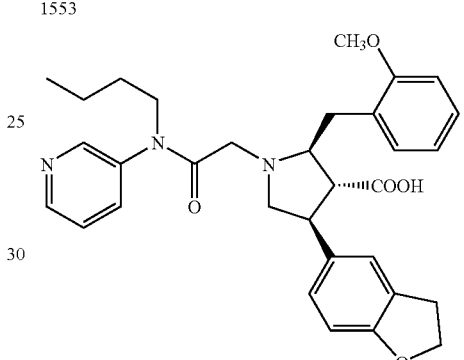
1554
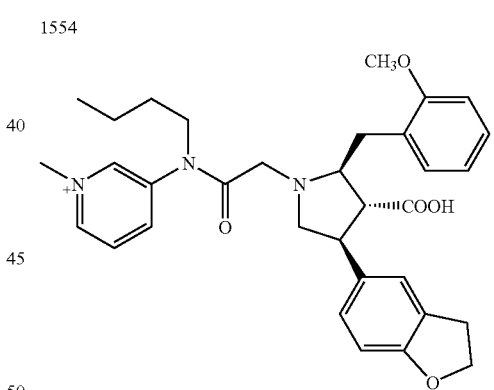
1555
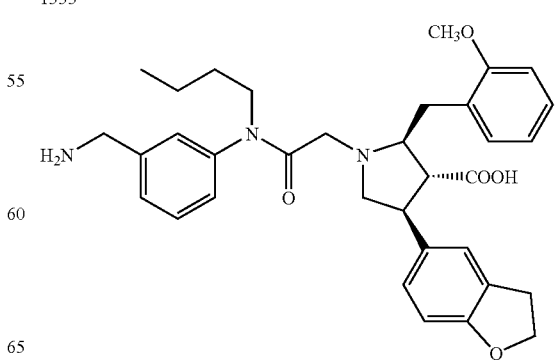

TABLE 3C-continued
1556
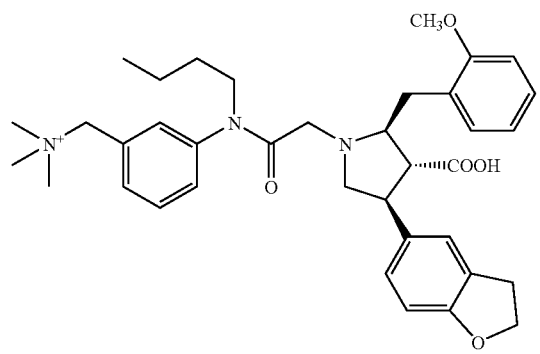
1559
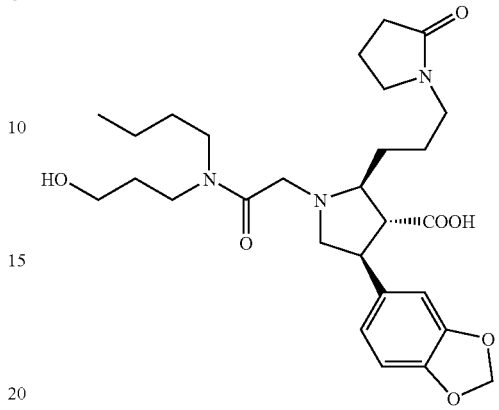
1557
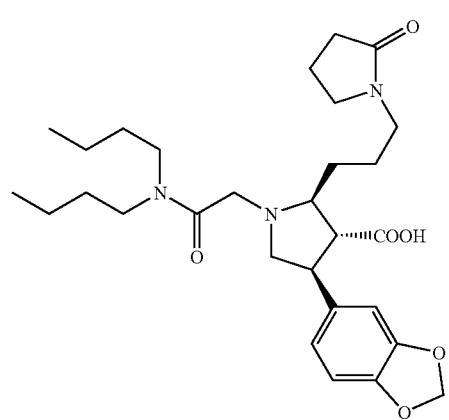
1560
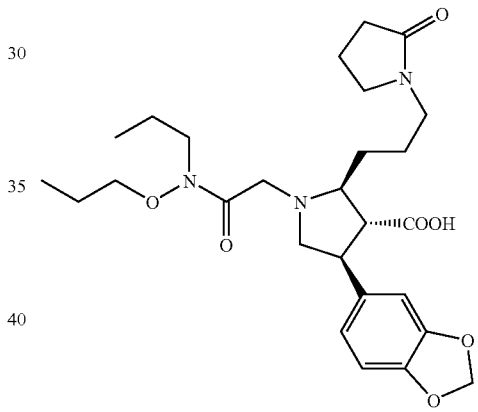
1558
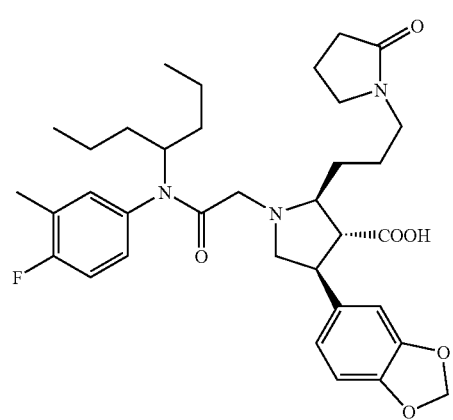
1561
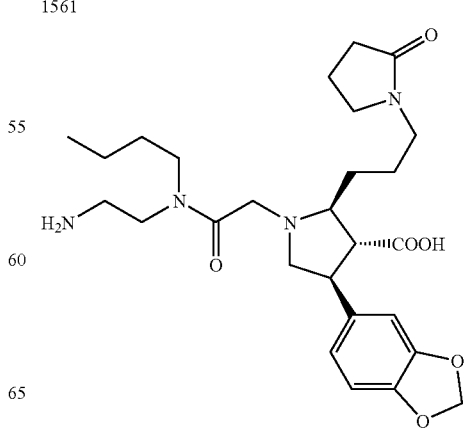

1063 1064
TABLE 3C-continued | TABLE 3C-continued
1562 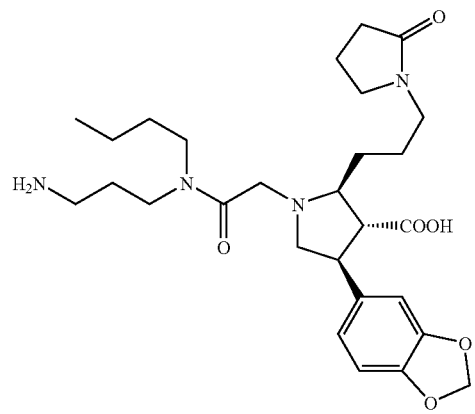
1565 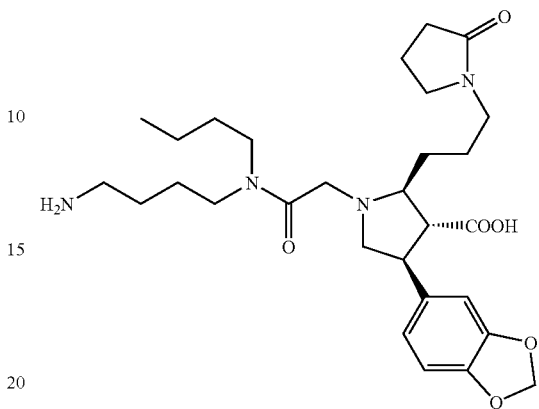
1563 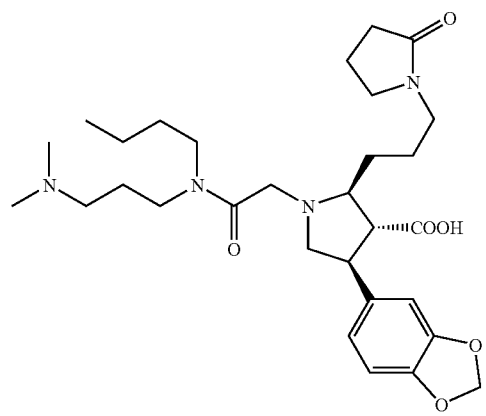
1566 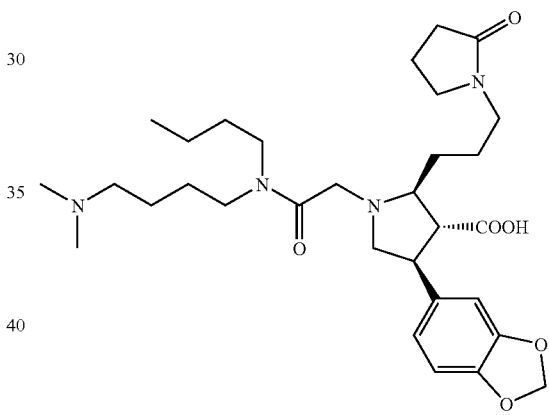
1564 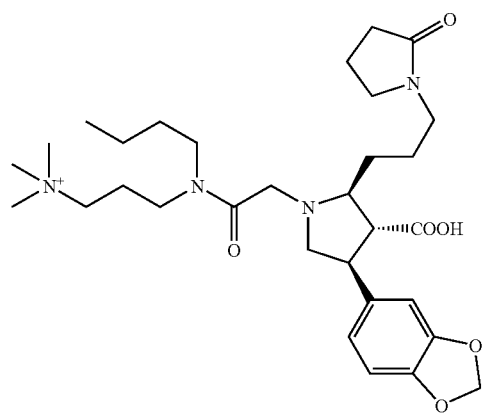
1567 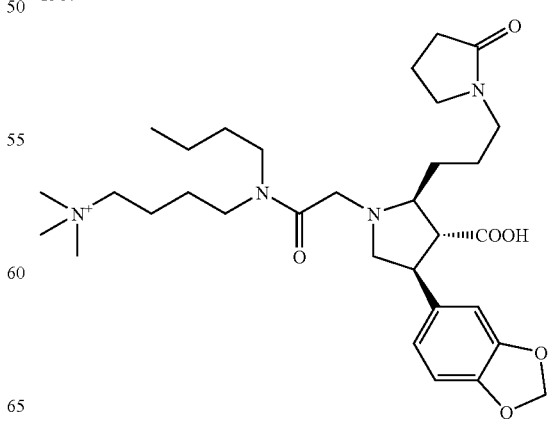

TABLE 3C-continued
1568
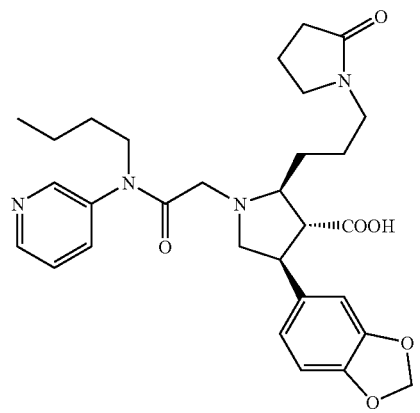
1569
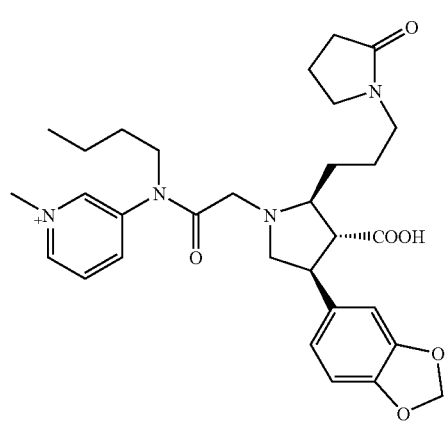
1570
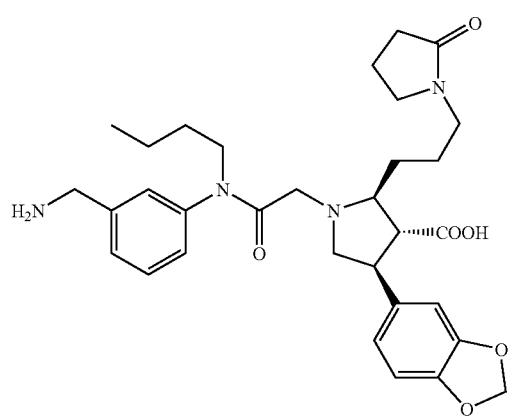
TABLE 3C-continued
1571
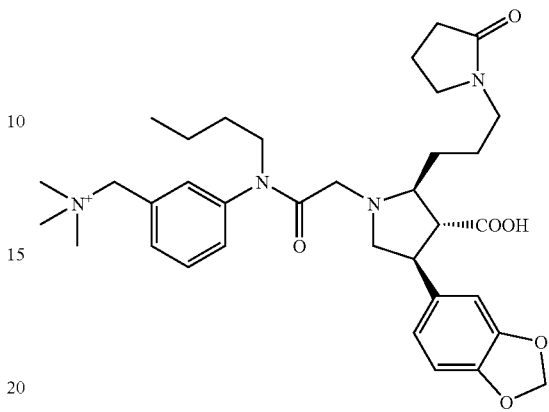
1572
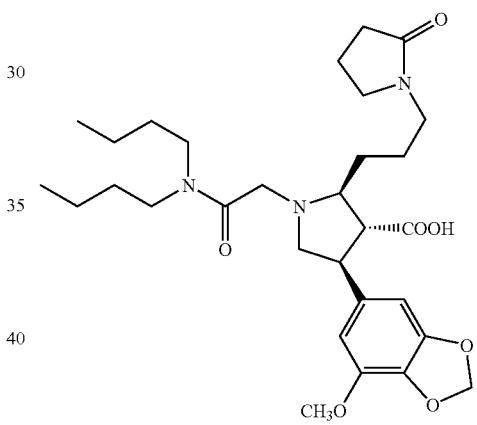
1573
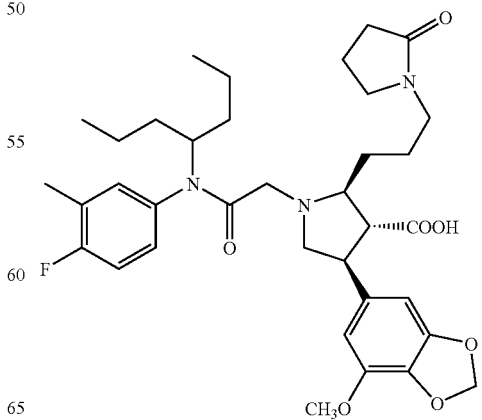

TABLE 3C-continued
1574
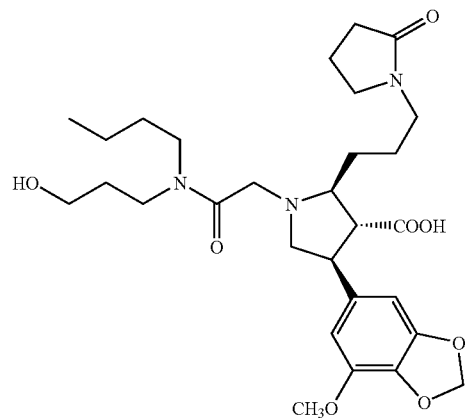
1577
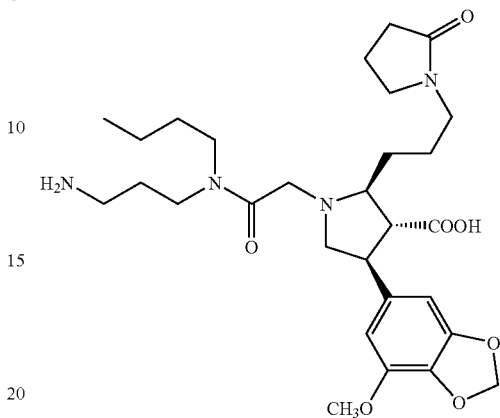
1575
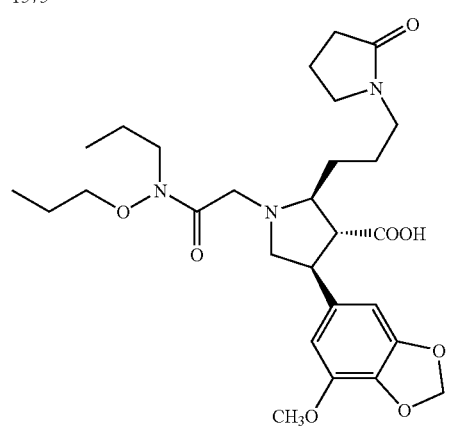
1578
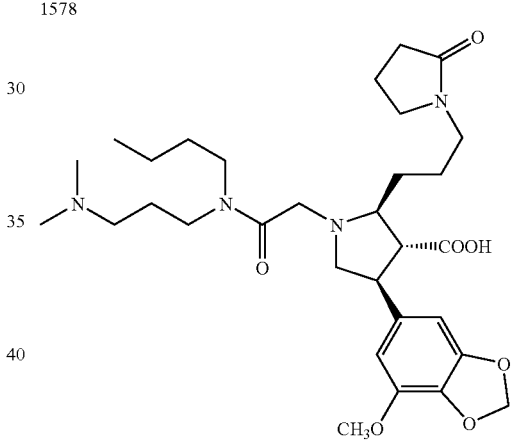
1576
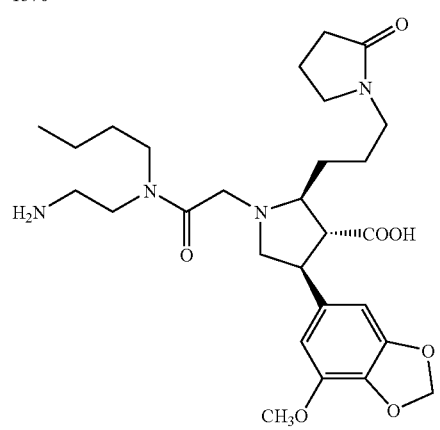
1579
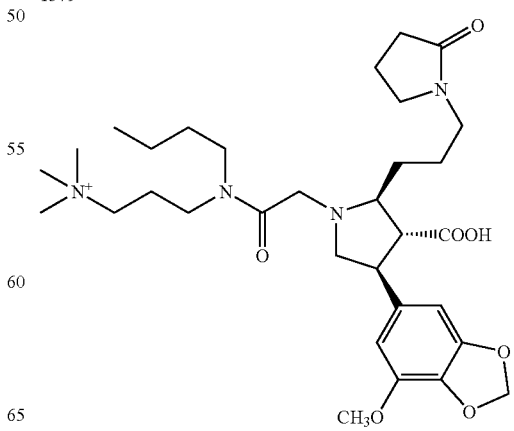

TABLE 3C-continued
1580
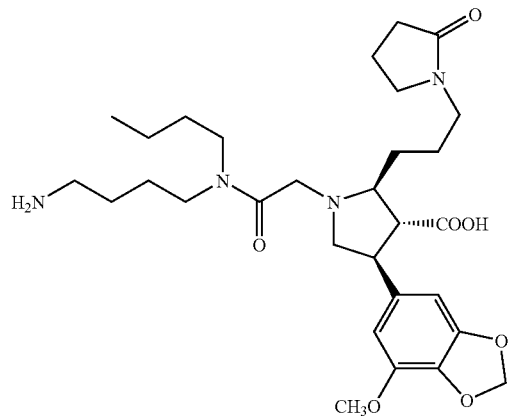
1581
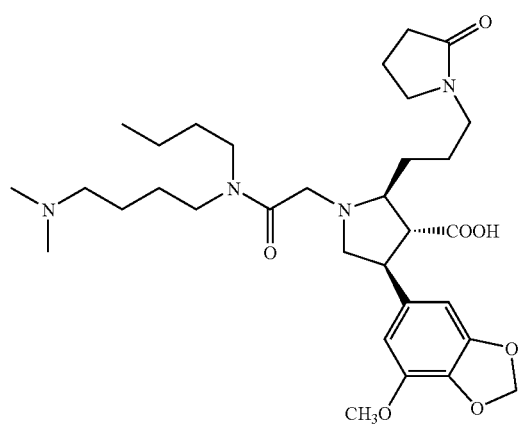
1582
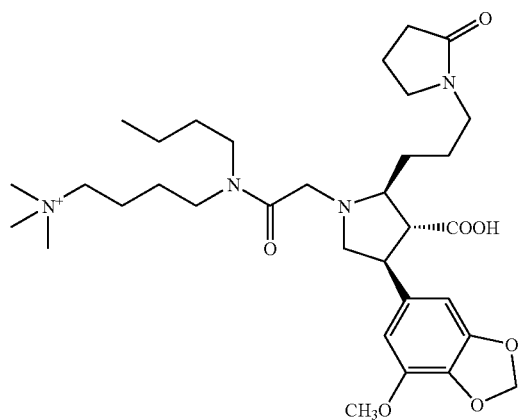
TABLE 3C-continued
1583
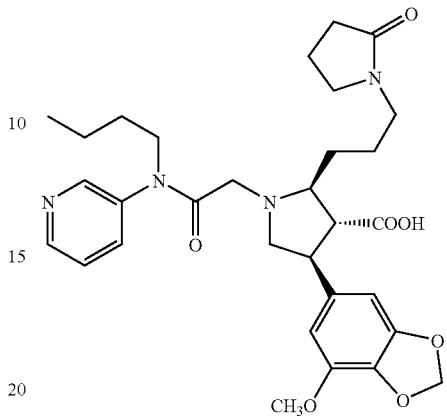
1584
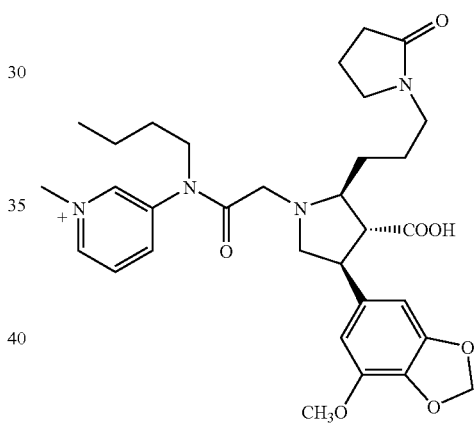
1585
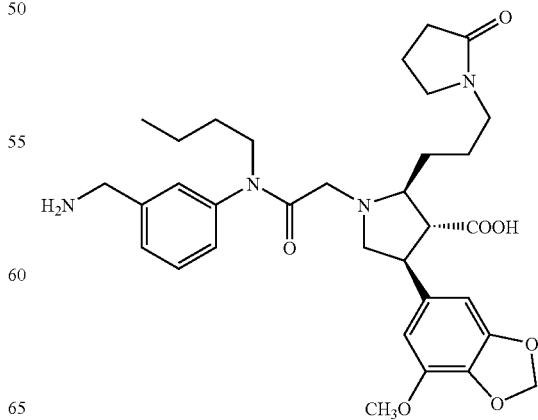

TABLE 3C-continued
1586
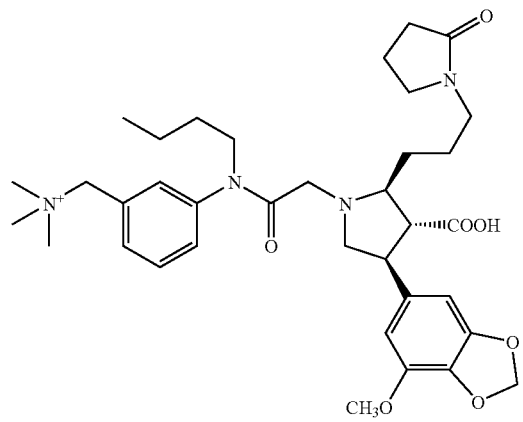
1587
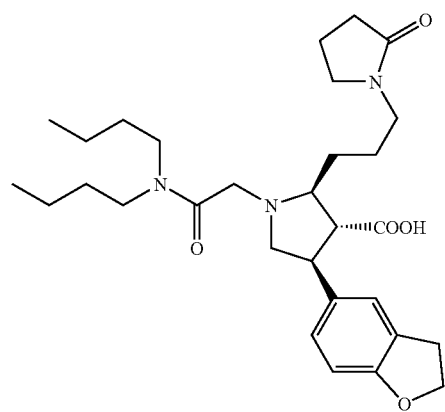
1588
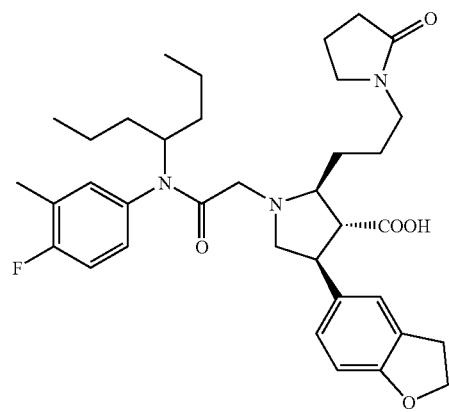
TABLE 3C-continued
1589
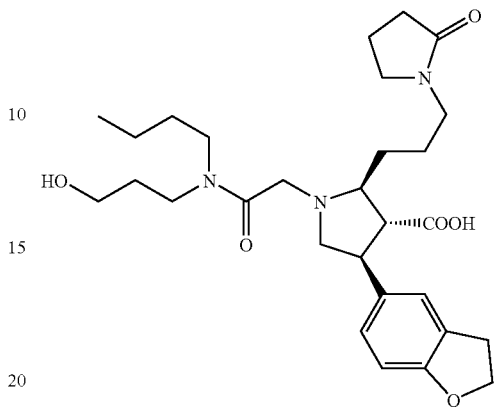
1590
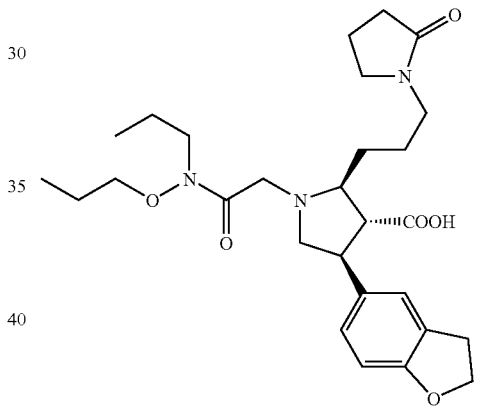
1591
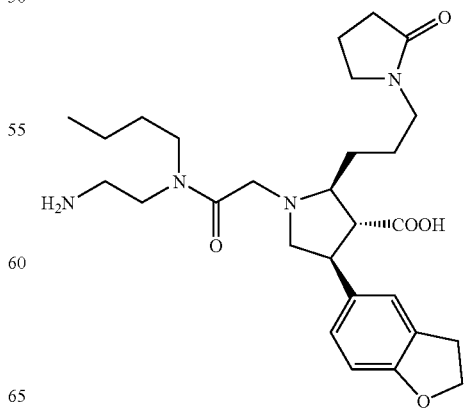

TABLE 3C-continued
1592
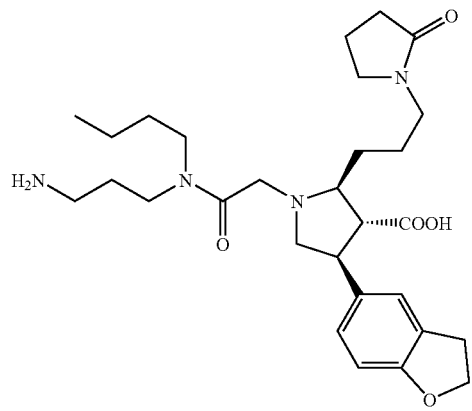
1595
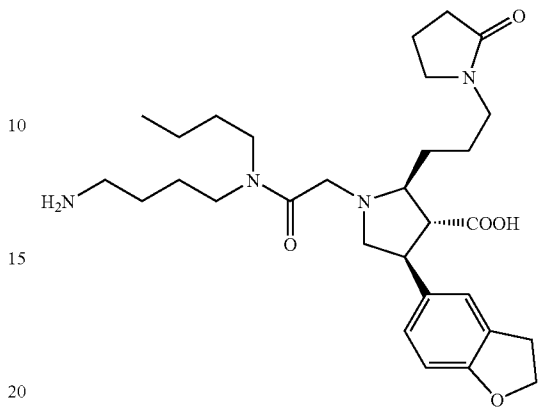
1593
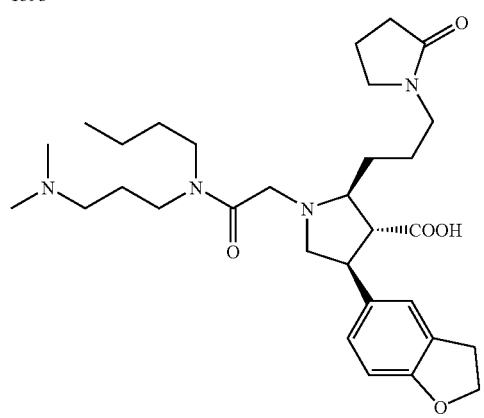
1596
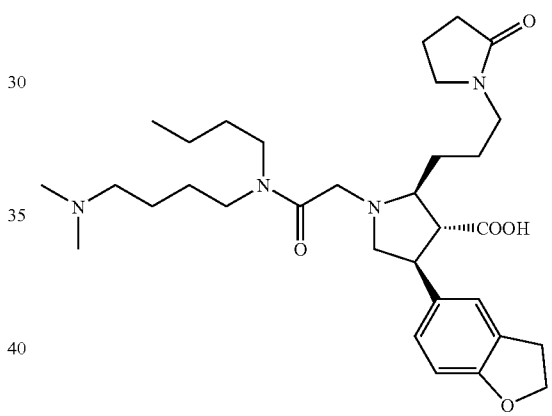
1594
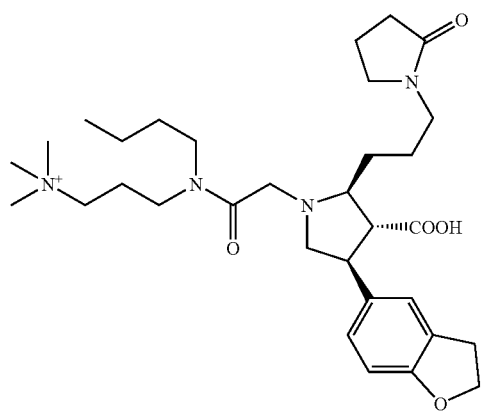
1597
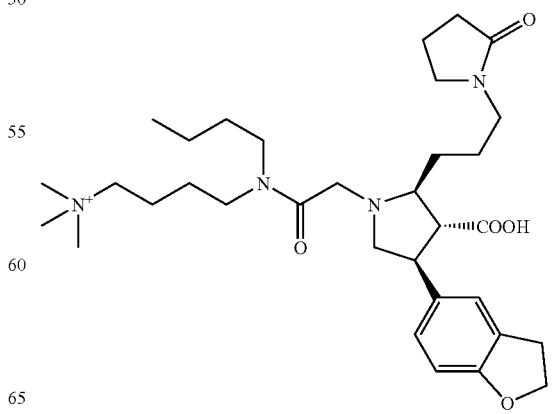

TABLE 3C-continued
1598
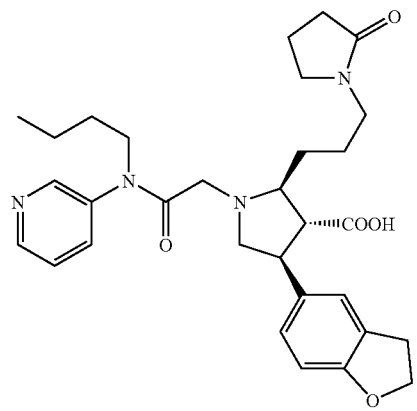
1601
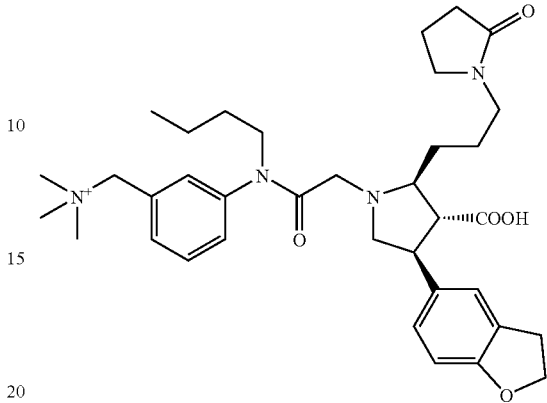
1599
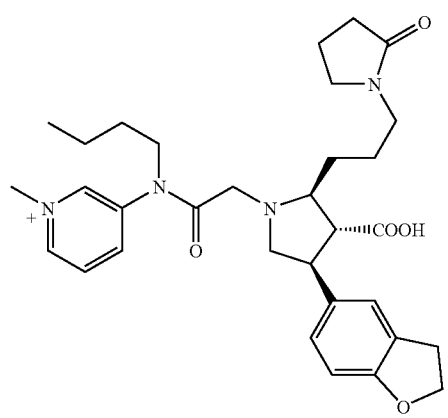
1602
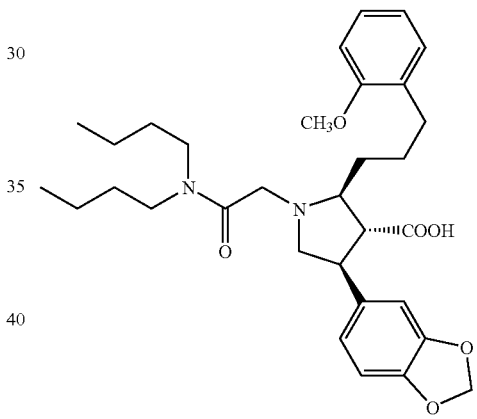
1600
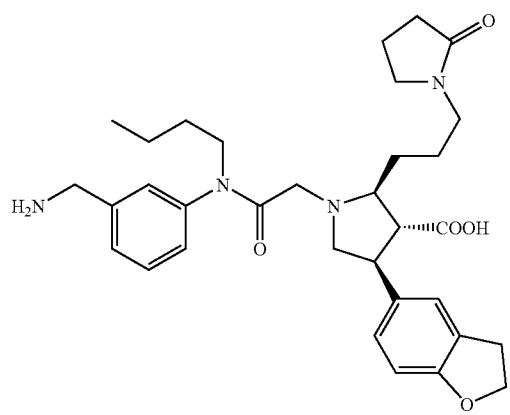
1603
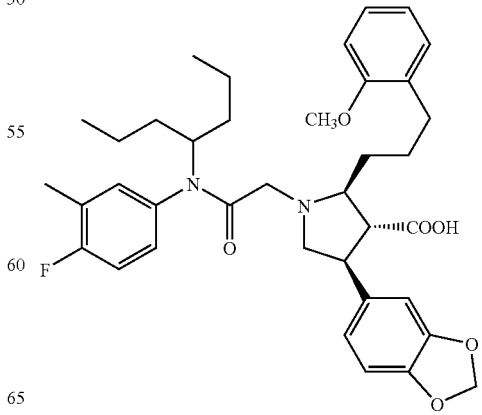

TABLE 3C-continued
1604
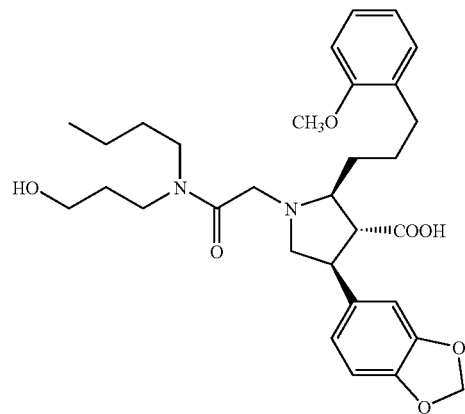
1605
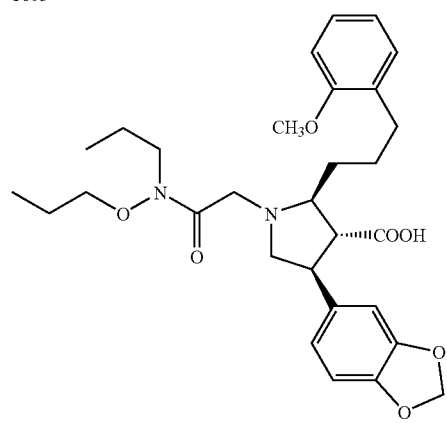
1606
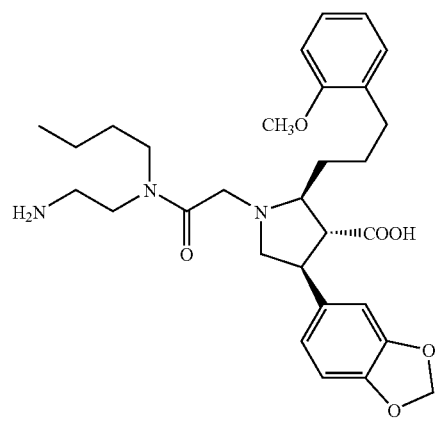
TABLE 3C-continued
1607
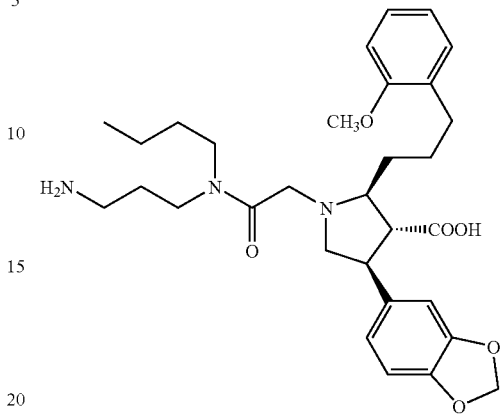
1608
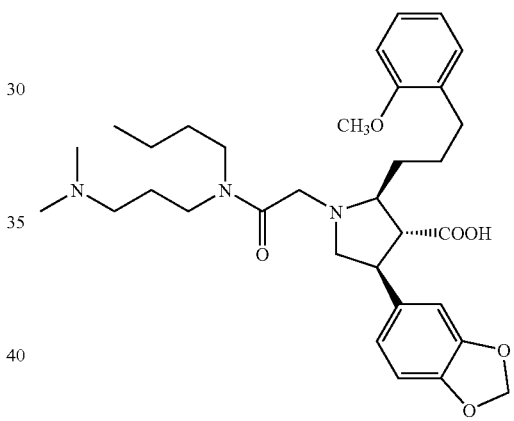
1609
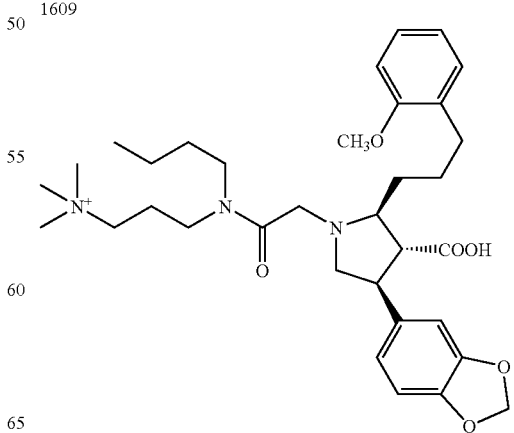

1079
TABLE 3C-continued
1610
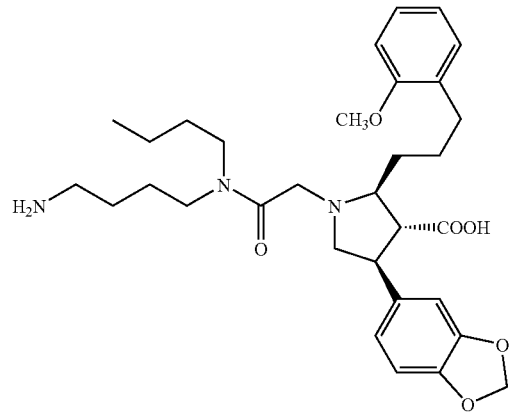
1611
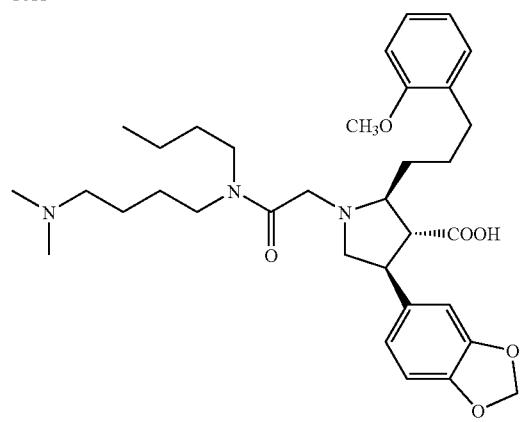
1612
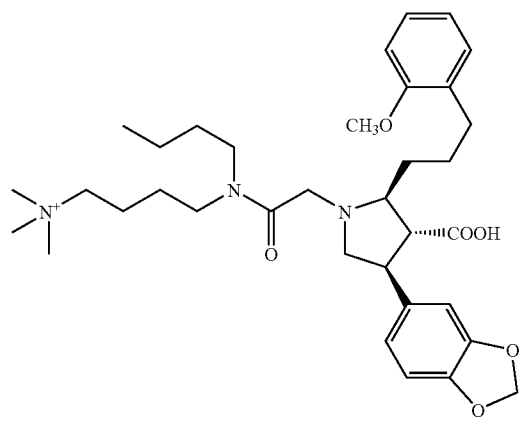
1080
TABLE 3C-continued
1613
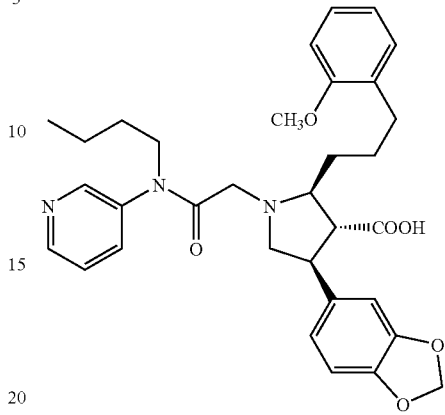
1614
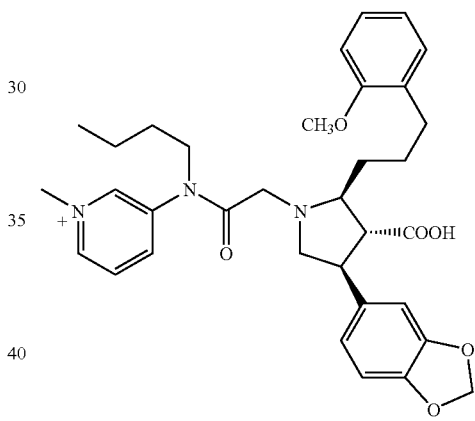
1615
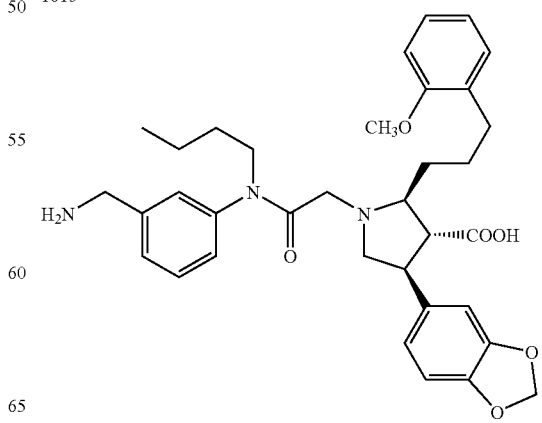

TABLE 3C-continued
1616
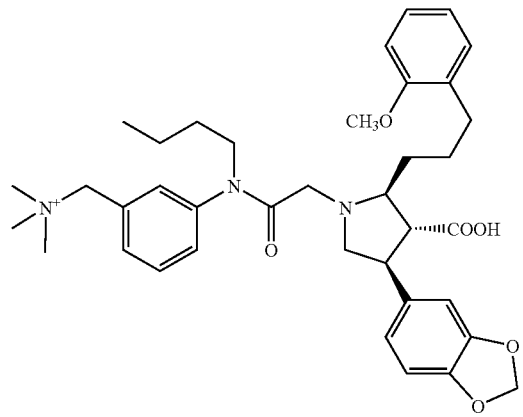
1617
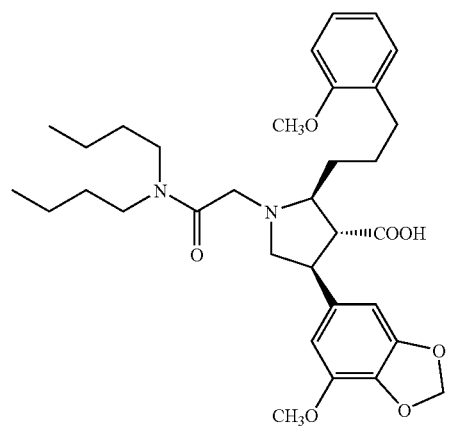
1618
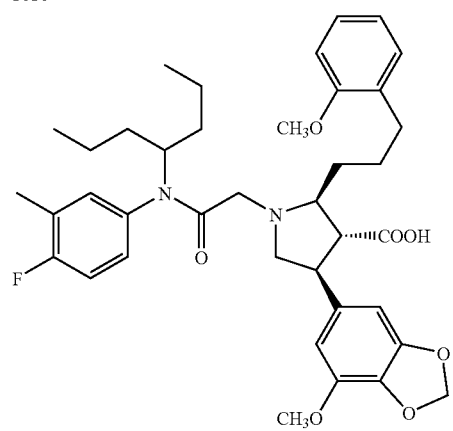
TABLE 3C-continued
1619
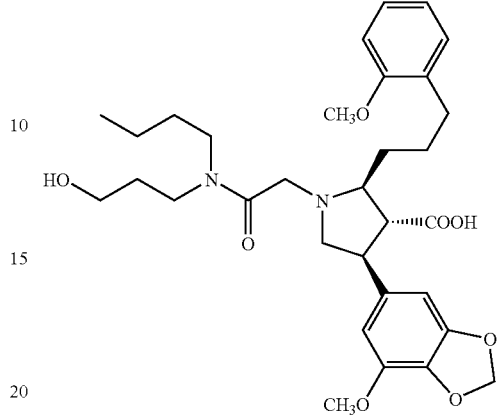
1620
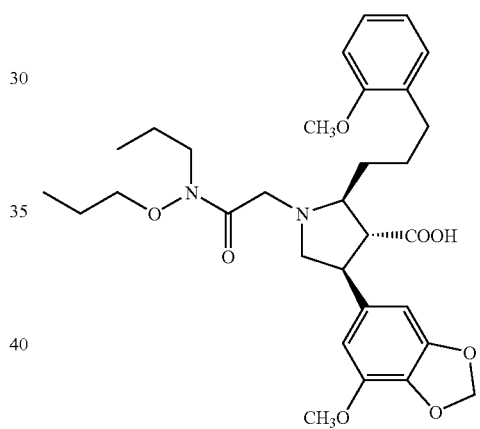
1621
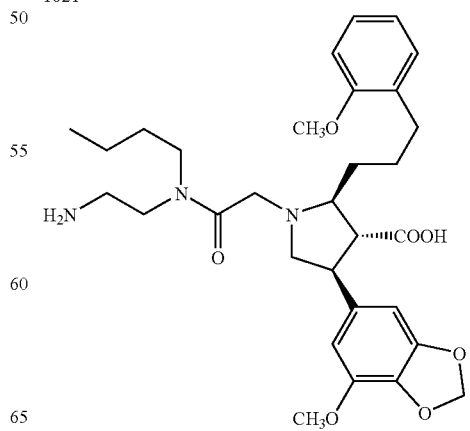

TABLE 3C-continued
1622
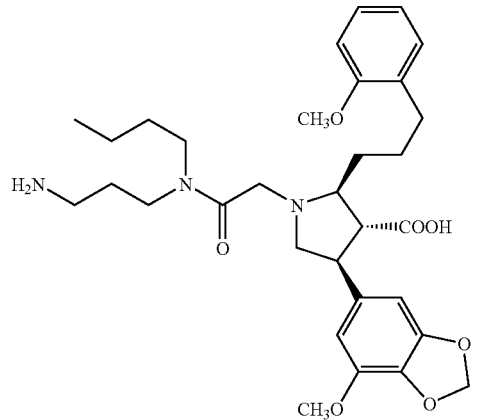
1623
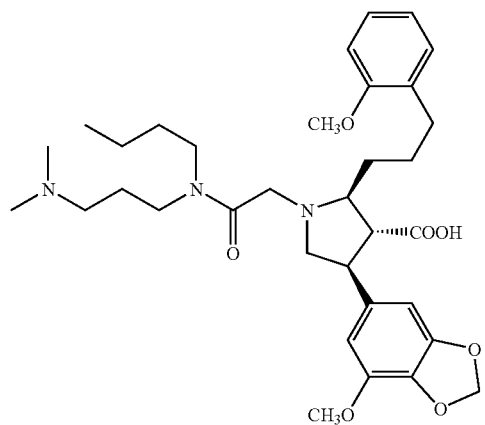
1624
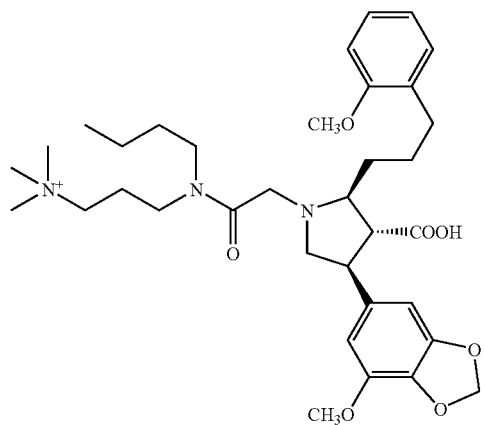
TABLE 3C-continued
1625
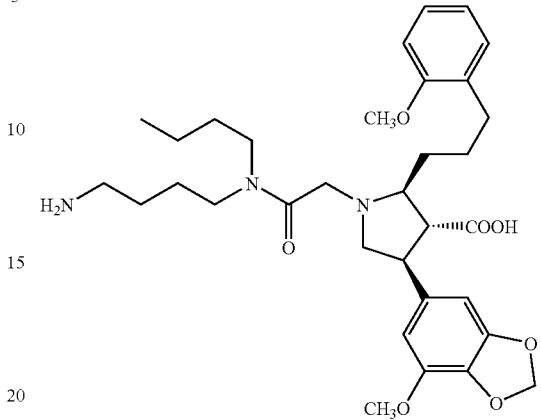
1626
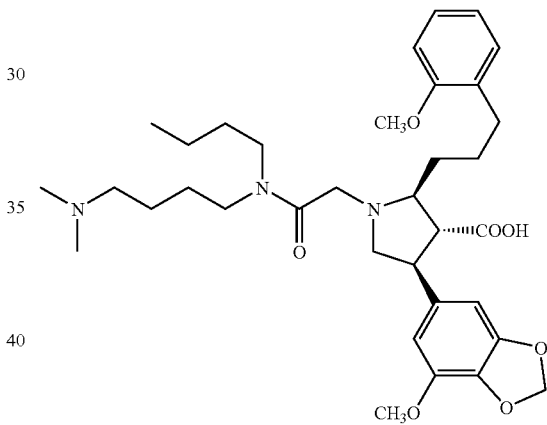
1627
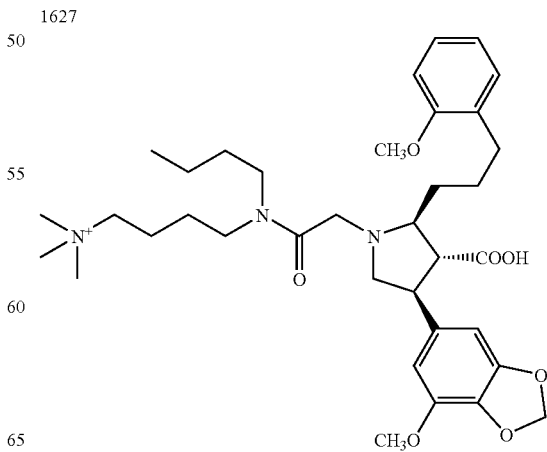

TABLE 3C-continued
1628
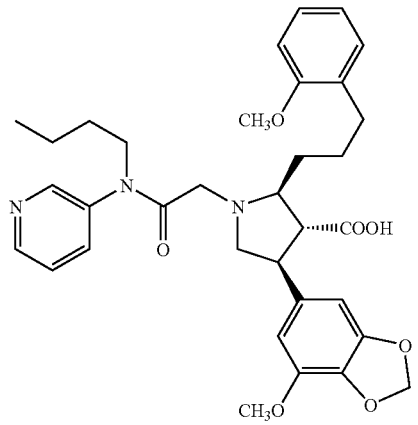
1631
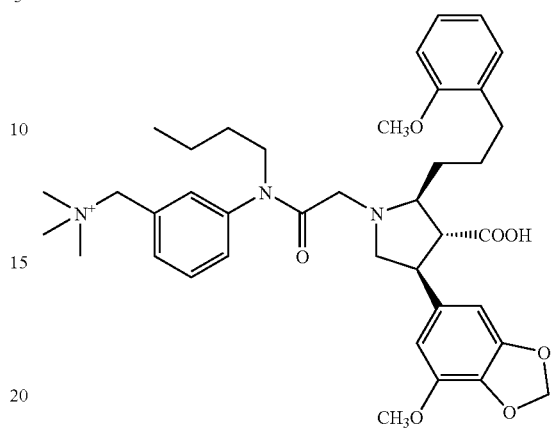
1629
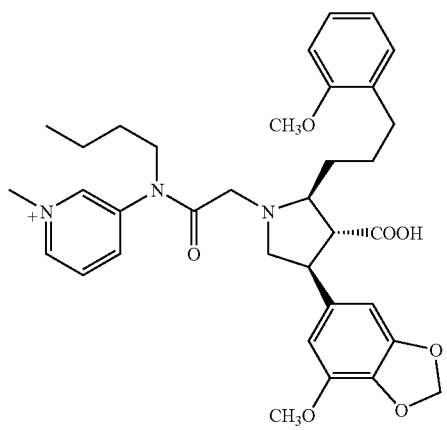
1632
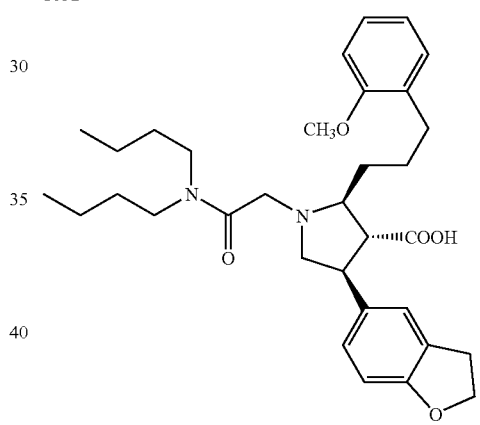
1630
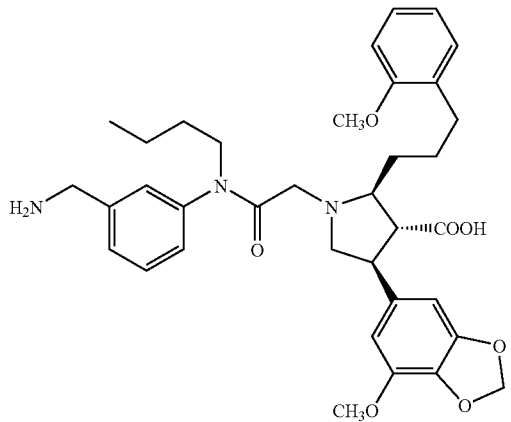
1633
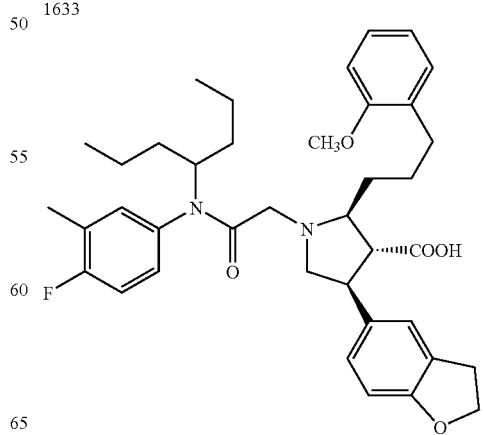

TABLE 3C-continued
1634
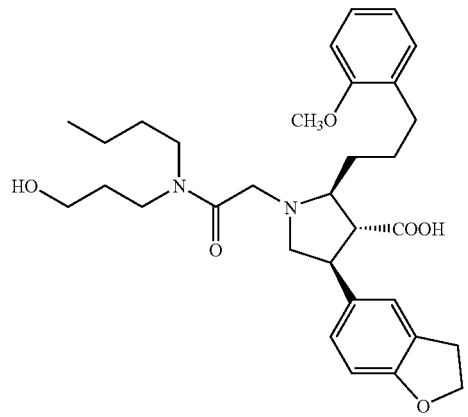
1635
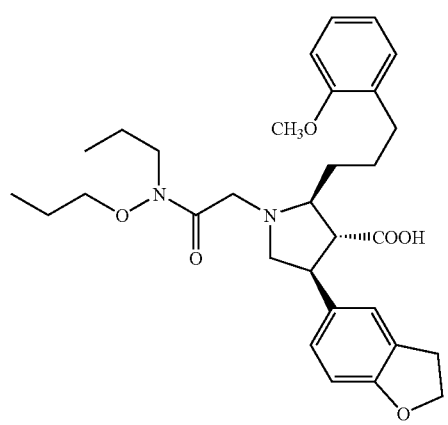
1636
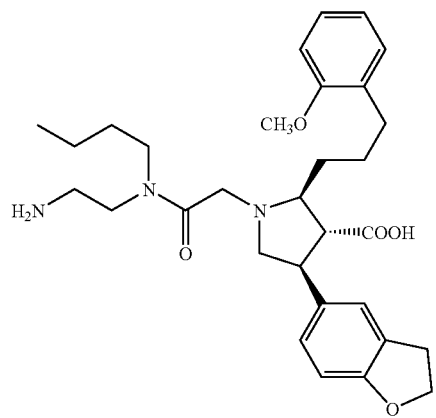
TABLE 3C-continued
1637
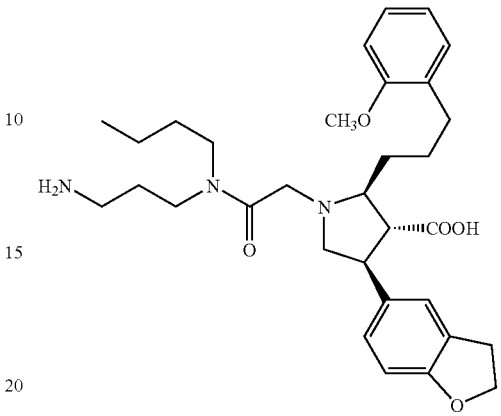
1638
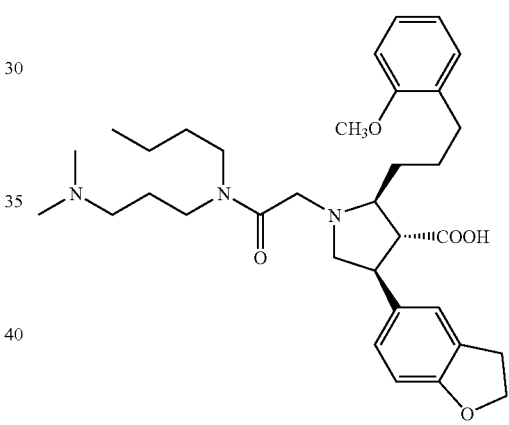
1639
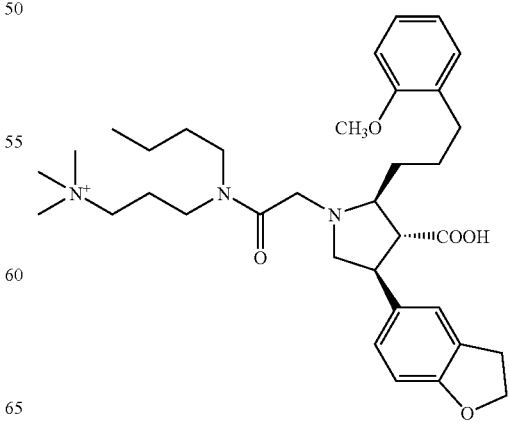

TABLE 3C-continued
1640
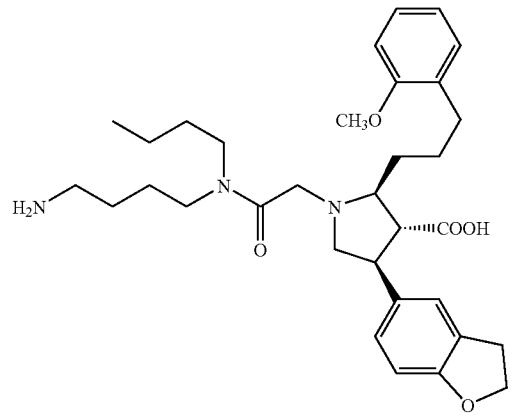
1641
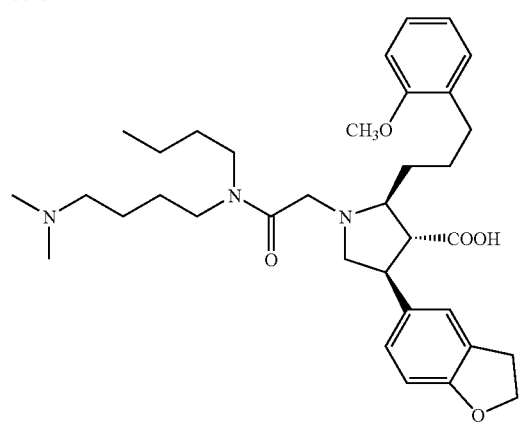
1642
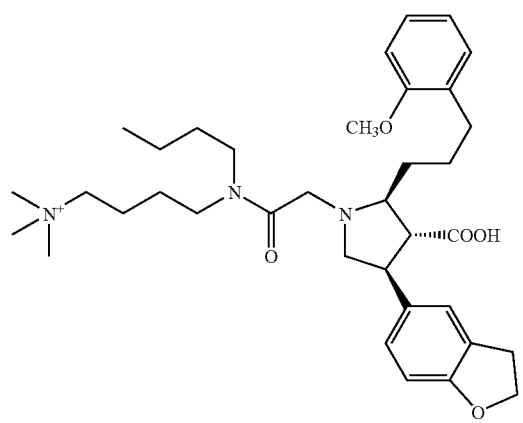
TABLE 3C-continued
1643
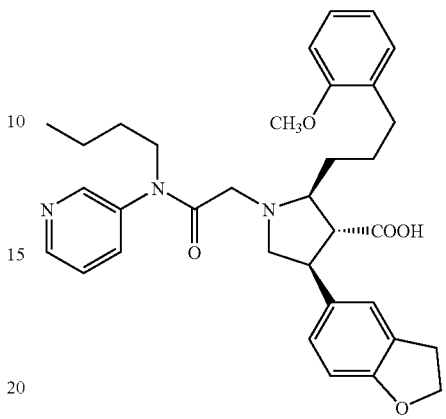
1644
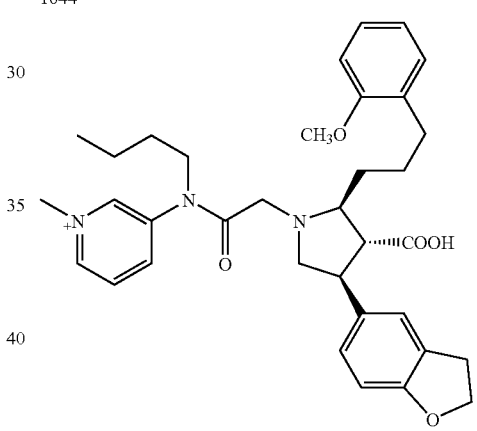
1645
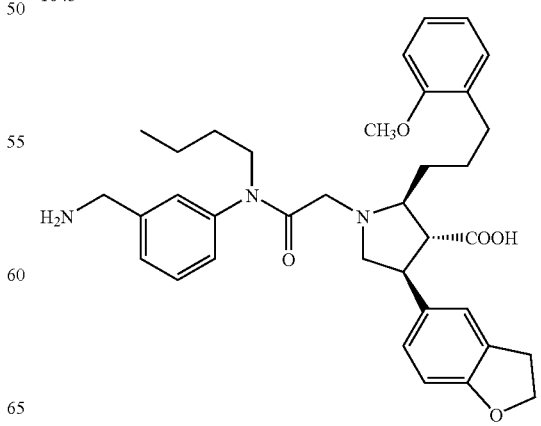

TABLE 3C-continued
1646
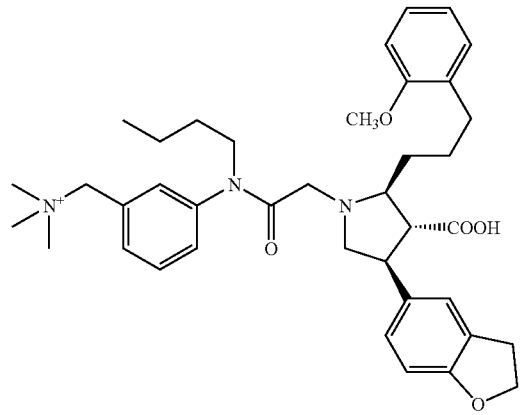
1649
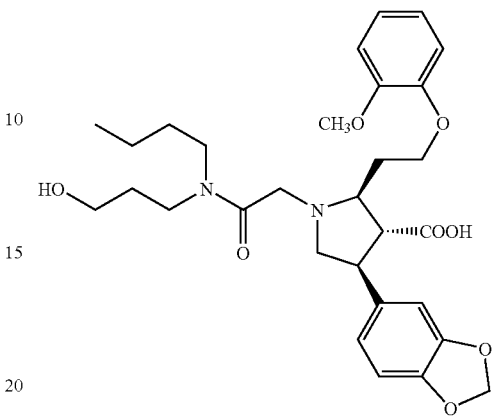
1647
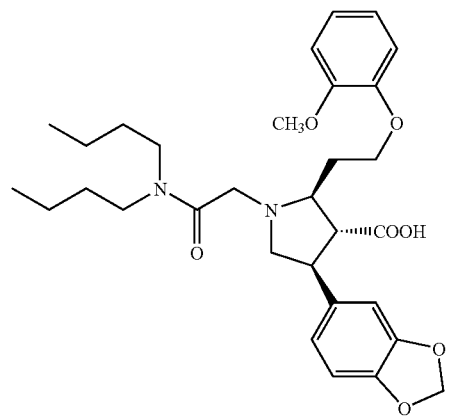
1650
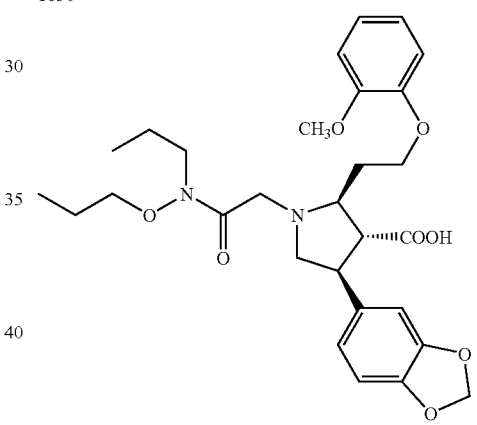
1648
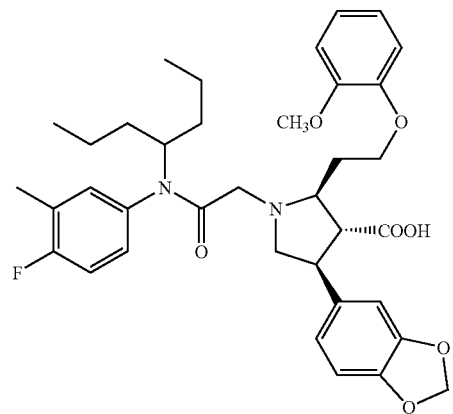
1651
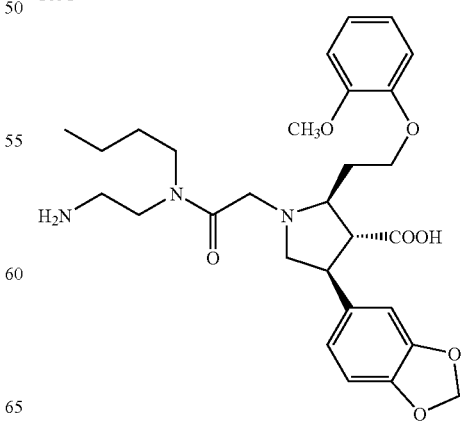

TABLE 3C-continued
1652
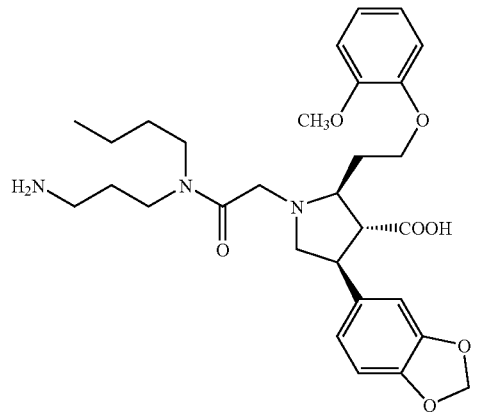
1653
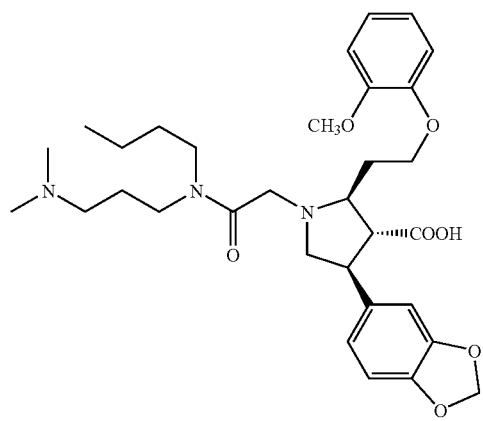
1654
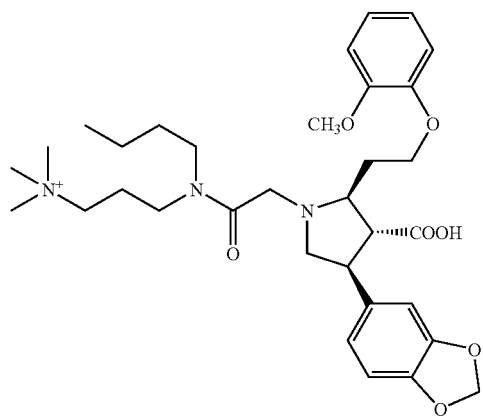
TABLE 3C-continued
1655
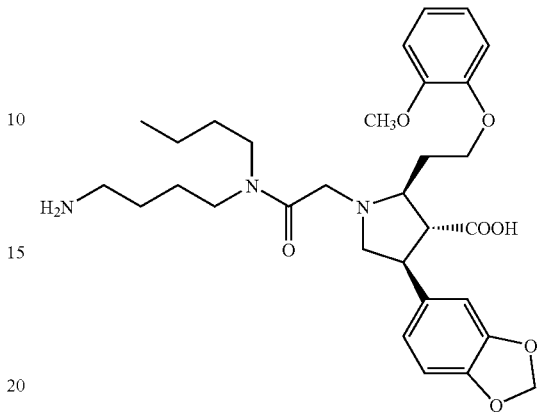
1656
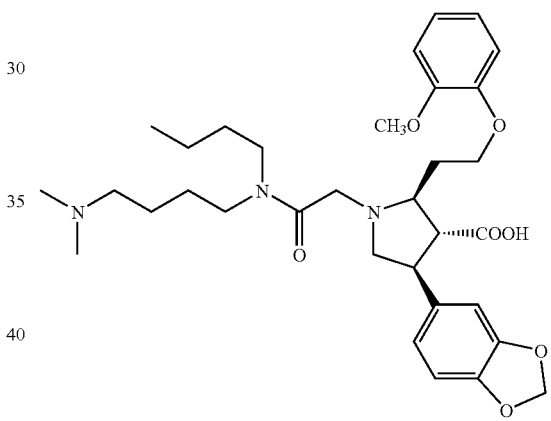
1657
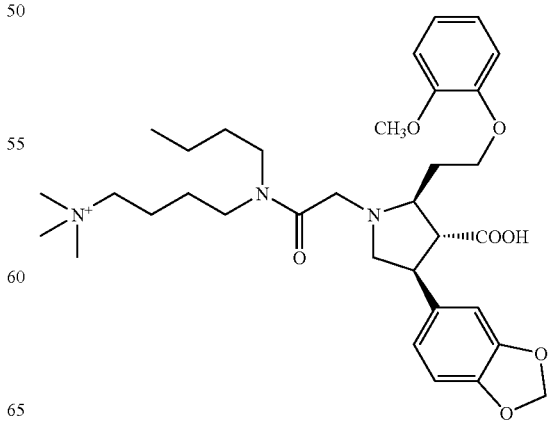

TABLE 3C-continued
1658
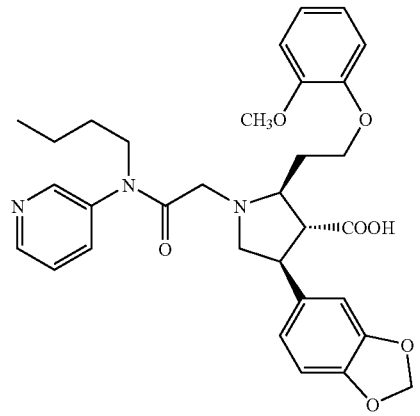
1659
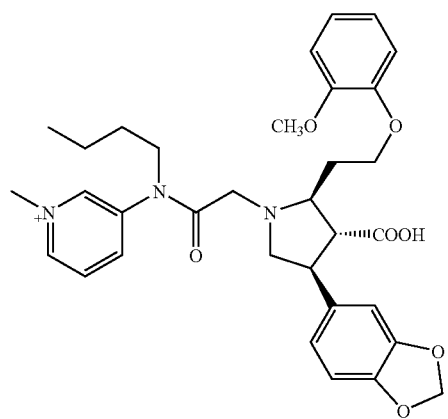
1660
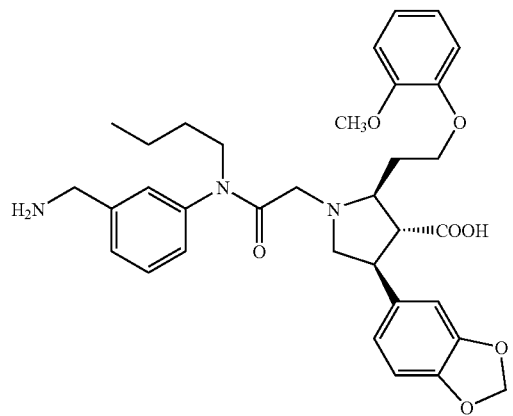
TABLE 3C-continued
1661
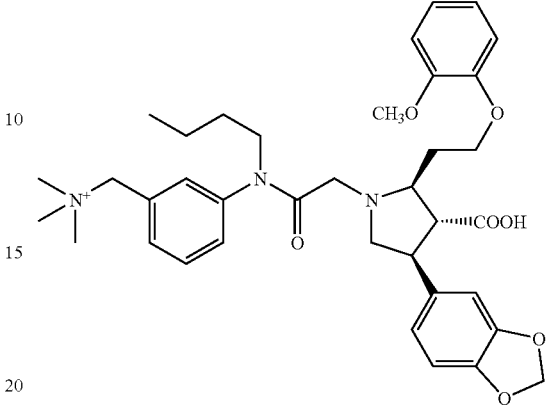
1662
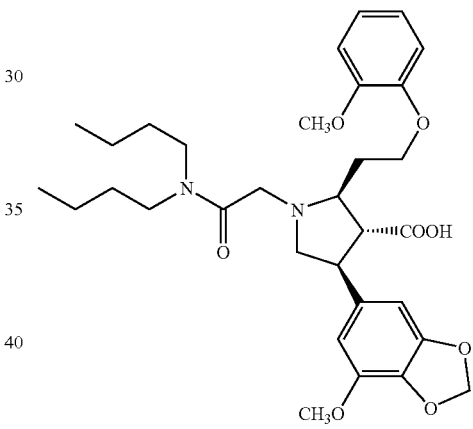
1663
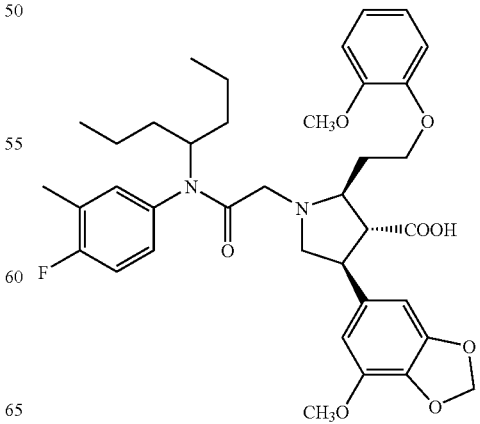

1097
TABLE 3C-continued
1664
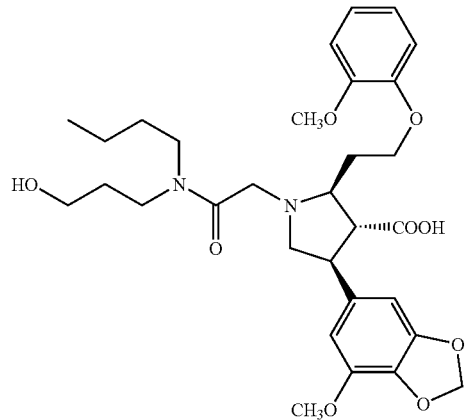
1665
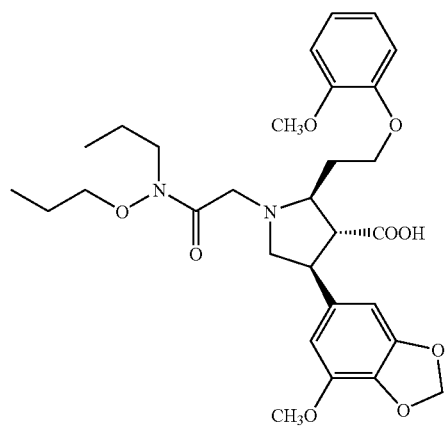
1666
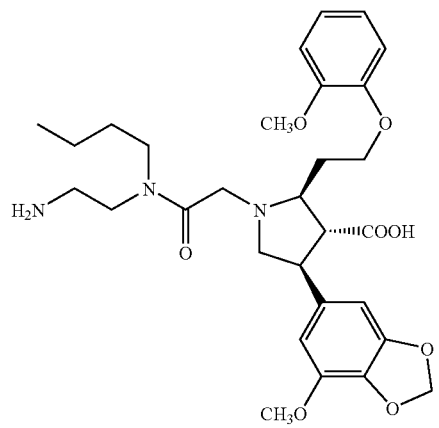
1098
TABLE 3C-continued
1667
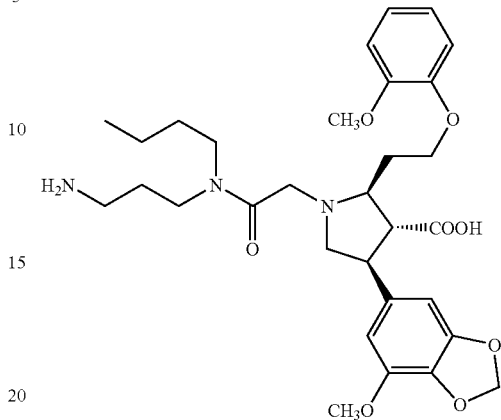
1668
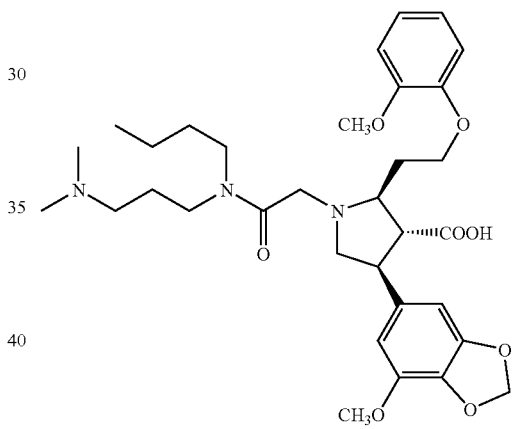
1669
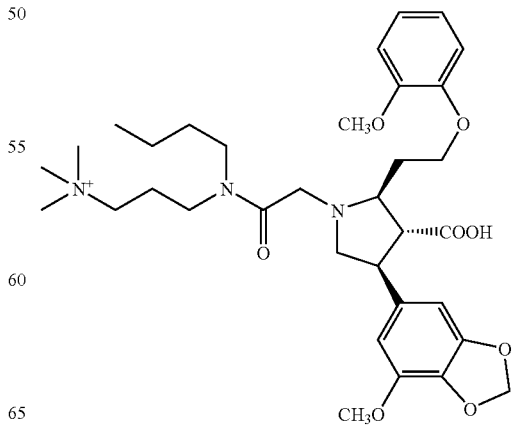

TABLE 3C-continued
1670
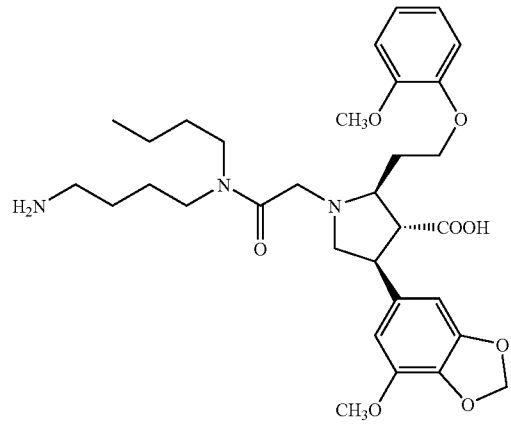
1671
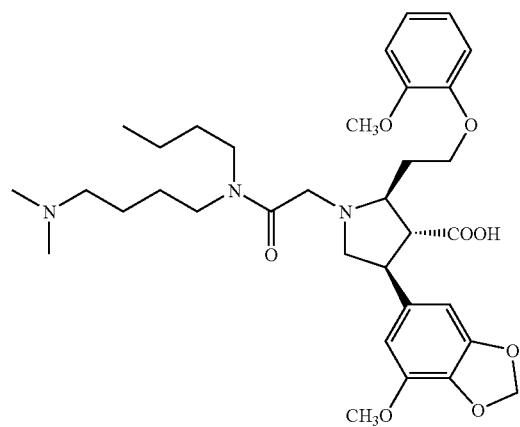
1672
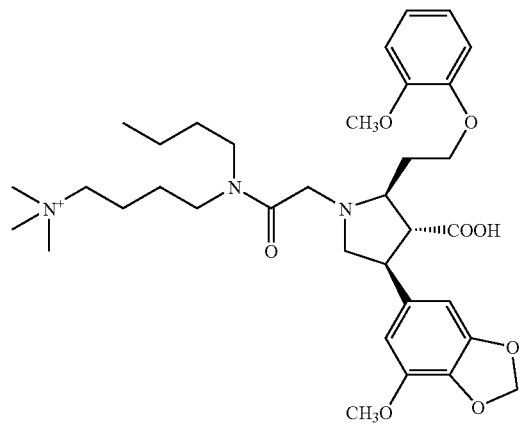
TABLE 3C-continued
1673
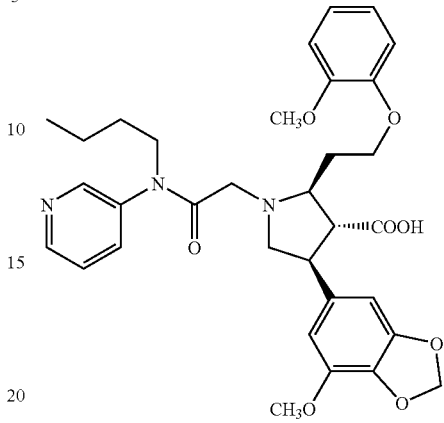
1674
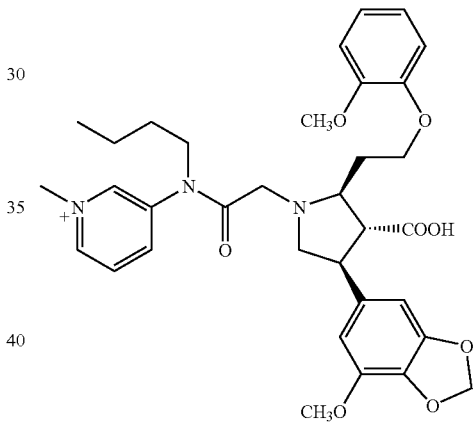
1675
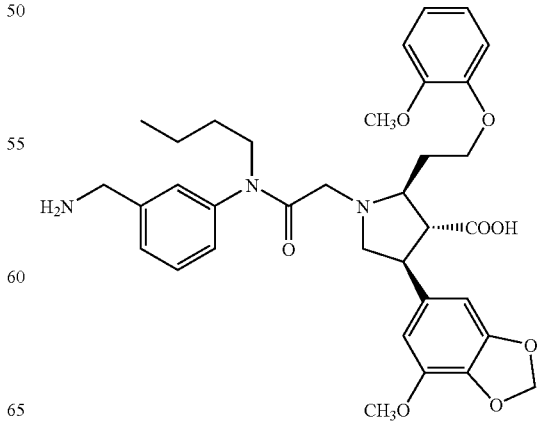

TABLE 3C-continued
1676
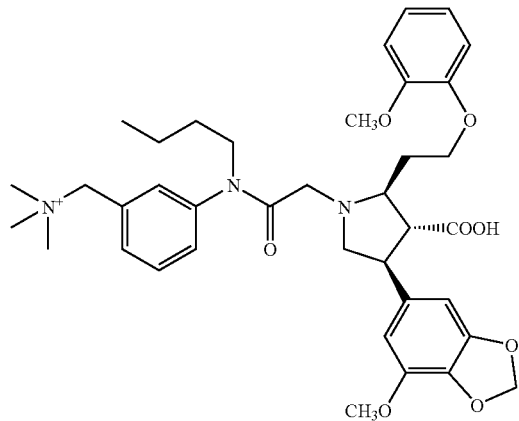
1677
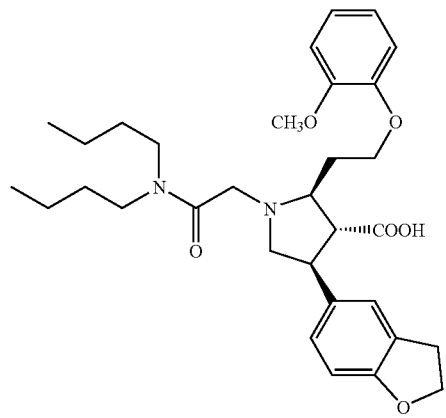
1678
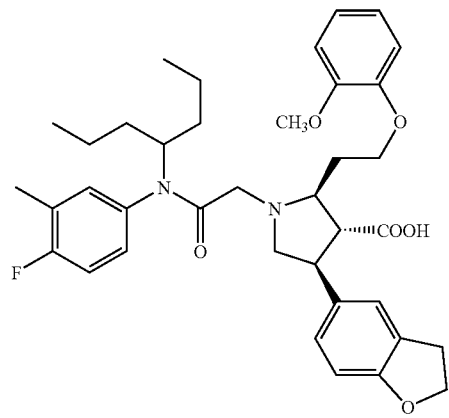
TABLE 3C-continued
1679
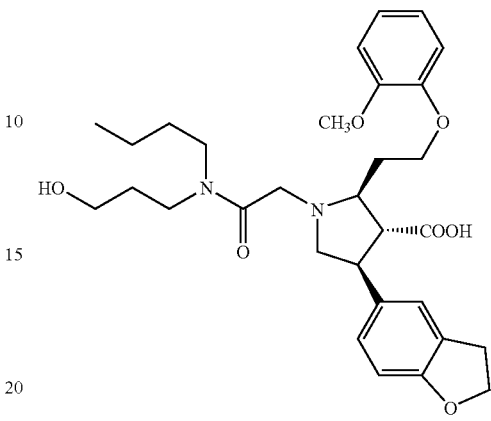
1680
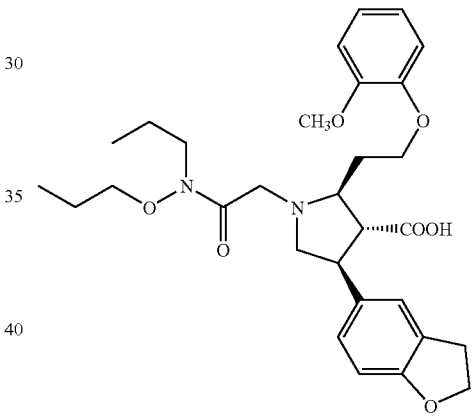
1681
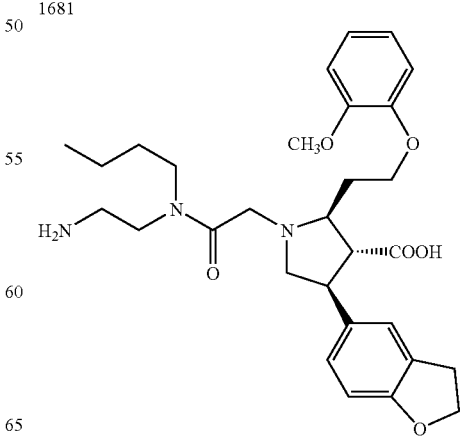

TABLE 3C-continued
1682
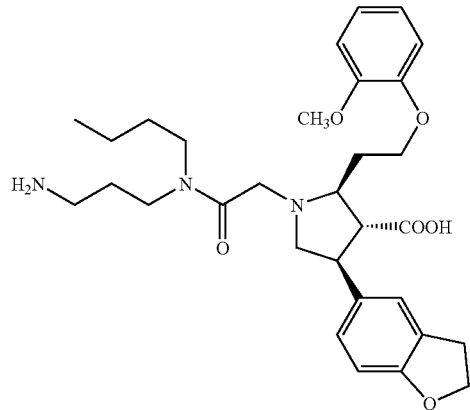
1683
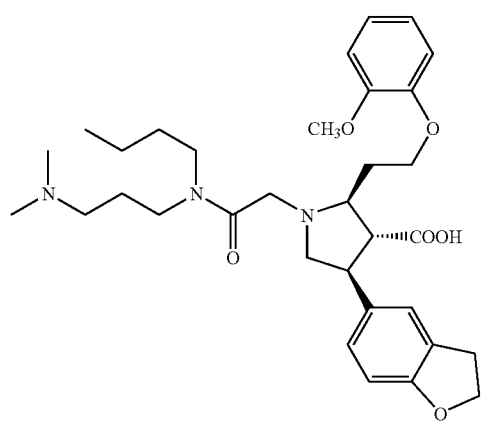
1684
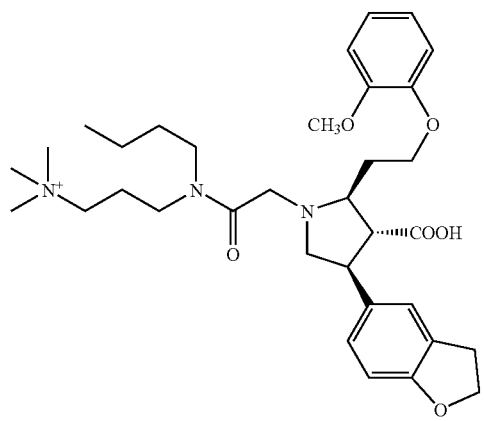
TABLE 3C-continued
1685
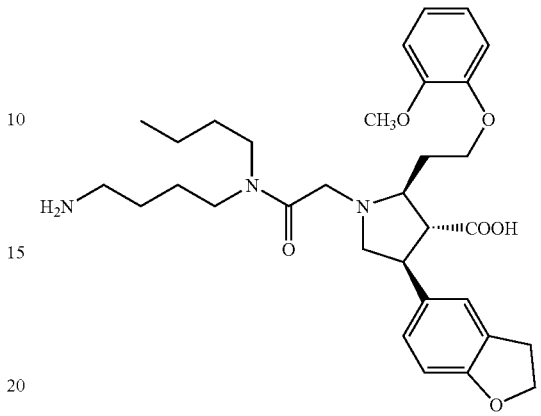
1686
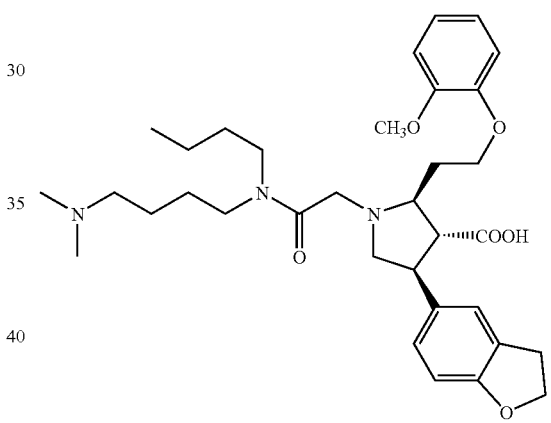
1687
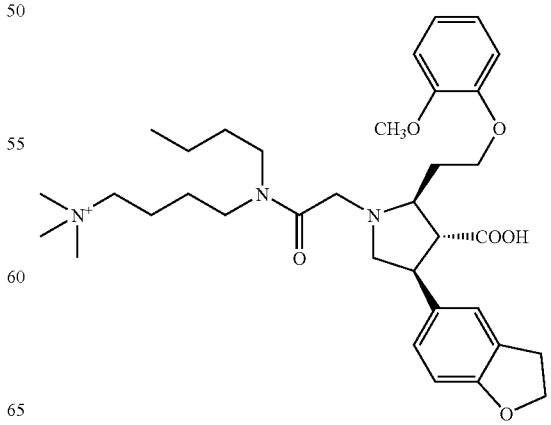

TABLE 3C-continued
1688
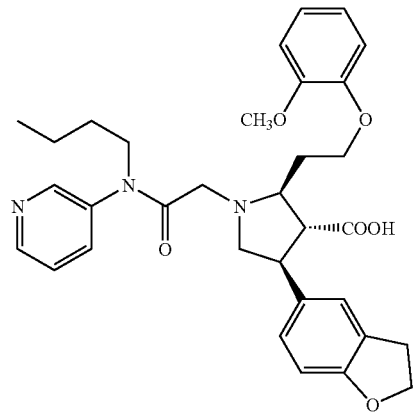
1689
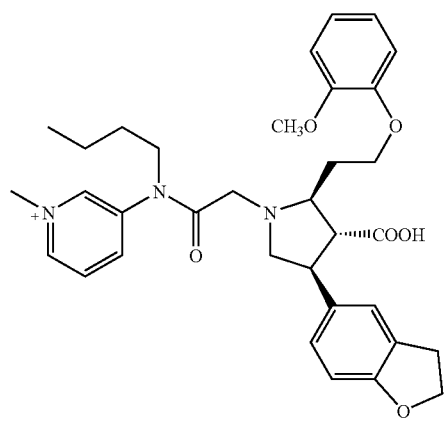
1690
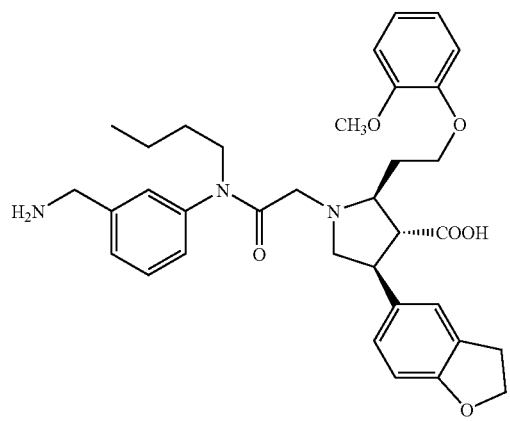
TABLE 3C-continued
1691
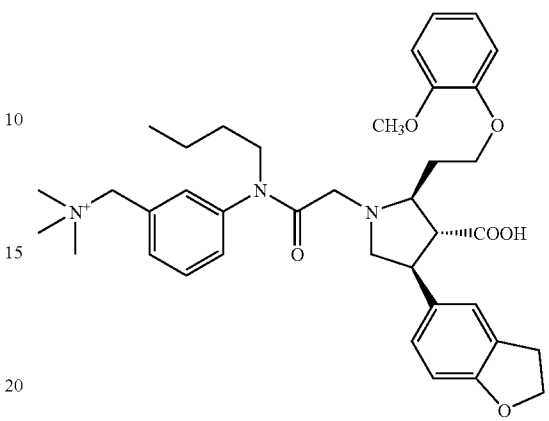
1692
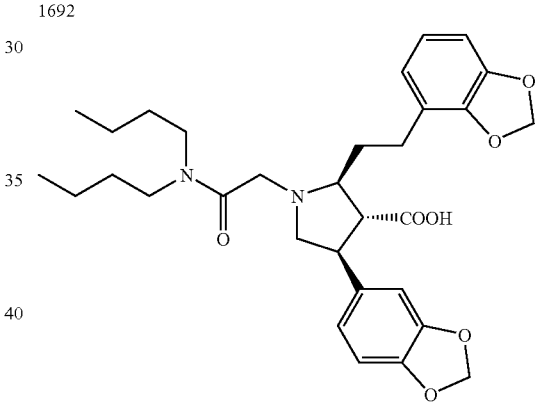
1693
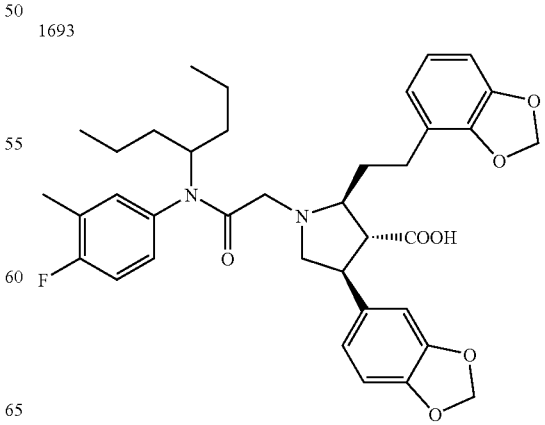

TABLE 3C-continued
1694
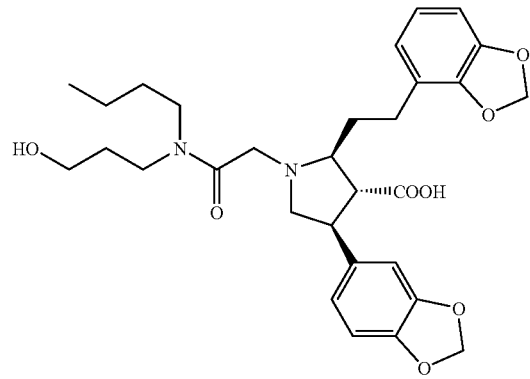
1695
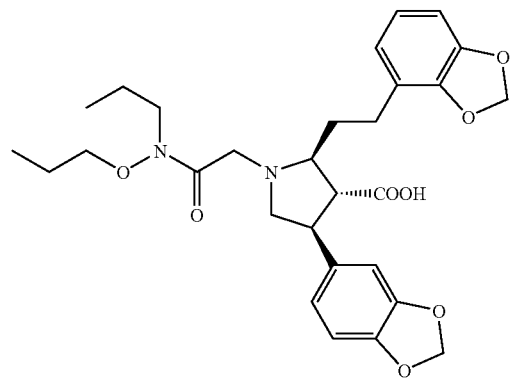
1696
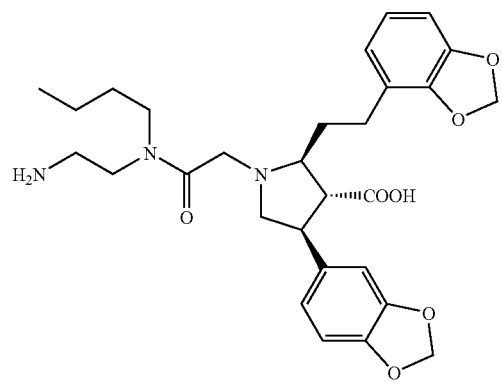
1697
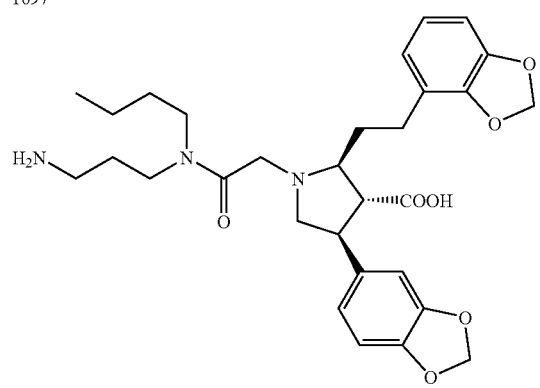
TABLE 3C-continued
1698
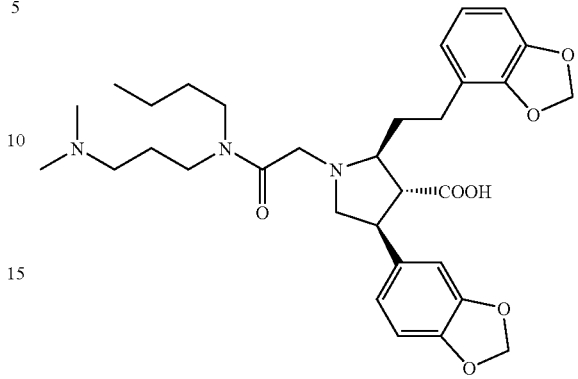
1699
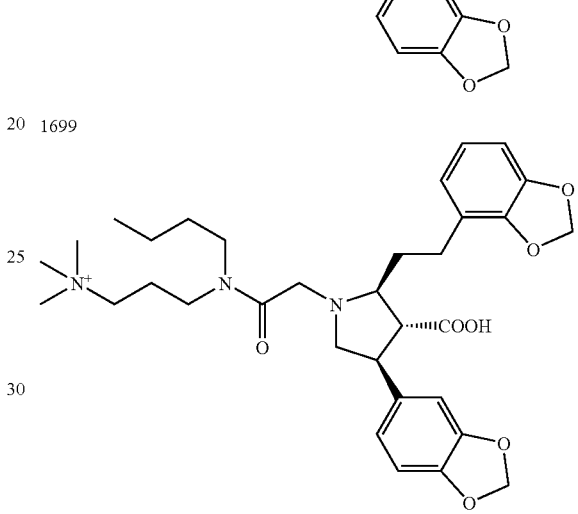
1700
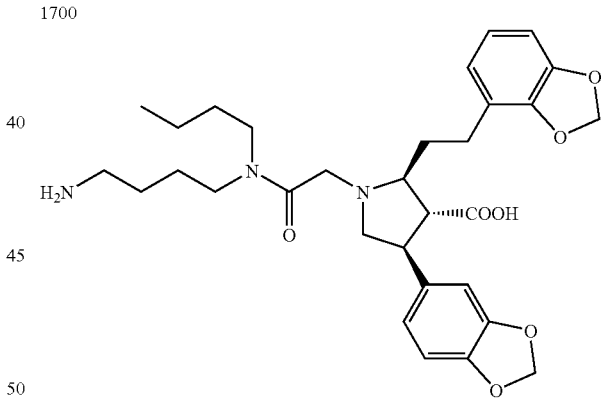
1701
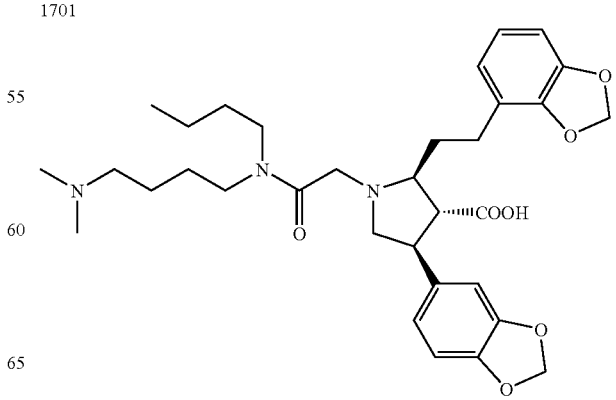

TABLE 3C-continued
1702
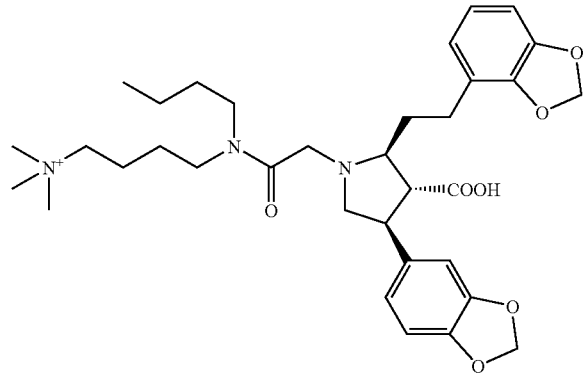
1703
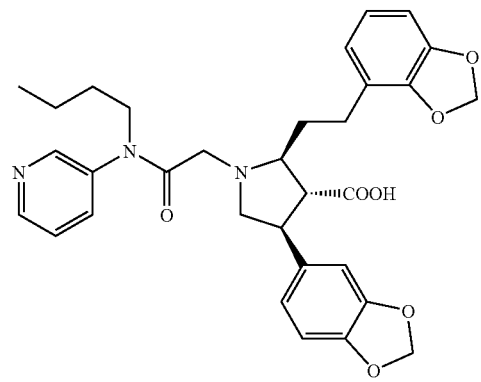
1704
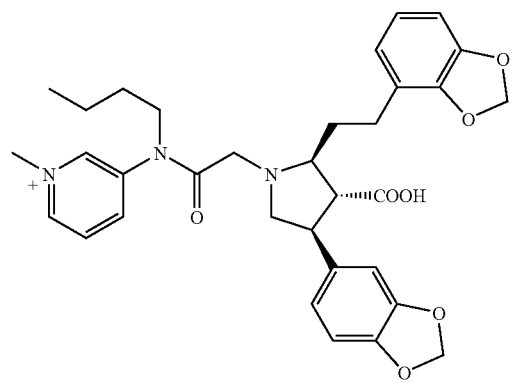
1705
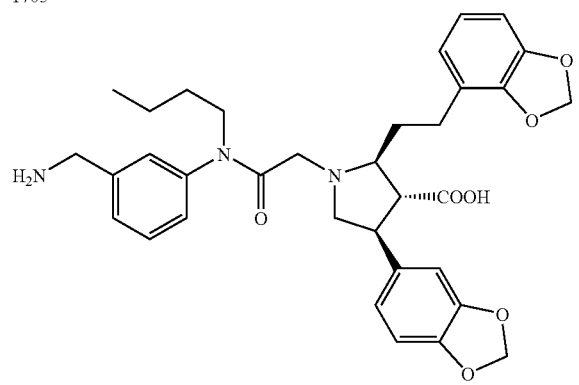
TABLE 3C-continued
1706
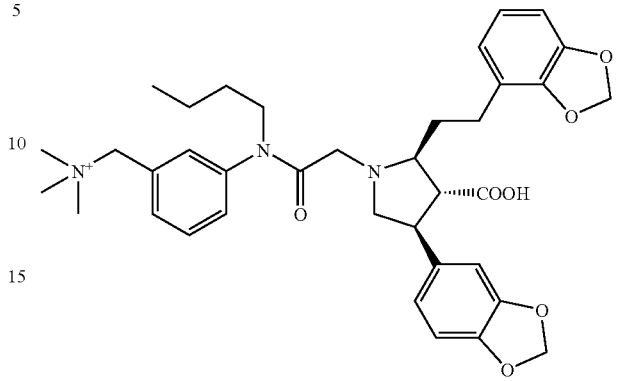
1707
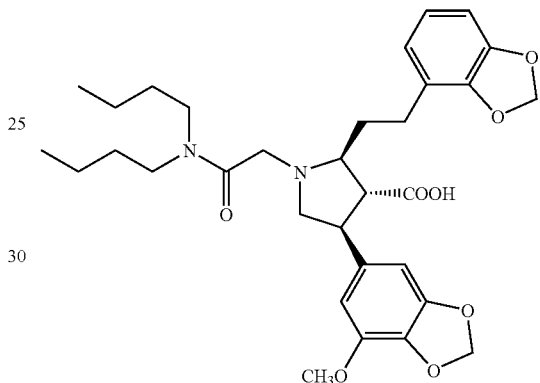
1708
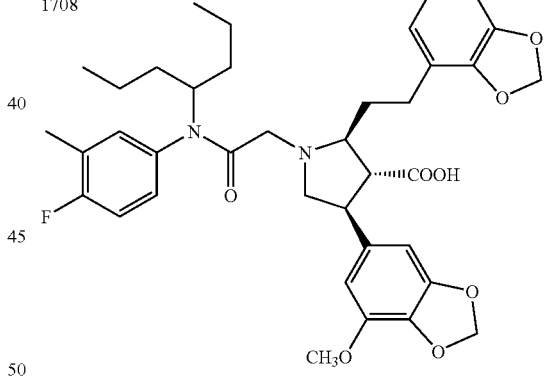
1709
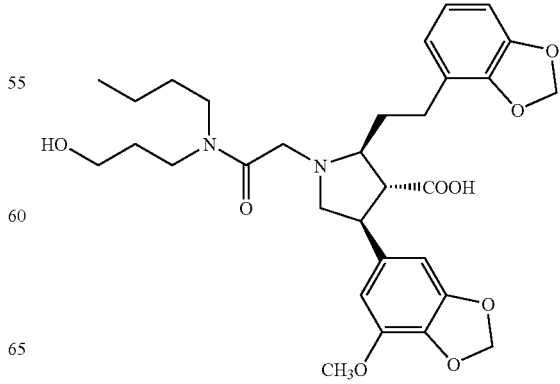

TABLE 3C-continued
1710
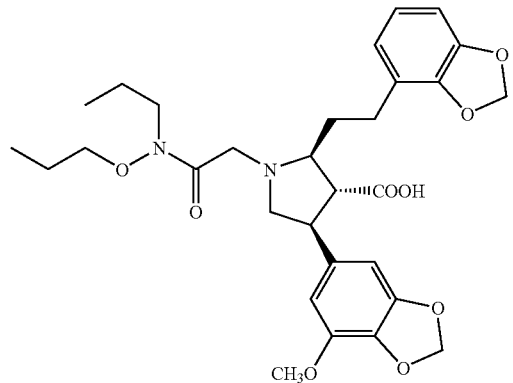
1711
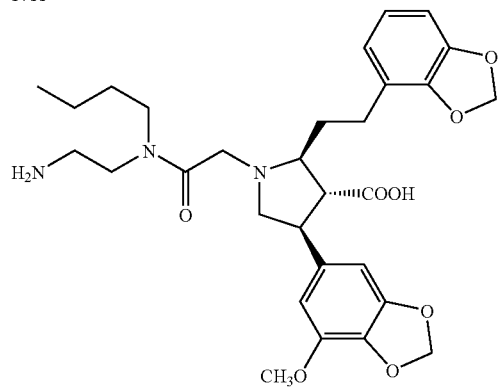
1712
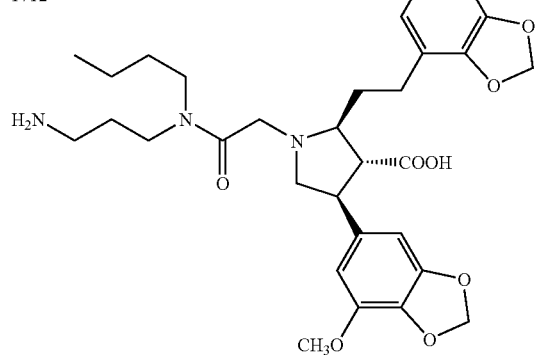
1713
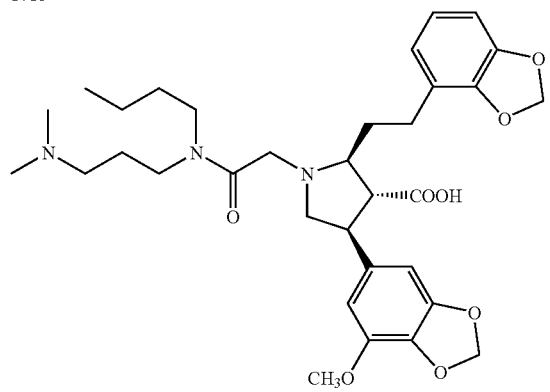
1714
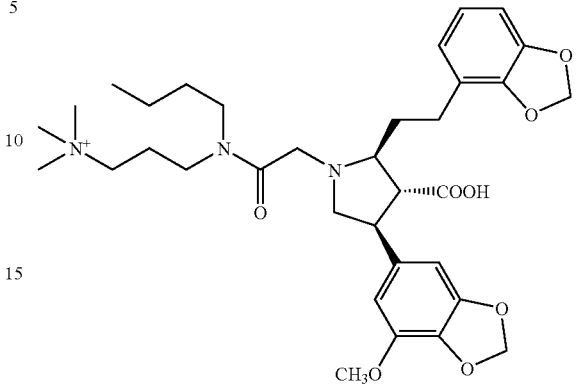
1715
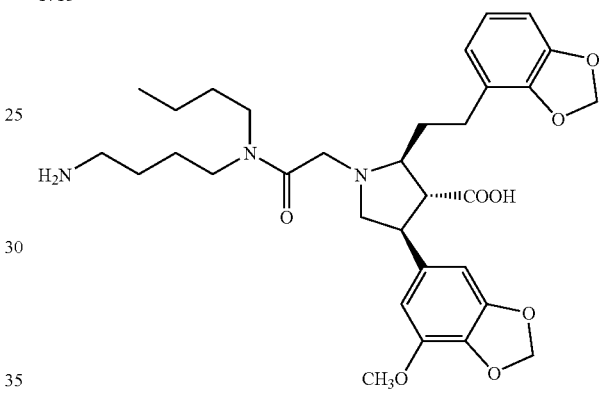
1716
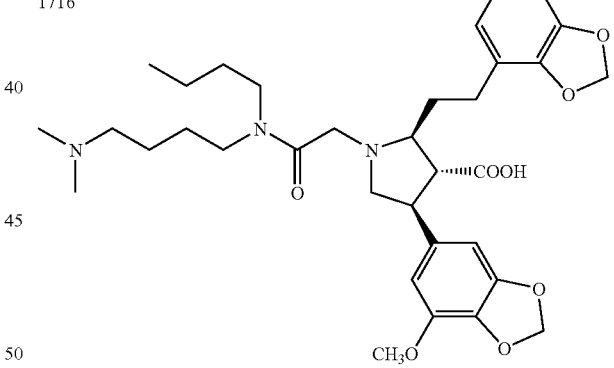
1717
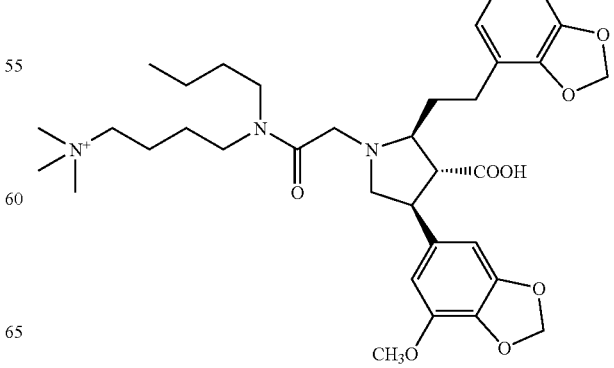

TABLE 3C-continued
1718
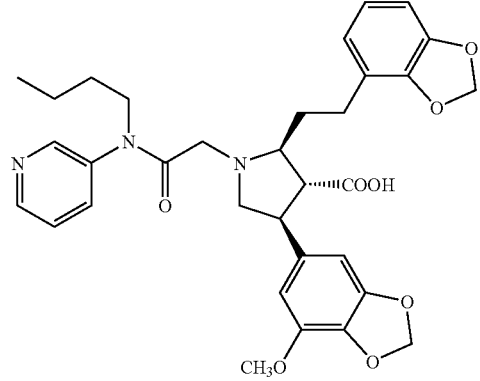
1719
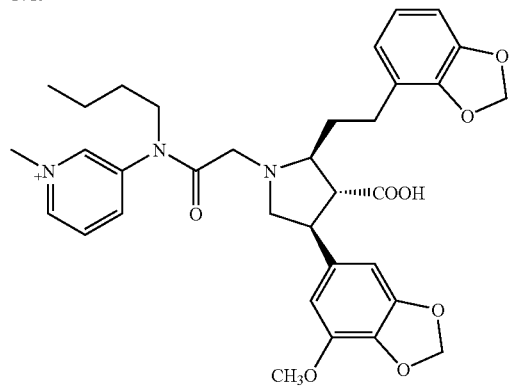
1720
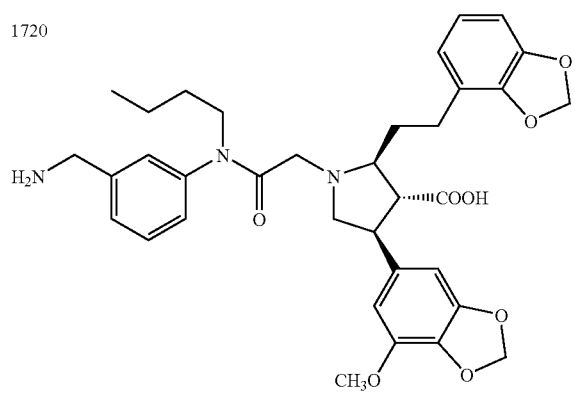
1721
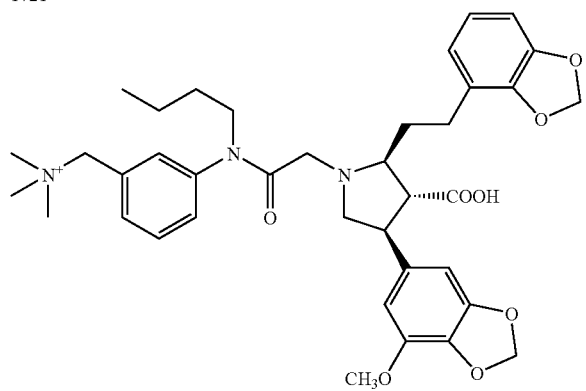
TABLE 3C-continued
1722
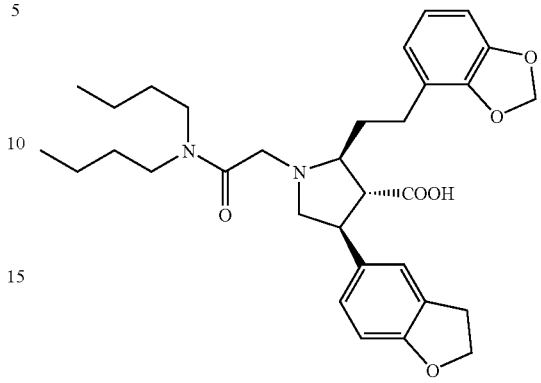
1723
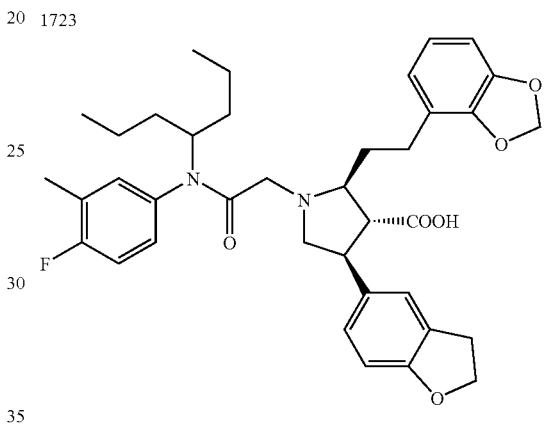
1724
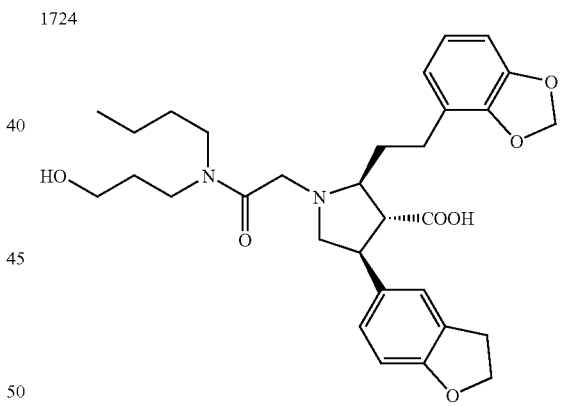
1725
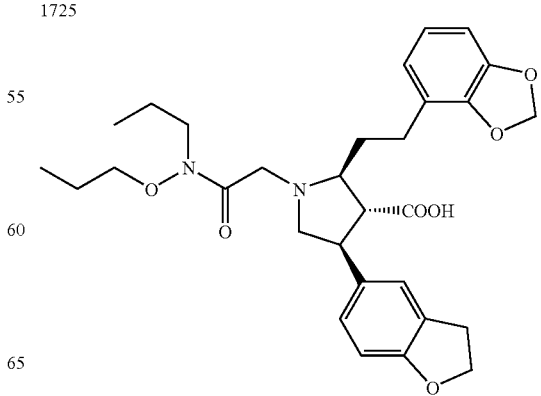

1115
TABLE 3C-continued
1726
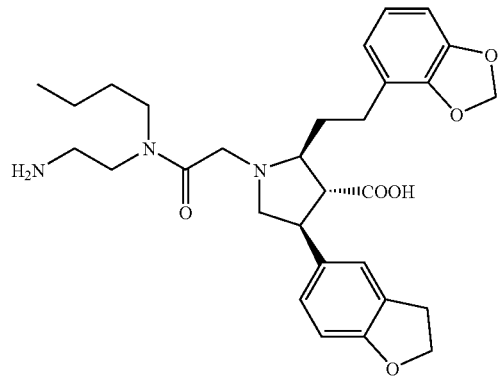
1727
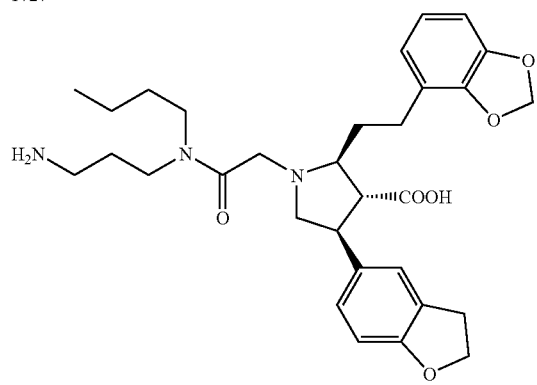
1728
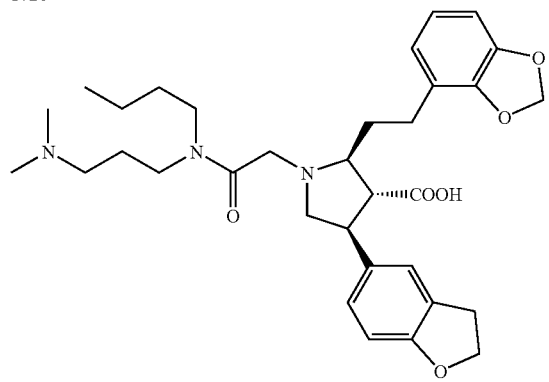
1729
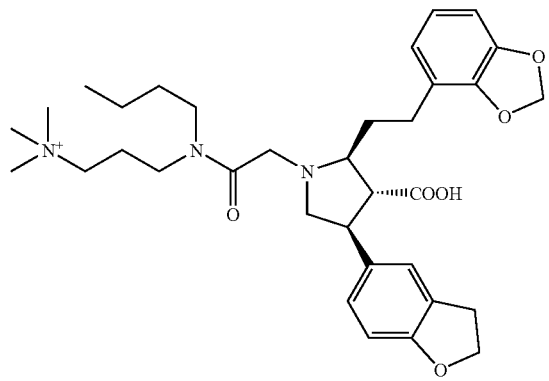
1116
TABLE 3C-continued
1730
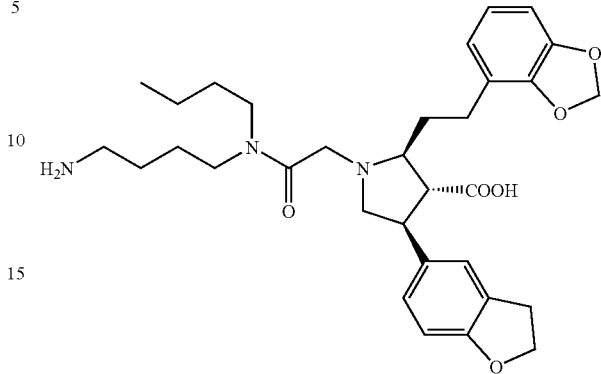
1731
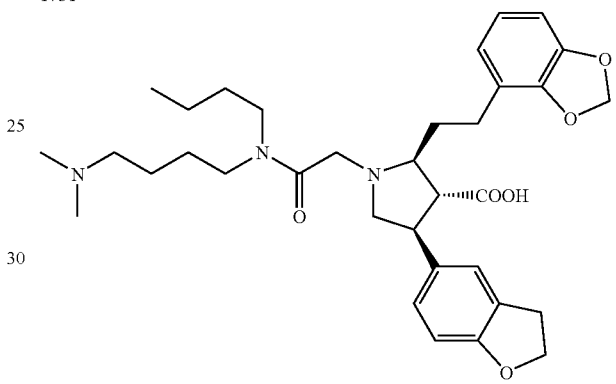
1732
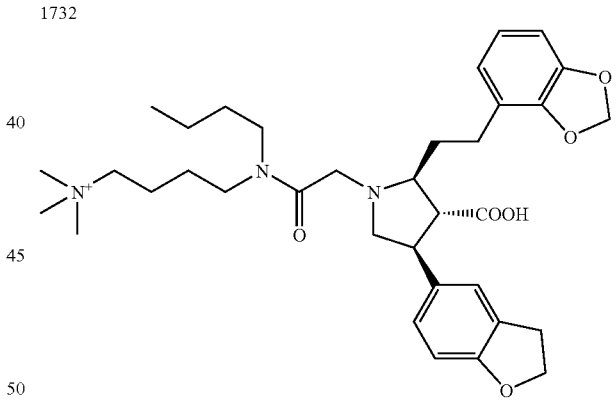
1733
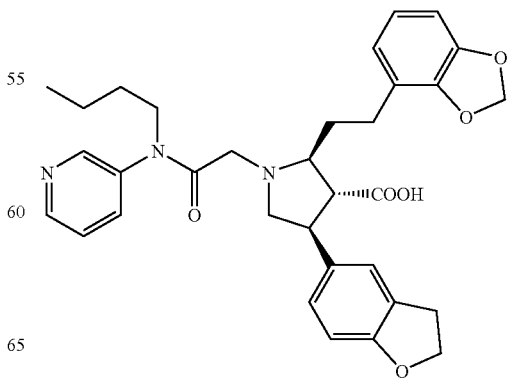

1117
TABLE 3C-continued
1734
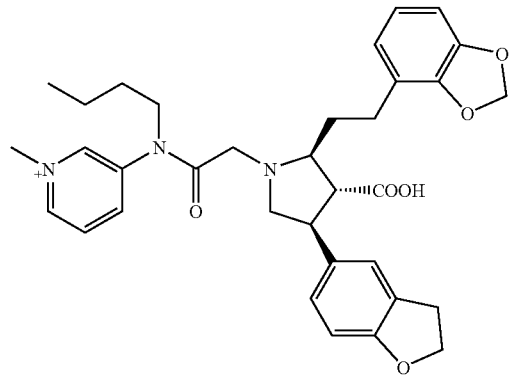
1735
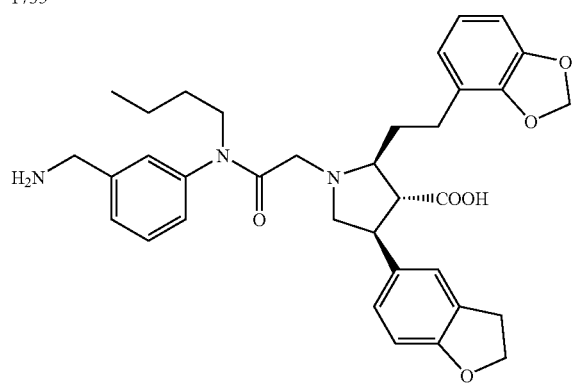
1736
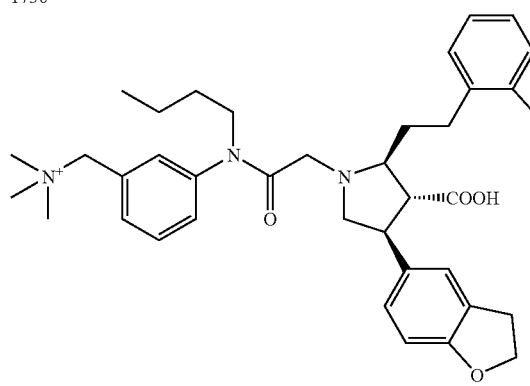
1737
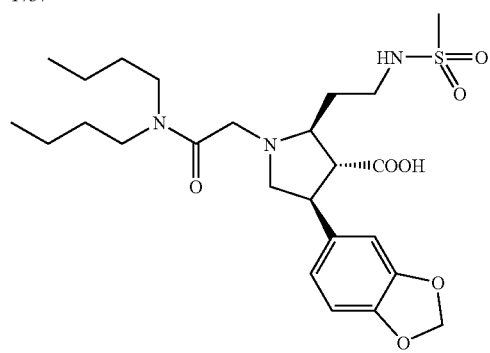
1118
TABLE 3C-continued
1738
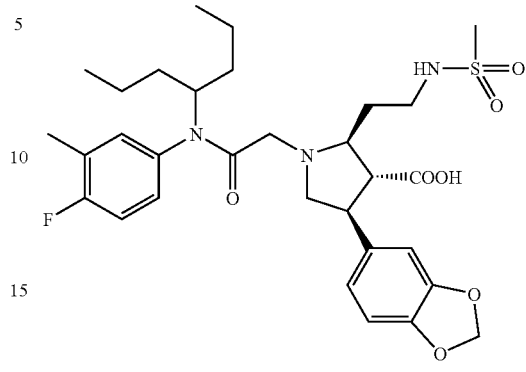
1739
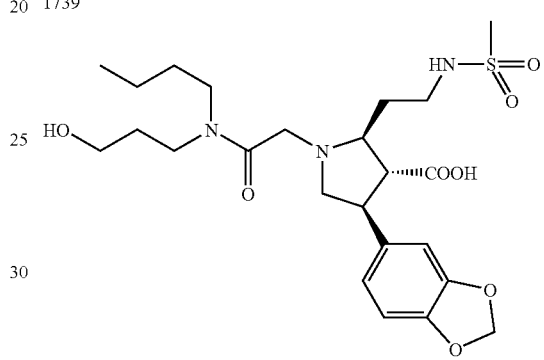
1740
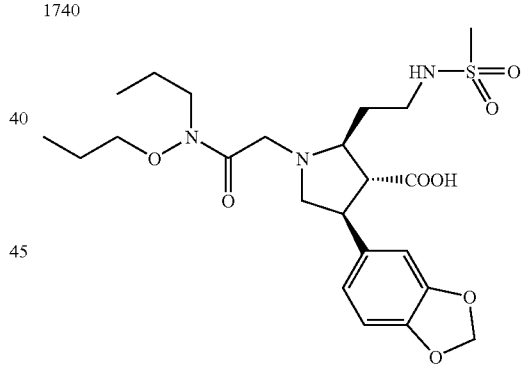
1741
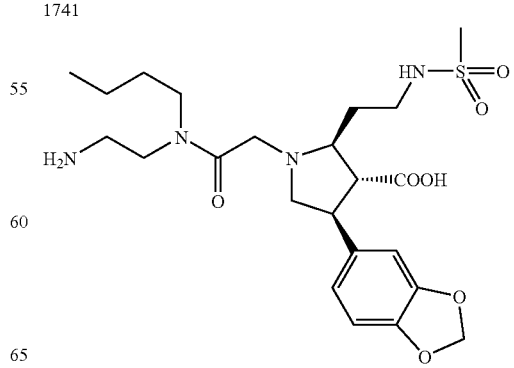

1119
TABLE 3C-continued
1742
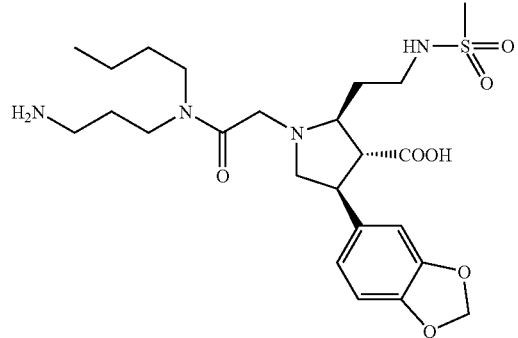
1743
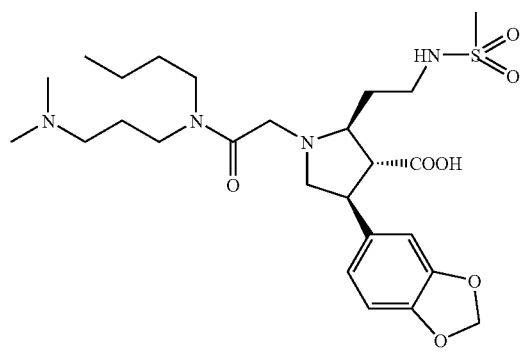
1744
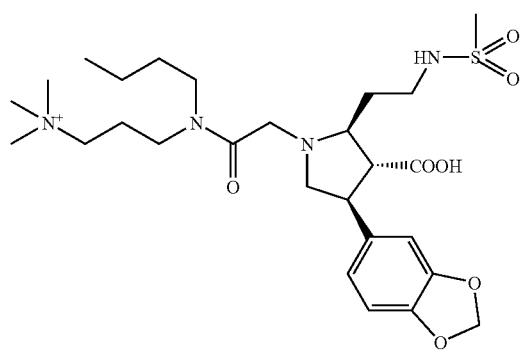
1745
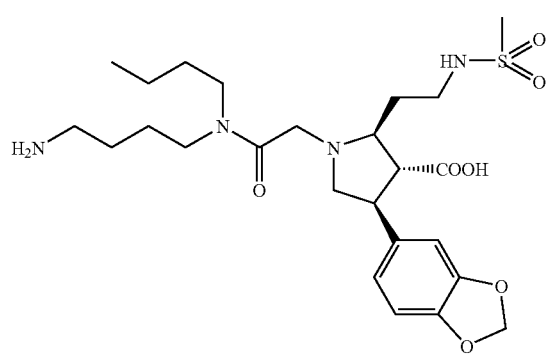
1120
TABLE 3C-continued
1746
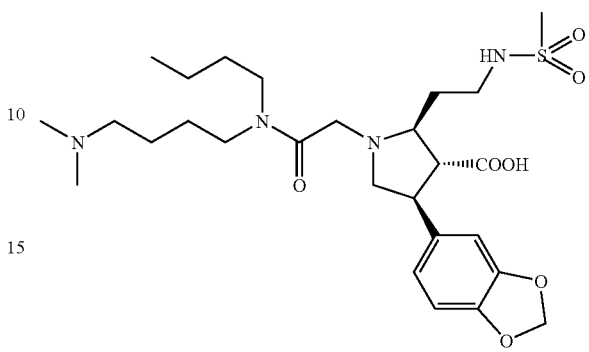
1747
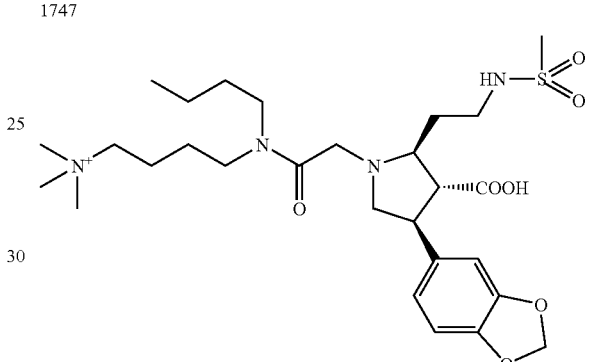
1748
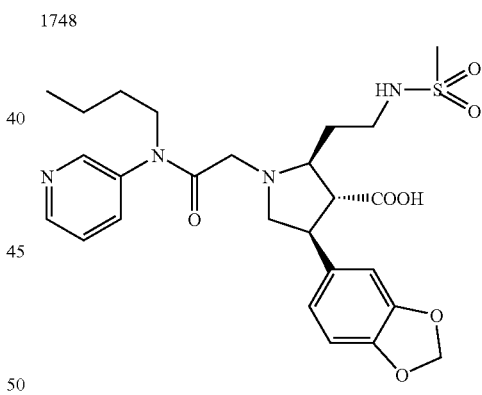
1749
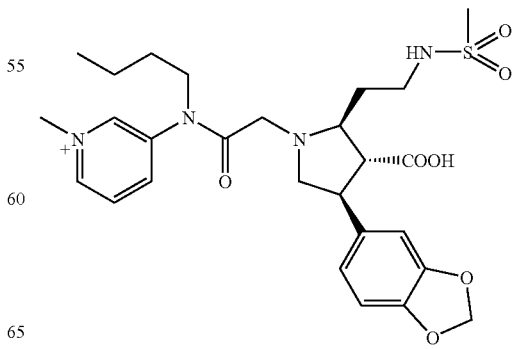

TABLE 3C-continued
1750
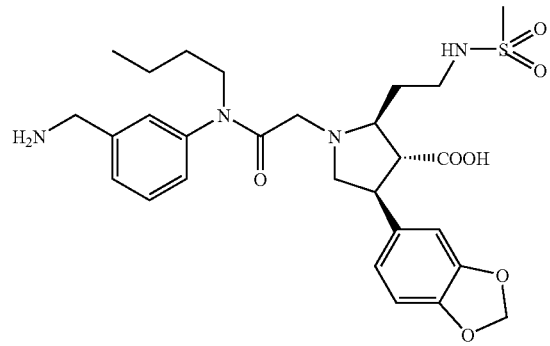
1751
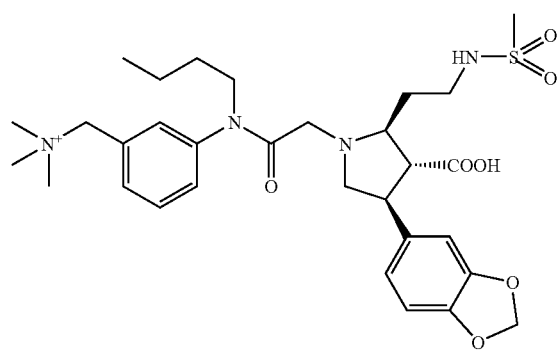
1752
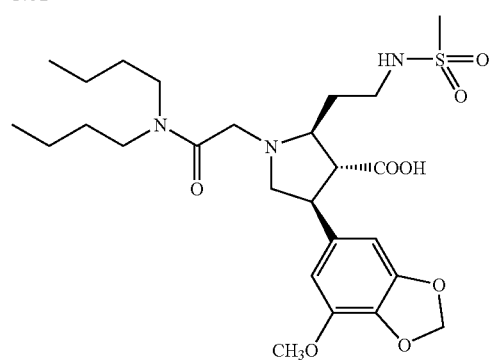
1753
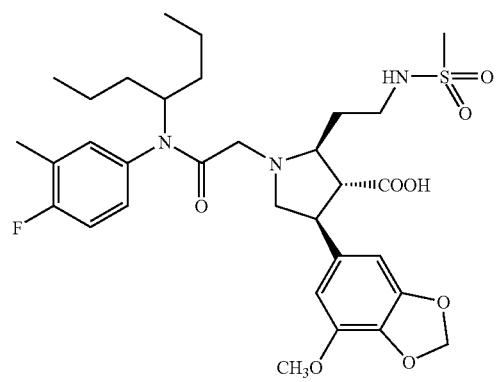
TABLE 3C-continued
1754
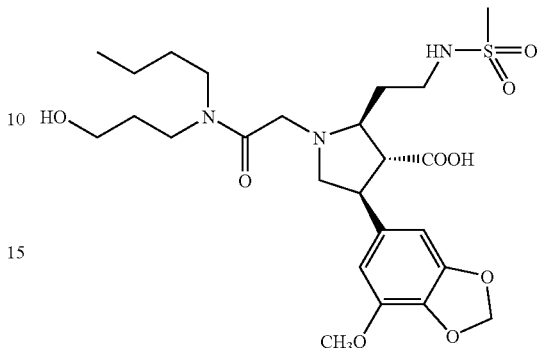
1755
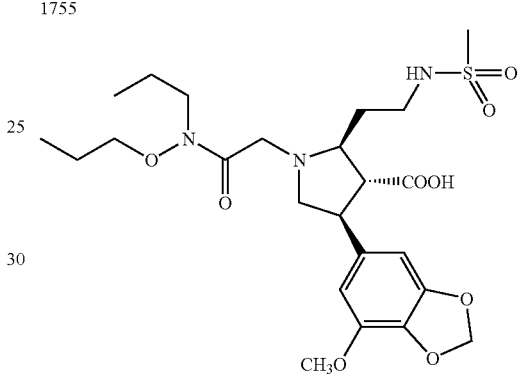
1756
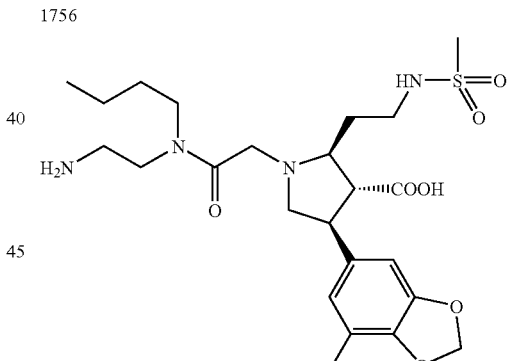
1757
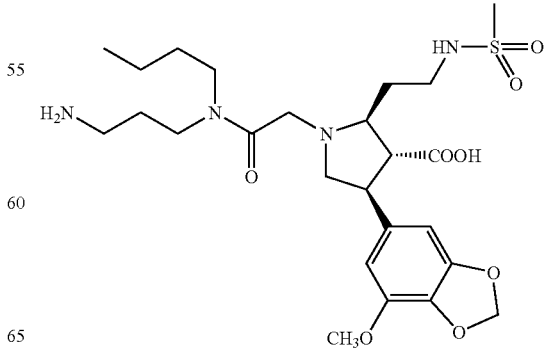

TABLE 3C-continued
1758
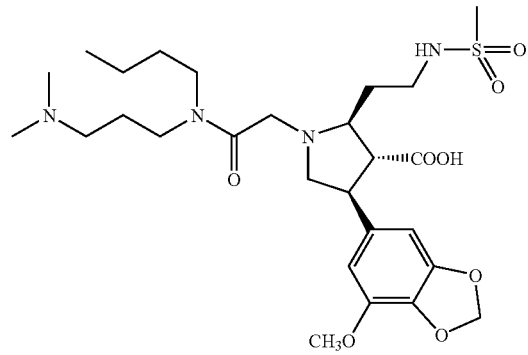
1759
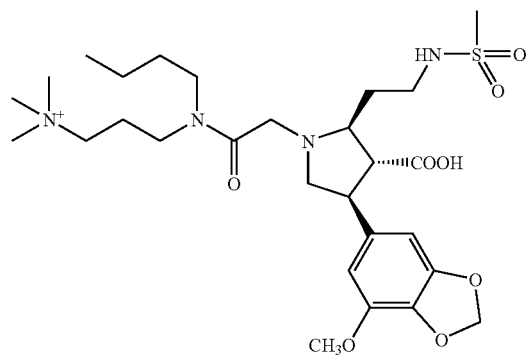
1760
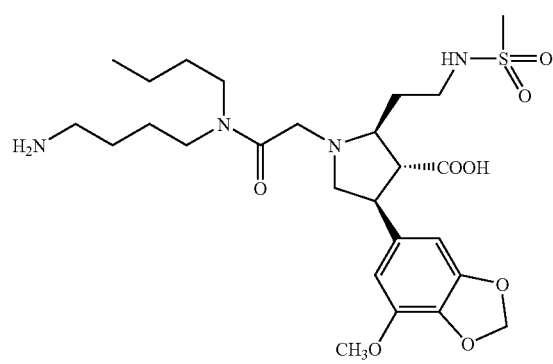
1761
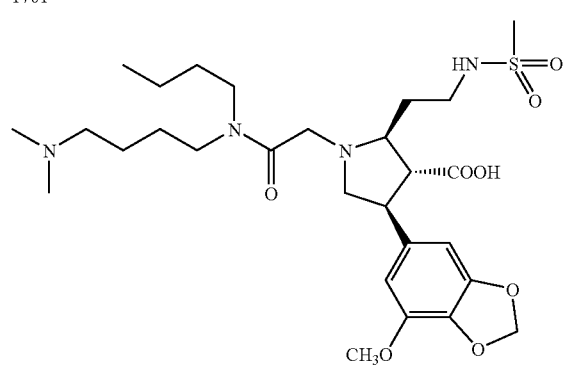
TABLE 3C-continued
1762
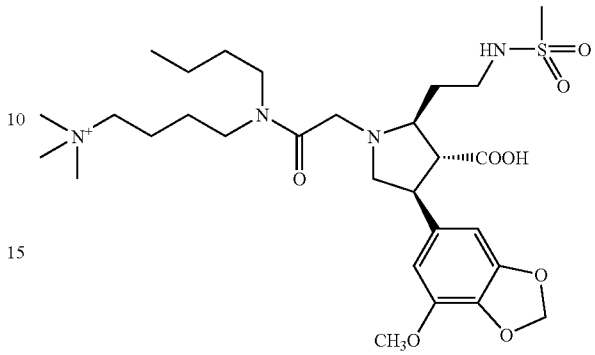
1763
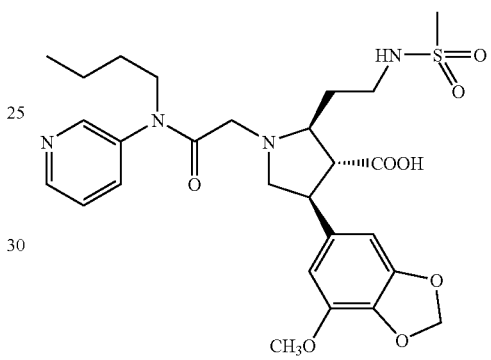
1764
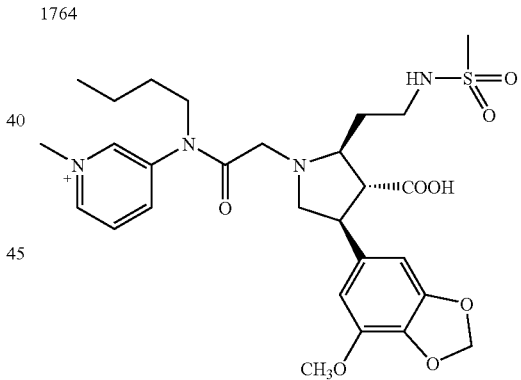
1765
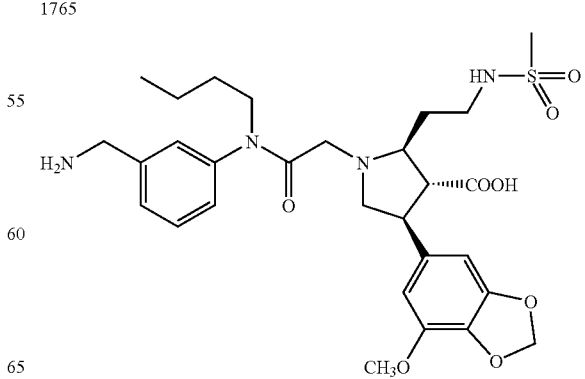

TABLE 3C-continued
1766
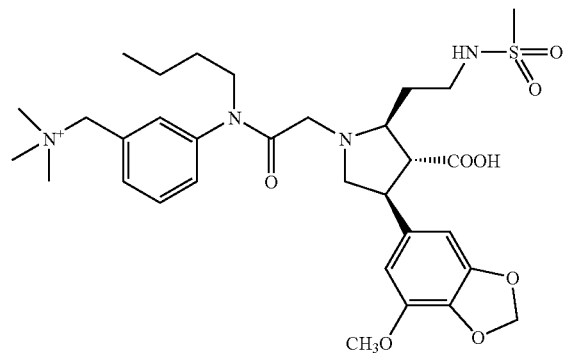
1767
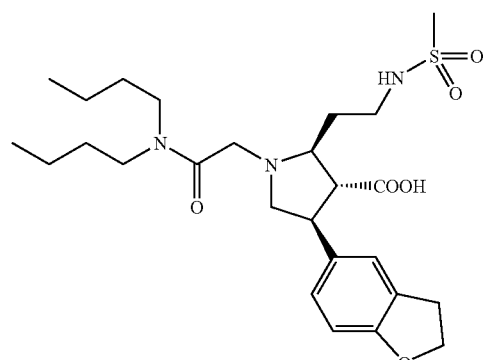
1768
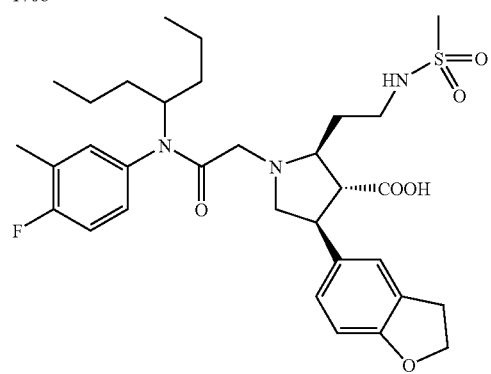
1769
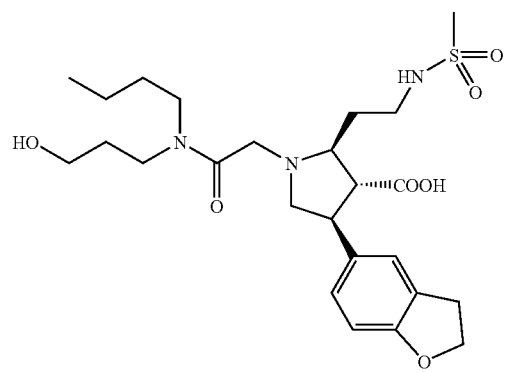
TABLE 3C-continued
1770
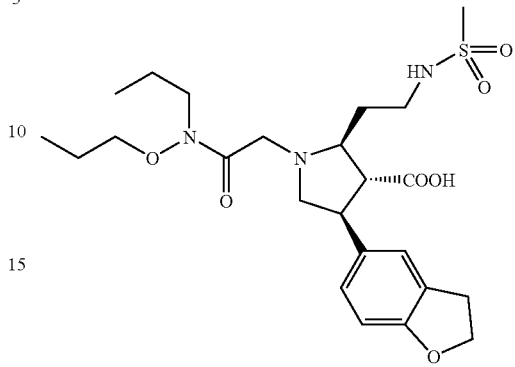
1771
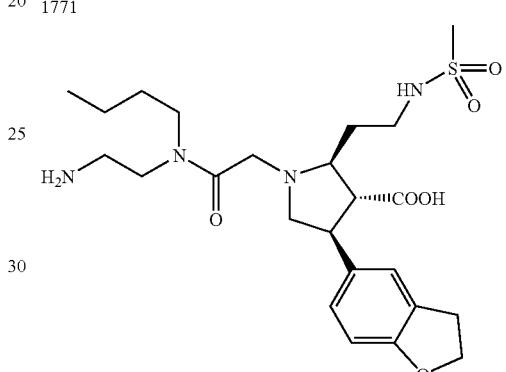
1772
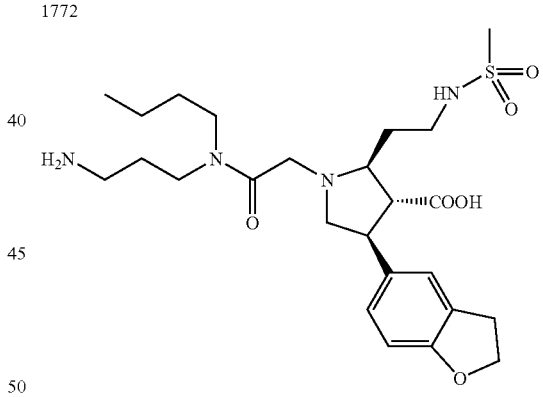
1773
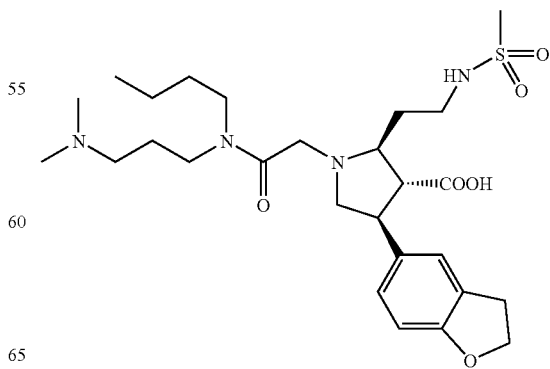

TABLE 3C-continued
1774
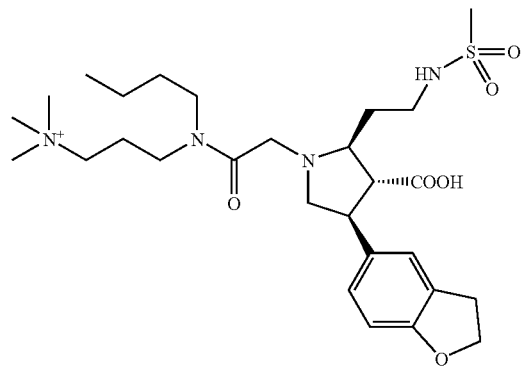
1775
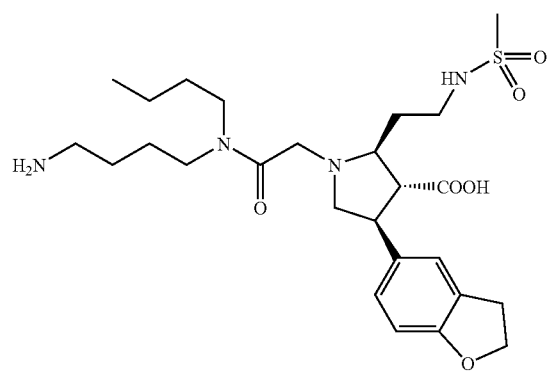
1776
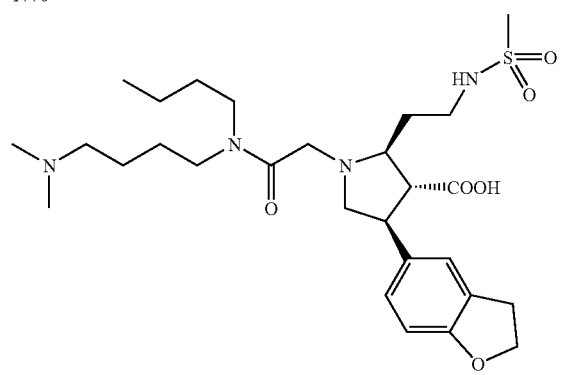
1777
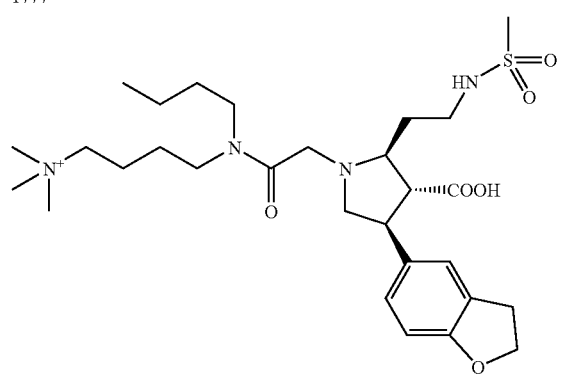
TABLE 3C-continued
1778
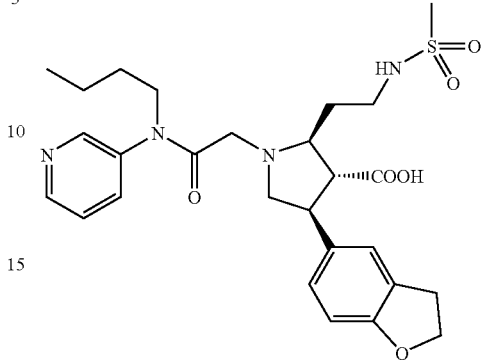
1779
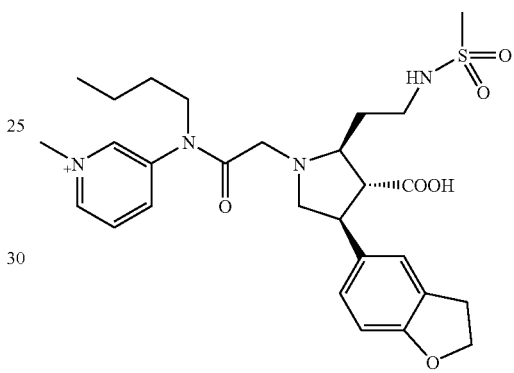
1780
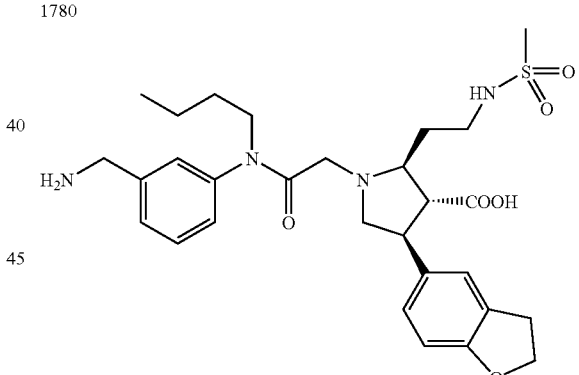
1781
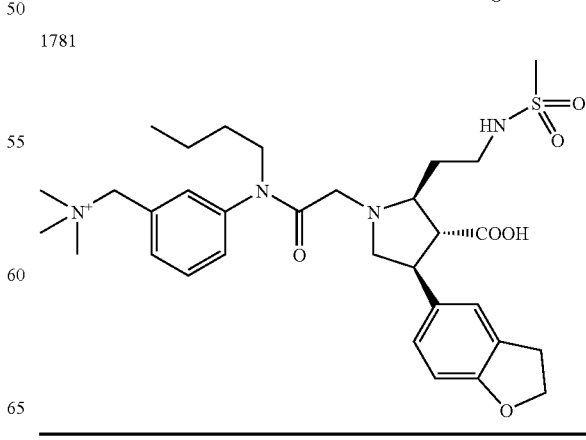

EXAMPLE 536

(2S,3R,4S)-2-(2,2-Dimethylpentyl)-4-(7-methoxy-1,3-benzodioxol-5-yl)-1-(N,N-di(n-butyl)aminocarbonylmethyl)-pyrrolidine-3-carboxylic acid

EXAMPLE 536A

Ethyl 5,5-dimethyl-3-oxooctanoate

Ethyl 3,3-dimethylhexanoate was prepared using the general procedure of Cahiez et al., Tetrahedron Lett., 31, 7425 (1990). To a solution of 63.8 g (370 mmol) of this compound in 400 mL of ethanol, cooled to 0° C., was added a solution of 30 g of NaOH in 150 mL of water. The resultant solution was warmed to ambient temperature and stirred overnight. Solvents were removed in vacuo; the residue was taken up in 700 mL of water, and extracted twice with 1:1 ether/hexanes. The aqueous layer was acidified to pH3 with 1N HCl and extracted twice with hexanes. The combined hexane extracts were washed with brine, dried over sodium sulfate, filtered and concentrated. A 20.2 g (150 mmol) sample of the crude product is dissolved in 150 mL of THF; 27.3 g of 1,1'-carbonyldiimidazole is added portionwise, to control gas evolution. In meantime, 33.4 g of potassium ethylmalonate and 13.4 g of magnesium chloride are combined in 350 mL of THF (overhead mechanical stirring) and warmed to 50° C. for 3 hrs. This mixture is cooled to ambient temperature, and the above acid imidazolide solution is added. The resultant slurry is stirred overnight. Ether (600 mL), hexanes (600 mL) and aqueous 1N phosphoric acid (500 mL) are added, and the mixture is sitrred for 30 min. The aqueous layer is separated; the organics are washed sequentially with bicarb (2×), water and brine. The organics are dried over sodium sulfate, filtered and concentrated to give 30.2 g (95% yield) of a colorless liquid.

EXAMPLE 536B

4-Methoxy-6-(2-nitrovinyl)-1,3-benzodioxole

3-Methoxypiperonal (50.0 g) is combined with 71.9 mL of nitromethane in 250 mL of acetic acid; 36 g of ammonium acetate is added, and the mixture is heated to 50° C. for 4 hrs. Solvents are removed in vacuo; the residue is taken up in water and stirred for 20 min. The solution is filtered; the filtrate is washed with water, then ether, to give 51.8 g of a yellow solid.

EXAMPLE 536C

Ethyl trans,trans-2-(2,2-Dimethylpentyl)-4-(7-methoxy-1,3-benzodioxol-5-yl)-pyrrolidine-3-carboxylate The compound of Example 536A (6.42 g, 30 mmol) was combined with 5.79 g of the compound of Example 536B in 40 mL of THF. DBU (0.5 mL) was added, and the mixture was stirred at ambient temperature for 6 hrs, during which time it turns reddish brown, and homogeneous. The solvents were removed in vacuo; the residue was taken up in EtOAc and washed sequentially with aqueous 1N phosphoric acid and brine. The organic phase was dried over sodium sulfate, filtered and concentrated. The residue was dissolved in 50 mL of THF; 12 g of Raney Nickel catalyst (washed sequentially with water and ethanol) was added, followed by 10 mL of acetic acid. The resultant mixture was hydrogenated under 4 atmospheres of hydrogen until hydrogen uptake ceased (~3 hrs). The catalyst was removed by filtration: solvents were removed in vacuo. The residue was dissolved in 90 mL of 2:1 ethanol/THF; 30 mg of bromcresol green indicator was added, followed by 30 mL of 1N sodium cyanoborohydride in THF. Concentrated HCl was added dropwise to maintain pH at the indicator point, over 1 hr. The resultant solution was stirred overnight at ambient temperature. Bicarb was added, and the solvents were removed in vacuo: the residue was partitioned between water and EtOAc. The organic material was washed with water (2×) and brine. The organic phase was dried over sodium sulfate, filtered and concentrated. The crude product was dissolved in 100 mL of acetonitrile; 10 mL of Hünig's base was added, and the solution was warmed to 40° C. overnight. Removal of solvents in vacuo provided 5.0 g of a yellowish oil.

EXAMPLE 536D

Ethyl (2S,3R,4S)-2-(2,2-Dimethylpentyl)-4-(7-methoxy-1,3-benzodioxol-5-yl)-pyrrolidine-3-carboxylate The crude compound of Example 536C (2.0 g) was combined with 4 mL of triethylamine in 40 mL of THF; 2.0 g of di-tert-butyldicarbonate was added, and the mixture was stirred at ambient temperature for 5 hrs. Solvents were removed in vacuo, and the residue was taken up in 60 mL of ethanol. Aqueous sodium hydroxide (10 mL of 2.5 N solution) was added, and the resultant solution was stirred overnight. Solvents were removed in vacuo; the residue was taken up in water and extracted with ether. The aqueous phase was acidified with aqueous 1N phosphoric acid and extracted with EtOAc. The organic extracts were washed with brine, dried over sodium sulfate, filtered, and concentrated to give 1.0 g of a colorless oil. A sample of this material (0.734 g, 1.58 mmol) was combined with 0.35 g of pentafluorophenol and 0.364 g of EDAC in 5 mL of DMF. The resultant solution was stirred at ambient temperature for 1 hr, then was poured onto 50 mL of 0.6M sodium bicarbonate solution and extracted (3×15 mL) with ether. The combined ether extracts were washed with brine, dried over magnesium sulfate, filtered, and concentrated in vacuo to give a foam, which was dissolved in 5 mL of THF and cooled to 0° C. Simultaneously, 0.418 g (2.37 mmol) of R-4-benzyl-2-oxazolidinone was combined with ~0.1 mg of pyreneacetic acid in 5 mL of THF and cooled to 0° C. N-butyllithium (1.6M in hexanes) was added to a red endpoint (persists ~10 sec), and the solution was stirred for 10 min. The solution was transferred into the solution of the pentafluorophenyl ester, and the resultant solution was stirred at 0° C. for 40 min. Solvents were removed in vacuo; the residue was taken up in bicarb and extracted with ether (3×10 mL). The combined ether extracts were washed with brine, dried over magnesium sulfate, filtered, and concentrated in vacuo. The crude mixture of diasteromeric products was separated by flash chromatography on silica gel, eluting with a gradient from 4:1→3:1→2:1 hexanes/EtOAc, giving 423 mg of the faster-moving and 389 mg of the slower-moving diastereomer, respectively. The faster-moving diastereomer was dissolved in 2 mL of a 2.0M solution of sodium methoxide in methanol (freshly prepared, containing 5% methyl formate by volume) and stirred at ambient temperature for 16 hrs. Solvents were removed in vacuo, and the residue was partitioned between ether and aqueous 1N sodium hydroxide. The ether layer was washed with brine, dried over magnesium sulfate, filtered, and concentrated in vacuo. The residue was purified by flash chromatography on silica gel, eluting with 4:1 hexanes/EtOAc. The resultant material was dissolved in 5 mL of TFA and stirred at ambient temperature for 1 hr. Solvents were removed in vacuo; the residue was suspended in bicarb and extracted with EtOAc. The organic phase was washed with brine, dried over magnesium sulfate, filtered, and concentrated in vacuo to give 98 mg of product.

EXAMPLE 536E (2S,3R,4S)-2-(2,2-Dimethylpentyl)-4-(7-methoxy-1, 3-benzodioxol-5-yl)-1-(N,N-di(n-butyl)aminocarbonylmethyl)-pyrrolidine-3-carboxylic acid The compound of Example 536D (48 mg) was combined with 35 mg of the compound of Example 501A in 3 mL of acetonitrile; 0.5 mL of Hünig's base was added, and the solution was allowed to stir overnight at ambient temperature. Solvents were removed in vacuo: the residue was partitioned between EtOAc and aqueous 1N phosphoric acid. The organic layer was washed with bicarb and brine, then dried over sodium sulfate, filtered and concentrated. The residue was purified by flash chromatography on silica gel, eluting with 2:1 hexanes/EtOAc. The product was dissolved in 4 mL of ethanol; 1 mL of 2.5N aqueous sodium hydroxide was added, and the resultant solution was stirred overnight at ambient temperature. Solvents were removed in vacuo; the residue was taken up in water and extracted with ether. The aqueous phase was acidified to pH 3 with aqueous 1N phosphoric acid and extracted with EtOAc. The organic extracts were washed with brine, dried over sodium sulfate, filtered and concentrated to give a colorless oil. Lyophilization from acetonitrile/0.1% aqueous TFA gave 56 mg of a white solid.

$^1$H NMR (CDCl$_3$, 300 MHz) d 0.81 (s, 3H), 0.84 (s, 3H), 0.86 (t, J=6.9 Hz, 3H), 0.93 (t, J=6.9 Hz, 3H), 0.96 (t, J=6.9 Hz, 3H), 1.09–1.38 (m, 8H), 1.45–1.59 (m, 4H), 1.84–2.00 (m, 2H), 3.15 (dd, J=6.9 Hz, 10.0 Hz, 2H), 3.30–3.42 (m, 3H), 3.72 (t, J=10.5 Hz, 1H), 3.86 (t, J=10.5 Hz, 1H), 3.88 (s, 3H), 4.02 (q, J=10.0 Hz, 1H), 4.12 (d, J=16.8 Hz, 1H), 4.29 (d, J=16.8 Hz, 1H), 4.41 (brm, 1H), 5.94 (s, 1H), 6.52 (d, J=1.8 Hz, 1H), 6.67 (d, J=1.8 Hz, 1H). MS (ESI) (M+H)+at m/e 533. Anal calcd for C$_{30}$H$_{48}$N$_2$O$_6$.0.7 TFA: C, 61.57; H, 8.01; N, 4.57. Found: C, 61.59; H, 8.20; N, 4.63.

EXAMPLE 537

(2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid

EXAMPLE 537A

Ethyl trans,trans-2-(2,2-Dimethylpentyl)-4-(1,3-benzodioxol-5-yl)-pyrrolidine-3-carboxylate Prepared according to the procedures of Example 536C above, substituting the compound of Example 501B (5-(2-nitrovinyl)-1,3-benxodioxole) for 4-methoxy-6-(2-nitrovinyl)-1,3-benzodioxole.

EXAMPLE 537B

Ethyl (2S,3R,4S)-2-(2,2-Dimethylpentyl)-4-(1,3-benzodioxol-5-yl)-pyrrolidine-3-carboxylate The compound of Example 537A (6.8 g) was dissolved in 100 mL of ether; a solution of 1.6 g of (S)-(+)-mandelic acid in 60 mL of ether was added, the total volume was made up to ~200 mL, and the solution was seeded. The mixture was stirred slowly overnight. The resultant crystals were collected by filtration and recrystallized from ether/EtOAc to give 1.8 g of a white solid. Thsi material was partitioned between bicarb and ether; the ether layer was washed with brine, dried over sodium sulfate, filtered, and concentrated in vacuo to give the enantiomerically pure product (>98% e.e.).

EXAMPLE 537C (2S,3R,4S)-2-(2,2-Dimethylpentyl)-4-(1,3-benzodioxol-5-yl)-1-(N,N-di(n-butyl)aminocarbonylmethyl)-pyrrolidine-3-carboxylic acid Prepared from the compound of Example 537B according to the procedures of Example 536E. $^1$H NMR (CDCl$_3$, 300 MHz) d 0.80–0.99 (m, 15H), 1.10–1.37 (m, 8H), 1.43–1.58 (m, 4H), 1.77–1.97 (m, 2H), 3.48–3.12 (m, 5H), 3.60–3.69 (m, 1H), 3.75–3.86 (m, 1H), 3.95–4.16 (m, 2H), 4.28–4.4 (m, 2H), 5.94 (s, 2H), 6.74 (d, J=7.8 Hz, 1H), 6.8 (dd, J=8.1, 1.5 Hz, 1H), 6.87 (d, J=1.8 Hz, 1H). MS (APCI+) m/e 503 (M+H)+.

EXAMPLE 538

(2S,3R,4S)-2-(2,2-Dimethylpentyl)-4-(1,3-benzodioxol-5-yl)-1-((N-propoxy, N-(n-butyl))aminocarbonylmethyl)-pyrrolidine-3-carboxylic acid

EXAMPLE 538A

N-Boc-N-butyl-O-allylhydroxylamine

O-Allylhydroxylamine hydrochloride hydrate (5.0 g) was dissolved in THF (15 mL). The solution was cooled to 0° C. in an ice bath. Diisopropylethylamine (8 mL) and di-t-butyldicarbonate (10.0 g) were added. The mixture was stirred at 0° C. for one hour at which point the bath was removed and the reaction allowed to warm to room temperature and stirred overnight. The THF was removed in vacuo and the residue taken up in EtOAc (25 mL), and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil (6.5 g). This crude product was dissolved in dry THF (25 mL) and the solution cooled to 0° C. in an ice bath. Sodium hydride (1.5 g, 60% dispersion in oil) was added portionwise over five minutes. The resulting mixture was stirred for 30 minutes at 0° C. 1-Iodobutane (4.1 mL) was added dropwise to the mixture. The reaction was stirred at 0° C. for one hour, then stirred overnight at room temperature. The THF was removed in vacuo and the residue taken up in EtOAc (50 mL) and washed with water (1×50 mL), saturated sodium bicarbonate solution (3×50 mL), 1N phosphoric acid (3×50 mL), and brine (1×50 mL). The organic layer was dried with sodium sulfate and evaporated to give a light yellow oil, which was purified by flash chromatography on silica gel eluting with 5% EtOAc/hexanes to give the title compound as a colorless oil (6.0 g).

EXAMPLE 538B

N-butyl-N-propoxyamine trifluoroacetate

The compound of Example 538A (6.0 g) was dissolved in EtOAc (100 mL). 10% Palladium-on-carbon (0.5 g) was added, and the mixture was purged with nitrogen. The nitrogen line was exchanged for a balloon of hydrogen, and the mixture was stirred at room temperature for 6 hours. The catalyst was removed by filtration through a pad of Celite and the solvents were removed in vacuo to give a yellow oil which was purified by flash chromatography on silica gel eluting with 5% EtOAc/hexanes to give a colorless oil (5.8 g). A sample of the resultant material (1.15 g) was dissolved in $CH_2Cl_2$ (5 mL) and cooled in an ice bath. Trifluoroacetic acid (3 mL) was added and the solution stirred cold for two hours. The solvent was removed in vacuo, care being taken not to allow the solution to warm above room temperature. The residue contained considerable TFA and was used without further purification.

EXAMPLE 538C

N-butyl-N-propoxy-bromoacetamide

The salt of Example 538B (0.60 g) was dissolved in acetonitrile (5 mL) and cooled to −20° C. Hünig's base (5.5 mL) was added slowly. Bromoacetyl bromide (0.5 mL) was added dropwise over five minutes. The solution was stirred at −20° C. for 30 minutes. The bath was removed and the solution was stirred for six hours at room temperature. The solvent was removed in vocuo and the residue taken up in EtOAc (50 mL) and washed with water (1×25 mL), 1N phosphoric acid (3×25 mL), and brine (1×25 mL). The organic layer was dried with sodium sulfate and evaporated to give a dark orange oil (0.65 g) which was used without further purification.

EXAMPLE 538D (2S,3R,4S)-2-(2,2-Dimethylpentyl)-4-(1,3-benzo-dioxol-5-yl)-1-((N-propoxy, N-(n-butyl))aminocar-bonylmethyl)-pyrrolidine-3-carboxylic acid The compound of Example 537B was reacted with the compound of Example 538C according to the procedures of Example 536E.

EXAMPLE 539

(2S,3R,4S)-2-(2,2-Dimethylpentyl)-4-(1,3-benzo-dioxol-5-yl)-1-((N-propoxy, N-(n-propyl))aminocar-bonylmethyl)-pyrrolidine-3-carboxylic acid

EXAMPLE 539A

N-propyl-N-propoxy bromoacetamide

Prepared according to the procedures of Example 538A–C, substituting iodopropane for iodobutane in Example 538A.

EXAMPLE 539B (2S,3R,4S)-2-(2,2-Dimethylpentyl)-4-(1,3-benzo-dioxol-5-yl)-1-((N-propoxy, N-(n-propyl))aminocar-bonylmethyl)-pyrrolidine-3-carboxylic acid The compound of Example 537B was reacted with the compound of Example 539A according to the procedures of Example 536E.

EXAMPLE 540

(2S,3R,4S)-2-(2,2-Dimethylpentyl)-4-(7-methoxy-1,3-benzodioxol-5-yl)-1-((N-propoxy, N-(n-butyl)) aminocarbonylmethyl)-pyrrolidine-3-carboxylic acid The compound of Example 536D was reacted with the compound of Example 538C according to the procedures of Example 536E.

EXAMPLE 541

(2S,3R,4S)-2-(2,2-Dimethylpentyl)-4-(7-methoxy-1,3-benzodioxol-5-vi)-1-((N-propoxy, N-(n-propyl)) aminocarbonylmethyl)-pyrrolidine-3-carboxylic acid The compound of Example 536D was reacted with the compound of Example 539A according to the procedures of Example 536E.

EXAMPLE 542

(2S,3R,4S)-2-(2,2-Dimethylpent-3-enyl)-4-(1,3-ben-zodioxol-5-yl)-1-((N-propoxy, N-(n-butyl))ami-nocarbonylmethyl)-pyrrolidine-3-carboxylic acid

EXAMPLE 542A trans-Ethyl 3,3-dimethyl-4-hexenoate

A mixture of 4-methyl-3-penten-2-ol (7.4 g, 74 mmol), triethyl orthoacetate (13.6 mL, 74 mmol) and propionic acid (0.28 mL, 3.7 mmol) was heated at 150° C. for 7 hr. The product was then distilled under normal pressure (200–220° C.) to give 5.0 g of crude ester as a colorless oil.

EXAMPLE 542B

Ethyl trans,trans-2-(2,2-Dimethylpent-3-enyl)-4-(1,3-benzodioxol-5-yl)-pyrrolidine-3-carboxylate The title compound is prepared according to the procedures of Examples 536A and 536C, substituting the compound of Example 542A for ethyl 3,3-dimethylhexanoate in Example 536A and the compound of Example 501B (5-(2-nitrovinyl)-1,3-benxodioxole) for 4-methoxy-6-(2-nitrovi-nyl)-1,3-benzodioxole in Example 536C.

EXAMPLE 542C

Ethyl (2S,3R,4S)-2-(2,2-Dimethylpent-3-enyl)-4-(1,3-benzodioxol-5-yl)-pyrrolidine-3-carboxylate The compound of Example 542B was resolved according to the procedure described in Example 537B.

EXAMPLE 542D (2S,3R,4S)-2-(2,2-Dimethylpent-3-enyl)-4-(1,3-ben-zodioxol-5-yl)-1-((N-propoxy, N-(n-butyl))ami-nocarbonylmethyl)-pyrrolidine-3-carboxylic acid The compound of Example 542C was reacted with the compound of Example 538C according to the procedures of Example 536E.

EXAMPLE 543

(2S,3R,4S)-2-(2,2-Dimethylpent-3-enyl)-4-(1,3-benzodioxol-5-yl)-1-((N-propoxy, N-(n-propyl))aminocarbonylmethyl)-pyrrolidine-3-carboxylic acid The compound of Example 542C was reacted with the compound of Example 539A according to the procedures of Example 536E.

EXAMPLE 544

(2S,3R,4S)-2-(2,2-Dimethylpent-3-enyl)-4-(7-methoxy-1,3-benzodioxol-5-yl)-1-((N-propoxy, N-(n-butyl))aminocarbonylmethyl)-pyrrolidine-3-carboxylic acid

EXAMPLE 544A

Ethyl trans,trans-2-(2,2-Dimethylpent-3-enyl)-4-(7-methoxy-1,3-benzodioxol-5-yl)-pyrrolidine-3-carboxylate The title compound is prepared according to the procedures of Examples 536A and 536C, substituting the compound of Example 542A for ethyl 3,3-dimethylhexanoate in Example 536A.

EXAMPLE 544B

Ethyl (2S,3R,4S)-2-(2,2-Dimethylpent-3-enyl)-4-(7-methoxy-1,3-benzodioxol-5-yl)-pyrrolidine-3-carboxylate The compound of Example 544A was resolved according to the procedure described in Example 536D.

EXAMPLE 544C (2S,3R,4S)-2-(2,2-Dimethylpent-3-enyl)-4-(7-methoxy-1,3-benzodioxol-5-yl)-1-((N-propoxy, N-(n-butyl))aminocarbonylmethyl)-pyrrolidine-3-carboxylic acid The compound of Example 544B was reacted with the compound of Example 538C according to the procedures of Example 536E.

EXAMPLE 545

(2S,3R,4S)-2-(2,2-Dimethylpent-3-enyl)-4-(7-methoxy-1,3-benzodioxol-5-yl)-1-((N-propoxy, N-(n-propyl))aminocarbonylmethyl)-pyrrolidine-3-carboxylic acid The compound of Example 544B was reacted with the compound of Example 539A according to the procedures of Example 536E.

EXAMPLE 546

(2S,3R,4S)-2-(2-(2-pyridyl)ethyl)-4-(1,3-benzodioxol-5-yl)-1-[(N-4-heptyl-N-(2-methyl-3-fluorophenyl)]amino carbonylmethyl-pyrrolidine-3-carboxylic acid

EXAMPLE 546A

Ethyl trans,trans-2-(2-(2-pyridyl)ethyl)-4-(1,3-benzodioxol-5-yl)-pyrrolidine-3-carboxylate The title compound is prepared according to the procedures of Examples 536A and 536C, substituting the compound of Example 519A for 3,3-dimethylhexanoic acid in Example 536A.

EXAMPLE 546B

Ethyl (2S,3R,4S)-2-(2-(2-pyridyl)ethyl)-4-(1,3-benzodioxol-5-yl)-pyrrolidine-3-carboxylate The compound of Example 546A (1.5 g) was dissolved in $CH_2Cl_2$ (25 mL). Di-t-butyldicarbonate (0.9 g) was added and the solution stirred overnight at room temperature. The solvent was evaporated in vacuo and the residue taken up in EtOAc (50 mL), washed with water (1×50 mL), saturated sodium bicarbonate solution (3×50 mL), and brine (1×50 mL). The organic layer was dried with sodium sulfate and evaporated in vacuo to give an oil with was purified by flash chromatography on silica gel eluting with 1/10/10 EtOH/EtOAc/hexanes to give a colorless oil (1.5 g). The oil was dissolved in EtOH (10 mL) and 50% NaOH solution (0.5 mL) and water (5 mL) were added. The mixture was stirred overnight at room temperature. The solvents were evaporated in vocuo and the residue taken up in EtOAc (25 mL) and acidified with 1N $H_3PO_4$ (10 mL). The layers were separated and the organic layer dried with sodium sulfate and evaporated to give a white semi-solid (1.3 g). A sample of the resultant Boc-protected amino acid (0.9 g) was dissolved in DMF (5 mL). (S)-Phenylalaninol (0.32 g), HOOBt (0.33 g), and EDCI (0.40 g) were added and the solution sitrred overnight at room temperature. Water (50 mL) was added and the mixture extracted with EtOAc (3×25 mL). The organic layers were combined, washed with water (2×50 mL), saturated sodium bicarbonate solution (3×50 mL), and brine (1×50 mL), and evaporated to give a yellow oil; tlc indicated the presence of two diastereomeric products. The diastereomeric amides were separated by flash chromatography on silica gel eluting with 1/12/12 EtOH/EtOAc/hexanes to give faster-(450 mg) and slower-moving isomers (400 mg). The faster-moving diastereomer (400 mg) was taken up in 6N HCl and heated at reflux overnight. The solvent was evaporated and the residue was taken up in toluene (75 mL) and evaporated. This was repeated two additional times to give a brown solid, which was dissolved in EtOH (50 mL). 4N HCl/dioxane (10 mL) was added and the solution heated at reflux overnight. The EtOH was evaporated and the residue taken up in EtOAc which was treated with saturated sodium bicarbonate solution (3×50 mL), and brine (1×50 mL), and evaporated to give a brown solid. Flash chromatography on silica gel eluting with 30% EtOH/EtOAc gave a mixture of products (130 mg) which was approximately 70% desired material. This product was carried forward without additional purification.

EXAMPLE 546C (2S,3R,4S)-2-(2-(2-pyridyl)ethyl)-4-(1,3-benzo-dioxol-5-yl)-1-((N-4-heptyl-N-(2-methyl-3-fluorophenyl))amino carbonylmethyl)-pyrrolidine-3-carboxylic acid The compound of Example 546B was reacted with the compound of Example 508E according to the procedures of Example 536E.

EXAMPLE 547

(2S,3R,4S)-2-(4-Methoxyphenyl)-4-(1,3-benzo-dioxol-5-yl)-1-((N-butyl-N-(4-dimethylaminobutyl) amino)carbonylmethyl)-pyrrolidine-3-carboxylic acid

EXAMPLE 547A

N-butyl-4-hydroxybutyramide

To 30 mL (390 mmol) of g-butyrolactone was added 45 ml (455 mmol) of n-butylamine. The solution was heated at 85° C. for 1.5 hr, then the excess n-butylamine was removed in vocuo. The product crystallized on standing to give about 62 g of a colorless, low melting solid.

EXAMPLE 547B

N-butyl-4-hydroxybutyl chloroacetamide

To an ice cooled solution of 3.40 g (91.9 mmol) of LiAlH$_4$ in 90 mL of THF was added 2.4 mL of 98% H$_2$SO$_4$, dropwise, with stirring. After bubbling had ceased, a solution of 4.7 g of the compound of Example 547A in 10 mL of THF was added. The mixture was stirred at reflux for 24 hr, then cooled with an ice bath and quenched by sequential dropwise addition of 1.7 mL H$_2$O, and 17 mL of 25% w/v aqueous NaOH. The white precipitate was filtered, and washed with about 50 mL of THF. The combined filtrate and washings were concentrated to 3.85 g of an oil. To an ice cooled solution of this material in 35 mL of ethyl acetate was added a solution of 5.0 g (29.2 mmol) of chloroacetic anhydride in 10 mL of ethyl acetate. The solution was stirred at 0° C. for 30 min, then extracted with saturated aqueous NaHCO$_3$ solution (1×25 mL), 2M NaOH (1×25 mL), 5% NH$_4$OH (1×25 mL), 1M HCl (1×25 mL), and brine (1×25 mL), dried over MgSO$_4$, filtered, and concentrated in vacuo to an oil. The product was purified via silica gel chromatography, eluting with 98:2 diethyl ether: methanol, to give 1.52 g (31%) of a colorless oil.

EXAMPLE 547C

Ethyl (2S,3R,4S)-2-(4-Methoxyphenyl)-4-(1,3-ben-zodioxol-5-yl)-1-((N-butyl-N-(4-hydroxybutyl)amino)carbonylmethyl)-pyrrolidine-3-carboxylate To 1.52 g (6.85 mmol) of the compound of Example 547B was added 2.75 g (7.44 mmol) of the ethyl (2S,3R,4S)-2-(4-Methoxyphenyl)-4-(1,3-benzodioxol-5-yl)-pyrrolidine-3-carboxylate (prepared by neutralization of the compound of Example 501G), 10 mL of DMSO, and 2 mL of N,N-diisopropylethylamine. The solution was stirred at ambient temperature for 22 h, then poured into 100 mL of water and extracted with diethyl ether (3×25 mL). The combined ether layers were washed with water (1×25 mL), 4% (v/v) H$_3$PO$_4$ (1×25 mL), saturated aqueous NaHCO$_3$ solution (1×25 mL), and brine (1×25 mL), dried over MgSO$_4$, filtered, and concentrated to an oil. This was purified via silica gel chromatography, eluting with 98:2 diethyl ether: methanol to give 3.0 g (79%) of a colorless oil.

EXAMPLE 547D

Ethyl (2S,3R,4S)-2-(4-Methoxyphenyl)-4-(1,3-ben-zodioxol-5-yl)-1-((N-butyl-N-(4-bromobutyl)amino) carbonylmethyl-pyrrolidine-3-carboxylate To an ice cooled solution of 2.80 g (5.05 mmol) of the compound of Example 547C in 27 mL of diethyl ether was added 1.4 mL (10 mmol) of triethylamine, then 0.58 mL of methanesulfonyl chloride. A white precipitate formed, and the suspension was stirred at 0° C. for 20 min. The reaction was diluted with 75 mL of diethyl ether, then extracted with saturated aqueous NaHCO$_3$ solution (2×25 mL), 5% NH$_4$OH (2×25 mL), and brine (1×25 mL), dried over MgSO$_4$, filtered, and concentrated to 3.0 g of a colorless oil. To this material in 45 mL of DMF was added 6.0 g (69 mmol) of LiBr. The reaction warmed to about 50° C., then gradually cooled. The solution was stirred at ambient temperature for 4 h, then poured into 450 mL of water, and extracted with diethyl ether (3×100 mL). The combined ether layers were back extracted with water (1×100 mL), and brine (1×100 mL), dried over MgSO$_4$, filtered, and concentrated in vacuo to an oil. The product was purified via silica gel chromatography, eluting with 3:1 diethyl ether: petroleum ether, to give 2.65 g (90%) of a colorless oil.

EXAMPLE 547E (2S,3R,4S)-2-(4-Methoxyphenyl)-4-(1,3-benzo-dioxol-5-yl)-1-((N-butyl-N-(4-dimethylaminobutyl) amino)carbonylmethyl)-pyrrolidine-3-carboxylic acid To a solution of the compound of Example 547D (0.825 g, 1.34 mmol) in 3 mL of ethanol was added 5 mL of 4.07M dimethylamine in ethanol; the resultant solution was heated at reflux for 75 min. Solvents were removed in vacuo. The residue was purified by flash chromatography on silica gel, eluting with 9:1 dichloromethane/methanol. The resultant material was taken up in 5 mL of 1.4N NaOH in 5:1 ethanol/water and stirred at ambient temperature for 14 hrs. Solvents were removed in vacuo; the residue was taken up in water, then adjusted to pH 6–7 with 1M HCl (~7 mL required). The mixture was extracted with EtOAc (3×); the aqueous layer was concentrated in vacuo. The residue was washed 3× with acetonitrile; the combined washes were filtered through Celite and concentrated to give 596 mg of a white foam.

EXAMPLE 548

(2S,3R,4S)-2-(2,2-Dimethylpentyl)-4-(1,3-benzo-dioxol-5-yl)-1-((N-butyl-N-(4-dimethylaminobutyl) amino)carbonylmethyl)-pyrrolidine-3-carboxylic acid Prepared according to the procedures of Example 547, substituting the compound of Example 537B (ethyl (2S,3R,4S)-2-(2,2-Dimethylpentyl)-4-(1,3-benzodioxol-5-yl)-pyr-rolidine-3-carboxylate) in Example 547C.

EXAMPLE 549

(2S,3R,4S)-2-(2,2-Dimethylpentyl)-4-(7-methoxy-1,3-benzodioxol-5-yl)-1-((N-butyl-N-(4-dimethylaminobutyl)amino)carbonylmethyl)-pyrrolidine-3-carboxylic acid Prepared according to the procedures of Example 547, substituting the compound of Example 536D (ethyl (2S,3R,4S)-2-(2,2-Dimethylpentyl)-4-(7-methoxy-1,3-benzodioxol-5-yl)-pyrrolidine-3-carboxylate) in Example 547C.

EXAMPLE 550

(2S,3R,4S)-2-(2,2-Dimethylpent-3-enyl)-4-(1,3-benzodioxol-5-yl)-1-((N-butyl-N-(4-dimethylaminobutyl)amino)carbonylmethyl)-pyrrolidine-3-carboxylic acid Prepared according to the procedures of Example 547, substituting the compound of Example 542C (ethyl(2S,3R,4S)-2-(2,2-Dimethylpent-3-enyl)-4-(1,3-benzodioxol-5-yl)-pyrrolidine-3-carboxylate) in Example 547C.

EXAMPLE 551

(2S,3R,4S)-2-(2,2-Dimethylpent-3-enyl)-4-(7-methoxy-1,3-benzodioxol-5-yl)-1-((N-butyl-N-(4-dimethylaminobutyl)amino)carbonylmethyl)-pyrrolidine-3-carboxylic acid Prepared according to the procedures of Example 547, substituting the compound of Example 544A (ethyl(2S,3R,4S)-2-(2,2-Dimethylpent-3-enyl)-4-(7-methoxy-1,3-benzodioxol-5-yl)-pyrrolidine-3-carboxylate) in Example 547C.

EXAMPLE 552

(2S,3R,4S)-2-(2,2-Dimethylpent-3-enyl)-4-(1,3-benzodioxol-5-yl)-1-((N,N-di(nbutyl)amino)carbonylmethyl)-pyrrolidine-3-carboxylic acid Prepared according to the procedures of Example 1, substituting the compound of Example 541C (ethyl(2S,3R,4S)-2-(2,2-Dimethylpent-3-enyl)-4-(1,3-benzodioxol-5-yl)-pyrrolidine-3-carboxylate).

EXAMPLE 553

[2S,3R,4S]-2-(2,2-Dimethylpent-3-enyl)-4-(7-methoxy-1,3-benzodioxol-5-yl)-1-[(N,N-di(n-butyl)amino)carbonylmethyl)-]pyrrolidine-3-carboxylic acid Prepared according to the procesures of Example 1, substituting the compound of Example 544B (ethyl(2S,3R,4S)-2-(2,2-Dimethylpent-3-enyl)-4-(7-methoxy-1,3-benzodioxol-5-yl)-pyrrolidine-3-carboxylate).

EXAMPLE 554 trans,trans-2-(4-Methoxyphenyl)-4-(1,3-benzodioxol-5-yl)-1-(N-((bis-(o-tolyl)methyl)amino)carbonylmethyl)-(pyrrolidine-3-carboxylic acid

EXAMPLES 554A THROUGH 554E

These compounds were prepared in Examples 501B–F.

EXAMPLE 554F

Bis-(o-tolyl)methylamine

In a 50 mL round-bottom flask were placed 2,2'-dimethylbenzophenone (prepared from commercially available methyl-2-methylbenzoate according to the procedure in *J. Chem. Soc.*, 1929, 1631) (2.50 g, 10 mmol), hydroxylamine hydrochloride (0.76 g, 11 mmol), pyridine (5 mL) and ethanol (5 mL). The mixture was stirred under reflux for 8 h, cooled to r.t., diluted with EtOAc (25 mL) and transferred into a separatory funnel. The aqueous layer was removed, and organic layer was washed in turns with $CuSO_4$ (25 mL), water (25 mL) and brine (25 mL). After concentration of the organic phase, the residual oil obtained was purified by column chromatography (elution with 10% EtOAc in Hexanes) to give 1.31 g (73%) of oxime as a white crystalline solid.

To 55 mL of ammonia cooled in a dry ice-acetone bath was added 130 mg (6 mmol) of sodium metal. To the resulting blue solution at −78° C. was added slowly 650 mg (3 mmol) of the above oxime in 25 mL of anhydrous THF. The solution was stirred for 1 h followed by the addition of 1 g of ammonium chloride. The resulting colorless reaction mixture was warmed to r.t., transferred to a separatory funnel, diluted with 50 mL of water and extracted with dichloromethane (3×50 mL). The combined organic layers were dried ($Na_2SO_4$) and concentrated to give a yellowish oil. The residue was purified by a column chromatography (elution with 60% EtOAc in hexanes, followed by elution with 2% $Et_3N$ in EtOAc) to give 500 mg (66%) of the pure amine.

EXAMPLE 554G

N-(Bis-(o-tolyl)methyl) bromoacetamide

The compound of Example 554F (100 mg, 0.47 mmol) was dissolved in 2 mL of 1,2-dichloroethane. To this solution at −78° C. was added $Et_3N$ (0.05 mL) and then dropwise bromoacetyl bromide (40 mL, 0.47 mmol in 1 mL of 1,2-dichloroethane). The reaction mixture was stirred at −78° C. for 10 min, then at r.t. for 2 h., diluted with water (10 mL), and extracted with 1,2-dichloroethane (2×25 mL). The combined organic layers were concentrated to give the bromoacetamide as a white solid (184 mg, 96%) suitable for further use without additional purification.

EXAMPLE 554H

Ethyl trans,trans-2-(4-Methoxyphenyl)-4-(1,3-benzodioxol-5-yl)-1-(N-((bis-(o-tolyl)methyl)amino)carbonylmethyl)-pyrrolidine-3-carboxylate The compound of Example 554G was dissolved in 5 mL of $CH_3CN$ and added to a solution of 0.20 g (0.54 mmol) of the compound of Example 1E, N,N-diisopropylethylamine (0.1 mL) and $CH_3CN$ (10 mL). The reaction mixture was stirred overnight at r.t., diluted with $H_2O$ (25 mL) and extracted with EtOAc (2×25 mL). The combined organic fractions were concentrated to give a yellow oil, which was purified by a column chromatography (elution with 40% of EtOAc in Hexanes) to give 250 mg (73%) of the title compound.

EXAMPLE 554J trans,trans-2-(4-Methoxyphenyl)-4-(1,3-benzodioxol-5-yl)-1-(N-((bis-(o-tolyl)methyl)amino)carbonylmethyl)-pyrrolidine-3-carboxylic acid The compound of Example 554H was dissolved in a solution of 50 mL of ethanol and 10 mL of aqueous sodium hydroxide (6N) and stirred overnight at room temperature. The solution was then diluted with 30 mL of water, transferred to a separatory funnel and extracted with a mixture of 20% Hexanes in EtOAc (2×50 mL). The aqueous phase was treated with hydrochloric acid (3N) until pH=4 and extracted with chloroform (3×50 mL). The combined organic fractions containing the acid product were concentrated to get a yellow viscous oil. The title compound was then isolated by lyophylization from dilute $CH_3CN/TFA/H_2O$ as an amorphous solid: $^1H$ NMR (300 MHz, $CDCl_3$) δ 2.14 (s, 3H), 2.20 (s, 3H), 3.02–3.33 (m, 2H), 3.40–3.72 (m, 3H), 3.80 (s, 3H), 4.16–4.24 (broad s, 1H), 5.92 (m, 2H), 6.36–6.42 (m, 1H), 6.58–6.67 (m, 2H), 6.81 (t, J=9 Hz, 4H), 6.88–7.00 (m, 2H), 7.05–7.27 (m, 8H). MS (ESI+) m/e 593 (M+H$^+$). Anal. Calc for $C_{36}H_{36}N_2O_6$*0.4 TFA: C, 69.25H, 5.75 N, 4.39. Found: C, 69.20H, 5.68 N, 4.22.

EXAMPLE 555 trans,trans-2-[4-(2-Methoxyethoxy)phenyl]-4-(1,3-benzodioxol-5-yl)-1-(N-(2,2-dimethyl-1-phenylpropyl)-1-amino)carbonylmethyl)-pyrrolidine-3-carboxylic acid The title compound was prepared by using the procedures of Example 554, substituting 2,2-dimethyl-1-phenylpropan-1-one for 2,2'-dimethylbenzophenone in Example 554F and ethyl [4-(2-methoxyethoxy)benzoyl]acetate for ethyl (4-methoxybenzoyl) acetate in Example 1C. $^1H$ NMR (300 MHz, $CDCl_3$) δ 0.85 (s, 9H, minor diastereomer), 0.88 (s, 9H, major diastereomer), 3.44 (s, 2H), 3.10–3.42 (m, 3H), 3.46 (s, 3H), 3.51–3.75 (m, 4H), 4.06–4.13 (m, 2H), 4.72 (m, 1H), 5.97 (m, 2H), 6.77–7.45 (m, 12H). MS (ESI+) m/e 589 (M+H$^+$). Anal. Calc for $C_{34}H_{40}N_2O_7$*0.75 TFA: C, 63.24H, 6.09 N, 4.15. Found: C, 63.33H, 6.18 N, 4.05.

EXAMPLE 556 trans,trans-2-[4-(2-Methoxyethoxy)phenyl]-4-(1,3-benzodioxol-5-yl)-1-(N-((bis-(o-tolyl)methyl)amino)carbonylmethyl)-pyrrolidine-3-carboxylic acid The title compound was prepared by using the procedures of Example 554, substituting ethyl [4-(2-methoxyethoxy)benzoyl]acetate for ethyl (4-methoxybenzoyl) acetate in Example 554C. $^1H$ NMR (300 MHz, $CDCl_3$) δ 2.13 (s, 3H), 2.20 (s, 3H), 2.94–3.23 (m, 3H), 3.32–3.51 (m, 2H), 3.47 (s, 3H), 3.58–3.69 (broad s, 1H), 3.76 (dd, J=6, 1.5 Hz, 4H), 4.09 (t, J=4.5 Hz, 1H), 5.93 (m, 2H), 6.34–6.41 (d, J=7.5 Hz, 2H), 6.58 (broad s, 2H), 6.72–6.98 (m, 3H), 7.05–7.28 (m, 8H). MS (ESI+) m/e 637 (M+H$^+$). Anal. Calc for $C_{38}H_{40}N_2O_7$*0.2 TFA: C, 69.93H, 6.14 N, 4.25. Found: C, 70.03H, 6.08 N, 4.21.

EXAMPLE 557 trans,trans-2-[4-(2-Isopropoxyethoxy)phenyl]-4-(1,3-benzodioxol-5-yl)-1-(N-(2,2-dimethyl-1-phenylpropyl)-1-amino)carbonylmethyl)-pyrrolidine-3-carboxylic acid The title compound was prepared by using the procedures of Example 554, substituting 2,2-dimethyl-1-phenylpropan-1-one for 2,2'-dimethylbenzophenone in Example 554F and ethyl [4-(2-isopropoxyethoxy)benzoyl]acetate for ethyl (4-methoxybenzoyl) acetate in Example 1C. $^1H$ NMR (300 MHz, $CDCl_3$) δ 0.83 (s, 9H, major diastereomer), 0.88 (s, 9H, minor diastereomer), 1.19 (d, J=7 Hz, 6H), 3.14–3.83 (m, 9H), 4.07 (p, J=10.5, 4.5 Hz, 2H), 4.27–4.47 (m, 1H), 4.70 (t, J=9 Hz, 1H), 5.93–6.00 (m, 2H), 6.73–7.38 (m, 12H). MS (ESI+) m/e 617 (M+H$^+$). Anal. Calc for $C_{36}H_{44}N_2O_7$*0.6 TFA: C, 65.21H, 6.56 N, 4.09. Found: C, 65.15H, 6.59 N, 4.01.

EXAMPLE 558 trans,trans-2-(4-Methoxyphenyl)-4-(1,3-benzodioxol-5-yl)-1-(N-(3,3-dimethyl-1-phenylbutyl)-1-amino)carbonylmethyl)-pyrrolidine-3-carboxylic acid The title compound was prepared according to the procedures of Example 554, substituting 3,3-dimethyl-1-phenylbutan-1-one (prepared from commercially available 3,3-dimethyl-butyryl chloride according to the procedure in *J. Amer. Chem. Soc.*, 72, 1950, 222–227) for 2,2'-dimethylbenzophenone in Example 554F. $^1H$ NMR (300 MHz, $CDCl_3$) δ 0.84 (s, 9H, minor diastereomer), 0.89 (s, 9H, major diastereomer), 1.68 (t, J=7.5 Hz, 2H), 3.05–3.30 (m, 2H), 3.34–3.53 (m, 2H), 3.62–2.74 (m, 1H), 3.77 (s, 2H), 3.80 (s, 3H), 4.92–5.02 (m, 1H), 5.97–6.01(m, 2H), 6.77 (t, J=6 Hz, 2H), 6.88 (q, J=18, 7.5 Hz, 2H), 6.97 (d, J=6 Hz, 1H), 7.10–7.40 (m, 7H). MS (ESI+) m/e 559 (M+H$^+$). Anal. Calc for $C_{33}H_{38}N_2O_6$*0.45 TFA: C, 66.75H, 6.35 N, 4.59. Found: C, 66.69H, 6.32 N, 4.46.

EXAMPLE 559 trans,trans-2-[4-(2-Isoproopoxyethoxy)phenyl]-4-(1,3-benzodioxol-5-yl)-1-(N-((1-(o-tolyl)-1-(o-ethylphenyl)-methyl)amino)carbonylmethyl)-pyrrolidine-3-carboxylic acid The title compound was prepared by using the procedures of Example 554, substituting ethyl [4-(2-isopropoxyethoxy) benzoyl]acetate for ethyl (4-methoxybenzoyl) acetate in Example 554C and 2-ethyl-2'-methylbenzophenone (prepared from commercially available methyl-2-methylbenzoate according to the procedure in *J. Chem. Soc.,* 1929, 1631) for 2,2'-dimethylbenzophenone in Example 554F. $^1H$ NMR (300 MHz, $CDCl_3$) δ1.04–1.28 (m, 9H) 2.20 (s, 3H), 2.53 (broad s, 2H), 2.94–3.23 (m, 3H), 3.35–3.87 (m, 6H), 4.08 (broad s, 3H), 4.52 (broad s, 1H), 5.96 (s, 2H), 6.48–7.35 (m, 15H). MS (ESI+) m/e 678 (M+H$^+$). Anal. Calc for $C_{41}H_{46}N_2O_7$*0.95 TFA: C, 65.46H, 6.01 N, 3.46. Found: C, 65.47H, 6.00 N, 3.10.

EXAMPLE 560 trans,trans-2-(4-(2-(2-Propoxy)ethoxy)phenyl)-4-(1,3-benzodioxol-5-yl)-1-N-phenyl-N-t-butylhydrazino carbonylmethyl)-pyrrolidine-3-carboxylic acid

EXAMPLE 560A

N-phenyl-t-butylamine t-Butylamine (2.0 eq.) was stirred in dry THF at r.t. and n-butyllithium (1.2 eq.) was added slowly. The resulting mixture was stirred for 30 min. and then bromobenzene (1.0 eq.) added, refluxed for 4 hr. After work-up, it was purified and separated by a column(silica) to elute with hexane and ethyl acetate (9:1). Yield 50%.

EXAMPLE 560B

Phenyl-t-butylnitrosoamine

Phenyl-t-butylamine (6 g, 0.04 mol) was treated with conc.HCl (5 ml) and a solution of $NaNO_2$(6.4 g, 2.4 eq.) in 20 ml of water was added slowly. The resulting mixture was stirred for 2 hr at r.t. to produce an oily layer which was extracted with EtOAc, washed with brine, and dried over $Na_2SO_4$.Yield 6 g (85%). This nitrosoamine was used for the next step without further purification.

EXAMPLE 560C

N-phenyl-t-butylhydrazine

To a stirred suspension of zinc dust (5.14 g, 0.079 mol) in water (15 ml) was added dropwise a solution of the compound of Example 560B (3.5 g, 0.02 mol) in acetic acid (9 ml) and the resultant mixture was stirred for 1 hr at r.t. Dichloromethane (20 ml) was added, the mixture was adjusted to pH 8–9 with 15% NaOH, The zinc dust was removed by filtration, and the crude reaction mixture was extracted with dichloromethane. The combined organic layers were dried ($MgSO_4$). Yield 1.97 g (60%).

EXAMPLE 560D

N-phenyl,N-t-butyl-N'-(bromoacetyl) hydrazine

The title compound was prepared by the procedure described Example 554G, substituting the compound of Example 560C.

EXAMPLE 560E trans,trans-2-(4-(2-(2-Propoxy)ethoxy)phenyl)-4-(1,3-benzodioxol-5-yl)-1-(N-phenyl-N-t-butylhydrazino carbonylmethyl)-pyrrolidine-3-carboxylic acid The title compound was prepared by the procedures described in Example 554. $^1$H NMR (300 MHz, DMSO) δ 0.92(d, J=24 Hz, 6H), 1.10(s, 9H), 2.59–2.80(m, 2H), 2.95–3.10(m, 1H), 3.25–3.51(m, 3H), 3.58–3.70(m, 3H), 3.73–3.88(m, 1H), 4.02–4.07(m, 2H), 5.97–6.0(m, 2H), 6.78–6.93(m, 4H), 7.02–7.26(m, 7H), 7.35(d, J=8 Hz, 1H). MS(ESI+) m/e 618(M+H$^+$). Anal. Calc for C35H43N3O7.0.5H$_2$O: C, 67.07H, 7.08 N, 6.70. Found: C, 67.21H, 6.61 N, 6.40.

EXAMPLE 561 trans,trans-2-(4-(2-Methoxyethoxy)phenyl)-4-(1,3-benzodioxol-5-yl)-1-(N-phenyl-N-t-butylhydrazino carbonylmethyl)-pyrrolidine-3-carboxylic acid The title compound was prepared by the procedures described in Examples 554 and 560. $^1$H NMR (300 MHz, CD$_3$OD) δ 1.22(s, 9H), 2.87(d, J=15 Hz, 1H), 2.98–3.07(m, 2H), 3.27(bs, 1H), 3.42(s, 3H), 3.60–368(m, 2H), 3.72–3.76 (m, 2H), 3.92(d, J=9 Hz, 1H), 4.10–4.14(m, 2H), 5.95(dd, J=2 Hz,4 Hz, 2H), 6.82(d, J=8 Hz, 1H), 6.90(dd, J=2 Hz, 9 Hz, 1H), 7.96(d, J=8 Hz, 2H), 7.07(d, J=2 Hz, 1H), 7.10–7.23(m, 5H), 7.42(d, J=8 Hz, 2H). MS (ESI+) m/e590 (M+H$^+$). Anal. Calc for $C_{33}H_{39}N_3O_7$.1.0 AcOH: C, 64.70, H, 6.67, N, 6.47. Found: C, 64.40, H, 6.40, N, 6.70.

As an indication that the compounds described herein act through binding to endothelin receptors, the compounds have been evaluated for their ability to displace endothelin from its receptor.

As an indication that the compounds described herein act through binding to endothelin receptors, the compounds have been evaluated for their ability to displace endothelin from its receptor.

Binding Assay

ET$_A$ Receptor

Preparation of Membranes from MMQ Cells:

MMQ [MacLeod/MacQueen/Login cell line (prolactin secreting rat pituitary cells)] cells from 150 mL culture flasks were collected by centrifugation (1000×g for 10 min) and then homogenized in 25 mL of 10 mM Hepes (pH 7.4) containing 0.25 M sucrose and protease inhibitors [3 mM EDTA, 0.1 mM PMSF, and 5 μg/mL Pepstatin A] by a micro ultrasonic cell disrupter (Kontes). The mixture was centrifuged at 1000×g for 10 min. The supernatant was collected and centrifuged at 60,000×g for 60 min. The precipitate was resuspended in 20 mM Tris, pH 7.4 containing the above protease inhibitors and centrifuged again. The final pellet was resuspended in 20 mM Tris, pH 7.4 containing protease inhibitors and stored at −80° C. until used. Protein content was determined by the Bio-Rad dye-binding protein assay.

[$^{125}$I]ET-1 Binding to Membranes:

Binding assays were performed in 96-well microtiter plates pretreated with 0.1% BSA. Membranes prepared from cells were diluted 100 fold in Buffer B (20 mM Tris, 100 mM NaCl, 10 mM MgCl$_2$, pH 7.4, with 0.2% BSA, 0.1 mM PMSF, 5 μg/mL Pepstatin A, 0.025% bacitracin, and 3 mM EDTA) to a final concentration of 0.2 mg/mL of protein. In competition studies, membranes (0.02 mg) were incubated with 0.1 nM of [$^{125}$I]ET-1 in Buffer B (final volume: 0.2 mL) in the presence of increasing concentrations of unlabeled ET-1 or a test compound for 4 hours at 25° C. After incubation, unbound ligands were separated from bound ligands by a vacuum filtration method using glass-fiber filter strips in PHD cell harvesters (Cambridge Technology, Inc., MA), followed by washing the filter strips with saline (1 mL) for three times. Nonspecific binding was determined in the presence of 1 μM ET-1. The data are shown in Table 4. The percent inhibition at a concentration of 1 mM is shown. The data show that the compounds of the invention bind to the endothelin receptor.

TABLE 4

Binding Data

| Example | % Inhibition of ET$_A$ at 1 μM |
|---|---|
| 1D | 96.4 |
| 2 | 58.4 |
| 3 | 42.2 |
| 4 | 78.2 |
| 5 | 95.1 |
| 6B | 34.9 |
| 7 | 63.4 |
| 8 | 53.7 |
| 9 | 69.2 |
| 10 | 66.1 |
| 14 | 86.6 |
| 15 | 84.8 |
| 16 | 96.0 |
| 17 | 73.9 |
| 18 | 97.3 |
| 19 | 90.3 |
| 20 | 80.9 |
| 21 | 56.3 |
| 22 | 86.3 |
| 23 | 85.9 |
| 26 | 83.0 |
| 27 | 61.2 |
| 28 | 63.8 |
| 29 | 85.3 |
| 30 | 80.0 |
| 31B | 93.6 |
| 34 | 95.5 |
| 35 | 91.8 |
| 36 | 94.5 |
| 37 | 47.9 |
| 38 | 100.0 |
| 39 | 83.6 |
| 40 | 94.8 |
| 41 | 89.9 |
| 42 | 95.2 |
| 43 | 99.2 |
| 44 | 91.3 |
| 45 | 85.4 |
| 46 | 90.4 |
| 47 | 95.1 |
| 48 | 96.3 |
| 52 | 84.0 |
| 54 | 64.6 |
| 55 | 50.5 |
| 56 | 34.3 |
| 57 | 93.2 |
| 58 | 81.9 |
| 59 | 70.8 |
| 60 | 42.8 |
| 61C | 90.6 |
| 62 | 94.1 |
| 63 | 92.0 |
| 64 | 95.0 |
| 65 | 82.8 |
| 66 | 87.7 |
| 67 | 96.3 |
| 68 | 84.6 |
| 69D | 37.4 |
| 70 | 62.7 |
| 71 | 81.4 |
| 72C | 80.7 |
| 73C | 96.3 |
| 74 | 95.6 |
| 75C | 95.3 |
| 76 | 93.1 |
| 79 | 100.4 |
| 80 | 89.4 |
| 82 | 90.3 |
| 83 | 85.0 |
| 84 | 65.3 |
| 86 | 52.6 |
| 87 | 62.4 |
| 88 | 84.3 |
| 89 | 84.6 |
| 91C | 91.6 |
| 92C | 107.4 |
| 93C | 59.2 |
| 95D | 82.1 |
| 96 | 86.1 |
| 97 | 89.0 |
| 98 | 86.8 |
| 99 | 92.1 |
| 100 | 76.8 |
| 101 | 89.2 |
| 102 | 75.2 |
| 103 | 69.0 |
| 104 | 98.0 |
| 105 | 98.6 |
| 106 | 90.0 |
| 107 | 97.2 |
| 109 | 96.8 |
| 110 | 94.4 |
| 111 | 101.8 |
| 112 | 94.9 |
| 113 | 94.3 |
| 114 | 86.2 |
| 115 | 88.4 |
| 116 | 79.3 |
| 117 | 95.2 |
| 118 | 93.2 |
| 119 | 86.6 |
| 120 | 99.5 |
| 121 | 98.6 |
| 122 | 95.3 |
| 125 | 97.2 |
| 126 | 91.7 |
| 127 | 91.4 |
| 128 | 95.4 |
| 123 | 89.7 |
| 124 | 91.0 |
| 129 | 100.1 |
| 130 | 91.0 |
| 131 | 89.5 |
| 132 | 90.0 |
| 133 | 88.6 |
| 134 | 92.2 |
| 135B | 77.7 |
| 136 | 79.4 |
| 138 | 83.0 |
| 139 | 98.6 |
| 140 | 106.3 |
| 141 | 92.8 |
| 142B | 78.7 |
| 143 | 20.6 |
| 144 | 78.2 |
| 145 | 32.4 |
| 146 | 25.0 |
| 147 | 73.0 |
| 148 | 94.7 |
| 149 | 84.6 |
| 150 | 93.6 |
| 151 | 80.5 |
| 152 | 86.9 |
| 153 | 97.1 |
| 154 | 80.2 |
| 155 | 92.7 |
| 156 | 92.6 |
| 157 | 83.8 |
| 158 | 91.8 |
| 159 | 36.2 |
| 160B | 80.3 |
| 161 | 93.6 |
| 162B | 91.5 |
| 163 | 90.6 |
| 164 | 98.6 |
| 165 | 54.1 |
| 166 | 91.6 |
| 167 | 94.4 |

TABLE 4-continued

Binding Data

| Example | % Inhibition of $ET_A$ at 1 μM |
|---|---|
| 291 | 100.0 |
| 293 | 89.8 |
| 294 | 77.7 |
| 295 | 93.0 |
| 296 | 87.1 |
| 297 | 84.4 |
| 298 | 93.3 |
| 299 | 90.4 |
| 300 | 96.1 |
| 301 | 96.7 |
| 302 | 86.6 |
| 303 | 87.2 |
| 304 | 89.7 |
| 305 | 87.4 |
| 306 | 93.3 |
| 307 | 92.2 |
| 308 | 93.0 |
| 309 | 80.7 |
| 310 | 87.1 |
| 311 | 92.3 |
| 312 | 88.2 |
| 313 | 96.3 |
| 314 | 86.0 |
| 315 | 82.7 |
| 316 | 74.0 |
| 317 | 68.5 |
| 318 | 79.0 |
| 319 | 79.0 |
| 320 | 82.2 |
| 322 | 95.6 |
| 323 | 91.3 |
| 324 | 95.0 |
| 334 | 88.0 |
| 335 | 84.1 |
| 340 | 94.0 |
| 341 | 87.4 |
| 342 | 89.9 |
| 343 | 98.7 |
| 344 | 95.6 |
| 345 | 86.6 |
| 346 | 88.9 |
| 348 | 91.3 |
| 349 | 73.0 |
| 350 | 92.1 |
| 351 | 99.0 |
| 352 | 96.2 |
| 353 | 73.7 |
| 354 | 79.3 |
| 355 | 100 |
| 356 | 93.5 |
| 357 | 96.3 |
| 358 | 62.7 |
| 359 | 94.7 |
| 360 | 93.7 |
| 361 | 92.8 |
| 362 | 94.1 |
| 363 | 82.3 |
| 365 | 59.2 |
| 366 | 91.5 |
| 367 | 71.0 |
| 368 | 94.6 |
| 370 | 84.3 |
| 371 | 97.2 |
| 372 | 91.6 |
| 373 | 92.9 |
| 374 | 91.4 |
| 375 | 97.8 |
| 376 | 90.2 |
| 377 | 85.6 |
| 378 | 91.1 |
| 379 | 90.7 |
| 380 | 99.0 |
| 381 | 95.7 |
| 382 | 96.8 |
| 383 | 91.4 |
| 384 | 79.4 |
| 385 | 86.2 |
| 386 | 47.8 |
| 387 | 98.7 |
| 388 | 69.2 |
| 389 | 100 |
| 390 | 98.2 |
| 391 | 45.6 |
| 392 | 93.7 |
| 393 | 100 |
| 394 | 97.8 |
| 395 | 79.8 |
| 396 | 98.7 |
| 397 | 100 |
| 398 | 90.0 |
| 399 | 59.9 |
| 400 | 93.0 |
| 401 | 96.5 |
| 402 | 80.5 |
| 403 | 96.1 |
| 404 | 95.4 |
| 405 | 86.4 |
| 406 | 94.5 |
| 407 | 100 |
| 408 | 100 |
| 409 | 89.4 |
| 410 | 91.4 |
| 411 | 93.5 |
| 412 | 86.4 |
| 413 | 99.5 |
| 414 | 91.4 |
| 415 | 87.3 |
| 416 | 86.4 |
| 417 | 98.7 |
| 418 | 100 |
| 420 | 100 |
| 421 | 100 |
| 422 | 96.6 |
| 423 | 89.1 |
| 424 | 85.8 |
| 425 | 90.8 |
| 426 | 97.2 |
| 427 | 100 |
| 428 | 100 |
| 429 | 100 |
| 430 | 94.1 |
| 431 | 99.1 |
| 432 | 95.5 |
| 433 | 99.6 |
| 434 | 100 |
| 435 | 97.8 |
| 436 | 100 |
| 437 | 100 |
| 438 | 94.3 |
| 439 | 94.3 |
| 440 | 100 |
| 441 | 98.3 |
| 442 | 100 |
| 443 | 100 |
| 444 | 100 |
| 445 | 98.1 |
| 446 | 97.8 |
| 447 | 96.9 |
| 448 | 97.4 |
| 449 | 100.0 |
| 450 | 99.7 |
| 451 | 100 |
| 452 | 100 |
| 453 | 94.4 |
| 454 | 96.8 |
| 455 | 99.1 |
| 456 | 95.3 |
| 457 | 88.9 |

TABLE 4-continued

Binding Data

| Example | % Inhibition of $ET_A$ at 1 µM |
|---|---|
| 458 | 93.4 |
| 459 | 97.4 |
| 460 | 91.6 |
| 461 | 99.6 |
| 462 | 98.3 |
| 463 | 96.1 |
| 464 | 97.1 |
| 465 | 95.1 |
| 466 | 94.2 |
| 467 | 93.6 |
| 468 | 88.7 |
| 469 | 98.7 |
| 470 | 100 |
| 471 | 100 |
| 475 | 91.6 |
| 476 | 82.3 |
| 477 | 80.1 |
| 479 | 96.5 |
| 495 | 95.9 |
| 496 | 92.7 |
| 497 | 83.7 |
| 498 | 81.6 |
| 499 | 68.5 |
| 500 | 55.7 |
| 502 | 95.7 |
| 503 | 97.0 |
| 504 | 97.1 |
| 505 | 95.8 |
| 506 | 99.7 |
| 507 | 99.3 |
| 508 | 97.6 |
| 509 | 100 |
| 510 | 100 |
| 511 | 99.2 |
| 512 | 98.9 |
| 513 | 98.0 |
| 514 | 100 |
| 515 | 99.1 |
| 516 | 99.7 |
| 517 | 94.1 |
| 518 | 96.3 |
| 519 | 99.1 |
| 520 | 97.4 |
| 521 | 100 |
| 523 | 99.0 |
| 524 | 99.2 |
| 525 | 100 |
| 526 | 100 |
| 527 | 96.6 |
| 528 | 98.3 |
| 529 | 98.1 |
| 531 | 99.8 |
| 532 | 100 |
| 533 | 97.9 |
| 536 | 100 |
| 537 | 97.2 |
| 554 | 58.2 |
| 555 | 66.7 |
| 556 | 24 |
| 557 | 72.2 |
| 558 | 79.8 |
| 559 | 5.8 |
| 560 | 0 |
| 561 | 0 |

As further demonstration of the efficacy of the described compounds as functional antagonists of endothelin, the ability of the described compounds to inhibit ET-1-induced phosphatidylinositol hydrolysis was measured.

Determination of Phosphatidylinositol (PI) Hydrolysis

MMQ cells ($0.4 \times 10^6$ cells/mL) were labeled with 10 µCi/mL of [$^3$H]myo-inositol in RPMI for 16 hours. The cells were washed with PBS, then incubated with Buffer A containing protease inhibitors and 10 mM LiCl for 60 minutes. The cells were then incubated with test compounds for 5 minutes, and then challenged with 1 nM ET-1. ET-1 challenge was terminated by the addition of 1.5 mL of 1:2 (v/v) chloroform-methanol. Total inositol phosphates were extracted after adding chloroform and water to give final proportions of 1:1:0.9 (v/v/v) chloroform-methanol-water as described by Berridge (Biochem. J. 206 587–595 (1982)). The upper aqueous phase (1 mL) was retained and a small portion (100 µL) was counted. The rest of the aqueous sample was analyzed by batch chromatography using anion-exchange resin AG1-X8 (Bio-Rad). The $IC_{50}$ is the concentration of test compound required to inhibit the ET-induced increase in PI turnover by 50%. The results of the above study clearly indicate that the compounds act as functional ET antagonists.

TABLE 5

Phosphatidylinositol Hydrolysis

| Example | $IC_{50}$ µM |
|---|---|
| 1D | 0.025 |
| 14 | 0.017 |
| 15 | 0.010 |
| 16 | 0.009 |
| 18 | 0.009 |
| 19 | 0.024 |
| 30 | 0.001 |
| 31B | 0.002 |
| 43 | 0.0001 |
| 46 | 0.002 |
| 47 | 0.0005 |
| 48 | 0.0004 |
| 291 | 0.0098 |
| 300 | 0.0012 |
| 534 | 0.05 |
| 553 | 0.0004 |

Table 6

$ET_A/ET_B$ Selectivity

MMQ cells, porcine cerebellar tissues (known to contain $ET_B$ receptors) and chinese hamster ovary cells (CHO) permanently transfected with the human ETA or ETB receptor were homogenized in 25 ml of 10 mM Hepes (pH 7.4) containing 0.25 M sucrose and a protease inhibitor [50 mM EDTA, 0.1 mM PMSF, 5 µg/ml Pepstatin A, and 0.025% Bacitracin] using a micro ultrasonic cell disrupter. The mixture was centrifuged at 1000×g for 10 min. The supernatant was collected and centrifuged at 60,000×g for 60 min. The precipitate was resuspended in 20 mM Tris, pH 7.4 containing protease inhibitor and centrifuged again. The final membrane pellet was resuspended in 20 mM Tris, pH 7.4 containing protease inhibitors and stored at −80° C. until used. Protein content was determined by the Bio-Rad dye-binding protein assay.

Binding assays were performed in 96-well microtiter plates pretreated with 0.1% BSA. Membranes prepared from cells were diluted 100 fold in Buffer B (20 mM Tris, 100 mM NaCl, 10 mM $MgCl_2$, pH 7.4, with 0.2% BSA, 0.1 mM PMSF, 5 µg/mL Pepstatin A, 0.025% bacitracin, and 50 mM EDTA) to a final concentration of 0.2 mg/mL of protein. In competition binding studies, membranes (0.02 mg) were incubated with 0.1 nM of ($^{125}$I)ET-1 (for ETA assay in MMQ or CHO cells transfected with human ETA receptor) or ($^{125}$I)ET-3 (for ETB assay in porcine cerebellum or CHO cells transfected with human ETB receptor) in Buffer B (final volume: 0.2 mL) in the presence of increasing concentrations of the test compound for 3 hours at 25° C. After incubation, unbound ligands were separated from bound ligands by a vacuum filtration method using glass-fiber filter strips in PHD cell harvesters (Cambridge Technology, Inc., MA), washing the filter strips three times with saline (1 mL). Nonspecific binding was determined in the presence of 1 μM ET-1. IC50 values are calculated using an average of at least two separate determinations. The data shows the selectivity of the compounds of the invention in binding to the endothelin receptors.

Determination of Plasma Protein Binding

A stock solution of the test compound in 50% ethanol (2 mg/mL) was diluted 10× into PBS. A 0.4 mL sample of this secondary stock solution was added to 3.6 mL of fresh plasma, and incubated at room temperature for 1 hour. A 1 mL sample of this incubation mixture was transferred to a Centrifree ultrafiltration tube. The sample was centrifuged in a fixed-bucket rotor for approximately 2 min and the filtrate was discarded. The sample was centrifuged for another 15–30 min. A 100 μL sample of the ultrafiltrate was transfered to a micro HPLC sample vial containing 150 ML of HPLC mobile phase and mixed thoroughly. A 50 μL sample was injected and the concentration of drug in the ultrafiltrate was determined by HPLC analysis compared against a standard sample prepared identically in the absence of

TABLE 6

| EXAMPLE NO. | rET-A (% I @ 1 μM) | rET-A IC$_{50}$ (nM) | pET-B IC$_{50}$ (nM) | Selectivity (rA/pB ratio) | hET-A IC$_{50}$ (nM) | hET-B IC$_{50}$ (nM) | Selectivity (hA/hB ratio) |
|---|---|---|---|---|---|---|---|
| 502 | 95.7 | 3.0 | 71,000 | 23,000 | | | |
| 503 | 97.0 | 1.4 | 50,000 | 35,000 | 0.92 | 52,000 | 56,000 |
| 504 | 97.1 | 3.1 | >100,000 | >32,000 | 4.6 | >100,000 | >21,000 |
| 505 | 95.8 | 2.0 | 60,000 | 30,000 | 5.7 | 68,000 | 12,000 |
| 506 | 99.7 | 3.2 | >100,000 | >31,000 | 3.0 | 61,000 | 20,000 |
| 507 | 99.3 | 3.0 | >100,000 | >33,000 | 1.63 | >100,000 | >60,000 |
| 508 | 97.6 | 1.9 | 45,000 | 23,000 | 2.1 | 51,000 | 24,000 |
| 509 | 100 | 0.56 | 30,000 | 53,000 | 0.51 | 23,000 | 45,000 |
| 510 | 100 | 0.50 | 35,000 | 68,000 | 1.0 | 11,000 | 11,000 |
| 511 | 99.2 | 0.81 | N.D. | — | 0.60 | 15,000 | 25,000 |
| 512 | 98.9 | 0.42 | >80,000 | >190,000 | 0.58 | 60,000 | >102,000 |
| 513 | 98.0 | 0.30 | 8,800 | 29,000 | 0.36 | 14,000 | 37,000 |
| 514 | 100 | 1.0 | 26,000 | 26,000 | 0.36 | 9,800 | 29,000 |
| 515 | 99.1 | 1.6 | >62,000 | >37,000 | 6.7 | >100,000 | >15,000 |
| 516 | 99.7 | 0.71 | 29,000 | 40,000 | 1.8 | 37,000 | 21,000 |
| 517 | 94.1 | 1.0 | 30,000 | 30,000 | 0.43 | 12,000 | 29,000 |
| 518 | 96.3 | 1.3 | 85,000 | 63,000 | 0.31 | 38,000 | 124,000 |
| 519 | 99.1 | 0.38 | 14,000 | 36,000 | 0.23 | 19,000 | 83,000 |
| 520 | 97.4 | 0.20 | 28,000 | 130,000 | | | |
| 521 | 100 | 0.67 | 37,000 | 54,000 | | | |
| 523 | 99.0 | 0.42 | 360 | 880 | 0.33 | 290 | 880 |
| 524 | 99.2 | 0.79 | 1,700 | 2,100 | 0.82 | 890 | 1,100 |
| 525 | 100 | 8.2 | 560 | 70 | | | |
| 526 | 100 | 42 | — | — | 17 | 7,400 | 440 |
| 527 | 96.6 | 7.9 | 10,000 | 1,300 | | | |
| 528 | 98.3 | 11 | 43,000 | 3,800 | | | |
| 529 | 98.1 | 3.6 | 6,300 | 1,700 | | | |
| 531 | 99.8 | 1.2 | — | — | 0.71 | 870 | 1,200 |
| 532 | 100 | 5.1 | 3,200 | 630 | | | |
| 533 | 97.9 | 76 | 7,900 | 100 | 40 | 22,000 | 560 |
| 534 | | 0.12 | 0.36 | 3.0 | 0.08 | 0.28 | 3.5 |
| 536 | 100 | 0.52 | 17,000 | 33,000 | 0.92 | 52,000 | 56,000 |
| 537 | 97.2 | 0.96 | 5,900 | 6,200 | 0.23 | 1,900 | 8,200 |
| 552 | 97.3 | 0.78 | 7100,000 | 7125,000 | 1.0 | >96,000 | >96,000 |
| 553 | 100 | 0.26 | 42,400 | 160,000 | 0.29 | 39,500 | 136,000 | plasma. Ultrafiltrate concentrations are calculated from a calibration curve. Protein binding is calculated according to the equation:

$$\% PB = [1-(Cu/Ci)]*100\%$$

where Cu is the ultrafiltrate concentration and Ci is the initial plasma concentration. The percent of bound compound is listed in Table 7.

TABLE 7

| Example #43 | >99.5% bound |
|---|---|
| Example #530 | 78% bound |
| Example #531 | 92% bound |
| Example #532 | 96.8% bound |
| Example #533 | 82.6% bound |

It has been demonstrated in the literature (Wu-Wong, et al., Life Sci. 1996, 58, 1839–1847, and references contained therein) that compounds which are highly protein bound show decreased potency in vitro in the presence of plasma proteins. A decrease in in vitro potency may correspondingly result in reduced in vivo potency. An endothelin antagonist which has reduced protein binding might be expected to be less susceptible to this effect, and thus be more potent as an in vivo agent.

The ability of "reduced protein binding" endothelin antagonists to exhibit enhanced activity in the presence of serum albumin has been demonstrated through the following study: A series of binding curves is recorded for a given antagonist, each experiment performed in the presence of increasing concentrations of serum albumin.

Protocol for Albumin-induced binding shift studies: Binding assays were performed in 96-well microtiter plates pre-coated with 0.1% BSA unless otherwise indicated. Membranes were diluted in Buffer B (20 mM Tris, 100 mM NaCl, 10 mM MgCl$_2$, pH 7.4, 0.1 mM PMSF, 5 mg/mL Pepstatin A, 0.025% bacitracin and 3 mM EDTA) to a final concentration of 0.05 mg/ml of protein. Varying concentrations of human serum albumin (HSA) were added as indicated. In competition studies, membranes were incubated with 0.1 nM of [$^{125}$I]ET in Buffer B (final volume: 0.2 ml) in the presence of increasing concentrations of unlabeled test ligands for 4 hours at 25° C. After incubation, unbound ligands were separated from bound ligands by vacuum filtration using glass-fiber filter strips in PHD cell harvesters (Cambridge Technology, Inc., Watertown, MA), followed by washing the filter strips with saline (1 ml) for three times. Nonspecific binding was determined in the presence of 1 μM ET-1.

Inhibition of [$^{125}$I]ET-1 binding to human ETA receptor by ETA antagonists. Each curve was determined in the presence of either 0%, 0.2%, 1%, or 5% HSA, and assays were performed as described above. The results are expressed as % of control binding, with [$^{125}$I]ET-1 binding in the absence of antagonist defining 100%. Each point represents the mean (±S.D.) of three determinations.

As observed in FIG. 1A, a compound which is highly protein bound (Example 43, >98% bound) shows a rightward shift of the binding curve (toward decreasing potency) in the presence of increasing albumin levels. The compound of Example 531 (FIG. 1B), in which protein binding is reduced to 92%, shows a substantial diminution of this rightward shift; the shift is completely eliminated with the compound of Example 530 (FIG. 1C), in which protein binding is reduced to 78%. This experiment demonstrates that a reduction in protein binding translates into increased potency in the presence of plasma proteins, and suggests that such compounds may exhibit enhanced in vivo activity.

The observed reduction in protein binding, in compounds which retain high affinity for endothelin receptors, appears linked to the placement of "basic" functionality (groups which carry a positive charge at physiological pH).

Such compounds also exhibit improved solubility in aqueous solutions, as demonstrated below (Table 1) in an experiment in which maximum solubility was measured in aqueous media at varying pH at about 25° C. These results indicate that compounds that contain charged groups on the amide sidechain exhibit increased solubility over a significant range of pH. Such increased aqueous solubility, coupled with the enhanced potency resulting from decreased protein binding, might make such compounds preferred for development as parenteral agents. Table 8 presents the pH-Solubility profiles for representative compounds c the present invention.

TABLE 8

| pH | [Example 43] (mg/mL) | [Example 531] (mg/ml) |
|---|---|---|
| 5.1 | 0.08 | >3.3 |
| 6.5 | 0.51 | >3.4 |
| 7.1 | 0.99 | 3.54 |
| 7.6 | 1.14 | 3.55 |

The present invention provides less protein bound compounds having improved in vitro and in vivo activity as pharmaceutical agents. The present invention also provides compounds that show that the affinity of hydrophobic acids for plasma protein may be reduced by attaching a counterbalanced charge at a biologically acceptable site. For example, protein binding is reduced by attaching a "basic" functionality (groups which carry a positive charge at physiological pH) on the amide sidechain (see Formula XII wherein R$_3$ has an amide sidechain).

A particularly preferred compound of formula I is a compound of formula IIIa, also known as ABT-627:

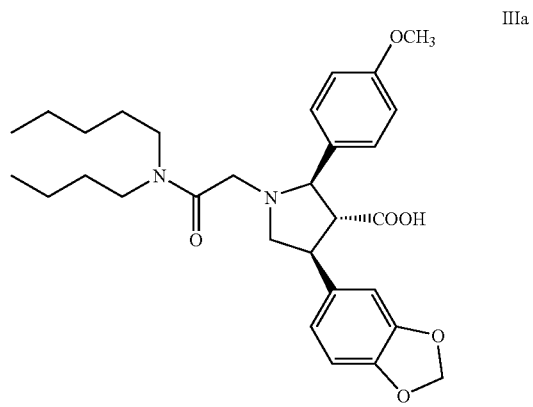

IIIa

Other suitable endothelin ET-A receptor antagonist may be used, such as those disclosed in U.S. Pat. Nos. 6,048,893, 6,017,951, and 5,998,468.

The term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

The methods of the present invention are useful in men as well as in women. Preferably, however, the methods of the present invention are useful in men, more preferably men with prostate cancer.

The ability of the compounds of the invention to treat cancers can be demonstrated according to the method described in J. Clin. Invest. 87 1867 (1991). Types of cancer includes primary cancer such as breast, prostate, lung, kidney, thyroid, myeloma, lymphoma, sarcoma, osteosarcoma, and ovarian.

The ability of the compounds of the invention to treat nociception can be demonstrated according to the method described in J. Pharmacol. Exp. Therap. 271 156 (1994).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula I, or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful for antagonizing endothelin in humans or other mammals. Total daily dose administered to a host in single or divided doses may be in amounts, for example, from 0.001 to 1000 mg/kg body weight daily and more usually 0.1 to 100 mg/kg for oral administration or 0.01 to 10 mg/kg for parenteral administeration. Dosage unit compositions may contain such amounts of submultiples thereof to make up the daily dose.

Pharmaceutical formulations may be prepared by procedures known in the art. The amount of active ingredient that may be combined with the carrier materials to produce a single dosage form will vary depending upon the host treated and the particular mode of administeration.

It will be understood, however, that the specific dose level for any particular patient will depend upon a variety of factors including the activity of the specific compound employed, the age, body weight, general health, sex, diet, time of administeration, route of administeration, rate of excretion, drug combination, and the severity of the particular disease undergoing therapy.

The compounds of the present invention may be administered orally, buccally, parenterally, sublingually, by inhalation spray, rectally, or topically in dosage unit formulations containing conventional nontoxic pharmaceutically acceptable carriers, adjuvants, and vehicles as desired. Topical administeration may also involve the use of transdermal administeration such as transdermal patches or iontophoresis devices. The term parenteral as used herein includes subcutaneous injections, intravenous, intramuscular, intrasternal injection, transcutaneous, intradermal, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A representative solid dosage form, for example, a tablet or a capsule, comprises:

| | |
|---|---|
| Compound of the invention: | 35% w/w |
| Starch, Pregelatinized, NF | 50% w/w |
| Microcrystalline Cellulose, NF | 10% w/w |
| Talc, Powder, USP | 5% w/w |

While the compounds of the invention can be administered as the sole active therapeutic agent, they can also be used in combination with one or more co-therapeutic agents, such as anticancer drugs or methods including, but not limited to, hormonal agents, such as leuprolide (Lupron®); gonadorelin antagonists, such as goserelin (Zoladex®) and abarelix; bicalutamide; nilutamide; flutamide; vitamin D; vitamin D analogues; estrogen and estrogen analogues, such as diethylstibestrol; prednisone; hydrocortisone; ketoconazole; cyproterone acetate; progesterone; 5-alpha reductase inhibitors, such as finasteride; bone-seeking radionuclides, such as samarium (Quadramet®), strontium (Metastron®), and $^{186}$rhenium; external beam radiation, including three dimensional conformal radiation; brachytherapy, which is the implantation of radioactive seeds directly into the prostate; monoclonal antibodies such as trastuzumab (Herceptin®); anti-angiogenic agents such as thrombospondin peptide or kringle 5; matrix metalloproteinase inhibitors; farnesyl transferase inhibitors; lycopenes; urokinase; plasminogen activator inhibitors; plasminogen activator receptor blockers; apoptosis inducers; selective and non-selective alpha blockers; platinum agents, such as cis-platinum and carbo-platinum; taxane class agents, such as docitaxil and paclitaxil; estramustine; gemcytabine; adriamycin; doxorubicin; daunorubicin; mitoxantrone; vinblastine; vincristine; capecitabine; irinotecan; topotecan; 5-fluorouracil; interferons; cytoxan; methotrexate; cytokines, such as IL-2; PPAR agonists, such as thiazolidine diones; retinoid-type agents, 5-lipooxygenase inhibitors, such as zyfo (Zilueton®), COX-2 inhibitors; gene-therapy based therapeutics, including sense and anti-sense genes; cholesterol lowering drugs, such as lovastatin, pravastatin, and simvistatin; bisphosphonates; osteoprotegrin; and antibodies, both monoclonal and polyclonal; antibody-coupled radionucleotides; antibody-coupled cytotoxic agents; antibody-coupled radionucleotides; viral-vector delivered agents; vaccines directed at protein, carbohydrate, or nucleic acid targets; aminoglutethimide; and suramin.

These combinations can be administered as separate compositions or as a single dosage form containing both or all agents. When administered as a combination, the therapeutic agents can be formulated as separate compositions, which are given at the same time or different times, or the therapeutic agents can be given as a single composition.

In addition, the compounds invention can be used in combination with one or more co-therapeutic agents which impede net bone loss, such as estrogens, bisphosphonates, and estrogen receptor modulators, such as raloxifene, and calcitonin.

The compounds of the invention can additionally be administered in combination with surgery, such as radical prostatectomy, cryotherapy, transurethral resection of the prostate as an adjuvant, and the like, or prior to surgery as a neoadjuvant agent.

The current major diseases or conditions of bone which are of public concern include, but are not limited to, post-menopausal osteoporosis, ovariectomy patients, senile osteoporosis, patients undergoing long-term treatment of corticosteroids, side effects from glucocorticoid or steroid treatment, patients suffering from Cushings's syndrome, gonadal dysgenesis, periarticular erosions in rheumatoid arthritis, osteoarthritis, Paget's disease, osteohalisteresis, osteomalacia, hypercalcemia of malignancy, osteopenia due to bone metastases, periodontal disease, hyperparathyroidism, osteroperosis from Lupron therapy, and starvation. All of these conditions are characterized by bone loss, resulting from an imbalance between the degradation of bone (bone resorption) and the formation of new healthy bone. This turnover of bone continues normally throughout life and is the mechanism by which bone regenerates. However, the conditions stated above will tip the balance towards bone loss such that the amount of bone resorbed is inadequately replaced with new bone, resulting in net bone loss.

EXAMPLES

Studies were performed on male subjects with asymptomatic hormone refractory prostate cancer with rising PSA levels and on male subjects with symptomatic hormone refractory prostate cancer with rising PSA levels and pain. Subjects in the phase II studies had castrate levels of testosterone, either due to pharmacologic intervention, via leuprolide (Lupron®) or goserelin (Zoladex®), or via surgical castration. Subjects received ABT-627 or placebo. The following tests were conducted:

ABT-627 was formulated in 2.5 and 10 mg doses. An oral liquid formulation of ABT-627 was also prepared as follows: 1 mg/ml ABT-627, 50% glycerin, 14% alcohol, and water. Matching placebos were also provided.

A number of recognized or putative biochemical markers of disease progression have been used to monitor treatment of individuals with prostate cancer. Among these markers are serum Prostate Specific Antigen (PSA), serum acid Phosphatase, Interleukin-6, and Chromagranin-A. As currently accepted, favorable treatment is marked by a decrease or slower rate of increase for PSA, acid phosphatase, and Interleukin-6, while a favorable response is marked by an increase in Chromagranin-A.

Serum samples were obtained from subjects during treatment with the ET antagonist ABT-627 in order to determine PSA, acid phosphatase, IL-6, and Chromagranin-A values.

Prostate Specific Antigen Level Assay

The effect of ABT-627 administration on prostate specific antigen (PSA) levels in human subject serum samples was determined using the procedure described in the *Chiron Diagnostics ACS: Centaur PSA2 Assay*. This assay is a two-site sandwich immunoassay which uses direct chemiluminescense and constant amounts of two antibodies. The first antibody, the Lite Reagent, is an affinity purified polyclonal sheep anti-PSA antibody labeled with acridinium ester. The Lite Reagent is purchased as a 5.0 mL reagent pack comprising the polyclonal sheep anti-PSA antibody (3.1 μg) in buffered saline with sodium azide (0.1%). The second antibody, the Solid Phase, is a monoclonal mouse anti-PSA antibody covalently coupled to paramagnetic particles. The Solid Phase is purchased as a 25.0 mL reagent pack comprising the covalently coupled monoclonal mouse anti-PSA antibody (316 μg) in buffered saline with sodium azide (0.1%). The assay was performed at Quintiles Laboratories (Smyrna, GA) using Chiron Diagnostics ACS: Centaur® Automated Chemiluminescence Systems.

Briefly, a subject population was treated with a placebo or 2.5 mg or 10 mg of ABT-627. Blood samples were collected, allowed to adequately clot, centrifuged at 1000×g for 15–20 minutes, and stored at −20° C. if not assayed within 48 hours. A cuvette was charged sequentially with serum, Lite Reagent (50 μL), and Solid Phase (250 μL). The resulting mixture was incubated for 7.5 minutes at 37° C., separated, and treated with the solution of Acid Reagent and Base Reagent to initiate the chemiluminescent reaction. A direct relationship exists between the amount of PSA present in the patient sample and the RLU's (relative light units) detected. As shown by the area under the curve (AUC) in FIG. 2, the rate of increase of PSA in the serum samples decreases after the adminsteration of ABT-627, demonstrating the effectivness of ABT-627 as an agent for treating prostate cancer.

Acid Phosphatase Levels

The effect of ABT-627 administeration on Acid Phosphatase levels in human subject serum samples was determined at Quintiles Laboratories using the chemical test described in *Sigma Diagnostics Acid Phosphatase (ACP) Procedure No.* 435. The enzyme Acid Phosphatase (ACP) catalyzes the hydrolysis of alpha-naphthyl phosphate to alpha-naphthol and inorganic phosphate. The alpha-naphthol immediately reacts with fast red TR salt to produce a yellow chromophore with an absorbance maximum at 405 nm. The rate of increase in absorbance at 405 nm is directly proportional to ACP activity in the sample. ACP activity was determined in the presence and absence of L-tartrate, the difference being attributed to prostatic acid phosphatase activity.

Briefly, a subject population was treated with a placebo or 2.5 mg or 10 mg of ABT-627. Blood samples were collected, allowed to adequately clot, centrifuged at 1000×g for 15–20 minutes, and stored at −20° C. if not assayed within 48 hours. Assays were performed on a Hitachi Spectrophotomer. A cuvette was charged sequentially with ACP reagent (1 mL), prepared as described in the assay protocol, and serum (0.1 mL). The mixture was agitated and incubated for 5 minutes, and an absorbance (A) at 405 nm (versus water as a reference) was read to provide an initial absorbance. The mixture was incubated for another 5 minutes, and a second absorbance was read to provide a final absorbance. A change A/5 minute value was obtained by subtracting the initial absorbance from the final absorbance and was used to calculate total ACP activity.

To provide the tartrate-resistant acid phosphatase activity, the above procedure was repeated with the addition of ACP tartrate reagent (0.01 mL) to the cuvette containing the ACP reagent and mixing before adding the serum. Prostatic acid phosphatase activity was calculated by subtracting the the tartrate-resistant acid phosphatase activity from the ACP activity. As shown shown by the (AUC) in FIG. 7, the rate of increase and the average change from baseline for acid phosphatase was decreased in those subjects treated with ABT-627, again demonstrating the effectivness of ABT-627 as an agent for treating prostate cancer.

Chromagranin-A Levels

The effect of ABT-627 adminstration on Chromagranin-A levels in human serum samples was determined by proprietary assay conducted at the Nichols Institute. The procedure is a two site chemiluminescence assay (ICMA) using one monoclonal antibody conjugated with biotin, another monoclonal antibody labeled with an acridinium ester, and an avidin-coated solid phase. The antibody/Chromagranin-A/antibody complex is bound to the solid phase by the avidin-biotin interaction and unbound materials are removed by washing. The bound, acridinium-labeled material produces light that is detected in a luminometer after addition of triggering agents. The Limit of Detection (LOD) for the assay was 0.07 ng/mL. As shown by the AUC in FIG. 8, the average change from baseline for Chromagranin-A was higher for subjects treated with 2.5 mg/day of ABT-627, again demonstrating the effectivness of ABT-627 as an agent for treating prostate cancer.

Interleukin-6 Levels

The effect of ABT-627 adminstration on Interleukin-6 levels in human serum samples was determined at Quintiles Laboratories using a sandwich immunoassay. Human serum samples and standards were incubated in microtiter plate wells coated with a monoclonal anti-IL-6 antibody, in the presence of a second monoclonal anti IL-6 antibody, linked to acetylcholinesterase. After incubation, the wells were washed, and the bound enzymatic activity was measured using a chromogenic substrate. The intensity of the color was proportional to the concentration of IL-6 in the sample or standard. As shown by the AUC FIG. 1, the average change in baseline for Interleukin-6 was lower in those subjects treated with ABT-627, demonstrating the effectivness of ABT-627 as an agent for reducing inflammation and ameliorating pain.

Bone Scan Methodology

Bone scans were performed with an NDA approved, Tc-99m phosphonate type radiopharmaceutical. This technique uses whole body format (skull to feet) so that anterior and posterior images are presented when using a 510 K-approved gamma camera. Alternatively, spot views covering both anterior and posterior projections of the total body can be obtained. Interpretation was performed according to standard nuclear medicine criteria, on a bone by bone basis, by recording the number of lesions at each site. Each site was evaluated against a confidence score of 1 to 5, where 1 is negative, 2 is probably negative, 3 is equivocal, 4 is probably positive, and 5 is definitely positive. The MSKCC (Clin. Can. Res. 1998; 4:1765–1772) was used to record these findings. For the purposes of scoring the extent of disease or the response to treatment, lesions with a confidence score of 4 and 5 were considered positive, and all other lesions were considered negative. In addition, in a blinded study, a reference nuclear medicine physician interpreted the bone scans quantitatively as follows: the percent of involved bone was estimated for each individual bone, and the individual bone involvement was summed to calculate a global percent bone scan index (BSI). More specifically, the bone scan was separated into three indices. The first was the appindicular scan which involved arms and legs (i.e. the humorous and all bones distal to the humerous and the femur and everything distal to the femur). The second was the axial (everything but the arms and the legs). The results of these scans were combined to provide the total BSI.

Bone scans were conducted on each subject on day one of the study, and on the final day of the study, and the changes from baseline in bone scan index scores were analysed by mean change and mean percent change, adjusting for baseline characteristics as co-variates using SAS version XXX software.

As shown in FIG. 6, bone scans indicated a decrease in the proportion of total skeketal involvement in those subjects receiving ABT-627 versus placebo, demonstrating the effectivness of ABT-627 as an agent for reducing the fraction of total skeletal involvement by tumor.

VAS Methodology/Administeration/Analysis

The Visual Analog Scale (VAS) is a common instrument of pain assessment performed by having a subject draw a vertical line on a 10 cm scale at the point that best describes his or her pain on average in the last 24 hours. A diagram of the scale is shown below:

No pain I—I Pain as bad as it could possibly be (not to scale)

During the course of the study, pain asessments were done daily, at bedtime, by the subject. If the subject was unable to maintain the log, a caregiver could complete the log on his or her behalf. The log also contained a table on which was recorded all daily pain medication consumed by the patient. The logs of daily VAS scores and analgesic consumption were collected at biweekly visits of the subject to the clinic when a new log was distributed. Clinical personnel who received the logs measured the score by measuring the distance (in mm) from the "no pain" end mark to the point where the subject's line crossed the VAS line. The number was written into the case report form next to the date the subject completed that page of the logbook.

Subjects with pain were initially stabilized in their pain so that their pain was treated to a tolerable and constant level. For this study, "tolerable and constant" refers to a pain score less than or equal to 5 cm on the VAS for an average of seven successive days while using four or less rescue doses of pain medication per day. A rescue medication dose refers to a dose equal to one single dose a patient used for common timed pain relief.

The weekly VAS scores were calculated excluding the lowest and highest score for each week and averaging the remaining five scores. If there were two days with the same VAS score, the day with the highest analgesic use was discarded.

The weekly mean VAS score was used to define subjects as responders or non-responders. A subject was considered a responder based on the reduction in the pain intensity: a weekly VAS score reduction of greater than or equal to 25% during at least two consecutive weeks without an increase of analgesic use during the same period (compared to baseline). Alternatively, a subject was considered a responder if his pain analgesic consumption was reduced by at least 25% during at least two consecutive weeks without a concomitant increase in VAS score.

The percentage of responders in each treatment group was compared to evaluate drug efficacy. The comparison was subjected to an adjustment for baseline characteristics and prognostic factors as co-variates, and the analysis was performed using the Cochran-Mantel-Haenszel test or a generalized linear model.

Figure 3:
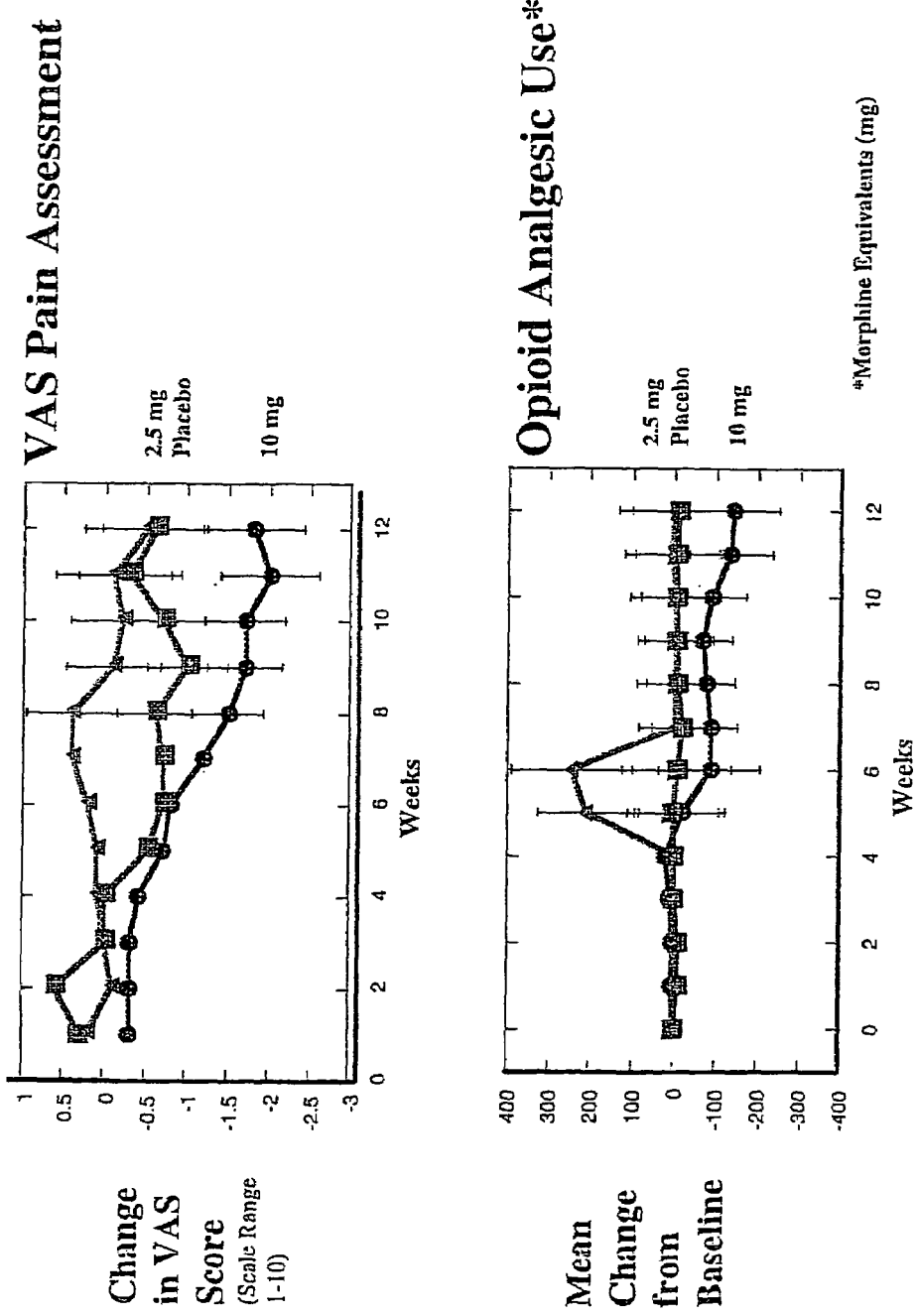
FIG. 3 illustrates VAS score levels relating to pain assessment in a subject population treated with a placebo or 2.5 mg or 10 mg of ABT-627.

Weekly VAS scores are examined using a longitudinal analysis method to explore trends over time. The duration of the response, defined as the time from baseline to the last weekly assessment for which the responder definition was satisfied, was analyzed using the Kaplan-Meier methodology and logrank test. Cox proportional hazard models were used as needed (see U.S. Department of Health and Human Services. Management of Cancer Pain Clinical Practice Guidelines. AHCPR Publication #94–0592, Rockville, Md. (1994). As shown by the AUC in FIG. 3, VAS scores showed a decrease in pain, independent of the effects of morphine, after treatment with with ABT-627, demonstrating the effectivness of ABT-627 as an agent for ameliorating pain.

Osteoblastic Activity and Bone Markers

Markers of osteoblastic activity were assessed using urine samples. Bone markers include bone alkaline phosphatase (BAP), deoxypridinoline, and N-telopeptide of Type I collagen. Blood samples were collected prior to dosing on Day 1, Day 42, Day 84, Day 168, and every 28 days after Day 168, with a final collection on the last day of the study.

Bone Alkaline Phosphatase

Figure 5:
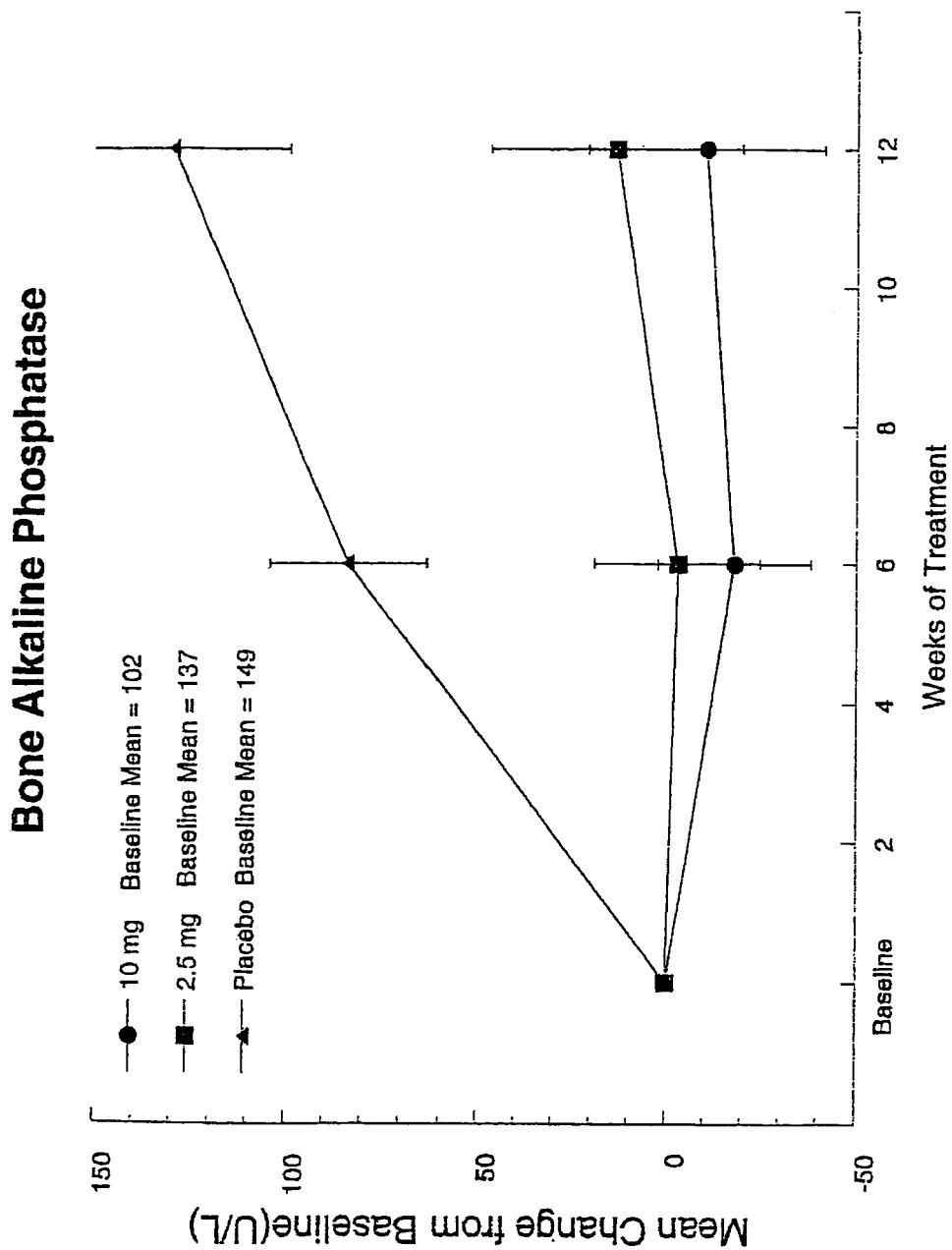
FIG. 5 illustrates bone alkaline phosphatase (BAP) formation in a subject population treated with a placebo or 10 mg ABT-627.

Bone Alkaline Phosphatase levels were determined using the bone-specific Alkphase-B® assay published by Metra Biosystems (Mountain View, Calif.). As shown by the AUC in FIG. 5, BAP levels decreased in subjects treated with ABT-627, demonstrating the effectivness of ABT-627 as an agent for inhibiting abnormal bone remodeling.

Crosslinked N-Telopeptide Levels

Figure 4:
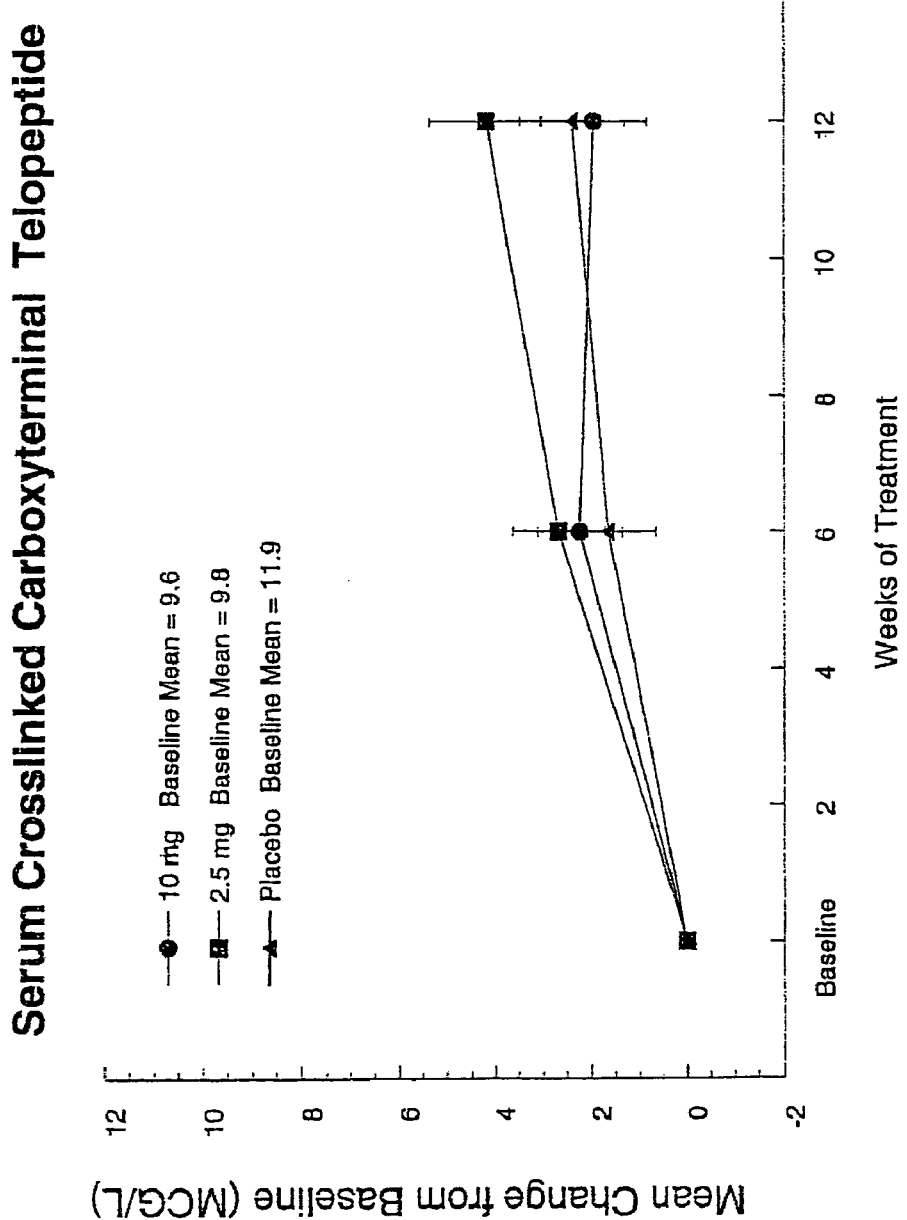
FIG. 4 illustrates crosslinked N-telopeptides (degradation) in a subject population treated with a placebo or 10 mg ABT-627.

Cross-linked N-telopeptide levels were determined using the DiaSorin (Stillwater, MN) assay for the quantitative determination of carboxyterminal cross-linked telopeptide of type I collagen (ICTP) in human serum by equilibrium radioimmunoassay (RIA). Briefly, samples were incubated with the $^{125}$, ICTP tracer and ICTP primary antibody for 2 hours at 37° C. Following the 2 hour incubation, a pre-precipitated second antibody complex was added to separate the bound from free tracer. The assay was then centrifuged and decanted after a 30 minute incubation at room temperature. The bound tracer in the pellet was counted with a gamma counter. Counts were inversely proportional to the amount of ICTP present in each sample. As shown by the AUC in FIG. 4, Crosslinked N-telopeptide levels decreased in subjects treated with ABT-627, demonstrating the effectivness of ABT-627 as an agent for inhibiting the bone remodeling associated with bone diseases.

The present invention covers compounds having the formula XII:

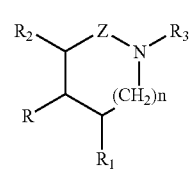

XII wherein

Z is —C(R$_{18}$)(R$_{19}$)— or —C(O)— wherein R$_{18}$ and R$_{19}$ are independently selected from hydrogen and loweralkyl;

n is 0 or 1;

R is —(CH$_2$)$_m$—W wherein m is an integer from 0 to 6 and W is
- (a) —C(O)$_2$-G wherein G is hydrogen or a carboxy protecting group,
- (b) —PO$_3$H$_2$,
- (c) —P(O)(OH)E wherein E is hydrogen, loweralkyl or arylalkyl,
- (d) —CN,
- (e) —C(O)NHR$_{17}$ wherein R$_{17}$ is loweralkyl,
- (f) alkylaminocarbonyl,
- (g) dialkylaminocarbonyl,
- (h) tetrazolyl,
- (i) hydroxy,
- (j) alkoxy,
- (k) sulfonamido,
- (l) —C(O)NHS(O)$_2$R$_{16}$ wherein R$_{16}$ is loweralkyl, haloalkyl, aryl or dialkylamino,
- (m) —S(O)$_2$NHC(O)R$_{16}$ wherein R$_{16}$ is defined as above,
- (n)

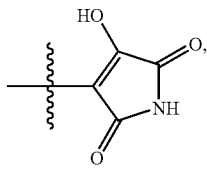

- (o)

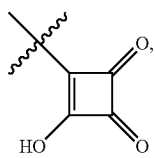

- (p)

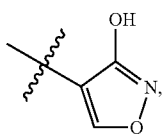

- (q)

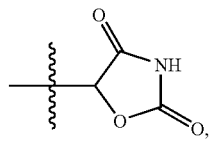

- (r)

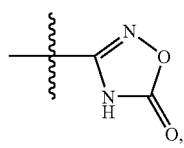

- (s)

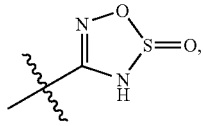

- (t)

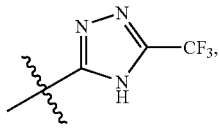

or
- (u)

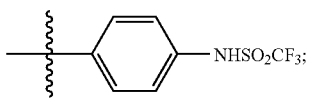

R$_1$ and R$_2$ are independently selected from hydrogen, loweralkyl, alkenyl, alkynyl, alkoxyalkyl, alkoxycarbonylalkyl, hydroxyalkyl, haloalkyl, haloalkoxyalkyl, alkoxyalkoxyalkyl, thioalkoxyalkoxyalkyl, cycloalkyl, cycloalkylalkyl, aminocarbonylalkyl, alkylaminocarbonylalkyl, dialkylaminocarbonylalkyl, aminocarbonylalkenyl, alkylaminocarbonylalkenyl, dialkylaminocarbonylalkenyl, hydroxyalkenyl, aryl, arylalkyl, aryloxyalkyl, arylalkoxyalkyl, (N-alkanoyl-N-alkyl)aminoalkyl, alkylsulonylamidoalkyl, heterocyclic, (heterocyclic)alkyl and (R$_{aa}$)(R$_{bb}$)N—R$_{cc}$ wherein R$_{aa}$ is aryl or arylalkyl, R$_{bb}$ is hydrogen or alkanoyl and R$_{cc}$ is alkylene, with the proviso that one or both of R$_1$ and R$_2$ is other than hydrogen;

R$_3$ is (a)R$_4$—C(O)—R$_5$—, R$_4$—C(O)—R$_5$—N(R$_6$)—, wherein R$_5$ is (i) a covalent bond, (ii) alkylene, (iii) alkenylene, (iv) —N(R$_{20}$)—R$_8$— or —R$_{8a}$—N(R$_{20}$)—R$_8$— wherein R$_8$ and R$_{8a}$ are independently selected from the group consisting of alkylene and alkenylene and R$_{20}$ is hydrogen, loweralkyl, alkenyl, haloalkyl, alkoxyalkyl, haloalkoxyalkyl, cycloalkyl or cycloalkylalkyl or (v) —O—R$_9$— or —R$_{9a}$—O—R$_9$— wherein R$_9$ and R$_{9a}$ are independently selected from alkylene;

R$_4$ and R$_6$ are (R$_{11}$)(R$_{12}$)N— wherein R$_{11}$ and R$_{12}$ are independently selected from
- (1) hydrogen,
- (2) loweralkyl,
- (3) haloalkyl,
- (4) alkoxyalkyl,
- (5) haloalkoxyalkyl,
- (6) alkenyl,
- (7) alkynyl,
- (8) cycloalkyl,
- (9) cycloalkylalkyl,
- (10) aryl,
- (11) heterocyclic,
- (12) arylalkyl,
- (13) (heterocyclic)alkyl,
- (14) hydroxyalkyl,
- (15) alkoxy,
- (16) aminoalkyl,
- (17) trialkylaminoalkyl,

(18) alkylaminoalkyl,
(19) dialkylaminoalkyl,
(20) carboxyalkyl,
(21) (cycloalkyl)aminoalkyl,
(22) (cycloalkyl)alkylaminoalkyl,
(23) (heterocyclic)aminoalkyl, and
(24) (heterocyclic)aminoalkyl, with the proviso that at least one of $R_{11}$ and $R_{12}$ is selected from heterocyclic, aminoalkyl, alkylaminoalkyl, dialkylaminoalkyl, trialkylaminoalkyl, alkylaminoalkyl, dialkylaminoalkyl, carboxyalkyl, (cycloalkyl)aminoalkyl, (cycloalkyl)alkylaminoalkyl, (heterocyclic)aminoalkyl, and (heterocyclic)alkylaminoalkyl;

or a pharmaceutically acceptable salt thereof.

Preferred compounds having reduced protein binding are shown in Table 9A wherein R may be selected from the substituents shown in Table 9B.

TABLE 9A

1

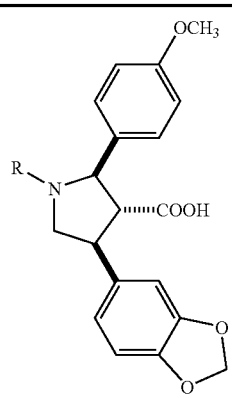

2

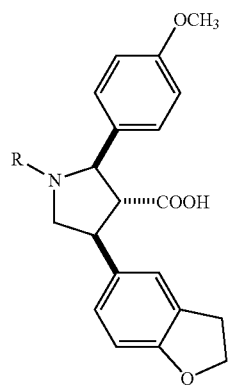

3

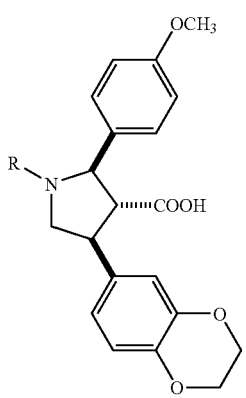

TABLE 9A-continued

4

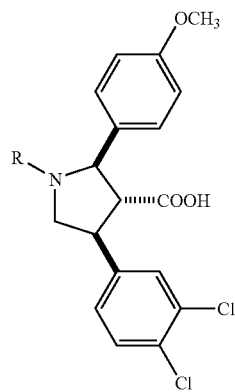

5

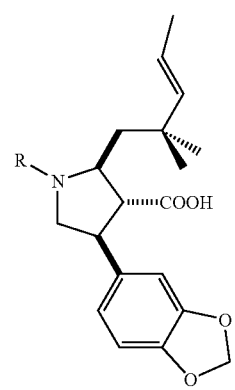

6

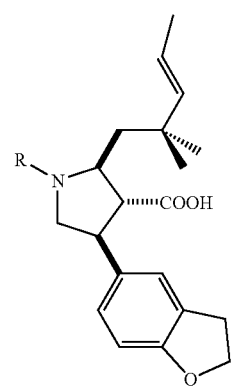

7

TABLE 9A-continued
| | |
|---|---|
| 8 | 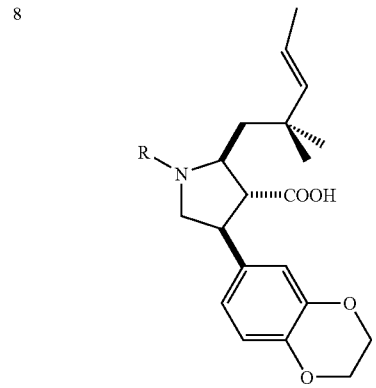 |
| 9 | 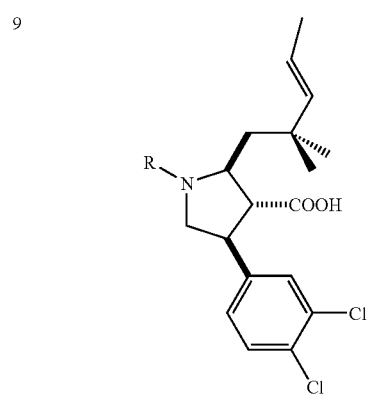 |
| 10 | 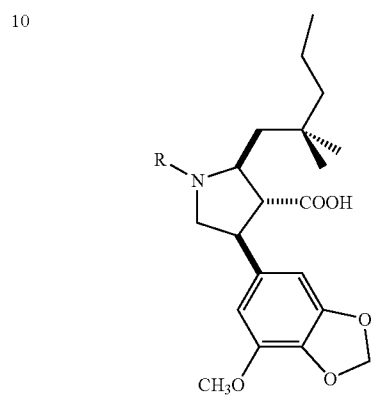 |
| 11 | 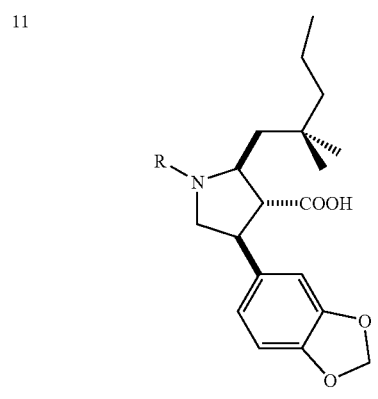 |
TABLE 9A-continued
| | |
|---|---|
| 12 | 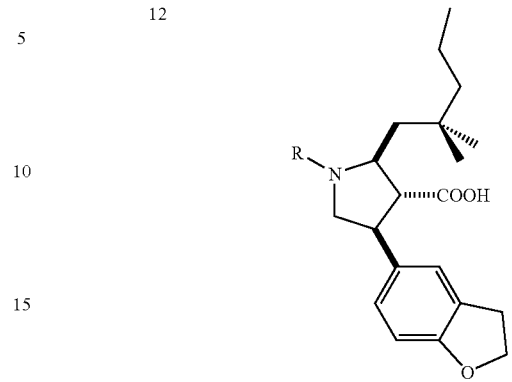 |
| 13 | 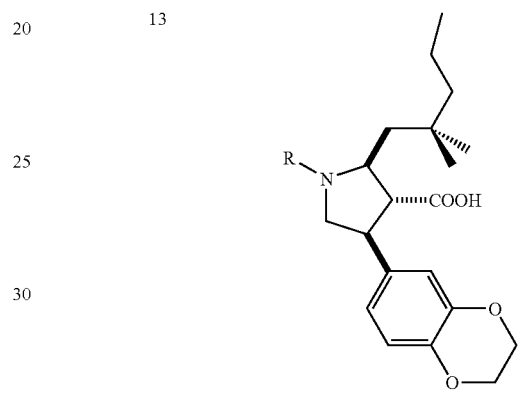 |
| 14 | 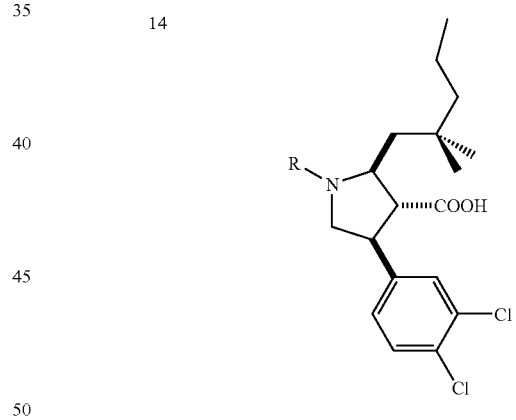 |
| 15 | 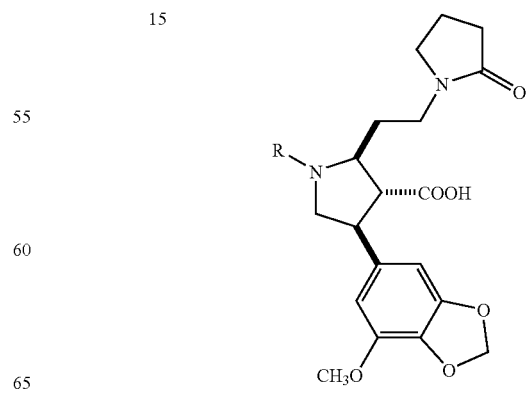 |

TABLE 9A-continued
| | |
|---|---|
| 16 | 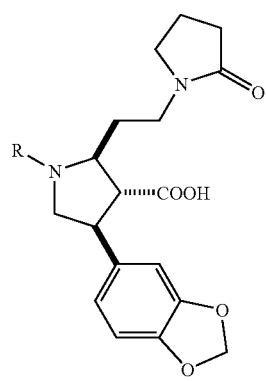 |
| 17 | 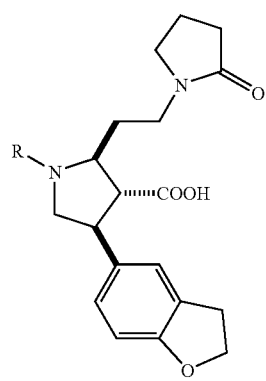 |
| 18 | 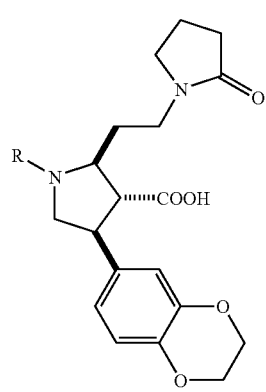 |
| 19 | 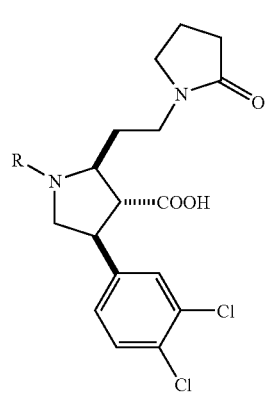 |
| 20 | 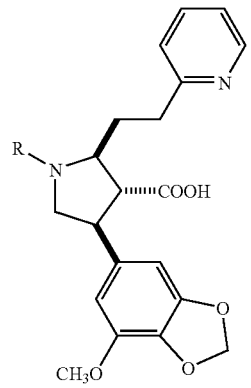 |
| 21 | 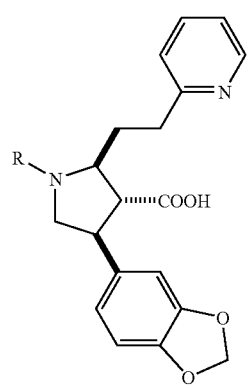 |
| 22 | 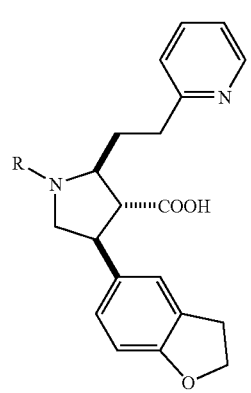 |
| 23 | 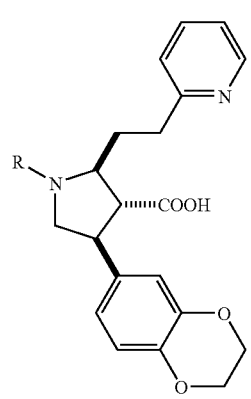 |

TABLE 9A-continued
| | |
|---|---|
| 24 | 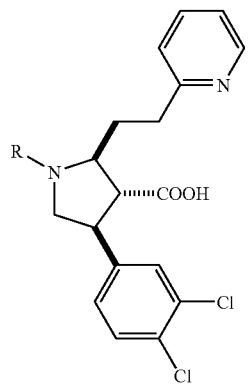 |
| 25 | 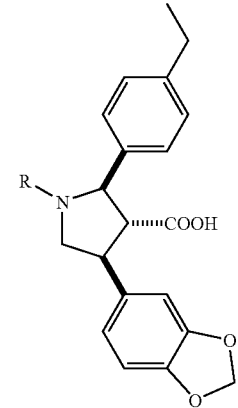 |
| 26 | 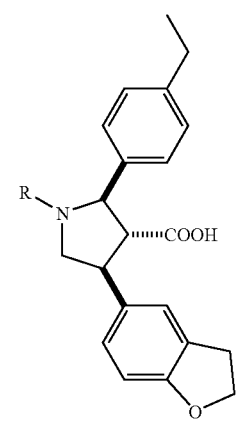 |
| 27 | 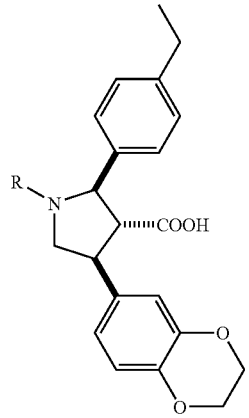 |
| 28 | 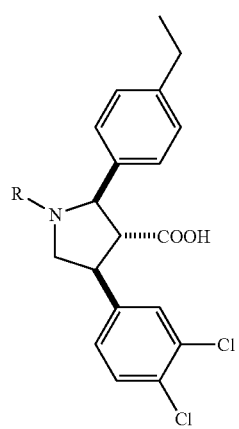 |
| 29 | 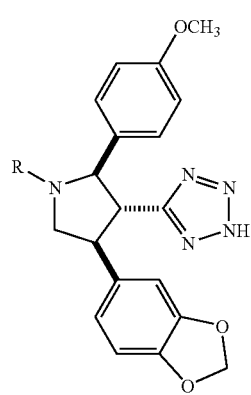 |
| 30 | 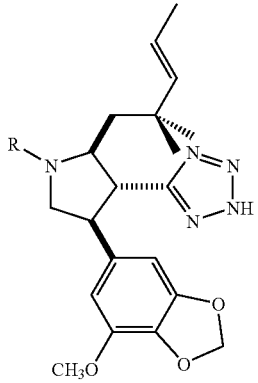 |
| 31 | 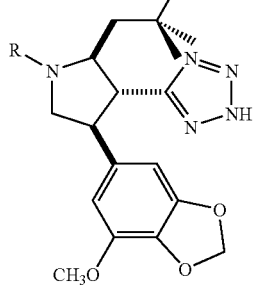 |

TABLE 9A-continued
32
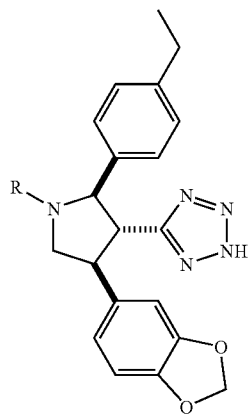
TABLE 9B
1 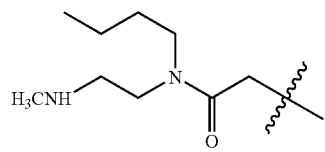
2 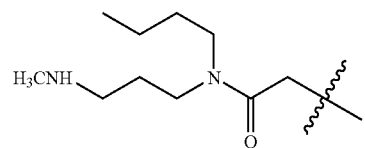
3 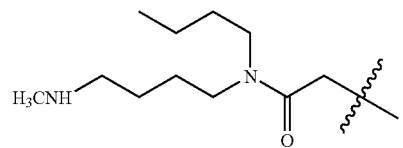
4 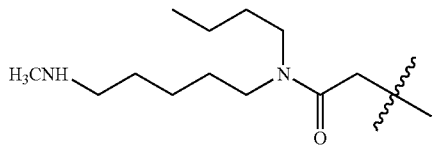
5 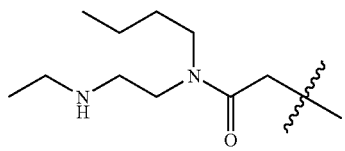
6 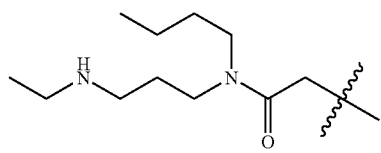
7 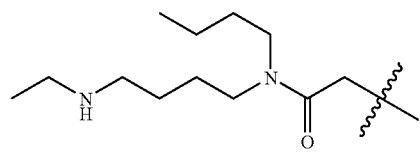
TABLE 9B-continued
8 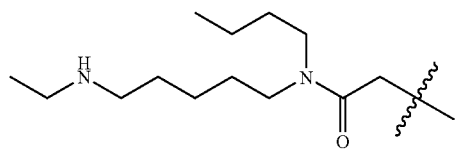
9 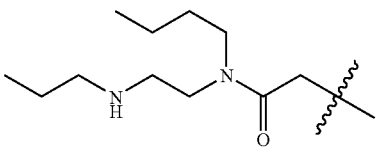
10 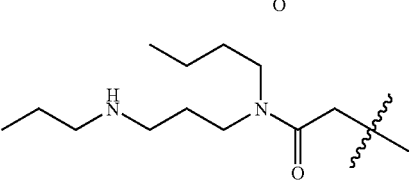
11 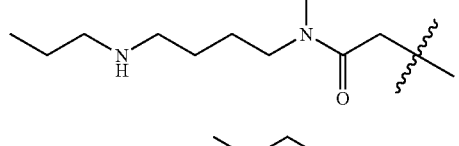
12 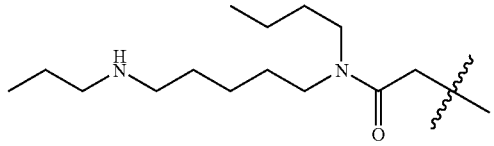
13 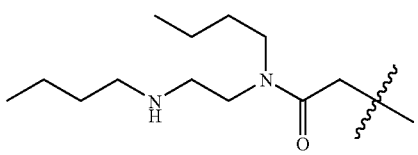
14 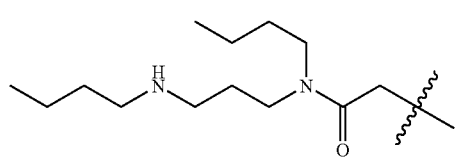
15 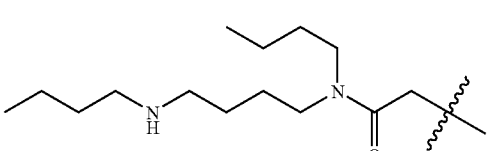
16 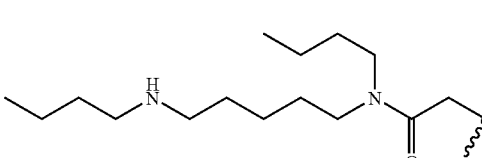
17 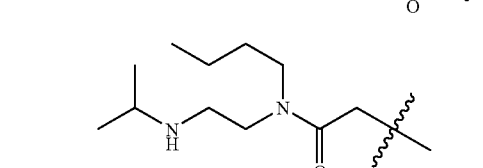

TABLE 9B-continued
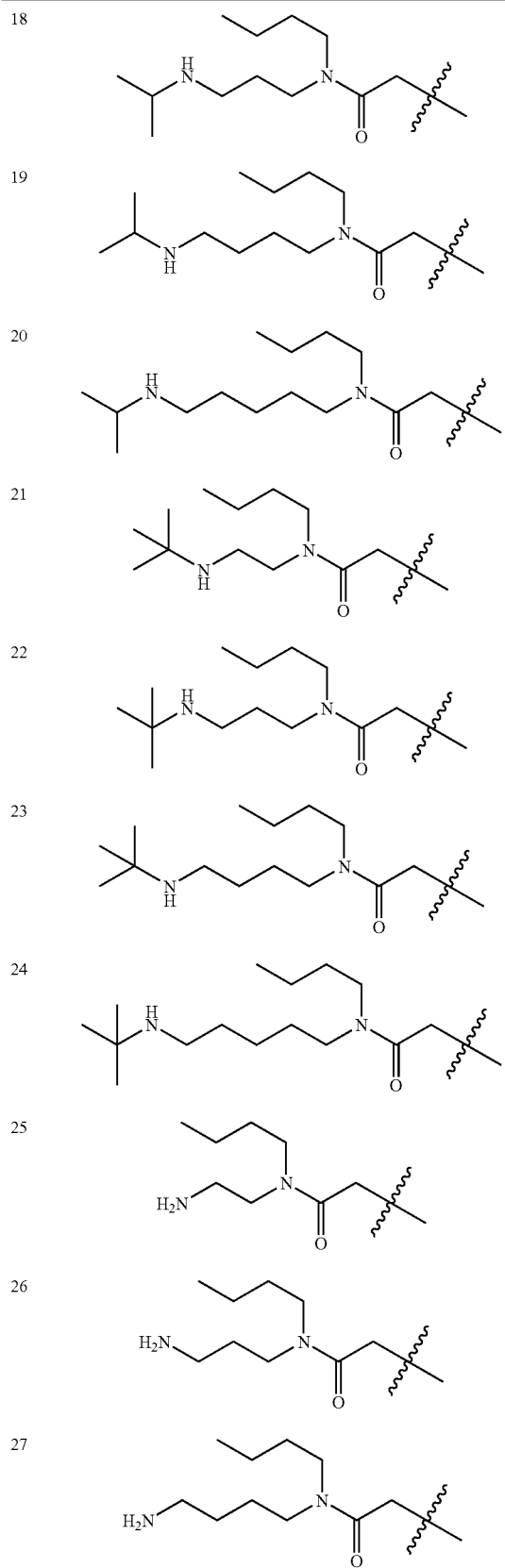
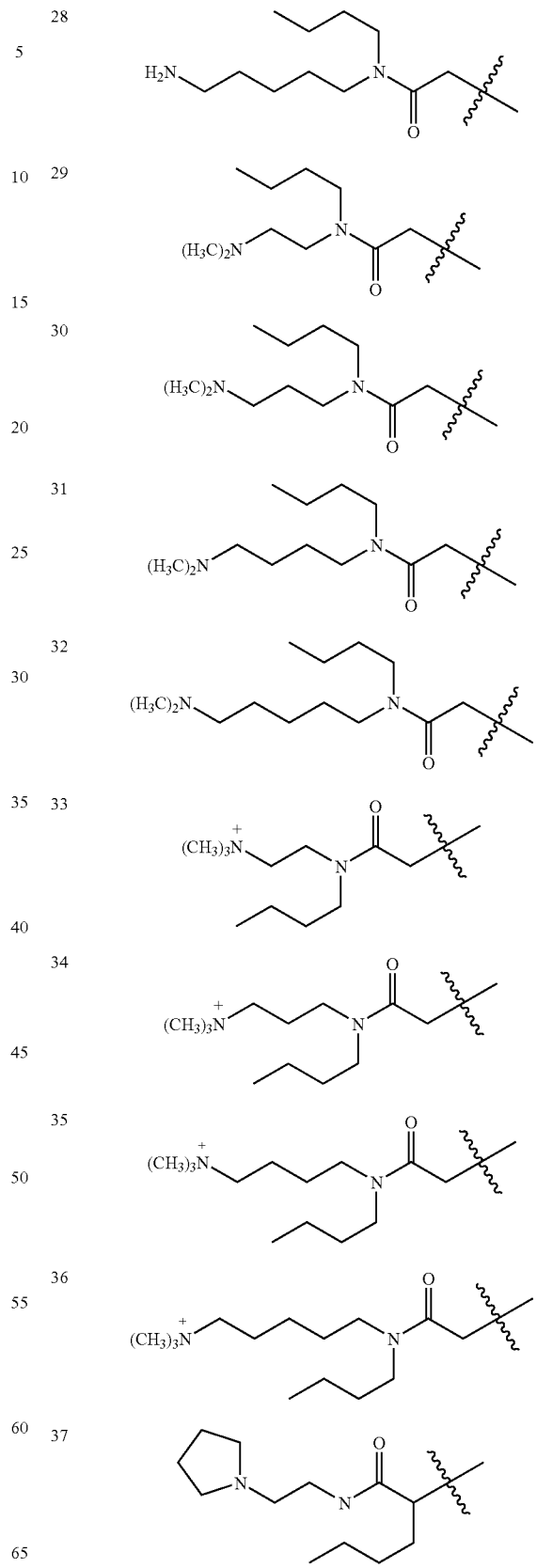

TABLE 9B-continued
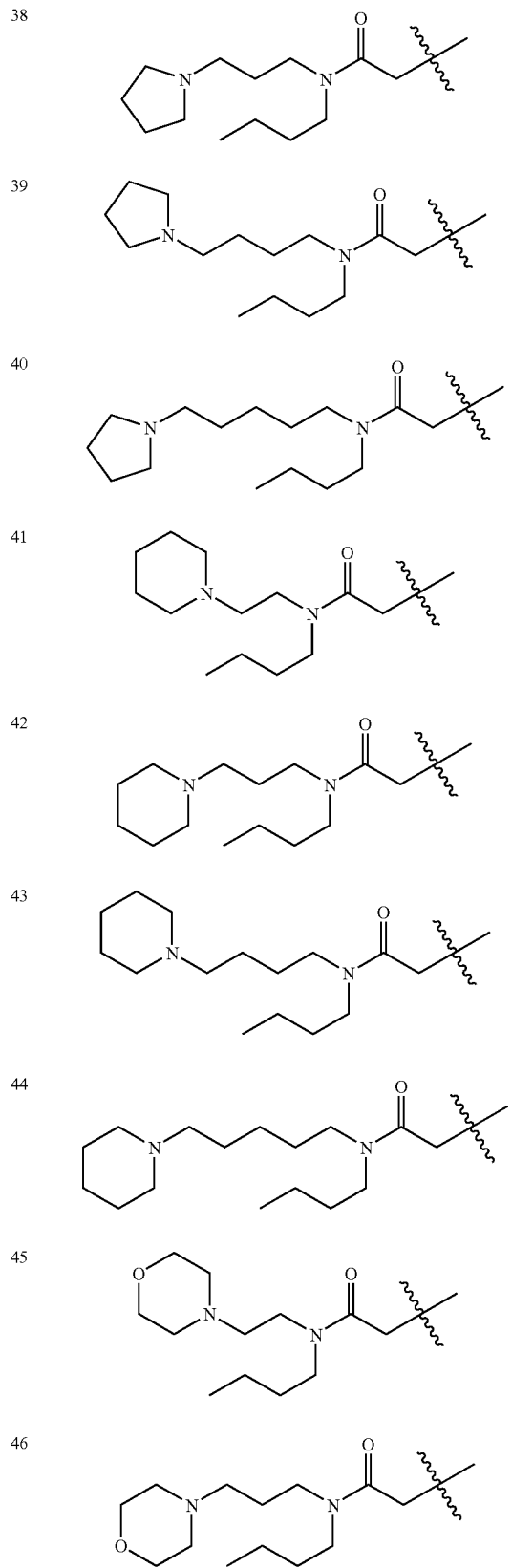
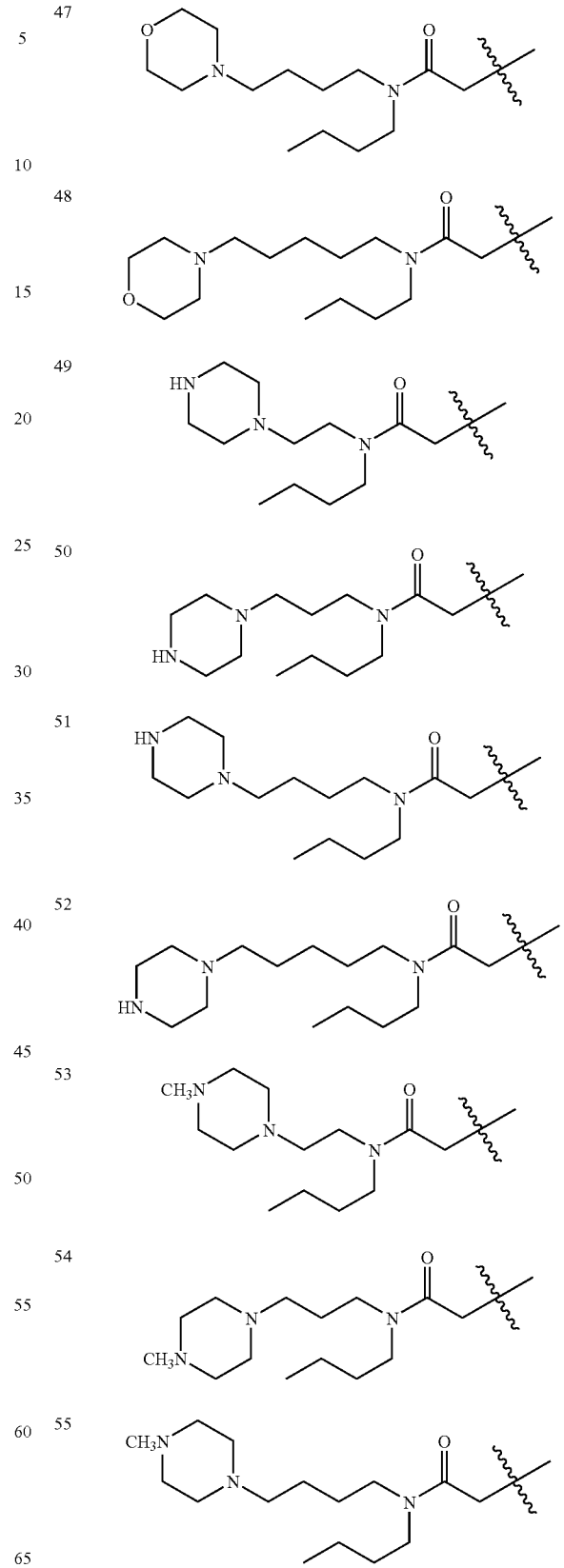

TABLE 9B-continued

| # | Structure |
|---|---|
| 56 | piperazine-N(CH3)-(CH2)4-N(butyl)-C(O)- |
| 57 | cyclohexyl-NH-(CH2)2-N(butyl)-C(O)- |
| 58 | cyclohexyl-NH-(CH2)3-N(butyl)-C(O)- |
| 59 | cyclohexyl-NH-(CH2)4-N(butyl)-C(O)- |
| 60 | cyclohexyl-NH-(CH2)5-N(butyl)-C(O)- |
| 61 | tetrahydropyran-4-yl-NH-(CH2)2-N(butyl)-C(O)- |
| 62 | tetrahydropyran-4-yl-NH-(CH2)3-N(butyl)-C(O)- |
| 63 | tetrahydropyran-4-yl-NH-(CH2)4-N(butyl)-C(O)- |
| 64 | tetrahydropyran-4-yl-NH-(CH2)5-N(butyl)-C(O)- |

For the purposes of this disclosure, the term "(cycloalkyl)aminoalkyl" as used herein refers a cycloalkyl moiety attached to the parent compound through an aminoalkyl. Examples of (cycloalkyl)aminoalkyl include (cyclohexane)aminopropyl, (cyclohexane)aminoethyl, and the like.

The term "(heterocyclic)aminoalkyl" as used herein refers to a heterocyclic moiety attached to the parent compound through an aminoalkyl. Examples of (heterocyclic)aminoalkyl include (pyridine)aminopropyl, (benzofuran)aminopropyl, (tetrahydopyran)aminoethyl, and the like.

The term "(cycloalkyl)alkylaminoalkyl" refers to a cycloalkyl moiety attached to the parent compound through an alkylaminoalkyl. Examples of (cycloalkyl)alkylaminoalkyl include (cyclohexane)ethylaminomethyl, (cyclopentane)methylaminoisopropyl, and the like.

The term "(heterocyclic)alkylaminoalkyl" as used herein refers to a heterocyclic moiety attached to the parent compound through an alkylaminoalkyl. Examples of (heterocyclic)alkylaminoalkyl include (pyridine)ethylaminopropyl, (benzofuran)methylaminoisobutyl, (tetrahydopyran)methylaminoethyl, and the like.

The ability of the compounds of the invention to lower blood pressure can be demonstrated according to the methods described in Matsumura, et al., Eur. J. Pharmacol. 185 103 (1990) and Takata, et al., Clin. Exp. Pharmacol. Physiol. 10 131 (1983).

The ability of the compounds of the invention to treat congestive heart failure can be demonstrated according to the method described in Margulies, et al., Circulation 82 2226 (1990).

The ability of the compounds of the invention to treat myocardial ischemia can be demonstrated according to the method described in Watanabe, et al., Nature 344 114 (1990).

The ability of the compounds of the invention to treat coronary angina can be demonstrated according to the method described in Heistad, et al., Circ. Res. 54 711 (1984).

The ability of the compounds of the invention to treat cerebral vasospasm can be demonstrated according to the methods described in Nakagomi, et al., J. Neurosurg. 66 915 (1987) or Matsumura, et al., Life Sci. 49 841–848 (1991).

The ability of the compounds of the invention to treat cerebral ischemia can be demonstrated according to the method described in Hara et al., European. J. Pharmacol. 197: 75–82, (1991).

The ability of the compounds of the invention to treat acute renal failure can be demonstrated according to the method described in Kon, et al., J. Clin. Invest. 83 1762 (1989).

The ability of the compounds of the invention to treat chronic renal failure can be demonstrated according to the method described in Benigni, et al., Kidney Int. 44 440–444 (1993).

The ability of the compounds of the invention to treat gastric ulceration can be demonstrated according to the method described in Wallace, et al., Am. J. Physiol. 256 G661 (1989).

The ability of the compounds of the invention to treat cyclosporin-induced nephrotoxicity can be demonstrated according to the method described in Kon, et al., Kidney Int. 37 1487 (1990).

The ability of the compounds of the invention to treat endotoxin-induced toxicity (shock) can be demonstrated according to the method described in Takahashi, et al., Clinical Sci. 79 619 (1990).

The ability of the compounds of the invention to treat asthma can be demonstrated according to the method described in Potvin and Varma, Can. J. Physiol. and Pharmacol. 67 1213 (1989).

The ability of the compounds of the invention to treat transplant-induced atherosclerosis can be demonstrated according to the method described in Foegh, et al., Atherosclerosis 78 229–236 (1989).

The ability of the compounds of the invention to treat atherosclerosis can be demonstrated according to the methods described in Bobik, et al., Am. J. Physiol. 258 C408 (1990) and Chobanian, et al., Hypertension 15 327 (1990).

The ability of the compounds of the invention to treat LPL-related lipoprotein disorders can be demonstrated according to the method described in Ishida, et al., Biochem. Pharmacol. 44 1431–1436 (1992).

The ability of the compounds of the invention to treat proliferative diseases can be demonstrated according to the methods described in Bunchman E T and C A Brookshire, Transplantation Proceed. 23 967–968 (1991); Yamagishi, et al., Biochem. Biophys. Res. Comm. 191 840–846 (1993); and Shichiri, et al., J. Clin. Invest. 87 1867–1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels.

The ability of the compounds of the invention to treat acute or chronic pulmonary hypertension can be demonstrated according to the method described in Bonvallet et al., Am. J. Physiol. 266H1327 (1994). Pulmonary hypertension can be associated with congestive heart failure, mitral valve stenosis, emphysema, lung fibrosis, chronic obstructive pulmonary disease (COPD), acute repiratory distress syndrome (ARDS), altitude sickness, chemical exposure, or may be idiopathic.

The ability of the compounds of the invention to treat plaletet aggregation, and thrombosis, can be demonstrated according to the method described in McMurdo et al. Eu. J. Pharmacol. 259 51 (1994).

The ability of the compounds of the invention to treat cancers can be demonstrated according to the method described in Shichiri, et al., J. Clin. Invest. 87 1867 (1991).

The ability of the compounds of the invention to treat IL-2 (and other cytokine) mediated cardiotoxicity and vascular permeability disorders can be demonstrated according to the method described in Klemm et al., Proc. Nat. Acad. Sci. 92 2691 (1995).

The ability of the compounds of the invention to treat nociception can be demonstrated according to the method described in Yamamoto et al., J. Pharmacol. Exp. Therap. 271 156 (1994).

The ability of the compounds of the invention to treat colitis can be demonstrated according to the method described in Hogaboam et al (EUR. J. Pharmacol. 1996, 309, 261–269).

The ability of the compounds of the invention to treat ischemia-repurfusion injury in kidney transplantation can be demonstrated according to the method described in Aktan et al (Transplant Int 1996, 9, 201–207).

The ability of the compounds of the invention to treat angina, pulmonary hypertension, raynaud's disease, and migraine can be demonstrated according to the method described in Ferro and Webb (Drugs 1996, 51,12–27).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (1), or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful for antagonizing endothelin in a human or other mammal. In addition, the compounds of the present invention are useful (in a human or other mammal) for the treatment of hypertension, acute or chronic pulmonary hypertension, Raynaud's disease, congestive heart failure, myocardial ischemia, reperfusion injury, coronary angina, cerebral ischemia, cerebral vasospasm, chronic or acute renal failure, non-steroidal antiinflammatory drug induced gastric ulceration, cyclosporin induced nephrotoxicity, endotoxin-induced toxicity, asthma, fibrotic or proliferative diseases, including smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels, LPL-related lipoprotein disorders, transplantation-induced atherosclerosis or atherosclerosis in general, platelet aggregation, thrombosis, cancers, prostate cancer, IL-2 and other cytokine mediated cardiotoxicity and permeability disorders, and nociception, especially treatment of bone pain associated with bone cancer.

Total daily dose administered to a host in single or divided doses may be in amounts, for example, from 0.001 to 1000 mg/kg body weight daily and more usually 0.1 to 100 mg/kg for oral administration or 0.01 to 10 mg/kg for parenteral administration. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according. to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa buffer and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A representative solid dosage form, for example, a tablet or a capsule, comprises:

| | |
|---|---|
| Compound of the invention: | 35% w/w |
| Starch, Pregelatinized, NF | 50% w/w |
| Microcrystalline Cellulose, NF | 10% w/w |
| Talc, Powder, USP | 5% w/w |

While the compounds of the invention can be administered as the sole active pharmaceutical agent, they can also be used in combination with one or more cardiovascular agents independently selected from diuretics, adrenergic blocking agents, vasodilators, calcium channel blockers, renin inhibitors, angiotensin converting enzyme (ACE) inhibitors, angiotensin II antagonists, potassium channel activators and other cardiovascular agents.

Representative diuretics include hydrochlorothiazide, chlorothiazide, acetazolamide, amiloride, bumetamide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative renin inhibitors include enalkiren, zankiren, RO 42-5892, PD-134672 and the like or a pharmaceutically acceptable salt thereof.

Representative angiotensin II antagonists include DUP 753, A-81988 and the like.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compounds of the invention and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds, processes, compositions and methods. Variations and changes which are obvious to one skilled in the art are intended to be within the scope and nature of the invention which are defined in the appended claims.

What is claimed is:

1. A method for treating nociception comprising administering to a mammal in need of such treatment a therapeutically effective amount of trans,trans-2-(4-methoxyphenyl)-4-(1,3-benzodioxol-5-yl)-1-(N,N-di(n-butyl) aminocarbonylmethyl)-pyrrolidine-3-carboxylic acid, or a pharmaceutically acceptable salt thereof.

2. A method for treating bone pain associated with bone cancer comprising administering to a mammal in need of such treatment a therapeutically effective amount of trans, trans-2-(4-methoxyphenyl)-4-(1,3-benzodioxol-5-yl)-1-(N,N-di(n-butyl)aminocarbonylmethyl)pyrrolidine-3-carboxylic acid, or a pharmaceutically acceptable salt thereof.

3. A method for treating nociception comprising administering to a mammal in need of such treatment a pharmaceutical composition comprising a therapeutically effective amount of trans,trans-2-(4-methoxyphenyl)$_4$-(1,3-benzodioxol-5-yl)-1-(N,N-di(n-butyl)aminocarbonylmethyl)pyrrolidine-3-carboxylic acid, or a pharmaceutically acceptable salt thereof.

4. A method for treating bone pain associated with bone cancer comprising administering to a mammal in need of such treatment a pharmaceutical composition comprising a therapeutically effective amount of trans,trans-2-(4-methoxyphenyl)-4-(1,3-benzodioxol-5-yl)-1-(N,N-di(n-butyl)aminocarbonylmethyl)-pyrrolidine-3-carboxylic acid, or a pharmaceutically acceptable salt thereof.

5. A method for treating nociception comprising administering to a mammal in need of such treatment a therapeutically effective amount of (2R,3R,4S)-(+)-2-(4-methoxyphenyl)-4-(1,3-benzodioxol-5-yl)-1-(N,N-di(n-butyl) aminocarbonylmethyl)-pyrrolidine-3-carboxylic acid, or a pharmaceutically acceptable salt thereof.

6. A method for treating bone pain associated with bone cancer comprising administering to a mammal in need of such treatment a therapeutically effective amount of (2R, 3R,4S)-(+)-2-(4-methoxyphenyl)-4-(1,3-benzodioxol-5-yl)-1-(N,N-di(n-butyl)aminocarbonylmethyl)pyrrolidine-3-carboxylic acid, or a pharmaceutically acceptable salt thereof.

7. A method for treating nociception comprising administering to a mammal in need of such treatment a pharmaceutical composition comprising a therapeutically effective amount of (2R,3R,4S)-(+)-2-(4-methoxyphenyl)-4-(1,3-benzodioxol-5-yl)-1-(N,N-di(n-butyl)aminocarbonylmethyl)pyrrolidine-3-carboxylic acid, or a pharmaceutically acceptable salt thereof.

8. A method for treating bone pain associated with bone cancer comprising administering to a mammal in need of such treatment a pharmaceutical composition comprising a therapeutically effective amount of (2R,3R,4S)-(+)-2-(4-methoxyphenyl)-4-(1,3-benzodioxol-5-yl)-1-(N,N-di(n-butyl)aminocarbonylmethyl)-pyrrolidine-3-carboxylic acid, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,208,517 B1 |
| APPLICATION NO. | : 09/653563 |
| DATED | : April 24, 2007 |
| INVENTOR(S) | : Martin Winn et al. |

It is certified that error appears in the above-identified patent and that said Letters Patent is hereby corrected as shown below:

Col. 1185, line 27
  replace "amount of tran,trans-2-(4-methoxyphenyl)$_4$-(1,3-benzo-"
  with --amount of tran,trans-2-(4-methoxyphenyl)-4-(1,3-benzo- --.

Signed and Sealed this

Twenty-sixth Day of June, 2007

JON W. DUDAS
*Director of the United States Patent and Trademark Office*